US011123439B2

(12) United States Patent
Lerchen et al.

(10) Patent No.: US 11,123,439 B2
(45) Date of Patent: Sep. 21, 2021

(54) ANTIBODY DRUG CONJUGATES (ADCS) AND ANTIBODY PRODRUG CONJUGATES (APDCS) WITH ENZYMATICALLY CLEAVABLE GROUPS

(71) Applicant: Bayer Pharma Aktiengesellschaft, Berlin (DE)

(72) Inventors: Hans-Georg Lerchen, Leverkusen (DE); Anne-Sophie Rebstock, Champagne au Mont d'Or (FR); Yolanda Cancho Grande, Leverkusen (DE); Leo Marx, Wuppertal (DE); Beatrix Stelte-Ludwig, Wülfrath (DE); Carsten Terjung, Bochum (DE); Christoph Mahlert, Wuppertal (DE); Simone Greven, Dormagen (DE); Anette Sommer, Berlin (DE); Sandra Berndt, Hohen Neuendorf (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 492 days.

(21) Appl. No.: 15/739,111

(22) PCT Filed: Jun. 20, 2016

(86) PCT No.: PCT/EP2016/064118

§ 371 (c)(1),
(2) Date: Dec. 21, 2017

(87) PCT Pub. No.: WO2016/207089

PCT Pub. Date: Dec. 29, 2016

(65) Prior Publication Data

US 2018/0169256 A1 Jun. 21, 2018

(30) Foreign Application Priority Data

Jun. 22, 2015 (EP) .................................... 15173102
Mar. 16, 2016 (EP) .................................... 16160738

(51) Int. Cl.
*A61K 47/68* (2017.01)
*A61K 47/65* (2017.01)
(Continued)

(52) U.S. Cl.
CPC ...... *A61K 47/6803* (2017.08); *A61K 31/4025* (2013.01); *A61K 31/4439* (2013.01);
(Continued)

(58) Field of Classification Search
None
See application file for complete search history.

(56) References Cited

U.S. PATENT DOCUMENTS 4,474,893 A 10/1984 Reading
4,714,681 A 12/1987 Reading
(Continued)

FOREIGN PATENT DOCUMENTS

CA 2990411 A1 12/2016
CA 3018630 A1 9/2017
(Continued)

OTHER PUBLICATIONS

Dubowchik et al., Bioorganic & Medicinal Chemistry Letters 8 (1998) 3341-3346 (Year: 1998).*
(Continued)

*Primary Examiner* — Karl J Puttlitz
(74) *Attorney, Agent, or Firm* — Wilson Sonsini Goodrich & Rosati

(57) ABSTRACT

The present invention relates to novel binder-prodrug conjugates (APDCs) where binders are conjugated with inactive
(Continued)

| | | 34 40 50 60 68 |
|---|---|---|
| SEQ ID NO: 169 | Human | APCSRGSSWSADLDKCMDCASCRARPHSDFCLGCA |
| SEQ ID NO: 134 | Rat | APCSSGSSWSADLDKCMDCASCPARPHSDFCLGCA |
| SEQ ID NO: 133 | Mac | APCSHGSSWSADLDKCMDCASCRARPHSDFCLGCS |
| SEQ ID NO: 135 | Pig | TPCSRGSSWSADLDKCMDCASCPARPHSDFCLGCA |
| SEQ ID NO: 137 | Mouse | SPCSSGSSWSADLDKCMDCASCPARPHSDFCLGCA |
| SEQ ID NO: 136 | Dog | TPCPRGSSWSADLDKCMDCASCRARPHSDFCLGCT |
| | | ^ ^ |

precursor compounds of kinesin spindle protein inhibitors, and to antibody-drug conjugates ADCs and to processes for producing these APDCs and ADCs.

51 Claims, 5 Drawing Sheets

Specification includes a Sequence Listing.

(51) Int. Cl.
*A61K 31/4025* (2006.01)
*A61K 31/4439* (2006.01)

(52) U.S. Cl.
CPC .......... *A61K 47/65* (2017.08); *A61K 47/6849* (2017.08); *A61K 47/6851* (2017.08); *A61K 47/6855* (2017.08); *A61K 47/6857* (2017.08); *A61K 47/6863* (2017.08); *A61K 47/6865* (2017.08); *A61K 2300/00* (2013.01)

(56) References Cited

U.S. PATENT DOCUMENTS

| | | | |
|---|---|---|---|
| 4,816,397 A | 3/1989 | Boss et al. | |
| 4,925,648 A | 5/1990 | Hansen et al. | |
| 5,270,163 A | 12/1993 | Gold et al. | |
| 5,573,920 A | 11/1996 | Randle | |
| 5,601,819 A | 2/1997 | Wong et al. | |
| 7,318,924 B2 | 1/2008 | McKenzie et al. | |
| 7,465,449 B2 | 12/2008 | Violette et al. | |
| 7,598,350 B2 | 10/2009 | Liu et al. | |
| 7,628,986 B2 | 12/2009 | Weber et al. | |
| 10,022,453 B2 | 7/2018 | Lerchen | |
| 10,485,880 B2 | 11/2019 | Lerchen | |
| 10,744,205 B2 | 8/2020 | Lerchen et al. | |
| 2007/0264253 A1 | 11/2007 | Liu et al. | |
| 2009/0175796 A1 | 7/2009 | Raitano et al. | |
| 2010/0028947 A1 | 2/2010 | Goletz et al. | |
| 2014/0322247 A1* | 10/2014 | Barsanti ............ | A61K 31/4196 424/178.1 |
| 2016/0346402 A1 | 12/2016 | Lerchen | |
| 2018/0015176 A1 | 1/2018 | Lerchen | |
| 2018/0185510 A1 | 7/2018 | Lerchen | |
| 2018/0318437 A1 | 11/2018 | Lerchen | |
| 2018/0318438 A1 | 11/2018 | Lerchen | |
| 2019/0077752 A1 | 3/2019 | Lerchen | |
| 2019/0262463 A1 | 8/2019 | Lerchen | |
| 2019/0328897 A1 | 10/2019 | Lerchen | |
| 2019/0330357 A1 | 10/2019 | Lerchen | |
| 2019/0351066 A1 | 11/2019 | Lerchen | |
| 2019/0365916 A1 | 12/2019 | Lerchen | |
| 2020/0138970 A1 | 5/2020 | Lerchen et al. | |

FOREIGN PATENT DOCUMENTS

| | | | |
|---|---|---|---|
| EP | 0719859 | A1 | 7/1996 |
| EP | 1735348 | A1 | 12/2006 |
| EP | 1900750 | A1 | 3/2008 |
| EP | 1911766 | A1 | 4/2008 |
| EP | 2073842 | A2 | 7/2009 |
| WO | WO-9000786 | A1 | 1/1990 |
| WO | WO-9100360 | A1 | 1/1991 |
| WO | WO-9105871 | A1 | 5/1991 |
| WO | WO-9205793 | A1 | 4/1992 |
| WO | WO-9208802 | A1 | 5/1992 |
| WO | WO-9215683 | A1 | 9/1992 |
| WO | WO-9317715 | A1 | 9/1993 |
| WO | WO-9708320 | A1 | 3/1997 |
| WO | WO-9735616 | A1 | 10/1997 |
| WO | WO-9947554 | A1 | 9/1999 |
| WO | WO-0109192 | A1 | 2/2001 |
| WO | WO-0162931 | A2 | 8/2001 |
| WO | WO-0188138 | A1 | 11/2001 |
| WO | WO-0212501 | A2 | 2/2002 |
| WO | WO-02077033 | A1 | 10/2002 |
| WO | WO-020881 70 | A2 | 11/2002 |
| WO | WO-02092771 | A2 | 11/2002 |
| WO | WO-02100348 | A2 | 12/2002 |
| WO | WO-03034903 | A2 | 5/2003 |
| WO | WO-03040979 | A1 | 5/2003 |
| WO | WO-03049527 | A2 | 6/2003 |
| WO | WO-03060064 | A2 | 7/2003 |
| WO | WO-03083041 | A2 | 10/2003 |
| WO | WO-03106495 | A2 | 12/2003 |
| WO | WO-2004056847 | A2 | 7/2004 |
| WO | WO-2004091375 | A2 | 10/2004 |
| WO | WO-2005009369 | A2 | 2/2005 |
| WO | WO-2005010151 | A2 | 2/2005 |
| WO | WO-2005051922 | A1 | 6/2005 |
| WO | WO-2005056606 | A2 | 6/2005 |
| WO | WO-2005081711 | A2 | 9/2005 |
| WO | WO-2005081854 | A2 | 9/2005 |
| WO | WO-2005090407 | A1 | 9/2005 |
| WO | WO-2006002236 | A1 | 1/2006 |
| WO | WO-2006044825 | A2 | 4/2006 |
| WO | WO-2006060737 | A2 | 6/2006 |
| WO | WO-2006062779 | A2 | 6/2006 |
| WO | WO-2006074418 | A2 | 7/2006 |
| WO | WO-2006089232 | A2 | 8/2006 |
| WO | WO-2006100036 | A1 | 9/2006 |
| WO | WO-2007002222 | A2 | 1/2007 |
| WO | WO-2007024536 | A2 | 3/2007 |
| WO | WO-2007038637 | A2 | 4/2007 |
| WO | WO-2007070538 | A2 | 6/2007 |
| WO | WO-2008004834 | A1 | 1/2008 |
| WO | WO-2008028686 | A2 | 3/2008 |
| WO | WO-2008031056 | A2 | 3/2008 |
| WO | WO-2008036688 | A2 | 3/2008 |
| WO | WO-2008047242 | A2 | 4/2008 |
| WO | WO-2008070593 | A2 | 6/2008 |
| WO | WO-2008092117 | A2 | 7/2008 |
| WO | WO-2008140603 | A2 | 11/2008 |
| WO | WO-2009000786 | A2 | 12/2008 |
| WO | 2009020933 | * | 2/2009 |
| WO | WO2009020933 | A2 | 2/2009 |
| WO | WO-2009023265 | A1 | 2/2009 |
| WO | WO-2009026274 | A1 | 2/2009 |
| WO | WO-2009033094 | A2 | 3/2009 |
| WO | WO-2009068204 | A1 | 6/2009 |
| WO | WO-2009080829 | A1 | 7/2009 |
| WO | WO-2009080830 | A1 | 7/2009 |
| WO | WO-2009123894 | A2 | 10/2009 |
| WO | 2009140177 | * | 11/2009 |
| WO | WO-2010022736 | A2 | 3/2010 |
| WO | WO2009140177 | A2 | 8/2010 |
| WO | WO-2010112413 | A1 | 10/2010 |
| WO | WO-2010115554 | A1 | 10/2010 |
| WO | WO-2011044368 | A1 | 4/2011 |
| WO | WO-2012143499 | A2 | 10/2012 |
| WO | WO-2012171020 | A1 | 12/2012 |
| WO | WO-2013076186 | A1 | 5/2013 |
| WO | WO-2013092983 | A2 | 6/2013 |
| WO | WO-2013092998 | A1 | 6/2013 |
| WO | WO2014093640 | A1 | 6/2014 |
| WO | WO2014151030 | A1 | 9/2014 |
| WO | WO-2014199817 | A1 | 12/2014 |
| WO | WO2015054659 | A1 | 4/2015 |
| WO | WO2015096982 | A1 | 7/2015 |
| WO | WO2015138615 | A2 | 9/2015 |
| WO | WO2015189143 | A1 | 12/2015 |
| WO | WO2016020791 | A1 | 2/2016 |
| WO | WO2016096610 | A1 | 6/2016 |
| WO | WO-2016207089 | A1 | 12/2016 |
| WO | WO2016207090 | A2 | 12/2016 |
| WO | WO2016207094 | A1 | 12/2016 |
| WO | WO2016207098 | A1 | 12/2016 |
| WO | WO2016207103 | A1 | 12/2016 |
| WO | WO2016207104 | A1 | 12/2016 |
| WO | WO2017162663 | A1 | 9/2017 |
| WO | WO2017216028 | A1 | 12/2017 |
| WO | WO2018114578 | A1 | 6/2018 |

(56) References Cited

FOREIGN PATENT DOCUMENTS

| | | |
|---|---|---|
| WO | WO2018114798 A1 | 6/2018 |
| WO | WO2018114804 A1 | 6/2018 |

OTHER PUBLICATIONS

Dubowchik et al. Bioorg. Med. Chem. Lett. 8 (1998) 3347-3352 (Year: 1998).*
Maltman et al., Org. Biomol. Chem., 2005, 3, 2505-2507 (Year: 2005).*
Jain et al., Pharm Res (2015) 32:3526-3540 (Year: 2015).*
International Search Report dated Sep. 13, 2016 for International Application No. PCT/EP2016/064118 filed Jun. 20, 2016, 10 pages.
U.S. Appl. No. 15/739,471, filed Feb. 22, 2019, for Lerchen et al. (Copy not attached) (U.S. Patent Application is not submitted herewith pursuant to the waiver of 37 C.F.R § 1.98(a)(2)(iii) issued by the Office on Sep. 21, 2004.).
Zhou H. et al. (2011). "Development and Characterization of a Potent Immunoconjugate Targeting the Fn14 Receptor on Solid Tumor Cells," Mol Cancer Therapeutics 10(7):276-1288.
Zhou H et al. (2012). "The TWEAK Receptor Fn14 is a Novel Therapeutic Target in Melanoma: Immunotoxins Targeting Fn14 Receptor for Malignant Melanoma Treatment," J. Invest Dermatol. 133(4):1052-1062.
Agarwal et al. Site-specific antibody-drug conjugates: the nexus of bioorthogonal chemistry, protein engineering, and drug development. Bioconjug. Chem. 26:176-192 (2015).
Amir et al. Prodrug activation gated by a molecular "OR" logic trigger. Angew Chem. Inter. Ed. 44:4378-4381 (2005).
Bajjuri et al. The legumain protease-activated auristatin prodrugs suppress tumor growth and metastasis without toxicity. ChemMedChem 6(1):54-59 (2011).
Behrens et al. Methods for site-specific drug conjugation to antibodies. MAbs 6:46-53 (2014).
Cal et al. Cysteine-selective reactions for antibody conjugation. Angewandte Chemi International Edition 53:10585-10587 (2014).
Chen et al. Cloning, isolation, and characterization of mammalian legumain, an asparaginyl endopeptidase. J. Biol. Chern. 272:8090-8098 (1997).
Clackson et al. Making antibody fragments using phage display libraries. Nature 352(6336):624-628 (1991).
Co-pending U.S. Appl. No. 17/253,086, inventors Johannes; Sarah Anna Liesa et al., filed on Dec. 16, 2020.
Culp et al. Antibodies to TWEAK receptor inhibit human tumor growth through dual mechanisms. Clin Cancer Res. 16(2):497-508 (2010).
Delfourne et al. Synthesis and in vitro antitumor activity of phenanthrolin-7-one derivatives, analogues of the marine pyridoacridine alkaloids ascididemin and meridine: structure-activity relationship. J. Med. Chern. 46(16):3536-3545 (2003).
Dennler et al. Chapter 12: Antibody Drug Conjuagtes (Ducry, L., Ed.), pp. 205-215, Humana Press. (2013).
Doronina et al. Development of potent monoclonal antibody auristatin conjugates for cancer therapy. Nat Biotechnol 21:778-784 (2003).
Dorsch et al. Identification and optimization of pyridazinones as potent and selective c-Met kinase inhibitors. Bioorg. Med. Chern. Lett. 7:1597-1602 (1999).
Dubowchik et al. Cathepsin B-labile dipeptide linkers for lysosomal release of doxorubicin from internalizing immunoconjugates: model studies of enzymatic drug release and antigen-specific in vitro anticancer activity. Bioconjugate Chem. 13:855-869 (2002).
Ducry et al. Antibody-drug conjugates: linking cytotoxic payloads to monoclonal antibodies. Bioconjug Chern. 21(1):5-13 (2010).
Gebauer et al. Engineered protein scaffolds as next-generation antibody therapeutics. Curr. Opinion in Chem. Biol. 13:245-255 (2009).
Hoet et al. Generation of high-affinity human antibodies by combining donor-derived and synthetic complementarity-determining-region diversity. Nature Biotechnology 23(3):344-348 (Mar. 2005).
Hoogenboom. Selecting and screening recombinant antibody libraries. Nat Biotechnol. 23(9):1105-16 (2005).
Ishii. Legumain: asparaginyl endopeptidase . Methods Enzymol. 244:604-615 (1994).
Jeger et al. Site-specific and stoichiometric modification of antibodies by bacterial transglutaminase. Ange Chem Int. Ed. Engl 49:9995-9997 (2010).
Josten et al. Use of microbial transglutaminase for the enzymatic biotinylation of antibodies. J. Immunol. Methods 240:47-54 (2000).
Junutula et al. Site-specific conjugation of a cytotoxic drug to an antibody improves the therapeutic index. Nat Biotechnol. 26(8):925-32 (2008).
Kabat et al. Sequences of proteins of immunological interest. NIH Publ. No. 91-3242 1:647-669 (1991).
Keefe et al. Aptamers as therapeutics. Nat. Rev. Drug Discov. 9:537-550 (2010).
Kohchi et al. Design and synthesis of novel prodrugs of 2'-deoxy-2'-methylidenecytidine activated by membrane dipeptidase overexpressed in tumor tissues. Bioorg. Med. Chem. Lett. 17:2241-2245 (2007).
Kohler et al. Continuous cultures of fused cells secreting antibody of predefined specificity. Nature256(5517):495-497 (1975).
Kostelny et al. Formation of a bispecific antibody by the use of leucine zippers. J. Immunol. 148(5):1547-1553 (1992).
Kumar et al. Modulating paclitaxel bioavailability for targeting prostate cancer. Bioorg. Med. Chem. 15:4973-4984 (2007).
Lambert. Drug-conjugated monoclonal antibodies for the treatment of cancer. Curr. Opin. Pharmacol. 5:543-549 (2005).
Lang et al. Cellular Incorporation of Unnatural Amino Acids and Bioorthogonal Labeling of Proteins, Chem.Rev. 114:4764-4806 (2014) .
Lhospice et al. Site-Specific Conjugation of Monomethyl Auristatin E to Anti-CD30 Antibodies Improves Their Pharmacokinetics and Therapeutic Index in Rodent Models. Mol Pharm 12:1863-1871 (2015).
Lonberg et al. Human antibodies from transgenic mice. Int Rev Immunol. 13(1):65-93 (1995).
Michaelson et al. Development of an Fn14 agonistic antibody as an anti-tumor agent. MAbs 3(4):362-375 (2011).
Mindt et al. Modification of different IgG1 antibodies via glutamine and lysine using bacterial and human tissue transglutaminase. Bioconjugate Chem. 19:271-278 (2008).
Nose et al. Biological significance of carbohydrate chains on monoclonal antibodies. PNAS USA 80(21):6632-6 (1983).
Nuttall et al. Display scaffolds: protein engineering for novel therapeutics. Curr. Opinion in Pharmacology 8:609-615 (2008).
Olsson et al. Human-human monoclonal antibody-producing hybridomas: Technical aspects. Meth Enzymol. 92:3-16 (1983).
Panowski et al. Site-specific antibody drug conjugates for cancer therapy MAbs 6:34-45 (2014).
Pellegrini et al. Structure of the extracellular domains of human and Xenopus Fn14: implications in the evolution of TWEAK and Fn14 interactions. FEBS 280:1818-1829 (2013).
Peterson et al. Cathepsin substrates as cleavable peptide linkers in bioconjugates, selected from a fluorescence quench combinatorial library. Bioconjugate Chem. 9:618-626 (1998).
Polson et al. Antibody-drug conjugates for the treatment of non-Hodgkin's lymphoma: target and linker-drug selection. Cancer Res. 69(6):2358-64 (2009).
Polson et al. Antibody-drug conjugates targeted to CD79 for the treatment of non-Hodgkin lymphoma. Blood 110(2):616-623 (2007).
Queen et al. A humanized antibody that binds to the interleukin 2 receptor. PNAS USA 86:10029-10032 (1989).
Rashidian et al. Enzymatic labeling of proteins: techniques and approaches. Bioconjugate Chem. 24:1277-1294 (2013).
Rawale et al. Synthesis and biological activity of the prodrug of class I major histocompatibility peptide GILGFVFTL activated by beta-glucuronidase. J. Med. Chem. 45:937-943 (2002).
Schmidt et al. Prodrug Mono Therapy: synthesis and biological evaluation of an etoposide glucuronide-prodrug. Bioorg. Med. Chem. 11:2277-2283 (2003).

(56) References Cited

OTHER PUBLICATIONS

Söderlind et al. Recombining germline-derived CDR sequences for creating diverse single-framework antibody libraries. Nature Biotechnology 18:852-856 (Aug. 1, 2000).
Senter. Potent antibody drug conjugates for cancer therapy. Curr. Opin. Chem. Biol 13:235-244 (2009).
Sochaj et al. Current methods for the synthesis of homogeneous antibody-drug conjugates. Biotechnology Advances 33:775-784 (2015).
Stern, L. et al., A novel antitumor prodrug platform designed to be cleaved by the endoprotease legumain, Bioconj. Chern., 20: 500-510 (2009).
Strop et al. Location matters: site of conjugation modulates stability and pharmacokinetics of antibody drug conjugates. Chem Biol 20(2):161-167 (2013).
Tao et al. Induction of apoptosis by an inhibitor of the mitotic kinesin KSP requires both activation of the spindle assembly checkpoint and mitotic slippage. Cancer Cell 8(1):49-59 (2005).
Tranoy-Opalinski et al. Design of self-immolative linkers for tumour-activated prodrug therapy. Anticancer Agents in Medicinal Chemistry 8:618-637 (2008).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Ueki et al. Selective cancer targeting with prodrugs activated by histone deacetylases and a tumour-associated protease. Nat. Commun. 4:2735 (2013).
Winkelhake et al. Aglycosylantibody. Effects of exoglycosidase treatments on autochthonous antibody survival time in the circulation. J Biol Chern. 251 (4):1074-80 (1976).
Wu et al. Arming antibodies: prospects and challenges for immunoconjugates. Nat. Biotechnol. 23:1137-1146 (2005).
Wu et al. Targeting cell-impermeable prodrug activation to tumor microenvironment eradicates multiple drug-resistant neoplasms. Cancer Res. 66:970-980 (2006).

* cited by examiner

| | | |
|---|---|---|
| | | 34 40 50 60 68 |
| SEQ ID NO: 169 | Human | APCSRGSSWSADLDKCMDCASCRARPHSDFCLGCA |
| SEQ ID NO: 134 | Rat | APCSSGSSWSADLDKCMDCASCPARPHSDFCLGCA |
| SEQ ID NO: 133 | Mac | APCSHGSSWSADLDKCMDCASCRARPHSDFCLGCS |
| SEQ ID NO: 135 | Pig | TPCSRGSSWSADLDKCMDCASCPARPHSDFCLGCA |
| SEQ ID NO: 137 | Mouse | SPCSSGSSWSADLDKCMDCASCPARPHSDFCLGCA |
| SEQ ID NO: 136 | Dog | TPCPRGSSWSADLDKCMDCASCRARPHSDFCLGCT |
| | | ^ ^ |

FIG. 1

ANTIBODY DRUG CONJUGATES (ADCS) AND ANTIBODY PRODRUG CONJUGATES (APDCS) WITH ENZYMATICALLY CLEAVABLE GROUPS

CROSS REFERENCE TO RELATED APPLICATIONS

This application is a National Phase application under 35 U.S.C. § 371 of International Application No. PCT/EP2016/064118, filed Jun. 20, 2016, which claims priority benefit of European Application No. 16160738.7, filed Mar. 16, 2016 and European Application No. 15173102.3, filed Jun. 22, 2015.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052019400seqlist.txt, date recorded: Dec. 18, 2017, size: 405 KB).

INTRODUCTION AND STATE OF THE ART

The invention relates to novel binder-prodrug conjugates (ADCs) in which binders are conjugated with inactive precursor compounds of kinesin spindle protein inhibitors, and to binder-drug conjugates ADCs, to active metabolites of these binder-prodrug conjugates and binder-drug conjugates, to processes for preparing these APDCs and ADCs, to the use of these conjugates for the treatment and/or prophylaxis of diseases and to the use of these conjugates for preparing medicaments for treatment and/or prevention of diseases, in particular hyperproliferative and/or angiogenic disorders such as, for example, cancer diseases. Such treatments can be effected as monotherapy or else in combination with other medicaments or further therapeutic measures. According to the invention, the binder is preferably an antibody.

Cancers are the consequence of uncontrolled cell growth of the most diverse tissues. In many cases the new cells penetrate into existing tissue (invasive growth), or they metastasize into remote organs. Cancers occur in a wide variety of different organs and often have tissue-specific courses. The term "cancer" as a generic term therefore describes a large group of defined diseases of different organs, tissue and cell types.

Some tumours at early stages can be removed by surgical and radiotherapy measures. Metastased tumours as a rule can only be treated palliatively by chemotherapeutics. The aim here is to achieve the optimum combination of an improvement in the quality of life and prolonging of life.

Conjugates of binder proteins with one or more drug molecules are known, in particular in the form of antibody drug conjugates (ADCs) in which an internalizing antibody directed against a tumour-associated antigen is covalently attached via a linker to a cytotoxic agent. Following introduction of the ADCs into the tumour cell and subsequent dissociation of the conjugate, either the cytotoxic agent itself or a cytotoxic metabolite formed therefrom is released within the tumour cell and can unfold its action therein directly and selectively. In this manner, in contrast to conventional chemotherapy, damage to normal tissue is contained in significantly narrower limits [see, for example, J. M. Lambert, *Curr. Opin. Pharmacol.* 5, 543-549 (2005); A. M. Wu and P. D. Senter, *Nat. Biotechnol.* 23, 1137-1146 (2005); *P. D. Senter, Curr. Opin.* 13, 235-244 (2009); L. Ducry and B. Stump, *Bioconjugate Chem.* Thus, WO2012/171020 describes ADCs in which a plurality of toxophore molecules are attached via a polymeric linker to an antibody. As possible toxophores, WO2012/171020 mentions, among others, the substances SB 743921, SB 715992 (Ispinesib), MK-0371, AZD8477, AZ3146 and ARRY-520.

The substances mentioned last are kinesin spindle protein inhibitors. Kinesin spindle protein (KSP, also known as Eg5, HsEg5, KNSL1 or KIF11) is a kinesin-like motorprotein which is essential for the bipolar mitotic spindle to function. Inhibition of KSP leads to mitotic arrest and, over a relatively long term, to apoptosis (Tao et al., Cancer Cell 2005 Jul. 8(1), 39-59). After the discovery of the first cell-penetrating KSP inhibitor, Monastrol, KSP inhibitors have established themselves as a class of novel chemotherapeutics (Mayer et al., Science 286: 971-974, 1999), and they are subject of a number of patent applications (e.g. WO2006/044825; WO2006/002236; WO2005/051922; WO2006/060737; WO03/060064; WO03/040979; and WO03/049527). However, since KSP is active only during a relatively short period of time during the mitosis phase, KSP inhibitors have to be present in a sufficiently high concentration during this phase. WO2014/151030 discloses ADCs including certain KSP inhibitors.

Legumain is a tumour-associated asparaginyl endopeptidase (S. Ishii, Methods Enzymol. 1994, 244, 604; J. M. Chen et al. J. Biol. Chem. 1997, 272, 8090) and has been utilized for processing of prodrugs of small cytotoxic molecules, for example of doxorubicin and etoposide derivatives among others (W. Wu et al. Cancer Res. 2006, 66, 970; L. Stern et al. Bioconjugate Chem. 2009, 20, 500; K. M. Bajjuri et al. Chem Med Chem 2011, 6, 54).

Other lysosomal enzymes are, for example, cathepsin or glycosidases, for example (3-glucuronidases, which have also been utilized for release of the active ingredients by enzymatic cleavage of prodrugs. Groups cleavable enzymatically in vivo are especially 2-8-oligopeptide groups or glycosides. Peptide cleaving sites are disclosed in *Bioconjugate Chem.* 2002, 13, 855-869 and *Bioorganic & Medicinal Chemistry Letters* 8 (1998) 3341-3346 and also *Bioconjugate Chem.* 1998, 9, 618-626. These include, for example, valine-alanine, valine-lysine, valine-citrulline, alanine-lysine and phenylalanine-lysine (optionally with additional amide group).

SUMMARY OF THE INVENTION

In order to further improve the tumour selectivity of ADCs and the metabolites thereof, binder conjugates have been provided with peptide derivatives which can be released by tumour-associated enzymes such as legumain or cathepsin. The tumour selectivity is thus determined not just by the choice of antibody but additionally by the enzymatic cleavage of the peptide derivative, for example by the tumour-associated enzyme legumain.

According to the invention, the peptide derivative may be present in the linker which connects the binder to the KSP inhibitor. These are the binder-drug conjugates (ADCs) according to the invention.

The kinesin spindle protein inhibitors used in accordance with the invention have an amino group which is essential to the effect. By modification of this amino group with peptide derivatives, the effect with respect to the kinesin spindle protein is blocked and hence the development of a cytotoxic effect is also inhibited. If this peptide residue, however, can be released by tumour-associated enzymes such as legumain, the effect can be re-established in a controlled manner in the tumour tissue. The modification of the amino group in this case is not part of the linker. Therefore, the present invention relates to binder conjugates having inactive precursor molecules of the kinesin spindle protein inhibitors which are only processed in the tumour by means of the tumour-associated lysosomal endopeptidase legumain to give the active metabolites, in order thus to be able to display their cytotoxic activity again in a controlled manner in the tumour. The binder conjugates with KSP inhibitors, wherein the free amino group thereof is correspondingly blocked, are also referred to in accordance with the invention as APDCs. The APDCs are particularly preferred.

Thus, the invention provides conjugates of a binder or derivative thereof with one or more drug molecules or one or more prodrugs thereof, of the following formula I:

$$BINDER-[L-KSP]_n$$

where BINDER represents binder or a derivative thereof (preferably an antibody), L represents a linker, n represents a number from 1 to 50, preferably 1.2 to 20 and more preferably 2 to 8, and KSP represents a kinesin spindle protein inhibitor or prodrug thereof, where L-KSP has the following formula (IIa):

(IIa)

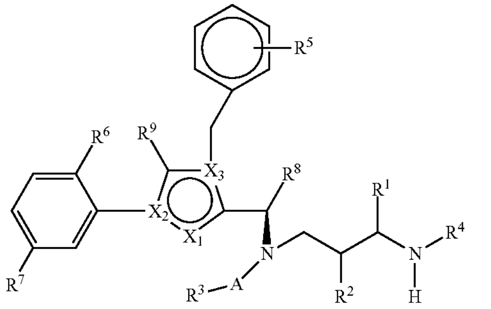

where $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH, $X_2$ represents N and $X_3$ represents C;

(with $X_1$ representing CH, $X_2$ representing C and $X_3$ representing N being preferred);

$R^1$ represents H, -L-#1, -MOD or —$(CH_2)_{0-3}Z$, where Z represents —H, —$NHY^3$, —$OY^3$, —$SY^3$, halogen, —CO—$NY^1Y^2$, or —CO—$OY^3$, where $Y^1$ and $Y^2$ independently of one another represent —H, —$NH_2$, —$(CH_2CH_2O)_{0-3}$—$(CH_2)_{0-3}Z'$ (e.g. —$(CH_2)_{0-3}Z'$), or —$CH(CH_2W)Z'$, and $Y^3$ represents —H or —$(CH_2)_{0-3}Z'$, where Z' represents —H, —$NH_2$, —$SO_3H$, —COOH, —NH—CO—$CH_2$—$CH_2$—$CH(NH_2)COOH$ or —$(CO—NH—CHY^4)_{1-3}COOH$; where W represents —H or —OH, where $Y^4$ represents straight-chain or branched $C_{1-6}$-alkyl which is optionally substituted by —$NHCONH_2$, or represents aryl or benzyl which are optionally substituted by —$NH_2$;

$R^2$ represents -L-#1, H, -MOD, —CO—$CHY^4$—$NHY^5$ or —$(CH_2)_{0-3}Z$, where Z represents —H, halogen, —$OY^3$, —$SY^3$, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or —COOH;

where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents —H or —CO—$CHY^6$—$NH_2$, where $Y^6$ represents straight-chain or branched $C_{1-6}$-alkyl;

$R^4$ represents -L-#1, —H, —CO—$CHY^4$—$NHY^5$ or —$(CH_2)_{0-3}Z$, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents —H or —$(CH_2)_{0-3}Z'$, where Z' represents H, $SO_3H$, $NH_2$ or —COOH;

where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents —H or —CO—$CHY^6$—$NH_2$, where $Y^6$ represents straight-chain or branched $C_{1-6}$-alkyl;

or $R^4$ represents a group of the formula $R^{21}$—$(CO)_{(0-1)}$—$(P3)_{(0-2)}$—P2-NH—CH(CH2CONH2)-CO— or $R^{21}$—$(CO)_{(0-1)}$—$(P3)_{(0-2)}$—P2-NH—CH(CH2COOH)—CO— or the cathepsin-cleavable group of the formula $R^{21}$—$(CO)_{(0-1)}$—$(P3)_{(1-2)}$—P2-, where $R^{21}$ represents a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroaryl-alkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH— alkyl, —$N(alkyl)_2$, NH—CO-alkyl, —N(alkyl)-COalkyl, —$SO_3H$, —$SO_2NH_2$, —$SO_2$—$N(alkyl)_2$, —COOH, —$CONH_2$, —$CON(alkyl)_2$, or —OH, —H or an —$Ox$-$(CH_2CH_2O)_v$—$R^{22}$ group (where x represents 0 or 1 and v represents a number from 1 to 20, and $R^{22}$ represents —H, -alkyl (preferably C1-12-alkyl), —CH2-COOH, —CH2-CH2-COOH, or —CH2-CH2-NH2);

P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably N-methyl amino acids (when more than one P3 is present, P3 may thus have different meanings);

or $R^2$ and $R^4$ together represent (forming a pyrrolidine ring) —$CH_2$—$CHR^{10}$— or —$CHR^{10}$—$CH_2$—, where $R^{10}$ represents H, —$NH_2$, —$SO_3H$, —COOH, —SH, halogen (especially F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl), —OH and where the hydrogen atom of the secondary amino group in the pyrrolidine ring may be replaced by $R^{21}$—CO—$P3_{(0-2)}$—P2-NH—CH($CH_2CONH_2$)—CO)—CO-SIG-, where SIG represents a self-immolative group which, after cleavage of the CO-SIG bond, releases the secondary amine;

A represents —C(═O)—, —S(═O)—, —S(═O)$_2$—, —S(═O)$_2$NH— or —C(═N—NH$_2$)—;

$R^3$ represents -L-#1, -MOD, or an optionally substituted alkyl, cycloalkyl, aryl, heteroaryl, heteroalkyl, heterocycloalkyl group, preferably -L-#1 or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group, which may be substituted by 1-3 —OH groups, 1-3 halogen atoms, 1-3 halogenated alkyl groups (which each have 1-3 halogen atoms), 1-3 O-alkyl groups, 1-3 —SH groups, 1-3 —S-alkyl groups, 1-3 —O—C(═O)-alkyl groups, 1-3 —O—C(═O)—NH-alkyl groups, 1-3 —NH—C(═O)-alkyl groups, 1-3 —NH—C(═O)—NH-alkyl groups, 1-3 —S(═O)$_n$-alkyl groups, 1-3 —S(═O)$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, n represents 0, 1 or 2, Y$^1$ and Y$^2$ independently of one another represent H, NH$_2$ or —(CH$_2$)$_{0-3}$Z' and Y$^3$ represents —H, —(CH$_2$)$_{0-3}$—CH(NHC(═O)CH$_3$)Z', —(CH$_2$)$_{0-3}$—CH(NH$_2$)Z', or —(CH$_2$)$_{0-3}$Z', where Z' represents —H, —SO$_3$H, —NH$_2$ or —COOH, (where "alkyl" preferably represents $C_{1-10}$-alkyl);

$R^5$ represents —H, —NH$_2$, —NO$_2$, halogen (in particular —F, —Cl, —Br), —CN, —CF$_3$, —OCF$_3$, —CH$_2$F, —CH$_2$F, —SH or —(CH$_2$)$_{0-3}$Z, where Z represents —H, —OY$^3$, —SY$^3$, halogen, —NHY$^3$, —CO—NY$^1$Y$^2$ or —CO—OY$^3$, where Y$^1$ and Y$^2$ independently of one another represent —H, —NH$_2$ or —(CH$_2$)$_{0-3}$Z', and Y$^3$ represents —H or —(CH$_2$)$_{0-3}$Z', where Z' represents —H, —SO$_3$H, —NH$_2$ or —COOH; darstellt, $R^6$ and $R^7$ independently of one another represent —H, cyano, (optionally fluorinated) $C_{1-10}$-alkyl, (optionally fluorinated) $C_{2-10}$-alkenyl, (optionally fluorinated) $C_{2-10}$-alkynyl, hydroxy, —NO$_2$, NH$_2$, —COOH or halogen (in particular —F, —Cl, —Br), $R^8$ represents (optionally fluorinated) $C_{1-10}$-alkyl, (optionally fluorinated) $C_{2-10}$-alkenyl, (optionally fluorinated) $C_{2-10}$-alkynyl, (optionally fluorinated) $C_{4-10}$-cycloalkyl or —(CH$_2$)$_{0-2}$—(HZ$^2$), where HZ$^2$ represents a 4- to 7-membered heterocycle having up to two heteroatoms selected from the group consisting of N, O and S, where each of these groups may be substituted by —OH, —CO$_2$H, —NH$_2$ or -L-#1;

$R^9$ represents —H, —F, —CH$_3$, —CF$_3$, —CH$_2$F or —CHF$_2$;

where one of the substituents $R^1$, $R^2$, $R^3$, $R^4$ and $R^8$ represents or (in the case of $R^8$) contains -L-#1, -L represents the linker and #1 represents the bond to the binder or derivative thereof, where -MOD represents —(NR$^{10}$)$_n$-(G1)$_o$-G2-G3, where $R^{10}$ represents H, halogen or $C_1$-$C_3$-alkyl;

G1 represents —NHCO—, —CONH— or

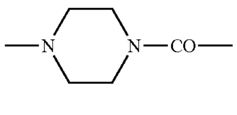

(where, if G1 represents —NHCO— or

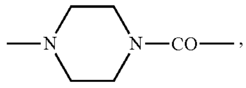

, $R^1$ is not —NH$_2$);

n is 0 or 1;

o is 0 or 1; and

G2 is a straight-chain and/or branched hydrocarbyl group which has 1 to 10 carbon atoms and may be interrupted once or more than once by one or more of the —O—, —S—, —SO—, SO$_2$, —NR$^y$—, —NR$^y$CO—, CONR$^y$—, —NR$^y$NR$^y$—, —SO2NR$^y$NR$^y$—, —CONR$^y$NR$^y$—, (where R$^y$ represents H, phenyl, $C_1$-$C_{10}$-alkyl, $C_2$-$C_{10}$-alkenyl or $C_2$-$C_{10}$-alkynyl, each of which may be substituted by —NHC(═O)NH$_2$, —COOH, —OH, —NH$_2$, —NH—(CH═N—NH$_2$), sulphonamide, sulphone, sulphoxide or sulphonic acid), —CO—, —CR$^x$═N—O— (where Rx represents H, $C_1$-$C_3$-alkyl or phenyl) groups, where the hydrocarbon chain including the side chains, if present, may be substituted by —NHCONH$_2$, —COOH, —OH, —NH$_2$, —NH—CNNH$_2$, sulphonamide, sulphone, sulphoxide or sulphonic acid, and G3 represents —H or —COOH;

where the -MOD group preferably has at least one —COOH group;

where one or more of the following conditions (i) to (iii) is fulfilled:

(i) -L-#1 comprises a group of the formula —(CO)$_{(0-1)}$—(P3)$_{(0-2)}$—P2—NH—CH(CH$_2$COX)—CO—,
where X represents —NH2 or —COOH, preferably —NH2; P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;
P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

(ii) $R^4$ represents the group of the formula R$^{21}$—(CO)$_{(0-1)}$—(P3)$_{(0-2)}$—P2—NH—CH(CH$_2$CONH$_2$)—CO— or the cathepsin-cleavable group of the formula R$^{21}$—(CO)$_{(0-1)}$—(P3)$_{(0-2)}$—P2-,
where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline, and His;
P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably N-methyl amino acids;

(iii) $R^2$ and $R^4$ together represent (forming a pyrrolidine ring) —CH$_2$—CHR$^{10}$— or —CHR$^{10}$—CH$_2$—, where the secondary hydrogen atom of the secondary amine group of the pyrrolidine ring is replaced by R$^{21}$—CO—P3$_{(0-2)}$—P2—NH—CH(CH$_2$CONH$_2$)—CO)—CO-SIG-, where SIG represents a self-immolative group which, after cleavage of the CO-SIG bond, releases the secondary amine;

and the salts, solvates, salts of the solvates and epimers thereof.

In the ADCs according to the invention, -L-#1—comprises or is the group of the formula —(CO)$_{(0-1)}$—(P3)$_{(0-2)}$—P2—NH—CH(CH$_2$COX)—CO—. Particular preference is given to those groups of the formula —(CO)$_{(0-1)}$—(P3)$_{(0-2)}$—P2—NH—CH(CH$_2$CONH$_2$)—

CO— which have thus been found to be cleavable in the legumain assay described in the Experimental section. More preferably, one of the $R^1$, $R^3$ or $R^4$ substituents is -L-#1. When $R^4$ represents -L-#1, the carbonyl group of the asparagine or aspartic acid binds directly to the nitrogen atom which binds to $R^4$ in the above formula.

In the APDCs according to the invention, $R^4$ is $R^{21}$—$(CO)((_{0-1)}$—$(P3)_{(0-2)}$—P2—NH—$CH(CH_2COX)$—CO— or the cathepsin-cleavable group of the formula $R^{21}$—$(CO)_{(0-1)}$—$(P3)_{(1-2)}$—P2-, or the hydrogen atom of the NH in the pyrrolidine ring is replaced by $R^{21}$—CO—$P3_{(0-2)}$—P2—NH—$CH(CH_2COX)$—CO-SIG-.

The $R^{21}$—$(CO)_{(0-1)}$—$(P3)_{(0-2)}$—P2—NH—CH $(CH_2COX)$—CO— and $R^{21}$—CO—P3-P2—NH—CH $(CH_2COX)$—CO-SIG- groups are cleaved in vivo, probably by the legumain enzyme.

These groups are therefore also referred to hereinafter as "legumain-cleavable groups". The legumain-cleavable group has the formula —$(CO)_{(0-1)}$—$(P3)_{(0-2)}$—P2—NH—$CH(CH_2CONX)$—CO—. In the APDCs according to the invention, the group preferably has the formula R21-$(CO)_{(0-1)}$—$(P3)_{(0-2)}$—P2—NH—$CH(CH_2COX)$—CO-#, meaning that the legumain-cleavable group has the $R^{21}$ group at one end, and at the other end (-#) it binds to the amino group corresponding to position $R^4$ in formula IIa.

In this case, NH—$CH(CH_2COX)$—CO— (i.e. asparagine or aspartic acid) is present in the natural L configuration. Particular preference is given to those groups which have been found to be cleavable in the legumain assay described in the Experimental section. The APDCs according to the invention may, in addition to the legumain- or cathepsin-cleavable $R^4$ group, have a linker -L-#1 having a legumain- or cathepsin-cleavable group.

—NH—$CH(CH_2CONH_2)$—CO— in the legumain-cleavable group is asparagine; —NH—$CH(CH_2COOH)$—CO— in the legumain-cleavable group is aspartic acid. Asparagine and aspartic acid are present here as L(−)-asparagine and L-aspartic acid respectively. The legumain-cleavable group has, as well as asparagine or aspartic acid, 1 to 3 further amino acids (i.e., in the case of asparagine, —P2—NH—$CH(CH_2CONH_2)$—CO—; —P3-P2—NH—$CH(CH_2 CONH_2)$—CO; —$(P3)_{(2)}$—P2—NH—$CH(CH_2CONH_2)$—CO—), and is thus a di-, tri- or tetrapeptide or derivative thereof (dipeptide: —P2—NH—$CH(CH_2CONH_2)$—CO—; tripeptide: —P3-P2—NH—$CH(CH_2CONH_2)$—CO; tetrapeptide: —$(P3)_2$-P2—NH—$CH(CH_2CONH_2)$—CO— (where the two amino acids P3 may be different).

P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably selected from Ala, Gly, Val, Leu, Ile, Pro, Ser, Thr, citrulline and Asn. P2 is regularly in the natural L configuration. Particular preference is given to L-Ala.

P3 is an amino acid selected from Gly, Pro, Ala, Val, Leu, Ile, Met, Phe, Tyr, Trp, Ser, Thr, Cys, Asn, Gln, Asp, Glu, Lys, Arg, citrulline, or one of the respective N-alkyl amino acids, preferably N-methyl amino acids. P3 is preferably selected from His, Pro, Ala, Val, Leu, Ile, Gly, Ser, Phe, citrulline and Gln. P3 is regularly in the natural L configuration. Particular preference is given to L-Ala. When more than one amino acid P3 is present, these amino acids may differ within the scope of the above definition.

More preferably, the legumain-cleavable group is -L-Ala-L-Ala-L-Asn- (i.e., in the case of the APDCs, $R^{21}$-L-Ala-L-Ala-L-Asn-#).

$R^{21}$ preferably represents —H, a $C_{1-5}$-alkyl-, $C_{5-10}$-aralkyl-, $C_{1-5}$-alkoxy-, $C_{6-10}$-aryloxy group, $C_{5-10}$-heteroalkyl, $C_{5-10}$-heterocycloalkyl, heteroaryl, heteroarylalkyl, $C_{5-10}$-heteroalkoxy or a $C_{5-10}$-heterocycloalkoxy group, each of which may be substituted by —COOH, COOalkyl, $COONH_2$, $NH_2$ or $N(alkyl)_2$, or an -Ox-$(CH_2CH_2O)_y$—$R^{22}$ group (where x represents 0 or 1 and v represents a number from 1 to 20, and $R^{22}$ is —H, -alkyl —CH2-COOH, —CH2-CH2-COOH, or —CH2-CH2-NH2). "Alkyl" here refers to an alkyl group having up to 20 carbon atoms, preferably C1-12-alkyl.

The cathepsin-cleavable group has the formula —$(CO)_{(0-1)}$—$(P3)_{(1-2)}$—P2-. In the APDCs according to the invention, the group has the formula $R^{21}$—$(CO)_{(0-1)}$—$(P3)_{(1-2)}$—P2-#, meaning that the cathepsin-cleavable group has the $R^{21}$ group at one end, and at the other end (-#) it binds to the amino group corresponding to position R4 in formula IIa. In this case, R21, P2 and P3 are as defined for the legumain-cleavable group. Whether the group of the formula $R^{21}$—$(CO)_{(0-1)}$—$(P3)_{(1-2)}$—P2-# is cleavable by cathepsin can be determined on the basis of the cathepsin assay described in the Experimental section. Particularly preferred cathepsin-cleavable groups are those in which P2 is selected from alanine, lysine and citrulline, and P3 is selected from valine, alanine and phenylalanine, especially those of the formula $R^{21}$—$(CO)_{(0-1)}$—P3-P2-.

DESCRIPTION OF THE FIGURES

FIG. 1 shows the alignment of the TWEAKR cysteine-rich domain (amino acid 34 to 68) of various species. (The numbers show the amino acid position in full-length constructs including the signal sequences; "Human" shows amino acids 34 to 68 of SEQ ID NO: 169, "Rat" shows amino acids 7 to 41 of SEQ ID NO: 134, "Mac" shows amino acids 7 to 41 of SEQ ID NO: 133, "Pig" shows amino acids 7 to 41 of SEQ ID NO: 135, "Mouse" shows amino acids 7 to 41 of SEQ ID NO: 137, "Dog" shows amino acids 7 to 41 of SEQ ID NO: 136).

DETAILED DESCRIPTION OF THE INVENTION

Figure 2A:
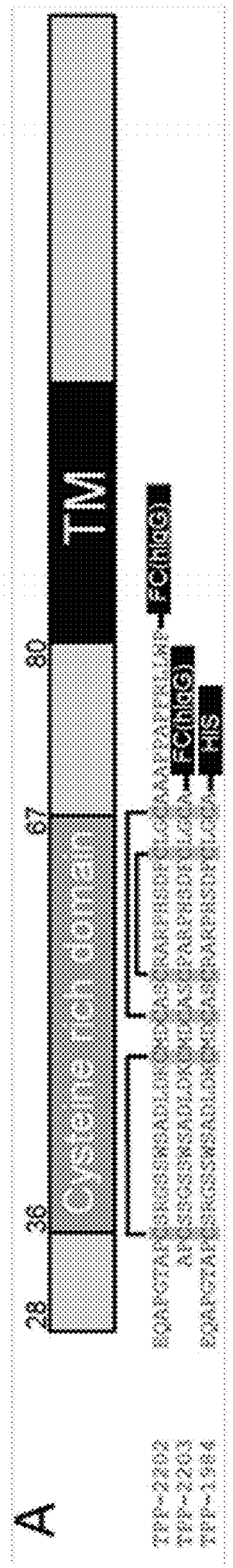
FIG. 2A shows a schematic diagram of the structure of TWEAKR (SEQ ID NO: 169). The diagram shows the extracellular domain (amino acids 28-80) (SEQ ID NO: 168) including the cysteine-rich domain (36-67), the transmembrane domain TM (81-101) and the intracellular domain (102-129). TPP-2202 the complete ectodomain (28-80), to which the Fc domain of hIgG1 fuses. TPP-2203—extracellular domain with N- and C-terminal truncation (34-68), fused to the Fc domain of hIgG1. Disulphide bridges Cys36-Cys49, Cys52-Cys67 and Cys55-Cys64 are indicated by black bars. TPP-2203 receives two amino acids more at the N-terminus and one amino acid more at the C-terminus, compared to the pure cysteine-rich domain, in order to assure respectable folding. TPP-1984—extracellular domain with C-terminal truncation (28-68), fused to an HIS6 tag. All three constructs show comparable binding to the antibodies according to the invention and PDL-192 (TPP-1104). P4A8 (TPP-1324) binds only to the full-length extracellular domain (TPP-2202).
Figure 2B:
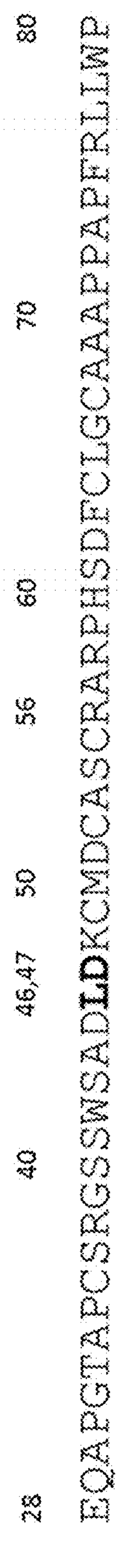
FIG. 2B shows the amino acid sequence of the extracellular domain (SEQ ID NO: 168). It has been published that amino acid 64 is essential to the TWEAK ligand binding, and amino acid 47 is essential to the binding of the antibodies according to the invention, as has been determined here.

The invention provides conjugates of a binder or derivative thereof with one or more drug molecules or prodrugs thereof, the drug molecule being a kinesin spindle protein inhibitor (KSP inhibitor).

There follows a description of binders usable in accordance with the invention, of KSP inhibitors usable in accordance with the invention or prodrugs thereof, and of linkers usable in accordance with the invention, which can be used in combination without restriction. More particularly, it is possible to use the binders described as preferred or particularly preferred in each case in combination with the KSP inhibitors or prodrugs described as preferred or particularly preferred in each case, optionally in combination with the linkers described as preferred or particularly preferred in each case.

KSP Inhibitors and their Binder Conjugates

According to the invention, KSP-L in formula I has the following formula (IIa):

(IIa)

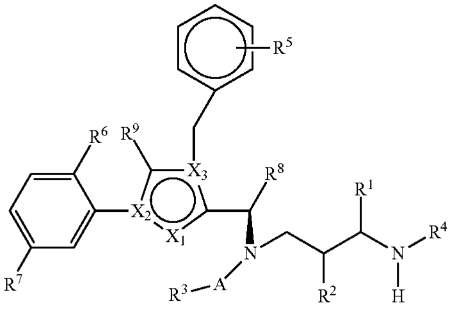

where $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH, $X_2$ represents N and $X_3$ represents C; (with $X_1$ representing CH, $X_2$ representing C and $X_3$ representing N being preferred);

$R^1$ represents H, -L-#1, -MOD or $—(CH_2)_{0-3}Z$, where Z represents —H, $—NHY^3$, $—OY^3$, $—SY^3$, halogen, $—CO—NY^1Y^2$ or $—CO—OY^3$, where $Y^1$ and $Y^2$ independently of one another represent H, $NH_2$, $—(CH_2CH_2O)_{0-3}—(CH_2)_{0-3}Z'$ (e.g. $—(CH_2)_{0-3}Z'$) or $—CH(CH_2W)Z'$, and $Y^3$ represents H or $—(CH_2)_{0-3}Z'$, where Z' represents H, $NH_2$, $SO_3H$, —COOH, —NH—CO—$CH_2$—$CH_2$—$CH(NH_2)COOH$ or $—(CO—NH—CHY^4)_{1-3}COOH$, where W represents —H or —OH, where $Y^4$ represents straight-chain or branched $C_{1-6}$-alkyl which is optionally substituted by $—NHCONH_2$, or represents aryl or benzyl which are optionally substituted by $—NH_2$;

$R^2$ represents -L-#1, —H, -MOD, $—CO—CHY^4—NHY^5$ or $—(CH_2)_{0-3}Z$, where Z represents —H, halogen, $—OY^3$, $—SY^3$, $—NHY^3$, $—CO—NY^1Y^2$ or $—CO—OY^3$, where $Y^1$ and $Y^2$ independently of one another represent —H, $—NH_2$ or $—(CH_2)_{0-3}Z'$, and $Y^3$ represents —H or $—(CH_2)_{0-3}Z'$, where Z' represents —H, $—SO_3H$, $—NH_2$ or —COOH;

where $Y^4$ represents straight-chain or branched $C_{1-6}$-alkyl which is optionally substituted by $—NHCONH_2$, or represents aryl or benzyl which are optionally substituted by $—NH_2$, and $Y^5$ represents —H or $—CO—CHY^6—NH_2$, where $Y^6$ represents straight-chain or branched $C_{1-6}$-alkyl;

$R^4$ represents -L-#1, H, $—CO—CHY^4—NHY^5$ or $—(CH_2)_{0-3}Z$, where Z represents —H, halogen, $—OY^3$, $—SY^3$, $NHY^3$, $—CO—NY^1Y^2$ or $—CO—OY^3$, where $Y^1$ and $Y^2$ independently of one another represent H, $NH_2$ or $—(CH_2)_{0-3}Z'$, and $Y^3$ represents —H or $—(CH_2)_{0-3}Z'$, where Z' represents H, $SO_3H$, $NH_2$ or —COOH;

where $Y^4$ represents straight-chain or branched $C_{1-6}$-alkyl which is optionally substituted by $—NHCONH_2$, or represents aryl or benzyl which are optionally substituted by $—NH_2$, and $Y^5$ represents —H or $—CO—CHY^6—NH_2$, where $Y^6$ represents straight-chain or branched $C_{1-6}$-alkyl;

or $R^4$ represents a group of the formula $R^{21}—(CO)_{(0-1)}—(P3)_{(0-2)}—P2—NH—CH(CH_2CONH_2)—CO—$ or $R^{21}—(CO)_{(0-1)}—(P3)_{(0-2)}—P2—NH—CH(CH_2COOH)—CO—$ or the cathepsin-cleavable group of the formula $R^{21}—(CO)_{(0-1)}—(P3)_{(1-2)}—P2$-, where $R^{21}$ represents a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroaryl-alkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by $—NH_2$, —NH— alkyl, $—N(alkyl)_2$, NH—CO-alkyl, N(alkyl)-COalkyl, $—SO_3H$, $—SO_2NH_2$, $—SO_2—N(alkyl)_2$, —COOH, $—CONH_2$, $—CON(alkyl)_2$, or —OH, —H or an $-Ox-(CH_2CH_2O)_v—R^{22}$ group (where x represents 0 or 1 and v represents a number from 1 to 20, and $R^{22}$ represents —H, -alkyl (preferably C1-12-alkyl), —CH2-COOH, —CH2-CH2-COOH, or —CH2-CH2-NH2);

P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably N-methyl amino acids;

or $R^2$ and $R^4$ together represent (forming a pyrrolidine ring) $—CH_2—CHR^{10}—$ or $—CHR^{10}—CH_2—$, where $R^{10}$ represents H, $NH_2$, $SO_3H$, COOH, SH, halogen (especially F or Cl), $C_{1-4}$-alkyl, $C_{1-4}$-haloalkyl, $C_{1-4}$-alkoxy, hydroxyl-substituted $C_{1-4}$-alkyl, $COO(C_{1-4}$-alkyl), OH or $R^{21}—CO—P3-P2—NH—CH(CH_2CONH_2)$—CO-SIG-, where SIG represents a self-immolative group which, after cleavage of the CO-SIG bond, releases the secondary amine;

A represents —C(=O)—, —S(=O)—, —$S(=O)_2$—, —$S(=O)_2NH$— or —C(=N—$NH_2$)—;

$R^3$ represents -L-#1, -MOD, or an optionally substituted alkyl, cycloalkyl, aryl, heteroaryl, heteroalkyl, heterocycloalkyl group, preferably -L-#1 or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group, which may be substituted by 1-3 —OH groups, 1-3 halogen atoms, 1-3 halogenated alkyl groups (which each have 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —$S(O)_n$-alkyl groups, 1-3 —$SO_2$—NH— alkyl groups, 1-3 —NH-alkyl groups, 1-3 —$N(alkyl)_2$ groups, 1-3 —$NH_2$ groups or 1-3 —$(CH_2)_{0-3}Z$ groups, where Z represents —H, halogen, —$OY^3$, —$SY^3$, —$NHY^3$, —CO—$NY^1Y^2$ or —CO—$OY^3$, n represents 0, 1 or 2, $Y^1$ and $Y^2$ independently of one another represent H, $NH_2$ or —$(CH_2)_{0-3}Z'$ and $Y^3$ represents H, —$(CH_2)_{0-3}$—CH($NHCOCH_3$)Z', —$(CH_2)_{0-3}$—CH($NH_2$)Z' or —$(CH_2)_{0-3}Z'$, where Z' represents H, $SO_3H$, $NH_2$ or COOH (where "alkyl" preferably represents $C_{1-10}$-alkyl);

$R^5$ represents —H, —$NH_2$, —$NO_2$, halogen (in particular F, Cl, Br), —CN, —$CF_3$, —$OCF_3$, —$CH_2F$, —$CH_2F$, —SH or —$(CH_2)_{0-3}Z$, where Z represents —H, —$OY^3$, —$SY^3$, halogen, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents —H or —$(CH_2)_{0-3}Z'$, where Z' represents H, $SO_3H$, $NH_2$ or —COOH; darstellt, $R^6$ and $R^7$ independently of one another represent —H, cyano, (optionally fluorinated) $C_{1-10}$-alkyl, (optionally fluorinated) $C_{2-10}$-alkenyl, (optionally fluorinated) $C_{2-10}$-alkynyl, hydroxy, —$NO_2$, $NH_2$, —COOH or halogen (in particular —F, —Cl, —Br), $R^8$ represents (optionally fluorinated) $C_{1-10}$-alkyl, (optionally fluorinated) $C_{2-10}$-alkenyl, (optionally fluorinated) $C_{2-10}$-alkynyl, (optionally fluorinated) $C_{4-10}$-cycloalkyl or —$(CH_2)_{0-2}$—($HZ^2$), where $HZ^2$ represents a 4- to 7-membered heterocycle having up to two heteroatoms selected from the group consisting of N, O and S, where each of these groups may be substituted by —OH, —$CO_2H$, —$NH_2$ or -L-#1;

$R^9$ represents —H, —F, —$CH_3$, —$CF_3$, —$CH_2F$ or —$CHF_2$;

where one of the substituents $R^1$, $R^2$, $R^3$, $R^4$ and $R^8$ represents or (in the case of $R^{8)}$ contains -L-#1, L represents a linker and #1 represents the bond to the binder or derivative thereof, where -MOD represents —$(NR^{10})_n$-$(G1)_o$-G2-G3, where $R^{10}$ represents —H or $C_1$-$C_3$-alkyl;

G1 represents —NHCO—, —CONH— or

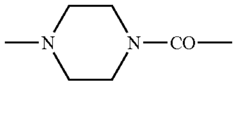

(where, if G1 represents —NHCO— or

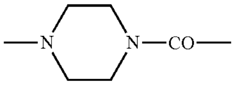, $R^{10}$ is not —$NH_2$);

n is 0 or 1;

o is 0 or 1; and

G2 is a straight-chain and/or branched hydrocarbon group which has 1 to 10 carbon atoms and which may be interrupted once or more than once by one or more of the groups —O—, —S—, —SO—, $SO_2$, —$NR^y$—, —$NR^yCO$—, —$CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by NHC(=O)$NH_2$, —COOH, —OH, —$NH_2$, NH—CNNH$_2$, sulphonamide, sulphone, sulphoxide or sulphonic acid), —C(=O)—, —$CR^x$=N—O— (where Rx represents H, $C_1$-$C_3$-alkyl or phenyl) groups, where the hydrocarbon chain including any side chains may be substituted by —$NHCONH_2$, —COOH, —OH, —$NH_2$, —NH—C(=$NNH_2$), sulphonamide, sulphone, sulphoxide or sulphonic acid, G3 represents —H or —COOH;

where the -MOD group preferably has at least one —COOH group;

where one or more of the following conditions (i) to (iii) is fulfilled:

(i) -L-#1 comprises a group of the formula —$(CO)_{(0-1)}$—$(P3)_{(0-2)}$—P2—NH—CH($CH_2COX$)—CO—, where X represents —$NH_2$ or —COOH, preferably —$NH_2$;

P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

(ii) $R^4$ represents the group of the formula $R^{21}$—$(CO)_{(0-1)}$—$(P3)_{(0-2)}$—P2—NH—CH($CH_2CONH_2$)—CO— or the cathepsin-cleavable group of the formula $R^{21}$—$(CO)_{(0-1)}$—$(P3)_{(1-2)}$—P2-, where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline, and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

(iii) $R^2$ and $R^4$ together represent (forming a pyrrolidine ring) —$CH_2$—$CHR^{10}$— or —$CHR^{10}$—$CH_2$—, where the secondary hydrogen atom of the secondary amine group of the pyrrolidine ring is replaced by $R^{21}$—CO—P3-P2—NH—CH($CH_2CONH_2$)—CO-SIG-, where SIG represents a self-immolative group which, after cleavage of the CO-SIG bond, releases the secondary amine;

and the salts, solvates, salts of the solvates and epimers thereof.

Definitions

The term "substituted" means that one or more hydrogens on the designated atom or the designated group has/have been replaced by a selection from the group specified, with the proviso that the normal valency of the designated atom is not exceeded under the circumstances in question. Combinations of substituents and/or variables are permissible.

The term "optionally substituted" means that the number of substituents can be equal to or different from zero. Unless stated otherwise, optionally substituted groups may be substituted by as many optional substituents as can be accommodated by replacement of a hydrogen atom by a non-hydrogen substituent on any available carbon or nitrogen or sulphur atom. Normally, the number of optional substituents (if present) may be 1, 2, 3, 4 or 5, especially 1, 2 or 3.

As used here, the expression "mono- or poly-", for example in the definition of the substituents of the compounds of the general formulae of the present invention, means "1, 2, 3, 4 or 5, preferably 1, 2, 3 or 4, more preferably 1, 2 or 3, most preferably 1 or 2".

If radicals in the compounds according to the invention are substituted, the radicals may be mono- or polysubstituted, unless stated otherwise. Within the scope of protection of the present invention, the definitions of all radicals which occur more than once are independent of one another. Substitution by one, two or three identical or different substituents is preferred. Substitution by one substituent is particularly preferred.

Alkyl

Alkyl is a linear or branched saturated monovalent hydrocarbon radical having 1 to 10 carbon atoms ($C_1$-$C_{10}$-alkyl), generally 1 to 6 ($C_1$-$C_6$-alkyl), preferably 1 to 4 ($C_1$-$C_4$-alkyl) and more preferably 1 to 3 carbon atoms ($C_1$-$C_3$-alkyl).

Preferred examples include:

methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, and 1,2-dimethylbutyl.

Particular preference is given to a methyl, ethyl, propyl, isopropyl or tert-butyl radical.

Heteroalkyl

Heteroalkyl is a straight-chain and/or branched hydrocarbon chain which has 1 to 10 carbon atoms and may be interrupted once or more than once by one or more of the groups —O—, —S—, —C(=O)—, —S(=O)—, —S(=O)$_2$—, —NR$^y$—, —NR$^y$C(=O)—, —C(=O)—NR$^y$—, —NR$^y$NR$^y$—, —S(=O)$_2$—NR$^y$NR$^y$—, —C(=O)—NR$^y$NR$^y$—, —CR$^x$=N—O—, and where the hydrocarbon chain including the side chains, if present, may be substituted by —NH—C(=O)—NH$_2$, —C(=O)—OH, —OH, —NH$_2$, —NH—C(=NNH$_2$)—, sulphonamide, sulphone, sulphoxide, or sulphonic acid.

In this context, R$^y$ in each case is —H, phenyl, $C_1$-$C_{10}$-alkyl, $C_2$-$C_{10}$-alkenyl or $C_2$-$C_{10}$-alkynyl, which may in turn be substituted in each case by —NH—C(=O)—NH$_2$, —C(=O)—OH, —OH, —NH$_2$, —NH—C(=NNH$_2$)—, sulphonamide, sulphone, sulphoxide, or sulphonic acid.

In this context, R$^x$ is —H, $C_1$-$C_3$-alkyl or phenyl.

Alkenyl

Alkenyl is a straight-chain or branched monovalent hydrocarbon chain having one or two double bonds and 2, 3, 4, 5, 6, 7, 8, 9 or 10 carbon atoms ($C_2$-$C_{10}$-alkenyl), especially 2 or 3 carbon atoms ($C_2$-$C_3$-alkenyl), where, as will be apparent, when the alkenyl group contains more than one double bond, the double bonds may be isolated from one another or conjugated to one another. The alkenyl group is, for example, an ethenyl (or vinyl), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl, buta-1,3-dienyl, penta-1,4-dienyl or hexa-1,5-dienyl group. More particularly, the group is vinyl or allyl.

Alkynyl

Alkynyl is a straight-chain or branched monovalent hydrocarbon chain having one triple bond and having 2, 3, 4, 5, 6, 7, 8, 9 or 10 carbon atoms ($C_2$-$C_{10}$-alkynyl), especially 2 or 3 carbon atoms ($C_2$-$C_3$-alkynyl). The $C_2$-$C_6$-alkynyl group is, for example, an ethynyl, prop-1-ynyl, prop-2-ynyl (or propargyl), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group. More particularly, the alkynyl group is ethynyl, prop-1-ynyl or prop-2-ynyl.

Cycloalkyl

Cycloalkyl is a saturated monovalent mono- or bicyclic hydrocarbyl radical having 3-12 carbon atoms ($C_3$-$C_{12}$-cycloalkyl).

In this context, a monocyclic hydrocarbyl radical is a monovalent hydrocarbyl radical having generally 3 to 10 ($C_3$-$C_{10}$-cycloalkyl), preferably 3 to 8 ($C_3$-$C_8$-cycloalkyl) and more preferably 3 to 7 ($C_3$-$C_7$-cycloalkyl) carbon atoms.

Preferred examples of monocyclic hydrocarbyl radicals include: cyclopropyl, cyclobutyl, cyclopentyl, cyclohexyl, cycloheptyl and cyclooctyl.

Particular preference is given to a cyclopropyl, cyclobutyl, cyclopentyl, cyclohexyl and cycloheptyl.

In this context, a bicyclic hydrocarbyl radical is a hydrocarbyl radical having generally 3 to 12 carbon atoms ($C_3$-$C_{12}$-cycloalkyl), which should be understood here to mean a fusion of two saturated ring systems which together share two directly adjacent atoms. Preferred examples of bicyclic hydrocarbyl radicals include: bicyclo[2.2.0]hexyl, bicyclo[3.3.0]octyl, bicyclo[4.4.0]decyl, bicyclo[5.4.0]undecyl, bicyclo[3.2.0]heptyl, bicyclo[4.2.0]octyl, bicyclo[5.2.0]

nonyl, bicyclo[6.2.0]decyl, bicyclo[4.3.0]nonyl, bicyclo[5.3.0]decyl and bicyclo[6.3.0]undecyl.

Heterocycloalkyl

Heterocycloalkyl is a nonaromatic mono- or bicyclic ring system having one, two, three or four heteroatoms which may be the same or different. The heteroatoms may be nitrogen atoms, oxygen atoms or sulphur atoms.

A monocyclic ring system according to the present invention may have 3 to 8, preferably 4 to 7 and more preferably 5 or 6 ring atoms.

Preferred examples of a heterocycloalkyl having 3 ring atoms include:

aziridinyl.

Preferred examples of a heterocycloalkyl having 4 ring atoms include:

azetidinyl, oxetanyl.

Preferred examples of a heterocycloalkyl having 5 ring atoms include:

pyrrolidinyl, imidazolidinyl, pyrazolidinyl, pyrrolinyl, dioxolanyl and tetrahydrofuranyl.

Preferred examples of a heterocycloalkyl having 6 ring atoms include:

piperidinyl, piperazinyl, morpholinyl, dioxanyl, tetrahydropyranyl and thiomorpholinyl.

Preferred examples of a heterocycloalkyl having 7 ring atoms include:

azepanyl, oxepanyl, 1,3-diazepanyl, 1,4-diazepanyl.

Preferred examples of a heterocycloalkyl having 8 ring atoms include:

oxocanyl, azocanyl.

Among monocyclic heterocycloalkyl, preference is given to 4- to 7-membered saturated heterocyclyl radicals having up to two heteroatoms from the group of O, N and S. Particular preference is given to morpholinyl, piperidinyl, pyrrolidinyl and tetrahydrofuranyl.

A bicyclic ring system having one, two, three or four heteroatoms which may be the same or different may, according to the present invention, have 6 to 12 and preferably 6 to 10 ring atoms, where one, two, three or four carbon atoms may be exchanged for identical or different heteroatoms from the group of O, N and S.

Examples include: azabicyclo[3.3.0]octyl, azabicyclo[4.3.0]nonyl, diazabicyclo[4.3.0]nonyl, oxazabicyclo[4.3.0]nonyl, thiazabicyclo[4.3.0]nonyl or azabicyclo[4.4.0]decyl, and radicals derived from further possible combinations as per the definition.

Particular preference is given to perhydrocyclopenta[c]pyrrolyl, perhydrofuro[3,2-c]pyridinyl, perhydropyrrolo[1,2-a]pyrazinyl, perhydropyrrolo[3,4-c]pyrrolyl and 3,4-methylenedioxyphenyl.

Aryl

Aryl is a monovalent mono- or bicyclic aromatic ring system consisting of carbon atoms. Examples are naphthyl and phenyl; preference is given to phenyl or a phenyl radical.

$C_6$-$C_{10}$-Aralkyl $C_{6-10}$-Aralkyl in the context of the invention is a monocyclic aromatic aryl, phenyl by way of example, to which a $C_1$-$C_4$-alkyl group is bonded.

An illustrative $C_{6-10}$-aralkyl group is benzyl.

Heteroaryl

Heteroaryl is a monovalent monocyclic, bicyclic or tricyclic aromatic ring system which has 5, 6, 8, 9, 10, 11, 12, 13 or 14 ring atoms (a "5- to 14-membered heteroaryl" group), especially 5, 6, 9 or 10 ring atoms, and contains at least one ring heteroatom and optionally one, two or three further ring heteroatoms from the group of N, O and S, and is bonded via a ring carbon atom or optionally (when permitted by the valency) via a ring nitrogen atom.

The heteroaryl group may be a 5-membered heteroaryl group, for example thienyl, furyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, for example pyridinyl, pyridazinyl, pyrimidinyl, pyrazinyl or triazinyl; or a tricyclic heteroaryl group, for example carbazolyl, acridinyl or phenazinyl; or a 9-membered heteroaryl group, for example benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, for example quinolinyl, quinazolinyl, isoquinolinyl, cinnolinyl, phthalazinyl, quinoxalinyl or pteridinyl.

In general, and unless stated otherwise, the heteroaryl radicals include all possible isomeric forms thereof, for example tautomers and positional isomers in relation to the attachment point to the rest of the molecule. Thus, as an illustrative, non-exclusive example, the term pyridinyl includes pyridin-2-yl, pyridin-3-yl and pyridin-4-yl; or the term thienyl includes thien-2-yl and thien-3-yl.

$C_5$-$C_{10}$-Heteroaryl $C_{5-10}$-Heteroaryl in the context of the invention is a mono- or bicyclic aromatic ring system having one, two, three or four heteroatoms which may be the same or different. The heteroatoms that can occur are: N, O, S, S(═O) and/or $S(═O)_2$. The bonding valence may be at any aromatic carbon atom or at a nitrogen atom.

A monocyclic heteroaryl radical according to the present invention has 5 or 6 ring atoms. Preference is given to heteroaryl radicals having one or two heteroatoms. Particular preference is given here to one or two nitrogen atoms.

Heteroaryl radicals having 5 ring atoms include, for example, the following rings: thienyl, thiazolyl, furyl, pyrrolyl, oxazolyl, imidazolyl, pyrazolyl, isoxazolyl, isothiazolyl, oxadiazolyl, triazolyl, tetrazolyl and thiadiazolyl.

Heteroaryl radicals having 6 ring atoms include, for example, the following rings: pyridinyl, pyridazinyl, pyrimidinyl, pyrazinyl and triazinyl.

A bicyclic heteroaryl radical in accordance with the present invention has 9 or 10 ring atoms.

Heteroaryl radicals having 9 ring atoms include, for example, the following rings: phthalidyl, thiophthalidyl, indolyl, isoindolyl, indazolyl, benzothiazolyl, benzofuryl, benzothienyl, benzimidazolyl, benzoxazolyl, azocinyl, indolizinyl, purinyl, indolinyl.

Heteroaryl radicals having 10 ring atoms include, for example, the following rings: isoquinolinyl, quinolinyl, quinolizinyl, quinazolinyl, quinoxalinyl, cinnolinyl, phthalazinyl, 1,7- and 1,8-naphthyridinyl, pteridinyl, chromanyl.

Heteroalkoxy

Heteroalkoxy is a straight-chain and/or branched hydrocarbyl chain which has 1 to 10 carbon atoms and is bonded via —O— to the rest of the molecule and may additionally be interrupted once or more than once by one or more of the groups —O—, —S—, —C(═O)—, —S(═O)—, $—S(═O)_2—$, $—NR_y—$, $—NR^yC(═O)—$, $—C(═O)—NR^y—$, $—NR^yNR^y—$, $—S(═O)_2—NR^yNR^y—$, $—C(═O)—NR^yNR^y—$, $—CR^x═N—O—$, and where the hydrocarbon chain, including the side chains, if present, may be substituted by $—NH—C(═O)—NH_2$, —C(═O)—OH, —OH, $—NH_2$, $—NH—C(═NNH_2)—$, sulphonamide, sulphone, sulphoxide, or sulphonic acid.

In this context, $R^y$ in each case is —H, phenyl, $C_1$-$C_{10}$-alkyl, $C_2$-$C_{10}$-alkenyl or $C_2$-$C_{10}$-alkynyl, which may in turn be substituted in each case by $—NH—C(═O)—NH_2$, —C(═O)—OH, —OH, —$NH_2$, —NH—C(═$NNH_2$)—, sulphonamide, sulphone, sulphoxide, or sulphonic acid.

In this context, $R^x$ is —H, $C_1$-$C_3$-alkyl or phenyl.

Halogen or halogen atom in the context of the invention is fluorine (—F), chlorine (—Cl), bromine (—Br), or iodine (—I).

Fluoroalkyl, fluoroalkenyl and fluoroalkynyl mean that the alkyl, alkenyl and alkynyl may be mono- or polysubstituted by fluorine.

The kinesin spindle protein inhibitor prodrugs preferably have the following formula (III):

(III)

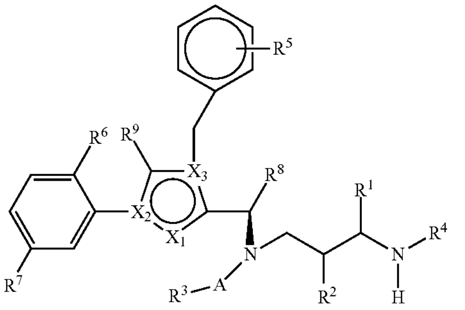

where $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH, $X_2$ represents N and $X_3$ represents C; (with $X_1$ representing CH, $X_2$ representing C and $X_3$ representing N being preferred);

$R^1$ represents —H, -MOD or —$(CH_2)_{0-3}Z$, where Z represents —H, —$NHY^3$, —$OY^3$, —$SY^3$, halogen, —CO—$NY^1Y^2$ or —CO—$OY^3$, where $Y^1$ and $Y^2$ independently of one another represent —H, —$NH_2$, —$(CH_2CH_2O)_{0-3}$—$(CH_2)_{0-3}Z'$ (e.g. —$(CH_2)_{0-3}Z'$) or —$CH(CH_2W)Z'$, and $Y^3$ represents —H or —$(CH_2)_{0-3}Z'$, where Z' represents —H, —$NH_2$, —$SO_3H$, —COOH, —NH—CO—$CH_2$—$CH_2$—$CH(NH_2)COOH$ or —$(CO—NH—CHY^4)_{1-3}COOH$, where W represents —H or —OH, where $Y^4$ represents straight-chain or branched $C_{1-6}$-alkyl which is optionally substituted by —$NHCONH_2$, or represents aryl or benzyl which are optionally substituted by —$NH_2$;

$R^2$ represents —H, -MOD, —CO—$CHY^4$—$NHY^5$ or —$(CH_2)_{0-3}Z$, where Z represents —H, halogen, —$OY^3$, —$SY^3$, $NHY^3$, —CO—$NY^1Y^2$ or —CO—$OY^3$, where $Y^1$ and $Y^2$ independently of one another represent —H, —$NH_2$ or —$(CH_2)_{0-3}Z'$, and $Y^3$ represents —H or —$(CH_2)_{0-3}Z'$, where Z' represents —H, —$SO_3H$, —$NH_2$ or —COOH;

where $Y^4$ represents straight-chain or branched $C_{1-6}$-alkyl which is optionally substituted by —NHC(═O)$NH_2$, or represents aryl or benzyl which are optionally substituted by —$NH_2$, and $Y^5$ represents —H or —CO—$CHY^6$—$NH_2$, where $Y^6$ represents straight-chain or branched $C_{1-6}$-alkyl;

$R^4$ represents a group of the formula $R^{21}$—$(CO)_{(0-1)}$—$(P3)_{(0-2)}$—P2—NH—$CH(CH_2CONH_2)$—CO— or $R^{21}$—$(CO)_{(0-1)}$—$(P3)_{(0-2)}$—P2—NH—CH($CH_2COOH$)—CO— or the cathepsin-cleavable group of the formula $R^{21}$—$(CO)_{(0-1)}$—$(P3)_{(1-2)}$—P2-, where $R^{21}$ represents a $C_{1-10}$-alkyl, $C_{510}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroaryl-alkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH— alkyl, —N(alkyl)$_2$, NH—CO-alkyl, N(alkyl)-COalkyl, —$SO_3H$, —$SO_2NH_2$, —$SO_2$—N(alkyl)$_2$, —COOH, —$CONH_2$, —CON(alkyl)$_2$, or —OH, —H or an -Ox-$(CH_2CH_2O)_v$—$R^{22}$ group (where x represents 0 or 1 and v represents a number from 1 to 20, and $R^{22}$ represents —H, -alkyl (preferably C1-12-alkyl), —CH2-COOH, —CH2-CH2-COOH, or —CH2-CH2-NH2);

P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably N-methyl amino acids;

A represents —C(═O)—, —S(═O)—, —S(═O)$_2$—, —S(═O)$_2$NH— or —C(═$NNH_2$)—;

$R^3$ represents -MOD, or an optionally substituted alkyl, cycloalkyl, aryl, heteroaryl, heteroalkyl, heterocycloalkyl group, a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group, which may be substituted by 1-3 —OH groups, 1-3 halogen atoms, 1-3 halogenated alkyl groups (which each have 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —$S(O)_n$-alkyl groups, 1-3 —$SO_2$—NH— alkyl groups, 1-3 —NH-alkyl groups, 1-3 —N(alkyl)$_2$ groups, 1-3 —$NH_2$ groups or 1-3 —$(CH_2)_{0-3}Z$ groups, where Z represents —H, halogen, —$OY^3$, —$SY^3$, —$NHY^3$, —CO—$NY^1Y^2$ or —CO—$OY^3$, n represents 0, 1 or 2, $Y^1$ and $Y^2$ independently of one another represent H, $NH_2$ or —$(CH_2)_{0-3}Z'$ and $Y^3$ represents H, —$(CH_2)_{0-3}$—CH($NHCOCH_3$)Z', —$(CH_2)_{0-3}$—$CH(NH_2)Z'$ or —$(CH_2)_{0-3}Z'$, where Z' represents —H, —$SO_3H$, —$NH_2$ or —COOH, (where “alkyl” preferably represents $C_{1-10}$-alkyl);

$R^5$ represents —H, —$NH_2$, —$NO_2$, halogen (in particular F, Cl, Br), —CN, —$CF_3$, —$OCF_3$, —$CH_2F$, —$CH_2F$, —SH or —$(CH_2)_{0-3}Z$, where Z represents —H, —$OY^3$, —$SY^3$, halogen, —$NHY^3$, —CO—$NY^1Y^2$ or —CO—$OY^3$, where $Y^1$ and $Y^2$ independently of one another represent —H, —$NH_2$ or —$(CH_2)_{0-3}Z'$, and $Y^3$ represents —H or —$(CH_2)_{0-3}Z'$, where Z' represents —H, —$SO_3H$, —$NH_2$ or —COOH;

$R^6$ and $R^7$ independently of one another represent —H, cyano, (optionally fluorinated) $C_{1-10}$-alkyl, (optionally fluorinated) $C_{2-10}$-alkenyl, (optionally fluorinated) $C_{2-10}$-alkynyl, hydroxy, —$NO_2$, $NH_2$, —COOH or halogen (in particular —F, —Cl, —Br), $R^8$ represents (optionally fluorinated) $C_{1-10}$-alkyl, (optionally fluorinated) $C_{2-10}$-alkenyl, (optionally fluorinated) $C_{2-10}$-alkynyl, (optionally fluorinated) $C_{4-10}$-cycloalkyl or $—(CH_2)_{0-2}—(HZ^2)$, where $HZ^2$ represents a 4- to 7-membered heterocycle having up to two heteroatoms selected from the group consisting of N, O and S, where each of these groups may be substituted by —OH, $—CO_2H$ or $—NH_2$;

$R^9$ represents —H, —F, $—CH_3$, $—CF_3$, $—CH_2F$ or $—CHF_2$;

where -MOD represents $—(NR^{10})_n$-$(G1)_o$-G2-G3, where $R^{10}$ represents —H or $C_1$-$C_3$-alkyl;

G1 represents —NHC(═O)—, —C(═O)NH— or

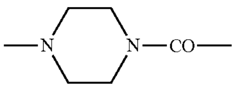

(where, if G1 represents —NHCO— or

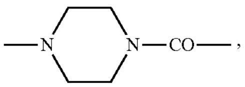

$R^{10}$ is not $—NH_2$);

n is 0 or 1;

o is 0 or 1; and

G2 is a straight-chain and/or branched hydrocarbon group which has 1 to 10 carbon atoms and which may be interrupted once or more than once by one or more of the groups —O—, —S—, —SO—, $SO_2$, $—NR^y—$, $—NR^yCO—$, $—CONR^y—$, $—NR^yNR^y—$, $—SO_2NR^yNR^y—$, $—CONR^yNR^y—$ (where $R^y$ represents H, phenyl, $C_1$-$C_{10}$-alkyl, $C_2$-$C_{10}$-alkenyl or $C_2$-$C_{10}$-alkynyl, each of which may be substituted by $—NHCONH_2$, —COOH, —OH, $—NH_2$, NH—$CNNH_2$, sulphonamide, sulphone, sulphoxide or sulphonic acid), —CO—, $—CR^x$═N—O— (where Rx represents H, $C_1$-$C_3$-alkyl or phenyl), where the hydrocarbon chain including any side chains may be substituted by $—NHCONH_2$, —COOH, —OH, $—NH_2$, —NH—$CNNH_2$, sulphonamide, sulphone, sulphoxide or sulphonic acid, and G3 represents H or COOH;

where the -MOD group preferably has at least one —COOH group;

and the salts, solvates and salts of the solvates thereof.

By substitution of a hydrogen atom at $R^1$, $R^2$, $R^3$, $R^4$, $R^5$ or $R^8$ or at the pyrrolidine ring ($R^{10}$) formed by $R^2$ and $R^4$, in a manner known to the person of average skill in the art, the compound of the formula (III) may be attached to a linker. This gives conjugates of the formula (IIa) where one of the substituents $R^1$, $R^2$, $R^3$, $R^4$, $R^5$, $R^8$ or $R^{10}$ represents -L-#1, L represents the linker and #1 represents the bond to the binder or the derivative thereof. If the KSP inhibitor (or KSP-L) according to formula (IIa) is conjugated with a binder, one of the substituents $R^1$, $R^2$, $R^3$, $R^4$, $R^5$, $R^8$ or $R^{10}$ thus represents -L-#1, where L represents the linker and #1 represents the bond to the binder or the derivative thereof. In other words, in the case of the conjugates, one of the substituents $R^1$, $R^2$, $R^3$, $R^4$, $R^5$, $R^8$ and $R^{10}$ represents -L-#1, where -L-#1 is attached to the binder, for example an antibody. With particular preference, one of the substituents $R^1$, $R^3$ or $R^4$ represents -L-#1. The binder is preferably a human, humanized or chimeric monoclonal antibody or an antigen-binding fragment thereof, in particular an anti-TWEAKR antibody or an antigen-binding fragment thereof or an anti-EGFR antibody or an antigen-binding fragment thereof or an anti-HER2 antibody. Particular preference is given to an anti-TWEAKR antibody which binds specifically to amino acid D in position 47 (D47) of TWEAKR (SEQ ID NO: 169), in particular the anti-TWEAKR antibodies TPP-2090 and TPP-2658, or the anti-EGFR antibodies cetuximab or nimotuzumab or the HER-2 antibody trastuzumab.

Instead of -L-#1, in the formula IIa, it is also possible for the group -L-#3 to be present in the compound, where L represents the linker and #3 represents the reactive group for binding to the binder or the derivative thereof. Compounds comprising -L-#3 are reactive compounds which react with the binder or the derivative thereof. #3 is preferably a group which reacts with an amino or thiol group with formation of a covalent bond, preferably with the cysteine residue in a protein. The cysteine residue in a protein may be present naturally in the protein, may be introduced by biochemical methods or, preferably, may be generated by prior reduction of disulphides of the binder.

When $R^1$ is not H, the carbon atom to which $R^1$ binds is a stereocenter which may be in the L and/or D configuration, preferably in the L configuration.

When $R^2$ is not H, the carbon atom to which $R^2$ binds is a stereocenter which may be in the L and/or D configuration.

The compounds of the formula (IIa) in which one of the substituents $R^1$, $R^3$, and $R^4$ represents -L-#1, and in which $X^1$ represents N, $X_2$ represents N and $X_3$ represents C;

$X_1$ represents CH or CF, $X_2$ represents C and $X_3$ represents N;

$X_1$ represents NH, $X_2$ represents C and $X_3$ represents C; or $X_1$ represents CH, $X_2$ represents N and $X_3$ represents C;

are particularly preferred, especially those in which $X_1$ represents N, $X_2$ represents N and $X_3$ represents C; or X1 represents CH, X2 represents C and X3 represents N. Particular preference is given to compounds in which $X_1$ represents CH, $X_2$ represents C and $X_3$ represents N.

For A, preference is given to CO (carbonyl).

Preferred for $R^1$ are -L-#1, -MOD, —H, —COOH, $—CONHNH_2$, $—(CH_2)_{1-3}NH_2$, $—CONZ''(CH_2)_{1-3}NH_2$ and $—CONZ''CH_2COOH$, where Z'' represents —H or $—NH_2$. If $R^4$ represents -L-#1, $R^3$ is preferably -MOD (especially if $R^3$ does not represent -MOD).

Preferred for $R^2$ is —H.

Preferred for $R^4$ is —H, -L-#1 or the legumain-cleavable group of the formula $R^{21}—(CO)_{(0-1)}—(P3)_{(0-2)}—P2—NH—CH(CH_2CONH_2)—CO—$. As described above, in this case, -L-#1 contains the group of the formula $—(CO)_{(0-1)}—(P3)_{(0-2)}—P2-NH—CH(CH_2COX)—CO^*—$, where the carbonyl group of the (L-)asparagine or the (L-)aspartic acid (identified by *) binds directly to the nitrogen atom which binds to $R^4$ in the above formula. If $R^4$ represents -L-#1, $R^1$ or $R^3$ is preferably -MOD.

Preferred for $R^3$ is -L-#1, -MOD or a $C_{1-10}$-alkyl-, which may optionally be substituted by —OH, —O-alkyl, —SH, —S-alkyl, —O—CO-alkyl, —O—C(═O)—NH-alkyl, NH—C(═O)-alkyl, NH—C(═O)—NH-alkyl, $S(O)_n$-alkyl, $SO_2$—NH-alkyl, NH-alkyl, $N(alkyl)_2$ or $NH_2$, n represents 0, 1 or 2, (where alkyl is preferably $C_{1-3}$-alkyl). If $R^4$ represents -L-#1, $R^3$ is preferably -MOD (especially if $R^1$ does not represent -MOD).

Preferred for $R^5$ is —H or —F.

Preferred for $R^6$ and $R^7$, independently of one another, are —H, (optionally fluorinated) $C_{1-3}$-alkyl, (optionally fluorinated) $C_{2-4}$-alkenyl, (optionally fluorinated) $C_{2-4}$-alkynyl, hydroxy or halogen.

Preferred for $R^8$ is a branched $C_{1-5}$-alkyl group, in particular a group of the formula —$C(CH_3)_2$—$(CH_2)_{0-2}$—$R_y$, where $R_y$ represents —H, —OH, —$CO_2H$ or —$NH_2$. Particular preference is given to the group of the formula —$C(CH_3)_2$—$(CH_2)$—$R_y$, where $R_y$ represents —H.

Preferred for $R^9$ is —H or —F.

Preferred for -MOD is HOOC—$(CHX)_x$-AM-$CH_2$—$CH_2$—NH—CO—, where x represents a number from 2 to 6, X represents —H, —$NH_2$ or —COOH, and represents AM —CO—NH— or —NH—CO— (particular preference is given to HOOC—$CH_2$—$CH_2$—CH(COOH)—NH—CO—$CH_2$—$CH_2$—NH—CO—; HOOC—CH($NH_2$)—$CH_2$—$CH_2$—CO—NH—$CH_2$—$CH_2$—NH—CO—; HOOC—CH($NH_2$)—$(CH_2)_4$—NH—CO—$CH_2$—$CH_2$—NH—CO—).

Especially preferred are compounds of the formula (Ha) in which one of the substituents $R^1$ and $R^3$ represents -L-#1, and in which $X_1$ represents N, $X_2$ represents N and $X_3$ represents C;

$X_1$ represents CH or CF, $X_2$ represents C and $X_3$ represents N;

$X_1$ represents NH, $X_2$ represents C and $X_3$ represents C; or $X_1$ represents CH, $X_2$ represents N and $X_3$ represents C;

A represents —C(=O)—;

$R^1$ represents —H, —COOH, —CONHNH$_2$, —$(CH_2)_{1-3}$ $NH_2$, —CONZ"$(CH_2)_{1-3}$ $NH_2$ and —CONZ"$CH_2$COOH, where Z" represents —H or $NH_2$;

$R^2$ represents —H;

$R^4$ represents the legumain-cleavable group of the formula $R^{21}$—$(CO)_{(0-1)}$—$(P3)_{(0-2)}$—P2—NH—CH($CH_2CONH_2$)—CO—;

$R^3$ represents a phenyl group which may be mono- or polysubstituted by halogen (in particular F) or optionally fluorinated $C_{1-3}$-alkyl, or represents an optionally fluorinated $C_{1-10}$-alkyl group which may optionally be substituted by —$OY^4$, —$SY^4$, —O—CO—$Y^4$, —O—CO—NH—$Y^4$, NH—CO—$Y^4$, —NH—CO—NH—$Y^4$, $S(O)_n$—$Y^4$ (where n represents 0, 1 or 2), —$SO_2$—NH—$Y^4$, NH—$Y^4$ or $N(Y^4)_2$, where $Y^4$ represents H, phenyl (optionally mono- or polysubstituted by halogen (in particular F) or optionally fluorinated $C_{1-3}$-alkyl), or alkyl (where the alkyl group may be substituted by —OH, —COOH, and/or —NHCO—$C_{1-3}$-alkyl and where alkyl preferably represents $C_{1-3}$-alkyl);

where particularly preferably $R^3$ may be substituted by —OH, —O-alkyl, —SH, —S-alkyl, —O—CO-alkyl, —O—CO—NH-alkyl, —NH—CO-alkyl, —NH—CO—NH-alkyl, —$S(O)_n$-alkyl, —$SO_2$—NH-alkyl, —NH-alkyl, —N(alkyl)$_2$ or —$NH_2$, n represents 0, 1 or 2, (where alkyl preferably means $C_{1-3}$-alkyl), $R^5$ is —H or —F;

$R^6$ and $R^7$ independently of one another represent —H, (optionally fluorinated) $C_{1-3}$-alkyl, (optionally fluorinated) $C_{2-4}$-alkenyl, (optionally fluorinated) $C_{2-4}$-alkynyl, hydroxy or halogen;

$R^8$ is a branched $C_{1-5}$-alkyl group; and $R^9$ represents —H or —F.

Especially preferred are also compounds of the formula (IIa) in which the substituent $R^4$ represents -L-#1, and in which $X_1$ represents N, $X_2$ represents N and $X_3$ represents C;

$X_1$ represents CH or CF, $X_2$ represents C and $X_3$ represents N;

$X_1$ represents NH, $X_2$ represents C and $X_3$ represents C; or $X_1$ represents CH, $X_2$ represents N and $X_3$ represents C;

A represents CO (carbonyl);

$R^1$ represents —H, —COOH, —CONHNH$_2$, —$(CH_2)_{13}$ $NH_2$, —CONZ"$(CH_2)_{1-3}$ $NH_2$, —CONZ"$CH_2$COOH, where Z" represents —H or —$NH_2$, or HOOC—$(CHX)_x$-AM-$CH_2$—$CH_2$—NH—CO—, where x is a number from 2 to 6, X represents —H, —$NH_2$ or —COOH, and AM represents —CO—NH— or —NH—CO—, (particular preference is given to HOOC—$CH_2$—$CH_2$—CH(COOH)—NH—CO—$CH_2$—$CH_2$—NH—CO—; HOOC—CH($NH_2$)—$CH_2$—$CH_2$—CO—NH—$CH_2$—$CH_2$—NH—CO—; HOOC—CH($NH_2$)—$(CH_2)_4$—NH—CO—$CH_2$—$CH_2$—NH—CO—).

$R^2$ represents —H;

$R^3$ represents —$(CH_2)$OH, —CH($CH_3$)OH, —$CH_2SCH_2CH(COOH)NHCOCH_3$, —CH($CH_3$)$OCH_3$, a phenyl group which may be substituted by 1-3 halogen atoms, 1-3 amino groups or 1-3 alkyl groups (which may optionally be halogenated) or HOOC—$(CHX)_x$-AM-$CH_2$—$CH_2$—NH—CO—, where x is a number from 2 to 6, X represents H, $NH_2$ or COOH, and AM represents —CO—NH— or —NH—CO—, (particular preference is given to HOOC—$CH_2$—$CH_2$—CH(COOH)—NH—CO—$CH_2$—$CH_2$—NH—CO—; HOOC—CH($NH_2$)—$CH_2$—$CH_2$—CO—NH—$CH_2$—$CH_2$—NH—CO—; HOOC—CH($NH_2$)—$(CH_2)_4$—NH—CO—$CH_2$—$CH_2$—NH—CO—) or —$CH_2$—$S_x$—$(CH_2)_{0-4}$—$CHY^5$—COOH, where x is 0 or 1, and $Y^5$ represents —H or —$NHY^6$, where $Y^6$ is —H or —$COCH_3$;

$R^5$ is —H or —F;

$R^6$ and $R^7$ independently of one another represent —H, (optionally fluorinated) $C_{1-3}$-alkyl, (optionally fluorinated) $C_{2-4}$-alkenyl, (optionally fluorinated) $C_{2-4}$-alkynyl, hydroxy or halogen;

$R^8$ is a branched $C_{1-5}$-alkyl group; and $R^9$ represents —H or —F.

Furthermore, it is preferred when (alone or in combination)

$R^1$ represents -L-#1, —COOH, HOOC—$CH_2$—$CH_2$—CH(COOH)—NH—CO—$CH_2$—$CH_2$—NH—CO—; HOOC—CH($NH_2$)—$CH_2$—$CH_2$—CO—NH—$CH_2$—$CH_2$—NH—CO—; HOOC—CH($NH_2$)—$(CH_2)_4$—NH—CO—$CH_2$—$CH_2$—NH—CO— or —H, $R^2$ represents —H, $R^4$ represents the legumain-cleavable group of the formula $R^{21}$—$(CO)_{(0-1)}$—$(P3)_{(0-2)}$—P2—NH—CH($CH_2CONH_2$)—CO—;

A represents —C(=O)—, $R^3$ represents —$(CH_2)$OH, —CH($CH_3$)OH, —$CH_2SCH_2CH(COOH)NHCOCH_3$, CH($CH_3$)$OCH_3$, a phenyl group which may be substituted by 1-3 halogen atoms, 1-3 amino groups or 1-3 alkyl groups (which may optionally be halogenated), HOOC—$CH_2$—$CH_2$—CH(COOH)—NH—CO—$CH_2$—$CH_2$—NH—CO—; HOOC—CH($NH_2$)—$CH_2$—$CH_2$—CO—NH—$CH_2$—$CH_2$—NH—CO—; HOOC—CH($NH_2$)—$(CH_2)_4$—NH—CO—$CH_2$—$CH_2$—NH—CO—), —$CH_2$—$S_x$—$(CH_2)_{0-4}$—$CHY^5$—COOH, where x is 0 or 1, and $Y^5$ represents —H or —$NHY^6$, where $Y^6$ is —H or —$COCH_3$, or represents -L-#1;

$R^5$ represents —H, $R^6$ and $R^7$ independently of one another represent —H, $C_{1-3}$-alkyl or halogen; in particular, $R^6$ and $R^7$ represent —F;

$R^8$ represents $C_{1-4}$-alkyl (preferably tert-butyl); and/or $R^9$ represents —H, where one of the substituents $R^1$ and $R^3$ represents -L-#1.

Additionally, in accordance with the invention it is preferred when $R^1$ represents -L-#1, —COOH, HOOC—$CH_2$—$CH_2$—CH(COOH)—NH—CO—$CH_2$—$CH_2$—NH—CO—; HOOC—CH($NH_2$)—$CH_2$—$CH_2$—CO—NH—$CH_2$—$CH_2$—NH—CO—; HOOC—CH($NH_2$)—$(CH_2)_4$—NH—CO—$CH_2$—$CH_2$—NH—CO— or —H, $R^2$ represents —H, $R^4$ represents —H or the legumain-cleavable group of the formula $R^{21}$—$(CO)_{(0-1)}$—$(P3)_{(0-2)}$—P2-NH—CH($CH_2CONH_2$)—CO—, A represents —C(═O), $R^3$ represents —($CH_2$)OH, —CH($CH_3$)OH, —$CH_2SCH_2CH$(COOH)$NHCOCH_3$, CH($CH_3$)$OCH_3$, a phenyl group which may be substituted by 1-3 halogen atoms, 1-3 amino groups or 1-3 alkyl groups (which may optionally be halogenated), or represents -L-#1, $R^5$ represents —H, $R^6$ and $R^7$ independently of one another represent —H, $C_{1-3}$-alkyl or halogen; in particular, $R^6$ and $R^7$ represent —F;

$R^8$ represents $C_{1-4}$-alkyl (preferably tert-butyl); and $R^9$ represents —H, where one of the substituents $R^1$ and $R^3$ represents -L-#1.

In addition, preference is given in accordance with the invention to the following ADCs or APDCs:

Formula (IIb):

(IIb)

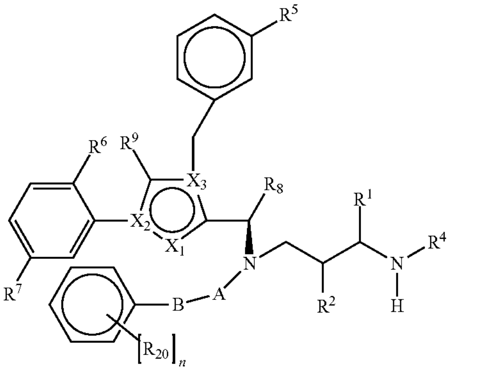

where $X_1$, $X_2$, $X_3$ have the same meaning as in formula (IIa) (where preferably $X_1$ represents CH, $X_2$ represents C and $X_3$ represents N), $R^1$, $R^2$, $R^4$, $R^5$, $R^6$, $R^7$, $R^8$ and $R^9$ have the same meaning as in formula (IIa), A represents —C(═O)—, B represents a single bond, —O—$CH_2$— or —$CH_2$—O— and $R^{20}$ represents NH2, F, CF3 or $CH_3$ and n represents 0, 1 or 2.

Formula (IIc):

(IIc)

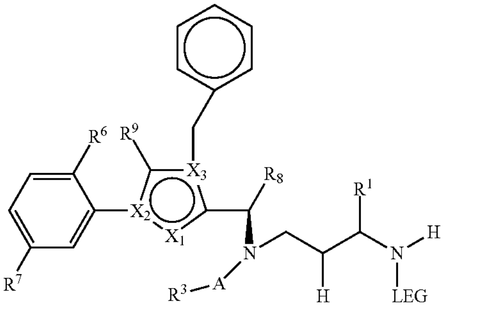

where $X_1$, $X_2$, $X_3$ have the same meaning as in formula (IIIa) or (III) (where preferably $X_1$ represents CH, $X_2$ represents C and $X_3$ represents N), A, $R^1$, $R^3$, $R^6$, $R^7$, $R^8$ and $R^9$ have the same meaning as in formula (IIa), where A preferably represents —C(═O)— and $R^3$ represents —$CH_2OH$, —$CH_2OCH_3$, —CH($CH_3$)OH or —CH($CH_3$)$OCH_3$, and LEG represents the legumain-cleavable $R^{21}$—$(CO)_{(0-1)}$—$(P3)_{(0-2)}$—P2—NH—CH($CH_2CONH_2$)—CO— group, where $R^{21}$, P2 and P3 have the same meaning as in formula (IIa).

Formula (IId):

(IId)

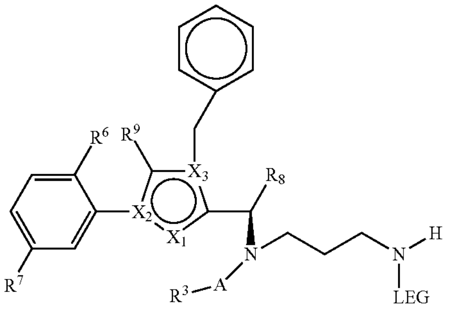

where $X_1$, $X_2$, $X_3$ have the same meaning as in formula (IIa) (where preferably $X_1$ represents CH, $X_2$ represents C and $X_3$ represents N), A, $R^3$, $R^6$, $R^7$, $R^8$ and $R^9$ have the same meaning as in formula (IIa), where A is preferably —C(═O)— and $R^3$ is —$CH_2$—$S_x$—$(CH_2)_{0-4}$—$CHY^5$—COOH, where x is 0 or 1, and $Y^5$ represents —H or —$NHY^6$, where $Y^6$ represents —H or —$COCH_3$, and LEG represents the legumain-cleavable $R^{21}$—$(CO)_{(0-1)}$—$(P3)_{(0-2)}$—P2—NH—CH($CH_2CONH_2$)—CO— group, where $R^{21}$, P2 and P3 have the same meaning as in formula (IIa).

Formula (IIe):

(IIe)

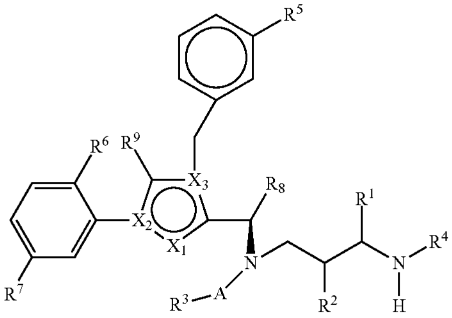

where $X_1$ represents CH, $X_2$ represents C and $X_3$ represents N, A, $R^3$, $R^6$, $R^7$, $R^8$ and $R^9$ have the same meaning as in formula (IIIa) or (III) and $R^1$ represents -L-#.

Furthermore, it is preferred when in the compounds of the formulae (IIa), (IIb), (IIc), (IId) and (IIe) (alone or in combination):

Z represents —Cl or —Br;

$R^1$ represents —$(CH_2)_{0-3}$Z, where Z represents —CO—$NY^1Y^2$, where $Y^2$ represents —$(CH_2CH_2O)_{0-3}$—$(CH_2)_{0-3}$Z' and $Y^1$ represents —H, —$NH_2$ or —$(CH_2CH_2O)_{0-3}$—$(CH_2)_{0-3}$Z';

$Y^1$ represents —H, $Y^2$ represents —$(CH_2CH_2O)_3$—$CH_2CH_2Z'$ and Z' represents —COOH;

$Y^1$ represents —H, $Y^2$ represents —$CH_2CH_2Z'$ and Z' represents —$(CONHCHY^4)_2COOH$;

$Y^1$ represents —H, $Y^2$ represents —$CH_2CH_2Z'$, Z' represents —$(CONHCHY^4)_2COOH$ and one of the $Y^4$ radicals represents i-propyl and the other —$(CH_2)_3$—$NHCONH_2$;

$Y^1$ represents —H, $Y^2$ represents —$CH_2CH_2Z'$, Z' represents —$(CONHCHY^4)_2COOH$ and one of the $Y^4$ radicals represents —$CH_3$ and the other —$(CH_2)_3$—$NHCONH_2$;

$Y^4$ represents straight-chain or branched $C_{1-6}$-alkyl which is optionally substituted by —$NHCONH_2$;

at least one $Y^4$ representative is selected from i-propyl and —$CH_3$.

$Y^1$ represents —H, $Y^2$ represents —$CH_2CH_2Z'$, Z' represents —$CONHCHY^4COOH$ and $Y^4$ represents aryl or benzyl which are optionally substituted by —$NH_2$;

$Y^4$ represents aminobenzyl;

$R^2$ represents —$(CH_2)_{0-3}Z$ and Z represents —$SY^3$;

$R^4$ represents —CO—$CHY^4$—$NHY^5$ and $Y^5$ represents H;

$R^4$ represents —CO—$CHY^4$—$NHY^5$ and $Y^5$ represents —CO—$CHY^6$—$NH_2$;

$Y^4$ represents straight-chain or branched $C_{1-6}$-alkyl which is optionally substituted by —$NHCONH_2$.

Furthermore, it is preferred when $R^1$, $R^2$ or $R^3$ in formula (IIa) represents -MOD, in particular when $R^4$ represents -L-#1 (in particular when -L is a cleavable linker which cleaves directly at —N—$R^4$ or —N-L-#1, such that $R^4$ or L is replaced by H).

Particularly preferably, $R^3$ represents -MOD and $R^1$ or $R^4$ represents -L-#1 or -L-BINDER, where -MOD represents —$(NR^{10})_n$-$(G1)_o$-G2-G3, where $R^{10}$ represents —H or $C_1$-$C_3$-alkyl;

G1 represents —NHCO—, —CONH— or

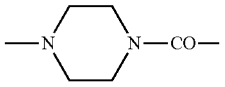

(where, if G1 represents —NHCO— or

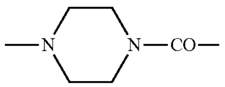

, $R^{10}$ is not —$NH_2$);

n is 0 or 1;

o is 0 or 1; and

G2 is a straight-chain and/or branched hydrocarbon group which has 1 to 10 carbon atoms and which may be interrupted once or more than once by one or more of the groups —O—, —S—, —SO—, $SO_2$, —$NR^y$—, —$NR^yCO$—, —$CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by —$NHCONH_2$, —COOH, —OH, —$NH_2$, NH—$CNNH_2$, sulphonamide, sulphone, sulphoxide or sulphonic acid), —C(═O)—, —$CR^x$═N—O— (where Rx represents H, $C_1$-$C_3$-alkyl or phenyl), where the hydrocarbon chain including any side chains may be substituted by —$NHCONH_2$, —COOH, —OH, —$NH_2$, —NH—$CNNH_2$, sulphonamide, sulphone, sulphoxide or sulphonic acid, G3 represents —H or —COOH; and where the -MOD group preferably has at least one —COOH group.

Particularly preferably, the group -MOD has a (preferably terminal) —COOH group, for example in a betaine group. Preferably, the group -MOD has the formula —$CH_2$—$S_x$—$(CH_2)_{0-4}$—$CHY^5$—COOH where x is 0 or 1, and $Y^5$ represents —H or —$NHY^6$, where Y6 represents —H or —$COCH_3$.

Furthermore, it is preferred when (alone or in combination) in formula (IIa), (IIb), (IIc), (IId) or (IIIe):

Z represents —Cl or —Br;

$R^1$ represents —$(CH_2)_{0-3}Z$, where Z represents —CO—$NY^1Y^2$, where $Y^2$ represents —$(CH_2CH_2O)_{0-3}$—$(CH_2)_{0-3}Z'$ and $Y^1$ represents —H, —$NH_2$ or —$(CH_2CH_2O)_{0-3}$—$(CH_2)_{0-3}Z'$;

$Y^1$ represents —H, $Y^2$ represents —$(CH_2CH_2O)_3$—$CH_2CH_2Z'$ and Z' represents —COOH;

$Y^1$ represents —H, $Y^2$ represents —$CH_2CH_2Z'$ and Z' represents —$(CONHCHY^4)_2COOH$;

$Y^1$ represents —H, $Y^2$ represents —$CH_2CH_2Z'$, Z' represents —$(CONHCHY^4)_2COOH$ and one $Y^4$ representative represents i-propyl and the other represents —$(CH_2)_3$—$NHCONH_2$;

$Y^1$ represents —H, $Y^2$ represents —$CH_2CH_2Z'$, Z' represents —$(CONHCHY^4)_2COOH$ and one $Y^4$ representative represents —$CH_3$ and the other represents —$(CH_2)_3$—$NHCONH_2$;

$Y^4$ represents straight-chain or branched $C_{1-6}$-alkyl which is optionally substituted by —$NHCONH_2$;

at least one $Y^4$ representative is selected from the group consisting of i-propyl and —$CH_3$.

$Y^1$ represents —H, $Y^2$ represents —$CH_2CH_2Z'$, Z' represents —$CONHCHY^4COOH$ and $Y^4$ represents aryl or benzyl which are optionally substituted by —$NH_2$;

$Y^4$ represents aminobenzyl;

$R^2$ represents —$(CH_2)_{0-3}Z$ and Z represents —$SY^3$;

$R^4$ represents —CO—$CHY^4$—$NHY^5$ and $Y^5$ represents —H;

$R^4$ represents —CO—$CHY^4$—$NHY^5$ and $Y^5$ represents —CO—$CHY^6$—$NH_2$;

$Y^4$ represents straight-chain or branched $C_{1-6}$-alkyl which is optionally substituted by —$NHCONH_2$.

Preference is furthermore given to compounds of the formula (IIa), (IIb), (IIc), (IId) or (IIIe):

where $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH or CF, $X_2$ represents N and $X_3$ represents C;

(with $X_1$ representing CH, $X_2$ representing C and $X_3$ representing N being preferred);

$R^1$ represents H, -L-#1, -MOD or —$(CH_2)_{0-3}Z$, where Z represents —H, —$NHY^3$, —$OY^3$, —$SY^3$, halogen, —CO—$NY^1Y^2$ or —CO—$OY^3$, where $Y^1$ and $Y^2$ independently of one another represent H, $NH_2$, —$(CH_2CH_2O)_{0-3}$—$(CH_2)_{0-3}Z'$ (e.g. —$(CH_2)_{0-3}Z'$) or —$CH(CH_2W)Z'$, and $Y^3$ represents —H or —$(CH_2)_{0-3}Z'$, where Z' represents —H, $NH_2$, —$SO_3H$, —COOH, —NH—CO—$CH_2$—$CH_2$—CH($NH_2$)COOH or —(CO—NH—$CHY^4$)$_{1-3}$COOH, where W represents —H or —OH, where $Y^4$ represents straight-chain or branched $C_{1-6}$-alkyl which is optionally substituted by —$NHCONH_2$, or represents aryl or benzyl which are optionally substituted by —$NH_2$;

$R^2$ represents —H, —CO—$CHY^4$—$NHY^5$ or —$(CH_2)_{0-3}$Z, where Z represents —H, halogen, —$OY^3$, —$SY^3$, —$NHY^3$, —CO—$NY^1Y^2$ or —CO—$OY^3$, where $Y^1$ and $Y^2$ independently of one another represent —H, —$NH_2$ or —$(CH_2)_{0-3}$Z', and $Y^3$ represents —H or —$(CH_2)_{0-3}$Z', where Z' represents —H, —$SO_3H$, —$NH_2$ or —COOH;

where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents —H or —CO—$CHY^6$—$NH_2$, where $Y^6$ represents straight-chain or branched $C_{1-6}$-alkyl;

$R^4$ represents —H or the legumain-cleavable group $R^{21}$—$(CO)_{(0-1)}$—$(P3)_{(0-2)}$—P2—NH—CH($CH_2CONH_2$)—CO—;

A represents —C(=O)—, —S(=O)—, —S(=O)$_2$—, —S(=O)$_2$NH— or —C(=$NNH_2$)—;

$R^3$ represents -L-#1, -MOD or an optionally substituted alkyl, cycloalkyl, aryl, heteroaryl, heteroalkyl, heterocycloalkyl group, preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —$S(O)_n$-alkyl groups, 1-3 —$SO_2$—NH-alkyl groups, 1-3 —NH-alkyl groups, 1-3 —N(alkyl)$_2$ groups, 1-3 —NH(($CH_2CH_2O$)1-20H) groups, 1-3 —NH2 groups or 1-3 —(CH2)$_{0-3}$Z groups, where n represents 0, 1 or 2, Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}$Z' and $Y^3$ represents H, —$(CH_2)_{0-3}$—CH($NHCOCH_3$)Z', —$(CH_2)_{0-3}$—CH($NH_2$)Z' or —$(CH_2)_{0-3}$Z', where Z' represents H, $SO_3H$, $NH_2$ or COOH (where "alkyl" is preferably $C_{1-10}$-alkyl);

$R^5$ represents —H, -MOD, —$NH_2$, —$NO_2$, halogen (in particular —F, —Cl, —Br), —CN, —$CF_3$, —$OCF_3$, —$CH_2F$, —$CH_2F$, —SH or —$(CH_2)_{0-3}$Z, where Z represents —H, —$OY^3$, —$SY^3$, halogen, —$NHY^3$, —CO—$NY^1Y^2$ or —CO—$OY^3$, where $Y^1$ and $Y^2$ independently of one another represent —H, —$NH_2$ or —$(CH_2)_{0-3}$Z', and $Y^3$ represents —H or —$(CH_2)_{0-3}$Z', where Z' represents —H, —$SO_3H$, —$NH_2$ or —COOH;

$R^6$ and $R^7$ independently of one another represent —H, cyano, (optionally fluorinated) $C_{1-10}$-alkyl, (optionally fluorinated) $C_{2-10}$-alkenyl, (optionally fluorinated) $C_{2-10}$-alkynyl, hydroxy, —$NO_2$, $NH_2$, —COOH or halogen (in particular —F, —Cl, —Br), $R^8$ represents (optionally fluorinated) $C_{1-10}$-alkyl, (optionally fluorinated) $C_{2-10}$-alkenyl, (optionally fluorinated) $C_{2-10}$-alkynyl or (optionally fluorinated) C4-10-cycloalkyl;

where one or none of the substituents $R^1$ and $R^3$ represents -L-#1,

L represents the linker and #1 represents the bond to the binder or derivative thereof, $R^9$ represents —H, —F, —$CH_3$, —$CF_3$, —$CH_2F$ or —$CHF_2$;

where -MOD represents —$(NR^{10})_n$-$(G1)_o$-G2-G3, where $R^{10}$ represents —H or $C_1$-$C_3$-alkyl;

G1 represents —NHCO—, —CONH— or

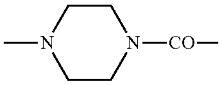

(where, if G1 represents —NHCO— or

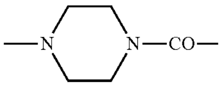

, $R^{10}$ is not —$NH_2$);

n is 0 or 1;

o is 0 or 1; and

G2 is a straight-chain and/or branched hydrocarbon group which has 1 to 10 carbon atoms and which may be interrupted once or more than once by one or more of the groups —O—, —S—, —SO—, $SO_2$, —$NR^y$—, —$NR^yCO$—, —$CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by —$NHCONH_2$, —COOH, —OH, —$NH_2$, NH—$CNNH_2$, sulphonamide, sulphone, sulphoxide or sulphonic acid), —CO—, —$CR^x$=N—O— (where Rx represents H, $C_1$-$C_3$-alkyl or phenyl), where the hydrocarbon chain including any side chains may be substituted by —$NHCONH_2$, —COOH, —OH, —$NH_2$, —NH—$CNNH_2$, sulphonamide, sulphone, sulphoxide or sulphonic acid, G3 represents —H or —COOH;

where the -MOD group preferably has at least one —COOH group;

and the salts, solvates and salts of the solvates thereof.

Preference is furthermore given to compounds of the formula (IIa), (IIb), (IIc), (IId) or (IIIe) in which $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH or CF, $X_2$ represents N and $X_3$ represents C;

(with $X_1$ representing CH, $X_2$ representing C and $X_3$ representing N being preferred);

$R^1$ represents H, -L-#1, -MOD or —$(CH_2)_{0-3}$Z, where Z represents —H, —$NHY^3$, —$OY^3$, —$SY^3$, halogen, —CO—$NY^1Y^2$ or —CO—$OY^3$, where $Y^1$ and $Y^2$ independently of one another represent —H, —$NH_2$, —$(CH_2CH_2O)_{0-3}$—$(CH_2)_{0-3}$Z' (e.g. —$(CH_2)_{0-3}$Z') or —CH($CH_2$W)Z', and $Y^3$ represents —H or —$(CH_2)_{0-3}$Z', where Z' represents —H, —$NH_2$, —$SO_3H$, —COOH, —NH—CO—$CH_2$—$CH_2$—CH $(NH_2)COOH$ or $-(CO-NH-CHY^4)_{1-3}COOH$, where W represents —H or —OH, where $Y^4$ represents straight-chain or branched $C_{1-6}$-alkyl which is optionally substituted by $-NHCONH_2$, or represents aryl or benzyl which are optionally substituted by $-NH_2$;

$R^2$ represents —H, $-CO-CHY^4-NHY^5$ or $-(CH_2)_{0-3}Z$, where Z represents —H, halogen, $-OY^3$, $-SY^3$, $NHY^3$, $-CO-NY^1Y^2$ or $-CO-OY^3$, where $Y^1$ and $Y^2$ independently of one another represent —H, $-NH_2$ or $-(CH_2)_{0-3}Z'$, and $Y^3$ represents —H or $-(CH_2)_{0-3}Z'$, where Z' represents —H, $-SO_3H$, $-NH_2$ or —COOH;

where $Y^4$ represents straight-chain or branched $C_{1-6}$-alkyl which is optionally substituted by $-NHCONH_2$, or represents aryl or benzyl which are optionally substituted by $-NH_2$, and $Y^5$ represents —H or $-CO-CHY^6-NH_2$, where $Y^6$ represents straight-chain or branched $C_{1-6}$-alkyl;

$R^4$ represents —H or the legumain-cleavable group $R^{21}-(CO)_{(0-1)}-(P3)_{(0-2)}-P2-NH-CH(CH_2CONH_2)-CO-$, A represents $-C(=O)$, $-S(=O)$, $-S(=O)_2-$, $-S(=O)_2NH-$ or $-C(=NNH_2)-$;

$R^3$ represents -L-#1, -MOD or an optionally substituted alkyl, cycloalkyl, aryl, heteroaryl, heteroalkyl, heterocycloalkyl group, preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 $-S(O)_n$-alkyl groups, 1-3 $-SO_2$—NH-alkyl groups, 1-3 —NH-alkyl groups, 1-3 $-N(alkyl)_2$ groups, 1-3 $-NH((CH_2CH_2O)1\text{-}20H)$ groups, 1-3 —NH2 groups or 1-3 $-(CH2)_{0-3}Z$ groups, where n represents 0, 1, or 2, Z represents —H, halogen, $-OY^3$, $-SY^3$, $-NHY^3$, $-CO-NY^1Y^2$ or $-CO-OY^3$, where $Y^1$ and $Y^2$ independently of one another represent H, $NH_2$ or $-(CH_2)_{0-3}Z'$ and $Y^3$ represents H, $-(CH_2)_{0-3}-CH(NHCOCH_3)Z'$, $-(CH_2)_{0-3}-CH(NH_2)Z'$ or $-(CH_2)_{0-3}Z'$, where Z' represents H, $SO_3H$, $NH_2$ or COOH (where "alkyl" is preferably $C_{1-10}$-alkyl);

$R^5$ represents —H, -MOD, $-NH_2$, $-NO_2$, halogen (in particular —F, —Cl, —Br), —CN, $-CF_3$, $-OCF_3$, $-CH_2F$, $-CH_2F$, —SH or $-(CH_2)_{0-3}Z$, where Z represents —H, $-OY^3$, $-SY^3$, halogen, $-NHY^3$, $-CO-NY^1Y^2$ or $-CO-OY^3$, where $Y^1$ and $Y^2$ independently of one another represent —H, $-NH_2$ or $-(CH_2)_{0-3}Z'$, and $Y^3$ represents —H or $-(CH_2)_{0-3}Z'$, where Z' represents —H, $-SO_3H$, $-NH_2$ or —COOH;

$R^6$ and $R^7$ independently of one another represent H or halogen (in particular —F, —Cl, —Br), $R^8$ represents (optionally fluorinated) $C_{1-10}$-alkyl;

where one or none of the substituents $R^1$ and $R^3$ represents -L-#1,

L represents the linker and #1 represents the bond to the binder or derivative thereof, $R^9$ represents —H, —F, $-CH_3$, $-CF_3$, $-CH_2F$ or $-CHF_2$;

where -MOD represents $-CH_2-S_x-(CH_2)_{0-4}-CHY^5-COOH$ where x is 0 or 1, and $Y^5$ represents —H or $-NHY^6$, where Y6 represents —H or $-COCH_3$, and the salts, solvates, salts of the solvates and epimers thereof.

Particular preference according to the invention is given to the following compounds of the formulae V, VI and VII, where $R^1$, $R^2$, $R^3$, $R^4$ and $R^5$ have the meanings mentioned above (as mentioned, for example for formula (IIa)):

Formula V

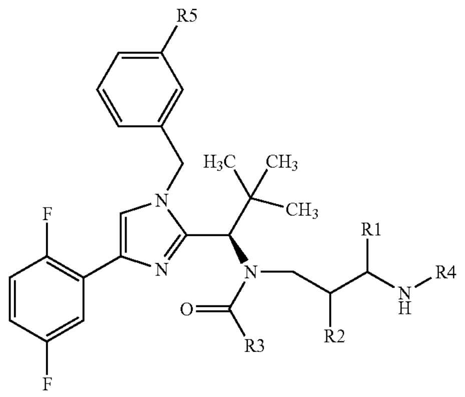

Formula VI

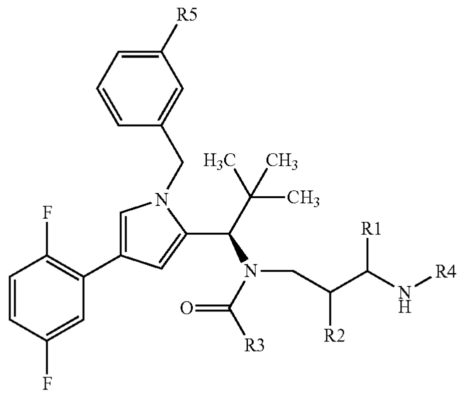

Formula VII

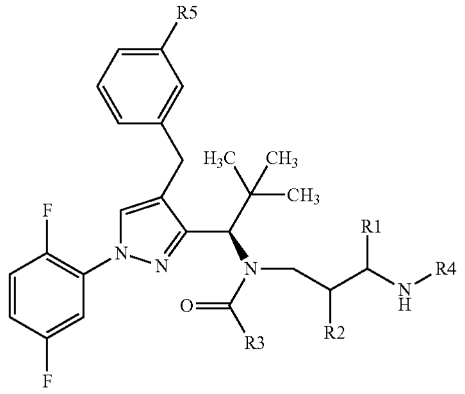

Particular preference is given to compounds of the formulae V, VI, VII, where $R^1$ and $R^5$ represent H or -L-#1; $R^2$ represents H; $R^4$ represents the group of the formula $R^{21}-(CO)_{(0-1)}-(P3)_{(0-2)}-P2-NH-CH(CH_2CONH_2)-CO-$ or the cathepsin-cleavable group of the formula $R^{21}-$ $(CO)_{(0-1)}$—$(P3)_{(0-2)}$—P2-, where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His; P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where one of the substituents $R^1$ and $R^3$ represents -L-#1. Especially preferred are the corresponding compounds of the formula VI.

The antibody-drug conjugates (ADCs) according to the invention preferably have the following formula VIII:

Formula VIII

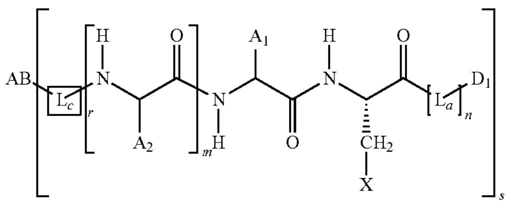

where m is a number from 0 to 2;

n is 0 or 1;

X is —$CONH_2$ or —COOH;

$L_a$ represents a self-immolative linker;

$L_c$ represents a linker;

$A_1$ is a radical which derives from one of the amino acids Gly, Pro, Ala, Val, Nva, Leu, Ile, Met, Phe, Tyr, Trp, Ser, Thr, Cys, Asn, Gln, Asp, Glu, Lys, Arg, citrulline and His;

$A_2$ is a radical which derives from one of the amino acids Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably N-methyl amino acids (when more than one P3 is present, P3 may thus have different meanings);

D1 is a compound of the formula III;

R represents $Z_1$—(CO)q-, where q is 0 or 1 and $Z_1$ represents a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{5-10}$-heteroarylalkoxy, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —$N(alkyl)_2$, —NH—CO-alkyl, N(alkyl)-COalkyl, —$SO_3H$, —$SO_2NH_2$, —$SO_2$—$N(alkyl)_2$, —COOH, —$CONH_2$, —$CON(alkyl)_2$, or —OH, —H or an -Ox-$(CH_2CH_2O)_v$—$R^1$ group (where x represents 0 or 1 and v represents a number from 1 to 20, and $R^1$ represents —H, -alkyl (preferably $C_{1-12}$-alkyl), —CH2-COOH, —CH2-CH2-COOH, or —CH2-CH2-NH2), and AB represents an antibody, and s is a number from 1 to 20, preferably 2 to 8, more preferably 3 to 5, for example 4.

The antibody-prodrug conjugates (APDCs) according to the invention preferably have the following formula IX:

Formula IX

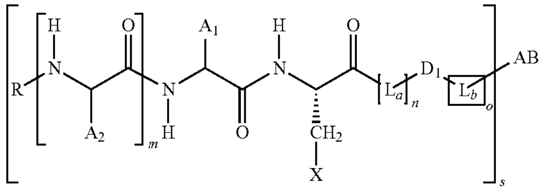

where m is a number from 0 to 2;

n is 0 or 1;

o is 0 or 1;

X is —$CONH_2$ or —COOH;

$L_a$ represents a self-immolative linker;

$L_b$ represents a linker;

$A_1$ is a radical which derives from one of the amino acids Gly, Pro, Ala, Val, Nva, Leu, Ile, Met, Phe, Tyr, Trp, Ser, Thr, Cys, Asn, Gln, Asp, Glu, Lys, Arg, citrulline and His;

$A_2$ is a radical which derives from one of the amino acids Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably N-methyl amino acids (when more than one P3 is present, P3 may thus have different meanings);

D1 is a compound of the formula III;

R represents $Z_1$—(CO)q-, where q is 0 or 1 and $Z_1$ represents a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{5-10}$-heteroarylalkoxy, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —$N(alkyl)_2$, —NH—CO-alkyl, N(alkyl)-COalkyl, —$SO_3H$, —$SO_2NH_2$, —$SO_2$—$N(alkyl)_2$, —COOH, —$CONH_2$, —$CON(alkyl)_2$, or —OH, —H or an -Ox-$(CH_2CH_2O)_v$—$R^1$ group (where x represents 0 or 1 and v represents a number from 1 to 20, and $R^1$ represents —H, -alkyl (preferably $C_{1-12}$-alkyl), —CH2-COOH, —CH2-CH2-COOH, or —CH2-CH2-NH2), and AB represents an antibody, and s is a number from 1 to 20, preferably 2 to 8, more preferably 3 to 5, for example 4.

Linkers

The literature discloses various options for covalently coupling (conjugating) organic molecules to binders such as, for example antibodies (see, for example, K. Lang and J. W. Chin. *Chem. Rev.* 2014, 114, 4764-4806, M. Rashidian et al. *Bioconjugate Chem.* 2013, 24, 1277-1294). Preference according to the invention is given to conjugation of the KSP inhibitors or prodrug to an antibody via one or more sulphur atoms of cysteine residues of the antibody which are either already present as free thiols or generated by reduction of disulphide bridges, and/or via one or more NH groups of lysine residues of the antibody. However, it is also possible to attach the KSP inhibitor or prodrug to the antibody via tyrosine residues, via glutamine residues, via residues of unnatural amino acids, via free carboxyl groups or via sugar residues of the antibody.

It is also possible in accordance with the invention to conjugate the drug molecules to specific conjugation sites of the binder, which improves product homogeneity. The literature describes various methods of conjugation site-specific conjugation (Agarwal et al., *Bioconjug. Chem.* 26, 176-192 (2015); Cal et al., *Angew. Chem. Int. Ed. Engl.* 53, 10585-10587 (2014); Behrens et al., *MAbs* 6, 46-53 (2014); Panowski et al., *MAbs* 6, 34-45 (2014)). These methods also include, in particular, enzymatic conjugation methods which use, for example, transglutaminases (TGases), glycosyltransferases or the formylglycine-generating enzyme ((Sochaj et al., *Biotechnology Advances* 33, 775-784, (2015)).

According to the invention, it is possible to provide conjugation site-specific binder conjugates of the kinesin spindle protein inhibitor, in which the kinesin spindle protein inhibitors are conjugated to glutamine side chains of the binders.

When the binder is an antibody, it contains an acceptor glutamine, preferably in the constant region. Such acceptor glutamines can be introduced via mutation of suitable positions to glutamine (for example the mutation N297Q of the heavy chain, Kabat EU numbering) or via generation of deglycosylated or aglycosylated antibodies (for example via enzymatic deglycosylation by means of PNGaseF or via mutation N297X of the heavy chain, Kabat EU numbering (X here may be any amino acid except N)). In the latter case of a deglycosylated or aglycosylated antibody, the glutamine residue Q295 (Kabat EU numbering) of the heavy chain becomes an acceptor glutamine. Particular preference is given to an antibody containing the N297A or N297Q mutation (Kabat EU numbering). Therefore, all the antibodies described in this invention likewise include aglycosylated variants of these antibodies, which are produced either via deglycosylation by means of PNGaseF or by mutation of N297 (Kabat EU numbering) (Kabat numbering system of antibodies, see Kabat et al., Sequences of Proteins of Immunological Interest, 5th Ed. Public Health Service, National Institutes of Health, Bethesda, Md. (1991)) of the heavy chain to any other amino acid except N. In addition, all the antibodies described here likewise contain variants of the antibodies described which, by virtue of engineering, contain one or more acceptor glutamine residues for transglutaminase-catalysed reactions.

One method for such conjugation site specific-conjugations is approaches described in the literature which are concerned with conjugation site-specific conjugation of binders by means of transglutaminase. Transglutaminases (TGases) which also include bacterial transglutaminase (BTG) (EC 2.3.2.13) are a family of enzymes which catalyse the formation of a covalent bond between the γ-carbonyl-amide group of glutamines and the primary amine group of lysines. Since such transglutaminases also accept substrates other than lysine as amine donor, they were used in order to modify proteins including antibodies at suitable acceptor glutamines (Jeger et al., *Angewandte Chemie Int. Ed. Engl* 49, 9995-9997 (2010); Josten et al., *J. Immunol. Methods* 240, 47-54 (2000); Mindt et al., *Bioconjugate Chem.* 19, 271-278 (2008); Dennler et al., in *Antibody Drug Conjugates* (Ducry, L., Ed.), pp 205-215, Humana Press. (2013)). On the one hand, transglutaminases have been used for the conjugation of drugs to antibodies containing artificial glutamine tags which are acceptor glutamine residues which have been introduced into the antibody by genetic engineering (Strop et al., *Chem. Biol.* 20, 161-167 (2013)). On the other hand, it has been stated that the conserved glutamine residue Q295 (Kabat EU numbering) of the constant region of the heavy chain of antibodies is the only γ-carbonyl-amide donor for the bacterial transglutaminase (EC 2.3.2.13) in the backbone of aglycosylated IgG1 molecules, and is thus an acceptor glutamine, whereas no acceptor glutamine is present in the backbone of IgG1 when the antibody has been glycosylated at position N297 (Kabat EU numbering) of the heavy chain (Jeger et al., *Angewandte Chemie Int. Ed. Engl* 49, 9995-9997 (2010)). In summary, bacterial transglutaminase can be used for the conjugation of an amine-donor substrate, for example a drug-linker construct, at an acceptor glutamine residue of an antibody. Such acceptor glutamines can be introduced by engineering of the antibody by mutations or by the generation of aglycosylated antibodies. Such aglycosylated antibodies can be introduced by deglycosylation using N-glycosidase F (PNGase F) or by mutation of N297 of the glycosylation site of the heavy chain (Kabat EU numbering) to any other amino acid except N. The enzymatic conjugation of such aglycosylated antibodies using bacterial transglutaminase has been described for aglycosylated antibody variants containing the mutations N297D, N297Q (Jeger et al., *Angewandte Chemie Int. Ed. Engl* 49, 9995-9997 (2010)) or N297S (see patent applications WO2013092998A1 and WO2013092983A2). The enzymatic conjugation of such aglycosylated antibodies by means of transglutaminase generally affords ADCs having a DAR of 2, in which both heavy chains are specifically functionalized at position Q295 (Kabat EU numbering). Only mutation N297Q of the heavy chain affords an additional conjugation site per heavy chain. The conjugation of such variants leads to ADCs having a DAR of 4, in which both heavy chains are specifically functionalized at positions Q295 and Q297.

Figure 3:
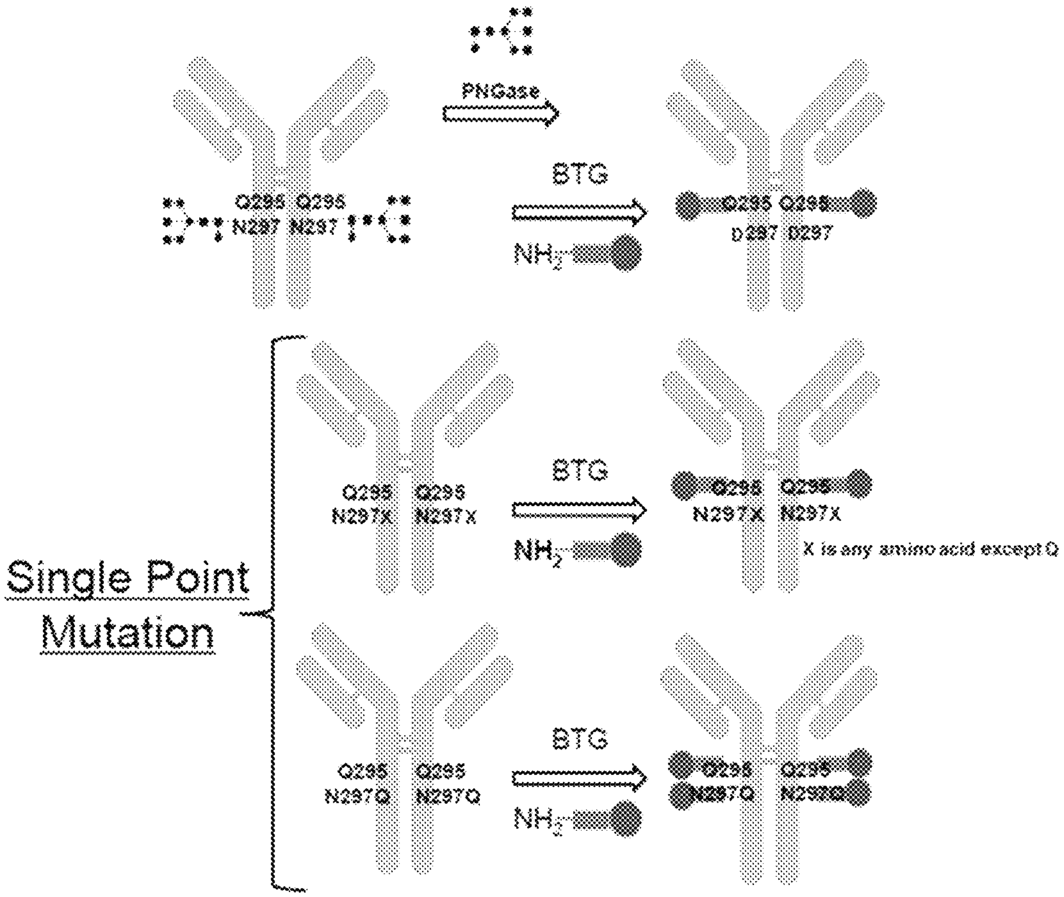
FIG. 3 shows a schematic diagram of the transglutaminase-catalysed conjugation site-specific functionalization of aglycosylated antibodies.

Antibody variants in which the heavy chains bear the mutations Q295N and N297Q have only one acceptor glutamine residue at position Q297 (Kabat numbering) per heavy chain (Simone Jeger, Site specific conjugation of tumour targeting antibodies using transglutaminase, Thesis at ETH Zurich (2009)). There exist several examples in the literature which describe the conjugation site-specific conjugation of aglycosylated antibodies using bacterial transglutaminase (for example Dennler et al., Bioconjugate Chemistry 19, 569-578 (2014); Lhospice et al., Molecular Pharmaceutics 12, 1863-1871 (2015)). The strategy of transglutaminase-catalysed conjugation site-specific functionalization of aglycosylated antibodies is summarized in FIG. 3.

Coupling—both in a conjugation site-specific and in a conjugation site-nonspecific manner—is accomplished using what are called linkers. Linkers can be categorized into the group of the linkers which can be cleaved in vivo and the group of the linkers which are stable in vivo (see L. Ducry and B. Stump, *Bioconjugate Chem.* 21, 5-13 (2010)). The linkers which can be cleaved in vivo have a group which can be cleaved in vivo, where, in turn, a distinction may be made between groups which are chemically cleavable in vivo and groups which are enzymatically cleavable in vivo. "Chemically cleavable in vivo" and "enzymatically cleavable in vivo" means that the linkers or groups are stable in circulation and are cleaved only at or in the target cell by the chemically or enzymatically different environment therein (lower pH; elevated glutathione concentration; presence of lysosomal enzymes such as legumain, cathepsin or plasmin, or glyosidases such as, for example, β-glucuronidases), thus releasing the low-molecular weight KSP inhibitor or a derivative thereof. Groups which can be cleaved chemically in vivo are in particular disulphide, hydrazone, acetal and aminal; groups which can be cleaved enzymatically in vivo are in particular the 2-8-oligopeptide group, especially a dipeptide group or glycoside. Peptide cleaving sites are disclosed in *Bioconjugate Chem.* 2002, 13, 855-869 and *Bioorganic & Medicinal Chemistry Letters* 8 (1998) 3341-3346 and also *Bioconjugate Chem.* 1998, 9, 618-626. These include, for example, alanine-alanine-asparagine, valine-alanine, valine-lysine, valine-citrulline, alanine-lysine and phenylalanine-lysine (optionally with additional amide group).

Figure 5:
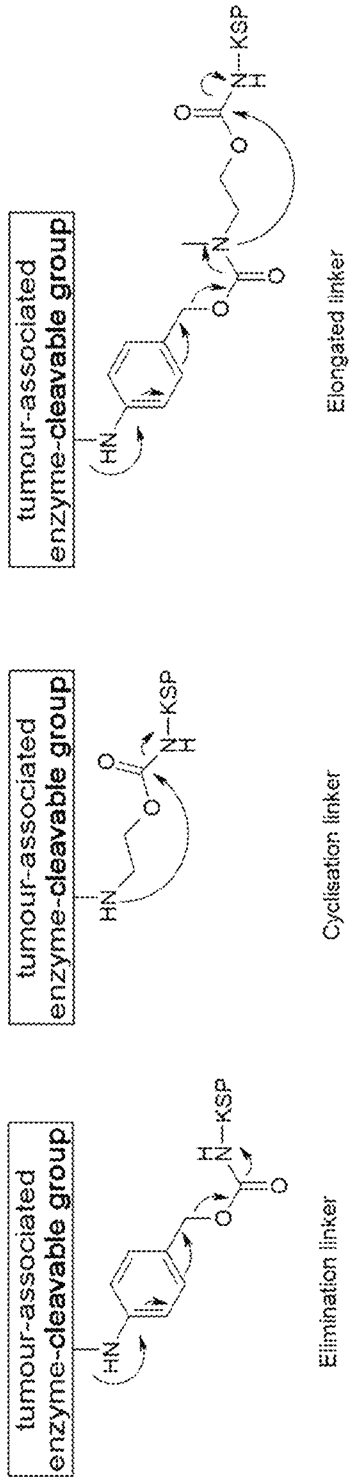
FIG. 5 shows a diagram of self-immolative linker elements and mechanisms for drug release.

In order to assure efficient release of the free drug, it is optionally also possible to incorporate what are called self-immolative linker elements (SIG, for example, in the above formula IIa or La in the above formulae VIII and IX) between the enzymatic cleavage site and drug (Anticancer Agents in Medicinal Chemistry, 2008, 8, 618-637). The drug can be released by various mechanisms, for example after initial enzymatic release of a nucleophilic group by subsequent elimination via an electronic cascade (Bioorg. Med. Chem., 1999, 7, 1597; J. Med. Chem., 2002, 45, 937; Bioorg. Med. Chem., 2002, 10,71) or by cyclization of the corresponding linker element (Bioorg. Med. Chem., 2003, 11, 2277; Bioorg. Med. Chem., 2007, 15, 4973; Bioorg. Med. Chem. Lett., 2007, 17, 2241) or by a combination of the two (Angew. Chem. Inter. Ed., 2005, 44, 4378). Examples of such linker elements are shown in FIG. 5.

Figure 4:
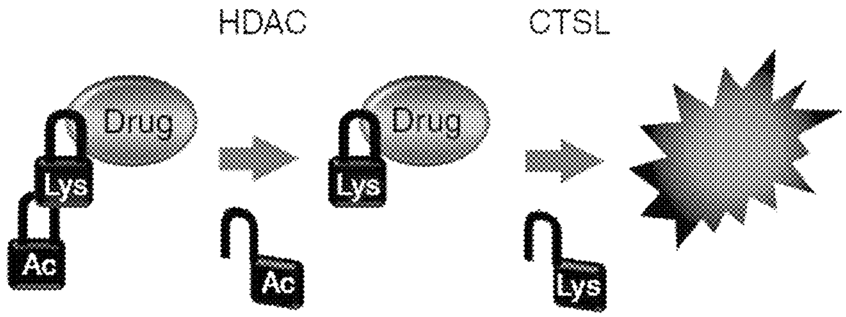
FIG. 4 shows a diagram Diagram of successive enzymatic steps for drug release by means of histone deacetylase and cathepsin L according to Nat. Commun., 2013, 4, 2735.

Examples of successive enzymatic steps for drug release, for example by means of histone deacetylase and cathepsin L, are described in Nat. Commun., 2013, 4, 2735 (cf. FIG. 4).

Linkers which are stable in vivo are distinguished by a high stability (less than 5% metabolites after 24 hours in plasma) and do not have the chemically or enzymatically in vivo cleavable groups mentioned above.

The linker -L- (like Lc in formula VIII and Lb in formula IX as well) preferably has one of the following base structures (i) to (iv):

(i) —(C═O)$_m$-SG1L1-L2

(ii) —(C═O)$_m$-L1-SG-L1-L2-

(iii) —(C═O)$_m$-L1-L2

(iv) —(C═O)$_m$-L1-SG-L2 where m is 0 or 1; SG is a (chemically or enzymatically) in vivo cleavable group (in particular disulphide, hydrazone, acetal and aminal; or a 2-8-oligopeptide group which can be cleaved by legumain, cathepsin or plasmin), SG1 is an oligopeptide group or preferably a dipeptide group, L1 represent in vivo stable organic groups, and L2 represents a coupling group to the binder or a single bond. Here, coupling is preferably to a cysteine residue or a lysine residue of the antibody. Alternatively, coupling can be to a tyrosine residue, glutamine residue or to an unnatural amino acid of the antibody. The unnatural amino acids may contain, for example, aldehyde or keto groups (such as, for example, formylglycine) or azide or alkyne groups (see Lan & Chin, Cellular Incorporation of Unnatural Amino Acids and Bioorthogonal Labeling of Proteins, Chem. Rev. 2014, 114, 4764-4806).

Particular preference according to the invention is given to the basic linker structure (iii). Via metabolization, the administration of a conjugate according to the invention having a basic linker structure (iii) and coupling of the linker to a cysteine or lysine residue of the antibody leads to cysteine or lysine derivatives of the following formulae:

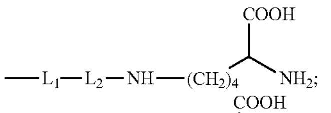;

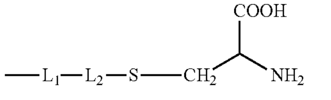

where L1 is joined in each case to the low molecular weight KSP inhibitor, for example a compound of the formula (III) or (IIa), (IIb), (IIc), (IId), (IIe), (IIf), or (IV), where -L-#1 represents one of the two radicals above which derive from lysine and cysteine respectively.

Preference according to the invention is also given to the basic linker structures (ii) and (iv), in particular when attachment is at position $R^1$, in particular when group L1 has one of the following structures:

(a) —NH—$(CH_2)_{0-4}$—$(CHCH_3)_{0-4}$—$CHY^5$—CO—$Y^7$, where $Y^5$ represents —H or —$NHY^6$, where $Y^6$ represents —H or —$COCH_3$, and $Y^7$ represents a single bond or —NH—$(CH_2)_{0-4}$—$CHNH_2$—CO—, such that after cleavage the corresponding structure —NH—$(CH_2)_{0-4}$—$(CHCH_3)_{0-4}$—$CHY^5$—COOH or —NH—$(CH_2)_{0-4}$—$(CHCH_3)_{0-4}$—$CHY^5$—CO—NH—$(CH_2)_{0-4}$—$CHNH_2$—COOH is obtained.

(b) —$CH_2$—$S_x$—$(CH_2)_{0-4}$—$CHY^5$—CO—, where x is 0 or 1, and $Y^5$ represents —H or —$NHY^6$, where $Y^6$ represents —H or —$COCH_3$, such that after cleavage the corresponding structure —$CH_2$—$S_x$—$(CH_2)_{0-4}$—$CHY^5$—COOH is obtained.

Preference according to the invention is also given to the basic linker structure (i) when attached to position $R^4$, in particular if m=0.

If the linker is attached to a cysteine side chain or a cysteine residue, L2 is preferably derived from a group which reacts with the sulphhydryl group of the cysteine. These include haloacetyls, maleimides, aziridines, acryloyls, arylating compounds, vinylsulphones, pyridyl disulphides, TNB thiols and disulphide-reducing agents. These groups generally react in an electrophilic manner with the sulphhydryl bond, forming a sulphide (e.g. thioether) or disulphide bridge. Preference is given to stable sulphide bridges. L2 is preferably

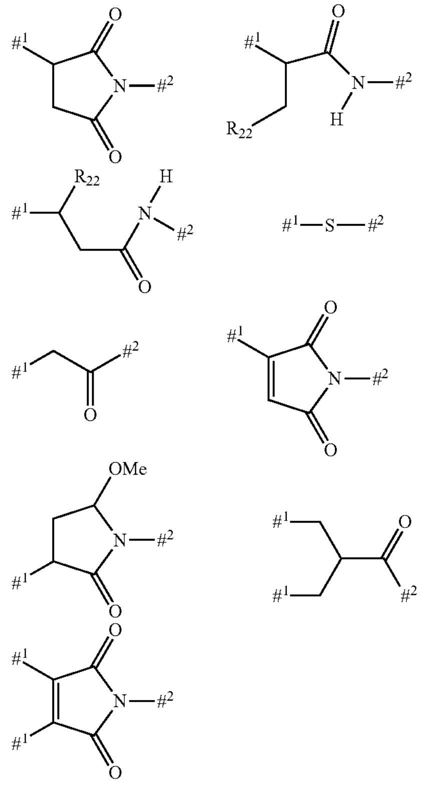

where $\#^1$ denotes the point of attachment to the sulphur atom of the antibody, $\#^2$ denotes the point of attachment to group $L^1$, and $R^{22}$ represents —COOH, —COOR, —COR, —CONHR, —$CONR_2$ (where R in each case represents C1-3-alkyl), —$CONH_2$, preferably —COOH.

Particularly preferred for L2 is:

Formula A3

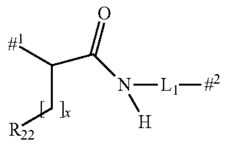

or

Formula A4

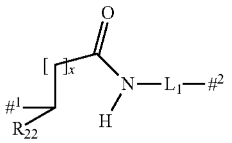

where $\#^1$ denotes the point of attachment to the sulphur atom of the antibody, $\#^2$ denotes the point of attachment to the drug, x represents 1 or 2, and $R^{22}$ represents —COOH, —COOR, —COR, —$CONR_2$, —CONHR (where R in each case represents $C_{1-3}$-alkyl), —CONH2, preferably —COOH. It is preferred when x=1 and $R^{22}$ represents —COOH.

In a conjugate according to the invention or in a mixture of the conjugates according to the invention, the bonds to a cysteine residue of the antibody are present, to an extent of preferably more than 80%, particularly preferably more than 90% (in each case based on the total number of bonds of the linker to the antibody), particularly preferably as one of the two structures of the formula A3 or A4. Here, the structures of the formula A3 or A4 are generally present together, preferably in a ratio of from 60:40 to 40:60, based on the number of bonds to the antibody. The remaining bonds are then present as the structure

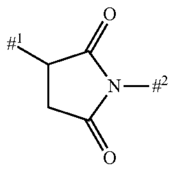

According to the invention, L1 is preferably represented by the formula $\#^1$—$(NR^{10})_n$-$(G1)_o$-G2-$\#^2$ where $R^{10}$ represents —H, —$NH_2$ or $C_1$-$C_3$-alkyl;

G1 represents —NHCO—, —CONH— or

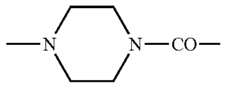

($R^{10}$ is preferably not NH2 if G1 represents —NHCO— or

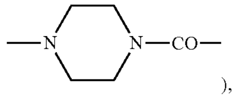

), n is 0 or 1;

o is 0 or 1; and

G2 represents a straight-chain or branched hydrocarbon chain which has 1 to 100 carbon atoms from arylene groups and/or straight-chain and/or branched and/or cyclic alkylene groups and which may be interrupted once or more than once by one or more of the groups —O—, —S—, —SO—, $SO_2$, —$NR^y$—, —$NR^yCO$—, —$C(NH)NR^y$—, $CONR^y$—, —$NR^yNR^y$—, —$SO_2NR^yNR^y$—, —$CONR^yNR^y$— (where $R^y$ represents —H, phenyl, $C_1$-$C_{10}$-alkyl, $C_2$-$C_{10}$-alkenyl or $C_2$-$C_{10}$-alkynyl, each of which may be substituted by $NHCONH_2$, —COOH, —OH, —$NH_2$, NH—$CNNH_2$, sulphonamide, sulphone, sulphoxide or sulphonic acid), —CO—, —$CR^x$═N—O— (where $R^x$ represents H, $C_1$-$C_3$-alkyl or phenyl) and/or a 3- to 10-membered aromatic or non-aromatic heterocycle having up to 4 heteroatoms selected from the group consisting of N, O and S, —SO— or —$SO_2$— (preferably

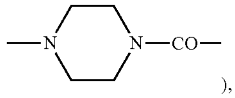

), where the hydrocarbon chain including any side chains may be substituted by —$NHCONH_2$, —COOH, —OH, —$NH_2$, —NH—$CNNH_2$, sulphonamide, sulphone, sulphoxide or sulphonic acid.

G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2NHNH$—, —CONHNH— and a 5- to 10-membered aromatic or non-aromatic heterocycle having up to 4 heteroatoms selected from the group consisting of N, O and S, or —SO— (preferably

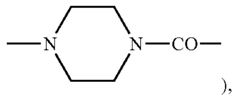

), where the side chains, if present, may be substituted by —$NHCONH_2$, —COOH, —OH, —$NH_2$, NH—$CNNH_2$, sulphonamide, sulphone, sulphoxide or sulphonic acid.

G2 preferably represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2NHNH$—, —CONHNH—, —$CR^x$═N—O— (where $R^x$ represents H, $C_1$-$C_3$-alkyl or phenyl) and a 3- to 10-membered, for example 5- to 10-membered, aromatic or non-aromatic heterocycle having up to 4 heteroatoms selected from the group consisting of N, O and S, —SO— or —$SO_2$— (preferably

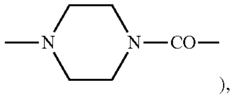

where the hydrocarbon chain including the side chains, if present, may be substituted by —$NHCONH_2$, —COOH, —OH, —$NH_2$, NH—$CNNH_2$, sulphonamide, sulphone, sulphoxide or sulphonic acid.

Further interrupting groups in G2 are preferably

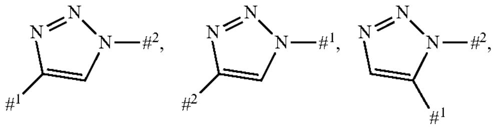

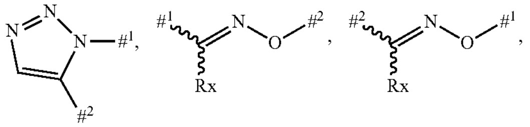

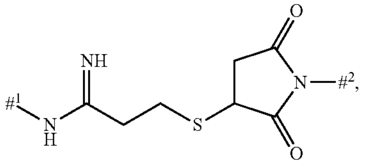

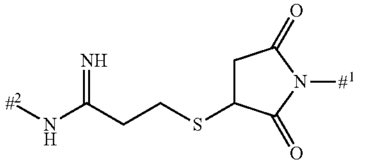

where $R^x$ represents H, $C_1$-$C_3$-alkyl or phenyl.

Here, #1 is the bond to the KSP inhibitor or prodrug and #2 is the bond to the coupling group to the antibody (e.g. L2).

A straight-chain or branched hydrocarbon chain of arylene groups and/or straight-chain and/or branched and/or cyclic alkylene groups generally comprises a α,ω-divalent alkyl radical having the respective number of carbon atoms stated. Preferred examples include: methylene, ethane-1,2-diyl (1,2-ethylene), propane-1,3-diyl (1,3-propylene), butane-1,4-diyl (1,4-butylene), pentane-1,5-diyl (1,5-pentylene), hexane-1,6-diyl (1,6-hexylene), heptane-1,7-diyl (1,7-hexylene), octane-1,8-diyl (1,8-octylene), nonane-1,9-diyl (1,9-nonylene), decane-1,10-diyl (1,10-decylene). However, the alkylene groups in the hydrocarbon chain may also be branched, i.e. one or more hydrogen atoms of the straight-chain alkylene groups mentioned above may optionally be substituted by $C_{1-10}$-alkyl groups, thus forming side chains. The hydrocarbon chain may furthermore contain cyclic alkylene groups (cycloalkanediyl), for example 1,4-cyclohexanediyl or 1,3-cyclopentanediyl. These cyclic groups may be unsaturated. In particular, aromatic groups (arylene groups), for example phenylene, may be present in the hydrocarbon group. In turn, in the cyclic alkylene groups and the arylene groups, too, one or more hydrogen atoms may optionally be substituted by $C_{1-10}$-alkyl groups. In this way, an optionally branched hydrocarbon chain is formed. This hydrocarbon chain has a total of 0 to 100 carbon atoms, preferably 1 to 50, particularly preferably 2 to 25 carbon atoms.

The side chains, if present, may be mono- or polysubstituted identically or differently by —$NHCONH_2$, —COOH, —OH, —$NH_2$, —NH—$CNNH_2$, sulphonamide, sulphone, sulphoxide or sulphonic acid.

The hydrocarbon chain may be interrupted once or more than once identically or differently by —O—, —S—, —SO—, —SO2-, —NH—, —CO—, —NHCO—, —CONH—, —NMe-, —NHNH—, —SO2NHNH—, —CONHNH— and a 5- to 10-membered aromatic or non-aromatic heterocycle having up to 4 heteroatoms selected from the group consisting of N, O and S, —SO— or —SO2- (preferably).

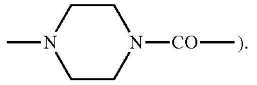

Further interrupting groups in G2 are preferably

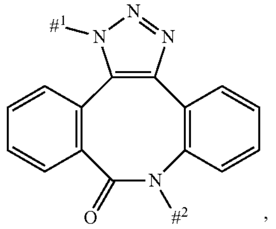

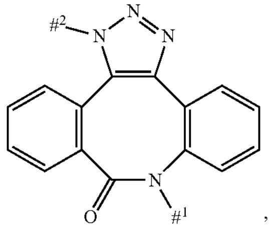

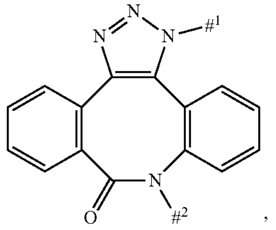

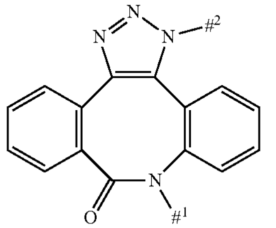

-continued
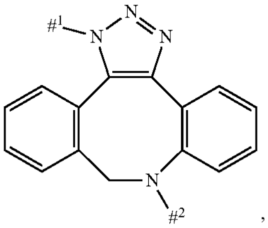
,
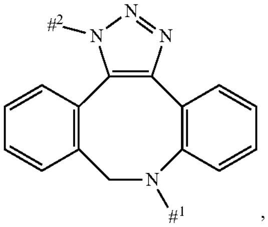
,
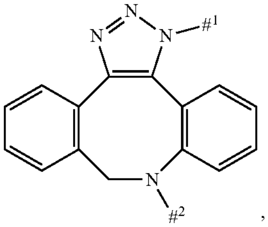
,
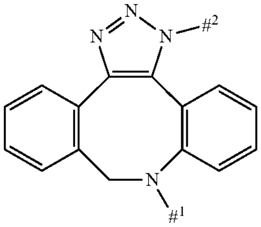
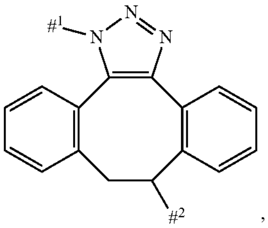
,
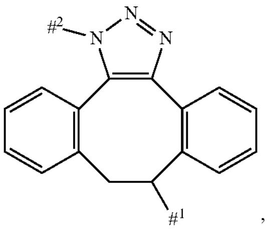
,
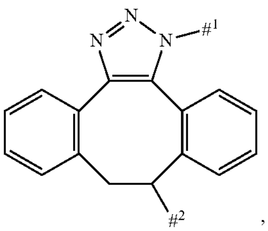
,
-continued
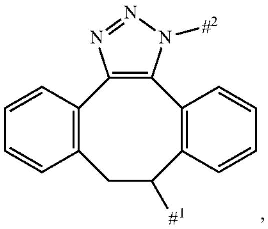
,
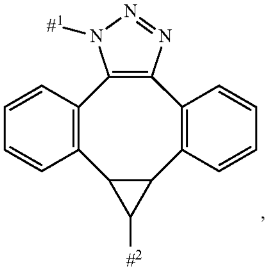
,
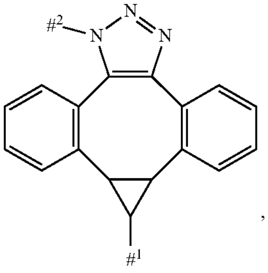
,
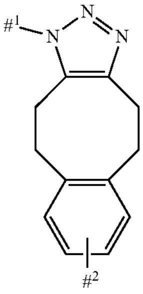
,
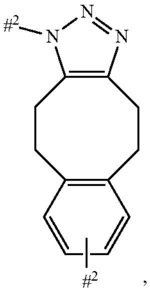
,
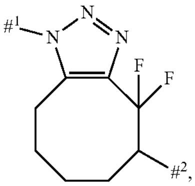
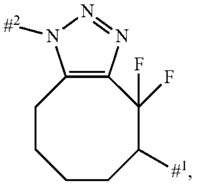
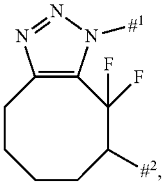
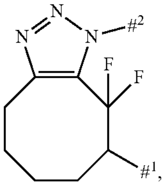
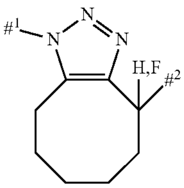
,
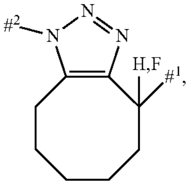
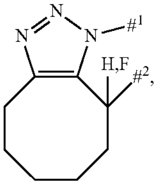
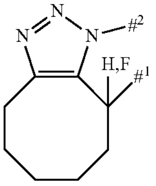
Preferably, the linker corresponds to the formula below:
§ —(CO)*m*-L1-L2-§§ where m is 0 or 1;

§ represents the bond to the drug molecule or prodrug and §§ represents the bond to the binder peptide or protein, and L1 and L2 have the meaning given above.

Particularly preferably, L1 has the formula $—NR^{11}B—$, where $R^{11}$ represents —H or $—NH_2$;

B represents $—[(CH_2)_x—(X^4)_y]_w—(CH_2)_z—$, w=0 to 20;

x=0 to 5;

x=0 to 5;

y=0 or 1;

z=0 to 5; and $X^4$ represents —O—, —CONH—, —NHCO— or

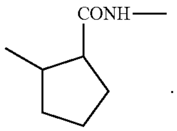

.

Linkers L which are preferred in accordance with the invention have the formula below:

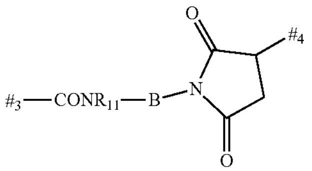

where

#3 represents the bond to the drug molecule or prodrug,

#4 represents the bond to the binder peptide or protein, $R^{11}$ represents —H or —NH2;

B represents $—[(CH_2)_x—(X^4)_y]_w—(CH_2)_z—$, w=0 to 20;

x=0 to 5;

y=0 or 1;

z=1 to 5; and $X^4$ represents —O—, —CONH—, —NHCO— or

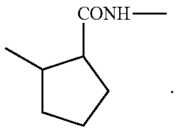

.

Preference is further given to linkers where the linker $L_1$ is one of the following groups:

§ $—NH—(CH_2)_2—$§§;

§ $—NH—(CH_2)_6—$§§;

§ $—NH—(CH_2)_2—O—(CH_2)_2—$§§;

§ $—NH—CH(COOH)—(CH_2)_4—$§§

§ $—NH—NH—C(=O)—(CH_2)_5—$§§;

§ $—NH—(CH_2)_2—C(=O)—O—(CH_2)_2—$§§;

§ $—NH—(CH_2)_2—C(=O)—NH—(CH_2)_2—$§§;

§ $—NH—(CH_2)_2—NH—C(=O)—CH_2—$§§;

§ $—NH—(CH_2)_3—NH—C(=O)—CH_2—$§§;

§ $—NH—(CH_2)_2—NH—C(=O)—(CH_2)_2—$§§;

§ $—NH—(CH_2)_2—NH—C(=O)—(CH_2)_5—$§§;

§ $—NH—(CH_2)_2—NH—C(=O)—CH(CH_3)—$§§;

§ $—NH—(CH_2)_2—O—(CH_2)_2—NH—C(=O)—CH_2—$§§;

§ $—NH—CH(COOH)—CH_2—NH—C(=O)—CH_2—$§§;

§ $—NH—CH(COOH)—(CH_2)_2—NH—C(=O)—CH_2—$§§;

§ $—NH—CH(COOH)—(CH_2)_4—NH—C(=O)—CH_2—$§§;

§ $—NH—CH(COOH)—CH_2—NH—C(=O)—(CH_2)_2—$§§;

§ $—NH—(CH_2)_2—NH—C(=O)—CH(C_2H_4COOH)—$§§;

§ $—NH—(CH_2)_2—NH—C(=O)—((CH_2)_2—O)_3—(CH_2)_2—$§§;

§ $—NH—(CH_2)_2—S(=O)_2—(CH_2)_2—NH—C(=O)—CH_2—$§§;

§ $—NH—(CH_2)_2—NH—C(=O)—CH_2—NH—C(=O)—CH_2—$§§;

§ $—NH—(CH_2)_3—NH—C(=O)—CH_2—NH—C(=O)—CH_2—$§§;

§ $—NH—CH(COOH)—CH_2—NH—C(=O)—CH(CH_2COOH)—$§§;

§ $—NH—(CH_2)_2—NH—C(=O)—CH(C_2H_4COOH)—NH—C(=O)—CH_2—$§§;

§ $—NH—CH(COOH)—CH_2—NH—C(=O)—(CH_2)_2—NH—C(=O)—CH_2—$§§;

§ $—NH—(CH_2)_2—NH—C(=O)—(CH_2)_2—CH(COOH)—NH—C(=O)—CH_2—$§§;

§ $—NH—CH(COOH)—CH_2—NH—C(=O)—CH(CH_2OH)—NH—C(=O)—CH_2—$§§;

§ $—NH—CH[C(=O)—NH—(CH_2)_2—O)_4—(CH_2)_2COOH]—CH_2—NH—C(=O)—CH_2—$§§;

§ $—NH—CH(COOH)—CH_2—NH—C(=O)—((CH_2)_2—O)_4—(CH_2)_2—NH—C(=O)—CH_2—$§§;

§ $—NH—(CH_2)_4—CH(COOH)—NH—C(=O)—CH(CH_3)—NH—C(=O)—CH(isoC_3H_7)—$§§;

§ $—NH—(CH_2)_4—CH(COOH)—NH—C(=O)—CH(CH_3)—NH—C(=O)—CH(isoC_3H_7)—NH—C(=O)—(CH_2)_5—$§§;

§ $—NH—(CH_2)_2—C(=O)—NH—(CH_2)_4—CH(COOH)—NH—C(=O)—CH(CH_3)—NH—C(=O)—CH(isoC_3H_7)—NH—C(=O)—CH_2—$§§;

§ $—NH—(CH_2)_2—C(=O)—NH—(CH_2)_4—CH(COOH)—NH—C(=O)—CH(CH)—NH—C(=O)—CH(isoC_3H_7)—NH—C(=O)—(CH_2)_5—$§§;

§ $—NH—(CH_2)_4—CH(COOH)—NH—C(=O)—CH[(CH_2)_3—NH—C(=O)—NH_2]—NH—C(=O)—CH(isoC_3H_7)—NH—C(=O)—(CH_2)_5—$§§;

§ $—NH—(CH_2)_2—NH—C(=O)—(CH_2)_2—CH(COOH)—NH—C(=O)— CH(CH_3)—NH—C(=O)—CH(isoC_3H_7)—NH—C(=O)—(CH_2)_5—$§§;

§ $—NH—CH(CH)—C(=O)—NH—(CH_2)_4—CH(COOH)—NH—C(=O)— CH(CH_3)—NH—C(=O)—CH(isoC_3H_7)—NH—C(=O)—(CH_2)_5—$§§;

§ $—NH—(CH_2)_2—C(=O)—NH—(CH_2)_4—CH(COOH)—NH—C(=O)—CH [(CH_2)_3—NH—C(=O)—NH_2]—NH—C(=O)—CH(isoC_3H_7)—NH—C(=O)—(CH_2)_5—$§§;

§ —NH

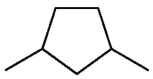

$C(=O)—NH—(CH_2)_2—$§§;

§ —NH

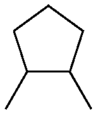

C(=O)—NH—$(CH_2)_2$—NH—C(=O)—$CH_2$—§§;

§ —NH

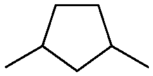

C(=O)—NH—$(CH_2)_4$—CH(COOH)—NH—C(=O)—CH[$(CH_2)_3$—NH—C(=O)—$NH_2$]—NH—C(=O)—CH($isoC_3H_2$)—NH—C(=O)—$(CH_2)_5$—§§;

§ —NH

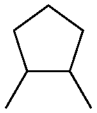

C(=O)—NH—$(CH_2)_4$—CH(COOH)—NH—C(=O)—CH[$(CH_2)_3$—NH—C(=O)—$NH_2$]—NH—C(=O)—CH($isoC_3H_2$)—NH—C(=O)—$(CH_2)_5$—§§;

§ —NH

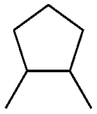

C(=O)—NH—$(CH_2)_4$—CH(COOH)—NH—C(=O)—CH($CH_3$)—NH—C(=O)—CH($isoC_3H_2$)—NH—C(=O)—$(CH_2)_5$—§§;

§ —NH—$(CH_2)_2$—C(=O)—NH—CH($isoC_3H_2$)—C(=O)—NH—CH[$(CH_2)_3$—NH—C(=O)—$NH_2$]—C(=O)—O

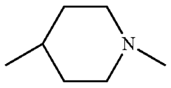

C(=O)—$CH_2$—§§;

§ —NH—$(CH_2)_2$—C(=O)—NH—CH($isoC_3H_2$)—C(=O)—NH—CH($CH_3$)—C(=O)—O

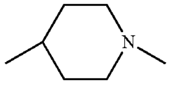

C(=O)—$CH_2$—§§;

§ —NH—$(CH_2)_2$—NH—C(=O)

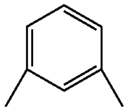

§§;

§ —NH—CH(COOH)—$CH_2$—NH—C(=O)

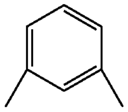

§§;

§ —NH—$(CH_2)_2$—C(=O)—NH—CH($CH_3$)—C(=O)—NH—CH[$(CH_2)_3$—NH—C(=O)—$NH_2$]—C(=O)—NH

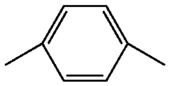

§§;

§ —$(CH_2)_2$—C(=O)—NH—$(CH_2)_2$—§§;

§ —$(CH_2)_2$—C(=O)—NH—$(CH_2)_2$—NH—C(=O)—$CH_2$—§§;

§ —CH($CH_3$)—NH—C(=O)—CH($isoC_3H_7$)—§§;

§ —CH($CH_3$)—NH—C(=O)—CH($isoC_3H_7$)—NH—C(=O)—$CH_2$—§§;

§ —CH($CH_3$)—NH—C(=O)—CH($isoC_3H_7$)—NH—C(=O)—$(CH_2)_5$—§§;

§ —$(CH_2)_2$—C(=O)—NH—($(CH_2)_2$—O$)_4$—$(CH_2)_2$—NH—C(=O)—$CH_2$—§§;

§ —CH($CH_3$)—NH—C(=O)—CH($isoC_3H_7$)—NH—C(=O)—($(CH_2)_2$—O$)_4$—$(CH_2)_2$—NH—C(=O)—$(CH_2)_2$—§§;

§

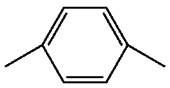

NH—C(=O)—CH($CH_3$)—NH—C(=O)—CH($isoC_3H_7$)—NH—C(=O)—($(CH_2)_2$—O$)_4$—$(CH_2)_2$—NH—C(=O)—$(CH_2)_2$—§§;

§ —$CH_2$—S—$(CH_2)_2$—C(=O)—NH—$(CH_2)_2$—§§;

§ —$CH_2$—S—$(CH_2)_5$—C(=O)—NH—$(CH_2)_2$—§§;

§ —$CH_2$—S—$CH_2$CH(COOH)—NH—C(=O)—$CH_2$—§§;

§ —$CH_2$—S—$CH_2$CH(COOH)—NH—C(=O)—$(CH_2)_5$—§§;

§ —$CH_2$—S—$(CH_2)_2$—C(=O)—NH—($(CH_2)_2$—O$)_2$—$(CH_2)_2$—§§;

§ —$CH_2$—S—$(CH_2)_2$—C(=O)—NH—($(CH_2)_2$—O$)_2$—$(CH_2)_5$—§§;

§ —$CH_2$—S—$(CH_2)_2$—C(=O)—NH—$(CH_2)_2$—NH—C(=O)—$CH_2$—§§;

§ —$CH_2$—S—$(CH_2)_2$—C(=O)—NH—$(CH_2)_2$—NH—C(=O)—$CH_5$—§§;

§ —$CH_2$—S—$(CH_2)_2$—C(=O)—NH—CH(COOH)—$CH_2$—NH—C(=O)—$CH_2$—§§;

§ —$CH_2$—S—$CH_2CH(NH_2)$—C(=O)—NH—$(CH_2)_2$—NH—C(=O)—$(CH_2)_5$—§§;

§ —$CH_2$—S—$(CH_2)_2$—C(=O)—NH—$((CH_2)_2$—$O)_2$—$(CH_2)_2$—NH—C(=O)—$CH_2$—§§;

§ —$CH_2$—S—$(CH_2)_2$—C(=O)—NH—$((CH_2)_2$—$O)_4$—$(CH_2)_2$—NH—C(=O)—$CH_2$—§§;

§ —$CH_2$—S—$(CH_2)_2$—C(=O)—NH—$((CH_2)_2$—$O)_2$—$(CH_2)_2$—NH—C(=O)—$(CH_2)_5$—§§;

§ —$CH_2$—S—$(CH_2)_2$—C(=O)—NH—$((CH_2)_2$—$O)_4$—$(CH_2)_2$—NH—C(=O)—$(CH_2)_5$—§§;

§ —$CH_2$—S—$CH_2CH$(COOH)—NH—C(=O)—$((CH_2)_2$—$O)_2$—$(CH_2)_2$—NH—C(=O)—$CH_2$—§§;

§ —$CH_2$—S—$CH_2CH$(COOH)—NH—C(=O)—$((CH_2)_2$—$O)_4$—$(CH_2)_2$—NH—C(=O)—$CH_2$—§§;

§ —$CH_2$—S—$CH_2CH$(COOH)—NH—C(=O)—$((CH_2)_2$—$O)_4$—$(CH_2)_2$—NH—C(=O)—$(CH_2)_2$—§§;

§ —$CH_2$—S—$(CH_2)_2$—CH(COOH)—NH—C(=O)—$((CH_2)_2$—$O)_4$—$(CH_2)_2$—NH—C(=O)—$(CH_2)_2$—§§;

§ —$CH_2$—S—$(CH_2)_2$—C(=O)—NH—CH($C_2H_4$COOH)—C(=O)—NH—$(CH_2)_2$—NH—C(=O)—$CH_2$—§§;

§ —$CH_2$—S—$CH_2CH$[NH—C(=O)—$(CH_2)_2$—COOH]—C(=O)—NH—$(CH_2)_2$—NH—C(=O)—$CH_2$—§§;

§ —$CH_2$—S—$CH_2CH$[NH—C(=O)—$((CH_2)_2$—$O)_4$—$CH_3$]—C(=O)—NH—$(CH_2)_2$—NH—C(=O)—$CH_2$—§§;

§ —$CH_2$—S—$CH_2CH$(COOH)—NH—C(=O)—CH($CH_3$)—NH—C(=O)—CH(iso$C_3H_7$)—NH—C(=O)—$CH_2$—§§;

§ —$CH_2$—S—$CH_2CH$[NH—C(=O)—$(CH_2)_2$—COOH]—C(=O)—NH—$(CH_2)_2$—S(=O)2-(CH2)2-NH—C(=O)—$CH_2$—§§;

§ —$CH_2$—S—$CH_2CH$[NH—C(=O)—$(CH_2)_2$—COOH]—C(=O)—NH—$((CH_2)_2$—$O)_4$—$(CH_2)_2$—NH—C(=O)—$CH_2$—§§;

§ —$CH_2$—S—$CH_2CH$[C(=O)—NH—$(CH_2)_2$—COOH]—NH—C(=O)—$((CH_2)_2$—$O)_4$—$(CH_2)_2$—NH—C(=O)—$CH_2$—§§;

§ —$CH_2$—S—$CH_2CH$[C(=O)—NH—$(CH_2)_2$—COOH]—NH—C(=O)—$((CH_2)_2$—$O)_4$—$(CH_2)_2$—NH—C(=O)—$(CH_2)_2$—§§;

§ —$CH_2$—S—$CH_2CH$(COOH)—NH—C(=O)—$(CH_2)_2CH$(COOH)—NH—C(=O)—$((CH_2)_2$—$O)_4$—$(CH_2)_2$—NH—C(=O)—$CH_2$—§§ or

§ —$CH_2$—S—$CH_2CH$(COOH)—NH—C(=O)—CH[$(CH_2)_2$—COOH]—NH—C(=O)—$((CH_2)_2$—$O)_4$—$(CH_2)_2$—NH—C(=O)—$(CH_2)_2$—§§, where § represents the bond to the active ingredient molecule §§ represents the bond to the antibody and iso$C_3H_7$ represents an isopropyl radical.

The linkers mentioned above are especially preferred in conjugates of the formula (IIa) in which the linker couples by substitution of a hydrogen atom at R1 or in combination with a cleavable linker SG1 at R4, i.e. R1 represents -L-#1 or R4 represents -SG1-L-#1, where #1 represents the bond to the antibody.

Preference in accordance with the invention is furthermore given to the linkers below: In a conjugate according to the invention or in a mixture of the conjugates according to the invention, the bonds to a cysteine residue of the antibody are present, to an extent of preferably more than 80%, particularly preferably more than 90% (in each case based on the total number of bonds of the linker to the antibody), particularly preferably as one of the two structures of the formula A5 or A6:

Formula A5

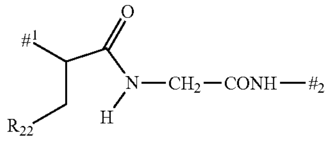

Formula A6

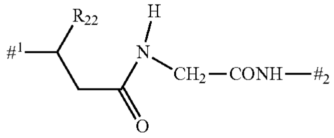

where $\#^1$ denotes the point of attachment to the sulphur atom of the antibody, $\#^2$ denotes the point of attachment to group $L^1$, and $R^{22}$ represents —COOH, —COOR, —COR, —$CONR_2$, —CONHR (where R in each case represents $C_{1-3}$-alkyl), —$CONH_2$, preferably —COOH.

Here, the structures of the formula A5 or A6 are generally present together, preferably in a ratio of from 60:40 to 40:60, based on the number of bonds to the antibody. The remaining bonds are then present as the structure

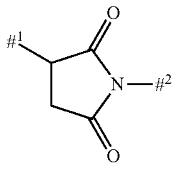

Other linkers -L- attached to a cysteine side chain or cysteine residue have the following formula:

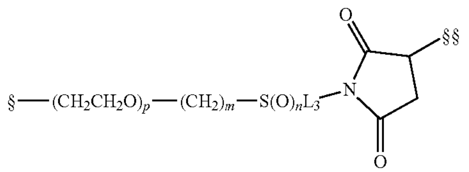

where

§ represents the bond to the drug molecule or prodrug and

§§ represents the bond to the binder peptide or protein, m represents 0, 1, 2 or 3;

n represents 0, 1 or 2;

p represents 0 to 20; and

L3 represents

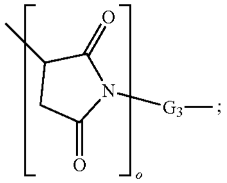

where o is 0 or 1;

and

G3 represents a straight-chain or branched hydrocarbon chain having 1 to 100 carbon atoms from arylene groups and/or straight-chain and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH— and a 3- to 10-membered (preferably 5- to 10-membered) aromatic or non-aromatic heterocycle having up to 4 heteroatoms selected from the group consisting of N, O and S, —SO— or $SO_2$ (preferably

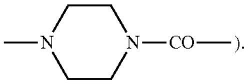

where the side chains, if present, may be substituted by —$NHCONH_2$, —COOH, —OH, —$NH_2$, NH—$CNNH_2$, sulphonamide, sulphone, sulphoxide or sulphonic acid.

In the formula above, preferably m is 1;

p is 0;

n is 0;

and L3 represents

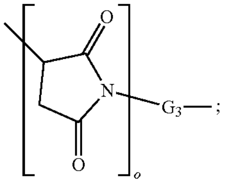

where o is 0 or 1; and

G3 represents —$(CH_2CH_2O)_s(CH_2)_t(CONH)_uCH_2CH_2O)_v(CH_2)_w$—, where s, t, v and w each independently of one another are from 0 to 20 and u is 0 or 1.

Preferred groups L1 in the formula § —(CO)m-L1-L2-§§ above are those below, where r represents a number from 0 to 20, preferably from 0 to 15, particularly preferably from 1 to 20, especially preferably from 2 to 10:

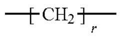
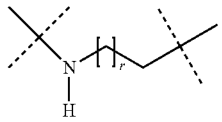
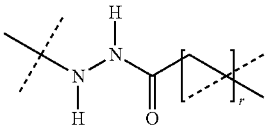
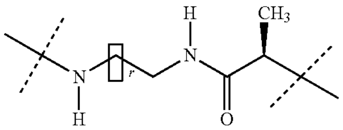
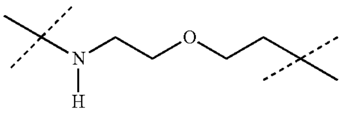
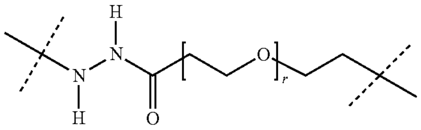
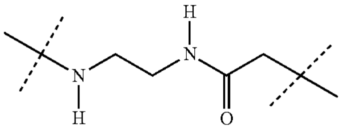
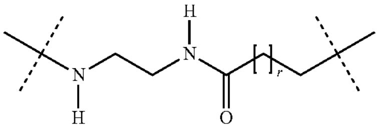
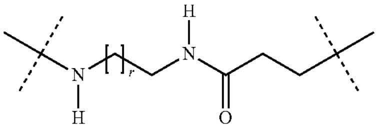
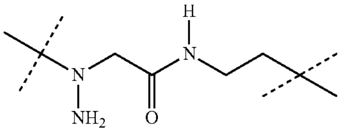
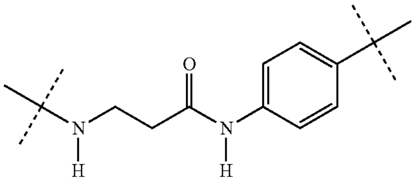
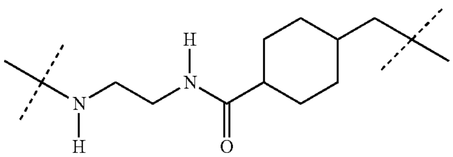
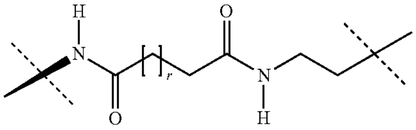
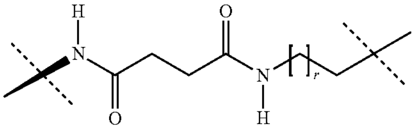
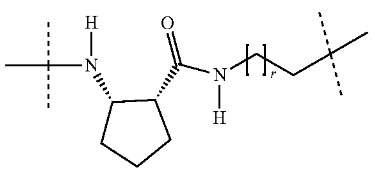
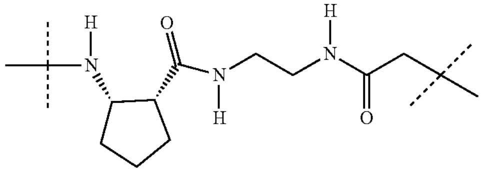

-continued
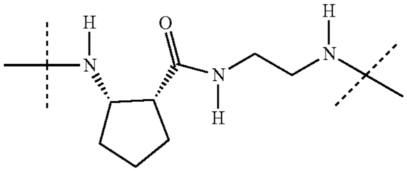
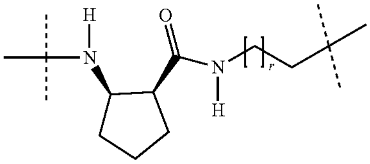
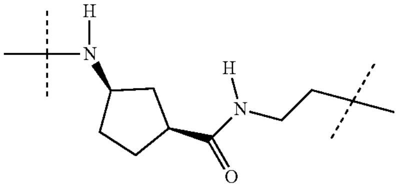
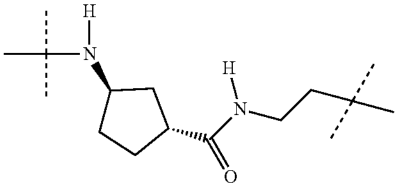
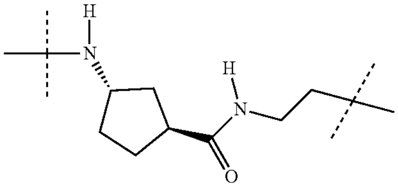
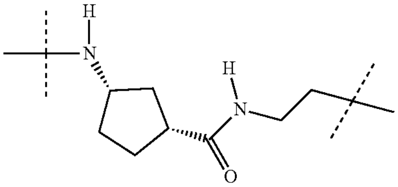
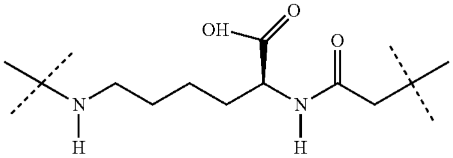
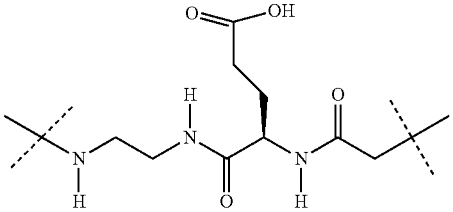
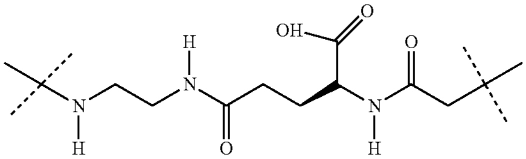
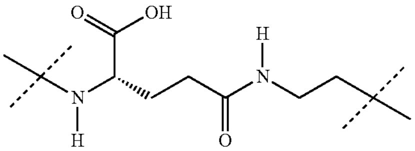
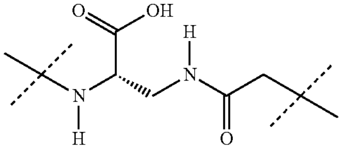
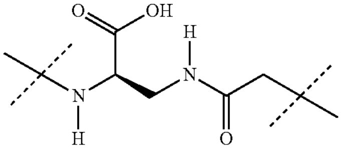
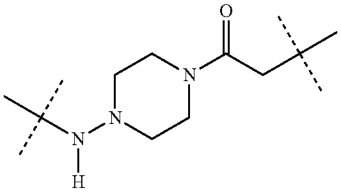
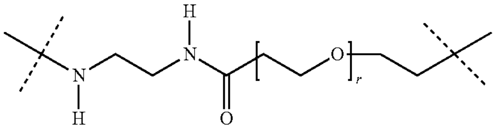
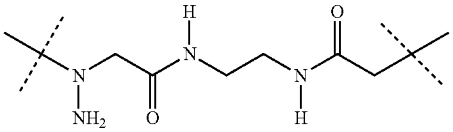
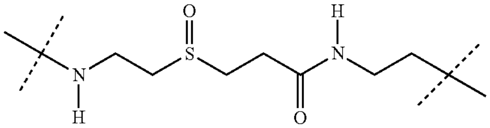
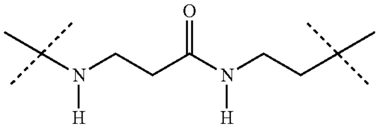
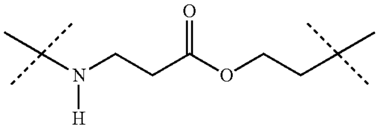
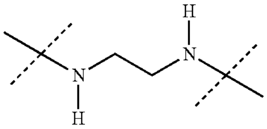
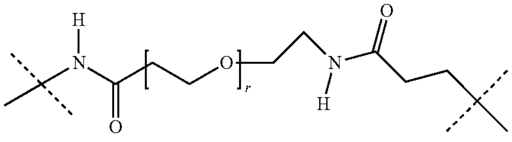

-continued
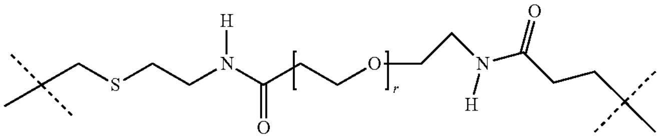
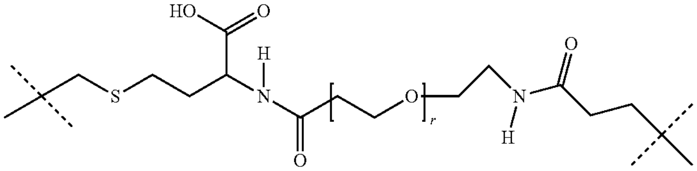
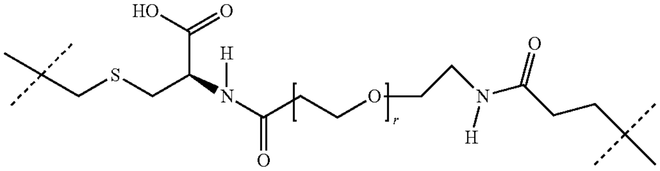
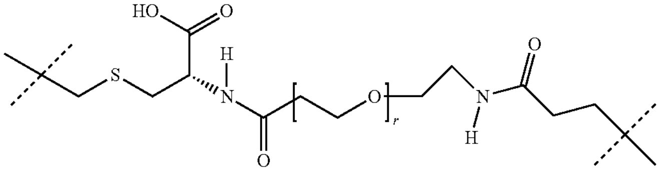
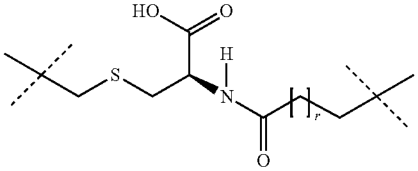
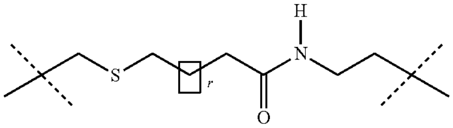
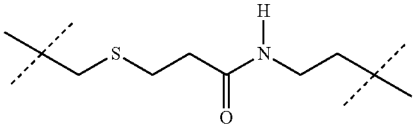
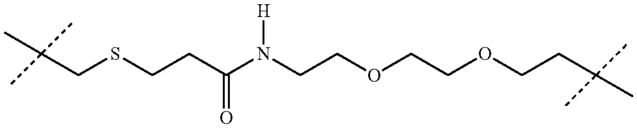
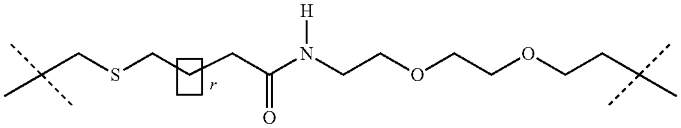
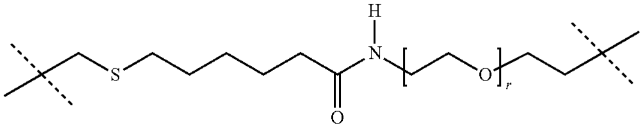
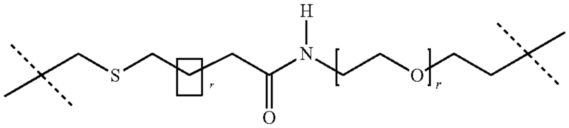
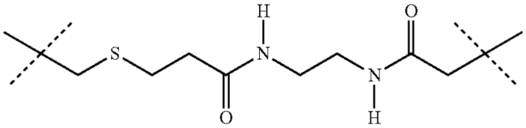
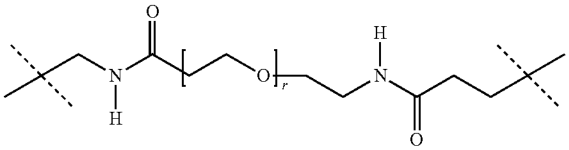
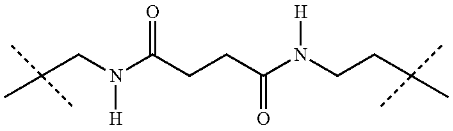
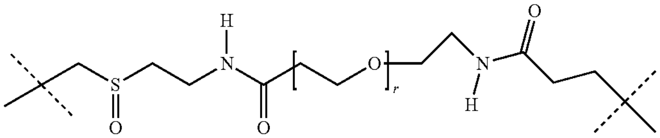
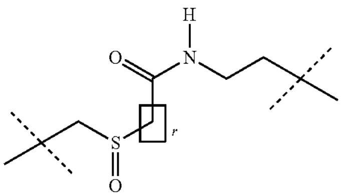

-continued
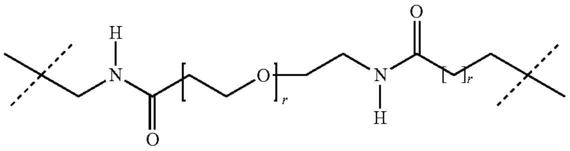
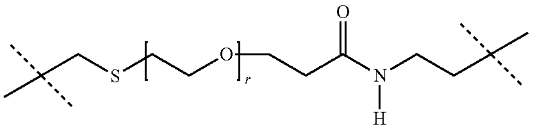
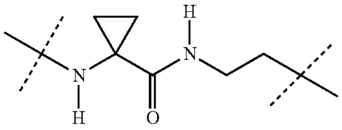
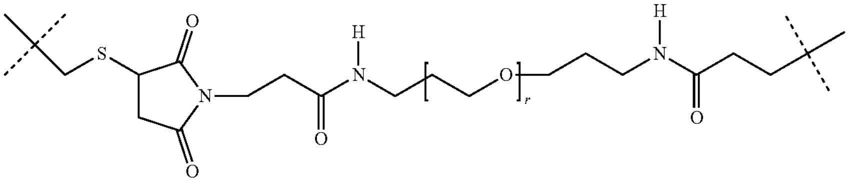
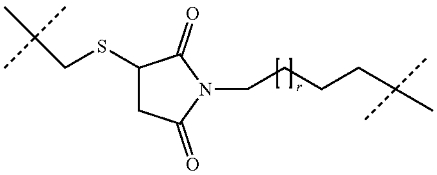
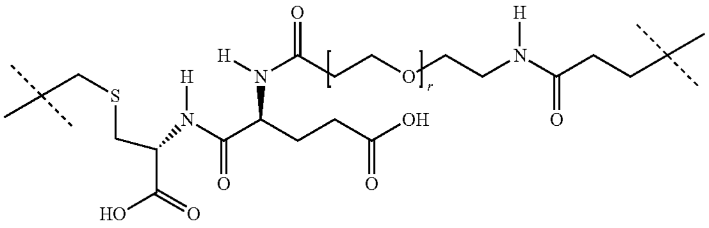
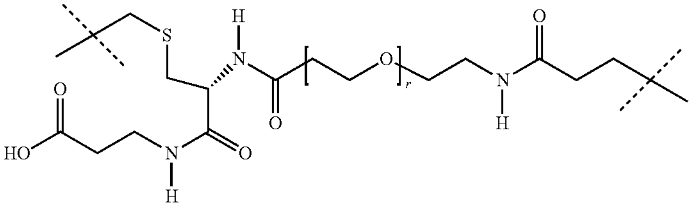
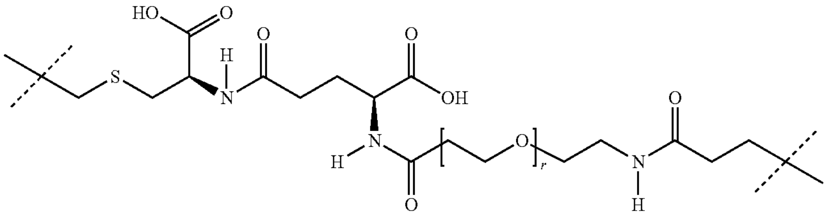
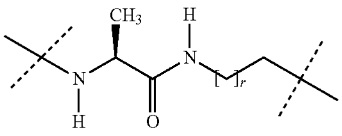
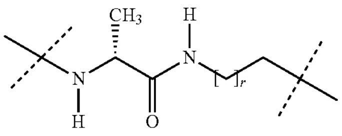
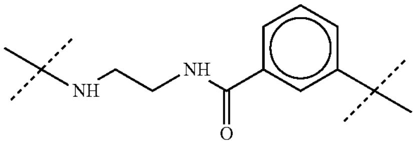
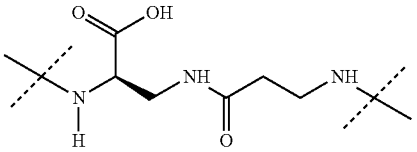
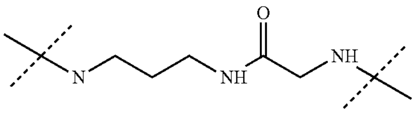

-continued
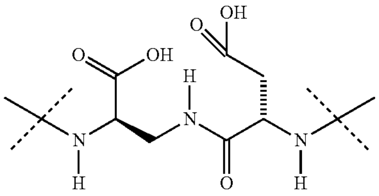
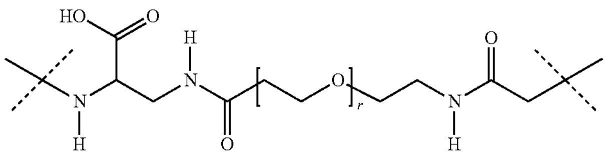
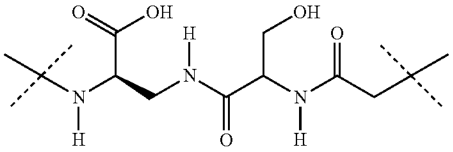
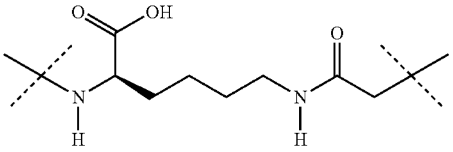
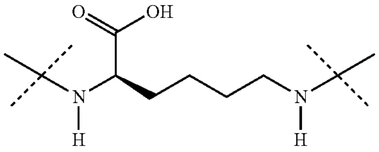
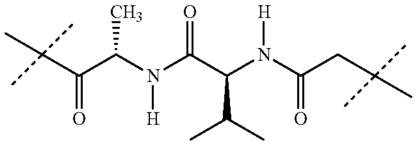
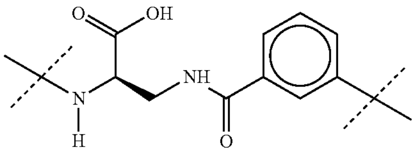
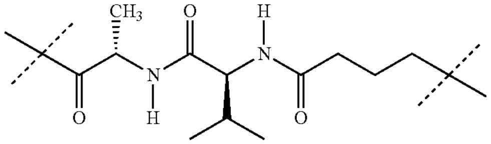
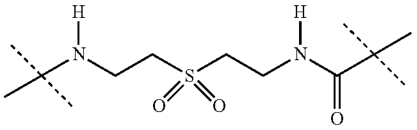
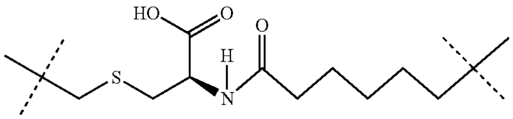
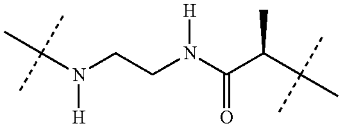
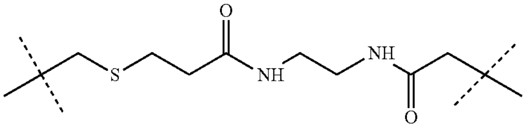
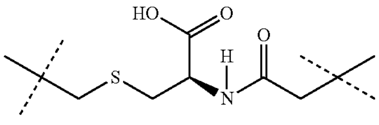
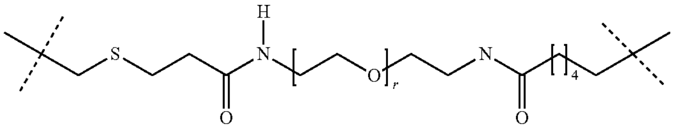
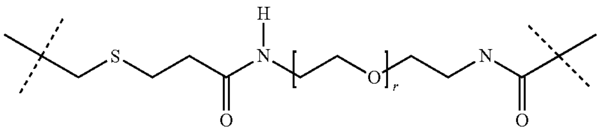
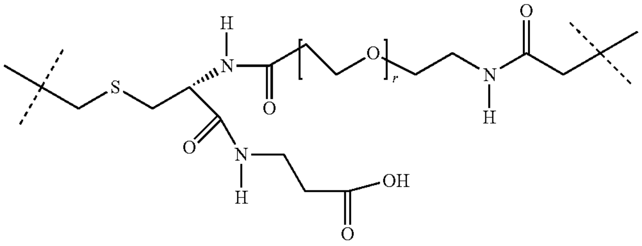
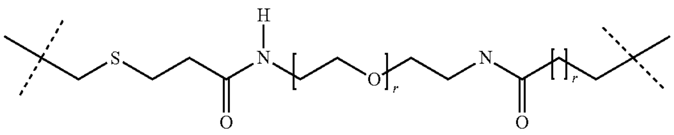

-continued
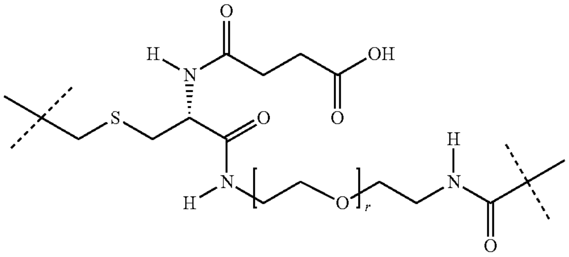
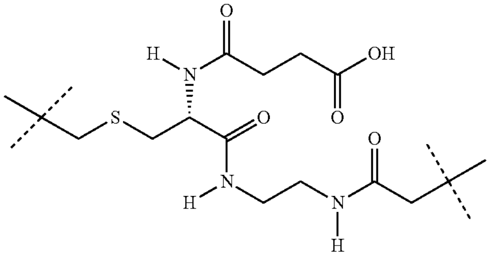
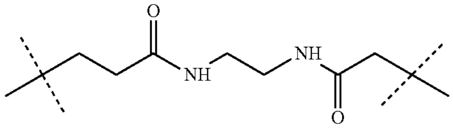
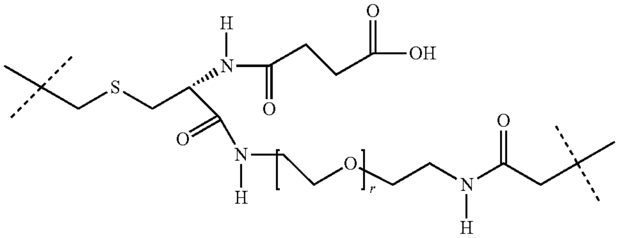
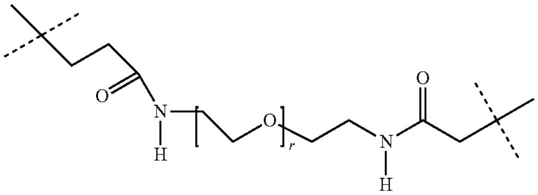
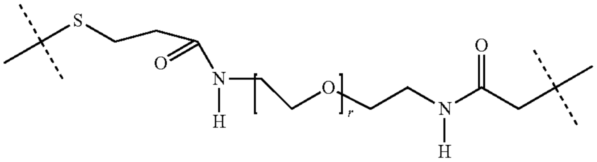
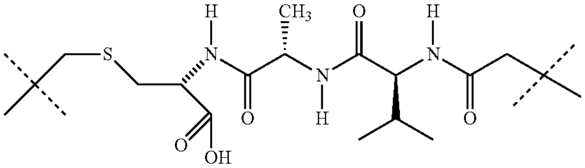
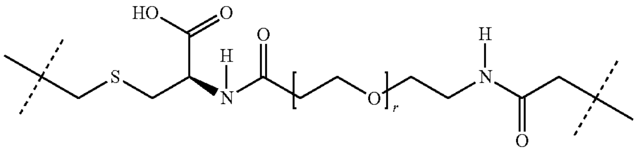
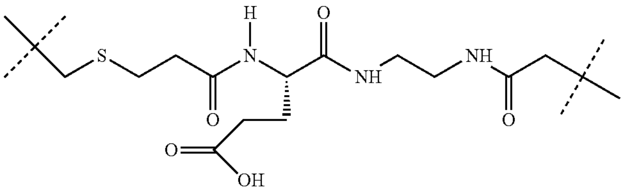
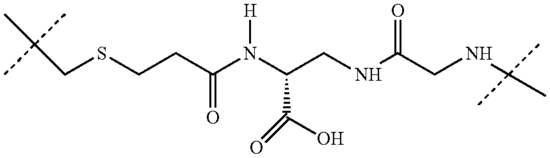

-continued

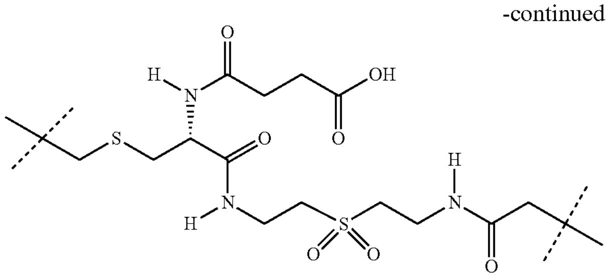

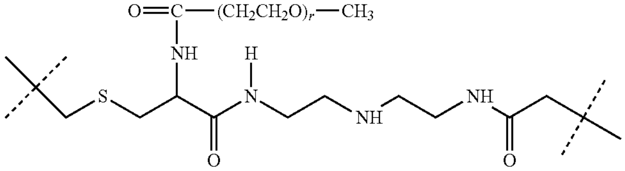

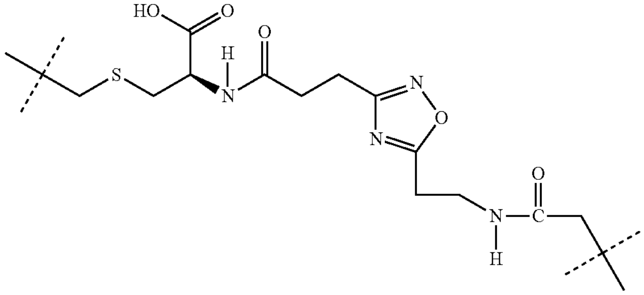

Further examples of L1 are given in Table C, in which this group is highlighted in a box.

Examples of a linker moiety L1 are given in Tables A and A' below. The table furthermore states with which group L2 these examples of L1 are preferably combined, and also the preferred coupling point ($R^1$ or $R^3$ or $R^4$) and the preferred value for m, this is whether there is a carbonyl group in front of L1 or not (cf. § —(CO)m-L1-L2-§§). These linkers are preferably coupled to a cysteine residue. If L2 is a succinimide or derived therefrom, this imide may also be fully or partially in the form of the hydrolysed open-chain succinamide, as described above. Depending on L1, this hydrolysis to open-chain succinamides may be more or less pronounced or not present at all.

TABLE A

| Subst. | m | L1 | L2 |
|---|---|---|---|
| $R^1$ | 1 | 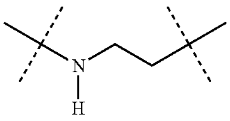 | 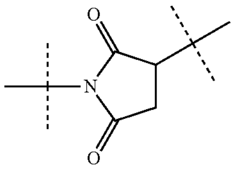 |
| $R^1$ | 1 | 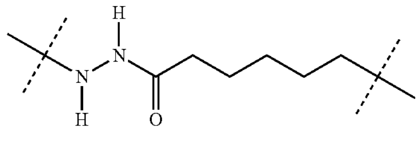 | 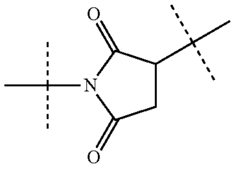 |
| $R^1$ | 1 | 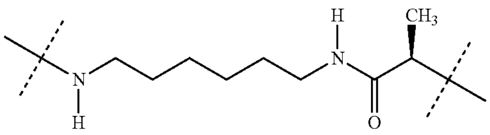 | 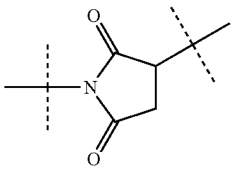 |

TABLE A-continued
| Subst. | m | L1 | L2 |
|---|---|---|---|
| $R^1$ | 1 | 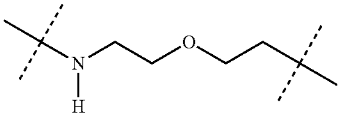 | 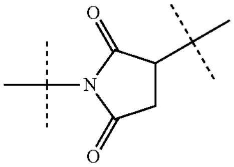 |
| $R^1$ | 1 | 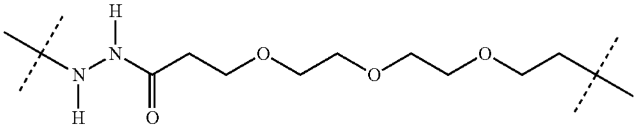 | 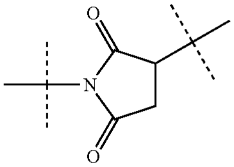 |
| $R^1$ | 1 | 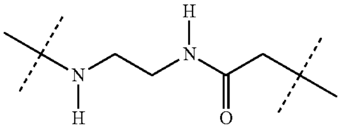 | 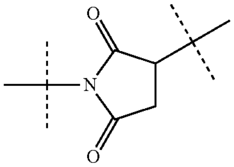 See note ** |
| $R^1$ | 1 | 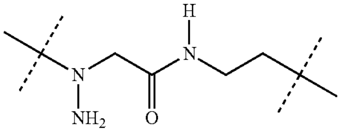 | 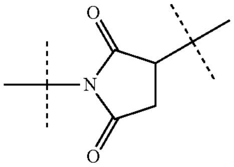 |
| $R^1$ | 1 | 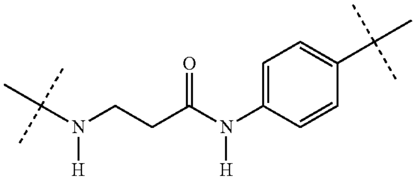 | 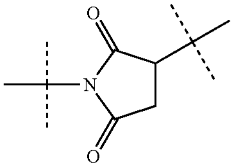 See note ** |
| $R^1$ | 1 | 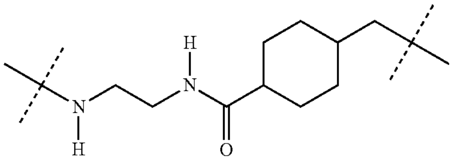 | 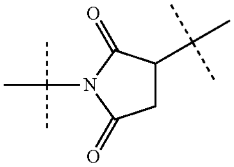 |
| $R^1$ | 1 | 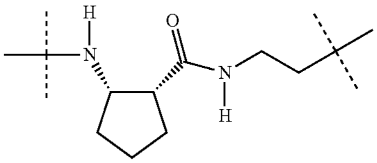 | 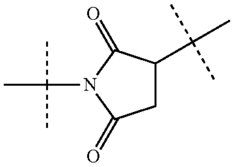 |
| $R^1$ | 1 | 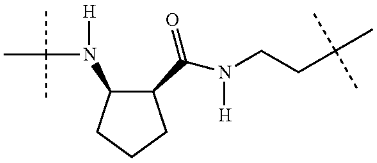 | 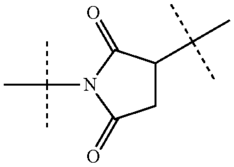 |

TABLE A-continued
| Subst. | m | L1 | L2 |
|---|---|---|---|
| $R^1$ | 1 | 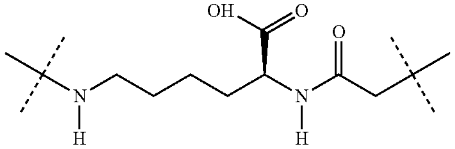 | 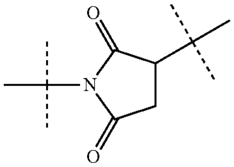 See note ** |
| $R^1$ | 1 | 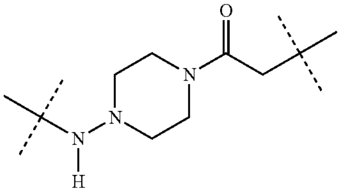 | 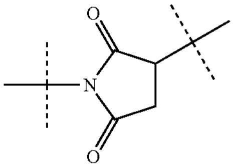 See note ** |
| $R^1$ | 1 | 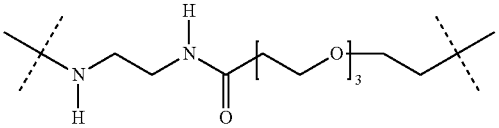 | 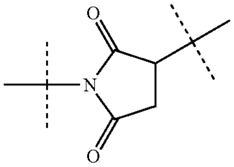 |
| $R^1$ | 1 | 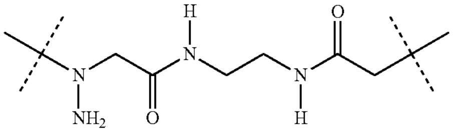 | 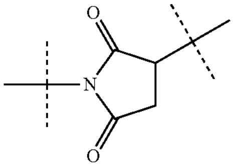 See note ** |
| $R^1$ | 1 | 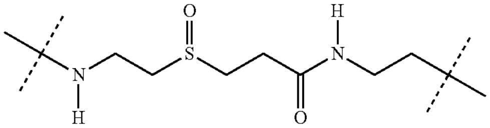 | 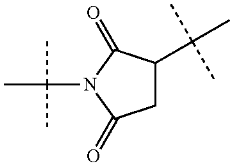 |
| $R^1$ | 1 | 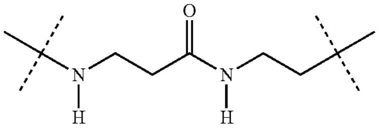 | 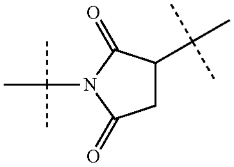 |
| $R^1$ | 1 | 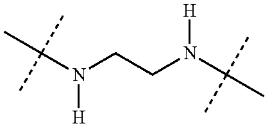 | 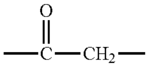 |
| $R^1$ | 1 | 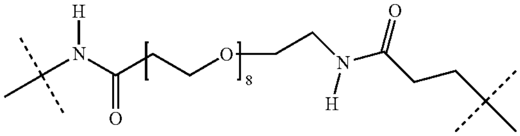 | 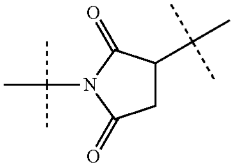 |

TABLE A-continued
| Subst. | m | L1 | L2 |
|---|---|---|---|
| $R^3$ | 0 | 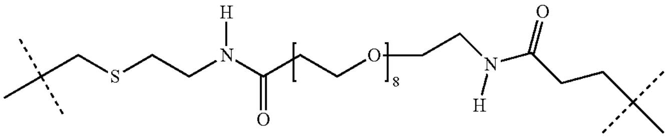 | 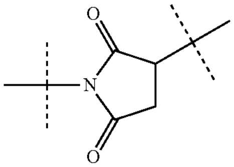 |
| $R^1$ | 1 | 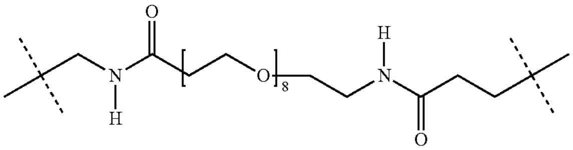 | 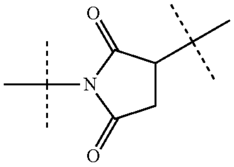 |
| $R^3$ | 0 | 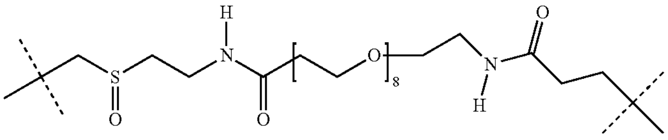 | 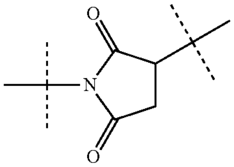 |
| $R^1$ | 1 | 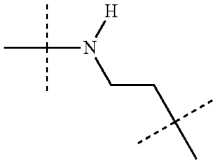 | 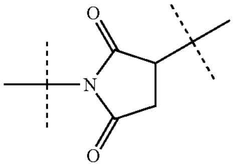 |
| $R^1$ | 0 | 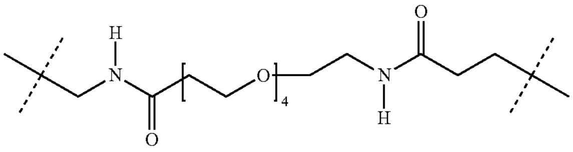 | 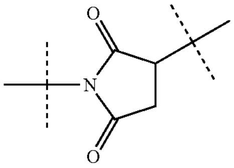 |
| $R^3$ | 0 | 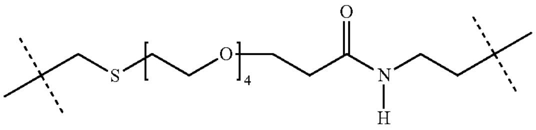 | 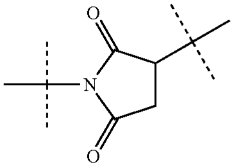 |
| $R^3$ | 0 | 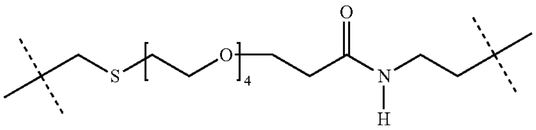 | 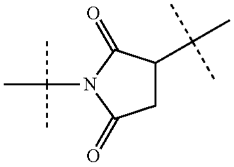 |

TABLE A-continued
| Subst. | m | L1 | L2 |
| --- | --- | --- | --- |
| $R^1$ | 1 | 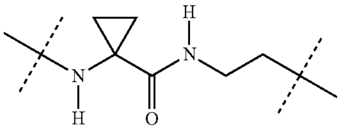 | 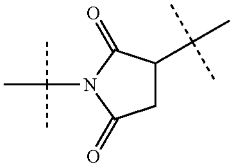 |
| $R^3$ | 0 | 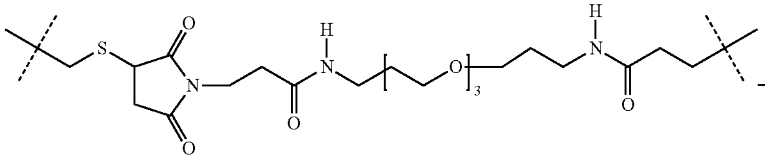 | 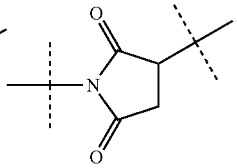 |
| $R^3$ | 0 | 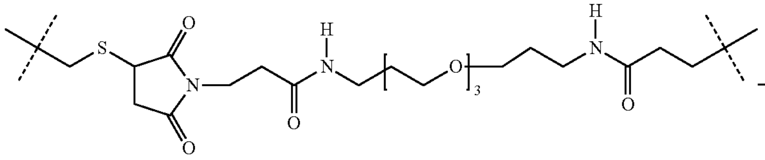 | 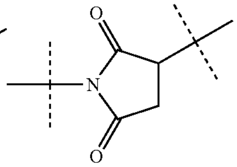 |
| $R^3$ | 0 | 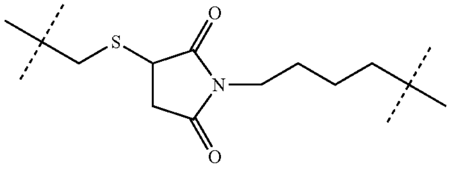 | 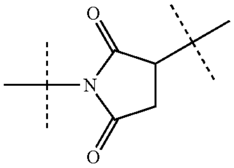 |
| $R^3$ | 0 | 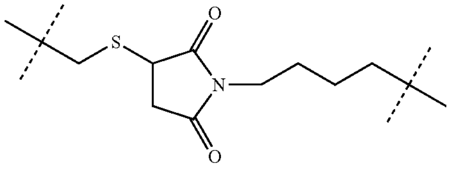 | 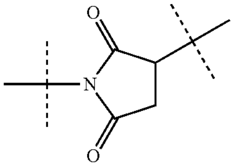 |
| $R^1$ | 1 | 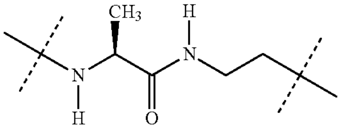 | 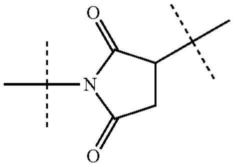 |

TABLE A-continued

| Subst. | m | L1 | L2 |
|---|---|---|---|
| $R^1$ | 1 | 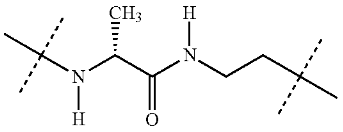 | 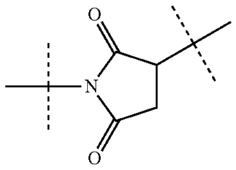 |

**With particular preference, the linkers L1 given in these rows are attached to a linker L2 selected from:

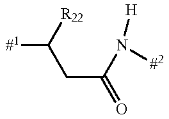

Formula A7 and/or

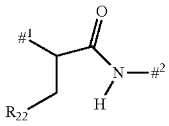

Formula A8 where #[1] denotes the point of attachment to the sulphur atom of the binder,

#[2] denotes the point of attachment to group L1,

R22 preferably represents COOH. In a conjugate according to the invention or in a mixture of the conjugates according to the invention, the bonds to a cysteine residue of the binder are present, to an extent of preferably more than 80%, particularly preferably more than 90% (in each case based on the total number of bonds of the linker to the binder), particularly preferably as one of the two structures of the formula A7 or A8. Here, the structures of the formula A7 or A8 are generally present together, preferably in a ratio of from 60:40 to 40:60, based on the number of bonds to the binder. The remaining bonds are then present as the structure

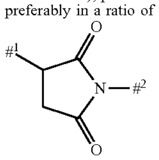

TABLE A'

| Subst. | m | L1 | L2 |
|---|---|---|---|
| $R^1$ | 1 | 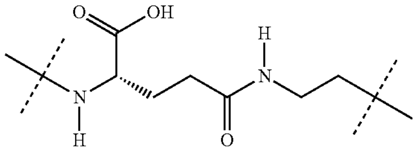 | 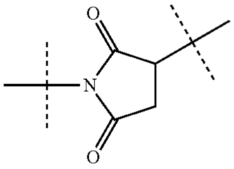 |
| $R^1$ | 1 | 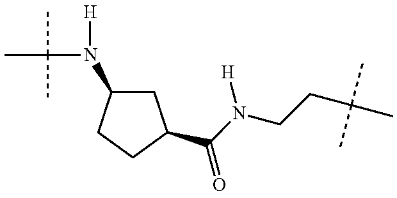 | 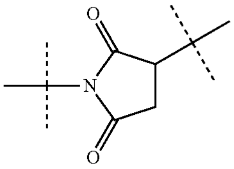 |
| $R^1$ | 1 | 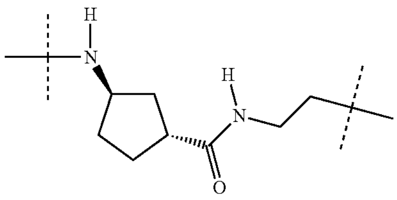 | 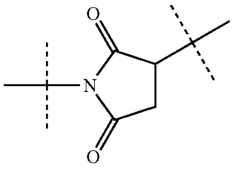 |
| $R^1$ | 1 | 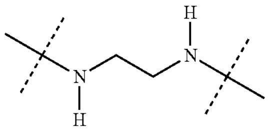 | 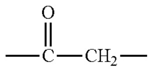 |

TABLE A'-continued
| Subst. | m | L1 | L2 |
| --- | --- | --- | --- |
| $R^1$ | 1 | 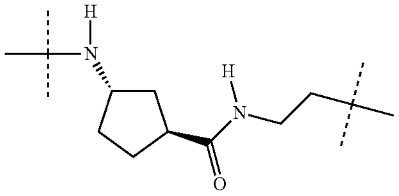 | 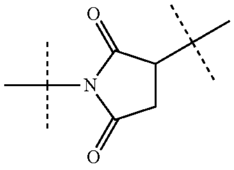 |
| $R^1$ | 1 | 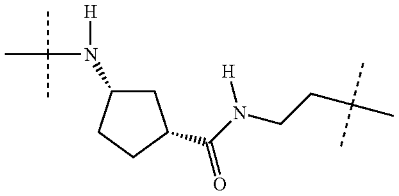 | 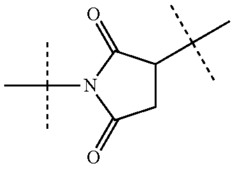 |
| $R^3$ | 0 | 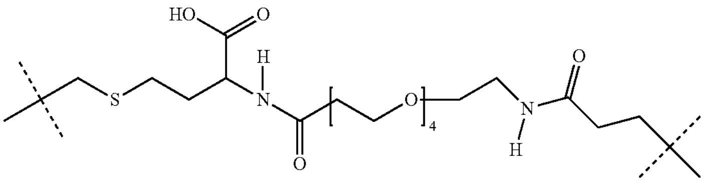 | 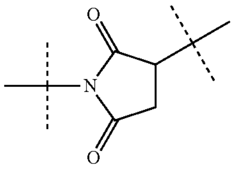 |
| $R^3$ | 0 | 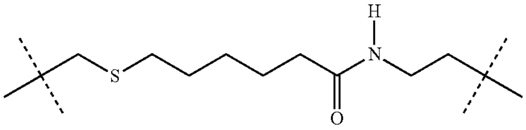 | 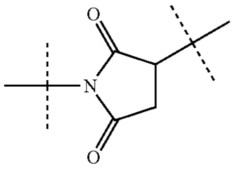 |
| $R^3$ | 0 | 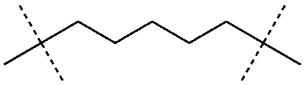 | 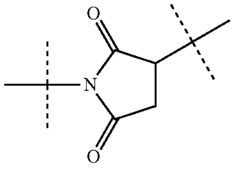 |
| $R^3$ | 0 | 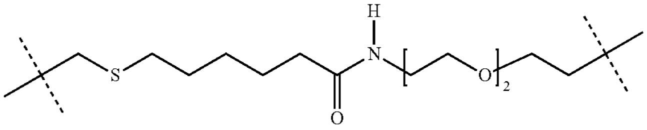 | 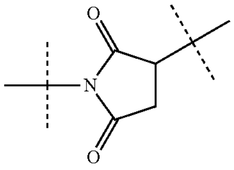 |
| $R^3$ | 0 | 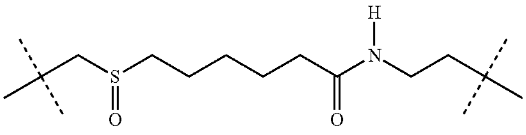 | 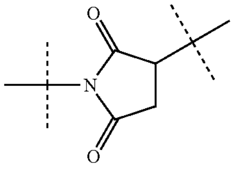 |
| $R^1$ | 1 | 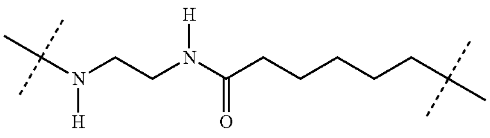 | 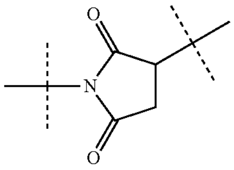 |

TABLE A'-continued
| Subst. | m | L1 | L2 |
|---|---|---|---|
| $R^1$ | 1 | 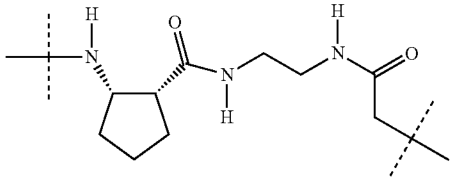 | 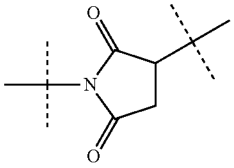 See note ** |
| $R^1$ | 1 | 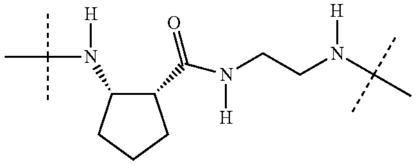 | 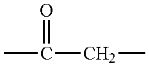 |
| $R^1$ | 1 | 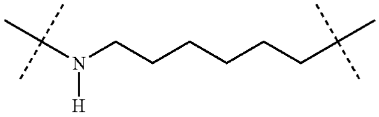 | 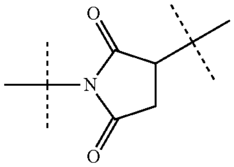 |
| $R^1$ | 1 | 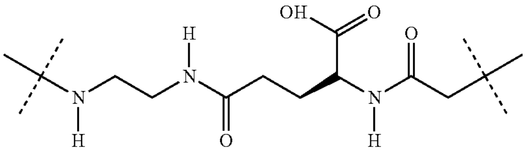 | 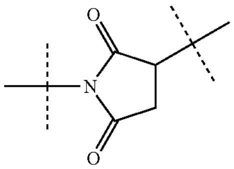 See note ** |
| $R^1$ | 1 | 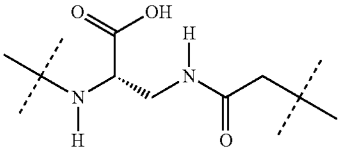 | 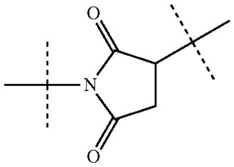 See note ** |
| $R^1$ | 1 | 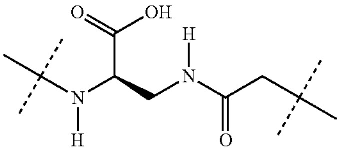 | 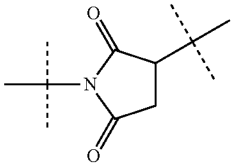 See note ** |
| $R^1$ | 0 | 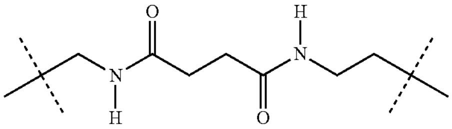 | 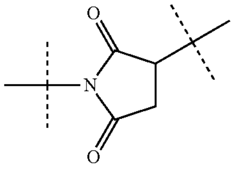 |
| $R^1$ | 1 | 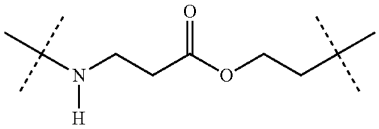 | 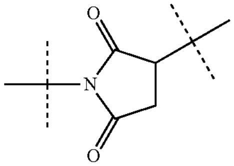 |

TABLE A'-continued
| Subst. | m | L1 | L2 |
|---|---|---|---|
| $R^1$ | 1 | 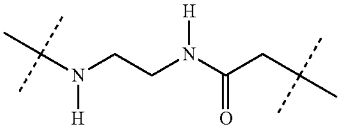 | 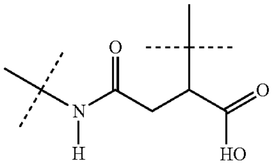 and 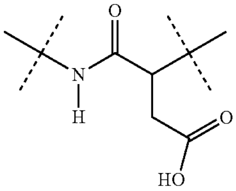 See note *** |
| $R^1$ | 1 | 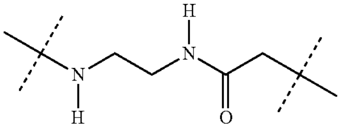 | 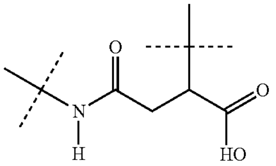 |
| $R^1$ | 1 | 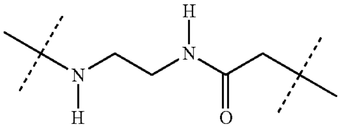 | 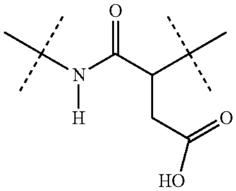 |
| $R^1$ | 1 | 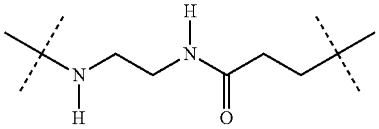 | 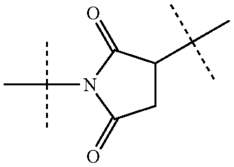 |
| $R^3$ | 0 | 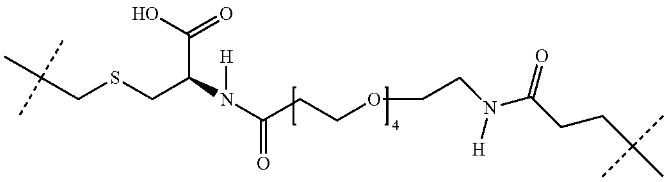 | 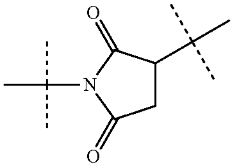 |
| $R^3$ | 0 | 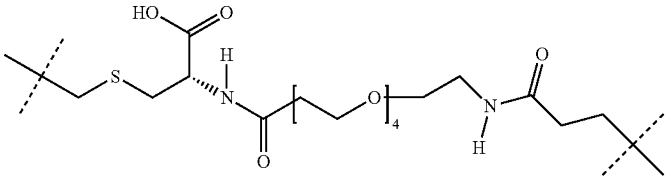 | 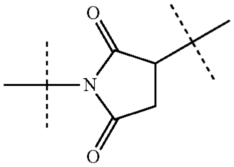 |
| $R^3$ | 0 | 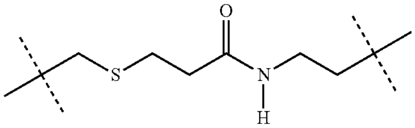 | 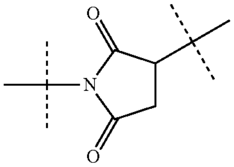 |

TABLE A'-continued
| Subst. | m | L1 | L2 |
|---|---|---|---|
| $R^3$ | 0 | 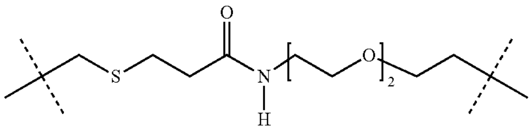 | 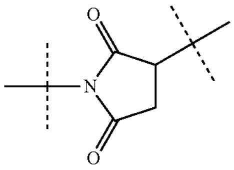 |
| $R^3$ | 0 | 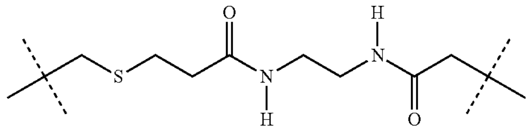 | 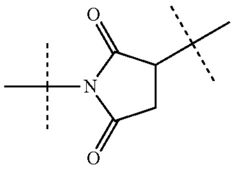 See note ** |
| $R^3$ | 0 | 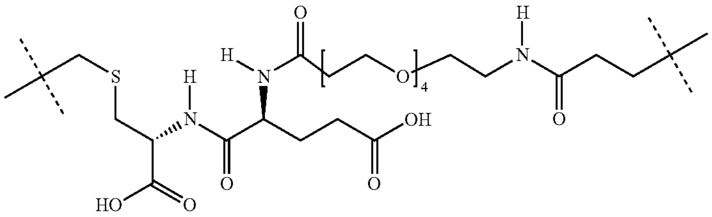 | 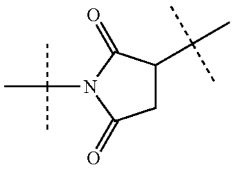 |
| $R^3$ | 0 | 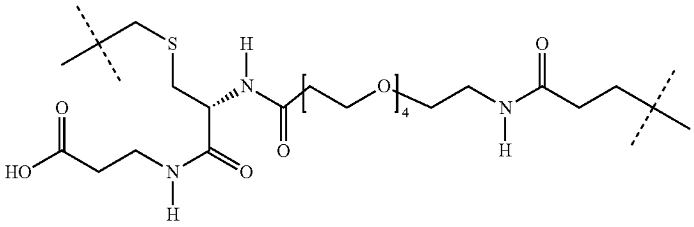 | 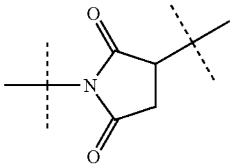 |
| $R^3$ | 0 | 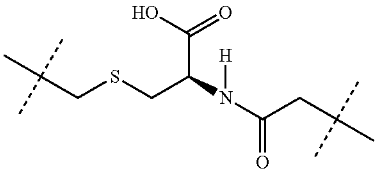 | 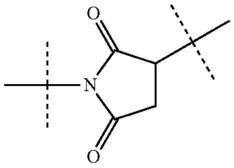 See note ** |
| $R^3$ | 0 | 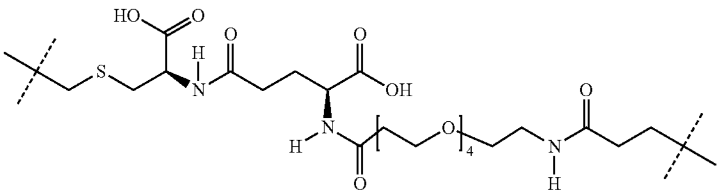 | 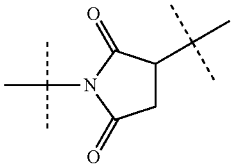 |
| $R^2$ | 0 | 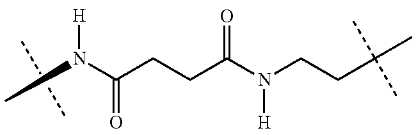 | 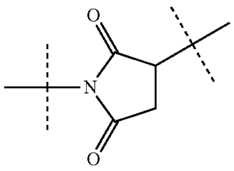 |

TABLE A'-continued
| Subst. | m | L1 | L2 |
|---|---|---|---|
| $R^1$ | 1 | 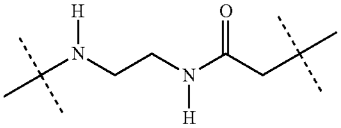 | 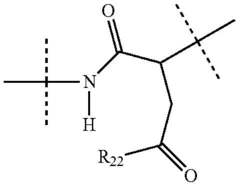 where $R_{22}$ = —OH or —$NH_2$ |
| $R^1$ | 1 | 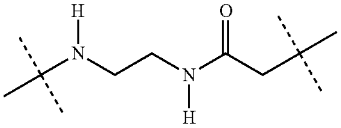 | 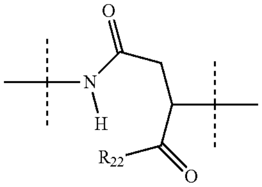 where $R_{22}$ = —OH or —$NH_2$ |
| $R^1$ | 1 | 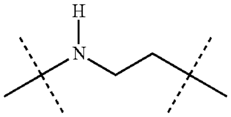 | 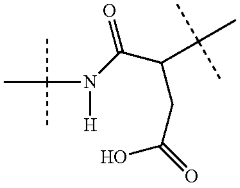 and 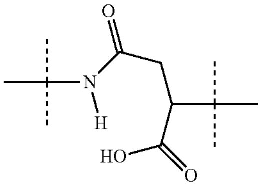 See note *** |
| $R^1$ | 1 | 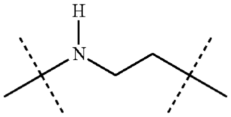 | 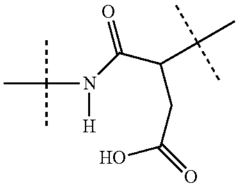 |
| $R^1$ | 1 | 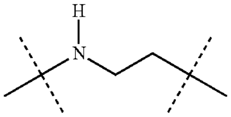 | 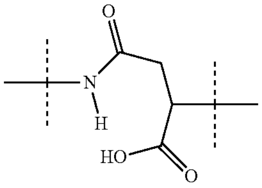 |

TABLE A'-continued
| Subst. | m | L1 | L2 |
|---|---|---|---|
| R[1] | 1 | 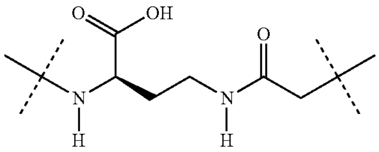 | 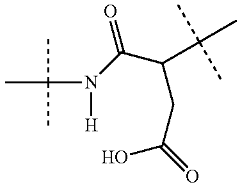<br>and<br>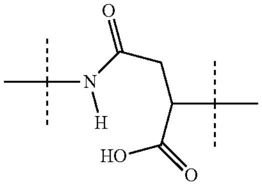<br>See note *** |
| R[1] | 1 | 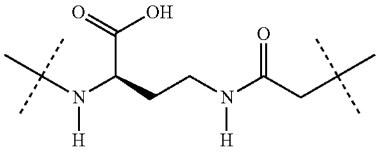 | 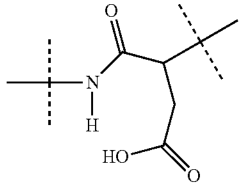 |
| R[1] | 1 | 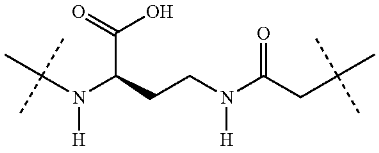 | 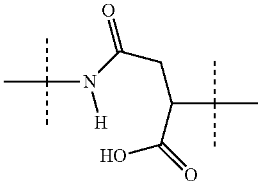 |
| R[3] | 0 | 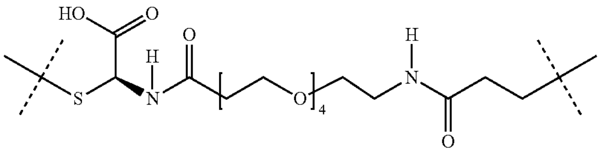 | 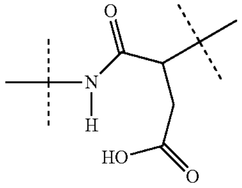<br>and<br>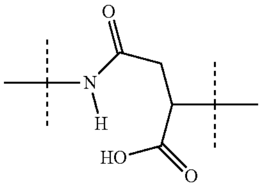<br>See note *** |
| R[3] | 0 | 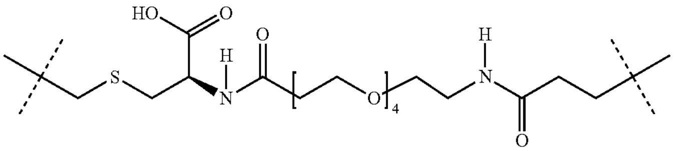 | 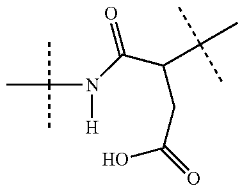 |

TABLE A'-continued
| Subst. | m | L1 | L2 |
|---|---|---|---|
| $R^3$ | 0 | 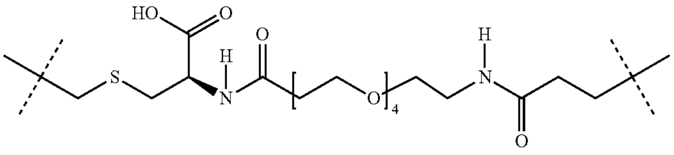 | 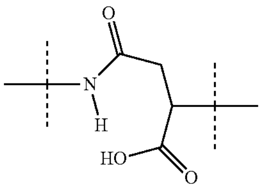 |
| $R^3$ | 0 | 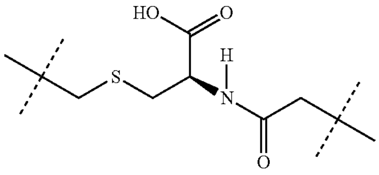 | 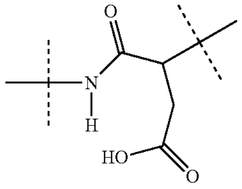<br>and<br>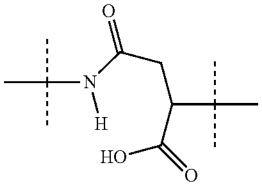<br>See note *** |
| $R^3$ | 0 | 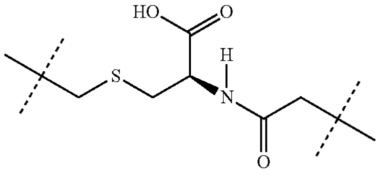 | 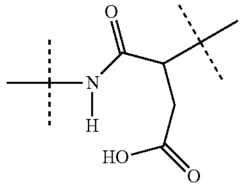 |
| $R^3$ | 0 | 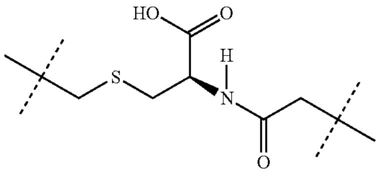 | 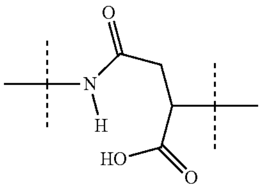 |
| $R^3$ | 0 | 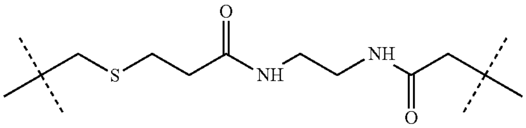 | 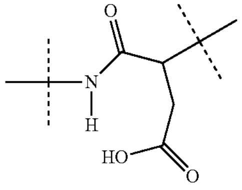<br>and<br>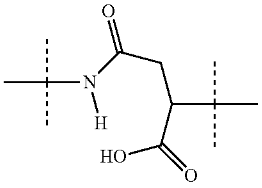<br>See note *** |

TABLE A'-continued
| Subst. | m | L1 | L2 |
|---|---|---|---|
| $R^3$ | 0 | 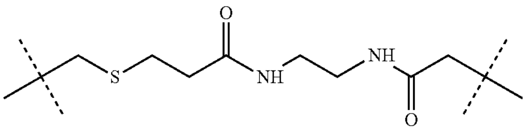 | 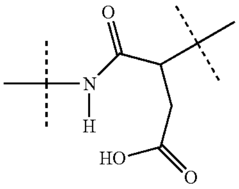 |
| $R^3$ | 0 | 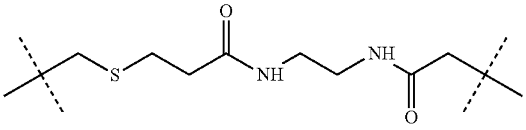 | 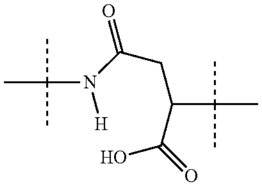 |
| $R^1$ | 1 | 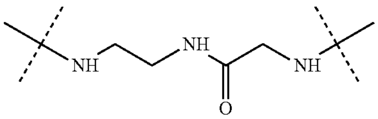 | 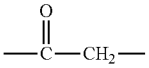 |
| $R^1$ | 1 | 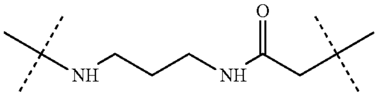 | 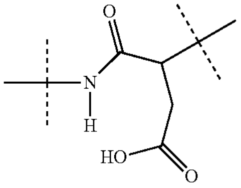 and 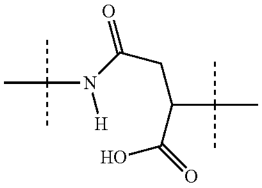 See note *** |
| $R^1$ | 1 | 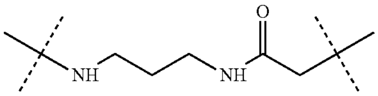 | 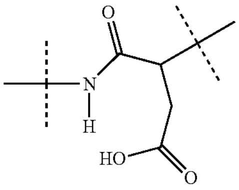 |
| $R^1$ | 1 | 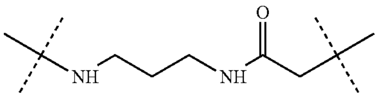 | 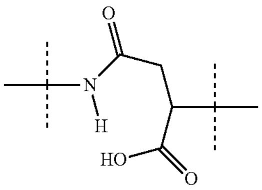 |

TABLE A'-continued
| Subst. | m | L1 | L2 |
|---|---|---|---|
| $R^1$ | 1 | 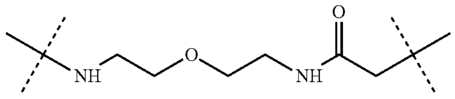 | 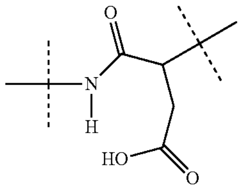<br>and<br>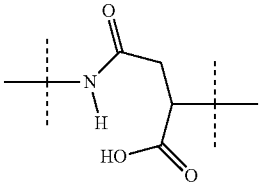<br>See note *** |
| $R^1$ | 1 | 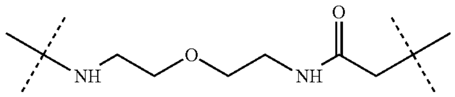 | 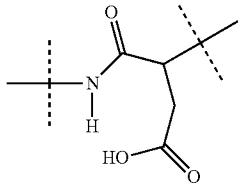 |
| $R^1$ | 1 | 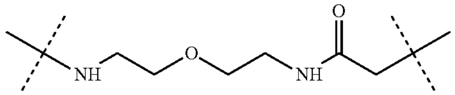 | 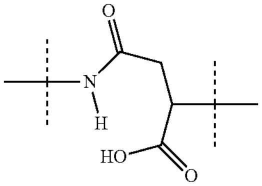 |
| R3 | 0 | 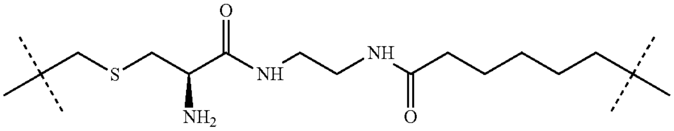 | 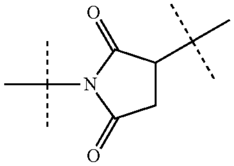 |
| R1 | 0 | 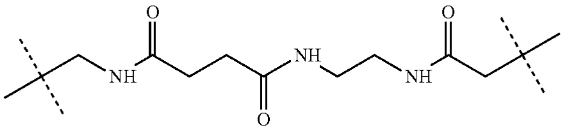 | 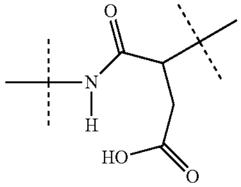<br>and<br>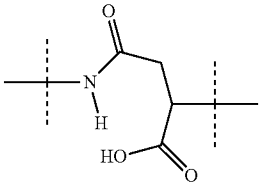<br>See note *** |

TABLE A'-continued
| Subst. | m | L1 | L2 |
|---|---|---|---|
| R1 | 0 | 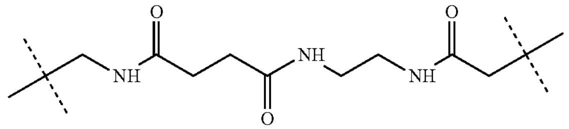 | 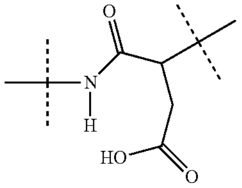 |
| R1 | 0 | 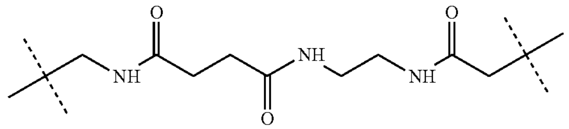 | 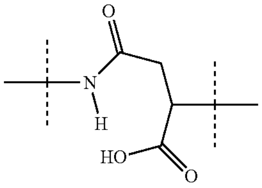 |
| R1 | 1 | 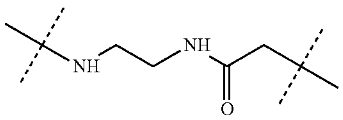 | 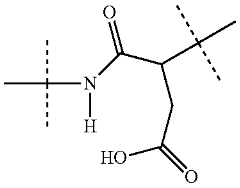 and 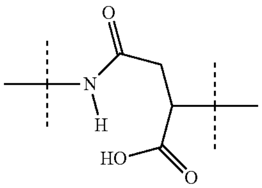 See note *** |
| R1 | 1 | 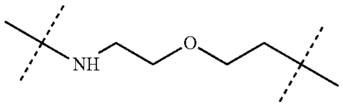 | 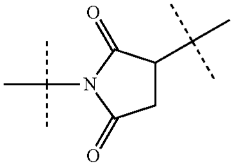 |
| R1 | 1 | 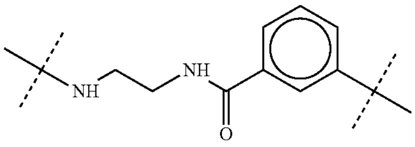 | 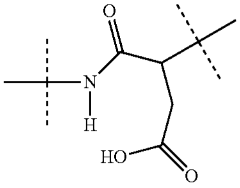 and 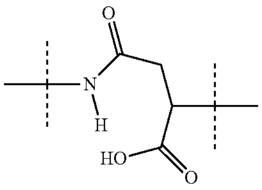 See note *** |

TABLE A'-continued
| Subst. | m | L1 | L2 |
|---|---|---|---|
| $R^1$ | 1 | 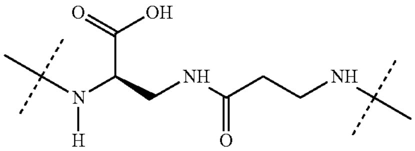 | 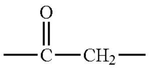 |
| $R^1$ | 1 | 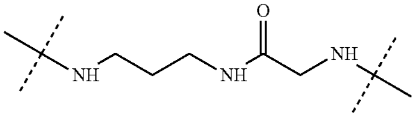 | 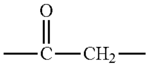 |
| $R^1$ | 1 | 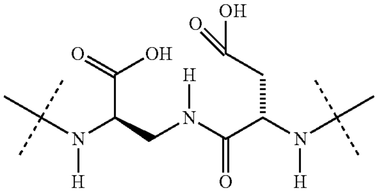 | 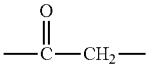 |
| $R^1$ | 1 | 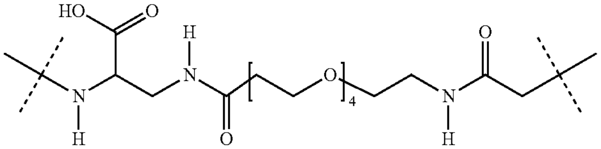 | 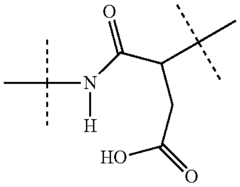 and 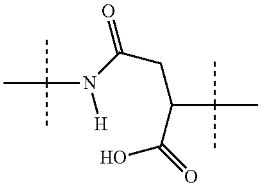 See note *** |
| $R^1$ | 1 | 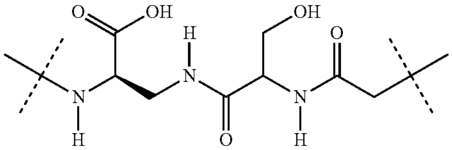 | 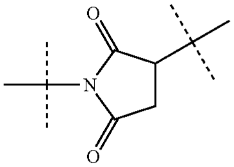 See note ** |
| $R^1$ | 1 | 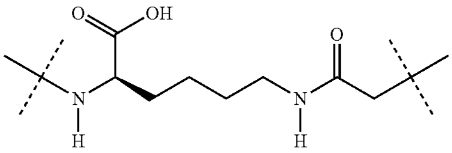 | 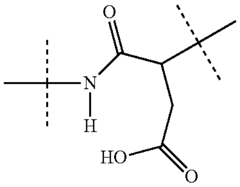 and 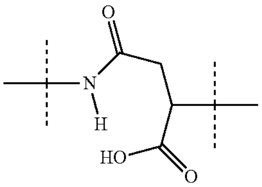 See note *** |

TABLE A'-continued
| Subst. | m | L1 | L2 |
|---|---|---|---|
| $R^1$ | 1 | 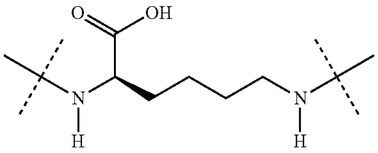 | 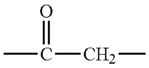 |
| $R^4$ | 0 | 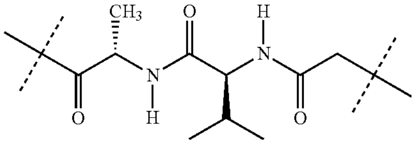 | 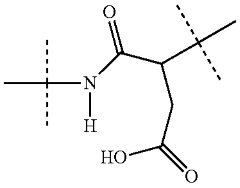<br>and<br>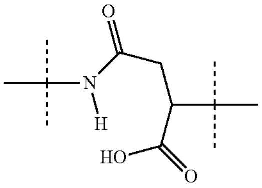<br>See note *** |
| $R^1$ | 1 | 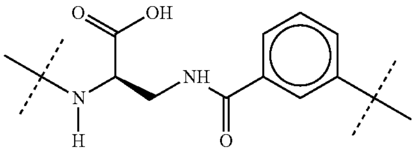 | 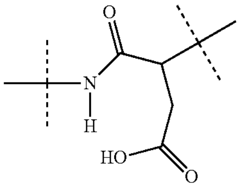<br>and<br>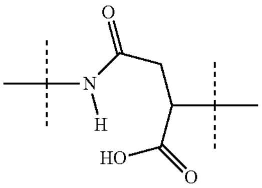<br>See note *** |
| $R^4$ | 0 | 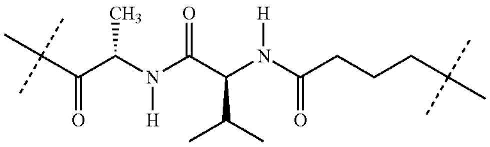 | 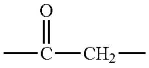 |

TABLE A'-continued
| Subst. | m | L1 | L2 |
|---|---|---|---|
| $R^1$ | 1 | 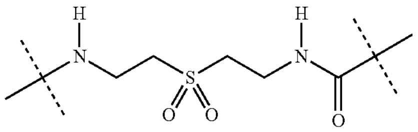 | 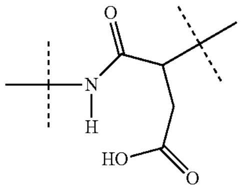<br>and<br>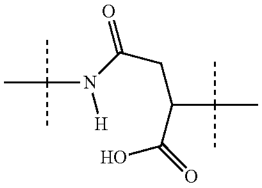<br>See note *** |
| $R^3$ | 0 | 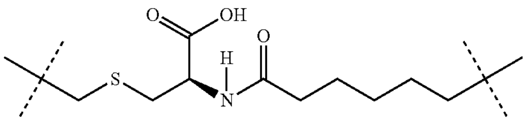 | 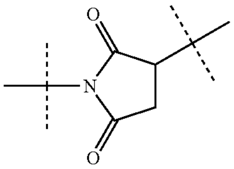<br>See note ** |
| $R^1$ | 1 | 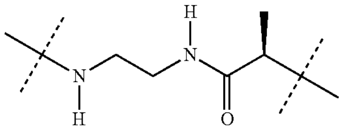 | 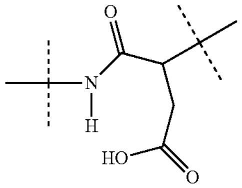<br>and<br>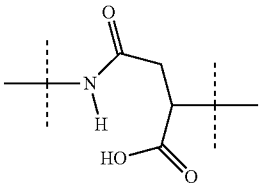<br>See note *** |
| $R^3$ | 0 | 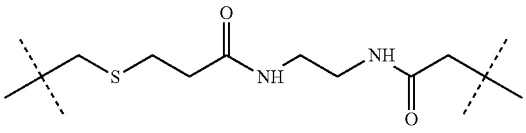 | 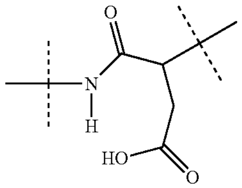<br>and<br>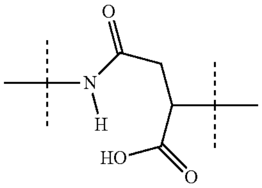<br>See note *** |

TABLE A'-continued
| Subst. | m | L1 | L2 |
|---|---|---|---|
| $R^3$ | 0 | 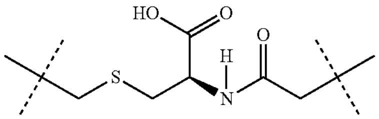 | 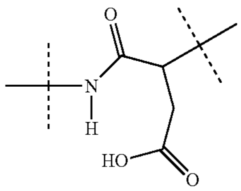<br>and<br>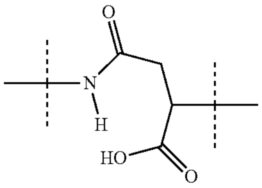<br>See note *** |
| $R^3$ | 0 | 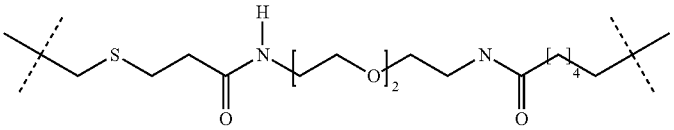 | 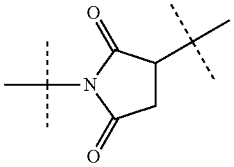 |
| $R^3$ | 0 | 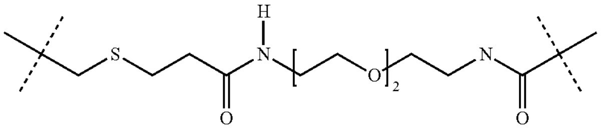 | 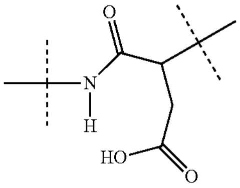<br>and<br>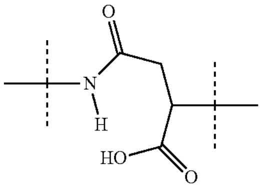<br>See note *** |
| $R^3$ | 0 | 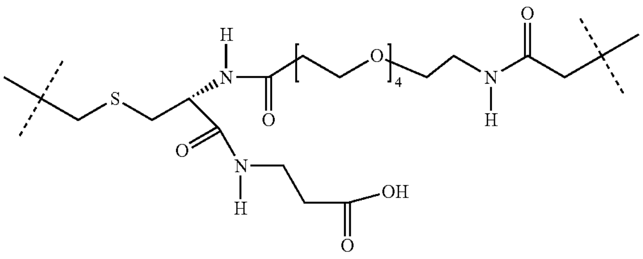 | 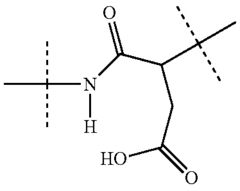<br>and<br>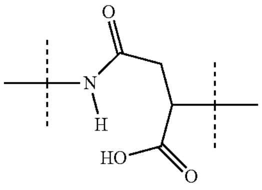<br>See note *** |

TABLE A'-continued
| Subst. | m | L1 | L2 |
|---|---|---|---|
| $R^3$ | 0 | 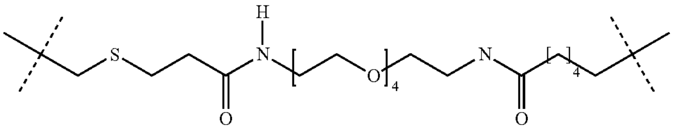 | 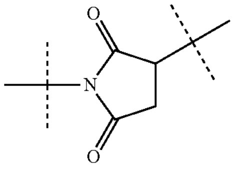 See note ** |
| $R^3$ | 0 | 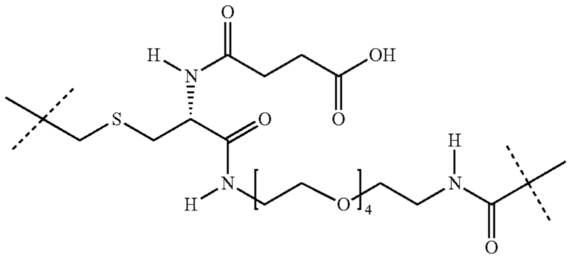 | 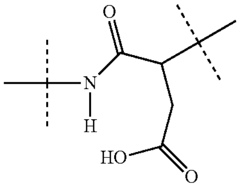 and 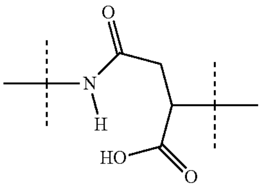 See note *** |
| $R^3$ | 0 | 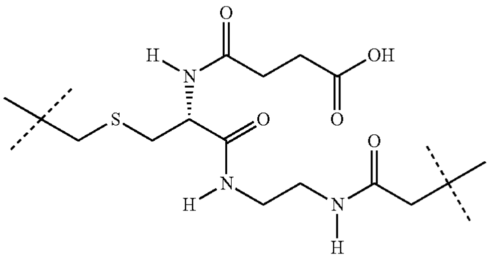 | 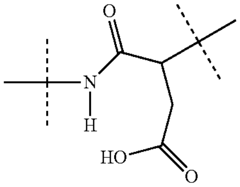 and 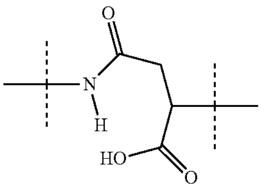 See note *** |

TABLE A'-continued
| Subst. | m | L1 | L2 |
|---|---|---|---|
| $R^3$ | 0 | 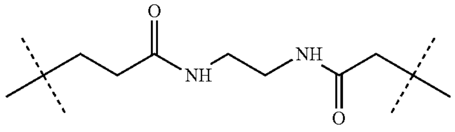 | 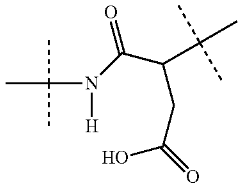 and 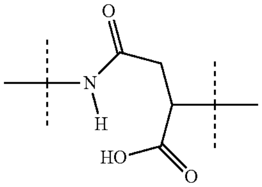 See note *** |
| $R^3$ | 0 | 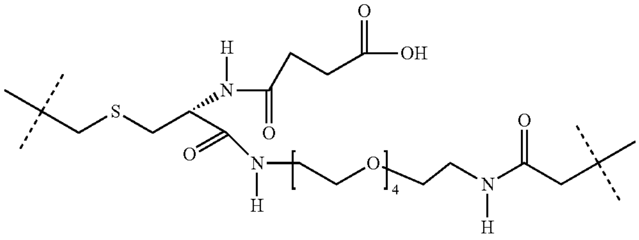 | 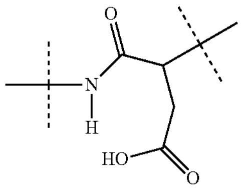 and 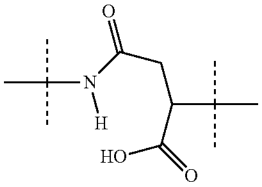 See note *** |
| $R^3$ | 0 | 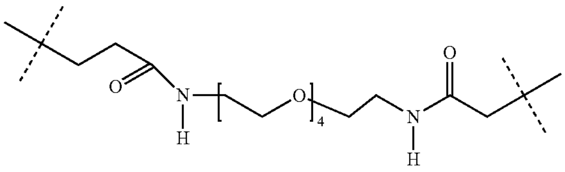 | 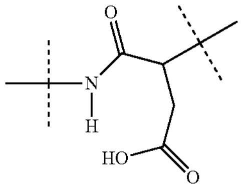 and 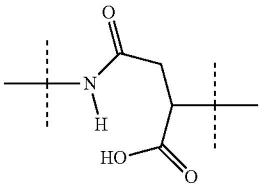 See note *** |

TABLE A'-continued
| Subst. | m | L1 | L2 |
|---|---|---|---|
| $R^3$ | 0 | 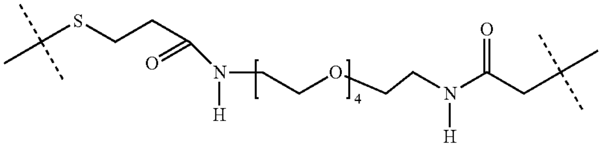 | 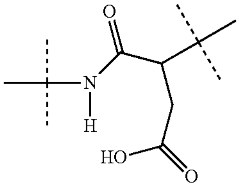 and 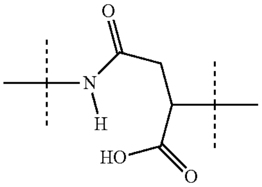 See note *** |
| $R^3$ | 0 | 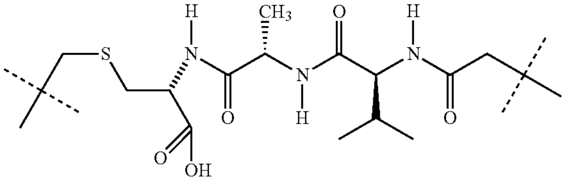 | 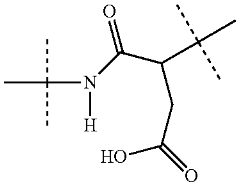 and 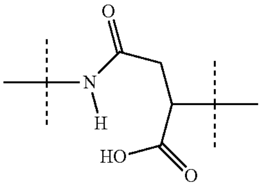 See note *** |
| $R^3$ | 0 | 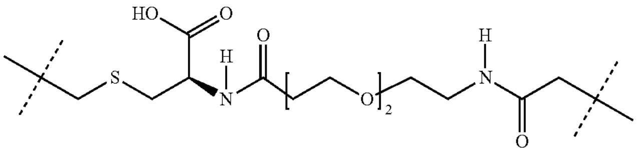 | 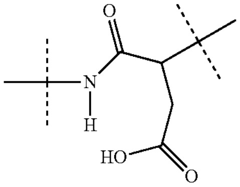 and 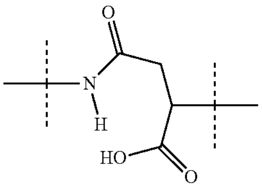 See note *** |

TABLE A'-continued

| Subst. | m | L1 | L2 |
| --- | --- | --- | --- |
| $R^3$ | 0 | 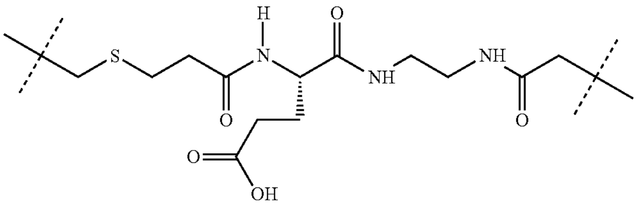 | 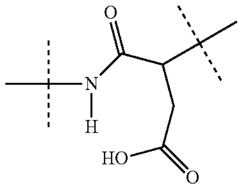 and 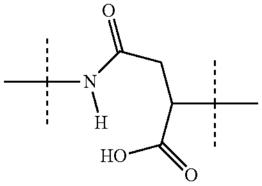 See note *** |
| $R^3$ | 0 | 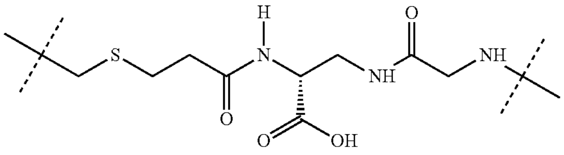 | 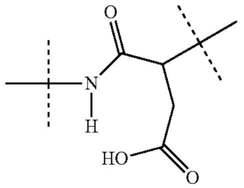 and 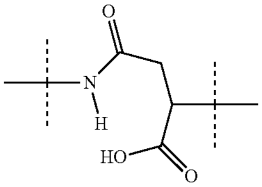 See note *** |
| $R^3$ | 0 | 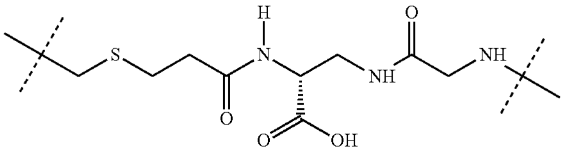 | 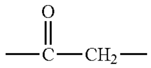 |

: See note  for Table A.

*** : When this structure L2 is present, there may simultaneously be a structure L2 of the formula below:

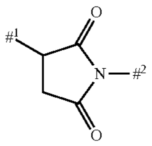

Examples of conjugates having corresponding linkers have the following structures, where X1 represents CH, X2 represents C and X3 represents N and L1 has the meaning given above, L2 and L3 have the same meaning as L1, AK1 represents an antibody attached via a cysteine residue and n is a number from 1 to 10. More preferably, AK1 is preferably a human, humanized or chimeric monoclonal antibody. Particular preference is given to an aglycosylated anti-TWEAKR antibody which binds specifically to amino acid D in position 47 (D47) of TWEAKR (SEQ ID NO:169), in particular the anti-TWEAKR antibody TPP-2658.

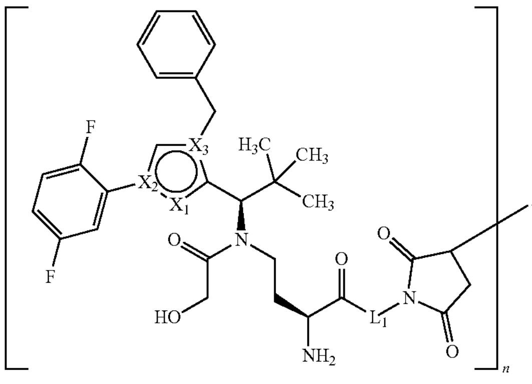

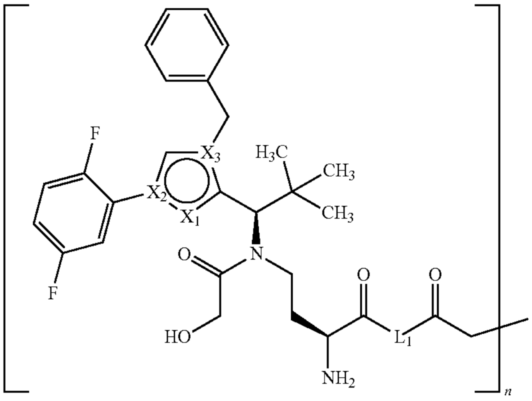

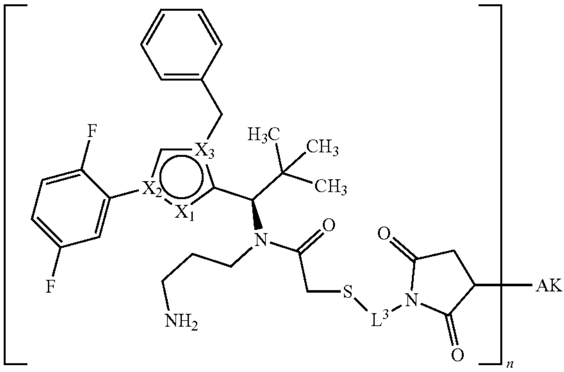

When the linker is attached to a lysine side chain or a lysine residue, it is possible to use the same linkers as described above for coupling to a cysteine side chain, except that L2 is preferably a carbonyl group (the coupling is effected, for example, via a corresponding activated carboxylic acid).

Examples of conjugates having the base structure (i) have one of the following structures, where X1 represents CH, X2 represents C and X3 represents N, L4 has the same meaning as L1, AK1 is an aglycosylated anti-TWEAKR antibody attached via a cysteine residue, and n is a number from 1 to 10, and the hydrogen atom in position $R^4$ of formula IIa (i.e. in the —$NH_2$ group) is replaced by a legumain-cleavable group of the formula $R^{21}$—CO—P3-P2—NH—CH($CH_2CONH_2$)—CO—:

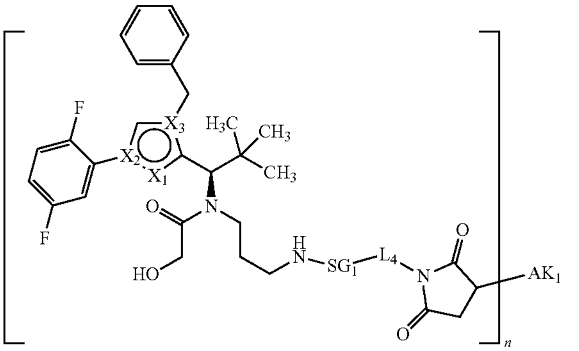

where $R^{21}$ represents a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —$SO_3H$, —COOH, —SH or —OH: P2 is a single bond or an amino acid selected from Gly, Pro, Ala, Val, Leu, Ile, Met, Phe, Tyr, Trp, Ser, Thr, Cys, Asn, Gln, Asp, Glu, Lys, Arg and His;

P3 is a single bond or an amino acid selected from Gly, Pro, Ala, Val, Leu, Ile, Met, Phe, Tyr, Trp, Ser, Thr, Cys, Asn, Gln, Asp, Glu, Lys, Arg and His.

Particular preference is given to the anti-TWEAKR antibody which binds specifically to amino acid D in position 47 (D47) of TWEAKR (SEQ ID NO: 169), in particular the aglycosylated anti-TWEAKR antibody TPP-2658.

In the case of transglutaminase-catalysed conjugation, the literature discloses various options for the covalent coupling (conjugation) of organic molecules to binders, for example antibodies, in a conjugation site-specific manner (see, for example Sochaj et al., *Biotechnology Advances,* 33, 775-784, (2015), Panowski et al., *MAbs* 6, 34-45 (2014)). Preference is given in accordance with the invention to the conjugation of the KSP inhibitors or prodrugs to an antibody via acceptor glutamine residues of the antibody using transglutaminase. Such acceptor glutamine residues can be generated by engineering of the antibody or by mutations which create aglycosylated antibodies. The number of these acceptor glutamines in the antibody is preferably 2 or 4. Suitable linkers are used for the coupling (conjugation). Suitable linker structures are those which possess a free amine donor functionality which constitutes a suitable substrate for the transglutaminase. The linker can be joined to the antibody in various ways.

Preferably, in the case of a transglutaminase-catalysed conjugation, the linker has one of the above base structures (i) to (iv), where L1, SG, SG1 and m have the meanings given above, but L2 is preferably one of the following groups:

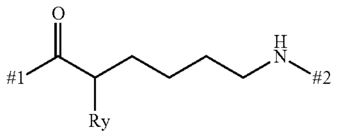

where Ry is —H, NHCOalkyl, —$NH_2$ or

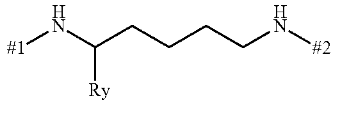

where Ry is —CONHalkyl, —$CONH_2$, where $\#^1$ represents the point of attachment to $L^1$, $\#^2$ represents the point of attachment to the glutamine residue of the binder.

Preferably, Ry is H or —NHCOMe.

Examples of corresponding conjugates have the following structures, where X1, X2, X3, Ry and L1 have the same meaning as above, AK represents a binder, preferably an antibody, where n is preferably 2 or 4:

Particularly Preferred KSP Inhibitor Conjugates

Particular preference is given in accordance with the invention to the KSP inhibitor conjugates which follow, where AK ($AK_1$; $AK_2$; $AK_3$) represent binders or a derivative thereof (preferably an antibody), and n is a number from 1 to 50, preferably 1.2 to 20 and more preferably 2 to 8. $AK_1$ is preferably an antibody bonded via a cysteine residue to the KSP inhibitor; $AK_2$; is preferably an antibody bonded via a lysine residue to the KSP inhibitor; $AK_3$ is preferably an antibody bonded via a glutamine residue to the KSP inhibitor. The binders or antibodies used here are preferably the binders and antibodies described as preferred in the description.

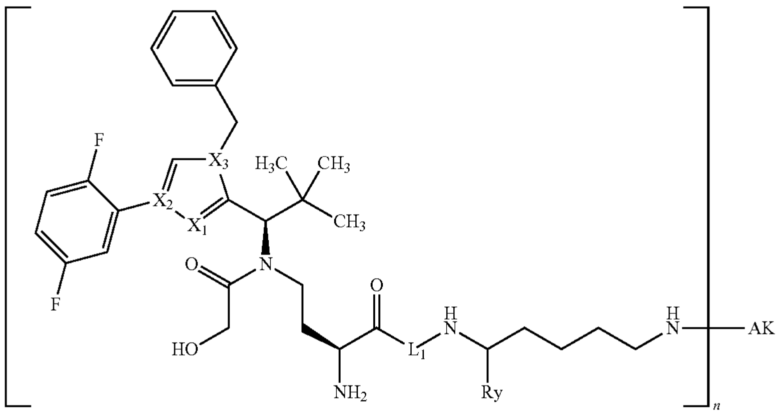

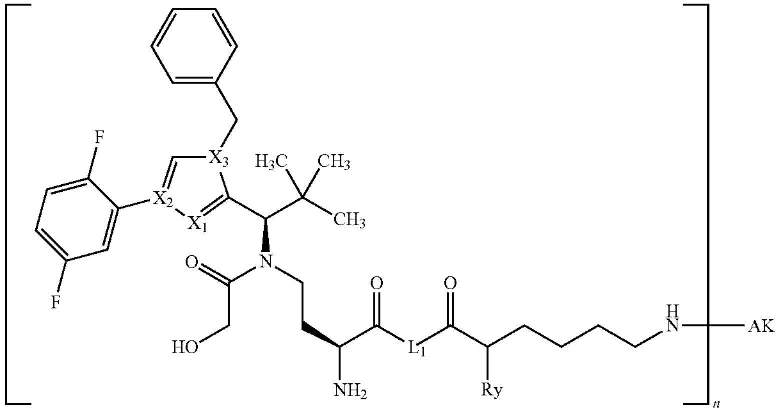

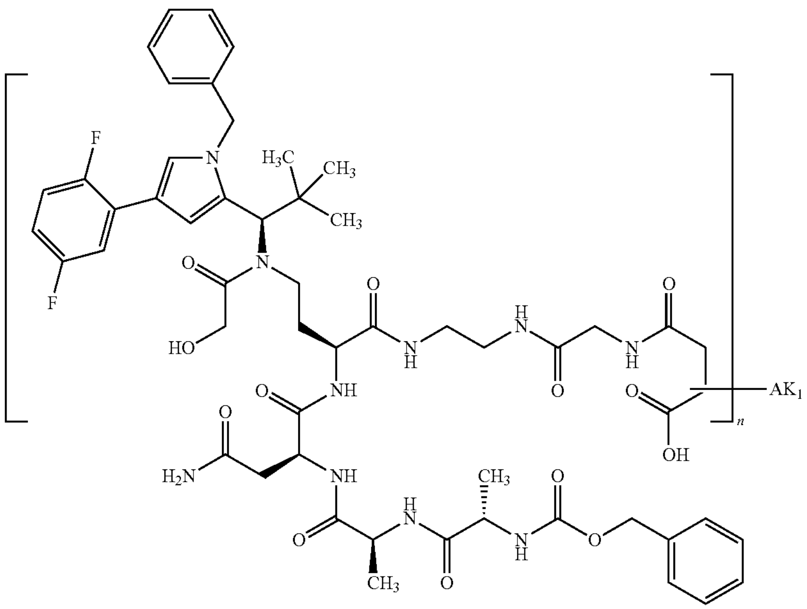
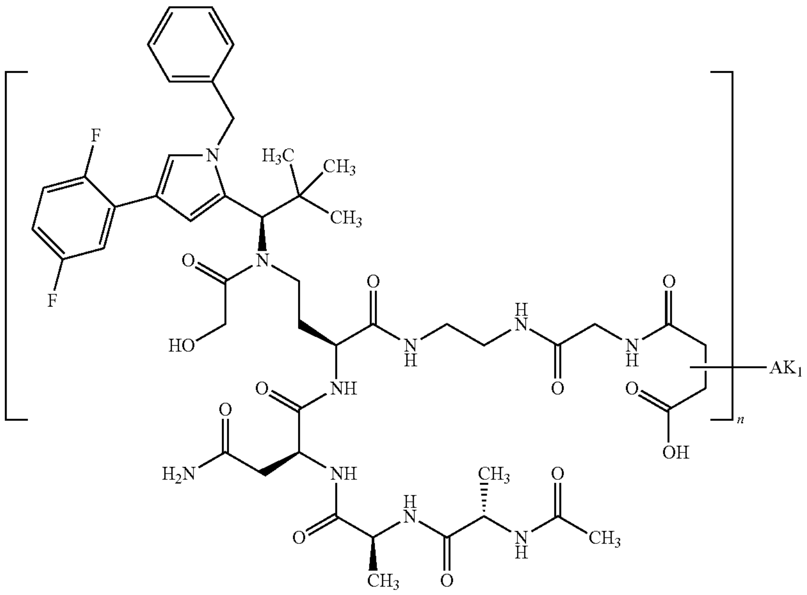

-continued
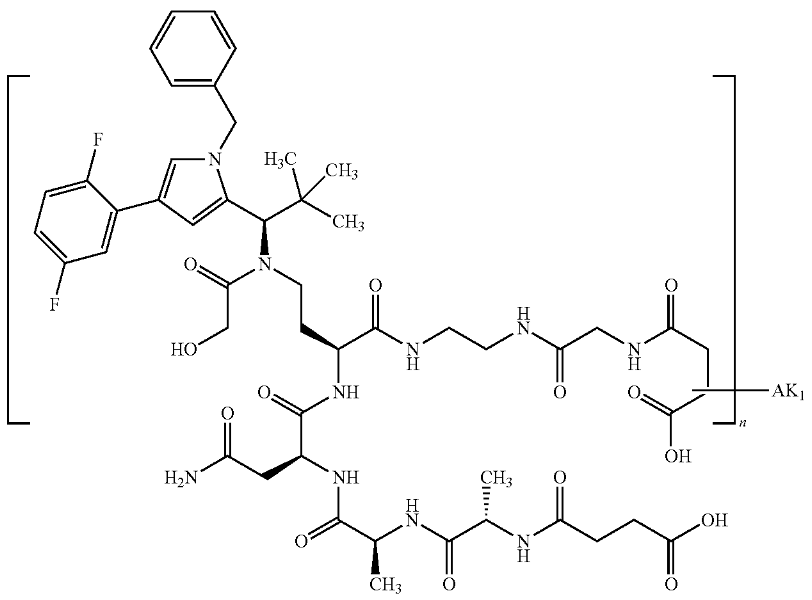
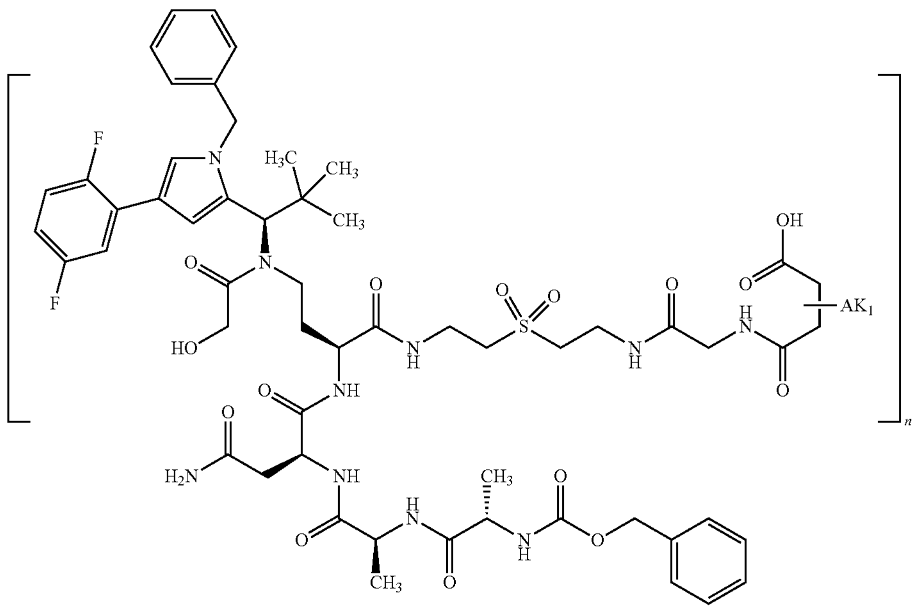

-continued
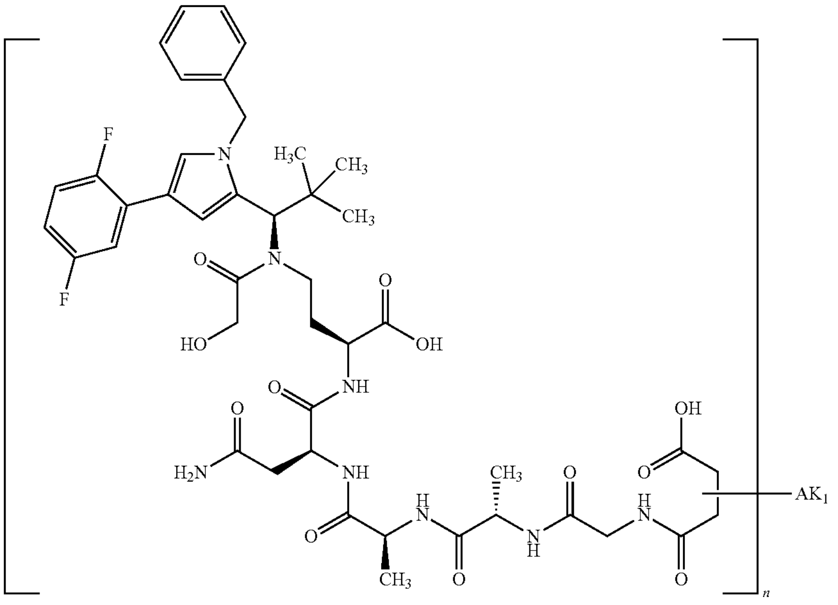
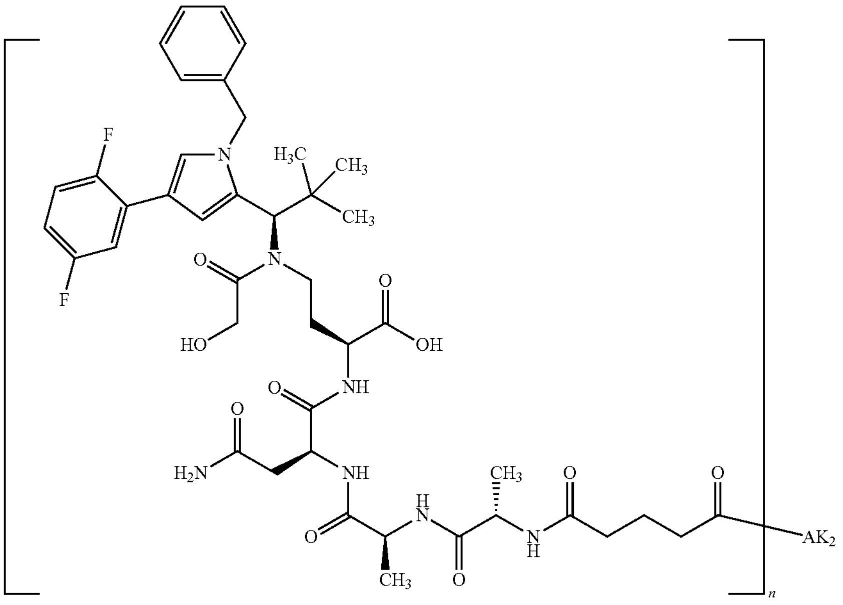

-continued
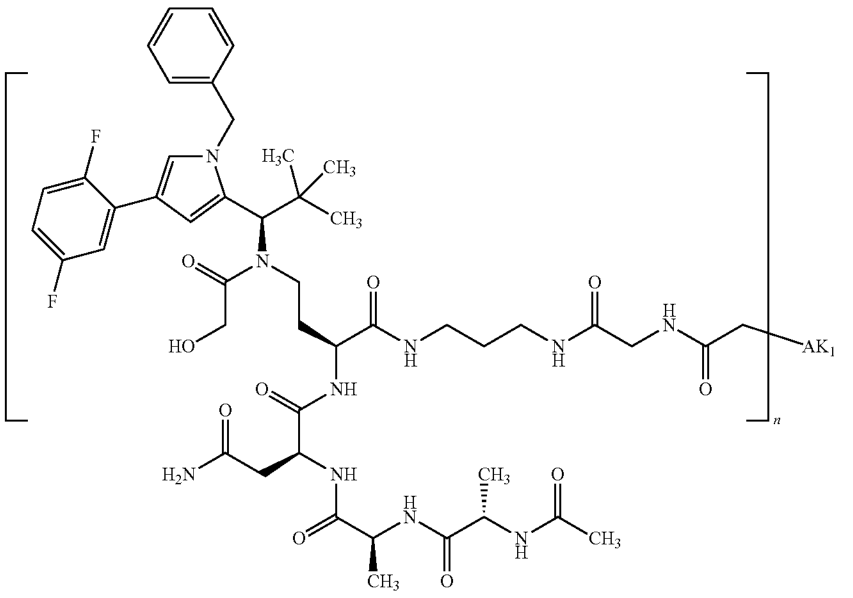
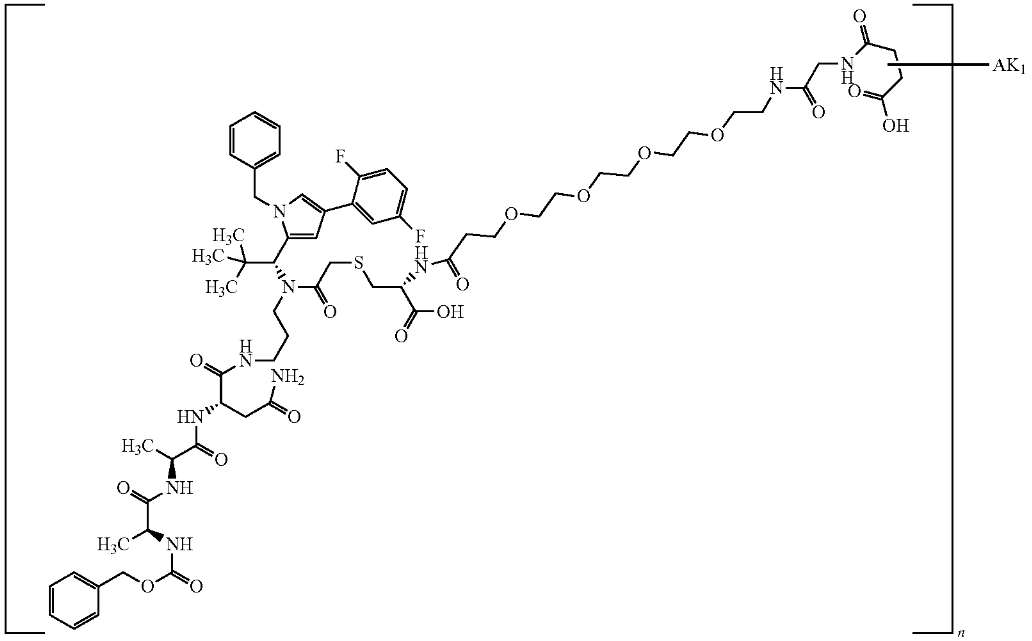

-continued
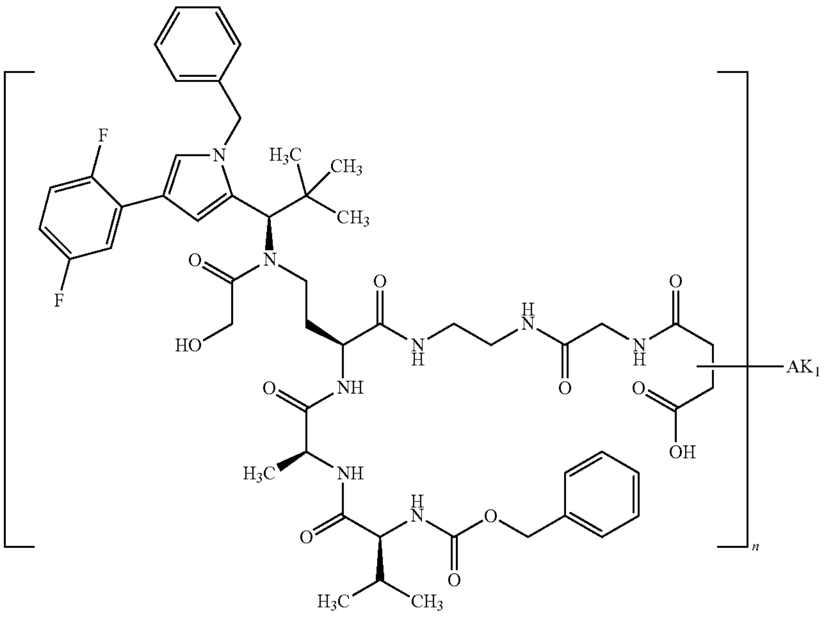
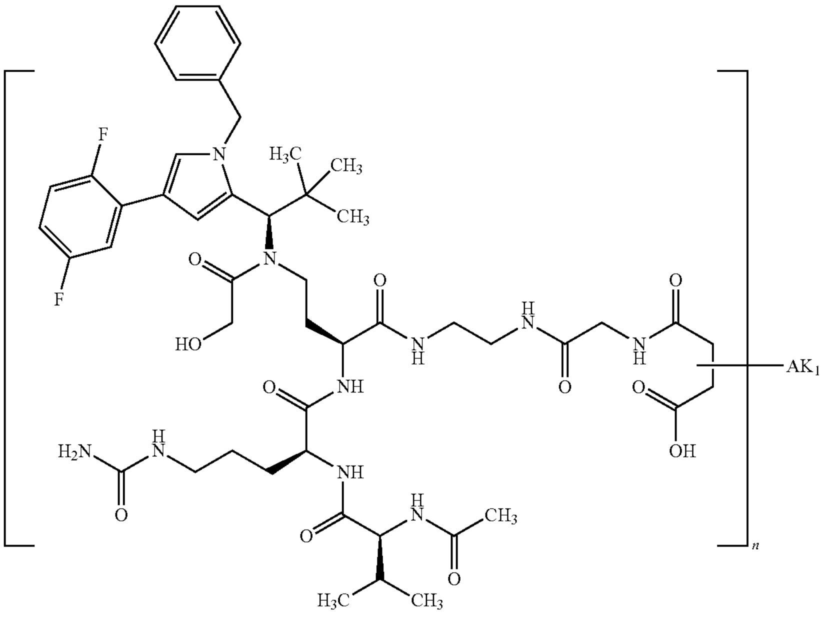

-continued
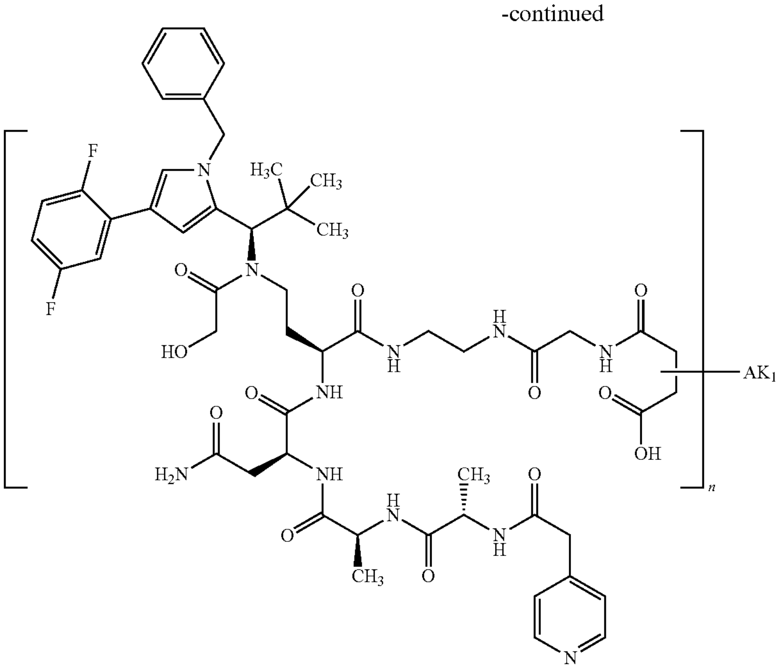
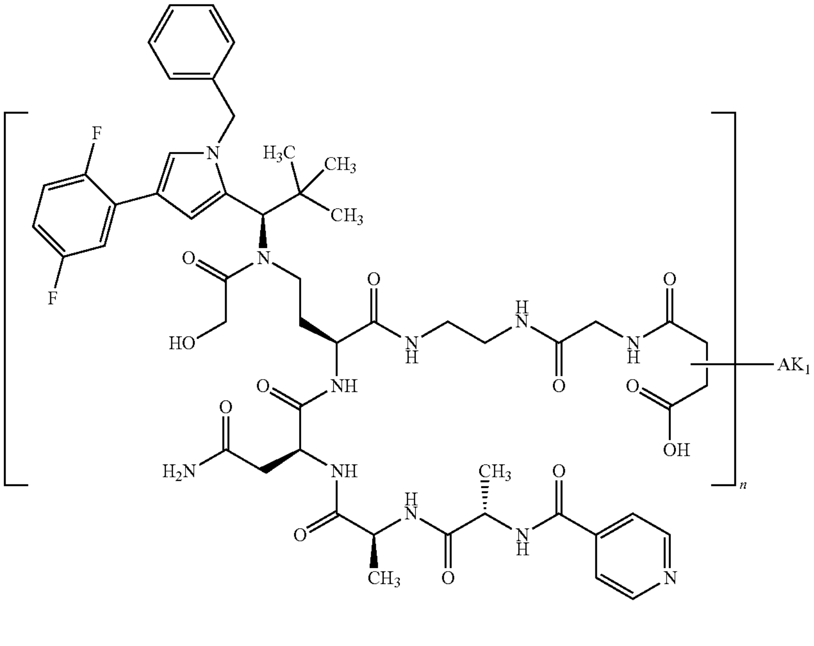

-continued
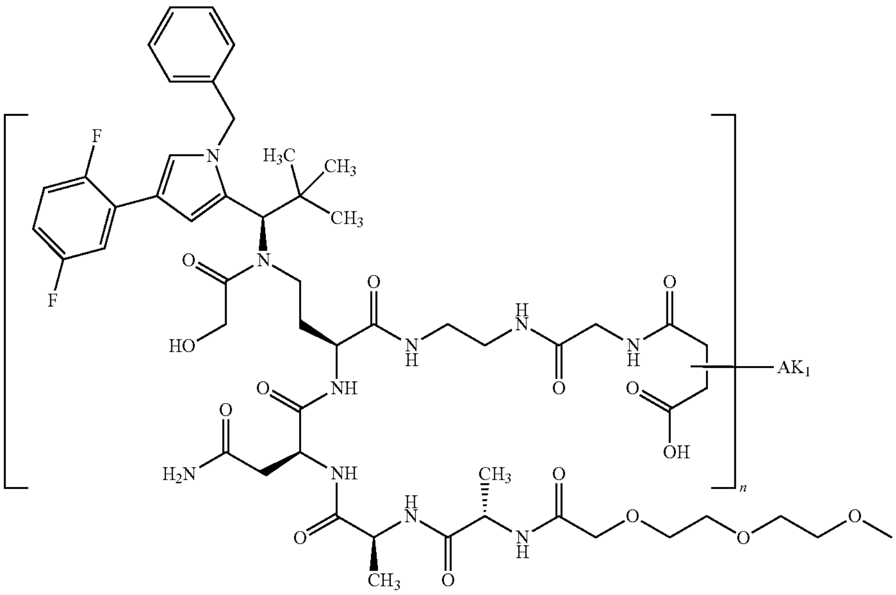
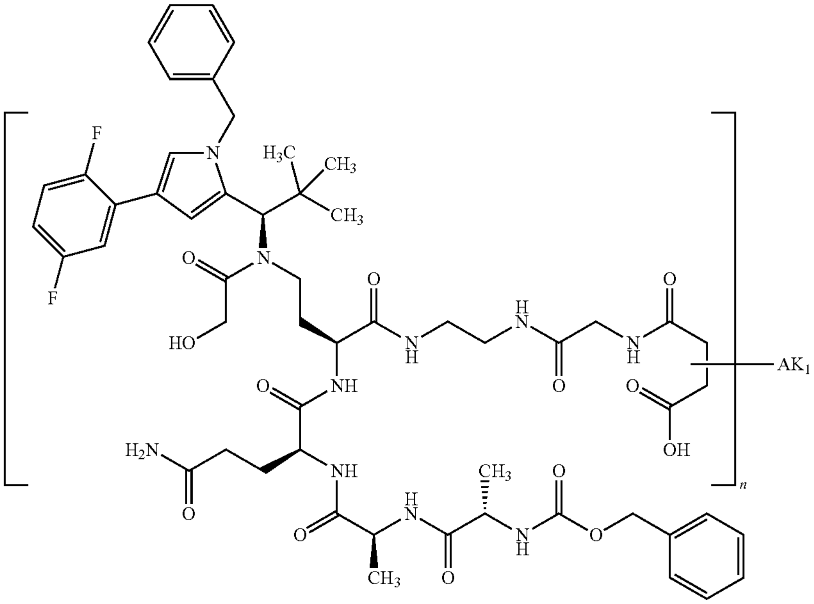

-continued
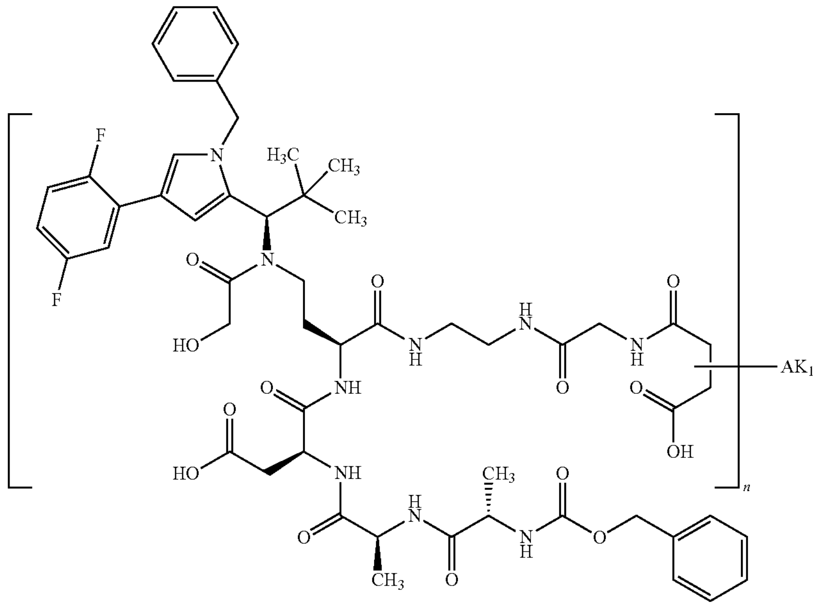
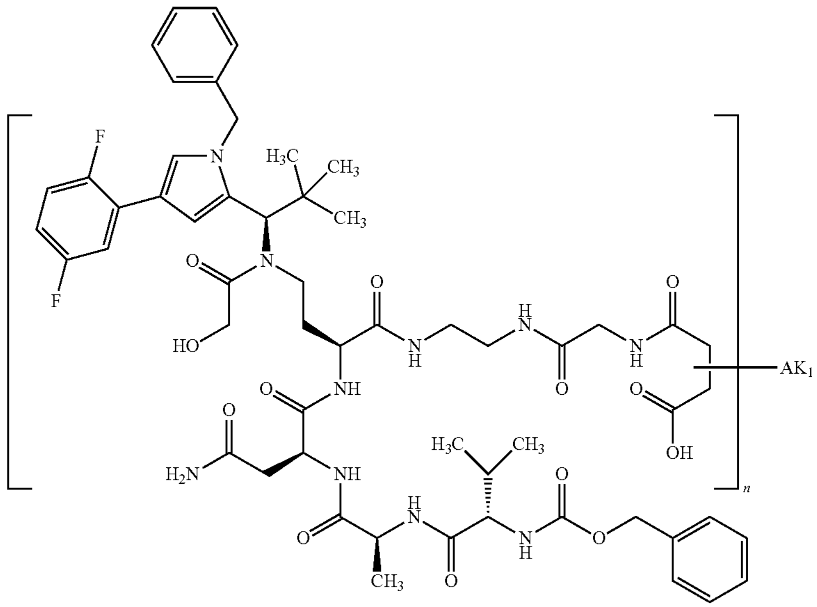

-continued
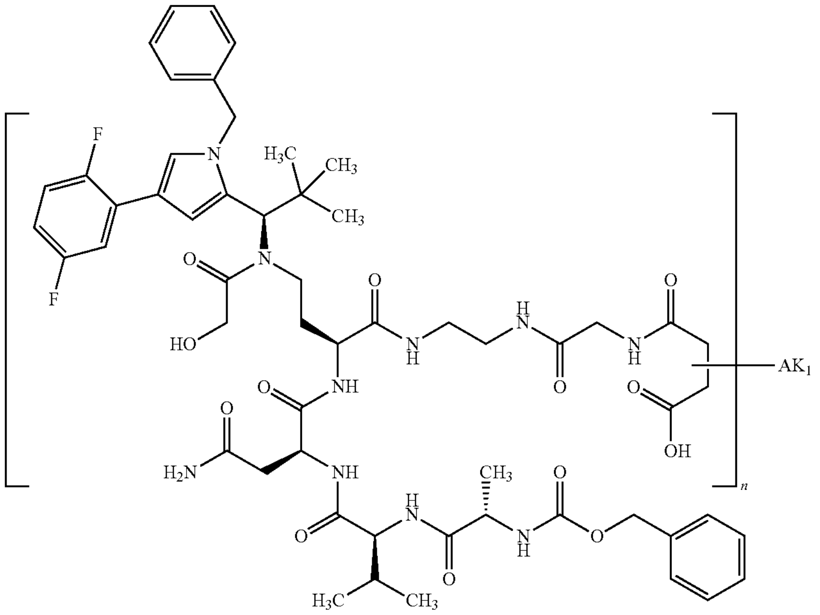
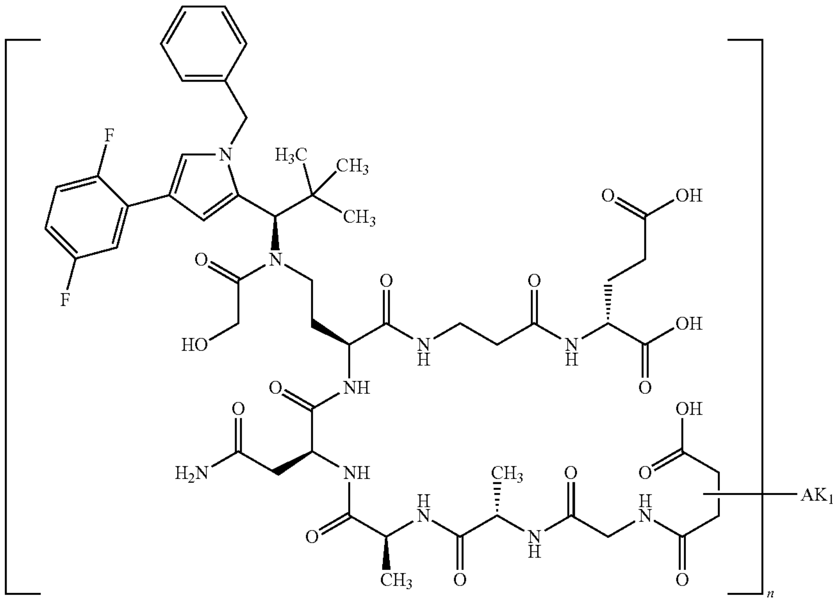

-continued
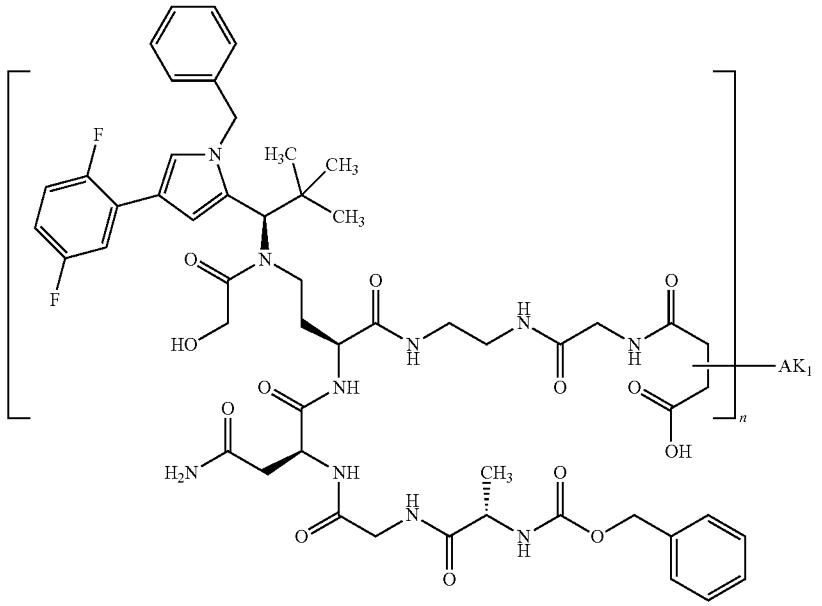
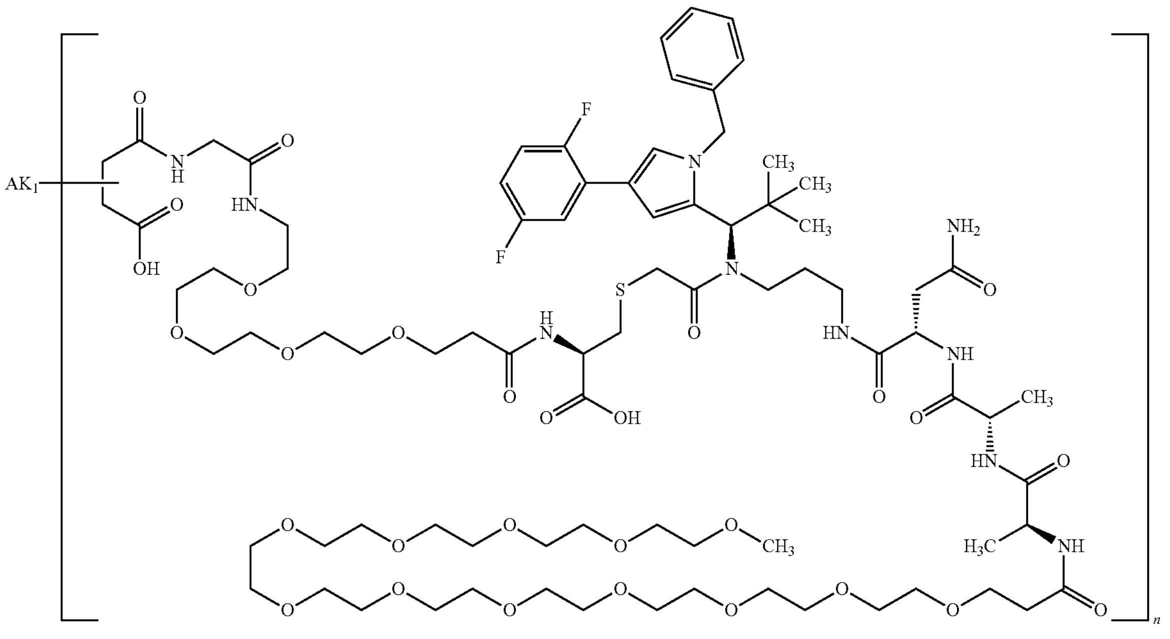

-continued
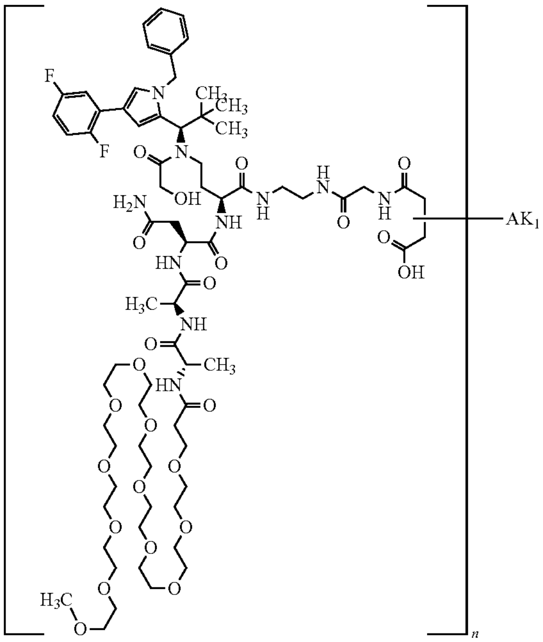
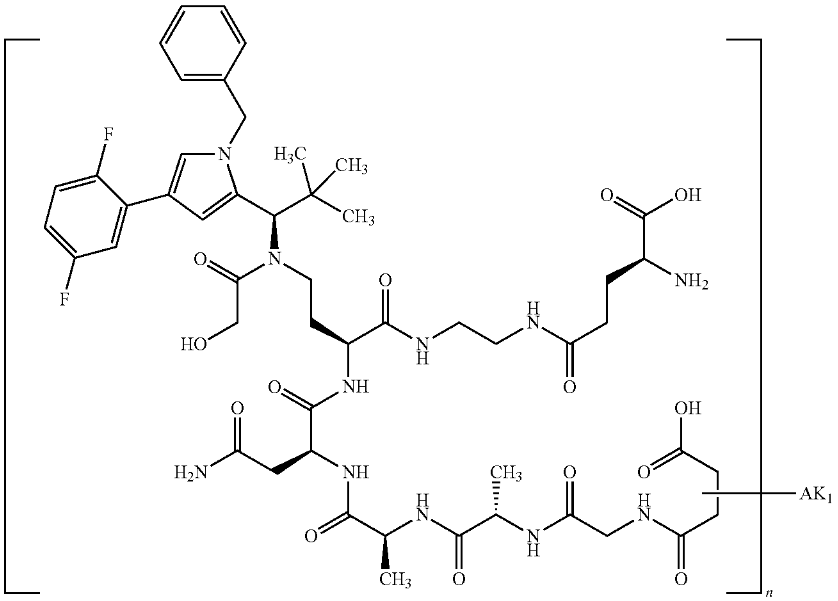

-continued
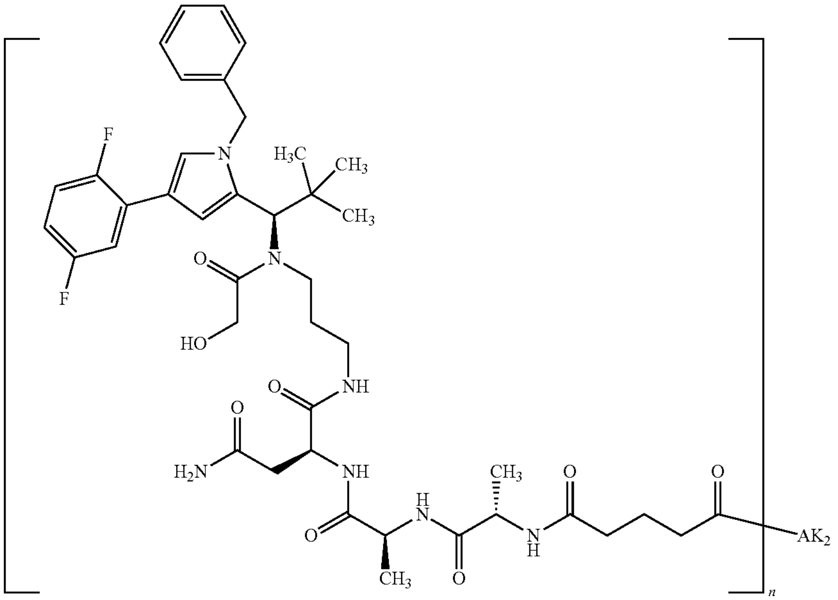
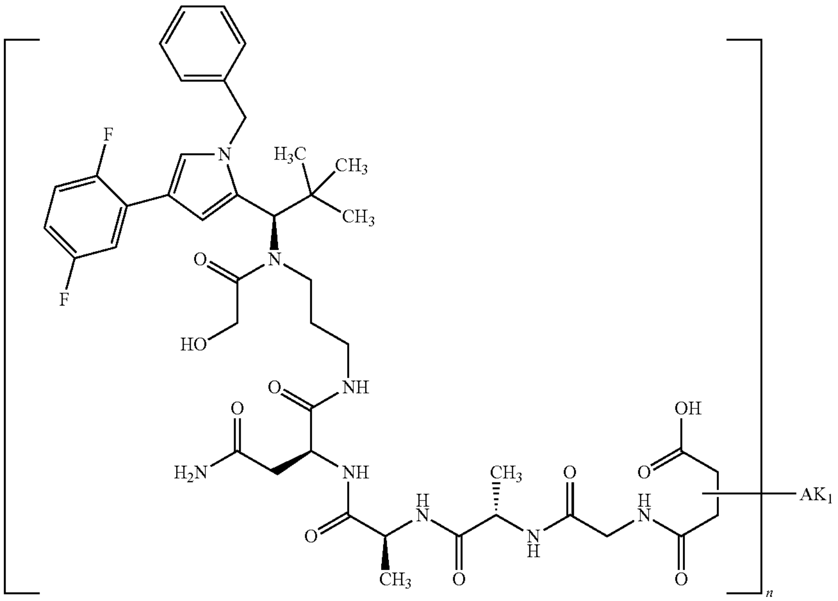

-continued
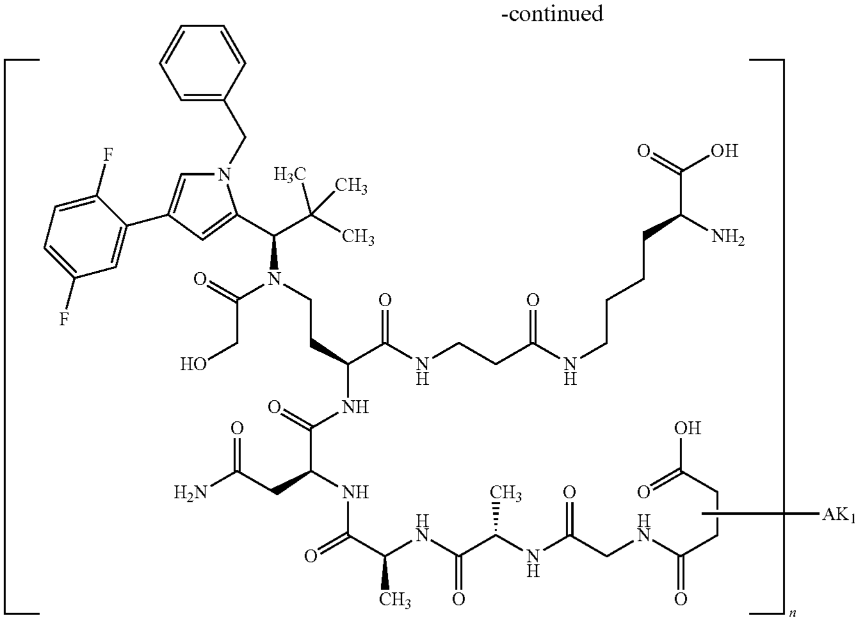
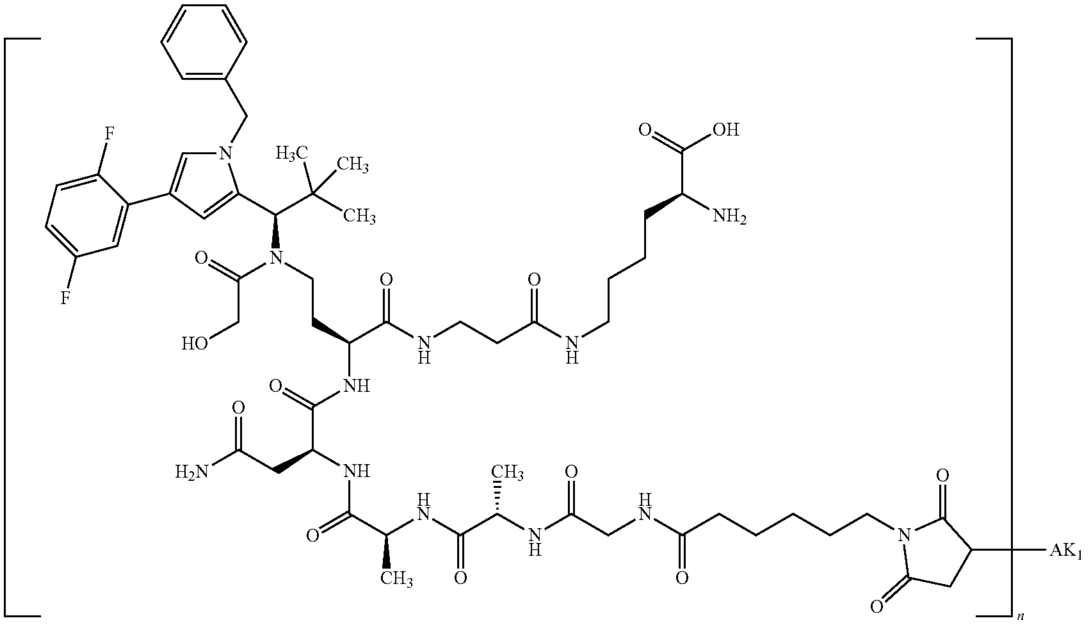

-continued
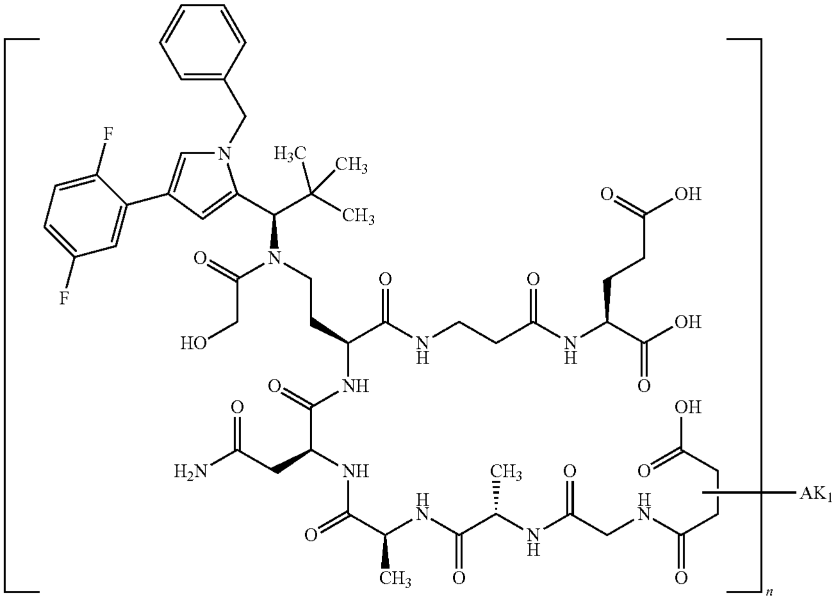
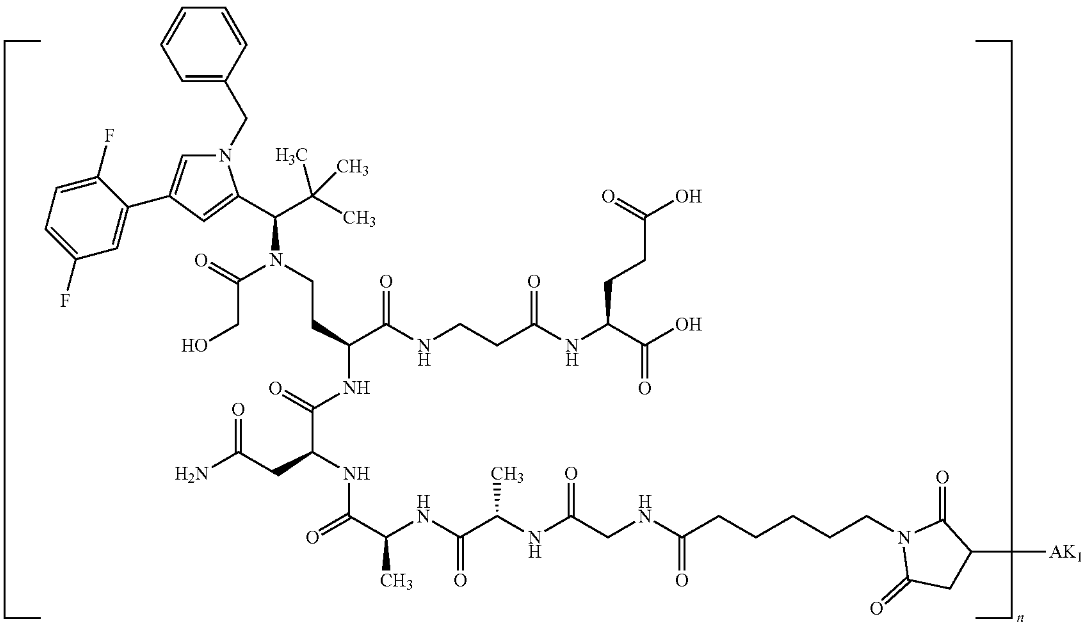

-continued
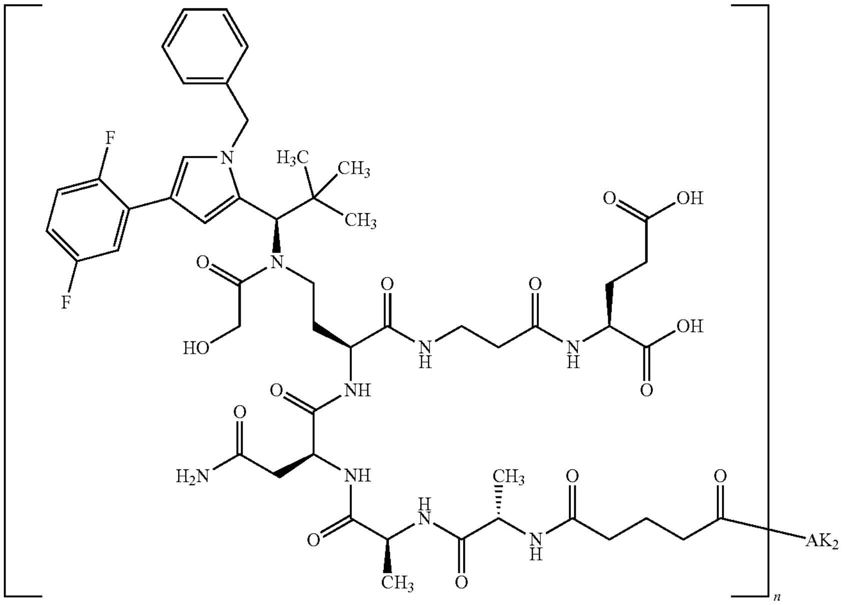
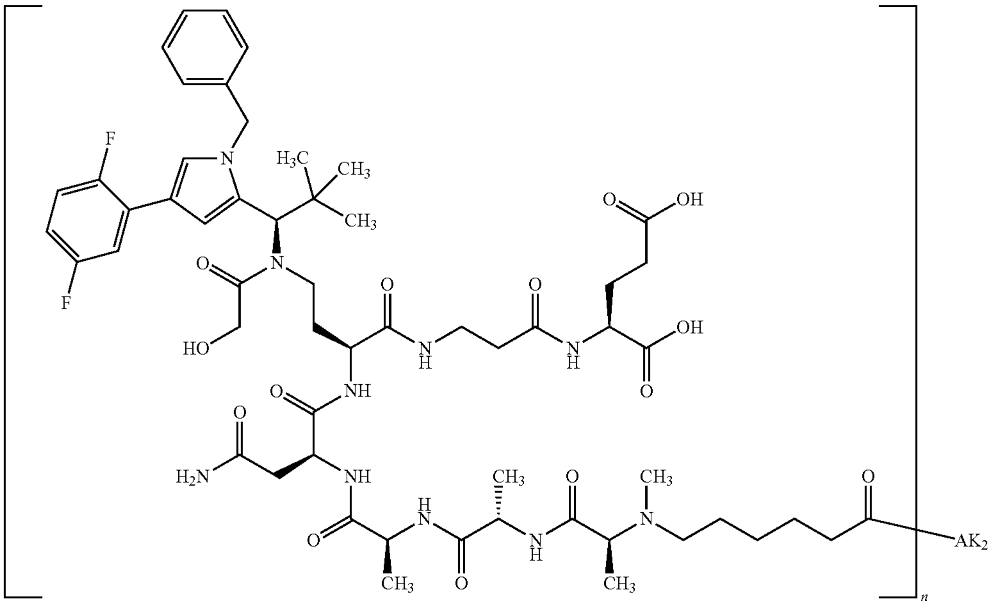

-continued
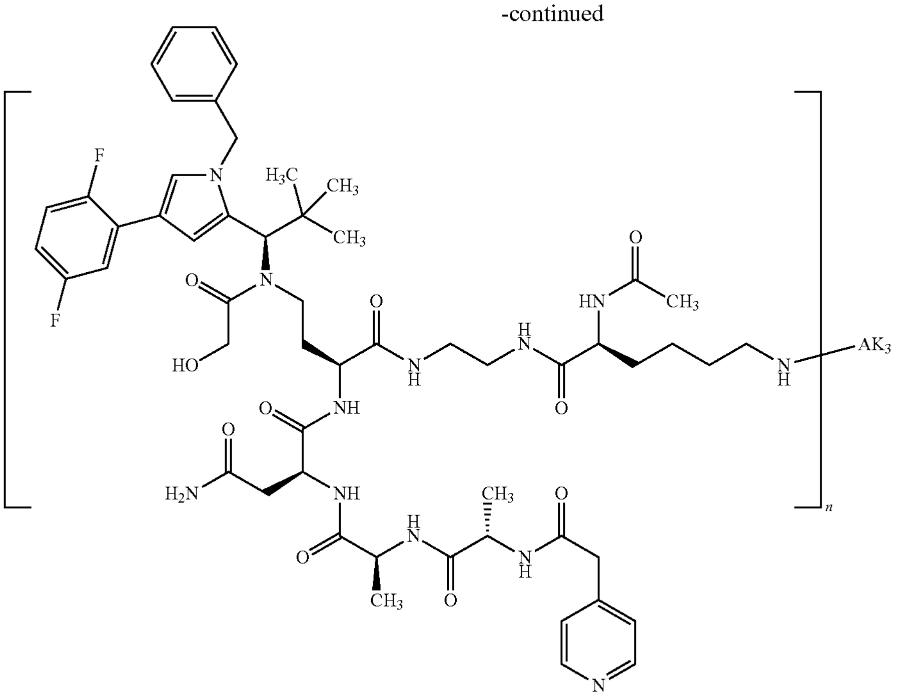
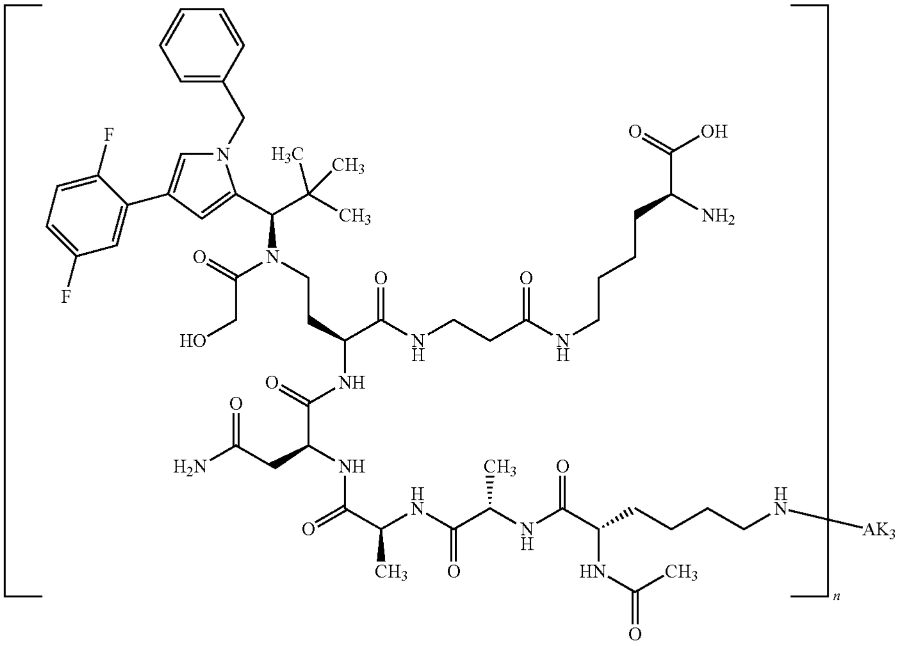

-continued
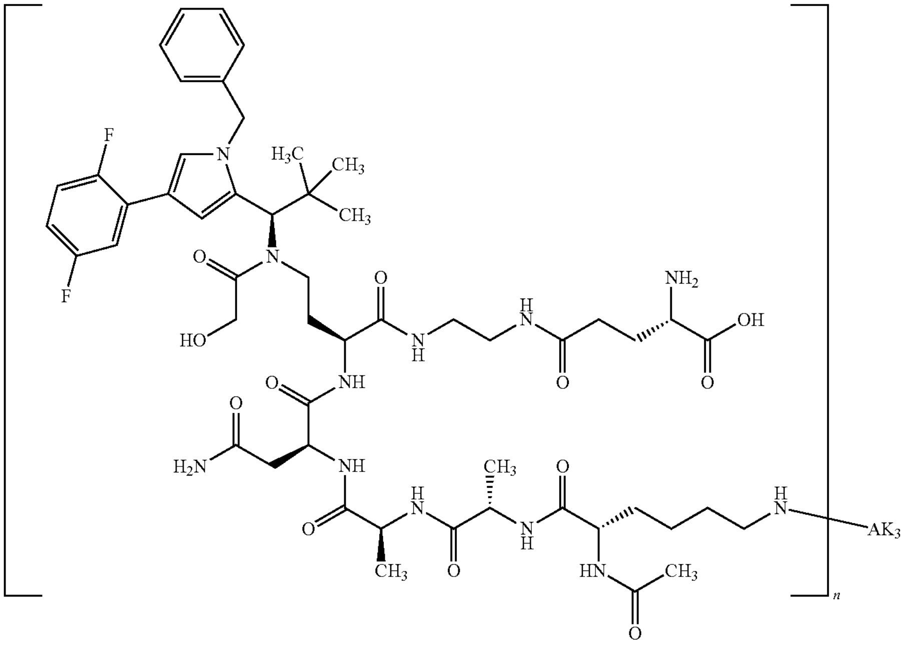
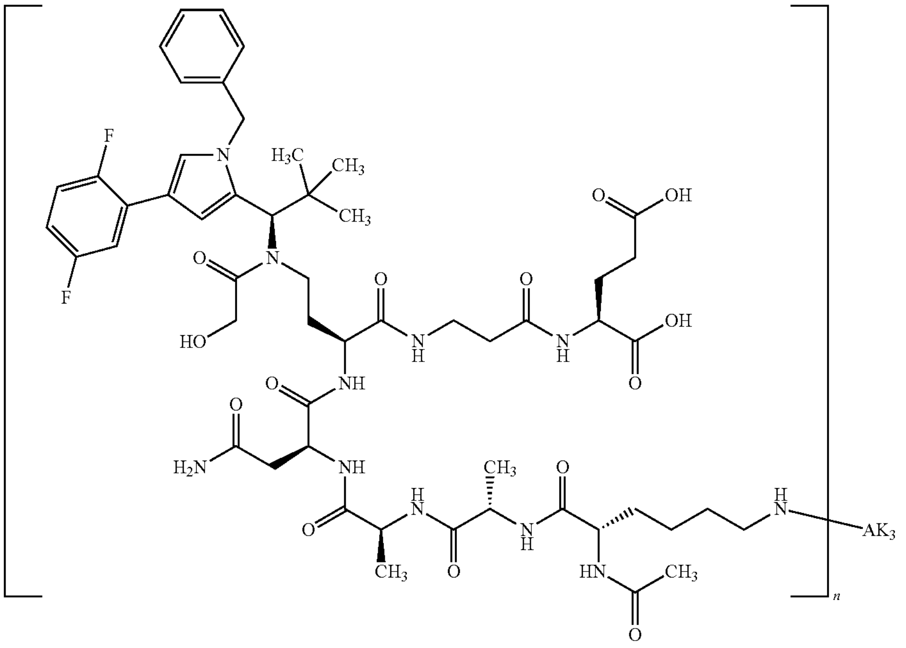

-continued
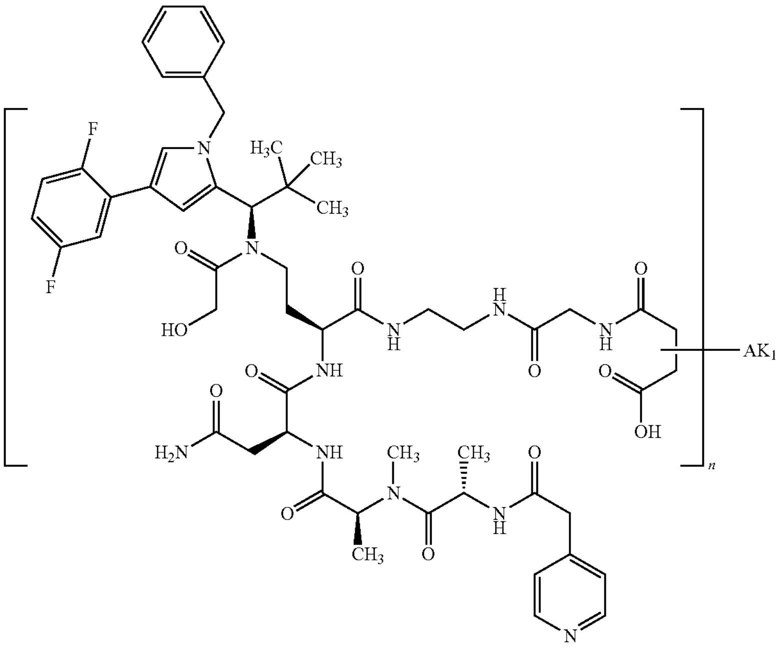
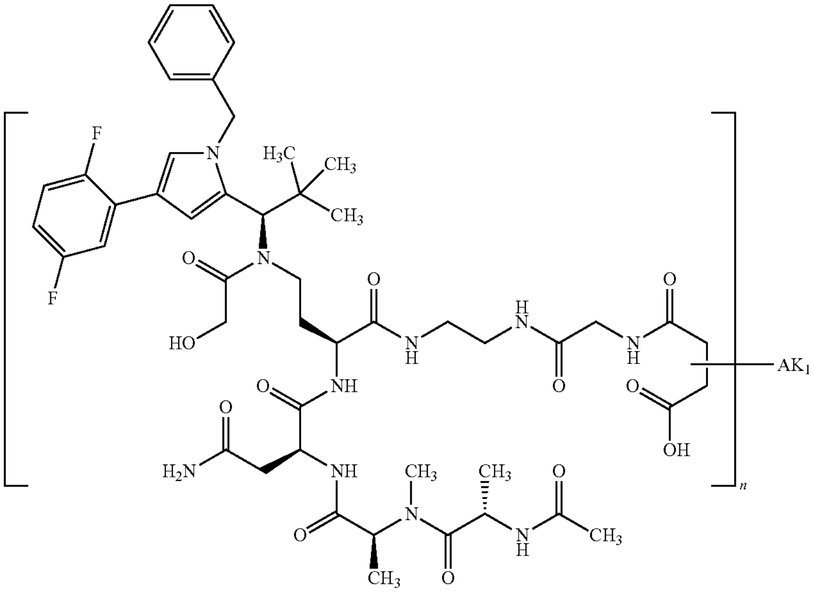

-continued
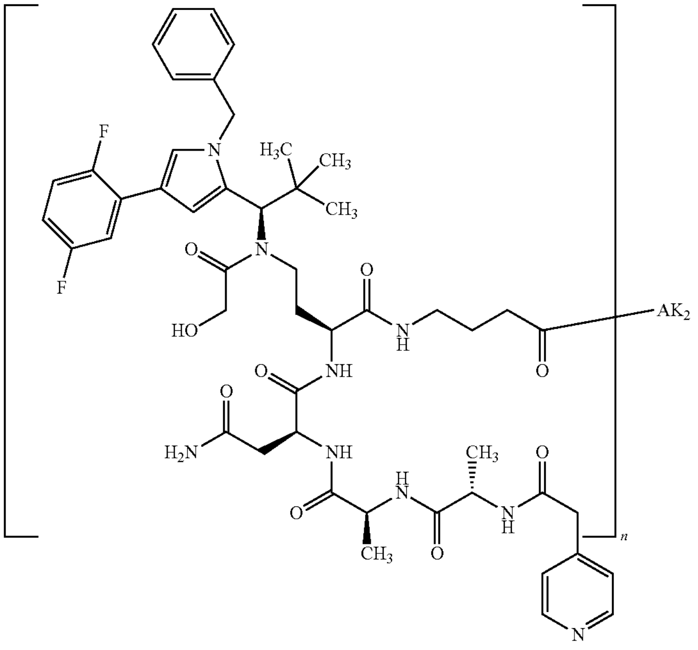
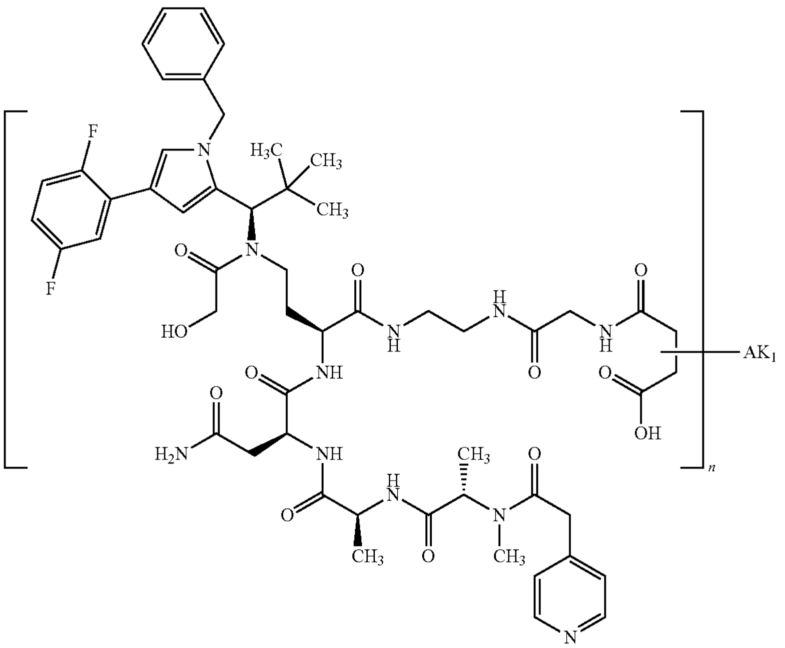

-continued
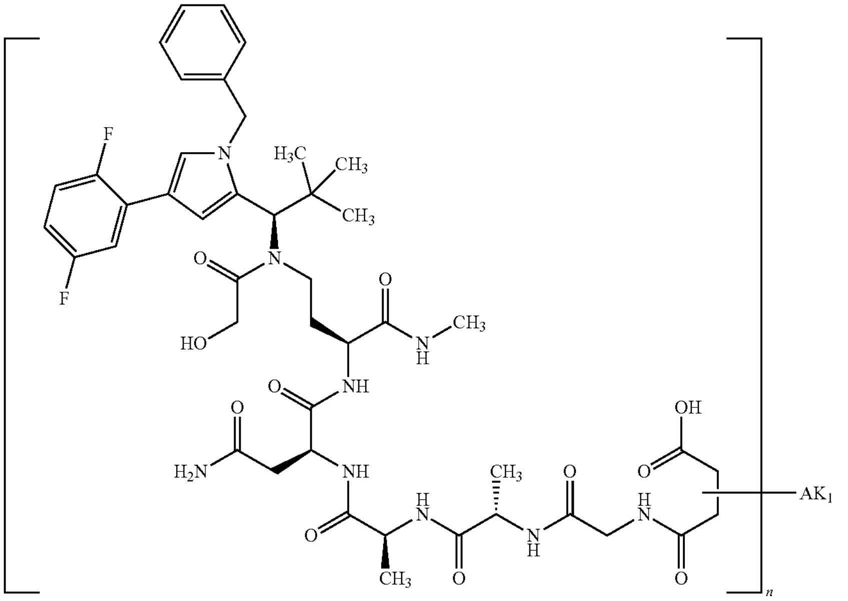
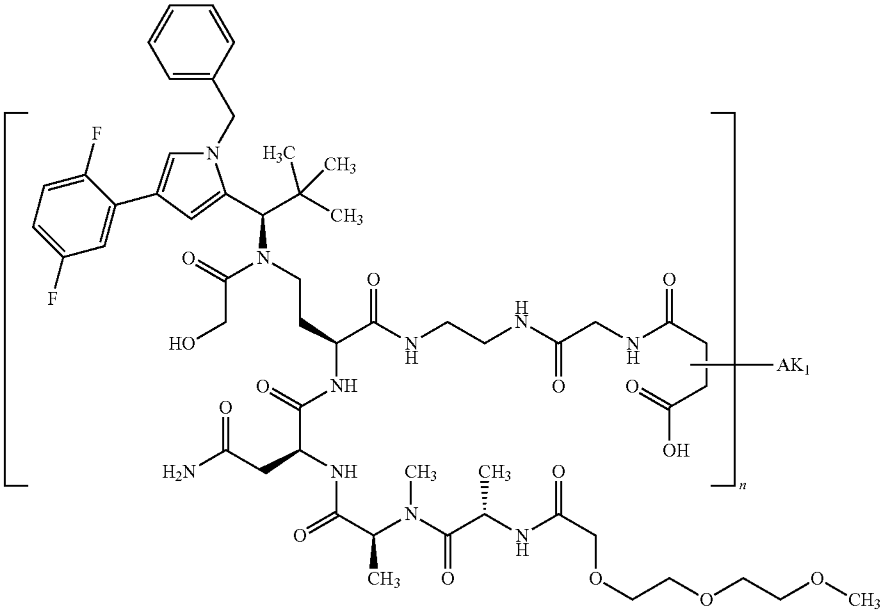

-continued
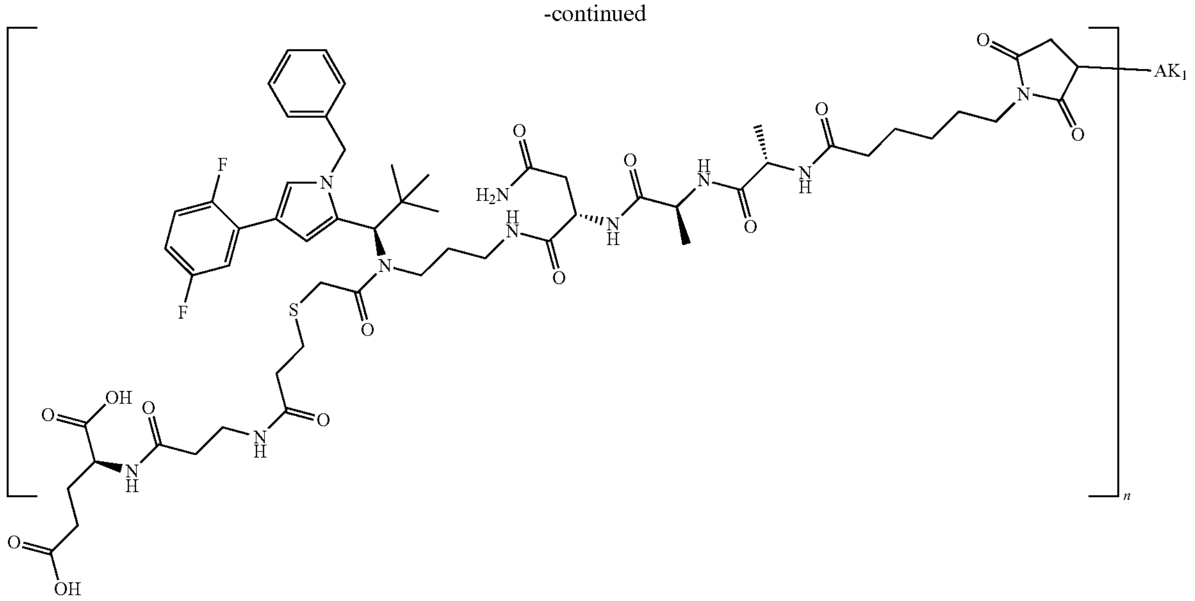
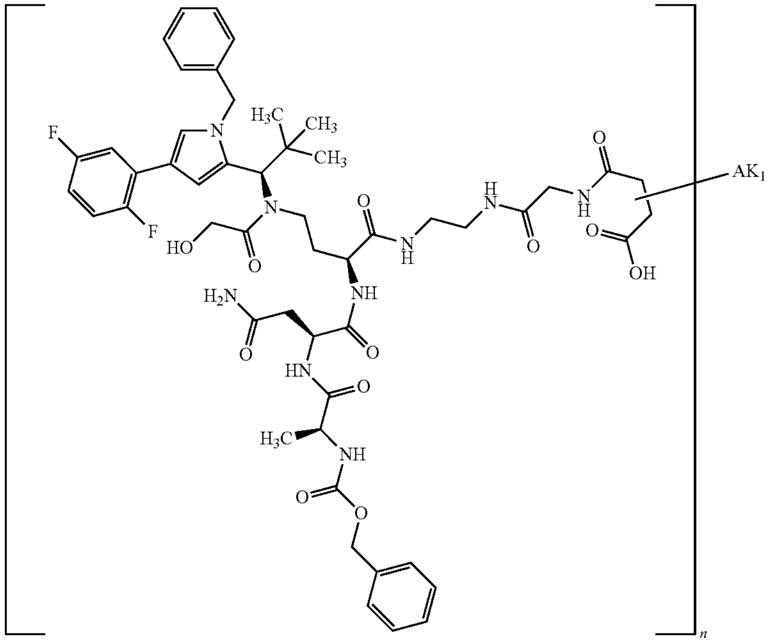

-continued

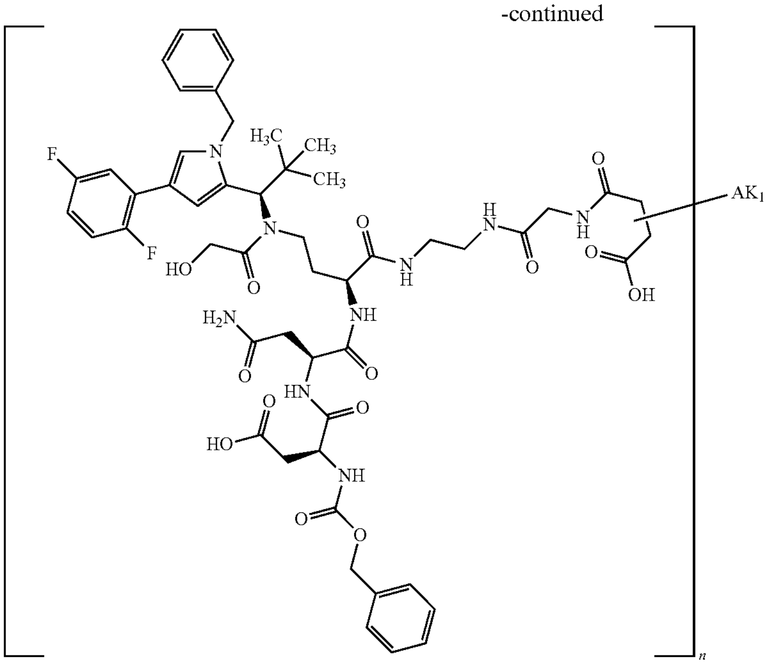

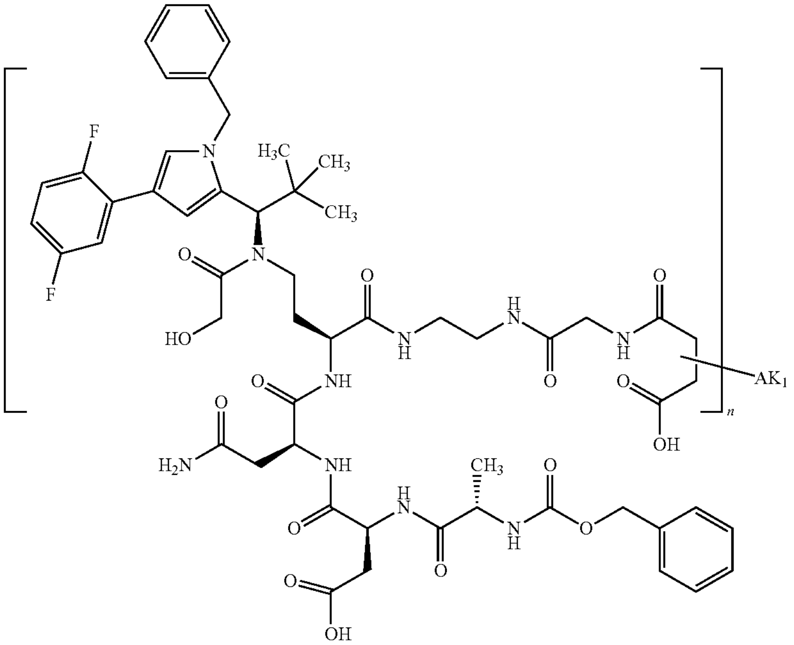

KSP Inhibitor-Linker Intermediates or Prodrug-Linker Intermediates and Preparation of the Conjugates The conjugates according to the invention are prepared by initially providing the low-molecular weight KSP inhibitor or prodrug thereof with a linker. The intermediate obtained in this manner is then reacted with the binder (preferably antibody).

Preferably, for coupling to a cysteine residue, one of the compounds below is reacted with the cysteine-containing binder such as an antibody, which is optionally partially reduced for this purpose:

-continued
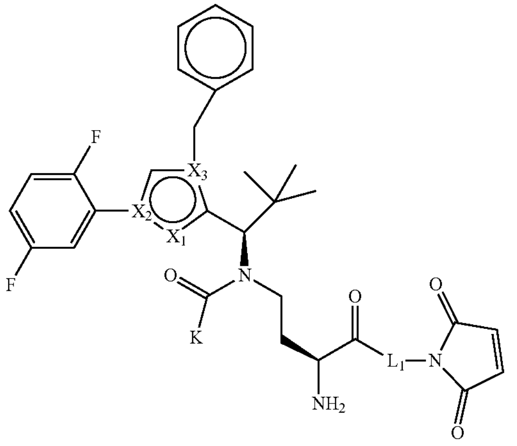
TFA
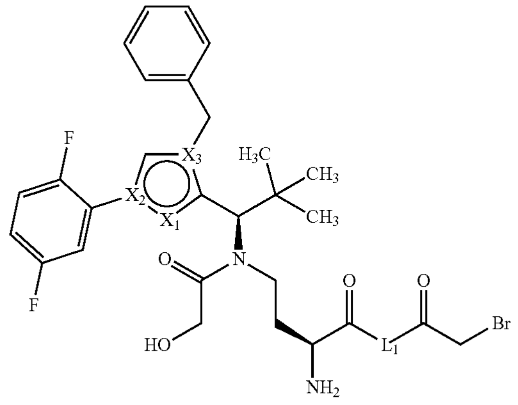
TFA
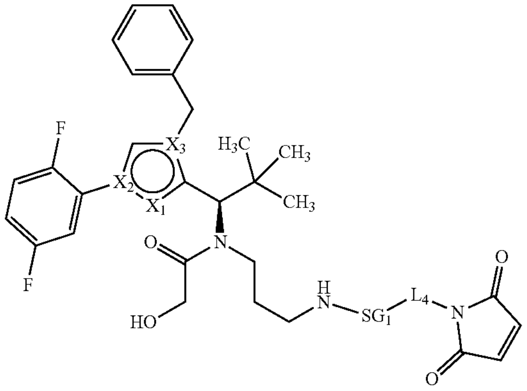
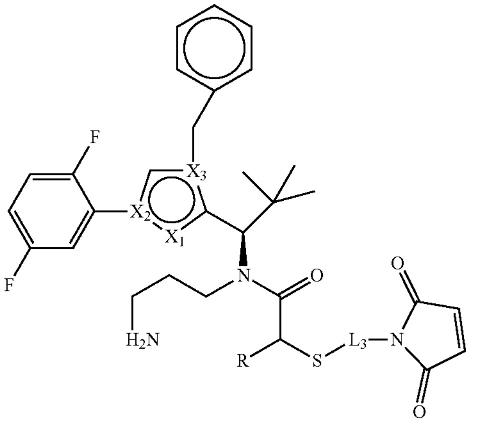
TFA
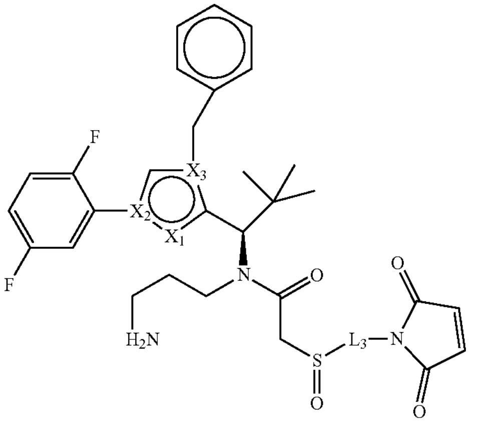
TFA
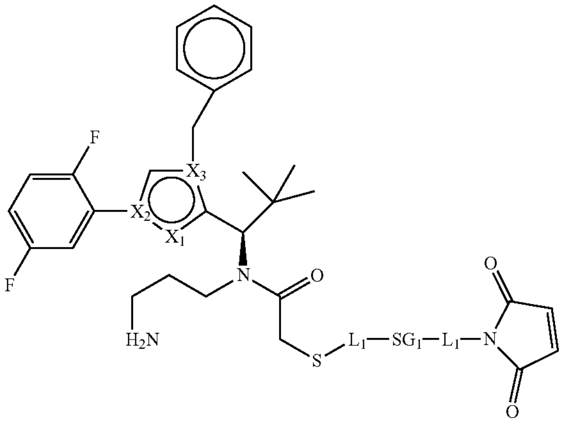
TFA -continued

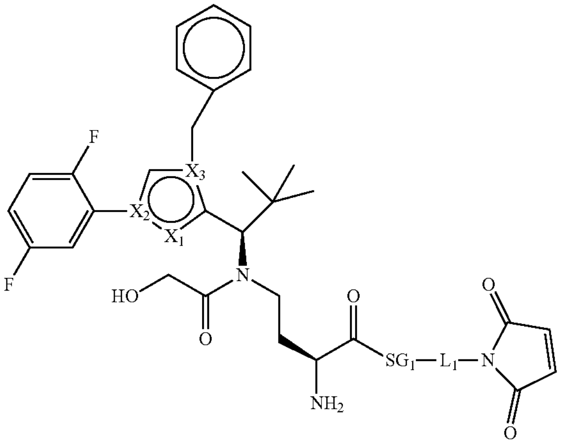

TFA

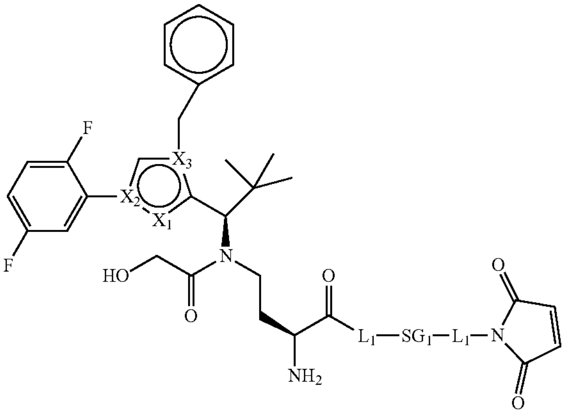

TFA

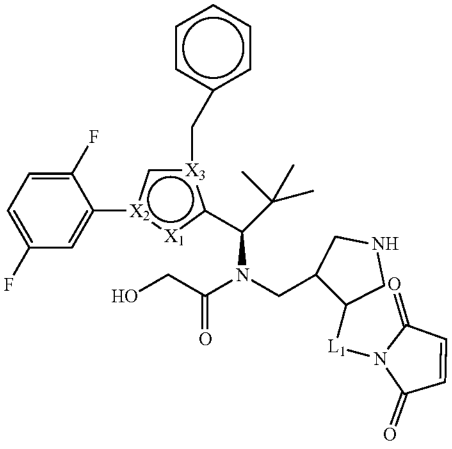

TFA

-continued

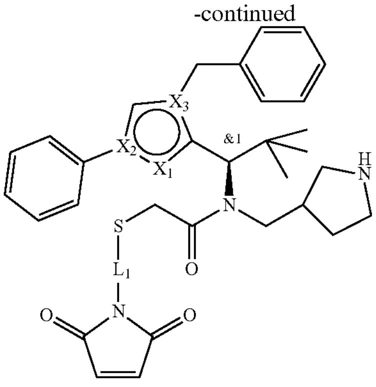

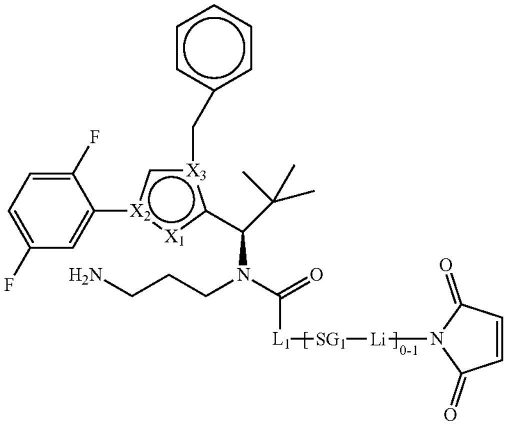

TFA where R represents —H or —COOH, where K represents straight-chain or branched $C_1$-$C_6$ alkyl which is optionally substituted by $C_1$-$C_6$-alkoxy or —OH, and where X1 represents CH, X2 represents C and X3 represents N, SG1, L1, L2, L3 and L4 have the same meaning as described above.

In the above-described formulae, as also in the reaction schemes and structural formulae which follow, the hydrogen atom in position $R^4$ of formula IIa (i.e. in the —$NH_2$ group) may be replaced by the group of the formula $R^{21}$—$(CO)_{(0-1)}$—$(P3)_{(0-2)}$—P2—NH—$CH(CH_2CONH_2)$—CO— or the cathepsin-cleavable group of the formula $R^{21}$—$(CO)_{(0-1)}$—$(P3)_{(1-2)}$—P2- where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline, and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where $R^{21}$ represents a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —$SO_3H$, —COOH, —SH or —OH.

In each of the above compounds and in the compounds below, the tert-butyl group may be replaced by cyclohexyl.

The compound may be employed, for example, in the form of its trifluoroacetic acid salt. For the reaction with the binder such as, for example, the antibody, the compound is preferably used in a 2- to 12-fold molar excess with respect to the binder.

Preferably, for coupling to a lysine residue, one of the compounds below is reacted with the lysine-containing binder such as an antibody:

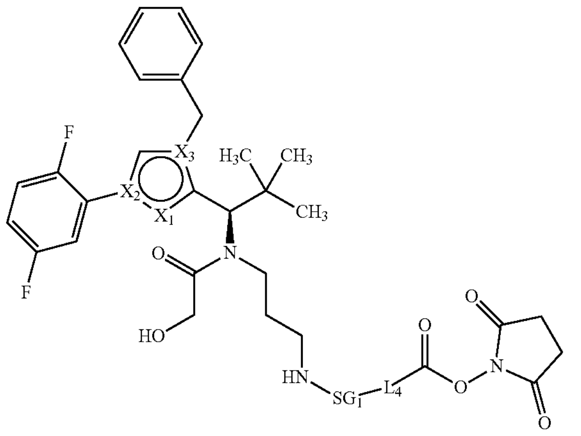

where X1 represents CH, X2 represents C and X3 represents N and L4 has the same meaning as L1 and L1 has the same meaning as described above.

For an intermediate coupling to a cysteine residue, the reactions can be illustrated as follows:

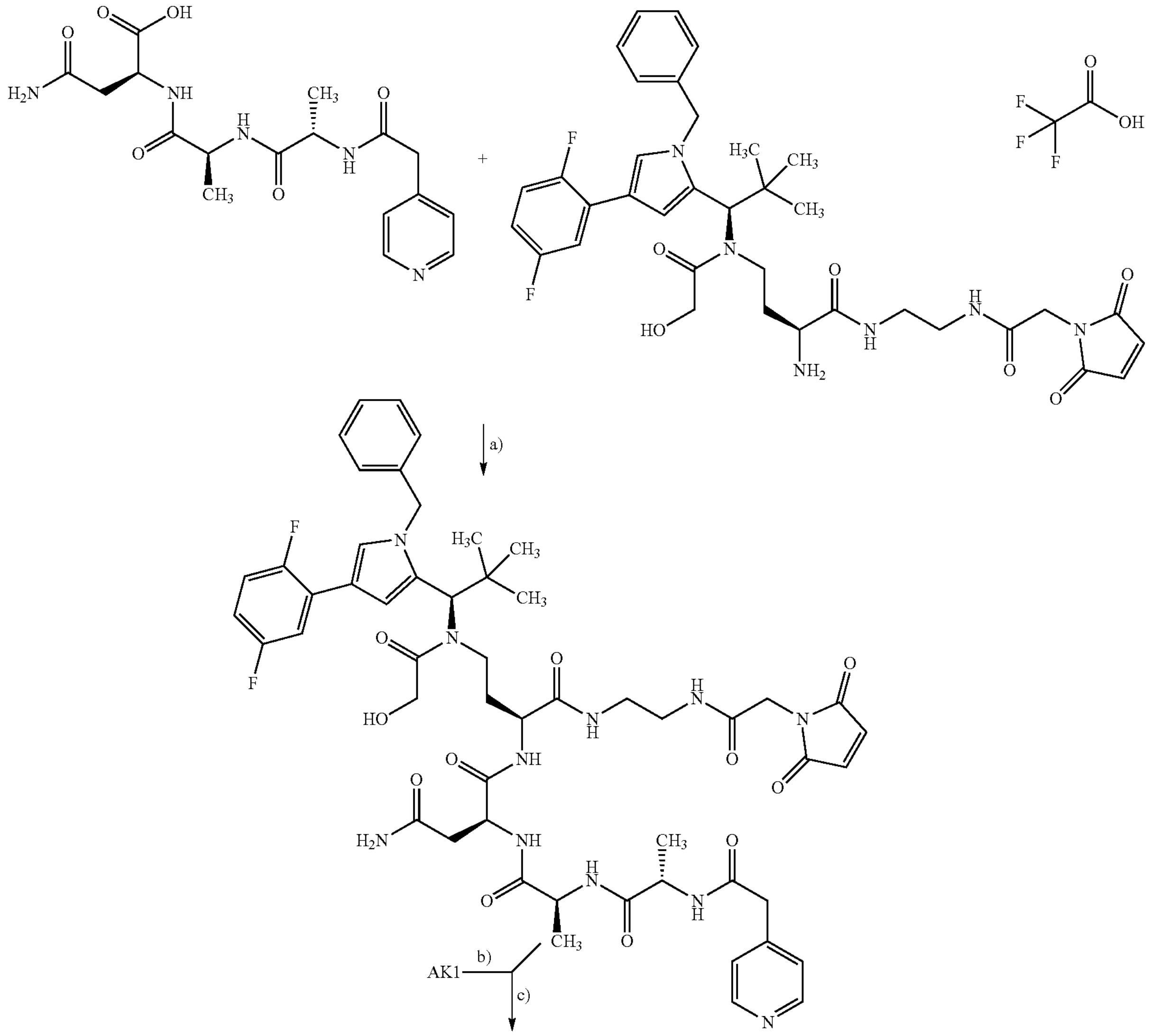

-continued
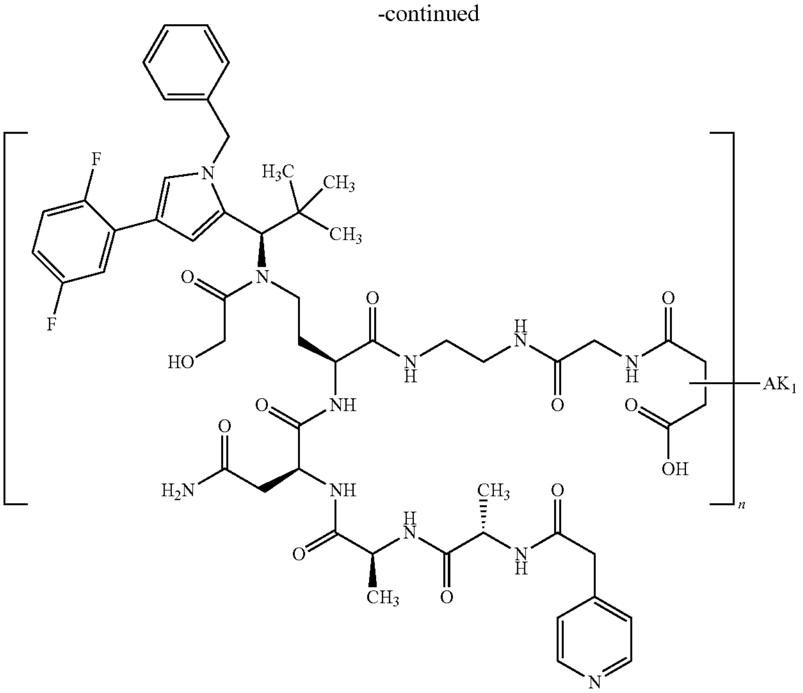
The other intermediates and other antibodies can be reacted correspondingly.
For an intermediate coupling to a lysine residue, the reaction can be illustrated as follows:
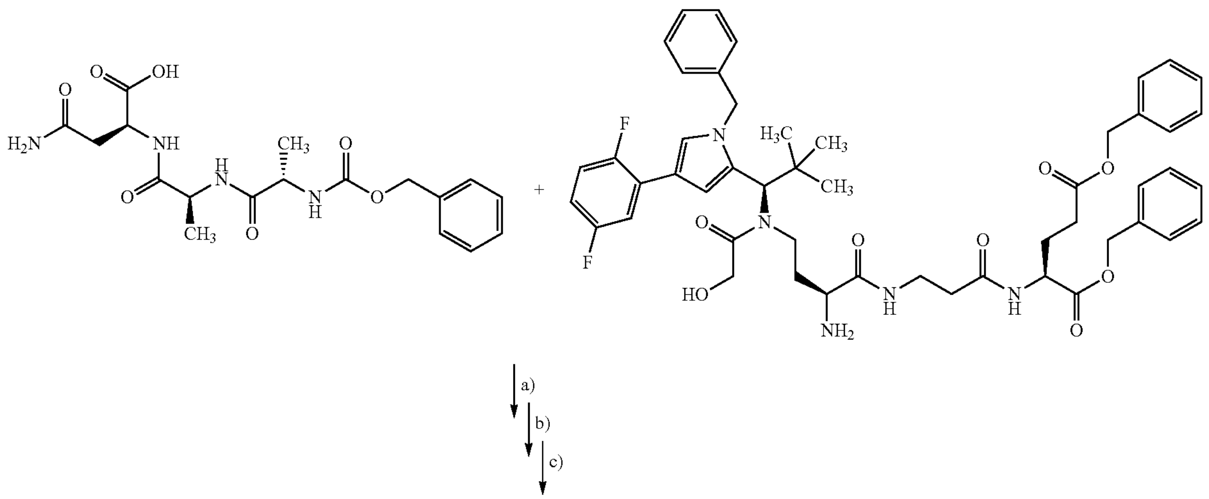

-continued
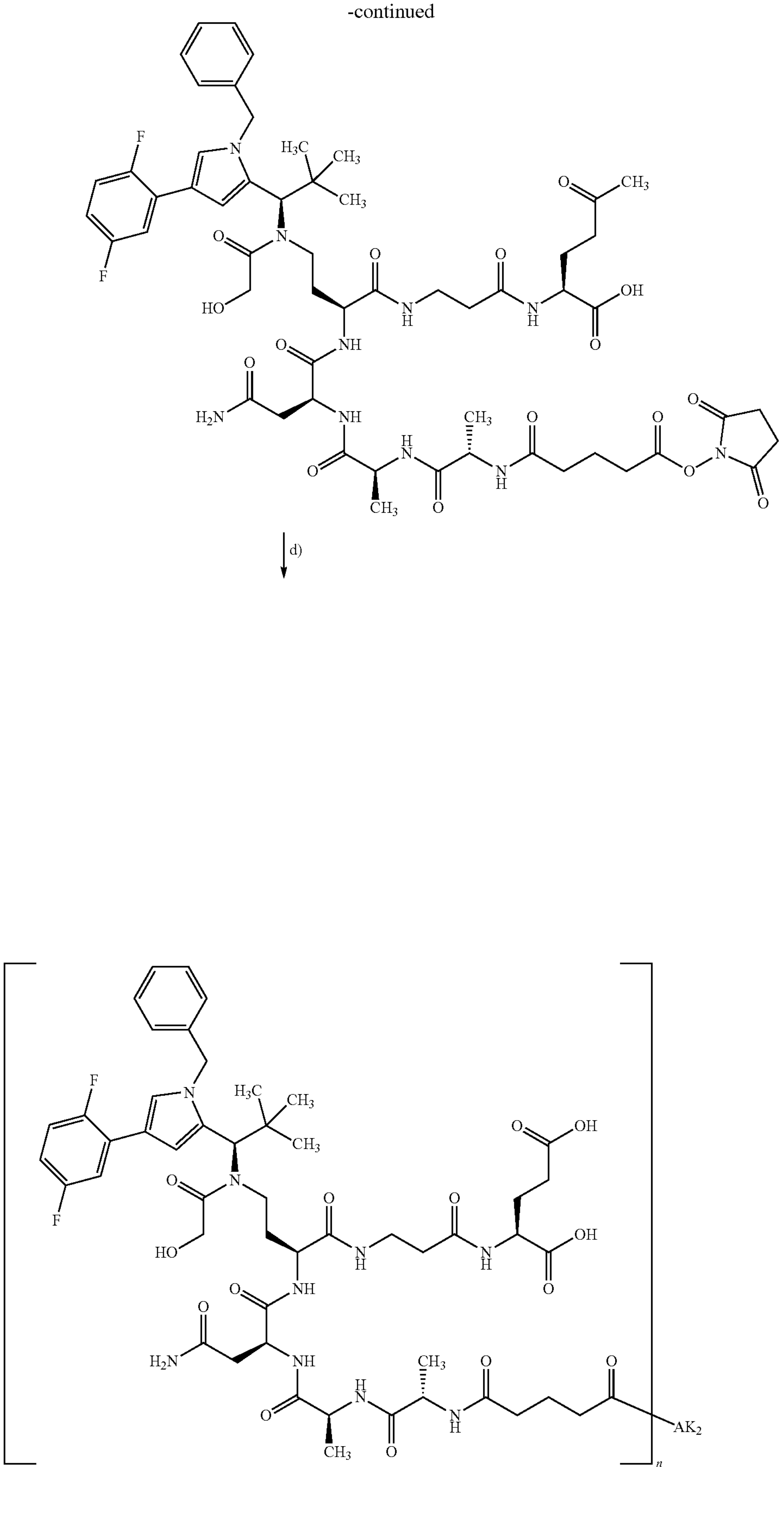

Depending on the linker, succinimide-linked ADCs may, after conjugation, be converted into the open-chain succinamides, which have an advantageous stability profile.

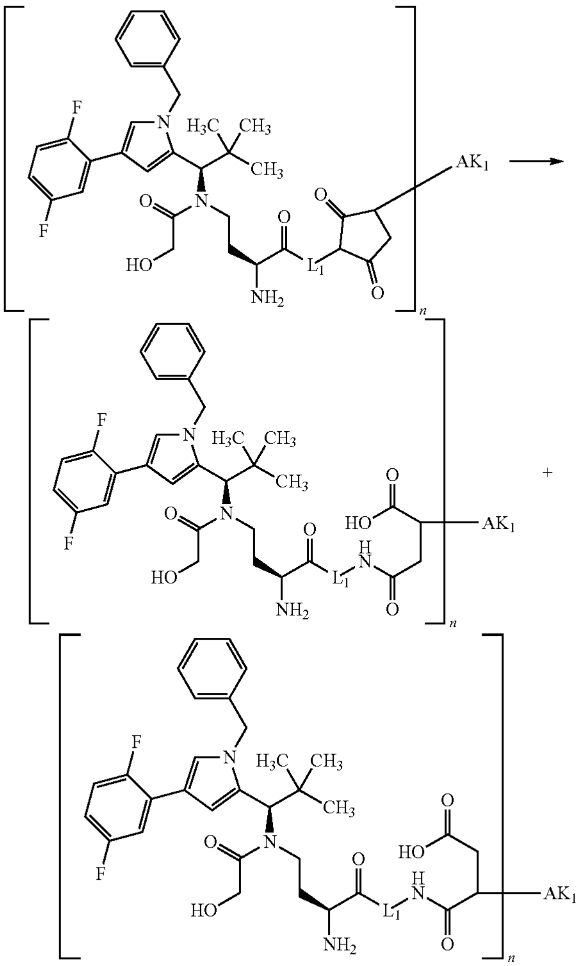

This reaction (ring opening) can be carried out at pH 7.5 to 9, preferably at pH 8, at a temperature of from 25° C. to 37° C., for example by stirring. The preferred stirring time is 8 to 30 hours.

In the above formulae, X1 represents CH, X2 represents C and X3 represents N, SG1 and L1 have the same meaning as described above and L2, L3 and L4 have the same meaning as L1; and R and K have the same meaning as described above. AK1 is an aglycosylated anti-TWEAKR antibody coupled via a cysteine residue, and AK2 is an aglycosylated anti-TWEAKR antibody coupled via a lysine residue. More preferably, AK1 and AK2 are an aglycosylated anti-TWEAKR antibody which binds specifically to amino acid D in position 47 (D47) of TWEAKR (SEQ ID NO:169), in particular the aglycosylated anti-TWEAKR antibody TPP-2658.

Further Definitions

The expression "transglutaminase", also used interchangeably as "TGase" or "TG", is understood to mean an enzyme having the ability to join proteins via an acyl transfer reaction between the γ-carboxamide group of peptide-bound glutamine and the ε-amino group of lysine or a structurally related primary amine, for example an aminopentyl group or, for example, a peptide-bound lysine, which results in an 8-(γ-glutamyl)-lysine isopeptide bond. TGases include bacterial transglutaminase (BTG), for example the enzyme having EC reference number 2.3.2.13 (protein-glutamine γ-glutamyltransferase).

The expression "acceptor glutamine" means, when referring to an amino acid residue of an antibody, a glutamine residue which, under suitable conditions, is recognized by a transglutaminase and can be joined therewith under transglutaminase catalysis by a reaction between this specific glutamine and a lysine or a structurally related primary amine, for example an aminopentyl group. The acceptor glutamine may be a surface-exposed glutamine.

"Amino acid modification" or "mutation" here means an amino acid substitution, insertion and/or deletion in a polypeptide sequence. The preferred amino acid modification here is a substitution. "Amino acid substitution" or "substitution" here means an exchange of an amino acid at a given position in a protein sequence for another amino acid. For example, the substitution Y50W describes a variant of a parent polypeptide in which the tyrosine at position 50 has been exchanged for a tryptophan. A "variant" of a polypeptide describes a polypeptide having an amino acid sequence substantially identical to a reference polypeptide, typically a native or "parent" polypeptide. The polypeptide variant may have one or more amino acid exchanges, deletions and/or insertions at particular positions in the native amino acid sequence.

The expression "conjugation site-specific conjugate" describes a conjugate of a binder, preferably an antibody, and a residue, preferably a linker-drug residue, where the binder is functionalized at one or more defined positions, preferably glutamine residues. Transglutaminases (TGases), including bacterial transglutaminase (BTG) (EC 2.3.2.13), show strong specificity in the recognition of glutamine-protein substrates and can catalyse "conjugation site-specific conjugation".

The expression "homogeneous conjugate" or "homogeneous ADC" describes a mixture of conjugation site-specific conjugates wherein at least 60%, 70%, 80% or 90% of the binders have the same number of conjugated residues per binder. In the case of an antibody, this number should be an even number, preferably 2 or 4.

Binders

In the broadest sense, the term "binder" is understood to mean a molecule which binds to a target molecule present at a certain target cell population to be addressed by the binder-drug conjugate. The term binder is to be understood in its broadest meaning and also comprises, for example, lectins, proteins capable of binding to certain sugar chains, and phospholipid-binding proteins. Such binders include, for example, high-molecular weight proteins (binding proteins), polypeptides or peptides (binding peptides), non-peptidic (e.g. aptamers (U.S. Pat. No. 5,270,163) review by Keefe A D., et al., Nat. Rev. Drug Discov. 2010; 9:537-550), or vitamins) and all other cell-binding molecules or substances. Binding proteins are, for example, antibodies and antibody fragments or antibody mimetics such as, for example, affibodies, adnectins, anticalins, DARPins, avimers, nanobodies (review by Gebauer M. et al., Curr. Opinion in Chem. Biol. 2009; 13:245-255; Nuttall S. D. et al., Curr. Opinion in Pharmacology 2008; 8:608-617). Binding peptides are, for example, ligands of a ligand/receptor pair such as, for example, VEGF of the ligand/receptor pair VEGF/KDR, such as transferrin of the ligand/receptor pair transferrin/transferrin receptor or cytokine/cytokine receptor, such as TNFalpha of the ligand/receptor pair TNFalpha/TNFalpha receptor.

The "binder" may contain an acceptor glutamine residue which can be functionalized by a transglutaminase (TGase) including bacterial transglutaminase (BTG) (EC 2.3.2.13). This acceptor glutamine may either be present in natural form in the binder or it is generated specially. An acceptor glutamine can be generated via an insertion of a glutamine residue at a suitable position (for example by means of a fusion tag containing an acceptor glutamine, or via a mutation of a suitable position to give a glutamine residue), or an acceptor glutamine is generated by a mutation of any amino acid which leads to conversion of a particular glutamine residue which was not recognized by the transglutaminase beforehand to an acceptor glutamine, or an acceptor glutamine is generated by a modification in a post-translational modification (for example a glycosylation), this change having the effect that a naturally occurring glutamine which has not been recognized by a transglutaminase beforehand becomes an acceptor glutamine. When the binder is an antibody, it contains an acceptor glutamine, preferably in the constant region. Such acceptor glutamines can be generated by mutations of suitable positions to glutamine (e.g. the mutation N297Q Kabat EU numbering) or by the generation of deglycosylated or aglycosylated antibodies (for example by deglycosylation by means of PNGase F or by the mutation N297X, Kabat EU numbering). In the latter case of the deglycosylated or aglycosylated antibody, the glutamine residue Q295 (Kabat EU numbering) of the heavy chain becomes an acceptor glutamine. Particular preference is given to an antibody containing the N297A or N297Q mutation (Kabat EU numbering).

The term "aglycosylated antibody" or "deglycosylated antibody" is used here to define an antibody or an antibody derivative containing an FC region lacking the glycans joined to the conserved L-glycosylation site in the CH2 domain. Aglycosylated antibodies can be produced, for example, by mutation of the glycosylation site N297 (Kabat Eu numbering) of the heavy chain or by expression of antibodies in expression systems lacking glycosylation capacity. Methods of antibody deglycosylation are common knowledge (e.g. Winkelhake & Nicolson (1976), J Biol Chem. 251(4):1074-80)). Deglycosylated antibodies can be generated, for example, by enzymatic deglycosylation by means of PNGase F. In one embodiment of the invention, aglycosylated antibodies can be obtained by expression in prokaryotic hosts. Suitable prokaryotic hosts include but are not limited to *E. coli, Bacillus subtilis, Salmonella typhimurium* and some species of the *Pseudomonas, Streptomyces* and *Staphylococcus* genera. In another embodiment of the invention, aglycosylated antibodies can be obtained by the use of mammalian cell expression systems together with the glycosylation inhibitor tunicamycin (Nose & Wigzell (1983), Proc Natl Acad Sci USA, 80(21):6632-6). Here, the modification is the prevention of glycosylation at the conserved N-glycosylation site N297 (Kabat numbering) of the heavy chain in the CH2 domain of the Fc portion of the antibody.

The literature also discloses various options for the conjugation site-specific covalent coupling (conjugation) of organic molecules to antibodies. Particular attention with regard to this invention is placed on the conjugation of toxophores to antibodies via two or four acceptor glutamine residues of the antibody.

The literature also discloses various options of covalent coupling (conjugation) of organic molecules to antibodies. Preference according to the invention is given to the conjugation of the toxophores to the antibody via one or more sulphur atoms of cysteine residues of the antibody and/or via one or more NH groups of lysine residues of the antibody. However, it is also possible to bind the toxophore to the antibody via free carboxyl groups or via sugar residues of the antibody.

A "target molecule" in the broadest sense is understood to mean a molecule which is present in the target cell population and which may be a protein (for example a receptor of a growth factor) or a non-peptidic molecule (for example a sugar or phospholipid). It is preferably a receptor or an antigen.

The term "extracellular" target molecule describes a target molecule, attached to the cell, which is located at the outside of a cell, or the part of a target molecule which is located at the outside of a cell, i.e. a binder may bind on an intact cell to its extracellular target molecule. An extracellular target molecule may be anchored in the cell membrane or be a component of the cell membrane. The person skilled in the art is aware of methods for identifying extracellular target molecules. For proteins, this may be by determining the transmembrane domain(s) and the orientation of the protein in the membrane. These data are usually deposited in protein databases (e.g. SwissProt).

The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

The binder can be attached to the linker via a bond. Attachment of the binder can be via a heteroatom of the binder. Heteroatoms according to the invention of the binder which can be used for attachment are sulphur (in one embodiment via a sulphhydryl group of the binder), oxygen (according to the invention by means of a carboxyl or hydroxyl group of the binder) and nitrogen (in one embodiment via a primary or secondary amine group or amide group of the binder). These heteroatoms may be present in the natural binder or are introduced by chemical methods or methods of molecular biology. According to the invention, the attachment of the binder to the toxophore has only a minor effect on the binding activity of the binder with respect to the target molecule. In a preferred embodiment, the attachment has no effect on the binding activity of the binder with respect to the target molecule.

In accordance with the present invention, the term "antibody" is to be understood in its broadest meaning and comprises immunoglobulin molecules, for example intact or modified monoclonal antibodies, polyclonal antibodies or multispecific antibodies (e.g. bispecific antibodies). An immunoglobulin molecule preferably comprises a molecule having four polypeptide chains, two heavy chains (H chains) and two light chains (L chains) which are typically linked by disulphide bridges. Each heavy chain comprises a variable domain of the heavy chain (abbreviated VH) and a constant domain of the heavy chain. The constant domain of the heavy chain may, for example, comprise three domains CH1, CH2 and CH3. Each light chain comprises a variable domain (abbreviated VL) and a constant domain. The constant domain of the light chain comprises a domain (abbreviated CL). The VH and VL domains may be subdivided further into regions having hypervariability, also referred to as complementarity determining regions (abbreviated CDR) and regions having low sequence variability (framework region, abbreviated FR). Typically, each VH and VL region is composed of three CDRs and up to four FRs. For example from the amino terminus to the carboxy terminus in the following order: FR1, CDR1, FR2, CDR2, FR3, CDR3, FR4. An antibody may be obtained from any suitable species, e.g. rabbit, llama, camel, mouse or rat. In one embodiment, the antibody is of human or murine origin. An antibody may, for example, be human, humanized or chimeric.

The term "monoclonal" antibody refers to antibodies obtained from a population of substantially homogeneous antibodies, i.e. individual antibodies of the population are identical except for naturally occurring mutations, of which there may be a small number. Monoclonal antibodies recognize a single antigenic binding site with high specificity. The term monoclonal antibody does not refer to a particular preparation process.

The term "intact" antibody refers to antibodies comprising both an antigen-binding domain and the constant domain of the light and heavy chain. The constant domain may be a naturally occurring domain or a variant thereof having a number of modified amino acid positions, and may also be aglycosylated.

The term "modified intact" antibody refers to intact antibodies fused via their amino terminus or carboxy terminus by means of a covalent bond (e.g. a peptide bond) with a further polypeptide or protein not originating from an antibody. Furthermore, antibodies may be modified such that, at defined positions, reactive cysteines are introduced to facilitate coupling to a toxophore (see Junutula et al. Nat Biotechnol. 2008 August; 26(8):925-32).

The term "human" antibody refers to antibodies which can be obtained from a human or which are synthetic human antibodies. A "synthetic" human antibody is an antibody which is partially or entirely obtainable in silico from synthetic sequences based on the analysis of human antibody sequences. A human antibody can be encoded, for example, by a nucleic acid isolated from a library of antibody sequences of human origin. An example of such an antibody can be found in Söderlind et al., Nature Biotech. 2000, 18:853-856. Such "human" and "synthetic" antibodies also include aglycosylated variants which have been produced either by deglycosylation by PNGaseF or by mutation of N297 (Kabat numbering) of the heavy chain to any other amino acid.

The term "humanized" or "chimeric" antibody describes antibodies consisting of a non-human and a human portion of the sequence. In these antibodies, part of the sequences of the human immunoglobulin (recipient) is replaced by sequence portions of a non-human immunoglobulin (donor). In many cases, the donor is a murine immunoglobulin. In the case of humanized antibodies, amino acids of the CDR of the recipient are replaced by amino acids of the donor. Sometimes, amino acids of the framework, too, are replaced by corresponding amino acids of the donor. In some cases the humanized antibody contains amino acids present neither in the recipient nor in the donor, which were introduced during the optimization of the antibody. In the case of chimeric antibodies, the variable domains of the donor immunoglobulin are fused with the constant regions of a human antibody. Such "humanized" and "chimeric" antibodies also include aglycosylated variants which have been produced either by deglycosylation by PNGaseF or by mutation of N297 (Kabat numbering) of the heavy chain to any other amino acid.

The term complementarity determining region (CDR) as used herein refers to those amino acids of a variable antibody domain which are required for binding to the antigen. Typically, each variable region has three CDR regions referred to as CDR1, CDR2 and CDR3. Each CDR region may embrace amino acids according to the definition of Kabat and/or amino acids of a hypervariable loop defined according to Chotia. The definition according to Kabat comprises, for example, the region from about amino acid position 24-34 (CDR1), 50-56 (CDR2) and 89-97 (CDR3) of the variable light chain and 31-35 (CDR1), 50-65 (CDR2) and 95-102 (CDR3) of the variable heavy chain (Kabat et al., Sequences of Proteins of Immunological Interest, 5th Ed. Public Health Service, National Institutes of Health, Bethesda, Md. (1991)). The definition according to Chotia comprises, for example, the region from about amino acid position 26-32 (CDR1), 50-52 (CDR2) and 91-96 (CDR3) of the variable light chain and 26-32 (CDR1), 53-55 (CDR2) and 96-101 (CDR3) of the variable heavy chain (Chothia and Lesk; J Mol Biol 196: In some cases, a CDR may comprise amino acids from a CDR region defined according to Kabat and Chotia.

Depending on the amino acid sequence of the constant domain of the heavy chain, antibodies may be categorized into different classes. There are five main classes of intact antibodies: IgA, IgD, IgE, IgG and IgM, and several of these can be divided into further subclasses. (Isotypes), e.g. IgG1, IgG2, IgG3, IgG4, IgA1 and IgA2. The constant domains of the heavy chain, which correspond to the different classes, are referred to as [alpha/α], [delta/δ], [epsilon/ε], [gamma/γ] and [my/μ]. Both the three-dimensional structure and the subunit structure of antibodies are known.

The term "functional fragment" or "antigen-binding antibody fragment" of an antibody/immunoglobulin is defined as a fragment of an antibody/immunoglobulin (e.g. the variable domains of an IgG) which still comprise the antigen binding domains of the antibody/immunoglobulin. The "antigen binding domain" of an antibody typically comprises one or more hypervariable regions of an antibody, for example the CDR, CDR2 and/or CDR3 region.

However, the "framework" or "skeleton" region of an antibody may also play a role during binding of the antibody to the antigen. The framework region forms the skeleton of the CDRs. Preferably, the antigen binding domain comprises at least amino acids 4 to 103 of the variable light chain and amino acids 5 to 109 of the variable heavy chain, more preferably amino acids 3 to 107 of the variable light chain and 4 to 111 of the variable heavy chain, particularly preferably the complete variable light and heavy chains, i.e. amino acids 1-109 of the VL and 1 to 113 of the VH (numbering according to WO97/08320).

"Functional fragments" or "antigen-binding antibody fragments" of the invention encompass, non-conclusively, Fab, Fab', F(ab')2 and Fv fragments, diabodies, Single Domain Antibodies (DAbs), linear antibodies, individual chains of antibodies (single-chain Fv, abbreviated to scFv); and multispecific antibodies, such as bi and tri-specific antibodies, for example, formed from antibody fragments C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag. Antibodies other than "multispecific" or "multifunctional" antibodies are those having identical binding sites.

Multispecific antibodies may be specific for different epitopes of an antigen or may be specific for epitopes of more than one antigen (see, for example WO 93/17715; WO 92/08802; WO 91/00360; WO 92/05793; Tutt, et al., 1991, J. Immunol. 147:6069; U.S. Pat. Nos. 4,474,893; 4,714,681; 4,925,648; 5,573,920; 5,601,819; or Kostelny et al., 1992, J. Immunol. 148: 15471553). An $F(ab')_2$ or Fab molecule may be constructed such that the number of intermolecular disulphide interactions occurring between the Ch1 and the CL domains can be reduced or else completely prevented.

"Epitopes" refer to protein determinants capable of binding specifically to an immunoglobulin or T cell receptors. Epitopic determinants usually consist of chemically active surface groups of molecules such as amino acids or sugar side chains or combinations thereof, and usually have specific 3-dimensional structural properties and also specific charge properties.

"Functional fragments" or "antigen-binding antibody fragments" may be fused with another polypeptide or protein, not originating from an antibody, via the amino terminus or carboxyl terminus thereof, by means of a covalent bond (e.g. a peptide linkage). Furthermore, antibodies and antigen-binding fragments may be modified by introducing reactive cysteines at defined locations, in order to facilitate coupling to a toxophore (see Junutula et al. Nat Biotechnol. 2008 August; 26(8):925-32).

Polyclonal antibodies can be prepared by methods known to a person of ordinary skill in the art. Monoclonal antibodies may be prepared by methods known to a person of ordinary skill in the art (Köhler and Milstein, Nature, 256, 495-497, 1975). Human and humanized monoclonal antibodies may be prepared by methods known to a person of ordinary skill in the art (Olsson et al., Meth Enzymol. 92, 3-16 or Cabilly et al U.S. Pat. No. 4,816,567 or Boss et al U.S. Pat. No. 4,816,397).

A person of ordinary skill in the art is aware of diverse methods for preparing human antibodies and fragments thereof, such as, for example, by means of transgenic mice (N Lonberg and D Huszar, Int Rev Immunol. 1995; 13(1): 65-93) or Phage Display Technologien (Clackson et al., Nature. 1991 Aug. 15; 352(6336):624-8). Antibodies of the invention may be obtained from recombinant antibody libraries consisting for example of the amino acid sequences of a multiplicity of antibodies compiled from a large number of healthy volunteers. Antibodies may also be produced by means of known recombinant DNA technologies. The nucleic acid sequence of an antibody can be obtained by routine sequencing or is available from publically accessible databases.

An "isolated" antibody or binder has been purified to remove other constituents of the cell. Contaminating constituents of a cell which may interfere with a diagnostic or therapeutic use are, for example, enzymes, hormones, or other peptidic or non-peptidic constituents of a cell. A preferred antibody or binder is one which has been purified to an extent of more than 95% by weight, relative to the antibody or binder (determined for example by Lowry method, UV-Vis spectroscopy or by SDS capillary gel electrophoresis). Moreover an antibody which has been purified to such an extent that it is possible to determine at least 15 amino acids of the amino terminus or of an internal amino acid sequence, or which has been purified to homogeneity, the homogeneity being determined by SDS-PAGE under reducing or non-reducing conditions (detection may be determined by means of Coomassie Blau staining or preferably by silver coloration). However, an antibody is normally prepared by one or more purification steps.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value; i.e. preferably those with Kd values smaller than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule. The antibodies preferably have an affinity of at least $10^{-7}$ M (as Kd value; in other words preferably those with smaller Kd values than $10^{-7}$ M), preferably of at least $10^{-8}$ M, more preferably in the range from $10^{-9}$ M to $10^{-11}$ M. The Kd values may be determined, for example, by means of surface plasmon resonance spectroscopy.

The antibody-drug conjugates of the invention likewise exhibit affinities in these ranges. The affinity is preferably not substantially affected by the conjugation of the drugs (in general, the affinity is reduced by less than one order of magnitude, in other words, for example, at most from $10^{-8}$ M to $10^{-7}$ M).

The antibodies used in accordance with the invention are also notable preferably for a high selectivity. A high selectivity exists when the antibody of the invention exhibits an affinity for the target protein which is better by a factor of at least 2, preferably by a factor of 5 or more preferably by a factor of 10, than for an independent other antigen, e.g. human serum albumin (the affinity may be determined, for example, by means of surface plasmon resonance spectroscopy).

Furthermore, the antibodies of the invention that are used are preferably cross-reactive. In order to be able to facilitate and better interpret preclinical studies, for example toxicological or activity studies (e.g. in xenograft mice), it is advantageous if the antibody used in accordance with the invention not only binds the human target protein but also binds the species target protein in the species used for the studies. In one embodiment the antibody used in accordance with the invention, in addition to the human target protein, is cross-reactive to the target protein of at least one further species. For toxicological and activity studies it is preferred to use species of the families of rodents, dogs and non-human primates. Preferred rodent species are mouse and rat. Preferred non-human primates are rhesus monkeys, chimpanzees and long-tailed macaques.

In one embodiment the antibody used in accordance with the invention, in addition to the human target protein, is cross-reactive to the target protein of at least one further species selected from the group of species consisting of mouse, rat and long-tailed macaque (*Macaca fascicularis*). Especially preferred are antibodies used in accordance with the invention which in addition to the human target protein are at least cross-reactive to the mouse target protein. Preference is given to cross-reactive antibodies whose affinity for the target protein of the further non-human species differs by a factor of not more than 50, more particularly by a factor of not more than ten, from the affinity for the human target protein.

Antibodies Directed Against a Cancer Target Molecule

The target molecule towards which the binder, for example an antibody or an antigen-binding fragment thereof, is directed is preferably a cancer target molecule. The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

Antibodies which are specific against an antigen, for example cancer cell antigen, can be prepared by a person of ordinary skill in the art by means of methods with which he or she is familiar (such as recombinant expression, for example) or may be acquired commercially (as for example from Merck KGaA, Germany). Examples of known commercially available antibodies in cancer therapy are Erbitux® (cetuximab, Merck KGaA), Avastin® (bevacizumab, Roche) and Herceptin® (trastuzumab, Genentech). Trastuzumab is a recombinant humanized monoclonal antibody of the IgG1kappa type which in a cell-based assay (Kd=5 nM) binds the extracellular domains of the human epidermal growth receptor with high affinity. The antibody is produced recombinantly in CHO cells. All these antibodies can also be produced as aglycosylated variants of these antibodies, either by deglycosylation by means of PNGase F or by mutation of N297 (Kabat numbering) of the heavy chain to any amino acid.

In a preferred embodiment, the target molecule is a selective cancer target molecule.

In a particularly preferred embodiment, the target molecule is a protein.

In one embodiment, the target molecule is an extracellular target molecule. In a preferred embodiment, the extracellular target molecule is a protein.

Cancer target molecules are known to those skilled in the art. Examples of these are listed below.

Examples of cancer target molecules are:

(1) EGF receptor (NCBI reference sequence NP_005219.2), SEQ ID NO: 213 (1210 amino acids):

```
>gi|29725609|ref|NP_005219.2|EGFR receptor
precursor [Homo sapiens]
MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGCTGPGLEGCPTNGPKIPSIATGM

VGALLLLLVVALGIGLFMRRRHIVRKRTLRRLLQERELVEPLTPSGEAPN

QALLRILKETEFKKIKVLGSGAFGTVYKGLWIPEGEKVKIPVAIKELREA
```

-continued

```
TSPKANKEILDEAYVMASVDNPHVCRLLGICLTSTVQLITQLMPFGCLLD

YVREHKDNIGSQYLLNWCVQIAKGMNYLEDRRLVHRDLAARNVLVKTPQH

VKITDFGLAKLLGAEEKEYHAEGGKVPIKWMALESILHRIYTHQSDVWSY

GVTVWELMTFGSKPYDGIPASEISSILEKGERLPQPPICTIDVYMIMVKC

WMIDADSRPKFRELIIEFSKMARDPQRYLVIQGDERMHLPSPTDSNFYRA

LMDEEDMDDVVDADEYLIPQQGFFSSPSTSRTPLLSSLSATSNNSTVACI

DRNGLQSCPIKEDSFLQRYSSDPTGALTEDSIDDTFLPVPEYINQSVPKR

PAGSVQNPVYHNQPLNPAPSRDPHYQDPHSTAVGNPEYLNTVQPTCVNST

FDSPAHWAQKGSHQISLDNPDYQQDFFPKEAKPNGIFKGSTAENAEYLRV

APQSSEFIGA
```

The extracellular domain is marked by underlining.

(2) mesothelin (SwissProt reference Q13421-3), SEQ ID NO: 214 (622 amino acids):

```
>sp|Q13421-3|MSLN_HUMAN Isoform 2 of Mesothelin
OS = Homo sapiens GN = MSLN
MALPTARPLLGSCGTPALGSLLFLLFSLGWVQPSRTLAGETGQEAAPLDG

VLANPPNISSLSPRQLLGFPCAEVSGLSTERVRELAVALAQKNVKLSTEQ

LRCLAHRLSEPPEDLDALPLDLLLFLNPDAFSGPQACTRFFSRITKANVD

LLPRGAPERQRLLPAALACWGVRGSLLSEADVRALGGLACDLPGRFVAES

AEVLLPRLVSCPGPLDQDQQEAARAALQGGGPPYGPPSTWSVSTMDALRG

LLPVLGQPIIRSIPQGIVAAWRQRSSRDPSWRQPERTILRPRFRREVEKT

ACPSGKKAREIDESLIFYKKWELEACVDAALLATQMDRVNAIPFTYEQLD

VLKHKLDELYPQGYPESVIQHLGYLFLKMSPEDIRKWNVTSLETLKALLE

VNKGHEMSPQVATLIDRFVKGRGQLDKDTLDTLTAFYPGYLCSLSPEELS

SVPPSSIWAVRPQDLDTCDPRQLDVLYPKARLAFQNMNGSEYFVKIQSFL

GGAPTEDLKALSQQNVSMDLATFMKLRTDAVLPLTVAEVQKLLGPHVEGL

KAEERHRPVRDWILRQRQDDLDTLGLGLQGGIPNGYLVLDLSMQEALSGT

PCLLGPGPVLTVLALLLASTLA
```

where mesothelin is encoded by amino acids 296-598. Amino acids 37-286 are coding for the megakaryocyte-potentiating factor. Mesothelin is anchored in the cell membrane via a GPI anchor and is localized extracellularly.

(3) carboanhydrase IX (SwissProt reference Q16790), SEQ ID NO: 215 (459 amino acids):

```
>sp|Q16790|CAH9_HUMAN Carbonic anhydrase 9
OS = Homo sapiens GN = CA9 PE = 1 SV = 2
MAPLCPSPWLPLLIPAPAPGLTVQLLLSLLLLVPVHPQRLPRMQEDSPLG

GGSSGEDDPLGEEDLPSEEDSPREEDPPGEEDLPGEEDLPGEEDLPEVKP

KSEEEGSLKLEDLPTVEAPGDPQEPQNNAHRDKEGDDQSHWRYGGDPPWP

RVSPACAGRFQSPVDIRPQLAAFCPALRPLELLGFQLPPLPELRLRNNGH

SVQLTLPPGLEMALGPGREYRALQLHLHWGAAGRPGSEHTVEGHRFPAEI

HVVHLSTAFARVDEALGRPGGLAVLAAFLEEGPEENSAYEQLLSRLEEIA

EEGSETQVPGLDISALLPSDFSRYFQYEGSLTTPPCAQGVIWTVFNQTVM

LSAKQLHTLSDTLWGPGDSRLQLNFRATQPLNGRVIEASFPAGVDSSPRA
```

-continued

AEPVQLNSCLAAGDILALVFGLLFAVTSVAFLVQMRRQHRRGTKGGVSYR

PAEVAETGA

The extracellular domain is marked by underlining.

(4) C4.4a (NCBI reference sequence NP_055215.2; synonym LYPD3), SEQ ID NO: 216 (346 amino acids):

>gi|93004088|ref|NP_055215.2|ly6/PLAUR domain-containing protein 3-precursor [*Homo sapiens*]
MDPARKAGAQAMIWTAGWLLLLLLRGGAQALECYSCVQKADDGCSPNKMK

TVKCAPGVDVCTEAVGAVETIHGQFSLAVRGCGSGLPGKNDRGLDLHGLL

AFIQLQQCAQDRCNAKLNLTSRALDPAGNESAYPPNGVECYSCVGLSREA

CQGTSPPVVSCYNASDHVYKGCFDGNVTLTAANVTVSLPVRGCVQDEFCT

RDGVTGPGFTLSGSCCQGSRCNSDLRNKTYFSPRIPPLVRLPPPEPTTVA

STTSVTTSTSAPVRPTSTTKPMPAPTSQTPRQGVEHEASRDEEPRLTGGA

AGHQDRSNSGQYPAKGGPQQPHNKGCVAPTAGLAALLLAVAAGVLL

The mature extracellular domain is marked by underlining.

(5) CD52 (NCBI reference sequence NP_001794.2), SEQ ID NO: 217

>gi|68342030|ref|NP_001794.2|CAMPATH-1 antigen-precursor [*Homo sapiens*]
MKRFLFLLLTISLLVMVQIQTGLSGQNDTSQTSSPSASSNISGGIFLFFV

ANAIIHLFCFS (6) Her2 (NCBI reference sequence NP_004439.2), SEQ ID NO: 218

>gi|54792096|ref|NP_004439.2|receptor tyrosine-protein kinase erbB-2 isoform a [*Homo sapiens*]
MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

GGVLIQRNPQLCYQDTILWKDIFHKNNQLALTLIDTNRSRACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

ETLEEITGYLYISAWPDSLPDLSVFQNLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL

PREYVNARHCLPCHPECQPQNGSVTCFGPEADQCVACAHYKDPPFCVARC

PSGVKPDLSYMPIWKFPDEEGACQPCPINCTHSCVDLDDKGCPAEQRASP

LTSIISAVVGILLVVVLGVVFGILIKRRQQKIRKYTMRRLLQETELVEPL

TPSGAMPNQAQMRILKETELRKVKVLGSGAFGTVYKGIWIPDGENVKIPV

AIKVLRENTSPKANKEILDEAYVMAGVGSPYVSRLLGICLTSTVQLVTQL

MPYGCLLDHVRENRGRLGSQDLLNWCMQIAKGMSYLEDVRLVHRDLAARN

-continued

VLVKSPNHVKITDFGLARLLDIDETEYHADGGKVPIKWMALESILRRRFT

HQSDVWSYGVTVWELMTFGAKPYDGIPAREIPDLLEKGERLPQPPICTID

VYMIMVKCWMIDSECRPRFRELVSEFSRMARDPQRFVVIQNEDLGPASPL

DSTFYRSLLEDDDMGDLVDAEEYLVPQQGFFCPDPAPGAGGMVHHRHRSS

STRSGGGDLTLGLEPSEEEAPRSPLAPSEGAGSDVFDGDLGMGAAKGLQS

LPTHDPSPLQRYSEDPTVPLPSETDGYVAPLTCSPQPEYVNQPDVRPQPP

SPREGPLPAARPAGATLERPKTLSPGKNGVVKDVFAFGGAVENPEYLTPQ

GGAAPQPHPPPAFSPAFDNLYYWDQDPPERGAPPSTFKGTPTAENPEYLG

LDVPV (7) CD20 (NCBI reference sequence NP_068769.2), SEQ ID NO: 219

>gi|23110987|ref|NP_068769.2|B-lymphocyte antigen CD20 [*Homo sapiens*]
MTTPRNSVNGTFPAEPMKGPIAMQSGPKPLFRRMSSLVGPTQSFFMRESK

TLGAVQIMNGLFHIALGGLLMIPAGIYAPICVTVWYPLWGGIMYIISGSL

LAATEKNSRKCLVKGKMIMNSLSLFAAISGMILSIMDILNIKISHFLKME

SLNFIRAHTPYINIYNCEPANPSEKNSPSTQYCYSIQSLFLGILSVMLIF

AFFQELVIAGIVENEWKRTCSRPKSNIVLLSAEEKKEQTIEIKEEVVGLT

ETSSQPKNEEDIEIIPIQEEEEEETETNFPEPPQDQESSPIENDSSP (8) the lymphocyte activation antigen CD30 (SwissProt ID P28908), SEQ ID NO: 220

>gi|68348711|ref|NP_001234.2|tumor necrosis factor receptor superfamily member 8 isoform 1-precursor [*Homo sapiens*]
MRVLLAALGLLFLGALRAFPQDRPFEDTCHGNPSHYYDKAVRRCCYRCPM

GLFPTQQCPQRPTDCRKQCEPDYYLDEADRCTACVTCSRDDLVEKTPCAW

NSSRVCECRPGMFCSTSAVNSCARCFFHSVCPAGMIVKFPGTAQKNTVCE

PASPGVSPACASPENCKEPSSGTIPQAKPTPVSPATSSASTMPVRGGTRL

AQEAASKLTRAPDSPSSVGRPSSDPGLSPTQPCPEGSGDCRKQCEPDYYL

DEAGRCTACVSCSRDDLVEKTPCAWNSSRTCECRPGMICATSATNSRARC

VPYPICAAETVTKPQDMAEKDTTFEAPPLGTQPDCNPTPENGEAPASTSP

TQSLLVDSQASKTLPIPTSAPVALSSTGKPVLDAGPVLFWVILVLVVVVG

SSAFLLCHRRACRKRIRQKLHLCYPVQTSQPKLELVDSRPRRSSTQLRSG

ASVTEPVAEERGLMSQPLMETCHSVGAAYLESLPLQDASPAGGPSSPRDL

PEPRVSTEHTNNKIEKIYIMKADTVIVGTVKAELPEGRGLAGPAEPELEE

ELEADHTPHYPEQETEPPLGSCSDVMLSVEEEGKEDPLPTAASGK (9) the lymphocyte adhesion molecule CD22 (SwissProt ID P20273), SEQ ID NO: 221

>gi|157168355|ref|NP_001762.2|B-cell receptor CD22 isoform 1-precursor [*Homo sapiens*]
MHLLGPWLLLLVLEYLAFSDSSKWVFEHPETLYAWEGACVWIPCTYRALD

GDLESFILFHNPEYNKNTSKFDGTRLYESTKDGKVPSEQKRVQFLGDKNK

NCTLSIHPVHLNDSGQLGLRMESKTEKWMERIHLNVSERPFPPHIQLPPE

-continued

IQESQEVTLTCLLNFSCYGYPIQLQWLLEGVPMRQAAVTSTSLTIKSVFT

RSELKFSPQWSHHGKIVTCQLQDADGKFLSNDTVQLNVKHTPKLEIKVTP

SDAIVREGDSVTMTCEVSSSNPEYTTVSWLKDGTSLKKQNTFTLNLREVT

KDQSGKYCCQVSNDVGPGRSEEVFLQVQYAPEPSTVQILHSPAVEGSQVE

FLCMSLANPLPTNYTWYHNGKEMQGRTEEKVHIPKILPWHAGTYSCVAEN

ILGTGQRGPGAELDVQYPPKKVTTVIQNPMPIREGDTVTLSCNYNSSNPS

VTRYEWKPHGAWEEPSLGVLKIQNVGWDNTTIACAACNSWCSWASPVALN

VQYAPRDVRVRKIKPLSEIHSGNSVSLQCDFSSSHPKEVQFFWEKNGRLL

GKESQLNFDSISPEDAGSYSCWVNNSIGQTASKAWTLEVLYAPRRLRVSM

SPGDQVMEGKSATLTCESDANPPVSHYTWFDWNNQSLPYHSQKLRLEPVK

VQHSGAYWCQGTNSVGKGRSPLSTLTVYYSPETIGRRVAVGLGSCLAILI

LAICGLKLQRRWKRTQSQQGLQENSSGQSFFVRNKKVRRAPLSEGPHSLG

CYNPMMEDGISYTTLRFPEMNIPRTGDAESSEMQRPPPDCDDTVTYSALH

KRQVGDYENVIPDFPEDEGIHYSELIQFGVGERPQAQENVDYVILKH

(10) the myloid cell surface antigen CD33 (SwissProt ID P20138), SEQ ID NO: 222

>gi|130979981|ref|NP_001763.3|myeloid cell surface antigen CD33 isoform 1-precursor [*Homo sapiens*]
MPLLLLLPLLWAGALAMDPNFWLQVQESVTVQEGLCVLVPCTFFHPIPYY

DKNSPVHGYWFREGAIISRDSPVATNKLDQEVQEETQGRFRLLGDPSRNN

CSLSIVDARRRDNGSYFFRMERGSTKYSYKSPQLSVHVTDLTHRPKILIP

GTLEPGHSKNLTCSVSWACEQGTPPIFSWLSAAPTSLGPRTTHSSVLIIT

PRPQDHGTNLTCQVKFAGAGVTTERTIQLNVTYVPQNPTTGIFPGDGSGK

QETRAGVVHGAIGGAGVTALLALCLCLIFFIVKTHRRKAARTAVGRNDTH

PTTGSASPKHQKKSKLHGPTETSSCSGAAPTVEMDEELHYASLNFHGMNP

SKDTSTEYSEVRTQ

(11) the transmembrane glycoprotein NMB (SwissProt ID Q14956), SEQ ID NO: 223

>gi|52694752|ref|NP_001005340.1|transmembrane glycoprotein NMB isoform a-precursor [*Homo sapiens*]
MECLYYFLGFLLLAARLPLDAAKRFHDVLGNERPSAYMREHNQLNGWSSD

ENDWNEKLYPVWKRGDMRWKNSWKGGRVQAVLTSDSPALVGSNITFAVNL

IFPRCQKEDANGNIVYEKNCRNEAGLSADPYVYNWTAWSEDSDGENGTGQ

SHHNVFPDGKPFPHHPGWRRWNFIYVFHTLGQYFQKLGRCSVRVSVNTAN

VTLGPQLMEVTVYRRHGRAYVPIAQVKDVYVVTDQIPVFVTMFQKNDRNS

SDETFLKDLPIMFDVLIHDPSHFLNYSTINYKWSFGDNTGLFVSTNHTVN

HTYVLNGTFSLNLTVKAAAPGPCPPPPPPPRPSKPTPSLATTLKSYDSNT

PGPAGDNPLELSRIPDENCQINRYGHFQATITIVEGILEVNIIQMTDVLM

PVPWPESSLIDFVVTCQGSIPTEVCTIISDPTCEITQNTVCSPVDVDEMC

LLTVRRTFNGSGTYCVNLTLGDDTSLALTSTLISVPDRDPASPLRMANSA

-continued

LISVGCLAIFVTVISLLVYKKHKEYNPIENSPGNVVRSKGLSVFLNRAKA

VFFPGNQEKDPLLKNQEFKGVS

(12) the adhesion molecule CD56 (SwissProt ID P13591), SEQ ID NO: 224

>gi|94420689|ref|NP_000606.3|neural cell adhesion molecule 1 isoform 1 [*Homo sapiens*]
MLQTKDLIWTLFFLGTAVSLQVDIVPSQGEISVGESKFFLCQVAGDAKDK

DISWFSPNGEKLTPNQQRISVVWNDDSSSTLTIYNANIDDAGIYKCVVTG

EDGSESEATVNVKIFQKLMFKNAPTPQEFREGEDAVIVCDVVSSLPPTII

WKHKGRDVILKKDVRFIVLSNNYLQIRGIKKTDEGTYRCEGRILARGEIN

FKDIQVIVNVPPTIQARQNIVNATANLGQSVTLVCDAEGFPEPTMSWTKD

GEQIEQEEDDEKYIFSDDSSQLTIKKVDKNDEAEYICIAENKAGEQDATI

HLKVFAKPKITYVENQTAMELEEQVTLTCEASGDPIPSITWRTSTRNISS

EEKTLDGHMVVRSHARVSSLTLKSIQYTDAGEYICTASNTIGQDSQSMYL

EVQYAPKLQGPVAVYTWEGNQVNITCEVFAYPSATISWFRDGQLLPSSNY

SNIKIYNTPSASYLEVTPDSENDFGNYNCTAVNRIGQESLEFILVQADTP

SSPSIDQVEPYSSTAQVQFDEPEATGGVPILKYKAEWRAVGEEVWHSKWY

DAKEASMEGIVTIVGLKPETTYAVRLAALNGKGLGEISAASEFKTQPVQG

EPSAPKLEGQMGEDGNSIKVNLIKQDDGGSPIRHYLVRYRALSSEWKPEI

RLPSGSDHVMLKSLDWNAEYEVYVVAENQQGKSKAAHFVFRTSAQPTAIP

ANGSPTSGLSTGAIVGILIVIFVLLLVVVDITCYFLNKCGLFMCIAVNLC

GKAGPGAKGKDMEEGKAAFSKDESKEPIVEVRTEEERTPNHDGGKHTEPN

ETTPLTEPEKGPVEAKPECQETETKPAPAEVKTVPNDATQTKENESKA

(13) the surface molecule CD70 (SwissProt ID P32970), SEQ ID NO: 225

>gi|4507605|ref|NP_001243.1|CD70 antigen [*Homo sapiens*]
MPEEGSGCSVRRRPYGCVLRAALVPLVAGLVICLVVCIQRFAQAQQQLPL

ESLGWDVAELQLNHTGPQQDPRLYWQGGPALGRSFLHGPELDKGQLRIHR

DGIYMVHIQVTLAICSSTTASRHHPTTLAVGICSPASRSISLLRLSFHQG

CTIASQRLTPLARGDTLCTNLTGTLLPSRNTDETFFGVQWVRP

(14) the surface molecule CD74 (SwissProt ID P04233), SEQ ID NO: 226

>gi|10835071|ref|NP_004346.1|HLA class II histocompatibility antigen gamma chain isoform b [*Homo sapiens*]
MHRRRSRSCREDQKPVMDDQRDLISNNEQLPMLGRRPGAPESKCSRGALY

TGFSILVTLLLAGQATTAYFLYQQQGRLDKLTVTSQNLQLENLRMKLPKP

PKPVSKMRMATPLLMQALPMGALPQGPMQNATKYGNMTEDHVMHLLQNAD

PLKVYPPLKGSFPENLRHLKNTMETIDWKVFESWMHHWLLFEMSRHSLEQ

KPTDAPPKESLELEDPSSGLGVTKQDLGPVPM

(15) the B-lymphocyte antigen CD19 (SwissProt ID P15391), SEQ ID NO: 227

>gi|296010921|ref|NP_001171569.1|B-lymphocyte antigen CD19 isoform 1-precursor [*Homo sapiens*]
MPPPRLLFFLLFLTPMEVRPEEPLVVKVEEGDNAVLQCLKGTSDGPTQQL
TWSRESPLKPFLKLSLGLPGLGIHMRPLAIWLFIFNVSQQMGGFYLCQPG
PPSEKAWQPGWTVNVEGSGELFRWNVSDLGGLGCGLKNRSSEGPSSPSGK
LMSPKLYVWAKDRPEIWEGEPPCLPPRDSLNQSLSQDLTMAPGSTLWLSC
GVPPDSVSRGPLSWTHVHPKGPKSLLSLELKDDRPARDMWVMETGLLLPR
ATAQDAGKYYCHRGNLTMSFHLEITARPVLWHWLLRTGGWKVSAVTLAYL
IFCLCSLVGILHLQRALVLRRKRKRMTDPTRRFFKVTPPPGSGPQNQYGN
VLSLPTPTSGLGRAQRWAAGLGGTAPSYGNPSSDVQADGALGSRSPPGVG
PEEEEGEGYEEPDSEEDSEFYENDSNLGQDQLSQDGSGYENPEDEPLGPE
DEDSFSNAESYENEDEELTQPVARTMDFLSPHGSAWDPSREATSLAGSQS
YEDMRGILYAAPQLRSIRGQPGPNHEEDADSYENMDNPDGPDPAWGGGGR
MGTWSTR

(16) the surface protein mucin-1 (SwissProt ID P15941), SEQ ID NO: 228

>gi|65301117|ref|NP_002447.4|mucin-1 isoform 1-precursor [*Homo sapiens*]
MTPGTQSPFFLLLLLTVLTVVTGSGHASSTPGGEKETSATQRSSVPSSTE
KNALSTGVSFFFLSFHISNLQFNSSLEDPSTDYYQELQRDISEMFLQIYK
QGGFLGLSNIKFRPGSVVVQLTLAFREGTINVHDVETQFNQYKTEAASRY
NLTISDVSVSDVPFPFSAQSGAGVPGWGIALLVLVCVLVALAIVYLIALA
VCQCRRKNYGQLDIFPARDTYHPMSEYPTYHTHGRYVPPSSTDRSPYEKV
SAGNGGSSLSYTNPAVAATSANL

(17) the surface protein CD138 (SwissProt ID P18827), SEQ ID NO: 229

>gi|29568086|ref|NP_002988.3|syndecan-1-precursor [*Homo sapiens*]
MRRAALWLWLCALALSLQPALPQIVATNLPPEDQDGSGDDSDNFSGSGAG
ALQDITLSQQTPSTWKDTQLLTAIPTSPEPTGLEATAASTSTLPAGEGPK
EGEAVVLPEVEPGLTAREQEATPRPRETTQLPTTHQASTTTATTAQEPAT
SHPHRDMQPGHHETSTPAGPSQADLHTPHTEDGGPSATERAAEDGASSQL
PAAEGSGEQDFTFETSGENTAVVAVEPDRRNQSPVDQGATGASQGLLDRK
EVLGGVIAGGLVGLIFAVCLVGFMLYRMKKKDEGSYSLEEPKQANGGAYQ
KPTKQEEFYA

(18) the integrin alphaV (Genbank Accession No.: NP_002201.1), SEQ ID NO: 230

>gi|4504763|ref|NP_002201.1|integrin alpha-V isoform 1-precursor [*Homo sapiens*]
MAFPPRRRLRLGPRGLPLLLSGLLLPLCRAFNLDVDSPAEYSGPEGSYFG
FAVDFFVPSASSRMFLLVGAPKANTTQPGIVEGGQVLKCDWSSTRRCQPI
EFDATGNRDYAKDDPLEFKSHQWFGASVRSKQDKILACAPLYHWRTEMKQ -continued EREPVGTCFLQDGTKTVEYAPCRSQDIDADGQGFCQGGFSIDFTKADRVL
LGGPGSFYWQGQLISDQVAEIVSKYDPNVYSIKYNNQLATRTAQAIFDDS
YLGYSVAVGDFNGDGIDDFVSGVPRAARTLGMVYIYDGKNMSSLYNFTGE
QMAAYFGFSVAATDINGDDYADVFIGAPLFMDRGSDGKLQEVGQVSVSLQ
RASGDFQTTKLNGFEVFARFGSAIAPLGDLDQDGFNDIAIAAPYGGEDKK
GIVYIFNGRSTGLNAVPSQILEGQWAARSMPPSFGYSMKGATDIDKNGYP
DLIVGAFGVDRAILYRARPVITVNAGLEVYPSILNQDNKTCSLPGTALKV
SCFNVRFCLKADGKGVLPRKLNFQVELLLDKLKQKGAIRRALFLYSRSPS
HSKNMTISRGGLMQCEELIAYLRDESEFRDKLTPITIFMEYRLDYRTAAD
TTGLQPILNQFTPANISRQAHILLDCGEDNVCKPKLEVSVDSDQKKIYIG
DDNPLTLIVKAQNQGEGAYEAELIVSIPLQADFIGVVRNNEALARLSCAF
KTENQTRQVVCDLGNPMKAGTQLLAGLRFSVHQQSEMDTSVKFDLQIQSS
NLFDKVSPVVSHKVDLAVLAAVEIRGVSSPDHIFLPIPNWEHKENPETEE
DVGPVVQHIYELRNNGPSSFSKAMLHLQWPYKYNNNTLLYILHYDIDGPM
NCTSDMEINPLRIKISSLQTTEKNDTVAGQGERDHLITKRDLALSEGDIH
TLGCGVAQCLKIVCQVGRLDRGKSAILYVKSLLWTETFMNKENQNHSYSL
KSSASFNVIEFPYKNLPIEDITNSTLVTTNVTWGIQPAPMPVPVWVIILA
VLAGLLLLAVLVFVMYRMGFFKRVRPPQEEQEREQLQPHENGEGNSET

(19) the teratocarcinoma-derived growth factor 1 protein TDGF1 (Genbank Accession No.: NP_003203.1), SEQ ID NO: 231

>gi|4507425|ref|NP_003203.1|teratocarcinoma-derived growth factor 1 isoform 1-precursor [*Homo sapiens*]
MDCRKMARFSYSVIWIMAISKVFELGLVAGLGHQEFARPSRGYLAFRDDS
IWPQEEPAIRPRSSQRVPPMGIQHSKELNRTCCLNGGTCMLGSFCACPPS
FYGRNCEHDVRKENCGSVPHDTWLPKKCSLCKCWHGQLRCFPQAFLPGCD
GLVMDEHLVASRTPELPPSARTTTFMLVGICLSIQSYY

(20) the prostate-specific membrane antigen PSMA (Swiss Prot ID: Q04609), SEQ ID NO: 232

>gi|4758398|ref|NP_004467.1|glutamate carboxypeptidase 2 isoform 1 [*Homo sapiens*]
MWNLLHETDSAVATARRPRWLCAGALVLAGGFFLLGFLFGWFIKSSNEAT
NITPKHNMKAFLDELKAENIKKFLYNFTQIPHLAGTEQNFQLAKQIQSQW
KEFGLDSVELAHYDVLLSYPNKTHPNYISIINEDGNEIFNTSLFEPPPPG
YENVSDIVPPFSAFSPQGMPEGDLVYVNYARTEDFFKLERDMKINCSGKI
VIARYGKVFRGNKVKNAQLAGAKGVILYSDPADYFAPGVKSYPDGWNLPG
GGVQRGNILNLNGAGDPLTPGYPANEYAYRRGIAEAVGLPSIPVHPIGYY
DAQKLLEKMGGSAPPDSSWRGSLKVPYNVGPGFTGNFSTQKVKMHIHSTN
EVTRIYNVIGTLRGAVEPDRYVILGGHRDSWVFGGIDPQSGAAVVHEIVR
SFGTLKKEGWRPRRTILFASWDAEEFGLLGSTEWAEENSRLLQERGVAYI
NADSSIEGNYTLRVDCTPLMYSLVHNLTKELKSPDEGFEGKSLYESWTKK -continued

SPSPEFSGMPRISKLGSGNDFEVFFQRLGIASGRARYTKNWETNKFSGYP

LYHSVYETYELVEKFYDPMFKYHLTVAQVRGGMVFELANSIVLPFDCRDY

AVVLRKYADKIYSISMKHPQEMKTYSVSFDSLFSAVKNFTEIASKFSERL

QDFDKSNPIVLRMMNDQLMFLERAFIDPLGLPDRPFYRHVIYAPSSHNKY

AGESFPGIYDALFDIESKVDPSKAWGEVKRQIYVAAFTVQAAAETLSEVA

(21) the tyrosine protein kinase EPHA2 (Swiss Prot ID: P29317), SEQ ID NO: 233

>gi|32967311|ref|NP_004422.2|ephrin type-A receptor 2-precursor [*Homo sapiens*]

MELQAARACFALLWGCALAAAAAAQGKEVVLLDFAAAGGELGWLTHPYGK

GWDLMQNIMNDMPIYMYSVCNVMSGDQDNWLRTNWVYRGEAERIFIELKF

TVRDCNSFPGGASSCKETFNLYYAESDLDYGTNFQKRLFTKIDTIAPDEI

TVSSDFEARHVKLNVEERSVGPLTRKGFYLAFQDIGACVALLSVRVYYKK

CPELLQGLAHFPETIAGSDAPSLATVAGTCVDHAVVPPGGEEPRMHCAVD

GEWLVPIGQCLCQAGYEKVEDACQACSPGFFKFEASESPCLECPEHTLPS

PEGATSCECEEGFFRAPQDPASMPCTRPPSAPHYLTAVGMGAKVELRWTP

PQDSGGREDIVYSVTCEQCWPESGECGPCEASVRYSEPPHGLTRTSVTVS

DLEPHMNYTFTVEARNGVSGLVTSRSFRTASVSINQTEPPKVRLEGRSTT

SLSVSWSIPPPQQSRVWKYEVTYRKKGDSNSYNVRRTEGFSVTLDDLAPD

TTYLVQVQALTQEGQGAGSKVHEFQTLSPEGSGNLAVIGGVAVGVVLLLV

LAGVGFFIHRRRKNQRARQSPEDVYFSKSEQLKPLKTYVDPHTYEDPNQA

VLKFTTEIHPSCVTRQKVIGAGEFGEVYKGMLKTSSGKKEVPVAIKTLKA

GYTEKQRVDFLGEAGIMGQFSHHNIIRLEGVISKYKPMMIITEYMENGAL

DKFLREKDGEFSVLQLVGMLRGIAAGMKYLANMNYVHRDLAARNILVNSN

LVCKVSDFGLSRVLEDDPEATYTTSGGKIPIRWTAPEAISYRKFTSASDV

WSFGIVMWEVMTYGERPYWELSNHEVMKAINDGFRLPTPMDCPSAIYQLM

MQCWQQERARRPKFADIVSILDKLIRAPDSLKTLADFDPRVSIRLPSTSG

SEGVPFRTVSEWLESIKMQQYTEHFMAAGYTAIEKVVQMTNDDIKRIGVR

LPGHQKRIAYSLLGLKDQVNTVGIPI

(22) the surface protein SLC44A4 (Genbank Accession No: NP_001171515), SEQ ID NO: 234

>gi|295849282|ref|NP_001171515.1|choline transporter-like protein 4 isoform 2 [*Homo sapiens*]

MGGKQRDEDDEAYGKPVKYDPSFRGPIKNRSCTDVICCVLFLLFILGYIV

VGIVAWLYGDPRQVLYPRNSTGAYCGMGENKDKPYLLYFNIFSCILSSNI

ISVAENGLQCPTPQTVITSLQQELCPSFLLPSAPALGRCFPWTNVTPPAL

PGITNDTTIQQGISGLIDSLNARDISVKIFEDFAQSWYWILVALGVALVL

SLLFILLLRLVAGPLVLVLILGVLGVLAYGIYYCWEEYRVLRDKGASISQ

LGFTTNLSAYQSVQETWLAALIVLAVLEAILLLMLIFLRQRIRIAIALLK

EASKAVGQMMSTMFYPLVTFVLLLICIAYWAMTALYLATSGQPQYVLWAS

NISSPGCEKVPINTSCNPTAHLVNSSCPGLMCVFQGYSSKGLIQRSVFNL

-continued

QIYGVLGLFWTLNWVLALGQCVLAGAFASFYWAFHKPQDIPTFPLISAFI

RTLRYHTGSLAFGALILTLVQIARVILEYIDHKLRGVQNPVARCIMCCFK

CCLWCLEKFIKFLNRNAYIMIAIYGKNFCVSAKNAFMLLMRNIVRVVVLD

KVTDLLLFFGKLLVVGGVGVLSFFFFSGRIPGLGKDFKSPHLNYYWLPIM

TSILGAYVIASGFFSVFGMCVDTLFLCFLEDLERNNGSLDRPYYMSKSLL

KILGKKNEAPPDNKKRKK

(23) the surface protein BMPR1B (SwissProt: 000238)
(24) the transport protein SLC7A5 (SwissProt: Q01650)
(25) the epithelial prostate antigen STEAP1 (SwissProt: Q9UHE8)
(26) the ovarial carcinoma antigen MUC16 (SwissProt: Q8WXI7)
(27) the transport protein SLC34A2 (SwissProt: 095436)
(28) the surface protein SEMA5b (SwissProt: Q9P283)
(29) the surface protein LYPD1 (SwissProt: Q8N2G4)
(30) the endothelin receptor type B EDNRB (SwissProt: P24530)
(31) the ring finger protein RNF43 (SwissProt: Q68DV7)
(32) the prostate carcinoma-associated protein STEAP2 (SwissProt: Q8NFT2)
(33) the cation channel TRPM4 (SwissProt: Q8TD43)
(34) the complement receptor CD21 (SwissProt: P20023)
(35) the B-cell antigen receptor complex-associated protein CD79b (SwissProt: P40259)
(36) the cell adhesion antigen CEACAM6 (SwissProt: P40199)
(37) the dipeptidase DPEP1 (SwissProt: P16444)
(38) the interleukin receptor IL20Ralpha (SwissProt: Q9UHF4)
(39) the proteoglycan BCAN (SwissProt: Q96GW7)
(40) the ephrin receptor EPHB2 (SwissProt: P29323)
(41) the prostate stem cell-associated protein PSCA (Genbank Accession No: NP_005663.2)
(42) the surface protein LHFPL3 (SwissProt: Q86UP9)
(43) the receptor protein TNFRSF13C (SwissProt: Q96RJ3)
(44) the B-cell antigen receptor complex-associated protein CD79a (SwissProt: P11912)
(45) the receptor protein CXCR5 (SwissProt: P32302)
(46) the ion channel P2X5 (SwissProt: Q93086)
(47) the lymphocyte antigen CD180 (SwissProt: Q99467)
(48) the receptor protein FCRL1 (SwissProt: Q96LA6)
(49) the receptor protein FCRL5 (SwissProt: Q96RD9)
(50) the MHC class II molecule Ia antigen HLA-DOB (Genbank Accession No: NP_002111.1)
(51) the T-cell protein VTCN1 (SwissProt: Q7Z7D3)
(52) TWEAKR (SEQ ID NO:169 (protein); SEQ ID NO: 170 (DNA).
(53) the lymphocyte antigen CD37 (Swiss Prot: P11049)
(54) the FGF receptor 2; FGFR2 (Gene ID: 2263; Official Symbol: FGFR2), The FGFR2 receptor occurs in different splice variants (alpha, beta, IIIb, IIIc). All splice variants may act as target molecule.
(55) the transmembrane glycoprotein B7H3 (CD276; Gene ID: 80381)
(56) the B cell receptor BAFFR (CD268; Gene ID: 115650)
(57) the receptor protein ROR 1 (Gene ID: 4919)
(58) the surface receptor IL3RA (CD123; Gene ID: 3561)
(59) the CXC chemokine receptor CXCR5 (CD185; Gene ID 643)
(60) the receptor protein syncytin (Gene ID 30816)

In a preferred subject of the invention, the cancer target molecule is selected from the group consisting of the cancer target molecules (1)-(60), in particular (1), (6) and (52).

In a further particularly preferred subject of the invention, the binder binds to an extracellular cancer target molecule which is selected from the group consisting of the cancer target molecules (1)-(60), in particular (1), (6) and (52).

In a further particularly preferred subject of the invention, the binder binds specifically to an extracellular cancer target molecule which is selected from the group consisting of the cancer target molecules (1)-(60), in particular (1), (6) and (52). In a preferred embodiment the binder is, after binding to its extracellular target molecule on the target cell, internalized by the target cell as a result of the binding. This causes the binder-drug conjugate, which may be an immunoconjugate or an ADC, to be taken up by the target cell. The binder is then processed, preferably intracellularly, with preference lysosomally.

In one embodiment the binder is a binding protein. In a preferred embodiment the binder is an antibody, an aglycosylated antibody, an antigen-binding antibody fragment, a multispecific antibody or an antibody mimetic.

Preferred antibody mimetics are affibodies, adnectins, anticalins, DARPins, avimers, or nanobodies. Preferred multispecific antibodies are bispecific and trispecific antibodies.

In a preferred embodiment the binder is an antibody or an antigen-binding antibody fragment, more preferably an isolated antibody or an isolated antigen-binding antibody fragment.

Preferred antigen-binding antibody fragments are Fab, Fab', F(ab')2 and Fv fragments, diabodies, DAbs, linear antibodies and scFv. Particularly preferred are Fab, diabodies and scFv.

In a particularly preferred embodiment the binder is an antibody. Particularly preferred are monoclonal antibodies or antigen-binding antibody fragments thereof. Further particularly preferred are human, humanized or chimeric antibodies or antigen-binding antibody fragments thereof.

Antibodies or antigen-binding antibody fragments which bind cancer target molecules may be prepared by a person of ordinary skill in the art using known processes, such as, for example, chemical synthesis or recombinant expression. Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The person skilled in the art knows how processes such as phage display libraries (e.g. Morphosys HuCAL Gold) can be compiled and used for discovering antibodies or antigen-binding antibody fragments (see WO 2007/070538, page 24 ff and AK Example 1 on page 70, AK Example 2 on page 72). Further processes for preparing antibodies that use DNA libraries from B cells are described for example on page 26 (WO 2007/070538). Processes for humanizing antibodies are described on page 30-32 of WO2007070538 and in detail in Queen, et al., Pros. Natl. Acad. Sci. USA 8610029-10033, 1989 or in WO 90/0786. Furthermore, processes for the recombinant expression of proteins in general and of antibodies in particular are known to the person skilled in the art (see, for example, in Berger and Kimrnel (Guide to Molecular Cloning Techniques, Methods in Enzymology, Vol. A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et al. [Eds.], Current Protocols, Green Publishing Associates, Inc./John Wiley & Sons, Inc.); Harlow et al., (Monoclonal Antibodies: A Laboratory Manual, Cold Spring Harbor Laboratory Press (1988, Paul [Ed.]); Fundamental Immunology, (Lippincott Williams & Wilkins (1998)); and Harlow, et al., (Using Antibodies: A Laboratory Manual, Cold Spring Harbor Laboratory Press (1998)). The person skilled in the art knows the corresponding vectors, promoters and signal peptides which are necessary for the expression of a protein/antibody. Commonplace processes are also described in WO 2007/070538 on pages 41-45. Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The person skilled in the art is able to use the processes described in WO 2007/070538 that have been used for preparing carboanhydrase IX (Mn) antibodies in analogy for the preparation of antibodies with different target molecule specificity.

Anti-EGFR Antibodies

Examples of antibodies which bind the cancer target molecules EGFR are cetuximab (INN number 7906), panitumumab (INN number 8499) and nimotuzumab (INN number 8545). Cetuximab (Drug Bank Accession Number DB00002) is a chimeric anti-EGFR1 antibody which is produced in SP2/0 mouse myeloma cells and is sold by ImClone Systems Inc/Merck KgaA/Bristol-Myers Squibb Co. Cetuximab is indicated for the treatment of metastasizing, EGFR expressing, colorectal carcinoma with wild type K-Ras gene. It has an affinity of $10^{-10}$ M.

Sequence:

```
Cetuximab Light Chain (kappa), SEQ ID NO: 235:
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Cetuximab Heavy Chain, SEQ ID NO: 236:
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

Panitumumab (INN number 8499) (Drug Bank Accession Number DB01269) is a recombinant monoclonal human IgG2 antibody which binds specifically to the human EGF receptor 1 and is sold by Abgenix/Amgen. Panitumumab originates from the immunization of transgenic mice (XenoMouse). These mice are capable of producing human immunoglobulin (light and heavy chains). A specific B-cell clone was selected which produces antibodies against EGFR, and this clone was immortalized with CHO cells (Chinese hamster ovary cells). These cells are now used for the production of a 100% human antibody. Panitumumab is indicated for the treatment of EGFR-expressing, metastasizing colorectal carcinoma, which is resistant to chemotherapeutic treatment with fluoropyrimidine, oxaliplatin and irinotecan. It has an affinity of $10^{-11}$ M.

Sequence:

```
Panitumumab Light Chain (kappa), SEQ ID NO: 237:
DIQMTQSPSSLSASVGDRVTITCQASQDISNYLNWYQQKPGKAPKLLIYD

ASNLETGVPSRFSGSGSGTDFTFTISSLQPEDIATYFCQHFDHLPLAFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Panitumumab Heavy Chain, SEQ ID NO: 238:
QVQLQESGPGLVKPSETLSLTCTVSGGSVSSGDYYWTWIRQSPGKGLEWI

GHIYYSGNTNYNPSLKSRLTISIDTSKTQFSLKLSSVTAADTAIYYCVRD

RVTGAFDIWGQGTMVTVSSASTKGPSVFPLAPCSRSTSESTAALGCLVKD

YFPEPVTVSWNSGALTSGVHTFPAVLQSSGLYSLSSVVTVPSSNFGTQTY

TCNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPG
```

Nimotuzumab (INN number 8545) (EP 00586002, EP 00712863) is a humanized monoclonal IgG1 antibody which binds specifically to the human EGF receptor 1 and is sold by YM BioScienecs Inc. (Mississauga Canada). It is produced in non-secreting NSO cells (mammalian cell line). Nimotuzumab is approved for the treatment of head-and-neck tumours, highly malignant astrocytoma and glioblastoma multiforms (not in EU and US) and pancreatic carcinoma (Orphan drug, EMA). It has an affinity of $10^{-8}$ M.

```
Nimotuzumab light chain (SEQ ID NO: 239):
DIQMTQSPSSLSASVGDRVTITCRSSQNIVHSNGNTYLDWYQQTPGKAPK

LLIYKVSNRFSGVPSRFSGSGSGTDFTFTISSLQPEDIATYYCFQYSHVP

WTFGQGTKLQITRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Nimotuzumab heavy chain (SEQ ID NO: 240):
QVQLQQSGAEVKKPGSSVKVSCKASGYTFTNYYIYWVRQAPGQGLEWIGG

INPTSGGSNFNEKFKTRVTITADESSTTAYMELSSLRSEDTAFYFCTRQG

LWFDSDGRGFDFWGQGTTVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR
```

-continued

```
EPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLS

PGK
```

Further embodiments of EGFR antibodies are as follows:

zalutumumab/2F8/HuMax-EGFr, from Genmab A/S (WO 02/100348, WO 2004/056847, INN number 8605)

necitumumab/11F8, ImClone/IMC-11F8, from ImClone Systems Inc. [Eli Lilly & Co](WO 2005/090407 (EP 01735348-A1, US 2007/0264253-A1, U.S. Pat. No. 7,598,350, WO 2005/090407-A1), INN number 9083)

matuzumab/anti-EGFR MAb, Merck KGaA/anti-EGFR MAb, Takeda/EMD 72000/EMD-6200/EMD-72000 and EMD-55900/MAb 425/monoclonal antibody 425, from Merck KGaA/Takeda (WO 92/15683, INN number 8103 (Matuzumab))

RG-7160/GA-201/GA201/R-7160/R7160/RG7160/RO-4858696/RO-5083945/R04858696/R05083945, from Glycart Biotechnology AG (Roche Holding AG) (WO 2010/112413-A1, WO 2010/115554)

GT-MAB 5.2-GEX/CetuGEX, from Glycotope GmbH (WO 2008/028686-A2 (EP 01900750-A1, EP 01911766-A1, EP 02073842-A2, US 2010/0028947-A1)

ISU-101, from Isu Abxis Inc (ISU Chemical Co Ltd)/Scancell (WO 2008/004834-A1)

ABT-806/mAb-806/ch-806/anti-EGFR monoclonal antibody 806, from Ludwig Institute for Cancer Research/Abbott/Life Science Pharmaceuticals (WO 02/092771, WO 2005/081854 and WO 2009/023265)

SYM-004 (consists of two chimeric IgG1 antibodies (992 and 1024)), from Symphogen A/S (WO 2010/022736-A2)

MR1-1/MR1-1KDEL, from IVAX Corp (Teva Pharmaceutical Industries Ltd) (Duke University), (patent: WO2001/062931-A2)

Antibody against the deletion mutant, EGFRvIII, from Amgen/Abgenix (WO 2005/010151, U.S. Pat. No. 7,628,986)

SC-100, from Scancell Ltd (WO 01/088138-A1)

MDX-447/EMD 82633/BAB-447/H 447/MAb, EGFR, Medarex/Merck KgaA, from Bristol-Myers Squibb (US)/Merck KGaA (DE)/Takeda (JP), (WO 91/05871, WO 92/15683)

anti-EGFR-Mab, from Xencor (WO 2005/056606)

DXL-1218/anti-EGFR monoclonal antibody (cancer), InNexus, from InNexus Biotechnology Inc, Pharmaprojects PH048638

In a preferred embodiment, the anti-EGFR antibodies are selected from the group consisting of cetuximab, panitumumab, nimotuzumab, zalutumumab, necitumumab, matuzumab, RG-716, GT-MAB 5.2-GEX, ISU-101, ABT-806, SYM-004, MR1-1, SC-100, MDX-447 and DXL-1218.

In a particularly preferred embodiment the anti-EGFR antibodies are selected from the group consisting of cetuximab, panitumumab, nimotuzumab, zalutumumab, necitumumab and matuzumab.

The person skilled in the art knows of processes which can be used to prepare further antibodies, from the CDR regions of the abovementioned antibodies by means of sequence variations, these further antibodies having a similar or better affinity and/or specificity for the target molecule.

In a further embodiment, the anti-EGFR antibodies or antigen-binding antibody fragments are selected from the group consisting of antibodies or antigen-binding antibody fragments comprising three CDR regions of the light chain and the three CDR regions of the heavy chain of one of the following antibodies: cetuximab, panitumumab, nimotuzumab, zalutumumab, necitumumab, matuzumab, RG-716, GT-MAB 5.2-GEX, ISU-101, ABT-806, SYM-004, MR1-1, SC-100, MDX-447 and DXL-1218.

In a further embodiment, the anti-EGFR antibodies or antigen-binding antibody fragments are selected from the group consisting of antibodies or antigen-binding antibody fragments comprising three CDR regions of the light chain and the three CDR regions of the heavy chain of one of the following antibodies: cetuximab, panitumumab, nimotuzumab, zalutumumab, necitumumab, matuzumab. By reference, these antibodies and antigen-binding fragments thereof are incorporated herein, and they can be used in the context of the present invention.

Anti-Carboanhydrase IX Antibodies

Examples of antibodies which bind the cancer target molecule carbonahydrase IX are described in WO 2007/070538-A2 (e.g. Claims 1-16).

In a preferred embodiment the anti-carboanhydrase IX antibodies or antigen-binding antibody fragments are selected from the group consisting of anti-carboanhydrase IX antibodies or antigen-binding antibody fragments 3ee9 (Claim 4 (a) in WO 2007/070538-A2), 3ef2 (Claim 4 (b) in WO2007/070538-A2), 1e4 (Claim 4 (c) in WO 2007/070538-A2), 3a4 (Claim 4 (d) in WO 2007/070538-A2), 3ab4 (Claim 4 (e) in WO 2007/070538-A2), 3ah10 (Claim 4 (f) in WO 2007/070538-A2), 3bb2 (Claim 4 (g) in WO 2007/070538-A2), 1aa1 (Claim 4 (h) in WO 2007/070538-A2), 5a6 (Claim 4 (i) in WO 2007/070538-A2) and 5aa3 (Claim 4 (j) in WO 2007/070538-A2).

Anti-C4.4a Antibodies:

According to the invention, use may be made of C4.4a antibodies.

Examples of C4.4a antibodies and antigen-binding fragments are described in WO 2012/143499 A2. By reference, all antibodies of WO 2012/143499 A2 are hereby incorporated into the description of the present invention, and they can be used in the present invention. The sequences of the antibodies are given in Table 1 of WO 2012/143499 A2, where each row shows the respective CDR amino acid sequences of the variable light chain or the variable heavy chain of the antibody listed in column 1.

In one embodiment, the anti-C4.4a antibodies or antigen-binding antibody fragments thereof are, after binding to a cell expressing C4.4a, internalized by the cell.

In a further embodiment, the anti-C4.4a antibodies or antigen-binding antibody fragments comprise at least one, two or three CDR amino acid sequences of an antibody listed in Table 1 of WO 2012/143499 A2 or Table 2 of WO 2012/143499 A2. Preferred embodiments of such antibodies are likewise listed in WO 2012/143499 A2 and incorporated herein by reference.

Anti-HER2 Antibodies

An example of an antibody binding to the cancer target molecule Her2 is trastuzumab (Genentech). Trastuzumab is a humanized antibody used inter alia for the treatment of breast cancer.

Further examples of antibodies binding to HER2 are, in addition to trastuzumab (INN 7637, CAS No.: RN: 180288-69-1) and Pertuzumab (CAS No.: 380610-27-5), the antibodies disclosed in WO 2009/123894-A2, WO 200/8140603-A2 or in WO 2011/044368-A2. An example of an anti-HER2 conjugate is trastuzumab-emtansine (INN-No. 9295). By reference, these antibodies and antigen-binding fragments thereof are incorporated herein, and they can be used in the context of the present invention. In addition, it is possible to use aglycosylated variants of trastuzumab which are produced either by deglycosylation by PNGaseF or by mutation of N297 (Kabat numbering) of the heavy chain to any amino acid. In addition, it is also possible to use variants of the antibodies which have been engineered to contain one or more acceptor glutamines for transglutaminase-mediated reactions.

Anti-CD20 Antibodies

An example of an antibody binding to the cancer target molecule CD20 is rituximab (Genentech). Rituximab (CAS Number: 174722-31-7) is a chimeric antibody used for the treatment of non-Hodgkin's lymphoma. By reference, these antibodies and antigen-binding fragments thereof are incorporated herein, and they can be used in the context of the present invention.

Anti-CD52 Antibodies

An example of an antibody binding to the cancer target molecule CD52 is alemtuzumab (Genzyme). Alemtuzumab (CAS Number: 216503-57-0) is a humanized antibody used for the treatment of chronic lymphocytic leukaemia. By reference, these antibodies and antigen-binding fragments thereof are incorporated herein, and they can be used in the context of the present invention.

Anti-Mesothelin Antibodies:

Examples of anti-mesothelin antibodies are described, for example, in WO 2009/068204. By reference, all antibodies described in WO 2009/068204 are hereby incorporated into the present description, such that these antibodies can be used in the context of the invention disclosed herein.

The anti-mesothelin antibodies used in accordance with the invention are also notable preferably for an invariant binding to mesothelin. Invariant binding is characterized, for example, in that the antibody used in accordance with the invention binds to an epitope of mesothelin which cannot be masked by a further extracellular protein. Such a further extracellular protein is, for example, the protein ovarian cancer antigen 125 (CA125). Antibodies which are used with preference are characterized in that their binding to mesothelin is not blocked by CA125.

Anti-CD30 Antibodies

Examples of antibodies which bind the cancer target molecule CD30 and can be used for the treatment of cancer, for example Hodgkin's lymphoma, are brentuximab, iratumumab and antibodies disclosed in WO 2008/092117, WO 2008/036688 or WO 2006/089232. An example of an anti-CD30 conjugate is brentuximab vedotin (INN No. 9144). By reference, these antibodies and antigen-binding fragments thereof are incorporated herein, and they can be used in the context of the present invention.

Anti-CD22 Antibodies

Examples of antibodies which bind the cancer target molecule CD22 and can be used for the treatment of cancer, for example lymphoma, are inotuzumab and epratuzumab. Examples of anti-CD22 conjugates are inotuzumab ozagamycin (INN No. 8574) or anti-CD22-MMAE and anti-CD22-MC-MMAE (CAS RN: 139504-50-0 and 474645-27-7, respectively). By reference, these antibodies and antigen-binding fragments thereof are incorporated herein, and they can be used in the context of the present invention.

Anti-CD33 Antibodies

Examples of antibodies which bind the cancer target molecule CD33 and can be used for the treatment of cancer, for example leukaemia, are gemtuzumab and lintuzumab (INN 7580). An example of an anti-CD33 conjugate is gemtuzumab-ozagamycin. By reference, these antibodies and antigen-binding fragments thereof are incorporated herein, and they can be used in the context of the present invention.

Anti-NMB Antibodies

An example of an antibody which binds the cancer target molecule NMB and can be used for the treatment of cancer, for example melanoma or breast cancer, is glembatumumab (INN 9199). An example of an anti-NMB conjugate is glembatumumab vedotin (CAS RN: 474645-27-7). By reference, these antibodies and antigen-binding fragments thereof are incorporated herein, and they can be used in the context of the present invention.

Anti-CD56 Antibodies

An example of an antibody which binds the cancer target molecule CD56 and can be used for the treatment of cancer, for example multiple myeloma, small-cell lung carcinoma, MCC or ovarial carcinoma is lorvotuzumab. An example of an anti-CD57 conjugate is lorvotuzumab mertansine (CAS RN: 139504-50-0). By reference, these antibodies and antigen-binding fragments thereof are incorporated herein, and they can be used in the context of the present invention.

Anti-CD70 Antibodies

Examples of antibodies which bind the cancer target molecule CD70 and can be used for the treatment of cancer, for example non-Hodgkin's lymphoma or renal cell cancer, are disclosed in WO 2007/038637-A2 and WO 2008/070593-A2. An example of an anti-CD70 conjugate is SGN-75 (CD70 MMAF). By reference, these antibodies and antigen-binding fragments thereof are incorporated herein, and they can be used in the context of the present invention.

Anti-CD74 Antibodies

An example of an antibody which binds the cancer target molecule CD74 and can be used for the treatment of cancer, for example multiple myeloma, is milatuzumab. An example of an anti-CD74 conjugate is milatuzumab-doxorubicin (CAS RN: 23214-92-8). By reference, these antibodies and antigen-binding fragments thereof are incorporated herein, and they can be used in the context of the present invention.

Anti-CD19 Antibodies

An example of an antibody which binds the cancer target molecule CD19 and can be used for the treatment of cancer, for example non-Hodgkin's lymphoma, is disclosed in WO 2008/031056-A2. Further antibodies and examples of an anti-CD19 conjugate (SAR3419) are disclosed in WO 2008/047242-A2. By reference, these antibodies and antigen-binding fragments thereof are incorporated herein, and they can be used in the context of the present invention.

Anti-Mucin Antibodies

Examples of antibodies which bind the cancer target molecule mucin-1 and can be used for the treatment of cancer, for example non-Hodgkin's lymphoma, are clivatuzumab and the antibodies disclosed in WO 2003/106495-A2, WO 2008/028686-A2. Examples of anti-mucin conjugates are disclosed in WO 2005/009369-A2. By reference, these antibodies and antigen-binding fragments thereof are incorporated herein, and they can be used in the context of the present invention.

Anti-CD138 Antibodies

Examples of antibodies which bind the cancer target molecule CD138 and conjugates thereof, which can be used for the treatment of cancer, for example multiple myeloma, are disclosed in WO 2009/080829-A1, WO 2009/080830-A1. By reference, these antibodies and antigen-binding fragments thereof are incorporated herein, and they can be used in the context of the present invention.

Anti-Integrin-Alpha V Antibodies

Examples of antibodies which bind the cancer target molecule integrin alphaV and can be used for the treatment of cancer, for example melanoma, sarcoma or carcinoma, are intetumumab (CAS RN: 725735-28-4), abciximab (CAS RN: 143653-53-6), etaracizumab (CAS RN: 892553-42-3) and the antibodies disclosed in U.S. Pat. No. 7,465,449, EP 719859-A1, WO 2002/012501-A1 and WO2006/062779-A2. Examples of anti-integrin AlphaV conjugates are intetumumab-DM4 and other ADCs disclosed in WO 2007/024536-A2. By reference, these antibodies and antigen-binding fragments thereof are incorporated herein, and they can be used in the context of the present invention.

Anti-TDGF1 Antibodies

Examples of antibodies which bind the cancer target molecule TDGF1 and can be used for the treatment of cancer are the antibodies disclosed in WO 02/077033-A1, U.S. Pat. No. 7,318,924, WO 2003/083041-A2 and WO 2002/088170-A2. Examples of anti-TDGF1 conjugates are disclosed in WO 2002/088170-A2. By reference, these antibodies and antigen-binding fragments thereof are incorporated herein, and they can be used in the context of the present invention.

Anti-PSMA Antibodies

Examples of antibodies which bind the cancer target molecule PSMA and can be used for the treatment of cancer, for example prostate carcinoma, are the antibodies disclosed in WO 97/35616-A1, WO 99/47554-A1, WO 01/009192-A1 and WO2003/034903. Examples of anti-PSMA conjugates are disclosed in WO 2009/026274-A1 and WO 2007/002222. By reference, these antibodies and antigen-binding fragments thereof are incorporated herein, and they can be used in the context of the present invention.

Anti-EPHA2 Antibodies

Examples of antibodies which bind the cancer target molecule EPHA2 and can be used for preparing a conjugate and for the treatment of cancer are disclosed in WO 2004/091375-A2. By reference, these antibodies and antigen-binding fragments thereof are incorporated herein, and they can be used in the context of the present invention.

Anti-SLC44A4 Antibodies

Examples of antibodies which bind the cancer target molecule SLC44A4 and can be used for preparing a conjugate and for the treatment of cancer, for example pancreas or prostate carcinoma, are disclosed in WO2009/033094-A2 and US2009/0175796-A1. By reference, these antibodies and antigen-binding fragments thereof are incorporated herein, and they can be used in the context of the present invention.

Anti-HLA-DOB Antibodies

An example of an antibody binding to the cancer target molecule HLA-DOB is the antibody Lym-1 (CAS RN: 301344-99-0) which can be used for the treatment of cancer, for example non-Hodgkin's lymphoma. Examples of anti-HLA-DOB conjugates are disclosed, for example, in WO 2005/081711-A2. By reference, these antibodies and antigen-binding fragments thereof are incorporated herein, and they can be used in the context of the present invention.

Anti-VTCN1 Antibodies

Examples of antibodies which bind the cancer target molecule VTCN1 and can be used for preparing a conjugate and for the treatment of cancer, for example ovarial carcinoma, pancreas, lung or breast cancer, are disclosed in WO 2006/074418-A2. By reference, these antibodies and antigen-binding fragments thereof are incorporated herein, and they can be used in the context of the present invention.

Anti-FGFR2 Antibodies

According to the invention, use may be made of anti-FGFR2 antibodies.

Examples of anti-FGFR2 antibodies and antigen-binding fragments are described in WO2013076186. By reference, all antibodies of WO2013076186 are hereby incorporated into the description of the present invention, and they can be used in the present invention. The sequences of the antibodies are shown in Table 9 and Table 10 of WO2013076186. Preference is given to antibodies, antigen-binding fragments and variants of the antibodies derived from the antibodies referred to as M048-D01 and M047-D08. Preferred anti-FGFR2 bind to the various splice variants known of FGFR2.

In one embodiment, the anti-FGFR2 antibodies or antigen-binding antibody fragments thereof are, after binding to a cell expressing FGFR2, internalized by the cell.

In a further embodiment, the anti-FGFR2 antibodies or antigen-binding antibody fragments comprise at least one, two or three CDR amino acid sequences of an antibody listed in Table 9 or Table 10 of WO2013076186. Preferred embodiments of such antibodies are likewise listed in WO2013076186 and incorporated herein by reference.

Anti-TWEAKR Antibodies

In a preferred embodiment, when an anti-TWEAKR antibody or an antigen-binding fragment thereof is used in the processes according to the present invention, this antibody or fragment is selected from those described below (likewise published in WO2014/199817 (A1)). In addition, antibodies which bind to TWEAKR are known to the person skilled in the art, see, for example, WO2009/020933(A2) or WO2009140177 (A2). In addition, it is possible to use aglycosylated variants of the anti-TWEAKR antibodies described, which are produced either by deglycosylation by PNGaseF or by mutation of N297 (Kabat numbering) of the heavy chain to any amino acid. In addition, it is also possible to use variants of the antibodies which have been engineered to contain one or more acceptor glutamines for transglutaminase-mediated reactions.

The invention relates in particular to conjugates with antibodies or antigen-binding antibody fragments thereof or variants thereof which lead to strong activation of the TWEAKR (SEQ ID NO: 169 (protein); SEQ ID NO: 170 (DNA)), resulting in a strong induction of apoptosis in various cancer cells overexpressing TWEAKR.

The agonistic activity of TWEAKR with regard to the induction of apoptosis and inhibition of the proliferation of the anti-TWEAKR antibodies already described (e.g. PDL-192) is limited and does not reach the efficacy of the endogenous ligand TWEAK. This lack of agonistic activity is not based on reduced affinity, since these antibodies bind at the TWEAKR with affinities which, compared to the endogenous ligand TWEAK, are in a similar range (Michaelson J S et al, MAbs. 2011 July-August; 3(4):362-75; Culp P A et al, Clin Cancer Res. 2010 Jan. 15; 16(2):497-508), and even antibodies having a higher binding affinity do not necessarily display a more effective signalling activity (Culp P A, et al, Clin Cancer Res. 2010 Jan. 15; 16(2):497-508). In addition, it has been shown that the antitumour activity of the antibodies already described depends on the Fc effector function, and it was shown that ADCC plays an important role for the in-vivo efficacy in mouse models.

Generation of the Anti-TWEAKR Antibodies

A complete human antibody phage library (Hoet R M et al, Nat Biotechnol 2005; 23(3):344-8) was employed to isolate TWEAKR-specific human monoclonal antibodies of the present invention by protein panning (Hoogenboom H. R., Nat Biotechnol 2005; 23(3):1105-16) using dimeric Fc-fused extracellular domains of human and mouse TWEAKR as immobilized target. 11 different Fab phages were identified, and the corresponding antibodies were cloned into a mammalian EgG expression vector which provides the CH2-CH3 domains missing in the soluble FAb. Following identification of preferred antibodies, these were expressed as full-length IgGs. Aglycosylated variants of the antibodies described have been produced by introducing the mutations N297A or N297Q in the heavy chain of the respective antibodies. These constructs were expressed, for example, transiently in mammalian cells as described by Tom et al., Chapter 12 in Methods Express: Expression Systems edited by Micheal R. Dyson and Yves Durocher, Scion Publishing Ltd, 2007 (see AK-Example 1). The antibodies were purified by protein-A chromatography and characterized further by their binding affinity to soluble monomeric TWEAKR using ELISA and BIAcore analysis, as described in AK-Example 2. To determine the cell binding characteristics of the anti-TWEAKR antibodies, binding was tested by flow cytometry on a number of cell lines (HT29, HS68, HS578). NFκB reporter gene assays were carried out to examine the agonistic activity of all 11 antibodies identified (human IgG1). The antibody having the highest in vitro activity (TPP-883) was selected for further activity and affinity maturation (see AK-Example 1 for details). A single substitution variant having improved agonistic activity was detected: G102T of CDR-H3. Lastly, 7 variants were selected on the basis of the elevated affinity compared to the best single substitution variant G102T. The corresponding DNA thereof was cloned into a mammalian IgG expression vector and examined for functional activity in the NF-kappaB reporter gene assay mentioned above. Lastly, the sequences obtained were compared with human germ line sequences, and deviations without any significant effect on the affinity and the efficacy were adapted. The following antibodies were obtained by antibody library screening and by affinity and/or activity maturation: "TPP-2090", "TPP-2149", "TPP-2093", "TPP-2148", "TPP-2084", "TPP-2077", "TPP-1538", "TPP-883", "TPP-1854", "TPP-1853", "TPP-1857", and "TPP-1858".

Antibodies of the invention can furthermore be obtained by methods known in the art such as antibody phage display screening (see, for example, Hoet R M et al., Nat Biotechnol 2005; 23(3):344-8), the well-established hybridoma technology (see, for example, Köhler and Milstein Nature. 1975 Aug. 7; 256(5517):495-7) or immunization of mice, inter alia immunization of hMAb mice (e.g. VelocImmune Mouse®).

Particular Embodiments of Anti-TWEAKR Antibodies

One embodiment of the invention is the provision of antibodies or antigen-binding antibody fragments thereof or variants thereof showing strong induction of caspase 3/7 in one or more TWEAKR-expressing cell lines. In a preferred embodiment, the one or more TWEAKR-expressing cell line(s) is/are present in the group consisting of WiDr, A253, NCI-H322, HT29 and 786-0. "Induction of caspase 3/7" can be measured by customary methods known in the art, including those described herein. In one embodiment, the "induction of caspase 3/7" is determined in accordance with the present invention using the activity determination with capase 3/7 solution (Promega, #G8093) and reading the luminescence on a VICTOR V (Perkin Elmer). At the end of the incubation time, the caspase 3/7 activity was determined and the induction factor of caspase 3/7 was determined in comparison to untreated cells. An antibody is said to show "strong induction" of caspase 3/7 when the induction factor is greater than 1.2, preferably greater than 1.5, even more preferably greater than 1.8, even more preferably greater than 2.1, even more preferably greater than 2.5. What is provided are anti-TWEAKR antibodies leading to stronger induction of caspase 3/7 in HT29 cells compared to agonistic antibodies already described [e.g. PDL-192(TPP-1104), P4A8(TPP-1324), 136.1(TPP-2194)] and also compared to 300 ng/ml recombinant human TWEAK. This strong activity of inducing caspase 3/7 in cancer cells was also observed in WiDr, A253, NIC-H322 and 786-0 cells where in most experiments the antibodies of the invention examined induced higher factors of change compared to the reference antibodies [PDL-192(TPP-1104), P4A8(TPP-1324)] and to 300 ng/ml TWEAK. Some antibodies of the invention bind to the TWEAKR only with moderate affinity (>10 nM) which is clearly less than the affinity of the endogenous ligand TWEAK, and also less compared to other known agonistic antibodies. This property offers further possible advantages such as, for example, potentially deeper penetration into the tumour.

In this regard, one embodiment of the invention is the provision of antibodies or antigen-binding antibody fragments thereof binding specifically to a TWEAKR at a novel epitope characterized by selective binding to aspartate (D) at position 47 (D47) of TWEAKR (SEQ ID NO:169; see also FIG. 1). The dependencies identified for certain TWEAKR amino acids for antibody interaction correlate with the agonistic activity determined for these antibodies. The native ligand TWEAK shows an effective activation of the TWEAKR and binds depending on leucine 46 in the cysteine-rich domain of TWEAKR (Pellegrini et al, FEBS 280: 1818-1829). P4A8 displays a very low agonistic activity and interacts at least partially with domains outside of the cysteine-rich domain of TWEAKR. PDL-192 displays a moderate agonistic activity and binds depending on R56 to the cysteine-rich domain, but opposite the TWEAK ligand site. Antibodies of the present invention (e.g. TPP-2090) bind depending on D47, and TWEAK binds depending on L46. Thus, TWEAK binds to a similar but different binding site (FIG. 7). Accordingly, the antibodies of the present invention displaying strong agonistic activity bind to a novel epitope (D47-dependent) for antibodies which is connected to very high agonistic activity.

The amino acid at position 47 (D47) of TWEAKR (SEQ ID NO:169) is considered to be critical for binding of the antibodies according to the invention, which means that the antibody binds specifically to the D at position 47 (D47) of TWEAKR (SEQ ID NO:169) when the antibody loses more than 20%, alternatively more than 30%, alternatively more than 40%, alternatively more than 50%, alternatively more than 60%, alternatively more than 70%, alternatively more than 80%, alternatively more than 90%, alternatively 100% of its ELISA signal by modification of this residue into alanine, as described in AK-Example 2. Alternatively, an antibody binds specifically to the D at position 47 (D47) of TWEAKR (SEQ ID NO:169) when the antibody loses more than 20%, alternatively more than 30%, alternatively more than 40%, alternatively more than 50%, alternatively more than 60%, alternatively more than 70%, alternatively more than 80%, alternatively more than 90%, alternatively 100% of its ELISA signal for TPP-2614 compared to TPP-2203. Preferably, an antibody binds specifically to the D at position 47 (D47) of TWEAKR (SEQ ID NO:169) when the antibody loses more than 80% of its ELISA signal for TPP-2614 compared to TPP-2203.

In the present application, reference is made to the following preferred antibodies of the invention, as shown in the table below: "TPP-2090", "TPP-2149", "TPP-2093", "TPP-2148", "TPP-2084", "TPP-2077", "TPP-1538", "TPP-883", "TPP-1854", "TPP-1853", "TPP-1857", "TPP-1858; "TPP-2658")".

TABLE

Protein sequences of the antibodies:

| | SEQ ID NO: IgG1 light chain | SEQ ID NO: IgG1 heavy chain | SEQ ID NO: L-CDR1 | SEQ ID NO: L-CDR2 | SEQ ID NO: L-CDR3 | SEQ ID NO: H-CDR1 | SEQ ID NO: H-CDR2 | SEQ ID NO: H-CDR3 | SEQ ID NO: VL protein | SEQ ID NO: VH protein |
|---|---|---|---|---|---|---|---|---|---|---|
| TPP-2090 | 1 | 2 | 3 | 4 | 5 | 6 | 7 | 8 | 9 | 10 |
| TPP-2149 | 11 | 12 | 13 | 14 | 15 | 16 | 17 | 18 | 19 | 20 |
| TPP-2093 | 21 | 22 | 23 | 24 | 25 | 26 | 27 | 28 | 29 | 30 |
| TPP-2148 | 31 | 32 | 33 | 34 | 35 | 36 | 37 | 38 | 39 | 40 |
| TPP-2084 | 41 | 42 | 43 | 44 | 45 | 46 | 47 | 48 | 49 | 50 |
| TPP-2077 | 51 | 52 | 53 | 54 | 55 | 56 | 57 | 58 | 59 | 60 |
| TPP-1538 | 61 | 62 | 63 | 64 | 65 | 66 | 67 | 68 | 69 | 70 |
| TPP-883 | 71 | 72 | 73 | 74 | 75 | 76 | 77 | 78 | 79 | 80 |
| TPP-1854 | 81 | 82 | 83 | 84 | 85 | 86 | 87 | 88 | 89 | 90 |
| TPP-1853 | 91 | 92 | 93 | 94 | 95 | 96 | 97 | 98 | 99 | 100 |
| TPP-1857 | 101 | 102 | 103 | 104 | 105 | 106 | 107 | 108 | 109 | 110 |
| TPP-1858 | 111 | 112 | 113 | 114 | 115 | 116 | 117 | 118 | 119 | 120 |
| TPP-2658 | 1 | 241 | 3 | 4 | 5 | 6 | 7 | 8 | 9 | 10 |

TABLE-continued

| Protein sequences of the antibodies: | | | | | | | | | | |
|---|---|---|---|---|---|---|---|---|---|---|
| | SEQ ID NO: IgG1 light chain | SEQ ID NO: IgG1 heavy chain | SEQ ID NO: L-CDR1 | SEQ ID NO: L-CDR2 | SEQ ID NO: L-CDR3 | SEQ ID NO: H-CDR1 | SEQ ID NO: H-CDR2 | SEQ ID NO: H-CDR3 | SEQ ID NO: VL protein | SEQ ID NO: VH protein |
| TPP-5442 | 1 | 242 | 3 | 4 | 5 | 6 | 7 | 8 | 9 | 10 |
| TPP-8825 | 1 | 243 | 3 | 4 | 5 | 6 | 7 | 8 | 9 | 10 |

TPP-2090 is: an antibody which comprises a region of the heavy chain corresponding to SEQ ID NO: 2 and a region of the light chain corresponding to SEQ ID NO: 1.
TPP-2658 is: an antibody which comprises a region of the heavy chain corresponding to SEQ ID NO: 241 and a region of the light chain corresponding to SEQ ID NO: 1.
TPP-5442 is: an antibody which comprises a region of the heavy chain corresponding to SEQ ID NO: 242 and a region of the light chain corresponding to SEQ ID NO: 1.
TPP-8825: is an antibody which comprises a region of the heavy chain corresponding to SEQ ID NO: 243 and a region of the light chain corresponding to SEQ ID NO: 1.
TPP-2149 is: an antibody which comprises a region of the heavy chain corresponding to SEQ ID NO: 12 and a region of the light chain corresponding to SEQ ID NO: 11.
TPP-2093 is: an antibody which comprises a region of the heavy chain corresponding to SEQ ID NO: 22 and a region of the light chain corresponding to SEQ ID NO: 21.
TPP-2148 is: an antibody which comprises a region of the heavy chain corresponding to SEQ ID NO: 32 and a region of the light chain corresponding to SEQ ID NO: 31.
TPP-2084 is: an antibody which comprises a region of the heavy chain corresponding to SEQ ID NO: 42 and a region of the light chain corresponding to SEQ ID NO: 41.
TPP-2077 is: an antibody which comprises a region of the heavy chain corresponding to SEQ ID NO: 52 and a region of the light chain corresponding to SEQ ID NO: 51.
TPP-1538 is: an antibody which comprises a region of the heavy chain corresponding to SEQ ID NO: 62 and a region of the light chain corresponding to SEQ ID NO: 61.
TPP-883 is: an antibody which comprises a region of the heavy chain corresponding to SEQ ID NO: 72 and a region of the light chain corresponding to SEQ ID NO: 71.
TPP-1854 is: an antibody which comprises a region of the heavy chain corresponding to SEQ ID NO: 82 and a region of the light chain corresponding to SEQ ID NO: 81.
TPP-1853 is: an antibody which comprises a region of the heavy chain corresponding to SEQ ID NO: 92 and a region of the light chain corresponding to SEQ ID NO: 91.
TPP-1857 is: an antibody which comprises a region of the heavy chain corresponding to SEQ ID NO: 102 and a region of the light chain corresponding to SEQ ID NO: 101.
TPP-1858 is: an antibody which comprises a region of the heavy chain corresponding to SEQ ID NO: 112 and a region of the light chain corresponding to SEQ ID NO: 111.
TPP-2090 is: an antibody which comprises a variable region of the heavy chain corresponding to SEQ ID NO: 10 and a variable region of the light chain corresponding to SEQ ID NO: 9.
TPP-2658 is: an antibody which comprises a variable region of the heavy chain corresponding to SEQ ID NO: 10 and a variable region of the light chain corresponding to SEQ ID NO: 9.
TPP-5442 is: an antibody which comprises a variable region of the heavy chain corresponding to SEQ ID NO: 10 and a variable region of the light chain corresponding to SEQ ID NO: 9.
TPP-8825 is: an antibody which comprises a variable region of the heavy chain corresponding to SEQ ID NO: 10 and a variable region of the light chain corresponding to SEQ ID NO: 9.
TPP-2149 is: an antibody which comprises a variable region of the heavy chain corresponding to SEQ ID NO: 20 and a variable region of the light chain corresponding to SEQ ID NO: 19.
TPP-2093 is: an antibody which comprises a variable region of the heavy chain corresponding to SEQ ID NO: 30 and a variable region of the light chain corresponding to SEQ ID NO: 29.
TPP-2148: is an antibody which comprises a variable region of the heavy chain corresponding to SEQ ID NO: 40 and a variable region of the light chain corresponding to SEQ ID NO: 39.
TPP-2084: is an antibody which comprises a variable region of the heavy chain corresponding to SEQ ID NO: 50 and a variable region of the light chain corresponding to SEQ ID NO: 49.
TPP-2077: is an antibody which comprises a variable region of the heavy chain corresponding to SEQ ID NO: 60 and a variable region of the light chain corresponding to SEQ ID NO: 59.
TPP-1538: is an antibody which comprises a variable region of the heavy chain corresponding to SEQ ID NO: 70 and a variable region of the light chain corresponding to SEQ ID NO: 69.
TPP-883: is an antibody which comprises a variable region of the heavy chain corresponding to SEQ ID NO: 80 and a variable region of the light chain corresponding to SEQ ID NO: 79.
TPP-1854: is an antibody which comprises a variable region of the heavy chain corresponding to SEQ ID NO: 90 and a variable region of the light chain corresponding to SEQ ID NO: 89.
TPP-1853: is: an antibody which comprises a variable region of the heavy chain corresponding to SEQ ID NO: 100 and a variable region of the light chain corresponding to SEQ ID NO: 99.
TPP-1857: is an antibody which comprises a variable region of the heavy chain corresponding to SEQ ID NO: 110 and a variable region of the light chain corresponding to SEQ ID NO: 109.
TPP-1858: is an antibody which comprises a variable region of the heavy chain corresponding to SEQ ID NO: 120 and a variable region of the light chain corresponding to SEQ ID NO: 119.

TABLE

| DNA sequences of the antibodies | | |
|---|---|---|
| Antibody | SEQ ID NO: IgG1 light chain | SEQ ID NO: IgG1 heavy chain |
| Antibodies according to the invention: | | |
| TPP-2090 | 177 | 178 |
| TPP-2149 | 179 | 180 |
| TPP-2093 | 181 | 182 |
| TPP-2148 | 183 | 184 |
| TPP-2084 | 185 | 186 |
| TPP-2077 | 187 | 188 |
| TPP-1538 | 189 | 190 |
| TPP-883 | 191 | 192 |
| TPP-1854 | 193 | 194 |
| TPP-1853 | 195 | 196 |
| TPP-1857 | 197 | 198 |
| TPP-1858 | 199 | 200 |

Preferred embodiments of the anti-TWEAKR antibody are those below:

An aglycosylated anti-TWEAKR antibody or an antigen-binding fragment thereof which binds specifically to the D at position 47 (D47) of the TWEAKR (SEQ ID NO: 169).

The antibody or an antigen-binding fragment thereof according to embodiment 1 where the antibody is an agonistic antibody.

The antibody or an antigen-binding fragment thereof according to embodiment 1 or 2 which comprises:

a variable heavy chain comprising:

a CDR1 of the heavy chain encoded by an amino acid sequence comprising the formula PYPMX (SEQ ID NO: 171), where X is I or M;

a CDR2 of the heavy chain encoded by an amino acid sequence comprising the formula YISPSGGXTHYADSVKG (SEQ ID NO: 172), where X is S or K; and a CDR3 of the heavy chain encoded by an amino acid sequence comprising the formula GGDTYFDYFDY (SEQ ID NO: 173);

and a variable light chain comprising:

a CDR1 of the light chain encoded by an amino acid sequence comprising the formula RASQSISXYLN (SEQ ID NO: 174), where X is G or S;

a CDR2 of the light chain encoded by an amino acid sequence comprising the formula XASSLQS (SEQ ID NO: 175), where X is Q, A or N; and a CDR3 of the light chain encoded by an amino acid sequence comprising the formula QQSYXXPXIT (SEQ ID NO: 176), where X at position 5 is T or S, X at position 6 is T or S and X at position 8 is G or F.

The antibody or an antigen-binding fragment thereof according to any of the preceding embodiments, comprising:

a variable heavy chain comprising the variable CDR1 sequence of the heavy chain, as shown in SEQ ID NO: 6, the variable CDR2 sequence of the heavy chain, as shown in SEQ ID NO: 7 and the variable CDR3 sequence of the heavy chain, as shown in SEQ ID NO: 8, and a variable light chain comprising the variable CDR1 sequence of the light chain shown in SEQ ID NO: 3, the variable CDR2 sequence of the light chain shown in SEQ ID NO: 4 and the variable CDR3 sequence of the light chain shown in SEQ ID NO: 5 or a variable heavy chain comprising the variable CDR1 sequence of the heavy chain, as shown in SEQ ID NO: 16, the variable CDR2 sequence of the heavy chain, as shown in SEQ ID NO: 17, the variable CDR3 sequence of the heavy chain, as shown in SEQ ID NO: 18, and also a variable light chain comprising the variable CDR1 sequence of the light chain shown in SEQ ID NO: 13, the variable CDR2 sequence of the light chain shown in SEQ ID NO: 14 and the variable CDR3 sequence of the light chain shown in SEQ ID NO: 15 or a variable heavy chain comprising the variable CDR1 sequence of the heavy chain, as shown in SEQ ID NO: 26, the variable CDR2 sequence of the heavy chain, as shown in SEQ ID NO: 27, the variable CDR3 sequence of the heavy chain, as shown in SEQ ID NO:28, and also a variable light chain comprising the variable CDR1 sequence of the light chain shown in SEQ ID NO: 23, the variable CDR2 sequence of the light chain shown in SEQ ID NO: 24 and the variable CDR3 sequence of the light chain shown in SEQ ID NO:25 or a variable heavy chain comprising the variable CDR1 sequence of the heavy chain, as shown in SEQ ID NO: 36, the variable CDR2 sequence of the heavy chain, as shown in SEQ ID NO: 37, the variable CDR3 sequence of the heavy chain, as shown in SEQ ID NO:38, and also a variable light chain comprising the variable CDR1 sequence of the light chain shown in SEQ ID NO: 33, the variable CDR2 sequence of the light chain shown in SEQ ID NO: 34 and the variable CDR3 sequence of the light chain shown in SEQ ID NO:35 or a variable heavy chain comprising the variable CDR1 sequence of the heavy chain, as shown in SEQ ID NO: 46, the variable CDR2 sequence of the heavy chain, as shown in SEQ ID NO: 47, the variable CDR3 sequence of the heavy chain, as shown in SEQ ID NO:48, and also a variable light chain comprising the variable CDR1 sequence of the light chain shown in SEQ ID NO: 43, the variable CDR2 sequence of the light chain shown in SEQ ID NO: 44 and the variable CDR3 sequence of the light chain shown in SEQ ID NO:45 or a variable heavy chain comprising the variable CDR1 sequence of the heavy chain, as shown in SEQ ID NO: 56, the variable CDR2 sequence of the heavy chain, as shown in SEQ ID NO: 57, the variable CDR3 sequence of the heavy chain, as shown in SEQ ID NO:58, and also a variable light chain comprising the variable CDR1 sequence of the light chain shown in SEQ ID NO: 53, the variable CDR2 sequence of the light chain shown in SEQ ID NO: 54 and the variable CDR3 sequence of the light chain shown in SEQ ID NO:55 or a variable heavy chain comprising the variable CDR1 sequence of the heavy chain, as shown in SEQ ID NO: 66, the variable CDR2 sequence of the heavy chain, as shown in SEQ ID NO: 67, the variable CDR3 sequence of the heavy chain, as shown in SEQ ID NO:68, and also a variable light chain comprising the variable CDR1 sequence of the light chain shown in SEQ ID NO: 63, the variable CDR2 sequence of the light chain shown in SEQ ID NO: 64 and the variable CDR3 sequence of the light chain shown in SEQ ID NO:65 or a variable heavy chain comprising the variable CDR1 sequence of the heavy chain, as shown in SEQ ID NO: 76, the variable CDR2 sequence of the heavy chain, as shown in SEQ ID NO: 77, the variable CDR3 sequence of the heavy chain, as shown in SEQ ID NO:78, and also a variable light chain comprising the variable CDR1 sequence of the light chain shown in SEQ ID NO: 73, the variable CDR2 sequence of the light chain shown in SEQ ID NO: 74 and the variable CDR3 sequence of the light chain shown in SEQ ID NO:75 or a variable heavy chain comprising the variable CDR1 sequence of the heavy chain, as shown in SEQ ID NO: 86, the variable CDR2 sequence of the heavy chain, as shown in SEQ ID NO: 87, the variable CDR3 sequence of the heavy chain, as shown in SEQ ID NO:88, and also a variable light chain comprising the variable CDR1 sequence of the light chain shown in SEQ ID NO: 83, the variable CDR2 sequence of the light chain shown in SEQ ID NO: 84 and the variable CDR3 sequence of the light chain shown in SEQ ID NO:85 or a variable heavy chain comprising the variable CDR1 sequence of the heavy chain, as shown in SEQ ID NO: 96, the variable CDR2 sequence of the heavy chain, as shown in SEQ ID NO: 97, the variable CDR3 sequence of the heavy chain, as shown in SEQ ID NO:98, and also a variable light chain comprising the variable CDR1 sequence of the light chain shown in SEQ ID NO: 93, the variable CDR2 sequence of the light chain shown in SEQ ID NO: 94 and the variable CDR3 sequence of the light chain shown in SEQ ID NO:95 or a variable heavy chain comprising the variable CDR1 sequence of the heavy chain, as shown in SEQ ID NO: 106, the variable CDR2 sequence of the heavy chain, as shown in SEQ ID NO: 107, the variable CDR3 sequence of the heavy chain, as shown in SEQ ID NO: 108, and also a variable light chain comprising the variable CDR1 sequence of the light chain shown in SEQ ID NO: 103, the variable CDR2 sequence of the light chain shown in SEQ ID NO: 104 and the variable CDR3 sequence of the light chain shown in SEQ ID NO: 105 or a variable heavy chain comprising the variable CDR1 sequence of the heavy chain, as shown in SEQ ID NO: 116, the variable CDR2 sequence of the heavy chain, as shown in SEQ ID NO: 117, the variable CDR3 sequence of the heavy chain, as shown in SEQ ID NO: 118, and also a variable light chain comprising the variable CDR1 sequence of the light chain shown in SEQ ID NO: 113, the variable CDR2 sequence of the light chain shown in SEQ ID NO: 114 and the variable CDR3 sequence of the light chain shown in SEQ ID NO: 115.

The antibody or the antigen-binding fragment thereof according to any of the preceding embodiments, comprising:

a variable sequence of the heavy chain, as shown in SEQ ID NO: 10, and also a variable sequence of the light chain, as shown in SEQ ID NO:9, or a variable sequence of the heavy chain, as shown in SEQ ID NO:20, and also a variable sequence of the light chain, as shown in SEQ ID NO: 19, or a variable sequence of the heavy chain, as shown in SEQ ID NO:30, and also a variable sequence of the light chain, as shown in SEQ ID NO:29, or a variable sequence of the heavy chain, as shown in SEQ ID NO:40, and also a variable sequence of the light chain, as shown in SEQ ID NO:39, or a variable sequence of the heavy chain, as shown in SEQ ID NO:50, and also a variable sequence of the light chain, as shown in SEQ ID NO:49, or a variable sequence of the heavy chain, as shown in SEQ ID NO:60, and also a variable sequence of the light chain, as shown in SEQ ID NO:59, or a variable sequence of the heavy chain, as shown in SEQ ID NO:70, and also a variable sequence of the light chain, as shown in SEQ ID NO:69, or a variable sequence of the heavy chain, as shown in SEQ ID NO:80, and also a variable sequence of the light chain, as shown in SEQ ID NO:79, or a variable sequence of the heavy chain, as shown in SEQ ID NO:90, and also a variable sequence of the light chain, as shown in SEQ ID NO:89, or a variable sequence of the heavy chain, as shown in SEQ ID NO: 100, and also a variable sequence of the light chain, as shown in SEQ ID NO:99, or a variable sequence of the heavy chain, as shown in SEQ ID NO:110, and also a variable sequence of the light chain, as shown in SEQ ID NO: 109, or a variable sequence of the heavy chain, as shown in SEQ ID NO: 120, and also a variable sequence of the light chain, as shown in SEQ ID NO: 119.

The antibody according to any of the preceding embodiments which is an IgG antibody.

The antibody according to any of the preceding embodiments, comprising:

a sequence of the heavy chain, as shown in SEQ ID NO:2, and also a sequence of the light chain, as shown in SEQ ID NO:1, or a sequence of the heavy chain, as shown in SEQ ID NO: 12, and also a sequence of the light chain, as shown in SEQ ID NO:11, or a sequence of the heavy chain, as shown in SEQ ID NO:22, and also a sequence of the light chain, as shown in SEQ ID NO:21, or a sequence of the heavy chain, as shown in SEQ ID NO:32, and also a sequence of the light chain, as shown in SEQ ID NO:31, or a sequence of the heavy chain, as shown in SEQ ID NO:42, and also a sequence of the light chain, as shown in SEQ ID NO:41, or a sequence of the heavy chain, as shown in SEQ ID NO:52, and also a sequence of the light chain, as shown in SEQ ID NO:51, or a sequence of the heavy chain, as shown in SEQ ID NO:62, and also a sequence of the light chain, as shown in SEQ ID NO:61, or a sequence of the heavy chain, as shown in SEQ ID NO:72, and also a sequence of the light chain, as shown in SEQ ID NO:71, or a sequence of the heavy chain, as shown in SEQ ID NO:82, and also a sequence of the light chain, as shown in SEQ ID NO:81, or a sequence of the heavy chain, as shown in SEQ ID NO:92, and also a sequence of the light chain, as shown in SEQ ID NO:91, or a sequence of the heavy chain, as shown in SEQ ID NO: 102, and also a sequence of the light chain, as shown in SEQ ID NO: 101, or a sequence of the heavy chain, as shown in SEQ ID NO: 112, and also a sequence of the light chain, as shown in SEQ ID NO: 111, or a sequence of the heavy chain, as shown in SEQ ID NO:241, and also a sequence of the light chain, as shown in SEQ ID NO: 1, or a sequence of the heavy chain, as shown in SEQ ID NO:242, and also a sequence of the light chain, as shown in SEQ ID NO: 1, or a sequence of the heavy chain, as shown in SEQ ID NO:243, and also a sequence of the light chain, as shown in SEQ ID NO: 1.

The antigen-binding fragment according to any of the preceding embodiments or an antigen-binding fragment of an antibody according to any of the preceding embodiments which is an scFv, Fab, Fab' fragment or a F(ab')2 fragment.

The antibody or the antigen-binding fragment according to any of the preceding embodiments which is a monoclonal antibody or an antigen-binding fragment thereof.

The antibody or the antigen-binding fragment according to any of the preceding embodiments which is a human, humanized or chimeric antibody or an antigen-binding fragment.

Particular preference is given to the anti-TWEAKR antibody TPP-2658.

It is one embodiment of the invention to provide antibodies that are suitable for a transglutaminase-mediated conjugation of a kinesin spindle protein inhibitor.

Wild-type full-length antibodies of the human isotype have a conserved acceptor glutamine at position 295 (Kabat EU numbering) in the heavy chain, which is accessible and reactive in the presence of transglutaminase, which leads to formation of a conjugate of the antibody and a suitable compound when the antibody is in non-glycosylated form. Such aglycosylated antibodies or deglycosylated antibodies lack the glycans joined to the conserved glycosylation site N297 in the CH2 domain of the Fc region. Aglycosylated antibodies can be produced, for example, by mutation of the glycosylation site N297 (Kabat Eu numbering) of the heavy chain or by expression of antibodies in expression systems lacking glycosylation capacity. Methods of antibody deglycosylation are common knowledge (e.g. Winkelhake & Nicolson (1976), J Biol Chem. 251(4):1074-80)). Deglycosylated antibodies can be generated, for example, by enzymatic deglycosylation by means of PNGase F. In one embodiment of the invention, aglycosylated antibodies can be obtained by expression in prokaryotic hosts. Suitable prokaryotic hosts include but are not limited to *E. coli, Bacillus subtilis, Salmonella typhimurium* and some species of the *Pseudomonas, Streptomyces* and *Staphylococcus* genera. In another embodiment of the invention, aglycosylated antibodies can be obtained by the use of mammalian cell expression systems together with the glycosylation inhibitor tunicamycin (Nose & Wigzell (1983), Proc Natl Acad Sci USA, 80(21):6632-6). Here, the modification is the prevention of glycosylation at the conserved N-glycosylation site N297 (Kabat numbering) of the heavy chain in the CH2 domain of the Fc portion of the antibody.

In another embodiment of the invention, aglycosylated antibodies are produced by the mutation of the glycosylation site N297 (Kabat numbering) in the heavy chain. The enzymatic conjugation of such engineered aglycosylated antibodies has been described for antibody variants containing the mutations N297D, N297Q (Jeger et al., Angewandte Chemie Int. Ed. Engl 49, 9995-9997 (2010)) or N297S (see patent applications WO2013092998A1 and WO2013092983A2). In addition, this invention shows that transglutaminase can efficiently catalyse the conjugation of aglycosylated antibody variants bearing the N297A mutation (Kabat EU numbering).

Additional or alternative reactive residues in the presence of transglutaminase can be created by antibody engineering. The compounds according to the invention include glutamine-engineered antibodies in which one or more amino acids of a wild-type or parent antibody have been replaced by glutamines, or in which a glutamine residue, optionally together with another amino acid (for example a tag containing the acceptor glutamine), is introduced into the parent or wild-type molecule.

The glutamine residues of an antibody which are reactive in the presence of the transglutaminase are in the heavy chain, typically in the constant domain. In one embodiment, an asparagine at position N297 (Kabat numbering) has been exchanged for a residue other than glutamine. Preference is given to N297D, N297Q, N297S or N297A, even more preference to N297A. An antibody having N297X substitution and a glutamine at position 295 (Kabat numbering) therefore has one acceptor glutamine per heavy chain. The complete IgG therefore has two conjugation sites per antibody.

The glutamine residues of an antibody which are reactive in the presence of the transglutaminase are in the heavy chain, typically in the constant domain. In one embodiment, an asparagine at position N297 (Kabat numbering) has been exchanged for a glutamine. The antibody therefore has N297Q substitution. An antibody having N297Q substitution and a glutamine at position 295 (Kabat numbering) therefore has two acceptor glutamines and therefore two conjugation sites per heavy chain. The complete IgG therefore has four conjugation sites per antibody.

The glutamine residues of an antibody which are reactive in the presence of the transglutaminase are in the heavy chain, typically in the constant domain. In one embodiment, an asparagine at position N297 (Kabat numbering) has been exchanged for a glutamine and the glutamine at position 295 has been exchanged. The antibody therefore has an N297Q and a Q295X substitution. Preference is given to a Q295N substitution. An antibody having N297Q substitution and no glutamine at position 295 (Kabat numbering) therefore has one acceptor glutamine and therefore one conjugation site per heavy chain. The complete IgG therefore has two conjugation sites per antibody.

Preferred antibodies suitable for a transglutaminase-mediated conjugation thus include:

i. N297X substitution, where X is any amino acid except asparagine; more preferred are N297D, N297Q, N297S or N297A, even more preferred are N297A and N297Q.
ii. N297Q substitution and a Q295X substitution, where X is any amino acid except glutamine, preference being given to Q295N.

Isotopes, Salts, Solvates, Isotopic Variants

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass from the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the drug distribution in the body; due to comparatively easy preparability and detectability, especially compounds labelled with $^{3}H$ or $^{14}C$ isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described further down and the procedures described in the working examples, by using corresponding isotopic modifications of the respective reagents and/or starting compounds.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, arginine, lysine and 1,2-ethylenediamine.

Designated as solvates in the context of the invention are those forms of the compounds according to the invention which form a complex in the solid or liquid state by coordination with solvent molecules. Hydrates are a specific form of the solvates in which the coordination is with water. Solvates preferred in the context of the present invention are hydrates.

The present invention additionally also encompasses prodrugs of the compounds according to the invention. The term "prodrugs" in this context refers to compounds which may themselves be biologically active or inactive but are converted (for example metabolically or hydrolytically) to compounds according to the invention during their residence time in the body.

PARTICULAR EMBODIMENTS

The following embodiments are particularly preferred:

Embodiment A

An APDC of the formula $$BINDER\text{-}[L\text{-}KSP]_n$$

where KSP-L- is a compound of the formula (IIa), (IIb), (IIc), (IId), (IIe) or of the following formula (IIf), the binder is a human, humanized or chimeric monoclonal antibody or an antigen-binding fragment thereof (preferably an anti-HER2 antibody, an anti-EGFR antibody or an anti-TWEAKR antibody, more preferably an anti-TWEAKR antibody which binds specifically to amino acid D in position 47 (D47) of TWEAKR (SEQ ID NO: 169), especially the anti-TWEAKR antibody TPP-2658), and n is a number from 1 to 10:

Formula (IIf)

(IIf)

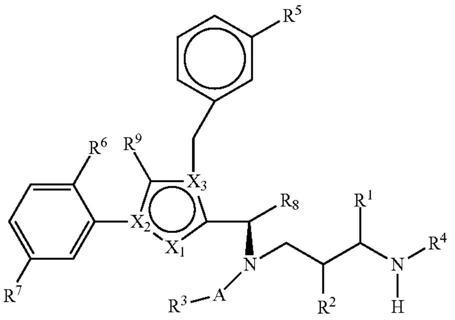

(IIf)

where $X_1$ represents N, $X_2$ represents N and $X_3$ represents C;

$X_1$ represents CH, $X_2$ represents C and $X_3$ represents N;

$X_1$ represents NH, $X_2$ represents C and $X_3$ represents C; or $X_1$ represents CH, $X_2$ represents N and $X_3$ represents C;

A is —C(=O)— (carbonyl);

$R^1$ represents -L-#1, —H, —COOH, —CONHNH$_2$, —$(CH_2)_{1-3}NH_2$, —CONZ"$(CH_2)_{1-3}$ $NH_2$ and —CONZ"$CH_2COOH$, where Z" represents —H or —$NH_2$;

$R^2$ is —H;

$R^4$ represents a group of the formula $R^{21}$—$(CO)_{(0-1)}$—$(P3)_{(0-2)}$—P2—NH—CH($CH_2CONH_2$)—CO— or the cathepsin-cleavable group of the formula $R^{21}$—$(CO)_{(0-1)}$—$(P3)_{(0-2)}$—P2-, where $R^{21}$ represents a $C_{1-10}$-alkyl, $C_{510}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —N(alkyl)$_2$, NH—CO-alkyl, N(alkyl)-COalkyl, —$SO_3H$, —$SO_2NH_2$, —$SO_2$—N(alkyl)$_2$, —COOH, —$CONH_2$, —CON(alkyl)$_2$, or —OH, —H or an —Ox-$(CH_2CH_2O)_y$—$R^{22}$ group (where x represents 0 or 1 and v represents a number from 1 to 20, and $R^{22}$ represents —H, -alkyl (preferably $C_{1-12}$-alkyl), —CH2-COOH, —CH2-CH2-COOH, or —CH2-CH2-NH2);

P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably N-methyl amino acids;

$R^3$ represents -L-#1 or a $C_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, $S(O)_n$-alkyl, $SO_2$—NH— alkyl, NH-alkyl, N(alkyl)$_2$ or $NH_2$, n represents 0, 1 or 2, (where alkyl is preferably $C_{1-3}$-alkyl);

$R^5$ is —H or —F;

$R^6$ and $R^7$ independently of one another represent —H, (optionally fluorinated) $C_{1-3}$-alkyl, (optionally fluorinated) $C_{2-4}$-alkenyl, (optionally fluorinated) $C_{2-4}$-alkynyl, hydroxy or halogen;

$R^8$ is a branched $C_{1-5}$-alkyl group; and $R^9$ is —H or —F, where one of the substituents $R^1$ and $R^3$ represents -L-#1, and -L- represents the linker and #1 represents the bond to the antibody, and salts, solvates and salts of the solvates of the APDC.

The linker is preferably a linker

§ —(CO)$m$-L1-L2-§§ where m is 0 or 1;

§ represents the bond to KSP and

§§ represents the bond to the antibody, and

L2

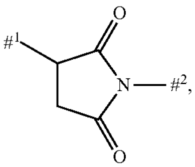 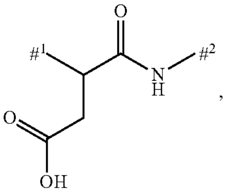 ,

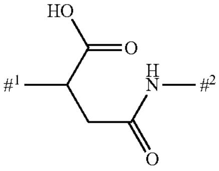 or 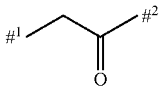

where $\#^1$ denotes the point of attachment to the sulphur atom of the antibody, $\#^2$ denotes the point of attachment to group $L^1$, and L1 is represented by formula $\#^1$—$(NR^{10})_n$-$(G1)_o$-G2-$\#^2$ where $R^{10}$ represents —H, —$NH_2$ or C1-C3-alkyl;

G1 represents —NHCO— or

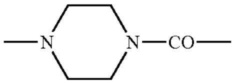 ;

n is 0 or 1;

o is 0 or 1; and

G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH— and a 3- to 10-membered aromatic or non-aromatic heterocycle having up to 4 heteroatoms selected from the group consisting of N, O and S, or —SO— (preferably

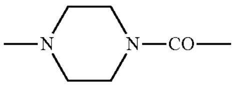

), where the side chains, if present, may be substituted by —NHCONH$_2$, —COOH, —OH, —$NH_2$, NH—CNNH$_2$, sulphonamide, sulphone, sulphoxide or sulphonic acid.

Here, #1 is the bond to the KSP inhibitor and #2 is the bond to the coupling group to the binder (e.g. L2).

Embodiment B

An APDC of the formula

BINDER-[-L-KSP]$_n$ where KSP-L- is a compound of the formula (IIa), (IIb), (IIc), (IId), (IIe), (IIf) or of the following formula (IIg), the binder is an antibody and n is a number from 1 to 10:

formula (IIg):

(IIg)

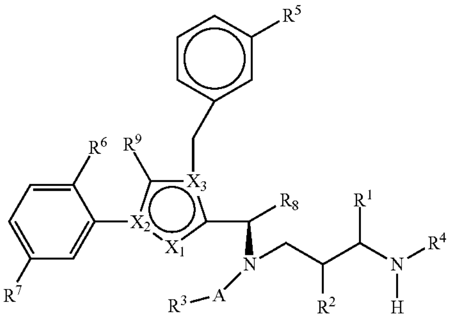

where $X_1$ represents N, $X_2$ represents N and $X_3$ represents C;
$X_1$ represents CH, $X_2$ represents C and $X_3$ represents N;
$X_1$ represents NH, $X_2$ represents C and $X_3$ represents C; or
$X_1$ represents CH, $X_2$ represents N and $X_3$ represents C;
A is CO (carbonyl);
$R^1$ is -L-#1, —H, —COOH, —$CONHNH_2$, —$(CH_2)_{1-3}NH_2$, —CONZ"$(CH_2)_{1-3}$ $NH_2$ and —CONZ"$CH_2COOH$, where Z" represents —H or —$NH_2$;
$R^2$ is —H;
$R^4$ represents a legumain-cleavable group of the formula $R^{21}$—$(CO)_{(0-1)}$—$(P3)_{(0-2)}$—P2—NH—CH($CH_2CONH_2$)—CO—;
where $R^{21}$ represents a $C_{1-10}$-alkyl, $C_{510}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —N(alkyl)$_2$, NH—CO-alkyl, —N(alkyl)-COalkyl, —$SO_3H$, —$SO_2NH_2$, —$SO_2$—N(alkyl)$_2$, —COOH, —$CONH_2$, —CON(alkyl)$_2$, or —OH, —H or a -Ox-(CH2CH2O)y-R22 group (where x represents 0 or 1 and v represents a number from 1 to 20, and
R22 represents —H, -alkyl (preferably C1-12-alkyl), —CH2-COOH, —CH2-CH2-COOH, or —CH2-CH2-NH2);
P2 is an amino acid selected from Gly, Pro, Ala, Val, Leu, Ile, Met, Phe, Tyr, Trp, Ser, Thr, Cys, Asn, Gln, Asp, Glu, Lys, Arg and His;
P3 is an amino acid selected from Gly, Pro, Ala, Val, Leu, Ile, Met, Phe, Tyr, Trp, Ser, Thr, Cys, Asn, Gln, Asp, Glu, Lys, Arg and His or one of the respective N-alkyl amino acids, preferably N-methyl amino acids;
$R^3$ represents -L-#1 or a $C_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, $S(O)_n$-alkyl, $SO_2$—NH-alkyl, NH-alkyl, N(alkyl)$_2$ or $NH_2$, n represents 0, 1 or 2, (where alkyl is preferably $C_{1-3}$-alkyl);
$R^5$ is —H or —F;
$R^6$ and $R^7$ independently of one another represent —H, (optionally fluorinated) $C_{1-3}$-alkyl, (optionally fluorinated) $C_{2-4}$-alkenyl, (optionally fluorinated) $C_{2-4}$-alkynyl, hydroxy or halogen;
$R^8$ is a branched $C_{1-5}$-alkyl group; and
$R^9$ is —H or —F,
where one of the substituents $R^1$ and $R^3$ represents -L-#1, and
-L- represents the linker and #1 represents the bond to the antibody.

The -L- is preferably represented by

§ —(CO)$m$-L1-L2-§§ where
m is 0 or 1;
§ represents the bond to KSP and
§§ represents the bond to the antibody, and
L2

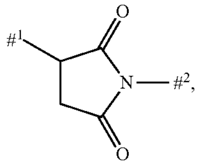
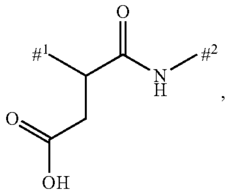
,
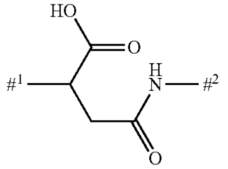
or
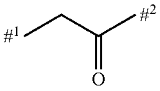

where
$\#^1$ denotes the point of attachment to the sulphur atom of the antibody,
$\#^2$ denotes the point of attachment to group $L^1$,
and L1 is represented by formula $\#^1$—$(NR^{10})_n$-$(G1)_o$-G2-$\#^2$ where
$R^{10}$ represents —H, —$NH_2$ or $C_1$-$C_3$-alkyl;
G1 represents —NHCO— or

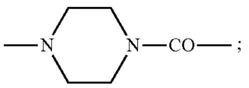

n is 0 or 1;
o is 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2NHNH$—, —CONHNH— and a 3- to 10-membered aromatic or non-aromatic heterocycle having up to 4 heteroatoms selected from the group consisting of N, O and S, or —SO— (preferably

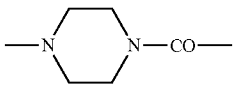

), where the side chains, if present, may be substituted by —NHCONH2, —COOH, —OH, —$NH_2$, NH—$CNNH_2$, sulphonamide, sulphone, sulphoxide or sulphonic acid,

#1 is the bond to the KSP inhibitor and #2 is the bond to the coupling group to the antibody (e.g. L2), and salts, solvates and salts of the solvates of the APDC.

Alternatively, the linker may be bonded to a lysine side chain or a lysine residue.

Embodiment C

An APDC of the formula

BINDER-[-L-KSP]$_n$ where KSP-L- is a compound of the following formula (IIa), (IIb), (IIc), (IId), (IIe), (IIf), (IIg) or of the following formula (IIh), the binder is an antibody and n is a number from 1 to 10:

formula (IIh):

(IIh)

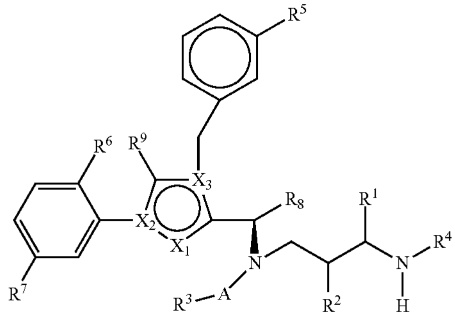

where $X_1$ represents N, $X_2$ represents N and $X_3$ represents C;

$X_1$ represents CH, $X_2$ represents C and $X_3$ represents N;

$X_1$ represents NH, $X_2$ represents C and $X_3$ represents C; or $X_1$ represents CH, $X_2$ represents N and $X_3$ represents C;

A is —C(═O)— (carbonyl);

$R^1$ is -L-#1;

$R^2$ is —H;

$R^4$ represents a group of the formula $R^{21}$—$(CO)_{(0-1)}$—$(P3)_{(0-2)}$—P2—NH—$CH(CH_2CONH_2)$—CO— or the cathepsin-cleavable group of the formula $R^{21}$—$(CO)_{(0-1)}$—$(P3)_{(1-2)}$—P2-, where $R^{21}$ represents a $C_{1-10}$-alkyl, $C_{510}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —$N(alkyl)_2$, NH—CO-alkyl, —N(alkyl)-COalkyl, —$SO_3H$, —$SO_2NH_2$, —$SO_2$—$N(alkyl)_2$, —COOH, —$CONH_2$, —$CON(alkyl)_2$, or —OH, —H or an —$O_x$—$(CH_2CH_2O)_y$—$R^{22}$ group (where x represents 0 or 1 and v represents a number from 1 to 20, and $R^{22}$ represents —H, -alkyl (preferably $C_{1-12}$-alkyl), —CH2-COOH, —CH2-CH2-COOH, or —CH2-CH2-NH2);

P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably N-methyl amino acids;

$R^3$ is a $C_{1-10}$-alkyl-, which may optionally be substituted by —OH, —O-alkyl, —SH, —S-alkyl, —O—CO-alkyl, —O—CO—NH-alkyl, —NH—CO-alkyl, —NH—CO—NH-alkyl, —$S(O)_n$-alkyl, —$SO_2$—NH— alkyl, —NH-alkyl, —$N(alkyl)_2$ or —$NH_2$, n represents 0, 1 or 2, (where alkyl is preferably $C_{1-3}$-alkyl), or -MOD;

where -MOD represents —$(NR^{10})_n$-$(G1)_o$-G2-H, where $R^{10}$ represents —H or $C_1$-$C_3$-alkyl;

G1 represents —NHCO—, —CONH— or

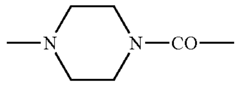

(where, if G1 represents —NHCO— or

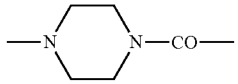

, $R^{10}$ is not $NH_2$);

n is 0 or 1;

o is 0 or 1; and

G2 is a straight-chain and/or branched hydrocarbon group which has 1 to 10 carbon atoms and which may be interrupted once or more than once by one or more of the groups —O—, —S—, —SO—, $SO_2$, —$NR^y$—, —$NR^yCO$—, $CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by —$NHCONH_2$, —COOH, —OH, —$NH_2$, NH—$CNNH_2$, sulphonamide, sulphone, sulphoxide or sulphonic acid), —CO—, —$CR^x$═N—O— (where Rx represents H, $C_1$-$C_3$-alkyl or phenyl), where the hydrocarbon chain including any side chains may be substituted by $NHCONH_2$, —COOH, —OH, —$NH_2$, NH—$CNNH_2$, sulphonamide, sulphone, sulphoxide or sulphonic acid, where the group -MOD preferably has at least one group —COOH;

$R^5$ is H or F;

$R^6$ and $R^7$ independently of one another represent H, (optionally fluorinated) $C_{1-3}$-alkyl, (optionally fluorinated) $C_{2-4}$-alkenyl, (optionally fluorinated) $C_{2-4}$-alkynyl, hydroxy or halogen;

$R^8$ is a branched $C_{1-5}$-alkyl group; and $R^9$ is H or F, where -L- represents the linker and #1 represents the bond to the antibody, where -L- is represented by § —$(CO)m$-L1-L2-§§ where m is 0 or 1;

§ represents the bond to KSP and

§§ represents the bond to the antibody, and

L2

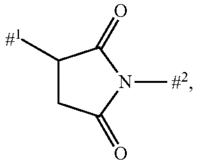

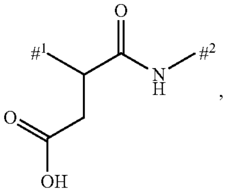

,

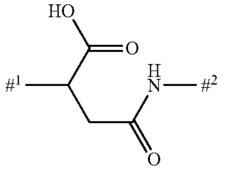

or

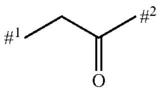

where $\#^1$ denotes the point of attachment to the sulphur atom of the antibody, $\#^2$ denotes the point of attachment to group $L^1$, and L1 is represented by formula $$\#^1\text{—}(NR^{10})_n\text{-}(G1)_o\text{-}G2\text{-}\#^2$$

where $R^{10}$ represents —H, —$NH_2$ or $C_1$-$C_3$-alkyl;

G1 represents —NHCO— or

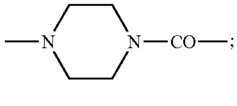

;

n is 0 or 1;

o is 0 or 1; and

G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH—, —$CR^x$=N—O— (where Rx represents H, $C_1$-$C_3$-alkyl or phenyl) and a 3- to 10-membered aromatic or non-aromatic heterocycle having up to 4 heteroatoms selected from the group consisting of N, O and S, —SO— or —$SO_2$— (preferably

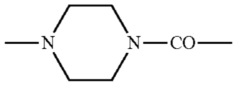

), where the hydrocarbon chain including the side chains, if present, may be substituted by —$NHCONH_2$, —COOH, —OH, —$NH_2$, NH—$CNNH_2$, sulphonamide, sulphone, sulphoxide or sulphonic acid, $\#^1$ is the bond to the KSP inhibitor and $\#^2$ is the bond to the coupling group to the antibody (e.g. L2), and salts, solvates and salts of the solvates of the APDC.

Embodiment D

An antibody conjugate of the formula

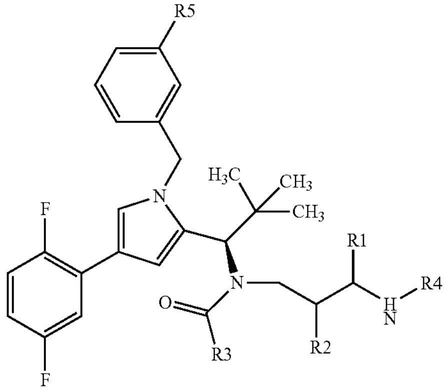

where $R^2$ and $R^5$ represent —H;

$R^4$ represents a group of the formula $R^{21}$—$(CO)_{(0\text{-}1)}$—$(P3)_{(0\text{-}2)}$—P2—NH—$CH(CH_2CONH_2)$—CO— or the cathepsin-cleavable group of the formula $R^{21}$—$(CO)_{(0\text{-}1)}$—$(P3)_{(0\text{-}2)}$—P2-, where $R^{21}$ represents a $C_{1\text{-}10}$-alkyl, $C_{510}$-aryl or $C_{6\text{-}10}$-aralkyl, $C_{5\text{-}10}$-heteroalkyl, $C_{1\text{-}10}$-alkyl-O—$C_{6\text{-}10}$-aryl, $C_{5\text{-}10}$-heterocycloalkyl, heteroaryl, heteroarylalkyl, $C_{1\text{-}10}$-alkoxy, $C_{6\text{-}10}$-aryloxy or $C_{6\text{-}10}$-aralkoxy, $C_{5\text{-}10}$-heteroalkoxy, $C_{1\text{-}10}$-alkyl-O—$C_{6\text{-}10}$-aryloxy, $C_{5\text{-}10}$-heterocycloalkoxy group which may be mono- or polysubstituted by —$NH_2$, —NH-alkyl, —$N(alkyl)_2$, NH—CO-alkyl, —N(alkyl)-COalkyl, —$SO_3H$, —$SO_2NH_2$, —$SO_2$—$N(alkyl)_2$, —COOH, —$CONH_2$, —$CON(alkyl)_2$, or —OH, —H or a —Ox-(CH2CH2O)y-R22 group (where x represents 0 or 1 and v represents a number from 1 to 20, and R22 represents —H, -alkyl (preferably C1-12-alkyl), —CH2-COOH, —CH2-CH2-COOH, or —CH2-CH2-NH2);

P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably N-methyl amino acids;

$R^3$ represents —CH2OH;

$R^1$ represents -L1-L2-BINDER, where

L1 represents

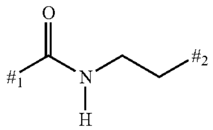

where #2 represents the attachment to L2 and #1 represents the attachment to L1;

and L2 represents one or both of the structure of the formulae A5 and A6 below:

Formula A5

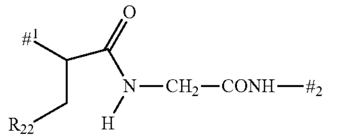

Formula A6

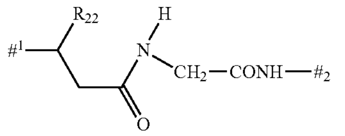

where $\#^1$ denotes the point of attachment to the sulphur atom of the binder, $\#^2$ denotes the point of attachment to group $L^1$, and $R_{22}$ represents —COOH, —COOR, —COR, —CONHR (where R in each case represents $C_{1-3}$-alkyl), —$CONH_2$, preferably —COOH.

In a conjugate according to the invention or in a mixture of the conjugates according to the invention, the bonds to a cysteine residue of the binder are present, to an extent of preferably more than 80%, particularly preferably more than 90% (in each case based on the total number of bonds of the linker to the binder) particularly preferably as one of the two structures of the formula A5 or A6.

Here, the structures of the formula A5 or A6 are generally present together, preferably in a ratio of from 60:40 to 40:60, based on the number of bonds to the binder. The remaining bonds are then present as the structure

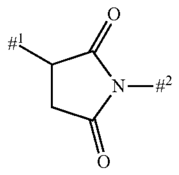

The binder is preferably a binder protein or peptide, particularly preferably a human, humanized or chimeric monoclonal antibody or an antigen-binding fragment thereof, in particular an anti-TWEAKR antibody or an antigen-binding fragment thereof or an anti-EGFR antibody or an antigen-binding fragment thereof. Particular preference is given to an anti-TWEAKR antibody which binds specifically to amino acid D in position 47 (D47) of TWEAKR (SEQ ID NO:169), in particular the anti-TWEAKR antibody TPP-2658, or the anti-EGFR antibodies cetuximab or nimotuzumab. As an alternative to the binder, a cysteine residue may also be present.

Embodiment E

An APDC of the formula

BINDER-[-L-KSP]$_n$ where KSP-L- is a compound of the following formula (IIa), (IIb), (IIc), (IId), (IIe), (IIf), (IIg), (IIh) or of the following formula (IIi), the binder is an antibody and n is a number from 1 to 10:

formula (IIi):

(II)

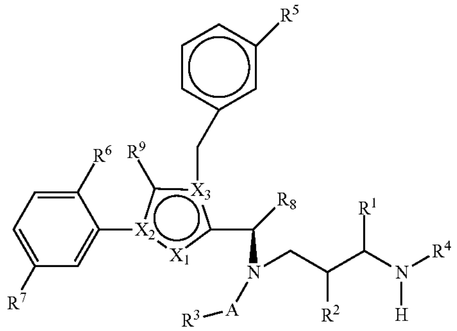

where $X_1$ represents N, $X_2$ represents N and $X_3$ represents C;
$X_1$ represents CH, $X_2$ represents C and $X_3$ represents N;
$X_1$ represents NH, $X_2$ represents C and $X_3$ represents C; or
$X_1$ represents CH, $X_2$ represents N and $X_3$ represents C;
A is CO (carbonyl);
$R^1$ is —H or —COOH,
$R^2$ is —H;
$R^4$ represents a group of the formula $R^{21}$—$(CO)_{(0-1)}$—$(P3)_{(0-2)}$—P2—NH—CH($CH_2CONH_2$)—CO— or the cathepsin-cleavable group of the formula $R^{21}$—$(CO)_{(0-1)}$—$(P3)_{(0-2)}$—P2-, where $R^{21}$ represents a $C_{1-10}$-alkyl, $C_5$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —N$(alkyl)_2$, NH—CO-alkyl, —N(alkyl)-COalkyl, —$SO_3H$, —$SO_2NH_2$, —$SO_2$—N$(alkyl)_2$, —COOH, —$CONH_2$, —CON$(alkyl)_2$, or —OH, —H or a —$O_x$—$(CH_2CH_2O)_y$—$R^{22}$ group (where x represents 0 or 1 and v represents a number from 1 to 20, and $R^{22}$ represents —H, -alkyl (preferably C1-12-alkyl), —CH2-COOH, —CH2-CH2-COOH, or —CH2-CH2-NH2);

P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids, preferably N-methyl amino acids;

$R^3$ is -L-#1;
$R^5$ is H or F;
$R^6$ and $R^7$ independently of one another represent H, (optionally fluorinated) $C_{1-3}$-alkyl, (optionally fluorinated) $C_{2-4}$-alkenyl, (optionally fluorinated) $C_{2-4}$-alkynyl, hydroxy or halogen;
$R^8$ is a branched $C_{1-5}$-alkyl group; and
$R^9$ is —H or —F, where -L- represents the linker and #1 represents the bond to the antibody, where -L- is represented by § —(C═O)$m$-L1-L2-§§ where m is 0 or 1;

§ represents the bond to KSP and

§§ represents the bond to the antibody, and

L2 represents

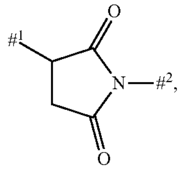
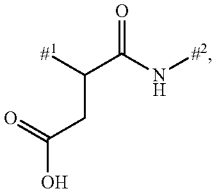
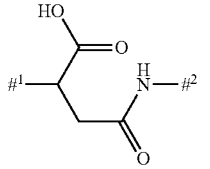
or
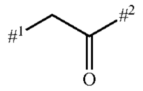

where $\#^1$ denotes the point of attachment to the sulphur atom or nitrogen atom of the antibody, $\#^2$ denotes the point of attachment to group $L^1$, and L1 is represented by formula $$\#^1—(NR^{10})_n-(G1)_o-G2-\#^2$$

where $R^{10}$ represents —H, —$NH_2$ or $C_1$-$C_3$-alkyl;

G1 represents —NHCO— or

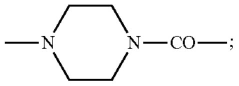

n is 0 or 1;

o is 0 or 1; and

G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH—, —$CR^x$═N—O— (where Rx represents H, $C_1$-$C_3$-alkyl or phenyl) and a 3- to 10-membered aromatic or non-aromatic heterocycle having up to 4 heteroatoms selected from the group consisting of N, O and S, —SO— or —$SO_2$— (preferably

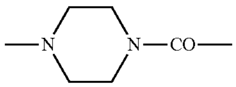

), where the hydrocarbon chain including the side chains, if present, may be substituted by —$NHCONH_2$, —COOH, —OH, —$NH_2$, NH—$CNNH_2$, sulphonamide, sulphone, sulphoxide or sulphonic acid,

#1 is the bond to the KSP inhibitor and #2 is the bond to the coupling group to the antibody (e.g. L2), and salts, solvates and salts of the solvates of the APDC.

Therapeutic Use

The hyper-proliferative diseases, for the treatment of which the compounds according to the invention may be employed, include in particular the group of cancer and tumour diseases. In the context of the present invention, these are understood to mean especially the following diseases, but without any limitation thereto: mammary carcinomas and mammary tumours (mammary carcinomas including ductal and lobular forms, also in situ), tumours of the respiratory tract (small-cell and non-small cell carcinoma, bronchial carcinoma), cerebral tumours (e.g. of the brain stem and of the hypothalamus, astrocytoma, ependymoma, glioblastoma, glioma, medulloblastoma, meningioma and neuro-ectodermal and pineal tumours), tumours of the digestive organs (carcinomas of the oesophagus, stomach, gall bladder, small intestine, large intestine, rectum and anal carcinomas), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity carcinomas, oral melanomas), skin tumours (basaliomas, spinaliomas, squamous cell carcinomas, Kaposi's sarcoma, malignant melanoma, non-melanomatous skin cancer, Merkel cell skin cancer, mast cell tumours), tumours of soft tissue (inter alia soft tissue sarcomas, osteosarcomas, malignant fibrous histiocytomas, chondrosarcomas, fibrosarcomas, hemangiosarcomas, leiomyosarcomas, liposarcomas, lymphosarcomas and rhabdomyosarcomas), tumours of the eyes (inter alia intraocular melanoma and retinoblastoma), tumours of the endocrine and exocrine glands (e.g. of the thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative diseases of the blood, the lymph system and the spinal cord, in solid form and as circulating cells, such as leukaemias, lymphomas and myeloproliferative diseases, for example acute myeloid, acute lymphoblastic, chronic lymphocytic, chronic myelogenous and hairy cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

These well-characterized diseases in humans can also occur with a comparable aetiology in other mammals and can likewise be treated there with the compounds of the present invention.

The treatment of the cancer diseases mentioned above with the compounds according to the invention comprises both a treatment of the solid tumors and a treatment of metastasizing or circulating forms thereof.

In the context of this invention, the term "treatment" or "treat" is used in the conventional sense and means attending to, caring for and nursing a patient with the aim of combating, reducing, attenuating or alleviating a disease or health abnormality, and improving the living conditions impaired by this disease, as, for example, in the event of a cancer.

The present invention thus further provides for the use of the compounds according to the invention for treatment and/or prevention of disorders, especially of the aforementioned disorders.

The present invention further provides for the use of the compounds according to the invention for production of a medicament for treatment and/or prevention of disorders, especially of the aforementioned disorders.

The present invention further provides for the use of the compounds according to the invention in a method for treatment and/or prevention of disorders, especially of the aforementioned disorders.

The present invention further provides a process for treatment and/or prevention of disorders, especially of the aforementioned disorders, using an effective amount of at least one of the compounds according to the invention.

The compounds according to the invention can be used alone or, if required, in combination with one or more other pharmacologically active substances, provided that this combination does not lead to undesirable and unacceptable side effects. Accordingly, the present invention further provides medicaments comprising at least one of the compounds according to the invention and one or more further drugs, especially for treatment and/or prevention of the aforementioned disorders.

For example, the compounds of the present invention can be combined with known anti-hyper-proliferative, cytostatic or cytotoxic substances for the treatment of cancer diseases. Examples of suitable combination drugs include:

131I-chTNT, abarelix, abiraterone, aclarubicin, ado-trastuzumab emtansine, afatinib, aflibercept, aldesleukin, alemtuzumab, alendronic acid, alitretinoin, altretamine, amifostine, aminoglutethimide, hexyl 5-aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, crizotinib, cyclophosphamide, cyproterone, cytarabine, dacarbazine, dactinomycin, dabrafenib, dasatinib, daunorubicin, decitabine, degarelix, denileukin-diftitox, denosumab, depreotide, deslorelin, dexrazoxane, dibrospidium chloride, dianhydrogalactitol, diclofenac, docetaxel, dolasetron, doxifluridine, doxorubicin, doxorubicin+oestrone, dronabinol, edrecolomab, elliptinium acetate, endostatin, enocitabine, enzalutamide, epirubicin, epitiostanol, epoetin-alfa, epoetin-beta, epoetin-zeta, eptaplatin, eribulin, erlotinib, esomeprazole, estramustine, etoposide, everolimus, exemestane, fadrozole, fentanyl, fluoxymesterone, floxuridine, fludarabine, fluorouracil, flutamide, folic acid, formestane, fosaprepitant, fotemustine, fulvestrant, gadobutrol, gadoteridol, gadoteric acid meglumine salt, gadoversetamide, gadoxetic acid disodium salt (gd-EOB-DTPA disodium salt), gallium nitrate, ganirelix, gefitinib, gemcitabine, gemtuzumab, glucarpidase, glutoxim, goserelin, granisetron, granulocyte colony stimulating factor (G-CSF), granulocyte macrophage colony stimulating factor (GM-CSF), histamine dihydrochloride, histrelin, hydroxycarbamide, I-125 seeds, ibandronic acid, ibritumomab-tiuxetan, idarubicin, ifosfamide, imatinib, imiquimod, improsulfan, indisetron, incadronic acid, ingenol mebutate, interferon-alfa, interferon-beta, interferon-gamma, iobitridol, iobenguane (123I), iomeprol, ipilimumab, irinotecan, itraconazole, ixabepilone, lanreotide, lansoprazole, lapatinib, lasocholine, lenalidomide, lentinan, letrozole, leuprorelin, levamisole, levonorgestrel, levothyroxin-sodium, lipegfilgrastim, lisuride, lobaplatin, lomustine, lonidamine, masoprocol, medroxyprogesteron, megestrol, melarsoprol, melphalan, mepitiostan, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotan, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumab pentetreotide, nilotinib, nilutamide, nimorazole, nimotuzumab, nimustine, nitracrine, nivolumab, obinutuzumab, octreotide, ofatumumab, omacetaxin mepesuccinate, omeprazole, ondansetron, orgotein, orilotimod, oxaliplatin, oxycodone, oxymetholone, ozogamicin, p53 gene therapy, paclitaxel, palladium-103 seed, palonosetron, pamidronic acid, panitumumab, pantoprazole, pazopanib, pegaspargase, pembrolizumab, Peg-interferon alfa-2b, pemetrexed, pentostatin, peplomycin, perflubutane, perfosfamide, pertuzumab, picibanil, pilocarpine, pirarubicin, pixantron, plerixafor, plicamycin, poliglusam, polyoestradiol phosphate, polyvinylpyrrolidone+sodium hyaluronate, polysaccharide-K, pomalidomide, ponatinib, porfimer-sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxan, refametinib, regorafenib, risedronic acid, rhenium-186 etidronate, rituximab, romidepsin, romurtid, roniciclib, samarium (153Sm) lexidronam, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, treosulfan, tretinoin, trifluridine+tipiracil, trametinib, trilostane, triptorelin, trofosfamide, thrombopoietin, ubenimex, valrubicin, vandetanib, vapreotide, vatalanib, vemurafenib, vinblastine, vincristine, vindesine, vinflunine, vinorelbine, vismodegib, vorinostat, yttrium-90 glass microbeads, zinostatin, zinostatin stimalamer, zoledronic acid, zorubicin.

In addition, the antibodies may be selected from the class of the MPS1 inhibitors or antibodies against the targets OX-40, CD137/4-1BB, DR3, IDO1/IDO2, LAG-3 and CD40.

In addition, the compounds according to the invention can also be used in combination with radiotherapy and/or surgical intervention.

Generally, the following aims can be pursued with the combination of compounds of the present invention with other cytostatically or cytotoxically active agents:

- improved efficacy in slowing the growth of a tumour, in reducing its size or even in completely eliminating it, compared with treatment with an individual active ingredient;
- the possibility of using the chemotherapeutics used in a lower dosage than in the case of monotherapy;
- the possibility of a more tolerable therapy with fewer side effects compared with individual administration;
- the possibility of treatment of a broader spectrum of tumours;

the achievement of a higher rate of response to the therapy;

a longer survival time of the patient compared with present-day standard therapy.

In addition, the compounds according to the invention can also be used in combination with radiotherapy and/or surgical intervention.

The present invention further provides medicaments which comprise at least one compound according to the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example parenterally, possibly inhalatively or as implants or stents.

The compounds according to the invention can be administered in administration forms suitable for these administration routes.

Parenteral administration can bypass an absorption step (for example intravenously, intraarterially, intracardially, intraspinally or intralumbally) or include an absorption (for example intramuscularly, subcutaneously, intracutaneously, percutaneously or intraperitoneally).

Administration forms suitable for parenteral administration include preparations for injection and infusion in the form of solutions, suspensions, emulsions or lyophilizates. Preference is given to parenteral administration, especially intravenous administration.

In general, it has been found to be advantageous in the case of parenteral administration to administer amounts of about 0.001 to 1 mg/kg, preferably about 0.01 to 0.5 mg/kg, of body weight to achieve effective results.

It may nevertheless be necessary in some cases to deviate from the stated amounts, specifically as a function of body weight, route of administration, individual response to the drug, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

EXAMPLES

The examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

Synthesis Routes:

By way of example for the working examples, the following schemes show illustrative synthesis routes leading to the working examples: In these schemes, the hydrogen atom in position $R^4$ of formula IIa (i.e. in the —$NH_2$ group) may be replaced by the group of the formula $R^{21}$—$(CO)_{(0-1)}$—$(P3)_{(0-2)}$—P2—NH—$CH(CH_2CONH_2)$—CO— or the cathepsin-cleavable group of the formula $R^{21}$—$(CO)_{(0-1)}$—$(P3)_{(0-2)}$—P2- where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline, and His;

P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where $R^{21}$ represents a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —$SO_3H$, —COOH, —SH or —OH.

Scheme 1: Synthesis of cysteine-linked ADCs

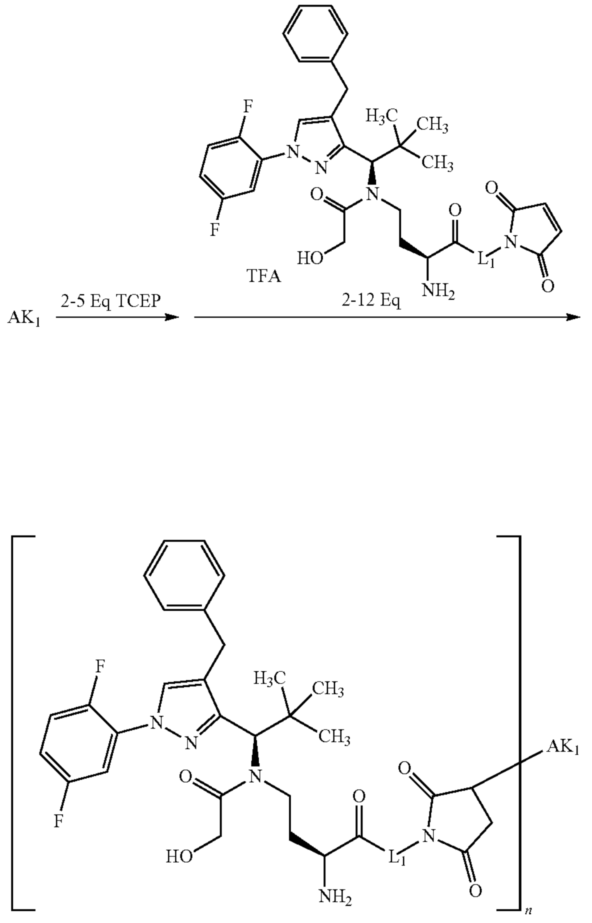

Scheme 2: Synthesis of cysteine-linked ADCs

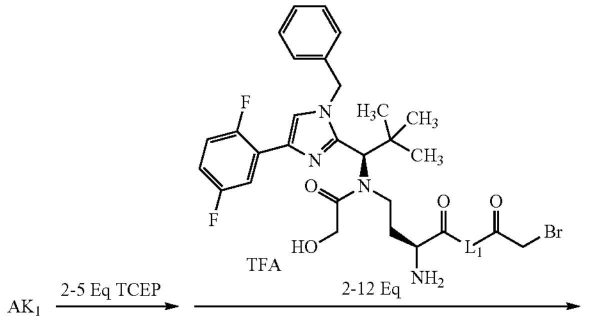

-continued
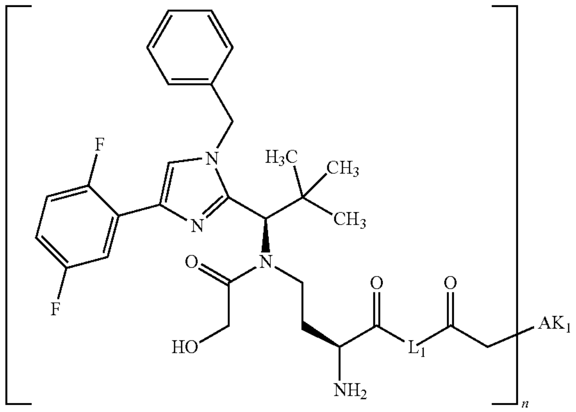
Scheme 3: Synthesis of cysteine-linked ADCs
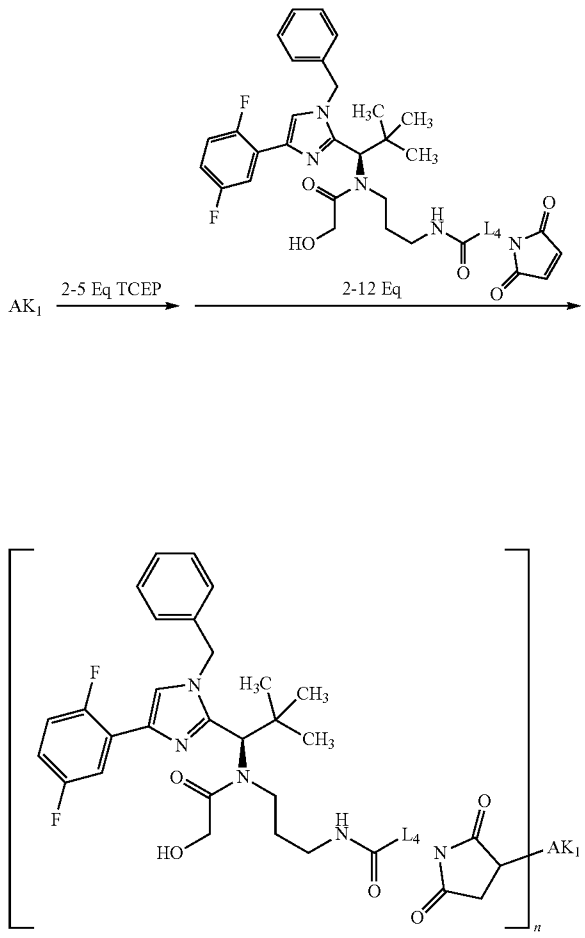
Scheme 4: Synthesis of cysteine-linked ADCs
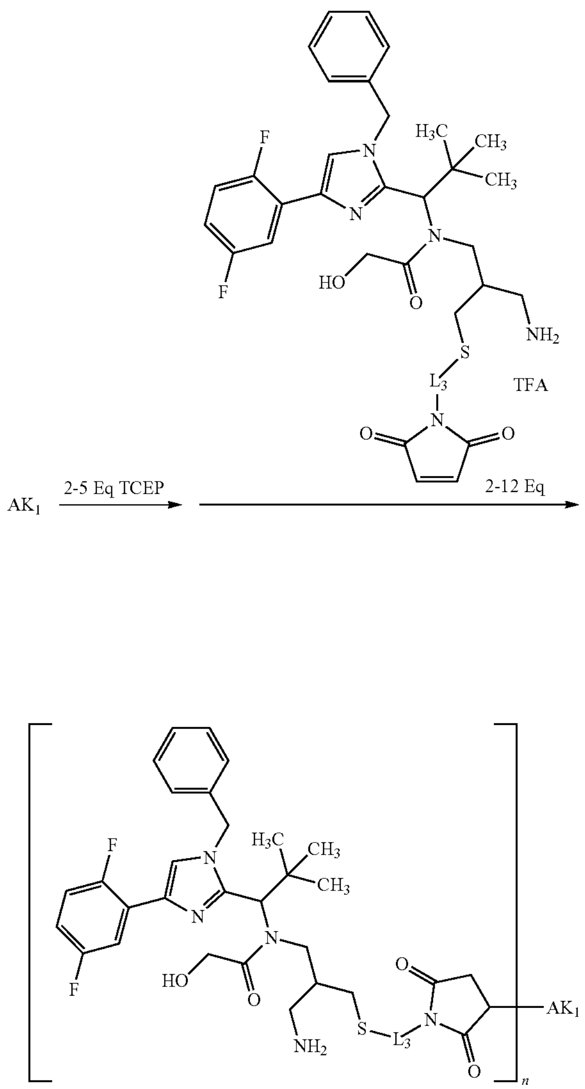
Scheme 5: Synthesis of lysine-linked ADCs
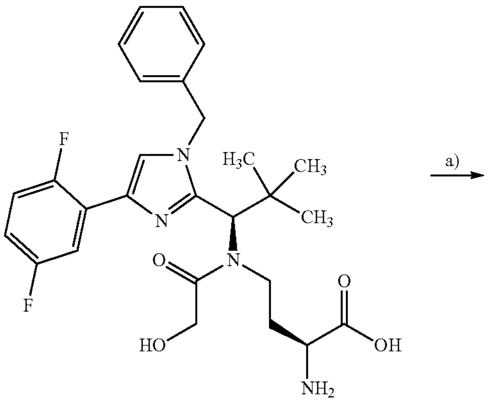

-continued
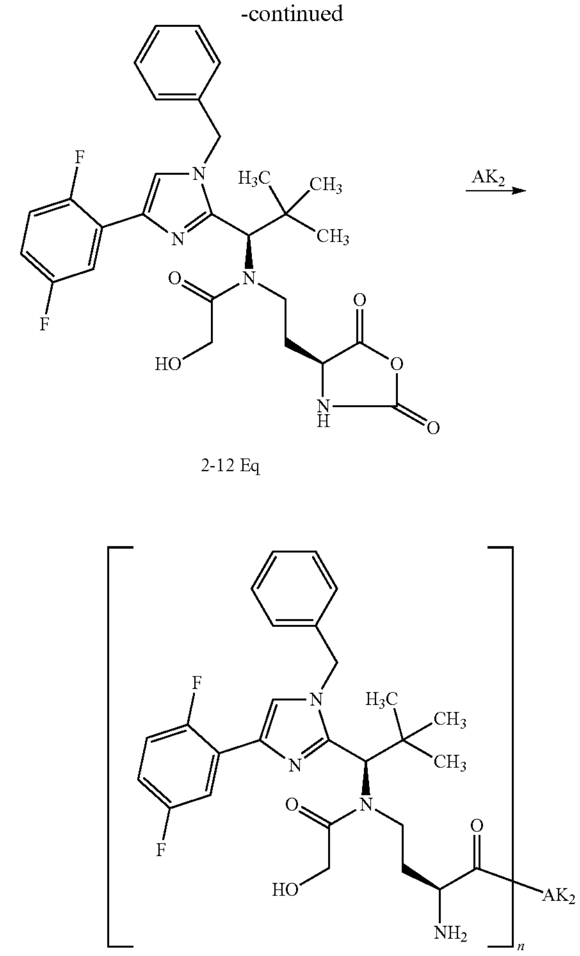
a) triphosgene, THF, under argon
Scheme 6: Synthesis of lysine-linked ADCs
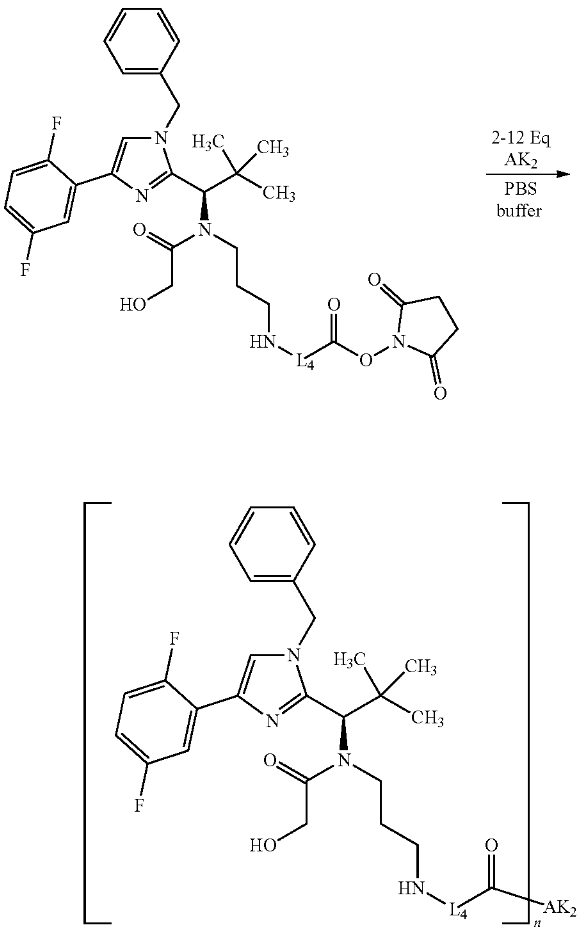
Scheme 7: Synthesis of ADC precursor molecules
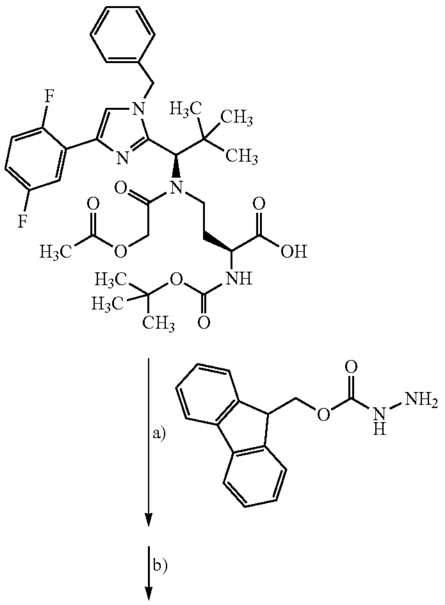

-continued
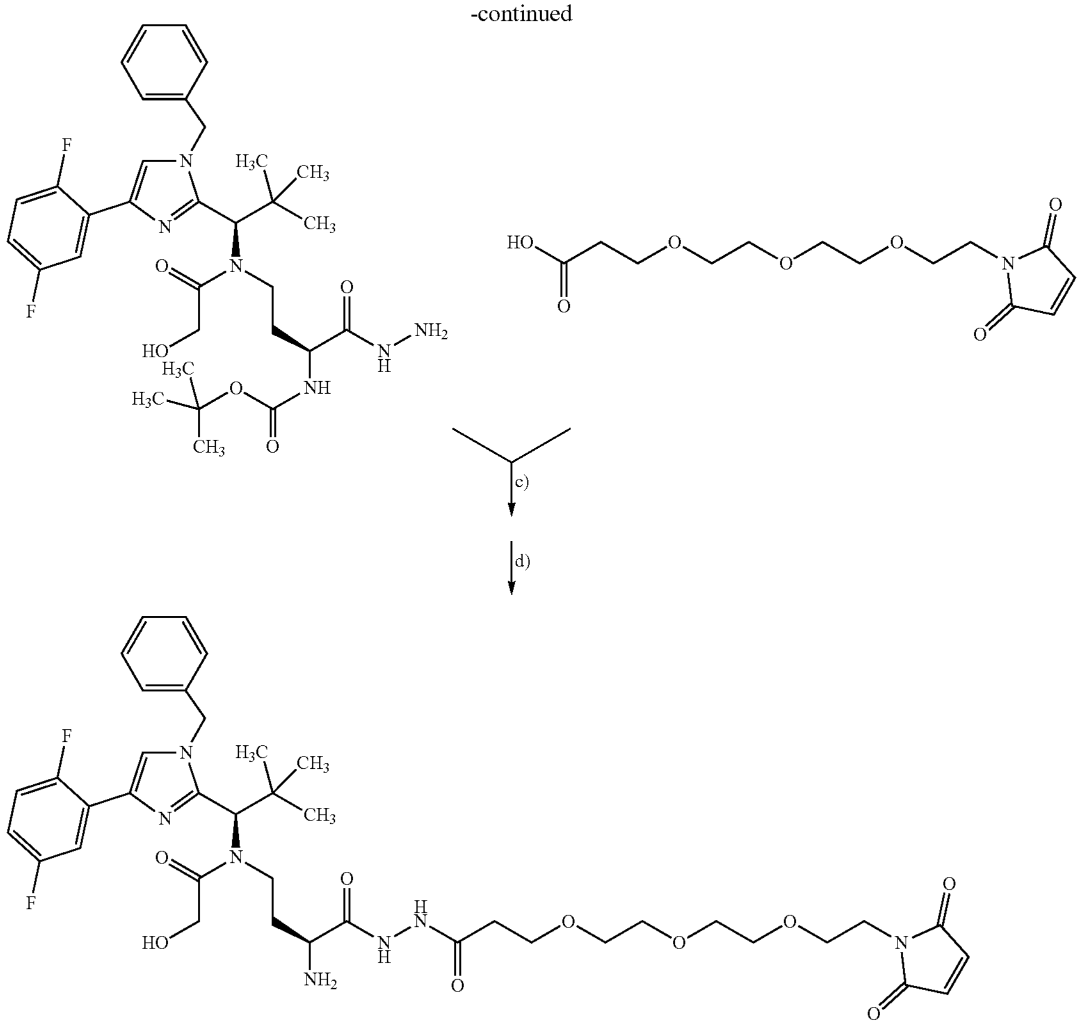
[a): EDCI, HOBT, diisopropylethylamine, RT; b) ethanol, piperidine, methylamine, water, RT; c) HATU, diisopropylethylamine, RT; d) TFA, DCM, RT]
Scheme 8: Synthesis of ADC precursor molecules
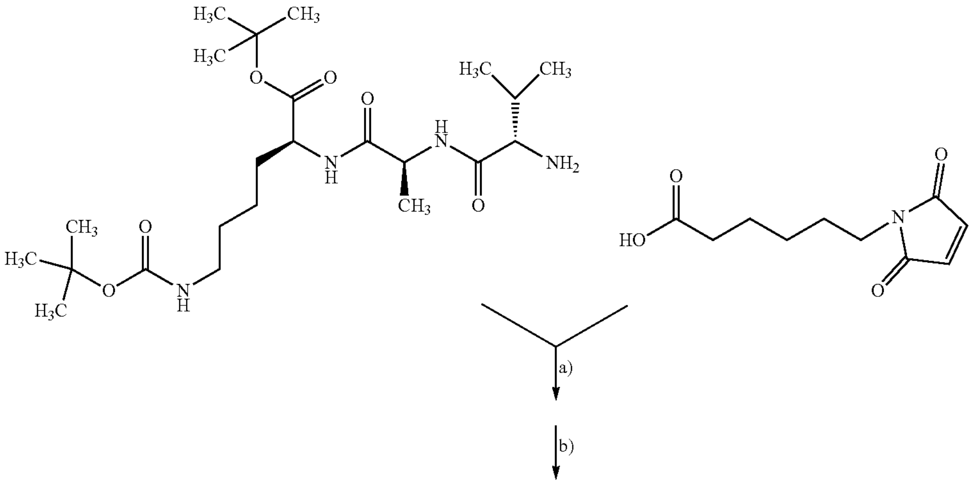

-continued
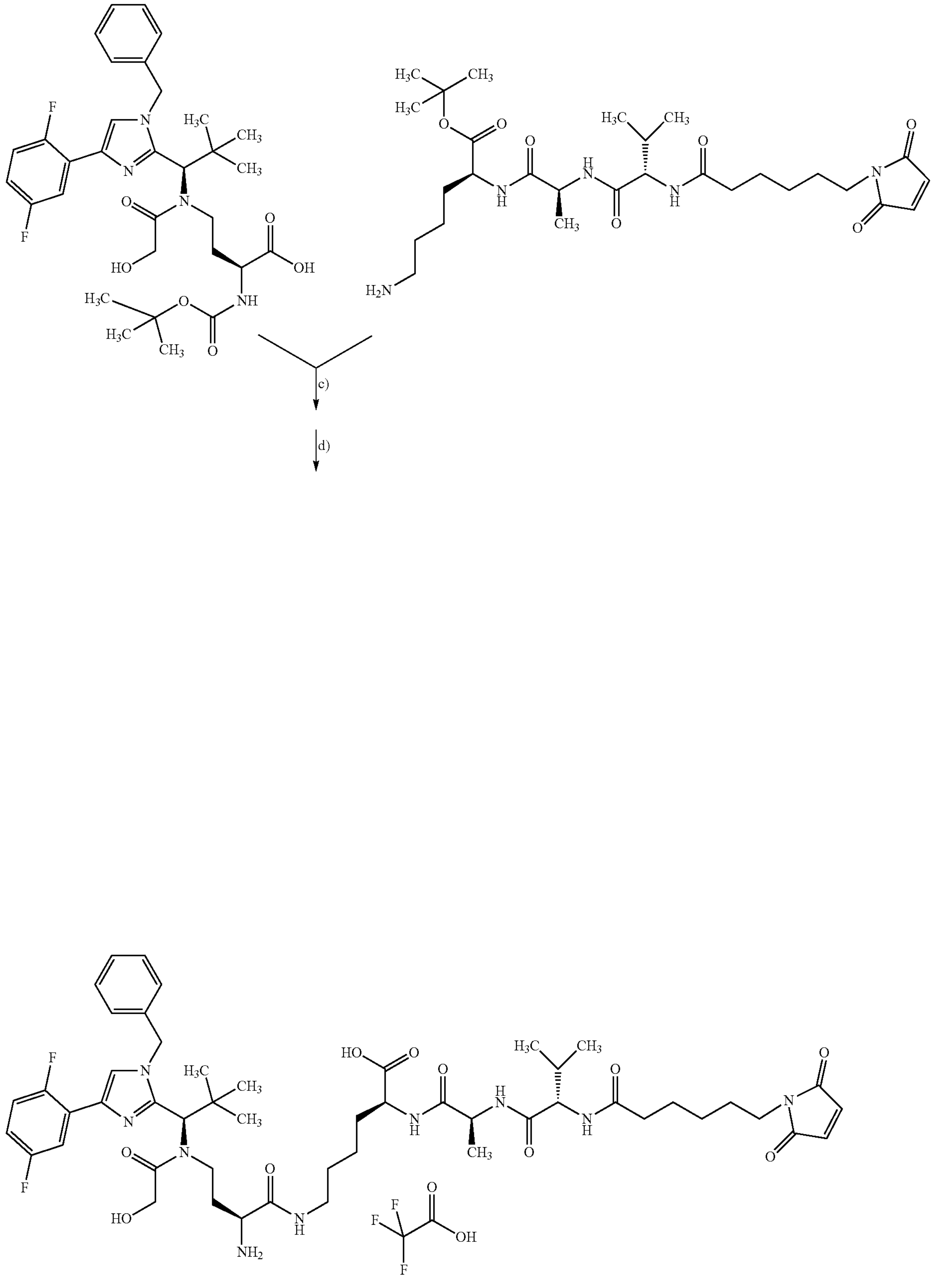
[a): for example EDCI, HOBT, diisopropylethylamine, DMF, RT; b) for example DCM/TFA 20:1, RT; c) for example HATU, diisopropylethylamine, DMF, RT; d) for example TFA, DCM, RT]

Scheme 9: Synthesis of ADC precursor molecules
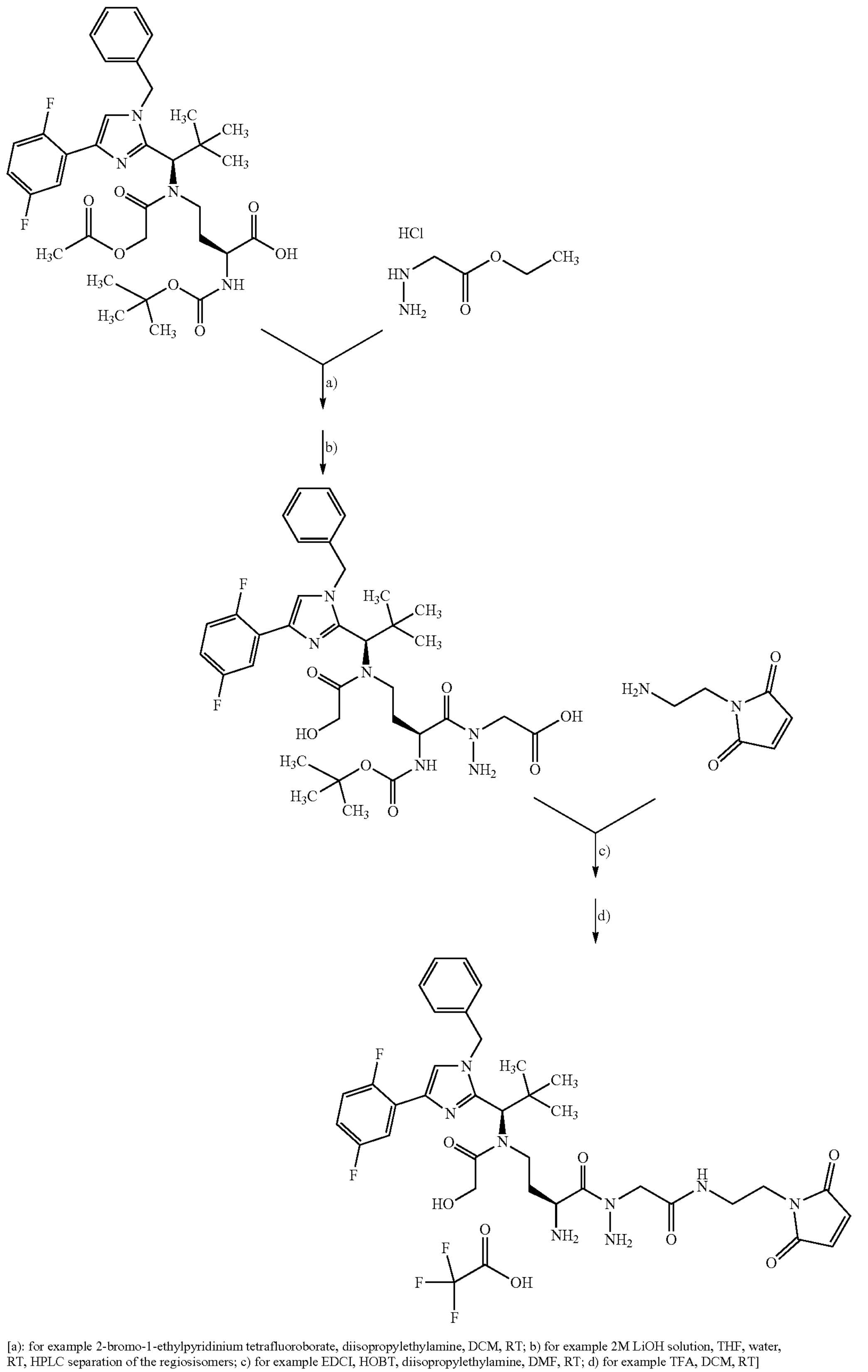
[a): for example 2-bromo-1-ethylpyridinium tetrafluoroborate, diisopropylethylamine, DCM, RT; b) for example 2M LiOH solution, THF, water, RT, HPLC separation of the regiosisomers; c) for example EDCI, HOBT, diisopropylethylamine, DMF, RT; d) for example TFA, DCM, RT]

Scheme 10: Synthesis of ADC precursor molecules
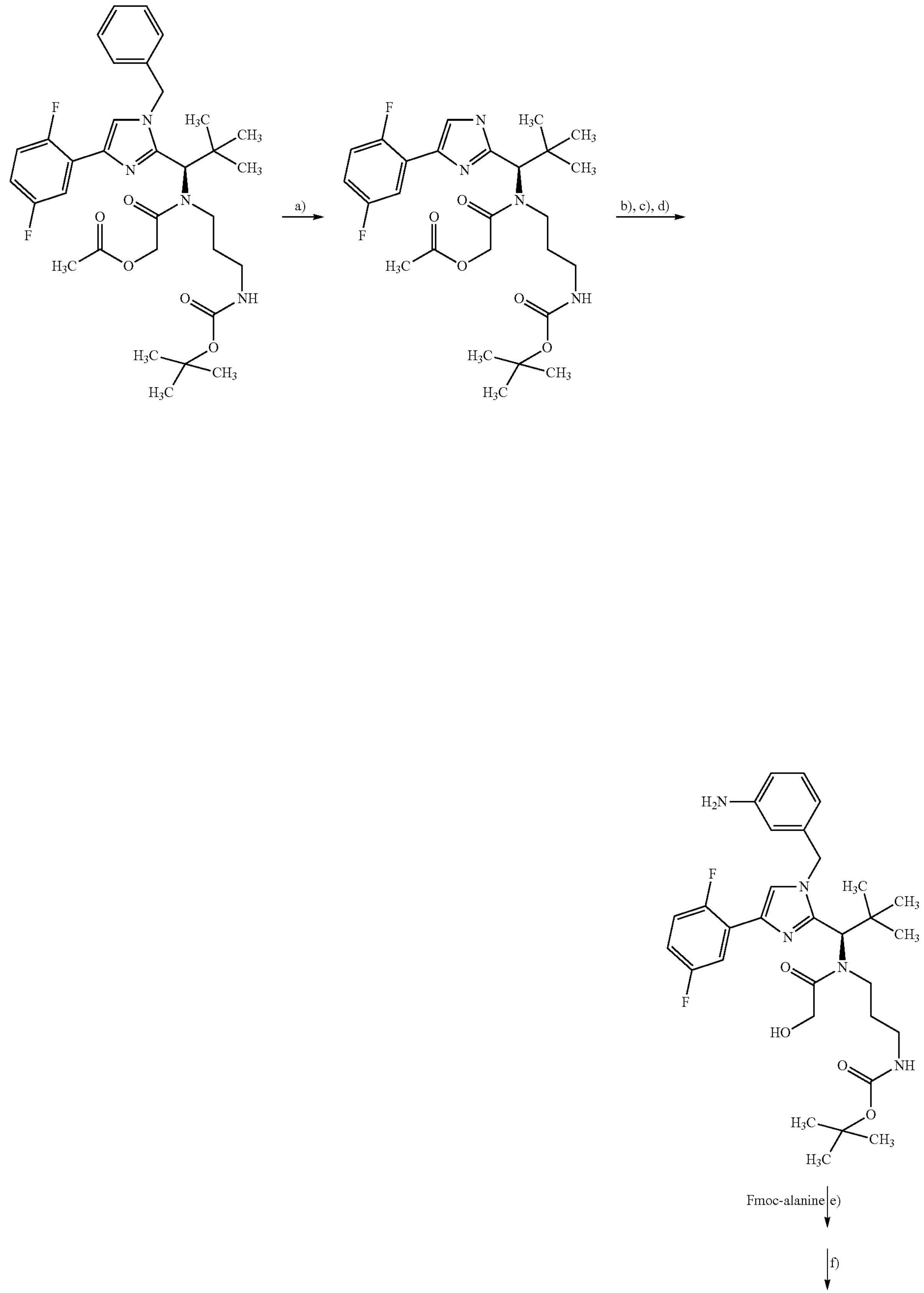

-continued

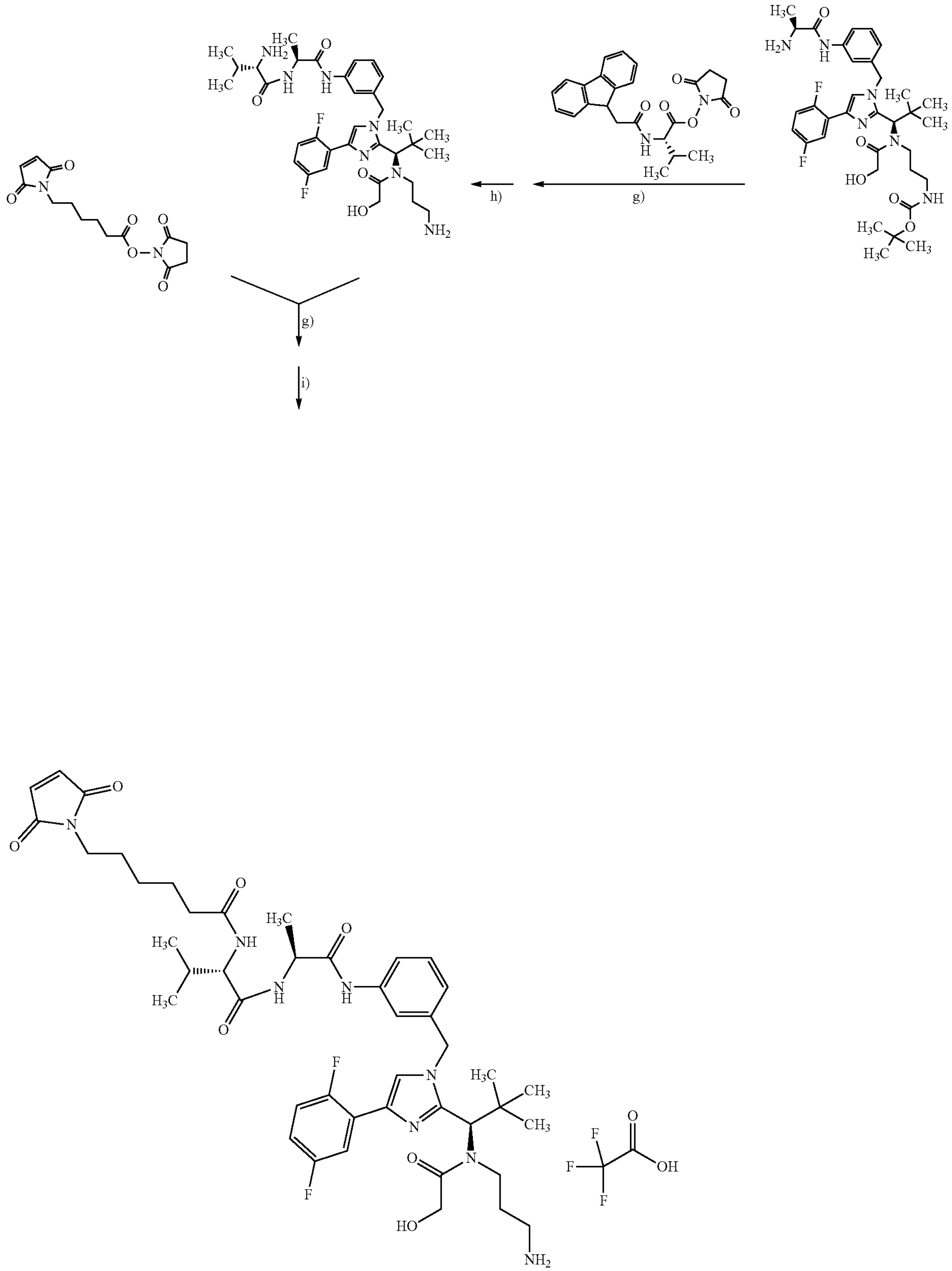

[a): for example $H_2$, Pd—C, EtOH, RT; b) for example p-nitrobenzyl bromide, $K_2CO_3$, DMF; c) for example ethanol, 40% strength methylamine solution in water, 50° C.; d) for example disodium dithionite, THF, water, 50° C.; e) for example HATU, diisopropylethylamine, DMF, RT; f) for example piperidine, 40% strength methylamine solution in water, ethanol, 50° C.; g) for example diisopropylethylamine, DMF, RT; h) for example piperidine, DMF, RT; i) TFA, DCM, RT]

Scheme 11: Synthesis of ADC precursor molecules
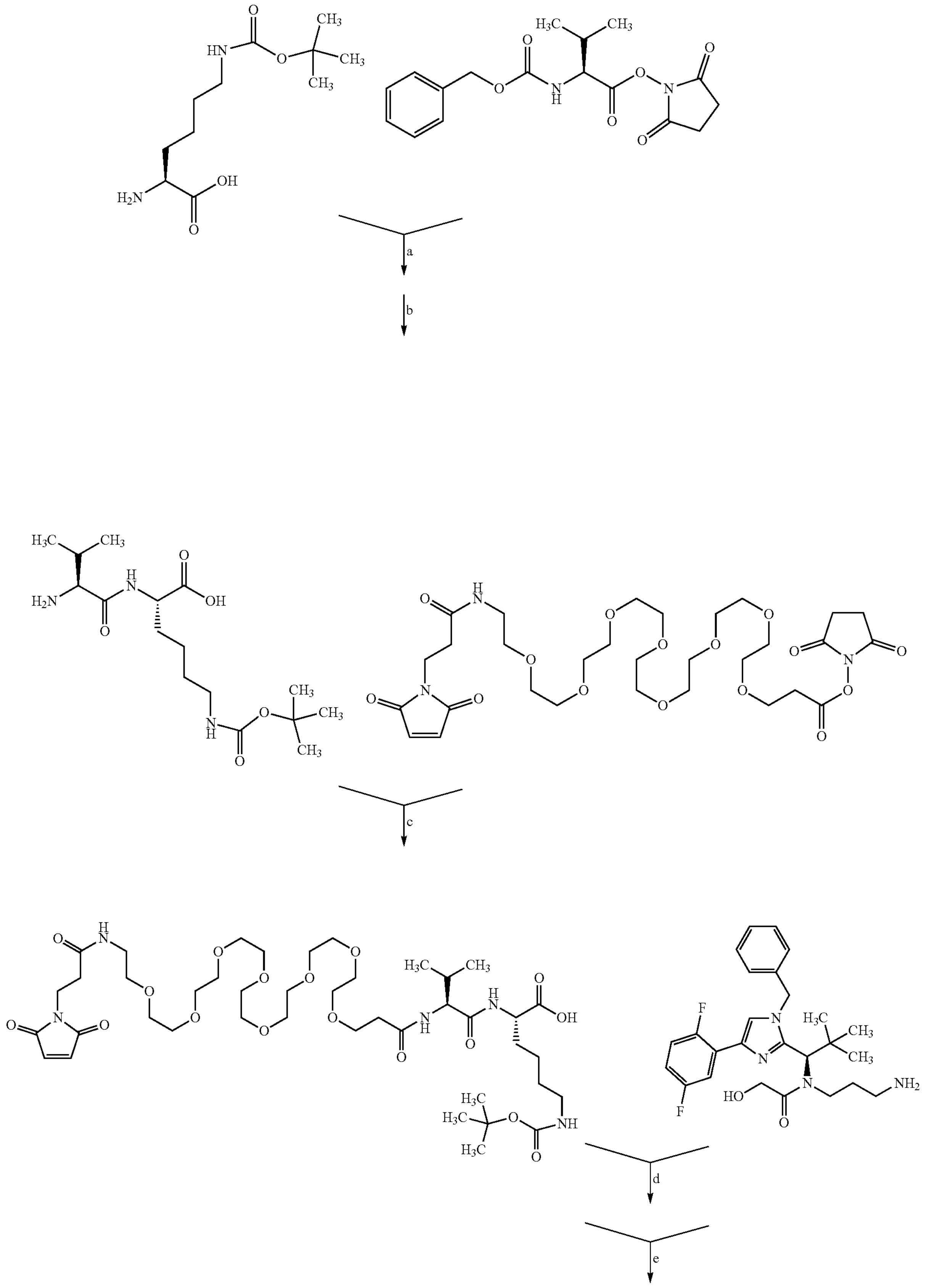

-continued
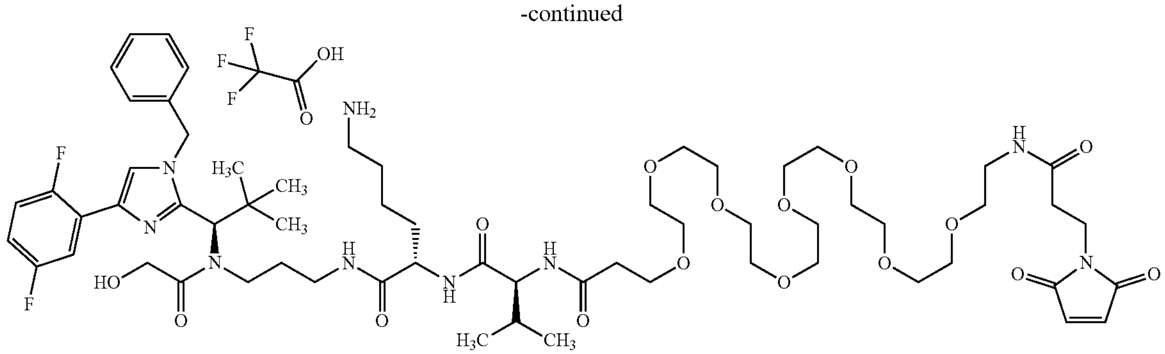
[a): for example $Et_3N$, DMF, RT; b) for example $H_2$, Pd—C, EtOH/ethyl acetate/THF (1:1:1), RT; c) for example 4-methylmorpholine, DMF, RT; d) for example HATU, HOAt, diisopropylethylamine, DMF, RT; e) for example TFA, RT]
Scheme 12: Synthesis of ADC precursor molecules
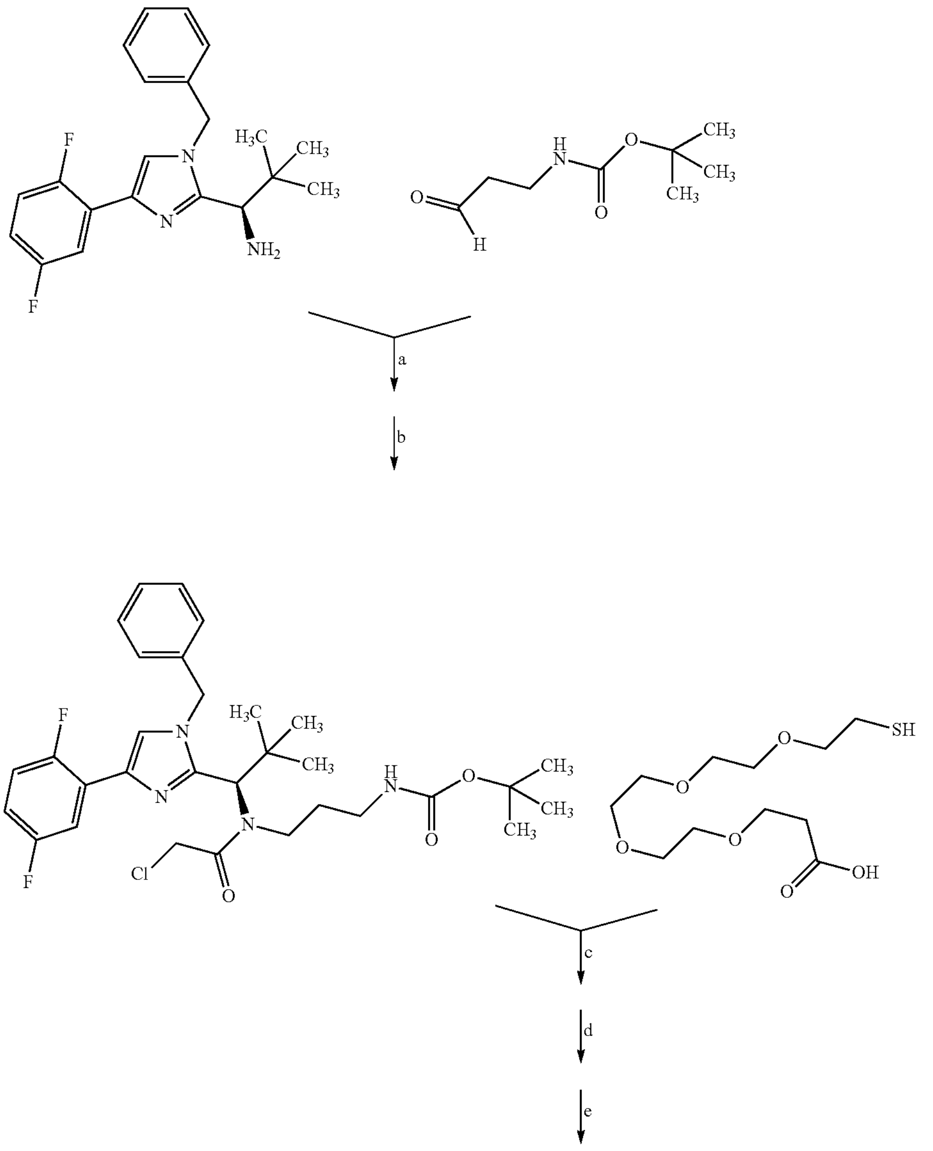

-continued
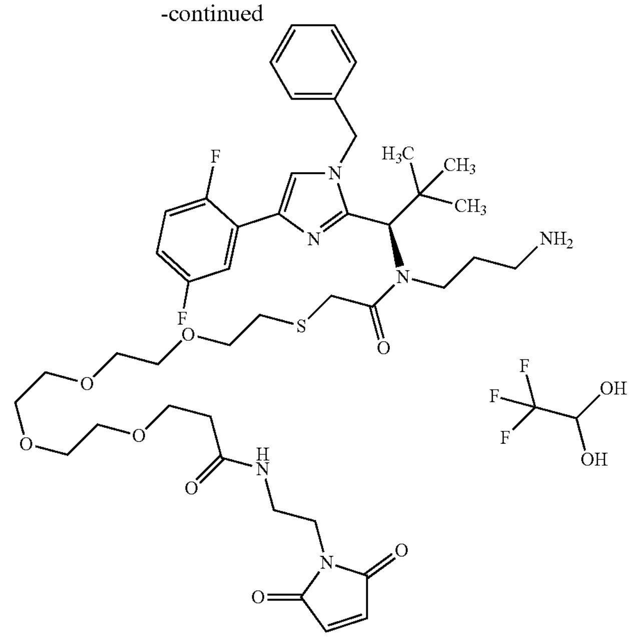
[a): for example $NaBH(OAc)_3$, HOAc, dichloromethane, RT; b) for example chloroacetyl chloride, $NEt_3$, DCM, RT; c) for example $Cs_2CO_3$, DMF, 50° C.; d) for example 1-(2-aminoethyl)-1H-pyrrole-2,5-dione hydrochloride (1:1), T3P[(R)], diisopropylethylamine, MeCN, RT; e) for example TFA, RT]
Scheme 13: Synthesis of ADC precursor molecules
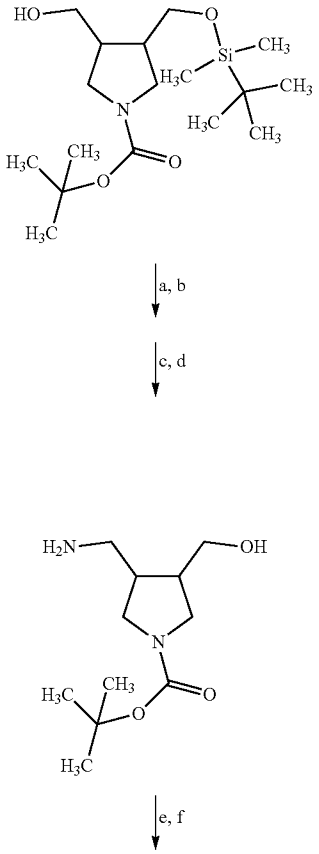

-continued

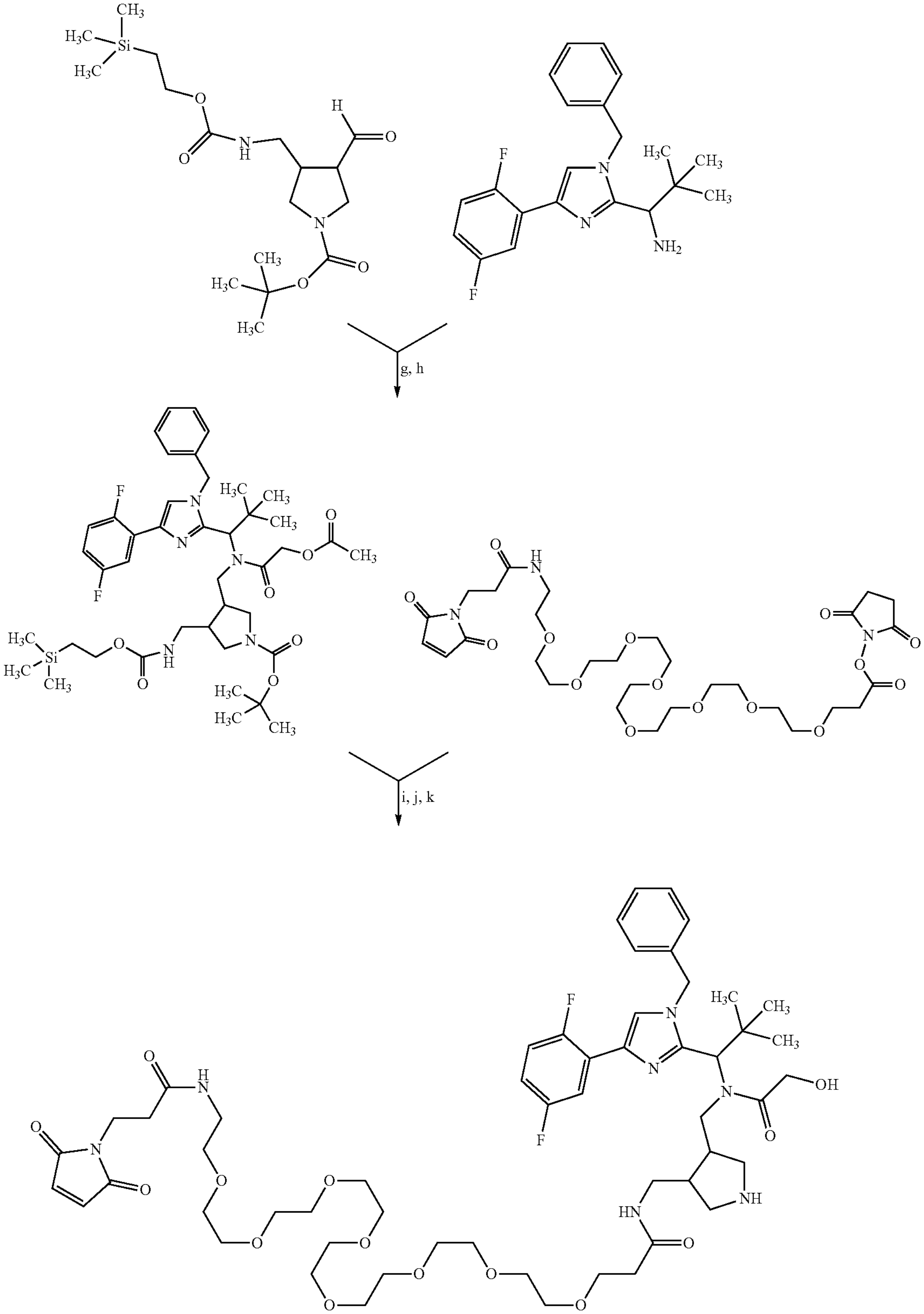

[a): for example methanesulphonyl chloride, $NEt_3$, dichloromethane, 0° C.; b) for example $NaN_3$, DMF, 40° C.; c) for example $H_2$, Pd—C, EtOH/ethyl acetate (1:1), RT; d) for example TBAF, THF, RT; e) for example 1-({[2-(trimethylsilyl)ethoxy] carbonyl}oxy)pyrrolidine-2,5-dione, $NEt_3$, $CaCO_3$, 1,4-dioxane, RT; f) for example N-chlorosuccinimide, TEMPO, tetra-n-butylammonium choride, chloroform, 0.05 N potassium carbonate/0.05 N sodium bicarbonate solution (1:1); g) for example $NaBH(OAc)_3$, HOAc, dichloromethane, RT; h) for example chloroacetyl chloride, $NEt_3$, DCM, RT; i) for example TBAF, THF, water, RT; j) for example 4-methylmorpholine, DMF, RT; k) for example TFA, RT]

Scheme 14: Synthesis of ADC precursor molecules

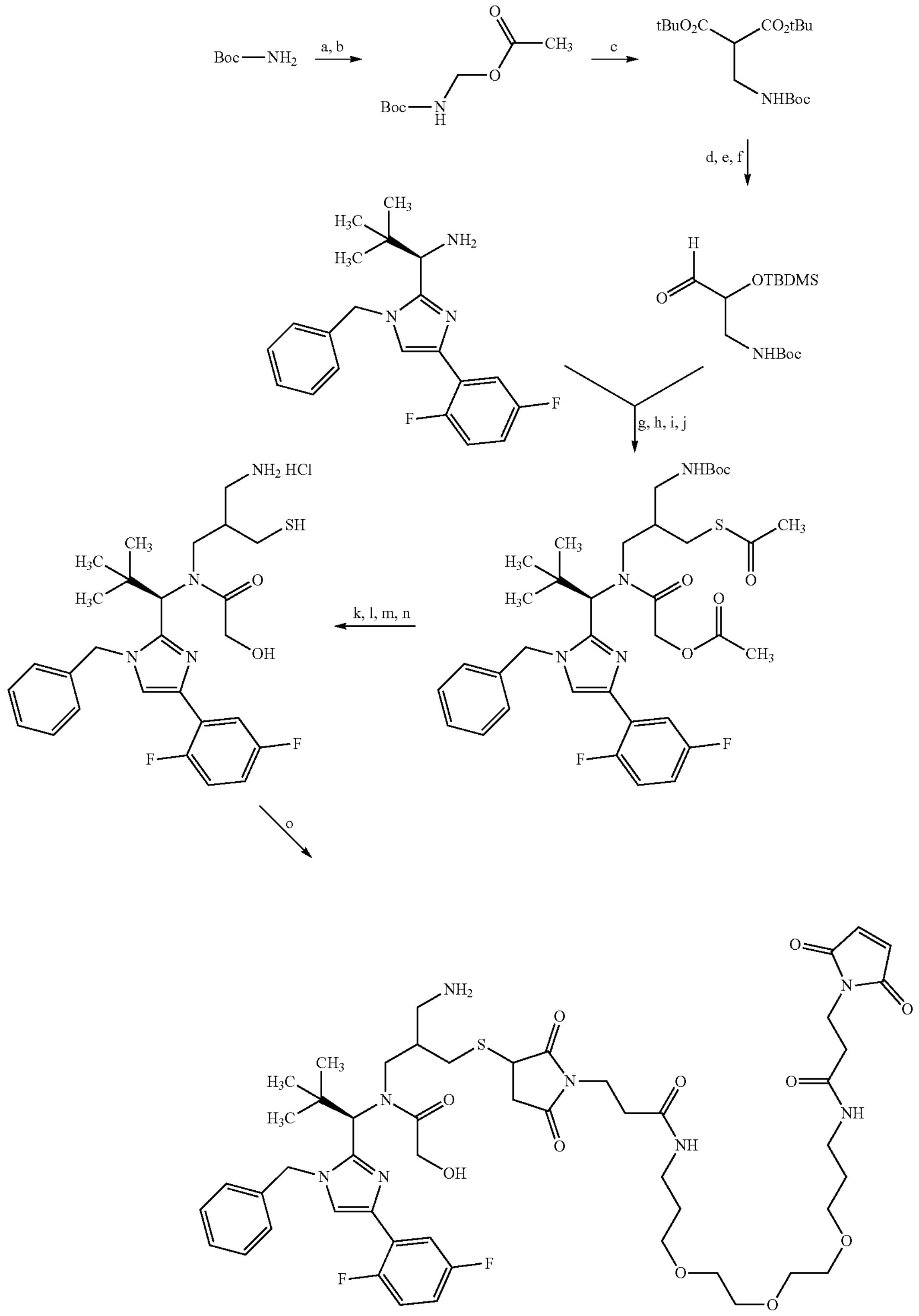

[a): for example formaldehyde, $Na_2CO_3$, water, RT; b) for example $Ac_2O$, pyridine, THF, RT; c) for example di-tert-butyl malonate, KOtBu, THF, RT; d) for example $LiBH_4$, THF, RT; e) for example TBDMSCl, imidazole, DCM, RT; f) for example Dess-Martin periodinane, DCM; g) for example sodium triacetoxyborohydride, AcOH, DCM, RT; h) for example $nBu_4NF$, THF, RT; i) for example $SOCl_2$, THF, RT; j) for AcSK, $nBu_4NI$, DMF, 90° C.; k) for example NaOH, MeOH, THF, RT; l) for example TCEP, dioxane, RT; m) for example separation of the epimers; n) for example 6N hydrochloric acid, THF, RT o) for example Mal-dPEG(3)-Mal, PBS buffer, ACN, RT]

Scheme 15: Synthesis of ADC precursor molecules

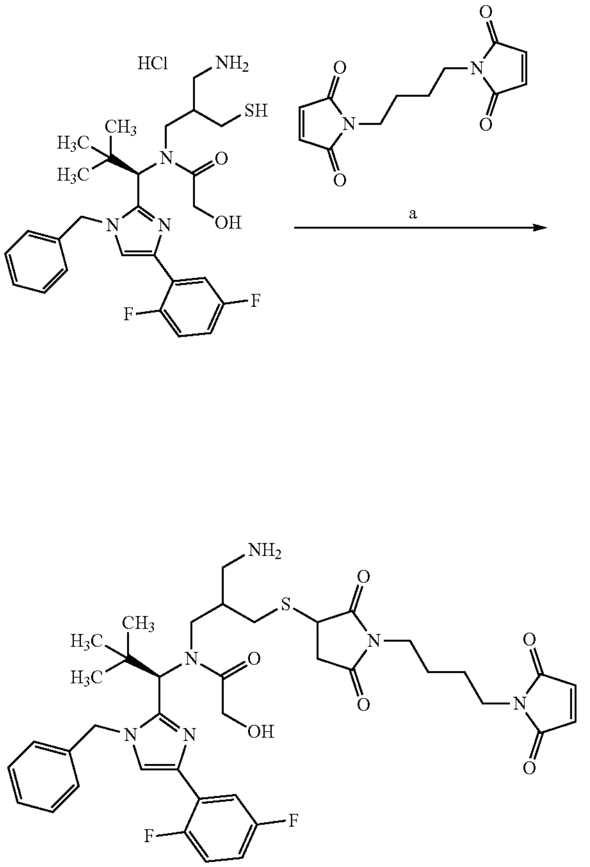

[a]: for example Mal-dPEG(3)-Mal, PBS buffer, ACN, RT]

Scheme 16: Synthesis of ADC precursor molecules

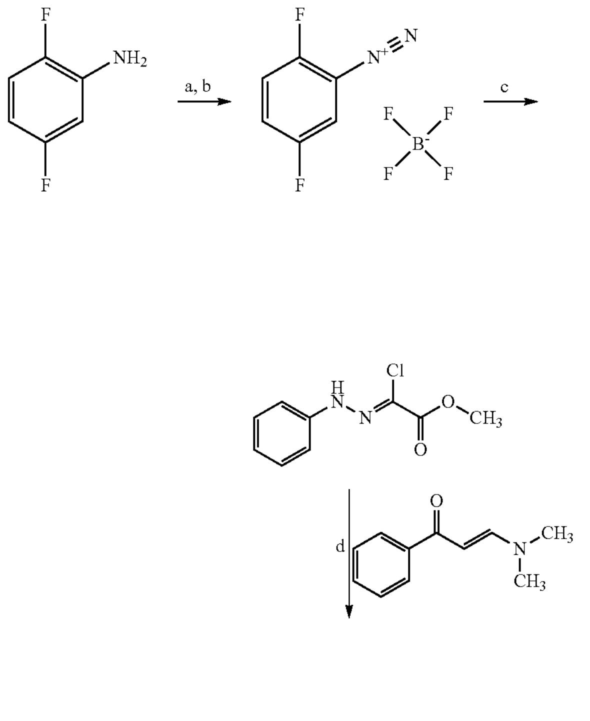

-continued

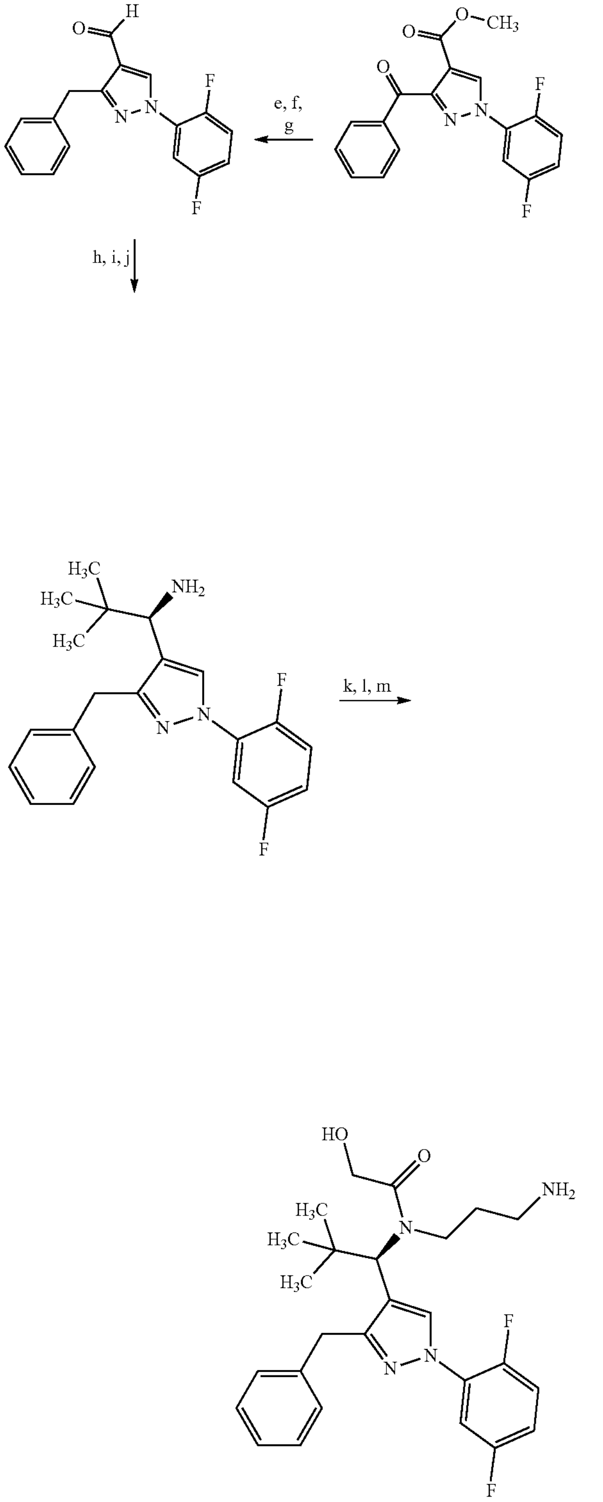

[a): for example $BF_3OEt_2$, THF, 0° C.; b): for example isoamyl nitrite, -10° C., 0.5 h; c): for example methyl 2-chloro-3-oxobutanoate, pyridine, water, -5° C.; d): for example $NEt_3$, toluene, RT; e); for example $Et_3SiH$, TFA, RT; f): for example $LiBH_4$, THF, 60° C.; g): for example Dess-Martin periodinane, DCM, RT; h): for example (R)-(+)-methyl-2-propanesulphinamide, titanium(IV) isopropoxide, THF, RT; i): for example tert-BuLi, pentane, THF, -78° C.; j): for example HCl in dioxane, THF, MeOH, RT; k): for example 3-(1,3-dioxo-1,3-dihydro-2H-isoindol-2-yl)propanol, $NaB(OAc)_3H$, AcOH, DCM, RT; 1): for example 2-chloro-2-oxoethyl acetate, $NEt_3$, DCM, RT; m): for example methylamine, water, EtOH, 50° C.]

Scheme 17: Synthesis of ADC precursor molecules

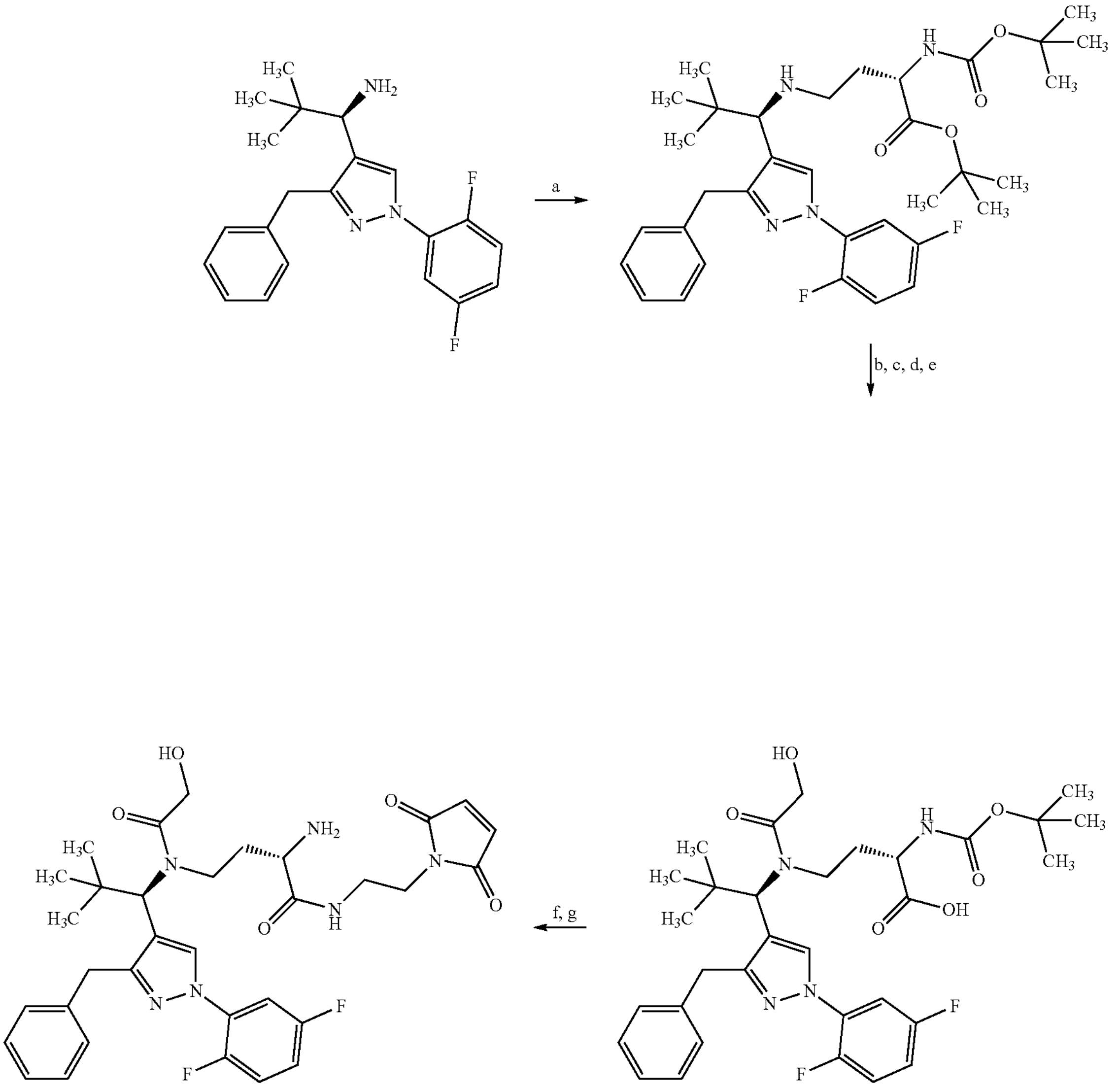

[a): for example tert-butyl N-(tert-butoxycarbonyl)-5-oxo-L-norvalinate, $NaB(OAc)_3H$, AcOH, DCM, RT; b): for example 2-chloro-2-oxoethyl acetate, $NEt_3$, DCM, RT; c): for example methylamine, water, EtOH, 60° C.; d): for example THF, DCM, 50° C.; e): for example $Boc_2O$, $NEt_3$, DCM, RT; f): for example trifluoroacetic acid/1-(2-aminoethyl)-1H-pyrrole-2,5-dione (1:1), HATU, diisopropylethylamine, DMF, RT; f): for example TFA, DCM, RT]

Scheme 18: Synthesis of cysteine-linked ADCs

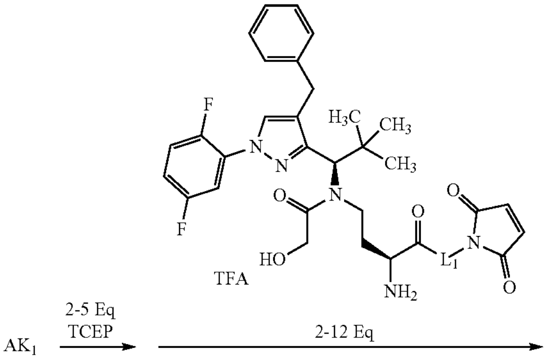

-continued

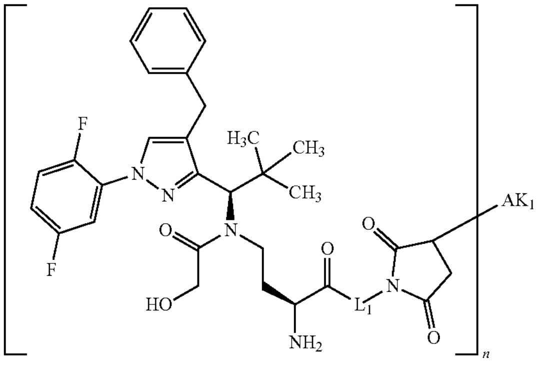

Scheme 19: Synthesis of cysteine-linked ADCs
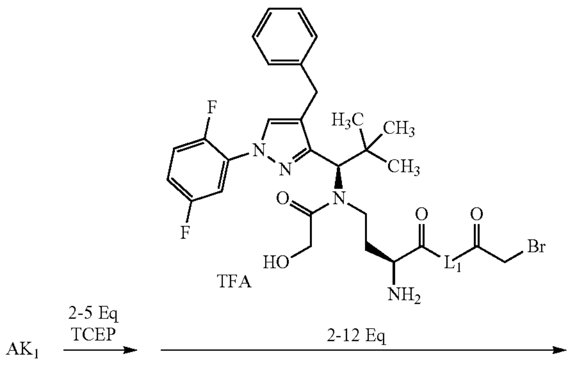
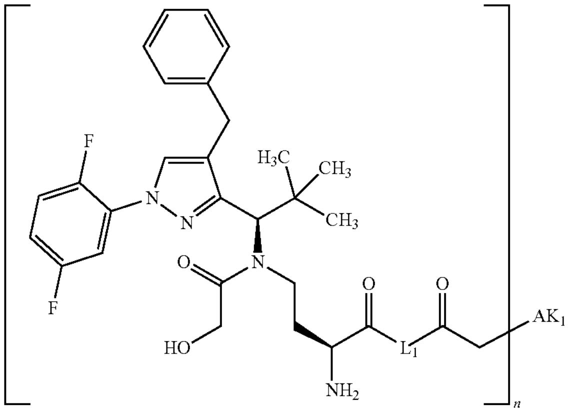
Scheme 20: Synthesis of cysteine-linked ADCs
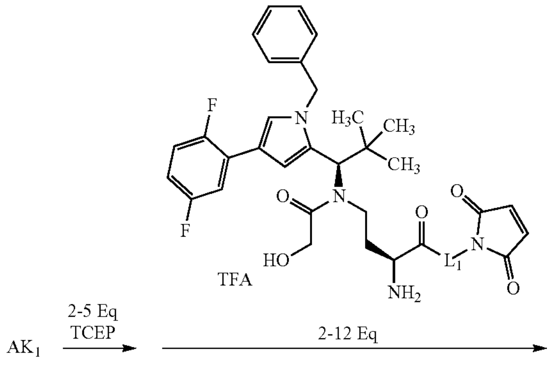
-continued
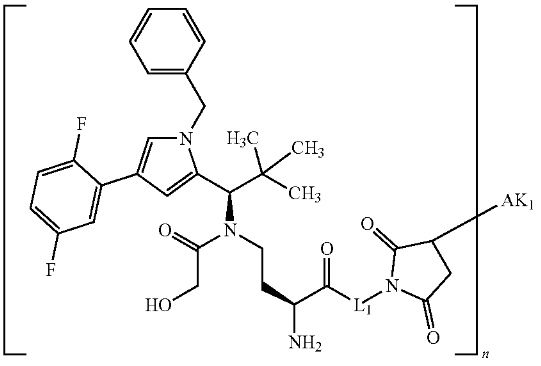
Scheme 21: Synthesis of cysteine-linked ADCs
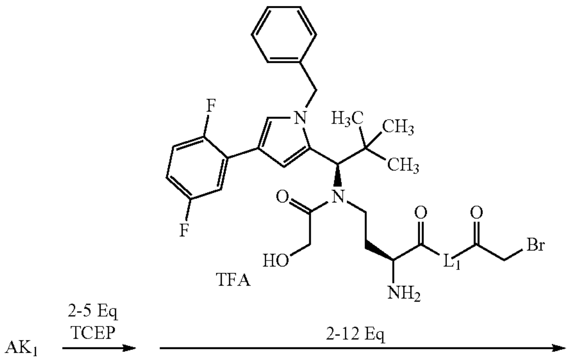
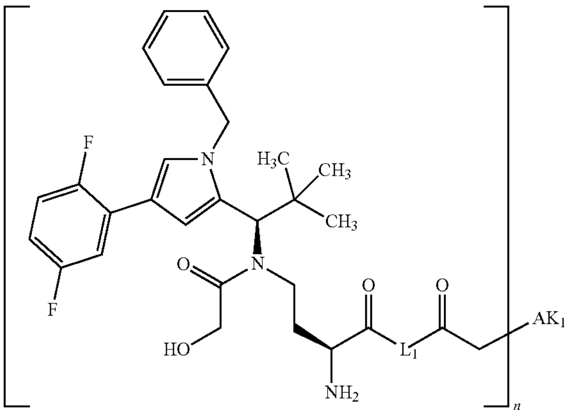

Scheme 22: Synthesis of intermediates
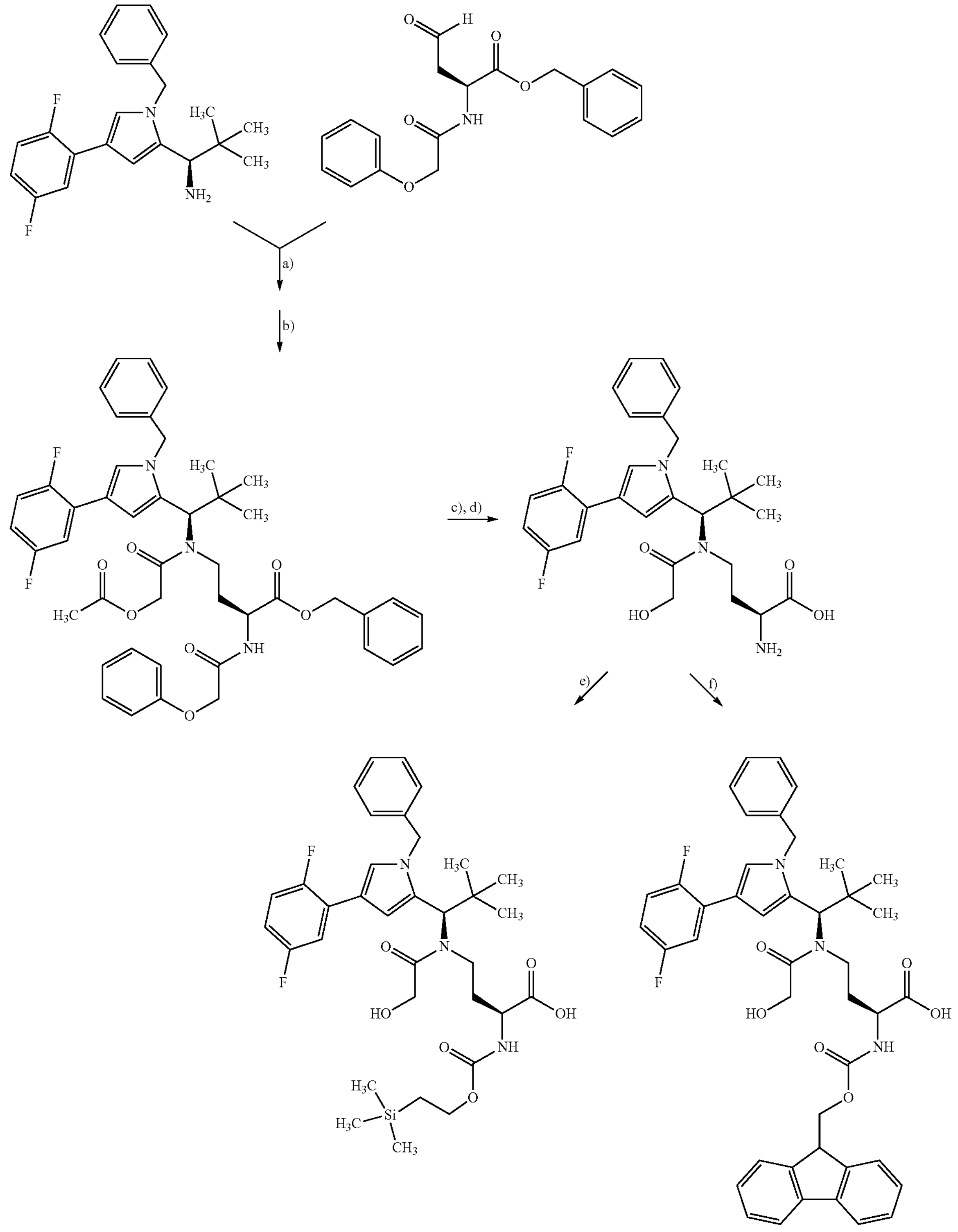
[a): for example sodium triacetoxyborohydride, acetic acid, DCM, RT; b) for example acetoxyacetyl chloride, NEt3, DCM, RT; c) for example LiOH, THF/water, RT; d) for example $H_2$, Pd—C, EtOH, RT; e) for example Teoc-OSu, NEt3, dioxane, RT; f) for example Fmoc—Cl, diisopropylethylamine, dioxane/water 2:1, RT]

Scheme 23: Synthesis of intermediates
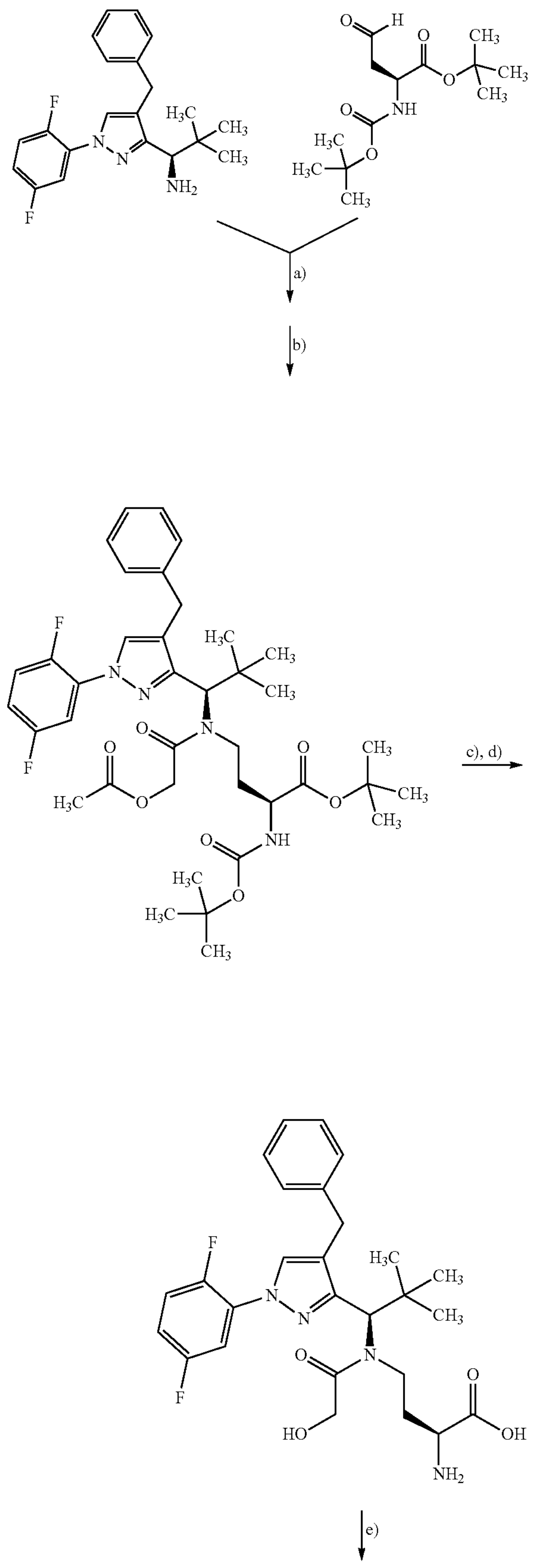
-continued
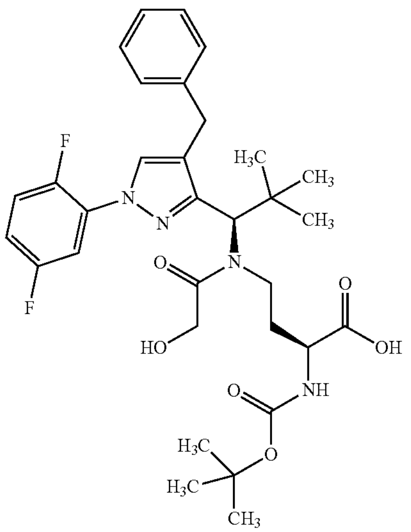
[a): for example sodium triacetoxyborohydride, acetic acid, DCM, RT; b) for example acetoxyacetyl chloride, NEt3, DCM, RT; c) for example LiOH, methanol, RT; d) for example TFA, DCM, RT; e) for example $Boc_2O$, diisopropylethylamine, DCM, RT]
Scheme 24: Synthesis of intermediates
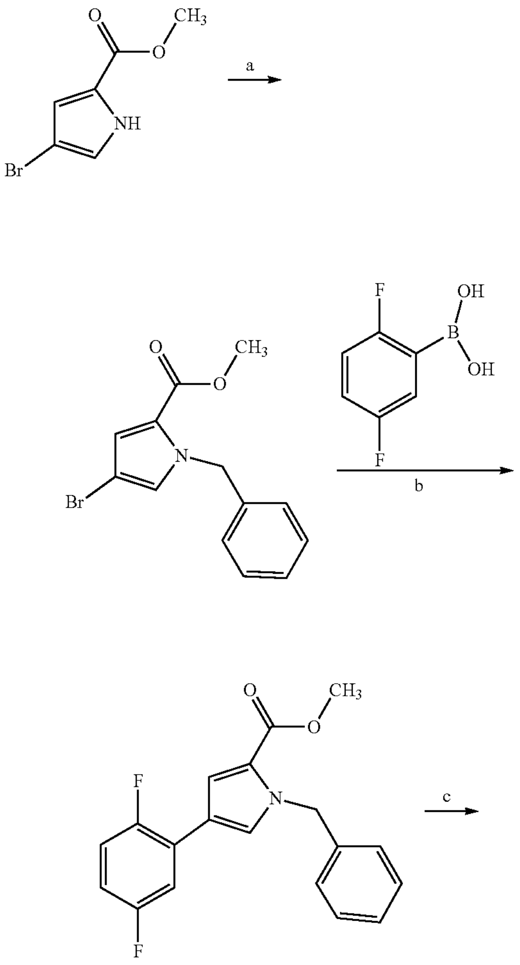

-continued

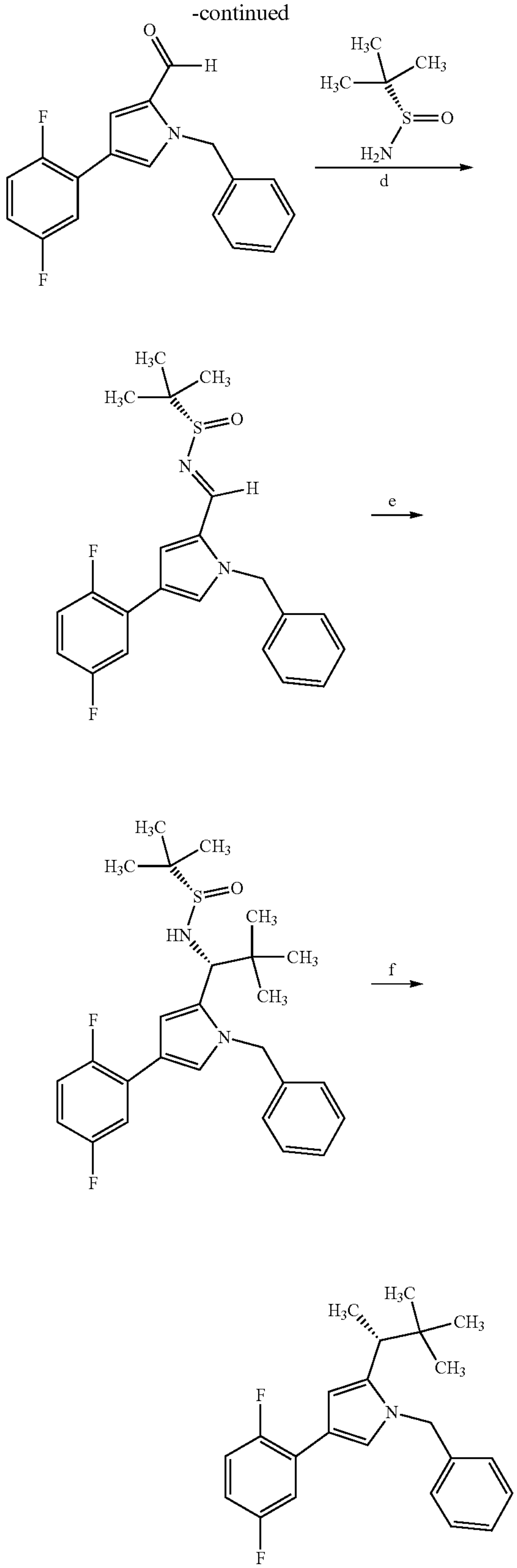

[a]: for example benzyl bromide, $Cs_2CO_3$, DMF, RT; b) for example $Pd(dppf)_2Cl_2$, DMF, $Na_2CO_3$, 85° C.; c) for example $LiAlH_4$, THF, 0° C.; $MnO_2$, DCM, RT; d) for example $Ti(iOPr)_4$, THF, RT; e) for example tBuLi, THF, -78° C.; MeOH, $NH_4Cl$; f) for example HCl/1,3-dioxane]

Scheme 25: Synthesis of cysteine-linked ADCs

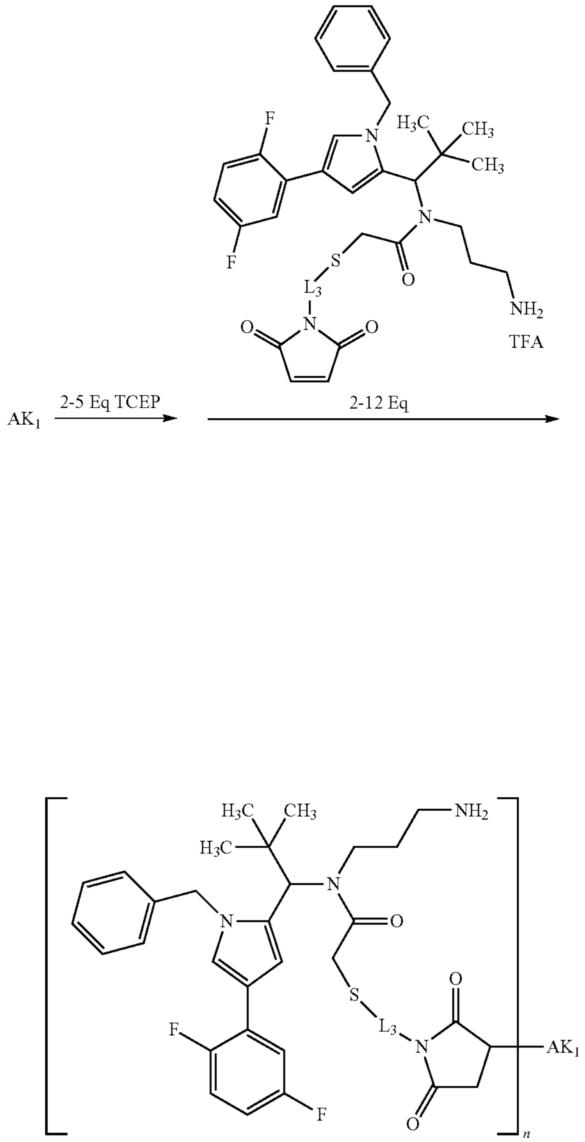

Scheme 26: Synthesis of cysteine-linked ADCs via hydrolysed succinamides

This process was used in particular for ADCs where L1 = CH2 to convert these ADCs into the open-chain linking form.

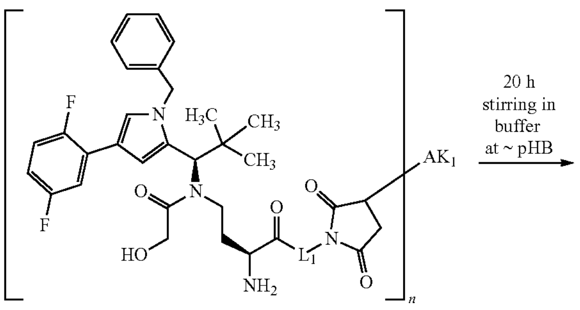

-continued
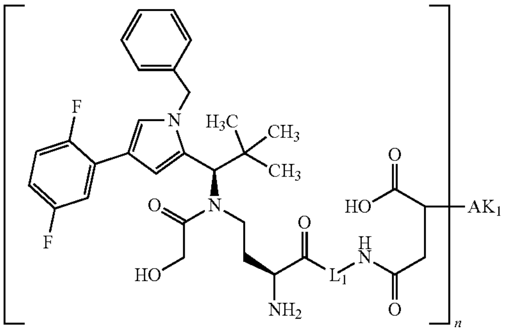
+
-continued
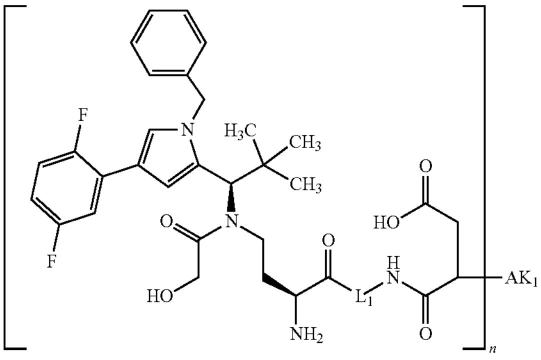
Scheme 27: Synthesis of ADC precursor molecules
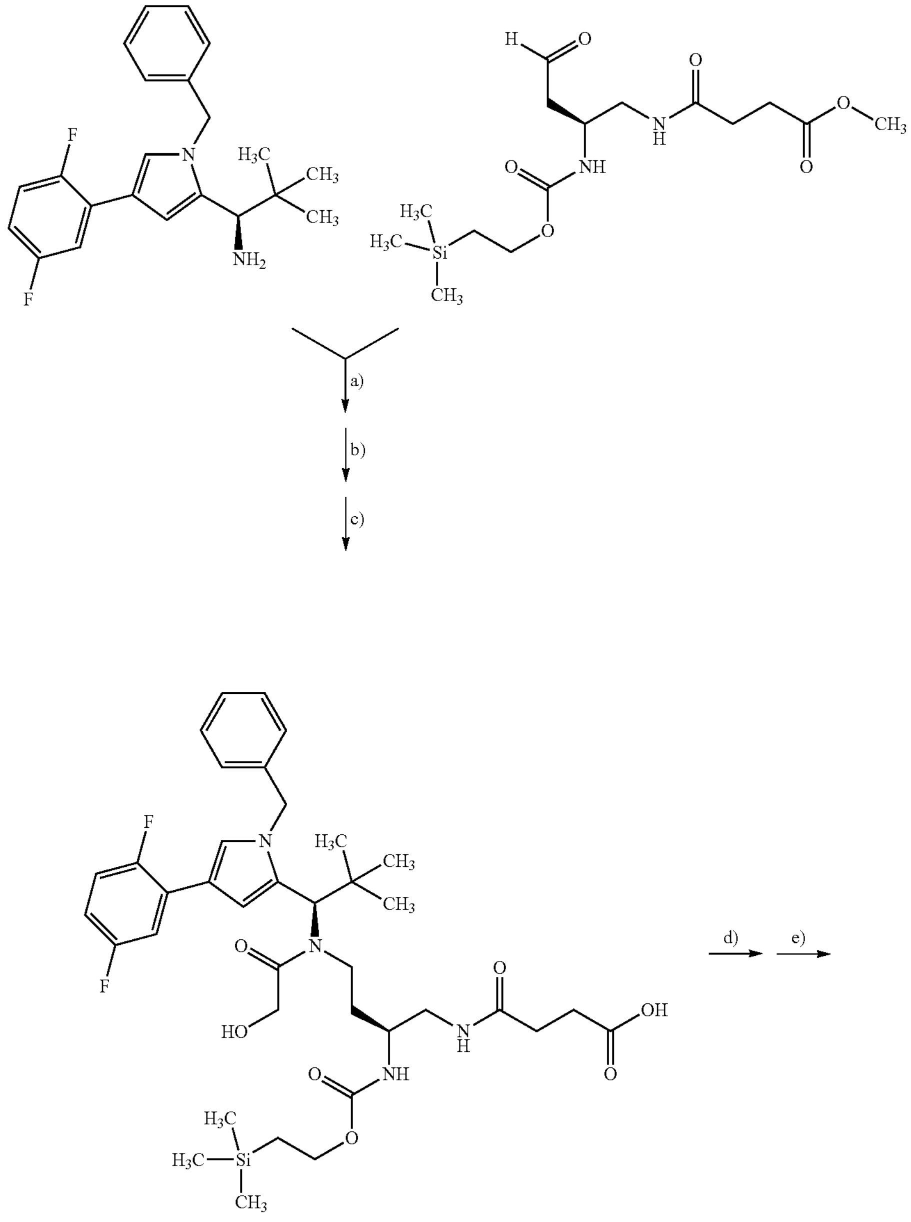

-continued
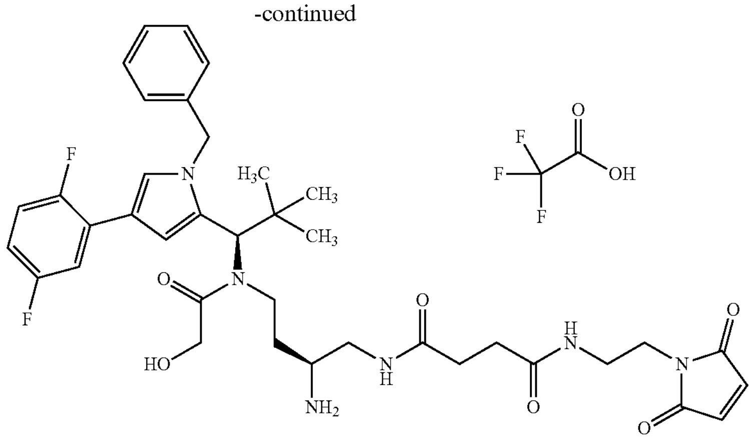
[a): sodium triacetoxyborohydride, acetic acid, DCM, RT; b) acetoxyacetyl chloride, diisopropylethylamine, DCM, RT; c) LiOH, MeOH, RT; d) trifluoroacetic acid/1-(2-aminoethyl)-1H-pyrrole-2,5-dione (1:1) HATU, DMF, diisorpopylethylamine, RT; e) zinc chloride, trifluoroethanol, 50° C., EDTA.]
Scheme 28: Synthesis of ADC precursor molecules
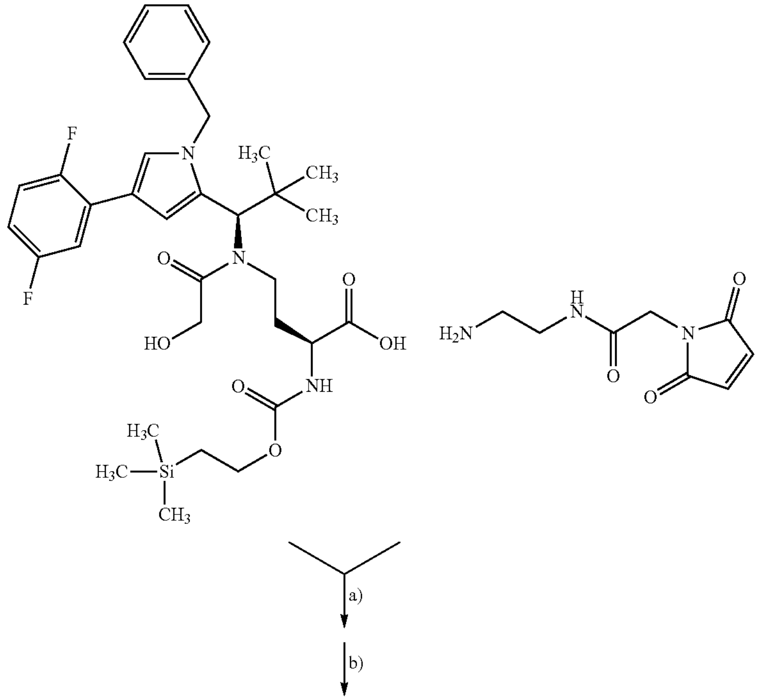

-continued
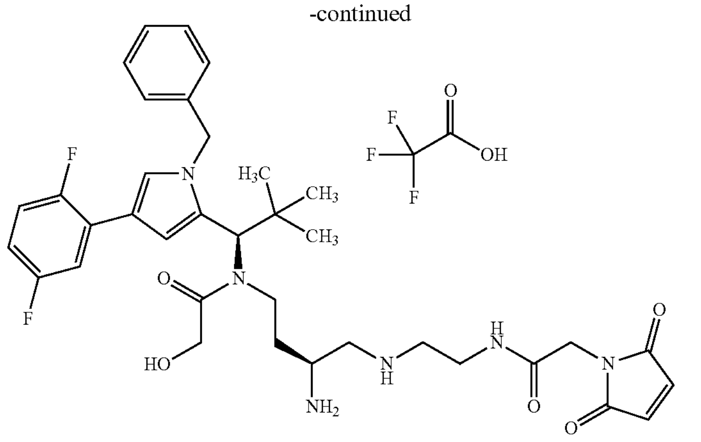
[a): HATU, DMF, diisopropylethylamine, RT; b) zinc chloride, trifluoroethanol, 50° C., EDTA.]
Scheme 29: Synthesis of ADC precursor molecules
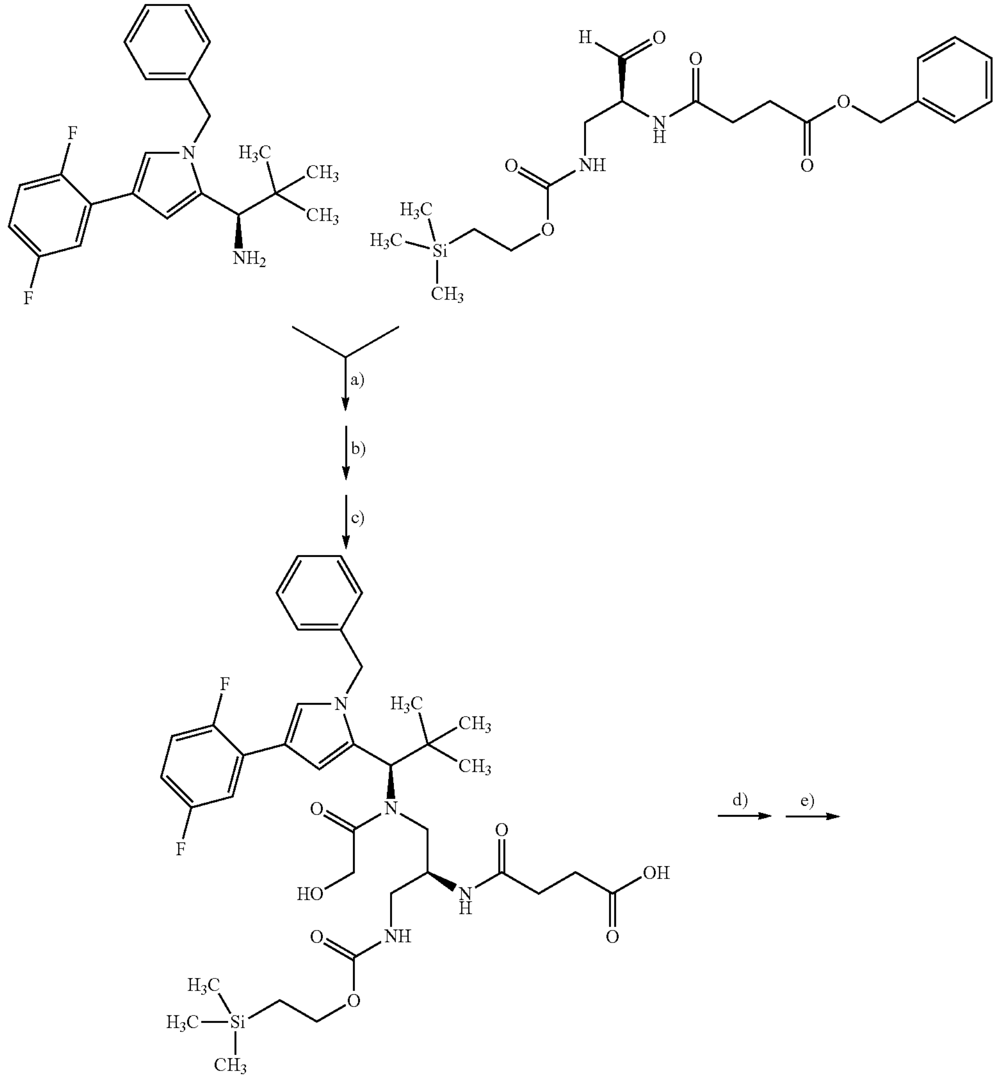

-continued
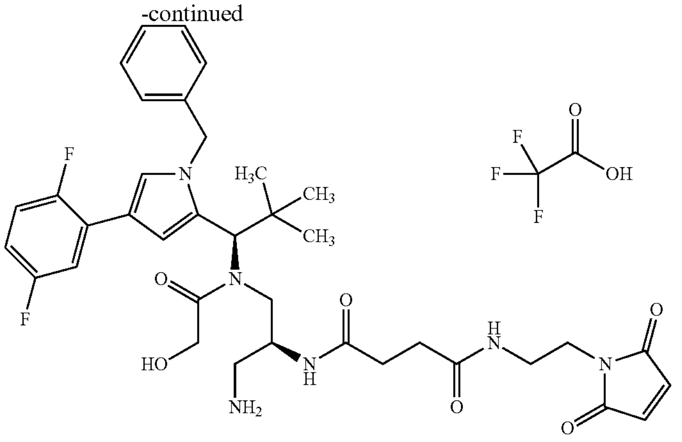
[a): sodium triacetoxyborohydride, acetic acid, DCM, RT; b) acetoxyacetyl chloride, triethylamine, DCM, RT; c) LiOH, MeOH, RT; d) trifluoroacetic acid/1-(2-aminoethyl)-1H-pyrrole-2,5-dione (1:1) HATU, DMF, diisorpopylethylamine, RT; e) zinc chloride, trifluoroethanol, 50° C., EDTA.]
Scheme 30: General method for synthesis of intermediates and ADC precursors
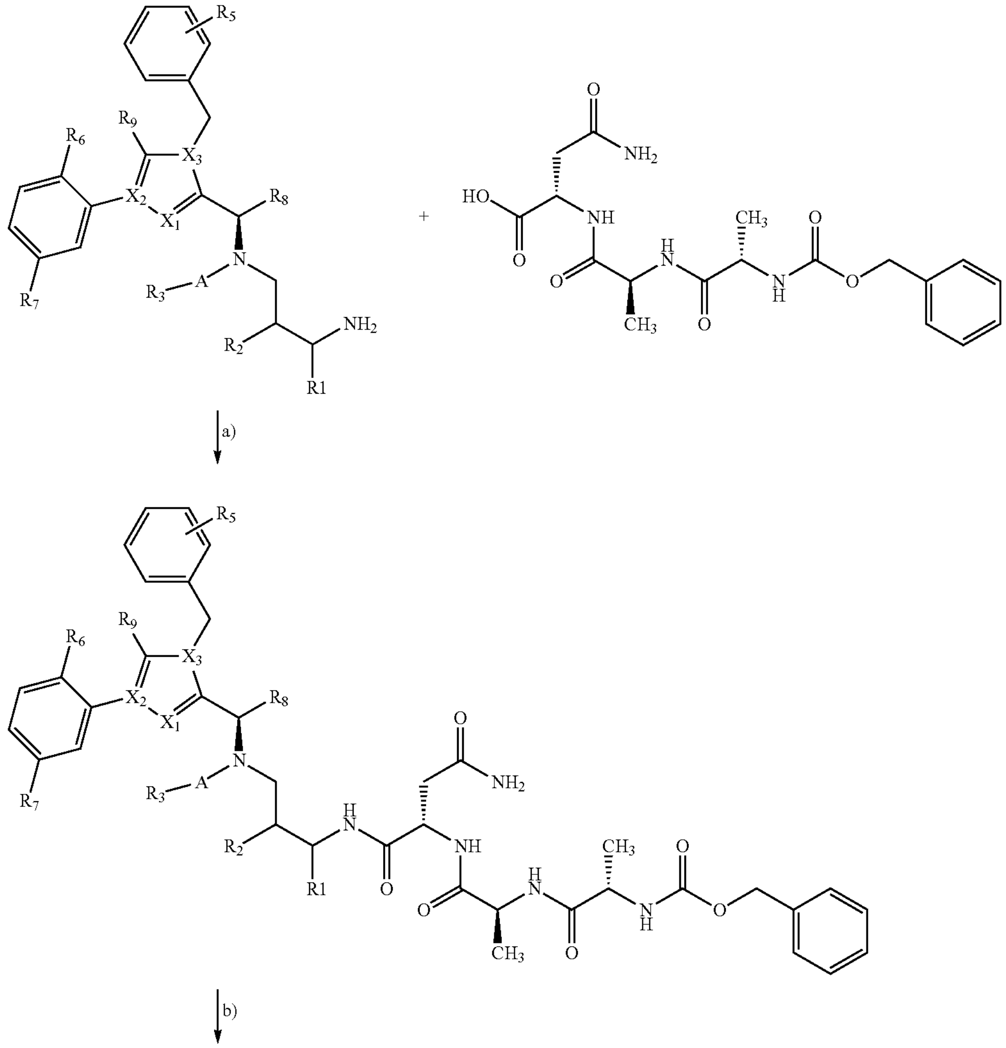

-continued
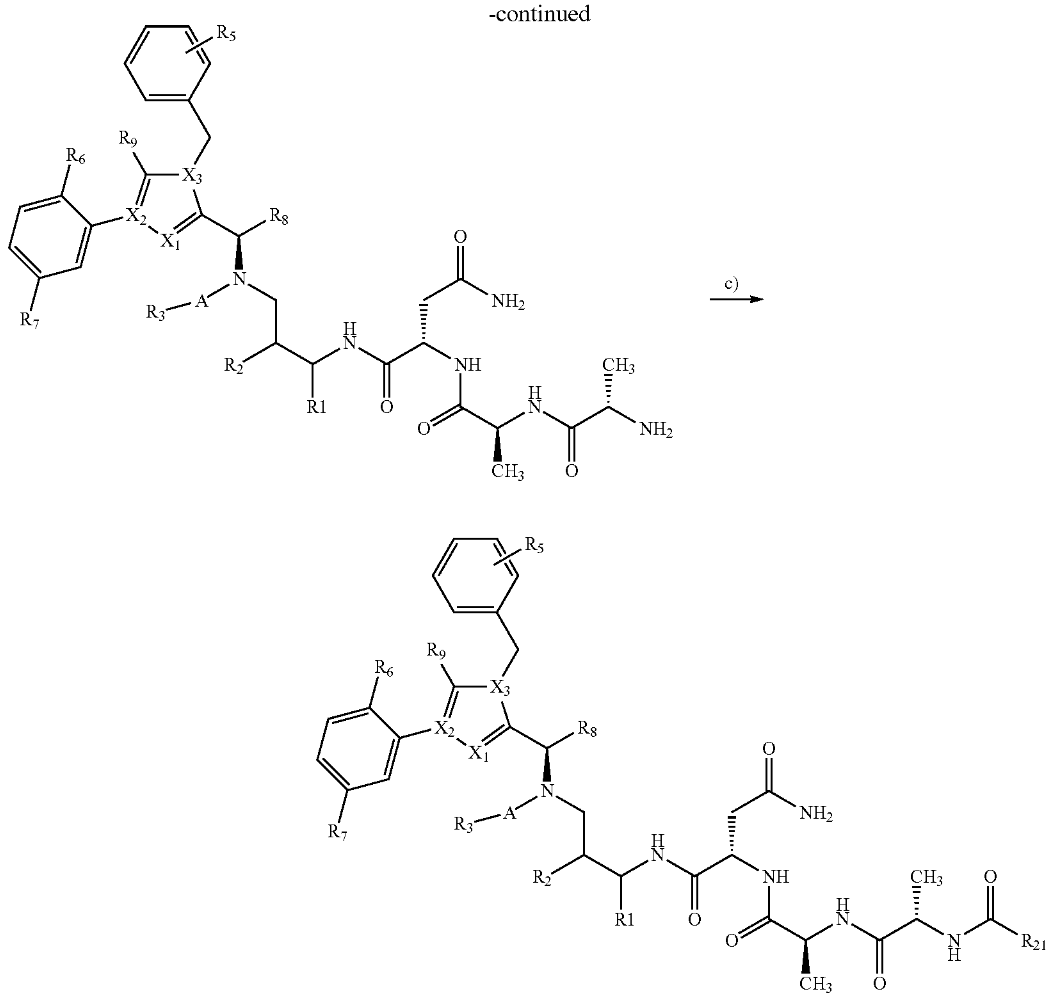
[a): HATU, DMF, N,N-diisopropylethylamine, RT or EDCI, HOBT, N,N-diisorpopylethylamine, DMF, RT b) $H_2$, 10% Pd—C, MeOH, RT; c) $R^{21}$ -COOH, EDCI, HOBT, N,N-diisopropylethylamine, DMF, RT or $R^{21}$ -COOH, HATU, N,N-diisopropylethylamine, DMF, RT or $R^{21}$ -COOSu, N,N-diisoproylethylamine, DMF, RT]
Scheme 31: Synthesis of ADC precursor molecules having legumain-cleavable linkers
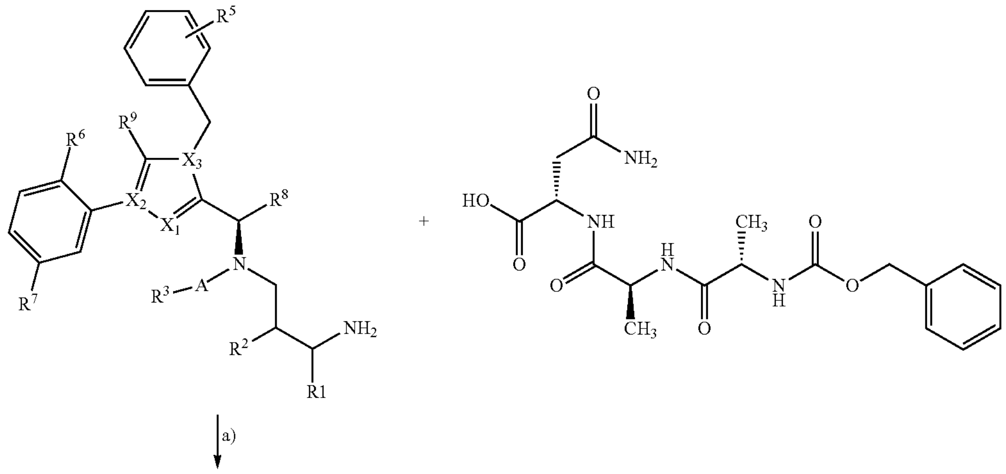

-continued
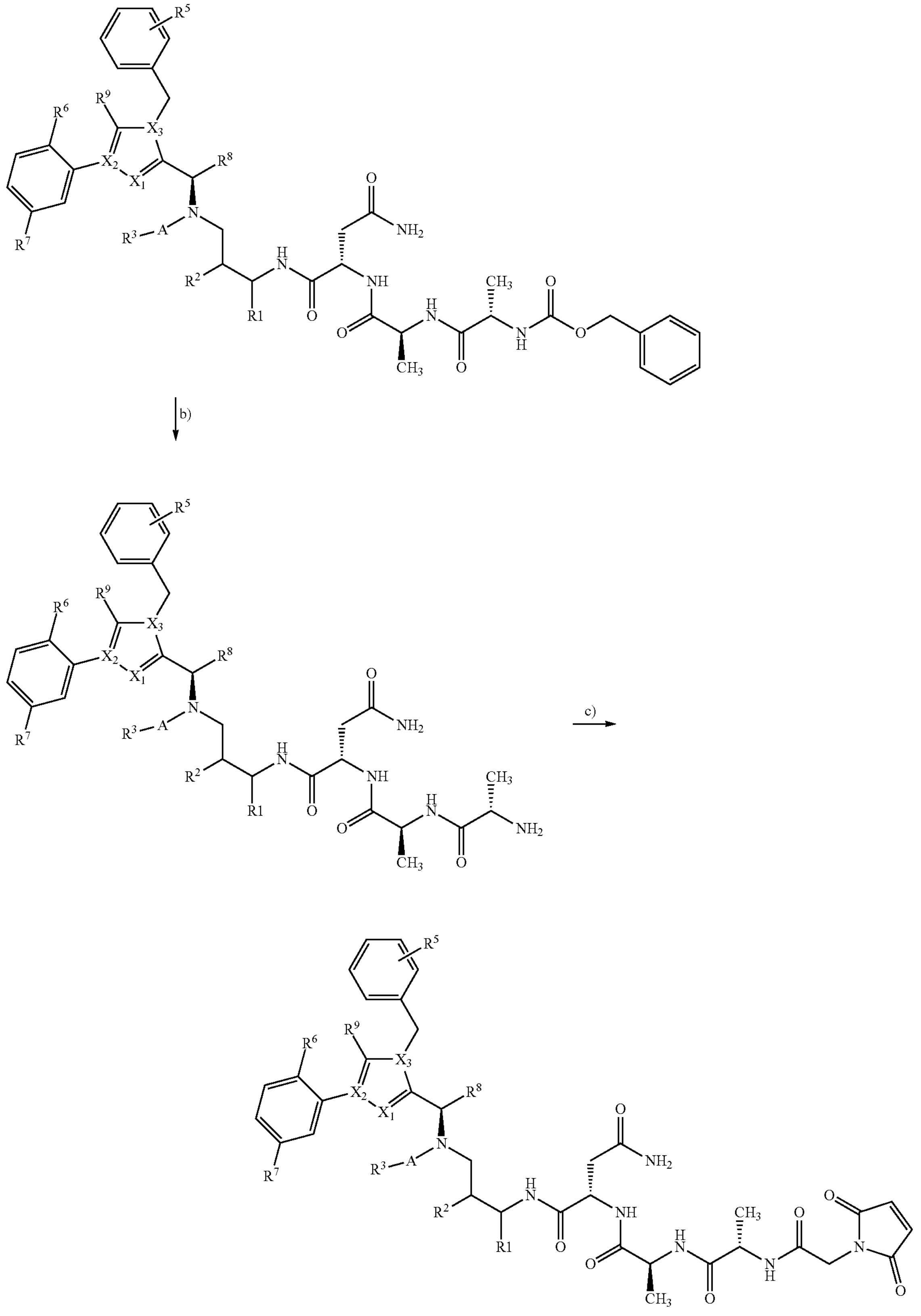
[a): HATU, DMF, N,N-diisopropylethylamine, RT or EDCI, HOBT, N,N-diisorpopylethylamine, DMF, RT b) $H_2$, 10% Pd—C, MeOH, RT; c) 1,1′-[(1,5-dioxopentane-1,5-diyl)bis(oxy)]dipyrrolidine-2,5-dione, N,N-diisopropylethylamine, DMF, RT]

Scheme 32: Synthesis of ADC precursor molecules having legumain-cleavable linkers
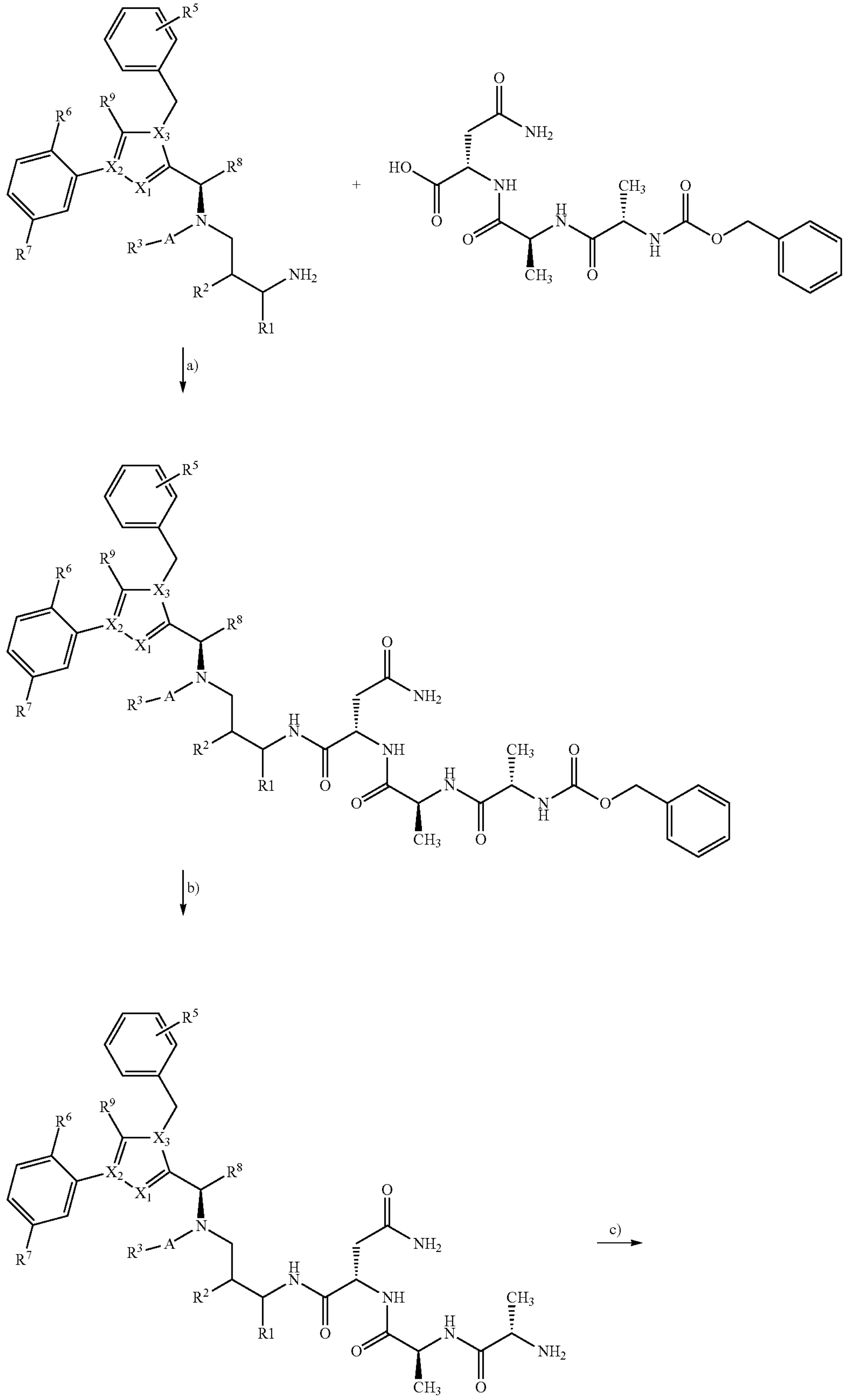

-continued

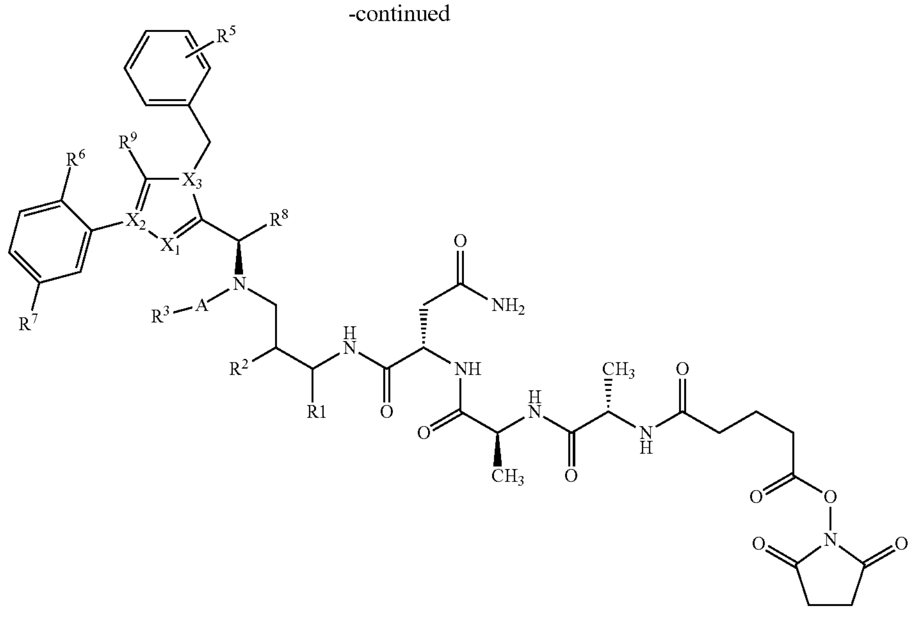

[a): HATU, DMF, N,N-diisopropylethylamine, RT or EDCI, HOBT, N,N-diisorpopylethylamine, DMF, RT b) $H_2$, 10% Pd—C, MeOH, RT; c) 1,1′-[(1,5-dioxopentane-1,5-diyl)bis(oxy)]dipyrrolidine-2,5-dione, N,N-diisopropylethylamine, DMF, RT]

In addition, other intermediates according to Schemes 32, 33 and 34 can be converted to legumain-cleavable ADC and APDC precursors.

As an alternative to the benzyloxycarbonyl group shown in Schemes 32-34, it is possible to use other protecting groups established in peptide chemistry and attach them by corresponding methods that are likewise known. The selection of the protecting group strategy is made according to requirements known to those skilled in the art relating to compatibility with other structural elements that occur in the molecule. If they are still present, further protecting groups in the molecule may be removed in a last step.

The syntheses may also optionally be rearranged in terms of their sequence.

Scheme 33: Synthesis of cysteine-bonded ADCs with legumain-cleavable head group

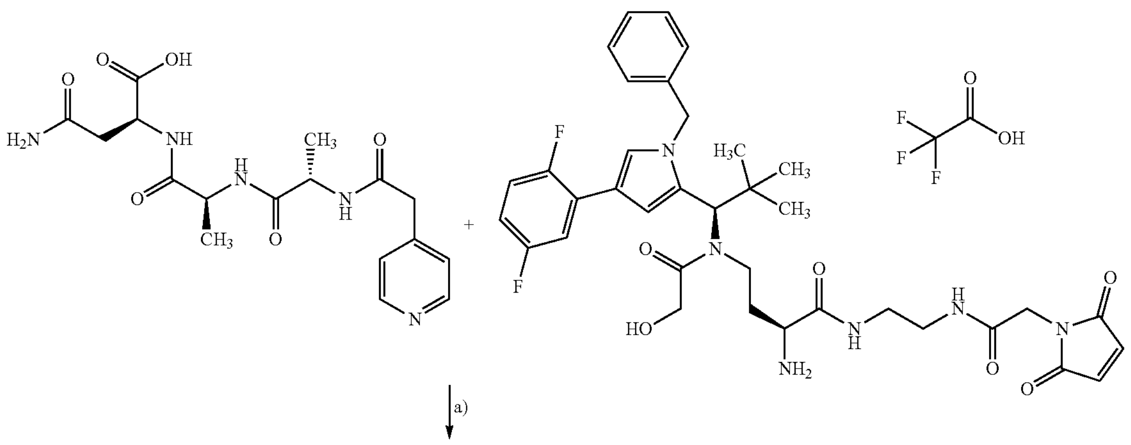

-continued
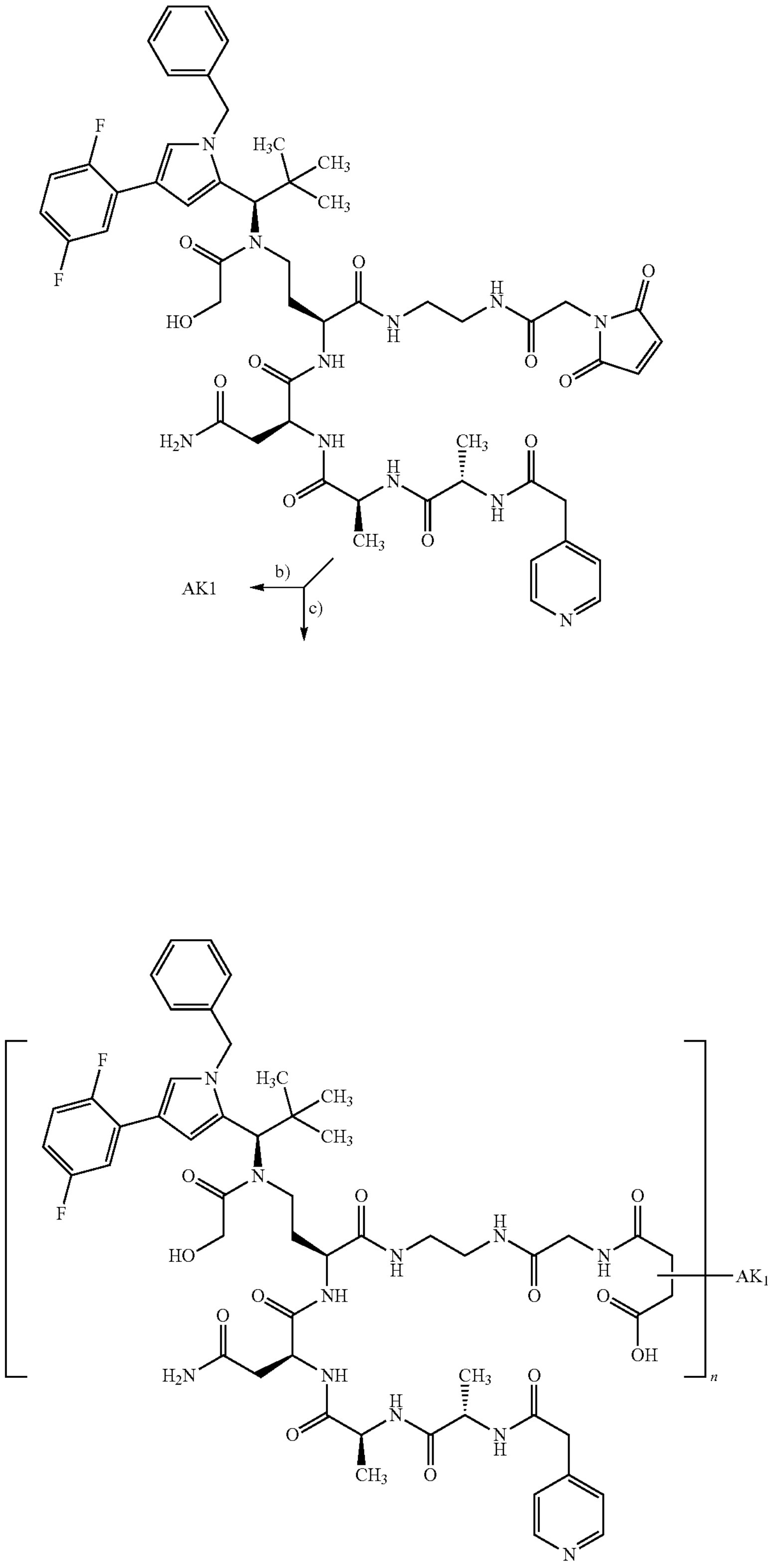
[a): HATU, DMF, N,N-diisopropylethylamine, RT; b) 2-5 eq TCEP, PBS pH7.2, stirring at RT for 30 min; c) stirring at RT under argon for 90 min, then rebuffering to pH 8 by means of PD 10 columns (Sephadex® G-25, GE Healthcare) and stirring under argon at RT overnight and subsequent concentration by means of ultracentrifugation and setting of the concentration desired with PBS at pH 7.2)]

Scheme 34: Synthesis of lysine-bonded ADCs with legumain-cleavable linker
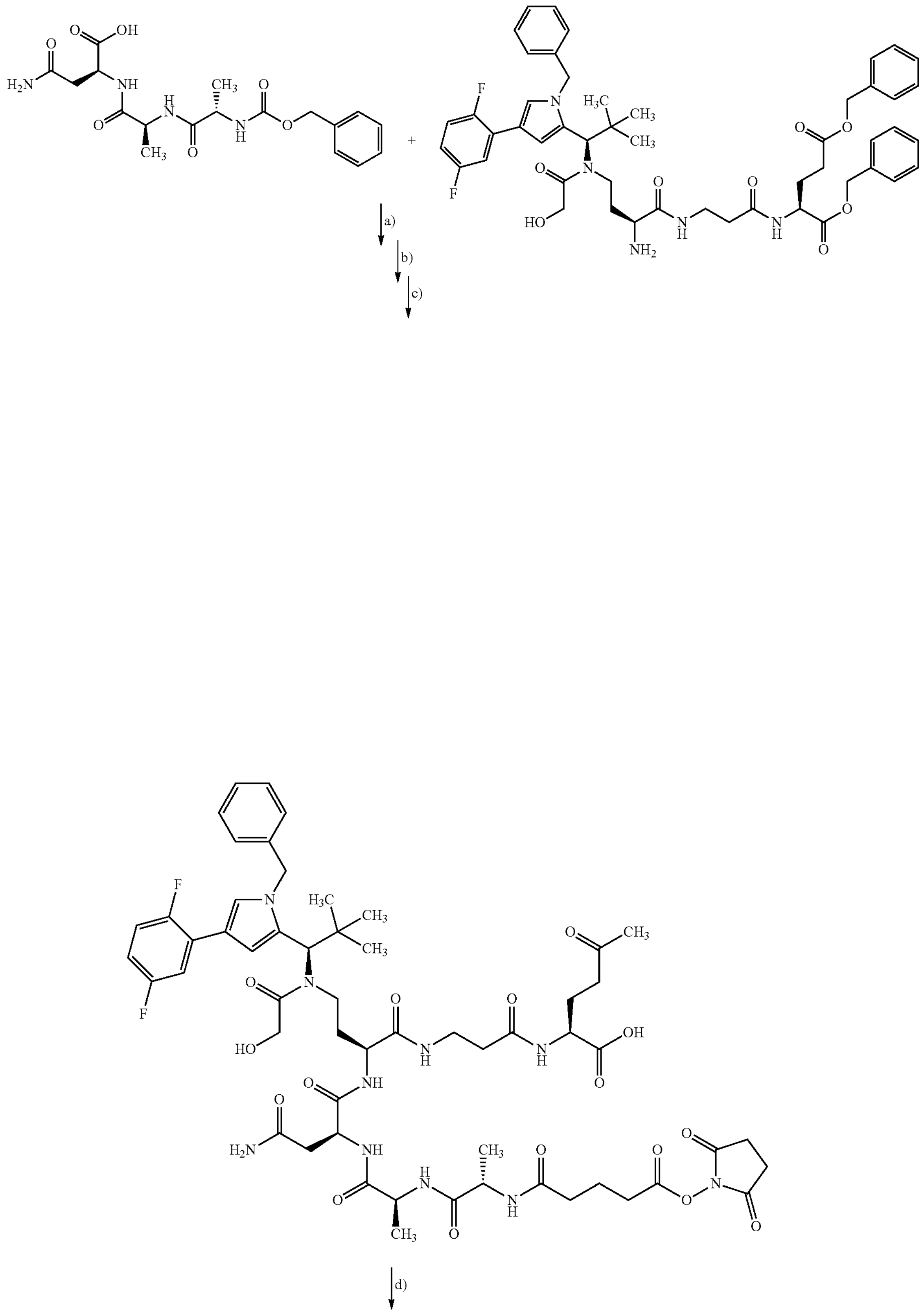

-continued

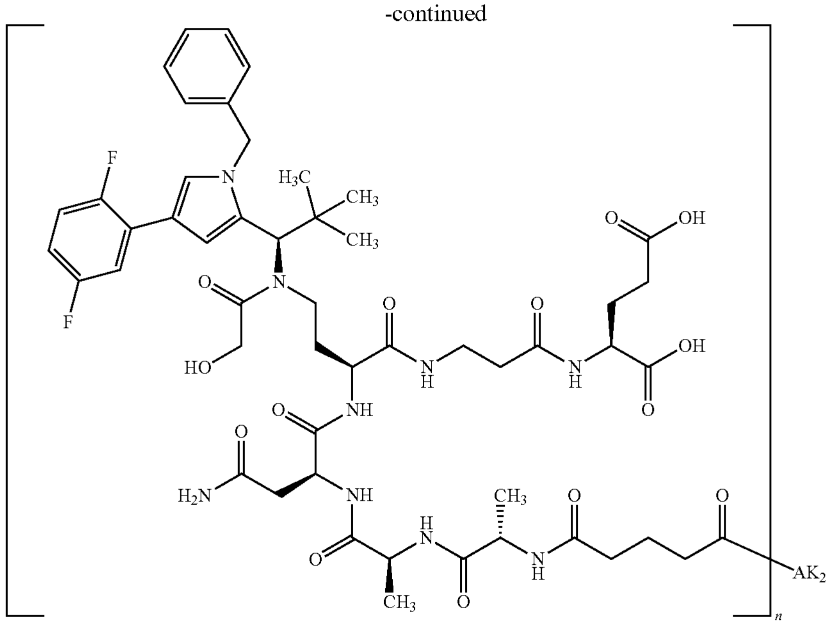

[a): HATU, DMF, N,N-diisopropylethylamine, RT; b) $H_2$, 10% Pd—C, methanol 1.5 h, RT; c) 1,1'-[(1,5-dioxopentane-1,5-diyl)bis(oxy)]dipyrrolidine-2,5-dione, N,N-diisopropylethylamine, DMF, stirring at RT overnight; d) AK2 in PBS, addition of 5 equiv. of active ester dissolved in DMSO, stirring at RT under argon for 60 min, addition of another 5 equiv. of active ester dissolved in DMSO, stirring at RT under argon for 60 min, then purification by means of PD 10 columns equilibrated with PBS buffer (pH 7.2) (Sephadex® G-25, GE Healthcare) and subsequent concentration by means of ultracentrifugation and setting of the concentration desired with PBS buffer (pH 7.2)]

Scheme 35: Synthesis of ADC precursors with legumain-cleavable head group

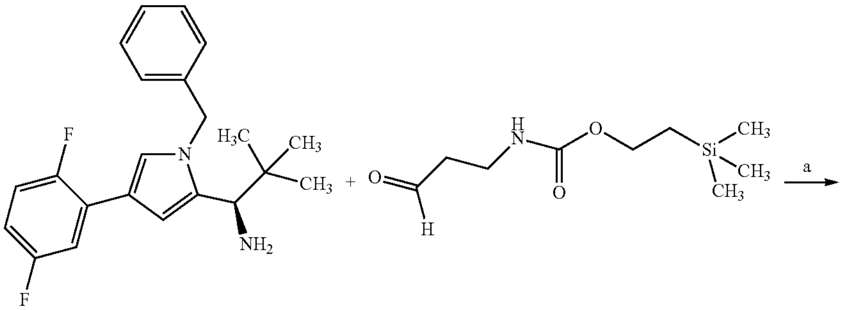

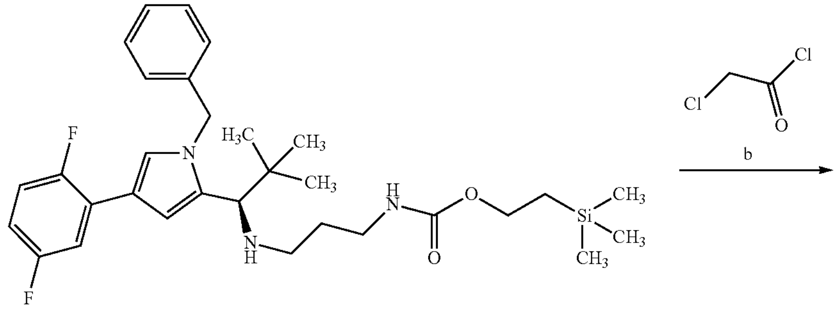

-continued
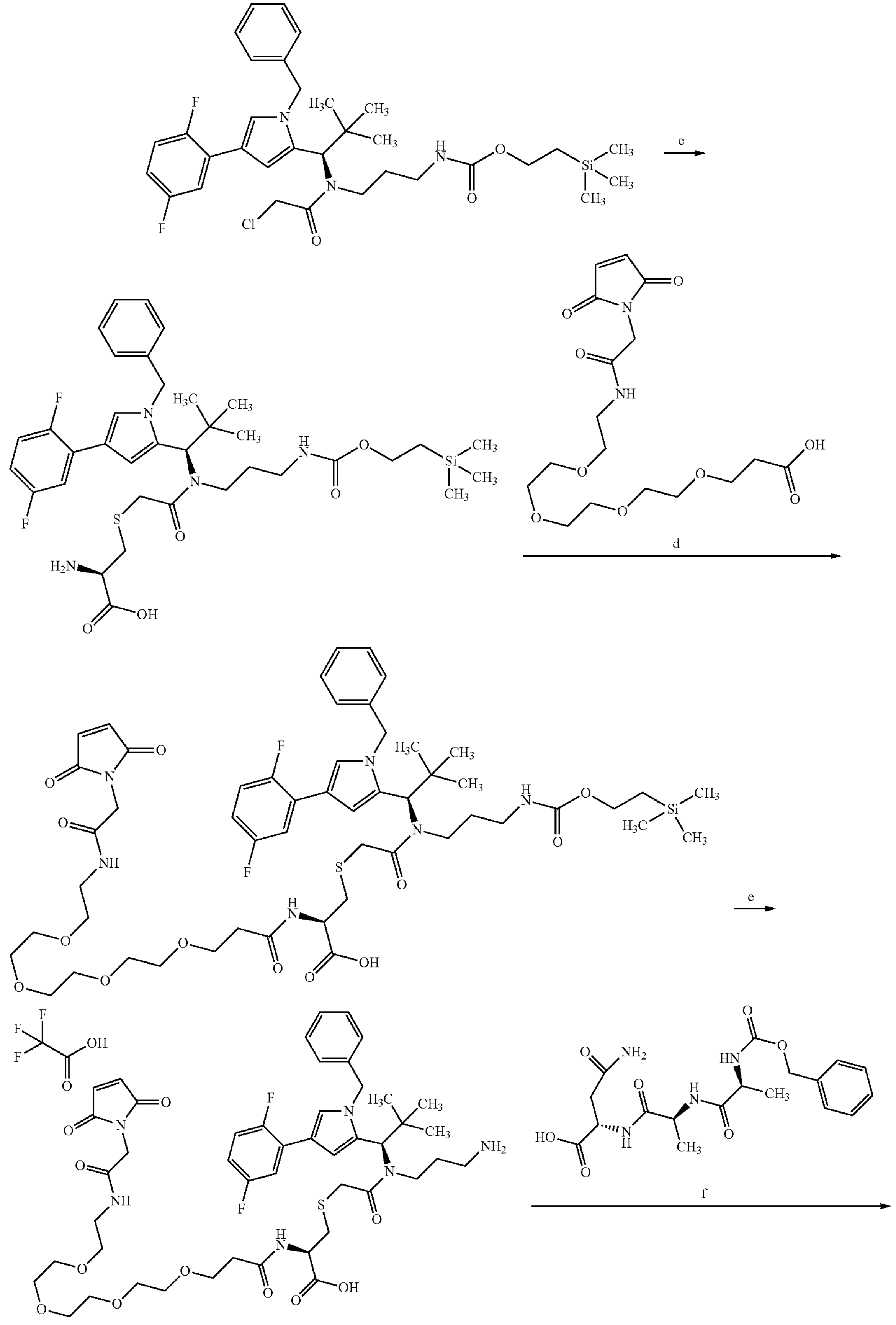

-continued
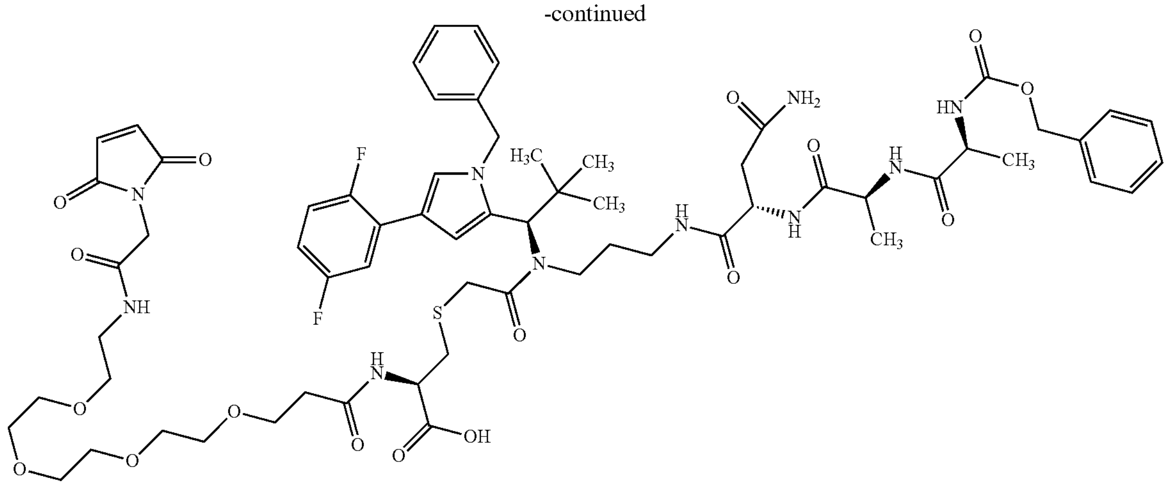
[a): NaBH(OAc)3, HOAc, dichloromethane, RT; b) chloroacetyl chloride, NEt3, DCM, RT; c) L-cysteine, NaHCO3, DBU, isopropanol/water, 50° C.; d) HATU, DMF, diisopropylethylamine, RT; e) zinc chloride, trifluoroethanol, 50° C.; f) d) HATU, DMF, diisopropylethylamine, RT]
Scheme 36: Synthesis of ADCs via transglutaminase coupling
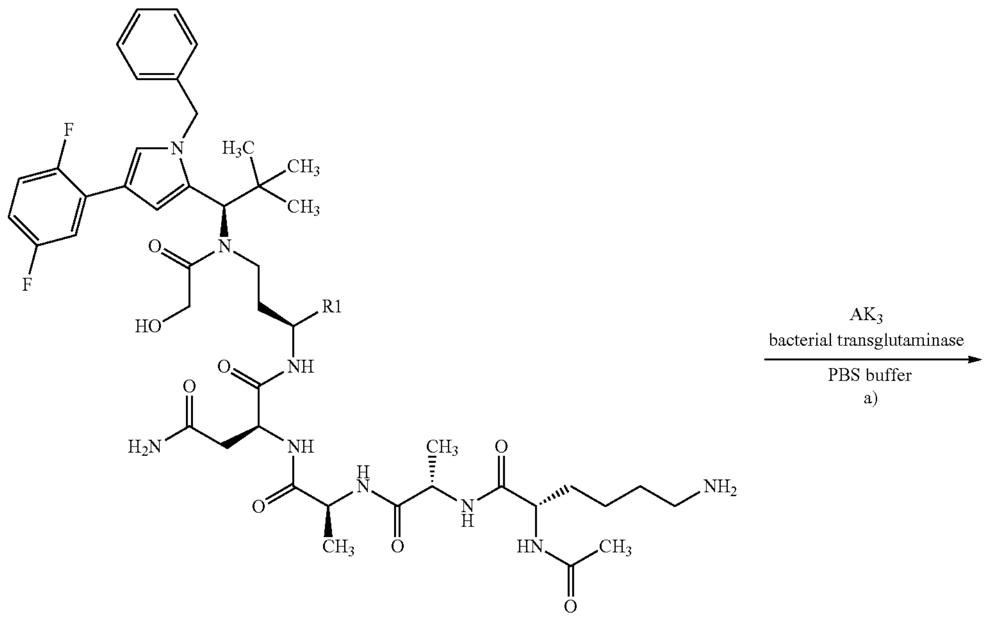

-continued

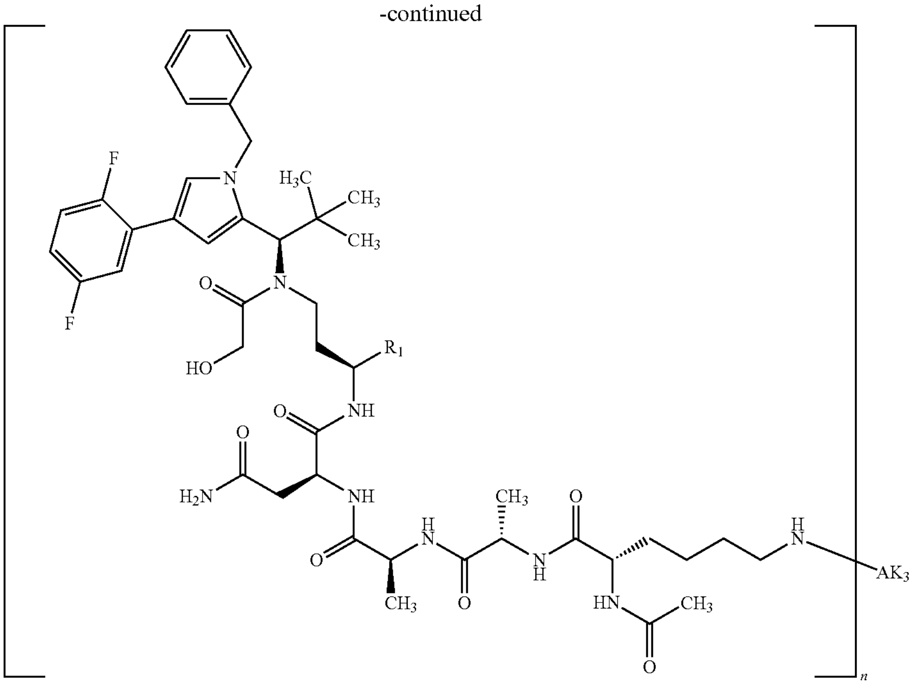

[a: 5 mg AK3 in DPBS pH 7.4 (c ~ 10 mg/mL), 6 equivalents of a toxophore-linker precursor (e.g. Intermediate Q31-Q34), add 50 μL of a solution of 12.5 μL (1.25 U) of recombinant bacterial transglutaminase solution in water (100 U/mL) and 37.5 μl of DPBS pH 7.4, incubate at 37° C. for 24 h]

A. Examples

Abbreviations and Acronyms

A431NS human tumour cell line
A549 human tumour cell line
ABCB1 ATP-binding cassette sub-family B member 1 (synonym for P-gp and MDR1)
abs. absolute
Ac acetyl
ACN acetonitrile
aq. aqueous, aqueous solution
ATP adenosine triphosphate
BCRP breast cancer resistance protein, an efflux transporter
BEP 2-bromo-1-ethylpyridinium tetrafluoroborate
Boc tert-butoxycarbonyl
br. broad (in NMR)
Ex. Example
BxPC3 human tumour cell line
ca. circa, about
CI chemical ionization (in MS)
D doublet (in NMR)
D day(s)
TLC thin-layer chromatography
DCI direct chemical ionization (in MS)
DCM dichloromethane
Dd doublet of doublets (in NMR)
DMAP 4-N,N-dimethylaminopyridine
DME 1,2-dimethoxyethane
DMEM Dulbecco's Modified Eagle Medium (standardized nutrient medium for cell culture)
DMF N,N-dimethylformamide
DMSO dimethyl sulphoxide
DPBS, D-PBS, PBS Dulbecco's phosphate-buffered salt solution PBS=DPBS=D-PBS, pH 7.4, from Sigma, No D8537
Composition:
0.2 g KCl
0.2 g $KH_2PO_4$ (anhyd)
8.0 g NaCl
1.15 g $Na_2HPO_4$ (anhyd)
made up ad 1 l with $H_2O$
Dt doublet of triplets (in NMR)
DTT DL-dithiothreitol
d. Th. of theory (in chemical yield)
EDC N'-(3-dimethylaminopropyl)-N-ethylcarbodiimide hydrochloride
EGFR epidermal growth factor receptor
EI electron impact ionization (in MS)
ELISA enzyme-linked immunosorbent assay
eq. equivalent(s)
ESI electrospray ionization (in MS)
ESI-MicroTofq ESI-MicroTofq (name of the mass spectrometer with Tof=time of flight and q=quadrupol)
FCS foetal calf serum
Fmoc (9H-fluoren-9-ylmethoxy)carbonyl
sat. saturated
GTP guanosine-5'-triphosphate
h hour(s)
HATU O-(7-azabenzotriazol-1-yl)-N,N,N',N'-tetramethyluronium hexafluorophosphate
HCT-116 human tumour cell line
HEPES 4-(2-hydroxyethyl)piperazine-1-ethanesulphonic acid
HOAc acetic acid
HOAt 1-hydroxy-7-azabenzotriazole
HOBt 1-hydroxy-1H-benzotriazole hydrate
HOSu N-hydroxysuccinimide
HPLC high-pressure, high-performance liquid chromatography
HT29 human tumour cell line
$IC_{50}$ half-maximal inhibitory concentration i.m. intramuscularly, administration into the muscle
i.v. intravenously, administration into the vein
conc. concentrated
KPL-4 human tumour cell lines
KU-19-19 human tumour cell line
LC-MS liquid chromatography-coupled mass spectrometry
LLC-PK1 cells Lewis lung carcinoma pork kidney cell line
L-MDR human MDR1 transfected LLC-PK1 cells
LoVo human tumour cell line
m multiplet (in NMR)
Me methyl
MDR1 Multidrug resistance protein 1
MeCN acetonitrile
min minute(s)
MS mass spectrometry
MTT 3-(4,5-dimethylthiazol-2-yl)-2,5-diphenyl-2H-tetrazolium bromide
NCI-H292 human tumour cell line
NCI-H520 human tumour cell line
NMM N-methylmorpholine
NMP N-methyl-2-pyrrolidinone
NMR nuclear magnetic resonance spectrometry
NMRI mouse strain originating from the Naval Medical Research Institute (NMRI)
Nude mice experimental animals
NSCLC non small cell lung cancer
PBS phosphate-buffered salt solution
Pd/C palladium on activated carbon
P-gp P-glycoprotein, a transporter protein
PNGaseF enzyme for cleaving sugar
quant. quantitative (in yield)
quart quartet (in NMR)
quint quintet (in NMR)
$R_f$ retention index (in TLC)
RT room temperature
$R_t$ retention time (in HPLC)
s singlet (in NMR)
s.c. subcutaneously, administration under the skin
SCC-4 human tumour cell line
SCC-9 human tumour cell line
SCID mice test mice with severe combined immunodeficiency
SK-HEP-1 human tumour cell line
t triplet (in NMR)
TBAF tetra-n-butylammonium fluoride
TCEP tris(2-carboxyethyl)phosphine
TEMPO (2,2,6,6-tetramethylpiperidin-1-yl)oxyl
tert tertiary
TFA trifluoroacetic acid
THF tetrahydrofuran
T3P® 2,4,6-tripropyl-1,3,5,2,4,6-trioxatriphosphinane 2,4,6-trioxide
UV ultraviolet spectrometry
v/v volume to volume ratio (of a solution)
Z benzyloxycarbonyl
786-O human tumour cell line Amino Acid Abbreviations Ala=alanine
Arg=arginine
Asn=asparagine
Asp=aspartic acid
Cys=cysteine
Glu=glutamic acid
Gln=glutamine
Gly=glycine
His=histidine
Ile=isoleucine
Leu=leucine
Lys=lysine
Met=methionine
Nva=norvaline
Phe=phenylalanine
Pro=proline
Ser=serine
Thr=threonine
Trp=tryptophan
Tyr=tyrosine
Val=valine HPLC and LC-MS Methods:

Method 1 (LC-MS):

Instrument: Waters ACQUITY SQD UPLC system; column: Waters Acquity UPLC HSS T31.8μ 50×1 mm; mobile phase A: 1 l of water+0.25 ml of 99% strength formic acid; mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 2 (LC-MS):

MS instrument type: Waters Synapt G2S; UPLC instrument type: Waters Acquity I-CLASS; column: Waters, BEH300, 2.1×150 mm, C181.7 μm; mobile phase A: 1 l of water+0.01% formic acid; mobile phase B: 1 l of acetonitrile+0.01% formic acid; gradient: 0.0 min 2% B→1.5 min 2% B→8.5 min 95% B→10.0 min 95% B; oven: 50° C.; flow rate: 0.50 ml/min; UV detection: 220 nm Method 3 (LC-MS):

MS instrument: Waters (Micromass) QM; HPLC instrument: Agilent 1100 series; column: Agilent ZORBAX Extend-C183.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm Method 4 (LC-MS):

MS instrument type: Waters Synapt G2S; UPLC instrument type: Waters Acquity I-CLASS; column: Waters, HSST3, 2.1×50 mm, C181.8 μm; mobile phase A: 1 l of water+0.01% formic acid; mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm Method 5 (LC-MS):

Instrument: Waters ACQUITY SQD UPLC system; column: Waters Acquity UPLC HSS T31.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 6 (LC-MS):

Instrument: Micromass Quattro Premier with Waters UPLC Acquity; column: Thermo Hypersil GOLD 1.9μ 50×1 mm; mobile phase A: 1 l of water+0.5 ml of 50% strength formic acid; mobile phase B: 1 l of acetonitrile+0.5 ml of 50% strength formic acid; gradient: 0.0 min 97% A→0.5 min 97% A→3.2 min 5% A→4.0 min 5% A oven: 50° C.; flow rate: 0.3 ml/min; UV detection: 210 nm.

Method 7 (LC-MS): Instrument: Agilent MS Quad 6150; HPLC: Agilent 1290; column: Waters Acquity UPLC HSS T3 1.8μ 50×2.1 mm; mobile phase A: 1 l of water+0.25 ml of 99% strength formic acid, mobile phase B: 1 l of acetonitrile+0.25 ml of 99% strength formic acid; gradient:

0.0 min 90% A→0.3 min 90% A→1.7 min 5% A→3.0 min 5% A oven: 50° C.; flow rate: 1.20 ml/min; UV detection: 205-305 nm.

Method 8 (LC-MS):

MS instrument type: Waters Synapt G2S; UPLC instrument type: Waters Acquity I-CLASS; column: Waters, HSST3, 2.1×50 mm, C181.8 μm; mobile phase A: 1 l of water+0.01% formic acid; mobile phase B: 1 l of acetonitrile+0.01% formic acid; gradient: 0.0 min 2% B→2.0 min 2% B→13.0 min 90% B→15.0 min 90% B; oven: 50° C.; flow rate: 1.20 ml/min; UV detection: 210 nm Method 9: LC-MS-Prep Purification Method for Examples 181-191 (Method LIND-LC-MS-Prep)

MS instrument: Waters; HPLC instrument: Waters (column Waters X-Bridge C18, 19 mm×50 mm, 5 μm, mobile phase A: water+0.05% ammonia, mobile phase B: acetonitrile (ULC) with gradient; flow rate: 40 ml/min; UV detection: DAD; 210-400 nm).

or

MS instrument: Waters; HPLC instrument: Waters (column Phenomenex Luna 5μ C18(2) 100A, AXIA Tech. 50×21.2 mm, mobile phase A: water+0.05% formic acid, mobile phase B: acetonitrile (ULC) with gradient; flow rate: 40 ml/min; UV detection: DAD; 210-400 nm).

Method 10: LC-MS Analysis Method for Examples 181-191 (LIND_SQD_SB_AQ)

MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 11 (HPLC):

Instrument: HP1100 Series column: Merck Chromolith SpeedROD RP-18e, 50-4.6 mm, Cat. No. 1.51450.0001, precolumn Chromolith Guard Cartridge Kit, RP-18e, 5-4.6 mm, Cat. No. 1.51470.0001

Gradient: flow rate 5 ml/min injection volume 5 μl

Solvent A: HClO4 (70% strength) in water (4 ml/1)

Solvent B: acetonitrile

Start 20% B 0.50 min 20% B 3.00 min 90% B 3.50 min 90% B 3.51 min 20% B 4.00 min 20% B column temperature: 40° C.

Wavelength: 210 nm

Method 12 (LC-MS):

MS instrument type: Thermo Scientific FT-MS; instrument type UHPLC+: Thermo Scientific UltiMate 3000; column: Waters, HSST3, 2.1×75 mm, C181.8 μm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/Optimum Integration Path 210-300 nm Method 13: (LC-MS):

MS instrument: Waters (Micromass) Quattro Micro; instrument Waters UPLC Acquity; column: Waters BEH C181.7μ 50×2.1 mm; mobile phase A: 1 l of water+0.01 mol of ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Method 14: (LC-MS) (MCW-LTQ-POROSHELL-TFA98-10 Min)

MS instrument type: ThermoFisherScientific LTQ-Orbitrap-XL; HPLC instrument type: Agilent 1200SL; column: Agilent, POROSHELL 120, 3×150 mm, SB—C182.7 μm; eluent A: 1 l of water+0.1% trifluoroacetic acid; mobile phase B: 1 l of acetonitrile+0.1% trifluoroacetic acid; gradient: 0.0 min 2% B→0.3 min 2% B→5.0 min 95% B→10.0 min 95% B; oven: 40° C.; flow rate: 0.75 ml/min; UV detection: 210 nm Starting Compounds and Intermediates:

Intermediate C1

Trifluoroacetic acid-(1R)-1-[1-benzyl-4-(2,5-difluorophenyl)-1H-imidazol-2-yl]-2,2-dimethylpropan-1-amine (1:1)

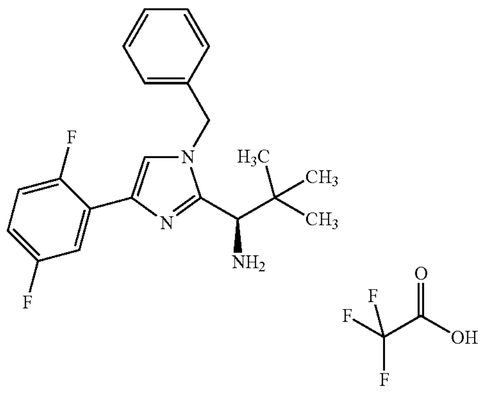 [SMILES: CC(C)(C)[C@@H](N)c1nc(-c2cc(F)ccc2F)cn1Cc1ccccc1 ; O=C(O)C(F)(F)F]

The title compound was prepared as described in WO2006/002326.

Intermediate C2 tert-Butyl (2S)-4-({(1R)-1-[1-benzyl-4-(2,5-difluorophenyl)-1H-imidazol-2-yl]-2,2-dimethylpropyl}amino)-2-[(tert-butoxycarbonyl)amino]butanoate

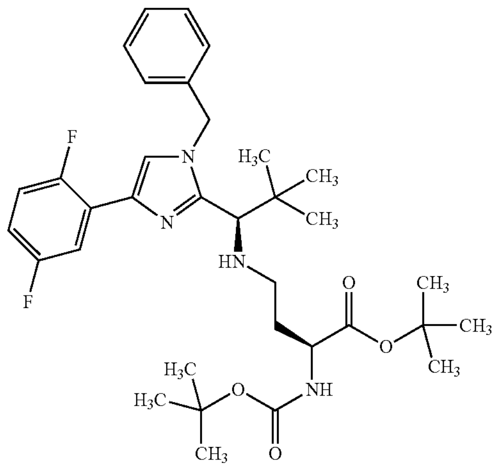 [SMILES: CC(C)(C)OC(=O)N[C@@H](CCN[C@@H](c1nc(-c2cc(F)ccc2F)cn1Cc1ccccc1)C(C)(C)C)C(=O)OC(C)(C)C]

4.22 g (14.5 mmol) of tert-butyl N-(tert-butoxycarbonyl)-L-homoserinate were dissolved in 180 ml of dichloromethane, and 3.5 ml of pyridine and 9.2 g (21.7 mmol) of 1,1,1-triacetoxy-1lambda5,2-benziodoxol-3(1H)-one were then added. The reaction was stirred at RT for 1 h and then diluted with 500 ml of dichloromethane and extracted twice with 10% strength sodium thiosulphate solution and then extracted successively twice with 5% strength citric acid and twice with 10% strength sodium bicarbonate solution. The organic phase was separated off, dried over magnesium sulphate and then dried under reduced pressure. The residue was taken up in diethyl ether, and HCl (solution in diethyl ether) was added. The precipitate was filtered off and the filtrate was then concentrated and lyophilized from acetonitrile/water. This gave 3.7 g (93%) of tert-butyl (2S)-2-[(tert-butoxycarbonyl)amino]-4-oxobutanoate which were used without further purification for the next step. ($R_f$: 0.5 (DCM/methanol 95/5).

3.5 g (9.85 mmol) of Intermediate C1 were dissolved in 160 ml of DCM, and 3.13 g (14.77 mmol) of sodium triacetoxyborohydride and 0.7 ml of acetic acid were added. After 5 min of stirring at RT, 3.23 g (11.85 mmol) of tert-butyl (2S)-2-[(tert-butoxycarbonyl)amino]-4-oxobutanoate were added and the reaction was stirred at RT for a further 30 min. The solvent was then evaporated under reduced pressure and the residue was taken up in acetonitrile/water. The precipitated solid was filtered off and dried, giving 5.46 g (84%) of the title compound.

HPLC (Method 11): $R_t$=2.5 min;

LC-MS (Method 1): $R_t$=1.13 min; MS (ESIpos): m/z=613 $(M+H)^+$.

Intermediate C3

(2S)-4-[(Acetoxyacetyl){(1R)-1-[1-benzyl-4-(2,5-difluorophenyl)-1H-imidazol-2-yl]-2,2-dimethylpropyl}amino]-2-[(tert-butoxycarbonyl)amino]butanoic Acid

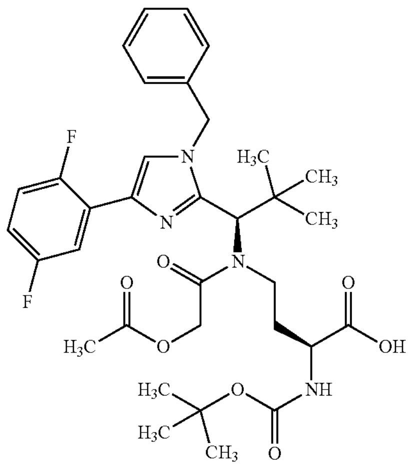 [SMILES: CC(=O)OCC(=O)N(CC[C@H](NC(=O)OC(C)(C)C)C(=O)O)[C@@H](c1nc(-c2cc(F)ccc2F)cn1Cc1ccccc1)C(C)(C)C]

5.46 g (8.24 mmol) of Intermediate C2 were dissolved in 160 ml of DCM, and 4.8 ml of triethylamine and 2.2 ml (20.6 mmol) of acetoxyacetyl chloride were added. The mixture was stirred at RT overnight and then concentrated under reduced pressure. The residue was taken up in ethyl acetate and extracted three times with saturated sodium bicarbonate solution and then with saturated sodium chloride solution. The organic phase was dried over sodium sulphate and then concentrated. The residue was purified by column chromatography on Biotage/Isolera (SNAP 340 g) using the mobile phase cyclohexane/ethyl acetate 2:1. This gave 4.57 g (75%) of the acylated intermediate.

LC-MS (Method 1): $R_t$=1.49 min; MS (ESIpos): m/z=713 $(M+H)^+$.

1 g (1.36 mmol) of this intermediate was dissolved in 20 ml of DCM, and 20 ml of TFA were added. After 5 h of stirring at RT, the mixture was concentrated and the residue was triturated twice with n-pentane. In each case, the n-pentane was decanted off and the solid that remained was dried under high vacuum. This gave 1.1 g of (2S)-4-[(acetoxyacetyl){(1R)-1-[1-benzyl-4-(2,5-difluorophenyl)-1H-imidazol-2-yl]-2,2-dimethylpropyl}amino]-2-aminobutanoic acid/trifluoroacetic acid (1:1). LC-MS (Method 1): $R_t$=0.93 min; MS (ESIpos): m/z=557 $(M+H)^+$.

0.91 g (1.57 mmol) of this intermediate were dissolved in 70 ml of DCM, and 3.43 g (15.7 mmol) of di-tert-butyl dicarbonate and 4.1 ml of N,N-diisopropylethylamine were added. After 30 min of stirring at RT, the reaction was diluted with DCM and extracted with 5% strength citric acid. The organic phase was dried over sodium sulphate and concentrated. The residue was triturated twice with n-pentane and in each case the n-pentane was decanted off. The solid that remained was lyophilized from acetonitrile/water 1:1, giving 1.11 g of the title compound.

HPLC (Method 11): $R_t$=2.55 min;

LC-MS (Method 1): $R_t$=1.3 min; MS (ESIpos): m/z=657 $(M+H)^+$.

Intermediate C4

(2S)-2-Amino-4-[{(1R)-1-[1-benzyl-4-(2,5-difluorophenyl)-1H-imidazol-2-yl]-2,2-dimethylpropyl}(glycoloyl)amino]butanoic Acid/Trifluoroacetic Acid (1:1)

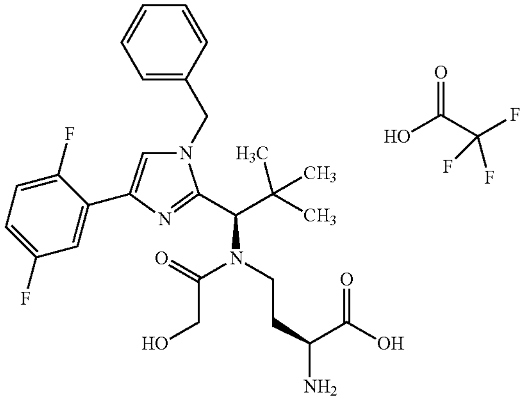 [SMILES: CC(C)(C)[C@H](c1nc(-c2cc(F)ccc2F)cn1Cc1ccccc1)N(CC[C@H](N)C(=O)O)C(=O)CO ; O=C(O)C(F)(F)F]

5.46 g (8.24 mmol) of Intermediate C2 were dissolved in 160 ml of DCM, and 4.8 ml of triethylamine and 2.2 ml (20.6 mmol) of acetoxyacetyl chloride were added. The mixture was stirred at RT overnight and then concentrated under reduced pressure. The residue was taken up in ethyl acetate and extracted three times with saturated sodium bicarbonate solution and then with saturated sodium chloride solution. The organic phase was dried over sodium sulphate and then concentrated. The residue was purified by column chromatography on Biotage/Isolera (SNAP 340 g) using the mobile phase cyclohexane/ethyl acetate 2:1. This gave 4.57 g (75%) of the acylated intermediate.

LC-MS (Method 1): $R_t$=1.49 min; MS (ESIpos): m/z=713 $(M+H)^+$.

1.5 g (2.035 mmol) of this intermediate were taken up in 50 ml of ethanol, and 5.8 ml of a 40% strength solution of methanamine in water was added. The reaction was stirred at 50° C. for 4 h and then concentrated. The residue was taken up in DCM and washed twice with water. The organic phase was dried over magnesium sulphate and then concentrated. The residue was dried under high vacuum. This gave 1.235 mg of this intermediate, which were reacted further without further purification.

1.235 mg (1.5 mmol) of this intermediate were dissolved in 15 ml of DCM, and 15 ml of TFA were added. After 4 h of stirring at RT, the mixture was concentrated. The residue was purified by preparative HPLC. The appropriate fractions were concentrated and the residue was lyophilized from acetonitrile. This gave 1.04 g (quant) of the title compound.

HPLC (Method 11): $R_t$=1.9 min;

LC-MS (Method 1): $R_t$=0.89 min; MS (ESIpos): m/z=515 $(M+H)^+$.

Intermediate C5

(2S)-4-[{(1R)-1-[1-Benzyl-4-(2,5-difluorophenyl)-1H-imidazol-2-yl]-2,2-dimethylpropyl}(glycoloyl)amino]-2-[(tert-butoxycarbonyl)amino]butanoic Acid

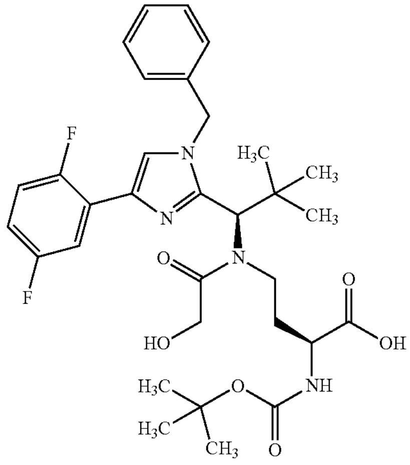 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)O]

0.9 g (1.24 mmol) of Intermediate C4 was dissolved in 60 ml of DCM, and 2.7 g (12.5 mmol) of di-tert-butyl dicarbonate and 3.3 ml of N,N-diisopropylethylamine were added. After 45 min of stirring at RT, the reaction was concentrated and the residue was taken up in diethyl ether, and n-pentane was added until the mixture started to get cloudy. The reaction was cooled to 0° C. and then decanted. Once more, n-pentane was added to the residue and the mixture was decanted. The solid that remained was lyophilized from acetonitrile/water 1:1, giving 0.95 g (quant) of the title compound.

HPLC (Method 11): $R_t$=2.5 min;

LC-MS (Method 1): $R_t$=1.27 min; MS (ESIpos): m/z=615 $(M+H)^+$.

Intermediate C6

Trifluoroacetic Acid/tert-butyl {(2S)-4-[{(1R)-1-[1-benzyl-4-(2,5-difluorophenyl)-1H-imidazol-2-yl]-2,2-dimethylpropyl}(glycoloyl)amino]-1-hydrazino-1-oxobutan-2-yl}carbamate (1:1)

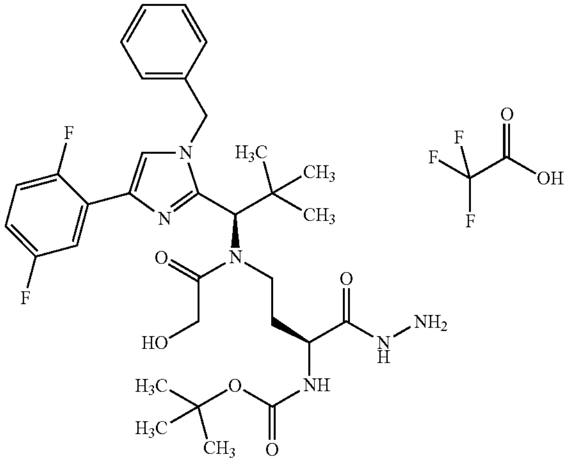 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)NN ; O=C(O)C(F)(F)F]

150 mg (0.16 mmol) of Intermediate C3 were dissolved in 21 ml of DMF, and then 37.2 mg (0.19 mmol) of N-(3-dimethylaminopropyl)-N'-ethylcarbodiimide hydrochloride (EDC), 37 mg (0.243 mmol) of 1-hydroxybenzotriazole, 85 μl of N,N-diisopropylethylamine and finally 45 mg (0.18 mmol) of commercially available 9H-fluoren-9-ylmethyl hydrazinecarboxylate were added. The mixture was stirred at RT overnight and then concentrated under reduced pressure. The residue was purified by preparative HPLC. The appropriate fractions were concentrated and the residue was lyophilized from acetonitrile/water. This gave 60 mg (41% of theory) of the protected intermediate.

HPLC (Method 11): $R_t$=2.9 min;

LC-MS (Method 1): $R_t$=1.47 min; MS (ESIpos): m/z=893 $(M+H)^+$.

60 mg (0.067 mmol) of this intermediate were dissolved in 19 ml of ethanol, and 681 μl of piperidine and 386 μl of a 40% strength solution of methanamine in water were added. The reaction was stirred at 50° C. for 18 h and then concentrated. The residue was taken up in acetonitrile/water 2:1 and adjusted to pH 2 with TFA. Then the mixture was concentrated again and the residue was purified by preparative HPLC. The appropriate fractions were concentrated and the residue was lyophilized from acetonitrile/water. This gave 25 mg (51% of theory) of the title compound.

HPLC (Method 11): $R_t$=2.2 min;

LC-MS (Method 1): $R_t$=1.27 min; MS (ESIpos): m/z=629 $(M+H)^+$.

Intermediate C7

1-{(2S)-4-[{(1R)-1-[1-Benzyl-4-(2,5-difluorophenyl)-1H-imidazol-2-yl]-2,2-dimethylpropyl}(glycoloyl)amino]-2-[(tert-butoxycarbonyl)amino]butanoyl}hydrazino)acetic Acid/Trifluoroacetic Acid (1:1)

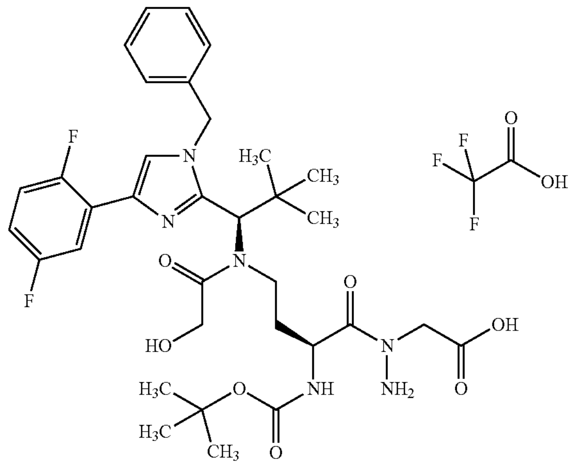 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)N(N)CC(=O)O ; O=C(O)C(F)(F)F]

0.2 g (0.305 mmol) of intermediate C3 were dissolved in 80 ml of DCM, 0.125 g (0.46 mmol) of 2-bromo-1-ethylpyridinium tetrafluoroborate (BEP), 94 mg (0.61 mmol) of commercially available ethylhydrazinoacetate hydrochloride and 159 μl of N,N-diisopropylethylamine were added and the mixture was then stirred at RT for 1 h. Ethyl acetate and water were then added to the reaction mixture, and the phases were separated. The organic phase was extracted with saturated sodium chloride solution and then dried over magnesium sulphate, filtered and concentrated. The residue was dried under reduced pressure and reacted further without purification. To this end, it was taken up in 20 ml of tetrahydrofuran, and 10 ml of water and 3.2 ml of a 2N lithium hydroxide solution were added. The reaction was stirred at RT for 1 h and then adjusted to pH 7 using TFA. The reaction was then concentrated and the residue was purified by preparative HPLC. In this manner, the title compound was separated from its earlier eluting regioisomer. Combination of the corresponding fractions, lyophilization and drying gave 19.7 g (8% of theory over 2 steps) of the title compound as a colourless foam.

HPLC (Method 11): $R_t$=2.4 min;

LC-MS (Method 1): $R_t$=1.22 min; MS (ESIpos): m/z=687 $(M+H)^+$.

The structural assignment of the regioisomers was effected in a separate experiment after separation of the regioisomers at the protected intermediate stage by NMR spectroscopy. The protected ethyl (1-{(2S)-4-[(acetoxyacetyl){(1R)-1-[1-benzyl-4-(2,5-difluorophenyl)-1H-imidazol-2-yl]-2,2-dimethylpropyl}amino]-2-[(tert-butoxycarbonyl)amino]butanoyl}hydrazino)acetate intermediate of the title compound had the following 1H NMR spectrum:

$^1$H-NMR (500 MHz, DMSO-$d_6$): δ=7.8 (m, 2H), 7.4-7.2 (m, 6H), 7.08 (m, 1H), 6.73 (d, 1H), 5.6 (s, 1H), 5.25 and 4.89 (2d, 2H), 4.89 and 4.77 (2d, 2H), 4.62 (t, 1H), 4.32 and 3.78 (2d, 2H), 4.1 (t, 2H), 3.62-3.47 (m), 2.13 (s, 3H), 1.41 and 0.72 (2m, 2H), 1.3 (s, 9H), 1.18 (t, 3H), 0.92 (s, 9H).

Intermediate C8

N-{(2S)-4-[{(1R)-1-[1-Benzyl-4-(2,5-difluorophenyl)-1H-imidazol-2-yl]-2,2-dimethylpropyl}(glycoloyl)amino]-2-[(tert-butoxycarbonyl)amino]butanoyl}-beta-alanine

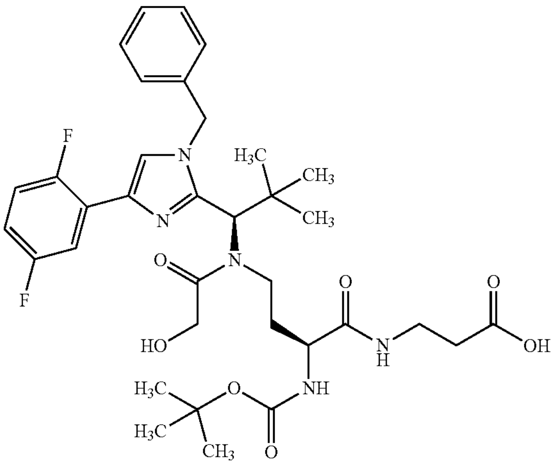 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)NCCC(=O)O]

293 mg (0.41 mmol) of Intermediate C3 were dissolved in 25 ml of DMF, and then 144 mg (0.75 mmol) of N-(3-dimethylaminopropyl)-N'-ethylcarbodiimide hydrochloride (EDC), 128 mg (0.83 mmol) of 1-hydroxybenzotriazole, 218 μl of N,N-diisopropylethylamine and finally 70 mg (0.5 mmol) of commercially available 3-methoxy-3-oxopropan-1-aminium chloride were added. The reaction was stirred at RT for 4 h and then concentrated under reduced pressure. The residue was purified by preparative HPLC. The appropriate fractions were concentrated and the residue was dried under high vacuum. This gave 177 mg (53% of theory) of the protected intermediate.

HPLC (Method 11): $R_t$=2.6 min;

LC-MS (Method 1): $R_t$=1.33 min; MS (ESIpos): m/z=742 $(M+H)^+$.

177 mg (0.22 mmol) of this intermediate were taken up in 20 ml of methanol, and 2.8 ml of 2N lithium hydroxide solution were added. The reaction was stirred at RT for 18 h. The mixture was then concentrated, the residue was taken up in water and the solution was adjusted to pH 5 using 5% strength citric acid. The mixture was then extracted twice with DCM and the organic phase was dried over magnesium sulphate and concentrated. The residue was finally lyophilized from acetonitrile/water, giving 133 mg (81% of theory) of the title compound.

HPLC (Method 11): $R_t$=2.3 min;

LC-MS (Method 3): $R_t$=7.4 min; MS (ESIpos): m/z=686 $(M+H)^+$.

Intermediate C9

(6S)-6-{2-[{(1R)-1-[1-Benzyl-4-(2,5-difluorophenyl)-1H-imidazol-2-yl]-2,2-dimethylpropyl}(glycoloyl)amino]ethyl}-2,2-dimethyl-4,7-dioxo-3,11,14,17-tetraoxa-5,8-diazaicosan-20-oic Acid

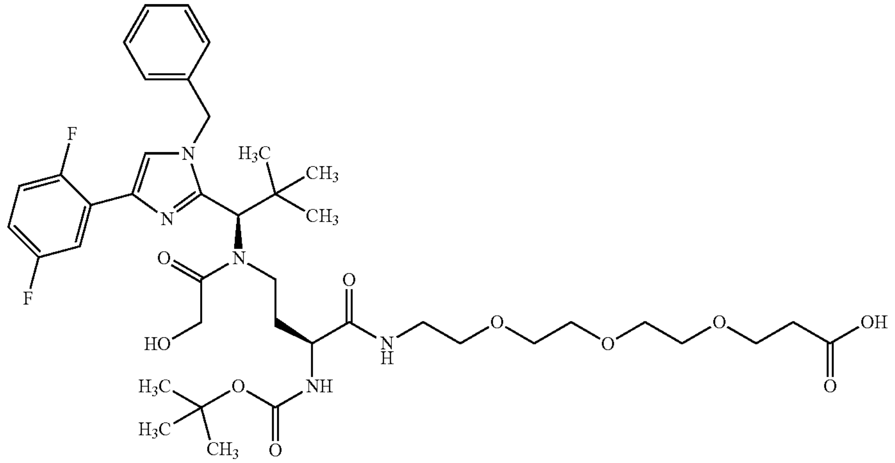 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)NCCOCCOCCOCCC(=O)O]

In the first step, 70 mg (0.114 mmol) of Intermediate C5 were coupled with 32 mg (0.114 mmol) of tert-butyl 3-{2-[2-(2-aminoethoxy)ethoxy]ethoxy}propanoate in 15 ml of DMF in the presence of 44 mg (0.228 mmol) of 1-(3-dimethylaminopropyl)-3-ethylcarbodiimide hydrochloride, 35 mg (0.228 mmol) of 1-hydroxy-1H-benzotriazole hydrate and 60 μl of N,N-diisopropylethylamine.

The reaction was stirred at RT overnight and the product was purified by preparative HPLC. This gave 33 mg (33% of theory) of the protected intermediate. This was stirred with 1.1 ml of trifluoroacetic acid in 11 ml of dichloromethane for 1 h giving, after work-up, 26 mg (98%) of the fully deprotected compound.

Finally, the intermediate was taken up in 2 ml of DCM and the tert-butoxycarbonyl protective group was introduced by twice adding in each case 10 mg of di-tert-butyl dicarbonate and 79 μl of N,N-diisopropylethylamine with stirring at RT for 3 days. Purification of the product by preparative HPLC gave 16.4 mg (66% of theory) of the title compound.

HPLC (Method 11): $R_t$=2.3 min;

LC-MS (Method 1): $R_t$=1.22 min; MS (ESIpos): m/z=818 $(M+H)^+$.

Intermediate C10 tert-Butyl {3-[{(1R)-1-[1-(3-aminobenzyl)-4-(2,5-difluorophenyl)-1H-imidazol-2-yl]-2,2-dimethylpropyl}(glycoloyl)amino]propyl}carbamate

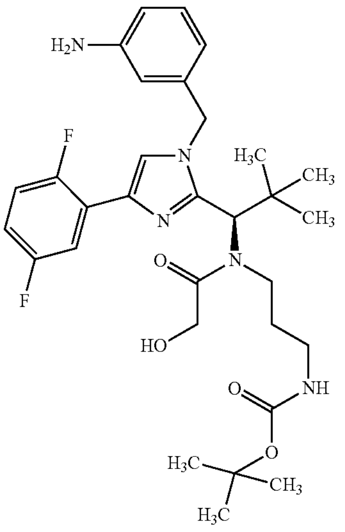 [SMILES: CC(C)(C)OC(=O)NCCCN(C(=O)CO)[C@@H](c1nc(-c2cc(F)ccc2F)cn1Cc1cccc(N)c1)C(C)(C)C]

The title compound was prepared from Intermediate C1 over 6 steps: In the first step, 1 g (2.77 mmol) of Intermediate C1 and 0.864 g (5 mmol) of tert-butyl (3-oxopropyl) carbamate were combined in 100 ml of methanol, and 400 ml of acetic acid and 1.288 g (13.9 mmol) of borane-pyridine complex were added. The reaction was stirred at RT for 3 days. The mixture was then concentrated under reduced pressure and the residue was purified by flash chromatography on silica gel (mobile phase: dichloromethane/ethyl acetate 9:1→dichloromethane/methanol 95:5). Concentration of the appropriate fractions and drying under high vacuum gave 1.255 g (80% of theory) of the N-alkylated intermediate.

LC-MS (Method 1): $R_t$=1.0 min; MS (ESIpos): m/z=513 $(M+H)^+$.

1.255 g (2.2 mmol) of this intermediate were dissolved in 50 ml of DCM, and 1.2 ml of triethylamine and 0.52 ml (4.85 mmol) of acetoxyacetyl chloride were then added. The mixture was stirred at RT overnight and then concentrated under reduced pressure. The residue was taken up in ethyl acetate and extracted three times with saturated sodium bicarbonate solution and then with saturated sodium chloride solution. The organic phase was dried over sodium sulphate and then concentrated. The residue was purified by preparative HPLC.

This gave 593 mg (41% of theory) of the acylated intermediate.

LC-MS (Method 1): $R_t$=1.4 min; MS (ESIpos): m/z=613 $(M+H)^+$.

993 mg (0.91 mmol) of this intermediate were dissolved in 100 ml of ethanol and, after addition of 60 mg of 10% palladium on activated carbon, hydrogenated under standard hydrogen pressure at RT for 3 min. The catalyst was then filtered off and the solvent was removed under reduced pressure. This gave 494 mg (91% of theory) of the debenzylated imidazole derivative as a virtually colourless oil. LC-MS (Method 1): $R_t$=1.17 min; MS (ESIpos): m/z=523 $(M+H)^+$.

150 mg (0.25 mmol) of this intermediate were initially charged in 15 ml of DMF, and 69.2 mg (0.5 mmol) of potassium carbonate were added. After 15 min of stirring at RT, 60 mg (0.28 mmol) of p-nitrobenzyl bromide were added and the mixture was stirred overnight. The solvent was then removed under reduced pressure, and the residue was taken up in ethyl acetate and extracted with saturated sodium bicarbonate solution. The organic phase was washed with saturated sodium chloride solution, concentrated on a rotary evaporator and purified by preparative HPLC. The appropriate fractions were concentrated on a rotary evaporator and the residue was lyophilized from 1,4-dioxane. This gave 169 mg (quant.) of the intermediate.

LC-MS (Method 1): $R_t$=1.39 min; MS (ESIpos): m/z=658 $(M+H)^+$.

165 mg (0.251 mmol) of this intermediate were taken up in 30 ml of ethanol, and 0.35 ml of a 40% strength aqueous solution of methanamine was added. The reaction was stirred at 50° C. for 5 h, and the same amount of the methylamine solution was then added again. After 10 h of stirring, the reaction was concentrated under reduced pressure. The distillate was redistilled twice with diethyl ether and the residue was then lyophilized from acetonitrile/water. This gave 148 mg (89% of theory) of this intermediate.

LC-MS (Method 6): $R_t$=2.97 min; MS (ESIpos): m/z=616 $(M+H)^+$.

98 mg (0.15 mmol) of the precursor were dissolved in 15 ml of THF, and a solution of 569 mg (3.27 mmol) of disodium dithionite in 6 ml of water was then added at RT.

After 8 h of stirring at 50° C., the same amount of dithionite—dissolved in 1 ml of H2O—was added again. After a further 16 hours of stirring at 50° C., the reaction was cooled to RT and extracted with ethyl acetate. The organic phase was concentrated and the residue was purified by preparative HPLC. Lyophilization of the residue from 1,4-dioxane gave 44.5 mg (47% of theory) of the title compound.

LC-MS (Method 1): $R_t$=1.24 min; MS (ESIpos): m/z=586 $(M+H)^+$.

Intermediate C11

R/S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-homocysteine/trifluoroacetate (1:1)

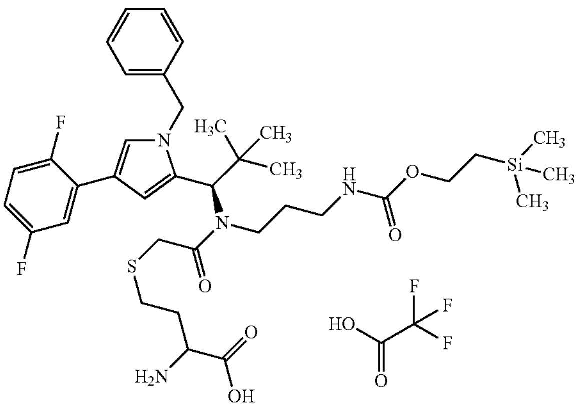 [SMILES: CC(C)(C)[C@H](c1cc(-c2cc(F)ccc2F)cn1Cc1ccccc1)N(CCCNC(=O)OCC[Si](C)(C)C)C(=O)CSCCC(N)C(=O)O ; O=C(O)C(F)(F)F]

990.0 mg (2.79 mmol) of (1R)-1-[1-benzyl-4-(2,5-difluorophenyl)-1H-pyrrol-2-yl]-2,2-dimethylpropan-1-amine were initially charged in 15.0 ml of dichloromethane, and 828.8 mg (3.91 mmol) of sodium triacetoxyborohydride and 129.9 mg (3.21 mmol) of acetic acid were added, and the mixture was stirred at RT for 5 min. 698.1 mg (3.21 mmol) of 2-(trimethylsilyl)ethyl (3-oxopropyl)carbamate (Intermediate L58) dissolved in 15.0 ml of dichloromethane were added, and the reaction mixture was stirred at RT overnight. The reaction mixture was diluted with ethyl acetate and the organic phase was washed in each case twice with saturated sodium carbonate solution and saturated NaCl solution. The organic phase was dried over magnesium sulphate and the solvent was evaporated under reduced pressure. The residue was chromatographed by means of silica gel (mobile phase: dichloromethane/methanol 100:2). The solvents were evaporated under reduced pressure and the residue was dried under high vacuum. This gave 1.25 g (73% of theory) of the compound 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate.

LC-MS (Method 1): $R_t$=1.09 min; MS (ESIpos): m/z=556 $(M+H)^+$.

151.4 mg (1.5 mmol) of triethylamine and 161.6 mg (1.43 mmol) of chloroacetyl chloride were added to 400.0 mg (0.65 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate. The reaction mixture was stirred at RT overnight. Ethyl acetate was added to the reaction mixture and the organic phase was washed three times with water and once with saturated NaCl solution. The organic phase was dried over magnesium sulphate and the solvent was evaporated under reduced pressure. The residue was chromatographed by means of silica gel (mobile phase: cyclohexane/ethyl acetate=3:1). The solvents were evaporated under reduced pressure and the residue was dried under high vacuum. This gave 254.4 mg (57% of theory) of the compound 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate.

LC-MS (Method 1): $R_t$=1.49 min; MS (ESIneg): m/z=676 $(M+HCOO^-)^-$.

117.4 mg (0.19 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate were dissolved in 10.0 ml of isopropanol, and 928.4 µl of 1M NaOH and 50.2 mg (0.37 mmol) of DL-homocysteine were added. The reaction mixture was stirred at 50° C. for 4.5 h. Ethyl acetate was added to the reaction mixture and the organic phase was washed with saturated sodium bicarbonate solution and saturated NaCl solution. The organic phase was dried over magnesium sulphate and the solvent was evaporated under reduced pressure. The residue was purified by preparative RP-HPLC (column: Reprosil 250×40; 10µ, flow rate: 50 ml/min, MeCN/water, 0.1% TFA). The solvents were evaporated under reduced pressure and the residue was dried under high vacuum. This gave 75.3 mg (48% of theory) of the title compound.

LC-MS (Method 1): $R_t$=1.24 min; MS (ESIpos): m/z=731 $(M+H)^+$.

$^1$H-NMR (400 MHz, DMSO-$d_6$): δ [ppm]=0.03 (s, 9H), 0.40 (m, 1H), 0.75-0.91 (m, 11H), 1.30 (m, 1H), 1.99-2.23 (m, 2H), 2.63-2.88 (m, 4H), 3.18-3.61 (m, 5H), 3.79-4.10 (m, 3H), 4.89 (d, 1H), 4.89 (d, 1H), 5.16 (d, 1H), 5.56 (s, 1H), 6.82 (m, 1H), 6.91 (s, 1H), 6.97 (m, 1H), 7.13-7.38 (m, 6H), 7.49 (s, 1H), 7.63 (m, 1H), 8.26 (s, 3H).

Intermediate C12

R/S-[(8S)-11-{(1R)-1-[1-Benzyl-4-(2,5-difluorophenyl)-1H-pyrrol-2-yl]-2,2-dimethylpropyl}-8-carboxy-2,2-dimethyl-6,12-dioxo-5-oxa-7,11-diaza-2-silatridecan-13-yl]homocysteine

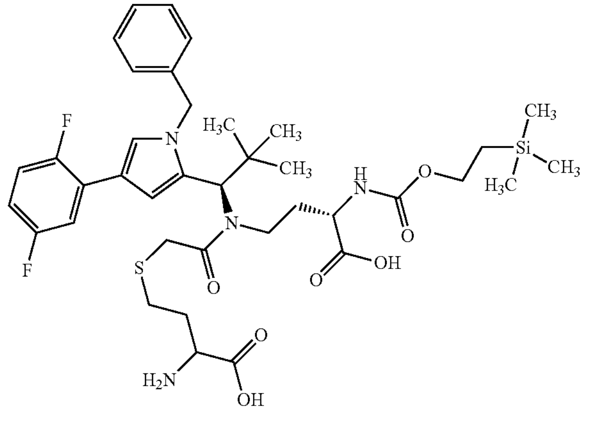 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CSCCC(N)C(=O)O]

The synthesis was carried out analogously to the synthesis of Intermediate C11 using methyl (2S)-4-oxo-2-({[2-(trimethylsilyl)ethoxy]carbonyl}amino)butanoate (Intermediate L57) and Intermediate C52 as starting materials.

LC-MS (Method 1): $R_t$=1.18 min; MS (ESIpos): m/z=775 $(M+H)^+$.

Intermediate C13

9-{(1R)-1-[1-Benzyl-4-(2,5-difluorophenyl)-1H-imidazol-2-yl]-2,2-dimethylpropyl}-2,2-dimethyl-4,10-dioxo-3-oxa-12-thia-5,9-diazaoctadecan-18-oic Acid

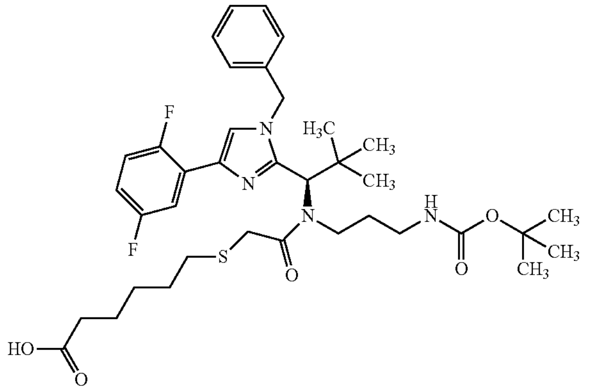 [SMILES: CC(C)(C)OC(=O)NCCCN(C(=O)CSCCCCCC(=O)O)[C@@H](c1nc(-c2cc(F)ccc2F)cn1Cc1ccccc1)C(C)(C)C]

90.0 mg (0.15 mmol) of intermediate C16 and 43.6 mg (0.23 mmol) of 6-(acetylsulphanyl)hexanoic acid were dissolved in 9.0 ml of methanol, and a drop of water and 73.9 mg (0.54 mmol) of potassium carbonate were added. The reaction mixture was stirred at 50° C. for 4 h and then diluted with ethyl acetate. The organic phase was washed with water/saturated NaCl solution and saturated NaCl solution and subsequently dried over magnesium sulphate. The solvent was evaporated under reduced pressure and the residue was chromatographed on silica gel (mobile phase: dichloromethane/methanol=100:2). The solvents were evaporated under reduced pressure and the residue was dried under high vacuum. This gave the title compound in 83% of theory.

LC-MS (Method 1): $R_t$=1.44 min; MS (ESIpos): m/z=701 $(M+H)^+$.

Intermediate C14

R/S-[2-({(1R)-1-[1-Benzyl-4-(2,5-difluorophenyl)-1H-imidazol-2-yl]-2,2-dimethylpropyl}{3-[(tert-butoxycarbonyl)amino]propyl}amino)-2-oxoethyl]homocysteine

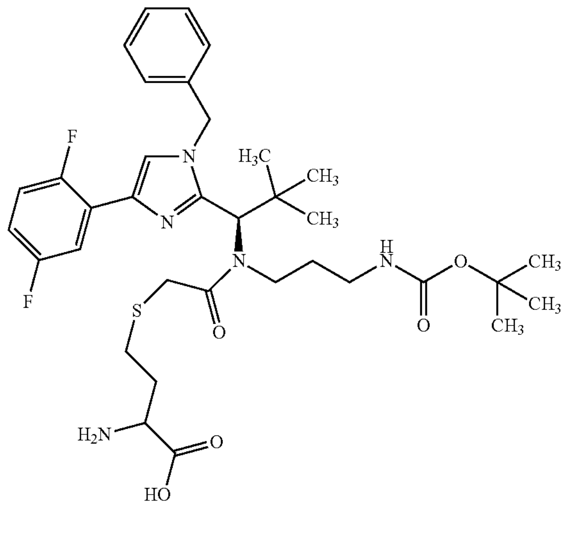 [SMILES: CC(C)(C)OC(=O)NCCCN(C(=O)CSCCC(N)C(=O)O)[C@@H](c1nc(-c2cc(F)ccc2F)cn1Cc1ccccc1)C(C)(C)C]

100.0 mg (0.17 mmol) of tert-butyl {3-[{(1R)-1-[1-benzyl-4-(2,5-difluorophenyl)-1H-imidazol-2-yl]-2,2-dimethylpropyl}(chloroacetyl)amino]propyl}carbamate (Intermediate C16) were initially charged in 4.0 ml of isopropanol, and 276.5 mg (0.85 mmol) of 1 M NaOH solution and 45.9 mg (0.34 mmol) of D/L-homocysteine were added. The reaction mixture was stirred at 50° C. for 1 h. The reaction mixture was diluted with ethyl acetate. The organic phase was washed with saturated sodium bicarbonate solution and saturated NaCl solution. Drying was over magnesium sulphate, and the solvent was evaporated under reduced pressure. The residue was purified by preparative RP-HPLC (column: Reprosil 250×40; 10μ, flow rate: 50 ml/min, MeCN/water). The solvents were evaporated under reduced pressure and the residue was dried under high vacuum.

This gave 92.6 mg (66% of theory) of the title compound.

LC-MS (Method 1): $R_t$=1.07 min; MS (ESIpos): m/z=688 $(M+H)^+$.

Intermediate C15 tert-Butyl [3-({(1R)-1-[1-benzyl-4-(2,5-difluorophenyl)-1H-imidazol-2-yl]-2,2-dimethylpropyl}amino)propyl]carbamate

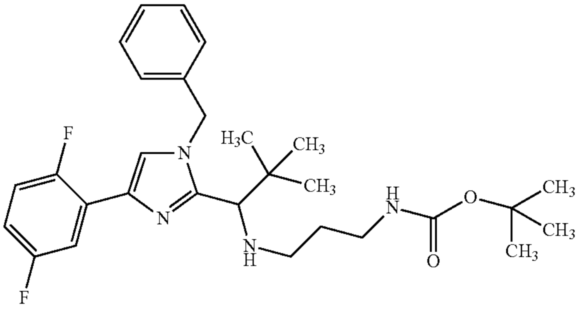 [SMILES: CC(C)(C)OC(=O)NCCCNC(c1nc(-c2cc(F)ccc2F)cn1Cc1ccccc1)C(C)(C)C]

750.0 mg (2.11 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C1) were dissolved in 15.0 ml of dichloromethane, and 626.0 mg (2.95 mmol) of sodium triacetoxyborohydride and 139 μl (2.43 mmol) of HOAc were added and the mixture was stirred at RT for 5 min. 420.3 mg (2.43 mmol) of tert-butyl (3-oxopropyl)carbamate (synthesis according to literature procedure J. Med. Chem. 2003, 46, 3536) were then added, and the mixture was stirred at RT overnight. Ethyl acetate was added and the reaction mixture was extracted twice with saturated sodium carbonate solution. The organic phase was washed with saturated NaCl solution and dried over magnesium sulphate. The solvent was evaporated under reduced pressure and the residue was chromatographed on silica gel (mobile phase: cyclohexane/ethyl acetate=4:1). The solvents were evaporated under reduced pressure and the residue was dried under high vacuum. This gave 881.0 mg (82% of theory) of the title compound.

LC-MS (Method 1): $R_t$=1.07 min; MS (ESIpos): m/z=513 $[M+H]^+$.

Intermediate C16 tert-Butyl {3-[{(1R)-1-[1-benzyl-4-(2,5-difluorophenyl)-1H-imidazol-2-yl]-2,2-dimethylpropyl}(chloroacetyl)amino]propyl}carbamate

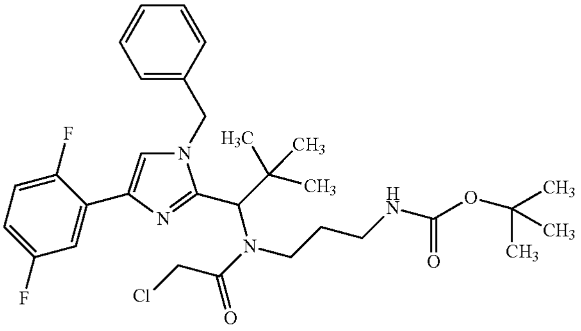 [SMILES: CC(C)(C)OC(=O)NCCCN(C(=O)CCl)C(c1nc(-c2cc(F)ccc2F)cn1Cc1ccccc1)C(C)(C)C]

373.4 mg (0.73 mmol) of tert-butyl [3-({(1R)-1-[1-benzyl-4-(2,5-difluorophenyl)-1H-imidazol-2-yl]-2,2-dimethylpropyl}amino)propyl]carbamate (Intermediate C15) were initially charged in 5.0 ml of dichloromethane, and 169.5 mg (1.68 mmol) of triethylamine and 181.0 mg (1.60 mmol) of chloroacetyl chloride were added. The reaction mixture was stirred at RT overnight, ethyl acetate was then added and the mixture was extracted repeatedly with water. The organic phase was washed with saturated NaCl solution and dried over magnesium sulphate. The solvent was evaporated under reduced pressure and the residue was chromatographed on silica gel (mobile phase: dichloromethane/methanol=100:0.5). The solvents were evaporated under reduced pressure and the residue was dried under high vacuum. This gave 336.0 mg (75% of theory) of the title compound.

LC-MS (Method 1): $R_t$=1.48 min; MS (ESIpos): m/z=589 $[M+H]^+$.

Intermediate C17

9-{(1R)-1-[1-Benzyl-4-(2,5-difluorophenyl)-1H-imidazol-2-yl]-2,2-dimethylpropyl}-2,2-dimethyl-4,10-dioxo-3,15,18,21,24-pentaoxa-12-thia-5,9-diazaheptacosan-27-oic Acid

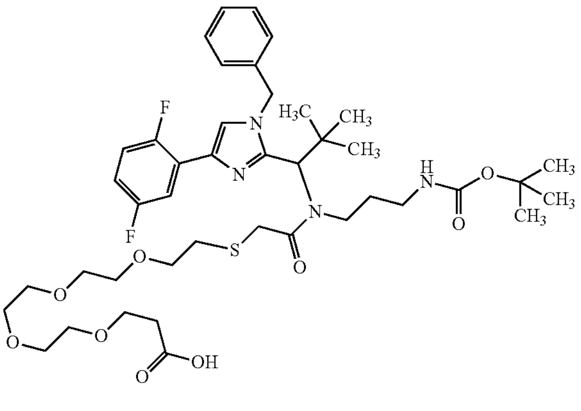 [SMILES: CC(C)(C)OC(=O)NCCCN(C(=O)CSCCOCCOCCOCCOCCC(=O)O)C(c1nc(-c2cc(F)ccc2F)cn1Cc1ccccc1)C(C)(C)C]

50.0 mg (0.09 mmol) of tert-butyl {3-[{(1R)-1-[1-benzyl-4-(2,5-difluorophenyl)-1H-imidazol-2-yl]-2,2-dimethylpropyl}(chloracetyl)amino]propyl}carbamate (Intermediate C16) were initially charged in 2.0 ml of DMF, and 69.1 mg (0.21 mmol) of caesium carbonate and 28.8 mg (0.10 mmol) of 1-sulphanyl-3,6,9,12-tetraoxapentadecan-15-oic acid were added. The mixture was stirred at 50° C. overnight. Water was added and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum.

This gave 25.1 mg (35% of theory) of the title compound.

LC-MS (Method 1): $R_t$=1.42 min; MS (ESIpos): m/z=835 [M+H]$^+$.

Intermediate C18 tert-Butyl [22-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-4,21-dioxo-7,10,13,16-tetraoxa-19-thia-3,22-diazapentacosan-25-yl] carbamate

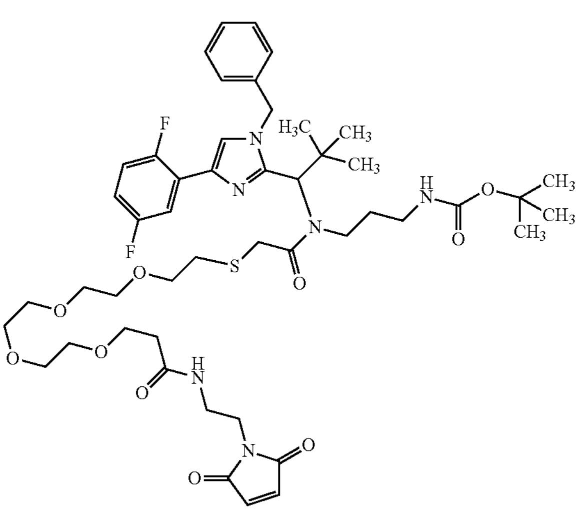 [SMILES: CC(C)(C)OC(=O)NCCCN(C(=O)CSCCOCCOCCOCCOCCC(=O)NCCN1C(=O)C=CC1=O)C(c1nc(-c2cc(F)ccc2F)cn1Cc1ccccc1)C(C)(C)C]

21.0 mg (0.03 mmol) of 9-{(1R)-1-[1-benzyl-4-(2,5-difluorophenyl)-1H-imidazol-2-yl]-2,2-dimethylpropyl}-2,2-dimethyl-4,10-dioxo-3,15,18,21,24-pentaoxa-12-thia-5,9-diazaheptacosan-27-oic acid (Intermediate C17) and 5.8 mg (0.0.3 mmol) of 1-(2-aminoethyl)-1H-pyrrole-2,5-dione hydrochloride (1:1) were initially charged in 1.0 ml of acetonitrile, and 26.1 mg (0.20 mmol) of N,N-diisopropylethylamine and 20.9 mg (0.03 mmol) of T3P (50% in ethyl acetate) were added. The mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 19.7 mg (79% of theory) of the title compound.

LC-MS (Method 1): $R_t$=1.42 min; MS (ESIpos): m/z=835 [M+H]$^+$.

Intermediate C19 tert-Butyl (13-{(1R)-1-[1-benzyl-4-(2,5-difluorophenyl)-1H-imidazol-2-yl]-2,2-dimethylpropyl}-2,2-dimethyl-6,12-dioxo-5-oxa-10-thia-7,13-diaza-2-silahexadecan-16-yl)carbamate

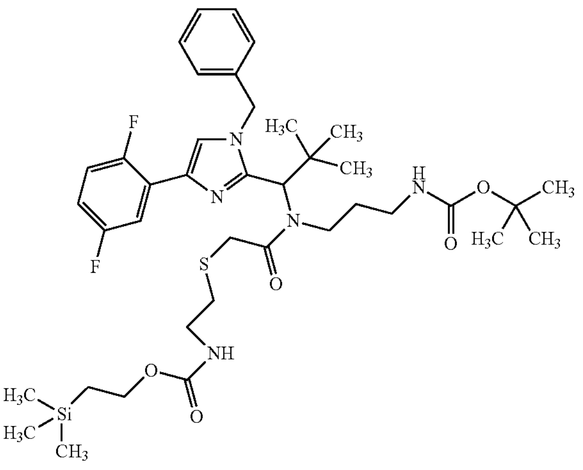 [SMILES: CC(C)(C)OC(=O)NCCCN(C(=O)CSCCNC(=O)OCC[Si](C)(C)C)C(c1nc(-c2cc(F)ccc2F)cn1Cc1ccccc1)C(C)(C)C]

58.5 mg (0.10 mmol) of tert-butyl {3-[{(1R)-1-[1-benzyl-4-(2,5-difluorophenyl)-1H-imidazol-2-yl]-2,2-dimethylpropyl}(chloroacetyl)amino]propyl}carbamate (Intermediate C16) were initially charged in 2.0 ml of DMF, and 44.0 mg (0.20 mmol) of 2-(trimethylsilyl)ethyl (2-sulphanylethyl) carbamate (Intermediate L39) and 64.7 mg (0.20 mmol) of caesium carbonate were added. The mixture was stirred at 50° C. for 4 h. The reaction was repeated with 46.6 mg (0.079 mmol) of Intermediate C16. The two reaction mixtures were combined and purified directly by preparative RP-HPLC (column: Reprosil 250×30; 10μ, flow rate: 50 ml/min, MeCN/water). The solvents were evaporated under reduced pressure and the residue was dried under high vacuum. This gave 98.0 mg (71% of theory) of the title compound.

LC-MS (Method 1): $R_t$=1.62 min; MS (ESIpos): m/z=774 [M+H]$^+$.

Intermediate C20

Trifluoroacetic Acid/tert-butyl [3-({[(2-aminoethyl) sulphanyl]acetyl}{(1R)-1-[1-benzyl-4-(2,5-difluorophenyl)-1H-imidazol-2-yl]-2,2-dimethylpropyl}amino)propyl]carbamate

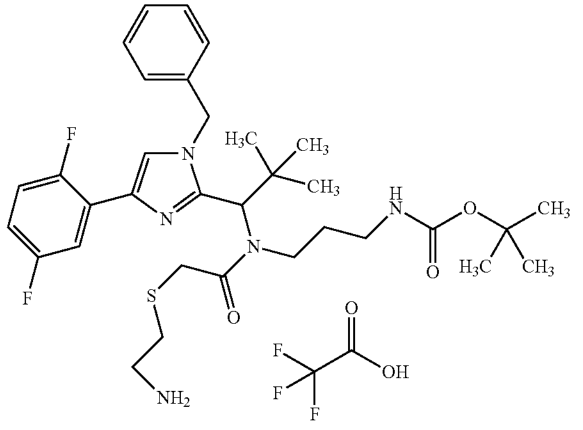

98.0 mg (0.13 mmol) of tert-butyl (13-{(1R)-1-[1-benzyl-4-(2,5-difluorophenyl)-1H-imidazol-2-yl]-2,2-dimethylpropyl}-2,2-dimethyl-6,12-dioxo-5-oxa-10-thia-7,13-diaza-2-silahexadecan-16-yl)carbamate (Intermediate C19) were initially charged in 2.0 ml of DMF/tert-butanol (9:1), and 96.2 mg (0.63 mmol) of CsF were added. The mixture was stirred at 90° C. for 16 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was lyophilized. This gave 57.1 mg (61% of theory) of the title compound. The compound also comprises the corresponding sulphoxide.

LC-MS (Method 1): $R_t$=1.08 min; MS (ESIpos): m/z=630 $[M+H]^+$.

Intermediate C21 tert-Butyl [38-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-3,31,37-trioxo-7,10,13,16,19,22,25,28-octaoxa-35-thia-4,32,38-triazahentetracontan-41-yl]carbamate

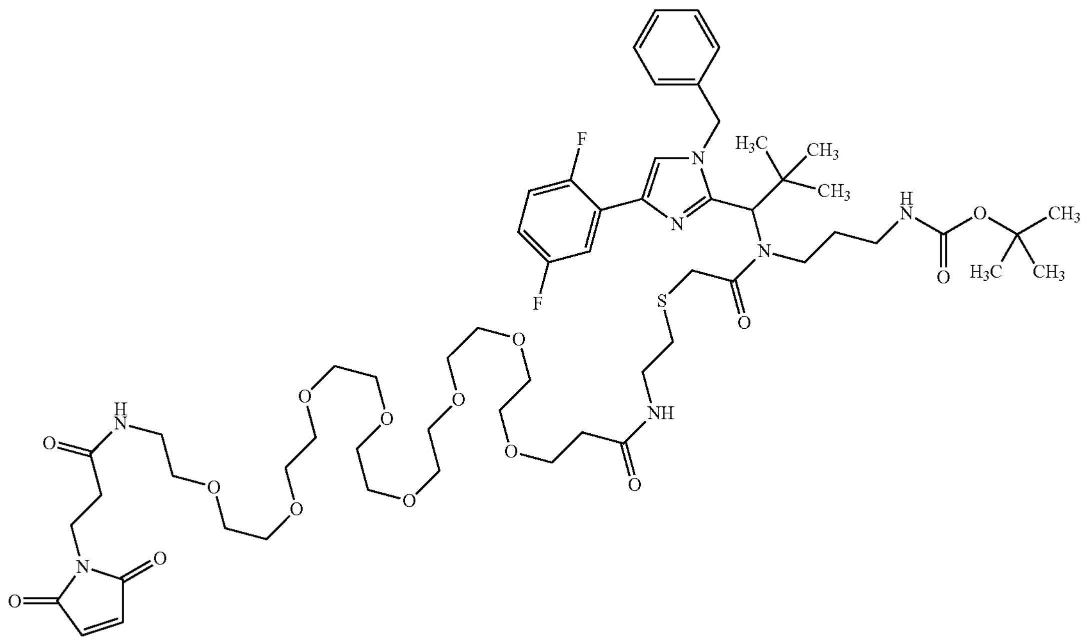 [SMILES: CC(C)(C)OC(=O)NCCCN(C(=O)CSCCNC(=O)CCOCCOCCOCCOCCOCCOCCOCCOCCNC(=O)CCN1C(=O)C=CC1=O)C(c1nc(-c2cc(F)ccc2F)cn1Cc1ccccc1)C(C)(C)C]

57.1 mg (0.08 mmol) of trifluoroacetic acid/tert-butyl [3-({[(2-aminoethyl)sulphanyl]acetyl}{(1R)-1-[1-benzyl-4-(2,5-difluorophenyl)-1H-imidazol-2-yl]-2,2-dimethylpropyl}amino)propyl]carbamate (Intermediate C20) were initially charged in 3.0 ml of DMF, and 53.0 mg (0.08 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide and 15.5 mg (0.15 mmol) of triethylamine were added. The mixture was stirred at RT for 16 h. The reaction mixture was purified directly by preparative RP-HPLC (column: Reprosil 250×30; 10μ, flow rate: 50 ml/min, MeCN/water). The solvents were evaporated under reduced pressure and the residue was lyophilized. This gave 49.7 mg (49% of theory) of the title compound.

LC-MS (Method 1): $R_t$=1.34 min; MS (ESIpos): m/z=1204 $[M+H]^+$.

Intermediate C22 tert-Butyl [38-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-35-oxido-3,31,37-trioxo-7,10,13,16,19,22,25,28-octaoxa-35lambda4-thia-4,32,38-triazahentetracontan-41-yl] carbamate 411.2 mg (1.15 mmol) of tert-butyl 3-formyl-4-({[2-(trimethylsilyl)ethoxy]carbonyl}amino)pyrrolidine-1-carboxylate (Intermediate L28) and 339.7 mg (0.96 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C1) were initially charged in 6.0 ml of dichloromethane, and 68.9 mg (1.15 mmol) of HOAc were added and the mixture was stirred at RT for 1

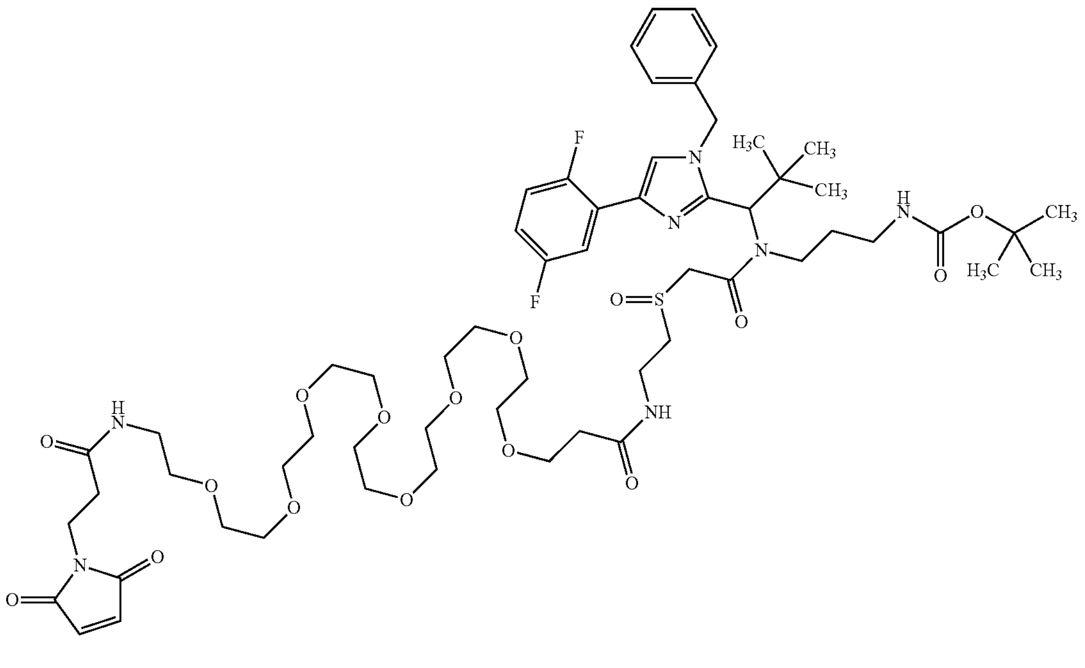 [SMILES: CC(C)(C)OC(=O)NCCCN(C(=O)CS(=O)CCNC(=O)CCOCCOCCOCCOCCOCCOCCOCCOCCNC(=O)CCN1C(=O)C=CC1=O)C(c1nc(-c2cc(F)ccc2F)cn1Cc1ccccc1)C(C)(C)C]

The title compound was formed as a by-product in the synthesis of Intermediate C21. This gave 15.5 mg (15% of theory) of the title compound.

LC-MS (Method 1): $R_t$=1.25 min; MS (ESIpos): m/z=1220 $[M+H]^+$.

Intermediate C23 tert-Butyl 3-amino-4-{[{(1R)-1-[1-benzyl-4-(2,5-difluorophenyl)-1H-imidazol-2-yl]-2,2-dimethylpropyl}(glycoloyl)amino]methyl}pyrrolidine-1-carboxylate Mixture of Stereoisomers

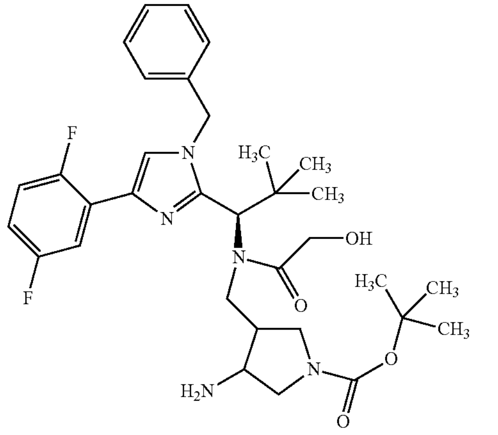 [SMILES: CC(C)(C)OC(=O)N1CC(N)C(CN(C(=O)CO)[C@@H](c2nc(-c3cc(F)ccc3F)cn2Cc2ccccc2)C(C)(C)C)C1]

h. 405.2 mg (1.91 mmol) of sodium triacetoxyborohydride were added and the mixture was stirred at RT for 2 h. The solvent was evaporated under reduced pressure and ethyl acetate and water were added to the residue. The aqueous phase was extracted three times with ethyl acetate. The combined organic phases were washed once with sat. NaCl solution and dried over magnesium sulphate. The solvent was evaporated under reduced pressure and the residue was purified using Biotage Isolera (silica gel, column 50 g SNAP, flow rate 40 ml/min, petroleum ether/ethyl acetate). The solvents were evaporated under reduced pressure and the residue was dried under high vacuum. This gave 541.5 mg (81% of theory) of the compound tert-butyl 3-[({(1R)-1-[1-benzyl-4-(2,5-difluorophenyl)-1H-imidazol-2-yl]-2,2-dimethylpropyl}amino)methyl]-4-({[2-(trimethylsilyl)ethoxy]carbonyl}amino)pyrrolidine-1-carboxylate.

LC-MS (Method 1): $R_t$=1.24 and 1.29 min; MS (ESIpos): m/z=698 $[M+H]^+$.

541.5 mg (0.78 mmol) of tert-butyl 3-[({(1R)-1-[1-benzyl-4-(2,5-difluorophenyl)-1H-imidazol-2-yl]-2,2-dimethylpropyl}amino)methyl]-4-({[2-(trimethylsilyl)ethoxy]carbonyl}amino)pyrrolidine-1-carboxylate were dissolved in 13.0 ml of dichloromethane, and 180.6 mg (1.78 mmol) of triethylamine were added. The reaction solution was cooled to 0° C., 233.1 mg (1.71 mmol) of acetoxyacetyl chloride were added and the mixture was stirred at RT for 16 h. Another 180.6 mg (1.78 mmol) of triethylamine and 233.1 mg (1.71 mmol) of acetoxyacetyl chloride were added, and the mixture was stirred at RT for another 80 h. The solvent was evaporated under reduced pressure and the residue was partitioned between water and ethyl acetate. The aqueous phase was extracted three times with ethyl acetate. The combined organic phases were washed once with sat. NaCl solution and dried over magnesium sulphate. The solvent was evaporated under reduced pressure and the residue was purified using Biotage Isolera (silica gel, column 50 g SNAP, flow rate 40 ml/min, petroleum ether/ethyl acetate). The solvents were evaporated under reduced pressure and the residue was dried under high vacuum. This gave 529.2 mg (86% of theory) of the compound tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-({[2-(trimethylsilyl)ethoxy]carbonyl}amino)pyrrolidine-1-carboxylate.

LC-MS (Method 1): $R_t$=1.53 and 1.56 min; MS (ESIpos): m/z=798 $[M+H]^+$.

529.2 mg (0.66 mmol) of tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-({[2-(trimethylsilyl)ethoxy]carbonyl}amino)pyrrolidine-1-carboxylate were initially charged in 10.0 ml of DMF/tert-butanol (9:1), and 503.7 mg (3.32 mmol) of CsF were added. The reaction mixture was stirred at 90° C. for 16 h. The reaction mixture was partitioned between water and ethyl acetate. The aqueous phase was extracted three times with ethyl acetate. The combined organic phases were washed once with sat. NaCl solution and dried over magnesium sulphate. The solvent was evaporated under reduced pressure and the residue was purified using Biotage Isolera (silica gel, column 50 g SNAP, flow rate 25 ml/min, dichloromethane/methanol). The solvents were evaporated under reduced pressure and the residue was dried under high vacuum. This gave 172.4 mg (40% of theory) of the compound tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-aminopyrrolidine-1-carboxylate.

LC-MS (Method 1): $R_t$=1.05 and 1.35 min; MS (ESIpos): m/z=654 $[M+H]^+$.

172.4 mg (0.26 mmol) of tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-aminopyrrolidine-1-carboxylate were initially charged in 4.5 ml of methanol/water (2:1), and 80.2 mg (0.58 mmol) potassium carbonate were added and the mixture was stirred at RT for 16 h. The reaction mixture was partitioned between water and ethyl acetate. The aqueous phase was extracted three times with ethyl acetate. The combined organic phases were washed once with sat. NaCl solution and dried over magnesium sulphate. The solvent was evaporated under reduced pressure and the residue was purified by preparative RP-HPLC (column: Reprosil 250×30; 10µ, flow rate: 50 ml/min, MeCN/water). The solvents were evaporated under reduced pressure and the residue was dried under high vacuum.

This gave 116.0 mg (72% of theory) of the title compound.

LC-MS (Method 1): $R_t$=1.01 min and 1.03 min; MS (ESIpos): m/z=612 $[M+H]^+$.

Intermediate C24

Trifluoroacetic Acid/tert-butyl 3-(aminomethyl)-4-{[{(1R)-1-[1-benzyl-4-(2,5-difluorophenyl)-1H-imidazol-2-yl]-2,2-dimethylpropyl}(glycoloyl)amino]methyl}pyrrolidine-1-carboxylate (1:1)

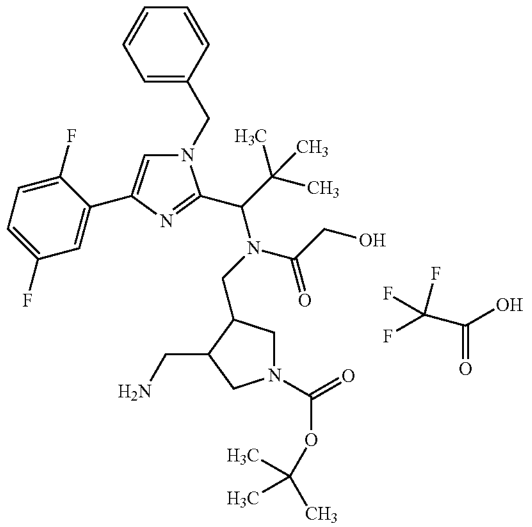

26.8 mg of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C1) were dissolved in 3.0 ml of dichloromethane, and 5.2 mg (0.09 mmol) of HOAc and 22.4 mg (0.11 mmol) of sodium triacetoxyborohydride were added and the mixture was stirred at RT for 5 min. 62.4 mg (0.09 mmol) of tert-butyl 3-formyl-4-[({[2-(trimethylsilyl)ethoxy]carbonyl}amino)methyl]pyrrolidine-1-carboxylate (Intermediate L29) were added and the mixture was stirred at RT overnight. The solvent was evaporated under reduced pressure and the residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 57.6 mg (91% of theory) of the compound trifluoroacetic acid/tert-butyl 3-[({(1R)-1-[1-benzyl-4-(2,5-difluorophenyl)-1H-imidazol-2-yl]-2,2-dimethylpropyl}amino)methyl]-4-[({[2-(trimethylsilyl)ethoxy]carbonyl}amino)methyl]pyrrolidine-1-carboxylate.

LC-MS (Method 1): $R_t$=1.25 and 1.27 min; MS (ESIpos): m/z=712 $[M+H]^+$.

77.0 mg (0.11 mmol) of tert-butyl 3-[({(1R)-1-[1-benzyl-4-(2,5-difluorophenyl)-1H-imidazol-2-yl]-2,2-dimethylpropyl}amino)methyl]-4-[({[2-(trimethylsilyl)ethoxy]carbonyl}amino)methyl]pyrrolidine-1-carboxylate were initially charged in 1.5 ml of dichloromethane, and 21.9 mg (0.22 mmol) of triethylamine were added. At 0° C., 29.5 mg (0.22 mmol) of acetoxyacetyl chloride were then added and the reaction mixture was stirred at RT overnight. The solvent was evaporated under reduced pressure and the residue was taken up in ethyl acetate. The organic phase was washed in each case once with water, saturated sodium bicarbonate solution and saturated NaCl solution. After drying over magnesium sulphate, the solvent was evaporated under reduced pressure. The reaction was repeated with 77.0 mg (0.11 mmol) of tert-butyl 3-[({(1R)-1-[1-benzyl-4-(2,5-difluorophenyl)-1H-imidazol-2-yl]-2,2-dimethylpropyl}amino)methyl]-4-[({[2-(trimethylsilyl)ethoxy]carbonyl}amino)methyl]pyrrolidine-1-carboxylate. The combined residues were purified on silica gel (mobile phase: cyclohexane/ethyl acetate=2:1). This gave 171.1 mg (85% of theory) of the compound tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-[({[2-(trimethylsilyl)ethoxy]carbonyl}amino)methyl]pyrrolidine-1-carboxylate.

LC-MS (Method 1): $R_t$=1.56 and 1.57 min; MS (ESIpos): m/z=812 $[M+H]^+$.

30.0 mg (0.04 mmol) of tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-[({[2-(trimethylsilyl)ethoxy]carbonyl}amino)methyl]pyrrolidine-1-carboxylate were initially charged in 0.5 ml of TBAF solution (1M in THF). The mixture was stirred at RT overnight. The solvent was evaporated under reduced pressure and the residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 25.0 mg (92% of theory) of the title compound.

LC-MS (Method 1): $R_t$=0.98 min; MS (ESIpos): m/z=626 $[M+H]^+$.

Intermediate C25

4-{[{(1R)-1-[1-Benzyl-4-(2,5-difluorophenyl)-1H-imidazol-2-yl]-2,2-dimethylpropyl}(glycoloyl)amino]methyl}-1-(tert-butoxycarbonyl)pyrrolidine-3-carboxylic Acid

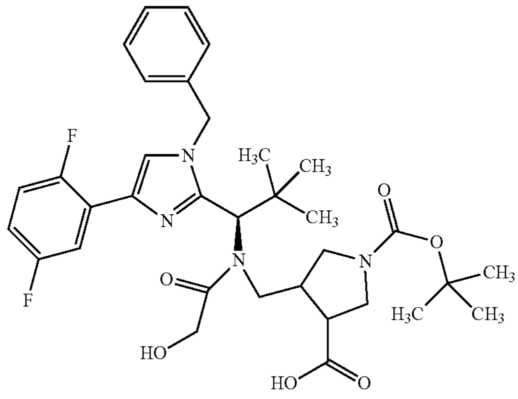 [SMILES: CC(C)(C)OC(=O)N1CC(CN(C(=O)CO)[C@@H](c2nc(-c3cc(F)ccc3F)cn2Cc2ccccc2)C(C)(C)C)C(C(=O)O)C1]

171.4 mg (0.48 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C1) were initially charged in 4.0 ml of dichloromethane, and 248.5 mg (0.72 mmol) of tert-butyl 3-({[tert-butyl(dimethyl)silyl]oxy}methyl)-4-formylpyrrolidine-1-carboxylate (Intermediate L30) and 34.8 mg (0.58 mmol) of HOAc were added. The reaction mixture was stirred at RT for 1 h. 204.4 mg (0.97 mmol) of sodium triacetoxyborohydride were added and the mixture was stirred at RT for 60 h. The solvent was removed under reduced pressure and the residue was purified using Biotage Isolera (silica gel, column 25 g SNAP, flow rate 25 ml/min, petroleum ether/ethyl acetate). The solvents were evaporated under reduced pressure and the residue was dried under high vacuum. This gave 267.0 mg (77% of theory) of the compound tert-butyl 3-[({(1R)-1-[1-benzyl-4-(2,5-difluorophenyl)-1H-imidazol-2-yl]-2,2-dimethylpropyl}amino)methyl]-4-({[tert-butyl(dimethyl)silyl]oxy}methyl)pyrrolidine-1-carboxylate.

LC-MS (Method 1): $R_t$=1.49 min; MS (ESIpos): m/z=683 $[M+H]^+$.

267.0 mg (0.39 mmol) of tert-butyl 3-[({(1R)-1-[1-benzyl-4-(2,5-difluorophenyl)-1H-imidazol-2-yl]-2,2-dimethylpropyl}amino)methyl]-4-({[tert-butyl(dimethyl)silyl]oxy}methyl)pyrrolidine-1-carboxylate were dissolved in 5.0 ml of dichloromethane, and 91.0 mg (0.90 mmol) of triethylamine were added and the mixture was cooled to 0° C. 117.4 mg (0.86 mmol) of acetoxyacetyl chloride were added, and the mixture was stirred at RT for 16 h. Another 593.4 mg (5.87 mmol) of triethylamine and 427.0 mg (3.13 mmol) of acetoxyacetyl chloride were added, and the mixture was stirred at RT for another 10 h. The solvent was evaporated under reduced pressure and the residue was purified by preparative RP-HPLC (column: Reprosil 250×30; 10μ, flow rate: 50 ml/min, MeCN/water). The solvents were then evaporated under reduced pressure and the residue was dried under high vacuum. This gave 216.3 mg (71% of theory) of the compound tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-({[tert-butyl(dimethyl)silyl]oxy}methyl)pyrrolidine-1-carboxylate.

LC-MS (Method 1): $R_t$=1.70 and 1.72 min; MS (ESIpos): m/z=783 $[M+H]^+$.

216.3 mg (0.28 mmol) of tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-({[tert-butyl(dimethyl)silyl]oxy}methyl)pyrrolidine-1-carboxylate were initially charged in 4.0 ml of THF, and 16.6 mg (0.28 mmol) of HOAc and 361.1 mg (1.38 mmol) of TBAF solution (1M in THF) were added. The reaction solution was stirred at RT for 4 h. The solvent was evaporated under reduced pressure and the residue was purified by preparative RP-HPLC (column: Reprosil 250×30; 10μ, flow rate: 50 ml/min, MeCN/water). The solvents were then evaporated under reduced pressure and the residue was dried under high vacuum. This gave 94.0 mg (51% of theory) of the compound tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-(hydroxymethyl)pyrrolidine-1-carboxylate.

LC-MS (Method 1): $R_t$=1.34 min; MS (ESIpos): m/z=669 $[M+H]^+$.

52.0 mg (0.08 mmol) of tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-(hydroxymethyl)pyrrolidine-1-carboxylate were initially charged in 4.0 ml of PBS buffer/acetonitrile (9:1), and 1.2 mg (0.01 mmol) of TEMPO were added. 14.1 mg (0.16 mmol) of sodium chlorite in 1.0 ml of water and 115.8 μl of (0.16 mmol) 10% strength sodium hypochlorite solution were then added simultaneously. The reaction mixture was stirred at RT for 16 h. The reaction mixture was poured into a 10% strength sodium sulphite solution, and ethyl acetate was added. The aqueous phase was extracted three times with ethyl acetate and the combined organic phases were washed once with saturated NaCl solution and dried over magnesium sulphate. The solvent was evaporated under reduced pressure and the residue was used for the next synthesis step without further purification.

LC-MS (Method 1): $R_t$=1.34 min; MS (ESIpos): m/z=683 $[M+H]^+$.

103.0 mg (0.15 mmol) of 4-{[(acetoxyacetyl){(1R)-1-[1-benzyl-4-(2,5-difluorophenyl)-1H-imidazol-2-yl]-2,2-dimethylpropyl}amino]methyl}-1-(tert-butoxycarbonyl) pyrrolidin-3-carboxylic acid were initially charged in 4.5 ml of methanol/water (2:1), and 45.9 mg (0.33 mmol) potassium carbonate were added and the mixture was stirred at RT for 3 h. The reaction mixture was partitioned between water and ethyl acetate. The aqueous phase was extracted three times with ethyl acetate and the combined organic phases were washed once with saturated NaCl solution and dried over magnesium sulphate. The solvent was evaporated under reduced pressure and the title compound was used for the next synthesis step without further purification.

LC-MS (Method 1): $R_t$=1.35 min; MS (ESIpos): m/z=641 $[M+H]^+$.

Intermediate C26 tert-Butyl [3-({(1R)-1-[1-benzyl-4-(2,5-difluorophenyl)-1H-imidazol-2-yl]-2,2-dimethylpropyl}amino)-2-({[tert-butyl(dimethyl)silyl]oxy}methyl)propyl] carbamate

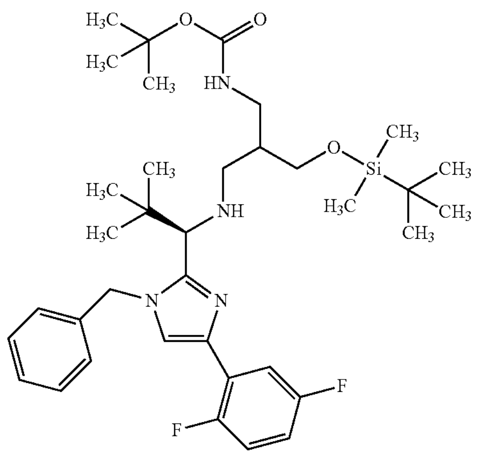 [SMILES: CC(C)(C)OC(=O)NCC(CN[C@@H](c1nc(-c2cc(F)ccc2F)cn1Cc1ccccc1)C(C)(C)C)CO[Si](C)(C)C(C)(C)C]

590 mg (1.69 mmol) of sodium triacetoxyborohydride and 155 µl (2.70 mmol, 162 mg) of acetic acid were initially charged in 30 ml of dichloromethane, and the mixture was stirred at RT for 30 min. 600 mg (1.687 mmol) of (1R)-1-[1-benzyl-4-(2,5-difluorophenyl)-1H-imidazol-2-yl]-2,2-dimethylpropan-1-amine (obtained from trifluoroacetic acid/(1R)-1-[1-benzyl-4-(2,5-difluorophenyl)-1H-imidazol-2-yl]-2,2-dimethylpropan-1-amine (1:1) by extraction with 1N aqueous sodium hydroxide solution) and 750 mg (2.362 mmol) of tert-butyl (3-{[tert-butyl(dimethyl)silyl]oxy}-2-formylpropyl)carbamate dissolved in 40 ml of dichloromethane were then added dropwise. The mixture was stirred at RT for 2 h. Ethyl acetate was then added, the mixture was washed with saturated sodium carbonate solution and the organic phase was concentrated. The residue was separated by preparative HPLC (mobile phase: ACN/water, gradient). This gave 510 mg (46% of theory) of the target compound as a diastereomer mixture.

Isomer 1:

LC-MS (Method 1): $R_t$=1.36 min (51%); MS (EIpos): m/z=657 $[M+H]^+$.

Isomer 2:

LC-MS (Method 1): $R_t$=1.41 min (49%); MS (EIpos): m/z=657 $[M+H]^+$.

Intermediate C27

2-({(1R)-1-[1-Benzyl-4-(2,5-difluorophenyl)-1H-imidazol-2-yl]-2,2-dimethylpropyl}{3-[(tert-butoxycarbonyl)amino]-2-({[tert-butyl(dimethyl)silyl]oxy}methyl)propyl}amino)-2-oxoethyl Acetate

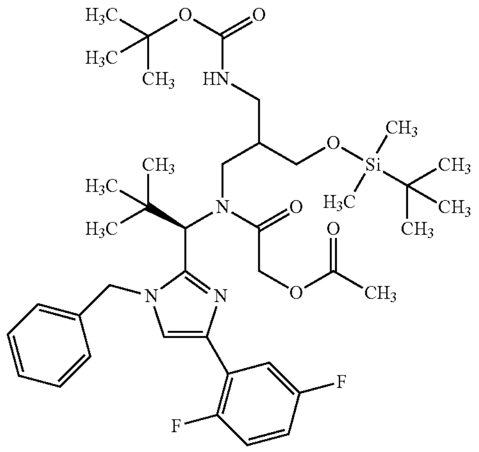 [SMILES: CC(=O)OCC(=O)N(CC(CNC(=O)OC(C)(C)C)CO[Si](C)(C)C(C)(C)C)[C@@H](c1nc(-c2cc(F)ccc2F)cn1Cc1ccccc1)C(C)(C)C]

510 mg (0,776 mmol) of tert-butyl [3-({(1R)-1-[1-benzyl-4-(2,5-difluorophenyl)-1H-imidazol-2-yl]-2,2-dimethylpropyl}amino)-2-({[tert-butyl(dimethyl)silyl]oxy}methyl)propyl]carbamate were initially charged in 30 ml of dichloromethane, and 181 mg (249 µl, 1.786 mmol) of triethylamine and 219 mg (1.553 mmol) of 2-chloro-2-oxoethyl acetate were added. The reaction mixture was stirred at RT for 2 h and then washed with saturated sodium bicarbonate solution. The organic phase was dried over sodium sulphate and concentrated on a rotary evaporator. The residue was separated by preparative HPLC (mobile phase: ACN/water, gradient). This gave 290 mg (49% of theory) of the target compound as an epimer mixture.

Isomer 1:

LC-MS (METHOD 1): $R_t$=1.70 min; MS (EIpos): m/z=757 $[M+H]^+$.

Isomer 2:

LC-MS (Method 1): $R_t$=1.72 min; MS (EIpos): m/z=757 $[M+H]^+$.

Intermediate C28

2-({(1R)-1-[1-Benzyl-4-(2,5-difluorophenyl)-1H-imidazol-2-yl]-2,2-dimethylpropyl}{3-[(tert-butoxycarbonyl)amino]-2-(hydroxymethyl)propyl}amino)-2-oxoethyl Acetate

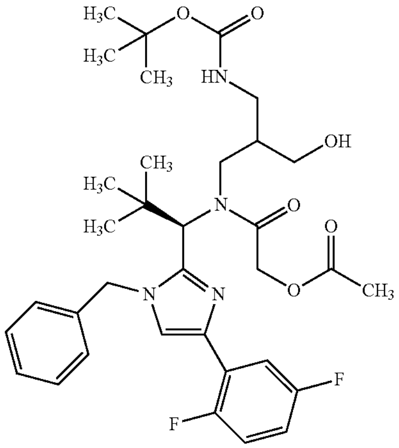 [SMILES: CC(=O)OCC(=O)N(CC(CO)CNC(=O)OC(C)(C)C)[C@@H](c1nc(-c2cc(F)ccc2F)cn1Cc1ccccc1)C(C)(C)C]

285 mg (0.376 mmol) of 2-({(1R)-1-[1-benzyl-4-(2,5-difluorophenyl)-1H-imidazol-2-yl]-2,2-dimethylpropyl}{3-[(tert-butoxycarbonyl)amino]-2-({[tert-butyl(dimethyl)silyl]oxy}methyl)propyl}amino)-2-oxoethyl acetate were dissolved in 5 ml of THF. 452 μl (0.452 mmol) of a 1 M solution of tetra-n-butylammonium fluoride in THF were added, and the reaction mixture was stirred at RT for 3 h. The reaction mixture was separated by preparative HPLC (mobile phase: ACN/water, gradient) and lyophilized. This gave 214 mg (81% of theory, purity according to LC/MS=92%) of the target compound as an epimer mixture.

Isomer 1:

LC-MS (Method 1): $R_t$=1.37 min; MS (EIpos): m/z=643 $[M+H]^+$.

Isomer 2:

LC-MS (METHOD 1): $R_t$=1.40 min; MS (EIpos): m/z=643 $[M+H]^+$.

Intermediate C29

2-([3-(Acetylsulphanyl)-2-{[(tert-butoxycarbonyl)amino]methyl}propyl]{(1R)-1-[1-benzyl-4-(2,5-difluorophenyl)-1H-imidazol-2-yl]-2,2-dimethylpropyl}amino)-2-oxoethyl Acetate

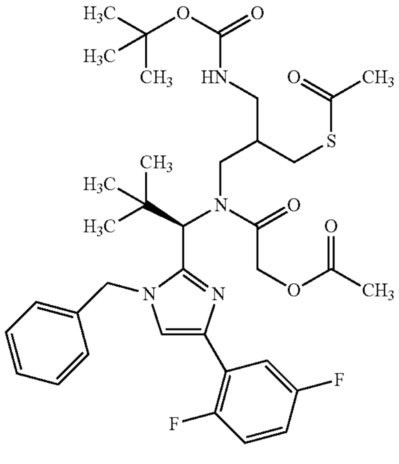 [SMILES: CC(=O)OCC(=O)N(CC(CNC(=O)OC(C)(C)C)CSC(C)=O)[C@@H](c1nc(-c2cc(F)ccc2F)cn1Cc1ccccc1)C(C)(C)C]

210 mg (0.301 mmol) of 2-({(1R)-1-[1-benzyl-4-(2,5-difluorophenyl)-1H-imidazol-2-yl]-2,2-dimethylpropyl}{3-[(tert-butoxycarbonyl)amino]-2-(hydroxymethyl)propyl}amino)-2-oxoethyl acetate were initially charged in 8 ml of absolute THF, 178 mg (1.503 mmol, 109 μl) of thionyl chloride dissolved in 8 ml of absolute THF were added dropwise at RT and the mixture was stirred at RT for 40 min. The reaction mixture was concentrated on a rotary evaporator and dried under high vacuum. The residue was taken up in 16 ml of absolute DMF, 172 mg (1.503 mmol) of potassium thioacetate and 133 mg (0.361 mmol) of tetra-n-butylammonium iodide were added and the mixture was stirred at 90° C. for 2 h. After cooling, water was added and the mixture was extracted with ethyl acetate. The organic phase was concentrated on a rotary evaporator and the residue was purified by preparative HPLC (mobile phase: ACN/water, gradient) and lyophilized. This gave 155 mg (69% of theory, purity according to LC/MS=94%) of the target compound as an epimer mixture.

Isomer 1:

LC-MS (METHOD 1): $R_t$=1.50 min; MS (EIpos): m/z=701 $[M+H]^+$.

Isomer 2:

LC-MS (METHOD 1): $R_t$=1.51 min; MS (EIpos): m/z=701 $[M+H]^+$.

Intermediate C30

Di-tert-butyl [disulphanediylbis(2-{[{(1R)-1-[1-benzyl-4-(2,5-difluorophenyl)-1H-imidazol-2-yl]-2,2-dimethylpropyl}(glycoloyl)amino]methyl}propane-3,1-diyl)]biscarbamate

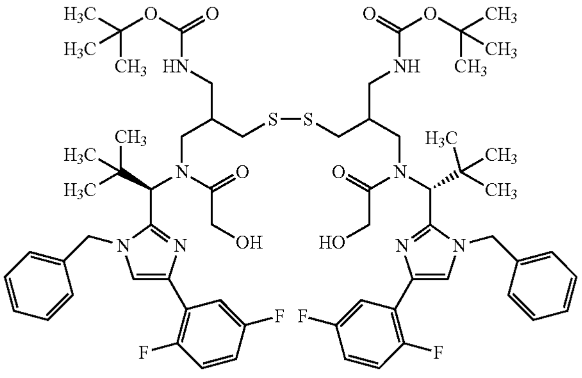 [SMILES: CC(C)(C)OC(=O)NCC(CSSCC(CNC(=O)OC(C)(C)C)CN(C(=O)CO)[C@@H](c1nc(-c2cc(F)ccc2F)cn1Cc1ccccc1)C(C)(C)C)CN(C(=O)CO)[C@@H](c1nc(-c2cc(F)ccc2F)cn1Cc1ccccc1)C(C)(C)C]

1.220 g (1.010 mmol, purity according to LC/MS=58%) of 2-([3-(acetylsulphanyl)-2-{[(tert-butoxycarbonyl)amino]methyl}propyl]{(1R)-1-[1-benzyl-4-(2,5-difluorophenyl)-1H-imidazol-2-yl]-2,2-dimethylpropyl}amino)-2-oxoethyl acetate were initially charged in 30 ml of THF and 30 ml of methanol, 10 ml of a 1 N aqueous sodium hydroxide solution were added and the mixture was stirred at RT for 2 h. Water was added and the reaction mixture was extracted with dichloromethane. The organic phase was dried over sodium sulphate and concentrated on a rotary evaporator. The residue was separated by preparative HPLC (mobile phase: ACN/water, gradient). This gave 390 mg (54% of theory, purity according to LC/MS=86%) of the target compound as a diastereomer mixture.

Isomers:

LC-MS (METHOD 1): $R_t$=1.81 min; MS (EIpos): m/z=1232 [M+H]$^+$.

Intermediate C31 tert-Butyl 3-[{(1R)-1-[1-benzyl-4-(2,5-difluorophenyl)-1H-imidazol-2-yl]-2,2-dimethylpropyl}(glycoloyl)amino]-2-(sulphanylmethyl)propyl}carbamate

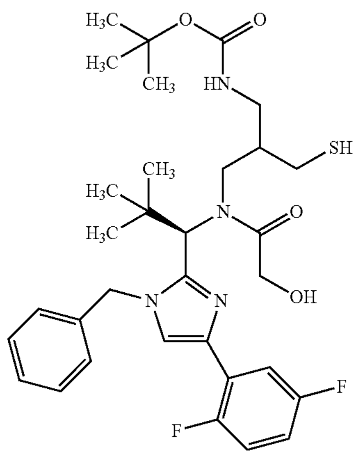 [SMILES: CC(C)(C)OC(=O)NCC(CS)CN(C(=O)CO)[C@@H](c1nc(-c2cc(F)ccc2F)cn1Cc1ccccc1)C(C)(C)C]

390 mg (0.272 mmol, purity according to LC/MS=86%) of di-tert-butyl [disulphanediylbis(2-{[{(1R)-1-[1-benzyl-4-(2,5-difluorophenyl)-1H-imidazol-2-yl]-2,2-dimethylpropyl}(glycoloyl)amino]methyl}propan-3,1-diyl)]biscarbamate were taken up in 20 ml of 1,4-dioxane and 10 ml of PBS buffer, and 234 mg (0.817 mmol) of 3,3',3"-phosphanetriyltripropanoic acid hydrochloride (1:1) were added. The mixture was stirred at RT for 16 h. The reaction mixture was then concentrated on a rotary evaporator and triturated with dichloromethane, and the filtrate was concentrated and dried under high vacuum. The residue was dissolved in 8 ml of isopropanol and purified by chiral chromatography (column: 250×30 mm filled with Daicel Chiralpak AZ-H, mobile phase: isohexane/isopropanol=90:10). This gave two fractions of the target compound. Fraction 1 contained 181.2 mg (50% of theory) of Isomer 1 and fraction 2 yielded 90.2 mg (25% of theory) of Isomer 2.

Isomer 1:

Chiral HPLC (column: 250×4.6 mm, filled with Diacel Chiralpak AZ-H, mobile phase: isohexane/ethanol 90:10): $R_t$=6.98 min.

LC-MS (METHOD 1): $R_t$=1.47 min; MS (EIpos): m/z=617 [M+H]$^+$.

Isomer 2:

Chiral HPLC (column: 250×4.6 mm, filled with Diacel Chiralpak AZ-H, mobile phase: isohexane/ethanol 90:10): $R_t$=9.39 min.

LC-MS (METHOD 1): $R_t$=1.47 min; MS (EIpos): m/z=617 [M+H]$^+$.

Intermediate C32

N-[3-Amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide Hydrochloride (1:1) (Isomer 1)

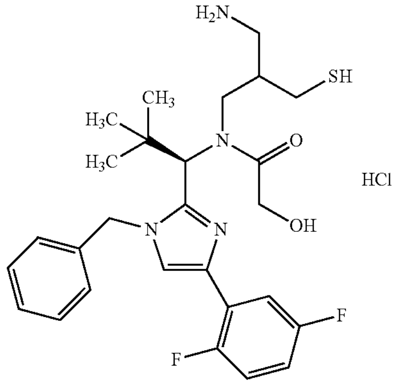 [SMILES: CC(C)(C)[C@H](c1nc(-c2cc(F)ccc2F)cn1Cc1ccccc1)N(CC(CN)CS)C(=O)CO ; Cl]

123 mg (199.42 μmol) of tert-butyl {3-[{(1R)-1-[1-benzyl-4-(2,5-difluorophenyl)-1H-imidazol-2-yl]-2,2-dimethylpropyl}(glycoloyl)amino]-2-(sulphanylmethyl)propyl}carbamate (Isomer 1) were dissolved in 2 ml of THF and stirred with 10 ml of semiconcentrated hydrochloric acid at RT for 1 h. The reaction solution was degassed under argon and then lyophilized. This gave 108 mg (98% of theory) of the target compound.

Isomer 1

LC-MS (METHOD 1): $R_t$=0.95 min; MS (EIpos): m/z=517 [M+H]$^+$.

Intermediate C33

N-[3-Amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide Hydrochloride (1:1) (Isomer 2)

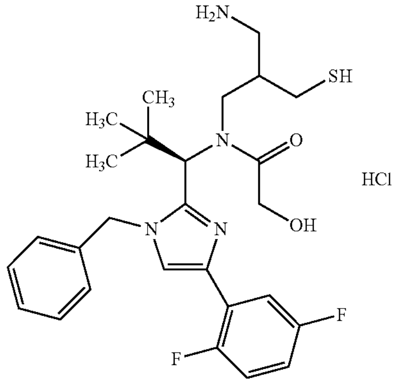 [SMILES: CC(C)(C)[C@H](c1nc(-c2cc(F)ccc2F)cn1Cc1ccccc1)N(CC(CN)CS)C(=O)CO ; Cl]

123 mg (199.42 μmol) of tert-butyl {3-[{(1R)-1-[1-benzyl-4-(2,5-difluorophenyl)-1H-imidazol-2-yl]-2,2-dimethylpropyl}(glycoloyl)amino]-2-(sulphanylmethyl)propyl}carbamate (Isomer 2) were dissolved in 2 ml of THF and stirred with 10 ml of semiconcentrated hydrochloric acid at RT for 1 h. The reaction solution was degassed under argon and then lyophilized. This gave 58 mg (63% of theory, purity according to LC/MS=91%) of the target compound.

Isomer 2

LC-MS (METHOD 1): $R_t$=0.97 min; MS (EIpos): m/z=517 $[M+H]^+$.

Intermediate C34 tert-Butyl [3-({(1R)-1-[1-benzyl-4-(2,5-difluorophenyl)-1H-imidazol-2-yl]-2,2-dimethylpropyl}amino)propyl]carbamate

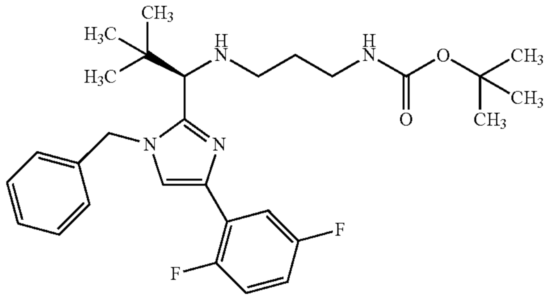 [SMILES: CC(C)(C)OC(=O)NCCCN[C@@H](c1nc(-c2cc(F)ccc2F)cn1Cc1ccccc1)C(C)(C)C]

3.790 g (10.02 mmol) of (1R)-1-[1-benzyl-4-(2,5-difluorophenyl)-1H-imidazol-2-yl]-2,2-dimethylpropan-1-amine (obtained from trifluoroacetic acid/(1R)-1-[1-benzyl-4-(2,5-difluorophenyl)-1H-imidazol-2-yl]-2,2-dimethylpropan-1-amine (1:1) by extraction with 1N aqueous sodium hydroxide solution), 3.186 g (15.04 mmol) of sodium triacetoxyborohydride and 690 μl (12.03 mmol, 722 mg) were initially charged in 100 ml of dichloromethane. The mixture was stirred at RT for 5 min. 4.687 g (27.06 mmol) of tert-butyl (3-oxopropyl)carbamate were then added, and the mixture was stirred at RT for 16 h. The reaction mixture was diluted with dichloromethane and washed with saturated sodium bicarbonate solution. The organic phase was dried over sodium sulphate and concentrated on a rotary evaporator. The residue was purified by chromatography on silica gel (mobile phase: dichloromethane/ethyl acetate, gradient=4:1→1:1). This gave 2.57 g (48% of theory, purity according to LC/MS=96%) of the target compound.

LC-MS (Method 1): $R_t$=1.00 min; MS (EIpos): m/z=513 $[M+H]^+$.

Intermediate C35 tert-Butyl {3-[{(1R)-1-[1-benzyl-4-(2,5-difluorophenyl)-1H-imidazol-2-yl]-2,2-dimethylpropyl}(4-nitrobenzoyl)amino]propyl}carbamate

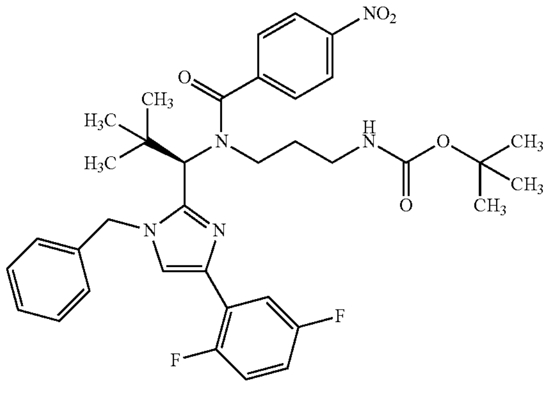 [SMILES: CC(C)(C)OC(=O)NCCCN(C(=O)c1ccc([N+](=O)[O-])cc1)[C@@H](c1nc(-c2cc(F)ccc2F)cn1Cc1ccccc1)C(C)(C)C]

200 mg (0.38 mmol) of tert-butyl [3-({(1R)-1-[1-benzyl-4-(2,5-difluorophenyl)-1H-imidazol-2-yl]-2,2-dimethylpropyl}amino)propyl]carbamate were initially charged in 9 ml of absolute dichloromethane, and 120 μl (0.86 mmol, 87 mg) of triethylamine were added at RT. At RT, 83 mg (0.45 mmol) of 4-nitrobenzoyl chloride dissolved in 1 ml of absolute dichloromethane were added dropwise, and the mixture was stirred at RT for 1 h. Water was added, and the mixture was concentrated on a rotary evaporator. The residue was separated by preparative HPLC (mobile phase: ACN/water+0.1% TFA, gradient) and dried. This gave 181 mg (73% of theory) of the target compound.

LC-MS (Method 1): $R_t$=1.47 min; MS (EIpos): m/z=662 $[M+H]^+$.

Intermediate C36 tert-Butyl {3-[(4-aminobenzoyl) {(1R)-1-[1-benzyl-4-(2,5-difluorophenyl)-1H-imidazol-2-yl]-2,2-dimethylpropyl}amino]propyl}carbamate

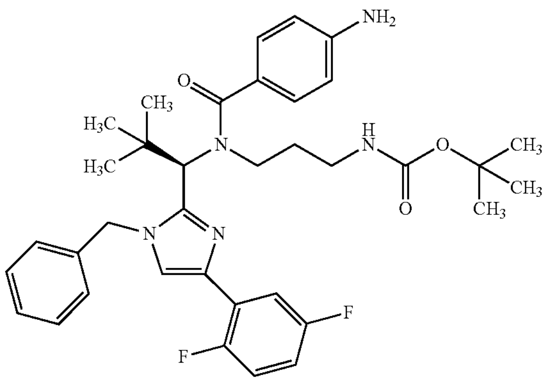 [SMILES: CC(C)(C)OC(=O)NCCCN(C(=O)c1ccc(N)cc1)[C@@H](c1nc(-c2cc(F)ccc2F)cn1Cc1ccccc1)C(C)(C)C]

170 mg (0.26 mmol) of tert-butyl {3-[{(1R)-1-[1-benzyl-4-(2,5-difluorophenyl)-1H-imidazol-2-yl]-2,2-dimethylpropyl}(4-nitrobenzoyl)amino]propyl}carbamate were initially charged in 10 ml of acetic acid. 143 mg (2.57 mmol) of iron powder were added, and the mixture was stirred at 50° C. for 16 h. After cooling, water was added and the mixture was extracted with ethyl acetate. The organic phase was dried over sodium sulphate and concentrated on a rotary evaporator. The residue was dried under HV. This gave 154 mg (77% of theory, purity according to LC/MS=82%) of the target compound.

LC-MS (Method 5): $R_t$=4.73 min; MS (EIpos): m/z=632 $[M+H]^+$.

Intermediate C37

N-[19-(2,5-Dioxo-2,5-dihydro-1H-pyrrol-1-yl)-17-oxo-4,7,10,13-tetraoxa-16-azanonadecan-1-oyl]-L-valyl-N-[4-({(1R)-1-[1-benzyl-4-(2,5-difluorophenyl)-1H-imidazol-2-yl]-2,2-dimethylpropyl}{3-[(tert-butoxycarbonyl)amino]propyl}carbamoyl)phenyl]-L-alaninamide

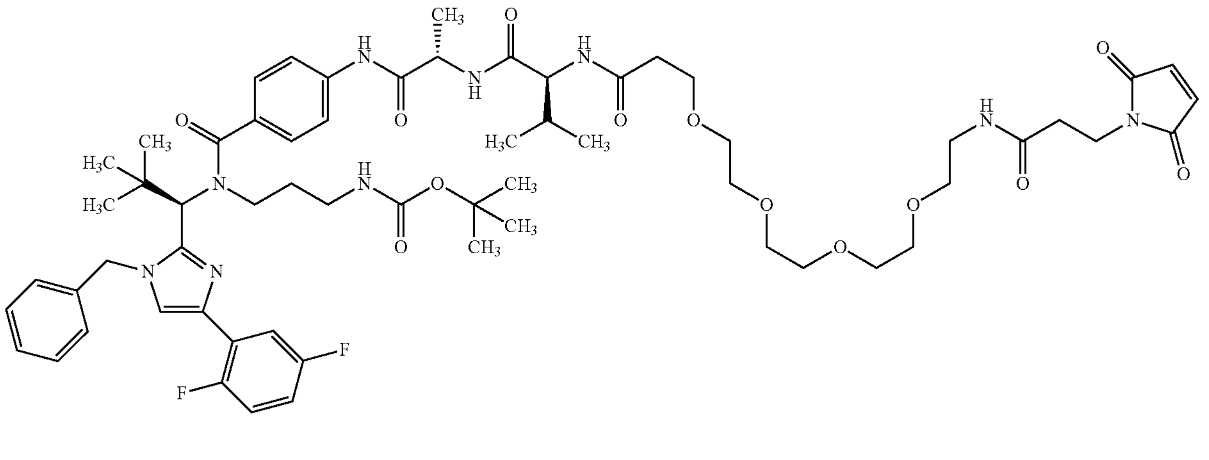 [SMILES: CC(C)[C@H](NC(=O)CCOCCOCCOCCOCCNC(=O)CCN1C(=O)C=CC1=O)C(=O)N[C@@H](C)C(=O)Nc1ccc(C(=O)N(CCCNC(=O)OC(C)(C)C)[C@@H](c2nc(-c3cc(F)ccc3F)cn2Cc2ccccc2)C(C)(C)C)cc1]

38.6 mg (0.05 mmol, LC/MS purity=82%) of tert-butyl {3-[(4-aminobenzoyl) {(1R)-1-[1-benzyl-4-(2,5-difluorophenyl)-1H-imidazol-2-yl]-2,2-dimethylpropyl}amino]propyl}carbamate were dissolved in absolute DMF, and 24.8 mg (0.06 mmol) of HATU and 13.0 mg (0.10 mmol) of N,N-diisopropylethylamine were added. The mixture was stirred at RT for 5 min, 63 mg (0.06 mmol) of N-[19-(2,5-dioxo-2,5-dihydro-1H-pyrrol-1-yl)-17-oxo-4,7,10,13-tetraoxa-16-azanonadecan-1-oyl]-L-valyl-L-alanine were added and the mixture was stirred at RT for 3 h. 7.5 mg (0.06 mmol) of 3H-[1,2,3]triazolo[4,5-b]pyridin-3-ol (HOAt) were added, and the mixture was stirred for 16 h. 19.1 mg (0.05 mmol) of HATU were added, and the mixture was stirred at 50° C. for 2 h. After cooling, the reaction mixture was purified directly by preparative HPLC (mobile phase: ACN/water+0.1% TFA, gradient). This gave 6.5 mg (9% of theory, purity according to LC/MS=83%) of the target compound.

LC-MS (Method 2): $R_t$=7.89 min; MS (EIpos): m/z=1200.6 $[M+H]^+$.

Intermediate C38

2-[3-({(1R)-1-[1-Benzyl-4-(2,5-difluorophenyl)-1H-imidazol-2-yl]-2,2-dimethylpropyl}amino)propyl]-1H-isoindole-1,3(2H)-dione

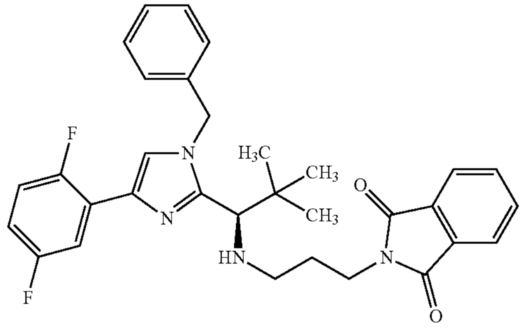 [SMILES: CC(C)(C)[C@@H](NCCCN1C(=O)c2ccccc2C1=O)c1nc(-c2cc(F)ccc2F)cn1Cc1ccccc1]

300.0 mg (0.84 mmol) of 2-[3-({(1R)-1-[1-benzyl-4-(2,5-difluorophenyl)-1H-imidazol-2-yl]-2,2-dimethylpropyl}amino)propyl]-1H-isoindole-1,3(2H)-dione (Intermediate C1) were initially charged in 4.0 ml of dichloromethane, and 58.3 mg (0.97 mmol) of HOAc and 250.4 mg (1.18 mmol) of sodium triacetoxyborohydride were added and the mixture was stirred at RT for 5 min. 197.2 mg (0.97 mmol) of 3-(1,3-dioxo-1,3-dihydro-2H-isoindol-2-yl)propanal were added. The reaction mixture was stirred at RT overnight. The reaction mixture was diluted with ethyl acetate and the organic phase was washed twice with saturated sodium carbonate solution and once with saturated NaCl solution. After drying over magnesium sulphate, the solvent was evaporated under reduced pressure and the residue was purified on silica gel (mobile phase: ethyl acetate/cyclohexane 1:5). The solvents were evaporated under reduced pressure and the residue was dried under high vacuum. This gave 333.3 mg (70%) of the title compound.

LC-MS (Method 1): $R_t$=1.05 min; MS (ESIpos): m/z=543 $[M+H]^+$.

Intermediate C39

2-({(1R)-1-[1-Benzyl-4-(2,5-difluorophenyl)-1H-imidazol-2-yl]-2,2-dimethylpropyl}[3-(1,3-dioxo-1,3-dihydro-2H-isoindol-2-yl)propyl]amino)-2-oxoethyl Acetate

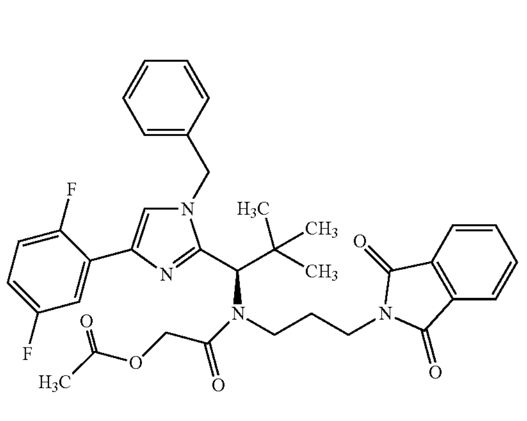 [SMILES: CC(=O)OCC(=O)N(CCCN1C(=O)c2ccccc2C1=O)[C@@H](c1nc(-c2cc(F)ccc2F)cn1Cc1ccccc1)C(C)(C)C]

332.3 mg (0.61 mmol) of 2-[3-({(1R)-1-[1-benzyl-4-(2,5-difluorophenyl)-1H-imidazol-2-yl]-2,2-dimethylpropyl}amino)propyl]-1H-isoindole-1,3(2H)-dione (Intermediate C38) were initially charged in 8.0 ml of dichloromethane, and 142.5 mg (1.35 mmol) of triethylamine were added. At 0° C., 184.0 mg (1.35 mmol) of acetoxyacetyl chloride were added, and the reaction mixture was stirred at RT overnight. The reaction mixture was diluted with ethyl acetate and the organic phase was washed twice with saturated sodium bicarbonate solution and once with sat. NaCl solution. After drying over magnesium sulphate, the solvent was evaporated under reduced pressure and the residue was purified on silica gel (mobile phase: ethyl acetate/cyclohexane 1:3). The solvents were evaporated under reduced pressure and the residue was dried under high vacuum. This gave 367.1 mg (63%) of the title compound.

LC-MS (Method 1): $R_t$=1.42 min; MS (ESIpos): m/z=643 $[M+H]^+$.

Intermediate C40

N-(3-Aminopropyl)-N-{(1R)-1-[1-benzyl-4-(2,5-difluorophenyl)-1H-imidazol-2-yl]-2,2-dimethylpropyl}-2-hydroxyacetamide

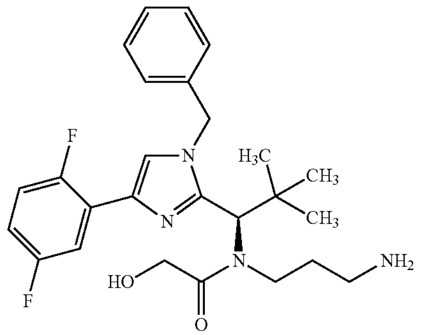 [SMILES: CC(C)(C)[C@H](c1nc(-c2cc(F)ccc2F)cn1Cc1ccccc1)N(CCCN)C(=O)CO]

583.1 mg (0.91 mmol) of 2-({(1R)-1-[1-benzyl-4-(2,5-difluorophenyl)-1H-imidazol-2-yl]-2,2-dimethylpropyl}[3-(1,3-dioxo-1,3-dihydro-2H-isoindol-2-yl)propyl]amino)-2-oxoethyl acetate (Intermediate C39) were initially charged in 15.0 ml of ethanol, and 1.41 g (18.15 mmol) of methanamine (40% in water) were added. The reaction mixture was stirred at 50° C. overnight. The solvent was evaporated under reduced pressure and the residue co-distilled three times with toluene. The residue was chromatographed by means of silica gel (mobile phase: dichloromethane/methanol=100:5). The solvents were evaporated under reduced pressure and the residue was dried under high vacuum. This gave 324.9 mg (73%) of the title compound.

LC-MS (Method 1): $R_t$=0.97 min; MS (ESIpos): m/z=471 $[M+H]^+$.

Intermediate C41

Trifluoroacetic Acid/L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide (1:1)

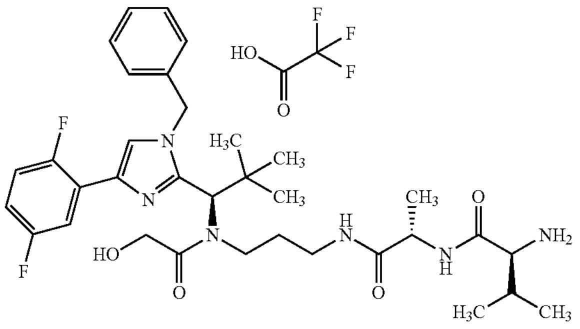

50.0 mg (0.11 mol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) and 30.4 mg (0.11 mmol) of 2,5-dioxopyrrolidin-1-yl-N-(tert-butoxycarbonyl)-L-alaninate were initially charged in 2.0 ml of DMF, and 32.2 mg (0.32 mmol) of 4-methylmorpholine were added. The reaction mixture was stirred at RT overnight. 19.1 mg (0.32 mmol) of HOAc were added, and the reaction mixture purified directly by preparative RP-HPLC (column: Reprosil 250×30; 10μ, flow rate: 50 ml/min, MeCN/water). The solvents were evaporated under reduced pressure and the residue was dried under high vacuum. This gave 38.0 mg (56%) of the compound tert-butyl [(2S)-1-({3-[{(1R)-1-[1-benzyl-4-(2,5-difluorophenyl)-1H-imidazol-2-yl]-2,2-dimethylpropyl}(glycoloyl)amino]propyl}amino)-1-oxopropan-2-yl]carbamate.

LC-MS (Method 1): $R_t$=1.26 min; MS (ESIpos): m/z=642 $[M+H]^+$.

33.6 mg (0.05 mmol) of tert-butyl [(2S)-1-({3-[{(1R)-1-[1-benzyl-4-(2,5-difluorophenyl)-1H-imidazol-2-yl]-2,2-dimethylpropyl}(glycoloyl)amino]propyl}amino)-1-oxopropan-2-yl]carbamate were initially charged in 3.0 ml of dichloromethane. 119.4 mg (1.05 mmol) of TFA were added and the reaction mixture was stirred at RT overnight. The solvent was evaporated under reduced pressure and the residue was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 32.8 mg (96%) of the compound trifluoroacetic acid/N-{3-[{(1R)-1-[1-benzyl-4-(2,5-difluorophenyl)-1H-imidazol-2-yl]-2,2-dimethylpropyl}(glycoloyl)amino]propyl}-L-alaninamide (1:1).

LC-MS (Method 1): $R_t$=0.93 min; MS (ESIpos): m/z=542 $[M+H]^+$.

29.5 mg (0.05 mmol) of trifluoroacetic acid/N-{3-[{(1R)-1-[1-benzyl-4-(2,5-difluorophenyl)-1H-imidazol-2-yl]-2,2-dimethylpropyl}(glycoloyl)amino]propyl}-L-alaninamide (1:1) and 14.1 mg (0.05 mmol) of 2,5-dioxopyrrolidin-1-yl-N-(tert-butoxycarbonyl)-L-valinate were initially charged in 1.0 ml of DMF, and 18.2 mg (0.18 mmol) of 4-methylmorpholine were added. The reaction mixture was stirred at RT overnight and purified directly by preparative RP-HPLC (column: Reprosil 250×30; 10μ, flow rate: 50 ml/min, MeCN/water). The solvents were evaporated under reduced pressure and the residue was dried under high vacuum. This gave 23.1 mg (69%) of the compound N-(tert-butoxycarbonyl)-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide.

LC-MS (Method 1): $R_t$=1.30 min; MS (ESIpos): m/z=741 $[M+H]^+$.

19.4 mg (0.03 mmol) of N-(tert-butoxycarbonyl)-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide were dissolved in 1.5 ml of dichloromethane, and 59.7 mg (0.52 mmol) of TFA were added. The reaction mixture was stirred at RT overnight. 119.4 mg (1.04 mmol) of TFA were added, and the mixture was once more stirred at RT overnight. The solvent was evaporated under reduced pressure and the residue was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 19.2 mg (97%) of the title compound.

LC-MS (Method 1): $R_t$=0.96 min; MS (ESIpos): m/z=641 $[M+H]^+$.

Intermediate C42

2,5-Difluorobenzenediazonium Tetrafluoroborate

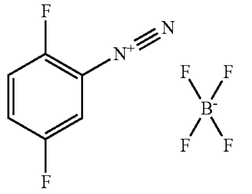 [SMILES: N#[N+]c1cc(F)ccc1F ; F[B-](F)(F)F]

3.00 g (21.16 mmol, 2.68 ml) of boron trifluoride-diethyl ether complex were initially charged, and 1.37 g (10.58 mmol) of 2,5-difluoroaniline dissolved in 27 ml of absolute THF were slowly added dropwise at 0° C. At −10° C., a solution of 1.61 g (13.75 mmol, 1.85 ml) of isoamyl nitrite dissolved in 3 ml of absolute THF was added dropwise, and stirring was continued at the same temperature for 30 min. 15 ml of diethyl ether were added and the precipitated diazonium salt was filtered off, washed with a little diethyl ether and dried under high vacuum. This gave 2.27 g of the target compound (94% of theory).

LC-MS (Method 6): $R_t$=0.24 min; MS (ESIpos): m/z=141 $[M]^+$.

$^1$H-NMR (400 MHz, DMSO-$d_6$): δ [ppm]=8.11-8.17 (m, 1H), 8.36-8.43 (m, 1H), 8.69-8.73 (m, 1H).

Intermediate C43

Methyl chloro[2-(2,5-difluorophenyl)hydrazinylidene]acetate

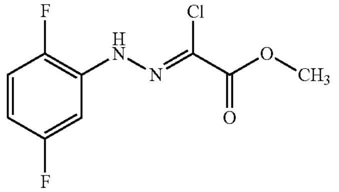 [SMILES: COC(=O)/C(Cl)=N/Nc1cc(F)ccc1F]

Under an atmosphere of argon, 3.63 g (24.13 mmol) of methyl 2-chloro-3-oxobutanoate were initially charged in 100 ml of water, and 48.90 g (618.19 mmol, 50.00 ml) of pyridine were added at −5° C. and the mixture was stirred at this temperature for 10 min. t−5° C., 5.00 g (21.94 mmol) of 2,5-difluorobenzenediazonium tetrafluoroborate were then added, resulting in the formation of an orange suspension. The mixture was stirred at this temperature for 30 min and the reaction was diluted with water and extracted three times with dichloromethane. The combined organic phases were washed with saturated sodium chloride solution, dried over sodium sulphate, concentrated on a rotary evaporator and dried under high vacuum. This gave 5.52 g of the target compound (97% of theory, purity according to LC/MS=96%).

LC-MS (Method 1): $R_t$=1.03 min; MS (ESIpos): m/z=249 $[M+H]^+$.

$^1$H-NMR (400 MHz, DMSO-$d_6$): δ [ppm]=3.85 (s, 3H), 6.88-6.94 (m, 1H), 7.16-7.21 (m, 1H), 7.31-7.37 (m, 1H), 10.00 (s, 1H).

Intermediate C44

Methyl 4-benzoyl-1-(2,5-difluorophenyl)-1H-pyrazole-3-carboxylate

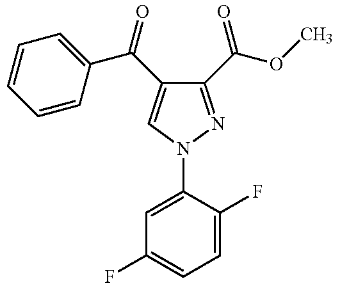 [SMILES: COC(=O)c1nn(-c2cc(F)ccc2F)cc1C(=O)c1ccccc1]

3.50 g (13.52 mmol) of methyl chloro[2-(2,5-difluorophenyl)hydrazinyliden]acetate (purity according to LC/MS 96%) were dissolved in 9 ml of absolute toluene, 2.61 g (14.87 mmol) of (2E)-3-(dimethylamino)-1-phenylprop-2-en-1-one and 3.01 g (29.73 mmol), 4.14 ml) of triethylamine were added and the mixture was stirred at room temperature for 16 h. The reaction mixture was concentrated on a rotary evaporator and the residue separated by preparative HPLC (mobile phase: ACN/water with 0.1% formic acid, gradient). This gave 1.79 g (39% of theory) of the target compound.

LC-MS (Method 1): $R_t$=1.07 min; MS (ESIpos): m/z=343 $[M+H]^+$.

$^1$H-NMR (400 MHz, DMSO-$d_6$): δ [ppm]=3.86 (s, 3H), 7.44-7.50 (m, 1H), 7.55-7.72 (m, 4H), 7.81-7.87 (m, 3H), 8.80 (d, 1H).

Intermediate C45

[4-Benzyl-1-(2,5-difluorophenyl)-1H-pyrazol-3-yl] methanol

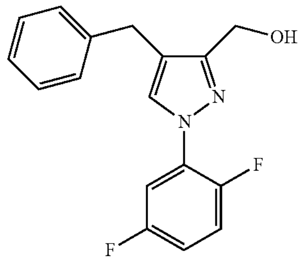 [SMILES: OCc1nn(-c2cc(F)ccc2F)cc1Cc1ccccc1]

3.18 g (8.92 mmol) of methyl 4-benzoyl-1-(2,5-difluorophenyl)-1H-pyrazole-3-carboxylate (purity according to LC/MS=96%) were initially charged in 50 ml of trifluoroacetic acid, 8.74 g (75.13 mmol, 12 ml) of triethylsilane were added dropwise and the mixture was stirred at room temperature for 1 h. The reaction mixture was concentrated on a rotary evaporator and dried under high vacuum. The residue obtained was taken up in 120 ml of absolute THF, and 2.89 g (33.63 mmol, 33.63 ml) of borane-tetrahydrofuran complex were added dropwise at 0° C. The mixture was stirred overnight. Owing to the low conversion, another 12.33 ml (12.33 mmol) of a 1M lithium borohydride solution in THF were added. The mixture was stirred at room temperature for 1 h, at 60° C. for 30 min and at 80° C. for 2 h. At 0° C., the reaction was carefully quenched with 60 ml of saturated sodium bicarbonate solution. The mixture was extracted twice with in each case 100 ml of ethyl acetate, the combined organic phases were dried over sodium sulphate and concentrated on a rotary evaporator and the residue was dried under high vacuum. This gave 2.67 g (76% of theory, purity=96%) of the target compound.

LC-MS (Method 3): $R_t$=2.79 min; MS (ESIpos): m/z=329 $[M+H]^+$.

$^1$H-NMR (400 MHz, DMSO-$d_6$): δ [ppm]=3.91 (s, 2H), 4.45 (d, 2H), 6.51 (s, 1H), 7.18-7.23 (m, 2H), 7.27-7.32 (m, 4H), 7.46-7.53 (m, 1H), 7.60-7.65 (m, 1H), 7.95 (d, 1H).

Intermediate C46

4-Benzyl-1-(2,5-difluorophenyl)-1H-pyrazole-3-carbaldehyde

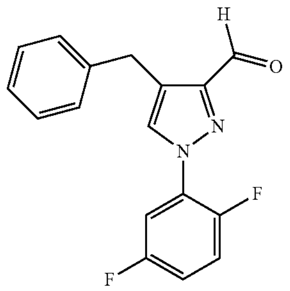 [SMILES: O=Cc1nn(-c2cc(F)ccc2F)cc1Cc1ccccc1]

2.66 g (8.50 mmol) of [4-benzyl-1-(2,5-difluorophenyl)-1H-pyrazol-3-yl]methanol (purity 96%) were dissolved in 150 ml of dichloromethane, and 4.33 g (10.20 mmol) of Dess-Martin periodinane were added a little at a time. The mixture was stirred at room temperature for 2 h, 100 ml of a semiconcentrated sodium bicarbonate solution and 100 ml of a 10% strength sodium thiosulphate solution were then added and the mixture was stirred for 20 min. The organic phase was separated off, dried over sodium sulphate and concentrated under high vacuum. This gave 2.35 g (88% of theory, purity=95%) of the target compound.

LC-MS (Method 7): $R_t$=1.49 min; MS (ESIpos): m/z=299 $[M+H]^+$.

$^1$H-NMR (400 MHz, DMSO-$d_6$): δ [ppm]=4.12 (s, 2H), 7.17-7.21 (m, 1H), 7.27-7.31 (m, 4H), 7.37-7.42 (m, 1H), 7.57-7.62 (m, 1H), 7.75-7.78 (m, 1H), 8.22 (d, 1H), 10.06 (s, 1H).

Intermediate C47

(1R)-1-[4-benzyl-1-(2,5-difluorophenyl)-1H-pyrazol-3-yl]-2,2-dimethylpropan-1-amine

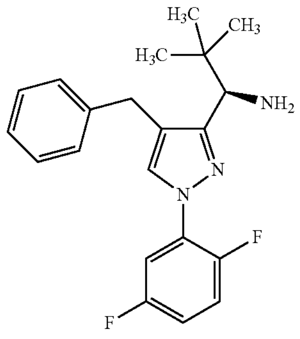 [SMILES: CC(C)(C)[C@@H](N)c1nn(-c2cc(F)ccc2F)cc1Cc1ccccc1]

2.35 g (7.56 mmol) of 4-benzyl-1-(2,5-difluorophenyl)-1H-pyrazole-3-carbaldehyde were dissolved in 25 ml of absolute THF, and 1.10 g (9.08 mmol) of (R)-(+)-2-methyl-2-propanesulphinamide and 4.73 g (16.64 mmol) of titanium (IV) isopropoxide were added. The reaction mixture was stirred at room temperature for 16 h, and 20 ml of a saturated sodium chloride solution and 30 ml of ethyl acetate were added. About 3 g of kieselguhr were then added, and the mixture was boiled under reflux for 1 h. The mixture was filtered and the organic phase was separated from the filtrate. The aqueous phase was extracted with ethyl acetate and the combined organic phases were washed with saturated sodium chloride solution, dried over sodium sulphate, concentrated on a rotary evaporator and dried under high vacuum. The residue was used further without further purification.

Under an atmosphere of argon, the residue was dissolved in 60 ml of absolute THF and cooled to −78° C., and 14.5 ml (23.24 mmol) of a solution of tert-butyllithium in pentane (c=1.6 mol/l) were added dropwise. The reaction was stirred at −78° C. for 3 h and then quenched with 5 ml of methanol and 15 ml of a saturated ammonium chloride solution. With stirring, the reaction mixture was allowed to warm to room temperature (about 30 min.). The mixture was extracted with ethyl acetate and the organic phase was extracted with saturated sodium chloride solution, concentrated on a rotary evaporator and dried under high vacuum. The residue was used further without further purification.

The residue was taken up in 30 ml of THF and 6 ml of methanol, 6 ml (24.00 mmol) of a 4N hydrogen chloride solution in dioxane were added and the mixture was stirred at room temperature for 1 h. 15 ml of saturated sodium carbonate solution were then added, and the mixture was extracted with ethyl acetate. The organic phase was separated off, concentrated on a rotary evaporator and dried under high vacuum. The residue was separated by preparative HPLC (mobile phase: ACN/water, gradient). This gave two fractions of the target compound. The first fraction yielded 1.31 g (72% of theory, LC/MS purity=97%) and the second 0.37 g (17% of theory, LC/MS purity=83%) of product.

LC-MS (Method 1): $R_t$=0.88 min; MS (ESIpos): m/z=356 $[M+H]^+$.

$^1$H-NMR (400 MHz, DMSO-$d_6$): δ [ppm]=0.91 (s, 9H), 1.71 (s, 2H), 3.59 (s, 1H), 3.87 (s, 2H), 7.17-7.32 (m, 6H), 7.45-7.51 (m, 1H), 7.61-7.65 (m, 1H), 7.84 (s br, 1H).

Intermediate C48 tert-Butyl (2S)-4-({(1R)-1-[4-benzyl-1-(2,5-difluorophenyl)-1H-pyrazol-3-yl]-2,2-dimethylpropyl}amino)-2-[(tert-butoxycarbonyl)amino]butanoate

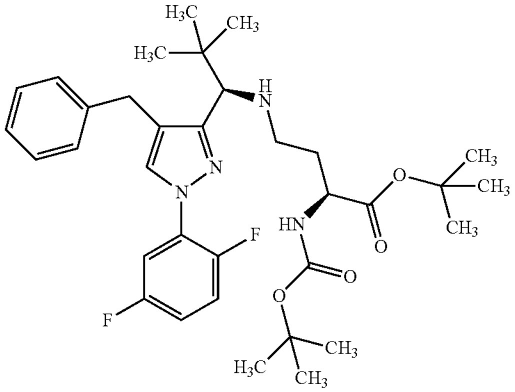 [SMILES: CC(C)(C)OC(=O)N[C@@H](CCN[C@@H](c1nn(-c2cc(F)ccc2F)cc1Cc1ccccc1)C(C)(C)C)C(=O)OC(C)(C)C]

1.28 g (3.35 mmol, LC/MS purity 93%) of (1R)-1-[4-benzyl-1-(2,5-difluorophenyl)-1H-pyrazol-3-yl]-2,2-dimethylpropan-1-amine were dissolved in 100 ml of absolute dichloromethane, and 261 mg (4.35 mmol, 250 μl) of acetic acid and 1.14 g (4.34 mmol) of sodium triacetoxyborohydride were added at room temperature followed after 5 min of stirring by 1.19 g (4.35 mmol) of tert-butyl (2S)-2-[(tert-butoxycarbonyl)amino]-4-oxobutanoate. The mixture was stirred at room temperature for 15 min, concentrated on a rotary evaporator, taken up in acetonitrile and water and purified by preparative HPLC (mobile phase: ACN/water+0.1% TFA, gradient). This gave 1.64 g (80% of theory) of the target compound.

LC-MS (Method 1): $R_t$=1.10 min; MS (ESIpos): m/z=613 $[M+H]^+$.

$^1$H-NMR (400 MHz, DMSO-$d_6$): δ [ppm]=1.01 (s, 9H), 1.32 (s, 9H), 1.35 (s, 9H), 1.80-1.89 (m, 1H), 2.01-2.11 (m, 1H), 2.54-2.71 (m, 2H), 3.75-3.81 (m, 1H), 3.90 (s, 2H), 4.18 (d, 1H), 7.13 (d, 1H), 7.20-7.24 (m, 1H), 7.28-7.34 (m, 5H), 7.52-7.58 (m, 1H), 7.76-7.80 (m, 1H), 8.10 (s br, 1H), 8.23 (s br, 1H).

Intermediate C49

(2S)-4-[{(1R)-1-[4-Benzyl-1-(2,5-difluorophenyl)-1H-pyrazol-3-yl]-2,2-dimethylpropyl}(glycoloyl)amino]-2-[(tert-butoxycarbonyl)amino]butanoic Acid

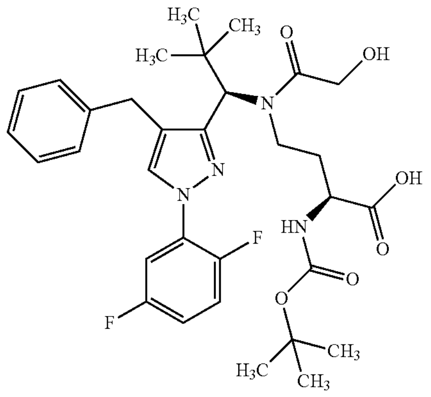 [SMILES: CC(C)(C)OC(=O)N[C@@H](CCN(C(=O)CO)[C@@H](c1nn(-c2cc(F)ccc2F)cc1Cc1ccccc1)C(C)(C)C)C(=O)O]

225 mg (0.37 mmol) of tert-butyl (2S)-4-({(1R)-1-[4-benzyl-1-(2,5-difluorophenyl)-1H-pyrazol-3-yl]-2,2-dimethylpropyl}amino)-2-[(tert-butoxycarbonyl)amino]butanoate were dissolved in 10 ml of absolute dichloromethane, and 156 mg (1.54 mmol) of triethylamine were added. At 0° C., 125 mg (0.92 mmol) of acetoxyacetyl chloride were added, and the mixture was stirred at RT for 16 h. Another 251 mg (1.84 mmol) of acetoxyacetyl chloride and 186 mg (1.84 mmol) of triethylamine were added, and the mixture was stirred at RT for 3 h. A little dichloromethane was added and the mixture was washed with saturated sodium bicarbonate solution and saturated sodium chloride solution. The organic phase was dried over sodium sulphate, concentrated on a rotary evaporator and dried under high vacuum. The residue was taken up in 10 ml of ethanol, 0.91 ml (12.67 mmol) of a 40% strength aqueous methylamine solution was added and the mixture was stirred at 50° C. for 3 h. The mixture was concentrated on a rotary evaporator, the residue was taken up in dichloromethane and the organic phase was washed twice with water. The organic phase was dried over sodium sulphate, concentrated on a rotary evaporator and dried under high vacuum. The residue was taken up in 2 ml of dichloromethane, 2 ml (25.96 mmol) of trifluoroacetic acid were added and the mixture was stirred at 50°

C. for 4 h. The mixture was concentrated on a rotary evaporator and the residue was dried under high vacuum. The residue was taken up in 10 ml of absolute dichloromethane, 298 mg (2.95 mmol) of triethylamine and 429 mg (1.97 mmol) of di-tert-butyl dicarbonate were added and the mixture was stirred at RT for 1 h. The mixture was concentrated on a rotary evaporator and the residue was purified by preparative HPLC (mobile phase: ACN/water, gradient). This gave 62 mg (27% of theory) of the target compound.

LC-MS (Method 1): $R_t$=1.32 min; MS (ESIpos): m/z=615 $[M+H]^+$.

$^1$H-NMR (400 MHz, DMSO-$d_6$): δ [ppm]=0.91 (s, 9H), 1.32 (s, 9H), 2.64-2.72 (m, 4H), 3.50-3.58 (m, 1H), 3.72 (dd, 2H), 4.07-4.22 (m, 2H), 4.47-4.54 (m, 1H), 5.75 (s, 1H), 6.84-6.89 (m, 1H), 7.15-7.30 (m, 6H), 7.47-7.53 (m, 1H), 7.70-7.75 (m, 1H), 8.09-8.13 (m, 1H), 11.66 (s br, 1H).

Intermediate C50 tert-Butyl [(2S)-4-[{(1R)-1-[4-benzyl-1-(2,5-difluorophenyl)-1H-pyrazol-3-yl]-2,2-dimethylpropyl}(glycoloyl)amino]-1-({[2-(2,5-dioxo-2,5-dihydro-1H-pyrrol-1-yl)ethyl)ethyl]amino}-1-oxobutan-2-yl] carbamate

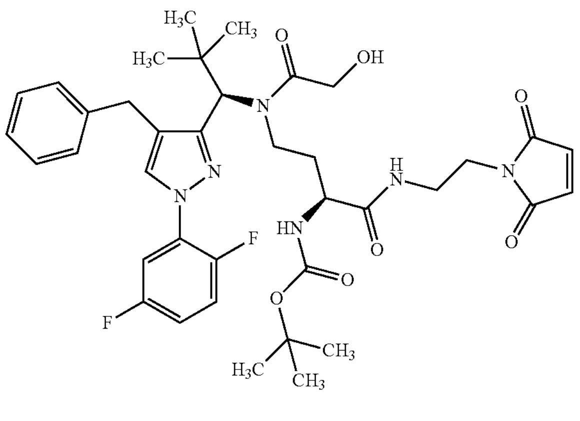 [SMILES: CC(C)(C)OC(=O)N[C@@H](CCN(C(=O)CO)[C@@H](c1nn(-c2cc(F)ccc2F)cc1Cc1ccccc1)C(C)(C)C)C(=O)NCCN1C(=O)C=CC1=O]

60 mg (0.1 mmol) of (2S)-4-[{(1R)-1-[4-benzyl-1-(2,5-difluorophenyl)-1H-pyrazol-3-yl]-2,2-dimethylpropyl}(glycoloyl)amino]-2-[(tert-butoxycarbonyl)amino]butanoic acid were dissolved in 10 ml of absolute DMF, and 74 mg (0.20 mmol) of HATU were added. 74 mg (0.29 mmol) of trifluoroacetic acid/1-(2-aminoethyl)-1H-pyrrole-2,5-dione (1:1) were dissolved separately in 2 ml of absolute DMF, 38 mg (0.29 mmol) of N,N-diisopropylethylamine were added and the mixture was added dropwise to the reaction mixture. The reaction was stirred at RT for 3 d. The mixture was purified directly by preparative HPLC mobile phase: ACN/water+0.1% TFA, gradient). This gave 9.3 mg (13% of theory) of the target compound.

LC-MS (Method 1): $R_t$=1.34 min; MS (ESIpos): m/z=737 $[M+H]^+$.

Intermediate C51

N-{(2S)-4-[{(1R)-1-[4-Benzyl-1-(2,5-difluorophenyl)-1H-pyrazol-3-yl]-2,2-dimethylpropyl}(glycoloyl)amino]-2-[(tert-butoxycarbonyl)amino]butanoyl}-beta-alanine

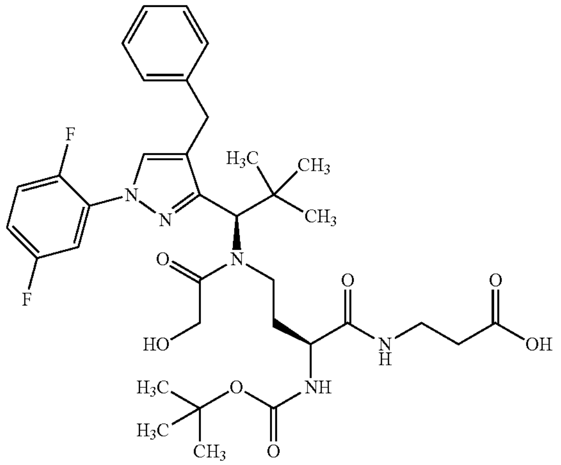 [SMILES: CC(C)(C)OC(=O)N[C@@H](CCN(C(=O)CO)[C@@H](c1nn(-c2cc(F)ccc2F)cc1Cc1ccccc1)C(C)(C)C)C(=O)NCCC(=O)O]

First, Intermediate C47 was reductively alkylated with benzyl N-{(2S)-2-[(tert-butoxycarbonyl)amino]-4-oxobutanoyl}-beta-alaninate analogously to Intermediate C2. The secondary amino group was then acylated with 2-chloro-2-oxoethyl acetate as described for Intermediate C27, and the two ester groups were then hydrolysed with 2M lithium hydroxide solution in methanol. 23 mg of the title compound were obtained.

LC-MS (Method 1): $R_t$=1.24 min; MS (ESIpos): m/z=686 $(M+H)^+$.

Intermediate C52

(1R)-1-[1-Benzyl-4-(2,5-difluorophenyl)-1H-pyrol-2-yl]-2,2-dimethylpropan-1-amine

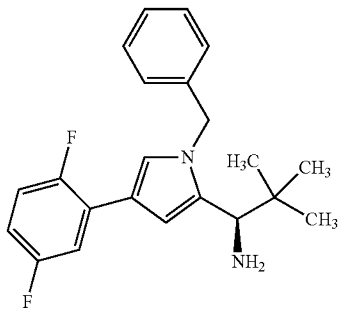 [SMILES: CC(C)(C)[C@@H](N)c1cc(-c2cc(F)ccc2F)cn1Cc1ccccc1]

10.00 g (49.01 mmol) of methyl 4-bromo-1H-pyrrole-2-carboxylate were initially charged in 100.0 ml of DMF, and 20.76 g (63.72 mmol) of caesium carbonate and 9.22 g (53.91 mmol) of benzyl bromide were added. The reaction mixture was stirred at RT overnight. The reaction mixture was partitioned between water and ethyl acetate and the aqueous phase was extracted with ethyl acetate. The combined organic phases were dried over magnesium sulphate and the solvent was evaporated under reduced pressure. The reaction was repeated with 90.0 g of methyl 4-bromo-1H-pyrrole-2-carboxylate.

The two combined reactions were purified by preparative RP-HPLC (column: Daiso 300×100; 10 j, flow rate: 250 ml/min, MeCN/water). The solvents were evaporated under reduced pressure and the residue was dried under high vacuum. This gave 125.15 g (87% of theory) of the compound methyl 1-benzyl-4-bromo-1H-pyrrole-2-carboxylate.

LC-MS (Method 1): $R_t$=1.18 min; MS (ESIpos): m/z=295 $[M+H]^+$.

Under argon, 4.80 g (16.32 mmol) of methyl 1-benzyl-4-bromo-1H-pyrrole-2-carboxylate were initially charged in DMF, and 3.61 g (22.85 mmol) of (2,5-difluorophenyl) boronic acid, 19.20 ml of saturated sodium carbonate solution and 1.33 g (1.63 mmol) of [1,1'-bis(diphenylphosphino) ferrocene]-dichloropalladium(II):dichloromethane were added. The reaction mixture was stirred at 85° C. overnight. The reaction mixture was filtered through Celite and the filter cake was washed with ethyl acetate. The organic phase was extracted with water and then washed with saturated NaCl solution. The organic phase was dried over magnesium sulphate and the solvent was evaporated under reduced pressure. The residue was chromatographed by means of silica gel (mobile phase: cyclohexane/ethyl acetate=100:3). The solvents were evaporated under reduced pressure and the residue was dried under high vacuum. This gave 3.60 g (67% of theory) of the compound methyl 1-benzyl-4-(2,5-difluorophenyl)-1H-pyrrole-2-carboxylate.

LC-MS (Method 7): $R_t$=1.59 min; MS (ESIpos): m/z=328 $[M+H]^+$.

3.60 g (11.00 mmol) of methyl 1-benzyl-4-(2,5-difluorophenyl)-1H-pyrrole-2-carboxylate were initially charged in 90.0 ml of THF, and 1.04 g (27.50 mmol) of lithium aluminium hydride (2.4 M in THF) were added at 0° C. The reaction mixture was stirred at 0° C. for 30 minutes. At 0° C., saturated potassium sodium tartrate solution was added, and ethyl acetate was added to the reaction mixture. The organic phase was extracted three times with saturated potassium sodium tartrate solution. The organic phase was washed once with saturated NaCl solution and dried over magnesium sulphate. The solvent was evaporated under reduced pressure and the residue was dissolved in 30.0 ml of dichloromethane. 3.38 g (32.99 mmol) of manganese(IV) oxide were added, and the mixture was stirred at RT for 48 h. Another 2.20 g (21.47 mmol) of manganese(IV) oxide were added, and the mixture was stirred at RT overnight. The reaction mixture was filtered through Celite and the filter cake was washed with dichloromethane. The solvent was evaporated under reduced pressure and the residue 2.80 g of (1-benzyl-4-(2,5-difluorophenyl)-1H-pyrrole-2-carbaldehyde) was used without further purification in the next step of the synthesis.

LC-MS (Method 7): $R_t$=1.48 min; MS (ESIpos): m/z=298 $[M+H]^+$.

28.21 g (94.88 mmol) of 1-benzyl-4-(2,5-difluorophenyl)-1H-pyrrole-2-carbaldehyde together with 23.00 g (189.77 mmol) of (R)-2-methylpropane-2-sulphinamide were initially charged in 403.0 ml of absolute THF, and 67.42 g (237.21 mmol) of titanium(IV) isopropoxide were added and the mixture was stirred at RT overnight. 500.0 ml of saturated NaCl solution and 1000.0 ml of ethyl acetate were added, and the mixture was stirred at RT for 1 h. The mixture was filtered through kieselguhr and the filtrate was washed twice with saturated NaCl solution. The organic phase was dried over magnesium sulphate, the solvent was evaporated under reduced pressure and the residue was purified using Biotage Isolera (silica gel, column 1500+340 g SNAP, flow rate 200 ml/min, ethyl acetate/cyclohexane 1:10).

LC-MS (Method 7): $R_t$=1.63 min; MS (ESIpos): m/z=401 $[M+H]^+$.

25.00 g (62.42 mmol) of (R)—N-{(E/Z)-[1-benzyl-4-(2,5-difluorophenyl)-1H-pyrrol-2-yl]methylene}-2-methylpropane-2-sulphinamide were initially charged in absolute THF under argon and cooled to −78° C. 12.00 g (187.27 mmol) of tert-butyllithium (1.7 M solution in pentane) were then added at −78° C. and the mixture was stirred at this temperature for 3 h. At −78° C., 71.4 ml of methanol and 214.3 ml of saturated ammonium chloride solution were then added in succession, and the reaction mixture was allowed to warm to RT and stirred at RT for 1 h. The mixture was diluted with ethyl acetate and washed with water. The organic phase was dried over magnesium sulphate and the solvent was evaporated under reduced pressure. The residue (R)—N-{(1R)-1-[1-benzyl-4-(2,5-difluorophenyl)-1H-pyrrol-2-yl]-2,2-dimethylpropyl}-2-methylpropane-2-sulphinamide was used without further purification in the next step of the synthesis.

LC-MS (Method 6): $R_t$=2.97 min; MS (ESIpos): m/z=459 $[M+H]^+$.

28.00 g (61.05 mmol) of (R)—N-{(1R)-1-[1-benzyl-4-(2,5-difluorophenyl)-1H-pyrrol-2-yl]-2,2-dimethylpropyl}-2-methylpropane-2-sulphinamide were initially charged in 186.7 ml of 1,4-dioxane, and 45.8 ml of HCl in 1,4-dioxane solution (4.0 M) were then added. The reaction mixture was stirred at RT for 2 h and the solvent was evaporated under reduced pressure. The residue was purified by preparative RP-HPLC (column: (column: Kinetix 100×30; flow rate: 60 ml/min, MeCN/water). The acetonitrile was evaporated under reduced pressure and dichloromethane was added to the aqueous residue. The organic phase was washed with sodium bicarbonate solution and dried over magnesium sulphate. The solvent was evaporated under reduced pressure and the residue was dried under high vacuum. This gave 16.2 g (75% of theory) of the title compound.

LC-MS (Method 6): $R_t$=2.10 min; MS (ESIpos): m/z=338 $[M-NH_2]^+$, 709 $[2M+H]^+$.

$^1$H-NMR (400 MHz, DMSO-$d_6$): δ [ppm]=0.87 (s, 9H), 1.53 (s, 2H), 3.59 (s, 1H), 5.24 (d, 2H), 6.56 (s, 1H), 6.94 (m, 1H), 7.10 (d, 2H), 7.20 (m, 1H), 7.26 (m, 2H), 7.34 (m, 2H), 7.46 (m, 1H).

Intermediate C53

(2S)-4-[{(1R)-1-[1-Benzyl-4-(2,5-difluorophenyl)-1H-pyrrol-2-yl]-2,2-dimethylpropyl}(glycoloyl)amino]-2-{[(9H-fluoren-9-ylmethoxy)carbonyl]amino}butanoic Acid

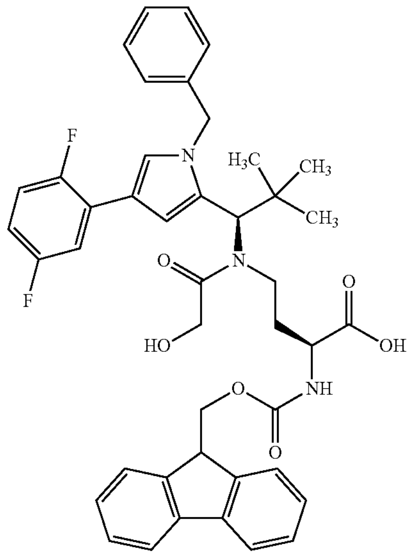 [SMILES: CC(C)(C)[C@H](c1cc(-c2cc(F)ccc2F)cn1Cc1ccccc1)N(CC[C@H](NC(=O)OCC1c2ccccc2-c2ccccc21)C(=O)O)C(=O)CO]

First, intermediate C52 was reductively alkylated with benzyl (2S)-2-{[(benzyloxy)carbonyl]amino}-4-oxobutanoate analogously to intermediate C2. The secondary amino group was then acylated with 2-chloro-2-oxoethyl acetate as described for Intermediate C27, and the two ester groups were then hydrolysed with 2M lithium hydroxide solution in methanol. The intermediate obtained in this manner was dissolved in ethanol, palladium on carbon (10%) was added and the mixture was hydrogenated at RT with hydrogen under standard pressure for 1 h. The deprotected compound was taken up in dioxane/water 2:1 and in the last step the Fmoc protective group was introduced using 9H-fluoren-9-ylmethyl chlorocarbonate in the presence of N,N-diisopropylethylamine.

LC-MS (Method 1): $R_t$=1.37 min; MS (ESIpos): m/z=734 $(M-H)^-$.

Intermediate C54

N-[(2S)-4-[{(1R)-1-[1-Benzyl-4-(2,5-difluorophenyl)-1H-pyrrol-2-yl]-2,2-dimethylpropyl}(glycoloyl)amino]-2-{[(9H-fluoren-9-ylmethoxy)carbonyl]amino}butanoyl]-beta-alanine

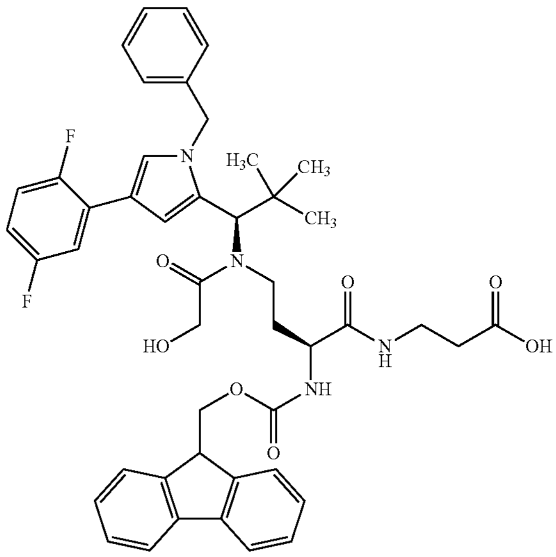 [SMILES: CC(C)(C)[C@H](c1cc(-c2cc(F)ccc2F)cn1Cc1ccccc1)N(CC[C@H](NC(=O)OCC1c2ccccc2-c2ccccc21)C(=O)NCCC(=O)O)C(=O)CO]

First, Intermediate C52 was reductively alkylated with benzyl N-[(2S)-2-{[(benzyloxy)carbonyl]amino}-4-oxobutanoyl]-beta-alaninate analogously to Intermediate C2. The secondary amino group was then acylated with 2-chloro-2-oxoethyl acetate as described for Intermediate C27. The intermediate obtained in this manner was dissolved in methanol, palladium on carbon (10%) was added and the mixture was hydrogenated at RT with hydrogen under standard pressure for 1 h. The ester group was then hydrolyzed with 2M lithium hydroxide solution in methanol. The deprotected compound was taken up in dioxane/water 2:1 and in the last step the Fmoc protective group was introduced using 9H-fluoren-9-ylmethyl chlorocarbonate in the presence of N,N-diisopropylethylamine. 48 mg of the title compound were obtained.

LC-MS (Method 1): $R_t$=1.38 min; MS (ESIpos): m/z=807 $(M+H)^+$.

Intermediate C55

2-[3-({(1R)-1-[4-Benzyl-1-(2,5-difluorophenyl)-1H-pyrazol-3-yl]-2,2-dimethylpropyl}amino)propyl]-1H-isoindole-1,3(2H)-dione

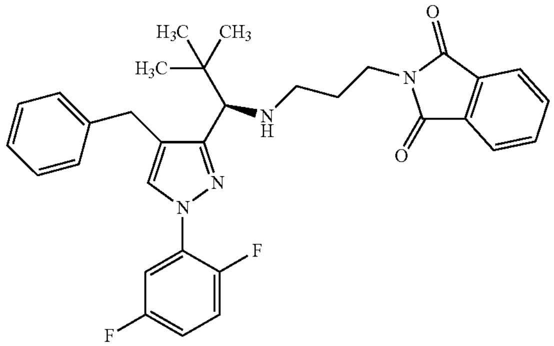 [SMILES: CC(C)(C)[C@@H](NCCCN1C(=O)c2ccccc2C1=O)c1nn(-c2cc(F)ccc2F)cc1Cc1ccccc1]

340 mg (0.96 mmol) of (1R)-1-[4-benzyl-1-(2,5-difluorophenyl)-1H-pyrazol-3-yl]-2,2-dimethylpropan-1-amine were dissolved in 7 ml of absolute DCM, and 69 mg (1.15 mmol, 60 µl) acetic acid and 284 mg (1.34 mmol) of sodium triacetoxyborohydride were added at RT. The mixture was stirred for 15 min, and 233 mg (1.15 mmol) of 3-(1,3-dioxo-1,3-dihydro-2H-isoindol-2-yl)propanal were then added. The mixture was stirred at RT for 4.5 h. Another 233 mg (1.15 mmol) of 3-(1,3-dioxo-1,3-dihydro-2H-isoindol-2-yl) propanal, 69 mg (1.15 mmol, 60 µl) acetic acid and 284 mg (1.34 mmol) of sodium triacetoxyborohydride were added, and the mixture was stirred at RT for 7 h. Ethyl acetate was added and the reaction mixture was washed with saturated sodium carbonate solution. The organic phase was concentrated and the residue was purified twice by preparative HPLC [1.) mobile phase: ACN/water+0.1% TFA, gradient; 2.) mobile phase: ACN/water+1% TFA+1.0% $NEt_3$)]. This gave 108 mg (21% of theory) of the target compound.

LC-MS (Method 1): $R_t$=0.96 min; MS (ESIpos): m/z=543 $[M+H]^+$.

Intermediate C56

2-({(1R)-1-[4-Benzyl-1-(2,5-difluorophenyl)-1H-pyrazol-3-yl]-2,2-dimethylpropyl}[3-(1,3-dioxo-1,3-dihydro-2H-isoindol-2-yl)propyl]amino)-2-oxoethyl Acetate

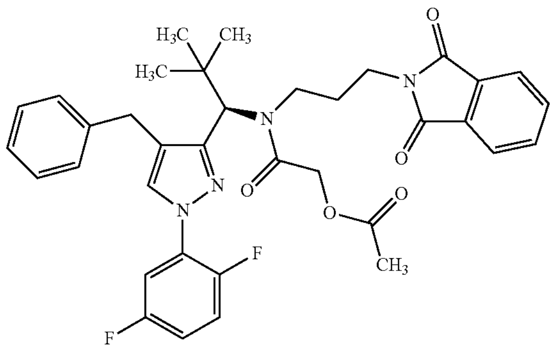 [SMILES: CC(=O)OCC(=O)N(CCCN1C(=O)c2ccccc2C1=O)[C@@H](c1nn(-c2cc(F)ccc2F)cc1Cc1ccccc1)C(C)(C)C]

102 mg (0.19 mmol) of 2-[3-({(1R)-1-[4-benzyl-1-(2,5-difluorophenyl)-1H-pyrazol-3-yl]-2,2-dimethylpropyl} amino)propyl]-1H-isoindole-1,3(2H)-dione were initially charged in 2 ml of absolute DCM, and 44 mg (0.43 mmol) of triethylamine were added at RT. At 0° C., 31 mg (0.23 mmol) of 2-chloro-2-oxoethyl acetate dissolved in 1 ml of absolute DCM were added. The mixture was stirred at RT for 40 min. Another 26 mg of 2-chloro-2-oxoethyl acetate dissolved in 0.5 ml of absolute DCM and 19 mg (0.19 mmol) of triethylamine were added, and the mixture was stirred at RT for 60 min.

Water was added, the mixture was concentrated on a rotary evaporator and the residue was purified by preparative HPLC (mobile phase: ACN/water+0.1% TFA, gradient). This gave 106 mg (88% of theory) of the target compound.

LC-MS (Method 1): $R_t$=1.37 min; MS (ESIpos): m/z=643 $[M+H]^+$.

Intermediate C57

Trifluoroacetic Acid/tert-butyl {(2S)-1-[(2-aminoethyl)amino]-4-[{(1R)-1-[4-benzyl-1-(2,5-difluorophenyl)-1H-pyrazol-3-yl]-2,2-dimethylpropyl}(glycoloyl)amino]-1-oxobutan-2-yl}carbamate (1:1)

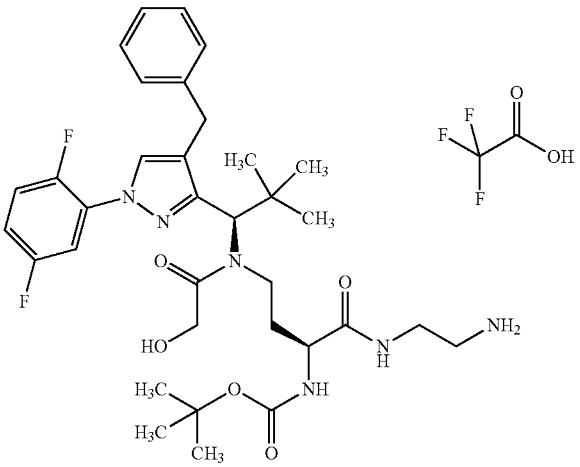 [SMILES: CC(C)(C)OC(=O)N[C@@H](CCN(C(=O)CO)[C@@H](c1nn(-c2cc(F)ccc2F)cc1Cc1ccccc1)C(C)(C)C)C(=O)NCCN ; O=C(O)C(F)(F)F]

The title compound was prepared according to standard methods by coupling Intermediate C49 with 9H-fluoren-9-ylmethyl (2-aminoethyl)carbamate in the presence of HATU and subsequent removal of the Fmoc protective group with piperidine. This gave 14 mg of the title compound (40% of theory over 2 steps).

LC-MS (Method 1): $R_t$=0.98 min; MS (ESIpos): m/z=657 $(M+H)^+$.

Intermediate C58

(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic Acid

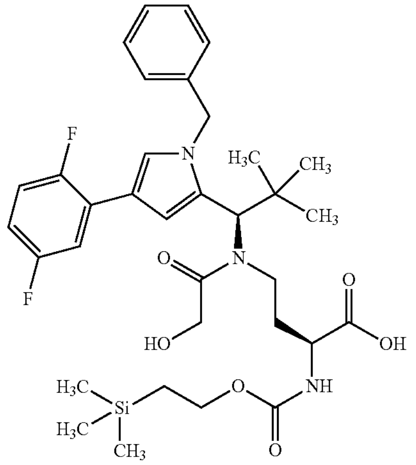 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CO]

4.3 g (12.2 mmol) of Intermediate C52 were dissolved in 525 ml of DCM, and 3.63 g (17.12 mmol) of sodium triacetoxyborohydride and 8.4 ml of acetic acid were added. After 5 min of stirring at RT, 8.99 g (24.5 mmol) of Intermediate L57 dissolved in 175 ml of DCM were added and the reaction was stirred at RT for a further 45 min. The reaction was then diluted with 300 ml of DCM and washed twice with 100 ml of sodium bicarbonate solution and once with saturated NaCl solution. The organic phase was dried over magnesium sulphate, the solvent was evaporated under reduced pressure and the residue was dried under high vacuum. The residue was then purified by preparative RP-HPLC (column: Chromatorex C18). After combination of the appropriate fractions, the solvent was evaporated under reduced pressure and the residue was dried under high vacuum. This gave 4.6 g (61% of theory) of methyl (2S)-4-({(1R)-1-[1-benzyl-4-(2,5-difluorophenyl)-1H-pyrrol-2-yl]-2,2-dimethylpropyl}amino)-2-({[2-(trimethylsilyl)ethoxy]carbonyl}amino)butanoate.

LC-MS (Method 12): $R_t$=1.97 min; MS (ESIpos): m/z=614 $(M+H)^+$.

2.06 g (3.36 mmol) of this intermediate were initially charged in 76 ml of DCM and acylated with 0.81 ml (7.17 mmol) of 2-chloro-2-oxoethyl acetate in the presence of 2.1 ml of triethylamine. After 20 h of stirring at RT, 0.36 ml of 2-chlor-2-oxoethyl acetate and 0.94 ml of triethylamine were added and the reaction was stirred at RT for a further 15 min. The mixture was then diluted with 500 ml of ethyl acetate and extracted successively twice with 300 ml of 5% strength citric acid, twice with 300 ml of saturated sodium bicarbonate solution and once with 100 ml of saturated sodium chloride solution and then dried over magnesium sulphate and concentrated. Drying under high vacuum gave 2.17 g (79% of theory) of the protected intermediate.

LC-MS (Method 1): $R_t$=1.48 min; MS (ESIpos): m/z=714 $(M+H)^+$.

2.17 mg (2.64 mmol) of this intermediate were dissolved in 54 ml of THF and 27 ml of water, and 26 ml of a 2-molar lithium hydroxide solution were added. The mixture was stirred at RT for 30 min and then adjusted to a pH between 3 and 4 using 1.4 ml of TFA. The mixture was concentrated under reduced pressure. Once most of the THF had been distilled off, the aqueous solution was extracted twice with DCM and then concentrated to dryness under reduced pressure. The residue was purified by preparative HPLC (column: Chromatorex C18). After combination of the appropriate fractions, the solvent was evaporated under reduced pressure and the residue was lyophilized from acetonitrile/water. This gave 1.1 g (63% of theory) of the title compound.

LC-MS (Method 1): $R_t$=1.34 min; MS (ESIpos): m/z=656 $(M-H)^-$.

$^1$H-NMR (400 MHz, DMSO-$d_6$): δ [ppm]=0.03 (s, 9H), 0.58 (m, 1H), 0.74-0.92 (m, 11H), 1.40 (m, 1H), 3.3 (m, 2H), 3.7 (m, 1H), 3.8-4.0 (m, 2H), 4.15 (q, 2H), 4.9 and 5.2 (2d, 2H), 5.61 (s, 1H), 6.94 (m, 2H), 7.13-7.38 (m, 7H), 7.48 (s, 1H), 7.60 (m, 1H), 12.35 (s, 1H).

Intermediate C59

(2S)-4-({(1R)-1-[1-Benzyl-4-(2,5-difluorophenyl)-1H-pyrrol-2-yl]-2,2-dimethylpropyl}[(2S)-2-methoxypropanoyl]amino)-2-{[(9H-fluoren-9-ylmethoxy)carbonyl]amino}butanoic acid

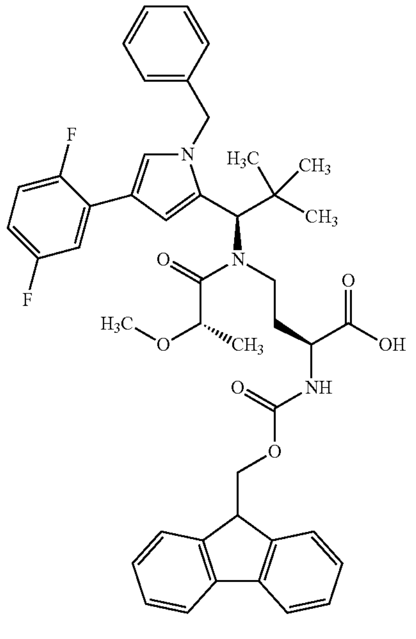 [SMILES: CO[C@@H](C)C(=O)N(CC[C@H](NC(=O)OCC1c2ccccc2-c2ccccc21)C(=O)O)[C@@H](c1cc(-c2cc(F)ccc2F)cn1Cc1ccccc1)C(C)(C)C]

Initially, the secondary amino group of benzyl (2S)-4-({(1R)-1-[1-benzyl-4-(2,5-difluorophenyl)-1H-pyrrol-2-yl]-2,2-dimethylpropyl}amino)-2-{[(benzyloxy)carbonyl]amino}butanoate was acylated with (2S)-2-methoxypropanoyl chloride (intermediate of Intermediate C53) in the presence of triethylamine as described for Intermediate C53. The intermediate obtained was taken up in ethanol, palladium on carbon (10%) was added and the mixture was hydrogenated at RT with hydrogen under standard pressure for 1 h. The deprotected compound was taken up in dioxane/water 2:1 and in the last step the Fmoc protective group was introduced using 9H-fluoren-9-ylmethyl chlorocarbonate in the presence of N,N-diisopropylethylamine.

LC-MS (Method 1): $R_t$=1.39 min; MS (ESIpos): m/z=764 $(M-H)^-$.

Intermediate C60

(2S)-4-({(1R)-1-[1-Benzyl-4-(2,5-difluorophenyl)-1H-pyrrol-2-yl]-2,2-dimethylpropyl}[(2S)-2-methoxypropanoyl]amino)-2-{[(9H-fluoren-9-yl-methoxy)carbonyl]amino}butanoic Acid

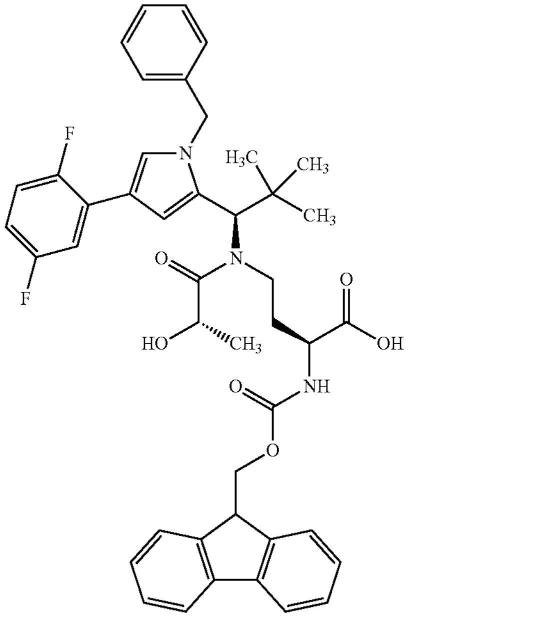 [SMILES: C[C@H](O)C(=O)N(CC[C@H](NC(=O)OCC1c2ccccc2-c2ccccc21)C(=O)O)[C@@H](c1cc(-c2cc(F)ccc2F)cn1Cc1ccccc1)C(C)(C)C]

The synthesis was carried out analogously to Intermediate C53.

LC-MS (Method 1): $R_t$=1.41 min; MS (ESIpos): m/z=750 $(M+H)^+$.

Intermediate C61

N-[(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-beta-alanine

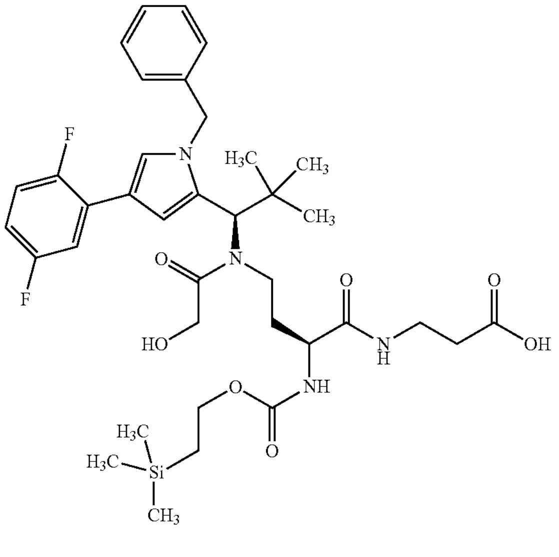 [SMILES: CC(C)(C)[C@H](c1cc(-c2cc(F)ccc2F)cn1Cc1ccccc1)N(CC[C@H](NC(=O)OCC[Si](C)(C)C)C(=O)NCCC(=O)O)C(=O)CO]

The title compound was prepared by coupling 60 mg (0.091 mmol) of Intermediate C58 with methyl 1-alaninate, followed by ester cleavage with 2M lithium hydroxide solution. This gave 67 mg (61% of theory) of the title compound over 2 steps.

LC-MS (Method 1): $R_t$=1.29 min; MS (ESIpos): m/z=729 $(M+H)^+$.

Intermediate C62

N-[(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alanine

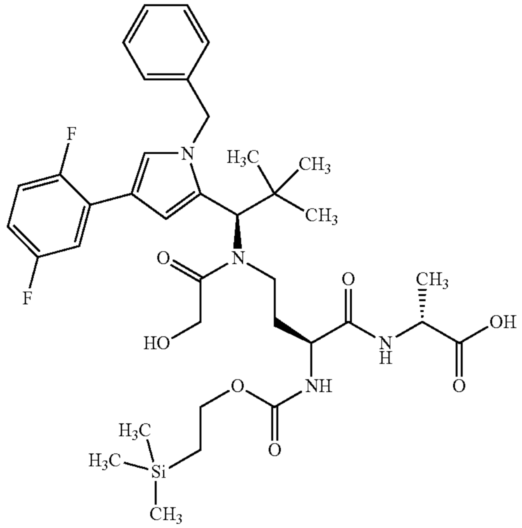 [SMILES: C[C@@H](NC(=O)[C@H](CCN(C(=O)CO)[C@@H](c1cc(-c2cc(F)ccc2F)cn1Cc1ccccc1)C(C)(C)C)NC(=O)OCC[Si](C)(C)C)C(=O)O]

The title compound was prepared analogously to Intermediate C61 from Intermediate C58 and methyl D-alaninate.

LC-MS (Method 1): $R_t$=1.32 min; MS (ESIpos): m/z=729 $(M+H)^+$.

Intermediate C63

Trifluoroacetic Acid/tert-butyl {(2S)-1-[(2-aminoethyl)amino]-4-[{(1R)-1-[1-benzyl-4-(2,5-difluorophenyl)-1H-imidazol-2-yl]-2,2-dimethylpropyl}(glycoloyl)amino]-1-oxobutan-2-yl}carbamate (1:1)

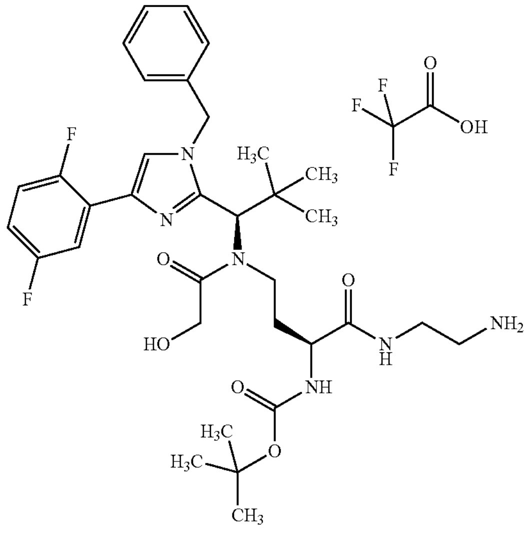 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)NCCN ; O=C(O)C(F)(F)F]

The synthesis of this intermediate began in the first step with the coupling of 50 mg (0.075 mmol) of Intermediate C3 with 26.2 mg (0.082 mmol) of 9H-fluoren-9-ylmethyl (2-aminoethyl)carbamate hydrochloride (1:1) in the presence of 28.7 mg (0.15 mmol) of 1-(3-dimethylaminopropyl)-3-ethyl carbodiimide hydrochloride, 22.9 mg (0.15 mmol) of 1-hydroxy-1H-benzotriazole hydrate and 39 μl of N,N-diisopropylethylamine. After 18 h of stirring at RT, the mixture was concentrated and the residue was purified by preparative HPLC. This gave 45 mg (65% of theory) of this intermediate.

LC-MS (Method 1): $R_t$=1.51 min; MS (ESIpos): m/z=921 $(M+H)^+$.

45 mg (0.049 mmol) of this intermediate were taken up in 10 ml of ethanol, and 176 μl of a 40% strength solution of methanamine in water were added. The reaction was stirred at 50° C., with the same amount of methanamine solution being added after 6 h and after 9 h. After a further 14 h of stirring at 50° C., another 700 μl of the methanamine solution were added, and after a further 20 h of stirring the mixture was finally concentrated. The residue was taken up in DCM and washed with water. The organic phase was concentrated and the residue was purified by preparative HPLC. Concentration of the appropriate fractions and drying of the residue under high vacuum gave 32 mg (99% of theory) of tert-butyl {(2S)-1-[(2-aminoethyl)amino]-4-[{(1R)-1-[1-benzyl-4-(2,5-difluorophenyl)-1H-imidazol-2-yl]-2,2-dimethylpropyl}(glycoloyl)amino]-1-oxobutan-2-yl}carbamate.

LC-MS (Method 1): $R_t$=0.95 min; MS (ESIpos): m/z=657 $(M+H)^+$.

Intermediate C64

Trifluoroacetic Acid/2-(trimethylsilyl)ethyl {(2S)-1-[(2-aminoethyl)amino]-4-[{(1R)-1-[1-benzyl-4-(2,5-difluorophenyl)-1H-pyrrol-2-yl]-2,2-dimethylpropyl}(glycoloyl)amino]-1-oxobutan-2-yl}carbamate (1:1)

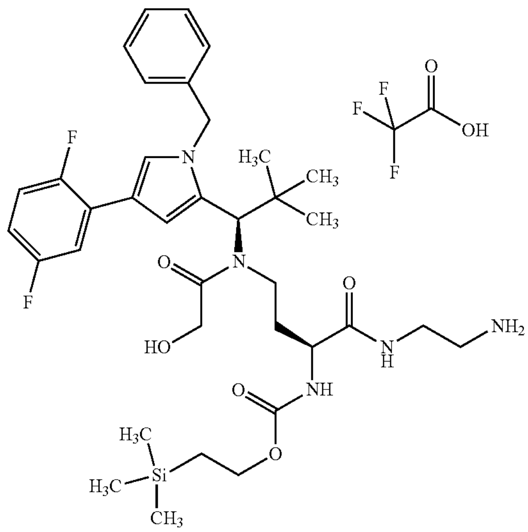 [SMILES: CC(C)(C)[C@H](c1cc(-c2cc(F)ccc2F)cn1Cc1ccccc1)N(CC[C@H](NC(=O)OCC[Si](C)(C)C)C(=O)NCCN)C(=O)CO ; O=C(O)C(F)(F)F]

The title compound was prepared from Intermediate C58 analogously to Intermediate C63.

HPLC (Method 11): $R_t$=2.4 min;

LC-MS (Method 1): $R_t$=1.01 min; MS (ESIpos): m/z=700 $(M+H)^+$.

Intermediate C65

(8S)-8-{2-[{(1R)-1-[1-Benzyl-4-(2,5-difluorophenyl)-1H-pyrrol-2-yl]-2,2-dimethylpropyl}-(glycoloyl)amino]ethyl}-2,2-dimethyl-6,11-dioxo-5-oxa-7,10-diaza-2-silatetradecan-14-oic Acid

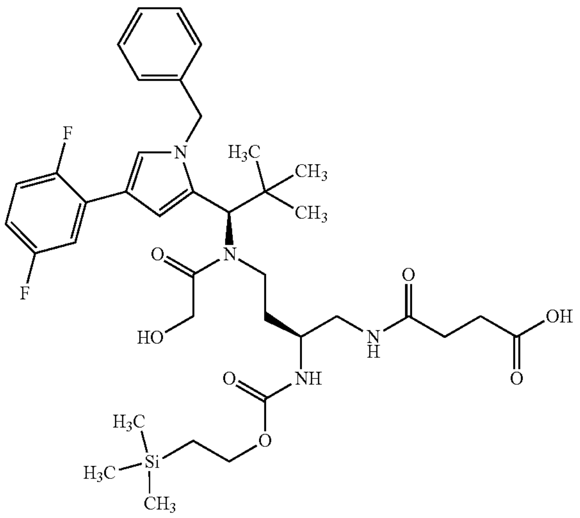 [SMILES: CC(C)(C)[C@H](c1cc(-c2cc(F)ccc2F)cn1Cc1ccccc1)N(CC[C@@H](CNC(=O)CCC(=O)O)NC(=O)OCC[Si](C)(C)C)C(=O)CO]

215 mg (0.59 mmol) of Intermediate L66 were initially charged in 25 ml of dichloromethane, and 377 mg (0.89 mmol) of Dess-Martin periodinane and 144 μl (1.78 mmol) of pyridine were added. The mixture was stirred at RT for 30 min. The reaction was then diluted with 300 ml of dichloromethane and the organic phase was washed in each case twice with 10% strength $Na_2S_2O_3$ solution, 10% strength citric acid solution and saturated sodium bicarbonate solution. The organic phase was dried over magnesium sulphate and the solvent was evaporated under reduced pressure. This gave 305 mg of the aldehyde which was reacted without further purification.

175 mg (0.49 mmol) of Intermediate C52 were dissolved in 50 ml of dichloromethane, and 147 mg (0.69 mmol) of sodium triacetoxyborohydride and 32.5 μl of acetic acid were added. After 5 min of stirring at RT, 214 mg (0.593 mmol) of the aldehyde described above were added, and the reaction was stirred at RT overnight. Here, instead of the expected product, 2-(trimethylsilyl)ethyl [(2S)-4-({(1R)-1-[1-benzyl-4-(2,5-difluorophenyl)-1H-pyrrol-2-yl]-2,2-dimethylpropyl}amino)-1-(2,5-dioxopyrrolidin-1-yl)butan-2-yl]carbamate was formed. Since this imide can also be converted into the title compound, the reaction was concentrated and the residue was purified by preparative HPLC. After combination of the appropriate imide-containing fractions, the solvent was evaporated under reduced pressure and the residue was dried under high vacuum. This gave 195 mg (58%) of the imide named above.

LC-MS (Method 5): $R_t$=3.32 min; MS (ESIpos): m/z=667 $(M+H)^+$.

65 mg (97.5 μmol) of this imide were taken up in 15 ml of dichloromethane, and 367 μl (3.4 mmol) of acetoxyacetyl chloride and 595 μl of N,N-diisopropylethylamine were added. After 30 min of stirring at RT, the reaction was concentrated without heating under reduced pressure and the residue was purified by preparative HPLC. The appropriate fractions were combined giving, after evaporation of the solvents and drying under high vacuum, 28 mg (37% of theory) of (8S)-11-{(1R)-1-[1-benzyl-4-(2,5-difluorophenyl)-1H-pyrrol-2-yl]-2,2-dimethylpropyl}-8-[(2,5-dioxopyrrolidin-1-yl)methyl]-2,2-dimethyl-6,12-dioxo-5-oxa-7,11-diaza-2-silatridecan-13-yl acetate.

LC-MS (Method 1): $R_t$=1.44 min; MS (ESIpos): m/z=767 $(M+H)^+$.

28 mg (37 μmol) of this intermediate were dissolved in 3 ml of methanol, and 548 μl of a 2M lithium hydroxide solution were added. After 10 min of stirring at RT, the reaction was adjusted to pH 4 with trifluoroacetic acid and then concentrated. The residue was purified by preparative HPLC. The appropriate fractions were combined, the solvent was evaporated and the residue was dried under high vacuum, giving 26 mg (96% of theory) of the title compound as a white solid.

LC-MS (Method 1): $R_t$=1.33 min; MS (ESIpos): m/z=743 $(M+H)^+$.

Intermediate C66

2-(Trimethylsilyl)ethyl [(2S)-4-[{(1R)-1-[1-benzyl-4-(2,5-difluorophenyl)-1H-pyrrol-2-yl]-2,2-dimethylpropyl}(glycoloyl)amino]-1-{[2-(glycylamino)ethyl]amino}-1-oxobutan-2-yl]carbamate

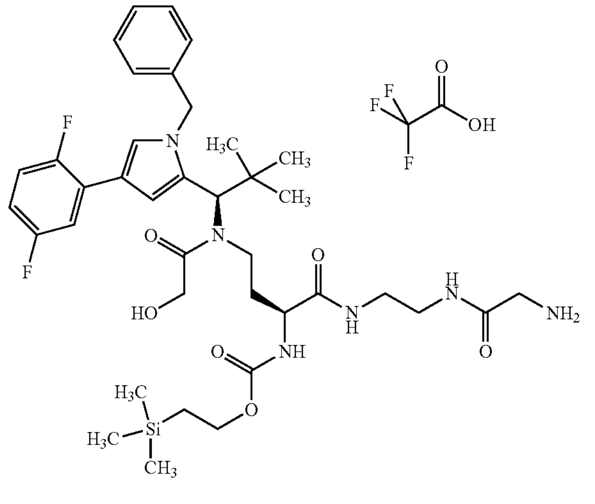 [SMILES: CC(C)(C)[C@H](c1cc(-c2cc(F)ccc2F)cn1Cc1ccccc1)N(CC[C@H](NC(=O)OCC[Si](C)(C)C)C(=O)NCCNC(=O)CN)C(=O)CO ; O=C(O)C(F)(F)F]

First, trifluoroacetic acid/benzyl {2-[(2-aminoethyl)amino]-2-oxoethyl}carbamate (1:1) was prepared from N-[(benzyloxy)carbonyl]glycine and tert-butyl (2-aminoethyl)carbamate according to classical methods of peptide chemistry (HATU coupling and Boc removal). 13 mg (0.036 mmol) of this intermediate and 25 mg (0.033 mmol) of Intermediate C58 were taken up in 3 ml of DMF, and 19 mg (0.05 mmol) of HATU and 17 μl of N,N-diisopropylethylamine were added. After 10 min of stirring at RT, the mixture was concentrated and the residue was purified by preparative HPLC. This gave 17.8 mg (60% of theory) of the intermediate.

LC-MS (Method 1): $R_t$=1.36 min; MS (ESIpos): m/z=891 $(M+H)^+$.

17 mg (0.019 mmol) of this intermediate were dissolved in 10 ml of ethanol, palladium on carbon (10%) was added and the mixture was hydrogenated at RT with hydrogen at standard pressure for 2 h. The catalyst was filtered off, the solvents were evaporated under reduced pressure and the residue was dried under high vacuum. This gave 9 mg (62% of theory) of the title compound.

LC-MS (Method 1): $R_t$=1.03 min; MS (ESIpos): m/z=757 $(M+H)^+$.

Intermediate C67

9H-Fluoren-9-ylmethyl [3-({(1R)-1-[1-benzyl-4-(2,5-difluorophenyl)-1H-pyrrol-2-yl]-2,2-dimethylpropyl}amino)propyl]carbamate

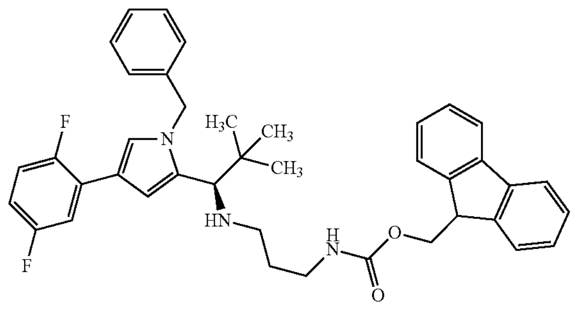 [SMILES: CC(C)(C)[C@@H](NCCCNC(=O)OCC1c2ccccc2-c2ccccc21)c1cc(-c2cc(F)ccc2F)cn1Cc1ccccc1]

605.3 mg (1.71 mmol) of (1R)-1-[1-benzyl-4-(2,5-difluorophenyl)-1H-pyrrol-2-yl]-2,2-dimethylpropan-1-amine (Intermediate C52) were initially charged in 10.0 ml of dichloromethane, and 506.7 mg (2.39 mmol) of sodium triacetoxyborohydride and 117.9 mg (1.96 mmol) of acetic acid were added and the mixture was stirred at RT for 5 min. 580.0 mg (1.96 mmol) of 9H-fluoren-9-ylmethyl (3-oxopropyl)carbamate (Intermediate L70) dissolved in 10.0 ml of dichloromethane were added and the reaction mixture stirred at RT overnight. The reaction mixture was diluted with ethyl acetate and the organic phase was washed in each case twice with saturated sodium carbonate solution and saturated NaCl solution. The organic phase was dried over magnesium sulphate and the solvent was evaporated under reduced pressure. The residue was chromatographed by means of silica gel (mobile phase: cyclohexane/ethyl acetate=3:1). The solvents were evaporated under reduced pressure and the residue was dried under high vacuum. This gave 514.7 mg (46% of theory) of the title compound.

LC-MS (Method 1): $R_t$=1.10 min; MS (ESIpos): m/z=634 $(M+H)^+$.

Intermediate C68 tert-Butyl [3-({(1R)-1-[4-benzyl-1-(2,5-difluorophenyl)-1H-pyrazol-3-yl]-2,2-dimethylpropyl}amino)propyl]carbamate

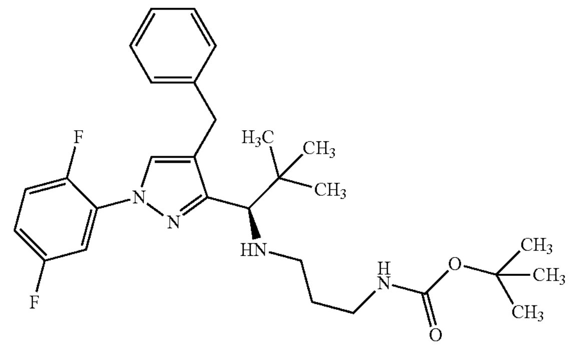 [SMILES: CC(C)(C)OC(=O)NCCCN[C@@H](c1nn(-c2cc(F)ccc2F)cc1Cc1ccccc1)C(C)(C)C]

The synthesis was carried out analogously to the synthesis of the compound Intermediate C67.

1000.0 mg (2.81 mmol) of (1R)-1-[4-benzyl-1-(2,5-difluorophenyl)-1H-pyrazol-3-yl]-2,2-dimethylpropan-1-amine (Intermediate C47)

835.0 mg (3.94 mmol) of sodium triacetoxyborohydride 194.0 mg (3.24 mmol) of acetic acid 560.0 mg (3.24 mmol) of tert-butyl (3-oxopropyl)carbamate This gave 695.8 mg (48% of theory) of the title compound.

LC-MS (Method 1): $R_t$=1.02 min; MS (ESIpos): m/z=513 $(M+H)^+$.

Intermediate C69

11-{(1R)-1-[1-Benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic Acid

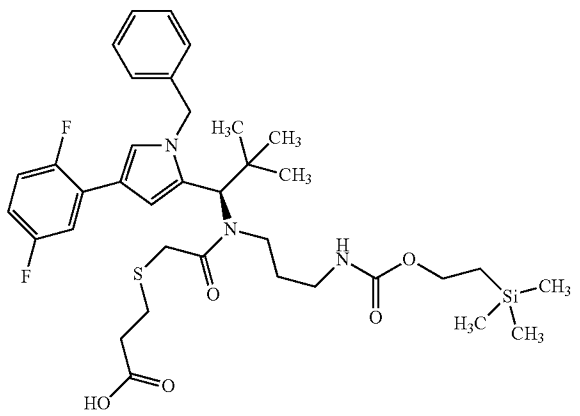 [SMILES: CC(C)(C)[C@H](c1cc(-c2cc(F)ccc2F)cn1Cc1ccccc1)N(CCCNC(=O)OCC[Si](C)(C)C)C(=O)CSCCC(=O)O]

117.0 mg (0.19 mmol) of (2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) and 21.6 mg (0.20 mmol) of 3-sulphanylpropanoic acid were initially charged in 3.0 ml of methanol, 89.5 mg (0.65 mmol) of potassium carbonate were added and the mixture was stirred at 50° C. for 4 h. The reaction mixture was diluted with ethyl acetate and the organic phase was washed with water and saturated NaCl solution. The organic phase was dried over magnesium sulphate, the solvent was evaporated under reduced pressure and the residue was dried under high vacuum. The residue was used without further purification in the next step of the synthesis. This gave 106.1 mg (73% of theory) of the title compound.

LC-MS (Method 1): $R_t$=1.42 min; MS (ESIneg): m/z=700 $(M-H)^-$.

Intermediate C70

(2-(Trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate

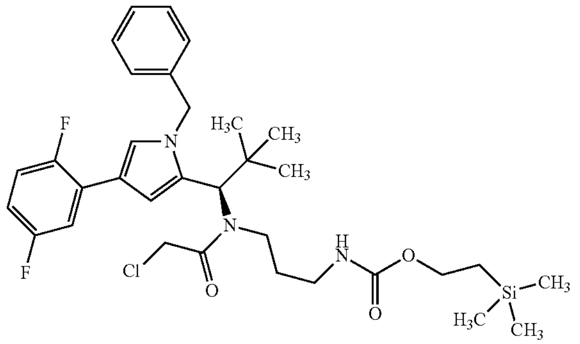 [SMILES: CC(C)(C)[C@H](c1cc(-c2cc(F)ccc2F)cn1Cc1ccccc1)N(CCCNC(=O)OCC[Si](C)(C)C)C(=O)CCl]

908.1 mg (1.63 mmol) of 2-(trimethylsilyl)ethyl [3-(({(1R)-1-[1-benzyl-4-(2,5-difluorophenyl)-1H-pyrrol-2-yl]-2,2-dimethylpropyl}amino)propyl]carbamate (see synthesis of Intermediate C11) and 545.6 mg (5.39 mmol) of triethylamine were initially charged in 10.0 ml of dichloromethane, and the mixture was cooled to 0° C. At this temperature, 590.5 mg (5.23 mmol) of chloroacetyl chloride were added and the mixture was stirred at RT overnight. The reaction mixture was diluted with ethyl acetate and the organic phase was washed in each case three times with saturated sodium bicarbonate solution and saturated ammonium chloride solution. The organic phase was washed with saturated NaCl solution and dried over magnesium sulphate. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 673.8 mg (65% of theory) of the title compound.

LC-MS (Method 1): $R_t$=1.53 min; MS (ESIneg): m/z=676 $(M+HCOO^-)^-$.

Intermediate C71

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic Acid (1:1)

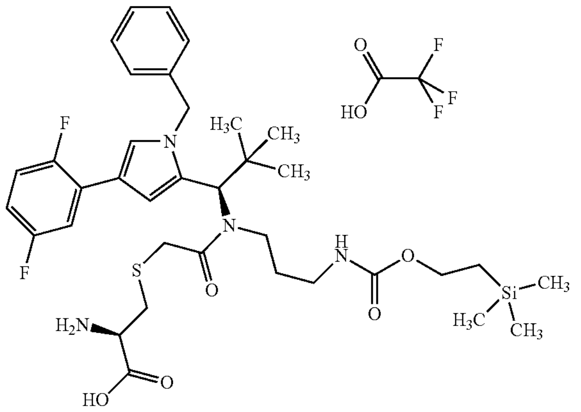 [SMILES: CC(C)(C)[C@H](c1cc(-c2cc(F)ccc2F)cn1Cc1ccccc1)N(CCCNC(=O)OCC[Si](C)(C)C)C(=O)CSC[C@H](N)C(=O)O ; O=C(O)C(F)(F)F]

536.6 mg (4.43 mmol) of L-cysteine were suspended in 2.5 ml of water together with 531.5 mg (6.33 mmol) of sodium bicarbonate. 400.0 mg (0.63 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) dissolved in 25.0 ml of isopropanol and 1.16 g (7.59 mmol) of 1,8-diazabicyclo[5.4.0]undec-7-ene were added. The reaction mixture was stirred at 50° C. for 1.5 h. Ethyl acetate was added to the reaction mixture and the organic phase was washed repeatedly with saturated sodium bicarbonate solution and once with sat. NaCl solution. The organic phase was dried over magnesium sulphate, the solvent was evaporated under reduced pressure and the residue was dried under high vacuum. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 449.5 mg (86% of theory) of the title compound.

LC-MS (Method 1): $R_t$=1.20 min; MS (ESIpos): m/z=717 $(M+H)^+$.

Intermediate C72

(9S)-9-{[{(1R)-1-[1-Benzyl-4-(2,5-difluorophenyl)-1H-pyrrol-2-yl]-2,2-dimethylpropyl}(glycoloyl)amino]methyl}-2,2-dimethyl-6,11-dioxo-5-oxa-7,10-diaza-2-silatetradecan-14-oic Acid

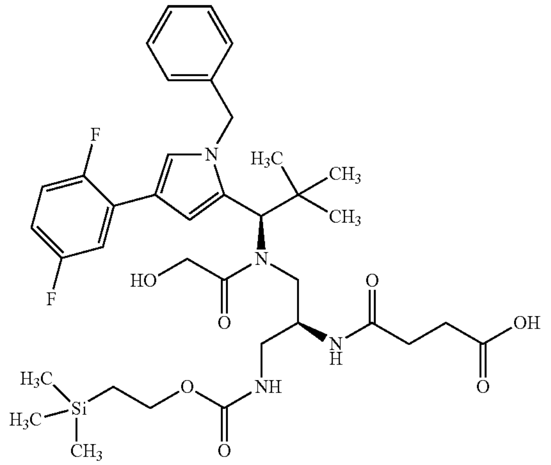 [SMILES: CC(C)(C)[C@H](c1cc(-c2cc(F)ccc2F)cn1Cc1ccccc1)N(C[C@H](CNC(=O)OCC[Si](C)(C)C)NC(=O)CCC(=O)O)C(=O)CO]

90 mg (0.212 mmol) of Intermediate L72 were initially charged in 6 ml of dichloromethane, and 86 μl (1.06 mmol) of pyridine and 135 mg (0.318 mmol) of Dess-Martin periodinane were added. The mixture was stirred at RT for 30 min. The reaction was then diluted with 30 ml of dichloromethane and the organic phase was washed twice with 10% strength $Na_2S_2O_3$ solution and once with 5% strength citric acid solution. The organic phase was dried over magnesium sulphate and the solvent was evaporated under reduced pressure. The aldehyde obtained in this manner was reacted without further purification.

63 mg (0.177 mmol) of Intermediate C52 were dissolved in 15 ml of dichloromethane, and 52.4 mg (0.247 mmol) of sodium triacetoxyborohydride and 20.2 μl of acetic acid were added. After 5 min of stirring at RT, 89.6 mg (0.212 mmol) of the aldehyde described above were added, and the reaction was stirred at RT for 20 min. The reaction was concentrated under reduced pressure and the residue was purified by preparative HPLC. After combination of the appropriate fractions, the solvent was evaporated under reduced pressure and the residue was lyophilized from acetonitrile/water. This gave 71 mg (53% of theory over 2 steps) of benzyl (9R)-9-[({(1R)-1-[1-benzyl-4-(2,5-difluorophenyl)-1H-pyrrol-2-yl]-2,2-dimethylpropyl}amino)methyl]-2,2-dimethyl-6,11-dioxo-5-oxa-7,10-diaza-2-silatetradecan-14-oate.

LC-MS (Method 1): $R_t$=1.21 min; MS (ESIpos): m/z=761 $(M+H)^+$.

70 mg (92 μmol) of this intermediate were taken up in 15 ml of dichloromethane, the mixture was cooled to 10° C. and 54 μl of triethylamine and 25.5 μl (0.23 mmol) of acetoxyacetyl chloride were added. After 1 h of stirring at RT, the same amounts of acid chloride and triethylamine were added, and once more after a further hour of stirring at RT. The reaction was then stirred at RT for a further 30 min and then concentrated under reduced pressure, and the residue was purified by preparative HPLC. The appropriate fractions were combined giving, after evaporation of the solvents and lyophilization of the residue from acetonitrile/water, 46.5 mg (59% of theory) of the acylated intermediate.

LC-MS (Method 1): $R_t$=1.53 min; MS (ESIpos): m/z=861 $(M+H)^+$.

46 mg (53 μmol) of this intermediate were dissolved in 5 ml of methanol, and 2.7 ml of a 2M lithium hydroxide solution were added. After 10 min of stirring at RT, the reaction was adjusted to pH 3-4 with acetic acid and then diluted with 15 ml of water. The aqueous phase was extracted with ethyl acetate and the organic phase was dried over magnesium sulphate and concentrated. The residue was lyophilized from acetonitrile/water giving, after drying of the residue under high vacuum, 37 mg (90% of theory) of the title compound as a white solid.

LC-MS (Method 1): $R_t$=1.32 min; MS (ESIpos): m/z=729 $(M+H)^+$.

Intermediate C73

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[3-(trimethylsilyl)propanoyl]-L-cysteine

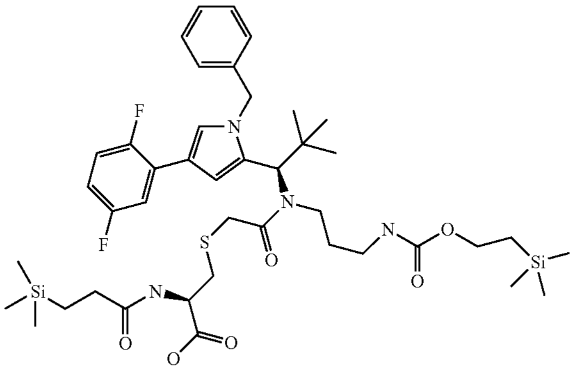

619 mg (0.86 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) were initially charged in 8.8 ml of dichloromethane, and 87 mg (0.86 mmol) of triethylamine and 224 mg (0.86 mmol) of N-[2-(trimethylsilyl)ethoxycarbonyloxy]pyrrolidine-2,5-dione were added. After 1 h, 45 mg (0.17 mmol) of N-[2-(trimethylsilyl)ethoxycarbonyloxy]pyrrolidine-2,5-dione were added. The reaction mixture was stirred at RT for 1 h. The mixture was concentrated under reduced pressure, the residue was taken up in dichloromethane and the organic phase was then washed twice with water and a saturated sodium bicarbonate solution. The organic phase was dried over magnesium sulphate, concentrated on a rotary evaporator and dried under high vacuum. The residue was used further without further purification. This gave 602 mg (71%, purity 87%) of the title compound.

LC-MS (Method 1): $R_t$=1.58 min; MS (ESIpos): m/z=861 $(M+H)^+$.

Intermediate C74

Trifluoroacetic Acid 2-(trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alaninate (11)

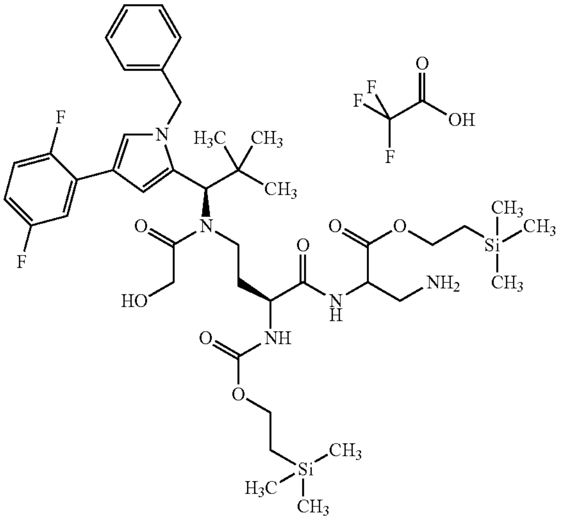 [SMILES: CC(C)(C)[C@H](c1cc(-c2cc(F)ccc2F)cn1Cc1ccccc1)N(CC[C@H](NC(=O)OCC[Si](C)(C)C)C(=O)NC(CN)C(=O)OCC[Si](C)(C)C)C(=O)CO ; O=C(O)C(F)(F)F]

75 mg (0.114 mmol) of Intermediate C58 were taken up in 12.5 ml of DMF and coupled with 78 mg (0.171 mmol) of Intermediate L75 in the presence of 65 mg (0.11 mmol) of HATU and 79 μl of N,N-diisopropylethylamine. After purification by preparative HPLC, the intermediate was taken up in 20 ml of ethanol and hydrogenated over 10% palladium on activated carbon at RT under hydrogen standard pressure for 1 h. The catalyst was then filtered off, the solvent was removed under reduced pressure and the product was purified by preparative HPLC. Lyophilization from acetonitrile/water 11 gave 63 mg (64% of theory over 2 steps) of the title compound.

LC-MS (Method 1): $R_t$=1.16 min; MS (EIpos): m/z=844 $[M+H]^+$.

Intermediate C75

Methyl (2S)-4-[(acetoxyacetyl){(1R)-1-[1-benzyl-4-(2,5-difluorophenyl)-1H-pyrrol-2-yl]-2,2-dimethylpropyl}amino]-2-({[2-(trimethylsilyl)ethoxy]carbonyl}amino)butanoate

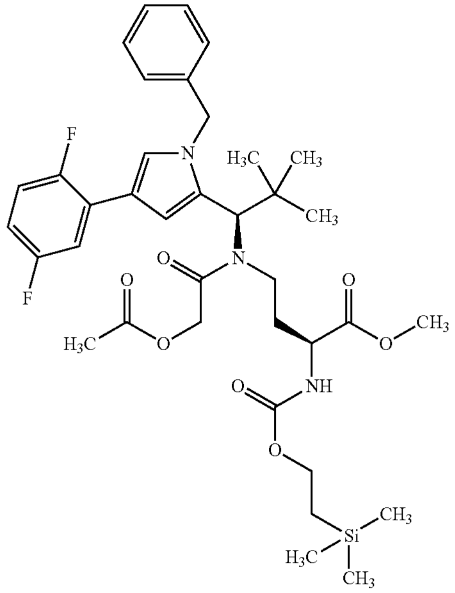 [SMILES: COC(=O)[C@H](CCN(C(=O)COC(C)=O)[C@@H](c1cc(-c2cc(F)ccc2F)cn1Cc1ccccc1)C(C)(C)C)NC(=O)OCC[Si](C)(C)C]

4.3 g (12.2 mmol) of Intermediate C52 were dissolved in 525 ml of DCM, and 3.63 g (17.12 mmol) of sodium triacetoxyborohydride and 8.4 ml of acetic acid were added. After 5 min of stirring at RT, 3.23 g (11.85 mmol) of methyl (2S)-4-oxo-2-({[2-(trimethylsilyl)ethoxy]carbonyl}amino) butanoate (prepared from (3S)-3-amino-4-methoxy-4-oxobutanoic acid by classical methods) dissolved in 175 ml of DCM were added, and the mixture was stirred at RT for a further 45 min. The mixture was then diluted with DCM and extracted twice with 100 ml of saturated sodium bicarbonate solution and then with saturated sodium chloride solution. The organic phase was dried over magnesium sulphate, filtered and concentrated. The residue was purified by preparative HPLC. Combination of the appropriate fractions, concentration and drying of the residue under high vacuum gave 4.6 g (61% of theory) of the intermediate.

LC-MS (Method 12): $R_t$=1.97 min; MS (ESIpos): m/z=614.32 $(M+H)^+$.

200 mg (0.33 mmol) of this intermediate were dissolved in 10 ml of DCM, and 105 µl of triethylamine and 77 µl (0.717 mmol) of acetoxyacetyl chloride were then added. The mixture was stirred at RT overnight and then concentrated under reduced pressure. The residue was taken up in ethyl acetate and extracted twice with saturated sodium bicarbonate solution and then with saturated sodium chloride solution. The organic phase was dried over magnesium sulphate and then concentrated. This gave 213 mg (75%) of the title compound as a beige foam.

LC-MS (Method 1): $R_t$=1.46 min; MS (ESIpos): m/z=714 $(M+H)^+$.

Intermediate C76

N-[(Benzyloxy)carbonyl]-L-valyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-alaninamide

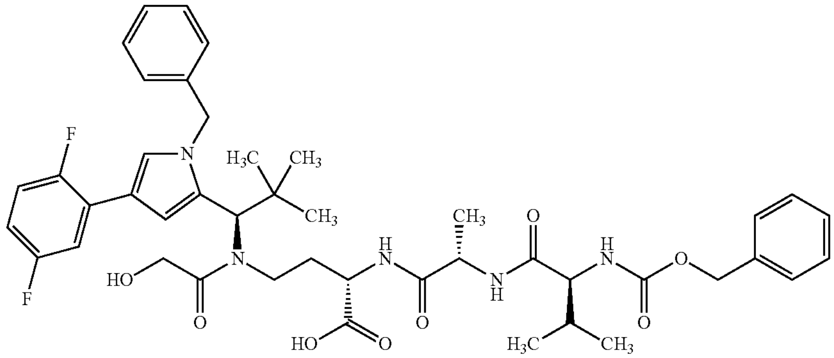 [SMILES: CC(C)[C@H](NC(=O)OCc1ccccc1)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)O]

The title compound was prepared from Intermediate C75 according to classical methods of peptide chemistry (removal of the Teoc protective group with zinc chloride, acylation with N-[(benzyloxy)carbonyl]-L-valyl-L-alanine in the presence of HATU and ester cleavage with lithium hydroxide in THF/water).

LC-MS (Method 1): $R_t$=1.23 min; MS (ESIpos): m/z=818 $(M+H)^+$.

Intermediate C77

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine

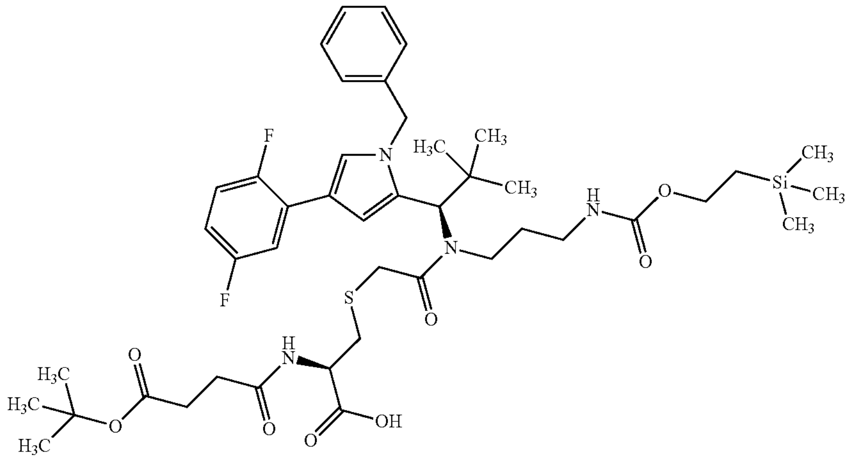 [SMILES: CC(C)(C)OC(=O)CCC(=O)N[C@@H](CSCC(=O)N(CCCNC(=O)OCC[Si](C)(C)C)[C@@H](c1cc(-c2cc(F)ccc2F)cn1Cc1ccccc1)C(C)(C)C)C(=O)O]

4-tert-Butoxy-4-oxobutanoic acid (8.39 mg, 48.1 μmol) was initially charged in 1.0 ml of DMF, 7.37 mg (48.1 μmol) of 1-hydroxy-1H-benzotriazole hydrate, 15.5 mg ((48.1 μmol) of (benzotriazol-1-yloxy)bisdimethylaminomethylium fluoroborat and 8.60 μl (48.1 μmol) of N,N-diisopropylethylamine were added and the mixture was stirred at RT for 10 minutes. 40.0 mg (0.048 mmol) S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (11) (Intermediate C71) were initially charged in 1.0 ml of DMF, 25.4 μl (141.9 μmol) of N,N-diisopropylethylamine were added, the mixture was added to the reaction and the reaction mixture was stirred at RT for 4 h. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 35.0 mg (83% of theory) of the title compound.

LC-MS (Method 12): $R_t$=2.76 min; MS (ESIpos): m/z=873 $[M+H]^+$

Intermediate C78

11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecane-15-acid

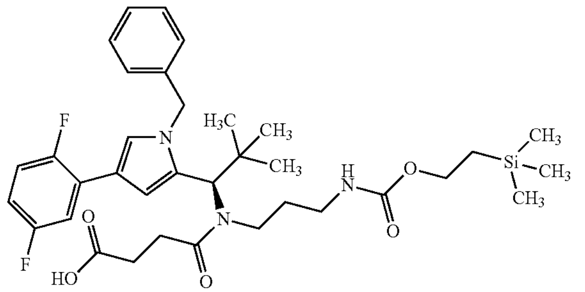 [SMILES: CC(C)(C)[C@H](c1cc(-c2cc(F)ccc2F)cn1Cc1ccccc1)N(CCCNC(=O)OCC[Si](C)(C)C)C(=O)CCC(=O)O]

197 mg (0.354 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate (see synthesis of Intermediate C11) were initially charged in 5.0 ml of dichloromethane, and the mixture was heated to 40° C. At this temperature, 240 μl (3.0 mmol) of pyridine and 220 μl (1.8 mmol) of methyl 4-chloro-4-oxobutanoate were added, and the mixture was stirred at RT for 1 h. 240 μl (3.0 mmol) of pyridine and 220 μl (1.8 mmol) of methyl 4-chloro-4-oxobutanoate were then added, and the mixture was stirred at RT for 1 h. 240 μl (3.0 mmol) of pyridine and 220 μl (1.8 mmol) of methyl 4-chloro-4-oxobutanoate were then added, and the mixture was stirred at RT for 1 h. The reaction mixture was diluted with ethyl acetate and the organic phase was extracted in each case three times with 5% strength $KHSO_4$ solution. The organic phase was washed with saturated NaCl solution and dried over magnesium sulphate. The solvents were evaporated under reduced pressure. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 74.1 mg (31% of theory) of methyl 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oate.

LC-MS (Method 1): $R_t$=1.49 min; MS (ESIpos): m/z=670 $[M+H]^+$ 78.3 mg (117 μmol) of methyl 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oate were initially charged in 4.0 ml of THF, and 800 μl of methanol, 160 μl of water and 230 μl (230 μmol) of aqueous LiOH solution (1M) were added. The reaction mixture was stirred at RT for 3 h, quenched with acetic acid and purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 64.8 mg (85% of theory) of the title compound.

LC-MS (Method 12): $R_t$=2.61 min; MS (ESIneg): m/z=654 $[M-H]^-$

Intermediate C79

Trifluoroacetic Acid 2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1)

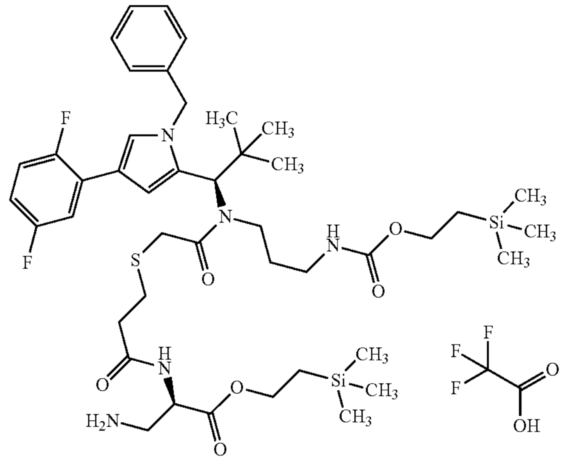 [SMILES: CC(C)(C)[C@H](c1cc(-c2cc(F)ccc2F)cn1Cc1ccccc1)N(CCCNC(=O)OCC[Si](C)(C)C)C(=O)CSCCC(=O)N[C@H](CN)C(=O)OCC[Si](C)(C)C ; O=C(O)C(F)(F)F]

57.4 mg (81.8 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged in 5.7 ml of DMF, 74.0 mg (164 μmol) of trifluoroacetic acid 2-(trimethylsilyl)ethyl 3-{[(benzyloxy)carbonyl]amino}-D-alaninate (1:1) (Intermediate L75), 43 μl (250 μmol) of N,N-diisopropylethylamine and 62.2 mg (164 μmol) of HATU were added and the mixture was stirred at RT for 1 h. The reaction mixture was stirred at RT for 1 h, quenched with acetic acid and purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 52.4 mg (63% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-

2,2-dimethyl-6,12,17-trioxo-5-oxa-14-thia-7,11-diaza-2-silaheptadecan-17-yl)-3-{[(benzyloxy)carbonyl]amino}-D-alaninate.

LC-MS (Method 1): $R_t$=1.64 min; MS (ESIpos): m/z=1022 $[M]^+$

Under argon, 6.23 mg (27.7 μmol) of palladium(II) acetate were initially charged in 3.0 ml of dichloromethane, 12 μl (83 μmol) of triethylamine and 89 μl (550 μmol) of triethylsilane were added and the mixture was stirred for 5 minutes. 56.7 mg (55.5 μmol) of 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-{[(benzyloxy)carbonyl]amino}-D-alaninate in 3.0 ml of dichloromethane were then added, and the mixture was stirred at RT overnight. The mixture was concentrated almost to dryness, acetonitrile/water was added, and the mixture was filtered and purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 37.4 mg (67% of theory) of the title compound.

LC-MS (Method 12): $R_t$=2.15 min; MS (ESIpos): m/z=888 $[M+H]^+$

Intermediate C80

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine Trifluoroacetic Acid (1:1)

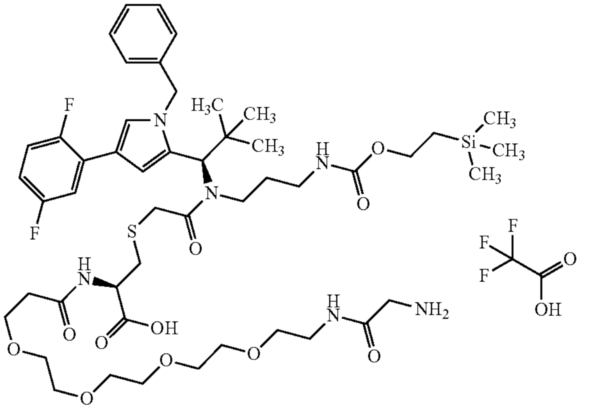 [SMILES: CC(C)(C)[C@H](c1cc(-c2cc(F)ccc2F)cn1Cc1ccccc1)N(CCCNC(=O)OCC[Si](C)(C)C)C(=O)CSC[C@H](NC(=O)CCOCCOCCOCCOCCNC(=O)CN)C(=O)O ; O=C(O)C(F)(F)F]

Under argon, 43.4 mg (95.1 μmol) of 1-({N-[(benzyloxy)carbonyl]glycyl}amino)-3,6,9,12-tetraoxapentadecan-15-oic acid (Intermediate L90) were initially charged in 2.5 ml of DMF, 14.6 mg (95.1 μmol) of 1-hydroxy-1H-benzotriazole hydrate, 30.5 mg (95.1 μmol) of (benzotriazol-1-yloxy)bisdimethylaminomethylium fluoroborate and 16.5 μl (95.1 μmol) of N,N-diisopropylethylamine were added and the mixture was stirred for 10 min. 79.0 mg (95.1 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (1:1) (Intermediate C71) were dissolved in 2.5 ml of DMF, 49.5 μl (285.3 μmol) of N,N-diisopropylethylamine were added and the mixture was added to the reaction. The reaction mixture was stirred at RT for 2 h and purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 44.2 mg (40% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(benzyloxy)carbonyl]glycyl}amino)-4,7,10,13-tetraoxapentadecan-1-oyl]-L-cysteine.

LC-MS (Method 12): $R_t$=2.57 min; MS (ESIpos): m/z=1156 $[M+H]^+$ 60.2 mg (52.1 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(benzyloxy)carbonyl]glycyl}amino)-4,7,10,13-tetraoxapentadecan-1-oyl]-L-cysteine were suspended in 3.0 ml of ethanol, 6.0 mg of palladium on activated carbon (10%) were added and the mixture was hydrogenated with hydrogen at RT and standard pressure for 1 h. Twice, 6.0 mg of palladium on activated carbon (10%) were added and the mixture was hydrogenated with hydrogen at RT and standard pressure for 1 h. The catalyst was filtered off and the reaction mixture was freed from the solvent under reduced pressure and dried under high vacuum. The residue was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 29.4 mg (50% of theory) of the title compound.

LC-MS (Method 5): $R_t$=3.77 min; MS (ESIpos): m/z=1021 $[M+H]^+$

Intermediate C81

(R)-1-[1-Benzyl-4-(2,5-difluorophenyl)-1H-pyrrol-2-yl]-1-cyclohexylmethanamine

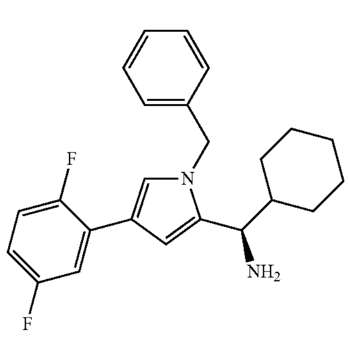 [SMILES: N[C@@H](c1cc(-c2cc(F)ccc2F)cn1Cc1ccccc1)C1CCCCC1]

Under argon and at −78° C., 18.7 ml (37.45 mmol) of cyclohexylmagnesium chloride in diethyl ether (2M) were added to a solution of 3.12 ml (6.24 mmol) of dimethylzinc in toluene (2.0 M), and the mixture was stirred at −78° C. for 30 minutes. A solution of 5.0 g (12.48 mmol) of (R)—N-{(E/Z)-[1-benzyl-4-(2,5-difluorophenyl)-1H-pyrrol-2-yl]methylene}-2-methylpropane-2-sulphinamide in THF was then added at −78° C., and the reaction mixture was stirred at this temperature for 1 h and then at RT for 4 h. At −78° C., ml of saturated ammonium chloride solution were then added and the reaction mixture was allowed to warm to RT. The mixture was diluted with ethyl acetate and washed with water. The organic phase was dried over magnesium sulphate and the solvent was evaporated under reduced pressure. The residue was purified using Biotage Isolera (silica gel, ethyl acetate/cyclohexane 25:75). This gave 1.59 g (26% of theory) of the intermediate.

LC-MS (Method 12): $R_t$=2.76 min; MS (ESIneg): m/z=483 $[M-H]^-$

Under argon, 264.0 mg (0.54 mmol) of this intermediate were initially charged in 0.5 ml of 1,4-dioxane, and 1.36 ml of HCl in 1,4-dioxane solution (4.0 M) were then added. The reaction mixture was stirred at RT for 1 h. Dichloromethane was added, and the reaction mixture was washed with an aqueous 1M sodium hydroxide solution. The organic phase was dried with magnesium sulphate and the solvent was evaporated under reduced pressure. The residue was purified using Biotage Isolera (silica gel, methanol/dichloromethane 98:2). The solvent was evaporated under reduced pressure and the residue was dissolved in dichloromethane, washed with a sodium bicarbonate solution and dried over sodium sulphate. The solvent was evaporated under reduced pressure and the residue was dried under high vacuum. This gave 148 mg (72% of theory) of the title compound.

LC-MS (Method 13): $R_t$=2.07 min; MS (ESIpos): m/z=364 $[M-NH_2]^+$

Intermediate C82

2-(Trimethylsilyl)ethyl (3-{[(R)-[1-benzyl-4-(2,5-difluorophenyl)-1H-pyrrol-2-yl](cyclohexyl)methyl]amino}propyl)carbamate

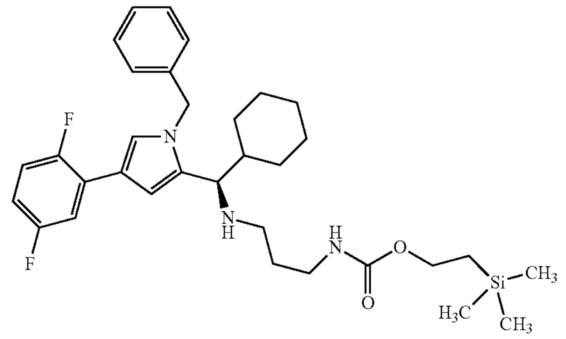 [SMILES: C[Si](C)(C)CCOC(=O)NCCCN[C@@H](c1cc(-c2cc(F)ccc2F)cn1Cc1ccccc1)C1CCCCC1]

Under argon, 392.2 mg (1.85 mmol) of sodium triacetoxyborohydride and 91.29 mg (1.52 mmol) of acetic acid were added to a solution of 503.0 mg (1.32 mmol) of 1-[1-benzyl-4-(2,5-difluorophenyl)-1H-pyrrol-2-yl]-1-cyclohexylmethanamine (Intermediate C81) in 1.4 ml of dichloromethane, and the reaction mixture was stirred at RT for 10 minutes. A solution of 574.6 (2.38 mmol) of 2-(trimethylsilyl)ethyl (3-oxopropyl)carbamate in dichloromethane was then added, and the mixture was stirred at RT overnight. After addition of 143 mg (0.66 mmol) of 2-(trimethylsilyl)ethyl (3-oxopropyl)carbamate, the mixture was stirred for a further 2 h. The reaction mixture was diluted with dichloromethane and the organic phase was washed twice each with saturated sodium carbonate solution and with saturated NaCl solution, dried over sodium sulphate and concentrated. The residue was purified by preparative HPLC. The solvents were evaporated under reduced pressure and the residue was dried under high vacuum. This gave 488 g (63% of theory) of the title compound.

LC-MS (Method 12): $R_t$=1.89 min; MS (ESIpos): m/z=582 $(M+H)^+$.

Intermediate C83

2-(Trimethylsilyl)ethyl (3-{[(R)-[1-benzyl-4-(2,5-difluorophenyl)-1H-pyrrol-2-yl](cyclohexyl)methyl](chloroacetyl)amino}propyl)carbamate

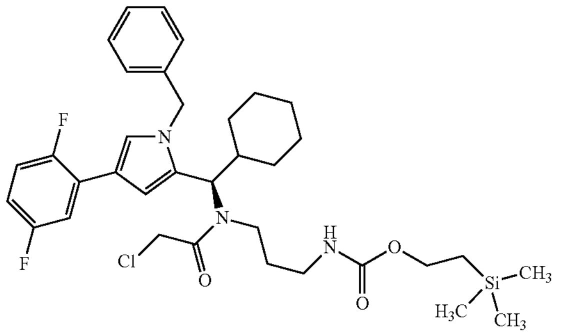 [SMILES: C[Si](C)(C)CCOC(=O)NCCCN(C(=O)CCl)[C@@H](c1cc(-c2cc(F)ccc2F)cn1Cc1ccccc1)C1CCCCC1]

280.0 mg (2.77 mmol) of triethylamine and 397.8 mg (3.52 mmol) of chloroacetyl chloride were added to a solution of 487.9 mg (0.84 mmol) 2-(trimethylsilyl)ethyl (3-{[(R)-[1-benzyl-4-(2,5-difluorophenyl)-1H-pyrrol-2-yl](cyclohexyl)methyl]amino}propyl)carbamate (Intermediate C82) in 8.40 ml of dichloromethane with 4 Å molecular sieve, and the reaction mixture was stirred at RT for 6 h. The reaction mixture was diluted with dichloromethane and the organic phase was washed with saturated sodium bicarbonate solution and saturated ammonium chloride solution. The organic phase was dried over sodium sulphate and concentrated. The residue was used further without purification. This gave 470 mg (85% of theory) of the title compound.

LC-MS (Method 12): $R_t$=2.88 min; MS (ESIpos): m/z=680 $(M+Na)^+$.

Intermediate C84

S-{11-[(R)-[1-Benzyl-4-(2,5-difluorophenyl)-1H-pyrrol-2-yl](cyclohexyl)methyl]-2,2-dimethyl-6,12-dioxo-5-oxa-7,11-diaza-2-silatridecan-13-yl}-L-cysteine

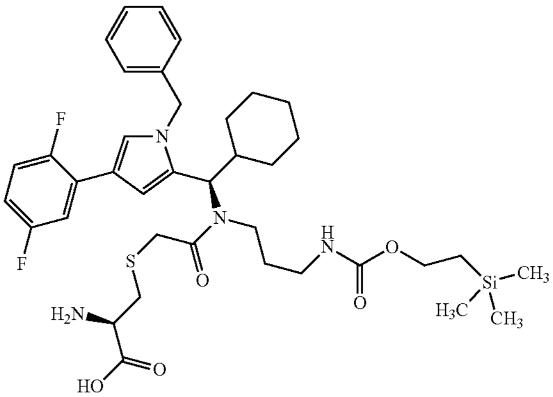 [SMILES: C[Si](C)(C)CCOC(=O)NCCCN(C(=O)CSC[C@H](N)C(=O)O)[C@@H](c1cc(-c2cc(F)ccc2F)cn1Cc1ccccc1)C1CCCCC1]

322.1 mg (2.66 mmol) of L-cysteine were suspended in 0.19 ml of water together with 319.0 mg (3.80 mmol) of sodium bicarbonate. 250.0 mg (0.38 mmol) of 2-(trimethylsilyl)ethyl (3-{[(R)-[1-benzyl-4-(2,5-difluorophenyl)-1H-pyrrol-2-yl](cyclohexyl)methyl](chloroacetyl)amino}propyl)carbamate (Intermediate C83) dissolved in 1.90 ml of iso-propanol and 693.8 g (4.56 mmol) of 1,8-diazabicyclo[5.4.0]undec-7-ene were added. The reaction mixture was stirred at 50° C. for 3.5 h. Ethyl acetate was added to the reaction mixture and the organic phase was washed repeatedly with saturated sodium bicarbonate solution and once with saturated NaCl solution. The organic phase was dried over sodium sulphate and the solvent was evaporated under reduced pressure. The residue was used further without further purification. This gave 276 mg (97% of theory) of the title compound.

LC-MS (Method 12): $R_t$=2.34 min; MS (ESIpos): m/z=744 $(M+H)^+$.

Intermediate C85

S-{11-[(R)-[1-Benzyl-4-(2,5-difluorophenyl)-1H-pyrrol-2-yl](cyclohexyl)methyl]-2,2-dimethyl-6,12-dioxo-5-oxa-7,11-diaza-2-silatridecan-13-yl}-N-[6-(2,5-dioxo-2,5-dihydro-1H-pyrrol-1-yl)hexanoyl]-L-cysteine

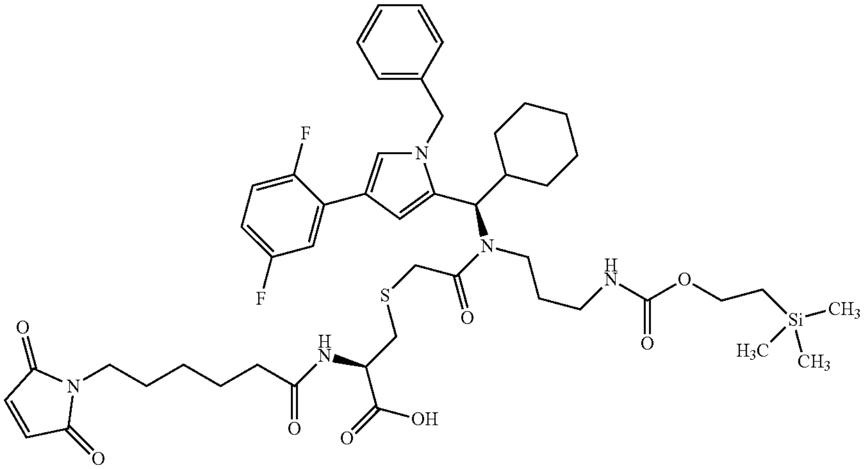 [SMILES: C[Si](C)(C)CCOC(=O)NCCCN(C(=O)CSC[C@H](NC(=O)CCCCCN1C(=O)C=CC1=O)C(=O)O)[C@@H](c1cc(-c2cc(F)ccc2F)cn1Cc1ccccc1)C1CCCCC1]

34.8 mg (0.27 mmol) of N,N-diisopropylethylamine were added to a mixture of 100 mg (0.13 mmol) of S-{11-[(R)-[1-benzyl-4-(2,5-difluorophenyl)-1H-pyrrol-2-yl](cyclohexyl)methyl]-2,2-dimethyl-6,12-dioxo-5-oxa-7,11-diaza-2-silatridecan-13-yl}-L-cysteine (1:1) (Intermediate C84) and 41.5 mg (0.13 mmol) of 1-{6-[(2,5-dioxopyrrolidin-1-yl)oxy]-6-oxohexyl}-1H-pyrrole-2,5-dione in 4.0 ml of DMF, and the reaction mixture was stirred at RT for 3 h. Without work-up, the mixture was purified by preparative HPLC. This gave 88 mg (70% of theory) of the title compound.

LC-MS (Method 12): $R_t$=2.71 min; MS (ESIpos): m/z=936 $(M+H)^+$.

Intermediate C86

11-[(R)-[1-Benzyl-4-(2,5-difluorophenyl)-1H-pyrrol-2-yl](cyclohexyl)methyl]-2,2-dimethyl-6,12-dioxo-5-oxa-14-thia-7,11-diaza-2-silaheptadecan-17-oic Acid

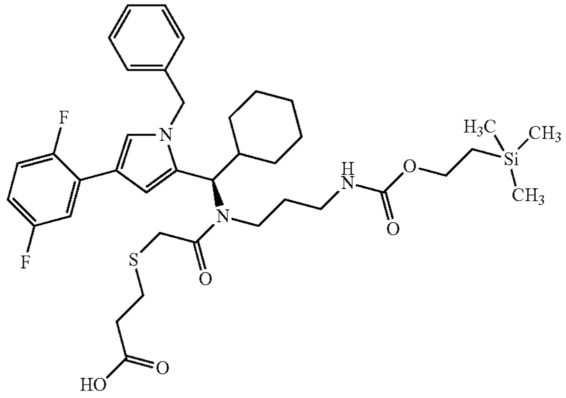 [SMILES: C[Si](C)(C)CCOC(=O)NCCCN(C(=O)CSCCC(=O)O)[C@@H](c1cc(-c2cc(F)ccc2F)cn1Cc1ccccc1)C1CCCCC1]

161.65 mg (1.17 mmol) of potassium carbonate were added to a mixture of 220.0 mg (0.33 mmol) of 2-(trimethylsilyl)ethyl (3-{[(R)-[1-benzyl-4-(2,5-difluorophenyl)-1H-pyrrol-2-yl](cyclohexyl)methyl](chloroacetyl)amino} propyl)carbamate (Intermediate C83) and 39.02 mg (0.37 mmol) of 3-sulphanylpropanoic acid in 7.45 ml of methanol and a few drops of water. The reaction mixture was stirred at 50° C. for 4 h. Ethyl acetate was added to the reaction mixture and the organic phase was washed repeatedly with water and with saturated NaCl solution. The organic phase was dried over sodium sulphate and the solvent was evaporated under reduced pressure. The residue was used further without work-up. This gave 201 mg (83% of theory) of the title compound.

LC-MS (Method 12): $R_t$=2.72 min; MS (ESIneg): m/z=726 $(M-H)^-$.

Intermediate C87

2-(Trimethylsilyl)ethyl {13-[(R)-[1-benzyl-4-(2,5-difluorophenyl)-1H-pyrrol-2-yl](cyclohexyl)methyl]-1-(2,5-dioxo-2,5-dihydro-1H-pyrrol-1-yl)-2,7,12-trioxo-10-thia-3,6,13-triazahexadecan-16-yl}carbamate

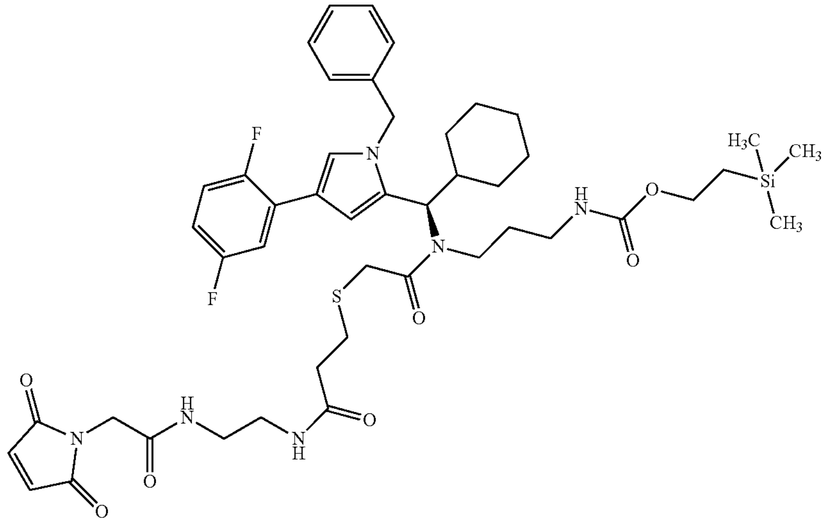 [SMILES: C[Si](C)(C)CCOC(=O)NCCCN(C(=O)CSCCC(=O)NCCNC(=O)CN1C(=O)C=CC1=O)[C@@H](c1cc(-c2cc(F)ccc2F)cn1Cc1ccccc1)C1CCCCC1]

54.18 mg (0.28 mmol) of N-(2-aminoethyl)-2-(2,5-dioxo-2,5-dihydro-1H-pyrrol-1-yl)acetamide (Intermediate L1), 71.01 mg (0.50 mmol) of N,N-diisopropylethylamine, 104.46 mg (0.27 mmol) of HATU and 0.23 ml (0.14 mmol) of 1-hydroxy-7-azabenzotriazole 0.5 M in DMF were added to a solution of 100 mg (0.14 mmol) of 11-[(R)-[1-benzyl-4-(2,5-difluorophenyl)-1H-pyrrol-2-yl](cyclohexyl)methyl]-2,2-dimethyl-6,12-dioxo-5-oxa-14-thia-7,11-diaza-2-silaheptadecan-17-oic acid (Intermediate C86) in 1.37 ml of DMF. The reaction mixture was stirred at RT for 5 h. Without further work-up, the mixture was purified by preparative HPLC. This gave 41 mg (33% of theory) of the title compound.

LC-MS (Method 12): $R_t$=2.61 min; MS (ESIpos): m/z=907 $(M+H)^+$.

Intermediate C88 tert-Butyl 3-[({1 (1R)-1-[1-benzyl-4-(2,5-difluorophenyl)-1H-pyrrol-2-yl]-2,2-dimethylpropyl}amino)methyl]pyrrolidine-1-carboxylate Trifluoroacetic Acid (1:1)

Mixture of Stereoisomers

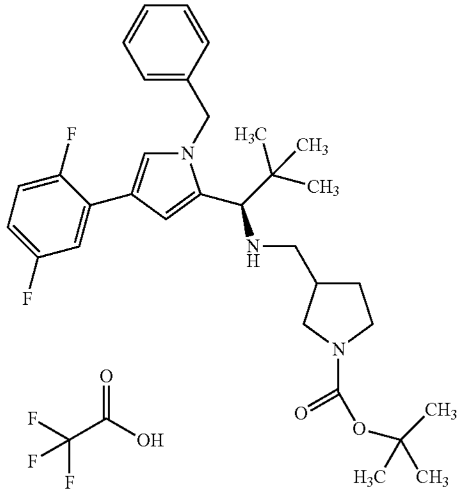 [SMILES: CC(C)(C)OC(=O)N1CCC(CN[C@@H](c2cc(-c3cc(F)ccc3F)cn2Cc2ccccc2)C(C)(C)C)C1 ; O=C(O)C(F)(F)F]

1.71 g (8.05 mmol) of sodium triacetoxyborohydride and 0.40 g (6.61 mmol) of acetic acid were added to a solution of 2.04 mg (5.75 mmol) of (1R)-1-[1-benzyl-4-(2,5-difluorophenyl)-1H-pyrrol-2-yl]-2,2-dimethylpropane-1-amine (Intermediate C52) in 51 ml of dichloromethane, and the reaction mixture was stirred at RT for 5 minutes. A solution of 1.32 g (6.61 mmol) of tert-butyl 3-formylpyrrolidine-1-carboxylate in 20 ml of dichloromethane was then added, and the mixture was stirred at RT overnight. The reaction mixture was diluted with ethyl acetate and the organic phase was washed in each case twice with saturated sodium carbonate solution and with saturated NaCl solution, dried over magnesium sulphate and concentrated. The residue was purified by preparative HPLC. The solvents were evaporated under reduced pressure and the residue was dried under high vacuum. This gave 1.86 g (50% of theory) of the title compound.

LC-MS (Method 1): $R_t$=0.99 min; MS (ESIpos): m/z=538 $(M+H-CF_3CO_2H)^+$.

Intermediate C89 tert-Butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate

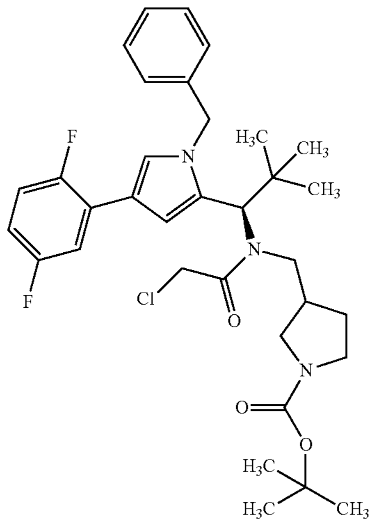 [SMILES: CC(C)(C)OC(=O)N1CCC(CN(C(=O)CCl)[C@@H](c2cc(-c3cc(F)ccc3F)cn2Cc2ccccc2)C(C)(C)C)C1]

1.36 g (13.42 mmol) of triethylamine and 2.13 g (18.87 mmol) of chloracetyl chloride were added to a solution of 2.89 g (4.19 mmol, 80% pure) of tert-butyl 3-[({(1R)-1-[1-benzyl-4-(2,5-difluorophenyl)-1H-pyrrol-2-yl]-2,2-dimethylpropyl}amino)methyl]pyrrolidine-1-carboxylate (Intermediate C88) in 42 ml of dichloromethane with 4 Å molecular sieve. The reaction mixture was stirred at RT for 5 h. The mixture was concentrated on a rotary evaporator and the residue was purified by preparative HPLC. This gave 449 mg (17% of theory) of Isomer 1 and 442 mg (17% of theory) of Isomer 2 of the title compound.

Isomer 1 LC-MS (Method 1): $R_t$=2.74 min; MS (ESIpos): m/z=614 $(M+H)^+$.

Isomer 2 LC-MS (Method 1): $R_t$=2.78 min; MS (ESIpos): m/z=614 $(M+H)^+$.

Intermediate C90

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Isomer 1)

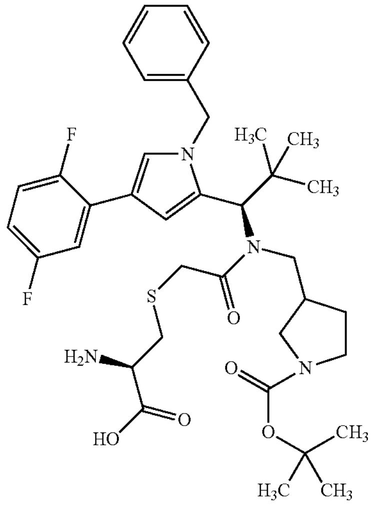 [SMILES: CC(C)(C)OC(=O)N1CCC(CN(C(=O)CSC[C@H](N)C(=O)O)[C@@H](c2cc(-c3cc(F)ccc3F)cn2Cc2ccccc2)C(C)(C)C)C1]

357.3 mg (0.58 mmol) of L-cysteine were suspended in 2.3 ml of water together with 488.7 mg (4.07 mmol) of sodium bicarbonate. 357.0 mg (0.58 mmol) of tert-butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (Isomer 1)

(Intermediate C89, Isomer 1) dissolved in 23.0 ml of isopropanol and 1.06 g (6.98 mmol) of 1,8-diazabicyclo[5.4.0]undec-7-ene were added. The reaction mixture was stirred at 50° C. for 3 h. Ethyl acetate was added to the reaction mixture and the organic phase was washed repeatedly with saturated sodium bicarbonate solution and once with sat. NaCl solution. The organic phase was dried over magnesium sulphate and the solvent was evaporated under reduced pressure. The residue was used further without purification. This gave 255.0 mg (62% of theory) of the title compound.

LC-MS (Method 1): $R_t$=1.09 min; MS (ESIpos): m/z=699 $(M+H)^+$.

Intermediate C91

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Isomer 2)

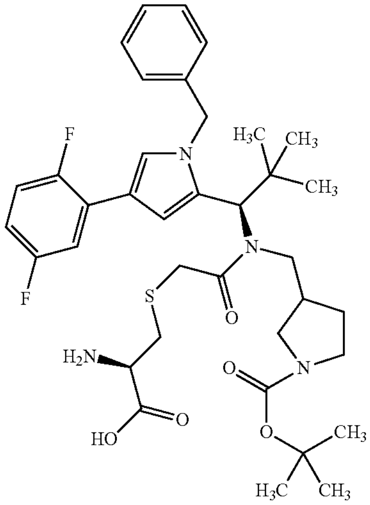 [SMILES: CC(C)(C)OC(=O)N1CCC(CN(C(=O)CSC[C@H](N)C(=O)O)[C@@H](c2cc(-c3cc(F)ccc3F)cn2Cc2ccccc2)C(C)(C)C)C1]

453.5 mg (3.74 mmol) of L-cysteine were suspended in 2.1 ml of water together with 449.2 mg (5.35 mmol) of sodium bicarbonate. 3287.4 mg (0.54 mmol) of tert-butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (Intermediate C89, Isomer 2) dissolved in 21.1 ml of iso-propanol and 0.98 g (6.42 mmol) of 1,8-diazabicyclo[5.4.0]undec-7-ene were added. The reaction mixture was stirred at 50° C. for 3 h. Ethyl acetate was added to the reaction mixture and the organic phase was washed repeatedly with saturated sodium bicarbonate solution and once with sat. NaCl solution. The organic phase was dried over magnesium sulphate and the solvent was evaporated under reduced pressure. The residue was used further without purification. This gave 221.0 mg (59% of theory) of the title compound.

LC-MS (Method 1): $R_t$=1.12 min; MS (ESIpos): m/z=699 $(M+H)^+$.

Intermediate C92

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Isomer 1)

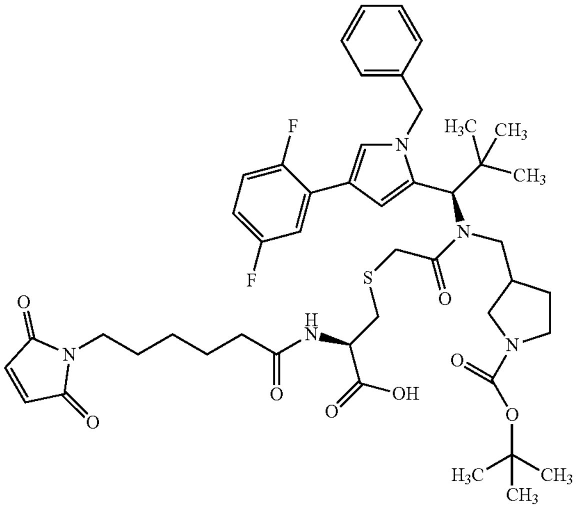 [SMILES: CC(C)(C)OC(=O)N1CCC(CN(C(=O)CSC[C@H](NC(=O)CCCCCN2C(=O)C=CC2=O)C(=O)O)[C@@H](c2cc(-c3cc(F)ccc3F)cn2Cc2ccccc2)C(C)(C)C)C1]

18.49 mg (0.14 mmol) of N,N-diisopropylethylamine were added to a mixture of 50 mg (0.07 mmol) of S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Intermediate C90) and 22.06 mg (0.07 mmol) of 1-{6-[(2,5-dioxopyrrolidin-1-yl)oxy]-6-oxohexyl}-1H-pyrrole-2,5-dione in 3.3 ml of DMF, and the reaction mixture was stirred at RT for 45 minutes. Without work-up, the mixture was purified by preparative HPLC. This gave 65 mg (100% of theory, 71% pure) of the title compound.

LC-MS (Method 1): $R_t$=1.31 min; MS (ESIpos): m/z=892 $(M+H)^+$.

Intermediate C93

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Isomer 2)

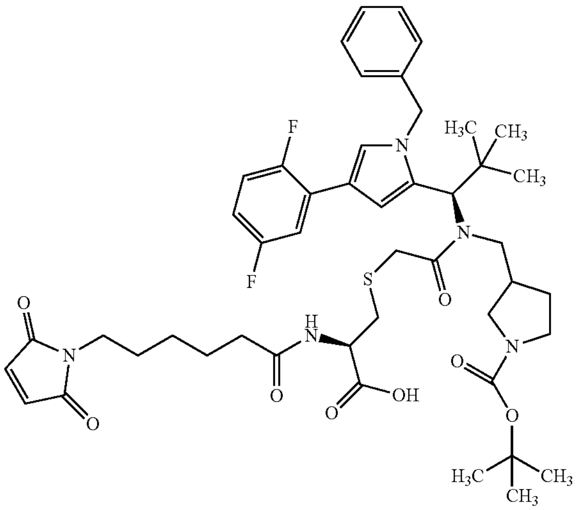 [SMILES: CC(C)(C)OC(=O)N1CCC(CN(C(=O)CSC[C@H](NC(=O)CCCCCN2C(=O)C=CC2=O)C(=O)O)[C@@H](c2cc(-c3cc(F)ccc3F)cn2Cc2ccccc2)C(C)(C)C)C1]

18.49 mg (0.14 mmol) of N,N-diisopropylethylamine were added to a mixture of 50.0 mg (0.07 mmol) of S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Intermediate C91) and 22.06 mg (0.07 mmol) of 1-{6-[(2,5-dioxopyrrolidin-1-yl)oxy]-6-oxohexyl}-1H-pyrrole-2,5-dione in 3.0 ml of DMF, and the reaction mixture was stirred at RT for 90 minutes. Without work-up, the mixture was purified by preparative HPLC. This gave 63 mg (98% of theory, 73% pure) of the title compound.

LC-MS (Method 1): $R_t$=1.34 min; MS (ESIpos): m/z=892 $(M+H)^+$.

Intermediate C94

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[(2,5-dioxo-2,5-dihydro-1H-pyrrol-1-yl)acetyl]-L-cysteine (Isomer 1)

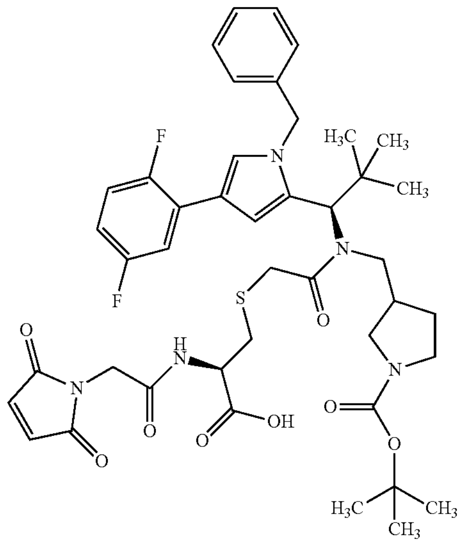 [SMILES: CC(C)(C)OC(=O)N1CCC(CN(C(=O)CSC[C@H](NC(=O)CN2C(=O)C=CC2=O)C(=O)O)[C@@H](c2cc(-c3cc(F)ccc3F)cn2Cc2ccccc2)C(C)(C)C)C1]

18.5 mg (0.14 mmol) of N,N-diisopropylethylamine were added to a mixture of 50.0 mg (0.07 mmol) of S-[2-({(1R)-1-[1-benzyl-4-(2,5-difluorophenyl)-1H-pyrrol-2-yl]-2,2-dimethylpropyl}{[-1-(tert-butoxycarbonyl)pyrrolidin-3-yl]methyl}amino)-2-oxoethyl]-L-cysteine (Intermediate C90) and 18.0 mg (0.07 mmol) of -{2-[(2,5-dioxopyrrolidin-1-yl)oxy]-2-oxoethyl}-1H-pyrrole-2,5-dione in 3.3 ml of DMF, and the reaction mixture was stirred at RT for 30 minutes. Ethyl acetate was added to the reaction mixture and the organic phase was washed repeatedly with saturated $NH_4Cl$ solution and with saturated NaCl solution. The organic phase was dried over magnesium sulphate and the solvent was evaporated under reduced pressure. The residue was employed without further purification. This gave 57 mg (81% of theory, 85% pure) of the title compound.

LC-MS (Method 1): $R_t$=0.96 min; MS (ESIpos): m/z=836 $(M+H)^+$.

Intermediate C95

3-{[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic Acid (Isomer 1)

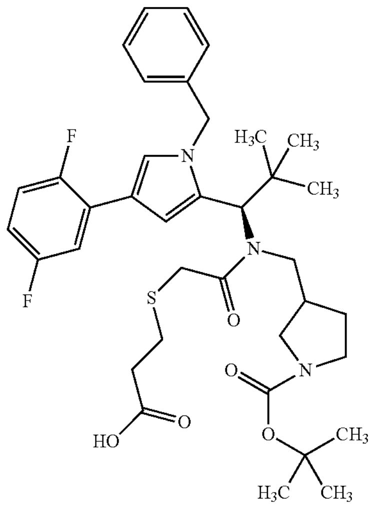 [SMILES: CC(C)(C)OC(=O)N1CCC(CN(C(=O)CSCCC(=O)O)[C@@H](c2cc(-c3cc(F)ccc3F)cn2Cc2ccccc2)C(C)(C)C)C1]

302.5 mg (2.19 mmol) of potassium carbonate were added to a mixture of 384.0 mg (0.62 mmol) of tert-butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (Intermediate C89, Isomer 1) and 73.0 mg (0.69 mmol) of 3-sulphanylpropanoic acid in 14 ml of methanol and a few drops of water. The reaction mixture was stirred at 50° C. for 2.5 h. Ethyl acetate was added to the reaction mixture and the organic phase was washed repeatedly with water and with saturated NaCl solution. The organic phase was dried over magnesium sulphate, the solvent was evaporated under reduced pressure and the residue was dried under high vacuum. The residue was used further without work-up. This gave 358.0 mg (84% of theory) of the title compound.

LC-MS (Method 1): $R_t$=1.33 min; MS (ESIpos): m/z=684 $(M+H)^+$.

Intermediate C96

3-{[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic Acid (Isomer 2)

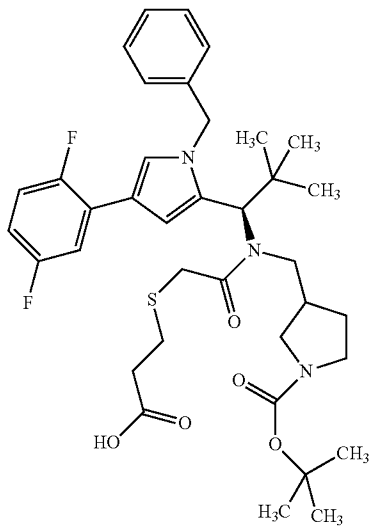 [SMILES: CC(C)(C)OC(=O)N1CCC(CN(C(=O)CSCCC(=O)O)[C@@H](c2cc(-c3cc(F)ccc3F)cn2Cc2ccccc2)C(C)(C)C)C1]

226.0 mg (1.64 mmol) of potassium carbonate were added to a mixture of 287.0 mg (0.45 mmol) of tert-butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (Intermediate C89, Isomer 2) and 54.6 mg (0.51 mmol) of 3-sulphanylpropanoic acid in 14 ml of methanol and a few drops of water. The reaction mixture was stirred at 50° C. for 2.5 h. Ethyl acetate was added to the reaction mixture and the organic phase was washed repeatedly with water and with saturated NaCl solution. The organic phase was dried over magnesium sulphate, the solvent was evaporated under reduced pressure and the residue was dried under high vacuum. The residue was used further without work-up. This gave 318.7 mg (88% of theory, 88% pure) of the title compound.

LC-MS (Method 1): $R_t$=1.36 min; MS (ESIpos): m/z=684 $(M+H)^+$.

Intermediate C97 tert-Butyl 3-[2-{(1R)-1-[1-benzyl-4-(2,5-difluorophenyl)-1H-pyrrol-2-yl]-2,2-dimethylpropyl}-14-(2,5-dioxo-2,5-dihydro-1H-pyrrol-1-yl)-3,8,13-trioxo-5-thia-2,9,12-triazatetradec-1-yl]pyrrolidine-1-carboxylate (Isomer 2)

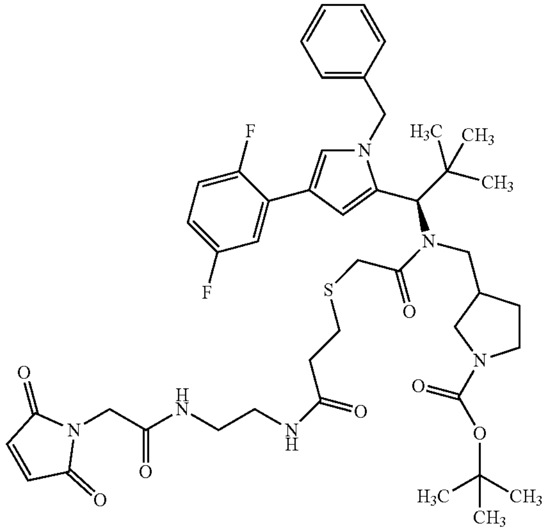 [SMILES: CC(C)(C)OC(=O)N1CCC(CN(C(=O)CSCCC(=O)NCCNC(=O)CN2C(=O)C=CC2=O)[C@@H](c2cc(-c3cc(F)ccc3F)cn2Cc2ccccc2)C(C)(C)C)C1]

Under argon, 14.17 mg (0.11 mmol) of N,N-diisopropylethylamine and 27.80 mg (0.07 mmol) of HATU were added to a solution of 25.0 mg (0.04 mmol) of 3-{[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Intermediate C96) in 2.81 ml of DMF. The reaction mixture was stirred at RT for 10 minutes. A solution of 22.75 mg (0.07 mmol) of N-(2-aminoethyl)-2-(2,5-dioxo-2,5-dihydro-1H-pyrrol-1-yl)acetamide-ethane (1:1) trifluoroacetic acid (Intermediate L1) in 1.4 ml of DMF and 5 mg (0.04 mmol) of N,N-diisopropylethylamine was then added, and the mixture was stirred at RT overnight. The mixture was admixed with water and extracted with dichloromethane. The organic phase was dried over magnesium sulphate and the solvent was evaporated under reduced pressure. The residue was used further without work-up. This gave 26 mg (84% of theory) of the title compound. LC-MS (Method 5): $R_t$=4.39 min; MS (ESIpos): m/z=863 $(M+H)^+$.

Intermediate C98 tert-Butyl 3-[2-{(1R)-1-[1-benzyl-4-(2,5-difluorophenyl)-1H-pyrrol-2-yl]-2,2-dimethylpropyl}-18-(2,5-dioxo-2,5-dihydro-1H-pyrrol-1-yl)-3,8,13-trioxo-5-thia-2,9,12-triazaoctadec-1-yl]pyrrolidine-1-carboxylate (Isomer 2)

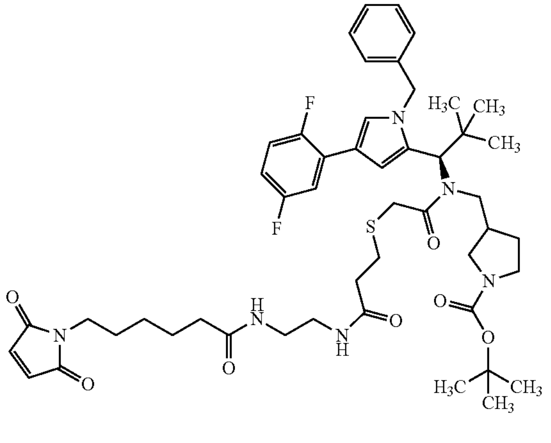 [SMILES: CC(C)(C)OC(=O)N1CCC(CN(C(=O)CSCCC(=O)NCCNC(=O)CCCCCN2C(=O)C=CC2=O)[C@@H](c2cc(-c3cc(F)ccc3F)cn2Cc2ccccc2)C(C)(C)C)C1]

Under argon, 14.17 mg (0.11 mmol) of N,N-diisopropylethylamin and 27.80 mg (0.07 mmol) of HATU were added to a solution of 25.0 mg (0.04 mmol) of 3-{[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Intermediate C96) in 2.81 ml of DMF. The reaction mixture was stirred at RT for 10 minutes. A solution of 37.30 mg (0.07 mmol) of N-(2-aminoethyl)-6-(2,5-dioxo-2,5-dihydro-1H-pyrrol-1-yl)hexanamide-ethane (1:1) trifluoroacetic acid in 1.4 ml of DMF and 5 mg (0.04 mmol) of N,N-diisopropylethylamine was then added, and the mixture was stirred at RT overnight. Water was added and the mixture was extracted with dichloromethane. The organic phase was dried over magnesium sulphate and the solvent was evaporated under reduced pressure. The residue was employed without further purification. This gave 22 mg (63% of theory) of the title compound.

LC-MS (Method 5): $R_t$=4.54 min; MS (ESIpos): m/z=919 $(M+H)^+$.

Intermediate C99 tert-Butyl 3-[2-{(1R)-1-[1-benzyl-4-(2,5-difluorophenyl)-1H-pyrrol-2-yl]-2,2-dimethylpropyl}-24-(2,5-dioxo-2,5-dihydro-1H-pyrrol-1-yl)-3,8,19-trioxo-12,15-dioxa-5-thia-2,9,18-triazatetracos-1-yl]pyrrolidine-1-carboxylate (Isomer 2)

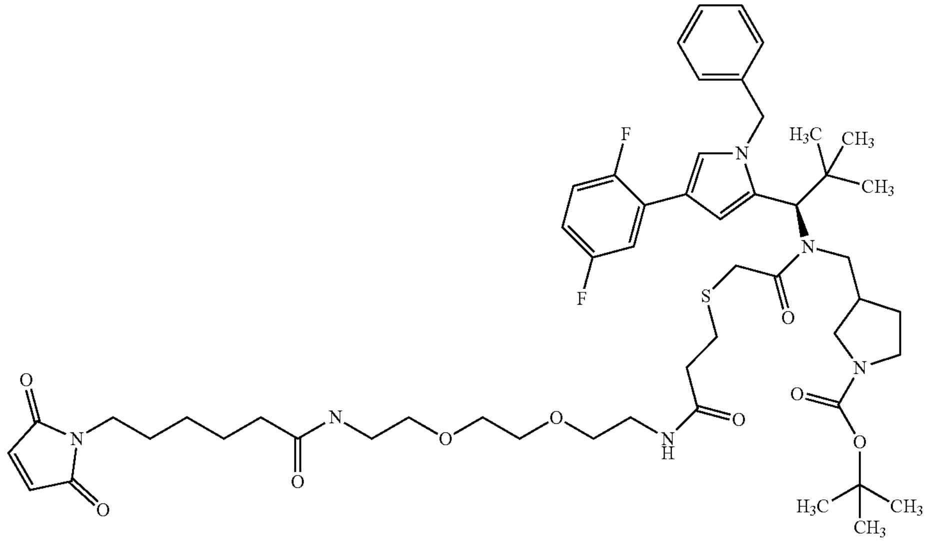 [SMILES: CC(C)(C)OC(=O)N1CCC(CN(C(=O)CSCCC(=O)NCCOCCOCCNC(=O)CCCCCN2C(=O)C=CC2=O)[C@@H](c2cc(-c3cc(F)ccc3F)cn2Cc2ccccc2)C(C)(C)C)C1]

Under argon, 14.17 mg (0.11 mmol) of N,N-diisopropylethylamin and 27.80 mg (0.07 mmol) of HATU were added to a solution of 25.0 mg (0.04 mmol) of 3-{[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Intermediate C96) in 2.81 ml of DMF. The reaction mixture was stirred at RT for 10 minutes. A solution of 35.05 mg (0.07 mmol) of N-{2-[2-(2-aminoethoxy)ethoxy]ethyl}-6-(2,5-dioxo-2,5-dihydro-1H-pyrrol-1-yl)hexanamide-ethane (1:1) trifluoroacetic acid (Intermediate L82) in 1.4 ml of DMF and 5 mg (0.04 mmol) of N,N-diisopropylethylamine was then added, and the mixture was stirred at RT overnight. Water was added and the mixture was extracted with dichloromethane. The organic phase was dried over magnesium sulphate, the solvent was evaporated under reduced pressure and the residue was dried under high vacuum. The residue was purified by preparative HPLC. This gave 25 mg (60% of theory) of the title compound.

LC-MS (Method 1): $R_t$=4.52 min; MS (ESIpos): m/z=1007 $(M+H)^+$.

Intermediate C100

2-(Trimethylsilyl)ethyl {(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2R)-2-(2,5-dioxo-2,5-dihydro-1H-pyrrol-1-yl)propanoyl]amino}ethyl)amino]-1-oxobutan-2-yl}carbamate

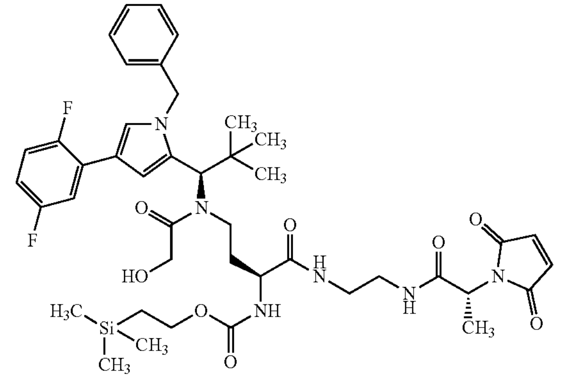 [SMILES: C[C@H](C(=O)NCCNC(=O)[C@H](CCN(C(=O)CO)[C@@H](c1cc(-c2cc(F)ccc2F)cn1Cc1ccccc1)C(C)(C)C)NC(=O)OCC[Si](C)(C)C)N1C(=O)C=CC1=O]

22.2 mg (0.068 mmol) of (2R)—N-(2-aminoethyl)-2-(2,5-dioxo-2,5-dihydro-1H-pyrrol-1-yl)propanamide (1:1) trifluoroacetic acid were added to a solution of 45 mg (0.068 mmol) of (2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic acid (Intermediate C58) in 5.8 ml of DMF. After 30 minutes of stirring at RT, 39 mg (0.10 mmol) of HATU and 36 mg (0.27 mmol) of N,N-diisopropylethylamine were added to the mixture. The reaction mixture was stirred at RT for 1 h. Without work-up, the mixture was purified by preparative HPLC. This gave 7 mg (12% of theory) of the title compound.

LC-MS (Method 1): $R_t$=1.41 min; MS (ESIpos): m/z 851 $(M+H)^+$.

Intermediate C101

Trifluoroacetic Acid/methyl (2S)-4-[(acetoxyacetyl){(1R)-1-[1-benzyl-4-(2,5-difluorophenyl)-1H-pyrrol-2-yl]-2,2-dimethylpropyl}amino]-2-aminobutanoate (1:1)

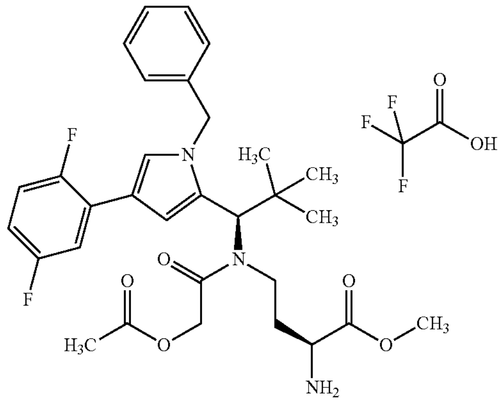 [SMILES: COC(=O)[C@@H](N)CCN(C(=O)COC(C)=O)[C@@H](c1cc(-c2cc(F)ccc2F)cn1Cc1ccccc1)C(C)(C)C ; O=C(O)C(F)(F)F]

4.3 g (12.2 mmol) of Intermediate C52 were dissolved in 525 ml of DCM, and 3.63 g (17.12 mmol) of sodium triacetoxyborohydride and 8.4 ml of acetic acid were added. After 5 min of stirring at RT, 3.23 g (11.85 mmol) of methyl (2S)-4-oxo-2-({[2-(trimethylsilyl)ethoxy]carbonyl}amino) butanoate (prepared from (3S)-3-amino-4-methoxy-4-oxobutanoic acid by classical methods) dissolved in 175 ml of DCM were added, and the mixture was stirred at RT for a further 45 min. The mixture was then diluted with DCM and extracted twice with 100 ml of saturated sodium bicarbonate solution and then with saturated sodium chloride solution. The organic phase was dried over magnesium sulphate, filtered and concentrated. The residue was purified by preparative HPLC. Combination of the appropriate fractions, concentration and drying of the residue under high vacuum gave 4.6 g (61% of theory) of the intermediate.

LC-MS (Method 12): $R_t$=1.97 min; MS (ESIpos): m/z=614.32 $(M+H)^+$.

2.06 g (3.36 mmol) of this intermediate were initially charged in 76 ml of DCM and acylated with 0.81 ml (7.17 mmol) of 2-chloro-2-oxoethyl acetate in the presence of 2.1 ml of triethylamine. After 20 h of stirring at RT, 0.36 ml of 2-chlor-2-oxoethyl acetate and 0.94 ml of triethylamine were added and the reaction was stirred at RT for a further 15 min. The mixture was then diluted with 500 ml of ethyl acetate and extracted successively twice with 300 ml of 5% strength citric acid, twice with 300 ml of saturated sodium bicarbonate solution and once with 100 ml of saturated sodium chloride solution and then dried over magnesium sulphate and concentrated. Drying under high vacuum gave 2.17 g (79% of theory) of the protected intermediate.

LC-MS (Method 1): $R_t$=1.48 min; MS (ESIpos): m/z=714 $(M+H)^+$.

321 mg (0.342 mmol) of this intermediate were dissolved in 7 ml of 2,2,2-trifluoroethanol. 279.5 mg (2.05 mmol) of zinc chloride were added, and the reaction mixture was stirred at 50° C. for 2 h. 599 mg (2.05 mmol) of ethylene-diamine-N,N,N',N'-tetraacetic acid and 2 ml of a 0.1% strength aqueous trifluoroacetic acid solution in water were then added, and the mixture was then concentrated under reduced pressure. The residue was purified by preparative HPLC. Concentration of the appropriate fractions and lyophilization of the residue from acetonitrile/water gave 60 mg (26% of theory) of the title compound, which still contained a portion of the deacetylated compound.

LC-MS (Method 1): $R_t$=0.91 min and 0.95 min; MS (ESIpos): m/z=528 and 570 $(M+H)^+$.

Intermediate C102

(2S)-4-[{(1R)-1-[1-Benzyl-4-(2,5-difluorophenyl)-1H-pyrrol-2-yl]-2,2-dimethylpropyl}(glycoloyl)amino]-2-{[(benzyloxy)carbonyl]amino}butanoic Acid

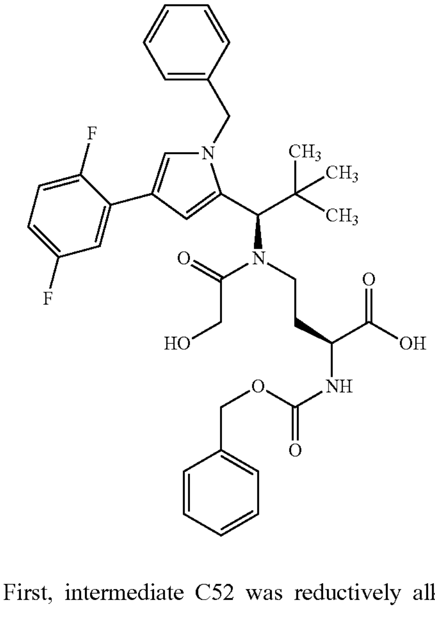

First, intermediate C52 was reductively alkylated with benzyl (2S)-2-{[(benzyloxy)carbonyl]amino}-4-oxobutanoate analogously to intermediate C2. The secondary amino group was then acylated with 2-chloro-2-oxoethyl acetate, and the two ester groups were then hydrolysed with 2M lithium hydroxide solution in methanol.

LC-MS (Method 1): $R_t$=1.31 min; MS (ESIpos): m/z=646 $(M-H)^-$.

Intermediate C103

2-(Trimethylsilyl)ethyl N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N2-{[2-(trimethylsilyl)ethoxy]carbonyl}-L-glutaminate

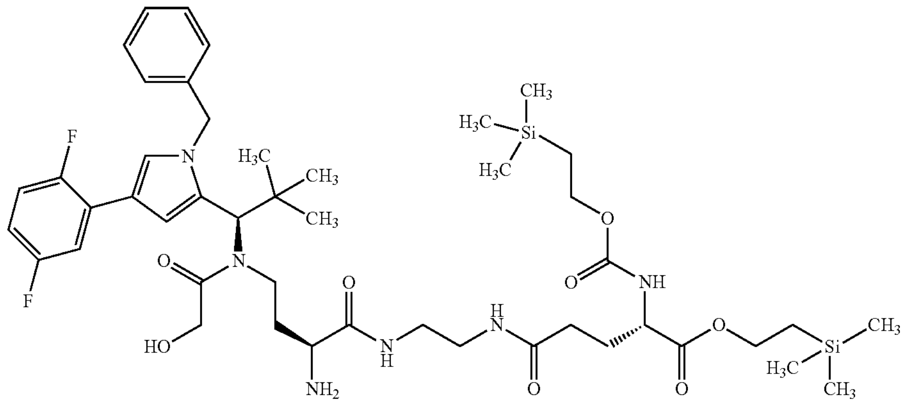 [SMILES: CC(C)(C)[C@H](c1cc(-c2cc(F)ccc2F)cn1Cc1ccccc1)N(CC[C@H](N)C(=O)NCCNC(=O)CC[C@H](NC(=O)OCC[Si](C)(C)C)C(=O)OCC[Si](C)(C)C)C(=O)CO]

The title compound was first prepared by coupling 151 mg (0.23 mmol) of Intermediate C102 with 128 g (0.234 mmol) of Intermediate L98 in DMF in the presence of HATU and N,N-diisopropylethylamine. Subsequently, the Z protecting group was removed by hydrogenation over 10% palladium on activated carbon at RT under standard hydrogen pressure for 30 minutes, giving the title compound.

Yield: 30% of theory over 2 stages

LC-MS (Method 1): $R_t$=1.14 min; MS (ESIpos): m/z=929 $(M+H)^+$.

Intermediate C104

2-(Trimethylsilyl)ethyl (3R,4R)-3-[({(1R)-1-[1-benzyl-4-(2,5-difluorophenyl)-1H-pyrrol-2-yl]-2,2-dimethylpropyl}amino)methyl]-4-fluoropyrrolidine-1-carboxylate

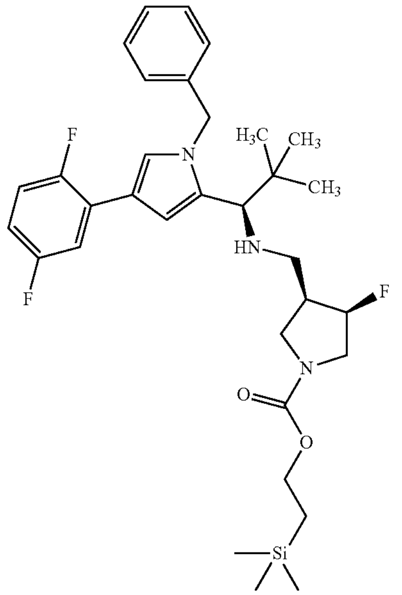 [SMILES: CC(C)(C)[C@@H](NC[C@@H]1CN(C(=O)OCC[Si](C)(C)C)C[C@@H]1F)c1cc(-c2cc(F)ccc2F)cn1Cc1ccccc1]

To a solution of 2.24 g (6.31 mmol) of (1R)-1-[1-benzyl-4-(2,5-difluorophenyl)-1H-pyrrol-2-yl]-2,2-dimethylpropan-1-amine in 56.0 ml of dichloromethane together with 4 Å molecular sieve were added 1.87 g (8.84 mmol) of sodium triacetoxyborohydride, and the mixture was stirred at room temperature for 15 minutes. Subsequently, 2.20 g (7.58 mmol) of 2-(trimethylsilyl)ethyl (3R,4S)-3-fluoro-4-formylpyrrolidine-1-carboxylate (Ref: WO 2014/151030A1) were added, and the reaction mixture was stirred at room temperature for 3.5 h. The mixture was diluted with dichloromethane and the organic phase was washed with saturated sodium hydrogencarbonate solution and water. The organic phase was dried over sodium sulphate and concentrated. The residue was purified by preparative HPLC. This gave 1.39 g (24% of theory) of the title compound.

LC-MS (Method 1): $R_t$=1.15 min; MS (ESIpos): m/z=600 $(M+H)^+$.

Intermediate C105

2-(Trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate

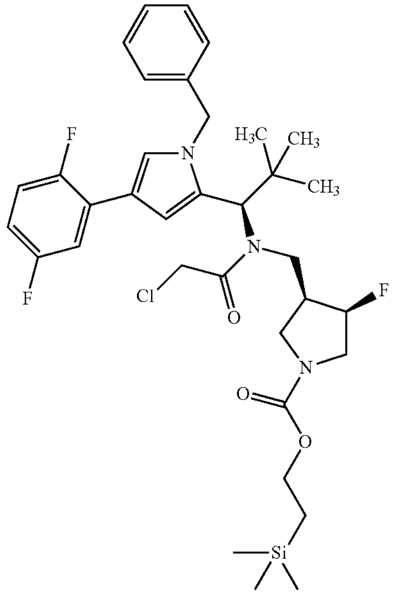 [SMILES: CC(C)(C)[C@H](c1cc(-c2cc(F)ccc2F)cn1Cc1ccccc1)N(C[C@@H]1CN(C(=O)OCC[Si](C)(C)C)C[C@@H]1F)C(=O)CCl]

To a solution of 692.8 mg (0.88 mmol) of 2-(trimethylsilyl)ethyl (3R,4R)-3-[({(1R)-1-[1-benzyl-4-(2,5-difluorophenyl)-1H-pyrrol-2-yl]-2,2-dimethylpropyl}amino)methyl]-4-fluoropyrrolidine-1-carboxylate (Intermediate C104) in 8.7 ml of dichloromethane together with 4 Å molecular sieve were added 295.0 mg (2.91 mmol) of triethylamine and 418.9 mg (3.71 mmol) of chloroacetyl chloride, and the reaction mixture was stirred at RT for 2.5 h. The reaction mixture was diluted with dichloromethane and the organic phase was washed with saturated sodium bicarbonate solution and saturated ammonium chloride solution. The organic phase was dried over sodium sulphate and concentrated. The residue was once again dissolved in 8.7 ml of dichloromethane together with 4 Å molecular sieve and 295.0 mg (2.91 mmol) of triethylamine and 418.9 mg (3.71 mmol) of chloroacetyl chloride were added and the reaction mixture was stirred at RT for 3 h. The reaction mixture was diluted with dichloromethane and the organic phase was washed with saturated sodium bicarbonate solution and saturated ammonium chloride solution. The organic phase was dried over sodium sulphate and concentrated. The organic phase was dried over sodium sulphate, concentrated and used further without purification. This gave 691 mg (74% of theory, 64% pure) of the title compound.

LC-MS (Method 1): $R_t$=1.78 min; MS (ESIpos): m/z=676 $(M+H)^+$.

Intermediate C106

3-{[2-({(1R)-1-[1-Benzyl-4-(2,5-difluorophenyl)-1H-pyrrol-2-yl]-2,2-dimethylpropyl}{[(3R,4R)-4-fluoro-1-({[2-(trimethylsilyl)ethoxy]carbonyl}pyrrolidin-3-yl]methyl}amino)-2-oxoethyl]sulphanyl}propanoic Acid

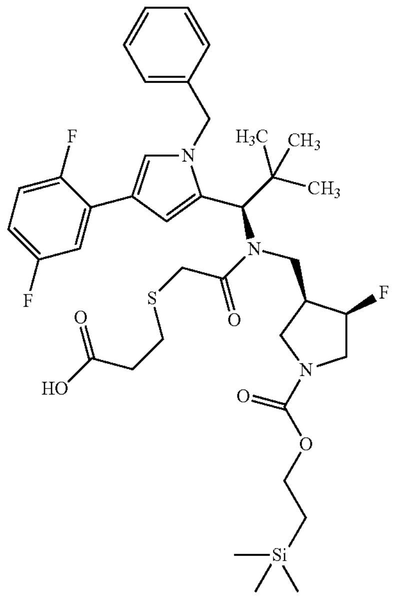 [SMILES: CC(C)(C)[C@H](c1cc(-c2cc(F)ccc2F)cn1Cc1ccccc1)N(C[C@@H]1CN(C(=O)OCC[Si](C)(C)C)C[C@@H]1F)C(=O)CSCCC(=O)O]

To a mixture of 691.0 mg (0.65 mmol) of 2-(trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate (Intermediate C105) and 76.3 mg (0.72 mmol) of 3-sulphanylpropanoic acid in 15 ml of methanol and a few drops of water were added 316 mg (2.29 mmol) of potassium carbonate. The reaction mixture was stirred at 50° C. for 1.5 h. Ethyl acetate was added to the reaction mixture and the organic phase was washed repeatedly with water and with saturated NaCl solution. The organic phase was dried over magnesium sulphate, the solvent was evaporated under reduced pressure and the residue was dried under high vacuum. The residue was used further without work-up. This gave 502 mg (67% of theory, 65% pure) of the title compound.

LC-MS (Method 1): $R_t$=1.48 min; MS (ESIneg): m/z=744 $(M-H)^-$.

Intermediate C107

S-{[2-({(1R)-1-[1-Benzyl-4-(2,5-difluorophenyl)-1H-pyrrol-2-yl]-2,2-dimethylpropyl}{[(3R,4R)-4-fluoro-1-({[2-(trimethylsilyl)ethoxy]carbonyl}pyrrolidin-3-yl]methyl}amino)-2-oxoethyl]-L-cysteine

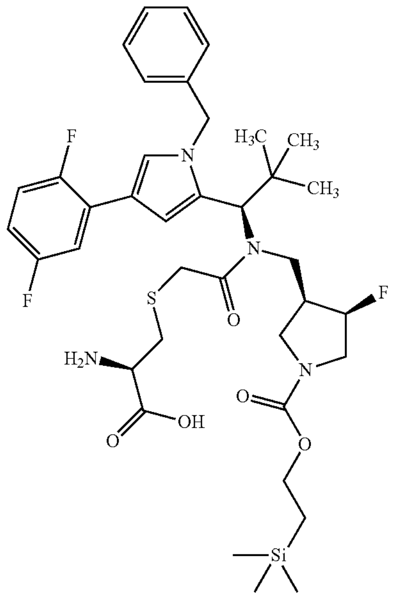 [SMILES: CC(C)(C)[C@H](c1cc(-c2cc(F)ccc2F)cn1Cc1ccccc1)N(C[C@@H]1CN(C(=O)OCC[Si](C)(C)C)C[C@@H]1F)C(=O)CSC[C@H](N)C(=O)O]

203.6 mg (1.68 mmol) of L-cysteine were suspended in 0.95 ml of water together with 201.7 mg (2.40 mmol) of sodium bicarbonate. To this were added 170.0 mg (0.24 mmol) of 2-(trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate (Intermediate 105) dissolved in 9.5 ml of iso-propanol and 438.5 g (2.40 mmol) of 1,8-diazabicyclo[5.4.0]undec-7-ene. The reaction mixture was stirred at 50° C. for 3 h. Ethyl acetate was added to the reaction mixture and the organic phase was washed repeatedly with saturated sodium bicarbonate solution and once with saturated NaCl solution. The organic phase was dried over sodium sulphate and the solvent was evaporated under reduced pressure. The residue was used further without further purification. This gave 152 mg (83% of theory) of the title compound.

LC-MS (Method 1): $R_t$=1.26 min; MS (ESIpos): m/z=762 $(M+H)^+$.

Intermediate C108

2-(Trimethylsilyl)ethyl $N^6$—(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$-{[2-(trimethylsilyl)ethoxy]carbonyl}-L-lysinate

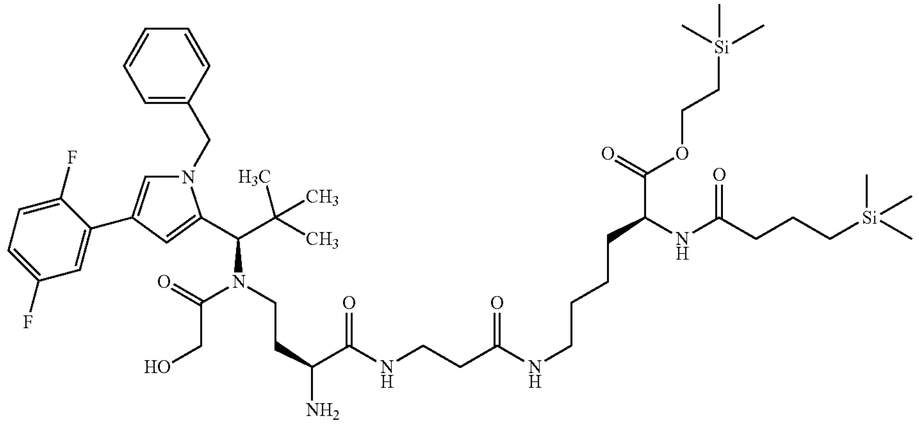 [SMILES: CC(C)(C)[C@H](c1cc(-c2cc(F)ccc2F)cn1Cc1ccccc1)N(CC[C@H](N)C(=O)NCCC(=O)NCCCC[C@H](NC(=O)CCC[Si](C)(C)C)C(=O)OCC[Si](C)(C)C)C(=O)CO]

The title compound was prepared by coupling 103 mg (0.16 mmol) of Intermediate C102 with 110 mg (0.175 mmol) of 2-(trimethylsilyl)ethyl $N^6$-beta-alanyl-$N^2$-{[2-(trimethylsilyl)ethoxy]carbonyl}-L-lysinate in DMF in the presence of EDCI, HOBT and N,N-diisopropylethylamine. Subsequently, the Z protecting group was removed by hydrogenation over 10% palladium on activated carbon in dichloromethane/methanol 1:1 at RT under standard hydrogen pressure for 1 hour, giving the title compound in a yield of 113 mg (75% of theory over 2 stages).

LC-MS (Method 1): $R_t$=1.17 min; MS (ESIpos): m/z=957 $(M+H)^+$.

The intermediate used here was prepared by conventional methods of peptide chemistry by coupling of commercially available N-(tert-butoxycarbonyl)-beta-alanine and 2-(trimethylsilyl)ethyl $N^2$-[(benzyloxy)carbonyl]-L-lysinate in the presence of HATU, hydrogenolytic detachment of the Z protecting group, introduction of the trimethylsilylethyloxycarbonyl (Teoc) protecting group with 1-({[2-(trimethylsilyl)ethoxy]carbonyl}oxy)pyrrolidine-2,5-dione and final gentle detachment of the Boc protecting group by stirring in a 7.5% trifluoroacetic acid solution in dichloromethane for 45 minutes.

LC-MS (Method 1): $R_t$=0.83 min; MS (ESIpos): m/z=462 $(M+H)^+$.

Intermediate C109

Di-tert-butyl N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-L-glutamate

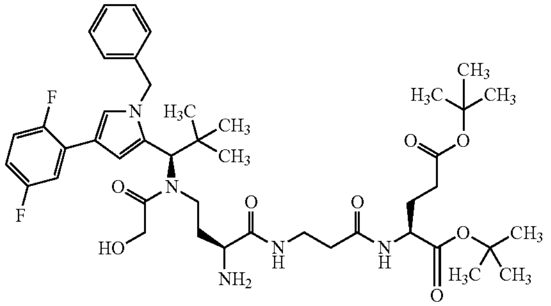 [SMILES: CC(C)(C)OC(=O)CC[C@H](NC(=O)CCNC(=O)[C@@H](N)CCN(C(=O)CO)[C@@H](c1cc(-c2cc(F)ccc2F)cn1Cc1ccccc1)C(C)(C)C)C(=O)OC(C)(C)C]

First of all, the dipeptide derivative di-tert-butyl beta-alanyl-L-glutamate was prepared by conventional methods of peptide chemistry by coupling of commercially available N-[(benzyloxy)carbonyl]-beta-alanine and di-tert-butyl L-glutamate hydrochloride (1:1) in the presence of HATU and subsequent hydrogenolytic detachment of the Z protecting group. The title compound was then prepared by coupling this intermediate with Intermediate C102 in the presence of HATU and N,N-diisopropylethylamine and subsequent detachment of the Z protecting group by hydrogenation over 10% palladium on activated carbon in methanol at RT under standard hydrogen pressure for 45 minutes.

LC-MS (Method 1): $R_t$=0.99 min; MS (ESIpos): m/z=826 $[M+H]^+$.

Intermediate C110

Dibenzyl N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-L-glutamate

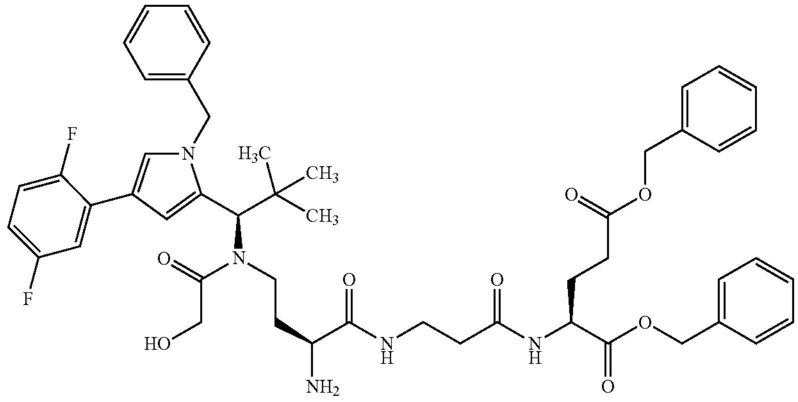 [SMILES: CC(C)(C)[C@H](c1cc(-c2cc(F)ccc2F)cn1Cc1ccccc1)N(CC[C@H](N)C(=O)NCCC(=O)N[C@@H](CCC(=O)OCc1ccccc1)C(=O)OCc1ccccc1)C(=O)CO]

The title compound was prepared by coupling dibenzyl L-glutamate, which had been released beforehand from its p-toluenesulphonic acid salt by partitioning between ethyl acetate and 5% sodium hydrogencarbonate solution, with Intermediate C61 in the presence of HATU and N,N-diisopropylethylamine and subsequent detachment of the Teoc protecting group with zinc chloride in trifluoroethanol.

LC-MS (Method 1): $R_t$=1.09 min; MS (ESIpos): m/z=894 $[M+H]^+$.

Intermediate C111

Di-tert-butyl N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamate

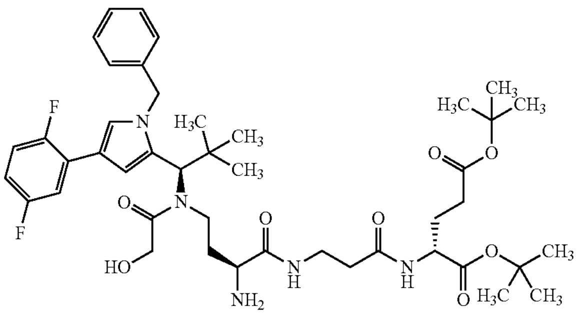 [SMILES: CC(C)(C)OC(=O)CC[C@@H](NC(=O)CCNC(=O)[C@@H](N)CCN(C(=O)CO)[C@@H](c1cc(-c2cc(F)ccc2F)cn1Cc1ccccc1)C(C)(C)C)C(=O)OC(C)(C)C]

The title compound was synthesized analogously to Intermediate C109.

LC-MS (Method 1): $R_t$=1.06 min; MS (ESIpos): m/z=826 $[M+H]^+$.

Intermediate C112

$N^2$-Acetyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-$N^6$-(tert-butoxycarbonyl)-L-lysinamide

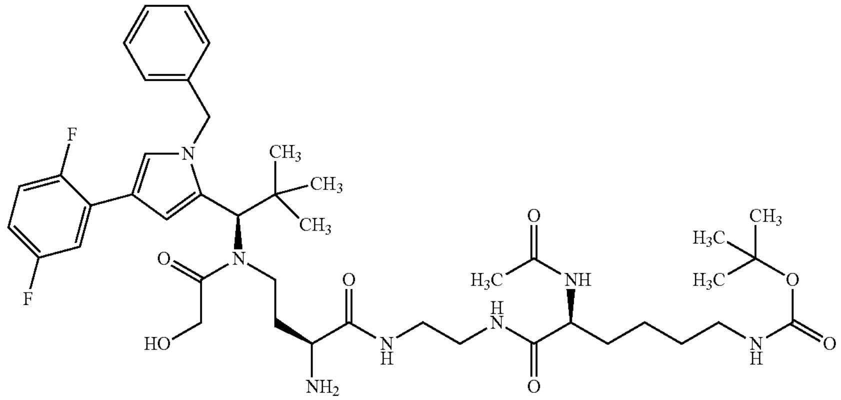 [SMILES: CC(=O)N[C@@H](CCCCNC(=O)OC(C)(C)C)C(=O)NCCNC(=O)[C@@H](N)CCN(C(=O)CO)[C@@H](c1cc(-c2cc(F)ccc2F)cn1Cc1ccccc1)C(C)(C)C]

The title compound was prepared by HATU coupling of Intermediate C102 and Intermediate L108 in DMF in the presence of N,N-diisopropylethylamine and subsequent detachment of the Z protecting group by hydrogenation in DCM/methanol 1:1 over 10% palladium on activated carbon under standard pressure.

LC-MS (Method 1): $R_t$=0.96 min; MS (ESIpos): m/z=826 $(M+H)^+$.

Intermediate C113

Trifluoroacetic Acid/benzyl N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-3-{[(benzyloxy)carbonyl]amino}-D-alaninate (1:1)

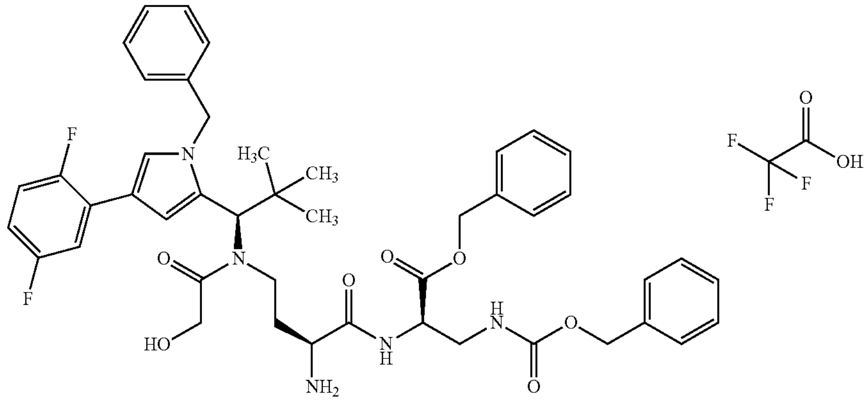 [SMILES: CC(C)(C)[C@H](c1cc(-c2cc(F)ccc2F)cn1Cc1ccccc1)N(CC[C@H](N)C(=O)N[C@H](CNC(=O)OCc1ccccc1)C(=O)OCc1ccccc1)C(=O)CO ; O=C(O)C(F)(F)F]

First of all, trifluoroacetic acid/benzyl-3-{[(benzyloxy)carbonyl]amino}-D-alaninate (1:1) was prepared proceeding from commercially available 3-{[(benzyloxy)carbonyl]amino}-N-(tert-butoxycarbonyl)-D-alanine by esterification with benzyl alcohol in the presence of EDC/DMAP, followed by elimination of the Boc protecting group with trifluoroacetic acid. This amino acid unit was then coupled to Intermediate C58 in the presence of HATU and N,N-diisopropylethylamine in DMF. In the last step, by stirring at 50° C. in trifluoroethanol with 6 equivalents of zinc chloride for 2 hours and purification by preparative HPLC, the title compound was obtained.

LC-MS (Method 1): $R_t$=1.05 min; MS (ESIpos): m/z=824 $[M+H]^+$.

Intermediate C114

Trifluoroacetic Acid/tert-butyl 4-({(2S)-2-amino-4-[{(1R)-1-[1-benzyl-4-(2,5-difluorophenyl)-1H-pyrrol-2-yl]-2,2-dimethylpropyl}(glycoloyl)amino] butanoyl}amino)butanoate (1:1)

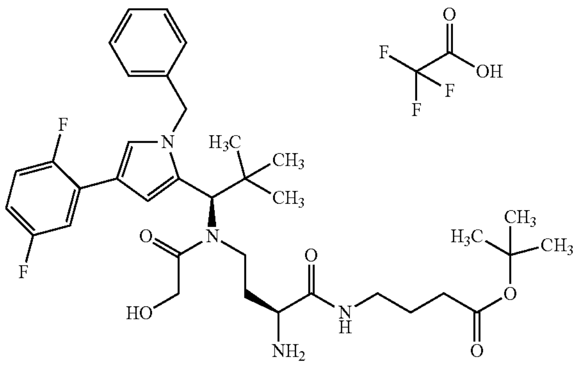 [SMILES: CC(C)(C)OC(=O)CCCNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

First of all, Intermediate C102 was coupled to tert-butyl 4-aminobutanoate hydrochloride (1:1) in the presence of HATU and N,N-diisopropylethylamine. Subsequently, by hydrogenating over 10% palladium on activated carbon in DCM/methanol 1:1 at RT under standard hydrogen pressure for 1 hour, the title compound was obtained.

LC-MS (Method 1): $R_t$=1.0 min; MS (ESIpos): m/z=655 $[M+H]^+$.

Intermediate C115

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1)

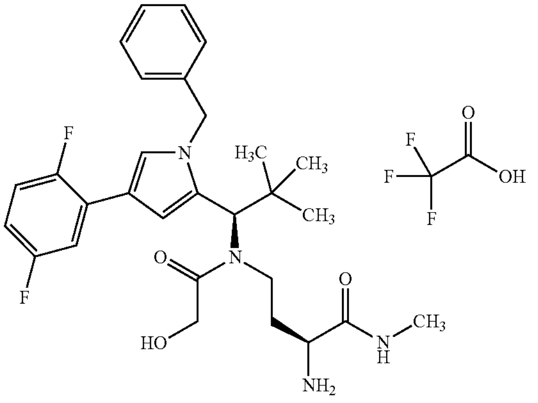 [SMILES: CNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

First of all, Intermediate C52 was reductively alkylated with benzyl (2S)-2-{[(benzyloxy)carbonyl]amino}-4-oxobutanoate in analogy to Intermediate C2. Subsequently, the secondary amino group was acylated with 2-chloro-2-oxoethyl acetate as described in Intermediate C27.

190 mg (0.244 mmol) of this intermediate were taken up in 7.5 ml of ethanol, and 0.35 ml of a 40% methanamine solution in water was added. The mixture was stirred at 50° C. for 3 h and then the same amount of methanamine again was added. After stirring at 50° C. for another 5 h, the mixture was concentrated and the residue was purified by preparative HPLC. 78 mg (48% of theory) of this intermediate were obtained.

LC-MS (Method 1): $R_t$=1.32 min; MS (EIpos): m/z=661 $[M+H]^+$.

78 mg (0.118 mmol) of this intermediate were dissolved in 8 ml of ethanol and, after addition of 15 mg of 10% palladium on activated carbon, hydrogenated at RT under standard hydrogen pressure for 3 h. The catalyst was then filtered off and the solvent was removed under reduced pressure and the product was purified by preparative HPLC. After lyophilisation from acetonitrile/water, 33 mg (44% of theory) of the title compound were obtained.

LC-MS (Method 1): $R_t$=0.88 min; MS (ESIpos): m/z=527 $(M+H)^+$.

$^1$H-NMR (500 MHz, DMSO-$d_6$): δ=8.1 (m, 1H), 8.0 (m, 3H), 7.9 (m, 1H), 7.65 (m, 1H), 7.5 (s, 1H), 7.15-7.35 (m, 5H) 7.0 (m, 1H), 6.85 (m, 1H), 5.6 (s, 1H), 4.9 and 5.2 (2d, 2H), 4.02 and 4.22 (2d, 2H), 3.2-3.5 (m, 6H), 0.7 and 1.46 (2m, 2H), 0.8 (s, 9H).

Intermediate C116

Trifluoroacetic Acid/N$^1$-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide (1:1)

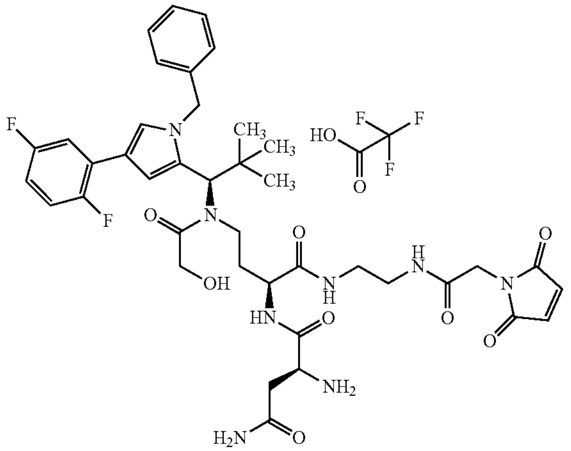 [SMILES: CC(C)(C)[C@H](c1cc(-c2cc(F)ccc2F)cn1Cc1ccccc1)N(CC[C@H](NC(=O)[C@@H](N)CC(N)=O)C(=O)NCCNC(=O)CN1C(=O)C=CC1=O)C(=O)CO ; O=C(O)C(F)(F)F]

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[(2,5-dioxo-2,5-dihydro-1H-pyrrol-1-yl)acetyl]amino}ethyl)butanamide (1:1) (81.0 mg, 100 μmol) (Intermediate F104) and 2,5-dioxopyrrolidin-1-yl N$^2$-(tert-butoxycarbonyl)-L-asparaginate (43.0 mg, 131 μmol) were dissolved in 5.0 ml of DMF. The reaction mixture was stirred with N,N-diisopropylethylamine (61 μl, 350 μmol), at RT for 1 h, and then purified directly by means of preparative RP-HPLC (column: Chromatorex 125×30; 10μ, flow rate: 75 ml/min, MeCN/water, 0.1% TFA). The solvents were evaporated under reduced pressure and the residue was lyophilized. This gave 84 mg (88% of theory) of the compound tert-butyl [(2S)-4-amino-1-({(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}amino)-1,4-dioxobutan-2-yl]carbamate.

LC-MS (Method 1): $R_t$=1.09 min; MS (ESIpos): m/z=907 $[M+H]^+$ tert-Butyl [(2S)-4-amino-1-({(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}amino)-1,4-dioxobutan-2-yl]carbamate (83.0 mg, 91.5 μmol) was dissolved in 5.0 ml of trifluoroethanol. Zinc chloride (74.8 mg, 549 μmol) was added to the reaction mixture, which was stirred at 50° C. for a further 15 min. Ethylenediamine-N,N,N',N'-tetraacetic acid (160 mg, 549 μmol) was added to the mixture, which was diluted with 5.0 ml of acetonitrile/water, TFA (20 μl) was added and the mixture was stirred for 10 min. The mixture was filtered through a syringe filter and purified by means of preparative RP-HPLC (column: Chromatorex 125×30; 10μ, flow rate: 75 ml/min, MeCN/water, 0.1% TFA). The solvents were evaporated under reduced pressure and the residue was dried under high vacuum. This gave 50 mg (58% of theory) of the title compound.

LC-MS (Method 1): $R_t$=0.81 min; MS (ESIpos): m/z=807 $[M+H]^+$

Intermediate L1

Trifluoroacetic Acid/N-(2-aminoethyl)-2-(2,5-dioxo-2,5-dihydro-1H-pyrrol-1-yl)acetamide (1:1)

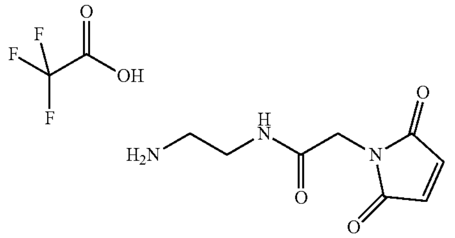 [SMILES: O=C(O)C(F)(F)F ; NCCNC(=O)CN1C(=O)C=CC1=O]

The title compound was prepared by classical methods of peptide chemistry from commercially available (2,5-dioxo-2,5-dihydro-1H-pyrrol-1-yl)acetic acid and tert-butyl (2-aminoethyl)carbamate.

HPLC (Method 11): $R_t$=0.19 min;

LC-MS (Method 1): $R_t$=0.17 min; MS (ESIpos): m/z=198 $(M+H)^+$.

Intermediate L2

Trifluoroacetic Acid/rel-(1R,2S)-2-amino-N-[2-(2,5-dioxo-2,5-dihydro-1H-pyrrol-1-yl)ethyl]cyclopentanecarboxamide (1:1)

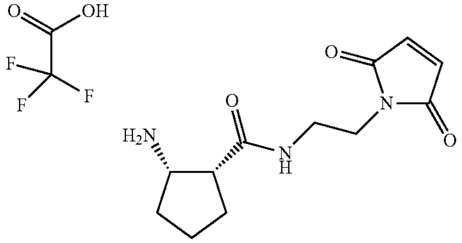 [SMILES: O=C(O)C(F)(F)F ; N[C@H]1CCC[C@H]1C(=O)NCCN1C(=O)C=CC1=O]

The title compound was prepared from 50 mg (0.214 mmol) of commercially available cis-2-[(tert-butoxycarbonyl)amino]-1-cyclopentanecarboxylic acid and 60 mg (0.235 mmol) of likewise commercially available trifluoroacetic acid/1-(2-aminoethyl)-1H-pyrrole-2,5-dione (1:1) by coupling with EDC/HOBT and subsequent deprotection with TFA. This gave 36 mg (38% of theory over 2 steps) of the title compound.

HPLC (Method 11): $R_t$=0.2 min;

LC-MS (Method 1): $R_t$=0.17 min; MS (ESIpos): m/z=252 $(M+H)^+$.

Intermediate L3

Trifluoroacetic Acid/(1S,2R)-2-amino-N-[2-(2,5-dioxo-2,5-dihydro-1H-pyrrol-1-yl)ethyl]cyclopentanecarboxamide (1:1)

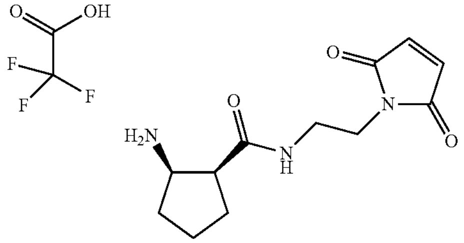 [SMILES: O=C(O)C(F)(F)F ; N[C@@H]1CCC[C@@H]1C(=O)NCCN1C(=O)C=CC1=O]

The title compound was prepared from 50 mg (0.214 mmol) of commercially available (1S,2R)-2-[(tert-butoxycarbonyl)amino]cyclopentanecarboxylic acid with 72 mg (0.283 mmol) of likewise commercially available trifluoroacetic acid/1-(2-aminoethyl)-1H-pyrrole-2,5-dione (1:1) by coupling with EDC/HOBT and subsequent deprotection with TFA. This gave 13 mg (16% of theory over 2 steps) of the title compound.

HPLC (Method 11): $R_t$=0.2 min;

LC-MS (Method 1): $R_t$=0.2 min; MS (ESIpos): m/z=252 $(M+H)^+$.

Intermediate L4

Trifluoroacetic Acid/N-(2-aminoethyl)-4-(2,5-dioxo-2,5-dihydro-1H-pyrrol-1-yl)cyclohexanecarboxamide (1:1)

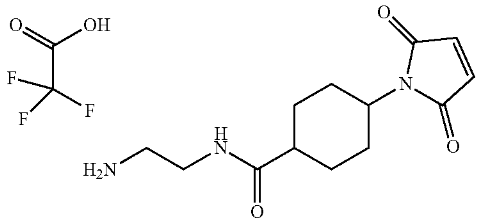 [SMILES: O=C(O)C(F)(F)F ; NCCNC(=O)C1CCC(N2C(=O)C=CC2=O)CC1]

The title compound was prepared by classical methods of peptide chemistry from commercially available 1-[(4-{[(2,5-dioxopyrrolidin-1-yl)oxy]carbonyl}cyclohexyl)methyl]-1H-pyrrole-2,5-dione and tert-butyl (2-aminoethyl)carbamate.

HPLC (Method 11): $R_t$=0.26 min;

LC-MS (Method 1): $R_t$=0.25 min; MS (ESIpos): m/z=280 $(M+H)^+$.

Intermediate L5

Trifluoroacetic Acid/N-[4-(2,5-dioxo-2,5-dihydro-1H-pyrrol-1-yl)phenyl]-beta-alaninamide (1:1)

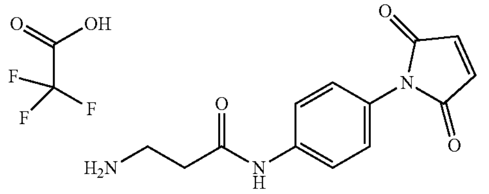 [SMILES: O=C(O)C(F)(F)F ; NCCC(=O)Nc1ccc(N2C(=O)C=CC2=O)cc1]

The title compound was prepared by classical methods of peptide chemistry from commercially available 1-(4-aminophenyl)-1H-pyrrole-2,5-dione and N-(tert-butoxycarbonyl)-beta-alanine.

HPLC (Method 11): $R_t$=0.22 min;

LC-MS (Method 1): $R_t$=0.22 min; MS (ESIpos): m/z=260 $(M+H)^+$.

Intermediate L6

Trifluoroacetic Acid/tert-butyl-N-[6-(2,5-dioxo-2,5-dihydro-1H-pyrrol-1-yl)hexanoyl]-L-valyl-L-alanyl-L-lysinate (1:1)

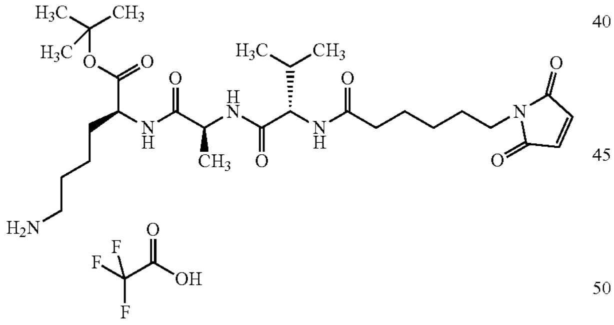

The title compound was prepared by initially coupling, in the presence of EDC/HOBT, commercially available 6-(2,5-dioxo-2,5-dihydro-1H-pyrrol-1-yl)hexanoic acid with the partially protected peptide tert-butyl L-valyl-L-alanyl-N6-(tert-butoxycarbonyl)-L-lysinate, prepared by classical methods of peptide chemistry. This was followed by deprotection at the amino group under gentle conditions by stirring in 5% strength trifluoroacetic acid in DCM at RT, which gave the title compound in a yield of 37%.

HPLC (Method 11): $R_t$=1.29 min;

LC-MS (Method 1): $R_t$=0.62 min; MS (ESIpos): m/z=566 $(M+H)^+$.

Intermediate L7

Trifluoroacetic Acid/beta-alanyl-L-valyl-$N^5$-carbamoyl-N-[4-(2,5-dioxo-2,5-dihydro-1H-pyrrol-1-yl)phenyl]-L-ornithinamide (1:1)

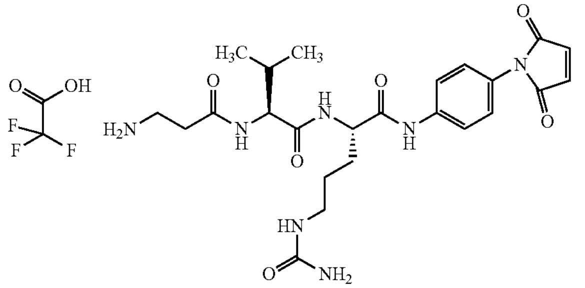 [SMILES: O=C(O)C(F)(F)F ; CC(C)[C@H](NC(=O)CCN)C(=O)N[C@@H](CCCNC(N)=O)C(=O)Nc1ccc(N2C(=O)C=CC2=O)cc1]

The title compound was prepared according to classical methods of peptide chemistry from commercially available 1-(4-aminophenyl)-1H-pyrrole-2,5-dione by sequential coupling with N2-(tert-butoxycarbonyl)-N5-carbamoyl-L-ornithine in the presence of HATU, deprotection with TFA, coupling with 2,5-dioxopyrrolidin-1-yl N-(tert-butoxycarbonyl)-L-valinate, deprotection with TFA, coupling with 2,5-dioxopyrrolidin-1-yl N-(tert-butoxycarbonyl)-beta-alaninate and another deprotection with TFA. 32 mg of the title compound were obtained.

HPLC (Method 11): $R_t$=0.31 min;

LC-MS (Method 1): $R_t$=0.47 min; MS (ESIpos): m/z=516 $(M+H)^+$.

Intermediate L8

Trifluoroacetic Acid/L-alanyl-$N^5$-carbamoyl-N-[4-(2,5-dioxo-2,5-dihydro-1H-pyrrol-1-yl)phenyl]-L-ornithinamide (1:1)

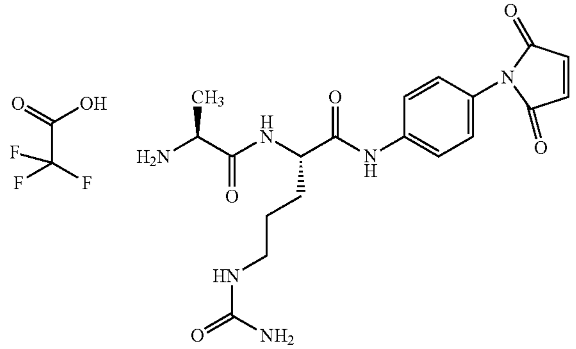 [SMILES: O=C(O)C(F)(F)F ; C[C@H](N)C(=O)N[C@@H](CCCNC(N)=O)C(=O)Nc1ccc(N2C(=O)C=CC2=O)cc1]

The title compound was prepared according to classical methods of peptide chemistry from commercially available 1-(4-aminophenyl)-1H-pyrrole-2,5-dione by sequential coupling with $N^2$-(tert-butoxycarbonyl)-$N^5$-carbamoyl-L-ornithine in the presence of HATU, deprotection with TFA, coupling with 2,5-dioxopyrrolidin-1-yl N-(tert-butoxycarbonyl)-L-alaninate and another deprotection with TFA. 171 mg of the title compound were obtained.

HPLC (Method 11): $R_t$=0.23 min;

LC-MS (Method 7): $R_t$=0.3 min; MS (ESIpos): m/z=417 $(M+H)^+$.

Intermediate L9

Trifluoroacetic Acid/beta-alanyl-L-valyl-$N^5$-carbamoyl-N-[4-(2-methoxy-2-oxoethyl)phenyl]-L-ornithinamide (1:1)

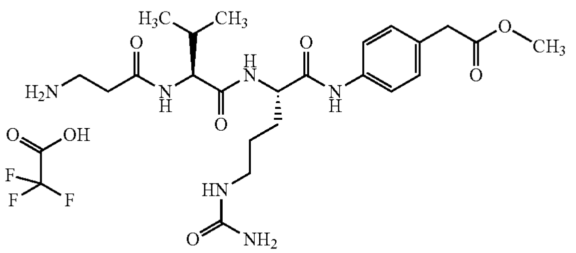 [SMILES: O=C(O)C(F)(F)F ; COC(=O)Cc1ccc(NC(=O)[C@H](CCCNC(N)=O)NC(=O)[C@@H](NC(=O)CCN)C(C)C)cc1]

The title compound was prepared analogously to Intermediate L7 from commercially available methyl (4-aminophenyl)acetate. 320 mg of the title compound were obtained.

HPLC (Method 11): $R_t$=0.45 min;

LC-MS (Method 1): $R_t$=0.48 min; MS (ESIpos): m/z=493 $(M+H)^+$.

Intermediate L10

N-[6-(2,5-Dioxo-2,5-dihydro-1H-pyrrol-1-yl)hexanoyl]-L-valyl-L-alanyl-rel-$N^6$-{[(1R,2S)-2-aminocyclopentyl]carbonyl}-L-lysine/trifluoroacetic Acid (1:2)

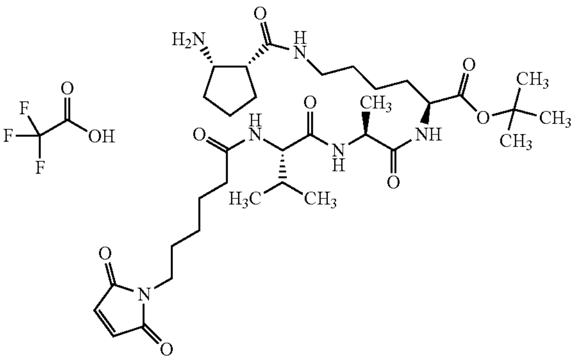 [SMILES: O=C(O)C(F)(F)F ; CC(C)[C@H](NC(=O)CCCCCN1C(=O)C=CC1=O)C(=O)N[C@@H](C)C(=O)N[C@@H](CCCCNC(=O)[C@@H]1CCC[C@@H]1N)C(=O)OC(C)(C)C]

The title compound was prepared from Intermediate L6 by coupling with cis-2-[(tert-butoxycarbonyl)amino]-1-cyclopentanecarboxylic acid with EDC/HOBT and subsequent deprotection with TFA. This gave 12 mg (52% of theory over 2 steps) of the title compound.

HPLC (Method 11): $R_t$=1.45 min;

LC-MS (Method 1): $R_t$=0.73 min; MS (ESIpos): m/z=677 $(M+H)^+$.

Intermediate L11

N-[6-(2,5-Dioxo-2,5-dihydro-1H-pyrrol-1-yl)hexanoyl]-L-valyl-L-alanyl-$N^6$-{[(1S,2R)-2-aminocyclopentyl]carbonyl}-L-lysine/trifluoroacetic Acid (1:2)

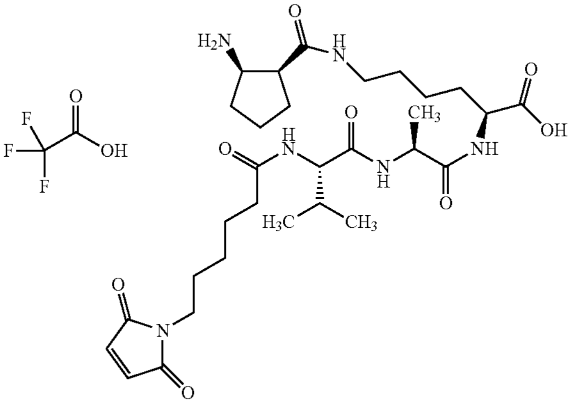 [SMILES: O=C(O)C(F)(F)F ; CC(C)[C@H](NC(=O)CCCCCN1C(=O)C=CC1=O)C(=O)N[C@@H](C)C(=O)N[C@@H](CCCCNC(=O)[C@H]1CCC[C@H]1N)C(=O)O]

The title compound was prepared from Intermediate L6 by coupling with (1S,2R)-2-[(tert-butoxycarbonyl)amino]cyclopentanecarboxylic acid with EDC/HOBT and subsequent deprotection with TFA. This gave 11 mg (39% of theory over 2 steps) of the title compound.

HPLC (Method 11): $R_t$=1.45 min;

LC-MS (Method 1): $R_t$=0.74 min; MS (ESIpos): m/z=677 $(M+H)^+$.

Intermediate L12

Trifluoroacetic Acid/1-[2-(2-aminoethoxy)ethyl]-1H-pyrrole-2,5-dione (1:1)

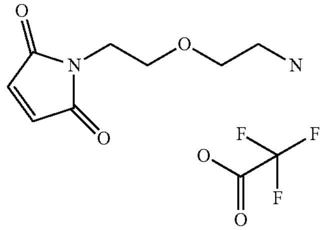 [SMILES: NCCOCCN1C(=O)C=CC1=O ; O=C(O)C(F)(F)F]

381 mg (2.46 mmol) of methyl 2,5-dioxo-2,5-dihydro-1H-pyrrole-1-carboxylate were added to 228 mg (1.12 mmol) of tert-butyl [2-(2-aminoethoxy)ethyl]carbamate dissolved in 7 ml of dioxane/water 1:1. 1.2 ml of a saturated sodium bicarbonate solution were then added and the reaction was stirred at RT. After a total of 5 days of stirring and 2 further additions of the same amounts of the sodium bicarbonate solution, the reaction was worked up by acidification with trifluoroacetic acid, concentration on a rotary evaporator and purification of the residue by preparative HPLC. The appropriate fractions were combined, the solvent was removed under reduced pressure and the residue was lyophilized from acetonitrile/water 1:1.

The residue was taken up in 3 ml of dichloromethane, and 1 ml of trifluoroacetic acid was added. After 15 min of stirring at RT, the solvent was removed under reduced pressure and the residue was lyophilized from acetonitrile/ water 1:1. This gave 70 mg (67% of theory over 2 steps) of the title compound as a resinous residue.

HPLC (Method 11): $R_t$=0.2 min;

LC-MS (Method 1): $R_t$=0.18 min; MS (ESIpos): m/z=185 $(M+H)^+$.

Intermediate L13

Trifluoroacetic Acid/tert-butyl N2-[(2,5-dioxo-2,5-dihydro-1H-pyrrol-1-yl)acetyl]-L-lysinate (1:1)

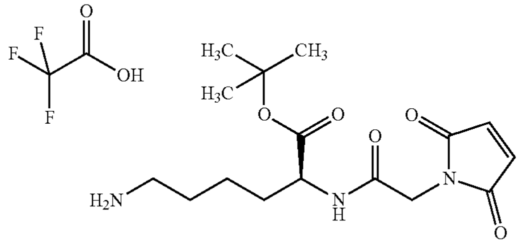 [SMILES: O=C(O)C(F)(F)F ; CC(C)(C)OC(=O)[C@H](CCCCN)NC(=O)CN1C(=O)C=CC1=O]

The title compound was prepared by coupling of (2,5-dioxo-2,5-dihydro-1H-pyrrol-1-yl)acetic acid with tert-butyl N6-(tert-butoxycarbonyl)-L-lysinate hydrochloride (1:1) in the presence of EDC/HOBT and subsequent gentle removal of the tert-butoxycarbonyl protective group analogously to Intermediate L6.

HPLC (Method 11): $R_t$=0.42 min;

LC-MS (Method 1): $R_t$=0.43 min; MS (ESIpos): m/z=340 $(M+H)^+$.

Intermediate L14

Trifluoroacetic Acid/1-[2-(4-aminopiperazin-1-yl)-2-oxoethyl]-1H-pyrrole-2,5-dione (1:1)

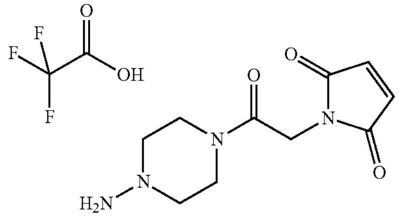 [SMILES: O=C(O)C(F)(F)F ; NN1CCN(C(=O)CN2C(=O)C=CC2=O)CC1]

The title compound was prepared analogously to Intermediate L2 over 2 steps from tert-butyl piperazin-1-ylcarbamate and (2,5-dioxo-2,5-dihydro-1H-pyrrol-1-yl)acetic acid.

HPLC (Method 11): $R_t$=0.2 min;

LC-MS (Method 3): $R_t$=0.25 min; MS (ESIpos): m/z=239 $(M+H)^+$.

Intermediate L15

Trifluoroacetic Acid/N-(2-aminoethyl)-3-(2-{2-[2-(2,5-dioxo-2,5-dihydro-1H-pyrrol-1-yl)ethoxy]ethoxy}ethoxy)propanamide (1:1)

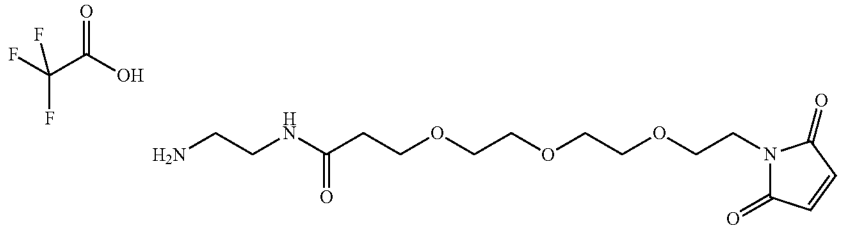 [SMILES: O=C(O)C(F)(F)F ; NCCNC(=O)CCOCCOCCOCCN1C(=O)C=CC1=O]

2.93 g (10.58 mmol) of tert-butyl 3-{2-[2-(2-aminoethoxy)ethoxy]ethoxy}propanoate were dissolved in 100 ml of dioxane/water 1:1, and 3.28 g (21.15 mmol) of methyl 2,5-dioxo-2,5-dihydro-1H-pyrrole-1-carboxylate and a saturated sodium bicarbonate solution were added until a pH of 6-7 had been reached. The solution was stirred at RT for 30 min and the 1,4-dioxane was then evaporated under reduced pressure. 200 ml of water were then added, and the mixture was extracted three times with in each case 300 ml of ethyl acetate. The organic extracts were combined, dried over magnesium sulphate and filtered. Concentration gave tert-butyl 3-(2-{2-[2-(2,5-dioxo-2,5-dihydro-1H-pyrrol-1-yl)ethoxy]ethoxy}ethoxy)propanoate as a brown oil which was then dried under high vacuum.

HPLC (Method 11): $R_t$=1.5 min;

LC-MS (Method 3): $R_t$=0.88 min; MS (ESIpos): m/z=375 $(M+NH_4)^+$.

This intermediate was converted by standard methods (deprotection with TFA, coupling with tert-butyl (2-aminoethyl)carbamate and another deprotection with TFA) into the title compound.

HPLC (Method 11): $R_t$=0.2 min;

LC-MS (Method 3): $R_t$=0.25 min; MS (ESIpos): m/z=344 $(M+H)^+$.

Intermediate L16

N-[6-(2,5-Dioxo-2,5-dihydro-1H-pyrrol-1-yl)hexanoyl]-L-valyl-$N^5$-carbamoyl-L-ornithine

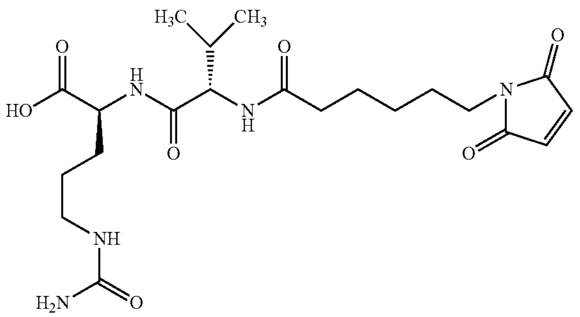 [SMILES: CC(C)[C@H](NC(=O)CCCCCN1C(=O)C=CC1=O)C(=O)N[C@@H](CCCNC(N)=O)C(=O)O]

535 mg (1.73 mmol) of commercially available 1-{6-[(2,5-dioxopyrrolidin-1-yl)oxy]-6-oxohexyl}-1H-pyrrole-2,5-dione and 930 ml of N,N-diisopropylethylamine were added to a solution of 266 mg (1.33 mmol) of L-valyl-N5-carbamoyl-L-ornithine in 24 ml of DMF. The reaction was treated in an ultrasonic bath for 24 h and then concentrated to dryness under reduced pressure. The residue that remained was purified by preparative HPCL and gave, after concentration of the appropriate fractions and drying of the residue under high vacuum, 337 mg (50% of theory) of the title compound.

HPLC (Method 11): $R_t$=0.4 min;

LC-MS (Method 3): $R_t$=0.58 min; MS (ESIpos): m/z=468 $(M+H)^+$.

Intermediate L17

Trifluoroacetic Acid/tert-butyl N-[6-(2,5-dioxo-2,5-dihydro-1H-pyrrol-1-yl)hexanoyl]-L-valyl-$N^5$-carbamoyl-L-ornithyl-L-lysinate (1:1)

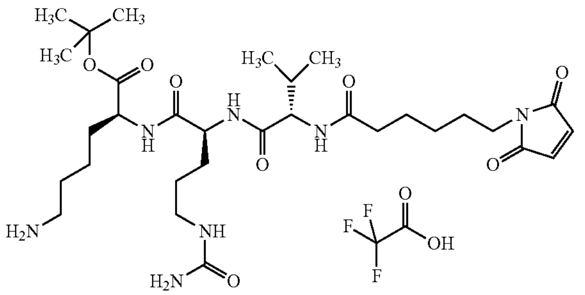 [SMILES: CC(C)[C@H](NC(=O)CCCCCN1C(=O)C=CC1=O)C(=O)N[C@@H](CCCNC(N)=O)C(=O)N[C@@H](CCCCN)C(=O)OC(C)(C)C ; O=C(O)C(F)(F)F]

The title compound was prepared by initially coupling 172 mg (0.37 mmol) of Intermediate L16 and 125 mg (0.37 mmol) of tert-butyl N6-(tert-butoxycarbonyl)-L-lysinate hydrochloride (1:1) in the presence of EDC/HOBT and N,N-diisopropylethylamine and then deprotecting the amino group under gentle conditions by stirring for 2 h in 10% strength trifluoroacetic acid in DCM at RT. Freeze-drying from acetonitrile/water gave 194 mg (49% of theory) of the title compound over 2 steps.

HPLC (Method 11): $R_t$=1.1 min;

LC-MS (Method 1): $R_t$=0.58 min; MS (ESIpos): m/z=652 $(M+H)^+$.

Intermediate L18

Trifluoroacetic Acid/beta-alanyl-L-alanyl-$N^5$-carbamoyl-N-[4-(2-methoxy-2-oxoethyl)phenyl]-L-ornithinamide (1:1)

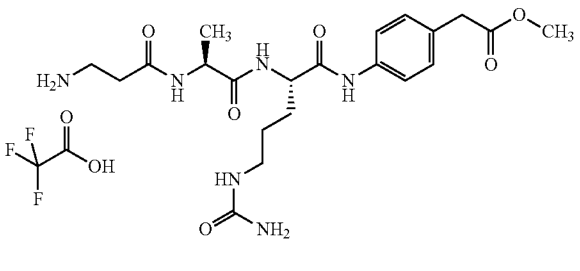

The title compound was prepared from methyl (4-aminophenyl)acetate analogously to Intermediate L7 sequentially according to classical methods of peptide chemistry by linking $N^2$-(tert-butoxycarbonyl)-$N^5$-carbamoyl-L-ornithine in the presence of HATU, deprotection with TFA, coupling with 2,5-dioxopyrrolidin-1-yl N-(tert-butoxycarbonyl)-L-alaninate, deprotection with TFA, coupling with 2,5-dioxopyrrolidin-1-yl N-(tert-butoxycarbonyl)-beta-alaninate and another deprotection with TFA. 330 mg of the title compound were obtained.

HPLC (Method 11): $R_t$=0.29 min;

LC-MS (Method 1): $R_t$=0.41 min; MS (ESIpos): m/z=465 $(M+H)^+$.

Intermediate L19

Trifluoroacetic Acid/L-alanyl-N5-carbamoyl-N-(4-{[(2,5-dioxo-2,5-dihydro-1H-pyrrol-1-yl)acetyl]amino}phenyl)-L-ornithinamide (1:1)

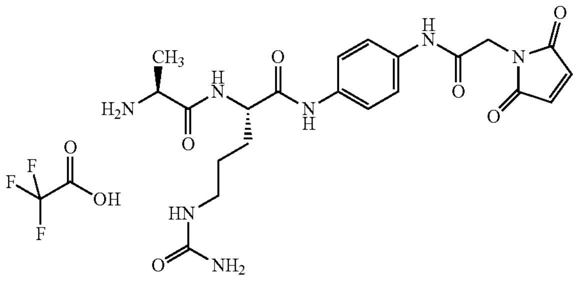 [SMILES: O=C(O)C(F)(F)F ; C[C@H](N)C(=O)N[C@@H](CCCNC(N)=O)C(=O)Nc1ccc(NC(=O)CN2C(=O)C=CC2=O)cc1]

The title compound was prepared from 1,4-phenylenediamine sequentially according to classical methods of peptide chemistry. In the first step, 942 mg (8.72 mmol) of 1,4-phenylenediamine were monoacylated with 0.8 g (2.9 mmol) of $N^2$-(tert-butoxycarbonyl)-$N^5$-carbamoyl-L-ornithine in the presence of HATU and N,N-diisopropylethylamine. In the second step, in an analogous manner, the second anilinic amino group was acylated with (2,5-dioxo-2,5-dihydro-1H-pyrrol-1-yl)acetic acid in the presence of HATU and N,N-diisopropylethylamine. Deprotection with TFA, coupling with 2,5-dioxopyrrolidin-1-yl N-(tert-butoxycarbonyl)-L-alaninate and another deprotection with TFA then gave, in 3 further synthesis steps, the title compound, 148 mg of which were obtained by this route.

LC-MS (Method 1): $R_t$=0.21 min; MS (ESIpos): m/z=474 $(M+H)^+$.

LC-MS (Method 4): $R_t$=0.2 min; MS (ESIpos): m/z=474 $(M+H)^+$.

Intermediate L20

Trifluoroacetic Acid/L-valyl-$N^5$-carbamoyl-N-[4-(2,5-dioxo-2,5-dihydro-1H-pyrrol-1-yl)phenyl]-L-ornithinamide (1:1)

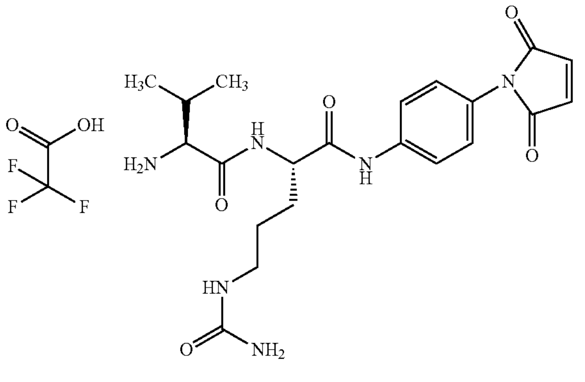 [SMILES: O=C(O)C(F)(F)F ; CC(C)[C@H](N)C(=O)N[C@@H](CCCNC(N)=O)C(=O)Nc1ccc(N2C(=O)C=CC2=O)cc1]

The title compound was prepared according to classical methods of peptide chemistry analogously to Intermediate L8 from commercially available 1-(4-aminophenyl)-1H-pyrrole-2,5-dione by sequential coupling with $N^2$-(tert-butoxycarbonyl)-$N^5$-carbamoyl-L-ornithine in the presence of HATU, deprotection with TFA, coupling with 2,5-dioxopyrrolidin-1-yl N-(tert-butoxycarbonyl)-L-valinate and another deprotection with TFA. 171 mg of the title compound were obtained.

HPLC (Method 11): $R_t$=0.28 min;

LC-MS (Method 1): $R_t$=0.39 min; MS (ESIpos): m/z=445 $(M+H)^+$.

Intermediate L21

L-Valyl-$N^6$-(tert-butoxycarbonyl)-N-[4-(2-methoxy-2-oxoethyl)phenyl]-L-lysinamide

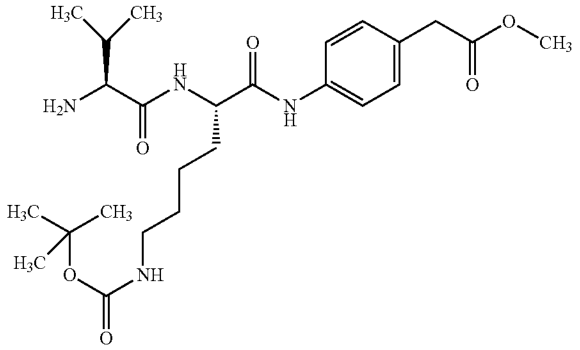 [SMILES: COC(=O)Cc1ccc(NC(=O)[C@H](CCCCNC(=O)OC(C)(C)C)NC(=O)[C@@H](N)C(C)C)cc1]

The title compound was prepared according to classical methods of peptide chemistry from commercially available 0.42 g (2.56 mmol) of methyl (4-aminophenyl)acetate by sequential coupling with N6-(tert-butoxycarbonyl)-N2-[(9H-fluoren-9-ylmethoxy)carbonyl]-L-lysine in the presence of HATU and N,N-diisopropylethylamine, deprotection with piperidine, coupling with 2,5-dioxopyrrolidin-1-yl N-[(benzyloxy)carbonyl]-L-valinate in the presence of N,N-diisopropylethylamine and subsequent hydrogenolytic removal of the benzyloxycarbonyl protective group over 10% palladium on activated carbon. 360 mg (32% of theory over 4 stages) of the title compound were obtained.

HPLC (Method 11): $R_t$=1.5 min;

LC-MS (Method 1): $R_t$=0.73 min; MS (ESIpos): m/z=493 $(M+H)^+$.

Intermediate L22

Trifluoroacetic Acid/N-[(9H-fluoren-9-ylmethoxy)carbonyl]-L-valyl-N-{4-[(2S)-2-amino-3-methoxy-3-oxopropyl]phenyl}-$N^5$-carbamoyl-L-ornithinamide (1:1)

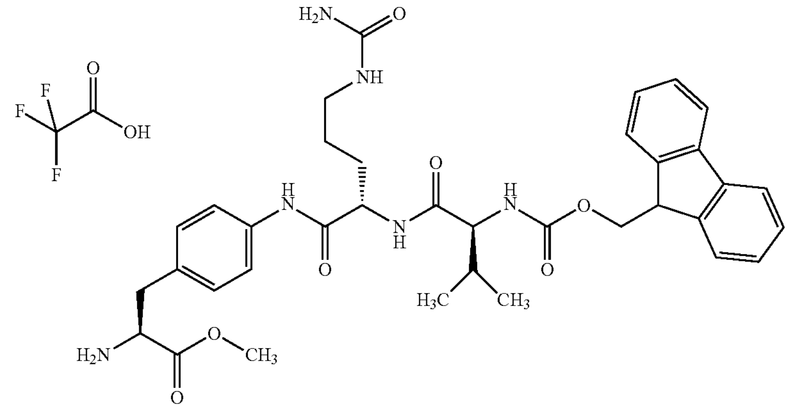 [SMILES: O=C(O)C(F)(F)F ; COC(=O)[C@@H](N)Cc1ccc(NC(=O)[C@H](CCCNC(N)=O)NC(=O)[C@@H](NC(=O)OCC2c3ccccc3-c3ccccc32)C(C)C)cc1]

The title compound was prepared from N-(tert-butoxycarbonyl)-4-nitro-L-phenylalanine sequentially according to classical methods of peptide chemistry. 2.5 g (8.06 mmol) of this starting material were in the first step initially converted into the caesium salt and then with iodomethane in DMF into the methyl ester.

Hydrogenolytically in methanol over 10% palladium on activated carbon, the nitro group was then converted into an amino group.

The amino group generated in this manner was then acylated with N5-carbamoyl-N2-[(9H-fluoren-9-ylmethoxy)carbonyl]-L-ornithine in DMF in the presence of HATU and N,N-diisopropylethylamine. In the next step, the Fmoc group was removed with piperidine in DMF. Coupling was then carried out in DMF with N-[(9H-fluoren-9-ylmethoxy)carbonyl]-L-valine in the presence of 1-(3-dimethylaminopropyl)-3-ethylcarbodiimide hydrochloride, 1-hydroxy-1H-benzotriazole hydrate and N,N-diisopropylethylamine and finally removal of the tert-butoxycarbonyl group with trifluoroacetic acid.

HPLC (Method 11): $R_t$=1.6 min;

LC-MS (Method 1): $R_t$=0.77 min; MS (ESIpos): m/z=673 $(M+H)^+$.

Intermediate L23

Trifluoroacetic Acid/N-[2-(2,5-dioxo-2,5-dihydro-1H-pyrrol-1-yl)ethyl]-beta-alaninamide (1:1)

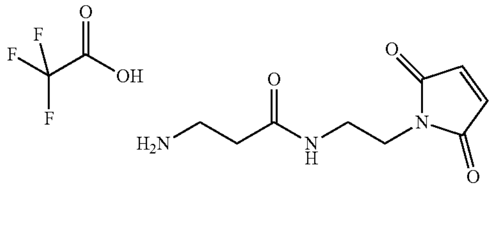 [SMILES: O=C(O)C(F)(F)F ; NCCC(=O)NCCN1C(=O)C=CC1=O]

The title compound was prepared from commercially available trifluoroacetic acid/1-(2-aminoethyl)-1H-pyrrole-2,5-dione (1:1) by coupling with N-(tert-butoxycarbonyl)-beta-alanine in the presence of EDCI/HOBT and N,N-diisopropylethylamine and subsequent deprotection with trifluoroacetic acid.

HPLC (Method 11): $R_t$=0.19 min.

Intermediate L24

Trifluoroacetic Acid/1-amino-N-[2-(2,5-dioxo-2,5-dihydro-1H-pyrrol-1-yl)ethyl]cyclopropanecarboxamide (1:1)

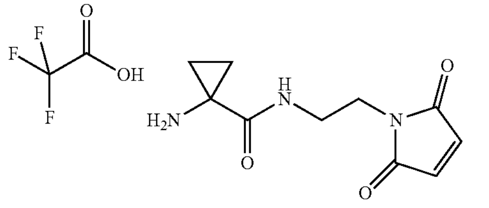 [SMILES: O=C(O)C(F)(F)F ; NC1(C(=O)NCCN2C(=O)C=CC2=O)CC1]

114 mg (0.67 mmol) of commercially available 1-[(tert-butoxycarbonyl)amino]cyclopropanecarboxylic acid were dissolved in 25 ml of DCM, 110 mg (0.623 mmol) of commercially available trifluoroacetic acid/1-(2-aminoethyl)-1H-pyrrole-2,5-dione (1:1) and 395 µl of N,N-diisopropylethylamine were added and the mixture was cooled to −10° C. 217 mg (0.793 mmol) of 2-bromo-1-ethylpyridinium tetrafluoroborate were then added, and the mixture was stirred at RT for 2 h. The mixture was then diluted with ethyl acetate and extracted successively with 10% strength citric acid, saturated sodium bicarbonate solution and saturated sodium chloride solution, then dried over magnesium sulphate and concentrated. Drying under high vacuum gave 152 mg of the protected intermediate.

These were then taken up in 10 ml of DCM and deprotected with 1 ml of trifluoroacetic acid. Lyophilization from acetonitrile/water gave 158 mg (71% of theory over 2 steps) of the title compound.

HPLC (Method 11): $R_t$=0.19 min.

LC-MS (Method 3): $R_t$=0.98 min; MS (ESIpos): m/z=224 $(M+H)^+$.

Intermediate L25

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-L-alanine

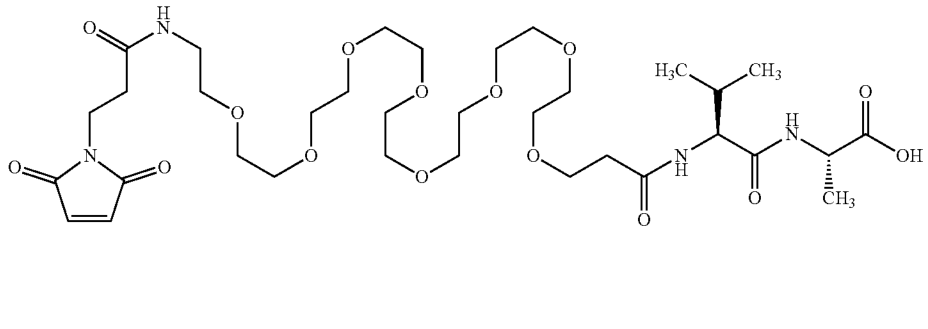 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)O]

31.4 mg (0.17 mmol) of valyl-L-alanine were dissolved in 3.0 ml of DMF, and 115.0 mg (0.17 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide and 33.7 mg (0.33 mmol) of triethylamine were added. The mixture was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 74.1 mg (58% of theory) of the title compound.

LC-MS (Method 1): $R_t$=0.61 min; MS (ESIpos): m/z=763 $[M+H]^+$.

Intermediate L26

L-Valyl-N6-(tert-butoxycarbonyl)-L-lysine

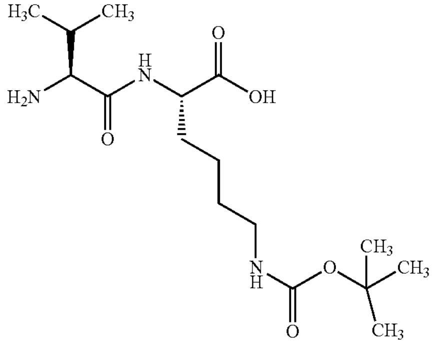 [SMILES: CC(C)[C@H](N)C(=O)N[C@@H](CCCCNC(=O)OC(C)(C)C)C(=O)O]

600.0 mg (1.58 mmol) of N2-[(benzyloxy)carbonyl]-N6-(tert-butoxycarbonyl)-L-lysine were suspended in 25.0 ml of water/ethanol/THF (1:1:0.5), palladium on carbon (10%) was added and the mixture was hydrogenated at RT with hydrogen under standard pressure for 5 h. The catalyst was filtered off and the solvents were evaporated under reduced pressure. The compound obtained was used in the next step without further purification.

LC-MS (Method 1): $R_t$=0.42 min; MS (ESIpos): m/z=247 $[M+H]^+$.

180 mg (0.73 mmol) of N6-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were then added. The reaction mixture was stirred at RT for 3.5 h. The reaction solution was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 294.1 mg (76% of theory) of N-[(benzyloxy)carbonyl]-L-valyl-N6-(tert-butoxycarbonyl)-L-lysine.

LC-MS (Method 1): $R_t$=0.97 min; MS (ESIpos): m/z=480 $[M+H]^+$.

272.2 mg (0.57 mmol) of N-[(benzyloxy)carbonyl]-L-valyl-N6-(tert-butoxycarbonyl)-L-lysine were initially charged in 20.0 ml of ethyl acetate/ethanol/THF (1:1:1), and 27.2 mg of palladium on activated carbon were added. The mixture was hydrogenated with hydrogen at RT under standard pressure for 5 h. The mixture was filtered off with the aid of Celite® and the filter cake was washed with ethyl acetate/ethanol/THF (1:1:1). The solvents were evaporated under reduced pressure and the residue was dried under high vacuum. The title compound (182 mg, 72% of theory) was used in the next reaction step without further purification.

LC-MS (Method 1): $R_t$=0.53 min; MS (ESIpos): m/z=346 $[M+H]^+$.

Intermediate L27

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N6-(tert-butoxycarbonyl)-L-lysine

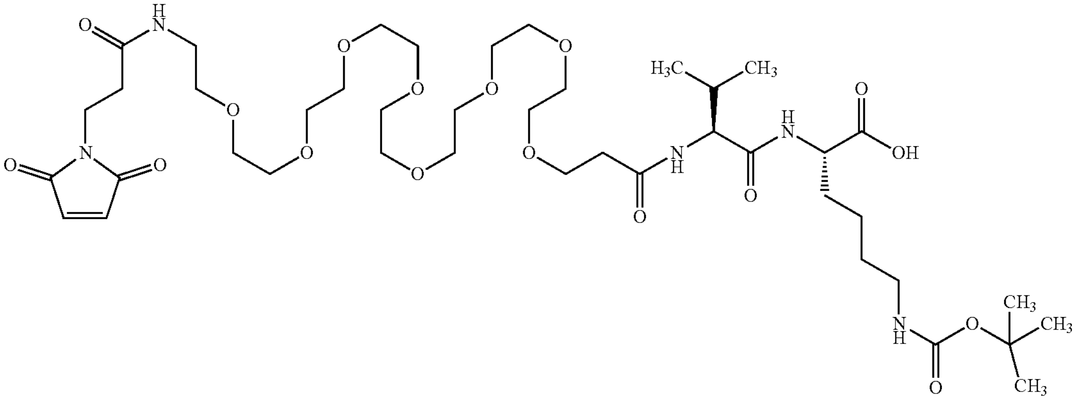 [SMILES: CC(C)[C@H](NC(=O)CCOCCOCCOCCOCCOCCOCCOCCOCCNC(=O)CCN1C(=O)C=CC1=O)C(=O)N[C@@H](CCCCNC(=O)OC(C)(C)C)C(=O)O]

30 mg (0.07 mmol) of L-valyl-N6-(tert-butoxycarbonyl)-L-lysine (Intermediate L26) and 46.1 mg (0.07 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide were initially charged in 1.5 ml of DMF, and 6.8 mg (0.07 mmol) of 4-methylmorpholine were added. The reaction solution was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 55.6 mg (90% of theory) of the title compound.

LC-MS (Method 1): $R_t$=0.77 min; MS (ESIpos): m/z=920 $[M+H]^+$.

Intermediate L28 tert-Butyl 3-formyl-4-({[2-(trimethylsilyl)ethoxy]carbonyl}amino)pyrrolidine-1-carboxylate

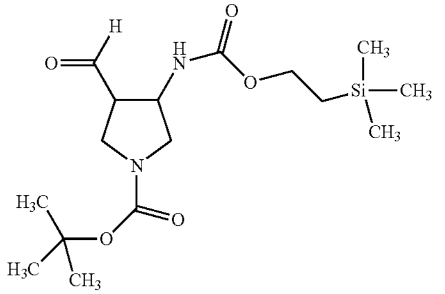 [SMILES: CC(C)(C)OC(=O)N1CC(C=O)C(NC(=O)OCC[Si](C)(C)C)C1]

461.7 mg (1.15 mmol) of 1-tert-butyl 3-ethyl-4-({[2-(trimethylsilyl)ethoxy]carbonyl}amino)pyrrolidine-1,3-dicarboxylate (this compound was prepared according to the literature procedure of WO 2006/066896) were initially charged in 5.0 ml of absolute dichloromethane and the mixture was cooled to −78° C. 326.2 mg (2.29 mmol) of diisobutylaluminium hydride solution (1 M in THF) were then slowly added dropwise and the mixture was stirred at −78° C. for 2 h (monitored by thin-layer chromatography (petroleum ether/ethyl acetate=3:1). 1.3 g (4.59 mmol) of potassium sodium tartrate dissolved in 60 ml of water were added dropwise and the reaction mixture was allowed to warm to RT. Ethyl acetate was added to the reaction mixture and the aqueous phase was extracted three times with ethyl acetate. The combined organic phases were washed once with sat. NaCl solution and dried over magnesium sulphate. The solvent was evaporated under reduced pressure and the residue was dried under high vacuum. This gave 629.0 mg of the title compound as a crude product which was used immediately without further purification in the next reaction step.

Intermediate L29 tert-Butyl 3-formyl-4-[({[2-(trimethylsilyl)ethoxy]carbonyl}amino)methyl]pyrrolidine-1-carboxylate Mixture of Diastereomers.

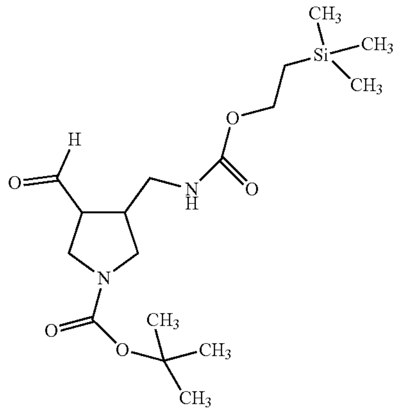 [SMILES: CC(C)(C)OC(=O)N1CC(C=O)C(CNC(=O)OCC[Si](C)(C)C)C1]

807.1 mg (2.34 mmol) of tert-butyl 3-({[tert-butyl(dimethyl)silyl]oxy}methyl)-4-(hydroxymethyl)pyrrolidine-1-carboxylate (prepared according to the literature procedure of WO 2006/100036) were initially charged in 8.0 ml of dichloromethane, and 236.4 mg (2.34 mmol) of triethylamine were added. At 0° C., 267.6 mg (2.34 mmol) of methanesulphonyl chloride were added dropwise, and the reaction mixture stirred at RT overnight. A further 133.8 mg (1.17 mmol) of methanesulphonyl chloride and 118.2 mg (1.17 mmol) of triethylamine were added. The reaction mixture was stirred at RT overnight. The mixture was diluted with dichloromethane and the organic phase was washed in each case once with saturated sodium bicarbonate solution, 5% strength potassium hydrogen sulphate solution and saturated NaCl solution. After drying over magnesium sulphate, the solvent was evaporated under reduced pressure and the residue was purified on Biotage Isolera (silica gel, column 50 g SNAP, flow rate 66 ml/min, cyclohexane/ethyl acetate). The solvents were evaporated under reduced pressure and the residue was dried under high vacuum. This gave 402.0 mg (41% of theory) of the compound tert-butyl 3-({[tert-butyl(dimethyl)silyl]oxy}methyl)-4-{[(methylsulphonyl)oxy]methyl}pyrrolidine-1-carboxylate.

LC-MS (Method 1): $R_t$=1.38 min; MS (ESIpos): m/z=424 $[M+H]^+$.

400.0 mg (0.94 mmol) of tert-butyl 3-({[tert-butyl(dimethyl)silyl]oxy}methyl)-4-{[(methylsulphonyl)oxy]methyl}pyrrolidine-1-carboxylate were initially charged in 5.0 ml of DMF, and 98.2 mg (1.51 mmol) of sodium azide were added. The reaction mixture was stirred at 40° C. for 10 h. Another 30.7 mg (0.47 mmol) of sodium azide were then added, and the mixture was stirred at 40° C. for a further 10 h. Ethyl acetate was added and the organic phase was washed repeatedly with water. After drying of the organic phase over magnesium sulphate, the solvent was evaporated under reduced pressure and the residue was dried under high vacuum. This gave 309.5 mg (89% of theory) of the compound tert-butyl 3-(azidomethyl)-4-({[tert-butyl(dimethyl)silyl]oxy}methyl)pyrrolidine-1-carboxylate. The compound was used without further purification in the next step of the synthesis.

LC-MS (Method 1): $R_t$=1.50 min; MS (ESIpos): m/z=371 $[M+H]^+$.

250 mg (0.68 mmol) of tert-butyl 3-(azidomethyl)-4-({[tert-butyl(dimethyl)silyl]oxy}methyl)pyrrolidine-1-carboxylate were dissolved in 10.0 ml of ethyl acetate/ethanol (1:1), and 25.0 mg of palladium on activated carbon (10%) were added. The mixture was hydrogenated with hydrogen at RT under standard pressure for 8 h. The reaction was filtered through Celite® and the filter cake was washed thoroughly with ethyl acetate. The solvent was evaporated under reduced pressure and the residue was dried under high vacuum. This gave 226.2 mg (82% of theory) of the compound tert-butyl 3-(aminomethyl)-4-({[tert-butyl(dimethyl)silyl]oxy}methyl)pyrrolidine-1-carboxylate. The compound was used without further purification in the next step of the synthesis.

LC-MS (Method 1): $R_t$=0.89 min; MS (ESIpos): m/z=345 $[M+H]^+$.

715.0 mg (2.08 mmol) of tert-butyl 3-(aminomethyl)-4-({[tert-butyl(dimethyl)silyl]oxy}methyl)pyrrolidine-1-carboxylate were dissolved in 15.0 ml of THF, and 2.28 ml (2.28 mmol) of TBAF solution (1M in THF) were added. The reaction mixture was stirred at RT overnight. The solvent was evaporated under reduced pressure and the residue (1.54 g) used without further purification in the next step of the synthesis.

LC-MS (Method 1): $R_t$=0.41 min; MS (ESIpos): m/z=231 $[M+H]^+$.

1.54 g (4.88 mmol) of tert-butyl 3-(aminomethyl)-4-(hydroxymethyl)pyrrolidine-1-carboxylate were initially charged in 1,4-dioxane, and 541.8 mg (4.88 mmol) of calcium chloride (anhydrous) and 488.6 mg (4.88 mmol) of calcium carbonate were added and the mixture was stirred vigorously. 592.8 mg (5.86 mmol) of triethylamine and 1.52 g (5.86 mmol) of 1-({[2-(trimethylsilyl)ethoxy]carbonyl}oxy)pyrrolidine-2,5-dione were then added and the reaction mixture stirred at RT overnight. 644.9 mg (10.7 mmol) of HOAc and ethyl acetate were added. The organic phase was washed twice with water and once with saturated NaCl solution. After drying over magnesium sulphate, the solvent was evaporated under reduced pressure and the residue was purified on silica gel (mobile phase: dichloromethane/methanol=100:1). The solvents were evaporated under reduced pressure and the residue was dried under high vacuum. This gave 346.9 mg (19% of theory) of the compound tert-butyl 3-(hydroxymethyl)-4-[({[2-(trimethylsilyl)ethoxy]carbonyl}amino)methyl]pyrrolidine-1-carboxylate.

LC-MS (Method 1): $R_t$=1.08 min; MS (ESIpos): m/z=375 $[M+H]^+$.

804.0 mg (2.15 mmol) of tert-butyl 3-(hydroxymethyl)-4-[({[2-(trimethylsilyl)ethoxy]carbonyl}amino)methyl]pyrrolidine-1-carboxylate were initially charged in 20.0 ml of chloroform and 20.0 ml of 0.05 N potassium carbonate/0.05 N sodium bicarbonate solution (1:1). 59.7 mg (0.22 mmol) of tetra-n-butylammonium chloride, 429.9 mg (3.22 mmol) of N-chlorosuccinimide and 33.5 mg (0.22 mmol) of TEMPO were then added and the reaction mixture was stirred vigorously at RT overnight. The organic phase was separated off and freed from the solvent under reduced pressure. The residue was chromatographed by means of silica gel (mobile phase: cyclohexane/ethyl acetate=3:1). This gave 517.0 mg (46% of theory) of the title compound.

LC-MS (Method 1): $R_t$=1.13 min; MS (ESIpos): m/z=373 $[M+H]^+$.

Intermediate L30 tert-Butyl 3-({[tert-butyl(dimethyl)silyl]oxy}methyl)-4-formylpyrrolidine-1-carboxylate Mixture of Stereoisomers

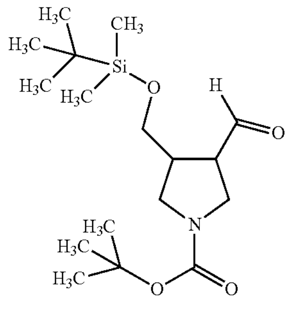 [SMILES: CC(C)(C)OC(=O)N1CC(C=O)C(CO[Si](C)(C)C(C)(C)C)C1]

250.0 mg (0.72 mmol) of tert-butyl 3-({[tert-butyl(dimethyl)silyl]oxy}methyl)-4-(hydroxymethyl)pyrrolidine-1-carboxylate (the compound was prepared according to the literature procedure of WO2006/100036) were initially charged in 12.5 ml of dichloromethane/DMSO (4:1), and 219.6 mg (2.17 mmol) of triethylamine were added. At 2° C., 345.5 mg (2.17 mmol) of sulphur trioxide-pyridine complex were added a little at a time and the mixture was stirred at 2° C. for 3 h. Another 345.5 mg (2.17 mmol) of sulphur trioxide-pyridine complex were added a little at a time and the mixture was stirred at RT for 17 h. The reaction mixture was partitioned between dichloromethane and water. The aqueous phase was extracted three times with dichloromethane and the combined organic phases were washed once with water and dried over magnesium sulphate. The solvent was evaporated under reduced pressure and the residue was dried under high vacuum. The residue was used without further purification in the next step of the synthesis (thin-layer chromatography: petroleum ether/ethyl acetate 7:3).

Intermediate L31

Di-tert-butyl {[(tert-butoxycarbonyl)amino]methyl}malonate

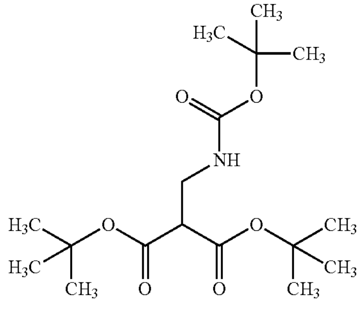 [SMILES: CC(C)(C)OC(=O)NCC(C(=O)OC(C)(C)C)C(=O)OC(C)(C)C]

57.2 g (488.27 mmol) of tert-butyl carbamate, 51.2 ml (683.57 mmol) of a 37% strength solution of formaldehyde in water and 25.9 g (244.13 mmol) of sodium carbonate were added to 600 ml of water. The mixture was warmed until a solution was formed and then stirred at RT for 16 h. The suspension formed was extracted with 500 ml of dichloromethane and the organic phase was separated off, washed with saturated sodium chloride solution and dried over sodium sulphate. The mixture was concentrated on a rotary evaporator and the residue was dried under high vacuum, giving a crystalline solid. The residue was taken up in 1000 ml of absolute THF, and a mixture of 322 ml (3.414 mol) of acetic anhydride and 138 ml (1.707 mol) of pyridine was added dropwise at RT. The reaction mixture was stirred at RT for 16 h and then concentrated on a rotary evaporator, with the water bath at room temperature. The residue was taken up in diethyl ether and washed three times with a saturated sodium bicarbonate solution and once with a saturated sodium chloride solution. The organic phase was dried over sodium sulphate and concentrated on a rotary evaporator and the residue was dried under high vacuum for 2 d. The residue was taken up in 2000 ml of absolute THF, and 456 ml (456.52 mmol) of a 1 M solution of potassium tert-butoxide in THF were added with ice cooling. The mixture was stirred at 0° C. for 20 min, and 100.8 g (456.52 mmol) of di-tert-butyl malonate dissolved in 200 ml of absolute THF were then added dropwise. The mixture was stirred at RT for 48 h, and water was then added. The reaction mixture was concentrated on a rotary evaporator and taken up in 500 ml of ethyl acetate. The mixture was washed with 500 ml of water and 100 ml of a saturated sodium chloride solution and the organic phase was dried over sodium sulphate. The organic phase was concentrated on a rotary evaporator and the residue was dried under high vacuum. The residue was purified by filtration through silica gel (mobile phase: cyclohexane/ethyl acetate, gradient=30:1→5:1). This gave 37.07 g (22% of theory) of the target compound.

LC-MS (Method 6): $R_t$=2.87 min; MS (ESIpos): m/z=346 $[M+H]^+$.

Intermediate L32 tert-Butyl [3-hydroxy-2-(hydroxymethyl)propyl]carbamate

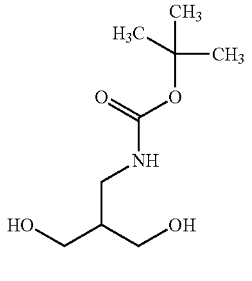

37.0 g (107.11 mmol) of di-tert-butyl (acetoxymethyl)malonate were dissolved in 1000 ml of absolute THF, and 535.5 ml (1071.10 mmol) of a 2 M solution of lithium borohydride in THF were added dropwise with ice cooling. 19.3 ml (1071.10 mmol) of water were added dropwise and the mixture was stirred at RT for 4.5 h. The reaction mixture was concentrated on a rotary evaporator and dried under high vacuum. The residue was taken up in 1500 ml of ethyl acetate, 100 ml of water were added and the mixture was stirred with water cooling (slightly exothermic) for 30 min. The organic phase was separated off and the aqueous phase was extracted twice with 500 ml of ethyl acetate. The organic phase was concentrated on a rotary evaporator and the residue was dried under high vacuum. This gave 20.7 g (94% of theory) of the target compound.

LC-MS (Method 6): $R_t$=1.49 min; MS (EIpos): m/z=106 $[M-C_5H_8O_2]^+$.

Intermediate L33 tert-Butyl [3-{[tert-butyl(dimethyl)silyl]oxy}-2-(hydroxymethyl)propyl]carbamate

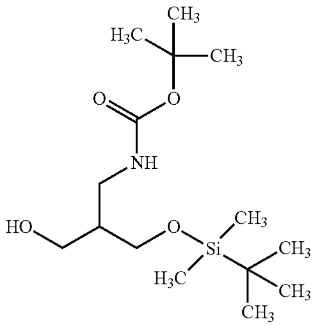 [SMILES: CC(C)(C)OC(=O)NCC(CO)CO[Si](C)(C)C(C)(C)C]

20.00 g (97.44 mmol) of tert-butyl [3-hydroxy-2-(hydroxymethyl)propyl]carbamate were dissolved in 1000 ml of absolute dichloromethane, and 6.63 g (97.44 mmol) of imidazole and 16.16 g (107.18 mmol) of tert-butyl(chloro)dimethylsilane were added at RT. The reaction mixture was stirred at RT for 16 h and washed with semiconcentrated sodium chloride solution. The aqueous phase was extracted with ethyl acetate and the combined organic phases were dried over sodium sulphate, concentrated on a rotary evaporator and dried under high vacuum. This gave 28.50 g (92% of theory) of the target compound.

$^1$H-NMR (400 MHz, DMSO-$d_6$): δ [ppm]=0.02 (s, 6H), 0.86 (s, 9H), 1.37 (s, 9H), 1.58-1.73 (m, 1H), 2.91 (q, 2H), 3.33-3.36 [m, (2H, hidden)], 3.53-3.58 (m, 2H), 6.65-6.72 (m, 1H).

Intermediate L34 tert-Butyl (3-{[tert-butyl(dimethyl)silyl]oxy}-2-formylpropyl)carbamate

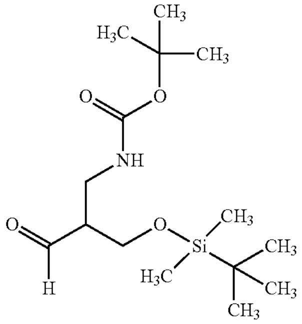 [SMILES: CC(C)(C)OC(=O)NCC(C=O)CO[Si](C)(C)C(C)(C)C]

12.65 g (39.591 mmol) of tert-butyl [3-{[tert-butyl(dimethyl)silyl]oxy}-2-(hydroxy-methyl)propyl]carbamate were dissolved in 200 ml of dichloromethane, and 19.31 g (45.53 mmol) of Dess-Martin periodinane dissolved in 150 ml of dichloromethane were added dropwise at RT. The mixture was stirred at room temperature for 2 h, 250 ml of a semiconcentrated sodium bicarbonate solution and 250 ml of a 10% strength sodium thiosulphate solution were then added and the mixture was stirred for 20 min. The organic phase was separated off and the aqueous phase was extracted with ethyl acetate. The combined organic phases were washed with 300 ml of water, dried over sodium sulphate, concentrated on a rotary evaporator and dried under high vacuum. This gave 11.35 g (90% of theory) of the target compound.

$^1$H-NMR (400 MHz, DMSO-$d_6$): δ [ppm]=0.02 (s, 6H), 0.84 (s, 9H), 1.36 (s, 9H), 1.48-1.51 (m, 1H), 3.08-3.32 [m, (1H, hidden)], 3.50-3.58 (m, 2H), 3.81-3.91 (m, 1H), 6.71 (t, 1H), 9.60 (d, 1H).

Intermediate L35 tert-Butyl (3-oxopropyl)carbamate

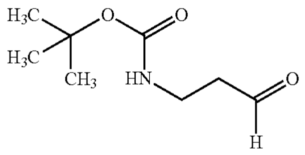

The title compound was prepared according to a method known from the literature (e.g. Jean Bastide et al. *J. Med. Chem.* 2003, 46(16), 3536-3545).

Intermediate L36

N-[(Benzyloxy)carbonyl]-L-valyl-N5-carbamoyl-L-ornithine

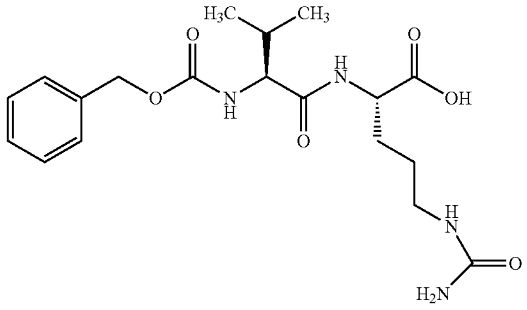 [SMILES: CC(C)[C@H](NC(=O)OCc1ccccc1)C(=O)N[C@@H](CCCNC(N)=O)C(=O)O]

100 mg (0.57 mmol) of N5-carbamoyl-L-ornithine were taken up in 4.0 ml of DMF, and 0.08 ml (0.57 mmol) of triethylamine was added. 199.0 mg (0.57 mmol) of 2,5-dioxopyrrolidin-1-yl N-[(benzyloxy)carbonyl]-L-valine and 0.08 ml (0.57 mmol) of triethylamine were then added. The mixture was stirred at RT for 48 h. The reaction mixture was purified directly by preparative RP-HPLC (column: Reprosil 250×30; 10μ, flow rate: 50 ml/min, MeCN/water with 0.1% TFA). The solvents were evaporated under reduced pressure and the residue was dried under high vacuum. This gave 75.7 mg (33% of theory) of the title compound.

LC-MS (Method 1): $R_t$=0.69 min; MS (ESIpos): m/z=409 $[M+H]^+$.

Intermediate L37

L-Valyl-N5-carbamoyl-L-ornithine

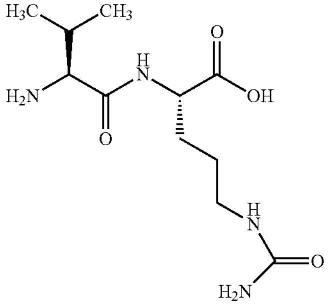 [SMILES: CC(C)[C@H](N)C(=O)N[C@@H](CCCNC(N)=O)C(=O)O]

75.7 mg (0.19 mmol) of Intermediate L36 were suspended in 25 ml of water/ethanol/THF, and 7.5 mg of palladium on activated carbon (10%) were added and the mixture was hydrogenated at RT with hydrogen under standard pressure for 4.5 h. The catalyst was filtered off and the reaction mixture was freed from the solvent under reduced pressure and dried under high vacuum. The residue was used for the next step without further purification. This gave 64.9 mg (93% of theory) of the title compound.

LC-MS (Method 6): $R_t$=0.25 min; MS (ESIpos): m/z=275 $[M+H]^+$.

Intermediate L38

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N5-carbamoyl-L-ornithine

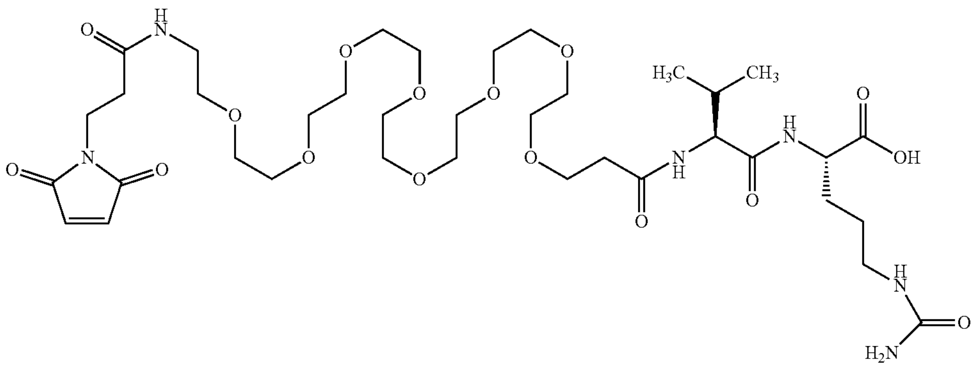 [SMILES: CC(C)[C@H](NC(=O)CCOCCOCCOCCOCCOCCOCCOCCOCCNC(=O)CCN1C(=O)C=CC1=O)C(=O)N[C@@H](CCCNC(N)=O)C(=O)O]

38.3 mg (0.14 mmol) of Intermediate L37 were initially charged in 3.0 ml of DMF, and 96.4 mg (0.14 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide and 39.0 μl (0.28 mmol) of triethylamine were added. The mixture was stirred at RT overnight. 16.0 μl (0.28 mmol) of HOAc were then added, and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 58.9 mg (45% of theory) of the title compound.

LC-MS (Method 1): $R_t$=0.61 min; MS (ESIpos): m/z=849 $[M+H]^+$.

Intermediate L39

2-(Trimethylsilyl)ethyl (2-sulphanylethyl)carbamate

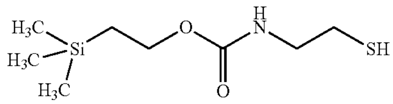

300 mg (2.64 mmol) of 2-aminoethanethiol hydrochloride (1:1) were initially charged in 3.0 ml of dichloromethane, and 668.0 mg (6.60 mmol) of triethylamine and 719.1 mg (2.77 mmol) of 1-({[2-(trimethylsilyl)ethoxy]carbonyl}oxy)pyrrolidine-2,5-dione were added. The mixture was stirred at RT for 2 days (monitored by thin-layer chromatography: dichloromethane/methanol=100:1.5). Ethyl acetate was added and the reaction mixture was washed three times with water. The organic phase was washed twice with saturated NaCl solution and dried over magnesium sulphate. The solvent was evaporated under reduced pressure and the residue was dried under high vacuum. The compound was used without further purification in the next step of the synthesis.

Intermediate L40

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N6-(tert-butoxycarbonyl)-L-lysine

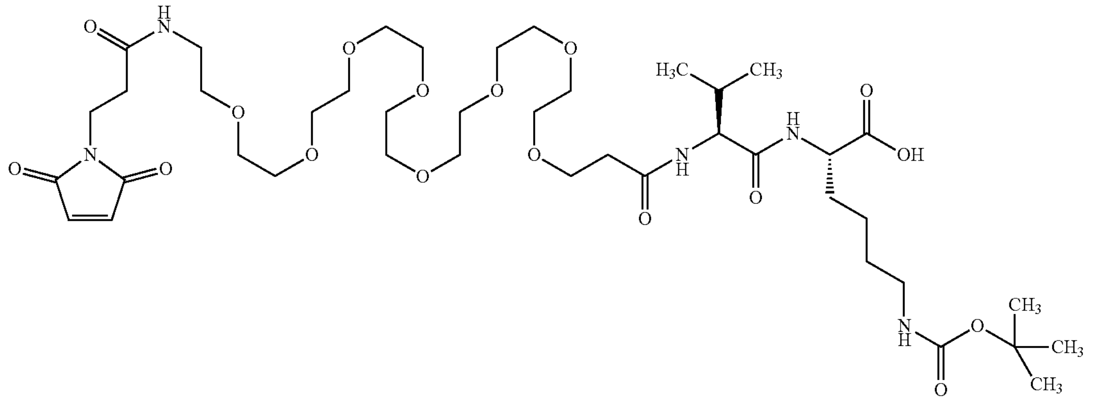 [SMILES: CC(C)[C@H](NC(=O)CCOCCOCCOCCOCCOCCOCCOCCOCCNC(=O)CCN1C(=O)C=CC1=O)C(=O)N[C@@H](CCCCNC(=O)OC(C)(C)C)C(=O)O]

600 mg (1.58 mmol) of N2-[(benzyloxy)carbonyl]-N6-(tert-butoxycarbonyl)-L-lysine were hydrogenated in 25.0 ml of water/ethanol/THF (1:1:0.5) using palladium on carbon (10%) at RT under standard pressure with hydrogen. The compound N6-(tert-butoxycarbonyl)-L-lysine is used without further purification in the next step of the synthesis.

LC-MS (Method 1): $R_t$=0.99 min; MS (ESIpos): m/z=247 $[M+H]^+$.

180.0 (0.73 mmol) of N6-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were added. The reaction mixture was stirred at RT for 3.5 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 294.1 mg (76% of theory) of the compound N-[(benzyloxy)carbonyl]-L-valyl-N6-(tert-butoxycarbonyl)-L-lysine.

LC-MS (Method 1): $R_t$=0.97 min; MS (ESIpos): m/z=480 $[M+H]^+$.

272.2 mg (0.57 mmol) of N-[(benzyloxy)carbonyl]-L-valyl-N6-(tert-butoxycarbonyl)-L-lysine were dissolved in 20 ml of ethyl acetate/ethanol/THF (1:1:1), 27.2 mg of palladium on activated carbon were added and the mixture was hydrogenated under standard pressure and at RT with hydrogen. The mixture was filtered through Celite® and the filter cake was washed thoroughly with ethyl acetate/ethanol/THF (1:1:1). The solvents were evaporated under reduced pressure and the residue was dried under high vacuum. This gave 182.0 mg (72% of theory) of the compound L-valyl-N6-(tert-butoxycarbonyl)-L-lysine.

LC-MS (Method 1): $R_t$=0.53 min; MS (ESIpos): m/z=346 $[M+H]^+$.

30.0 mg (0.07 mmol) of L-valyl-N6-(tert-butoxycarbonyl)-L-lysine and 46.1 mg (0.07 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide were dissolved in 1.5 ml of DMF, and 6.8 mg (0.07 mmol) of 4-methylmorpholine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 55.6 mg (90% of theory) of the title compound.

LC-MS (Method 1): $R_t$=0.77 min; MS (ESIpos): m/z=920 $[M+H]^+$.

Intermediate L41

N-[19-(2,5-Dioxo-2,5-dihydro-1H-pyrrol-1-yl)-17-oxo-4,7,10,13-tetraoxa-16-azanonadecan-1-oyl]-L-valyl-N6-(tert-butoxycarbonyl)-L-lysine

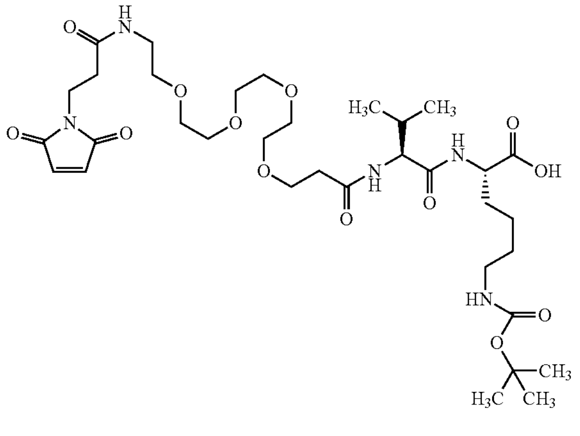 [SMILES: CC(C)[C@H](NC(=O)CCOCCOCCOCCOCCNC(=O)CCN1C(=O)C=CC1=O)C(=O)N[C@@H](CCCCNC(=O)OC(C)(C)C)C(=O)O]

600 mg (1.58 mmol) of N2-[(benzyloxy)carbonyl]-N6-(tert-butoxycarbonyl)-L-lysine were hydrogenated in 25.0 ml of water/ethanol/THF (1:1:0.5) using palladium on carbon (10%) at RT under standard pressure with hydrogen. The compound N6-(tert-butoxycarbonyl)-L-lysine is used without further purification in the next step of the synthesis.

LC-MS (Method 1): $R_t$=0.99 min; MS (ESIpos): m/z=247 $[M+H]^+$.

180.0 (0.73 mmol) of N6-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were added. The reaction mixture was stirred at RT for 3.5 h. The reaction mixture was purified directly by preparative RP-HPLC (column: Reprosil 250×30; 10μ, flow rate: 50 ml/min, MeCN/water, 0.1% TFA). The solvents were then evaporated under reduced pressure and the residue was dried under high vacuum. This gave 294.1 mg (76% of theory) of the compound N-[(benzyloxy)carbonyl]-L-valyl-N6-(tert-butoxycarbonyl)-L-lysine.

LC-MS (Method 1): $R_t$=0.97 min; MS (ESIpos): m/z=480 $[M+H]^+$.

272.2 mg (0.57 mmol) of N-[(benzyloxy)carbonyl]-L-valyl-N6-(tert-butoxycarbonyl)-L-lysine were dissolved in 20.0 ml of ethyl acetate/ethanol/THF (1:1:1), 27.2 mg of palladium on activated carbon were added and the mixture was hydrogenated under standard pressure and at RT with hydrogen. The mixture was filtered through Celite® and the filter cake was washed thoroughly with ethyl acetate/ethanol/THF (1:1:1). The solvents were evaporated under reduced pressure and the residue was dried under high vacuum. This gave 182.0 mg (72% of theory) of the compound L-valyl-N6-(tert-butoxycarbonyl)-L-lysine.

LC-MS (Method 1): $R_t$=0.53 min; MS (ESIpos): m/z=346 $[M+H]^+$.

30.0 mg (0.07 mmol) of L-valyl-N6-(tert-butoxycarbonyl)-L-lysine and 34.3 mg (0.07 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were dissolved in 1.5 ml of DMF, and 6.8 mg (0.07 mmol) of 4-methylmorpholine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 40.6 mg (82% of theory) of the title compound.

LC-MS (Method 1): $R_t$=0.73 min; MS (ESIpos): m/z=744 $[M+H]^+$.

Intermediate L42

N-[19-(2,5-Dioxo-2,5-dihydro-1H-pyrrol-1-yl)-17-oxo-4,7,10,13-tetraoxa-16-azanonadecan-1-oyl]-L-valyl-N5-carbamoyl-L-ornithine

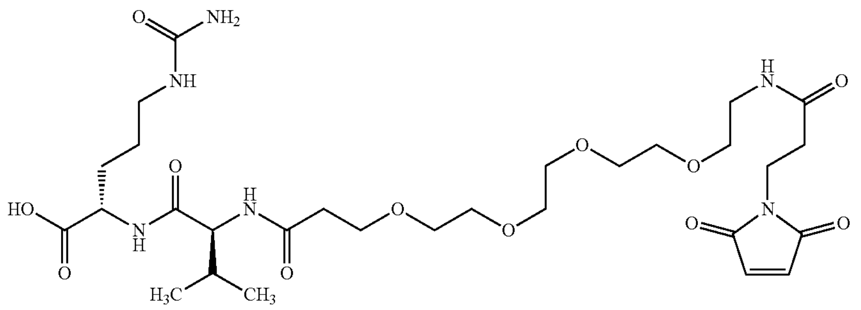 [SMILES: CC(C)[C@H](NC(=O)CCOCCOCCOCCOCCNC(=O)CCN1C(=O)C=CC1=O)C(=O)N[C@@H](CCCNC(N)=O)C(=O)O]

50.0 mg (0.18 mmol) of L-valyl-N5-carbamoyl-L-ornithine (Intermediate L37) were initially charged in DMF, and 93.6 mg (0.18 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide and 36.9 mg (0.37 mmol) of triethylamine were added. The reaction mixture was stirred at RT overnight. 21.9 mg (0.37 mmol) of HOAc were added and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 20.6 mg (14% of theory) of the title compound.

LC-MS (Method 1): $R_t$=0.55 min; MS (ESIpos): m/z=673 $[M+H]^+$.

Intermediate L43

N-[67-(2,5-Dioxo-2,5-dihydro-1H-pyrrol-1-yl)-65-oxo-4,7,10,13,16,19,22,25,28,31,34,37,40,43,46,49,52,55,58,61-icosaoxa-64-azaheptahexacontan-1-oyl]-L-valyl-N5-carbamoyl-L-ornithine

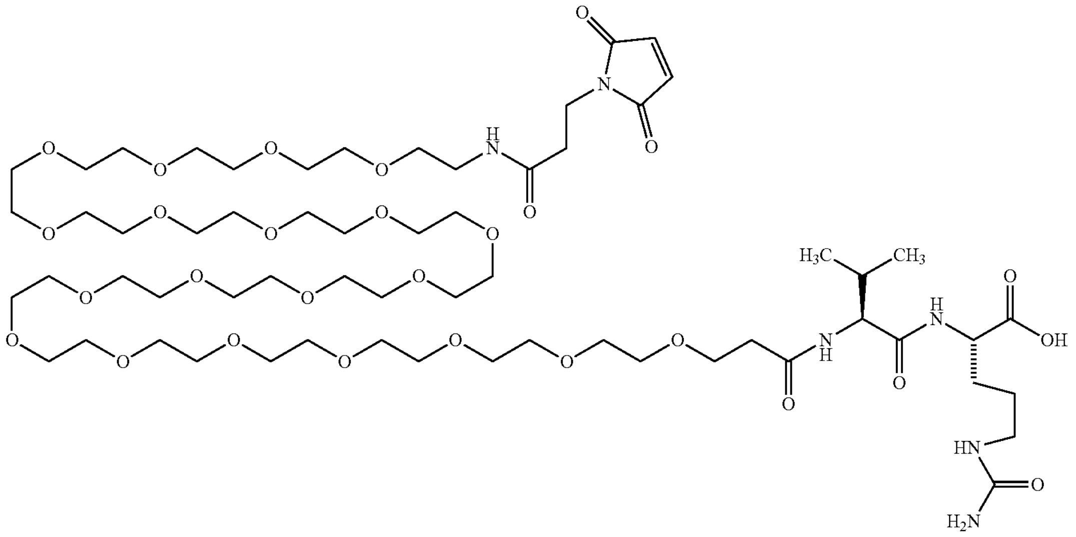 [SMILES: CC(C)[C@H](NC(=O)CCOCCOCCOCCOCCOCCOCCOCCOCCOCCOCCOCCOCCOCCOCCOCCOCCOCCOCCOCCOCCNC(=O)CCN1C(=O)C=CC1=O)C(=O)N[C@@H](CCCNC(N)=O)C(=O)O]

11.3 mg (0.04 mmol) of L-valyl-N5-carbamoyl-L-ornithine (Intermediate L37) were initially charged in DMF, and 50.0 mg (0.04 mmol) of 3-(2,5-dioxo-2,5-dihydro-1H-pyrrol-1-yl)-N-{63-[(2,5-dioxopyrrolidin-1-yl)oxy]-63-oxo-3,6,9,12,15,18,21,24,27,30,33,36,39,42,45,48,51,54,57,60-icosaoxatrihexacont-1-yl}propanamide and 8.3 mg (0.08 mmol) of triethylamine were added. The reaction mixture was stirred at RT overnight. 4.9 mg (0.08 mmol) of HOAc were added and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 15.8 mg (20% of theory) of the title compound.

LC-MS (Method 4): $R_t$=0.94 min; MS (ESIpos): m/z=1377 $[M+H]^+$.

Intermediate L44

N-[19-(2,5-Dioxo-2,5-dihydro-1H-pyrrol-1-yl)-7-oxo-4,7,10,13-tetraoxa-16-azanonadecan-1-oyl]-L-valyl-L-alanine

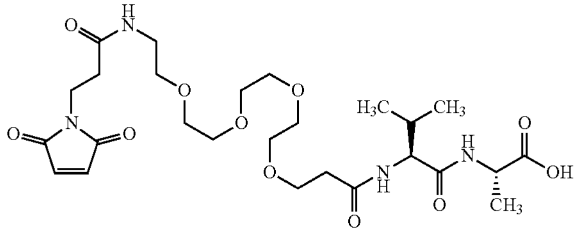 [SMILES: CC(C)[C@H](NC(=O)CCOCCOCCOCCOCCNC(=O)CCN1C(=O)C=CC1=O)C(=O)N[C@@H](C)C(=O)O]

73.3 mg (0.39 mmol) of L-valyl-L-alanine were dissolved in 7.0 ml of DMF, and 200.0 mg (0.39 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide and 78.8 mg (0.78 mmol) of triethylamine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 103.3 mg (45% of theory) of the title compound.

LC-MS (Method 1): $R_t$=0.58 min; MS (ESIpos): m/z=587 $[M+H]^+$.

Intermediate L45 tert-Butyl (2S)-2-[(tert-butoxycarbonyl)amino]-4-oxobutanoate

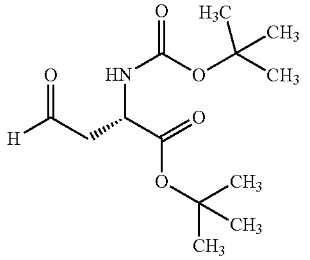 [SMILES: CC(C)(C)OC(=O)N[C@@H](CC=O)C(=O)OC(C)(C)C]

2.00 g (7.26 mmol) of tert-butyl N-(tert-butoxycarbonyl)-L-homoserinate were dissolved in 90 ml of dichloromethane, and 1.76 ml of pyridine and 4.62 g (10.90 mmol) of 1,1,1-triacetoxy-1lambda$^5$,2-benziodoxol-3(1H)-on (Dess-Martin periodinane) were then added. The reaction was stirred at RT for 2 h and then diluted with 200 ml of dichloromethane and extracted twice with 10% strength sodium thiosulphate solution and then successively twice with 5% strength citric acid and twice with saturated sodium bicarbonate solution. The organic phase was separated off, dried over sodium sulphate and then concentrated under reduced pressure. 100 ml of diethyl ether and cyclohexane (v/v=1:1) were added to the residue, resulting in the formation of a white precipitate. This was filtered off with suction. The filtrate was concentrated on a rotary evaporator and dried under high vacuum, giving 1.74 g (88% of theory) of the target compound as a light-yellow oil.

LC-MS (Method 1): $R_t$=0.85 min; MS (ESIpos): m/z=274 $[M+H]^+$.

$^1$H-NMR (400 MHz, DMSO-$d_6$): δ [ppm]=1.38 (s, 18H), 2.64-2.81 (m, 2H), 4.31-4.36 (m, 1H), 7.23 (d, 1H), 9.59 (s, 1H).

Intermediate L46

Trifluoroacetic Acid/tert-butyl N-[2-(2,5-dioxo-2,5-dihydro-1H-pyrrol-1-yl)ethyl]-L-glutaminate (1:1)

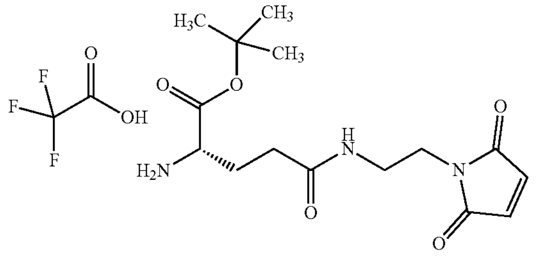

The title compound was prepared by first coupling 200 mg (0.79 mmol) of trifluoroacetic acid/1-(2-aminoethyl)-1H-pyrrole-2,5-dione (1:1) with 263 mg (0.87 mmol) of (4S)-5-tert-butoxy-4-[(tert-butoxycarbonyl)amino]-5-oxopentanoic acid/trifluoroacetic acid (1:1) in the presence of EDC/HOBT and N,N-diisopropylethylamine and then deprotecting the amino group under gentle conditions by stirring for 1 h in 10% strength trifluoroacetic acid in DCM at RT. Freeze-drying from acetonitrile/water gave 85 mg (20% of theory) of the title compound over 2 steps.

LC-MS (Method 1): $R_t$=0.37 min; MS (ESIpos): m/z=326 $[M+H]^+$.

Intermediate L47

Trifluoroacetic Acid/beta-alanyl-L-alanyl-N5-carbamoyl-N-[4-(2,5-dioxo-2,5-dihydro-1H-pyrrol-1-yl)phenyl]-L-ornithinamide (1:1)

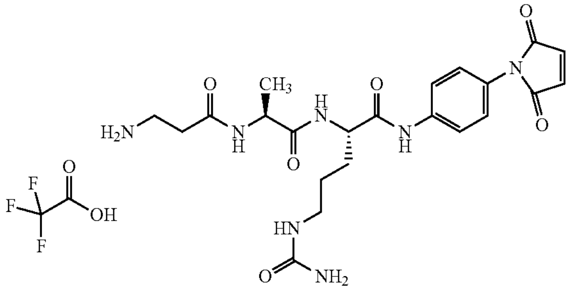 [SMILES: O=C(O)C(F)(F)F ; C[C@H](NC(=O)CCN)C(=O)N[C@@H](CCCNC(N)=O)C(=O)Nc1ccc(N2C(=O)C=CC2=O)cc1]

The title compound was prepared by coupling Intermediate L8 with 2,5-dioxopyrrolidin-1-yl N-(tert-butoxycarbonyl)-beta-alaninate and subsequent deprotection with TFA.

LC-MS (Method 3): $R_t$=1.36 min; MS (ESIpos): m/z=488 $(M+H)^+$.

Intermediate L48

Trifluoroacetic Acid/(1R,2S)-2-amino-N-[2-(2,5-dioxo-2,5-dihydro-1H-pyrrol-1-yl)ethyl]cyclopentanecarboxamide (1:1)

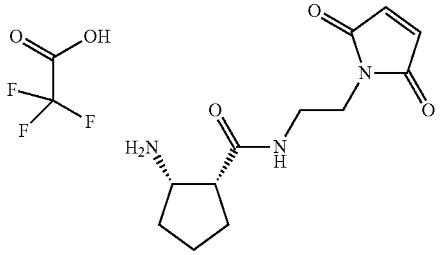 [SMILES: O=C(O)C(F)(F)F ; N[C@H]1CCC[C@H]1C(=O)NCCN1C(=O)C=CC1=O]

The title compound was prepared from commercially available (1R,2S)-2-[(tert-butoxycarbonyl)amino]cyclopentanecarboxylic acid analogously to Intermediate L2.

LC-MS (Method 3): $R_t$=1.22 min; MS (ESIpos): m/z=252 $(M+H)^+$.

Intermediate L49

Trifluoroacetic Acid/tert-butyl N-(bromoacetyl)-L-valyl-L-alanyl-L-lysinate (1:1)

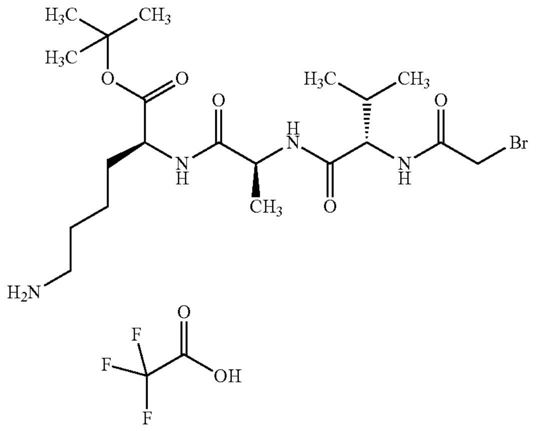 [SMILES: CC(C)[C@H](NC(=O)CBr)C(=O)N[C@@H](C)C(=O)N[C@@H](CCCCN)C(=O)OC(C)(C)C ; O=C(O)C(F)(F)F]

The title compound was prepared by first coupling commercially available bromoacetic anhydride with then partially protected peptide tert-butyl L-valyl-L-alanyl-$N^6$-(tert-butoxycarbonyl)-L-lysinate, prepared according to classical methods of peptide chemistry, in the presence of N,N-diisopropylethylamine in dichloromethane. This was followed by deprotection at the amino group under gentle conditions by stirring in 10% strength trifluoroacetic acid in DCM at RT, giving the title compound in 49% yield over 2 steps.

LC-MS (Method 1): $R_t$=1.09 min; MS (ESIpos): m/z=593 and 595 $(M+H)^+$.

Intermediate L50

Trifluoroacetic Acid/(1S,3R)-3-amino-N-[2-(2,5-dioxo-2,5-dihydro-1H-pyrrol-1-yl)ethyl]cyclopentanecarboxamide (1:1)

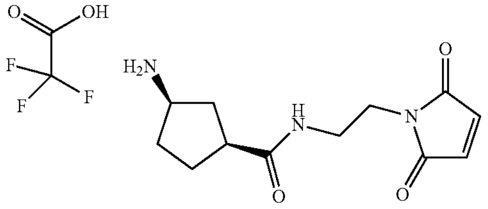 [SMILES: O=C(O)C(F)(F)F ; N[C@@H]1CC[C@H](C(=O)NCCN2C(=O)C=CC2=O)C1]

The title compound was prepared from commercially available (1S,3R)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

HPLC (Method 11): $R_t$=0.2 min;

LC-MS (Method 3): $R_t$=0.88 min; MS (ESIpos): m/z=252 $(M+H)^+$.

Intermediate L51

Trifluoroacetic Acid/(1R,3R)-3-amino-N-[2-(2,5-dioxo-2,5-dihydro-1H-pyrrol-1-yl)ethyl]cyclopentanecarboxamide (1:1)

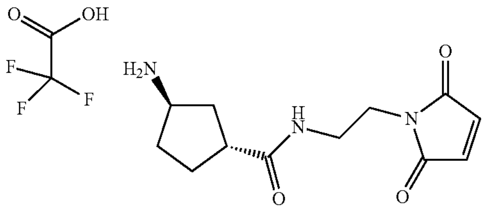 [SMILES: O=C(O)C(F)(F)F ; N[C@@H]1CC[C@@H](C(=O)NCCN2C(=O)C=CC2=O)C1]

The title compound was prepared from commercially available (1R,3R)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

LC-MS (Method 3): $R_t$=0.98 min; MS (ESIpos): m/z=250 $(M-H)^-$.

Intermediate L52

Trifluoroacetic Acid/N-(2-aminoethyl)-2-bromoacetamide (1:1)

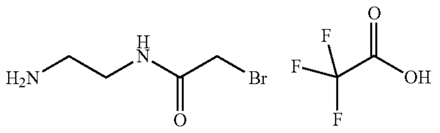

420 mg (2.62 mmol) of tert-butyl (2-aminoethyl)carbamate were taken up in 50 ml of dichloromethane, and 817 mg (3.15 mmol) of bromoacetic anhydride and 913 μl (5.24 mmol) of N,N-diisopropylethylamine were added. The reaction was stirred at RT for 1 h and then concentrated under reduced pressure. The residue was purified by preparative HPLC.

This gave 577 mg of the protected intermediate which were then taken up in 50 ml of dichloromethane, and 10 ml of trifluoroacetic acid were added. After 1 h of stirring at RT, the reaction was concentrated under reduced pressure and the residue was lyophilized from acetonitrile/water. This gave 705 mg (65% of theory) of the title compound.

LC-MS (Method 3): $R_t$=0.34 min; MS (ESIpos): m/z=181 and 183 $(M+H)^+$.

Intermediate L53

Trifluoroacetic Acid/(1S,3S)-3-amino-N-[2-(2,5-dioxo-2,5-dihydro-1H-pyrrol-1-yl)ethyl]cyclopentanecarboxamide (1:1)

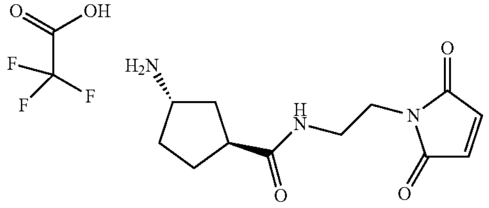 [SMILES: O=C(O)C(F)(F)F ; N[C@H]1CC[C@H](C(=O)NCCN2C(=O)C=CC2=O)C1]

The title compound was prepared from commercially available (1S,3S)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

HPLC (Method 11): $R_t$=0.19 min;

LC-MS (Method 3): $R_t$=0.88 min; MS (ESIpos): m/z=250 $(M-H)^-$.

Intermediate L54

Trifluoroacetic Acid/(1R,3S)-3-amino-N-[2-(2,5-dioxo-2,5-dihydro-1H-pyrrol-1-yl)ethyl]cyclopentanecarboxamide (1:1)

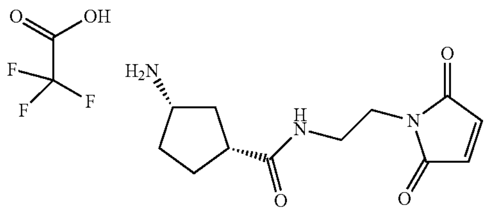 [SMILES: O=C(O)C(F)(F)F ; N[C@H]1CC[C@@H](C(=O)NCCN2C(=O)C=CC2=O)C1]

The title compound was prepared from commercially available (1R,3S)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

LC-MS (Method 3): $R_t$=0.89 min; MS (ESIpos): m/z=252 $(M+H)^+$.

Intermediate L55

Trifluoroacetic Acid/tert-butyl $N^6$-D-alanyl-$N^2$—{N-[6-(2,5-dioxo-2,5-dihydro-1H-pyrrol-1-yl)-hexanoyl]-L-valyl-L-alanyl}-L-lysinate (1:1)

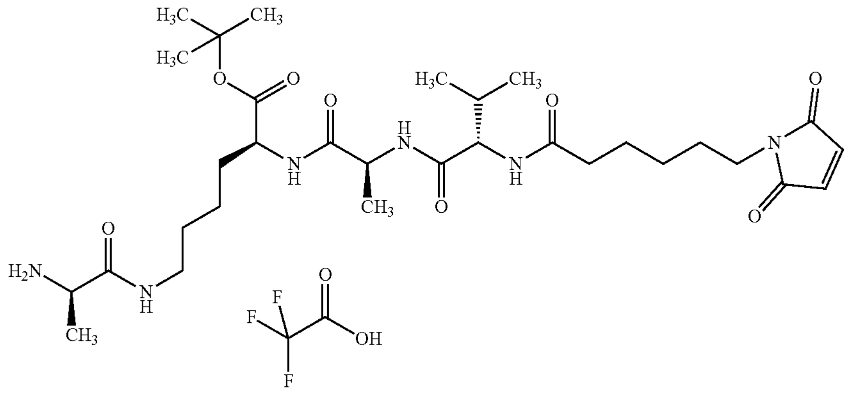 [SMILES: CC(C)[C@H](NC(=O)CCCCCN1C(=O)C=CC1=O)C(=O)N[C@@H](C)C(=O)N[C@@H](CCCCNC(=O)[C@@H](C)N)C(=O)OC(C)(C)C ; O=C(O)C(F)(F)F]

The title compound was prepared by first coupling Intermediate L6 with N-(tert-butoxycarbonyl)-D-alanine in the presence of HATU, followed by deprotection at the amino group under gentle conditions by stirring for 90 minutes in 5% strength trifluoroacetic acid in DCM at RT.

HPLC (Method 11): $R_t$=1.35 min;

LC-MS (Method 1): $R_t$=0.67 min; MS (ESIpos): m/z=637 $(M+H)^+$.

Intermediate L56

Trifluoroacetic Acid/tert-butyl-N-[6-(2,5-dioxo-2,5-dihydro-1H-pyrrol-1-yl)hexanoyl]-L-valyl-L-alanyl-$N^6$-{[(1R,3S)-3-aminocyclopentyl]carbonyl}-L-lysinate (1:1)

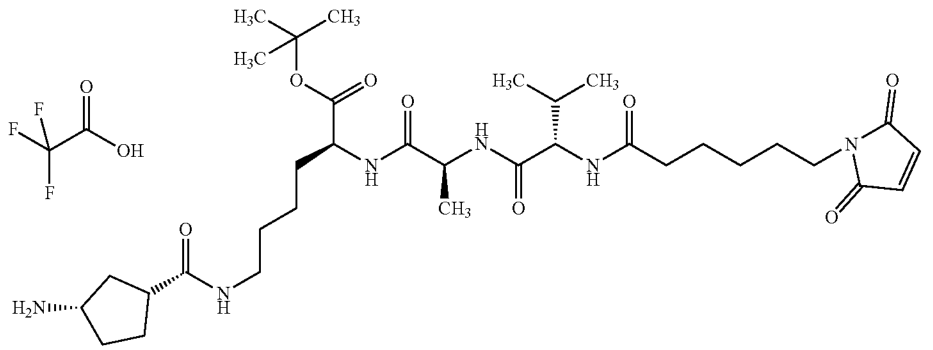

The title compound was prepared by first coupling Intermediate L6 with (1R,3S)-3-[(tert-butoxycarbonyl)amino]cyclopentanecarboxylic acid in the presence of HATU, followed by deprotection at the amino group under gentle conditions by stirring for 15 minutes in 25% strength trifluoroacetic acid in DCM at RT.

HPLC (Method 11): $R_t$=1.4 min;

LC-MS (Method 1): $R_t$=0.7 min; MS (ESIpos): m/z=677 $(M+H)^+$.

Intermediate L57

Methyl (2S)-4-oxo-2-({[2-(trimethylsilyl)ethoxy]carbonyl}amino)butanoate

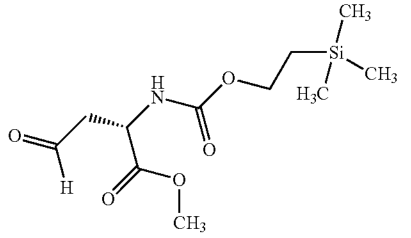 [SMILES: COC(=O)[C@H](CC=O)NC(=O)OCC[Si](C)(C)C]

500.0 mg (2.72 mmol) of methyl L-asparaginate hydrochloride and 706.3 mg (2.72 mmol) of 2-(trimethylsilyl)ethyl 2,5-dioxopyrrolidine-1-carboxylate were initially charged in 5.0 ml of 1,4-dioxane, and 826.8 mg (8.17 mmol) of triethylamine were added. The reaction mixture was stirred at RT overnight. The reaction mixture was purified directly by preparative RP-HPLC (column: Reprosil 250×40; 10μ, flow rate: 50 ml/min, MeCN/water, 0.1% TFA). The solvents were then evaporated under reduced pressure and the residue was dried under high vacuum. This gave 583.9 mg (74% of theory) of the compound (3S)-4-methoxy-4-oxo-3-({[2-(trimethylsilyl)ethoxy]carbonyl}amino)butanoic acid.

LC-MS (Method 1): $R_t$=0.89 min; MS (ESIneg): m/z=290 $(M-H)^-$.

592.9 mg of (3S)-4-methoxy-4-oxo-3-({[2-(trimethylsilyl)ethoxy]carbonyl}amino)butanoic acid were initially charged in 10.0 ml of 1,2-dimethoxyethane, the mixture was cooled to −15° C. and 205.8 mg (2.04 mmol) of 4-methylmorpholine and 277.9 mg (2.04 mmol) of isobutyl chloroformate were added. The precipitate was filtered off with suction after 15 min and twice with in each case 10.0 ml of 1,2-dimethoxyethane. The filtrate was cooled to −10° C., and 115.5 mg (3.05 mmol) of sodium borohydride dissolved in 10 ml of water were added with vigorous stirring. The phases were separated and the organic phase was washed in each case once with saturated sodium bicarbonate solution and saturated NaCl solution. The organic phase was dried over magnesium sulphate, the solvent was evaporated under reduced pressure and the residue was dried under high vacuum. This gave 515.9 mg (91% of theory) of the compound methyl N-{[2-(trimethylsilyl)ethoxy]carbonyl}-L-homoserinate.

LC-MS (Method 1): $R_t$=0.87 min; MS (ESIpos): m/z=278 $(M+H)^+$.

554.9 mg (2.00 mmol) of methyl N-{[2-(trimethylsilyl)ethoxy]carbonyl}-L-homoserinate were initially charged in 30.0 ml of dichloromethane, and 1.27 g (3.0 mmol) of Dess-Martin periodinane and 474.7 mg (6.00 mmol) of pyridine were added. The mixture was stirred at RT overnight. After 4 h, the reaction was diluted with dichloromethane and the organic phase was washed in each case three times with 10% strength $Na_2S_2O_3$ solution, 10% strength citric acid solution and saturated sodium bicarbonate solution. The organic phase was dried over magnesium sulphate and the solvent was evaporated under reduced pressure. This gave 565.7 mg (97% of theory) of the title compound.

$^1$H-NMR (400 MHz, DMSO-$d_6$): δ [ppm]=0.03 (s, 9H), 0.91 (m, 2H), 2.70-2.79 (m, 1H), 2.88 (dd, 1H), 3.63 (s, 3H), 4.04 (m, 2H), 4.55 (m, 1H), 7.54 (d, 1H), 9.60 (t, 1H).

Intermediate L58

2-(Trimethylsilyl)ethyl (3-oxopropyl)carbamate

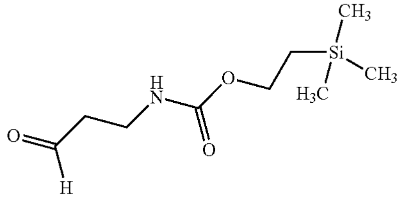

434.4 mg (5.78 mmol) of 3-amino-1-propanol and 1.50 g (5.78 mmol) of 2-(trimethylsilyl)ethyl 2,5-dioxopyrrolidine-1-carboxylate were dissolved in 10.0 ml of dichloromethane, 585.3 mg (5.78 mmol) of triethylamine were added and the mixture was stirred at RT overnight. The reaction mixture was diluted with dichloromethane and the organic phase was washed with water and saturated sodium bicarbonate solution and then dried over magnesium sulphate. The solvent was evaporated under reduced pressure. The residue 2-(trimethylsilyl)ethyl (3-hydroxypropyl)carbamate (996.4 mg, 79% of theory) was dried under high vacuum and used without further purification in the next step of the synthesis.

807.0 mg (3.68 mmol) of 2-(trimethylsilyl)ethyl (3-hydroxypropyl)carbamate were initially charged in 15.0 ml of chloroform and 15.0 ml of 0.05 N potassium carbonate/0.05 N sodium bicarbonate solution (1:1). 102.2 mg (0.37 mmol) of tetra-n-butylammonium chloride, 736.9 mg (5.52 mmol) of N-chlorosuccinimide and 57.5 mg (0.37 mmol) of TEMPO were then added and the reaction mixture was stirred vigorously at RT overnight. The reaction mixture was diluted with dichloromethane and the organic phase was washed with water and saturated NaCl solution. The organic phase was dried over magnesium sulphate and the solvent was evaporated under reduced pressure. The residue was dried under high vacuum and used without further purification in the next step of the synthesis (890.3 mg).

Intermediate L59

Trifluoroacetic Acid/1-{2-[2-(2-aminoethoxy)ethoxy]ethyl}-1H-pyrrole-2,5-dione (1:1)

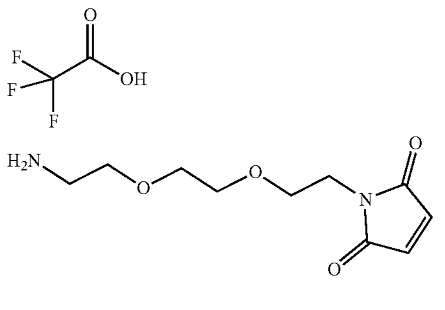

300.0 mg (0.91 mmol) of tert-butyl (2-{2-[2-(2,5-dioxo-2,5-dihydro-1H-pyrrol-1-yl)ethoxy]ethoxy}ethyl)carbamate were initially charged in dichloromethane, 4.2 g (36.54 mmol) of TFA were added and the mixture was stirred at RT for 1 h (monitored by TLC: dichloromethane/methanol 10:1). The volatile components were evaporated under reduced pressure and the residue was co-distilled four times with dichloromethane. The residue was dried under high vacuum and used without further purification in the next step of the synthesis.

LC-MS (Method 1): $R_t$=0.19 min; MS (ESIpos): m/z=229 $(M+H)^+$.

Intermediate L60

6-(2,5-Dioxo-2,5-dihydro-1H-pyrrol-1-yl)hexanoyl Chloride

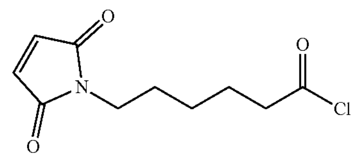 [SMILES: O=C(Cl)CCCCCN1C(=O)C=CC1=O]

200.0 mg (0.95 mmol) of 6-(2,5-dioxo-2,5-dihydro-1H-pyrrol-1-yl)hexanoic acid were dissolved in 4.0 ml of dichloromethane, and 338.0 mg (2.84 mmol) of thionyl chloride were added. The reaction mixture was stirred at RT for 3 h, and 1 drop of DMF was then added. The mixture was stirred for another 1 h. The solvent was evaporated under reduced pressure and the residue was co-distilled three times with dichloromethane. The crude product was used without further purification in the next step of the synthesis.

Intermediate L61

Trifluoroacetic Acid/2-(trimethylsilyl)ethyl-N-[6-(2,5-dioxo-2,5-dihydro-1H-pyrrol-1-yl)hexanoyl]-L-valyl-L-alanyl-L-lysinate (1:1)

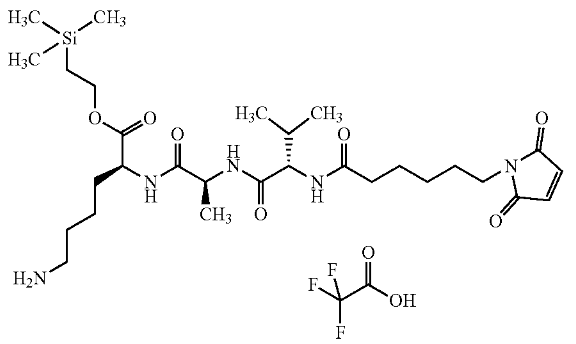 [SMILES: CC(C)[C@H](NC(=O)CCCCCN1C(=O)C=CC1=O)C(=O)N[C@@H](C)C(=O)N[C@@H](CCCCN)C(=O)OCC[Si](C)(C)C ; O=C(O)C(F)(F)F]

First, the tripeptide derivative 2-(trimethylsilyl)ethyl L-valyl-L-alanyl-N6-(tert-butoxycarbonyl)-L-lysinate was prepared from N2-[(benzyloxy)carbonyl]-N6-(tert-butoxycarbonyl)-L-lysine according to classical methods of peptide chemistry (esterification with 2-(trimethylsilylethanol using EDCI/DMAP, hydrogenolysis, coupling with N-[(benzyloxy)carbonyl]-L-valyl-L-alanine in the presence of HATU and another hydrogenolysis). The title compound was prepared by coupling this partially protected peptide derivative with commercially available 6-(2,5-dioxo-2,5-dihydro-1H-pyrrol-1-yl)hexanoic acid in the presence of HATU and N,N-diisopropylethylamine. This was followed by deprotection at the amino group under gentle conditions by stirring for 2.5 hours in 5% strength trifluoroacetic acid in DCM at RT with retention of the ester protective group. Work-up and purification by preparative HPLC gave 438 mg of the title compound.

HPLC (Method 11): $R_t$=1.69 min;

LC-MS (Method 1): $R_t$=0.78 min; MS (ESIpos): m/z=610 $(M+H)^+$.

Intermediate L62

Trifluoroacetic Acid/2-(trimethylsilyl)ethyl-N-[6-(2,5-dioxo-2,5-dihydro-1H-pyrrol-1-yl)hexanoyl]-L-valyl-$N^5$-carbamoyl-L-ornithyl-L-lysinate (1:1)

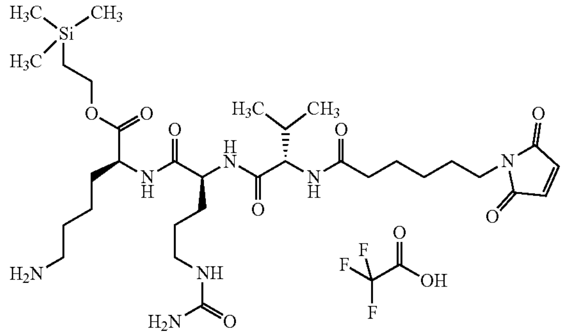 [SMILES: CC(C)[C@H](NC(=O)CCCCCN1C(=O)C=CC1=O)C(=O)N[C@@H](CCCNC(N)=O)C(=O)N[C@@H](CCCCN)C(=O)OCC[Si](C)(C)C ; O=C(O)C(F)(F)F]

First, 2-(trimethylsilyl)ethyl N6-(tert-butoxycarbonyl)-L-lysinate was prepared from N2-[(benzyloxy)carbonyl]-N6-(tert-butoxycarbonyl)-L-lysine according to classical methods of peptide chemistry. 148 mg (0.43 mmol) of this intermediate were then coupled in the presence of 195 mg (0.51 mmol) of HATU and 149 μl of N,N-diisopropylethylamine with 200 mg (0.43 mmol) of Intermediate L16. After concentration and purification of the residue by preparative HPLC, the protected intermediate was taken up in 20 ml of DCM and the tert-butoxycarbonyl protective group was removed by addition of 2 ml of trifluoroacetic acid and 1 h of stirring at RT. Concentration and lyophilization of the residue from acetonitrile/water gave 254 mg (63% of theory over 2 steps).

HPLC (Method 11): $R_t$=1.51 min;

LC-MS (Method 1): $R_t$=0.68 min; MS (ESIpos): m/z=696 $(M+H)^+$.

Intermediate L63

(4S)-4-{[(2S)-2-{[(2S)-2-{[6-(2,5-Dioxo-2,5-dihydro-1H-pyrrol-1-yl)hexanoyl]amino}-3-methylbutanoyl]amino}propanoyl]amino}-5-oxo-5-[2-(trimethylsilyl)ethoxy]pentanoic Acid

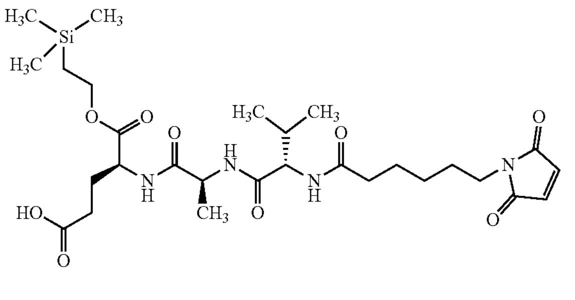 [SMILES: CC(C)[C@H](NC(=O)CCCCCN1C(=O)C=CC1=O)C(=O)N[C@@H](C)C(=O)N[C@@H](CCC(=O)O)C(=O)OCC[Si](C)(C)C]

First, the tripeptide derivative (4S)-4-{[(2S)-2-{[(2S)-2-amino-3-methylbutanoyl]amino}propanoyl]amino}-5-oxo-5-[2-(trimethylsilyl)ethoxy]pentanoic acid was prepared from (2S)-5-(benzyloxy)-2-[(tert-butoxycarbonyl)amino]-5-oxopentanoic acid according to classical methods of peptide chemistry (esterification with 2-(trimethylsilylethanol using EDCI/DMAP, removal of the Boc protective group with trifluoroacetic acid, coupling with N-[(benzyloxy)carbonyl]-L-valyl-L-alanine in the presence of HATU and hydrogenolysis in methanol over 10% palladium on activated carbon). The title compound was prepared by coupling of this partially protected peptide derivative with commercially available 1-{6-[(2,5-dioxopyrrolidin-1-yl)oxy]-6-oxohexyl}-1H-pyrrole-2,5-dione. Work-up and purification by preparative HPLC gave 601 mg of the title compound.

LC-MS (Method 1): $R_t$=0.96 min; MS (ESIpos): m/z=611 $(M+H)^+$.

Intermediate L64

(4S)-4-{[(2,5-Dioxo-2,5-dihydro-1H-pyrrol-1-yl)acetyl]amino}-5-oxo-5-[2-(trimethylsilyl)ethoxy]pentanoic Acid

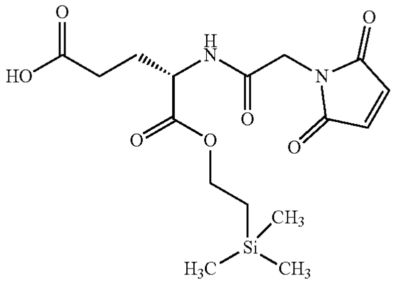 [SMILES: C[Si](C)(C)CCOC(=O)[C@H](CCC(=O)O)NC(=O)CN1C(=O)C=CC1=O]

The title compound was prepared from (2S)-5-(benzyloxy)-2-[(tert-butoxycarbonyl)amino]-5-oxopentanoic acid according to classical methods of peptide chemistry (esterification with 2-(trimethylsilylethanol using EDCI/DMAP, removal of the Boc protective group with trifluoroacetic acid, hydrogenolytic cleavage of the benzyl ester in methanol over 10% palladium on activated carbon and coupling with 1-{2-[(2,5-dioxopyrrolidin-1-yl)oxy]-2-oxoethyl}-1H-pyrrole-2,5-dione in the presence of N,N-diisopropylethylamine).

LC-MS (Method 1): $R_t$=0.84 min; MS (ESIpos): m/z=385 $(M+H)^+$.

Intermediate L65

Trifluoroacetic Acid/2-(trimethylsilyl)ethyl-3-{[(benzyloxy)carbonyl]amino}-L-alaninate (1:1)

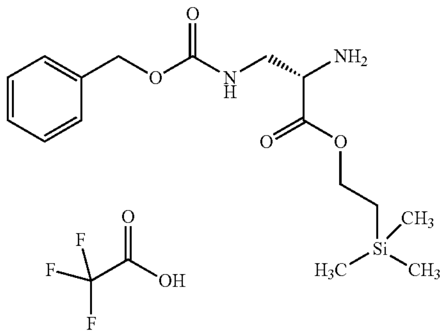 [SMILES: C[Si](C)(C)CCOC(=O)[C@@H](N)CNC(=O)OCc1ccccc1 ; O=C(O)C(F)(F)F]

The title compound was prepared from 3-{[(benzyloxy)carbonyl]amino}-N-(tert-butoxycarbonyl)-L-alanine according to classical methods of peptide chemistry (esterification with 2-(trimethylsilylethanol using EDCI/DMAP and removal of the Boc protective group with trifluoroacetic acid. This gave 373 mg (79% of theory over 2 steps) of the title compound.

LC-MS (Method 1): $R_t$=0.72 min; MS (ESIpos): m/z=339 $(M+H)^+$.

Intermediate L66

Methyl (8S)-8-(2-hydroxyethyl)-2,2-dimethyl-6,11-dioxo-5-oxa-7,10-diaza-2-silatetradecan-14-oate

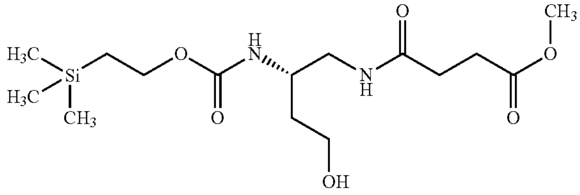

1000 mg (2.84 mmol) of (3S)-3-{[(benzyloxy)carbonyl]amino}-4-[(tert-butoxycarbonyl)amino]butanoic acid were initially charged in 10.0 ml of 1,2-dimethoxyethane, and 344.4 mg (3.4 mmol) of 4-methylmorpholine and 504 mg (3.69 mmol) of isobutyl chloroformate were added. After 10 min of stirring at RT, the reaction was cooled to 5° C. and 161 mg (4.26 mmol) of sodium borohydride dissolved in 3 ml of water were added a little at a time with vigorous stirring. After 1 h, the same amount of sodium borohydride was added again and the reaction was then slowly warmed to RT. 170 ml of water were added and the reaction was then extracted four times with in each case 200 ml of ethyl acetate. The phases were separated and the organic phase was washed once with citric acid and then with saturated sodium bicarbonate solution. The organic phase was dried over magnesium sulphate, the solvent was evaporated under reduced pressure and the residue was dried under high vacuum. This gave 760 mg (78% of theory) of the compound benzyl tert-butyl [(2S)-4-hydroxybutane-1,2-diyl]biscarbamate.

LC-MS (Method 1): $R_t$=0.84 min; MS (ESIpos): m/z=339 $(M+H)^+$.

760 mg (2.16 mmol) of this intermediate dissolved in 13 ml of hydrogen chloride/dioxane were stirred at RT for 20 min. The reaction was then concentrated to 5 ml, and diethyl ether was added. The precipitate was filtered off and lyophilized from acetonitrile/water 1:1.

The product obtained in this manner was dissolved in 132 ml of DMF, and 345.5 mg (2.35 mmol) of 4-methoxy-4-oxobutanoic acid, 970 mg (2.55 mmol) of HATU and 1025 µl of N,N-diisopropylethylamine were added. The mixture was stirred at RT for 5 min. The solvent was removed under reduced pressure and the residue that remained was purified by preparative HPLC. The appropriate fractions were combined and the acetonitrile was evaporated under reduced pressure. The aqueous phase that remained was extracted twice with ethyl acetate and the organic phase was then concentrated and dried under high vacuum.

The intermediate obtained in this manner was taken up in methanol and hydrogenated over 10% palladium on activated carbon at RT under hydrogen standard pressure for 1 h. The catalyst was then filtered off and the solvent was removed under reduced pressure.

247 mg of this deprotected compound were taken up in 20 ml of DMF, and 352 mg (1.36 mmol) of 1-({[2-(trimethylsilyl)ethoxy]carbonyl}oxy)pyrrolidine-2,5-dione and 592 µl of N,N-diisopropylethylamine were added. The reaction mixture was stirred at RT for 1 h and then concentrated, and the residue was purified by preparative HPLC. The solvents were then evaporated under reduced pressure and the residue was dried under high vacuum. This gave, over these 5 reaction steps, 218 mg of the title compound in a total yield of 21%.

LC-MS (Method 1): $R_t$=0.74 min; MS (ESIpos): m/z=363 $(M+H)^+$.

Intermediate L67

Trifluoroacetic Acid/2-(2,5-dioxo-2,5-dihydro-1H-pyrrol-1-yl)ethyl-beta-alaninate (1:1)

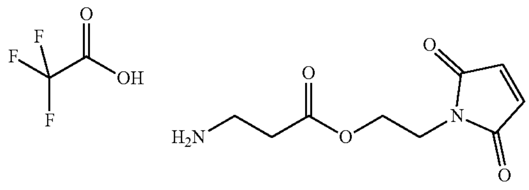 [SMILES: O=C(O)C(F)(F)F ; NCCC(=O)OCCN1C(=O)C=CC1=O]

The title compound was prepared from 50 mg (0.354 mmol) of commercially available 1-(2-hydroxyethyl)-1H-pyrrole-2,5-dione by coupling with 134 mg (0.71 mmol) of N-(tert-butoxycarbonyl)-beta-alanine in 10 ml of dichloromethane in the presence of 1.5 equivalents of EDCI and 0.1 equivalent of 4-N,N-dimethylaminopyridine and subsequent deprotection with trifluoroacetic acid.

Yield: 56 mg (48% of theory over 2 stages)

LC-MS (Method 3): $R_t$=1.15 min; MS (ESIpos): m/z=213 $(M+H)^+$.

Intermediate L68

Trifluoroacetic Acid/N-(2-aminoethyl)-2-(2,5-dioxo-2,5-dihydro-1H-pyrrol-1-yl)propanamide (1:1)

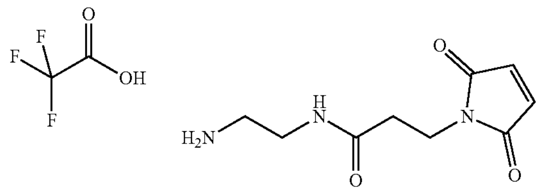 [SMILES: O=C(O)C(F)(F)F ; NCCNC(=O)CCN1C(=O)C=CC1=O]

The title compound was prepared analogously to Intermediate L1 according to classical methods of peptide chemistry from commercially available (2,5-dioxo-2,5-dihydro-1H-pyrrol-1-yl)propanoic acid and tert-butyl (2-aminoethyl) carbamate.

LC-MS (Method 1): $R_t$=0.17 min; MS (ESIpos): m/z=212 $(M+H)^+$.

Intermediate L69

Trifluoroacetic Acid/1-[(benzyloxy)carbonyl]piperidin-4-yl-L-valyl-N5-carbamoyl-L-ornithinate (1:1)

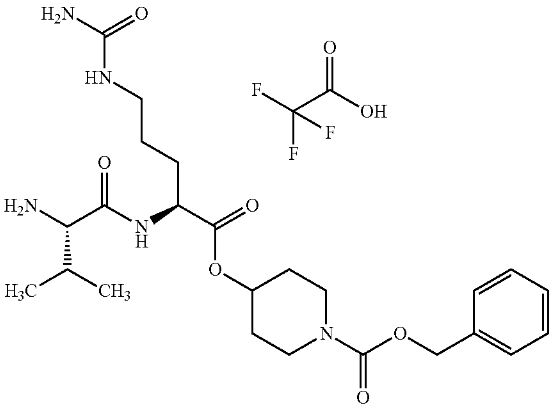 [SMILES: CC(C)[C@H](N)C(=O)N[C@@H](CCCNC(N)=O)C(=O)OC1CCN(C(=O)OCc2ccccc2)CC1 ; O=C(O)C(F)(F)F]

The title compound was prepared by classical methods of peptide chemistry from commercially available benzyl 4-hydroxypiperidine-1-carboxylate by esterification with N2-(tert-butoxycarbonyl)-N5-carbamoyl-L-ornithine using EDCI/DMAP, subsequent Boc removal with TFA, followed by coupling with N-[(tert-butoxy)carbonyl]-L-valine in the presence of HATU and N,N-diisopropylethylamine and finally another Boc removal with TFA.

LC-MS (Method 1): $R_t$=0.62 min; MS (ESIpos): m/z=492 $(M+H)^+$.

Intermediate L70

9H-Fluoren-9-ylmethyl (3-oxopropyl)carbamate

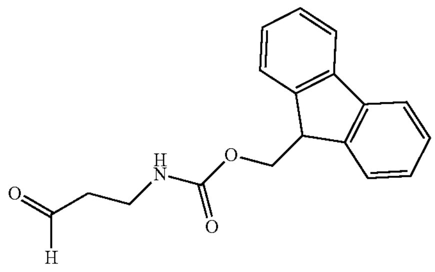 [SMILES: O=CCCNC(=O)OCC1c2ccccc2-c2ccccc21]

1000.0 mg (3.36 mmol) of 9H-fluoren-9-ylmethyl (3-hydroxypropyl)carbamate were initially charged in 15.0 ml of chloroform and 15.0 ml of 0.05 N potassium carbonate/0.05 N sodium bicarbonate solution (1:1). 93.5 mg (0.34 mmol) of tetra-n-butylammonium chloride, 673.6 mg (5.04 mmol) of N-chlorosuccinimide and 52.5 mg (0.34 mmol) of TEMPO were then added and the reaction mixture was stirred vigorously at RT overnight. The reaction mixture was diluted with dichloromethane and the organic phase was washed with water and saturated NaCl solution. The organic phase was dried over magnesium sulphate and the solvent was evaporated under reduced pressure. The residue was dried under high vacuum and purified on silica gel (mobile phase: cyclohexane/ethyl acetate 3:1-1:1). The solvents were evaporated under reduced pressure and the residue was dried under high vacuum. This gave 589.4 mg (58% of theory) of the title compound.

LC-MS (Method 6): $R_t$=2.15 min; MS (ESIpos): m/z=296 $(M-H)^+$.

Intermediate L71 tert-Butyl [4-(chlorocarbonyl)phenyl]carbamate

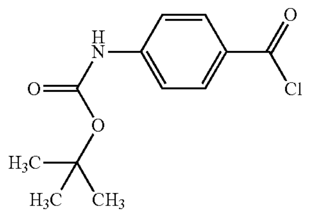 [SMILES: CC(C)(C)OC(=O)Nc1ccc(C(=O)Cl)cc1]

100.0 mg (0.42 mmol) of 4-[(tert-butoxycarbonyl)amino] benzoic acid were initially charged in 2.0 ml of dichloromethane, and 64.2 mg (0.51 mmol) of oxalyl dichloride were added. The reaction mixture was stirred at RT for 30 min (monitored by TLC: dichloromethane/methanol). Another 192.6 mg (1.53 mmol) of oxalyl dichloride and 1 drop of DMF were then added and the mixture was stirred at RT for 1 h. The solvent was evaporated under reduced pressure and the residue was co-distilled repeatedly with dichloromethane. The residue was used without further purification in the next step of the synthesis.

Intermediate L72

Benzyl (9S)-9-(hydroxymethyl)-2,2-dimethyl-6,11-dioxo-5-oxa-7,10-diaza-2-silatetradecan-14-oate

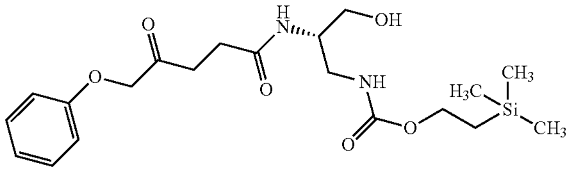 [SMILES: C[Si](C)(C)CCOC(=O)NC[C@@H](CO)NC(=O)CCC(=O)COc1ccccc1]

The title compound was prepared from commercially available benzyl tert-butyl [(2S)-3-hydroxypropan-1,2-diyl] biscarbamate according to classical methods of peptide chemistry by hydrogenolytic removal of the Z protective group, subsequent coupling with 4-(benzyloxy)-4-oxobutanoic acid in the presence of EDCI/HOBT, followed by removal of the Boc protective group with TFA and finally by reaction with 1-({[2-(trimethylsilyl)ethoxy]carbonyl}oxy) pyrrolidine-2,5-dione in the presence of triethylamine.

LC-MS (Method 1): $R_t$=0.94 min; MS (ESIpos): m/z=425 $[M+H]^+$.

Intermediate L73

N-(2-Aminoethyl)-6-(2,5-dioxo-2,5-dihydro-1H-pyrrol-1-yl)hexanamide

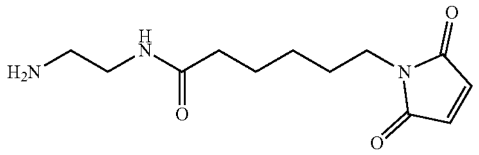 [SMILES: NCCNC(=O)CCCCCN1C(=O)C=CC1=O]

395.5 mg (1.87 mmol) of 6-(2,5-dioxo-2,5-dihydro-1H-pyrrol-1-yl)hexanoic acid, 1.21 g (9.36 mmol) of N,N-diisopropylethylamine and 854.3 mg (2.25 mmol) of HATU were added to a solution of 300 mg (1.87 mmol) of tert-butyl (2-aminoethyl)carbamate in 20 ml of dimethylformamide. The reaction mixture was stirred at RT for 5 minutes. After concentration of the mixture, the residue was taken up in DCM and washed with water. The organic phase was washed with brine, dried over magnesium sulphate, filtered off and concentrated. This gave 408 mg (33%, purity 53%) of the title compound which were used without further purification.

LC-MS (Method 1): $R_t$=0.75 min; MS (ESIpos): m/z=354 $(M+H)^+$.

1 ml of TFA was added to a solution of tert-butyl (2-{[6-(2,5-dioxo-2,5-dihydro-1H-pyrrol-1-yl)hexanoyl] amino}ethyl)carbamate (408 mg, 0.365 mmol) in 7 ml of dichloromethane. The reaction mixture was stirred at RT for 0.5 h. The reaction mixture was concentrated under reduced pressure and the residue was co-distilled twice with dichloromethane. The residue was used further without further purification. This gave 384 mg (94%, purity 57%) of the title compound.

LC-MS (Method 1): $R_t$=0.26 min; MS (ESIpos): m/z=254 $(M+H)^+$.

Intermediate L74

3-[2-[2-[2-[2-[[2-(2,5-Dioxopyrrol-1-yl)acetyl]amino]ethoxy]ethoxy]ethoxy]ethoxy]propanoic Acid

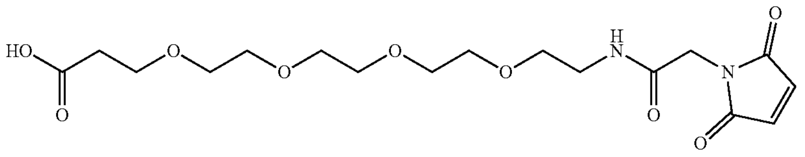 [SMILES: O=C(O)CCOCCOCCOCCOCCNC(=O)CN1C(=O)C=CC1=O]

107 mg (0.335 mmol) of tert-butyl 3-[2-[2-[2-(2-amino-ethoxy)ethoxy]ethoxy]ethoxy]propanoate and 93 mg (0.369 mmol) of (2,5-dioxopyrrolidin-1-yl) 2-(2,5-dioxopyrrol-1-yl)acetate were dissolved in 5 ml of dimethylformamide, and 0.074 ml (0.671 mmol) of N-methylmorpholine were added. The reaction mixture was stirred at RT overnight. 0.048 ml (0.838 mmol) of acetic acid were added and the reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 133 mg (86%, purity 100%) of tert-butyl 3-[2-[2-[2-[2-[[2-(2,5-dioxopyrrol-1-yl)acetyl]amino]ethoxy]ethoxy]ethoxy]ethoxy]propanoate.

LC-MS (Method 1): $R_t$=0.82 min; MS (ESIpos): m/z=459 $(M+H)^+$.

0.5 ml of TFA was added to a solution of tert-butyl 3-[2-[2-[2-[2-[[2-(2,5-dioxopyrrol-1-yl)acetyl]amino]ethoxy]ethoxy]ethoxy]ethoxy]propanoate (130 mg, 0.284 mmol) in 5 ml of dichloromethane. The reaction mixture was stirred at RT overnight. The reaction mixture was concentrated under reduced pressure and the residue was taken up in water and lyophilized. The residue was used further without further purification. This gave 102 mg (90%, purity 100%) of the title compound.

LC-MS (Method 1): $R_t$=0.52 min; MS (ESIpos): m/z=402 $(M+H)^+$.

Intermediate L75

Trifluoroacetic Acid/2-(trimethylsilyl)ethyl 3-{[(benzyloxy)carbonyl]amino}-D-alaninate (1:1)

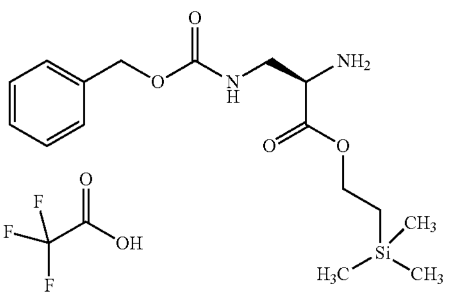

The title compound was prepared from 3-{[(benzyloxy)carbonyl]amino}-N-(tert-butoxycarbonyl)-D-alanine according to classical methods of peptide chemistry (esterification with 2-(trimethylsilylethanol using EDCI/DMAP and removal of the Boc protective group with trifluoroacetic acid. This gave 405 mg (58% of theory over 2 steps) of the title compound.

LC-MS (Method 1): $R_t$=0.75 min; MS (ESIpos): m/z=339 $(M+H)^+$.

Intermediate L76

(2S)-2-Bromo-4-oxo-4-[2-(trimethylsilyl)ethoxy]butanoic Acid

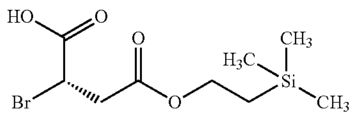

First, a suitably protected aspartic acid derivative was prepared from (3S)-4-(benzyloxy)-3-{[(benzyloxy)carbonyl]amino}-4-oxobutanoic acid according to classical methods of peptide chemistry (esterification with 2-(trimethylsilyl)ethanol using EDCI/DMAP and hydrogenolytic removal of the Z protective group and the benzyl ester.

470 mg (1.8 mmol) of the (2S)-2-amino-4-oxo-4-[2-(trimethylsilyl)ethoxy]butanoic acid obtained in this manner were suspended in 10 ml of water, and 1.8 ml of a 1 molar hydrochloric acid and 0.5 ml of concentrated sulphuric acid were added, followed by 863 mg (7.25 mmol) of potassium bromide. At 10° C., a solution of 150 mg (2.175 mmol) of sodium nitrite in 1 ml of water was then added dropwise over a period of 30 min, and the mixture was stirred at 10-15° C. for 2 h. The mixture was then extracted with 50 ml of ethyl acetate. The organic phase was washed with saturated sodium chloride solution and dried over magnesium sulphate. Evaporation of the solvent and purification of the product by preparative HPLC gave 260 mg (48% of theory) of the title compound.

LC-MS (Method 1): $R_t$=1.03 min; MS (ESIneg): m/z=295 and 297 $(M-H)^-$.

$^1$H-NMR (400 MHz, $CDCl_3$): δ [ppm]=0.03 (s, 9H), 0.95 (t, 2H), 2.94 and 3.2 (2dd, 2H), 4.18 (t, 2H), 4.57 (t, 1H).

Intermediate L77

Trifluoroacetic Acid/N-[2-(2-Aminoethoxy)ethyl]-2-bromoacetamide (1:1)

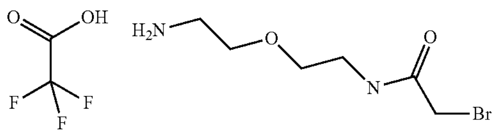 [SMILES: O=C(O)C(F)(F)F ; NCCOCCNC(=O)CBr]

418 mg (2.05 mmol) of tert-butyl [2-(2-aminoethoxy)ethyl]carbamate were initially reacted with 638 mg (2.46 mmol) of bromoacetic anhydride, and the Boc protective group was then removed with trifluoroacetic acid. This gave 551 mg (63% of theory over 2 steps) of the title compound.

LC-MS (Method): $R_t$=0.32 min; MS (ESIpos): m/z=227 and 225 $(M+H)^+$.

Intermediate L78

N-[(2,5-Dioxo-2,5-dihydro-1H-pyrrol-1-yl)acetyl]-beta-alanine

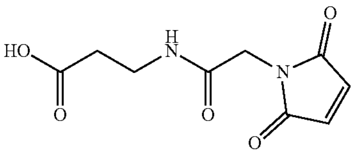 [SMILES: O=C(O)CCNC(=O)CN1C(=O)C=CC1=O]

The title compound was prepared from commercially available (2,5-dioxo-2,5-dihydro-1H-pyrrol-1-yl)acetic acid by coupling with tert-butyl beta-alaninate hydrochloride (1:1) in the presence of EDCI/HOBt and N,N-diisopropylethylamine and subsequent deprotection with trifluoroacetic acid.

LC-MS (Method 1): $R_t$=0.32 min; MS (ESIpos): m/z=227 $(M+H)^+$.

Intermediate L79

N-[(2,5-Dioxo-2,5-dihydro-1H-pyrrol-1-yl)hexanoyl]-beta-alanine

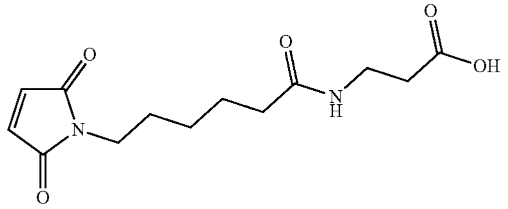 [SMILES: O=C(O)CCNC(=O)CCCCCN1C(=O)C=CC1=O]

64.8 mg (0.357 mmol) of tert-butyl beta-alaninate hydrochloride (1:1) and 100 mg (0.324 mmol) of 1-{6-[(2,5-dioxopyrrolidin-1-yl)oxy]-6-oxohexyl}-1H-pyrrole-2,5-dione were dissolved in 4 ml of dimethylformamide, and 65.6 mg (0.649 mmol) of N-methylmorpholine were added. The reaction mixture was stirred at RT overnight. 0.048 ml (0.838 mmol) of acetic acid were added and the reaction mixture was purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 84.5 mg (77%, purity 100%) of tert-butyl N-[6-(2,5-dioxo-2,5-dihydro-1H-pyrrol-1-yl)hexanoyl]-beta-alaninate.

LC-MS (Method 1): $R_t$=0.78 min; MS (ESIpos): m/z=339 $(M+H)^+$.

1.62 ml of TFA were added to a solution of tert-butyl N-[6-(2,5-dioxo-2,5-dihydro-1H-pyrrol-1-yl)hexanoyl]-beta-alaninate (82.8 mg, 0.244 mmol) in 8 ml of dichloromethane. The reaction mixture was stirred at RT for 2 hours. The reaction mixture was concentrated under reduced pressure and the residue was taken up in water and lyophilized. The residue was used further without further purification. This gave 62.7 mg (87%, purity 95%) of the title compound.

LC-MS (Method 1): $R_t$=0.75 min; MS (ESIpos): m/z=283 $(M+H)^+$.

Intermediate L80

2-(Trimethylsilyl)ethyl 3-[(15-amino-4,7,10,13-tetraoxapentadecan-1-oyl)amino]-N-(tert-butoxycarbonyl)-D-alaninate

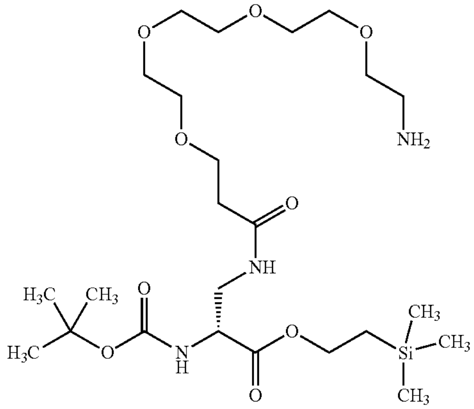 [SMILES: CC(C)(C)OC(=O)N[C@H](CNC(=O)CCOCCOCCOCCOCCN)C(=O)OCC[Si](C)(C)C]

The title compound was prepared from commercially available 3-{[(benzyloxy)carbonyl]amino}-N-(tert-butoxycarbonyl)-D-alanine/N-cyclohexylcyclohexanamine (1:1) according to classical methods of peptide chemistry (release from the salt and esterification with 2-(trimethylsilyl)ethanol using EDCI/DMAP, hydrogenolytic removal of the Z protective group, coupling with commercially available 3-oxo-1-phenyl-2,7,10,13,16-pentaoxa-4-azanonadecan-19-oic acid in the presence of HATU and N,N-diisopropylethylamine and another hydrogenolytic removal of the Z protective group).

LC-MS (Method 1): $R_t$=0.70 min; MS (ESIpos): m/z=552 $(M+H)^+$.

Intermediate L81

Trifluoroacetic Acid/benzyl {2-[(2-aminoethyl)sulphonyl]ethyl}carbamate (1:1)

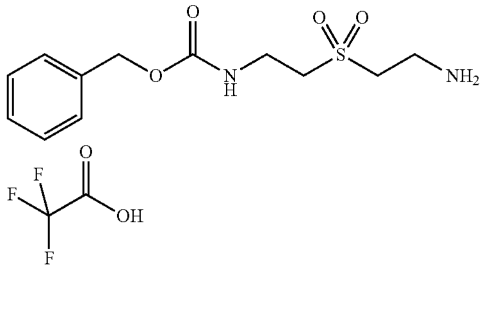

250 mg (1.11 mmol) of 2,2'-sulphonyldiethanamine were coupled with 92.3 mg (0.37 mmol) of 1-{[(benzyloxy)carbonyl]oxy}pyrrolidine-2,5-dione in the presence of N,N-diisopropylethylamine in DMF. Subsequent purification by HPLC gave 70 mg (47% of theory) of the title compound.

LC-MS (Method 12): $R_t$=0.64 min; MS (ESIpos): m/z=257.11 $(M+H)^+$.

Intermediate L82

Trifluoroacetic Acid/N-{2-[2-(2-aminoethoxy)ethoxy]ethyl}-6-(2,5-dioxo-2,5-dihydro-1H-pyrrol-1-yl)hexanamide (1:1)

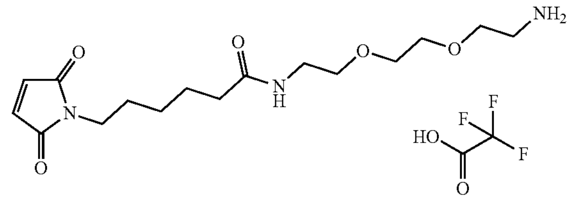 [SMILES: NCCOCCOCCNC(=O)CCCCCN1C(=O)C=CC1=O ; O=C(O)C(F)(F)F]

88.6 mg (0.357 mmol) of N-Boc-2,2'-(ethylenedioxy)diethylamine and 100 mg (0.324 mmol) of N-succinimidyl 6-maleimidohexanoate were dissolved in 4.0 ml of dimethylformamide, and 0.071 ml (0.650 mmol) of N-methylmorpholine were added. The reaction mixture was stirred at RT overnight. 0.048 ml (0.838 mmol) of acetic acid were added and the reaction mixture was purified directly by preparative RP-HPLC (column: Reprosil 125×30; 10μ, flow rate: 75 ml/min, MeCN/water/0.1% TFA). The solvents were evaporated under reduced pressure and the residue was dried under high vacuum. This gave 127 mg (81% of theory) of tert-butyl {2-[2-(2-{[6-(2,5-dioxo-2,5-dihydro-1H-pyrrol-1-yl)hexanoyl]amino}ethoxy)ethoxy]ethyl}carbamate.

LC-MS (Method 1): $R_t$=0.78 min; MS (ESIpos): m/z=442 $(M+H)^+$.

2.0 ml of TFA were added to a solution of 123 mg (225 μmol) tert-butyl {2-[2-(2-{[6-(2,5-dioxo-2,5-dihydro-1H-pyrrol-1-yl)hexanoyl]amino}ethoxy)ethoxy]ethyl}carbamate in 7.5 ml of dichloromethane. The reaction mixture was stirred at RT for 2 h. The reaction mixture was concentrated under reduced pressure and the residue was taken up in water and lyophilized. The residue was used further without further purification. This gave 111 mg (100% of theory) of the title compound.

LC-MS (Method 1): $R_t$=0.31 min; MS (ESIpos): m/z=342 $(M+H)^+$.

$^1$H-NMR (400 MHz, DMSO-$d_6$): δ [ppm]=1.17 (m, 2H), 1.47 (m, 4H), 2.04 (m, 2H), 2.98 (m, 2H), 3.19 (m, 2H), 3.39 (m, 4H), 3.56 (m, 6H), 7.01 (s, 2H), 7.72 (bs, 3H), 7.80 (m, 1H).

Intermediate L83

Trifluoroacetic Acid/N-{2-[2-(2-aminoethoxy)ethoxy]ethyl}-2-(2,5-dioxo-2,5-dihydro-1H-pyrrol-1-yl)acetamide (1:1)

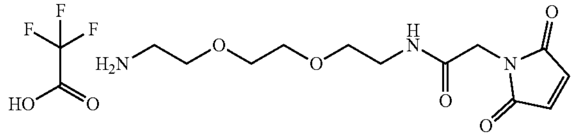

200 mg (0.805 mmol) of tert-butyl {2-[2-(2-aminoethoxy)ethoxy]ethyl}carbamate, 150 mg (0.966 mmol) of (2,5-dioxo-2,5-dihydro-1H-pyrrol-1-yl)acetic acid and 560 μl (3.2 mmol) of N,N-diisopropylethylamine were dissolved in 10 ml of dimethylformamide, and 459 mg (1.21 mmol) of HATU were added. The reaction mixture was stirred at RT for 30 minutes. The solvents were evaporated under reduced pressure and the residue was dissolved in dichloromethane. The organic phase was washed twice with 5% strength citric acid solution and dried over magnesium sulphate, and the solvent was evaporated under reduced pressure. The residue was purified using Biotage Isolera (silica gel, column 25 g SNAP, dichloromethane:methanol 98:2). This gave 276 mg (89% of theory) of tert-butyl {2-[2-(2-{[(2,5-dioxo-2,5-dihydro-1H-pyrrol-1-yl)acetyl]amino}ethoxy)ethoxy]ethyl}carbamate.

LC-MS (Method 1): $R_t$=0.67 min; MS (ESIpos): m/z=386 $(M+H)^+$.

4 ml of TFA were added to a solution of tert-butyl {2-[2-(2-{[(2,5-dioxo-2,5-dihydro-1H-pyrrol-1-yl)acetyl]amino}ethoxy)ethoxy]ethyl}carbamate (275 mg, 714 μmol) in 15 ml of dichloromethane. The reaction mixture was stirred at RT for 30 minutes. The reaction mixture was concentrated under reduced pressure and the residue was taken up in water and lyophilized. This gave 281 mg (99% of theory) of the title compound.

LC-MS (Method 1): $R_t$=0.17 min; MS (ESIpos): m/z=286 $(M+H)^+$.

Intermediate L84

Trifluoroacetic Acid/N-(14-amino-3,6,9,12-tetraoxatetradec-1-yl)-6-(2,5-dioxo-2,5-dihydro-1H-pyrrol-1-yl)hexanamide (1:1)

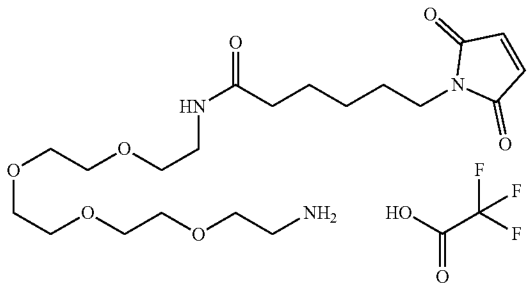

200 mg (0.594 mmol) of tert-butyl (14-amino-3,6,9,12-tetraoxatetradec-1-yl)carbamate and 202 mg (0.654 mmol) of 1-{6-[(2,5-dioxopyrrolidin-1-yl)oxy]-6-oxohexyl}-1H- pyrrole-2,5-dione were dissolved in 4.0 ml of dimethylformamide, and 0.130 ml (1.2 mmol) of N-methylmorpholine were added. The reaction mixture was stirred at RT overnight. 0.085 ml (1.5 mmol) of acetic acid were added and the reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 275 mg (73% of theory) of tert-butyl [21-(2,5-dioxo-2,5-dihydro-1H-pyrrol-1-yl)-16-oxo-3,6,9,12-tetraoxa-15-azahenicos-1-yl]carbamate.

LC-MS (Method 1): $R_t$=0.81 min; MS (ESIpos): m/z=530 $(M+H)^+$.

780 μl (10 mmol) of TFA were added to a solution of tert-butyl [21-(2,5-dioxo-2,5-dihydro-1H-pyrrol-1-yl)-16-oxo-3,6,9,12-tetraoxa-15-azahenicos-1-yl]carbamate (268 mg, 505 μmol) in 5.0 ml of dichloromethane. The reaction mixture was stirred at RT overnight. The reaction mixture was concentrated under reduced pressure and the residue was taken up in water and lyophilized. The residue was used further without further purification. This gave 266 mg (97% of theory) of the title compound.

LC-MS (Method 1): $R_t$=0.46 min; MS (ESIpos): m/z=430 $(M+H)^+$.

$^1$H-NMR (400 MHz, DMSO-$d_6$): δ [ppm]=1.17 (m, 2H), 1.47 (m, 4H), 2.03 (m, 2H), 2.99 (m, 2H), 3.18 (m, 2H), 3.38 (m, 4H), 3.52 (m, 8H), 3.58 (m, 6H), 7.01 (s, 2H), 7.73 (bs, 3H), 7.80 (m, 1H).

Intermediate L85

Trifluoroacetic Acid/N-(14-amino-3,6,9,12-tetraoxatetradec-1-yl)-2-(2,5-dioxo-2,5-dihydro-1H-pyrrol-1-yl)acetamide (1:1)

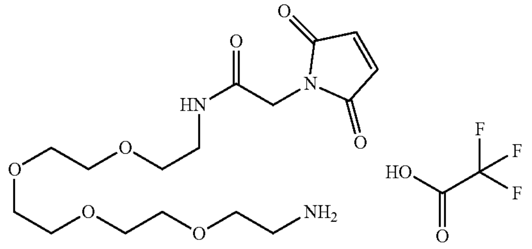

200 mg (0.594 mmol) of tert-butyl (14-amino-3,6,9,12-tetraoxatetradec-1-yl)carbamate, 111 mg (0.713 mmol) of (2,5-dioxo-2,5-dihydro-1H-pyrrol-1-yl)acetic acid and 410 μl (2.4 mmol) of N,N-diisopropylethylamine were dissolved in 6 ml of dimethylformamide, and 339 mg (0.892 mmol) of HATU were added. The reaction mixture was stirred at RT for 1 h and purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 130 mg (43% of theory) of tert-butyl [17-(2,5-dioxo-2,5-dihydro-1H-pyrrol-1-yl)-16-oxo-3,6,9,12-tetraoxa-15-azaheptadec-1-yl]carbamate.

LC-MS (Method 1): $R_t$=0.71 min; MS (ESIpos): m/z=474 $(M+H)^+$.

410 μl (5.3 mmol) of TFA were added to a solution of tert-butyl [17-(2,5-dioxo-2,5-dihydro-1H-pyrrol-1-yl)-16-oxo-3,6,9,12-tetraoxa-15-azaheptadec-1-yl]carbamate (126 mg, 267 μmol) in 4.0 ml of dichloromethane. The reaction mixture was stirred at RT overnight. The reaction mixture was concentrated under reduced pressure and the residue was dried under high vacuum. This gave 124 mg (95% of theory) of the title compound.

LC-MS (Method 13): $R_t$=0.74 min; MS (ESIpos): m/z=374 $(M+H)^+$.

$^1$H-NMR (400 MHz, DMSO-$d_6$): δ [ppm]=2.99 (m, 2H), 3.22 (m, 2H), 3.41 (m, 2H), 3.53 (m, 8H), 3.58 (m, 6H), 4.02 (s, 2H), 7.09 (s, 2H), 7.73 (bs, 3H), 8.21 (m, 1H).

Intermediate L86

N-[(2,5-Dioxo-2,5-dihydro-1H-pyrrol-1-yl)acetyl]-L-valyl-L-alanine

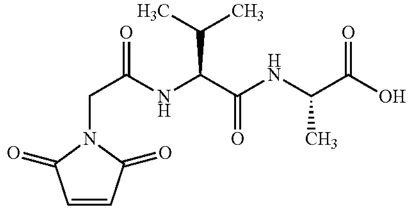 [SMILES: CC(C)[C@H](NC(=O)CN1C(=O)C=CC1=O)C(=O)N[C@@H](C)C(=O)O]

100 mg (0.531 mmol) of L-valyl-L-alanine and 134 mg (0.531 mmol) of 1-{2-[(2,5-dioxopyrrolidin-1-yl)oxy]-2-oxoethyl}-1H-pyrrole-2,5-dione were dissolved in 3 ml of dimethylformamide, and 0.150 ml (1.1 mmol) of triethylamine were added. The reaction mixture was stirred at RT for 8 h. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 71.5 mg (41% of theory) of the title compound.

LC-MS (Method 1): $R_t$=0.42 min; MS (ESIpos): m/z=326 $(M+H)^+$.

Intermediate L87

3-[2-(2-{[(2,5-Dioxo-2,5-dihydro-1H-pyrrol-1-yl)acetyl]amino}ethoxy)ethoxy]propanoic Acid

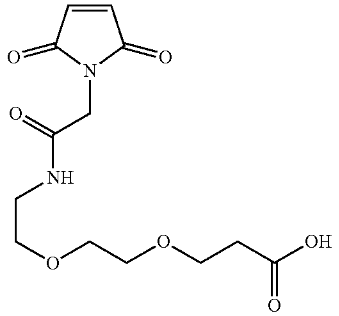 [SMILES: O=C(O)CCOCCOCCNC(=O)CN1C(=O)C=CC1=O]

250 mg (1.07 mmol) of tert-butyl 3-[2-(2-aminoethoxy)ethoxy]propanoate, 151 mg (0.974 mmol) of 2-(2,5-dioxo-2,5-dihydro-1H-pyrrol-1-yl)acetic acid, 224 mg (1.46 mmol) of 1-hydroxy-1H-benzotriazole hydrate and 224 mg (1.17 mmol) of 1-(3-dimethylaminopropyl)-3-ethylcarbodiimide hydrochloride were dissolved in 5.0 ml of dimethylformamide. The reaction mixture was stirred at RT for 1 h. Ethyl acetate was added and the mixture was extracted twice with 5% strength citric acid solution and with saturated sodium bicarbonate solution. The organic phase was washed twice with saturated sodium chloride solution and dried over magnesium sulphate, and the solvent was evaporated under reduced pressure. The residue was purified by preparative RP-HPLC (column: Reprosil 250×40; 10μ, flow rate: 50 ml/min, MeCN/water/0.1% TFA). The solvents were evaporated under reduced pressure and the residue was dried under high vacuum. This gave 267 mg (64% of theory) of tert-butyl 3-[2-(2-{[(2,5-dioxo-2,5-dihydro-1H-pyrrol-1-yl)acetyl]amino}ethoxy)ethoxy]propanoate.

LC-MS (Method 1): Rt=0.73 min; MS (ESIpos): m/z=371 $(M+H)^+$.

1.1 ml (14 mmol) of TFA were added to a solution of tert-butyl 3-[2-(2-{[(2,5-dioxo-2,5-dihydro-1H-pyrrol-1-yl)acetyl]amino}ethoxy)ethoxy]propanoate (263 mg, 710 μmol) in 10 ml of dichloromethane. The reaction mixture was stirred at RT overnight. The reaction mixture was concentrated under reduced pressure and the residue was dried under high vacuum. This gave 240 mg (94% of theory) of the title compound.

LC-MS (Method 12): $R_t$=0.57 min; MS (ESIpos): m/z=315 $(M+H)^+$.

Intermediate L88

2,5-Dioxopyrrolidin-1-yl N-[6-(2,5-dioxo-2,5-dihydro-1H-pyrrol-1-yl)hexanoyl]-L-valyl-L-alaninate

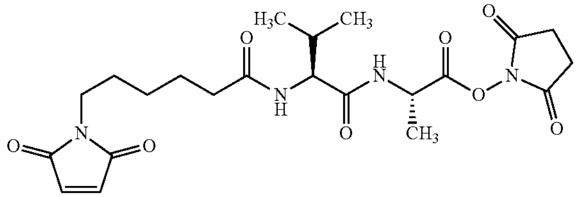 [SMILES: CC(C)[C@H](NC(=O)CCCCCN1C(=O)C=CC1=O)C(=O)N[C@@H](C)C(=O)ON1C(=O)CCC1=O]

150 mg (0.797 mmol) of L-valyl-L-alanine and 246 mg (0.797 mmol) of 1-{6-[(2,5-dioxopyrrolidin-1-yl)oxy]-6-oxohexyl}-1H-pyrrole-2,5-dione were dissolved in 4.0 ml of dimethylformamide, and 0.220 ml (1.6 mmol) of triethylamine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 302 mg (97% of theory) of N-[6-(2,5-dioxo-2,5-dihydro-1H-pyrrol-1-yl)hexanoyl]-L-valyl-L-alanine.

LC-MS (Method 12): $R_t$=1.02 min; MS (ESIpos): m/z=382 $(M+H)^+$.

$^1$H-NMR (400 MHz, DMSO-$d_6$): δ [ppm]=0.82 (dd, 6H), 1.17 (m, 2H), 1.27 (d, 3H), 1.48 (m, 4H), 1.94 (m, 1H), 2.13 (m, 2H), 3.38 (t, 2H), 4.17 (m, 2H), 7.00 (s, 2H), 7.75 (d, 1H), 8.19 (d, 1H).

130 mg (0.531 mmol) of N-[6-(2,5-dioxo-2,5-dihydro-1H-pyrrol-1-yl)hexanoyl]-L-valyl-L-alanine were dissolved in 6.5 ml of dichloromethane, and 58.8 mg (0.511 mmol) of 1-hydroxypyrrolidine-2,5-dione and 78.4 mg (0.409 mmol) of 1-(3-dimethylaminopropyl)-3-ethylcarbodiimide hydrochloride were added. Another 58.8 mg (0.511 mmol) of 1-hydroxypyrrolidine-2,5-dione and 78.4 mg (0.409 mmol) of 1-(3-dimethylaminopropyl)-3-ethylcarbodiimide hydrochloride were added. Dichloromethane was added and the mixture was washed three times with water. The organic phase was dried over magnesium sulphate, the solvent was evaporated under reduced pressure and the residue was dried under high vacuum. This gave 172 mg (87% of theory) of the title compound.

LC-MS (Method 12): $R_t$=1.28 min; MS (ESIpos): m/z=479 $(M+H)^+$.

Intermediate L89

1-Benzyl-5-[2-(trimethylsilyl)ethyl]-L-glutamate Hydrochloride (1:1)

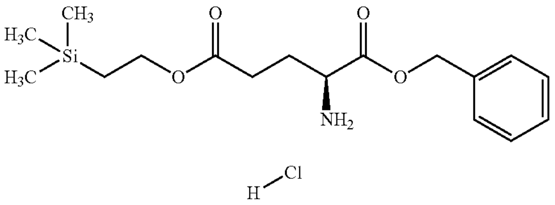 [SMILES: C[Si](C)(C)CCOC(=O)CC[C@H](N)C(=O)OCc1ccccc1 ; Cl]

1.00 g (2.96 mmol) of (4S)-5-(benzyloxy)-4-[(tert-butoxycarbonyl)amino]-5-oxopentanoic acid was initially charged in 13.0 ml of THF, and 510 μl (3.6 mmol) of 2-(trimethylsilyl)ethanol and 109 mg (889 μmol) of 4-dimethylaminopyridine were added. The reaction mixture was cooled to 0° C., and 682 mg (3.56 mmol) of N-ethyl-N'-3-(dimethylaminopropyl)carbodiimide hydrochloride were added. The reaction mixture was stirred at RT overnight. The solvents were evaporated under reduced pressure and the residue was dissolved in ethyl acetate. The organic phase was washed twice with 0.1 N HCl solution and saturated sodium chloride solution and dried over magnesium sulphate and the solvent was evaporated under reduced pressure. The residue was purified using Biotage Isolera (silica gel, column 25 g SNAP, cyclohexane:ethyl acetate 80:20). This gave 649 mg (50% of theory) of the compound 1-benzyl-5-[2-(trimethylsilyl)ethyl]-N-(tert-butoxycarbonyl)-L-glutamate.

LC-MS (Method 1): $R_t$=4.6 min; MS (ESIpos): m/z=438 $(M+H)^+$.

649 mg (1.48 mmol) of 1-benzyl-5-[2-(trimethylsilyl)ethyl]-N-(tert-butoxycarbonyl)-L-glutamate were dissolved in 7.0 ml of dioxane and, with ice bath cooling, 14 ml (59 mmol) of 4N HCl in dioxane were added. The reaction mixture was stirred at RT overnight. The reaction mixture was concentrated under reduced pressure and the residue was dried under high vacuum and purified by Biotage Isolera (silica gel, column 25 g SNAP, dichloromethane:methanol 90:10). This gave 320 mg (57% of theory) of the title compound.

LC-MS (Method 1): $R_t$=0.79 min; MS (ESIpos): m/z=338 $(M+H)^+$.

Intermediate L90

1-({N-[(Benzyloxy)carbonyl]glycyl}amino)-3,6,9,12-tetraoxapentadecan-15-oic Acid

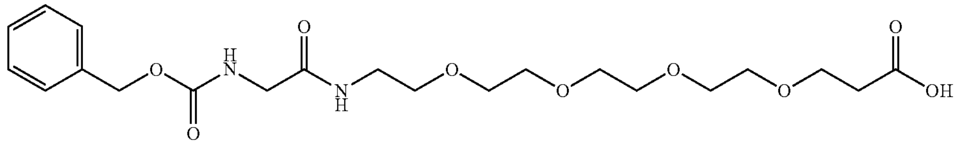 [SMILES: O=C(O)CCOCCOCCOCCOCCNC(=O)CNC(=O)OCc1ccccc1]

118 mg (566 μmol) of N-[(benzyloxy)carbonyl]glycine were initially charged in 5.0 ml of DMF, 200 mg (622 μmol) of tert-butyl 1-amino-3,6,9,12-tetraoxapentadecan-15-oate, 130 mg (849 μmol) of 1-hydroxy-1H-benzotriazole hydrate and 130 mg (679 μmol) of 1-(3-dimethylaminopropyl)-3-ethylcarbodiimide hydrochloride were added and the mixture was stirred at RT for 1 h. Ethyl acetate was added and the mixture was extracted twice with 5% strength citric acid solution and with saturated sodium bicarbonate solution. The organic phase was washed twice with saturated sodium chloride solution and dried over magnesium sulphate. The solvents were evaporated under reduced pressure and the residue was dried under high vacuum. This gave 274 mg (95% of theory) of tert-butyl 1-({N-[(benzyloxy)carbonyl]glycyl}amino)-3,6,9,12-tetraoxapentadecan-15-oate.

LC-MS (Method 12): $R_t$=1.69 min; MS (ESIpos): m/z=513 $(M+H)^+$.

820 μl (11 mmol) of TFA were added to a solution of 274 mg (535 μmol) of tert-butyl 1-({N-[(benzyloxy)carbonyl]glycyl}amino)-3,6,9,12-tetraoxapentadecan-15-oate in 5.0 ml of dichloromethane. The reaction mixture was stirred at RT for 3 h. The reaction mixture was concentrated under reduced pressure and the residue was taken up in water and lyophilized. This gave 262 mg (100% of theory) of the title compound.

LC-MS (Method 12): $R_t$=1.12 min; MS (ESIpos): m/z=457 $(M+H)^+$.

Intermediate L91

Trifluoroacetic Acid/2-(trimethylsilyl)ethyl 1-{[3-amino-N-(tert-butoxycarbonyl)-D-alanyl]amino}-3,6,9,12-tetraoxapentadecan-15-oate (1:1

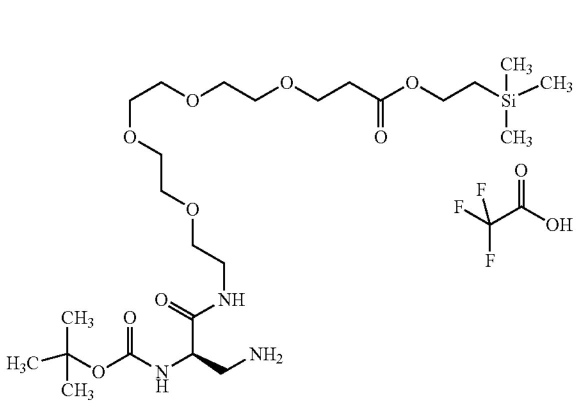

The title compound was prepared from commercially available 3-oxo-1-phenyl-2,7,10,13,16-pentaoxa-4-azanonadecan-19-oic acid by classical methods of peptide chemistry (esterification with 2-trimethylsilylethanol using EDCI/DMAP, hydrogenolytic removal of the Z protective group, coupling with commercially available N-(tert-butoxycarbonyl)-3-{[(9H-fluoren-9-ylmethoxy)carbonyl]amino}-D-alanine and removal of the Fmoc protective group).

LC-MS (Method 1): $R_t$=0.74 min; MS (ESIpos): m/z=552 $(M+H)^+$.

Intermediate L92

N-[(Benzyloxy)carbonyl]-L-alanyl-L-alanyl-L-asparagine

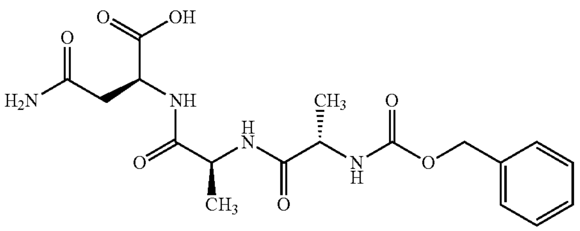 [SMILES: C[C@H](NC(=O)OCc1ccccc1)C(=O)N[C@@H](C)C(=O)N[C@@H](CC(N)=O)C(=O)O]

The title compound was prepared by conventional methods of peptide chemistry by HATU coupling, in the presence of N,N-diisopropylethylamine, of commercially available N-[(benzyloxy)carbonyl]-L-alanyl-L-alanine with tert-butyl L-asparaginate and subsequent deprotection of the carboxyl group with trifluoroacetic acid.

LC-MS (Method 1): $R_t$=0.5 min; MS (ESIpos): m/z=409 $(M+H)^+$.

Intermediate L93

N-Acetyl-L-alanyl-L-alanyl-L-asparagine

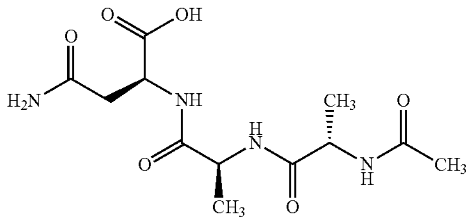 [SMILES: CC(=O)N[C@@H](C)C(=O)N[C@@H](C)C(=O)N[C@@H](CC(N)=O)C(=O)O]

The title compound was prepared by conventional methods of peptide chemistry by HATU coupling, in the presence of N,N-diisopropylethylamine, of commercially available N-[(benzyloxy)carbonyl]-L-alanyl-L-alanine with tert-butyl L-asparaginate, subsequent deprotection of the Z protecting group by hydrogenation in DCM/methanol over 10% palladium on activated carbon, followed by acetylation with acetic acid in DMF in the presence of HATU and N,N-diisopropylethylamine and finally deprotection of the carboxyl group with trifluoroacetic acid.

LC-MS (Method 1): $R_t$=0.16 min; MS (ESIpos): m/z=317 $(M+H)^+$.

$^1$H-NMR (400 MHz, DMSO-$d_6$): δ [ppm]=1.19 (2d, 6H), 1.82 (s, 3H), 2.5 (m, 2H), 4.26 (m, 2H), 4.48 (q, 1H), 6.9 (s, 1H), 7.36 (s, 1H), 8.0 (m, 3H), 12.54 (s, 1H).

Intermediate L94

N-{4-Oxo-4-[2-(trimethylsilyl)ethoxy]butanoyl}-L-alanyl-L-alanyl-L-asparagine

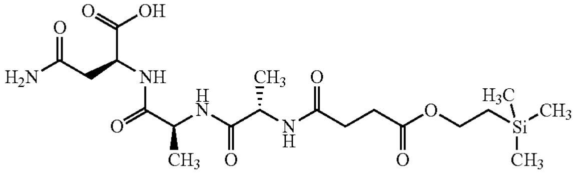 [SMILES: C[C@H](NC(=O)CCC(=O)OCC[Si](C)(C)C)C(=O)N[C@@H](C)C(=O)N[C@@H](CC(N)=O)C(=O)O]

First of all, 4-oxo-4-[2-(trimethylsilyl)ethoxy]butanoic acid was prepared by reaction of 4-(benzyloxy)-4-oxobutanoic acid with 2-(trimethylsilyl)ethanol in the presence of EDCI/DMAP in DCM and subsequent hydrogenolytic cleavage of the benzyl ester.

LC-MS (Method 1): $R_t$=0.89 min; MS (ESIpos): m/z=217 $(M-H)^-$.

In addition, trifluoroacetic acid/4-nitrobenzyl-L-alanyl-L-alanyl-L-asparaginate (1:1) was prepared by coupling N-(tert-butoxycarbonyl)-L-alanyl-L-alanine with 4-nitrobenzyl L-asparaginate hydrobromide (1:1) in DMF in the presence of HATU and N,N-diisopropylethylamine and then deprotecting the amino group with trifluoroacetic acid in DCM.

LC-MS (Method 1): $R_t$=0.43 min; MS (ESIpos): m/z=410 $(M+H)^+$.

The title compound was then prepared by coupling these two intermediates in DMF in the presence of HATU and N,N-diisopropylethylamine and then deprotecting the p-nitrobenzyl ester by hydrogenation in DCM-methanol 1:9 over 10% palladium on activated carbon.

LC-MS (Method 1): $R_t$=0.79 min; MS (ESIpos): m/z=475 $(M+H)^+$.

Intermediate L95

N-[(Benzyloxy)carbonyl]-L-valyl-L-alanine

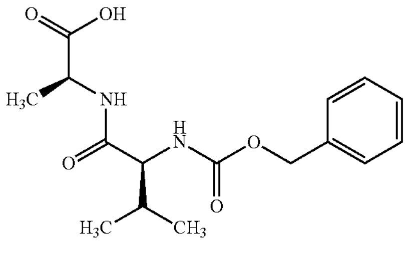 [SMILES: CC(C)[C@H](NC(=O)OCc1ccccc1)C(=O)N[C@@H](C)C(=O)O]

This intermediate was prepared proceeding from N-[(benzyloxy)carbonyl]-L-valine and tert-butyl L-alaninate hydrochloride (1:1) by conventional methods of peptide chemistry.

LC-MS (Method 12): $R_t$=1.34 min; MS (ESIpos): m/z=323.16 $(M+H)^+$.

Intermediate L96

N-Acetyl-L-valyl-$N^5$-carbamoyl-L-ornithinamide

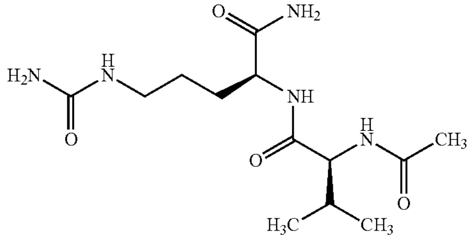 [SMILES: CC(=O)N[C@H](C(=O)N[C@@H](CCCNC(N)=O)C(N)=O)C(C)C]

This intermediate was prepared by conventional methods of peptide chemistry commencing with the coupling of 2,5-dioxopyrrolidin-1-yl-N-[(benzyloxy)carbonyl]-L-valinate with $N^5$-carbamoyl-L-ornithine, followed by hydrogenolytic cleavage of the Z protecting group over 10% palladium/activated carbon in ethanol and finally by reaction of the dipeptide obtained with 1-acetoxypyrrolidine-2,5-dione.

LC-MS (Method 1): $R_t$=0.25 min; MS (ESIpos): m/z=317 $(M+H)^+$.

Intermediate L97

1-(2,5-Dioxo-2,5-dihydro-1H-pyrrol-1-yl)-2-oxo-6,9,12,15,18,21,24,27-octaoxa-3-azatriacontan-30-oic Acid

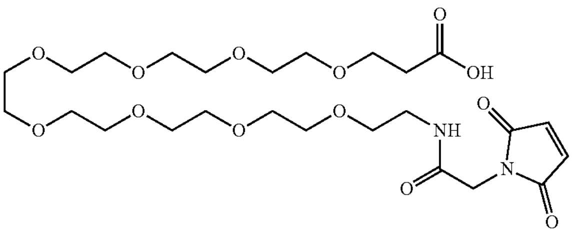 [SMILES: O=C(O)CCOCCOCCOCCOCCOCCOCCOCCOCCNC(=O)CN1C(=O)C=CC1=O]

tert-Butyl 1-amino-3,6,9,12,15,18,21,24-octaoxaheptacosan-27-oate (100 mg, 201 μmol) was initially charged in 1.0 ml of DMF, and (2,5-dioxo-2,5-dihydro-1H-pyrrol-1-yl)acetic acid (46.8 mg, 301 μmol), 1-hydroxy-1H-benzotriazole hydrate (76.9 mg, 502 μmol) and 1-(3-dimethylaminopropyl)-3-ethylcarbodiimide hydrochloride (77.0 mg, 402 μmol) were added. The reaction mixture was stirred at RT overnight, and ethyl acetate was then added. The organic phase was washed twice with 5% citric acid solution, with saturated sodium hydrogencarbonate solution and once with saturated sodium chloride solution. The organic phase was dried over magnesium sulphate. The solvents were evaporated under reduced pressure and the residue was purified by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 19.1 mg (13% of theory) of tert-butyl 1-(2,5-dioxo-2,5-dihydro-1H-pyrrol-1-yl)-2-oxo-6,9,12,15,18,21,24,27-octaoxa-3-azatriacontan-30-oate.

LC-MS (Method 1): $R_t$=0.87 min; MS (ESIpos): m/z=635 $[M+H]^+$

To a solution of tert-butyl 1-(2,5-dioxo-2,5-dihydro-1H-pyrrol-1-yl)-2-oxo-6,9,12,15,18,21,24,27-octaoxa-3-aza-triacontan-30-oate (19.1 mg, 30.1 μmol) in 1.0 ml of DCM was added TFA (62 μl, 600 μmol). The reaction mixture was stirred at RT for 3 h. The reaction mixture was concentrated under reduced pressure and the residue was taken up in water and lyophilized. The residue was used further without further purification. This gave 10.8 mg (46% of theory) of the title compound.

LC-MS (Method 1): $R_t$=0.55 min; MS (ESIneg): m/z=577 $[M-H]^-$.

Intermediate L98

2,2-Dimethylpropanoic Acid/2-(trimethylsilyl)ethyl N-(2-aminoethyl)-N2-{[2-(trimethylsilyl) ethoxy] carbonyl}-L-glutaminate (1:1)

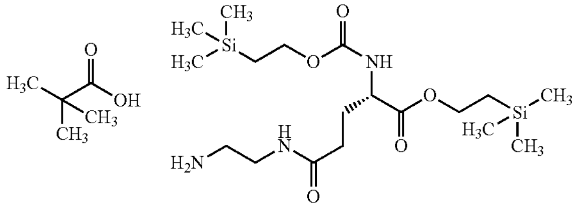

First of all, (4S)-5-tert-butoxy-4-[(tert-butoxycarbonyl) amino]-5-oxopentanoic acid was coupled in the presence of HATU and N,N-diisopropylethylamine with benzyl (2-aminoethyl)carbamate. Subsequently, by means of trifluoroacetic acid in DCM, the Boc protecting group and the tert-butyl ester were detached. Then, first the amino group was reprotected by reaction with 1-({[2-(trimethylsilyl) ethoxy]carbonyl}oxy)pyrrolidine-2,5-dione in DMF/water in the presence of N,N-diisopropylethylamine, and then the carboxyl group by reaction with 2-(trimethylsilyl)ethanol in DCM in the presence of EDCI/DMAP. In the last step, the terminal amino group was deprotected by means of hydrogenolysis over 10% palladium on activated carbon in ethanol under standard pressure. After removal of the catalyst by filtration, concentration, purification by preparative HPLC and freeze-drying of the residue from acetonitrile/water, the title compound was obtained.

LC-MS (Method 1): $R_t$=0.82 min; MS (ESIpos): m/z=434 $(M+H)^+$.

Intermediate L99

Trifluoroacetic Acid/2-(trimethylsilyl)ethyl N-[(2,5-dioxo-2,5-dihydro-1H-pyrrol-1-yl)acetyl]-L-valyl-L-alanyl-beta-alanyl-L-lysinate (1:1)

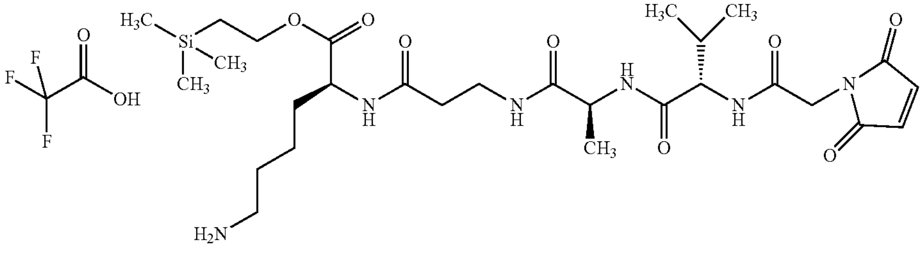 [SMILES: O=C(O)C(F)(F)F ; CC(C)[C@H](NC(=O)CN1C(=O)C=CC1=O)C(=O)N[C@@H](C)C(=O)NCCC(=O)N[C@@H](CCCCN)C(=O)OCC[Si](C)(C)C]

First, 2-(trimethylsilyl)ethyl N6-(tert-butoxycarbonyl)-L-lysinate was prepared from N2-[(benzyloxy)carbonyl]-N6-(tert-butoxycarbonyl)-L-lysine according to classical methods of peptide chemistry. This intermediate was then coupled in the presence of HATU and N,N-diisopropylethylamine with the tripeptide unit N-[(benzyloxy) carbonyl]-L-valyl-L-alanyl-beta-alanine prepared by standard methods. The Z protecting group was then removed by hydrogenolysis in methanol and the intermediate obtained was coupled with (2,5-dioxo-2,5-dihydro-1H-pyrrol-1-yl) acetic acid in the presence of HATU and N,N diisopropylethylamine. In the last step, the side-chain amino group was deprotected under gentle conditions by stirring in 10% trifluoroacetic acid in DMF at RT for 1 h. After concentration and freeze-drying from acetonitrile/water, the title compound was obtained.

LC-MS (Method 1): $R_t$=0.64 min; MS (ESIpos): m/z=625 $(M+H)^+$.

Intermediate L100

3-[5-(2-{[(2,5-Dioxo-2,5-dihydro-1H-pyrrol-1-yl) acetyl]amino}ethyl)-1,2,4-oxadiazol-3-yl]propanoic Acid

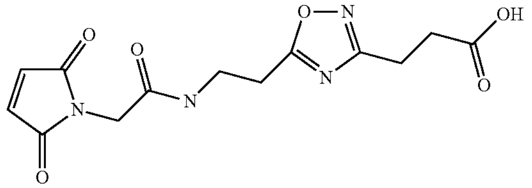 [SMILES: O=C(O)CCc1noc(CCNC(=O)CN2C(=O)C=CC2=O)n1]

To a solution of methyl 3-cyanopropanoate (4 g, 35.4 mmol) in 120 ml of ethanol were added 3.69 g (53 mmol) of hydroxylamine hydrochloride and 15 ml (110 mmol) of triethylamine. The reaction mixture was stirred at 50° C. for 3 h. The mixture was concentrated and the residue was dissolved in ethyl acetate and then washed with water and brine. The organic phase was dried over magnesium sulphate and concentrated. The residue was employed without further purification. This gave 5 g (97% of theory) of methyl (4Z)-4-amino-4-(hydroxyimino)butanoate.

To a solution of methyl (4Z)-4-amino-4-(hydroxyimino) butanoate (4.85 g, 33.19 mmol) in 120.0 ml of dioxane were added 6.91 g (36.50 mmol) of N-(tert-butoxycarbonyl)-beta-alanine and 8.22 g (39.82 mmol) of 1,3-dicyclohexylcarbodiimide. The reaction mixture was stirred at room temperature for 3 h. The mixture was concentrated and the residue was dissolved in water and extracted with ethyl acetate. The organic phase was dried over sodium sulphate and concentrated. The residue was purified by means of flash chromatography. This gave 6.0 g (57% of theory) of methyl (4E)-4-{[N-(tert-butoxycarbonyl)-beta-alanyl]amino}-4-(hydroxyimino)butanoate.

A solution of methyl (4E)-4-{[N-(tert-butoxycarbonyl)-beta-alanyl]amino}-4-(hydroxyimino)butanoate (6.0 g, 18.9 mmol) in 100 ml of DMF was stirred at 120° C. for 5 h. The mixture was admixed with water and extracted with ethyl acetate. The organic phase was dried over sodium sulphate and concentrated. The residue was purified by preparative HPLC. This gave 4 g (71% of theory) of methyl 3-(5-{2-[(tert-butoxycarbonyl)amino]ethyl}-1,2,4-oxadiazol-3-yl) propanoate.

To a solution of methyl (4E)-4-{[N-(tert-butoxycarbonyl)-beta-alanyl]amino}-4-(hydroxyimino)butanoate (4.00 g, 13.4 mmol) in 60 ml of THF was added a solution of LiOH (1.60 g, 66.8 mmol) in 10 ml of water. The reaction mixture was stirred at 60° C. overnight. The mixture was admixed with water and extracted with ethyl acetate. The organic phase was dried over sodium sulphate and concentrated. The residue was employed without further purification. This gave 3.60 g (87% of theory) of 3-(5-{2-[(tert-butoxycarbonyl)amino]ethyl}-1,2,4-oxadiazol-3-yl) propanoic acid.

To a solution of 3-(5-{2-[(tert-butoxycarbonyl)amino] ethyl}-1,2,4-oxadiazol-3-yl)propanoic acid (2.0 g, 7.01 mmol) in 30 ml of dichloromethane were added 2.0 ml (26 mmol) of trifluoroacetic acid. The reaction mixture was stirred at room temperature for 1 h. The mixture was admixed with water and extracted with dichloromethane. The organic phase was dried over sodium sulphate and concentrated. The residue was employed without further purification. This gave 1.50 g (72% of theory) of 3-[5-(2-aminoethyl)-1,2,4-oxadiazol-3-yl]propanoic acid/trifluoroacetic acid (1:1).

To a solution of 3-[5-(2-aminoethyl)-1,2,4-oxadiazol-3-yl]propanoic acid (1.5 g, 5.01 mmol) in 25 ml of DMF were added 1.30 g (5.52 mmol) of 1-[2-(2,5-dioxopyrrolidin-1-yl)-2-oxoethyl]-1H-pyrrole-2,5-dione and 1.52 g (15.04 mmol) of triethylamine. The reaction mixture was stirred at room temperature for 1 h. The mixture was admixed with water and extracted with dichloromethane. The organic phase was dried over sodium sulphate and concentrated. The residue was purified by preparative HPLC. This gave 774 mg (47% of theory) of the title compound.

$^1$H-NMR (300 MHz, DMSO-$d_6$): δ [ppm]=2.67 (t, 2H), 2.91 (t, 2H), 3.03 (t, 2H), 3.46 (q, 2H), 4.28 (s, 2H), 7.01 (s, 2H), 8.37 (t, 1H), 12.28 (bs, 1H).

Intermediate L101 tert-Butyl L-alanyl-L-alanyl-L-asparaginate

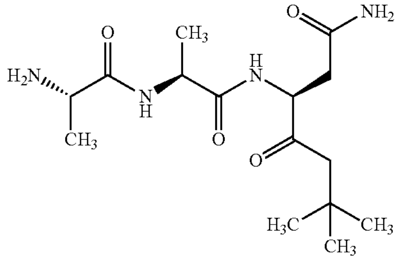 [SMILES: C[C@H](N)C(=O)N[C@@H](C)C(=O)N[C@@H](CC(N)=O)C(=O)CC(C)(C)C]

The title compound was prepared by conventional methods of peptide chemistry by HATU coupling, in the presence of N,N-diisopropylethylamine, of commercially available N-[(benzyloxy)carbonyl]-L-alanyl-L-alanine with tert-butyl L-asparaginate hydrochloride, followed by hydrogenolytic detachment of the Z protecting group over 10% palladium/activated carbon in methanol.

LC-MS (Method 7): $R_t$=0.23 min; MS (ESIneg): m/z=329 $(M-H)^-$.

Intermediate L102

N-(38-Oxo-2,5,8,11,14,17,20,23,26,29,32,35-dodecaoxaoctatriacontan-38-yl)-L-alanyl-L-alanyl-L-asparagine

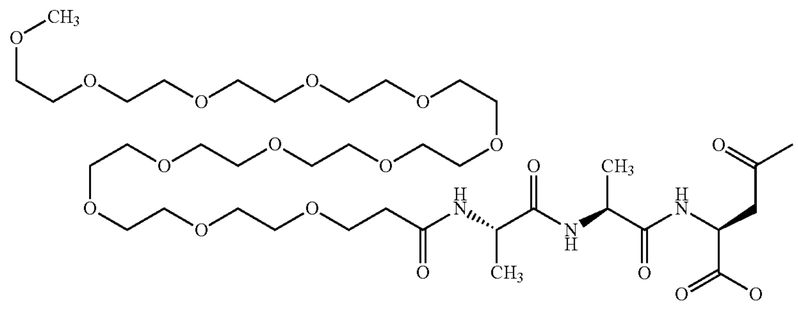 [SMILES: COCCOCCOCCOCCOCCOCCOCCOCCOCCOCCOCCOCCC(=O)N[C@@H](C)C(=O)N[C@@H](C)C(=O)N[C@@H](CC(C)=O)C(=O)O]

215 mg of 2,5,8,11,14,17,20,23,26,29,32,35-dodecaoxaoctatriacontan-38-oic acid (365 μmol) and 133 mg of Intermediate L101 (402 μmol) were initially charged in 1.4 ml of DMF, 146 mg of HATU (384 μmol) and 160 μl of N,N-diisopropylethylamine (910 μmol) were added and the mixture was stirred at RT for 3 h. Water (1.5 ml) and ACN (0.5 ml) were added. The reaction solution was purified by preparative HPLC (mobile phase: ACN/water+0.1% TFA, gradient=1:9→3:2) and subsequent detachment of the butoxycarbonyl protecting group with 2 ml of TFA in 2 ml of DCM (stirred at RT for 3 h).

LC-MS (Method 1): $R_t$=0.56 min; MS (ESIneg): m/z=844.5 (M+H)$^+$.

Intermediate L103

N-(Pyridin-4-ylacetyl)-L-alanyl-L-alanyl-L-asparagine trifluoroacetate (1:1)

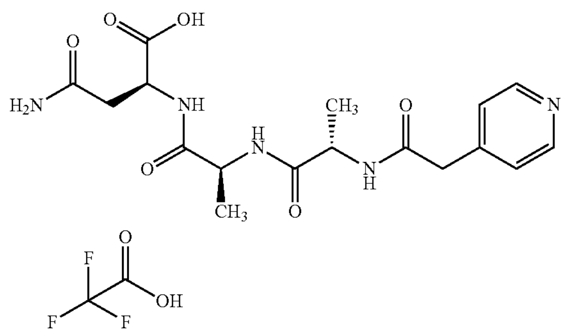

The title compound was prepared by conventional methods of peptide chemistry commencing with the coupling of 4-pyridineacetic acid with commercially available tert-butyl L-alanyl-L-alaninate in the presence of HATU and N,N-diisopropylethylamine, followed by deprotection with trifluoroacetic acid, coupling with tert-butyl L-asparaginate and subsequent deprotection of the carboxyl group with trifluoroacetic acid.

LC-MS (Method 1): $R_t$=0.15 min; MS (ESIpos): m/z=394 (M+H)$^+$.

Intermediate L104

N-Isonicotinoyl-L-alanyl-L-alanyl-L-asparagine Trifluoroacetate (1:1)

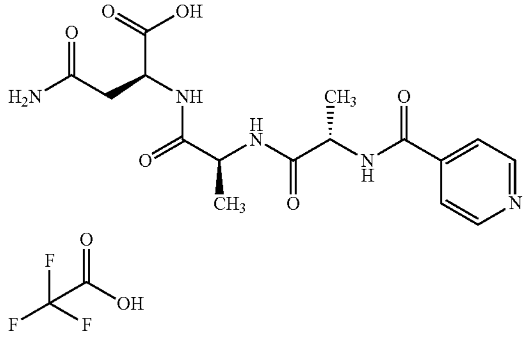

The title compound was prepared in analogy to intermediate L103 commencing with the coupling of isonicotinic acid with commercially available tert-butyl L-alanyl-L-alaninate.

LC-MS (Method 1): $R_t$=0.17 min; MS (ESIpos): m/z=380 (M+H)$^+$.

Intermediate L105 tert-Butyl N-{[2-(2-methoxyethoxy)ethoxy]acetyl}-L-alanyl-L-alanyl-L-asparaginate trifluoroacetate (1:1)

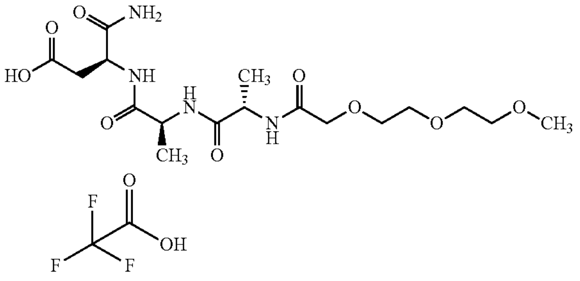

The title compound was prepared in analogy to intermediate L103 commencing with the coupling of [2-(2-methoxyethoxy)ethoxy]acetic acid with commercially available tert-butyl L-alanyl-L-alaninate.

LC-MS (Method 1): $R_t$=0.17 min; MS (ESIpos): m/z=380 (M+H)$^+$.

Intermediate L106

N-[(Benzyloxy)carbonyl]-L-alanyl-L-alanyl-L-asparagine

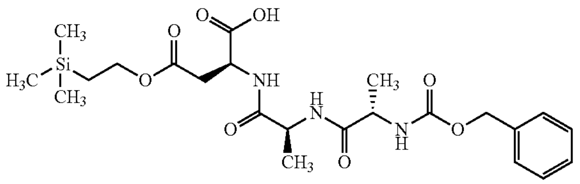 [SMILES: C[C@H](NC(=O)OCc1ccccc1)C(=O)N[C@@H](C)C(=O)N[C@@H](CC(=O)OCC[Si](C)(C)C)C(=O)O]

The title compound was prepared by conventional methods of peptide chemistry by coupling of commercially available N-[(benzyloxy)carbonyl]-L-alanyl-L-alanine with 1-tert-butyl 4-[2-(trimethylsilyl)ethyl]-L-aspartate in the presence of HATU and N,N-diisopropylethylamine. This amino acid unit was prepared from (3S)-4-tert-butoxy-3-[(tert-butoxycarbonyl)amino]-4-oxobutanoic acid by esterification with 2-(trimethylsilyl)ethanol in the presence of EDCI and DMAP and subsequent gentle removal of the tert-butoxycarbonyl protecting group by means of 5% trifluoroacetic acid in DCM. Subsequently, 745 mg (1.317 mmol) of the fully protected intermediate were dissolved in 43.5 ml of DCM and the tert-butyl ester was gently hydrolysed by adding 3.5 ml of trifluoroacetic acid and stirring at RT for 5 hours. 168 mg (25% of theory) of the title compound were isolated from the resultant product mixture after purification by preparative HPLC.

LC-MS (Method 1): $R_t$=0.95 min; MS (ESIpos): m/z=510 (M+H)$^+$.

Intermediate L107

N-[(2,5-Dioxo-2,5-dihydro-1H-pyrrol-1-yl)acetyl]-L-alanyl-L-alanyl-L-asparagine

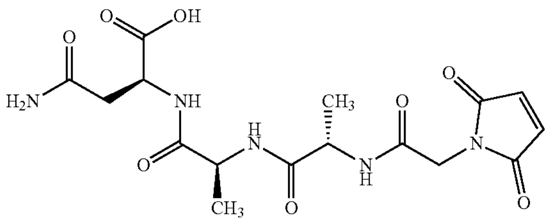 [SMILES: C[C@H](NC(=O)CN1C(=O)C=CC1=O)C(=O)N[C@@H](C)C(=O)N[C@@H](CC(N)=O)C(=O)O]

The title compound was prepared by conventional methods of peptide chemistry by HATU coupling of commercially available N-[(benzyloxy)carbonyl]-L-alanyl-L-alanine with tert-butyl L-asparaginate, in the presence of N,N-diisopropylethylamine, subsequent deprotection of the Z protecting group by hydrogenation in DCM/methanol over 10% palladium on activated carbon, followed by acylation with 1-{2-[(2,5-dioxopyrrolidin-1-yl)oxy]-2-oxoethyl}-1H-pyrrole-2,5-dione in DMF in the presence of N,N-diisopropylethylamine and finally deprotection of the carboxyl group by means of trifluoroacetic acid.

LC-MS (Method 1): $R_t$=0.35 min; MS (ESIpos): m/z=412 $(M+H)^+$.

Intermediate L108

$N^2$-Acetyl-N-(2-aminoethyl)-$N^6$-(tert-butoxycarbonyl)-L-lysinamide

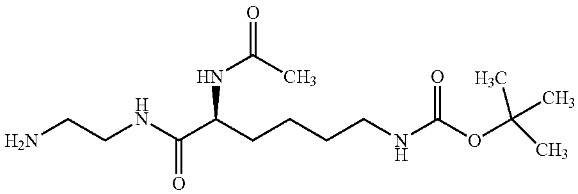 [SMILES: CC(=O)N[C@@H](CCCCNC(=O)OC(C)(C)C)C(=O)NCCN]

(1:1) in the presence of N,N-diisopropylethylamine and subsequent detachment of the Z protecting group by hydrogenation in DCM/methanol 1:1 over 10% palladium on activated carbon.

LC-MS (Method 1): $R_t$=0.43 min; MS (ESIpos): m/z=331 $(M+H)^+$.

Intermediate L109

$N^2$-Acetyl-$N^6$-{[2-(trimethylsilyl)ethoxy]carbonyl}-L-lysine

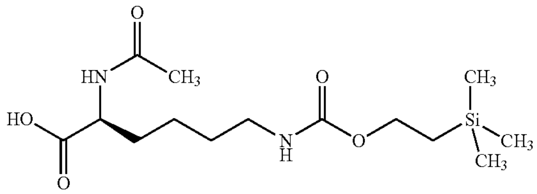 [SMILES: CC(=O)N[C@@H](CCCCNC(=O)OCC[Si](C)(C)C)C(=O)O]

This intermediate was obtained by reaction of commercially available $N^2$-acetyl-L-lysine with 1-({[2-(trimethylsilyl)ethoxy]carbonyl}oxy)pyrrolidine-2,5-dione in DMF/water 1:1 in the presence of N,N-diisopropylethylamine.

LC-MS (Method 1): $R_t$=0.87 min; MS (ESIpos): m/z=333 $(M+H)^+$.

Intermediate L110

$N^2$-Acetyl-$N^6$-{[2-(trimethylsilyl)ethoxy]carbonyl}-L-lysyl-L-alanyl-L-alanyl-L-asparagine

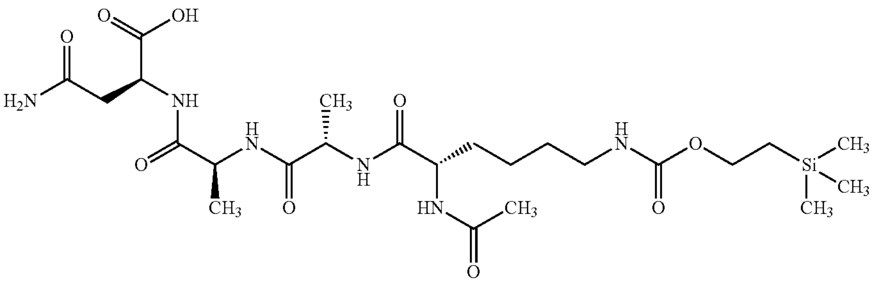 [SMILES: CC(=O)N[C@@H](CCCCNC(=O)OCC[Si](C)(C)C)C(=O)N[C@@H](C)C(=O)N[C@@H](C)C(=O)N[C@@H](CC(N)=O)C(=O)O]

The title compound was prepared by conventional methods of peptide chemistry by HATU coupling of commercially available $N^2$-acetyl-$N^6$-(tert-butoxycarbonyl)-L-lysine with benzyl (2-aminoethyl)carbamate hydrochloride The synthesis of the title compound commenced with the coupling of N-[(benzyloxy)carbonyl]-L-alanyl-L-alanine and tert-butyl L-asparaginate in DMF in the presence of HATU and N,N-diisopropylethylamine and subsequent detachment of the Z protecting group by hydrogenation over 10% palladium on activated carbon in methanol under standard pressure. Subsequently, the deprotected intermediate was coupled with Intermediate L109 in DMF in the presence of HATU and N,N-diisopropylethylamine. This was followed by complete deprotection by stirring in a 7.5% solution of trifluoroacetic acid in DCM for 1 h. In the last step, the title compound was prepared by reprotecting the free amino group by reaction with 1-({[2-(trimethylsilyl)ethoxy]carbonyl}oxy)pyrrolidine-2,5-dione in DMF/water 1:1 in the presence of N,N-diisopropylethylamine.

LC-MS (Method 1): $R_t$=0.71 min; MS (ESIpos): m/z=589 $(M+H)^+$.

Intermediate L111

N-(Pyridin-4-ylacetyl)-L-alanyl-N-methyl-L-alanyl-L-asparagine

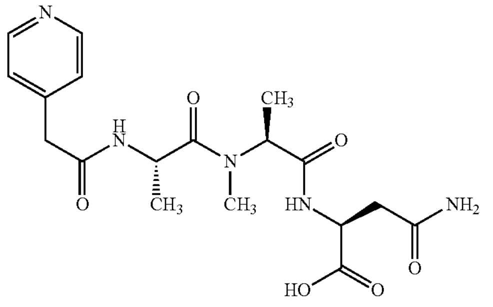 [SMILES: C[C@H](NC(=O)Cc1ccncc1)C(=O)N(C)[C@@H](C)C(=O)N[C@@H](CC(N)=O)C(=O)O]

The title compound was synthesized by classical methods of peptide chemistry commencing with the HATU coupling of N-[(benzyloxy)carbonyl]-L-alanine to tert-butyl N-methyl-L-alaninate hydrochloride (1:1) in the presence of N,N-diisopropylethylamine, followed by deprotection of the carboxyl group with trifluoroacetic acid in DCM. This was followed by coupling to tert-butyl L-aspartate in the presence of HATU and N,N-diisopropylethylamine and then the hydrolytic detachment of the Z protecting group in DCM/methanol 1:1 over 10% palladium on activated carbon at RT under standard hydrogen pressure. Finally, the intermediate obtained was converted to the title compound by coupling to 4-pyridineacetic acid in the presence of HATU and N,N-diisopropylethylamine, followed by deprotection of the carboxyl group with trifluoroacetic acid in DCM.

LC-MS (Method 1): $R_t$=0.16 min; MS (ESIpos): m/z=408 $(M+H)^+$.

Intermediate L112

N-(Pyridin-4-ylacetyl)-L-alanyl-N-methyl-L-alanyl-L-asparagine

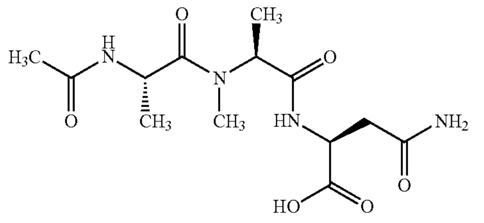 [SMILES: CC(=O)N[C@@H](C)C(=O)N(C)[C@@H](C)C(=O)N[C@@H](CC(N)=O)C(=O)O]

The title compound was synthesized by classical methods of peptide chemistry commencing with the HATU coupling of N-[(benzyloxy)carbonyl]-L-alanine to tert-butyl N-methyl-L-alaninate hydrochloride (1:1) in the presence of N,N-diisopropylethylamine, followed by deprotection of the carboxyl group with trifluoroacetic acid in DCM. This was followed by coupling to tert-butyl L-aspartate in the presence of HATU and N,N-diisopropylethylamine and then the hydrolytic detachment of the Z protecting group in DCM/methanol 1:1 over 10% palladium on activated carbon at RT under standard hydrogen pressure. Finally, the intermediate obtained was converted to the title compound by coupling to 1-acetoxypyrrolidine-2,5-dione in the presence of N,N-diisopropylethylamine, followed by deprotection of the carboxyl group with trifluoroacetic acid in DCM.

LC-MS (Method 1): $R_t$=0.16 min; MS (ESIpos): m/z=331 $(M+H)^+$.

Intermediate L113

N-Methyl-N-(pyridin-4-ylacetyl)-L-alanyl-L-alanyl-L-asparagine/trifluoroacetic Acid (1:1)

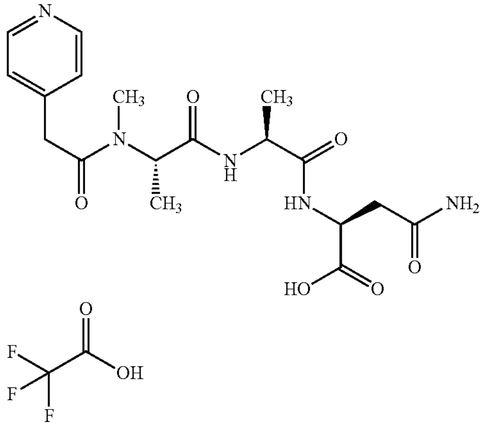

The title compound was synthesized by classical methods of peptide chemistry commencing with the HATU coupling of pyridin-4-ylacetic acid to tert-butyl N-methyl-L-alaninate hydrochloride (1:1) in the presence of N,N-diisopropylethylamine, followed by deprotection of the carboxyl group with trifluoroacetic acid in DCM. This was followed by coupling to tert-butyl L-alaninate in the presence of HATU and N,N-diisopropylethylamine and redeprotection of the carboxyl group with trifluoroacetic acid in DCM. Then coupling to tert-butyl L-aspartate was effected in the presence of HATU and N,N-diisopropylethylamine and finally deprotection of the carboxyl group with trifluoroacetic acid in DCM. After HPLC purification, the title compound was obtained.

LC-MS (Method 1): $R_t$=0.16 min; MS (ESIpos): m/z=408 $(M+H)^+$.

Intermediate L114

N-{[2-(2-Methoxyethoxy)ethoxy]acetyl}-L-alanyl-N-methyl-L-alanyl-L-asparagine

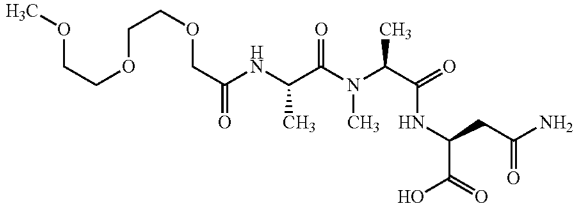 [SMILES: COCCOCCOCC(=O)N[C@@H](C)C(=O)N(C)[C@@H](C)C(=O)N[C@@H](CC(N)=O)C(=O)O]

The title compound was synthesized by classical methods of peptide chemistry commencing with the HATU coupling of N-[(benzyloxy)carbonyl]-L-alanine to tert-butyl N-methyl-L-alaninate hydrochloride (1:1) in the presence of N,N-diisopropylethylamine, followed by deprotection of the carboxyl group with trifluoroacetic acid in DCM. This was followed by coupling to tert-butyl L-aspartate in the presence of HATU and N,N-diisopropylethylamine and then the hydrolytic detachment of the Z protecting group in DCM/methanol 1:1 over 10% palladium on activated carbon at RT under standard hydrogen pressure. Finally, the intermediate obtained was converted to the title compound by coupling to [2-(2-methoxyethoxy)ethoxy]acetic acid in the presence of HATU and N,N-diisopropylethylamine, followed by deprotection of the carboxyl group with trifluoroacetic acid in DCM.

LC-MS (Method 1): $R_t$=0.36 min; MS (ESIpos): m/z=449 $(M+H)^+$.

Intermediate L115

Trifluoroacetic Acid/dibenzyl beta-alanyl-L-glutamate (1:1)

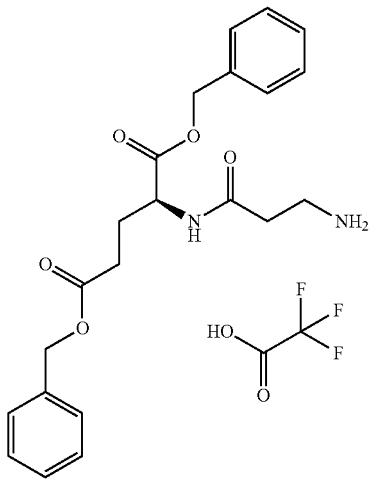 [SMILES: NCCC(=O)N[C@@H](CCC(=O)OCc1ccccc1)C(=O)OCc1ccccc1 ; O=C(O)C(F)(F)F]

The title compound was prepared proceeding from commercially available 4-methylbenzenesulphonic acid/dibenzyl L-glutamate (1:1) by classical methods of peptide chemistry by coupling to N-(tert-butoxycarbonyl)-beta-alanine in the presence of HATU, and finally by detachment of the Boc protecting group with TFA.

LC-MS (Method 1): $R_t$=0.72 min; MS (ESIpos): m/z=399 $[M+H]^+$

Intermediate F2

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-[2-(2,5-dioxo-2,5-dihydro-1H-pyrrol-1-yl)ethyl]butanamide (1:1)

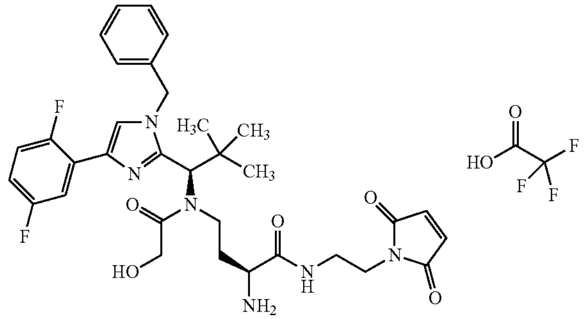 [SMILES: CC(C)(C)[C@H](c1nc(-c2cc(F)ccc2F)cn1Cc1ccccc1)N(CC[C@H](N)C(=O)NCCN1C(=O)C=CC1=O)C(=O)CO ; O=C(O)C(F)(F)F]

55 mg (0.089 mmol) of (2S)-4-[{(1R)-1-[1-benzyl-4-(2,5-difluorophenyl)-1H-imidazol-2-yl]-2,2-dimethylpropyl}(glycoloyl)amino]-2-[(tert-butoxycarbonyl)amino]butanoic acid (Intermediate C5) were taken up in 12 ml of DMF, and 68 mg (0.268 mmol) of commercially available trifluoroacetic acid/1-(2-aminoethyl)-1H-pyrrole-2,5-dione (1:1), 34.3 mg (0.18 mmol) of 1-(3-dimethylaminopropyl)-3-ethylcarbodiimide hydrochloride, 27.4 mg (0.18 mmol) of 1-hydroxy-1H-benzotriazole hydrate and 47 µl (0.27 mmol) of N,N-diisopropylethylamine were added in succession. The mixture was stirred at RT overnight. The solvent was removed under reduced pressure and the residue that remained was purified by preparative HPLC. The appropriate fractions were concentrated giving, after lyophilization from 1,4-dioxane, 20 mg (30% of theory) of the title compound.

HPLC (Method 11): $R_t$=2.48 min;

LC-MS (Method 1): $R_t$=1.29 min; MS (ESIpos): m/z=737 $(M+H)^+$.

20 mg (0.027 mmol) of this intermediate were taken up in 5 ml of dichloromethane, 1 ml of trifluoroacetic acid was added and the mixture was stirred at RT for 1 h. The reaction mixture was then concentrated under reduced pressure and the residue that remained was lyophilised from acetonitrile/water 1:1. In this way, 19 mg (95% of theory) of the title compound were obtained.

HPLC (Method 11): $R_t$=2.0 min;

LC-MS (Method 1): $R_t$=0.9 min; MS (ESIpos): m/z=637 $(M+H)^+$.

$^1$H-NMR (500 MHz, DMSO-$d_6$): δ=8.28 (t, 1H), 7.9-8.1 (m, 3H), 7.7-7.8 (m, 2H), 7.2-7.4 (m, 6H) 7.0-7.1 (m, 3H), 5.7 (s, 1H), 5.0 and 5.3 (2d, 2H), 4.08 and 4.25 (2d, 2H), 3.3-3.65 (m, 5H), 3.1-3.25 (m, 2H), 0.75 and 1.45 (2m, 2H), 0.9 (s, 9H).

Intermediate F3

Trifluoroacetic Acid/N-[(3S)-3-amino-4-{2-[6-(2,5-dioxo-2,5-dihydro-1H-pyrrol-1-yl)hexanoyl]hydrazino}-4-oxobutyl]-N-{(1R)-1-[1-benzyl-4-(2,5-difluorophenyl)-1H-imidazol-2-yl]-2,2-dimethylpropyl}-2-hydroxyacetamide (1:1)

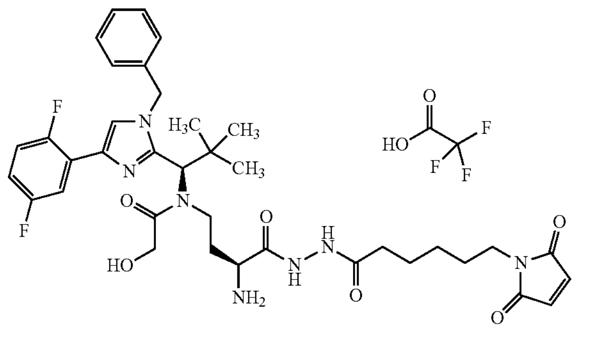 [SMILES: CC(C)(C)[C@H](c1nc(-c2cc(F)ccc2F)cn1Cc1ccccc1)N(CC[C@H](N)C(=O)NNC(=O)CCCCCN1C(=O)C=CC1=O)C(=O)CO ; O=C(O)C(F)(F)F]

13 mg (0.021 mmol) of (2S)-4-[{(1R)-1-[1-benzyl-4-(2,5-difluorophenyl)-1H-imidazol-2-yl]-2,2-dimethylpropyl}(glycoloyl)amino]-2-[(tert-butoxycarbonyl)amino]butanoic acid (Intermediate C5) were taken up in 5 ml of DMF, and 33 mg (86 μmol) of O-(7-azabenzotriazol-1-yl)-N,N,N',N'-tetramethyluronium hexafluorophosphate, 15 μl of N,N-diisopropylethylamine and 22 mg (64 μmol) of commercially available 6-(2,5-dioxo-2,5-dihydro-1H-pyrrol-1-yl)hexanehydrazide were then added. The reaction mixture was stirred at RT for 1 h. The mixture was then concentrated under high vacuum and the residue that remained was purified by preparative HPLC. This gave 9.5 mg (53% of theory) of the protected intermediate as a colourless foam.

HPLC (Method 11): $R_t$=2.1 min;

LC-MS (Method 1): $R_t$=1.33 min; MS (ESIpos): m/z=822 $(M+H)^+$.

9.5 mg (0.011 mmol) of this intermediate were taken up in 3 ml of dichloromethane, 1 ml of trifluoroacetic acid was added and the mixture was stirred at RT for 2 h. The reaction mixture was then concentrated under reduced pressure and the residue that remained was lyophilised from acetonitrile/water 1:1. In this way, 7 mg (70% of theory) of the title compound were obtained.

HPLC (Method 11): $R_t$=1.75 min;

LC-MS (Method 1): $R_t$=0.91 min; MS (ESIpos): m/z=722 $(M+H)^+$.

Intermediate F4

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-(6-{[(2R)-2-(2,5-dioxo-2,5-dihydro-1H-pyrrol-1-yl)propanoyl]amino}hexyl)butanamide (1:1)

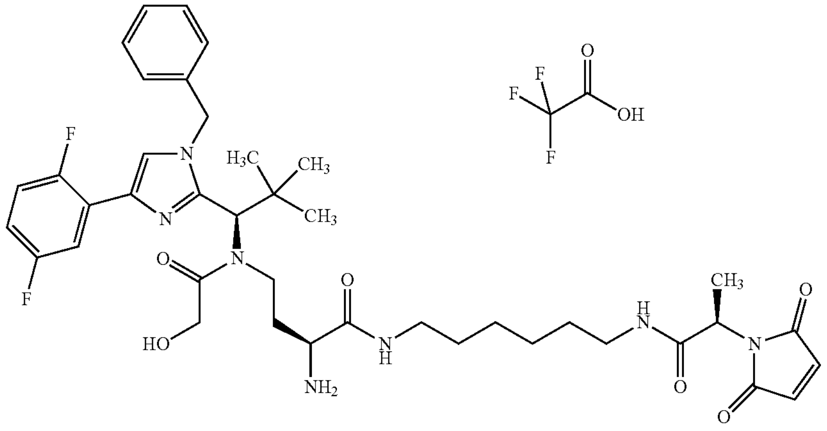 [SMILES: C[C@H](C(=O)NCCCCCCNC(=O)[C@@H](N)CCN(C(=O)CO)[C@@H](c1nc(-c2cc(F)ccc2F)cn1Cc1ccccc1)C(C)(C)C)N1C(=O)C=CC1=O ; O=C(O)C(F)(F)F]

First, 30 mg (0.049 mmol) of (2S)-4-[{(1R)-1-[1-benzyl-4-(2,5-difluorophenyl)-1H-imidazol-2-yl]-2,2-dimethylpropyl}(glycoloyl)amino]-2-[(tert-butoxycarbonyl)amino]butanoic acid (Intermediate C5) were coupled analogously to Intermediate F3 with trifluoroacetic acid/9H-fluoren-9-ylmethyl-(6-aminohexyl) carbamate (1:1) in the presence of HATU. Then the Fmoc protective group was removed with piperidine according to standard methods. This amine component was then, in the presence of N,N-diisopropylethylamine, coupled with (2R)-2-(2,5-dioxo-2,5-dihydro-1H-pyrrol-1-yl)propanoyl chloride which had been prepared from the free acid using thionyl chloride. In the last step, the Boc protective group was removed with trifluoroacetic acid in DCM. This gave 1.1 mg (3% over 4 steps) of the title compound.

HPLC (Method 11): $R_t$=1.83 min;

LC-MS (Method 1): $R_t$=0.96 min; MS (ESIpos): m/z=764 $(M+H)^+$.

Intermediate F5

Trifluoroacetic Acid/(2S)-2-amino-4-[{(1R)-1-[1-benzyl-4-(2,5-difluorophenyl)-1H-imidazol-2-yl]-2,2-dimethylpropyl}(propionyl)amino]-N-{2-[2-(2,5-dioxo-2,5-dihydro-1H-pyrrol-1-yl)ethoxy]ethyl}butanamide (1:1)

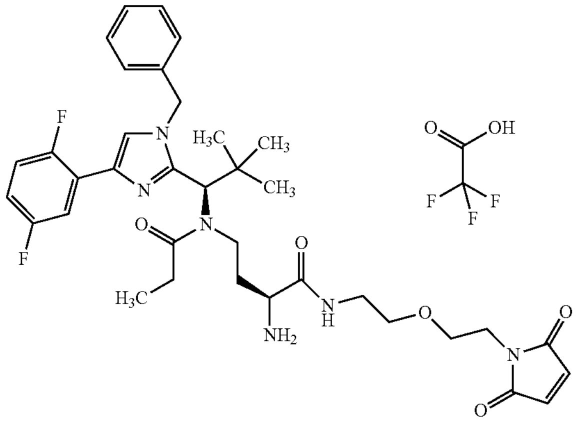 [SMILES: CCC(=O)N(CC[C@H](N)C(=O)NCCOCCN1C(=O)C=CC1=O)[C@@H](c1nc(-c2cc(F)ccc2F)cn1Cc1ccccc1)C(C)(C)C ; O=C(O)C(F)(F)F]

The title compound was prepared analogously to Intermediate F2 from 16 mg (0.026 mmol) of Intermediate C5 and 8.5 mg (0.03 mmol) of Intermediate L12. This gave 3 mg (13% of theory over 2 steps) of the title compound.

HPLC (Method 11): $R_t$=2.0 min;

LC-MS (Method 1): $R_t$=0.96 min; MS (ESIpos): m/z=681 $(M+H)^+$.

Intermediate F6

Trifluoroacetic Acid/N-[(16S)-16-amino-1-(2,5-dioxo-2,5-dihydro-1H-pyrrol-1-yl)-12,15-dioxo-3,6,9-trioxa-13,14-diazaoctadecan-18-yl]-N-{(1R)-1-[1-benzyl-4-(2,5-difluorophenyl)-1H-imidazol-2-yl]-2,2-dimethylpropyl}-2-hydroxyacetamide (1:1)

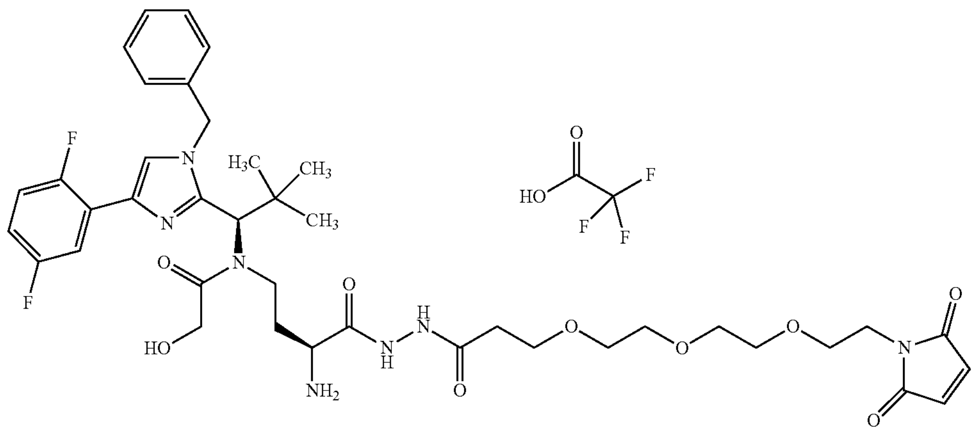 [SMILES: CC(C)(C)[C@H](c1nc(-c2cc(F)ccc2F)cn1Cc1ccccc1)N(CC[C@H](N)C(=O)NNC(=O)CCOCCOCCOCCN1C(=O)C=CC1=O)C(=O)CO ; O=C(O)C(F)(F)F]

8 mg (12.7 μmol) of trifluoroacetic acid/tert-butyl {(2S)-4-[{(1R)-1-[1-benzyl-4-(2,5-difluorophenyl)-1H-imidazol-2-yl]-2,2-dimethylpropyl}(glycoloyl)amino]-1-hydrazino-1-oxobutan-2-yl}carbamate (1:1) (Intermediate C6) were taken up in 8 ml of DMF, and 6 mg (19 μmol) of commercially available 3-(2-{2-[2-(2,5-dioxo-2,5-dihydro-1H-pyrrol-1-yl)ethoxy]ethoxy}ethoxy)propanoic acid, 5.8 mg (15 μmol) of O-(7-azabenzotriazol-1-yl)-N,N,N',N'-tetramethyluronium hexafluorophosphate (HATU) and 7 μl (38 μmol) of N,N-diisopropylethylamine were added. The mixture was stirred at RT for 15 min. The solvent was then removed under reduced pressure and the residue was taken up in acetonitrile/water 1:1 and adjusted to pH 2 with trifluoroacetic acid. Purification was by preparative HPLC. Combination of the appropriate fractions, concentration and freeze-drying from acetonitrile/water 1:1 gave 5 mg (41% of theory) of the Boc-protected intermediate. Removal of the Boc group with trifluoroacetic acid afforded 4 mg (32% of theory over 2 steps) of the title compound.

HPLC (Method 11): $R_t$=1.89 min;

LC-MS (Method 1): $R_t$=0.89 min; MS (ESIpos): m/z=812 $(M+H)^+$.

Intermediate F7

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-(2-{[(2,5-dioxo-2,5-dihydro-1H-pyrrol-1-yl)acetyl]amino}ethyl)butanamide (1:1)

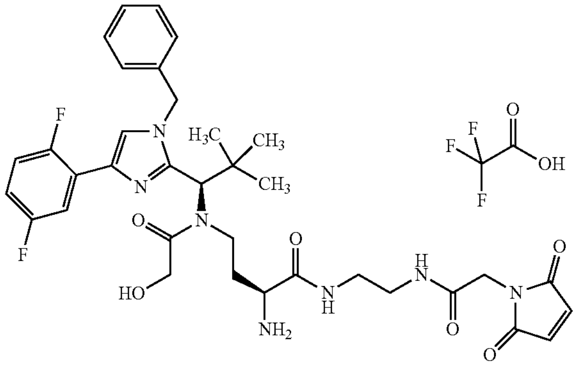 [SMILES: CC(C)(C)[C@H](c1nc(-c2cc(F)ccc2F)cn1Cc1ccccc1)N(CC[C@H](N)C(=O)NCCNC(=O)CN1C(=O)C=CC1=O)C(=O)CO ; O=C(O)C(F)(F)F]

The title compound was prepared analogously to Intermediate F2 from 25 mg (0.037 mmol) of Intermediate C5 and 35 mg (0,112 mmol) of Intermediate L1. This gave 14.4 mg (29% of theory over 2 steps) of the title compound.

HPLC (Method 11): $R_t$=2.0 min;

LC-MS (Method 1): $R_t$=0.9 min; MS (ESIpos): m/z=694 $(M+H)^+$.

$^1$H-NMR (500 MHz, DMSO-$d_6$): δ=8.2 (m, 1H), 7.9-8.1 (m, 3H), 7.7-7.8 (m, 2H), 7.2-7.4 (m, 6H), 7.0-7.12 (m, 3H), 5.7 (s, 1H), 4.95 and 5.3 (2d, 2H), 4.1 and 4.25 (2d, 2H), 4.0 (s, 2H), 3.3-3.65 (m, 5H), 3.0-3.15 (m, 2H), 0.7 and 1.45 (2m, 2H), 0.88 (s, 9H).

Intermediate F8

N-[6-(2,5-Dioxo-2,5-dihydro-1H-pyrrol-1-yl)hexanoyl]-L-valyl-L-alanyl-N6-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-L-lysine/trifluoroacetic Acid (1:1)

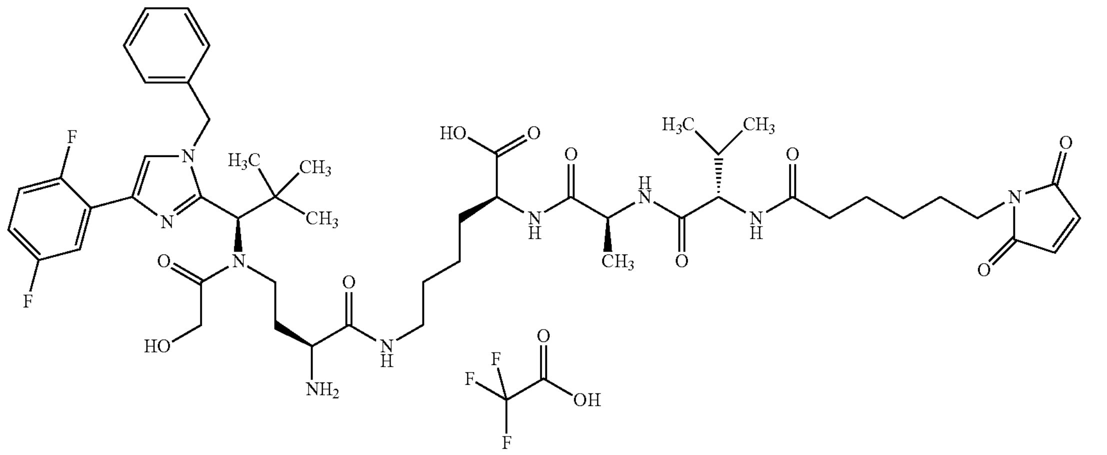 [SMILES: CC(C)[C@H](NC(=O)CCCCCN1C(=O)C=CC1=O)C(=O)N[C@@H](C)C(=O)N[C@@H](CCCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared analogously to Intermediate F2 from 10 mg (0.016 mmol) of Intermediate C5 and 13 mg (0.018 mmol) of Intermediate L6. This gave 10 mg (49% of theory over 2 steps) of the title compound.

HPLC (Method 11): $R_t$=1.97 min;

LC-MS (Method 1): $R_t$=0.93 min; MS (ESIpos): m/z=1006 $(M+H)^+$.

Intermediate F9

Trifluoroacetic Acid/N-{(3S)-3-amino-4-[1-(2-{[2-(2,5-dioxo-2,5-dihydro-1H-pyrrol-1-yl)ethyl]amino}-2-oxoethyl)hydrazino]-4-oxobutyl}-N-{(1R)-1-[1-benzyl-4-(2,5-difluorophenyl)-1H-imidazol-2-yl]-2,2-dimethylpropyl}-2-hydroxyacetamide (1:1)

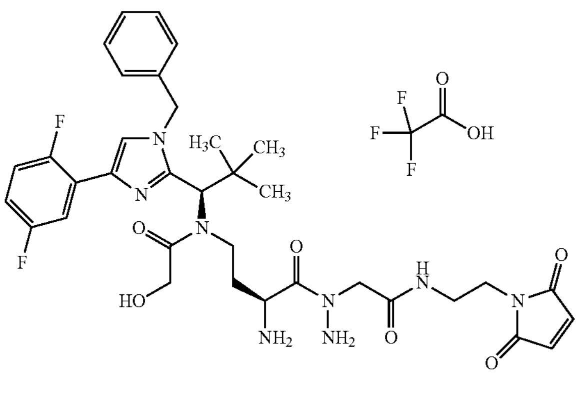 [SMILES: CC(C)(C)[C@H](c1nc(-c2cc(F)ccc2F)cn1Cc1ccccc1)N(CC[C@H](N)C(=O)N(N)CC(=O)NCCN1C(=O)C=CC1=O)C(=O)CO ; O=C(O)C(F)(F)F]

The title compound was prepared analogously to Intermediate F2 from 1.5 mg (0.002 mmol) of Intermediate C7 and 0.95 mg (0.004 mmol) of commercially available trifluoroacetic acid/1-(2-aminoethyl)-1H-pyrrole-2,5-dione (1:1). This gave 1.1 mg (52% of theory over 2 steps) of the title compound.

HPLC (Method 11): $R_t$=1.9 min;

LC-MS (Method 1): $R_t$=0.89 min; MS (ESIpos): m/z=709 $(M+H)^+$.

Intermediate F10

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-(3-{[4-(2,5-dioxo-2,5-dihydro-1H-pyrrol-1-yl)phenyl]amino}-3-oxopropyl)butanamide (1:1)

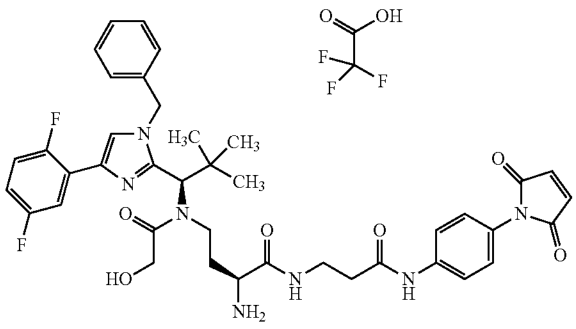 [SMILES: CC(C)(C)[C@H](c1nc(-c2cc(F)ccc2F)cn1Cc1ccccc1)N(CC[C@H](N)C(=O)NCCC(=O)Nc1ccc(N2C(=O)C=CC2=O)cc1)C(=O)CO ; O=C(O)C(F)(F)F]

The title compound was prepared analogously to Intermediate F2 from 14 mg (0.022 mmol) of Intermediate C5 and 10 mg (0.025 mmol) of Intermediate L5. This gave 4.5 mg (22% of theory over 2 steps) of the title compound.

HPLC (Method 11): $R_t$=2.0 min;

LC-MS (Method 1): $R_t$=0.93 min; MS (ESIpos): m/z=756 $(M+H)^+$.

Intermediate F11

Trifluoroacetic Acid/N-[2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)ethyl]-4-(2,5-dioxo-2,5-dihydro-1H-pyrrol-1-yl)cyclohexanecarboxamide (1:1)

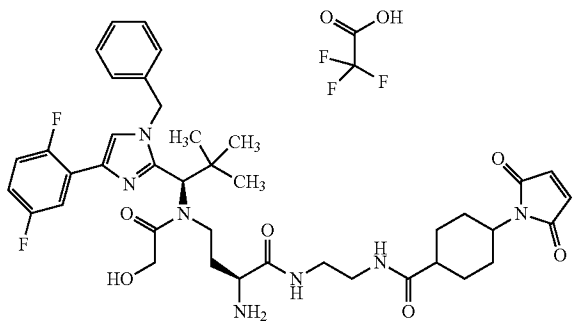 [SMILES: CC(C)(C)[C@H](c1nc(-c2cc(F)ccc2F)cn1Cc1ccccc1)N(CC[C@H](N)C(=O)NCCNC(=O)C1CCC(N2C(=O)C=CC2=O)CC1)C(=O)CO ; O=C(O)C(F)(F)F]

The title compound was prepared analogously to Intermediate F2 from 12 mg (0.019 mmol) of Intermediate C5 and 10 mg (0.021 mmol) of Intermediate L4. This gave 7 mg (38% of theory over 2 steps) of the title compound.

HPLC (Method 11): $R_t$=2.04 min;

LC-MS (Method 1): $R_t$=0.93 min; MS (ESIpos): m/z=776 $(M+H)^+$.

Intermediate F12

Trifluoroacetic Acid/(1R,2S)-2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

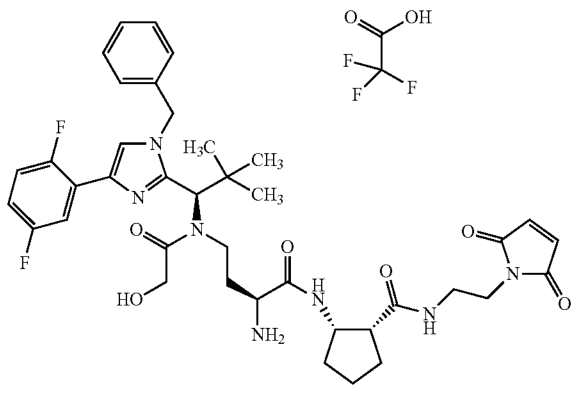 [SMILES: CC(C)(C)[C@H](c1nc(-c2cc(F)ccc2F)cn1Cc1ccccc1)N(CC[C@H](N)C(=O)N[C@H]1CCC[C@H]1C(=O)NCCN1C(=O)C=CC1=O)C(=O)CO ; O=C(O)C(F)(F)F]

The title compound was prepared analogously to Intermediate F2 from 43 mg (0.071 mmol) of Intermediate C5 and 30 mg (0.071 mmol) of Intermediate L2. At the stage of the Boc-protected intermediate, the diastereomers formed were separated by preparative HPLC (Chromatorex C18-10/125×30/12 ml/min). The stereochemistry of the separated diastereomers was assigned by comparison with the individual diastereomer prepared in an analogous manner from commercially available (1S,2R)-2-[(tert-butoxycarbonyl)amino]cyclopentanecarboxylic acid:

Fraction 1: 1S2R Diastereomer

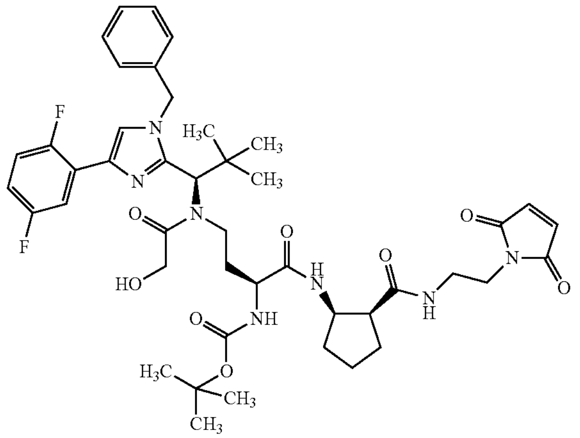 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)N[C@@H]1CCC[C@@H]1C(=O)NCCN1C(=O)C=CC1=O]

Yield: 13 mg (22%)

HPLC (Method 11): $R_t$=2.52 min;

LC-MS (Method 1): $R_t$=1.31 min; MS (ESIpos): m/z=848 $(M+H)^+$.

Fraction 2: 1R2S Diastereomer

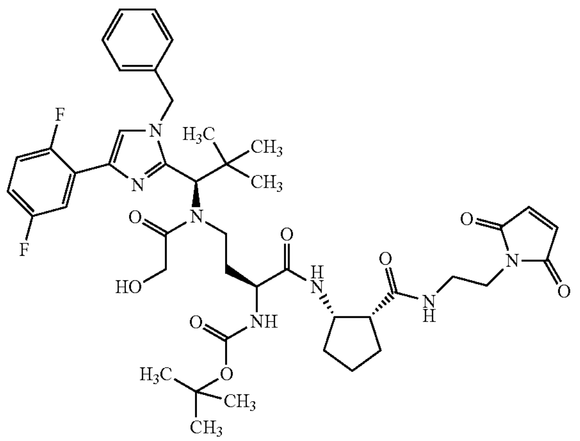 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)N[C@H]1CCC[C@H]1C(=O)NCCN1C(=O)C=CC1=O]

Yield: 10 mg (17%)

HPLC (Method 11): $R_t$=2.56 min;

LC-MS (Method 1): $R_t$=1.33 min; MS (ESIpos): m/z=848 $(M+H)^+$.

The deprotection of 10 mg (0.011 mmol) of the 1R2S diastereomer with TFA then yielded 8 mg (75% of theory) of the title compound.

HPLC (Method 11): $R_t$=2.04 min;

LC-MS (Method 1): $R_t$=0.92 min; MS (ESIpos): m/z=748 $(M+H)^+$.

Intermediate F13

Trifluoroacetic Acid/(1S,2R)-2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

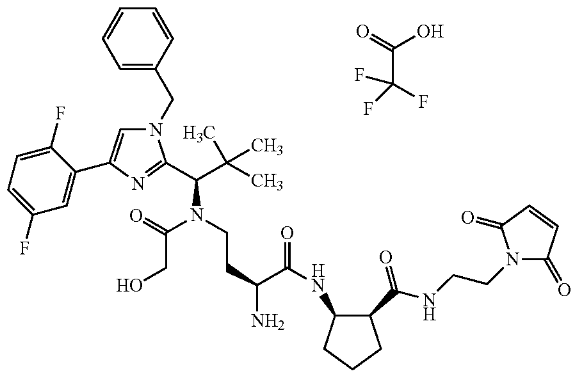 [SMILES: CC(C)(C)[C@H](c1nc(-c2cc(F)ccc2F)cn1Cc1ccccc1)N(CC[C@H](N)C(=O)N[C@@H]1CCC[C@@H]1C(=O)NCCN1C(=O)C=CC1=O)C(=O)CO ; O=C(O)C(F)(F)F]

The synthesis was carried out analogously to Intermediate F13 and the title compound was obtained by deprotection of the 1S2R diastereomer.

HPLC (Method 11): $R_t$=2.1 min;

LC-MS (Method 1): $R_t$=0.94 min; MS (ESIpos): m/z=748 $(M+H)^+$.

Intermediate F14

Trifluoroacetic Acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-$N^5$-carbamoyl-N-[4-(2,5-dioxo-2,5-dihydro-1H-pyrrol-1-yl)phenyl]-L-ornithinamide (1:1)

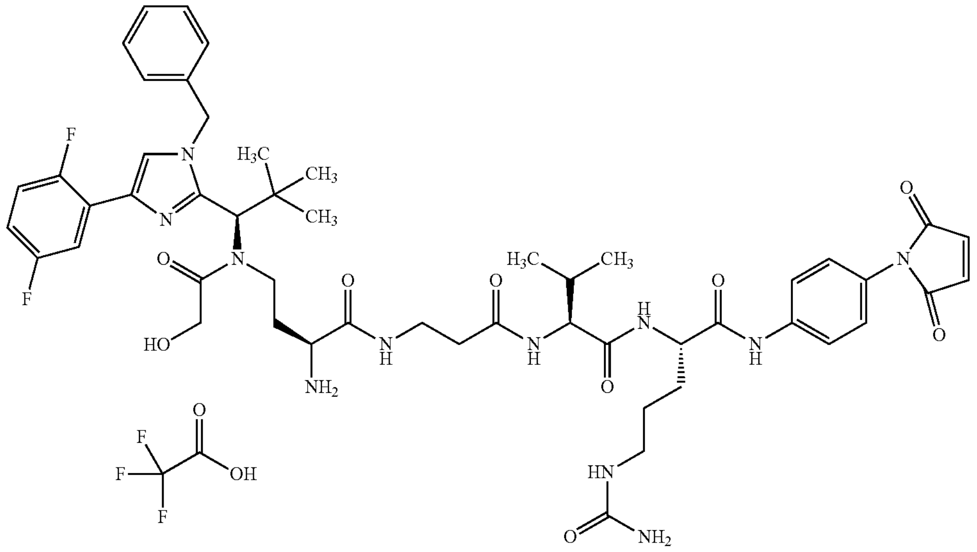 [SMILES: CC(C)[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

The title compound was prepared coupling of 20 mg (0.028 mmol) of Intermediate C5 and 18 mg (0.028 mmol) of Intermediate L7 in the presence of HATU and subsequent deblocking with TFA. This gave 15 mg (49% of theory over 2 steps) of the title compound.

HPLC (Method 11): $R_t$=1.97 min;

LC-MS (Method 1): $R_t$=0.91 min; MS (ESIpos): m/z=1012 $(M+H)^+$.

Intermediate F15

Trifluoroacetic Acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-N5-carbamoyl-N-[4-(2,5-dioxo-2,5-dihydro-1H-pyrrol-1-yl)phenyl]-L-ornithinamide (1:1)

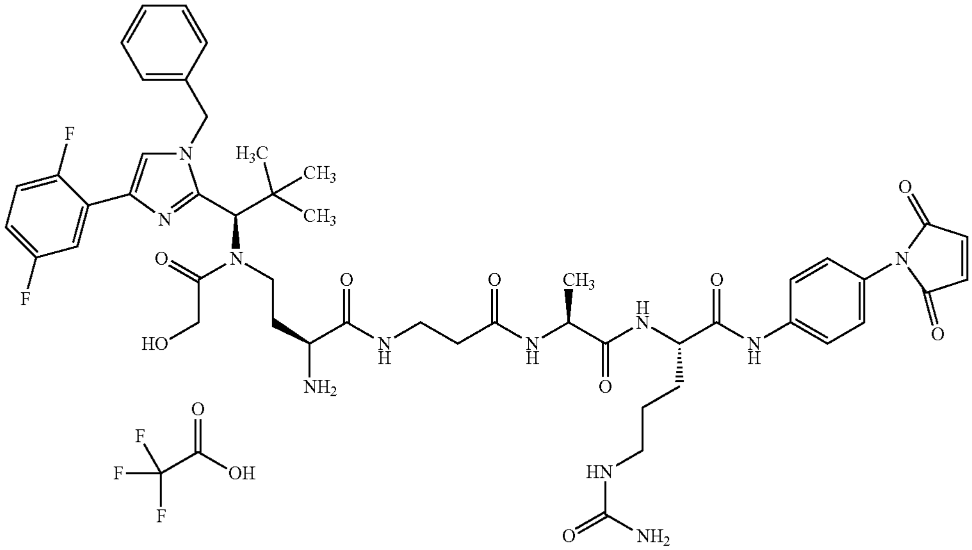 [SMILES: C[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

This Intermediate was prepared by coupling of 15 mg (0.022 mmol) of Intermediate C8 and 14 mg (0.026 mmol) of Intermediate L8 in the presence of HATU and subsequent deblocking with TFA. This gave 7 mg (27% of theory over 2 steps) of the title compound.

HPLC (Method 11): $R_t$=1.85 min;

LC-MS (Method 1): $R_t$=0.87 min; MS (ESIpos): m/z=984 $(M+H)^+$.

Intermediate F16

Trifluoroacetic Acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-N5-carbamoyl-N-[4-(2-{[2-(2,5-dioxo-2,5-dihydro-1H-pyrrol-1-yl)ethyl]amino}-2-oxoethyl)phenyl]-L-ornithinamide (1:1)

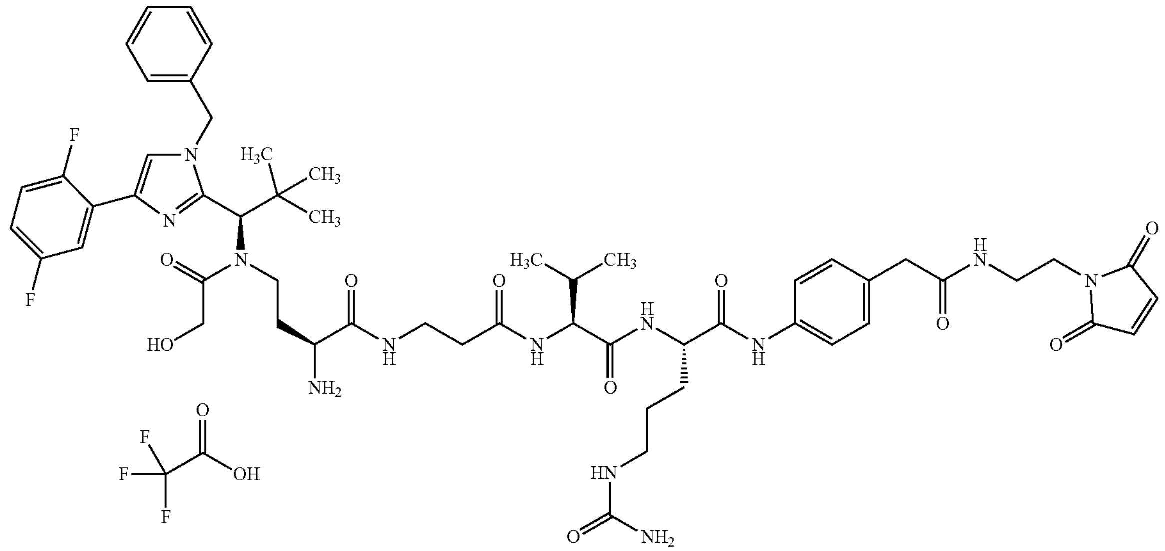 [SMILES: CC(C)[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(CC(=O)NCCN2C(=O)C=CC2=O)cc1 ; O=C(O)C(F)(F)F]

First, 20 mg (0.03 mmol) of Intermediate C3 were coupled analogously to Intermediate F3 with trifluoroacetic acid/beta-alanyl-L-valyl-N5-carbamoyl-N-[4-(2-methoxy-2-oxoethyl)phenyl]-L-ornithinamide (1:1) (Intermediate L9) in the presence of HATU (Yield: 15 mg (44% of theory). 26 mg (0.023 mmol) of this intermediate N-{(2S)-4-[(acetoxyacetyl){(1R)-1-[1-benzyl-4-(2,5-difluorophenyl)-1H-imidazol-2-yl]-2,2-dimethylpropyl}amino]-2-[(tert-butoxycarbonyl)amino]butanoyl}-beta-alanyl-L-valyl-N5-carbamoyl-N-[4-(2-methoxy-2-oxoethyl)phenyl]-L-ornithinamide were dissolved in 5 ml of methanol, 1 ml of a 2M lithium hydroxide solution were added and the reaction was stirred at RT for 90 min. The solvent was then removed under reduced pressure, the residue was taken up in acetonitrile/water and the mixture was adjusted to pH 2 using TFA. The mixture was then concentrated again giving, after purification of the residue by preparative HPLC, 20 mg (81%) of the carboxyl compound.

This intermediate was then taken up in 5 ml of DMF and coupled with 6 mg (0.022 mmol) of commercially available trifluoroacetic acid/1-(2-aminoethyl)-1H-pyrrole-2,5-dione (1:1) in the presence of 8.4 mg (0.022 mmol) of HATU and 1611 of N,N-diisopropylethylamine. Purification by preparative HPLC gave 17 mg (76% of theory) of the protected intermediate. These were taken up in 3 ml of DCM, and 1 ml of TFA was added. After 45 min of stirring at RT, the mixture was concentrated and the residue was digested with diethyl ether. Filtration with suction and drying of the residue under high vacuum yielded 15 mg (81%) of the title compound.

HPLC (Method 11): $R_t$=1.9 min;

LC-MS (Method 1): $R_t$=0.9 min; MS (ESIpos): m/z=1097 $(M+H)^+$.

Intermediate F17

N-[6-(2,5-Dioxo-2,5-dihydro-1H-pyrrol-1-yl)hexanoyl]-L-valyl-L-alanyl-$N^6$-{[(1R,2S)-2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)cyclopentyl]carbonyl}-L-lysine/trifluoroacetic Acid (1:1)

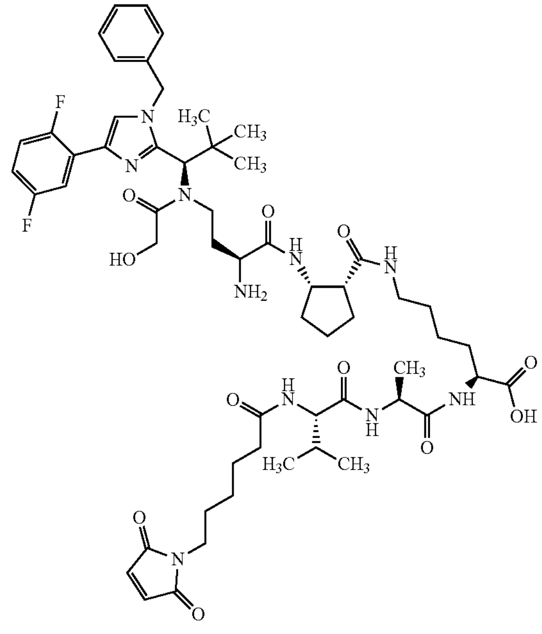 [SMILES: CC(C)[C@H](NC(=O)CCCCCN1C(=O)C=CC1=O)C(=O)N[C@@H](C)C(=O)N[C@@H](CCCCNC(=O)[C@@H]1CCC[C@@H]1NC(=O)[C@@H](N)CCN(C(=O)CO)[C@@H](c1nc(-c2cc(F)ccc2F)cn1Cc1ccccc1)C(C)(C)C)C(=O)O]

The title compound was prepared analogously to Intermediate F12 from 6 mg (0.01 mmol) of Intermediate C5 and 8 mg (0.01 mmol) of Intermediate L10. At the stage of the Boc-protected intermediate, the diastereomers formed were separated by preparative HPLC (Chromatorex C18-10/125×30/12 ml/min). The stereochemistry of the separated diastereomers was assigned by comparison with the individual diastereomer prepared in an analogous manner from commercially available (1S,2R)-2-[(tert-butoxycarbonyl)amino]cyclopentanecarboxylic acid:

Fraction 1: 1S2R Diastereomer

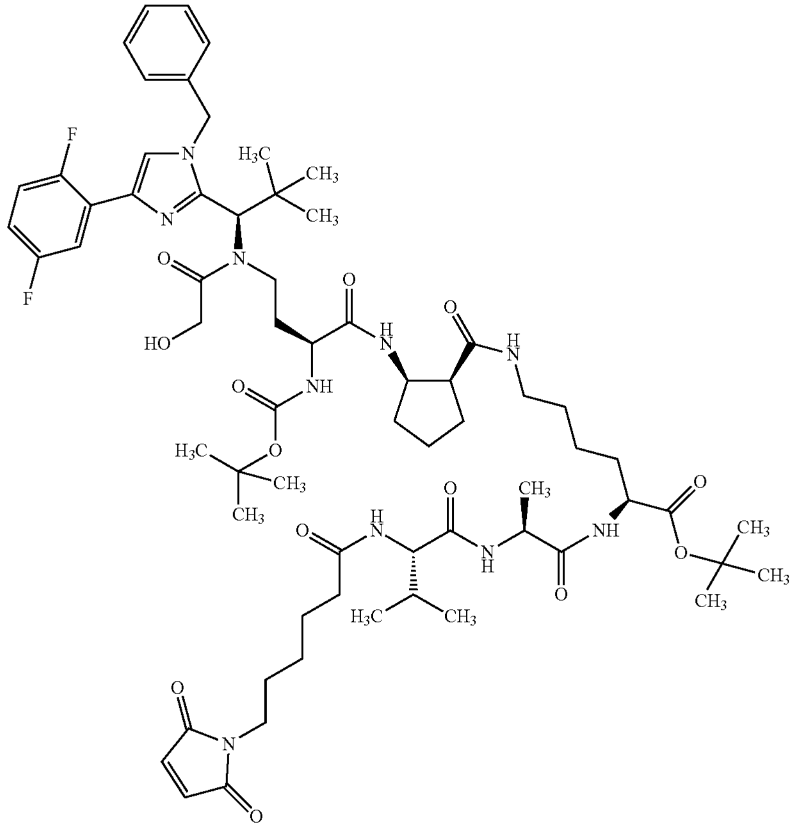 [SMILES: CC(C)[C@H](NC(=O)CCCCCN1C(=O)C=CC1=O)C(=O)N[C@@H](C)C(=O)N[C@@H](CCCCNC(=O)[C@H]1CCC[C@H]1NC(=O)[C@H](CCN(C(=O)CO)[C@@H](c1nc(-c2cc(F)ccc2F)cn1Cc1ccccc1)C(C)(C)C)NC(=O)OC(C)(C)C)C(=O)OC(C)(C)C]

Yield: 1 mg

HPLC (Method 11): $R_t$=2.73 min;

LC-MS (Method 1): $R_t$=1.37 min; MS (ESIpos): m/z=1274 $(M+H)^+$.

Fraction 2: 1R2S Diastereomer

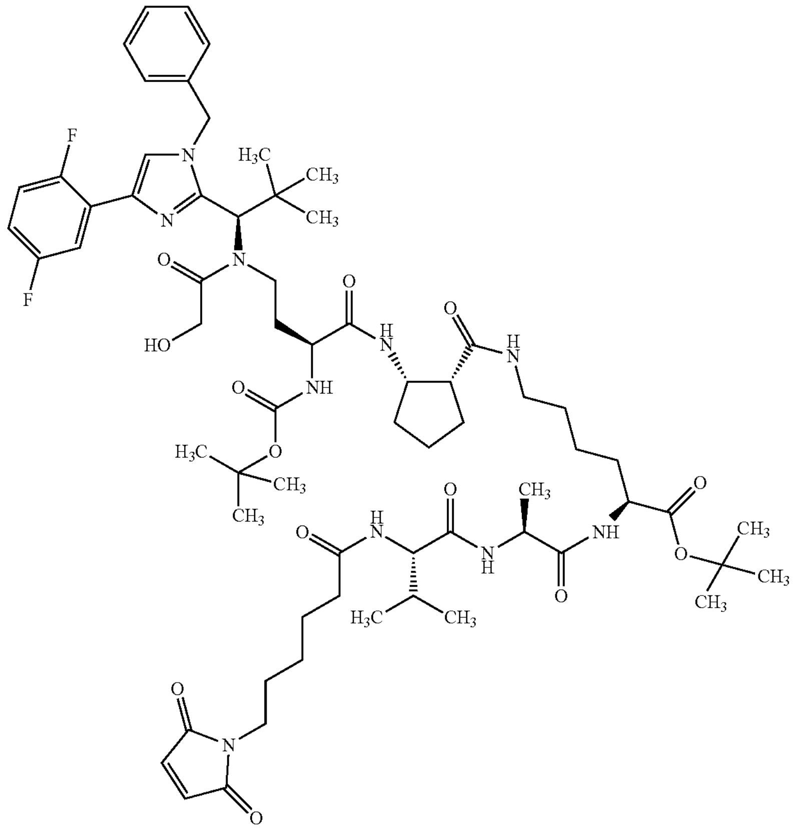 [SMILES: CC(C)[C@H](NC(=O)CCCCCN1C(=O)C=CC1=O)C(=O)N[C@@H](C)C(=O)N[C@@H](CCCCNC(=O)[C@@H]1CCC[C@@H]1NC(=O)[C@H](CCN(C(=O)CO)[C@@H](c1nc(-c2cc(F)ccc2F)cn1Cc1ccccc1)C(C)(C)C)NC(=O)OC(C)(C)C)C(=O)OC(C)(C)C]

Yield: 0.7 mg

HPLC (Method 11): $R_t$=2.81 min;

LC-MS (Method 1): $R_t$=1.41 min; MS (ESIpos): m/z=1274 $(M+H)^+$.

Complete deprotection of 0.7 mg (0.001 mmol) of the 1R2S diastereomer was achieved by dissolution in 1 ml of DCM, addition of 1 ml of TFA and 1 h of stirring at RT. Concentration under reduced pressure and lyophilization of the residue from acetonitrile/water gave 0.68 mg (94% of theory) of the title compound.

HPLC (Method 11): $R_t$=2.1 min;

LC-MS (Method 1): $R_t$=0.97 min; MS (ESIpos): m/z=1117 $(M+H)^+$.

Intermediate F18

N-[6-(2,5-Dioxo-2,5-dihydro-1H-pyrrol-1-yl)hexanoyl]-L-valyl-L-alanyl-$N^6$-{[(1S,2R)-2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)cyclopentyl]carbonyl}-L-lysine/trifluoroacetic Acid (1:1)

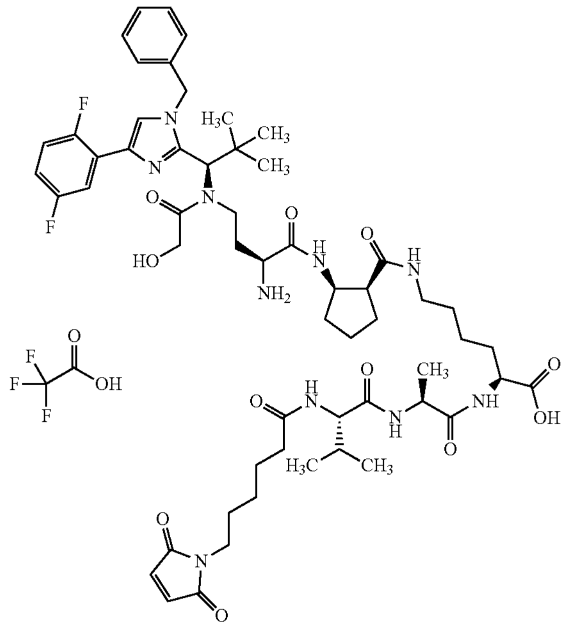 [SMILES: O=C(O)C(F)(F)F ; CC(C)[C@H](NC(=O)CCCCCN1C(=O)C=CC1=O)C(=O)N[C@@H](C)C(=O)N[C@@H](CCCCNC(=O)[C@H]1CCC[C@H]1NC(=O)[C@@H](N)CCN(C(=O)CO)[C@@H](c1nc(-c2cc(F)ccc2F)cn1Cc1ccccc1)C(C)(C)C)C(=O)O]

The title compound was prepared analogously to Intermediate F17 from 8.9 mg (0.014 mmol) of Intermediate C5 and 13 mg (0,014 mmol) of Intermediate L11.

HPLC (Method 11): $R_t$=2.2 min;

LC-MS (Method 1): $R_t$=1.01 min; MS (ESIpos): m/z=1117 $(M+H)^+$.

Intermediate F19

$N^6$-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-N-[(2,5-dioxo-2,5-dihydro-1H-pyrrol-1-yl)acetyl]-L-lysine/trifluoroacetic Acid (1:1)

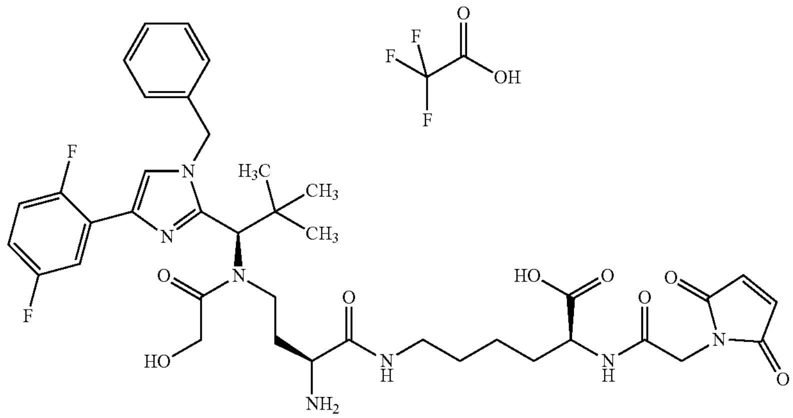 [SMILES: CC(C)(C)[C@H](c1nc(-c2cc(F)ccc2F)cn1Cc1ccccc1)N(CC[C@H](N)C(=O)NCCCC[C@H](NC(=O)CN1C(=O)C=CC1=O)C(=O)O)C(=O)CO ; O=C(O)C(F)(F)F]

The title compound was prepared analogously to Intermediate F2 by coupling of 25 mg (0.041 mmol) of Intermediate C5 with 55 mg (0.122 mmol) of Intermediate L13 and subsequent deprotection.

HPLC (Method 11): $R_t$=1.84 min;

LC-MS (Method 1): $R_t$=0.88 min; MS (ESIpos): m/z=780 $(M+H)^+$.

Intermediate F20

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-{4-[(2,5-dioxo-2,5-dihydro-1H-pyrrol-1-yl)acetyl]piperazin-1-yl}butanamide (1:1)

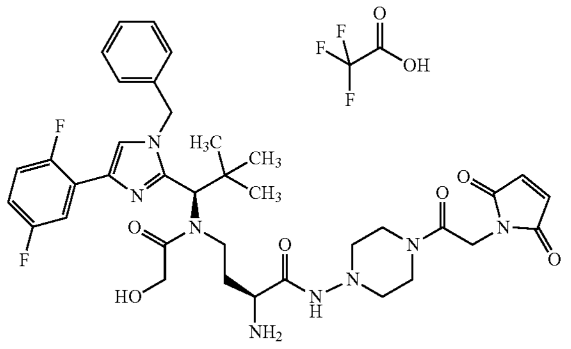 [SMILES: CC(C)(C)[C@H](c1nc(-c2cc(F)ccc2F)cn1Cc1ccccc1)N(CC[C@H](N)C(=O)NN1CCN(C(=O)CN2C(=O)C=CC2=O)CC1)C(=O)CO ; O=C(O)C(F)(F)F]

The title compound was prepared analogously to Intermediate F2 by coupling of 10 mg (0.015 mmol) of Intermediate C5 with 55 mg (0.122 mmol) of Intermediate L14 and subsequent deprotection.

HPLC (Method 11): $R_t$=1.9 min;

LC-MS (Method 1): $R_t$=0.87 min; MS (ESIpos): m/z=735 $(M+H)^+$.

Intermediate F21

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-[1-(2,5-dioxo-2,5-dihydro-1H-pyrrol-1-yl)-12-oxo-3,6,9-trioxa-13-azapentadecan-15-yl]butanamide (1:1)

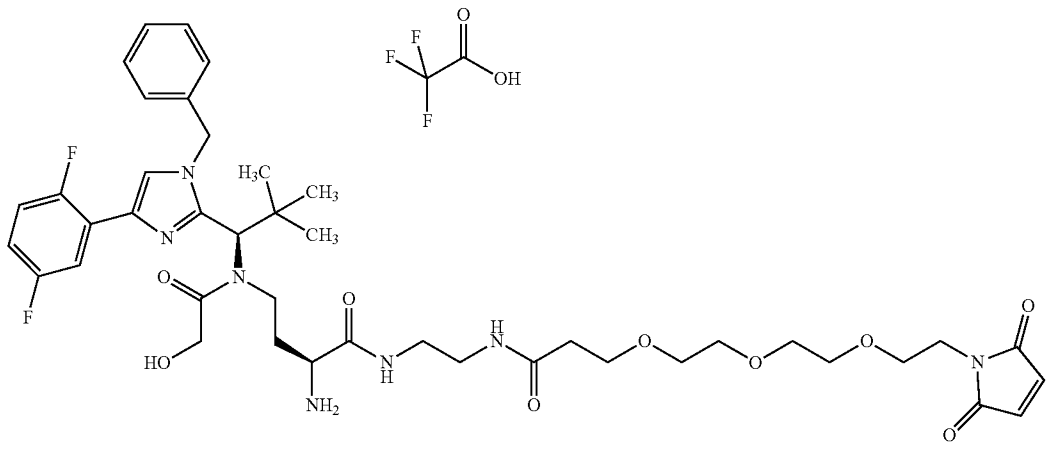 [SMILES: CC(C)(C)[C@H](c1nc(-c2cc(F)ccc2F)cn1Cc1ccccc1)N(CC[C@H](N)C(=O)NCCNC(=O)CCOCCOCCOCCN1C(=O)C=CC1=O)C(=O)CO ; O=C(O)C(F)(F)F]

The title compound was prepared analogously to Intermediate F2 by coupling of 10 mg (0.015 mmol) of Intermediate C5 with 7 mg (0.015 mmol) of Intermediate L15 and subsequent deprotection.

LC-MS (Method 1): $R_t$=0.89 min; MS (ESIpos): m/z=840 $(M+H)^+$.

Intermediate F22

Trifluoroacetic Acid/N-[(3S)-3-amino-4-(1-{2-[(2-{[(2,5-dioxo-2,5-dihydro-1H-pyrrol-1-yl)acetyl]amino}ethyl)amino]-2-oxoethyl}hydrazino)-4-oxobutyl]-N-{(1R)-1-[1-benzyl-4-(2,5-difluorophenyl)-1H-imidazol-2-yl]-2,2-dimethylpropyl}-2-hydroxyacetamide (1:1)

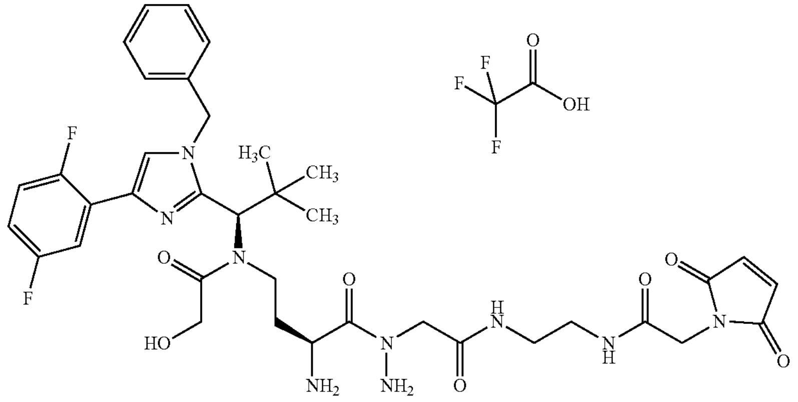 [SMILES: CC(C)(C)[C@H](c1nc(-c2cc(F)ccc2F)cn1Cc1ccccc1)N(CC[C@H](N)C(=O)N(N)CC(=O)NCCNC(=O)CN1C(=O)C=CC1=O)C(=O)CO ; O=C(O)C(F)(F)F]

The title compound was prepared analogously to Intermediate F9 by coupling of 13.7 mg (0.017 mmol) of Intermediate C7 with 5.9 mg (0.017 mmol) of Intermediate L1 and subsequent deprotection.

HPLC (Method 11): $R_t$=2.3 min;

LC-MS (Method 1): $R_t$=1.2 min; MS (ESIpos): m/z=866 $(M+H)^+$.

Intermediate F23

N-[6-(2,5-Dioxo-2,5-dihydro-1H-pyrrol-1-yl)hexanoyl]-L-valyl-$N^5$-carbamoyl-L-ornithyl-$N^6$-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-L-lysine/trifluoroacetic Acid (1:1)

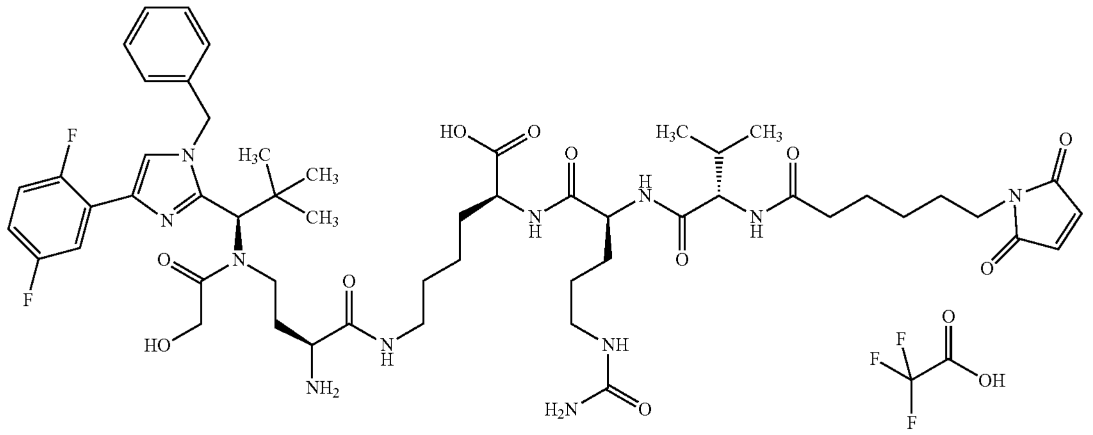 [SMILES: CC(C)[C@H](NC(=O)CCCCCN1C(=O)C=CC1=O)C(=O)N[C@@H](CCCNC(N)=O)C(=O)N[C@@H](CCCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared analogously to Intermediate F2 by coupling of 10 mg (0.016 mmol) of Intermediate C5 with 16.8 mg (0.016 mmol) of Intermediate L17 in the presence of EDC/HOBT and N,N-diisopropylethylamine and subsequent deprotection.

HPLC (Method 11): $R_t$=1.9 min;

LC-MS (Method 1): $R_t$=0.9 min; MS (ESIpos): m/z=1092 $(M+H)^+$.

Intermediate F24

Trifluoroacetic Acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-$N^5$-carbamoyl-N-[4-(2-{[2-(2,5-dioxo-2,5-dihydro-1H-pyrrol-1-yl)ethyl]amino}-2-oxoethyl)phenyl]-L-ornithinamide (1:1)

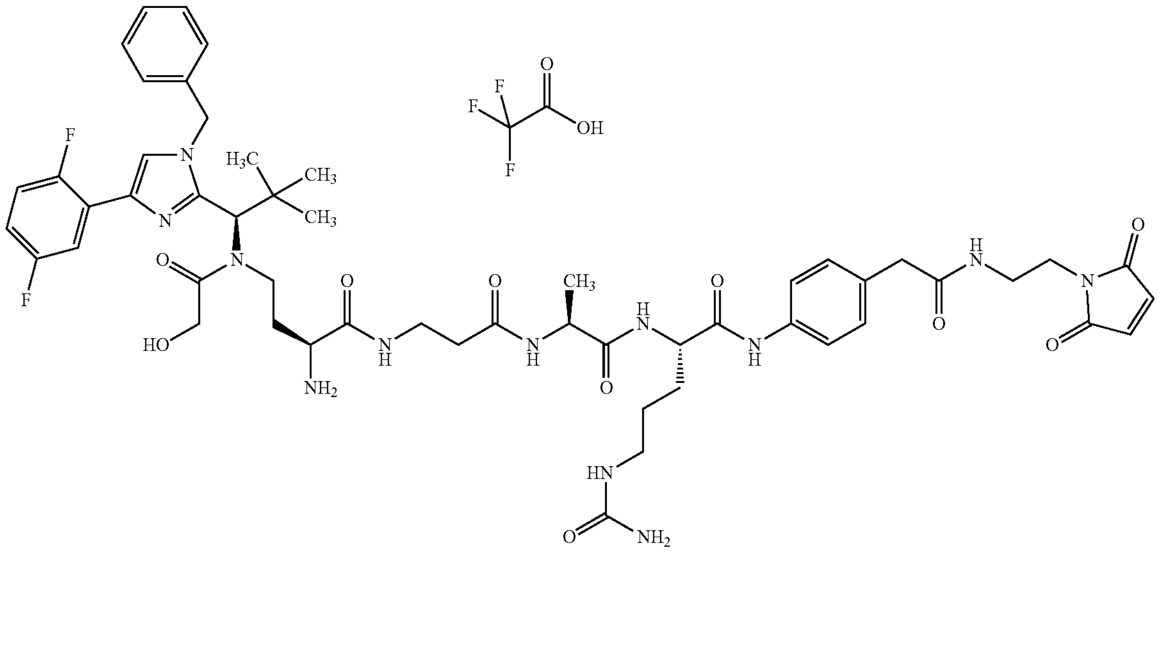 [SMILES: C[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(CC(=O)NCCN2C(=O)C=CC2=O)cc1 ; O=C(O)C(F)(F)F]

The preparation of the title compound was carried out analogously to Intermediate F16:

First, 30 mg (0.046 mmol) of Intermediate $C_3$ were coupled analogously to Intermediate F3 with Intermediate L18 in the presence of HATU (Yield: 25 mg (47% of theory). 27 mg (0.024 mmol) of this intermediate were dissolved in 5 ml of methanol, 1 ml of a 2M lithium hydroxide solution was added and the mixture was stirred at RT for 30 min, resulting in the cleavage of both the methyl ester and the acetyl group. The solvent was then removed under reduced pressure, the residue was taken up in acetonitrile/water and the mixture was adjusted to pH 2 using TFA. The mixture was then concentrated again giving, after purification of the residue by preparative HPLC, 15 mg (58%) of the carboxyl compound.

This intermediate was then taken up in 3 ml of DMF and coupled with 4.4 mg (0.017 mmol) of commercially available trifluoroacetic acid/1-(2-aminoethyl)-1H-pyrrole-2,5-dione (1:1) in the presence of 6.5 mg (0.017 mmol) of HATU and 12 μl of N,N-diisopropylethylamine. Purification by preparative HPLC gave 12 mg (72% of theory) of the protected intermediate. These were taken up in 2 ml of DCM, and 1 ml of TFA was added. After 30 min of stirring at RT, the mixture was concentrated and lyophilized from acetonitrile/water 1:1. Drying of the residue under high vacuum afforded 11 mg (91%) of the title compound.

LC-MS (Method 1): $R_t$=0.83 min; MS (ESIpos): m/z=1069 $(M+H)^+$.

Intermediate F25

Trifluoroacetic Acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-$N^5$-carbamoyl-N-(4-{[(2,5-dioxo-2,5-dihydro-1H-pyrrol-1-yl)acetyl]amino}phenyl)-L-ornithinamide (1:1)

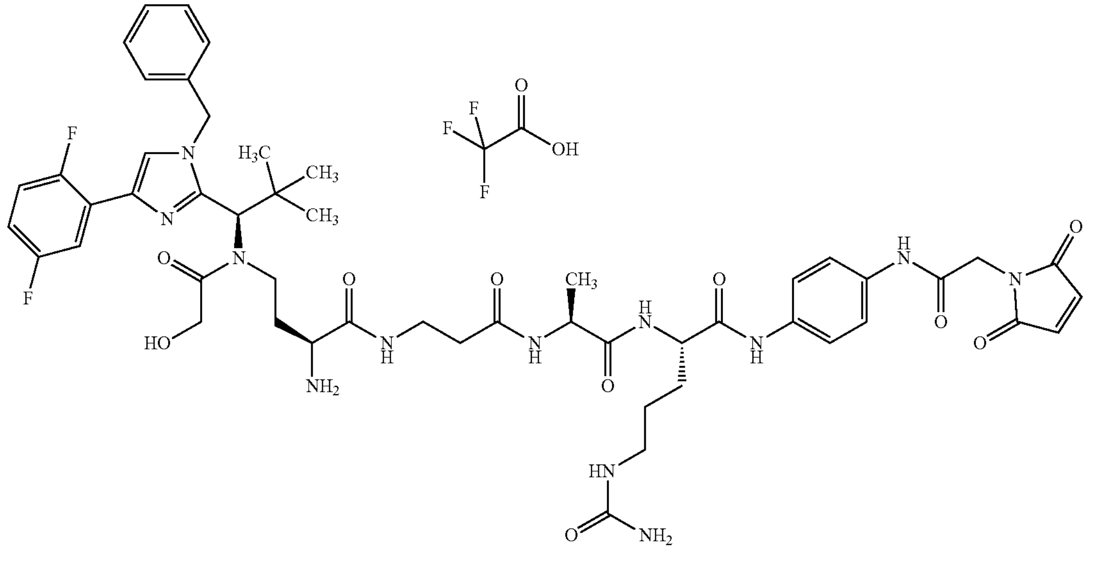 [SMILES: C[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(NC(=O)CN2C(=O)C=CC2=O)cc1 ; O=C(O)C(F)(F)F]

This intermediate was prepared by coupling of 9.6 mg (0.014 mmol) of Intermediate C8 with 10.8 mg (0.015 mmol) of Intermediate L19 in the presence of 6.4 mg (0.017 mmol) of HATU and 72 μl of N,N-diisopropylethylamine and subsequent deblocking with TFA. This gave 5 mg (31% of theory over 2 steps) of the title compound.

HPLC (Method 11): $R_t$=1.8 min;

LC-MS (Method 1): $R_t$=0.85 min; MS (ESIpos): m/z=1041 $(M+H)^+$.

Intermediate F26

Trifluoroacetic Acid/N-{(15S,19R)-15-amino-19-[1-benzyl-4-(2,5-difluorophenyl)-1H-imidazol-2-yl]-18-glycoloyl-20,20-dimethyl-14-oxo-4,7,10-trioxa-13,18-diazahenicosan-1-oyl}-L-valyl-$N^5$-carbamoyl-N-[4-(2,5-dioxo-2,5-dihydro-1H-pyrrol-1-yl)phenyl]-L-ornithinamide (1:1)

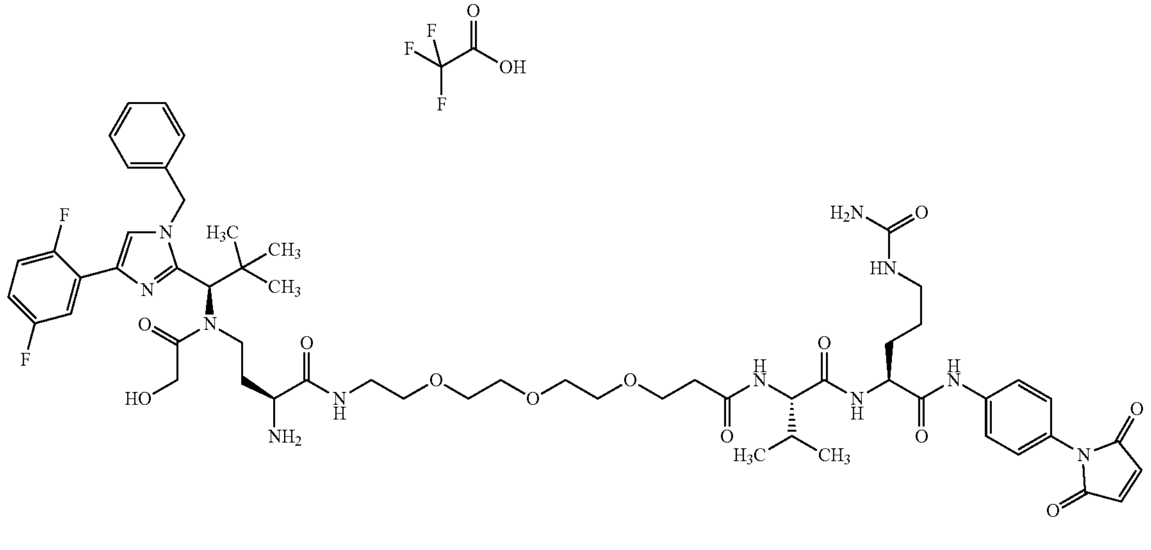 [SMILES: CC(C)[C@H](NC(=O)CCOCCOCCOCCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

This intermediate was prepared by coupling of 16.4 mg (0.02 mmol) of Intermediate C9 with 11.2 mg (0.02 mmol) of Intermediate L20 in the presence of 8 mg (0.04 mmol) of 1-(3-dimethylaminopropyl)-3-ethylcarbodiimide hydrochloride, 6 mg (0.04 mmol) of 1-hydroxy-1H-benzotriazole hydrate and 11 μl (0.06 mmol) of N,N-diisopropylethylamine and subsequent deblocking with TFA. This gave 10 mg (37% of theory over 2 steps) of the title compound.

HPLC (Method 11): $R_t$=2.0 min;

LC-MS (Method 1): $R_t$=0.91 min; MS (ESIpos): m/z=1144 $(M+H)^+$.

Intermediate F27

Trifluoroacetic Acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-N-[4-(2-{[2-(2,5-dioxo-2,5-dihydro-1H-pyrrol-1-yl)ethyl]amino}-2-oxoethyl)phenyl]-L-lysinamide (2:1)

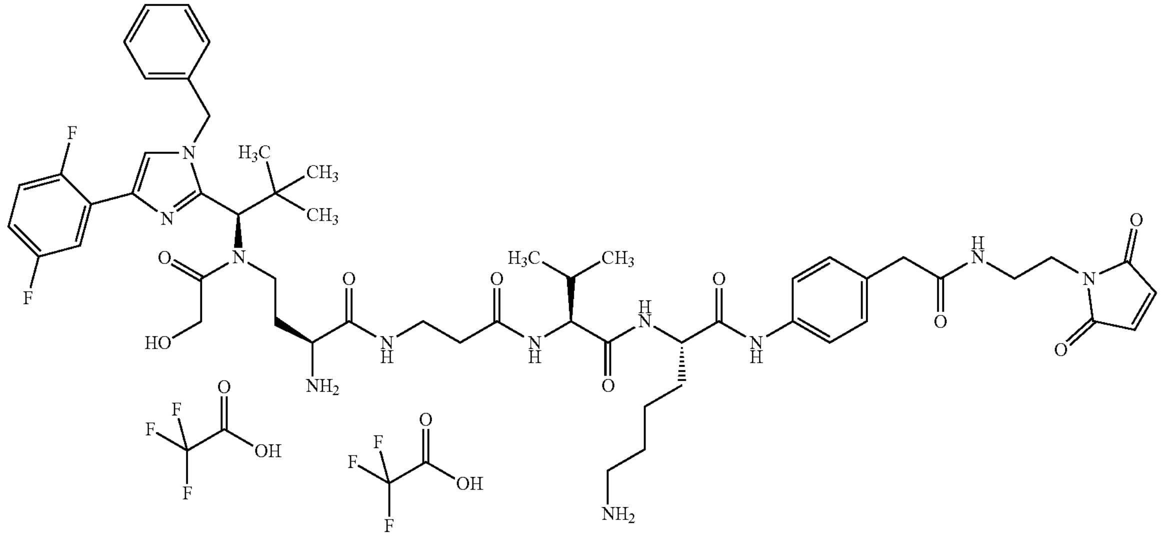 [SMILES: CC(C)[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCCN)C(=O)Nc1ccc(CC(=O)NCCN2C(=O)C=CC2=O)cc1 ; O=C(O)C(F)(F)F ; O=C(O)C(F)(F)F]

This intermediate was prepared over 4 steps:

In the first step, 20 mg (0.028 mmol) of Intermediate C8 were coupled with 16.7 mg (0.031 mmol) of Intermediate L21 in the presence of 11 mg (0.057 mmol) of 1-(3-dimethylaminopropyl)-3-ethylcarbodiimide hydrochloride, 8.7 mg (0.057 mmol) of 1-hydroxy-1H-benzotriazole hydrate and 15 μl (0.085 mmol) of N,N-diisopropylethylamine in 5 ml of DMF. After 4 days of stirring at RT, the reaction was concentrated and the product was purified by preparative HPLC. Yield: 18 mg (54.5% of theory).

18 mg (0.016 mmol) of this intermediate were dissolved in 4 ml of methanol, 194 μl of a 2M lithium hydroxide solution were added and the reaction was stirred at RT overnight. Another 116 μl of lithium hydroxide solution were then added, and the reaction was stirred at RT for a further 4 h. The solvent was then removed under reduced pressure, the residue was taken up in water and the reaction was then adjusted to pH 5 with 5% strength citric acid. The mixture was extracted twice with dichloromethane and the organic phase was dried over sodium sulphate. The organic phase was then filtered and concentrated and the residue was dried under high vacuum. This gave 10.5 mg (58%) of the carboxyl compound.

10.5 mg (0.009 mmol) of this intermediate were then taken up in 4 ml of DMF and coupled with 3 mg (0.012 mmol) of commercially available trifluoroacetic acid/1-(2-aminoethyl)-1H-pyrrole-2,5-dione (1:1) in the presence of 3.5 mg (0.018 mmol) of 1-(3-dimethylaminopropyl)-3-ethylcarbodiimide hydrochloride, 2.8 mg (0.018 mmol) of 1-hydroxy-1H-benzotriazole hydrate and 6 μl of N,N-diisopropylethylamine. After stirring overnight, the same amount of coupling reagents were added again and the reaction was stirred at RT for a further 3 days. The mixture was then concentrated and the product was purified by preparative HPLC. Yield: 6 mg (52% of theory). 6 mg (0.005 mmol) of this intermediate were then deprotected in 3 ml of DCM with 1 ml of trifluoroacetic acid. Lyophilization from acetonitrile/water gave 6 mg (83% of theory) of the title compound.

HPLC (Method 11): $R_t$=1.84 min;

LC-MS (Method 4): $R_t$=0.93 min; MS (ESIpos): m/z=1068 $(M+H)^+$.

Intermediate F28

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-4-({N-[6-(2,5-dioxo-2,5-dihydro-1H-pyrrol-1-yl)hexanoyl]-L-valyl-$N^5$-carbamoyl-L-ornithyl}amino)-L-phenylalanine/trifluoroacetic Acid (1:1)

This intermediate was prepared over 5 steps:

In the first step, 40 mg (0.058 mmol) of Intermediate C8 were coupled with 46 mg (0.058 mmol) of Intermediate L22 in the presence of 44.3 mg (0.117 mmol) of HATU and 30 μl of N,N-diisopropylethylamine. After 1 h of stirring at RT, the reaction was concentrated and the product was purified by preparative HPLC. Yield: 53 mg (62.5% of theory).

In the next step, the Fmoc group was removed with 0.6 ml of piperidine in 3 ml of DMF. After 1 h of stirring at RT, the reaction was concentrated and the product was purified by preparative HPLC.

Yield: 42 mg (82% of theory).

To cleave the methyl ester, 42 mg (0.033 mmol) of this intermediate were dissolved in 2 ml of THF and 1 ml of water, 330 μl of a 2M lithium hydroxide solution were added and the reaction was stirred at RT for 1 h. The reaction was then neutralized with TFA and concentrated and the residue was purified by preparative HPLC. Drying under high vacuum gave 32 mg (78%) of the carboxyl compound.

32 mg (0.026 mmol) of this intermediate were then coupled in 2.3 ml of DMF with 14.6 mg (0.047 mmol) of commercially available 1-{6-[(2,5-dioxopyrrolidin-1-yl)oxy]-6-oxohexyl}-1H-pyrrole-2,5-dione in the presence of 18 μl of N,N-diisopropylethylamine. After a 4-hour treatment in an ultrasonic bath, the reaction was concentrated and the product was purified by preparative HPLC Yield: 20.4 mg (60% of theory).

In the last step, 20.4 mg (0.016 mmol) of this intermediate were deprotected in DCM with trifluoroacetic acid. Lyophilization from acetonitrile/water gave 20 mg (85% of theory) of the title compound.

HPLC (Method 11): $R_t$=1.9 min;

LC-MS (Method 5): $R_t$=2.84 min; MS (ESIpos): m/z=1197 $(M+H)^+$.

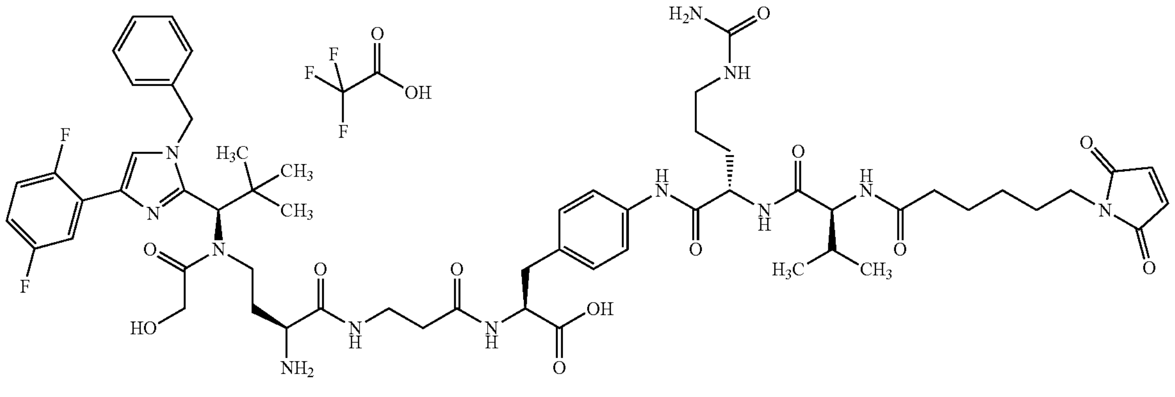 [SMILES: CC(C)[C@H](NC(=O)CCCCCN1C(=O)C=CC1=O)C(=O)N[C@@H](CCCNC(N)=O)C(=O)Nc1ccc(C[C@H](NC(=O)CCNC(=O)[C@@H](N)CCN(C(=O)CO)[C@@H](c2nc(-c3cc(F)ccc3F)cn2Cc2ccccc2)C(C)(C)C)C(=O)O)cc1 ; O=C(O)C(F)(F)F]

Intermediate F29

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-4-({N-[6-(2,5-dioxo-2,5-dihydro-1H-pyrrol-1-yl)hexanoyl]-L-valyl-L-alanyl}amino)-L-phenylalanine/trifluoroacetic Acid (1:1)

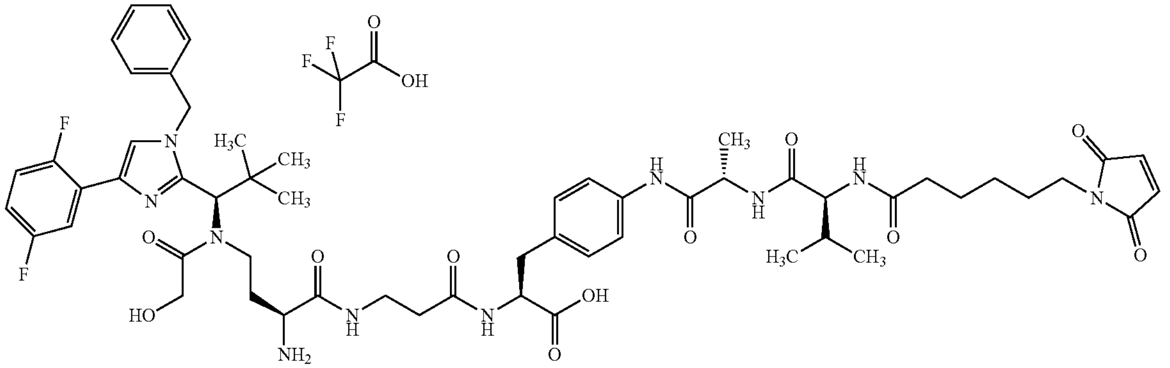 [SMILES: CC(C)[C@H](NC(=O)CCCCCN1C(=O)C=CC1=O)C(=O)N[C@@H](C)C(=O)Nc1ccc(C[C@H](NC(=O)CCNC(=O)[C@@H](N)CCN(C(=O)CO)[C@@H](c2nc(-c3cc(F)ccc3F)cn2Cc2ccccc2)C(C)(C)C)C(=O)O)cc1 ; O=C(O)C(F)(F)F]

The preparation of the title compound was carried out analogously to Intermediate F28.

HPLC (Method 11): $R_t$=2.0 min;

LC-MS (Method 1): $R_t$=0.92 min; MS (ESIpos): m/z=1111 $(M+H)^+$.

Intermediate F30

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-{2-[(3-{[2-(2,5-dioxo-2,5-dihydro-1H-pyrrol-1-yl)ethyl]amino}-3-oxopropyl)sulphinyl]ethyl}butanamide (1:1)

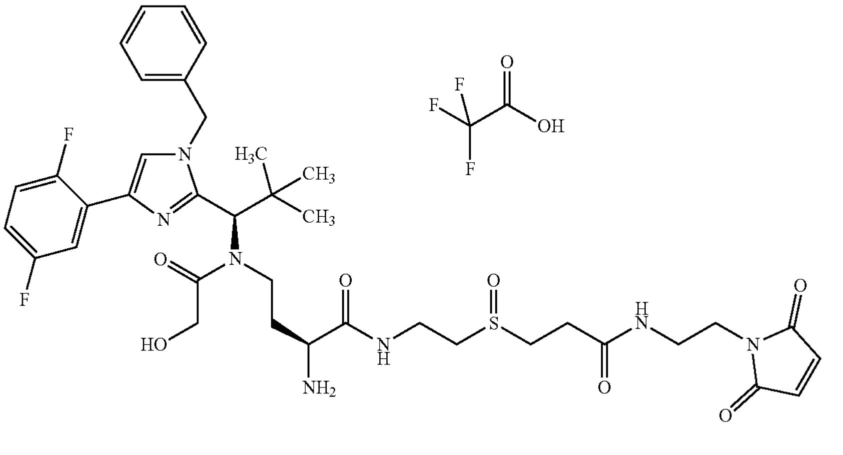 [SMILES: CC(C)(C)[C@H](c1nc(-c2cc(F)ccc2F)cn1Cc1ccccc1)N(CC[C@H](N)C(=O)NCCS(=O)CCC(=O)NCCN1C(=O)C=CC1=O)C(=O)CO ; O=C(O)C(F)(F)F]

This intermediate was prepared over 4 steps:

In the first step, 37.5 mg (0.055 mmol) of Intermediate C3 were coupled with 15 mg (0.066 mmol) of commercially available methyl 3-[(2-aminoethyl)sulphanyl]propanoate hydrochloride (1:1) in DMF in the presence of 25 mg (0.066 mmol) of HATU and 29 μl of N,N-diisopropylethylamine. After 15 min of stirring at RT, the coupling reagents were added again. The reaction was stirred at RT for another 15 min and then concentrated and the product was purified by preparative HPLC.

Yield: 21 mg (48% of theory).

LC-MS (Method 1): $R_t$=1.41 min; MS (ESIpos): m/z=802 $(M+H)^+$.

To cleave the methyl ester, 21 mg (0.026 mmol) of this intermediate were dissolved in 5 ml of methanol, 655 μl of a 2M lithium hydroxide solution were added and the reaction was stirred at RT overnight. During this time, partial oxidation at the sulphur occurred. The reaction was concentrated and the residue was taken up in water and then adjusted to pH 3 with acetic acid. The mixture was extracted twice with 50 ml of ethyl acetate and the organic phase was then dried over magnesium sulphate, filtered and concentrated. The mixture obtained after drying of the residue under high vacuum was used without further purification in the next step for coupling with 8.4 mg (0.033 mmol) of commercially available trifluoroacetic acid/1-(2-aminoethyl)-1H-pyrrole-2,5-dione (1:1) in the presence of 11.6 mg (0.031 mmol) of HATU and 22 μl of N,N-diisopropylethylamine. The reaction was stirred at RT for 5 min and then concentrated. The residue was taken up in ethyl acetate and the solution was extracted with 5% strength citric acid and then with water. The organic phase was then dried over magnesium sulphate, filtered and concentrated. The mixture obtained after drying of the residue under high vacuum was used without further purification in the next step. 22 mg of this crude material were then dissolved in 2 ml of DCM and deprotected with 0.5 ml of trifluoroacetic acid. After 10 min of stirring at RT, the reaction was concentrated and the residue was purified by preparative HPLC. Drying under high vacuum gave 2.1 mg of the title compound.

HPLC (Method 11): $R_t$=1.8 min;

LC-MS (Method 1): $R_t$=0.83 min; MS (ESIpos): m/z=784 $(M+H)^+$.

Intermediate F31

Trifluoroacetic Acid/N-[6-(2,5-dioxo-2,5-dihydro-1H-pyrrol-1-yl)hexanoyl]-L-valyl-N-(3-{[2-{(1R)-1-[(3-aminopropyl)(glycoloyl)amino]-2,2-dimethylpropyl}-4-(2,5-difluorophenyl)-1H-imidazol-1-yl]methyl}phenyl)-L-alaninamide (1:1)

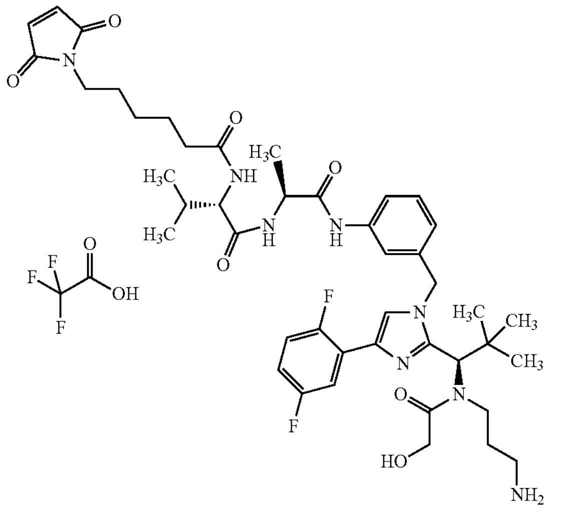 [SMILES: CC(C)[C@H](NC(=O)CCCCCN1C(=O)C=CC1=O)C(=O)N[C@@H](C)C(=O)Nc1cccc(Cn2cc(-c3cc(F)ccc3F)nc2[C@H](N(CCCN)C(=O)CO)C(C)(C)C)c1 ; O=C(O)C(F)(F)F]

This intermediate was synthesized from Intermediate C10 over 6 steps using classical methods of peptide chemistry.

In the first step, 42 mg (0.066 mmol) of Intermediate C10 were coupled with 20.7 mg (0.066 mmol) of N-[(9H-fluoren-9-ylmethoxy)carbonyl]-L-alanine in 5 ml of DMF in the presence of 100 mg (0.266 mmol) of HATU and 46 μl of N,N-diisopropylethylamine. The reaction was stirred at RT overnight and the product was purified by preparative HPLC. This gave 16 mg (27% of theory) of the N-acylated compound and 9 mg (12% of theory) of the N-, O-bisacylated compound.

The deprotection of the N-acylated compound was carried out in DMF with piperidine. The bisacylated compound was treated in ethanol both with piperidine and with an aqueous solution of methylamine. In both cases, tert-butyl (3-{[(1R)-1-{1-[3-(L-alanylamino)benzyl]-4-(2,5-difluorophenyl)-1H-imidazol-2-yl}-2,2-dimethylpropyl](glycoloyl)amino}propyl)carbamate was formed, and purification by preparative HPLC gave 13 mg in a purity of 95%.

LC-MS (Method 1): $R_t$=0.95 min; MS (ESIpos): m/z=657 $(M+H)^+$.

13 mg (0.019 mmol) of this intermediate in 2 ml of DMF were coupled with 9.1 mg (0.021 mmol) of 2,5-dioxopyrrolidin-1-yl N-[(9H-fluoren-9-ylmethoxy)carbonyl]-L-valinate in the presence of 7 μl of N,N-diisopropylethylamine. After stirring at RT for 20 h, the mixture was concentrated and the residue was purified by preparative HPLC. Lyophilization from 1,4-dioxane/water gave 10 mg (54% of theory).

The subsequent removal of the Fmoc protective group with piperidine in DMF gave 9 mg (quant.) of the partially deprotected intermediate. 9 mg (0.01 mmol) of this intermediate were then coupled in 2 ml of DMF with 3.2 mg (0.01 mmol) of commercially available 1-{6-[(2,5-dioxopyrrolidin-1-yl)oxy]-6-oxohexyl}-1H-pyrrole-2,5-dione in the presence of 5 μl of N,N-diisopropylethylamine. After stirring at RT overnight, the reaction was concentrated and the product was purified by preparative HPLC. Lyophilization from acetonitrile/water and a few drops of 1,4-dioxane afforded 3 mg (32% of theory) which were deprotected in the last step in 2 ml of DCM with 0.5 ml of trifluoroacetic acid. Lyophilization from acetonitrile/water gave 3.8 mg (quant.) of the title compound.

HPLC (Method 11): $R_t$=1.9 min;

LC-MS (Method 1): $R_t$=0.89 min; MS (ESIpos): m/z=849 $(M+H)^+$.

Intermediate F32

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-(3-{[2-(2,5-dioxo-2,5-dihydro-1H-pyrrol-1-yl)ethyl]amino}-3-oxopropyl)butanamide (1:1)

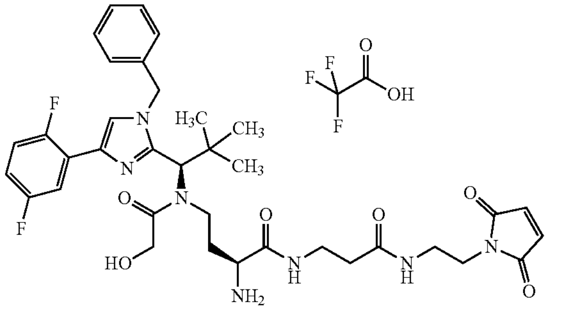 [SMILES: CC(C)(C)[C@H](c1nc(-c2cc(F)ccc2F)cn1Cc1ccccc1)N(CC[C@H](N)C(=O)NCCC(=O)NCCN1C(=O)C=CC1=O)C(=O)CO ; O=C(O)C(F)(F)F]

This intermediate was prepared by coupling of 15 mg (0,041 mmol) of Intermediate C5 with 16.8 mg (0.027 mmol) of Intermediate L23 in the presence of 10.5 mg (0.055 mmol) of 1-(3-dimethylaminopropyl)-3-ethylcarbodiimide hydrochloride, 8.4 mg (0,055 mmol) of 1-hydroxy-1H-benzotriazole hydrate and 14 μl (0.08 mmol) of N,N-diisopropylethylamine and subsequent deblocking with TFA. This gave 3.4 mg (15% of theory over 2 steps) of the title compound.

HPLC (Method 11): $R_t$=1.9 min;

LC-MS (Method 1): $R_t$=0.85 min; MS (ESIpos): m/z=708 $(M+H)^+$.

Intermediate F33

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-{2-[(bromoacetyl)amino]ethyl}butanamide (1:1)

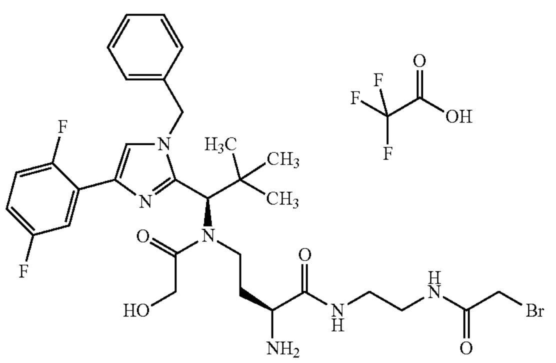 [SMILES: CC(C)(C)[C@H](c1nc(-c2cc(F)ccc2F)cn1Cc1ccccc1)N(CC[C@H](N)C(=O)NCCNC(=O)CBr)C(=O)CO ; O=C(O)C(F)(F)F]

The synthesis of this intermediate began in the first step with the coupling of 50 mg (0.075 mmol) of Intermediate C3 with 26.2 mg (0.082 mmol) of 9H-fluoren-9-ylmethyl (2-aminoethyl)carbamate hydrochloride (1:1) in the presence of 28.7 mg (0.15 mmol) of 1-(3-dimethylaminopropyl)-3-ethyl carbodiimide hydrochloride, 22.9 mg (0.15 mmol) of 1-hydroxy-1H-benzotriazole hydrate and 39 μl of N,N-diisopropylethylamine. After 18 h of stirring at RT, the mixture was concentrated and the residue was purified by preparative HPLC. This gave 45 mg (65% of theory) of this intermediate.

LC-MS (Method 1): $R_t$=1.51 min; MS (ESIpos): m/z=921 $(M+H)^+$.

solution were added, and after a further 20 h of stirring the mixture was finally concentrated. The residue was taken up in DCM and washed with water. The organic phase was concentrated and the residue was purified by preparative HPLC. Concentration of the appropriate fractions and drying of the residue under high vacuum gave 32 mg (99% of theory) of tert-butyl {(2S)-1-[(2-aminoethyl)amino]-4-[{(1R)-1-[1-benzyl-4-(2,5-difluorophenyl)-1H-imidazol-2-yl]-2,2-dimethylpropyl}(glycoloyl)amino]-1-oxobutan-2-yl}carbamate.

LC-MS (Method 1): $R_t$=0.95 min; MS (ESIpos): m/z=657 $(M+H)^+$.

8.3 mg (0.013 mmol) of this intermediate were dissolved in 4 ml of dichloromethane, and 3.3 mg (0.013 mmol) of bromoacetic anhydride and 2 μl of N,N-diisopropylethylamine were added. After 1 h of stirring at RT, the mixture was concentrated and the residue was purified by preparative HPLC. The appropriate fractions were concentrated and the residue was lyophilized from acetonitrile/water. The residue was taken up in 1 ml of dichloromethane and deprotected with 0.5 ml of trifluoroacetic acid. Concentration and lyophilization from acetonitrile/water gave 1.1 mg (9% of theory over 2 steps) of the title compound.

HPLC (Method 11): $R_t$=1.9 min;

LC-MS (Method 1): $R_t$=0.88 min; MS (ESIpos): m/z=677/679 $(M+H)^+$.

Intermediate F34

Trifluoroacetic Acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-L-alanyl-$N^5$-carbamoyl-N-[4-(2,5-dioxo-2,5-dihydro-1H-pyrrol-1-yl)phenyl]-L-ornithinamide (1:1)

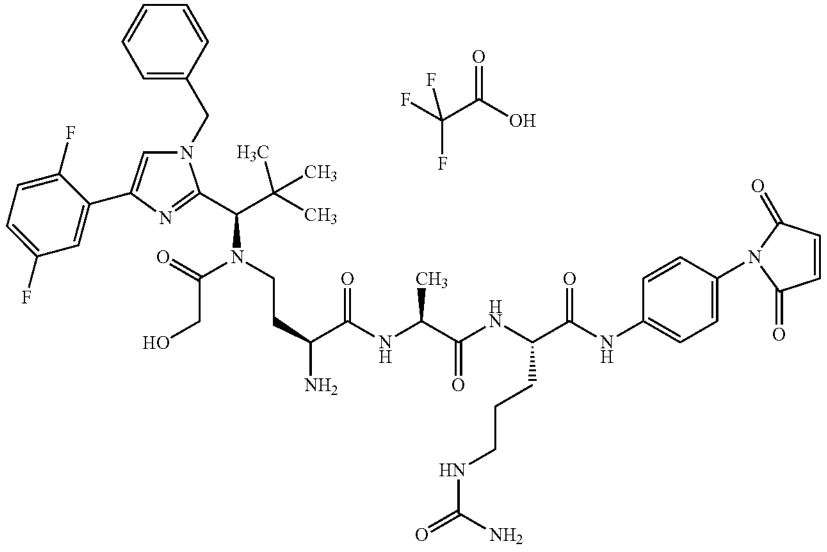 [SMILES: C[C@H](NC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

45 mg (0.049 mmol) of this intermediate were taken up in 10 ml of ethanol, and 176 μl of a 40% strength solution of methanamine in water were added. The reaction was stirred at 50° C., with the same amount of methanamine solution being added after 6 h and after 9 h. After a further 14 h of stirring at 50° C., another 700 μl of the methanamine This intermediate was prepared by coupling of 14 mg (0.022 mmol) of Intermediate C5 with 12.7 mg (0.024 mmol) of Intermediate L8 in the presence of 9.9 mg (0.026 mmol) of HATU and 19 μl of N,N-diisopropylethylamine. The reaction was stirred at RT for 30 min and the product was purified by preparative HPLC and then lyophilized from acetonitrile/water.

The intermediate obtained was taken up in 3 ml of dichloromethane and deblocked with 1 ml of trifluoroacetic acid. After 30 min of stirring at RT, the reaction was concentrated and the residue was lyophilized from acetonitrile/water. This gave 8.2 mg (36% of theory over 2 steps) of the title compound.

HPLC (Method 11): $R_t$=1.8 min;

LC-MS (Method 1): $R_t$=0.87 min; MS (ESIpos): m/z=913 $(M+H)^+$.

Intermediate F35

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide

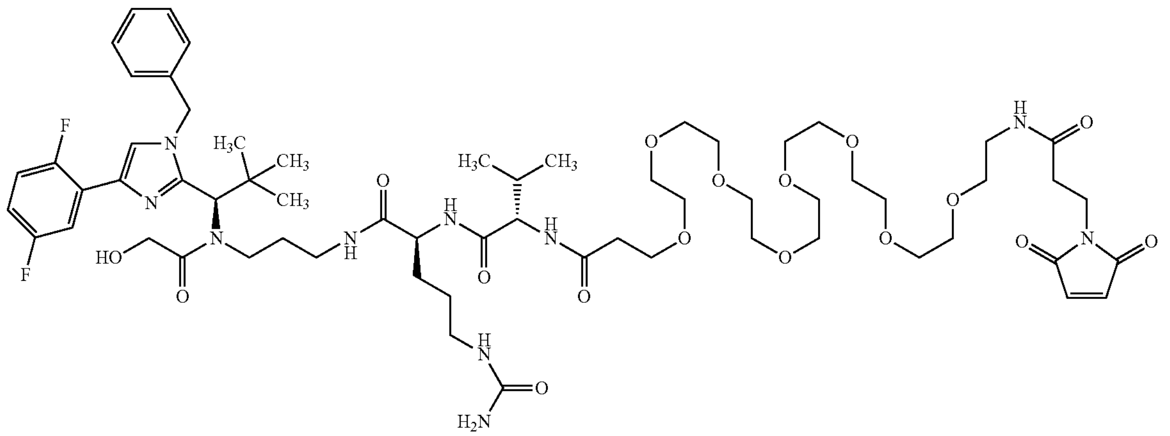 [SMILES: CC(C)[C@H](NC(=O)CCOCCOCCOCCOCCOCCOCCOCCOCCNC(=O)CCN1C(=O)C=CC1=O)C(=O)N[C@@H](CCCNC(N)=O)C(=O)NCCCN(C(=O)CO)[C@@H](c1nc(-c2cc(F)ccc2F)cn1Cc1ccccc1)C(C)(C)C]

Under argon and at 0° C., 57.3 mg (0.07 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N5-carbamoyl-L-ornithine (Intermediate L38), 9.2 mg (0.07 mmol) of HOAt and 32 mg (0.08 mmol) of HATU were added to 31.8 mg (0.07 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) in 4.0 ml of DMF. 23.5 µl (0.14 mmol) of N,N-diisopropylethylamine were then added, and the reaction was stirred at RT overnight. 7.7 µl of HOAc were added, and the reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 33.4 mg (38% of theory) of the title compound.

LC-MS (Method 1): $R_t$=1.12 min; MS (ESIpos): m/z=651 [M+2H]2+.

Intermediate F36

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide

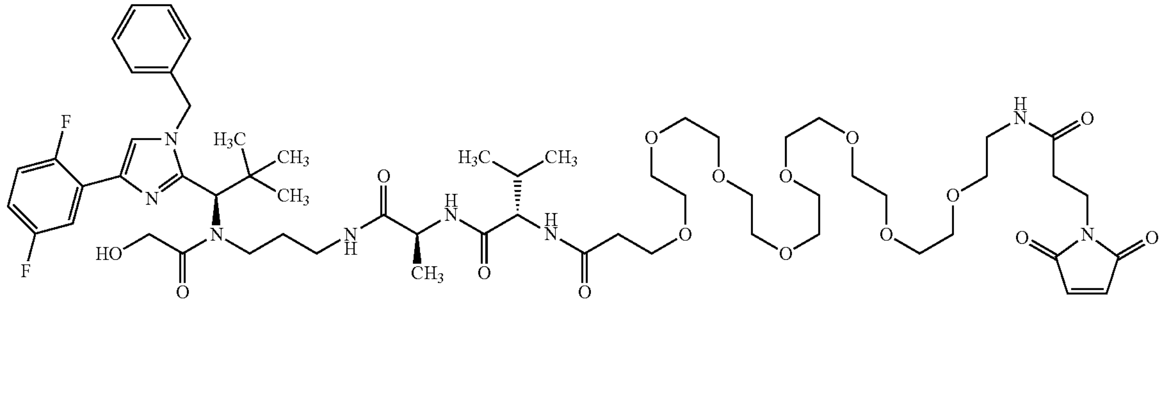 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)NCCCN(C(=O)CO)[C@@H](c1nc(-c2cc(F)ccc2F)cn1Cc1ccccc1)C(C)(C)C]

The synthesis of the title compound was carried out analogously to the preparation of Intermediate F35.

15.4 mg (0.03 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40). 25.0 mg (0.03 mmol) of N-[31-(2,5-doxo-2,5-dihydro-1H-pyrrol-1-yl)-29-oxo-4,7,10,13,16,19,22,25-octaoxa-28-aza-hentriacontan-1-oyl]-L-valyl-L-alanine (Intermediate L25). This gave 10.7 mg (27% of theory) of the title compound.

LC-MS (Method 1): $R_t$=1.13 min; MS (ESIpos): m/z=1215 $[M+H]^+$.

Intermediate F37

Trifluoroacetic Acid/N-(4-{[{(1R)-1-[1-benzyl-4-(2,5-difluorophenyl)-1H-imidazol-2-yl]-2,2-dimethyl-propyl}(glycoloyl)amino]methyl}pyrrolidin-3-yl)-31-(2,5-dioxo-2,5-dihydro-1H-pyrrol-1-yl)-29-oxo-4,7,10,13,16,19,22,25-octaoxa-28-azahentriacontan-1-amide (1:1)

Mixture of Diastereomers.

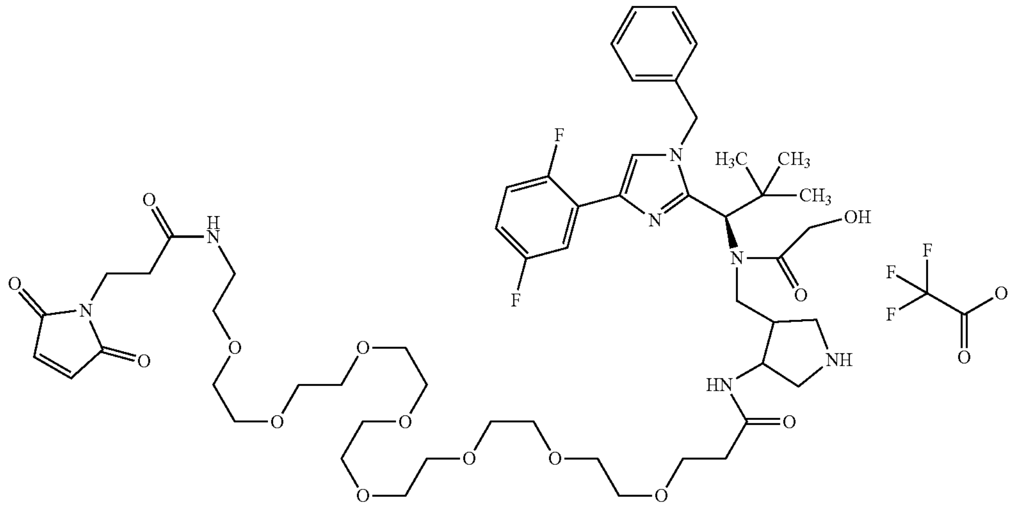 [SMILES: CC(C)(C)[C@H](c1nc(-c2cc(F)ccc2F)cn1Cc1ccccc1)N(CC1CNCC1NC(=O)CCOCCOCCOCCOCCOCCOCCOCCOCCNC(=O)CCN1C(=O)C=CC1=O)C(=O)CO ; O=C(O)C(F)(F)F]

The compound tert-butyl 3-{[{(1R)-1-[1-benzyl-4-(2,5-difluorophenyl)-1H-imidazol-2-yl]-2,2-dimethylpropyl}(glycoloyl)amino]methyl}-4-{[31-(2,5-dioxo-2,5-dihydro-1H-pyrrol-1-yl)-29-oxo-4,7,10,13,16,19,22,25-octaoxa-28-azahentriacontan-1-oyl]amino}pyrrolidine-1-carboxylate was prepared analogously to the synthesis of Intermediate C21.

8.0 (0.01 mmol) and 13.0 mg (0.02 mmol), respectively, of tert-butyl 3-amino-4-{[{(1R)-1-[1-benzyl-4-(2,5-difluorophenyl)-1H-imidazol-2-yl]-2,2-dimethylpropyl}(glycoloyl)amino]methyl}pyrrolidine-1-carboxylate (Intermediate C23).

9.0 mg (0.01 mmol) and 14.7 mg (0.02 mmol), respectively, of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide.

Yield (both reactions combined):

10.5 mg (42%) of diastereomer 1

11.6 mg (46%) of diastereomer 2

The title compound was prepared analogously to the synthesis of Intermediate F38.

10.5 mg (0.01 mmol) of tert-butyl 3-{[{(1R)-1-[1-benzyl-4-(2,5-difluorophenyl)-1H-imidazol-2-yl]-2,2-dimethylpropyl}(glycoloyl)amino]methyl}-4-{[31-(2,5-dioxo-2,5-dihydro-1H-pyrrol-1-yl)-29-oxo-4,7,10,13,16,19,22,25-octaoxa-28-azahentriacontan-1-oyl]amino}pyrrolidine-1-carboxylate (Diastereomer 1)

60.6 mg (0.54 mmol) of TFA.

This gave 7.4 mg (70% of theory) of the title compound.

LC-MS (Method 1): $R_t$=1.09 min; MS (ESIpos): m/z=1086 $[M+H]^+$.

Intermediate F38

Trifluoroacetic Acid/N-(3-aminopropyl)-N-{(1R)-1-[1-benzyl-4-(2,5-difluorophenyl)-1H-imidazol-2-yl]-2,2-dimethylpropyl}-37-(2,5-dioxo-2,5-dihydro-1H-pyrrol-1-yl)-7,35-dioxo-10,13,16,19,22,25,28,31-octaoxa-3-thia-6,34-diazaheptatriacontan-1-amide (1:1)

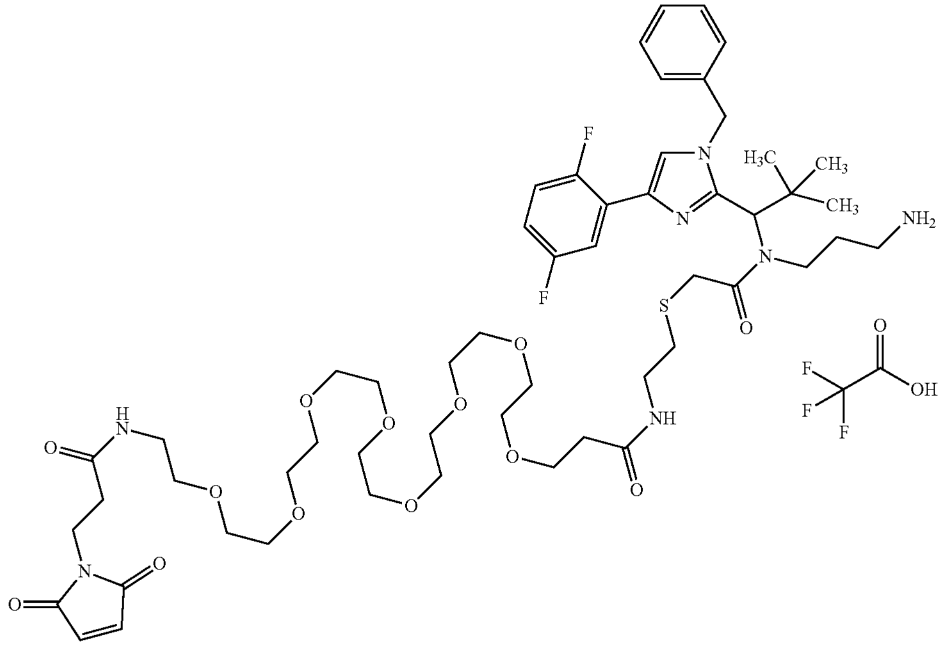 [SMILES: CC(C)(C)C(c1nc(-c2cc(F)ccc2F)cn1Cc1ccccc1)N(CCCN)C(=O)CSCCNC(=O)CCOCCOCCOCCOCCOCCOCCOCCOCCNC(=O)CCN1C(=O)C=CC1=O ; O=C(O)C(F)(F)F]

24.8 mg (0.02 mmol) of tert-butyl [38-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-3,31,37-trioxo-7,10,13,16,19,22,25,28-octaoxa-35-thia-4,32,38-triazahentetracontan-41-yl]carbamate (Intermediate C21) were initially charged in 1.0 ml of dichloromethane, and 85.8 mg (0.75 mmol) of TFA were added. The mixture was stirred at RT for 16 h. The solvent was evaporated under reduced pressure and the residue was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 23.0 mg (95% of theory) of the title compound.

LC-MS (Method 1): $R_t$=0.96 min; MS (ESIpos): m/z=1104 $[M+H]^+$.

Intermediate F39

N-[19-(2,5-Dioxo-2,5-dihydro-1H-pyrrol-1-yl)-7-oxo-4,7,10,13-tetraoxa-16-azanonadecan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide

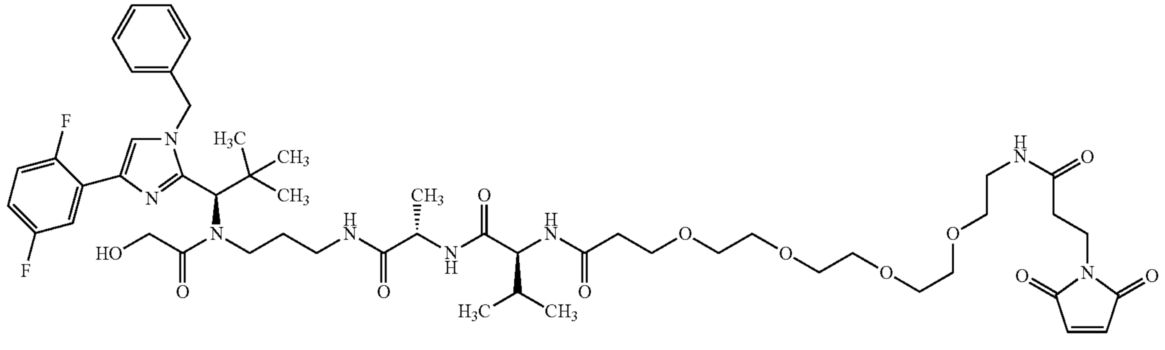 [SMILES: CC(C)[C@H](NC(=O)CCOCCOCCOCCOCCNC(=O)CCN1C(=O)C=CC1=O)C(=O)N[C@@H](C)C(=O)NCCCN(C(=O)CO)[C@@H](c1nc(-c2cc(F)ccc2F)cn1Cc1ccccc1)C(C)(C)C]

The title compound was prepared analogously to the synthesis of Intermediate F35.

56.1 mg (0.10 mmol) of N-[19-(2,5-dioxo-2,5-dihydro-1H-pyrrol-1-yl)-17-oxo-4,7,10,13-tetraoxa-16-azanonadecan-1-oyl]-L-valyl-L-alanine (Intermediate L44).

45.0 mg (0.10 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40).

This gave 20.9 mg (21% of theory) of the title compound.

LC-MS (Method 1): $R_t$=1.16 min; MS (ESIpos): m/z=1040 $[M+H]^+$.

Intermediate F40

Trifluoroacetic Acid/N-[(4-{[{(1R)-1-[1-benzyl-4-(2,5-difluorophenyl)-1H-imidazol-2-yl]-2,2-dimethylpropyl}(glycoloyl)amino]methyl}pyrrolidin-3-yl)methyl]-31-(2,5-dioxo-2,5-dihydro-1H-pyrrol-1-yl)-29-oxo-4,7,10,13,16,19,22,25-octaoxa-28-azahentriacontan-1-amide (1:1)

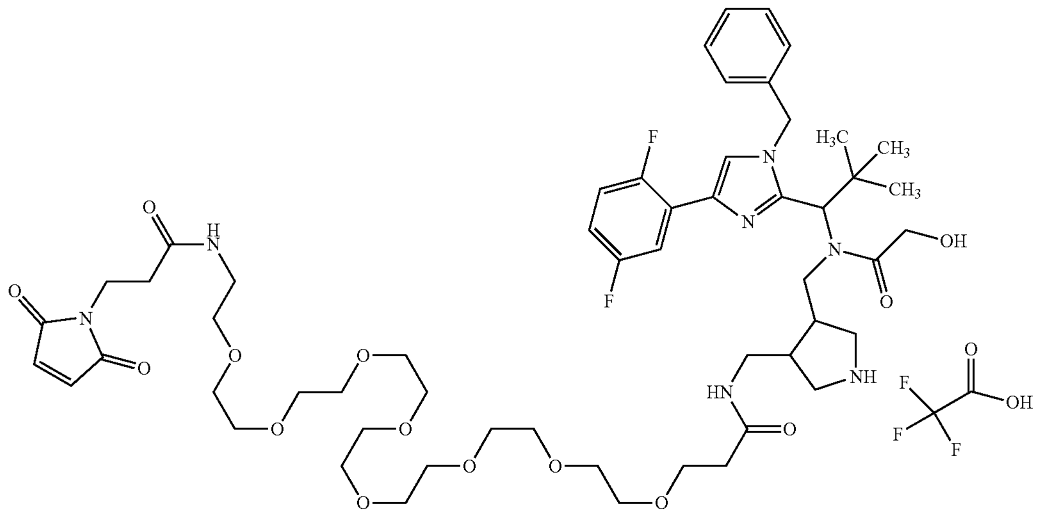

tert-Butyl 3-{[{(1R)-1-[1-benzyl-4-(2,5-difluorophenyl)-1H-imidazol-2-yl]-2,2-dimethylpropyl}(glycoloyl)amino]methyl}-4-[33-(2,5-dioxo-2,5-dihydro-1H-pyrrol-1-yl)-3,31-dioxo-6,9,12,15,18,21,24,27-octaoxa-2,30-diazatritriacont-1-yl]pyrrolidine-1-carboxylate was prepared analogously to the synthesis of Intermediate C21.

25.0 mg (0.04 mmol) of trifluoroacetic acid/tert-butyl 3-(aminomethyl)-4-{[{(1R)-1-[1-benzyl-4-(2,5-difluorophenyl)-1H-imidazol-2-yl]-2,2-dimethylpropyl}(glycoloyl)amino]methyl}pyrrolidine-1-carboxylate (1:1) (Intermediate C24).

27.6 mg (0.04 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide.

Yield: 20.6 mg (39% of theory)

LC-MS (Method 1): $R_t$=1.23 min; MS (ESIpos): m/z=1200 $[M+H]^+$.

The title compound was prepared analogously to the synthesis of Intermediate F37.

26.1 mg (0.02 mmol) of tert-butyl 3-{[{(1R)-1-[1-benzyl-4-(2,5-difluorophenyl)-1H-imidazol-2-yl]-2,2-dimethylpropyl}(glycoloyl)amino]methyl}-4-[33-(2,5-dioxo-2,5-dihydro-1H-pyrrol-1-yl)-3,31-dioxo-6,9,12,15,18,21,24,27-octaoxa-2,30-diazatritriacont-1-yl]pyrrolidine-1-carboxylate. 90.6 mg (0.80 mmol) of TFA.

This gave 22.9 mg (95% of theory) of the title compound.

LC-MS (Method 1): $R_t$=0.91 and 0.92 min; MS (ESIpos): m/z=1100 $[M+H]^+$.

Intermediate F41

Trifluoroacetic Acid/N-(3-aminopropyl)-N-{(1R)-1-[1-benzyl-4-(2,5-difluorophenyl)-1H-imidazol-2-yl]-2,2-dimethylpropyl}-37-(2,5-dioxo-2,5-dihydro-1H-pyrrol-1-yl)-7,35-dioxo-10,13,16,19,22,25,28,31-octaoxa-3-thia-6,34-diazaheptatriacontan-1-amide 3-oxide (1:1)

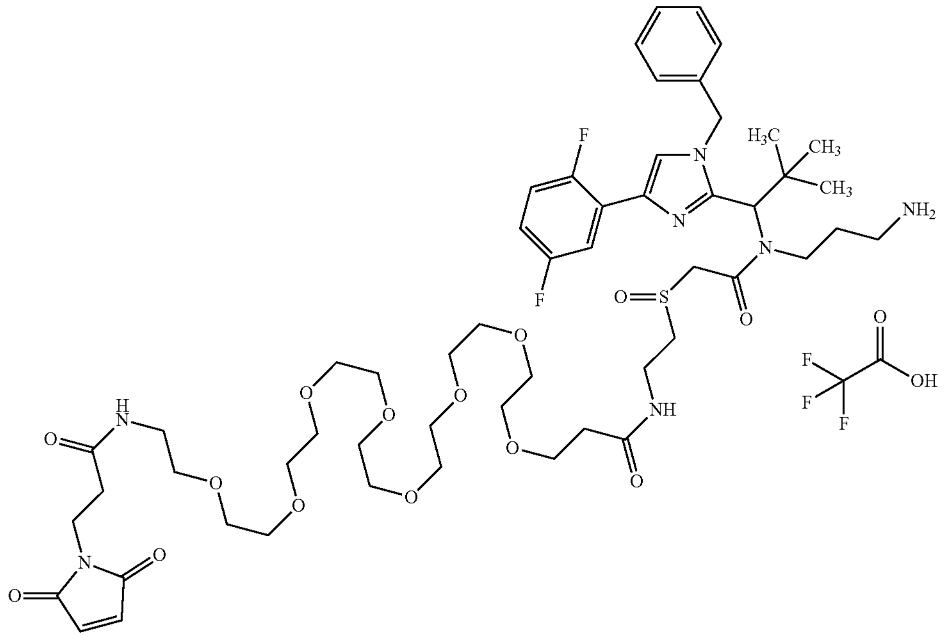 [SMILES: CC(C)(C)C(c1nc(-c2cc(F)ccc2F)cn1Cc1ccccc1)N(CCCN)C(=O)CS(=O)CCNC(=O)CCOCCOCCOCCOCCOCCOCCOCCOCCNC(=O)CCN1C(=O)C=CC1=O ; O=C(O)C(F)(F)F]

The title compound was prepared analogously to Intermediate F38 from 15.5 mg (0.01 mmol) of Intermediate C22. This gave 4.0 mg (27% of theory) of the title compound.

LC-MS (Method 1): $R_t$=0.90 min; MS (ESIpos): m/z=1120 $[M+H]^+$.

Intermediate F42

Trifluoroacetic Acid/4-{[{(1R)-1-[1-benzyl-4-(2,5-difluorophenyl)-1H-imidazol-2-yl]-2,2-dimethylpropyl}(glycoloyl)amino]methyl}-N-[2-(2,5-dioxo-2,5-dihydro-1H-pyrrol-1-yl)ethyl]pyrrolidine-3-carboxamide (1:1)

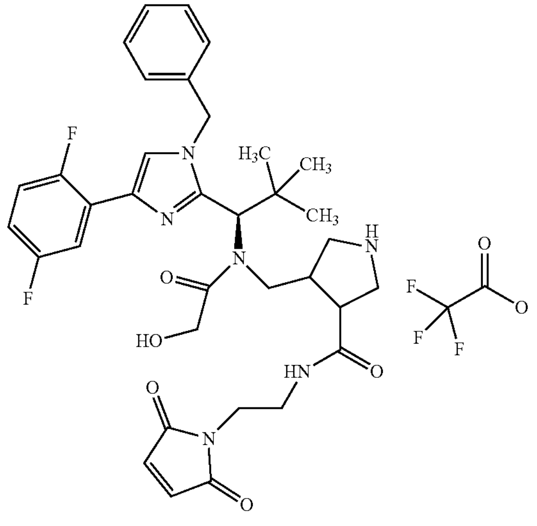

40.5 mg (0.06 mmol) of 4-{[{(1R)-1-[1-benzyl-4-(2,5-difluorophenyl)-1H-imidazol-2-yl]-2,2-dimethylpropyl}(glycoloyl)amino]methyl}-1-(tert-butoxycarbonyl)pyrrolidine-3-carboxylic acid (Intermediate C25) and 14.5 mg (0.08 mmol) of 1-(2-aminoethyl)-1H-pyrrole-2,5-dione hydrochloride (1:1) were initially charged in 1.0 ml of acetonitrile, and 64.4 mg (0.51 mmol) of N,N-diisopropylethylamine and 50.0 mg (0.08 mmol) of T3P were added and the mixture was stirred at RT for 16 h. The same amount of 1-(2-aminoethyl)-1H-pyrrole-2,5-dione hydrochloride (1:1), N,N-diisopropylethylamine and T3P were added again, and the mixture was stirred at RT for a further 4 h. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 7.2 mg (15% of theory) of the compound tert-butyl 3-{[{(1R)-1-[1-benzyl-4-(2,5-difluorophenyl)-1H-imidazol-2-yl]-2,2-dimethylpropyl}(glycoloyl)amino]methyl}-4-{[2-(2,5-dioxo-2,5-dihydro-1H-pyrrol-1-yl)ethyl]carbamoyl}pyrrolidine-1-carboxylate.

LC-MS (Method 1): $R_t$=1.30 min; MS (ESIpos): m/z=763 $[M+H]^+$.

7.2 mg (0.01 mmol) of tert-butyl 3-{[{(1R)-1-[1-benzyl-4-(2,5-difluorophenyl)-1H-imidazol-2-yl]-2,2-dimethylpropyl}(glycoloyl)amino]methyl}-4-{[2-(2,5-dioxo-2,5-dihydro-1H-pyrrol-1-yl)ethyl]carbamoyl}pyrrolidine-1-carboxylate were initially charged in 1.0 ml of dichloromethane, and 43.0 mg (0.38 mmol) of TFA were added. The reaction mixture was stirred at RT for 16 h. The solvent was evaporated under reduced pressure and the residue was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 4.5 mg (50% of theory) of the title compound.

LC-MS (Method 1): $R_t$=0.92 min; MS (ESIpos): m/z=663 $[M+H]^+$.

Intermediate F43

N-[19-(2,5-Dioxo-2,5-dihydro-1H-pyrrol-1-yl)-7-oxo-4,7,10,13-tetraoxa-16-azanonadecan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide

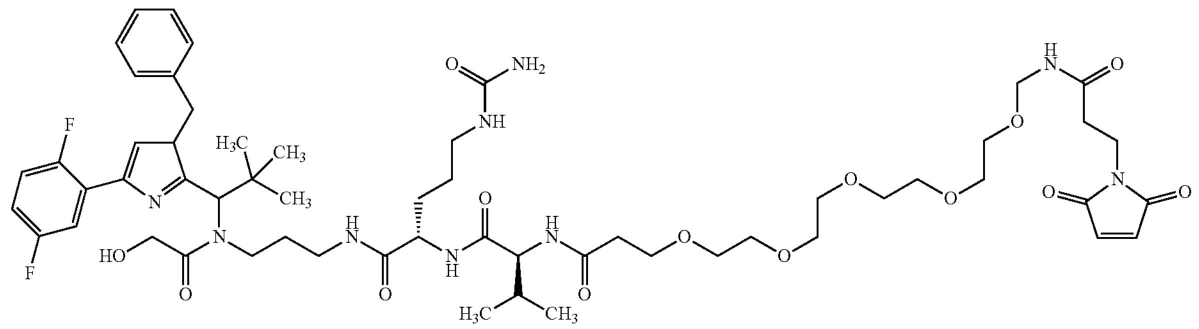 [SMILES: CC(C)[C@H](NC(=O)CCOCCOCCOCCOCCOCNC(=O)CCN1C(=O)C=CC1=O)C(=O)N[C@@H](CCCNC(N)=O)C(=O)NCCCN(C(=O)CO)C(C1=NC(c2cc(F)ccc2F)=CC1Cc1ccccc1)C(C)(C)C]

22.4 mg (0.03 mmol) of N-[19-(2,5-dioxo-2,5-dihydro-1H-pyrrol-1-yl)-17-oxo-4,7,10,13-tetraoxa-16-azanonadecan-1-oyl]-L-valyl-N5-carbamoyl-L-ornithine (Intermediate L42) were dissolved in 2.0 ml of DMF, and 4.5 mg (0.03 mmol) of HOAt, 15.8 mg (0.04 mmol) of HATU and 15.7 mg (0.03 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) were added. 8.6 mg (0.07 mmol) of N,N-diisopropylethylamine were added and the reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 16.7 mg (45% of theory) of the title compound.

LC-MS (Method 4): $R_t$=1.34 min; MS (ESIpos): m/z=1125 $[M+H]^+$.

Intermediate F44

Trifluoroacetic Acid/N-[(4-{[{(1R)-1-[1-benzyl-4-(2,5-difluorophenyl)-1H-imidazol-2-yl]-2,2-dimethylpropyl}(glycoloyl)amino]methyl}pyrrolidin-3-yl)methyl]-19-(2,5-dioxo-2,5-dihydro-1H-pyrrol-1-yl)-17-oxo-4,7,10,13-tetraoxa-16-azanonadecan-1-amide (1:1)

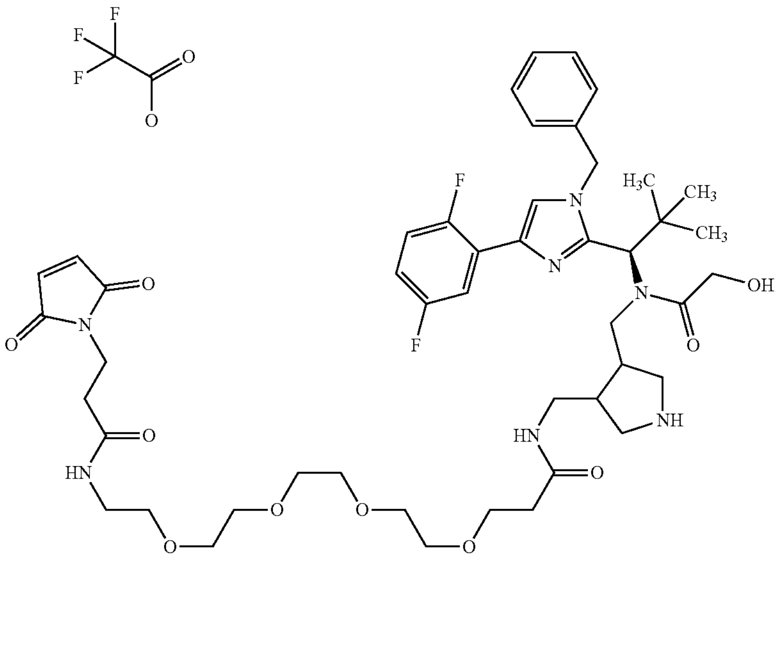 [SMILES: CC(C)(C)[C@H](c1nc(-c2cc(F)ccc2F)cn1Cc1ccccc1)N(CC1CNCC1CNC(=O)CCOCCOCCOCCOCCNC(=O)CCN1C(=O)C=CC1=O)C(=O)CO ; O=C(O)C(F)(F)F]

The title compound was prepared analogously to the synthesis of Intermediate F40.

25.0 mg (0.04 mmol) of trifluoroacetic acid/tert-butyl 3-(aminomethyl)-4-{[{(1R)-1-[1-benzyl-4-(2,5-difluoro-phenyl)-1H-imidazol-2-yl]-2,2-dimethylpropyl}(glycoloyl) amino]methyl}pyrrolidine-1-carboxylate (1:1) (Intermediate C24).

20.5 mg (0.04 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide.

This gave 21.8 mg (48% of theory) of the compound tert-butyl 3-{[{(1R)-1-[1-benzyl-4-(2,5-difluorophenyl)-1H-imidazol-2-yl]-2,2-dimethylpropyl}(glycoloyl)amino] methyl}-4-[21-(2,5-dioxo-2,5-dihydro-1H-pyrrol-1-yl)-3,19-dioxo-6,9,12,15-tetraoxa-2,18-diazahenicos-1-yl] pyrrolidine-1-carboxylate.

LC-MS (Method 1): $R_t$=1.22 min; MS (ESIpos): m/z=1025 $[M+H]^+$.

21.0 mg (0.02 mmol) of tert-butyl 3-{[{(1R)-1-[1-benzyl-4-(2,5-difluorophenyl)-1H-imidazol-2-yl]-2,2-dimethylpropyl}(glycoloyl)amino]methyl}-4-[21-(2,5-dioxo-2,5-dihydro-1H-pyrrol-1-yl)-3,19-dioxo-6,9,12,15-tetraoxa-2,18-diazahenicos-1-yl]pyrrolidine-1-carboxylate. 168.3 mg (1.48 mmol) of TFA.

This gave 17.3 mg (90% of theory) of the title compound.

LC-MS (Method 1): $R_t$=0.92 and 0.94 min; MS (ESIpos): m/z=924 $[M+H]^+$.

Intermediate F45

Trifluoroacetic Acid/N-[19-(2,5-dioxo-2,5-dihydro-1H-pyrrol-1-yl)-17-oxo-4,7,10,13-tetraoxa-16-azanonadecan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-lysinamide (1:1)

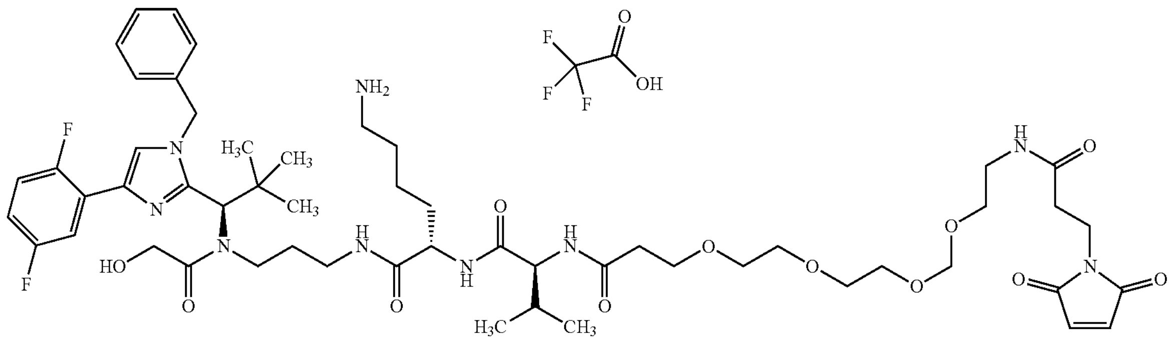 [SMILES: CC(C)[C@H](NC(=O)CCOCCOCCOCOCCNC(=O)CCN1C(=O)C=CC1=O)C(=O)N[C@@H](CCCCN)C(=O)NCCCN(C(=O)CO)[C@@H](c1nc(-c2cc(F)ccc2F)cn1Cc1ccccc1)C(C)(C)C ; O=C(O)C(F)(F)F]

The synthesis was carried out analogously to the synthesis of Intermediate F46.

22.9 mg (0.05 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40).

36.2 mg (0.05 mmol) of N-[19-(2,5-dioxo-2,5-dihydro-1H-pyrrol-1-yl)-17-oxo-4,7,10,13-tetraoxa-16-azanonadecan-1-oyl]-L-valyl-N6-(tert-butoxycarbonyl)-L-lysine (Intermediate L41).

This gave 19.8 mg (34%) of the compound N-[19-(2,5-dioxo-2,5-dihydro-1H-pyrrol-1-yl)-17-oxo-4,7,10,13-tetraoxa-16-azanonadecan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-N6-(tert-butoxycarbonyl)-L-lysinamide.

LC-MS (Method 1): $R_t$=1.20 min; MS (ESIpos): m/z=1196 $[M+H]^+$.

17.0 mg (0.01 mmol) of N-[19-(2,5-dioxo-2,5-dihydro-1H-pyrrol-1-yl)-17-oxo-4,7,10,13-tetraoxa-16-azanonadecan-1-oyl]-L-valyl-N-{3-[{(1R)-1-[1-benzyl-4-(2,5-difluorophenyl)-1H-imidazol-2-yl]-2,2-dimethylpropyl} (glycoloyl)amino]propyl}-N6-(tert-butoxycarbonyl)-L-lysinamide.

This gave 13.6 mg (79% of theory) of the title compound.

LC-MS (Method 1): $R_t$=0.94 min; MS (ESIpos): m/z=1096 $[M+H]^+$.

Intermediate F46

Trifluoroacetic Acid/N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-lysinamide (1:1)

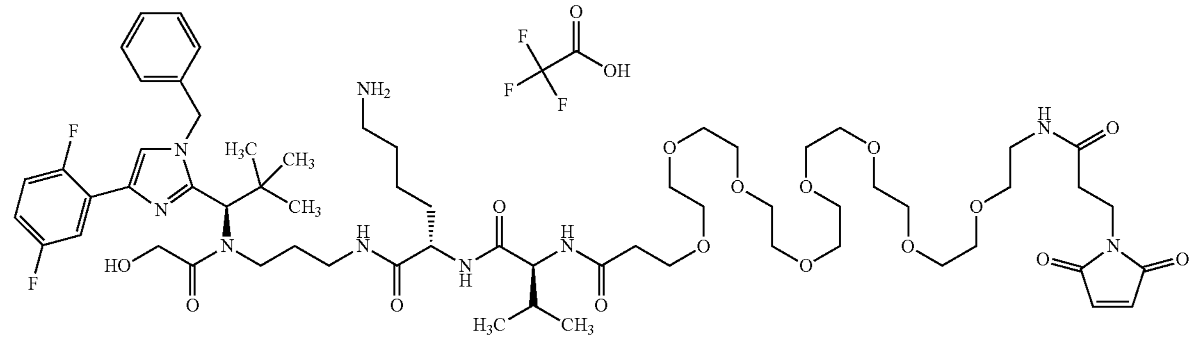 [SMILES: CC(C)[C@H](NC(=O)CCOCCOCCOCCOCCOCCOCCOCCOCCNC(=O)CCN1C(=O)C=CC1=O)C(=O)N[C@@H](CCCCN)C(=O)NCCCN(C(=O)CO)[C@@H](c1nc(-c2cc(F)ccc2F)cn1Cc1ccccc1)C(C)(C)C ; O=C(O)C(F)(F)F]

Under argon and at 0° C., 49.0 mg (0.05 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N6-(tert-butoxycarbonyl)-L-lysine (Intermediate L40), 7.3 mg (0.05 mmol) of HOAt and 25.3 mg (0.07 mmol) of HATU were added to 25.1 mg (0.05 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) in 2.0 ml of DMF. 18.6 μl (0.11 mmol) of N,N-diisopropylethylamine were then added, and the reaction was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 29.2 mg (37% of theory) of the compound N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-(3-{(1R)-1-[1-benzyl-4-(2,5-difluorophenyl)-1H-imidazol-2-yl]-2,2-dimethylpropyl}(glycoloyl)amino]propyl}-N6-(tert-butoxycarbonyl)-L-lysinamide.

LC-MS (Method 4): $R_t$=1.51 min; MS (ESIpos): m/z=1372 $[M+H]^+$.

25.2 mg (0.02 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-N6-(tert-butoxycarbonyl)-L-lysinamide were initially charged in 3.0 ml of dichloromethane, and 83.7 mg (0.73 mmol) of TFA were added. The reaction solution was stirred at RT for 48 h. The solvent was evaporated under reduced pressure and purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 24.5 mg (96% of theory) of the title compound.

LC-MS (Method 1): $R_t$=0.95 min; MS (ESIpos): m/z=1272 $[M+H]^+$.

Intermediate F47

N-[67-(2,5-Dioxo-2,5-dihydro-1H-pyrrol-1-yl)-65-oxo-4,7,10,13,16,19,22,25,28,31,34,37,40,43,46,49,52,55,58,61-icosaoxa-64-azaheptahexacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide

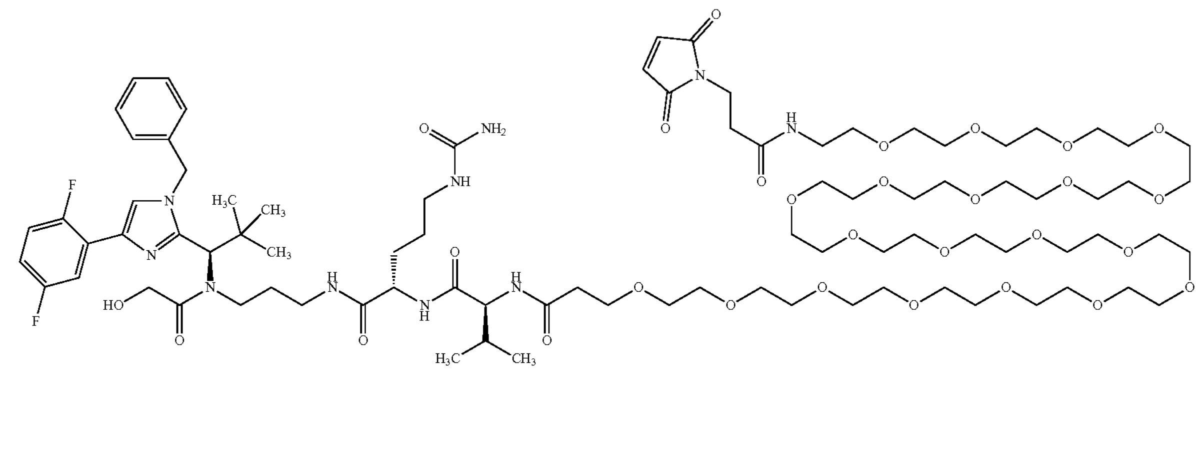

15.2 mg (0.01 mmol) of N-[67-(2,5-dioxo-2,5-dihydro-1H-pyrrol-1-yl)-65-oxo-4,7,10,13,16,19,22,25,28,31,34,37,40,43,46,49,52,55,58,61-icosaoxa-64-azaheptahexacontan-1-oyl]-L-valyl-N5-carbamoyl-L-ornithine (Intermediate L43) were dissolved in 1.0 ml of DMF, and 1.5 mg (0.01 mmol) of HOAt, 5.2 mg (0.01 mmol) of HATU and 5.2 mg (0.01 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) were added. 2.9 mg (0.02 mmol) of N,N-diisopropylethylamine were added and the reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 6.8 mg (33% of theory) of the title compound.

LC-MS (Method 4): $R_t$=1.37 min; MS (ESIpos): m/z=1831 $[M+H]^+$.

Intermediate F48

Trifluoroacetic Acid/N1-(3-aminopropyl)-N1-{(1R)-1-[1-benzyl-4-(2,5-difluorophenyl)-1H-imidazol-2-yl]-2,2-dimethylpropyl}-N18-[2-(2,5-dioxo-2,5-dihydro-1H-pyrrol-1-yl)ethyl]-6,9,12,15-tetraoxa-3-thiaoctadecane-1,18-diamide (1:1)

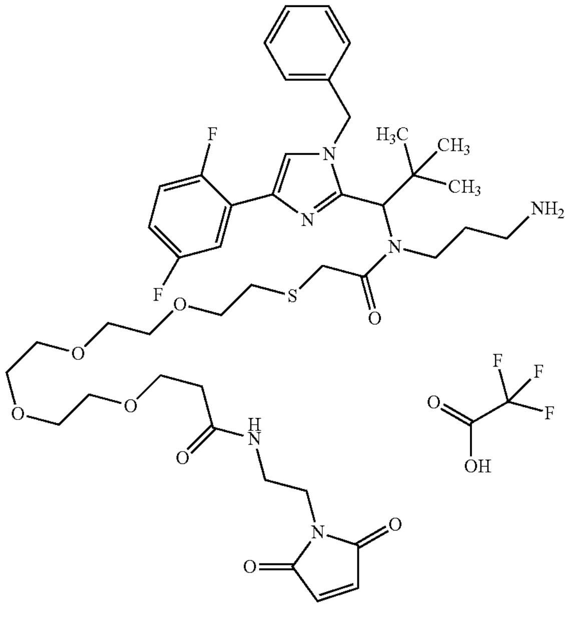 [SMILES: CC(C)(C)C(c1nc(-c2cc(F)ccc2F)cn1Cc1ccccc1)N(CCCN)C(=O)CSCCOCCOCCOCCOCCC(=O)NCCN1C(=O)C=CC1=O ; O=C(O)C(F)(F)F]

16.1 mg (0.02 mmol) of tert-butyl [22-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-4,21-dioxo-7,10,13,16-tetraoxa-19-thia-3,22-diazapentacosan-25-yl] carbamate (Intermediate C18) were initially charged in 1.5 ml of dichloromethane, and 26 μl (0.34 mmol) of TFA were added. The mixture was stirred at RT overnight, and another 26 μl (0.34 mmol) of TFA were then added. The mixture was once more stirred at RT overnight. The solvent was evaporated under reduced pressure and the residue was purified by preparative RP-HPLC (column: Reprosil 250×30; 10μ, flow rate: 50 ml/min, MeCN/water, 0.1% TFA). The solvents were evaporated under reduced pressure and the residue was taken up in water and lyophilized. This gave 10.8 mg (66% of theory) of the title compound.

LC-MS (Method 1): $R_t$=0.98 min; MS (ESIpos): m/z=857 $[M+H]^+$.

Intermediate F49

(25S)-25-Amino-22-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-4,21-dioxo-7,10,13,16-tetraoxa-19-thia-3,22-diazahexacosan-26-oic Acid/Trifluoroacetic Acid (1:1)

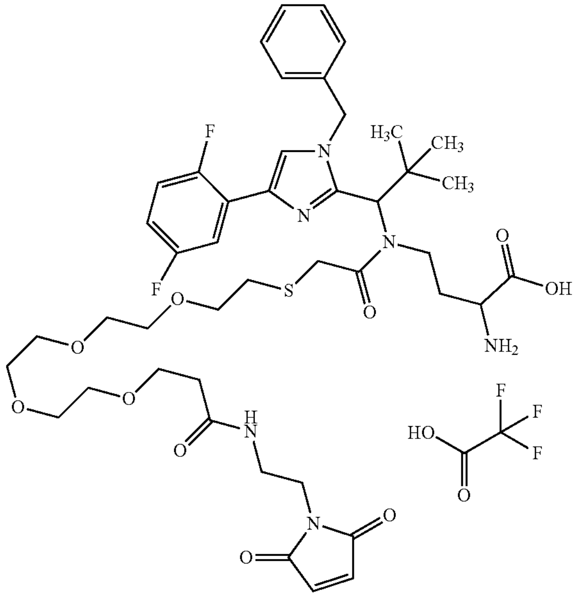

The synthesis of the compound tert-butyl (2S)-4-[{(1R)-1-[1-benzyl-4-(2,5-difluorophenyl)-1H-imidazol-2-yl]-2,2-dimethylpropyl}(chloroacetyl)amino]-2-[(tert-butoxycarbonyl)amino]butanoate was carried out analogously to the synthesis of Intermediate C16.

50.0 mg (0.08 mmol) of Intermediate C2

20.3 mg (0.18 mmol) of chloroacetyl chloride 19.0 mg (0.19 mmol) of triethylamine This gave 43.1 mg (77% of theory) of the compound tert-butyl (2S)-4-[{(1R)-1-[1-benzyl-4-(2,5-difluorophenyl)-1H-imidazol-2-yl]-2,2-dimethylpropyl}(chloroacetyl)amino]-2-[(tert-butoxycarbonyl)amino]butanoate.

LC-MS (Method 1): $R_t$=1.55 min; MS (ESIpos): m/z=689 $[M+H]^+$.

The synthesis of the compound (6S)-9-{(1R)-1-[1-benzyl-4-(2,5-difluorophenyl)-1H-imidazol-2-yl]-2,2-dimethylpropyl}-6-(tert-butoxycarbonyl)-2,2-dimethyl-4,10-dioxo-3,15,18,21,24-pentaoxa-12-thia-5,9-diazaheptacosan-27-oic acid was carried out analogously to the synthesis of Intermediate C17.

38.8 mg (0.06 mmol) of tert-butyl (2S)-4-[{(1R)-1-[1-benzyl-4-(2,5-difluorophenyl)-1H-imidazol-2-yl]-2,2-dimethylpropyl}(chloroacetyl)amino]-2-[(tert-butoxycarbonyl)amino]butanoate.

19.1 mg (0.07 mmol) of 1-sulphanyl-3,6,9,12-tetraoxapentadecan-15-oic acid 45.9 mg (0.14 mmol) of caesium carbonate This gave 40.7 mg (77% of theory) of the compound (6S)-9-{(1R)-1-[1-benzyl-4-(2,5-difluorophenyl)-1H-imidazol-2-yl]-2,2-dimethylpropyl}-6-(tert-butoxycarbonyl)-2,2-dimethyl-4,10-dioxo-3,15,18,21,24-pentaoxa-12-thia-5,9-diazaheptacosan-27-oic acid.

LC-MS (Method 1): $R_t$=1.45 min; MS (ESIpos): m/z=935 $[M+H]^+$.

The synthesis of the compound tert-butyl (25S)-22-{(1R)-1-[1-benzyl-4-(2,5-difluorophenyl)-1H-imidazol-2-yl]-2,2-dimethylpropyl}-25-[(tert-butoxycarbonyl)amino]-1-(2,5-dioxo-2,5-dihydro-1H-pyrrol-1-yl)-4,21-dioxo-7,10,13,16-tetraoxa-19-thia-3,22-diazahexacosan-26-oate was carried out analogously to the synthesis of Intermediate C18.

37.4 mg (0.04 mmol) of (6S)-9-{(1R)-1-[1-benzyl-4-(2,5-difluorophenyl)-1H-imidazol-2-yl]-2,2-dimethylpropyl}-6-(tert-butoxycarbonyl)-2,2-dimethyl-4,10-dioxo-3,15,18,21,24-pentaoxa-12-thia-5,9-diazaheptacosan-27-oic acid.

9.2 mg (0.05 mmol) of 1-(2-aminoethyl)-1H-pyrrole-2,5-dione hydrochloride (1:1).

This gave 23.4 mg (49% of theory) of the compound tert-butyl (25S)-22-{(1R)-1-[1-benzyl-4-(2,5-difluorophenyl)-1H-imidazol-2-yl]-2,2-dimethylpropyl}-25-[(tert-butoxycarbonyl)amino]-1-(2,5-dioxo-2,5-dihydro-1H-pyrrol-1-yl)-4,21-dioxo-7,10,13,16-tetraoxa-19-thia-3,22-diazahexacosan-26-oate.

LC-MS (Method 1): $R_t$=1.47 min; MS (ESIpos): m/z=1057 $[M+H]^+$.

The synthesis of the title compound was carried out analogously to the synthesis of Intermediate F38.

20.8 mg (0.02 mmol) of tert-butyl (25S)-22-{(1R)-1-[1-benzyl-4-(2,5-difluorophenyl)-1H-imidazol-2-yl]-2,2-dimethylpropyl}-25-[(tert-butoxycarbonyl)amino]-1-(2,5-dioxo-2,5-dihydro-1H-pyrrol-1-yl)-4,21-dioxo-7,10,13,16-tetraoxa-19-thia-3,22-diazahexacosan-26-oate. 157.0 mg (1.37 mmol) of TFA.

This gave 13.0 mg (65%) of the title compound.

LC-MS (Method 1): $R_t$=0.93 min; MS (ESIpos): m/z=901 $[M+H]^+$.

Intermediate F50

Trifluoroacetic Acid/1-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopropanecarboxamide (1:1)

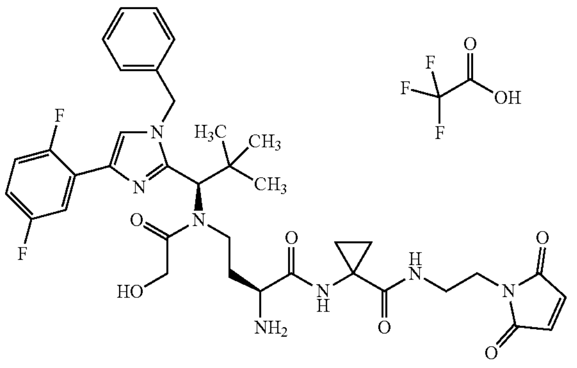 [SMILES: CC(C)(C)[C@H](c1nc(-c2cc(F)ccc2F)cn1Cc1ccccc1)N(CC[C@H](N)C(=O)NC1(C(=O)NCCN2C(=O)C=CC2=O)CC1)C(=O)CO ; O=C(O)C(F)(F)F]

15 mg (0.024 mmol) of Intermediate C5 were dissolved in 6.5 ml of DCM, and 19 mg (0.049 mmol) of Intermediate L24, 13 μl of N,N-diisopropylethylamine and 10 mg (0.037 mmol) of 2-bromo-1-ethylpyridinium tetrafluoroborate were added. The reaction was stirred at RT for 3 h and then concentrated under reduced pressure. The residue was purified by preparative HPLC, giving 2.4 mg of the protected intermediate.

These were then taken up in 1 ml of DCM and deprotected with 0.1 ml of trifluoroacetic acid. Lyophilization from acetonitrile/water gave 2.6 mg (11% of theory over 2 steps) of the title compound.

HPLC (Method 11): $R_t$=2.4 min.

LC-MS (Method 1): $R_t$=1.25 min; MS (ESIpos): m/z=819 $[M+H]^+$.

Intermediate F51

3-{3-[(3-Amino-2-{[{(1R)-1-[1-benzyl-4-(2,5-difluorophenyl)-1H-imidazol-2-yl]-2,2-dimethylpropyl}(glycoloyl)amino]methyl}propyl)sulphanyl]-2,5-dioxopyrrolidin-1-yl}-N-[17-(2,5-dioxo-2,5-dihydro-1H-pyrrol-1-yl)-15-oxo-4,7,10-trioxa-14-azaheptadec-1-yl]propanamide (Isomer 1)

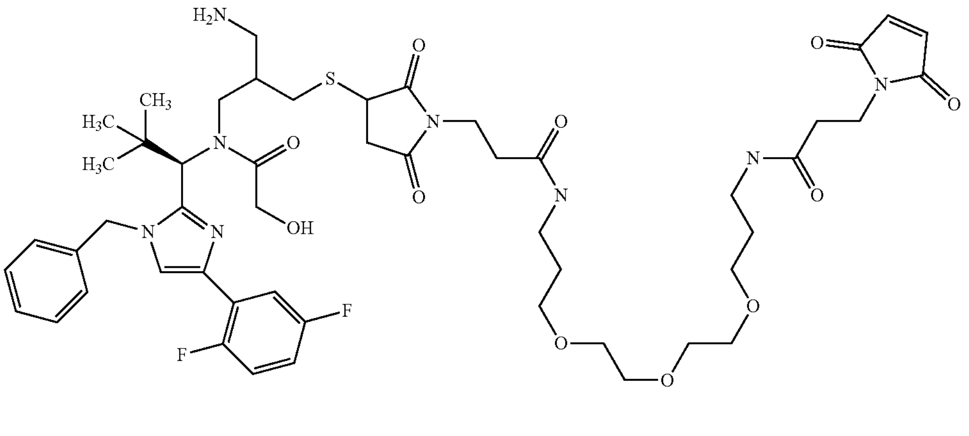 [SMILES: CC(C)(C)[C@H](c1nc(-c2cc(F)ccc2F)cn1Cc1ccccc1)N(CC(CN)CSC1CC(=O)N(CCC(=O)NCCCOCCOCCOCCCNC(=O)CCN2C(=O)C=CC2=O)C1=O)C(=O)CO]

10.0 mg (18.079 μmol) of N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 1) were initially charged in 100 μl of PBS buffer (Sigma D8537) and 200 μl of ACN. 17.1 mg (32.543 μmol) of 3-(2,5-dioxo-2,5-dihydro-1H-pyrrol-1-yl)-N-[17-(2,5-dioxo-2,5-dihydro-1H-pyrrol-1-yl)-15-oxo-4,7,10-trioxa-14-azaheptadec-1-yl]propanamide were added, and the mixture was stirred at RT for 16 h. The reaction solution was purified by preparative HPLC (mobile phase: ACN/water+0.1% TFA, gradient) and lyophilized. This gave 14.0 mg (75% of theory) of the target compound.

Isomer 1

LC-MS (Method 1): $R_t$=0.94 min; MS (ESIpos): m/z=1039 $[M+H]^+$.

Intermediate F52

3-{3-[(3-Amino-2-{[{(1R)-1-[1-benzyl-4-(2,5-difluorophenyl)-1H-imidazol-2-yl]-2,2-dimethylpropyl}(glycoloyl)amino]methyl}propyl)sulphanyl]-2,5-dioxopyrrolidin-1-yl}-N-[17-(2,5-dioxo-2,5-dihydro-1H-pyrrol-1-yl)-15-oxo-4,7,10-trioxa-14-azaheptadec-1-yl]propanamide (Isomer 2)

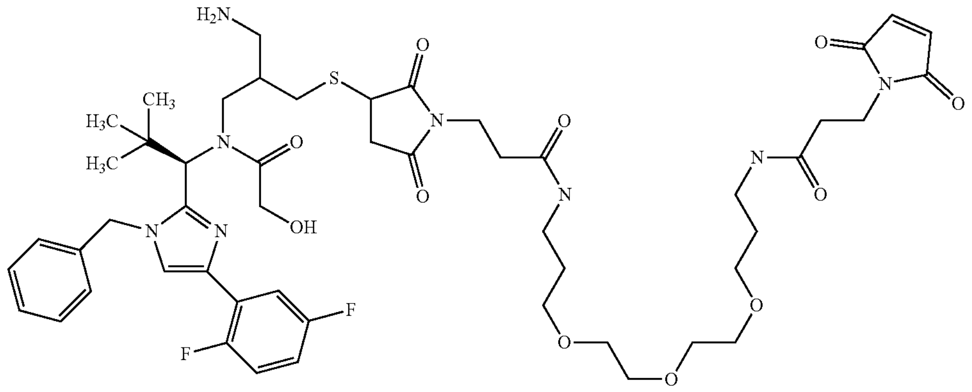 [SMILES: CC(C)(C)[C@H](c1nc(-c2cc(F)ccc2F)cn1Cc1ccccc1)N(CC(CN)CSC1CC(=O)N(CCC(=O)NCCCOCCOCCOCCCNC(=O)CCN2C(=O)C=CC2=O)C1=O)C(=O)CO]

6.5 mg (10.694 μmol, LC/MS purity=91%) of N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 2) were initially charged in 100 μl of PBS buffer (Sigma D8537) and 200 μl of ACN. 10.1 mg (19.249 μmol) of 3-(2,5-dioxo-2,5-dihydro-1H-pyrrol-1-yl)-N-[17-(2,5-dioxo-2,5-dihydro-1H-pyrrol-1-yl)-15-oxo-4,7,10-trioxa-14-azaheptadec-1-yl]propanamide were added, and the mixture was stirred at RT for 16 h. The reaction solution was purified by preparative HPLC (mobile phase: ACN/water+0.1% TFA, gradient) and lyophilized. This gave 5.0 mg (45% of theory) of the target compound.

Isomer 2

LC-MS (Method 5): $R_t$=2.87 min; MS (ESIpos): m/z=1039 $[M+H]^+$.

Intermediate F53

N-{3-Amino-2-[({1-[4-(2,5-dioxo-2,5-dihydro-1H-pyrrol-1-yl)butyl]-2,5-dioxopyrrolidin-3-yl}sulphanyl)methyl]propyl}-N-{(1R)-1-[1-benzyl-4-(2,5-difluorophenyl)-1H-imidazol-2-yl]-2,2-dimethylpropyl}-2-hydroxyacetamide (Isomer 1)

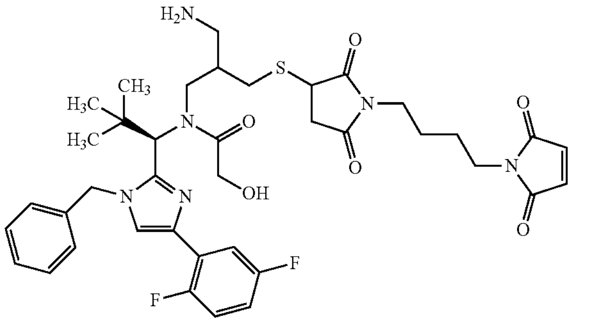 [SMILES: CC(C)(C)[C@H](c1nc(-c2cc(F)ccc2F)cn1Cc1ccccc1)N(CC(CN)CSC1CC(=O)N(CCCCN2C(=O)C=CC2=O)C1=O)C(=O)CO]

10.0 mg (18.079 μmol) of N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 1) were initially charged in 200 μl of PBS buffer (Sigma D8537) and 400 μl of ACN. 8.1 mg (32.543 μmol) of 1,1'-butane-1,4-diylbis(1H-pyrrole-2,5-dione) were added, and the mixture was stirred at RT for 1 h. 300 μl of DMF were then added, and the mixture was stirred for a further 1.5 h. The reaction solution was purified by preparative HPLC (mobile phase: ACN/water+0.1% TFA, gradient) and lyophilized. This gave 4.0 mg (29% of theory) of the target compound.

Isomer 1

LC-MS (Method 1): $R_t$=0.97 min; MS (ESIpos): m/z=765 $[M+H]^+$.

Intermediate F54

N-{3-Amino-2-[({1-[4-(2,5-dioxo-2,5-dihydro-1H-pyrrol-1-yl)butyl]-2,5-dioxopyrrolidin-3-yl}sulphanyl)methyl]propyl}-N-{(1R)-1-[1-benzyl-4-(2,5-difluorophenyl)-1H-imidazol-2-yl]-2,2-dimethylpropyl}-2-hydroxyacetamide (Isomer 2)

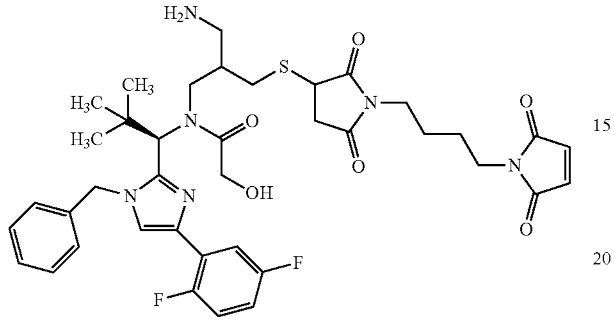

5.0 mg (9.040 μmol) of N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 2) were initially charged in 500 μl of DMF. 4.0 mg (16.271 μmol) of 1,1'-butane-1,4-diylbis(1H-pyrrole-2,5-dione) were added, and the mixture was stirred at RT for 16 h. The reaction solution was purified by preparative HPLC (mobile phase: ACN/water+0.1% TFA, gradient) and lyophilized. This gave 1.1 mg (16% of theory) of the target compound.

Isomer 2

LC-MS (Method 6): $R_t$=2.41 min; MS (ESIpos): m/z=765 $[M+H]^+$.

Intermediate F55

N-[19-(2,5-dioxo-2,5-dihydro-1H-pyrrol-1-yl)-17-oxo-4,7,10,13-tetraoxa-16-azanonadecan-1-oyl]-L-valyl-N-{4-[(3-aminopropyl) {(1R)-1-[1-benzyl-4-(2,5-difluorophenyl)-1H-imidazol-2-yl]-2,2-dimethylpropyl}carbamoyl]phenyl}-L-alaninamide

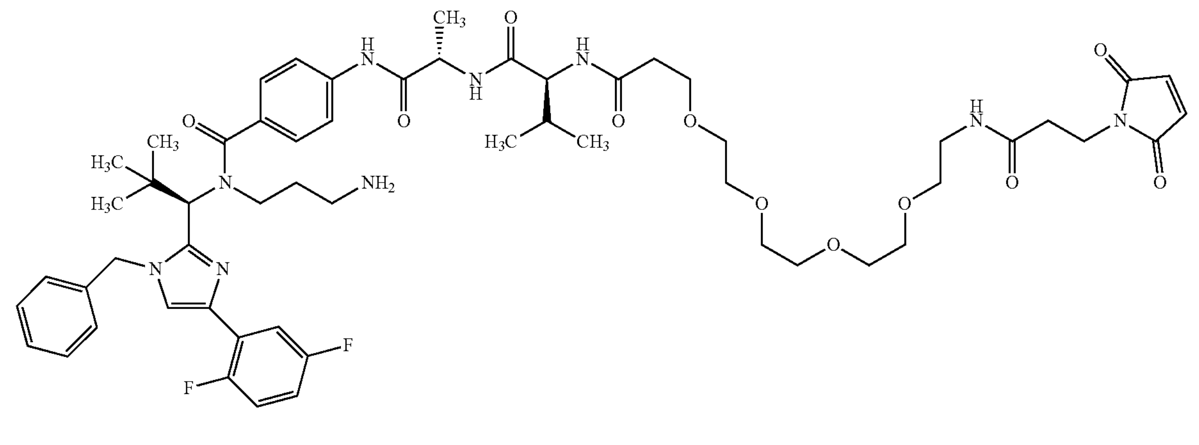 [SMILES: CC(C)[C@H](NC(=O)CCOCCOCCOCCOCCNC(=O)CCN1C(=O)C=CC1=O)C(=O)N[C@@H](C)C(=O)Nc1ccc(C(=O)N(CCCN)[C@@H](c2nc(-c3cc(F)ccc3F)cn2Cc2ccccc2)C(C)(C)C)cc1]

6.5 mg (4.5 μmol) of N-[19-(2,5-dioxo-2,5-dihydro-1H-pyrrol-1-yl)-17-oxo-4,7,10,13-tetraoxa-16-azanonadecan-1-oyl]-L-valyl-N-[4-({(1R)-1-[1-benzyl-4-(2,5-difluorophenyl)-1H-imidazol-2-yl]-2,2-dimethylpropyl}{3-[(tert-butoxycarbonyl)amino]propyl}carbamoyl)phenyl]-L-alaninamide were dissolved in 441 μl of dichloromethane, and 44 μl (573.1 μmol) of trifluoroacetic acid were added. The reaction was concentrated on a rotary evaporator at RT, taken up in water and ACN and lyophilized. This gave 5.6 mg (94% of theory, purity according to LC/MS=92%) of the target compound.

LC-MS (Method 1): $R_t$=1.01 min; MS (ESIpos): m/z=1100.6 $[M+H]^+$.

Intermediate F56

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-[(2S)-1-{[2-(2,5-dioxo-2,5-dihydro-1H-pyrrol-1-yl)ethyl]amino}-1-oxopropan-2-yl]butanamide (1:1)

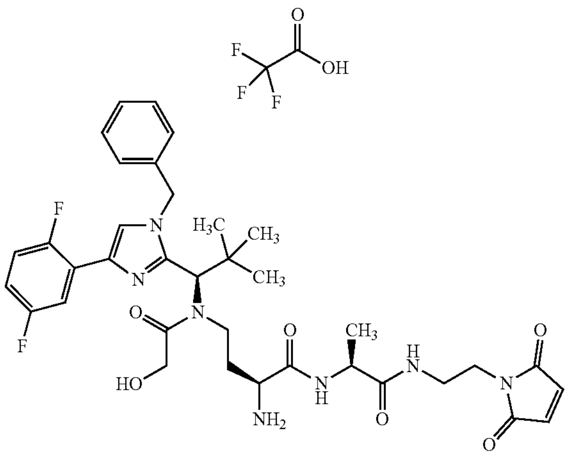 [SMILES: C[C@H](NC(=O)[C@@H](N)CCN(C(=O)CO)[C@@H](c1nc(-c2cc(F)ccc2F)cn1Cc1ccccc1)C(C)(C)C)C(=O)NCCN1C(=O)C=CC1=O ; O=C(O)C(F)(F)F]

The title compound was prepared analogously to Intermediate F50.

LC-MS (Method 1): $R_t$=0.9 min; MS (EIpos): m/z=708 $[M+H]^+$.

Intermediate F57

Trifluoroacetic Acid/(2S)-2-amino-4-[{(1R)-1-[1-benzyl-4-(2,5-difluorophenyl)-1H-imidazol-2-yl]-2,2-dimethylpropyl}(glycoloyl)amino]-N-[(2R)-1-{[2-(2,5-dioxo-2,5-dihydro-1H-pyrrol-1-yl)ethyl]amino}-1-oxopropan-2-yl]butanamide (1:1)

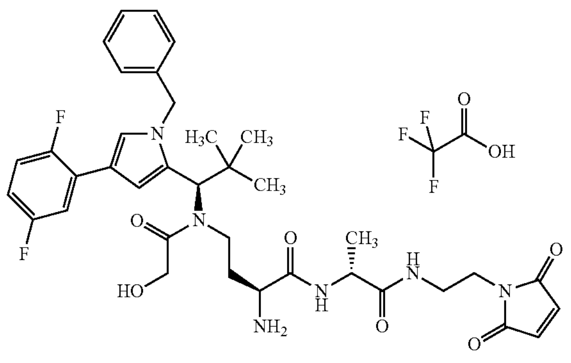 [SMILES: C[C@@H](NC(=O)[C@@H](N)CCN(C(=O)CO)[C@@H](c1cc(-c2cc(F)ccc2F)cn1Cc1ccccc1)C(C)(C)C)C(=O)NCCN1C(=O)C=CC1=O ; O=C(O)C(F)(F)F]

The title compound was prepared analogously to Intermediate F56.

LC-MS (Method 1): $R_t$=0.91 min; MS (EIpos): m/z=708 $[M+H]^+$.

Intermediate F58

N-{5-[(2,5-Dioxopyrrolidin-1-yl)oxy]-5-oxopentanoyl}-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide

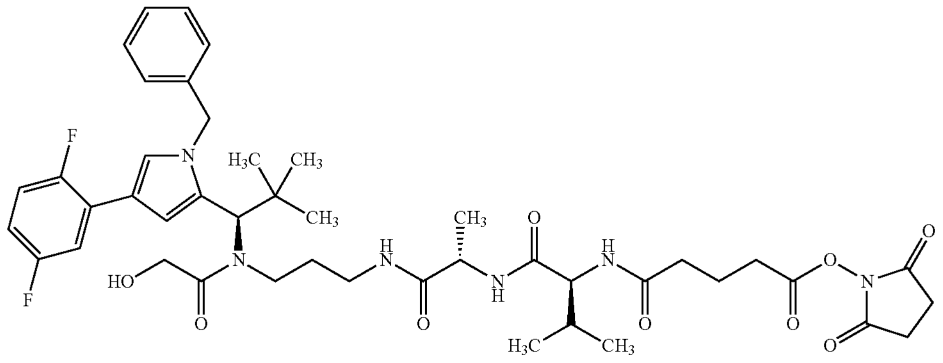 [SMILES: CC(C)[C@H](NC(=O)CCCC(=O)ON1C(=O)CCC1=O)C(=O)N[C@@H](C)C(=O)NCCCN(C(=O)CO)[C@@H](c1cc(-c2cc(F)ccc2F)cn1Cc1ccccc1)C(C)(C)C]

16.2 mg (0.02 mmol) of trifluoroacetic acid/L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide (1:1) (Intermediate C41) were initially charged in 1.0 ml of DMF, and 8.3 mg (0.06 mmol) of N,N-diisopropylethylamine and 12.6 mg (0.04 mmol) of 1,1'-[(1,5-dioxopentane-1,5-diyl)bis(oxy)]dipyrrolidine-2,5-dione were added. The reaction mixture was stirred at RT overnight and purified directly by preparative RP-HPLC (column: Reprosil 250×30; 10μ, flow rate: 50 ml/min, MeCN/water). The solvents were evaporated under reduced pressure and the residue was dried under high vacuum. This gave 11.0 mg (60% of theory) of the title compound.

LC-MS (Method 1): $R_t$=1.18 min; MS (ESIpos): m/z=852 $[M+H]^+$.

Intermediate F82

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N-{3-[{1-[1-benzyl-4-(2,5-difluorophenyl)-1H-pyrrol-2-yl]-2,2-dimethylpropyl}(glycoloyl)amino]propyl}-L-alaninamide

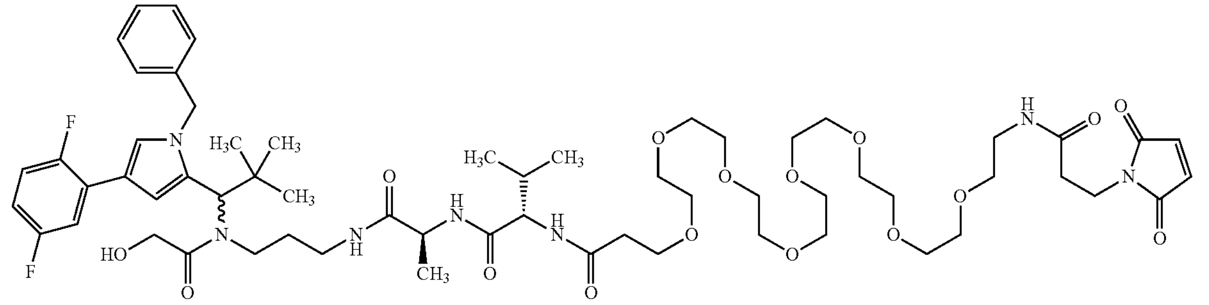 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)NCCCN(C(=O)CO)C(c1cc(-c2cc(F)ccc2F)cn1Cc1ccccc1)C(C)(C)C]

The synthesis of the title compound was carried out analogously to the synthesis of Intermediate F83. The racemic intermediates used were obtained analogously to the corresponding R-isomer intermediates.

LC-MS (Method 2): $R_t$=7.07 min; MS (EIpos): m/z=1236 [M+Na]$^+$.

Intermediate F83

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide

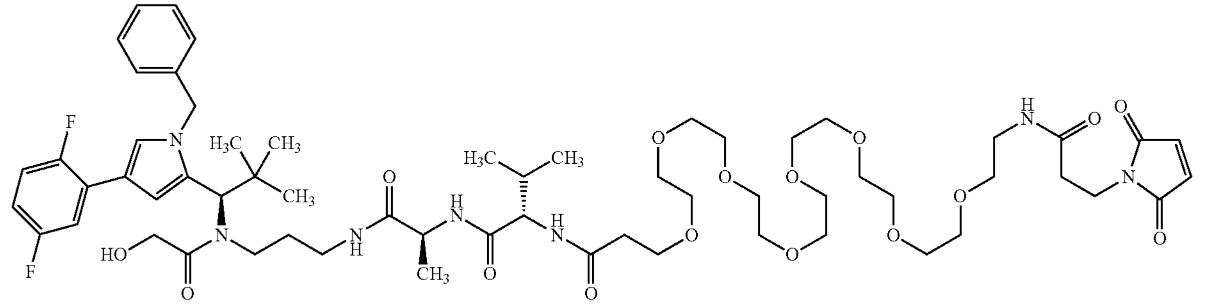 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)NCCCN(C(=O)CO)[C@@H](c1cc(-c2cc(F)ccc2F)cn1Cc1ccccc1)C(C)(C)C]

30.0 mg (0.06 mmol) of N-(3-aminopropyl)-N-{(1R)-1-[1-benzyl-4-(2,5-difluorophenyl)-1H-pyrrol-2-yl]-2,2-dimethylpropyl}-2-hydroxyacetamide (Example 98) and 26.1 mg (0.06 mmol) of 2,5-dioxopyrrolidin-1-yl-N-[(9H-fluoren-9-ylmethoxy)carbonyl]-L-alaninate were initially charged in 2.0 ml of DMF, and 19.4 mg (0.19 mmol) of 4-methylmorpholine were added. The reaction mixture was stirred at RT overnight, and 11.5 mg (0.19 mmol) of HOAc was added. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 41.9 mg (79% of theory) of the compound 9H-fluoren-9-ylmethyl [(2S)-1-({3-[{(1R)-1-[1-benzyl-4-(2,5-difluorophenyl)-1H-pyrrol-2-yl]-2,2-dimethylpropyl}(glycoloyl)amino]propyl}amino)-1-oxopropan-2-yl]carbamate.

LC-MS (Method 1): $R_t$=1.44 min; MS (ESIpos): m/z=763 [M+H]$^+$.

37.2 mg (0.05 mmol) of 9H-fluoren-9-ylmethyl [(2S)-1-({3-[{(1R)-1-[1-benzyl-4-(2,5-difluorophenyl)-1H-pyrrol-2-yl]-2,2-dimethylpropyl}(glycoloyl)amino]propyl}amino)-1-oxopropan-2-yl]carbamate were dissolved in 1.5 ml of DMF, and 124.6 mg (1.46 mmol) of 2-aminoethanol were added. The reaction mixture was stirred at RT overnight. The reaction mixture was partitioned between ethyl acetate and water and the organic phase was washed twice with water and once with saturated NaCl solution. After drying over magnesium sulphate, the solvent was evaporated under reduced pressure and the residue was purified on silica gel (mobile phase: dichloromethane/methanol 10:1). The solvents were evaporated under reduced pressure and the residue was dried under high vacuum. This gave 14.2 mg (50% of theory) of the compound N-{3-[{(1R)-1-[1-benzyl-4-(2,5-difluorophenyl)-1H-pyrrol-2-yl]-2,2-dimethylpropyl}(glycoloyl)amino]propyl}-L-alaninamide.

LC-MS (Method 1): $R_t$=0.92 min; MS (ESIpos): m/z=541 [M+H]$^+$.

14.1 mg (0.03 mmol) of N-{3-[{(1R)-1-[1-benzyl-4-(2,5-difluorophenyl)-1H-pyrrol-2-yl]-2,2-dimethylpropyl}(glycoloyl)amino]propyl}-L-alaninamide and 11.4 (0.03 mmol) of 2,5-dioxopyrrolidin-1-yl N-[(9H-fluoren-9-ylmethoxy)carbonyl]-L-valinate were dissolved in 1.5 ml of DMF, and 7.9 mg (0.08 mmol) of 4-methylmorpholine were added. The reaction mixture was stirred at RT overnight, and 4.7 mg (0.08 mmol) of HOAc was added. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 15.9 mg (71% of theory) of the compound N-[(9H-fluoren-9-yl-methoxy)carbonyl]-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide.

LC-MS (Method 1): $R_t$=1.46 min; MS (ESIpos): m/z=862 $(M+H)^+$.

14.9 mg (0.02 mmol) of N-[(9H-fluoren-9-ylmethoxy)carbonyl]-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide were dissolved in 1.5 ml of DMF, and 44.2 mg (0.52 mmol) of 2-aminoethanol were added. The reaction mixture was stirred at RT overnight. The reaction mixture was partitioned between ethyl acetate and water and the organic phase was washed twice with water and once with saturated NaCl solution. After drying over magnesium sulphate, the solvent was evaporated under reduced pressure and the residue was purified on silica gel (mobile phase: dichloromethane/methanol 10:1). The solvents were evaporated under reduced pressure and the residue was dried under high vacuum. This gave 5.7 mg (52% of theory) of the compound L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide.

LC-MS (Method 1): $R_t$=0.92 min; MS (ESIpos): m/z=640 $(M+H)^+$.

5.5 mg (8.6 μmol) of L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide and 6.5 mg (6.5 μmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide were dissolved in 1.0 ml of DMF, and 0.9 mg (8.6 mmol) of 4-methylmorpholine was added. The reaction mixture was stirred at RT overnight, and 0.8 mg (0.01 mmol) of HOAc was added. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 7.7 mg (74% of theory) of the title compound.

LC-MS (Method 1): $R_t$=1.10 min; MS (ESIpos): m/z=1214 $(M+H)^+$.

Intermediate F84

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(3-{[2-(2,5-dioxo-2,5-dihydro-1H-pyrrol-1-yl)ethyl]amino}-3-oxopropyl)butanamide (1:1)

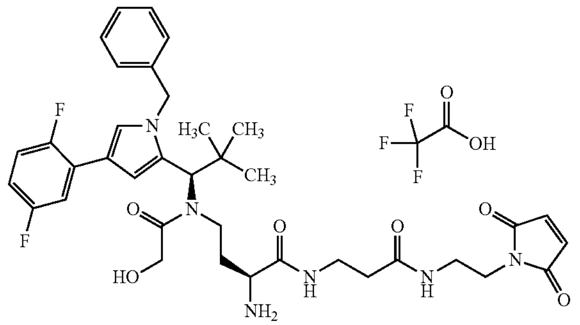 [SMILES: CC(C)(C)[C@H](c1cc(-c2cc(F)ccc2F)cn1Cc1ccccc1)N(CC[C@H](N)C(=O)NCCC(=O)NCCN1C(=O)C=CC1=O)C(=O)CO ; O=C(O)C(F)(F)F]

First, 16.5 mg (0.02 mmol) of Intermediate C54 were taken up in 5 ml of DMF and reacted with 10.4 mg (0.041 mmol) of trifluoroacetic acid/1-(2-aminoethyl)-1H-pyrrole-2,5-dione (1:1) in the presence of 11.7 mg (0.03 mmol) of HATU and 18 μl of N,N-diisopropylethylamine. After 5 min of stirring at RT, the mixture was concentrated and the residue was taken up in acetonitrile/water 1:1. The pH was adjusted to 2 with trifluoroacetic acid and the reaction was concentrated again. The residue that remained was purified by preparative HPLC. This gave 8 mg (42% of theory) of the protected intermediate.

LC-MS (Method 1): $R_t$=1.38 min; MS (EIpos): m/z=929 $[M+H]^+$.

7.6 mg (0.008 mmol) of this intermediate were taken up in 3 ml of DMF, and 92 mg (0.82 mmol) of 1,4-diazabicyclo[2.2.2]octane were added. The reaction was treated in an ultrasonic bath for 1 h. 31 μl of acetic acid were then added and the reaction was concentrated under high vacuum. The residue was purified by preparative HPLC. This gave 3 mg (45% of theory) of the title compound.

LC-MS (Method 1): $R_t$=0.86 min; MS (EIpos): m/z=707 $[M+H]^+$.

$^1$H-NMR (500 MHz, DMSO-$d_6$): δ=8.15 (t, 1H), 7.9-8.1 (m, 4H), 7.6 (m, 1H), 7.5 (s, 1H), 7.15-7.35 (m, 6H), 6.9-7.0 (m, 3H), 6.85 (s, 1H), 5.6 (s, 1H), 4.9 and 5.2 (2d, 2H), 4.05 and 4.2 (2d, 2H), 3.1-3.2 (m, 4H), 2.15 (m, 2H), 0.7 and 1.45 (2m, 2H), 0.8 (s, 9H).

Intermediate F85

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[2-(2,5-dioxo-2,5-dihydro-1H-pyrrol-1-yl)ethyl]butanamide (1:1)

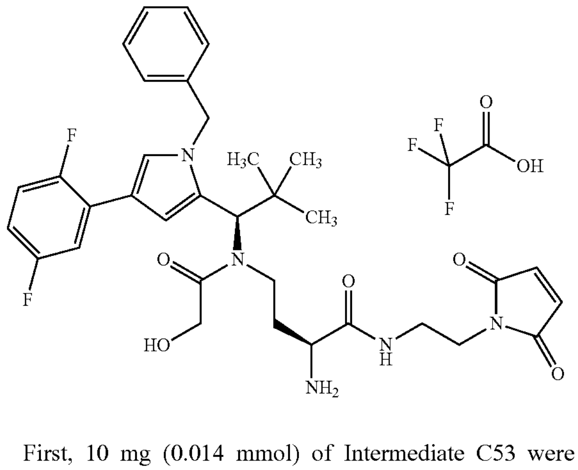

First, 10 mg (0.014 mmol) of Intermediate C53 were taken up in 3.4 ml of DMF and reacted with 7 mg (0.027 mmol) of trifluoroacetic acid/1-(2-aminoethyl)-1H-pyrrole-2,5-dione (1:1) in the presence of 7.8 mg (0.02 mmol) of HATU and 12 μl of N,N-diisopropylethylamine. After 15 min of stirring at RT, the mixture was concentrated and the residue was purified by preparative HPLC. This gave 6.6 mg (57% of theory) of the protected intermediate.

LC-MS (Method 1): $R_t$=1.4 min; MS (EIpos): m/z=858 $[M+H]^+$.

6.6 mg (0.008 mmol) of this intermediate were taken up in 2 ml of DMF, and 86 mg (0.77 mmol) of 1,4-diazabicyclo[2.2.2]octane were added. The reaction was treated in an ultrasonic bath for 2 h. 44 μl of acetic acid were then added and the reaction was concentrated under high vacuum. The residue was purified by preparative HPLC. This gave 3.3 mg (53% of theory) of the title compound.

LC-MS (Method 1): $R_t$=0.88 min; MS (EIpos): m/z=636 $[M+H]^+$.

Intermediate F86

Trifluoroacetic Acid/(2S)-2-amino-4-[{(1R)-1-[4-benzyl-1-(2,5-difluorophenyl)-1H-pyrazol-3-yl]-2,2-dimethylpropyl}(glycoloyl)amino]-N-(3-{[2-(2,5-dioxo-2,5-dihydro-1H-pyrrol-1-yl)ethyl]amino}-3-oxopropyl)butanamide (1:1)

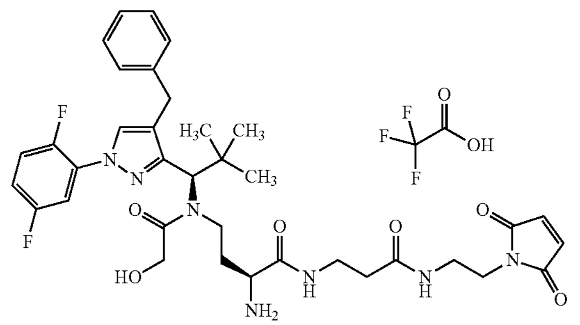 [SMILES: CC(C)(C)[C@H](c1nn(-c2cc(F)ccc2F)cc1Cc1ccccc1)N(CC[C@H](N)C(=O)NCCC(=O)NCCN1C(=O)C=CC1=O)C(=O)CO ; O=C(O)C(F)(F)F]

The title compound was prepared from 8 mg (0.012 mmol) of Intermediate C51 by reaction with 4.5 mg (0.017 mmol) of trifluoroacetic acid/1-(2-aminoethyl)-1H-pyrrole-2,5-dione (1:1) in the presence of 5.8 mg (0.015 mmol) of HATU and 10 μl of N,N-diisopropylethylamine and subsequent deprotection with trifluoroacetic acid. This gave 7 mg (78% of theory over 2 steps).

LC-MS (Method 1): $R_t$=0.83 min; MS (EIpos): m/z=708 $[M+H]^+$.

Intermediate F87

Trifluoroacetic Acid/(2S)-2-amino-4-[{(1R)-1-[4-benzyl-1-(2,5-difluorophenyl)-1H-pyrazol-3-yl]-2,2-dimethylpropyl}(glycoloyl)amino]-N-(3-{[2-(2,5-dioxo-2,5-dihydro-1H-pyrrol-1-yl)ethyl]amino}-3-oxopropyl)butanamide (1:1)

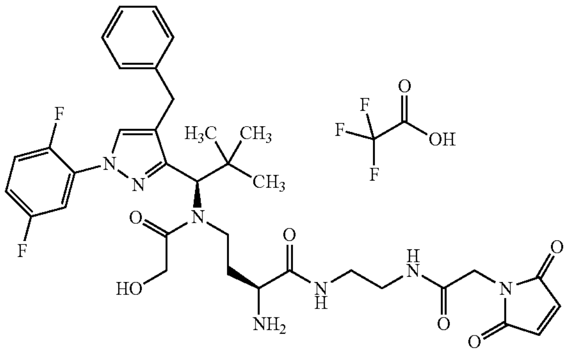 [SMILES: CC(C)(C)[C@H](c1nn(-c2cc(F)ccc2F)cc1Cc1ccccc1)N(CC[C@H](N)C(=O)NCCNC(=O)CN1C(=O)C=CC1=O)C(=O)CO ; O=C(O)C(F)(F)F]

The title compound was prepared analogously to Intermediate F2 from 16 mg (0.025 mmol) of Intermediate C49 by reaction with 24 mg (0.076 mmol) of Intermediate L1 in the presence of EDCI/HOBT and N,N-diisopropylethylamine and subsequent deprotection with trifluoroacetic acid. This gave 3 mg of the title compound (14% of theory over 2 steps).

LC-MS (Method 1): $R_t$=0.88 min; MS (EIpos): m/z=694 $[M+H]^+$.

Intermediate F88

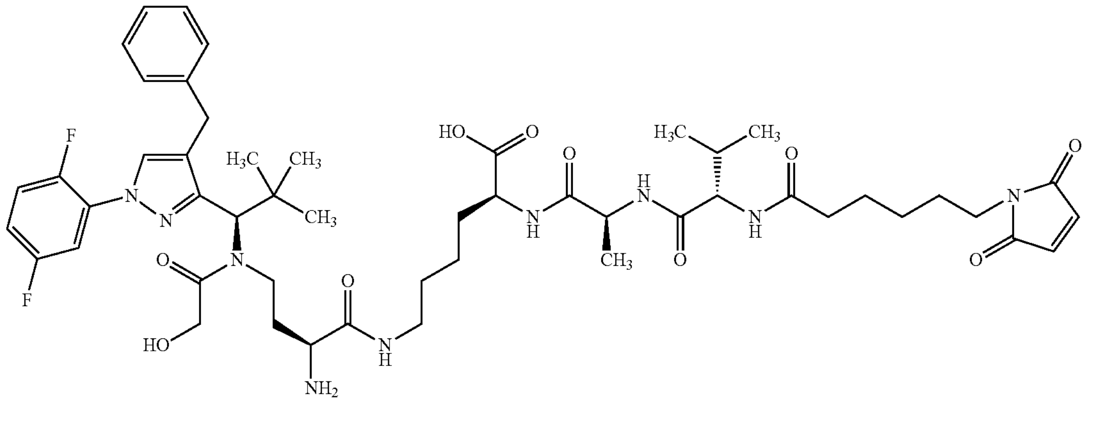 [SMILES: CC(C)[C@H](NC(=O)CCCCCN1C(=O)C=CC1=O)C(=O)N[C@@H](C)C(=O)N[C@@H](CCCCNC(=O)[C@@H](N)CCN(C(=O)CO)[C@@H](c1nn(-c2cc(F)ccc2F)cc1Cc1ccccc1)C(C)(C)C)C(=O)O]

The compound was prepared analogously to Intermediate F8.

LC-MS (Method 5): $R_t$=2.97 min; MS (EIpos): m/z=1006 [M+H]+.

Intermediate F89

Trifluoroacetic Acid/N-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-beta-alanyl-L-alanyl-$N^5$-carbamoyl-N-[4-(2,5-dioxo-2,5-dihydro-1H-pyrrol-1-yl)phenyl]-L-ornithinamide (1:1)

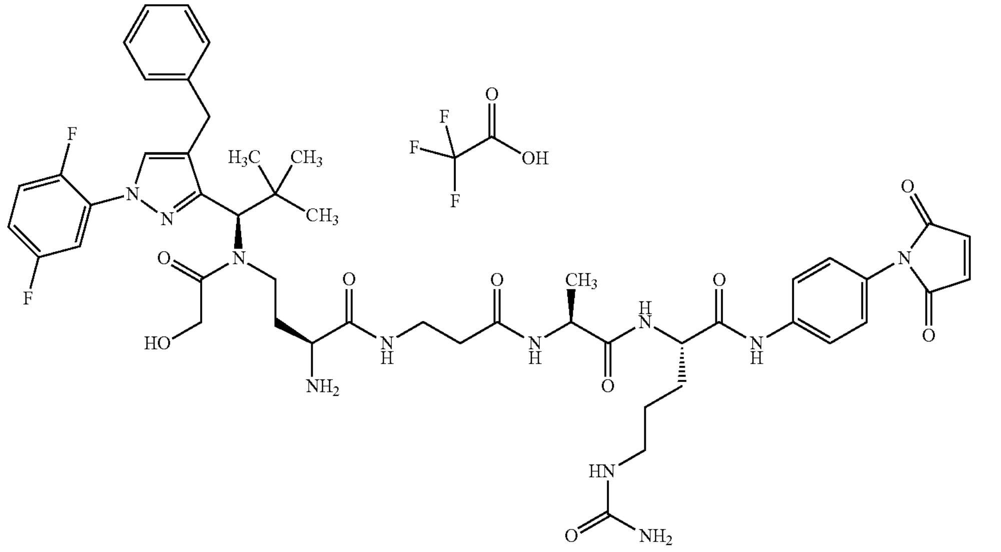 [SMILES: C[C@H](NC(=O)CCNC(=O)[C@@H](N)CCN(C(=O)CO)[C@@H](c1nn(-c2cc(F)ccc2F)cc1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

The title compound was prepared from 8 mg (0.012 mmol) of Intermediate C51 by reaction with 7.4 mg (0.014 mmol) of Intermediate L8 in the presence of 5.8 mg (0.015 mmol) of HATU and 10 µl of N,N-diisopropylethylamine and subsequent deprotection with trifluoroacetic acid. This gave 10 mg (78% of theory over 2 steps).

LC-MS (Method 1): $R_t$=0.87 min; MS (EIpos): m/z=984 $[M+H]^+$.

Intermediate F90

N-[6-(2,5-Dioxo-2,5-dihydro-1H-pyrrol-1-yl)hexanoyl]-L-valyl-$N^5$-carbamoyl-L-ornithyl-$N^6$-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-L-lysine/trifluoroacetic Acid (1:1)

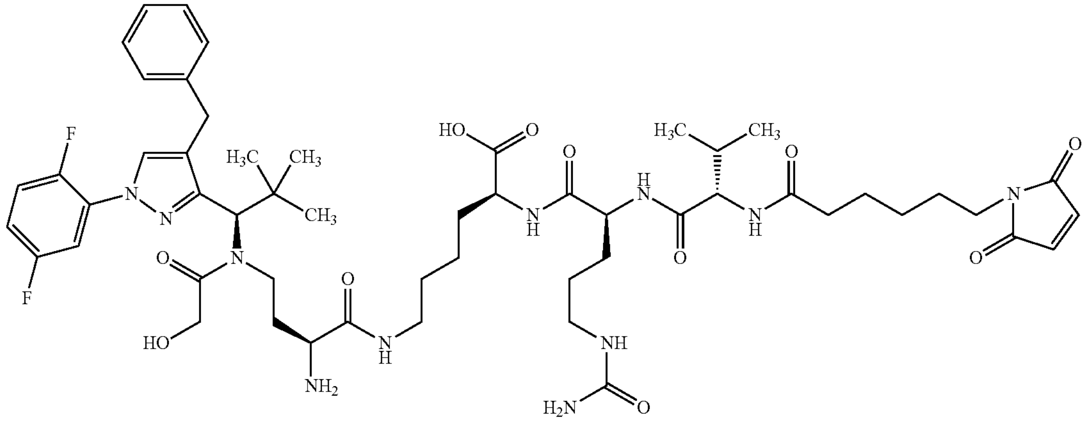 [SMILES: CC(C)[C@H](NC(=O)CCCCCN1C(=O)C=CC1=O)C(=O)N[C@@H](CCCNC(N)=O)C(=O)N[C@@H](CCCCNC(=O)[C@@H](N)CCN(C(=O)CO)[C@@H](c1nn(-c2cc(F)ccc2F)cc1Cc1ccccc1)C(C)(C)C)C(=O)O]

The title compound was prepared from 11 mg (0.018 mmol) of Intermediate C49 by reaction with 13.7 mg (0.018 mmol) of Intermediate L17 in the presence of 34 mg (0.089 mmol) of HATU and 19 μl of N,N-diisopropylethylamine and subsequent deprotection with trifluoroacetic acid. This gave 7.5 mg (35% of theory over 2 steps).

LC-MS (Method 8): $R_t$=6.78 min; MS (EIpos): m/z=1092 $[M+H]^+$.

Intermediate F91

Trifluoroacetic Acid/(2S)-2-amino-4-[{(1R)-1-[4-benzyl-1-(2,5-difluorophenyl)-1H-pyrazol-3-yl]-2,2-dimethylpropyl}(glycoloyl)amino]-N-[2-(2,5-dioxo-2,5-dihydro-1H-pyrrol-1-yl)ethyl]butanamide (1:1)

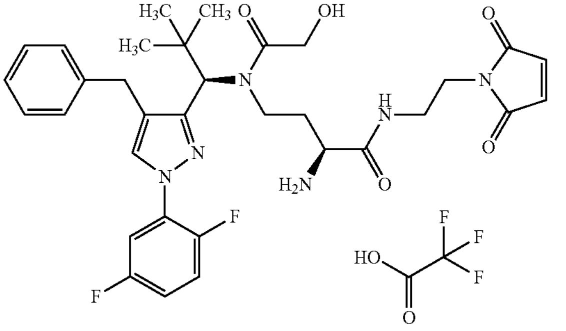 [SMILES: CC(C)(C)[C@H](c1nn(-c2cc(F)ccc2F)cc1Cc1ccccc1)N(CC[C@H](N)C(=O)NCCN1C(=O)C=CC1=O)C(=O)CO ; O=C(O)C(F)(F)F]

9.3 mg (0.01 mmol) of tert-butyl [(2S)-4-[{(1R)-1-[4-benzyl-1-(2,5-difluorophenyl)-1H-pyrazol-3-yl]-2,2-dimethylpropyl}(glycoloyl)amino]-1-{[2-(2,5-dioxo-2,5-dihydro-1H-pyrrol-1-yl)ethyl]amino}-1-oxobutan-2-yl] carbamate were dissolved in 2 ml of dichloromethane, and 740 mg (6.49 mmol, 0.50 ml) of trifluoroacetic acid were added and the mixture was stirred at RT for 1.5 h. The reaction mixture was then concentrated and the residue was taken up in acetonitrile and water and lyophilized. This gave 9.2 mg (96% of theory) of the target compound.

LC-MS (Method 1): $R_t$=0.88 min; MS (EIpos): m/z=637 $[M+H]^+$.

Intermediate F103

N-[19-(2,5-Dioxo-2,5-dihydro-1H-pyrrol-1-yl)-7-oxo-4,7,10,13-tetraoxa-16-azanonadecan-1-oyl]-L-valyl-N-(3-{[(1R)-1-(3-benzyl-7-chloro-4-oxo-3,4-dihydroquinazolin-2-yl)-2-methylpropyl](4-methylbenzoyl)amino}propyl)-L-alaninamide

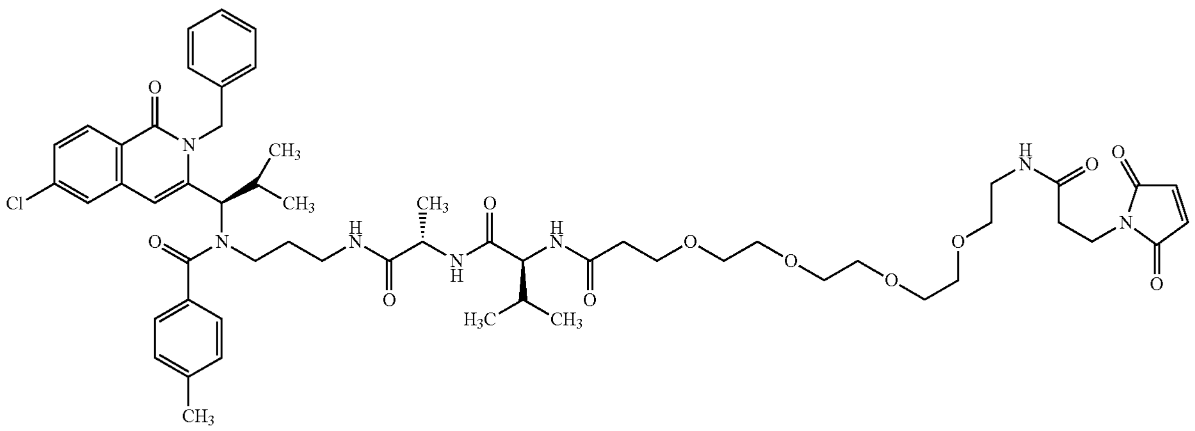 [SMILES: Cc1ccc(C(=O)N(CCCNC(=O)[C@H](C)NC(=O)[C@@H](NC(=O)CCOCCOCCOCCOCCNC(=O)CCN2C(=O)C=CC2=O)C(C)C)[C@@H](c2cc3cc(Cl)ccc3c(=O)n2Cc2ccccc2)C(C)C)cc1]

The title compound was prepared from 10 mg (0.019 mmol) of N-(3-aminopropyl)-N-[(1R)-1-(3-benzyl-7-chloro-4-oxo-3,4-dihydroquinazolin-2-yl)-2-methylpropyl]-4-methylbenzamide by reaction with 11.3 mg (0.019 mmol) of Intermediate L44 in the presence of 8.8 mg (0.023 mmol) of HATU and 10 μl of N,N-diisopropylethylamine. Purification was by preparative HPLC.

Yield: 8.5 mg (35% of theory)

LC-MS (Method 5): $R_t$=3.82 min; MS (EIpos): m/z=1085 $[M+H]^+$.

Intermediate F104

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[(2,5-dioxo-2,5-dihydro-1H-pyrrol-1-yl)acetyl]amino}ethyl) butanamide (1:1)

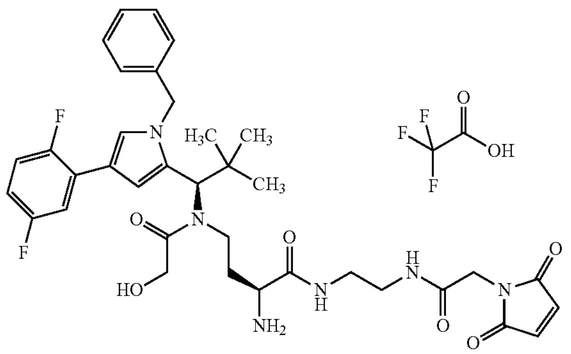 [SMILES: CC(C)(C)[C@H](c1cc(-c2cc(F)ccc2F)cn1Cc1ccccc1)N(CC[C@H](N)C(=O)NCCNC(=O)CN1C(=O)C=CC1=O)C(=O)CO ; O=C(O)C(F)(F)F]

15 mg (0.023 mmol) of Intermediate C58 were initially reacted with 11 mg (0.036 mmol) of Intermediate L1 in the presence of 13 mg (0.034 mmol) of HATU and 10 μl of N,N-diisopropylethylamine. After 60 min of stirring at RT, the mixture was concentrated and the residue was purified by preparative HPLC. This gave 12.3 mg (63% of theory) of the protected intermediate.

LC-MS (Method 1): $R_t$=1.3 min; MS (EIpos): m/z=837 $[M+H]^+$.

In the second step, this intermediate was dissolved in 3 ml of 2,2,2-trifluoroethanol. 12 mg (0.088 mmol) of zinc chloride were added, and the reaction was stirred at 50° C. for 2 h. 26 mg (0.088 mmol) of ethylenediamine-N,N,N',N'-tetraacetic acid and 2 ml of a 0.1% strength aqueous trifluoroacetic acid solution were then added. The reaction was purified by preparative HPLC. Concentration of the appropriate fractions and lyophilization of the residue from acetonitrile/water gave 8.1 mg (68% of theory) of the title compound.

LC-MS (Method 1): $R_t$=0.89 min; MS (ESIpos): m/z=693 $(M+H)^+$.

Intermediate F105

$N^2$-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-N-[2-(2,5-dioxo-2,5-dihydro-1H-pyrrol-1-yl)ethyl]-L-glutamine/trifluoroacetic Acid (1:1)

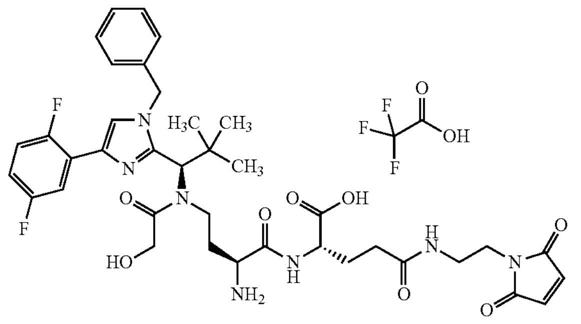 [SMILES: CC(C)(C)[C@H](c1nc(-c2cc(F)ccc2F)cn1Cc1ccccc1)N(CC[C@H](N)C(=O)N[C@@H](CCC(=O)NCCN1C(=O)C=CC1=O)C(=O)O)C(=O)CO ; O=C(O)C(F)(F)F]

The title compound was prepared analogously to Intermediate F32 from Intermediate C5 and Intermediate L46.

LC-MS (Method 1): $R_t$=0.82 min; MS (EIpos): m/z=766 $[M+H]^+$.

Intermediate F106

Trifluoroacetic Acid/N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-L-alanyl-N5-carbamoyl-N-[4-(2,5-dioxo-2,5-dihydro-1H-pyrrol-1-yl)phenyl]-L-ornithinamide (1:1)

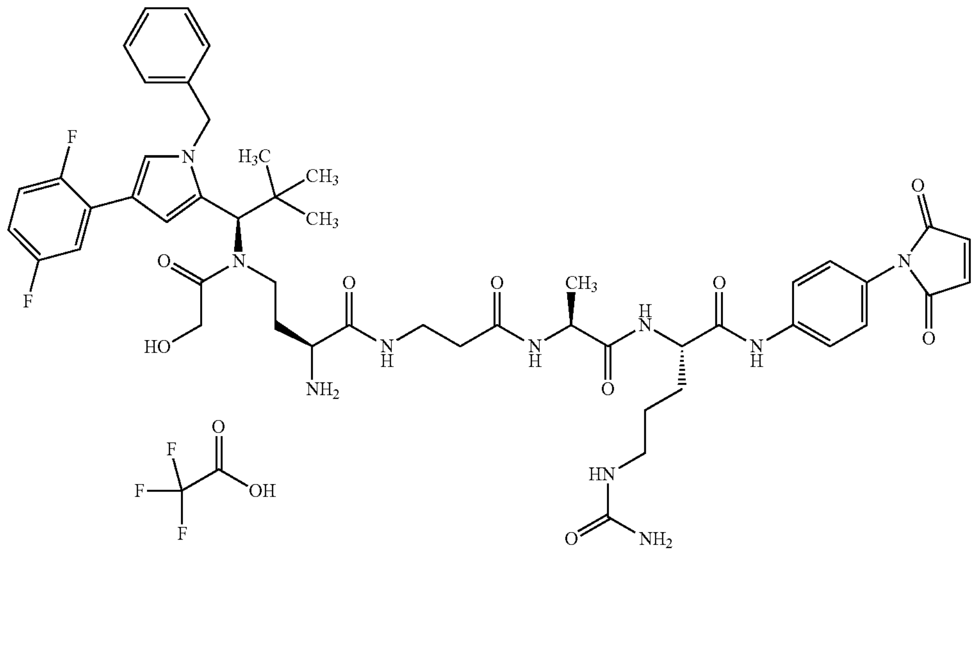 [SMILES: C[C@H](NC(=O)CCNC(=O)[C@@H](N)CCN(C(=O)CO)[C@@H](c1cc(-c2cc(F)ccc2F)cn1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

The title compound was prepared analogously to Intermediate F104 from Intermediate C53 and Intermediate L47.

HPLC (Method 11): $R_t$=1.85 min;

LC-MS (Method 1): $R_t$=0.86 min; MS (ESIpos): m/z=983 $(M+H)^+$.

Intermediate F107

Trifluoroacetic Acid/(1R,2S)-2-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

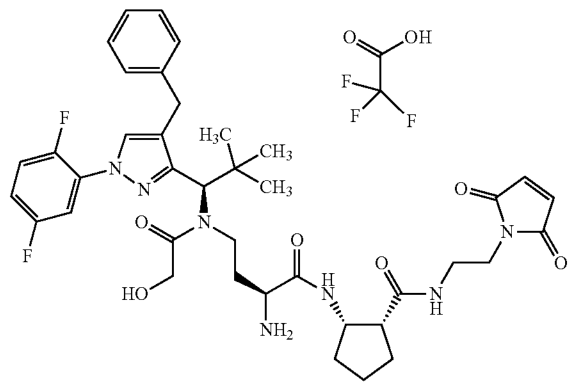 [SMILES: CC(C)(C)[C@H](c1nn(-c2cc(F)ccc2F)cc1Cc1ccccc1)N(CC[C@H](N)C(=O)N[C@H]1CCC[C@H]1C(=O)NCCN1C(=O)C=CC1=O)C(=O)CO ; O=C(O)C(F)(F)F]

The title compound was prepared from 15 mg (0.024 mmol) of Intermediate C49 by reaction with 22.3 mg (0.049 mmol) of Intermediate L48 in the presence of 14 mg (0.037 mmol) of HATU and 21 μl of N,N-diisopropylethylamine and subsequent deprotection with trifluoroacetic acid. This gave 13 mg (60% of theory over 2 steps).

LC-MS (Method 1): $R_t$=0.9 min; MS (EIpos): m/z=748 $[M+H]^+$.

Intermediate F108

Trifluoroacetic Acid/(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

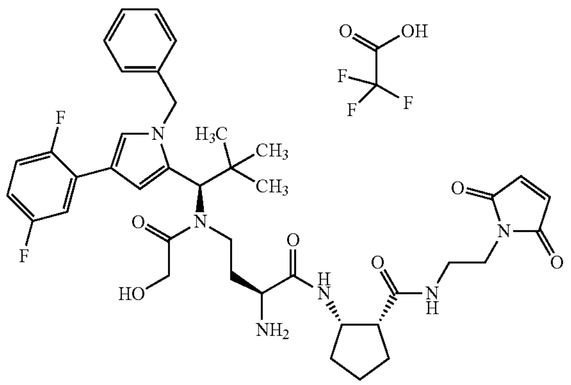 [SMILES: CC(C)(C)[C@H](c1cc(-c2cc(F)ccc2F)cn1Cc1ccccc1)N(CC[C@H](N)C(=O)N[C@H]1CCC[C@H]1C(=O)NCCN1C(=O)C=CC1=O)C(=O)CO ; O=C(O)C(F)(F)F]

The title compound was prepared analogously to Intermediate F104 from 20 mg (0.027 mmol) of Intermediate C53 and 24 mg (0.054 mmol) of Intermediate L48. This gave 3 mg (14% of theory over 2 steps).

LC-MS (Method 1): $R_t$=0.93 min; MS (EIpos): m/z=747 $[M+H]^+$.

Intermediate F109

Trifluoroacetic Acid/(2S)-2-amino-4-[{(1R)-1-[4-benzyl-1-(2,5-difluorophenyl)-1H-pyrazol-3-yl]-2,2-dimethylpropyl}(glycoloyl)amino]-N-{2-[(bromoacetyl)amino]ethyl}butanamide (1:1)

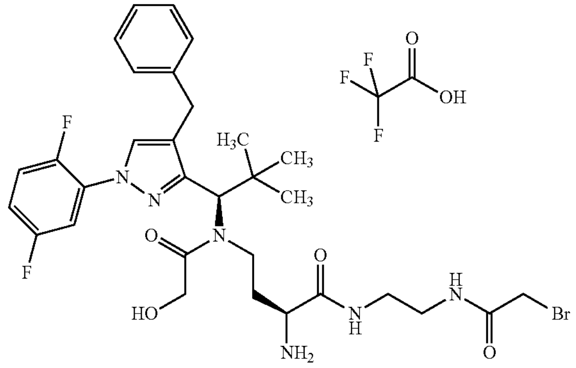 [SMILES: CC(C)(C)[C@H](c1nn(-c2cc(F)ccc2F)cc1Cc1ccccc1)N(CC[C@H](N)C(=O)NCCNC(=O)CBr)C(=O)CO ; O=C(O)C(F)(F)F]

17 mg (0.026 mmol) of Intermediate C57 were taken up in 3 ml of DMF and reacted with 7 mg (0.027 mmol) of commercially available 1-(2-bromoacetoxy)pyrrolidine-2,5-dione in the presence of 14 μl of N,N-diisopropylethylamine. After 15 min of stirring at RT, the mixture was concentrated and the residue was purified by preparative HPLC. This gave 7 mg (33% of theory) of this intermediate.

LC-MS (Method 1): $R_t$=1.29 min; MS (ESIpos): m/z=777 and 779 $(M+H)^+$.

This intermediate was taken up in 1 ml of dichloromethane and deprotected with 1 ml of trifluoroacetic acid. After concentration and lyophilization from acetonitrile/water, 6 mg (88% of theory) of the title compound were obtained.

LC-MS (Method 1): $R_t$=0.86 min; MS (ESIpos): m/z=677/679 $(M+H)^+$.

Intermediate F110

N-(Bromoacetyl)-L-valyl-L-alanyl-N6-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-L-lysine/trifluoroacetic Acid (1:1)

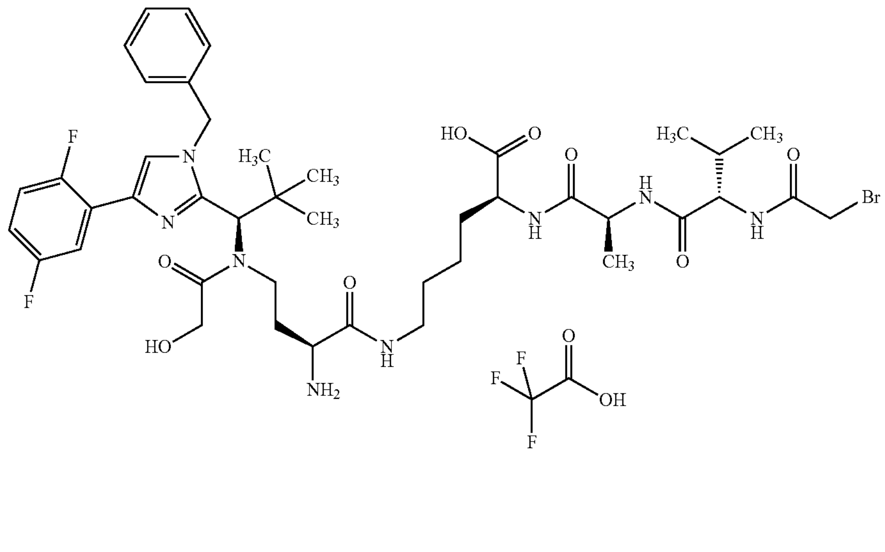 [SMILES: CC(C)[C@H](NC(=O)CBr)C(=O)N[C@@H](C)C(=O)N[C@@H](CCCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared analogously to Intermediate F109 from 16 mg (0.023 mmol) of Intermediate C5 and 17 mg (0.025 mmol) of Intermediate L49. This gave 6 mg (24% of theory over 2 steps) of the title compound.

HPLC (Method 11): $R_t$=1.93 min;

LC-MS (Method 1): $R_t$=0.88 min; MS (ESIpos): m/z=933 and 935 $(M+H)^+$.

Intermediate F111

Trifluoroacetic Acid/(1S,3R)-3-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

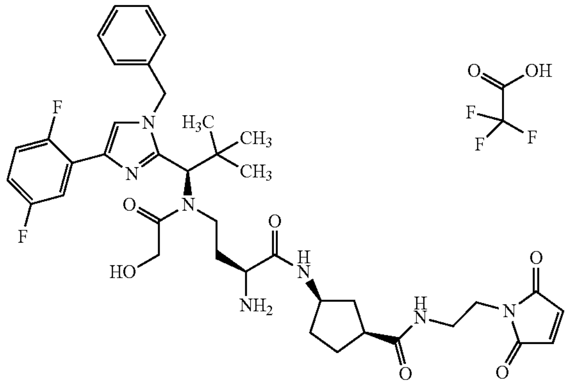 [SMILES: CC(C)(C)[C@H](c1nc(-c2cc(F)ccc2F)cn1Cc1ccccc1)N(CC[C@H](N)C(=O)N[C@@H]1CC[C@H](C(=O)NCCN2C(=O)C=CC2=O)C1)C(=O)CO ; O=C(O)C(F)(F)F]

The title compound was prepared from 15 mg (0.022 mmol) of Intermediate C5 by reaction with 16 mg (0.044 mmol) of Intermediate L50 in the presence of 12.5 mg (0.032 mmol) of HATU and 19 μl of N,N-diisopropylethylamine and subsequent deprotection with trifluoroacetic acid. This gave 13 mg (67% of theory over 2 steps).

LC-MS (Method 1): $R_t$=0.89 min; MS (EIpos): m/z=748 $[M+H]^+$.

Intermediate F112

Trifluoroacetic Acid/(1S,3R)-3-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

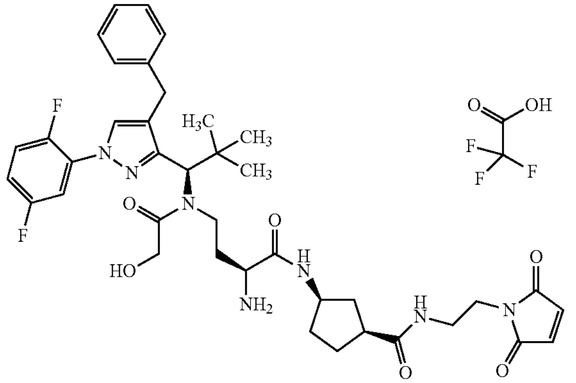 [SMILES: CC(C)(C)[C@H](c1nn(-c2cc(F)ccc2F)cc1Cc1ccccc1)N(CC[C@H](N)C(=O)N[C@@H]1CC[C@H](C(=O)NCCN2C(=O)C=CC2=O)C1)C(=O)CO ; O=C(O)C(F)(F)F]

The title compound was prepared from 15 mg (0.024 mmol) of Intermediate C49 by reaction with 18 mg (0.049 mmol) of Intermediate L50 in the presence of 14 mg (0.037 mmol) of HATU and 21 μl of N,N-diisopropylethylamine and subsequent deprotection with trifluoroacetic acid. This gave 12 mg (51% of theory over 2 steps).

LC-MS (Method 1): $R_t$=0.89 min; MS (EIpos): m/z=748 $[M+H]^+$.

Intermediate F113

Trifluoroacetic Acid/(1S,3R)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

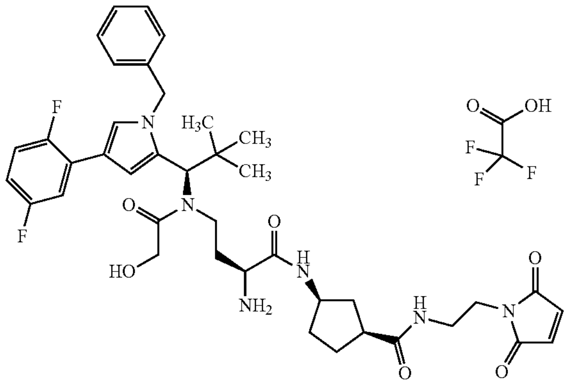 [SMILES: CC(C)(C)[C@H](c1cc(-c2cc(F)ccc2F)cn1Cc1ccccc1)N(CC[C@H](N)C(=O)N[C@@H]1CC[C@H](C(=O)NCCN2C(=O)C=CC2=O)C1)C(=O)CO ; O=C(O)C(F)(F)F]

The title compound was prepared from 15 mg (0.019 mmol) of Intermediate C53 by reaction with 14 mg (0.038 mmol) of Intermediate L50 in the presence of 11 mg (0.029 mmol) of HATU and 17 μl of N,N-diisopropylethylamine and subsequent deprotection with 133 mg of DABCO in 2 ml of DMF. Purification by HPLC gave 4 mg (24% of theory over 2 steps).

LC-MS (Method 5): $R_t$=2.77 min; MS (EIpos): m/z=747 $[M+H]^+$.

Intermediate F114

Trifluoroacetic Acid/(1R,3R)-3-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

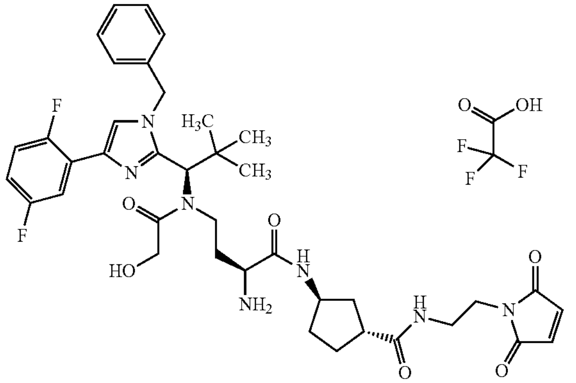 [SMILES: CC(C)(C)[C@H](c1nc(-c2cc(F)ccc2F)cn1Cc1ccccc1)N(CC[C@H](N)C(=O)N[C@@H]1CC[C@@H](C(=O)NCCN2C(=O)C=CC2=O)C1)C(=O)CO ; O=C(O)C(F)(F)F]

The title compound was prepared from 15 mg (0.022 mmol) of Intermediate C5 by reaction with 16 mg (0.044 mmol) of Intermediate L51 in the presence of 12.6 mg (0.032 mmol) of HATU and 19 μl of N,N-diisopropylethylamine and subsequent deprotection with trifluoroacetic acid. This gave 11 mg (53% of theory over 2 steps).

LC-MS (Method 1): $R_t$=0.89 min; MS (EIpos): m/z=748 $[M+H]^+$.

Intermediate F115

Trifluoroacetic Acid/(1R,3R)-3-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

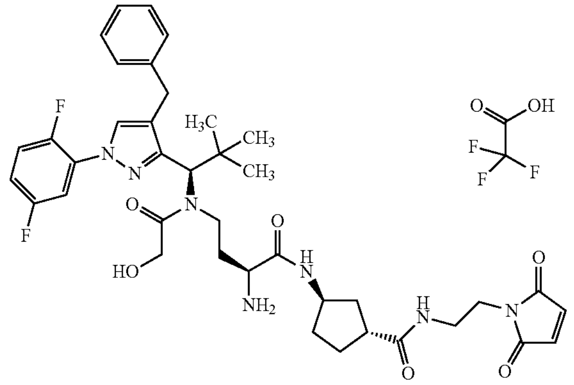 [SMILES: CC(C)(C)[C@H](c1nn(-c2cc(F)ccc2F)cc1Cc1ccccc1)N(CC[C@H](N)C(=O)N[C@@H]1CC[C@@H](C(=O)NCCN2C(=O)C=CC2=O)C1)C(=O)CO ; O=C(O)C(F)(F)F]

The title compound was prepared from 15 mg (0.024 mmol) of Intermediate C49 by reaction with 18 mg (0.047 mmol) of Intermediate L51 in the presence of 13 mg (0.035 mmol) of HATU and 21 μl of N,N-diisopropylethylamine and subsequent deprotection with trifluoroacetic acid. This gave 12 mg (51% of theory over 2 steps).

LC-MS (Method 1): $R_t$=0.87 min; MS (EIpos): m/z=748 $[M+H]^+$.

Intermediate F116

Trifluoroacetic Acid/(1R,3R)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

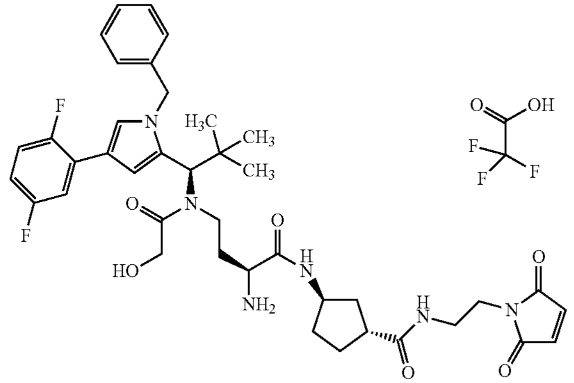 [SMILES: CC(C)(C)[C@H](c1cc(-c2cc(F)ccc2F)cn1Cc1ccccc1)N(CC[C@H](N)C(=O)N[C@@H]1CC[C@@H](C(=O)NCCN2C(=O)C=CC2=O)C1)C(=O)CO ; O=C(O)C(F)(F)F]

The title compound was prepared from 11 mg (0.014 mmol) of Intermediate C53 by reaction with 11 mg (0.028 mmol) of Intermediate L51 in the presence of 8 mg (0.021 mmol) of HATU and 12 μl of N,N-diisopropylethylamine and subsequent deprotection with 87 mg of DABCO in 2 ml of DMF. Purification by HPLC gave 3.3 mg (28% of theory over 2 steps).

LC-MS (Method 1): $R_t$=0.92 min; MS (EIpos): m/z=747 $[M+H]^+$.

Intermediate F117

Trifluoroacetic Acid/N-[(3S)-3-amino-4-{2-[6-(2,5-dioxo-2,5-dihydro-1H-pyrrol-1-yl)hexanoyl]hydrazino}-4-oxobutyl]-N-{(1R)-1-[4-benzyl-1-(2,5-difluorophenyl)-1H-pyrazol-3-yl]-2,2-dimethylpropyl}-2-hydroxyacetamide (1:1)

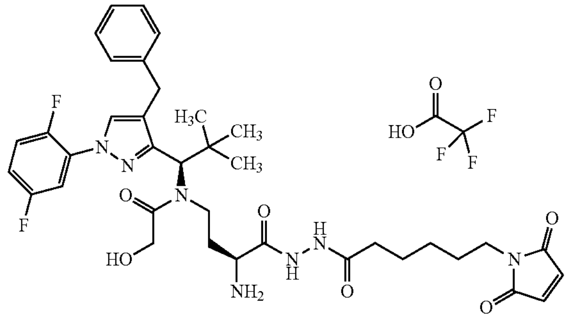 [SMILES: CC(C)(C)[C@H](c1nn(-c2cc(F)ccc2F)cc1Cc1ccccc1)N(CC[C@H](N)C(=O)NNC(=O)CCCCCN1C(=O)C=CC1=O)C(=O)CO ; O=C(O)C(F)(F)F]

The title compound was prepared according to classical methods of peptide chemistry from Intermediate C49. First, C49 was coupled with 9H-fluoren-9-ylmethyl hydrazinecarboxylate in the presence of HATU. The Fmoc protective group was then removed with piperidine in DMF and the hydrazide obtained was coupled with 6-(2,5-dioxo-2,5-dihydro-1H-pyrrol-1-yl)hexanoic acid in the presence of HATU. In the last step, the Boc protective group was removed with TFA in dichloromethane.

LC-MS (Method 1): $R_t$=0.93 min; MS (EIpos): m/z=722 $[M+H]^+$.

Intermediate F118

Trifluoroacetic Acid/N-[(3S)-3-amino-4-{2-[6-(2,5-dioxo-2,5-dihydro-1H-pyrrol-1-yl)hexanoyl]hydrazino}-4-oxobutyl]-N-{(1R)-1-[1-benzyl-4-(2,5-difluorophenyl)-1H-pyrrol-2-yl]-2,2-dimethylpropyl}-2-hydroxyacetamide (1:1)

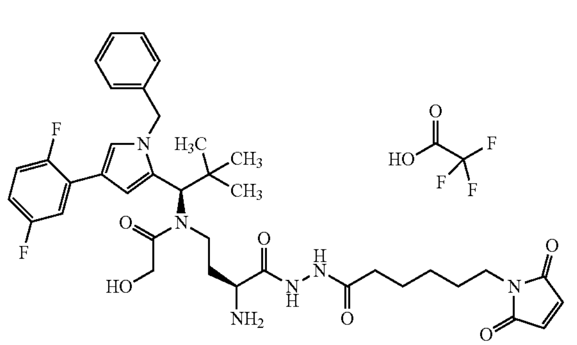 [SMILES: CC(C)(C)[C@H](c1cc(-c2cc(F)ccc2F)cn1Cc1ccccc1)N(CC[C@H](N)C(=O)NNC(=O)CCCCCN1C(=O)C=CC1=O)C(=O)CO ; O=C(O)C(F)(F)F]

In the first step, the title compound was prepared analogously to Intermediate F3 from 15 mg (0.019 mmol) of Intermediate C53 by coupling with commercially available 6-(2,5-dioxo-2,5-dihydro-1H-pyrrol-1-yl)hexanehydrazide in the presence of HATU. The Fmoc protective group was then removed with 142 mg of DABCO in DMF. Purification by HPLC gave 3 mg (19% of theory) of the title compound.

LC-MS (Method 1): $R_t$=0.90 min; MS (EIpos): m/z=721 $[M+H]^+$.

Intermediate F119

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[(bromoacetyl)amino]ethyl}butanamide (1:1)

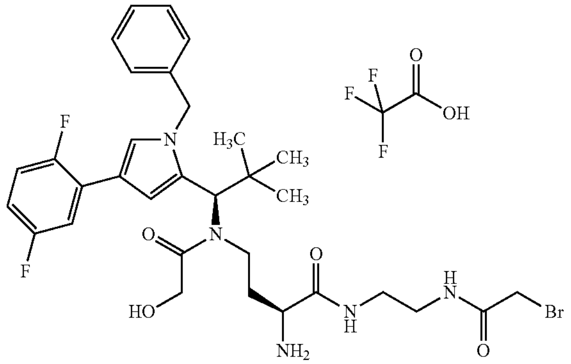 [SMILES: CC(C)(C)[C@H](c1cc(-c2cc(F)ccc2F)cn1Cc1ccccc1)N(CC[C@H](N)C(=O)NCCNC(=O)CBr)C(=O)CO ; O=C(O)C(F)(F)F]

29 mg (0.044 mmol) of Intermediate C58 were taken up in 3.4 ml of DMF, and 36 mg (0.087 mmol) of Intermediate L52, 25 mg (0.065 mmol) of HATU and 19 μl of N,N-diisopropylethylamine were added. After 60 min of stirring at RT, the mixture was concentrated and the residue was purified by preparative HPLC. This gave 26.4 mg (73% of theory) of the intermediate.

LC-MS (Method 1): $R_t$=1.34 min; MS (ESIpos): m/z=820 and 822 $(M+H)^+$.

This intermediate was dissolved in 3 ml of 2,2,2-trifluoroethanol. 6.5 mg (0,048 mmol) of zinc chloride were added, and the reaction was stirred at 50° C. for 4 h. 13.9 mg (0.048 mmol) of ethylenediamine-N,N,N',N'-tetraacetic acid and 2 ml of a 0.1% strength aqueous trifluoroacetic acid solution were added. The reaction was purified by preparative HPLC. Concentration of the appropriate fractions and lyophilization of the residue from acetonitrile/water gave 14.4 mg (58% of theory) of the title compound.

LC-MS (Method 1): $R_t$=0.88 min; MS (ESIpos): m/z=676 and 678 $(M+H)^+$.

Intermediate F120

Trifluoroacetic Acid/(1S,3S)-3-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

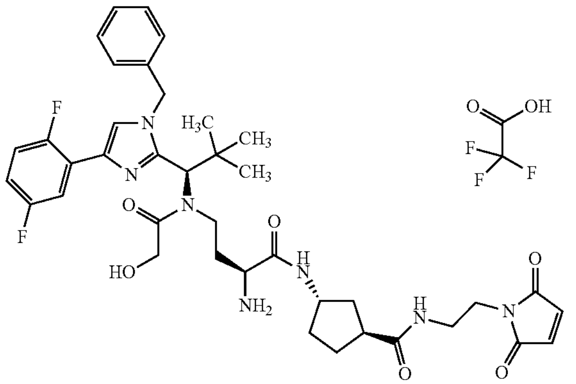 [SMILES: CC(C)(C)[C@H](c1nc(-c2cc(F)ccc2F)cn1Cc1ccccc1)N(CC[C@H](N)C(=O)N[C@H]1CC[C@H](C(=O)NCCN2C(=O)C=CC2=O)C1)C(=O)CO ; O=C(O)C(F)(F)F]

The title compound was prepared from 10 mg (0.015 mmol) of Intermediate C5 by reaction with 11 mg (0.03 mmol) of Intermediate L53 in the presence of 8.4 mg (0.022 mmol) of HATU and 13 μl of N,N-diisopropylethylamine and subsequent deprotection with trifluoroacetic acid. This gave 7.5 mg (59% of theory over 2 steps).

LC-MS (Method 1): $R_t$=0.85 min; MS (EIpos): m/z=748 $[M+H]^+$.

Intermediate F121

Trifluoroacetic Acid/(1S,3S)-3-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

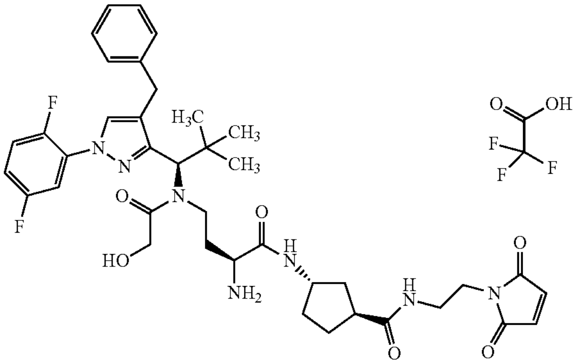 [SMILES: CC(C)(C)[C@H](c1nn(-c2cc(F)ccc2F)cc1Cc1ccccc1)N(CC[C@H](N)C(=O)N[C@H]1CC[C@H](C(=O)NCCN2C(=O)C=CC2=O)C1)C(=O)CO ; O=C(O)C(F)(F)F]

The title compound was prepared from 10 mg (0.016 mmol) of Intermediate C49 by reaction with 11.5 mg (0,031 mmol) of Intermediate L53 in the presence of 9 mg (0.024 mmol) of HATU and 14 μl of N,N-diisopropylethylamine and subsequent deprotection with trifluoroacetic acid. This gave 9 mg (61% of theory over 2 steps).

LC-MS (Method 1): $R_t$=0.84 min; MS (EIpos): m/z=748 $[M+H]^+$.

Intermediate F122

Trifluoroacetic Acid/(1S,3S)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

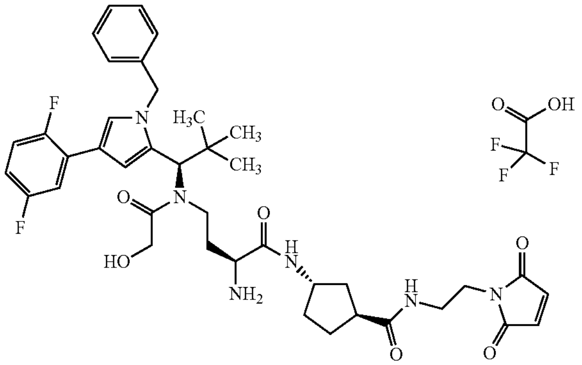 [SMILES: CC(C)(C)[C@H](c1cc(-c2cc(F)ccc2F)cn1Cc1ccccc1)N(CC[C@H](N)C(=O)N[C@H]1CC[C@H](C(=O)NCCN2C(=O)C=CC2=O)C1)C(=O)CO ; O=C(O)C(F)(F)F]

The title compound was prepared from 15 mg (0.019 mmol) of Intermediate C53 by reaction with 14 mg (0.038 mmol) of Intermediate L53 in the presence of 11 mg (0.029 mmol) of HATU and 17 μl of N,N-diisopropylethylamine and subsequent deprotection with 202 mg of DABCO in 3 ml of DMF. Purification by HPLC gave 4 mg (24% of theory over 2 steps).

LC-MS (Method 1): $R_t$=0.87 min; MS (EIpos): m/z=747 $[M+H]^+$.

Intermediate F123

Trifluoroacetic Acid/(1R,3S)-3-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

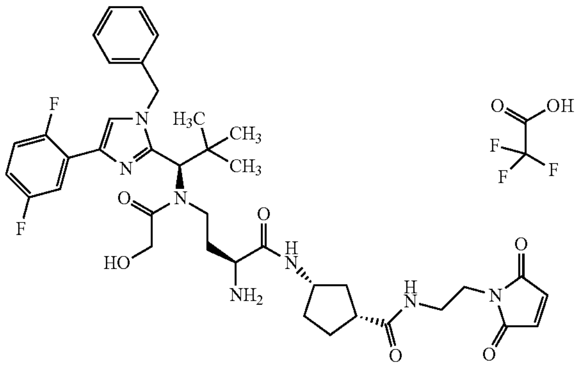 [SMILES: CC(C)(C)[C@H](c1nc(-c2cc(F)ccc2F)cn1Cc1ccccc1)N(CC[C@H](N)C(=O)N[C@H]1CC[C@@H](C(=O)NCCN2C(=O)C=CC2=O)C1)C(=O)CO ; O=C(O)C(F)(F)F]

The title compound was prepared from 10 mg (0.015 mmol) of Intermediate C5 by reaction with 11 mg (0.030 mmol) of Intermediate L54 in the presence of 8.4 mg (0.022 mmol) of HATU and 13 μl of N,N-diisopropylethylamine and subsequent deprotection with trifluoroacetic acid. This gave 4 mg (31% of theory over 2 steps).

LC-MS (Method 1): $R_t$=0.86 min; MS (EIpos): m/z=748 $[M+H]^+$.

Intermediate F124

Trifluoroacetic Acid/(1R,3S)-3-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

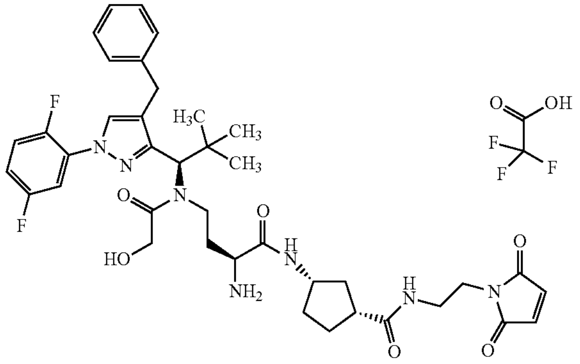 [SMILES: CC(C)(C)[C@H](c1nn(-c2cc(F)ccc2F)cc1Cc1ccccc1)N(CC[C@H](N)C(=O)N[C@H]1CC[C@@H](C(=O)NCCN2C(=O)C=CC2=O)C1)C(=O)CO ; O=C(O)C(F)(F)F]

The title compound was prepared from 10 mg (0.016 mmol) of Intermediate C49 by reaction with 11.5 mg (0.031 mmol) of Intermediate L54 in the presence of 9 mg (0.024 mmol) of HATU and 14 μl of N,N-diisopropylethylamine and subsequent deprotection with trifluoroacetic acid. This gave 9 mg (66% of theory over 2 steps).

LC-MS (Method 1): $R_t$=0.84 min; MS (EIpos): m/z=748 $[M+H]^+$.

Intermediate F125

Trifluoroacetic Acid/(1R,3S)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

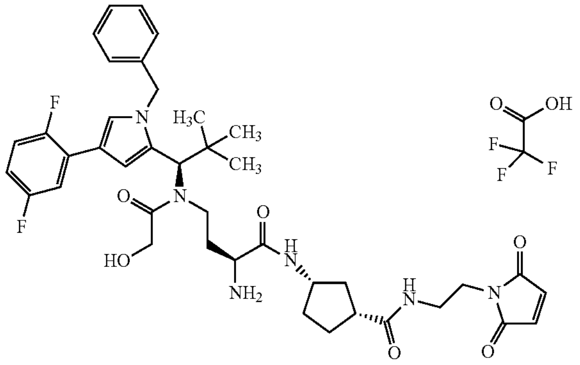 [SMILES: CC(C)(C)[C@H](c1cc(-c2cc(F)ccc2F)cn1Cc1ccccc1)N(CC[C@H](N)C(=O)N[C@H]1CC[C@@H](C(=O)NCCN2C(=O)C=CC2=O)C1)C(=O)CO ; O=C(O)C(F)(F)F]

The title compound was prepared from 15 mg (0.019 mmol) of Intermediate C53 by reaction with 14 mg (0.038 mmol) of Intermediate L54 in the presence of 11 mg (0.029 mmol) of HATU and 17 μl of N,N-diisopropylethylamine and subsequent deprotection with 127 mg of DABCO in 3 ml of DMF. Purification by HPLC gave 3 mg (17% of theory over 2 steps).

LC-MS (Method 4): $R_t$=1.08 min; MS (EIpos): m/z=769 $[M+Na]^+$.

Intermediate F126

N-(Bromoacetyl)-L-valyl-L-alanyl-$N^6$-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-L-lysine/trifluoroacetic Acid (1:1)

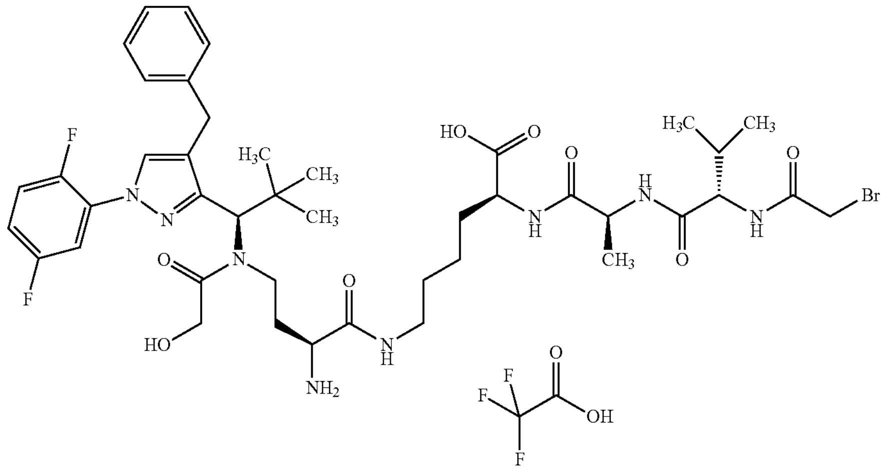 [SMILES: CC(C)[C@H](NC(=O)CBr)C(=O)N[C@@H](C)C(=O)N[C@@H](CCCCNC(=O)[C@@H](N)CCN(C(=O)CO)[C@@H](c1nn(-c2cc(F)ccc2F)cc1Cc1ccccc1)C(C)(C)C)C(=O)O ; O=C(O)C(F)(F)F]

The title compound was prepared analogously to Intermediate F110 from 18 mg (0.027 mmol) of Intermediate C49 and 21 mg (0.027 mmol) of Intermediate L49. This gave 8.7 mg (30% of theory over 2 stages) of the title compound.

HPLC (Method 11): $R_t$=1.94 min;

LC-MS (Method 1): $R_t$=0.86 min; MS (ESIpos): m/z=933 and 935 $(M+H)^+$.

Intermediate F127

Trifluoroacetic Acid/(2S)-2-amino-4-({(1R)-1-[1-benzyl-4-(2,5-difluorophenyl)-1H-pyrrol-2-yl]-2,2-dimethylpropyl}[(2S)-2-methoxypropanoyl]amino)-N-(2-{[(2,5-dioxo-2,5-dihydro-1H-pyrrol-1-yl)acetyl]amino}ethyl)butanamide (1:1)

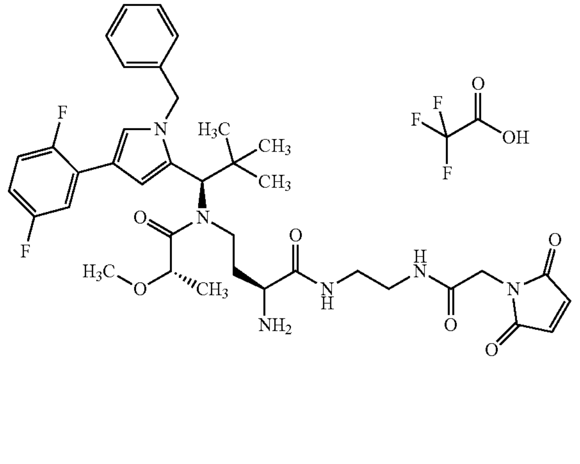 [SMILES: CO[C@@H](C)C(=O)N(CC[C@H](N)C(=O)NCCNC(=O)CN1C(=O)C=CC1=O)[C@@H](c1cc(-c2cc(F)ccc2F)cn1Cc1ccccc1)C(C)(C)C ; O=C(O)C(F)(F)F]

12 mg (0.015 mmol) of Intermediate C59 were dissolved in 2.4 ml of DMF, and 14.6 mg (0.046 mmol) of Intermediate L1, 6 mg (0.031 mmol) of 1-(3-dimethylaminopropyl)-3-ethylcarbodiimide hydrochloride, 5.9 mg (0.039 mmol) of 1-hydroxy-1H-benzotriazole hydrate and 8 μl of N,N-diisopropylethylamine were added. After 1 h of stirring at RT, the mixture was concentrated and the residue was purified by preparative HPLC. This gave 11 mg (70% of theory) of this intermediate.

LC-MS (Method 1): $R_t$=1.34 min; MS (ESIpos): m/z=942 $(M+H)^+$.

11 mg (0.011 mmol) of this intermediate were taken up in 2 ml of DMF, and 123 mg (1.1 mmol) of 1,4-diazabicyclo[2.2.2]octane were added. The reaction was treated in an ultrasonic bath for 2 h. 63 μl of acetic acid were then added and the reaction was concentrated under high vacuum. The residue was purified by preparative HPLC. This gave 2 mg (22% of theory) of the title compound.

LC-MS (Method 1): $R_t$=0.89 min; MS (EIpos): m/z=721 $[M+H]^+$.

HPLC (Method 11): $R_t$=1.95 min.

Intermediate F128

$N^6$—(N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-D-alanyl)-$N^2$—{N-[6-(2,5-dioxo-2,5-dihydro-1H-pyrrol-1-yl)hexanoyl]-L-valyl-L-alanyl}-L-lysine/trifluoroacetic Acid (1:1)

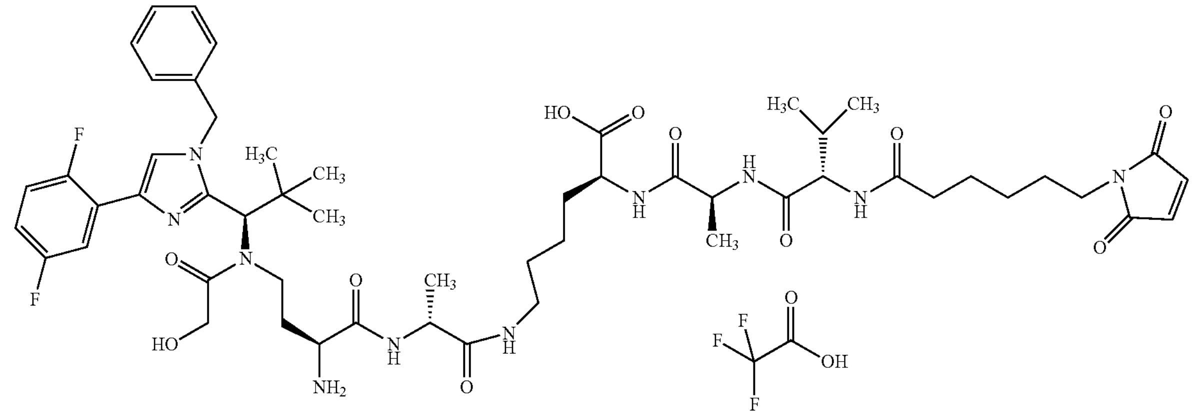

The title compound was prepared from 3 mg (0.005 mmol) of Intermediate C5 by reaction with 2.5 mg (0.003 mmol) of Intermediate L55 in the presence of 2.5 mg (0.007 mmol) of HATU and 3 μl of N,N-diisopropylethylamine and subsequent deprotection with trifluoroacetic acid. This gave 1.4 mg (32% of theory over 2 steps).

LC-MS (Method 1): $R_t$=0.93 min; MS (EIpos): m/z=1077 $[M+H]^+$.

Intermediate F129

N-[6-(2,5-Dioxo-2,5-dihydro-1H-pyrrol-1-yl)hexanoyl]-L-valyl-L-alanyl-$N^6$-{[(1R,3S)-3-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)cyclopentyl]carbonyl}-L-lysine/trifluoroacetic Acid

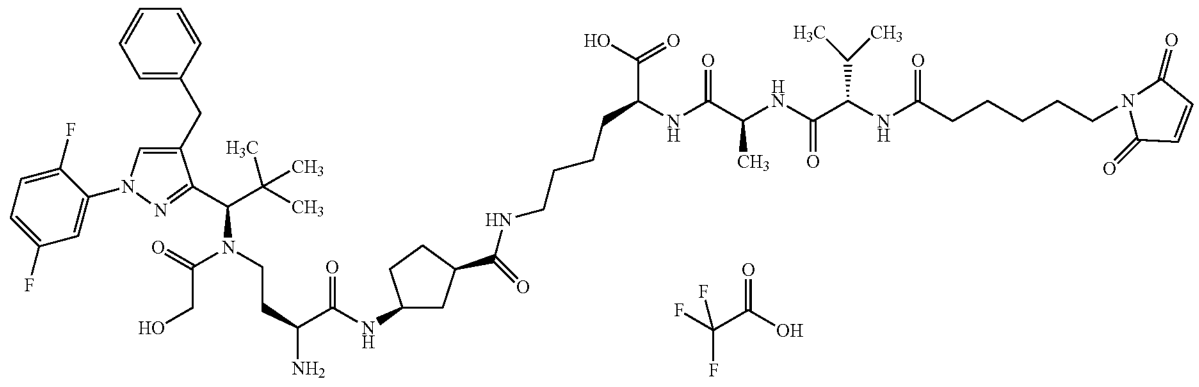 [SMILES: CC(C)[C@H](NC(=O)CCCCCN1C(=O)C=CC1=O)C(=O)N[C@@H](C)C(=O)N[C@@H](CCCCNC(=O)[C@@H]1CC[C@H](NC(=O)[C@@H](N)CCN(C(=O)CO)[C@@H](c2nn(-c3cc(F)ccc3F)cc2Cc2ccccc2)C(C)(C)C)C1)C(=O)O ; O=C(O)C(F)(F)F]

The title compound was prepared analogously to Intermediate F128 from 10 mg (0.016 mmol) of Intermediate C49 by reaction with 19 mg (0.024 mmol) of Intermediate L56 in the presence of 12 mg (0.031 mmol) of HATU and 14 μl of N,N-diisopropylethylamine and subsequent deprotection with trifluoroacetic acid. This gave 13.5 mg (70% of theory over 2 steps).

LC-MS (Method 1): $R_t$=0.9 min; MS (EIpos): m/z=1117 $[M+H]^+$.

Intermediate F142

R/S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-homocysteine/ trifluoroacetic Acid (1:1)

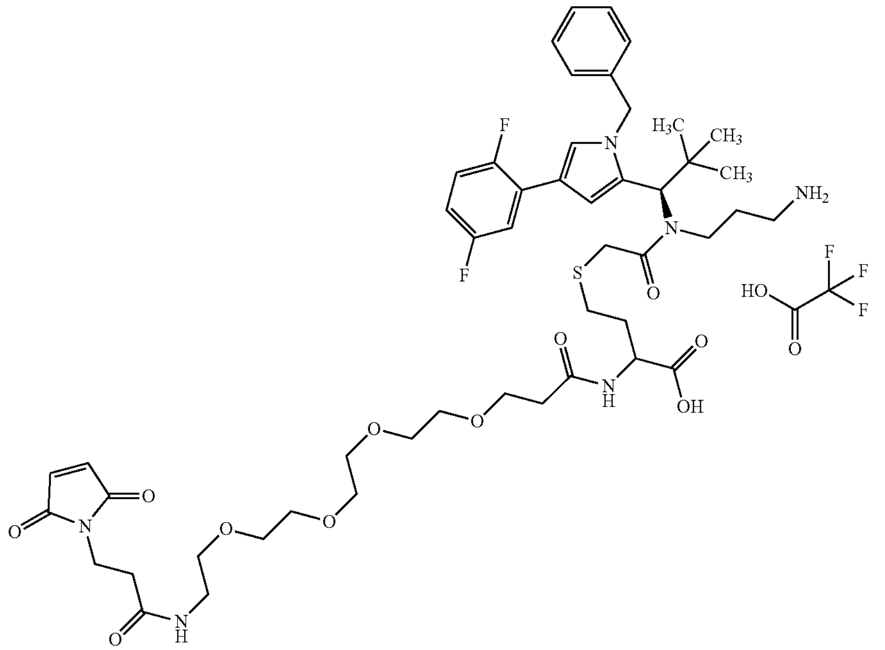 [SMILES: CC(C)(C)[C@H](c1cc(-c2cc(F)ccc2F)cn1Cc1ccccc1)N(CCCN)C(=O)CSCCC(NC(=O)CCOCCOCCOCCOCCNC(=O)CCN1C(=O)C=CC1=O)C(=O)O ; O=C(O)C(F)(F)F]

20.0 mg (23.7 µmol) of R/S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-homocysteine/trifluoroacetic acid (1:1) and 13.4 mg (26.04 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were dissolved in 1.0 ml of DMF, and 4.8 mg (47.34 µmol) of 4-methylmorpholine were added. The reaction mixture was stirred at RT overnight. 3.6 mg (0.06 mmol) of acetic acid were added and the reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 12.4 mg (44% of theory) of the compound R/S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]homocysteine.

LC-MS (Method 1): $R_t$=1.30 min; MS (ESIpos): m/z=1129 (M+H)$^+$.

10.0 mg (8.85 µmol) of R/S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]-L-homocysteine were dissolved in trifluoroethanol, and 3.1 mg (22.71 µmol) of zinc dichloride were added. The reaction mixture was stirred at 50° C. overnight. 3.9 mg (0.01 mmol) of ethylenediamine-N,N,N',N'-tetraacetic acid were added, the reaction mixture was stirred briefly and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was lyophilized with a little water. This gave 7.6 mg (78% of theory) of the title compound.

LC-MS (Method 1): $R_t$=0.94 min; MS (ESIpos): m/z=983 (M+H)$^+$.

$^1$H-NMR (400 MHz, DMSO-d$_6$): δ [ppm]=0.50 (m, 1H), 0.81 (s, 9H), 1.49 (m, 1H), 1.89 (m, 1H), 2.05 (m, 1H), 2.29-2.43 (m, 4H), 2.45-2.55 (m, 2H), 2.58-2.74 (m, 2H), 3.10-3.20 (m, 2H), 3.21-3.40 (m, 2H), 3.42-3.54 (m, 16H), 3.55-3.65 (m, 4H), 4.28 (m, 1H), 4.91 (dd, 1H), 5.18 (dd, 1H), 5.60 (s, 1H), 6.95 (m, 1H), 7.00 (s, 2H), 7.15-7.38 (m, 7H), 7.53 (s, 1H), 7.68 (m, 1H), 8.00 (m, 2H).

Intermediate F143

Trifluoroacetic Acid/6-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-N-[2-(2,5-dioxo-2,5-dihydro-1H-pyrrol-1-yl)ethyl]hexanamide (1:1)

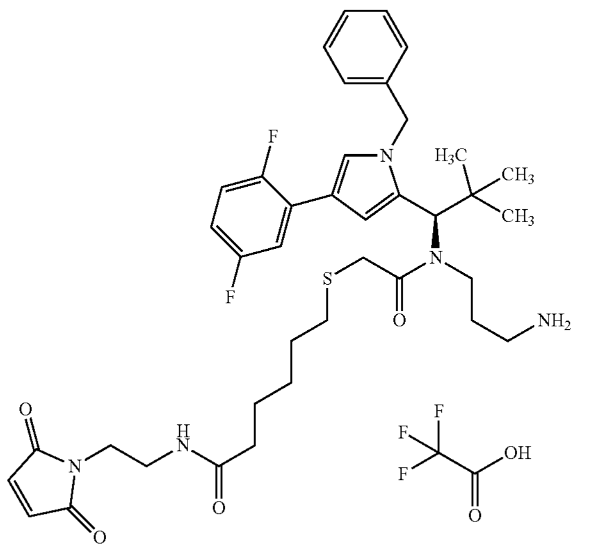 [SMILES: CC(C)(C)[C@H](c1cc(-c2cc(F)ccc2F)cn1Cc1ccccc1)N(CCCN)C(=O)CSCCCCCC(=O)NCCN1C(=O)C=CC1=O ; O=C(O)C(F)(F)F]

30.0 mg (0.05 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate and 13.5 mg (0.07 mmol) of 6-(acetylsulphanyl)hexanoic acid were initially charged in 2.0 ml of methanol with a drop of water. 23.0 mg (0.17 mmol) of potassium carbonate were added. The reaction mixture was stirred at 50° C. for 4 h. Ethyl acetate was added to the reaction mixture. The organic phase was washed with saturated NaCl solution and dried over magnesium sulphate. The solvent was evaporated under reduced pressure. The residue was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 54.2 mg (90% of theory) of the compound 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaicosan-20-oic acid.

LC-MS (Method 1): $R_t$=1.49 min; MS (ESIpos): m/z=1106 $(M+H)^+$.

54.0 mg (0.07 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaicosan-20-oic acid and 16.7 mg (0.09 mmol) of 1-(2-\minoethyl)-1H-pyrrole-2,5-dione hydrochloride (1:1) were initially charged in 3.0 ml of acetonitrile, and 75.0 mg (0.58 mmol) of N,N-diisopropylethylamine were added. 60.0 mg (0.09 mmol) of T3P (50% in acetonitrile) were added and the mixture was stirred at RT overnight. The reaction was quenched with water and the reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 42.8 mg (68% of theory) of the compound 2-(trimethylsilyl)ethyl [3-({(1R)-1-[1-benzyl-4-(2,5-difluorophenyl)-1H-pyrrol-2-yl]-2,2-dimethylpropyl}{[(6-{[2-(2,5-dioxo-2,5-dihydro-1H-pyrrol-1-yl)ethyl]amino}-6-oxohexyl)sulphanyl]acetyl}amino)propyl]carbamate.

LC-MS (Method 1): $R_t$=1.48 min; MS (ESIpos): m/z=866 $(M+H)^+$.

20.0 mg (0.02 mmol) of 2-(trimethylsilyl)ethyl [3-({(1R)-1-[1-benzyl-4-(2,5-difluorophenyl)-1H-pyrrol-2-yl]-2,2-dimethylpropyl}{[(6-{[2-(2,5-dioxo-2,5-dihydro-1H-pyrrol-1-yl)ethyl]amino}-6-oxohexyl)sulphanyl]acetyl}amino)propyl]carbamate were dissolved in 2.0 ml of trifluoroethanol, and 4.7 mg (0.04 mmol) of zinc dichloride were added. The reaction mixture was stirred at 50° C. overnight, and 10.1 mg (0.04 mmol) of ethylenediamine-N,N,N',N'-tetraacetic acid were then added and the mixture was stirred for 10 min. Water (0.1% TFA) was added and the reaction mixture was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 9.2 mg (48% of theory) of the title compound.

LC-MS (Method 1): $R_t$=0.98 min; MS (ESIpos): m/z=722 $(M+H)^+$.

Intermediate F144

Trifluoroacetic Acid/N-(3-aminopropyl)-N-{(1R)-1-[1-benzyl-4-(2,5-difluorophenyl)-1H-imidazol-2-yl]-2,2-dimethylpropyl}-6-(2,5-dioxo-2,5-dihydro-1H-pyrrol-1-yl)hexanamide (1:1)

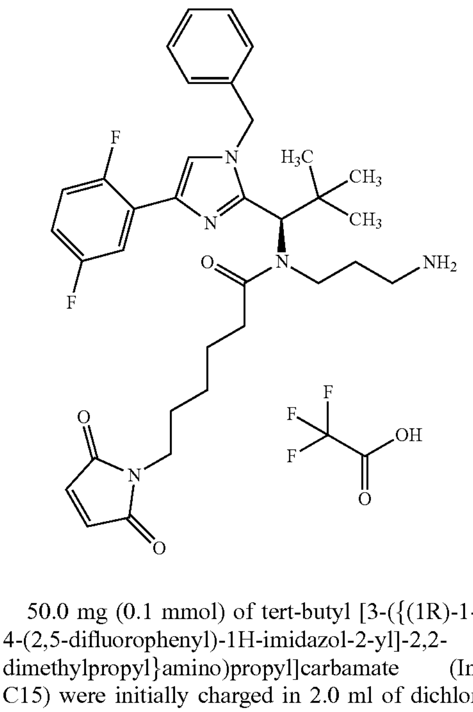

50.0 mg (0.1 mmol) of tert-butyl [3-({(1R)-1-[1-benzyl-4-(2,5-difluorophenyl)-1H-imidazol-2-yl]-2,2-dimethylpropyl}amino)propyl]carbamate (Intermediate C15) were initially charged in 2.0 ml of dichloromethane, and 22.7 mg (0.22 mmol) of triethylamine and 49.3 mg (0.22 mmol) of 6-(2,5-dioxo-2,5-dihydro-1H-pyrrol-1-yl)hexanoyl chloride (Intermediate L60) WISV1648-1-1 were added.

The reaction mixture was stirred at RT overnight. Every 2 h (three times) 1 equivalent of Intermediate L60 and 1.2 equivalents of triethylamine were added, and the mixture was then stirred at RT overnight. This procedure was repeated two more times. The solvent was removed under reduced pressure and the residue was purified by preparative RP-HPLC (column: Reprosil 125×30; 10μ, flow rate: 50 ml/min, MeCN/water). The solvents were evaporated under reduced pressure and the residue was dried under high vacuum. This gave 30.9 mg (43% of theory) of the compound tert-butyl [3-({(1R)-1-[1-benzyl-4-(2,5-difluorophenyl)-1H-imidazol-2-yl]-2,2-dimethylpropyl}[6-(2,5-dioxo-2,5-dihydro-1H-pyrrol-1-yl)hexanoyl]amino)propyl] carbamate.

LC-MS (Method 1): $R_t$=1.51 min; MS (ESIpos): m/z=706 $(M+H)^+$.

24.6 mg (0.04 mmol) of tert-butyl [3-({(1R)-1-[1-benzyl-4-(2,5-difluorophenyl)-1H-imidazol-2-yl]-2,2-dimethylpropyl}[6-(2,5-dioxo-2,5-dihydro-1H-pyrrol-1-yl)hexanoyl] amino)propyl]carbamate were dissolved in 3.0 ml of dichloromethane, 79.5 mg (0.7 mmol) of TFA were added and the mixture was stirred at RT for 6 h. Another 79.5 mg (0.7 mmol) of TFA were added and the mixture was stirred at RT overnight. The solvent was removed under reduced pressure and the residue was co-distilled three times with dichloromethane. The residue was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 24.2 mg (97% of theory) of the title compound.

LC-MS (Method 1): $R_t$=1.02 min; MS (ESIpos): m/z=606 $(M+H)^+$.

Intermediate F145

Trifluoroacetic Acid/6-({2-[(3-aminopropyl) {(1R)-1-[1-benzyl-4-(2,5-difluorophenyl)-1H-imidazol-2-yl]-2,2-dimethylpropyl}amino]-2-oxoethyl}sulphanyl)-N-[2-(2,5-dioxo-2,5-dihydro-1H-pyrrol-1-yl)ethyl]hexanamide

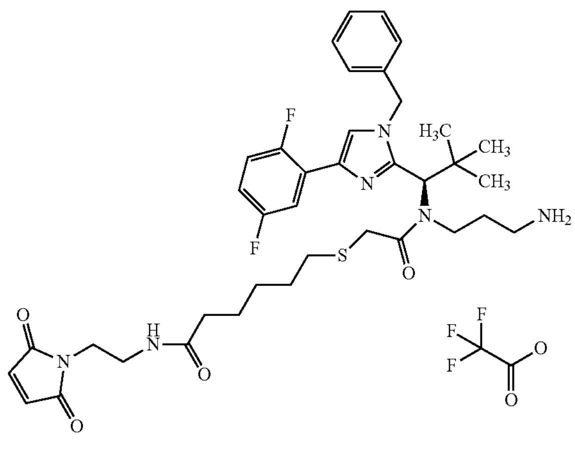 [SMILES: CC(C)(C)[C@H](c1nc(-c2cc(F)ccc2F)cn1Cc1ccccc1)N(CCCN)C(=O)CSCCCCCC(=O)NCCN1C(=O)C=CC1=O ; O=C(O)C(F)(F)F]

90.0 mg (0.15 mmol) of tert-butyl {3-[{(1R)-1-[1-benzyl-4-(2,5-difluorophenyl)-1H-imidazol-2-yl]-2,2-dimethylpropyl}(chloroacetyl)amino]propyl}carbamate, Intermediate C16, and 43.6 mg (0.23 mmol) of 6-(acetylsulphanyl) hexanoic acid were initially charged in 9.0 ml of methanol with a drop of water, and 73.9 mg (0.54 mmol) of potassium carbonate were added. The reaction mixture was stirred at RT for 4 h, and ethyl acetate was then added. The organic phase was washed with water/saturated NaCl solution and with saturated NaCl solution. The organic phase was dried over magnesium sulphate and the solvents were evaporated under reduced pressure. The residue was chromatographed by means of silica gel (mobile phase: dichloromethane/methanol 100:2). The solvents were evaporated under reduced pressure and the residue was dried under high vacuum. This gave 98.7 mg (83% of theory) of the compound 9-{(1R)-1-[1-benzyl-4-(2,5-difluorophenyl)-1H-imidazol-2-yl]-2,2-dimethylpropyl}-2,2-dimethyl-4,10-dioxo-3-oxa-12-thia-5,9-diazaoctadecan-18-oic acid.

LC-MS (Method 1): $R_t$=1.44 min; MS (ESIpos): m/z=701 $(M+H)^+$.

20.0 mg (0.03 mmol) of 9-{(1R)-1-[1-benzyl-4-(2,5-difluorophenyl)-1H-imidazol-2-yl]-2,2-dimethylpropyl}-2,2-dimethyl-4,10-dioxo-3-oxa-12-thia-5,9-diazaoctadecan-18-oic acid and 6.5 (0.04 mmol) of 1-(2-aminoethyl)-1H-pyrrole-2,5-dione hydrochloride (1:1) were initially charged in 1.5 ml of acetonitrile, and 23.6 mg (0.04 mmol) of T3P and 29.5 mg (0.23 mmol) of N,N-diisopropylethylamine were added. The reaction mixture was stirred at RT overnight, and water was then added. The reaction mixture was purified by preparative RP-HPLC (column: Reprosil 250×30; 10μ, flow rate: 50 ml/min, MeCN/water). The solvents were evaporated under reduced pressure and the residue was dried under high vacuum. This gave 16.7 mg (99% of theory) of the compound tert-butyl [3-({(1R)-1-[1-benzyl-4-(2,5-difluorophenyl)-1H-imidazol-2-yl]-2,2-dimethylpropyl}{[(6-{[2-(2,5-dioxo-2,5-dihydro-1H-pyrrol-1-yl)ethyl] amino}-6-oxohexyl) sulphanyl]acetyl}amino)propyl] carbamate.

LC-MS (Method 1): $R_t$=1.40 min; MS (ESIpos): m/z=823 $(M+H)^+$.

14.8 mg (0.02 mmol) of tert-butyl [3-({(1R)-1-[1-benzyl-4-(2,5-difluorophenyl)-1H-imidazol-2-yl]-2,2-dimethylpropyl}{[(6-{[2-(2,5-dioxo-2,5-dihydro-1H-pyrrol-1-yl)ethyl] amino}-6-oxohexyl)sulphanyl]acetyl}amino)propyl] carbamate were dissolved in 1.5 ml of dichloromethane, and 41.0 mg (0.36 mmol) of TFA were added. The reaction mixture was stirred at RT overnight. Then, two more times in each case 41.0 mg (0.36 mmol) of TFA were added and the mixture was stirred at RT overnight. The solvent was evaporated under reduced pressure and the residue was purified by prep. RP-HPLC (column: Reprosil 250×30; 10μ, flow rate: 50 ml/min, MeCN/water, 0.1% TFA). The solvents were evaporated under reduced pressure and the residue was taken up in 1,4-dioxane and water and lyophilized. This gave 2.9 mg (19% of theory) of the title compound.

LC-MS (Method 1): $R_t$=0.93 min; MS (ESIpos): m/z=723 $(M+H)^+$.

Intermediate F146

R/S-[2-([(3S)-3-Amino-3-carboxypropyl]{(1R)-1-[1-benzyl-4-(2,5-difluorophenyl)-1H-pyrrol-2-yl]-2,2-dimethylpropyl}amino)-2-oxoethyl]-N-[19-(2,5-dioxo-2,5-dihydro-1H-pyrrol-1-yl)-17-oxo-4,7,10,13-tetraoxa-16-azanonadecan-1-oyl]homocysteine/trifluoroacetic Acid (1:1)

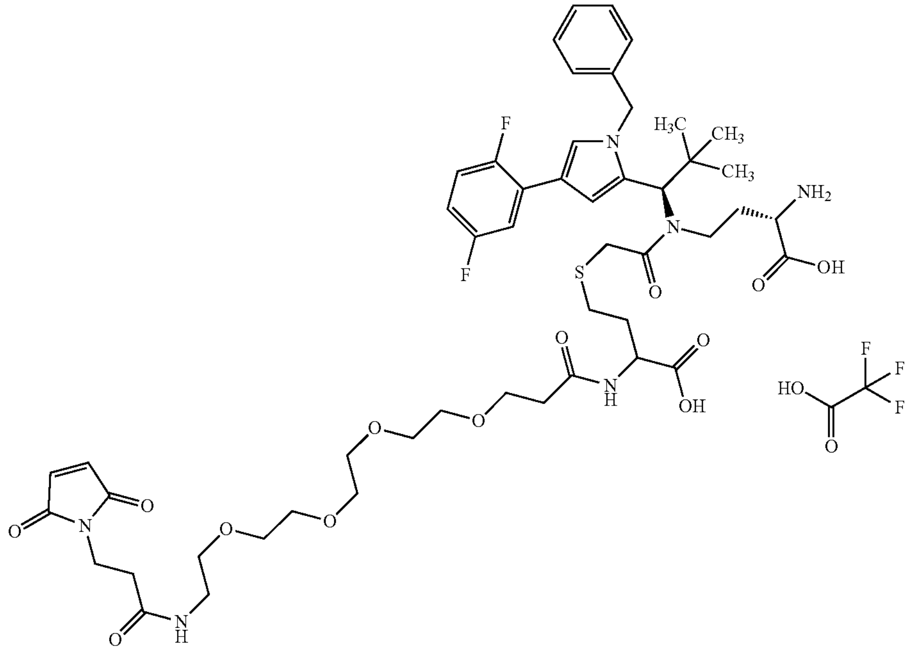 [SMILES: CC(C)(C)[C@H](c1cc(-c2cc(F)ccc2F)cn1Cc1ccccc1)N(CC[C@H](N)C(=O)O)C(=O)CSCCC(NC(=O)CCOCCOCCOCCOCCNC(=O)CCN1C(=O)C=CC1=O)C(=O)O ; O=C(O)C(F)(F)F]

25.0 mg (28.12 μmol) of R/S-[(8S)-11-{(1R)-1-[1-benzyl-4-(2,5-difluorophenyl)-1H-pyrrol-2-yl]-2,2-dimethylpropyl}-8-carboxy-2,2-dimethyl-6,12-dioxo-5-oxa-7,11-diaza-2-silatridecan-13-yl]homocysteine (Intermediate C12) and 15.9 mg (30.93 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were dissolved in 2.0 ml of DMF, and 11.4 mg (112.48 μmol) of 4-methylmorpholine were added. The reaction mixture was stirred at RT overnight. 7.6 mg (0.13 mmol) of acetic acid were added and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 23.9 mg (59% of theory) of the compound R/S-[(8S)-11-{(1R)-1-[1-benzyl-4-(2,5-difluorophenyl)-1H-pyrrol-2-yl]-2,2-dimethylpropyl}-8-carboxy-2,2-dimethyl-6,12-dioxo-5-oxa-7,11-diaza-2-silatridecan-13-yl]-N-[19-(2,5-dioxo-2,5-dihydro-1H-pyrrol-1-yl)-17-oxo-4,7,10,13-tetraoxa-16-azanonadecan-1-oyl] homocysteine.

LC-MS (Method 1): $R_t$=1.26 min; MS (ESIpos): m/z=1173 $(M+H)^+$.

11.8 mg (8.23 μmol) of R/S-[(8S)-11-{(1R)-1-[1-benzyl-4-(2,5-difluorophenyl)-1H-pyrrol-2-yl]-2,2-dimethylpropyl}-8-carboxy-2,2-dimethyl-6,12-dioxo-5-oxa-7,11-diaza-2-silatridecan-13-yl]-N-[19-(2,5-dioxo-2,5-dihydro-1H-pyrrol-1-yl)-17-oxo-4,7,10,13-tetraoxa-16-azanonadecan-1-oyl]homocysteine were dissolved in trifluoroethanol, and 1.7 mg (12.35 μmol) of zinc dichloride were added. The reaction mixture was stirred at 50° C. overnight. 3.6 mg (0.01 mmol) of ethylenediamine-N,N,N',N'-tetraacetic acid were added, the reaction mixture was stirred briefly and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 5.8 mg (62% of theory) of the title compound.

LC-MS (Method 4): $R_t$=1.20 min; MS (ESIpos): m/z=1029 $(M+H)^+$.

Intermediate F147

Trifluoroacetic Acid/N-(3-aminopropyl)-N-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-10-oxo-3,6-dioxa-16-thia-9-azaoctadecan-18-amide (1:1)

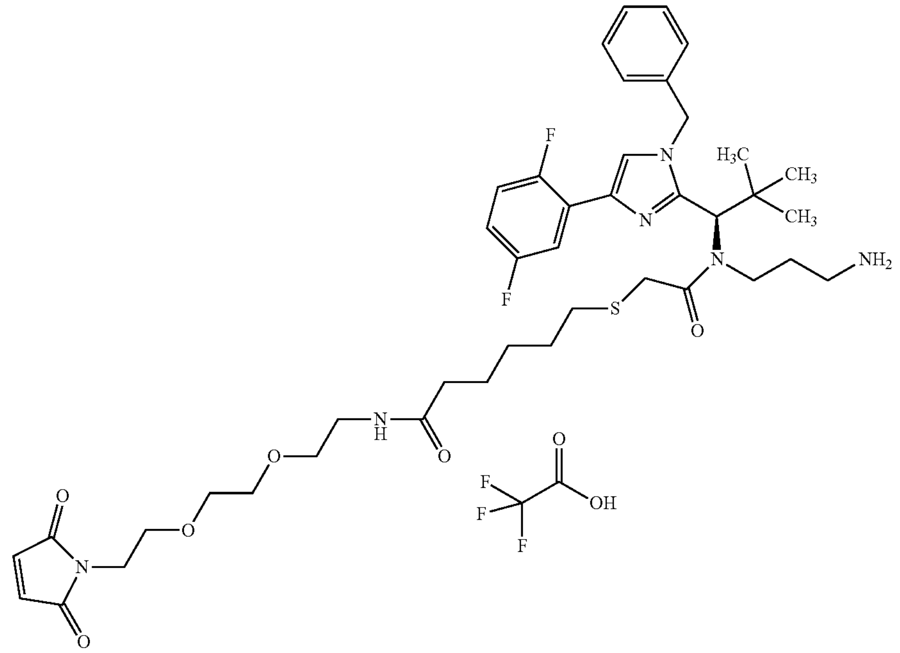

15.0 mg (0.03 mmol) of 9-{(1R)-1-[1-benzyl-4-(2,5-difluorophenyl)-1H-imidazol-2-yl]-2,2-dimethylpropyl}-2,2-dimethyl-4,10-dioxo-3-oxa-12-thia-5,9-diazaoctadecan-18-oic acid (Intermediate C13) were initially charged in 1.5 ml of acetonitrile, and 22.1 mg (0.17 mmol) of N,N-diisopropylethylamine and then 17.7 mg (0.03 mmol) of T3P were added. The mixture was stirred at RT for 5 min, and 9.5 mg (0.03 mmol) of trifluoroacetic acid/1-{2-[2-(2-aminoethoxy)ethoxy]ethyl}-1H-pyrrole-2,5-dione (1:1) (Intermediate L59) were then added. The reaction mixture was stirred at RT overnight and quenched with water. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 14.8 mg (57% of theory) of the compound tert-butyl [19-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-10,18-dioxo-3,6-dioxa-16-thia-9,19-diazadocosan-22-yl]carbamate.

LC-MS (Method 1): $R_t$=1.40 min; MS (ESIpos): m/z=911 $(M+H)^+$.

14.2 mg (0.02 mmol) of tert-butyl [19-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-10,18-dioxo-3,6-dioxa-16-thia-9,19-diazadocosan-22-yl]carbamate were dissolved in 1.5 ml of dichloromethane, 35.5 mg (0.31 mmol) of TFA were added and the mixture was stirred at RT overnight. Another 71.0 mg (0.62 mmol) of TFA were added and the mixture was stirred at RT overnight. The solvents were evaporated under reduced pressure and the residue was purified by preparative RP-HPLC (column: Reprosil 250×30; 10μ, flow rate: 50 ml/min, MeCN/water, 0.1% TFA). The solvents were evaporated under reduced pressure and the residue was taken up in a little water and lyophilized. This gave 14.0 mg (97% of theory) of the title compound.

LC-MS (Method 1): $R_t$=1.01 min; MS (ESIpos): m/z=811 $(M+H)^+$.

Intermediate F148

Trifluoroacetic Acid/6-({2-[(3-aminopropyl) {(1R)-1-[1-benzyl-4-(2,5-difluorophenyl)-1H-imidazol-2-yl]-2,2-dimethylpropyl}amino]-2-oxoethyl}sulphinyl)-N-[2-(2,5-dioxo-2,5-dihydro-1H-pyrrol-1-yl)ethyl]hexanamide (1:1)

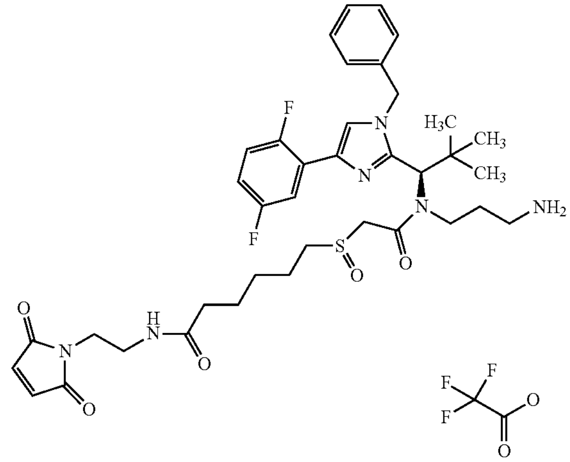 [SMILES: CC(C)(C)[C@H](c1nc(-c2cc(F)ccc2F)cn1Cc1ccccc1)N(CCCN)C(=O)CS(=O)CCCCCC(=O)NCCN1C(=O)C=CC1=O ; O=C(O)C(F)(F)F]

The title compound was formed as a by-product in the synthesis of Intermediate F145. This gave 8.1 mg (53% of theory) of the title compound.

LC-MS (Method 1): $R_t$=1.25 min; MS (ESIpos): m/z=739 $[M+H]^+$.

Intermediate F149

Trifluoroacetic Acid/R/S-{2-[(3-aminopropyl){(1R)-1-[1-benzyl-4-(2,5-difluorophenyl)-1H-imidazol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]homocysteine (1:1)

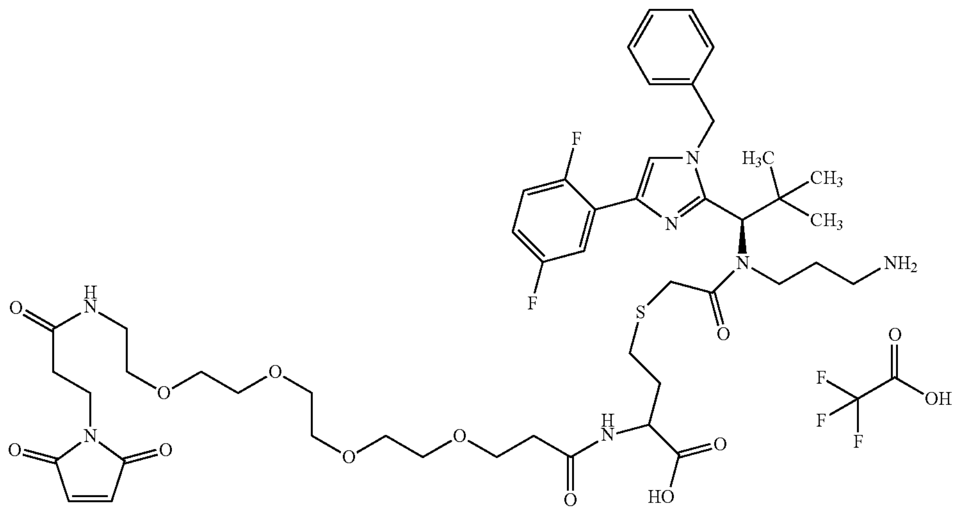 [SMILES: CC(C)(C)[C@H](c1nc(-c2cc(F)ccc2F)cn1Cc1ccccc1)N(CCCN)C(=O)CSCCC(NC(=O)CCOCCOCCOCCOCCNC(=O)CCN1C(=O)C=CC1=O)C(=O)O ; O=C(O)C(F)(F)F]

20.0 mg (24.94 μmol) of R/S-[2-({(1R)-1-[1-benzyl-4-(2,5-difluorophenyl)-1H-imidazol-2-yl]-2,2-dimethylpropyl}{3-[(tert-butoxycarbonyl)amino]propyl}amino)-2-oxoethyl]homocysteine (Intermediate C14) and 14.1 mg (27.44 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were initially charged in 1.0 ml of DMF, and 5.1 mg (49.88 μmol) of 4-methylmorpholine were added. The reaction mixture was stirred overnight. 3.7 mg (0.06 mmol) of acetic acid were added and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 18.2 mg (67% of theory) of the compound R/S-[2-({(1R)-1-[1-benzyl-4-(2,5-difluorophenyl)-1H-imidazol-2-yl]-2,2-dimethylpropyl}{3-[(tert-butoxycarbonyl)amino]propyl}amino)-2-oxoethyl]-N-[19-(2,5-dioxo-2,5-dihydro-1H-pyrrol-1-yl)-17-oxo-4,7,10,13-tetraoxa-16-azanonadecan-1-oyl]homocysteine.

LC-MS (Method 1): $R_t$=1.23 min; MS (ESIpos): m/z=1086 $(M+H)^+$.

17.6 mg (0.02 mmol) of R/S-[2-({(1R)-1-[1-benzyl-4-(2,5-difluorophenyl)-1H-imidazol-2-yl]-2,2-dimethylpropyl}{3-[(tert-butoxycarbonyl)amino]propyl}amino)-2-oxoethyl]-N-[19-(2,5-dioxo-2,5-dihydro-1H-pyrrol-1-yl)-17-oxo-4,7,10,13-tetraoxa-16-azanonadecan-1-oyl]homocysteine were dissolved in 1.5 ml of dichloromethane, 37.0 mg (0.32 mmol) of TFA were added, and the mixture was stirred at RT overnight. Another 74.0 mg (0.64 mmol) of TFA were added and the mixture was stirred at RT overnight. The solvents were evaporated under reduced pressure and the residue was purified by preparative RP-HPLC (column: Reprosil 250×30; 10μ, flow rate: 50 ml/min, MeCN/water, 0.1% TFA). The solvents were evaporated under reduced pressure and the residue was taken up in a little water and lyophilized. This gave 16.0 mg (90% of theory) of the title compound.

LC-MS (Method 1): $R_t$=0.92 min; MS (ESIpos): m/z=986 $(M+H)^+$.

Intermediate F150

Trifluoroacetic Acid/N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-[2-({2-[(3-aminopropyl) {(1R)-1-[1-benzyl-4-(2,5-difluorophenyl)-1H-imidazol-2-yl]-2,2-dimethylpropyl}amino]-2-oxoethyl}sulphanyl) ethyl]-L-alaninamide (1:1)

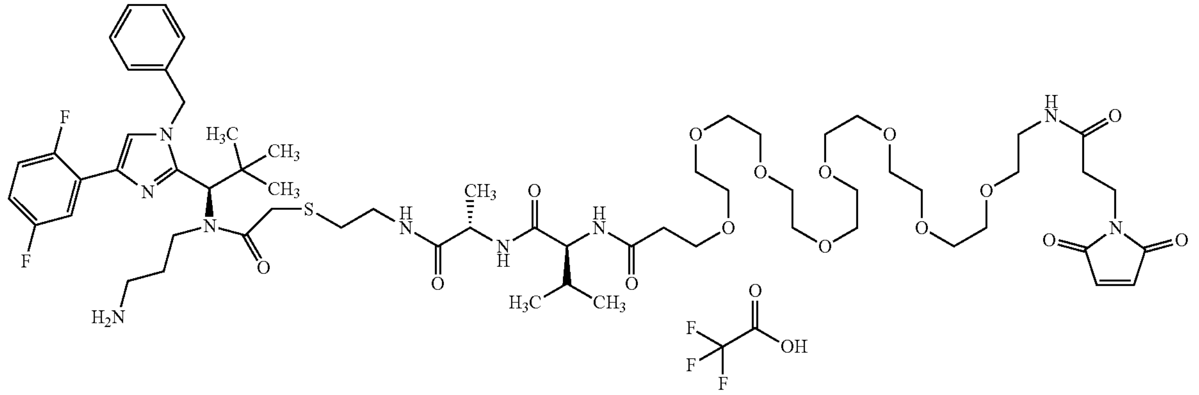 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)NCCSCC(=O)N(CCCN)[C@@H](c1nc(-c2cc(F)ccc2F)cn1Cc1ccccc1)C(C)(C)C ; O=C(O)C(F)(F)F]

Under argon and at 0° C., 10.0 mg (0.02 mmol) of trifluoroacetic acid/tert-butyl [3-({[(2-aminoethyl)sulphanyl]acetyl}{(1R)-1-[1-benzyl-4-(2,5-difluorophenyl)-1H-imidazol-2-yl]-2,2-dimethylpropyl}amino)propyl]carbamate (Intermediate C20) in 1.0 ml of DMF were treated with 12.1 mg (0.02 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-L-alanine (Intermediate L25), 2.2 mg (0.02 mmol) of HOAt and 7.6 mg (0.02 mmol) of HATU. 5.5 μl (0.03 mmol) of N,N-diisopropylethylamine were then added, and the reaction was stirred at RT overnight. 1.8 μl of HOAc were added, and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 10.4 mg (48% of theory) of the compound N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-(9-{(1R)-1-[1-benzyl-4-(2,5-difluorophenyl)-1H-imidazol-2-yl]-2,2-dimethylpropyl}-2,2-dimethyl-4,10-dioxo-3-oxa-12-thia-5,9-diazatetradecan-14-yl)-L-alaninamide.

LC-MS (Method 4): $R_t$=1.60 min; MS (ESIpos): m/z=687.5 $[M+2H]^{2+}$.

9.5 mg (0.01 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-(9-{(1R)-1-[1-benzyl-4-(2,5-difluorophenyl)-1H-imidazol-2-yl]-2,2-dimethylpropyl}-2,2-dimethyl-4,10-dioxo-3-oxa-12-thia-5,9-diazatetradecan-14-yl)-L-alaninamide were initially charged in 1.0 ml of dichloromethane, 15.8 mg (0.14 mmol) of TFA were added and the mixture was stirred overnight. Another 31.6 mg (0.28 mmol) of TFA were added, and the mixture was stirred overnight. The solvent was evaporated under reduced pressure and the residue was purified by preparative RP-HPLC (column: Reprosil 250×30; 10μ, flow rate: 50 ml/min, MeCN/water, 0.1% TFA). The solvents were evaporated under reduced pressure and the residue was taken up in a little water and lyophilized. This gave 10.2 mg (98% of theory) of the title compound.

LC-MS (Method 4): $R_t$=1.13 min; MS (ESIpos): m/z=637.5 $[M+2H]^{2+}$.

Intermediate F151

N-[19-(2,5-Dioxo-2,5-dihydro-1H-pyrrol-1-yl)-17-oxo-4,7,10,13-tetraoxa-16-azanonadecan-1-oyl]-L-valyl-N-(3-{(2S)-5-(2,5-difluorophenyl)-3-[methoxy(methyl)carbamoyl]-2-phenyl-2,3-dihydro-1,3,4-thiadiazol-2-yl}propyl)-L-alaninamide

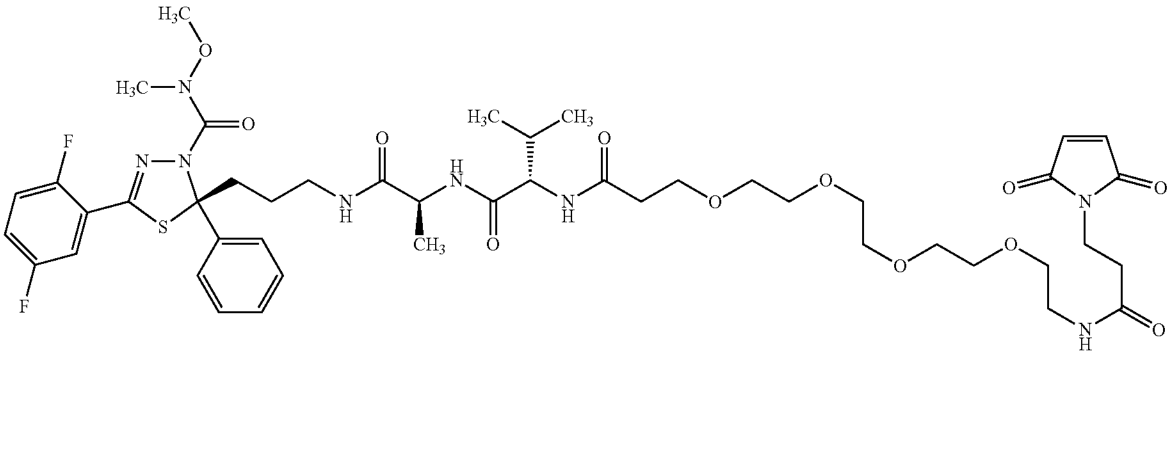 [SMILES: CON(C)C(=O)N1N=C(c2cc(F)ccc2F)S[C@@]1(CCCNC(=O)[C@H](C)NC(=O)[C@@H](NC(=O)CCOCCOCCOCCOCCNC(=O)CCN1C(=O)C=CC1=O)C(C)C)c1ccccc1]

5.0 mg (0.01 mmol) of (2S)-2-(3-aminopropyl)-5-(2,5-difluorophenyl)-N-methoxy-N-methyl-2-phenyl-1,3,4-thiadiazol-3(2H)-carboxamide were initially charged in 1.0 ml of acetonitrile, and 7.7 mg (0.06 mmol) of N,N-diisopropylethylamine and 9.8 (0.02 mmol) of T3P were added. The mixture was stirred at RT for 5 min, and 9.1 mg (0.02 mmol) of N-[19-(2,5-dioxo-2,5-dihydro-1H-pyrrol-1-yl)-17-oxo-4,7,10,13-tetraoxa-16-azanonadecan-1-oyl]-L-valyl-L-alanine (Intermediate L44) were then added. The reaction mixture was stirred at RT overnight. Water was added, and the reaction mixture was purified directly by preparative RP-HPLC (column: Reprosil 250×40; 10µ, flow rate: 50 ml/min, MeCN/water, 0.1% TFA). The solvents were evaporated under reduced pressure and the residue was dried under high vacuum. This gave 4.3 mg (35% of theory) of the title compound.

LC-MS (Method 1): $R_t$=1.02 min; MS (ESIpos): m/z=989 $[M+H]^+$.

Intermediate F152

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N-(3-{(2S)-5-(2,5-difluorophenyl)-3-[methoxy(methyl)carbamoyl]-2-phenyl-2,3-dihydro-1,3,4-thiadiazol-2-yl}propyl)-L-alaninamide

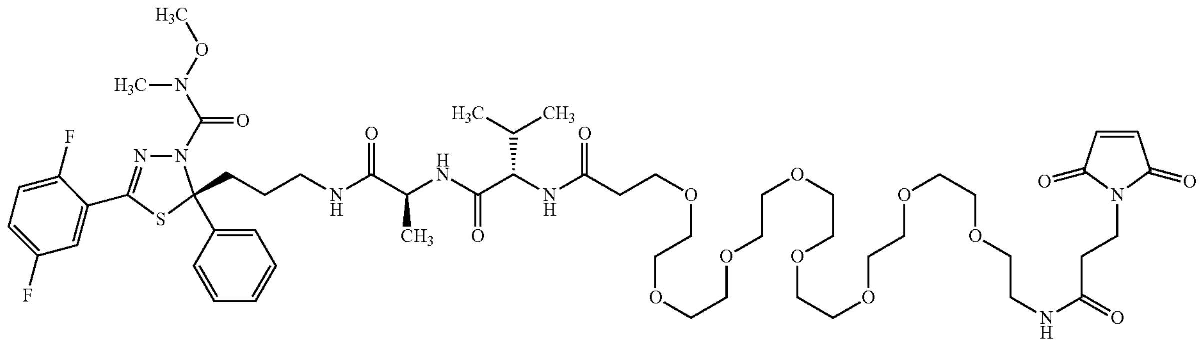 [SMILES: CON(C)C(=O)N1N=C(c2cc(F)ccc2F)S[C@@]1(CCCNC(=O)[C@H](C)NC(=O)[C@@H](NC(=O)CCOCCOCCOCCOCCOCCOCCOCCOCCNC(=O)CCN1C(=O)C=CC1=O)C(C)C)c1ccccc1]

5.0 mg (0.01 mmol) of (2S)-2-(3-aminopropyl)-5-(2,5-difluorophenyl)-N-methoxy-N-methyl-2-phenyl-1,3,4-thiadiazol-3(2H)-carboxamide were initially charged in 1.0 ml of acetonitrile, and 7.7 mg (0.06 mmol) of N,N-diisopropylethylamine and 9.8 (0.02 mmol) of T3P were added. The mixture was stirred at RT for 5 min, and 11.8 mg (0.02 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-L-alanine (Intermediate L25) were then added. The reaction mixture was stirred at RT overnight. Water was added, and the reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 4.7 mg (34% of theory) of the title compound.

LC-MS (Method 4): $R_t$=1.34 min; MS (ESIpos): m/z=1165 $[M+H]^+$.

Intermediate F153

Trifluoroacetic Acid/(2S)-2-amino-4-({(1R)-1-[1-benzyl-4-(2,5-difluorophenyl)-1H-pyrrol-2-yl]-2,2-dimethylpropyl}[(2S)-2-hydroxypropanoyl]amino)-N-(2-{[(2,5-dioxo-2,5-dihydro-1H-pyrrol-1-yl)acetyl]amino}ethyl)butanamide (1:1)

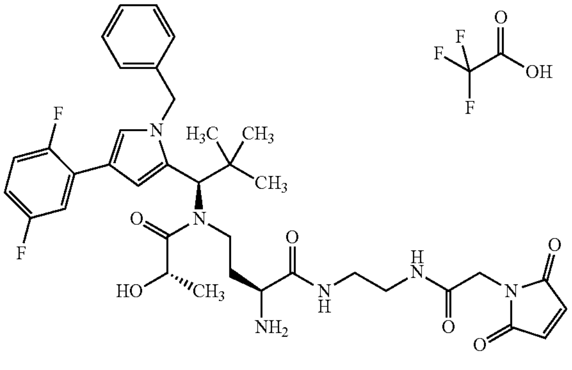 [SMILES: C[C@H](O)C(=O)N(CC[C@H](N)C(=O)NCCNC(=O)CN1C(=O)C=CC1=O)[C@@H](c1cc(-c2cc(F)ccc2F)cn1Cc1ccccc1)C(C)(C)C ; O=C(O)C(F)(F)F]

The synthesis was carried out analogously to Intermediate F104 from Intermediate C60.

LC-MS (Method 1): $R_t$=1.1 min; MS (ESIpos): m/z=707 $(M+H)^+$.

Intermediate F154

$N^6$—(N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl)-$N^2$—{N-[6-(2,5-dioxo-2,5-dihydro-1H-pyrrol-1-yl)hexanoyl]-L-valyl-L-alanyl}-L-lysine/trifluoroacetic Acid (1:1)

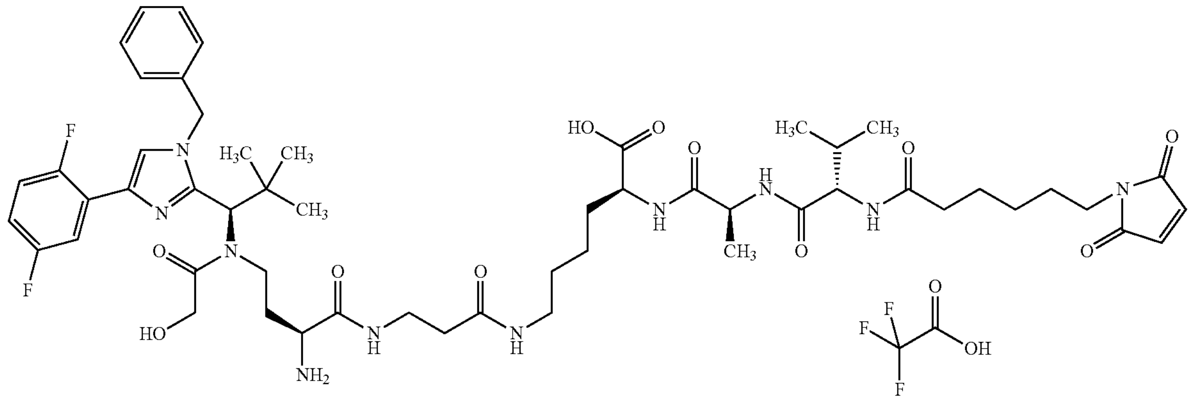

The title compound was prepared analogously to Intermediate F2 from 10 mg (0.015 mmol) of Intermediate C8 and 15 mg (0.022 mmol) of Intermediate L6.

HPLC (Method 11): $R_t$=1.91 min;

LC-MS (Method 1): $R_t$=0.89 min; MS (ESIpos): m/z=1077 $(M+H)^+$.

Intermediate F155

$N^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$—{N-[6-(2,5-dioxo-2,5-dihydro-1H-pyrrol-1-yl)hexanoyl]-L-valyl-L-alanyl}-L-lysine/trifluoroacetic Acid (1:1)

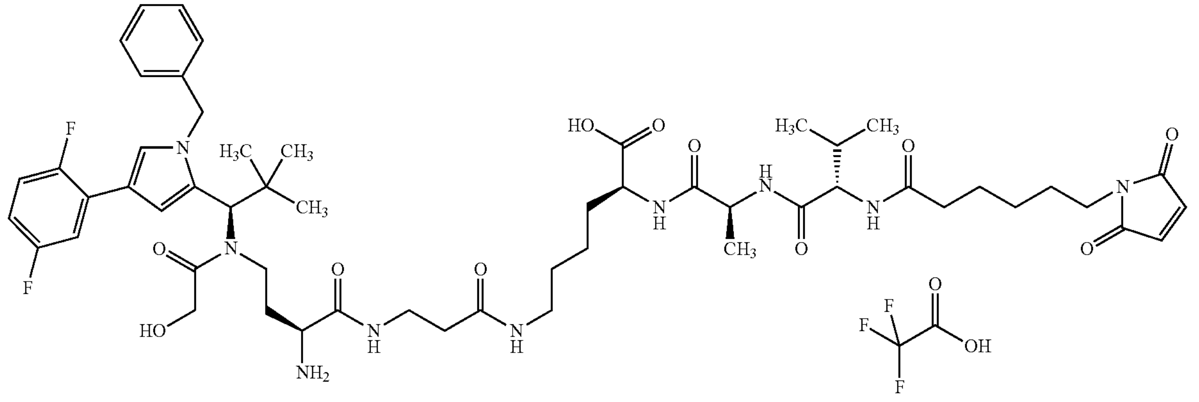 [SMILES: CC(C)[C@H](NC(=O)CCCCCN1C(=O)C=CC1=O)C(=O)N[C@@H](C)C(=O)N[C@@H](CCCCNC(=O)CCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared by coupling of 14 mg (0.019 mmol) of Intermediate C61 with 15 mg (0.021 mmol) of Intermediate L61 in the presence of 8.7 mg (0.023 mmol) of HATU and 17 μl of N,N-diisopropylethylamine and subsequent deprotection with zinc chloride in trifluoroethanol as described for Intermediate F119. Purification by preparative HPLC gave 13 mg (59% of theory over 2 steps) of the title compound.

LC-MS (Method 1): $R_t$=0.86 min; MS (ESIpos): m/z=1076 $(M+H)^+$.

Intermediate F156

N-(Bromoacetyl)-L-valyl-L-alanyl-$N^6$-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-lysine trifluoroacetic Acid (1:1)

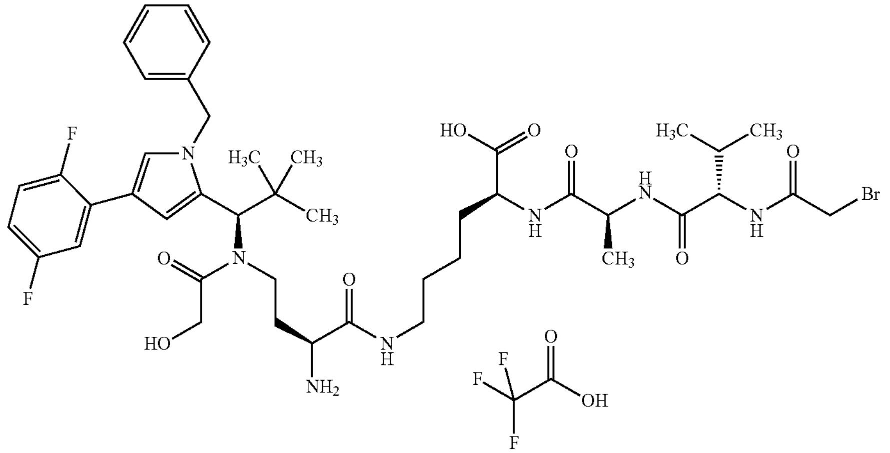 [SMILES: CC(C)[C@H](NC(=O)CBr)C(=O)N[C@@H](C)C(=O)N[C@@H](CCCCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

First, the tripeptide derivative 2-(trimethylsilyl)ethyl L-valyl-L-alanyl-N6-(tert-butoxycarbonyl)-L-lysinate was prepared from N2-[(benzyloxy)carbonyl]-N6-(tert-butoxycarbonyl)-L-lysine according to classical methods of peptide chemistry (esterification with 2-(trimethylsilylethanol using EDCI/DMAP, hydrogenolysis, coupling with N-[(benzyloxy)carbonyl]-L-valyl-L-alanine in the presence of HATU and another hydrogenolysis).

84 mg (0.163 mmol) of this Intermediate were taken up in 2.5 ml of DMF, and 58 mg (0.244 mmol) of 1-(2-bromoacetoxy)pyrrolidine-2,5-dione were added. After 10 min of stirring at RT, the mixture was concentrated, the residue was taken up in acetonitrile/water 1:1 and the mixture was adjusted with trifluoroacetic acid to pH 2 and purified by preparative HPLC. After concentration of the appropriate fractions, the residue was taken up in 15 ml of a 5% strength trifluoroacetic acid solution in DCM and stirred at RT for 2 h. The mixture was then concentrated with slight cooling and the residue was lyophilized from acetonitrile/water 1:1. 53 mg (50% of theory) of this intermediate were obtained over 2 steps.

LC-MS (Method 1): $R_t$=0.72 min; MS (ESIpos): m/z=537 and 539 $(M+H)^+$.

For the synthesis of the title compound, 18 mg (0.027 mmol) of this intermediate were taken up in 4 ml of DMF, and 16 mg (0.025 mmol) of Intermediate C61 and 19 mg of HATU and 9 µl of N,N-diisopropylethylamine were added. After 5 min of stirring at RT, a few drops of trifluoroacetic acid were added and the reaction was purified by preparative HPLC. After concentration of the appropriate fractions and lyophilization from acetonitrile/water 1:1, the intermediate obtained was dissolved in 3 ml of 2,2,2-trifluoroethanol. Following addition of 4.8 mg (0.035 mmol) of zinc chloride, the reaction was stirred at 50° C. for 2.5 h. 10 mg (0.035 mmol) of ethylenediamine-N,N,N',N'-tetraacetic acid were then added, and the reaction was diluted with acetonitrile/water and filtered. Purification was carried out by preparative HPLC. Concentration of the appropriate fractions and lyophilization of the residue from acetonitrile/water gave 3.2 mg (13% of theory) of the title compound over 2 steps.

HPLC (Method 11): $R_t$=1.94 min;

LC-MS (Method 5): $R_t$=2.79 min; MS (ESIpos): m/z=932 and 934 $(M+H)^+$.

Intermediate F163

N-[6-(2,5-Dioxo-2,5-dihydro-1H-pyrrol-1-yl)hexanoyl]-L-valyl-L-alanyl-N6-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-lysine/trifluoroacetic Acid (1:1)

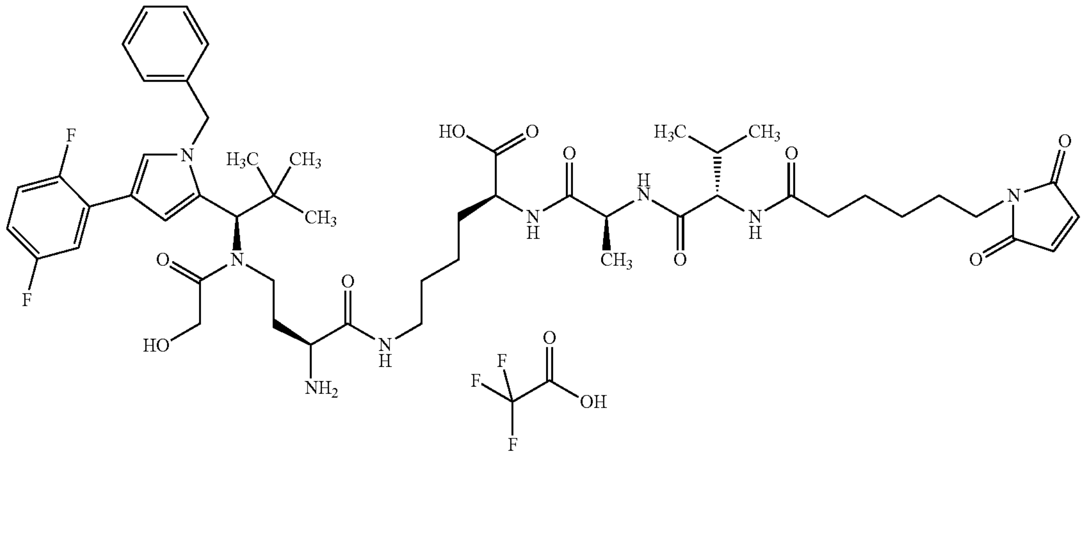 [SMILES: CC(C)[C@H](NC(=O)CCCCCN1C(=O)C=CC1=O)C(=O)N[C@@H](C)C(=O)N[C@@H](CCCCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared by coupling of 37 mg (0.056 mmol) of Intermediate C58 and 41 mg (0.056 mmol) of Intermediate L61 in the presence of HATU and subsequent deblocking with zinc chloride as described for Intermediate F119. This gave 12 mg (19% of theory over 2 steps) of the title compound.

HPLC (Method 11): $R_t$=1.49 min;

LC-MS (Method 1): $R_t$=0.89 min; MS (ESIpos): m/z=1005 $(M+H)^+$.

Intermediate F164

N-[6-(2,5-Dioxo-2,5-dihydro-1H-pyrrol-1-yl)hexanoyl]-L-valyl-N5-carbamoyl-L-ornithyl-N6-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-lysine/trifluoroacetic Acid (1:1)

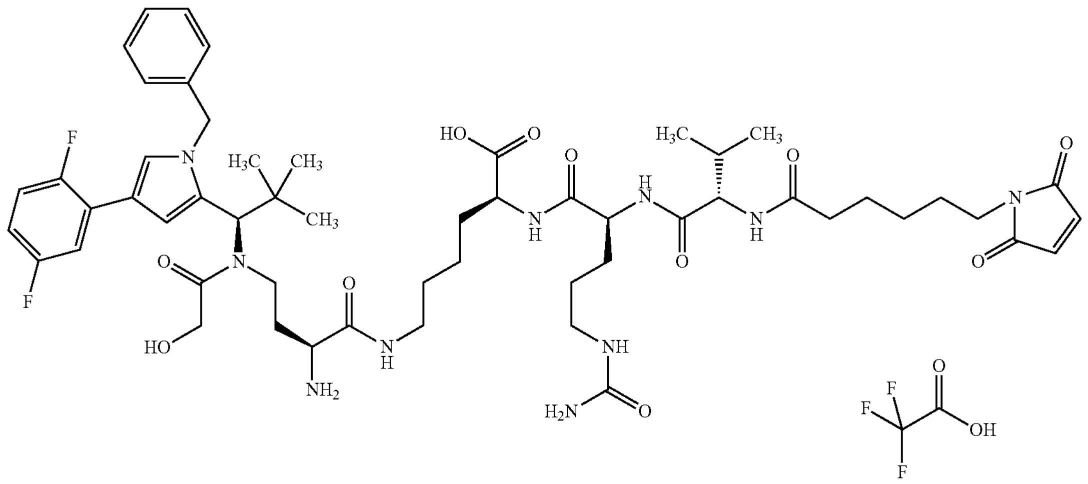 [SMILES: CC(C)[C@H](NC(=O)CCCCCN1C(=O)C=CC1=O)C(=O)N[C@@H](CCCNC(N)=O)C(=O)N[C@@H](CCCCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared analogously to Intermediate F155 by coupling of 20 mg (0.030 mmol) of Intermediate C58 with 27 mg (0.033 mmol) of Intermediate L62 in the presence of HATU and N,N-diisopropylethylamine and subsequent deprotection with zinc chloride in trifluoroethanol.

HPLC (Method 11): $R_t$=1.92 min;

LC-MS (Method 1): $R_t$=0.87 min; MS (ESIpos): m/z=1091 $(M+H)^+$.

Intermediate F165

$N^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$—{N-[6-(2,5-dioxo-2,5-dihydro-1H-pyrrol-1-yl)hexanoyl]-L-valyl-$N^5$-carbamoyl-L-ornithyl}-L-lysine/trifluoroacetic Acid (1:1)

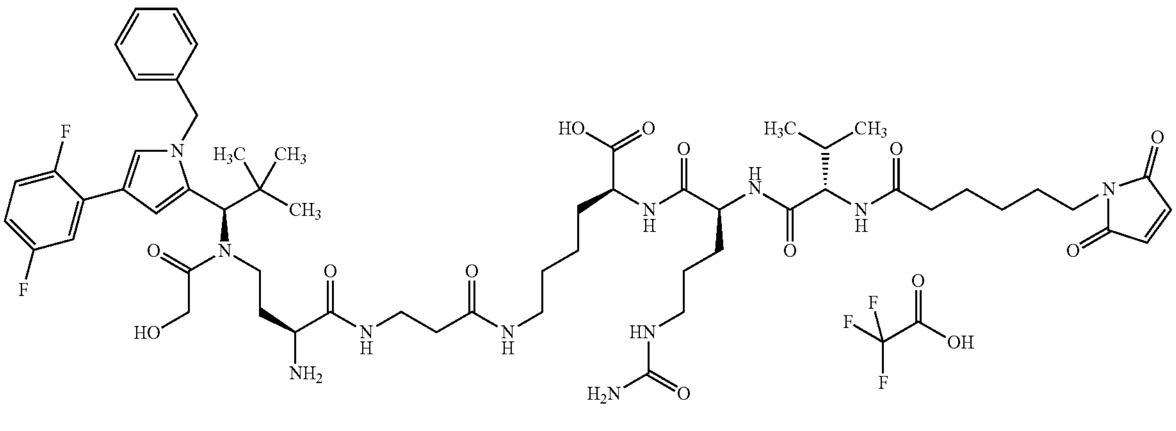 [SMILES: CC(C)[C@H](NC(=O)CCCCCN1C(=O)C=CC1=O)C(=O)N[C@@H](CCCNC(N)=O)C(=O)N[C@@H](CCCCNC(=O)CCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared analogously to Intermediate F155 by coupling of 15 mg (0.021 mmol) of Intermediate C61 with 18 mg (0.023 mmol) of Intermediate L62 in the presence of HATU and subsequent deprotection with zinc chloride in trifluoroethanol.

LC-MS (Method 1): $R_t$=0.88 min; MS (ESIpos): m/z=1162 $(M+H)^+$.

Intermediate F166

N-[6-(2,5-Dioxo-2,5-dihydro-1H-pyrrol-1-yl)hexanoyl]-L-valyl-$N^5$-carbamoyl-L-ornithyl-$N^6$-{[(1R,3S)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)cyclopentyl]carbonyl}-L-lysine/trifluoroacetic Acid (1:1)

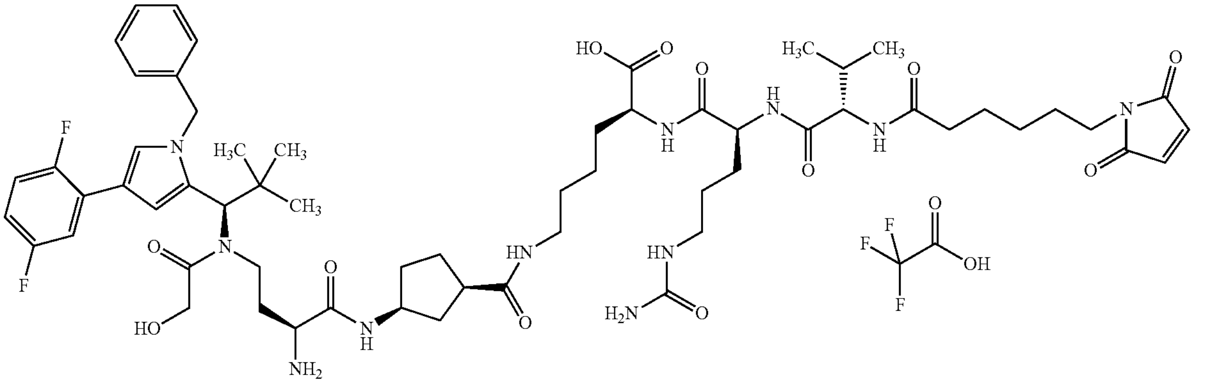 [SMILES: CC(C)[C@H](NC(=O)CCCCCN1C(=O)C=CC1=O)C(=O)N[C@@H](CCCNC(N)=O)C(=O)N[C@@H](CCCCNC(=O)[C@@H]1CC[C@H](NC(=O)[C@@H](N)CCN(C(=O)CO)[C@@H](c2cc(-c3cc(F)ccc3F)cn2Cc2ccccc2)C(C)(C)C)C1)C(=O)O ; O=C(O)C(F)(F)F]

First, trifluoroacetic acid/benzyl (1R,3S)-3-aminocyclopentanecarboxylate (1:1) was prepared from commercially available (1R,3S)-3-[(tert-butoxycarbonyl)amino]cyclopentanecarboxylic acid according to classical methods of peptide chemistry by esterification with benzyl alcohol using EDCI/DMAP and subsequent removal of the tert-butoxycarbonyl protective group with TFA in DCM.

51 mg (0.076 mmol) of this intermediate were taken up in 6 mN of DMF and coupled with 50 mg (0.076 mmol) of Intermediate C58 in the presence of HATU and N,N-diisopropylethylamine. After purification by preparative HPLC, the intermediate was taken up in methanol and hydrogenated over 10% palladium on activated carbon at RT under hydrogen standard pressure for 2 h. The catalyst was then filtered off, the solvent was removed under reduced pressure and the product was purified by preparative HPLC. Lyophilization from dioxane gave 21 mg (34% of theory over 2 steps) of (1R,3S)-3-{[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]amino}cyclopentanecarboxylic acid.

The title compound was prepared analogously to Intermediate F155 by coupling of 10.5 mg (0.013 mmol) of this intermediate with 11.4 mg (0.014 mmol) of Intermediate L62 in the presence of HATU and subsequent deprotection with zinc chloride in trifluoroethanol. Purification by preparative HPLC gave 8.6 mg (48% of theory over 2 steps) of the title compound.

LC-MS (Method 1): $R_t$=0.88 min; MS (ESIpos): m/z=1203 $(M+H)^+$.

Intermediate F167

N-[6-(2,5-Dioxo-2,5-dihydro-1H-pyrrol-1-yl)hexanoyl]-L-valyl-L-alanyl-$N^6$-{[(1R,3S)-3-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)cyclopentyl]carbonyl}-L-lysine/trifluoroacetic Acid (1:1)

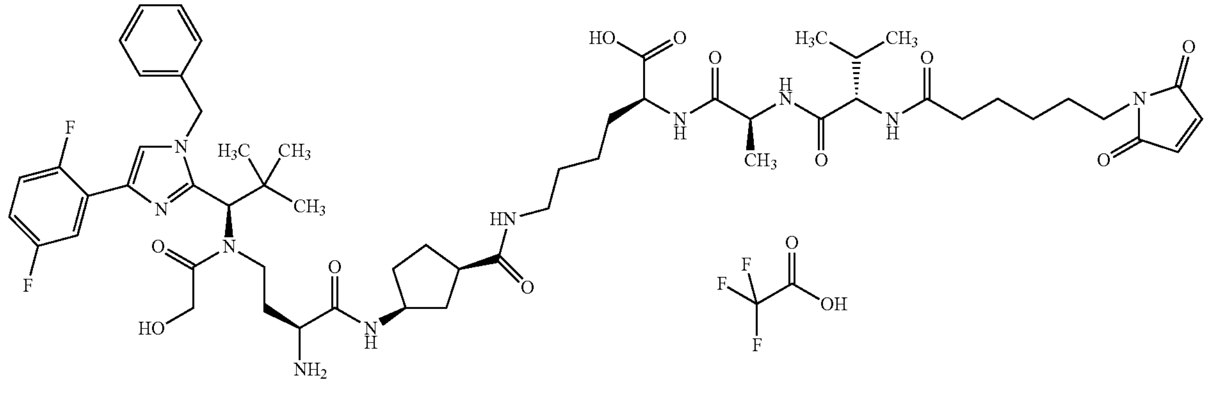 [SMILES: CC(C)[C@H](NC(=O)CCCCCN1C(=O)C=CC1=O)C(=O)N[C@@H](C)C(=O)N[C@@H](CCCCNC(=O)[C@@H]1CC[C@H](NC(=O)[C@@H](N)CCN(C(=O)CO)[C@@H](c2nc(-c3cc(F)ccc3F)cn2Cc2ccccc2)C(C)(C)C)C1)C(=O)O ; O=C(O)C(F)(F)F]

The title compound was prepared analogously to Intermediate F129 from 11 mg (0.016 mmol) of Intermediate C5 by reaction with 20 mg (0.024 mmol) of Intermediate L56 in the presence of 12 mg (0.032 mmol) of HATU and 14 μl of N,N-diisopropylethylamine and subsequent deprotection with trifluoroacetic acid. This gave 11 mg (46% of theory over 2 steps).

LC-MS (Method 4): $R_t$=1.13 min; MS (EIpos): m/z=1117 $[M+H]^+$.

Intermediate F168

N-[6-(2,5-Dioxo-2,5-dihydro-1H-pyrrol-1-yl)hexanoyl]-L-valyl-L-alanyl-$N^6$-{[(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)cyclopentyl]carbonyl}-L-lysine/trifluoroacetic Acid (1:1)

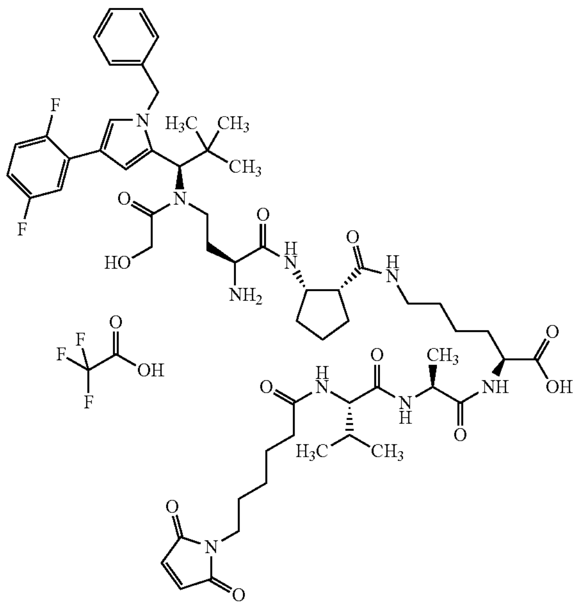 [SMILES: CC(C)[C@H](NC(=O)CCCCCN1C(=O)C=CC1=O)C(=O)N[C@@H](C)C(=O)N[C@@H](CCCCNC(=O)[C@@H]1CCC[C@@H]1NC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

First, trifluoroacetic acid/benzyl (1R,2S)-2-aminocyclopentanecarboxylate (1:1) was prepared from commercially available (1R,2S)-2-[(tert-butoxycarbonyl)amino]cyclopentanecarboxylic acid according to classical methods of peptide chemistry by esterification with benzyl alcohol using EDCI/DMAP and subsequent removal of the tert-butoxycarbonyl protective group with TFA in DCM.

102 mg (0.305 mmol) of this intermediate were taken up in 12 ml of DMF and coupled with 100 mg (0.152 mmol) of Intermediate C58 in the presence of HATU and N,N-diisopropylethylamine. After purification by preparative HPLC, the intermediate was taken up in methanol and hydrogenated over 10% palladium on activated carbon at RT under hydrogen standard pressure for 2 h. The catalyst was then filtered off, the solvent was removed under reduced pressure and the product was purified by preparative HPLC. Lyophilization from acetonitrile/water 1:1 gave 70 mg (59% of theory over 2 steps) of (1R,2S)-2-{[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]amino}cyclopentanecarboxylic acid.

The title compound was then prepared by coupling of 20 mg (0.013 mmol) of this intermediate with 16.6 mg (0.023 mmol) of Intermediate L61 in the presence of 9.5 mg (0.025 mmol) of HATU and 18 μl of N,N-diisopropylethylamine and subsequent deprotection with zinc chloride in trifluoroethanol as described for Intermediate F119. Purification by preparative HPLC gave 9.3 mg (30% of theory over 2 steps) of the title compound.

LC-MS (Method 1): $R_t$=0.98 min; MS (ESIpos): m/z=1116 $(M+H)^+$.

Intermediate F169

N-[6-(2,5-Dioxo-2,5-dihydro-1H-pyrrol-1-yl)hexanoyl]-L-valyl-$N^5$-carbamoyl-L-ornithyl-$N^6$-{[(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)cyclopentyl]carbonyl}-L-lysine/trifluoroacetic Acid (1:1)

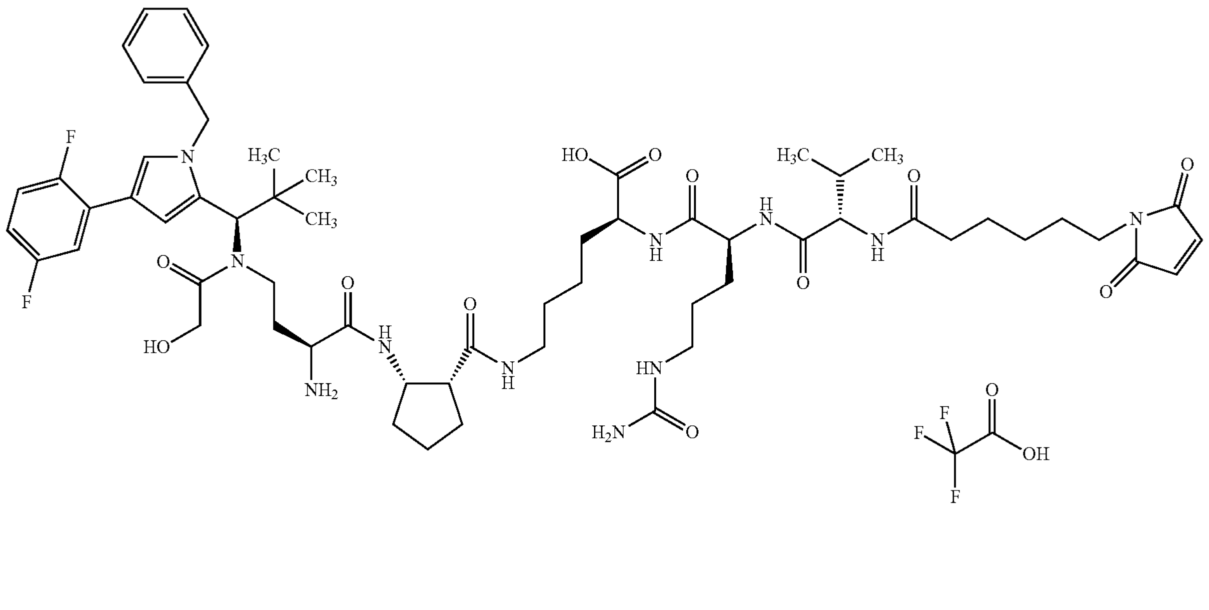 [SMILES: CC(C)[C@H](NC(=O)CCCCCN1C(=O)C=CC1=O)C(=O)N[C@@H](CCCNC(N)=O)C(=O)N[C@@H](CCCCNC(=O)[C@@H]1CCC[C@@H]1NC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The synthesis of the title compound was carried out analogously to Intermediate F168 from Intermediates C58 and L62.

LC-MS (Method 1): $R_t$=0.91 min; MS (ESIpos): m/z=1202 $(M+H)^+$.

Intermediate F170

N-[6-(2,5-Dioxo-2,5-dihydro-1H-pyrrol-1-yl)hexanoyl]-L-valyl-$N^5$-carbamoyl-L-ornithyl-$N^6$-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-D-lysine/trifluoroacetic Acid (1:1)

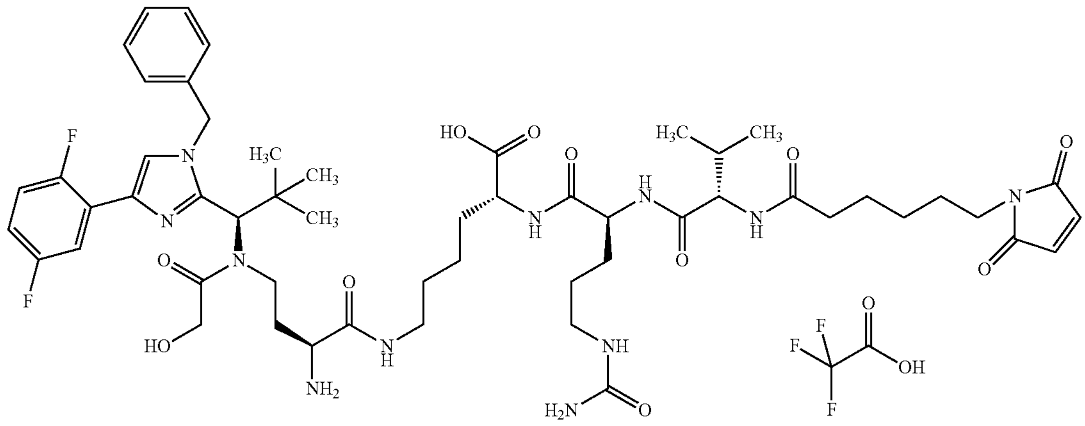 [SMILES: CC(C)[C@H](NC(=O)CCCCCN1C(=O)C=CC1=O)C(=O)N[C@@H](CCCNC(N)=O)C(=O)N[C@H](CCCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared analogously to its diastereomer Intermediate F23.

HPLC (Method 11): $R_t$=1.9 min;

LC-MS (Method 1): $R_t$=0.83 min; MS (ESIpos): m/z=1092 $(M+H)^+$.

Intermediate F171

$N^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-D-alanyl)-$N^2$—{N-[6-(2,5-dioxo-2,5-dihydro-1H-pyrrol-1-yl)hexanoyl]-L-valyl-L-alanyl}-L-lysine/trifluoroacetic Acid (1:1)

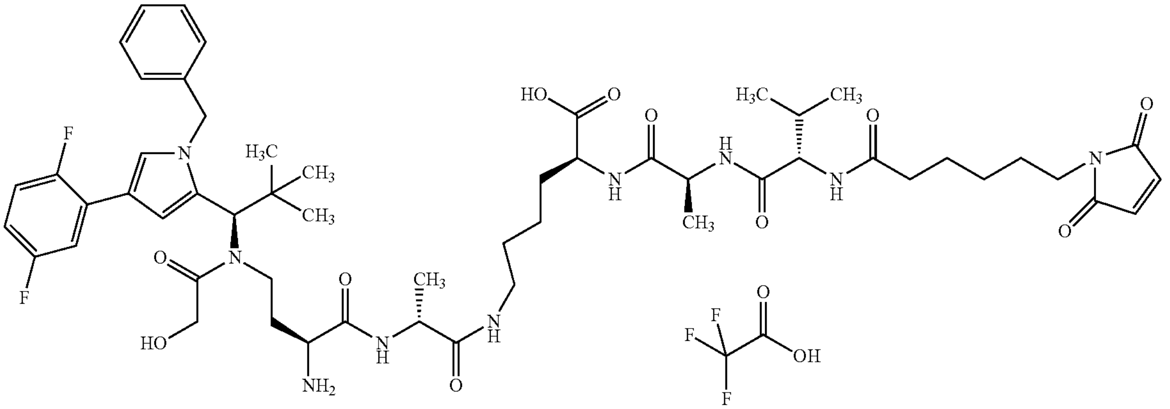 [SMILES: CC(C)[C@H](NC(=O)CCCCCN1C(=O)C=CC1=O)C(=O)N[C@@H](C)C(=O)N[C@@H](CCCCNC(=O)[C@@H](C)NC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The synthesis of the title compound was carried out analogously to Intermediate F155 from Intermediates C62 and L61.

LC-MS (Method 1): $R_t$=0.93 min; MS (ESIpos): m/z=1076 $(M+H)^+$.

Intermediate F172

N-[6-(2,5-Dioxo-2,5-dihydro-1H-pyrrol-1-yl) hexanoyl]-L-valyl-L-alanyl-N-[2-({(2S)-2-amino-4-[{(1R)-1-[1-benzyl-4-(2,5-difluorophenyl)-1H-imidazol-2-yl]-2,2-dimethylpropyl}(glycoloyl)amino] butanoyl}amino)ethyl]-L-glutamine/trifluoroacetic Acid (1:1)

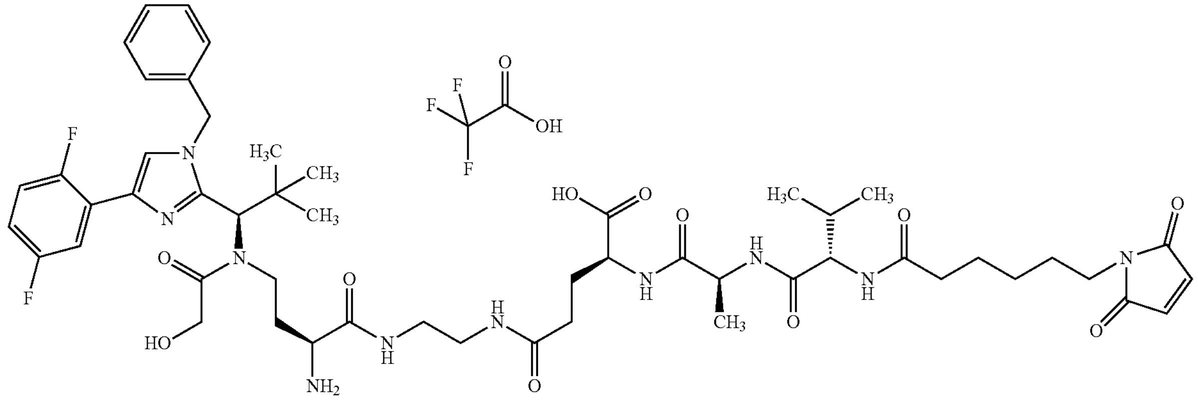 [SMILES: CC(C)[C@H](NC(=O)CCCCCN1C(=O)C=CC1=O)C(=O)N[C@@H](C)C(=O)N[C@@H](CCC(=O)NCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared from 10 mg (0.013 mmol) of Intermediate C63 by coupling with 9 mg (0.014 mmol) of Intermediate L63 in the presence of 5.5 mg (0.014 mmol) of HATU and 11 μl of N,N-diisopropylethylamine and subsequent deprotection by stirring in a solution of trifluoroacetic acid/dichloromethane 1:1 for 2.5 hours. This gave 11 mg (72% of theory over 2 steps).

LC-MS (Method 1): $R_t$=0.9 min; MS (EIpos): m/z=1049 $[M+H]^+$.

Intermediate F173

N-[6-(2,5-Dioxo-2,5-dihydro-1H-pyrrol-1-yl) hexanoyl]-L-valyl-L-alanyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino] butanoyl}amino)ethyl]-L-glutamine/trifluoroacetic Acid (1:1)

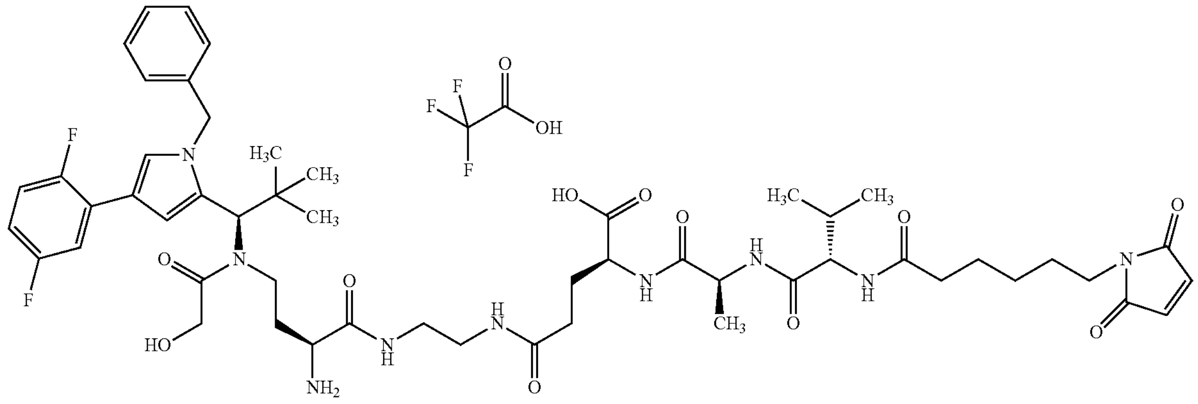 [SMILES: CC(C)[C@H](NC(=O)CCCCCN1C(=O)C=CC1=O)C(=O)N[C@@H](C)C(=O)N[C@@H](CCC(=O)NCCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared from 15 mg (0.018 mmol) of Intermediate C64 by coupling with 12 mg (0.02 mmol) of Intermediate L63 in the presence of 7.7 mg (0.02 mmol) of HATU and 16 μl of N,N-diisopropylethylamine and subsequent deprotection with zinc chloride in trifluoroethanol as described for Intermediate F119. Purification by preparative HPLC gave 12 mg (58% of theory over 2 steps) of the title compound.

LC-MS (Method 1): $R_t$=0.91 min; MS (EIpos): m/z=1048 $[M+H]^+$.

Intermediate F174

N-[6-(2,5-Dioxo-2,5-dihydro-1H-pyrrol-1-yl)hexanoyl]-L-valyl-L-alanyl-N-[2-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)ethyl]-L-glutamine/trifluoroacetic Acid (1:1)

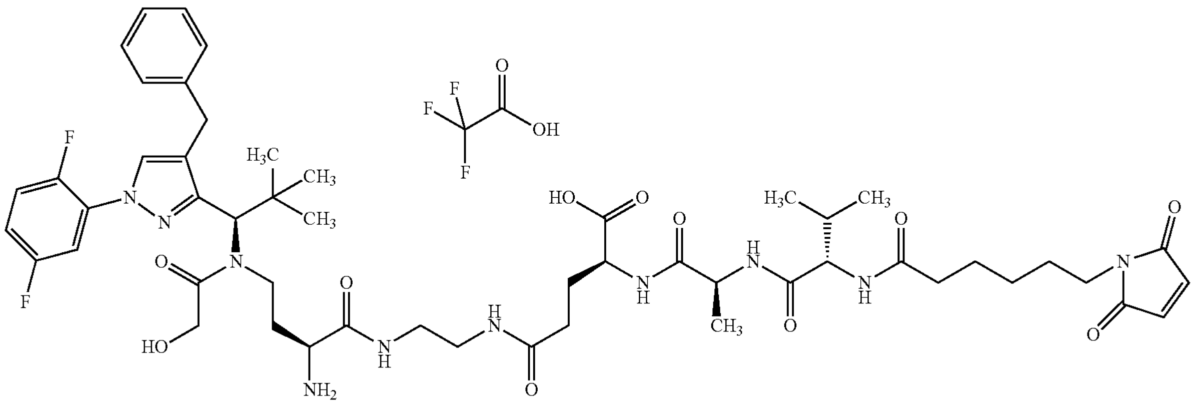 [SMILES: CC(C)[C@H](NC(=O)CCCCCN1C(=O)C=CC1=O)C(=O)N[C@@H](C)C(=O)N[C@@H](CCC(=O)NCCNC(=O)[C@@H](N)CCN(C(=O)CO)[C@@H](c1nn(-c2cc(F)ccc2F)cc1Cc1ccccc1)C(C)(C)C)C(=O)O ; O=C(O)C(F)(F)F]

The title compound was prepared analogously to Intermediate F172 from Intermediates C57 and L63.

LC-MS (Method 1): $R_t$=0.9 min; MS (EIpos): m/z=1049 $[M+H]^+$.

Intermediate F175

Trifluoroacetic Acid/N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-6-(2,5-dioxo-2,5-dihydro-1H-pyrrol-1-yl)hexanamide (1:1)

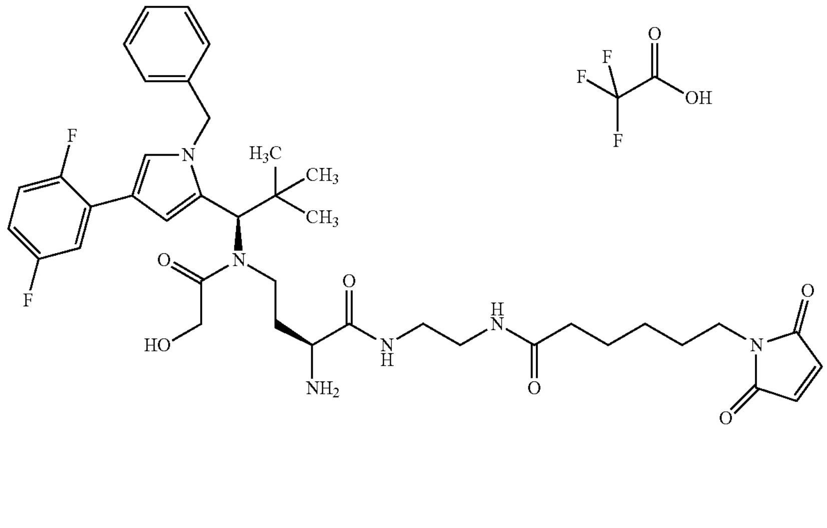 [SMILES: CC(C)(C)[C@H](c1cc(-c2cc(F)ccc2F)cn1Cc1ccccc1)N(CC[C@H](N)C(=O)NCCNC(=O)CCCCCN1C(=O)C=CC1=O)C(=O)CO ; O=C(O)C(F)(F)F]

The title compound was prepared by coupling of 11 mg (0.013 mmol) of Intermediate C64 with 3.4 mg (0.016 mmol) of 6-(2,5-dioxo-2,5-dihydro-1H-pyrrol-1-yl) hexanoic acid in the presence of 6.7 mg (0.018 mmol) of HATU and 9 μl of N,N-diisopropylethylamine and subsequent deprotection with zinc chloride in trifluoroethanol as described for Intermediate F119. Purification by preparative HPLC gave 8 mg (69% of theory over 2 steps) of the title compound.

LC-MS (Method 1): $R_t$=1.35 min; MS (EIpos): m/z=893 $[M+H]^+$.

Intermediate F176

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[1-(2,5-dioxo-2,5-dihydro-1H-pyrrol-1-yl)-12-oxo-3,6,9-trioxa-13-azapentadecan-15-yl]butanamide (1:1)

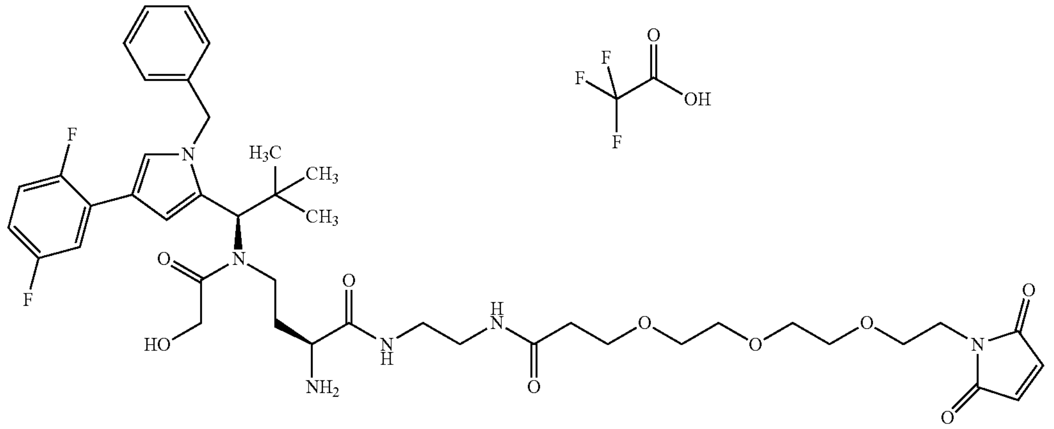 [SMILES: CC(C)(C)[C@H](c1cc(-c2cc(F)ccc2F)cn1Cc1ccccc1)N(CC[C@H](N)C(=O)NCCNC(=O)CCOCCOCCOCCN1C(=O)C=CC1=O)C(=O)CO ; O=C(O)C(F)(F)F]

The title compound was prepared by coupling of 5 mg (0.006 mmol) of Intermediate C64 with 2 mg (0.007 mmol) of 3-(2-{2-[2-(2,5-dioxo-2,5-dihydro-1H-pyrrol-1-yl)ethoxy]ethoxy}ethoxy)propanoic acid, the preparation of which is described under Intermediate L15, in the presence of 3.5 mg (0.009 mmol) of HATU and 4 μl of N,N-diisopropylethylamine and subsequent deprotection with zinc chloride in trifluoroethanol as described for Intermediate F119. Purification by preparative HPLC gave 2 mg (35% of theory over 2 steps) of the title compound.

LC-MS (Method 1): $R_t$=0.86 min; MS (EIpos): m/z=839 $[M+H]^+$.

Intermediate F177

Trifluoroacetic Acid/(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-(2-{[(2,5-dioxo-2,5-dihydro-1H-pyrrol-1-yl)acetyl]amino}ethyl)cyclopentanecarboxamide (1:1)

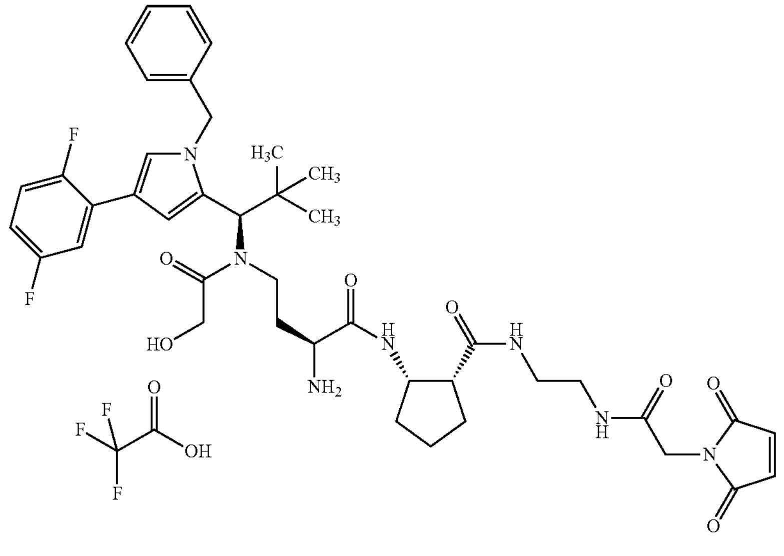

The title compound was prepared analogously to Intermediate F168 using, instead of Intermediate L61, the Intermediate L1.

LC-MS (Method 1): $R_t$=0.86 min; MS (EIpos): m/z=804 $[M+H]^+$.

Intermediate F178

Trifluoroacetic Acid/(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-{2-[(bromoacetyl)amino]ethyl}cyclopentanecarboxamide (1:1)

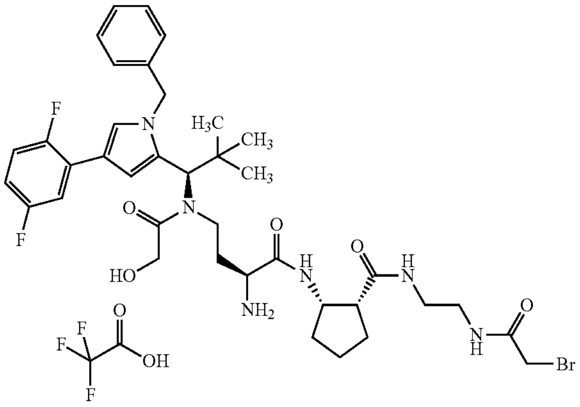

The title compound was prepared analogously to Intermediate F177 using, instead of Intermediate L1, the Intermediate L52.

LC-MS (Method 1): $R_t$=0.89 min; MS (EIpos): m/z=787 and 789 $[M+H]^+$.

Intermediate F179

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[6-(2,5-dioxo-2,5-dihydro-1H-pyrrol-1-yl)hexyl]butanamide (1:1)

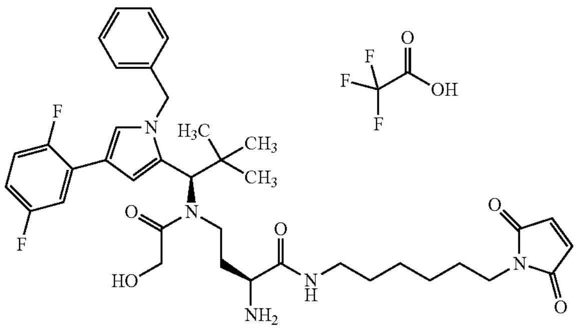 [SMILES: CC(C)(C)[C@H](c1cc(-c2cc(F)ccc2F)cn1Cc1ccccc1)N(CC[C@H](N)C(=O)NCCCCCCN1C(=O)C=CC1=O)C(=O)CO ; O=C(O)C(F)(F)F]

The title compound was prepared by coupling of 15 mg (0.023 mmol) of Intermediate C58 with 6 mg (0.025 mmol) of 1-(6-aminohexyl)-1H-pyrrole-2,5-dione in the presence of 13 mg (0.034 mmol) of HATU and 16 μl of N,N-diisopropylethylamine and subsequent deprotection with zinc chloride in trifluoroethanol as described for Intermediate F119. Purification by preparative HPLC gave 8.5 mg (46% of theory over 2 steps) of the title compound.

LC-MS (Method 6): $R_t$=2.22 min; MS (EIpos): m/z=692 $[M+H]^+$.

Intermediate F180

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N2-[(2,5-dioxo-2,5-dihydro-1H-pyrrol-1-yl)acetyl]-L-glutamine/trifluoroacetic Acid (1:1)

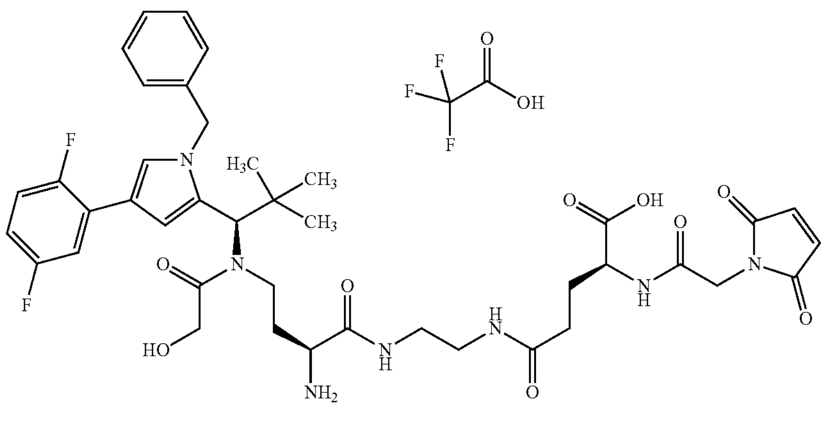 [SMILES: CC(C)(C)[C@H](c1cc(-c2cc(F)ccc2F)cn1Cc1ccccc1)N(CC[C@H](N)C(=O)NCCNC(=O)CC[C@H](NC(=O)CN1C(=O)C=CC1=O)C(=O)O)C(=O)CO ; O=C(O)C(F)(F)F]

The title compound was prepared by coupling of 9.6 mg (0.012 mmol) of Intermediate C64 with 5 mg (0.013 mmol) of Intermediate L64 in the presence of 7 mg (0.018 mmol) of HATU and 6 μl of N,N-diisopropylethylamine and subsequent deprotection with zinc chloride in trifluoroethanol as described for Intermediate F119. Purification by preparative HPLC gave 3.1 mg (28% of theory over 2 steps) of the title compound.

LC-MS (Method 1): $R_t$=0.85 min; MS (EIpos): m/z=822 $[M+H]^+$.

Intermediate F192

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl)acetyl]amino}-L-alanine/trifluoroacetic Acid (1:1)

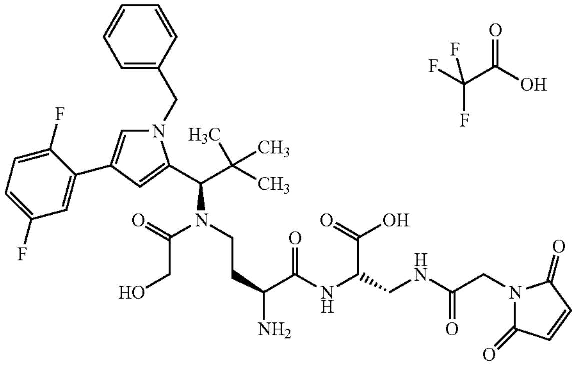

60 mg (0.091 mmol) of Intermediate C58 were taken up in 8 ml of DMF and coupled with 45 mg (0.100 mmol) of Intermediate L65 in the presence of 42 mg (0.11 mmol) of HATU and 64 μl of N,N-diisopropylethylamine. After purification by preparative HPLC, the intermediate was taken up in 10 ml of ethanol and hydrogenated over 10% palladium on activated carbon at RT under hydrogen standard pressure for 45 min. The catalyst was then filtered off, the solvent was removed under reduced pressure and the product was purified by preparative HPLC. Lyophilization from acetonitrile/water 1:1 gave 24.5 mg (31% of theory over 2 steps) of 2-(trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-L-alaninate.

LC-MS (Method 1): $R_t$=1.17 min; MS (EIpos): m/z=844 $[M+H]^+$.

The title compound was then prepared by coupling of 10 mg (0.012 mmol) of this intermediate with 2 mg (0.013 mmol) of commercially available (2,5-dioxo-2,5-dihydro-1H-pyrrol-1-yl)acetic acid intermediate in the presence of 5.4 mg (0.014 mmol) of HATU and 8 μl of N,N-diisopropylethylamine and subsequent deprotection with zinc chloride in trifluoroethanol as described for Intermediate F119. Purification by preparative HPLC gave 3.5 mg (33% of theory over 2 steps) of the title compound.

LC-MS (Method 1): $R_t$=0.81 min; MS (ESIpos): m/z=737 $(M+H)^+$.

Intermediate F193

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl)acetyl]amino}-D-alanine/trifluoroacetic Acid (1:1)

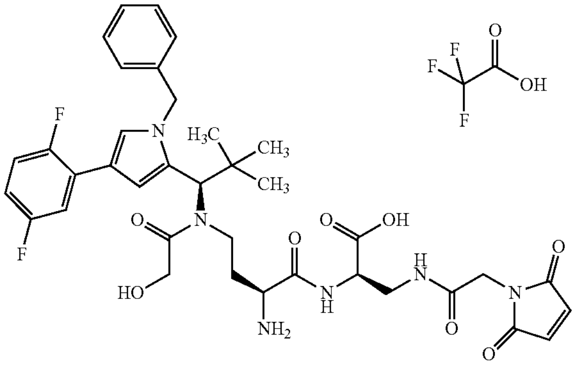 [SMILES: CC(C)(C)[C@H](c1cc(-c2cc(F)ccc2F)cn1Cc1ccccc1)N(CC[C@H](N)C(=O)N[C@H](CNC(=O)CN1C(=O)C=CC1=O)C(=O)O)C(=O)CO ; O=C(O)C(F)(F)F]

The synthesis of the title compound was carried out analogously to Intermediate F192 from 3-{[(benzyloxy)carbonyl]amino}-N-(tert-butoxycarbonyl)-D-alanine of HATU and N,N-cyclohexylcyclohexanamine (1:1).

LC-MS (Method 1): $R_t$=0.87 min; MS (ESIpos): m/z=737 $(M+H)^+$.

Intermediate F194

N-{5-[(2,5-Dioxopyrrolidin-1-yl)oxy]-5-oxopentanoyl}-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide

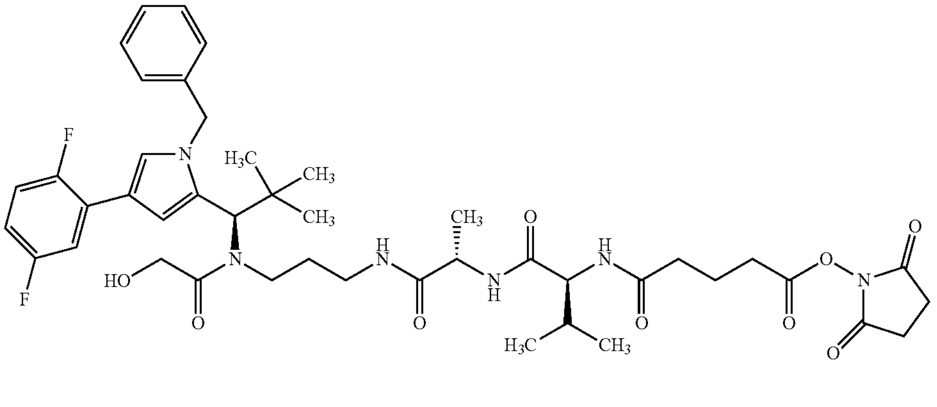 [SMILES: CC(C)[C@H](NC(=O)CCCC(=O)ON1C(=O)CCC1=O)C(=O)N[C@@H](C)C(=O)NCCCN(C(=O)CO)[C@@H](c1cc(-c2cc(F)ccc2F)cn1Cc1ccccc1)C(C)(C)C]

The title compound was prepared from Example 98 first by coupling with N-[(benzyloxy)carbonyl]-L-valyl-L-alanine in the presence of HATU and N,N-diisopropylethylamine. In the next step, the Z protective group was removed by hydrogenating for 1 hour over 10% palladium on activated carbon at RT under hydrogen standard pressure and then converting the deprotected intermediate as described for Intermediate F58 by reaction with 1,1'-[(1,5-dioxopentane-1,5-diyl)bis(oxy)]dipyrrolidine-2,5-dione into the title compound.

LC-MS (Method 1): $R_t$=1.19 min; MS (ESIpos): m/z=851 $[M+H]^+$.

Intermediate F195

Trifluoroacetic Acid/N-{(2S)-2-amino-4-[{(1R)-1-[1-benzyl-4-(2,5-difluorophenyl)-1H-pyrrol-2-yl]-2,2-dimethylpropyl}(glycoloyl)amino]butyl}-N'-[2-(2,5-dioxo-2,5-dihydro-1H-pyrrol-1-yl)ethyl]succinamide (1:1)

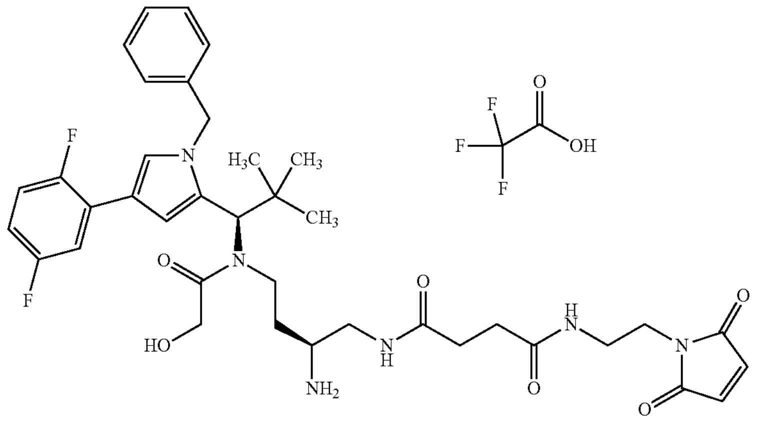 [SMILES: CC(C)(C)[C@H](c1cc(-c2cc(F)ccc2F)cn1Cc1ccccc1)N(CC[C@H](N)CNC(=O)CCC(=O)NCCN1C(=O)C=CC1=O)C(=O)CO ; O=C(O)C(F)(F)F]

The title compound was prepared by coupling of 26 mg (0.035 mmol) of Intermediate C65 with 18 mg (0.07 mmol) of commercially available trifluoroacetic acid/1-(2-aminoethyl)-1H-pyrrole-2,5-dione (1:1) in 8 ml of DMF in the presence of 40 mg (0.1054 mmol) of HATU and 61 µl of N,N-diisopropylethylamine and subsequent deprotection with zinc chloride in trifluoroethanol as described for Intermediate F119. Purification by preparative HPLC gave 16 mg (43% of theory over 2 steps) of the title compound.

LC-MS (Method 1): $R_t$=0.85 min; MS (ESIpos): m/z=721 $(M+H)^+$.

$^1$H-NMR (500 MHz, DMSO-$d_6$): δ=7.99 (t, 1H), 7.95 (t, 1H), 7.6-7.75 (m, 4H), 7.5 (s, 1H) 7.2-7.4 (m, 6H), 6.8-7.0 (m, 4H), 5.63 (s, 1H), 4.9 and 5.2 (2d, 2H), 4.26 and 4.0 (2d, 2H), 3.3-3.6 (m, 4H), 3.15-3.25 (m, 3H), 2.85-3.0 (m, 2H), 2.2-2.3 (m, 4H), 0.64 and 1.49 (2m, 2H), 0.81 (s, 9H).

Intermediate F196

Trifluoroacetic Acid/2-(2,5-dioxo-2,5-dihydro-1H-pyrrol-1-yl)ethyl-N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alaninate (1:1)

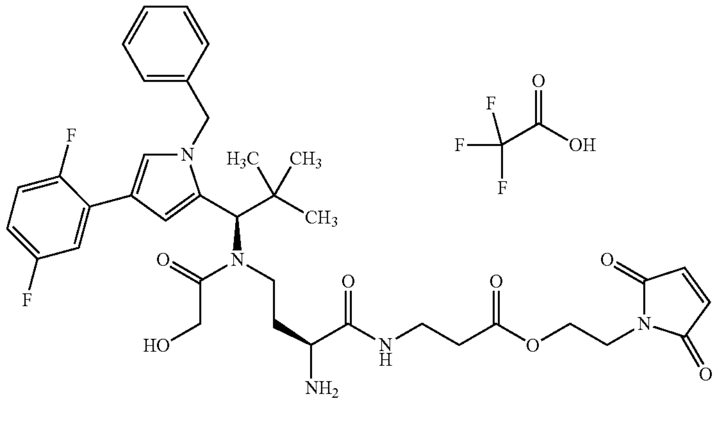 [SMILES: CC(C)(C)[C@H](c1cc(-c2cc(F)ccc2F)cn1Cc1ccccc1)N(CC[C@H](N)C(=O)NCCC(=O)OCCN1C(=O)C=CC1=O)C(=O)CO ; O=C(O)C(F)(F)F]

First, 15 mg (0.023 mmol) of Intermediate C58 were taken up in 4 ml of DMF and reacted with 8.2 mg (0.025 mmol) of Intermediate L67 in the presence of 13.0 mg (0.034 mmol) of HATU and 16 μl of N,N-diisopropylethylamine. After 30 min of stirring at RT, the mixture was concentrated and the residue was purified by preparative HPLC. After combination of the appropriate fractions and evaporation of the solvent, the residue was lyophilized from acetonitrile/water 1:1. This gave 4.3 mg (20% of theory) of the protected intermediate.

LC-MS (Method 1): $R_t$=1.35 min; MS (EIpos): m/z=852 $[M+H]^+$.

4.3 mg (4.5 μmol) of the intermediate were dissolved in 1 ml of trifluoroethanol and deprotected with 3.65 mg (27 μmol) zinc chloride as described for Intermediate F119. Purification by preparative HPLC gave 1 mg (25% of theory over 2 steps) of the title compound.

LC-MS (Method 1): $R_t$=0.88 min; MS (ESIpos): m/z=708 $(M+H)^+$

Intermediate F204

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[3-(2,5-dioxo-2,5-dihydro-1H-pyrrol-1-yl)propanoyl]amino}ethyl)butanamide (1:1)

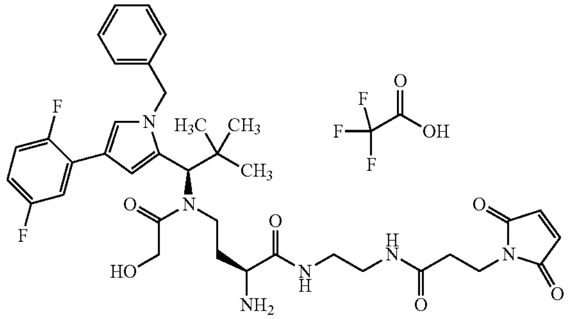 [SMILES: CC(C)(C)[C@H](c1cc(-c2cc(F)ccc2F)cn1Cc1ccccc1)N(CC[C@H](N)C(=O)NCCNC(=O)CCN1C(=O)C=CC1=O)C(=O)CO ; O=C(O)C(F)(F)F]

25 mg (0.038 mmol) of Intermediate C58 were initially reacted with 16.5 mg (75% pure) (0.038 mmol) of Intermediate L68 in the presence of 17 mg (0.046 mmol) of HATU and 20 μl of N,N-diisopropylethylamine. After 60 min of stirring at RT, the mixture was concentrated and the residue was purified by preparative HPLC. This gave 18.3 mg (56% of theory) of the protected intermediate.

LC-MS (Method 1): $R_t$=1.32 min; MS (EIpos): m/z=851 $[M+H]^+$.

In the second step, this intermediate was dissolved in 3 ml of 2,2,2-trifluoroethanol. 12 mg (0.086 mmol) of zinc chloride were added, and the reaction was stirred at 50° C. for 2 h. 25 mg (0.086 mmol) of ethylenediamine-N,N,N',N'-tetraacetic acid and 2 ml of a 0.1% strength aqueous trifluoroacetic acid solution were then added. The reaction was purified by preparative HPLC. Concentration of the appropriate fractions and lyophilization of the residue from acetonitrile/water gave 11 mg (62% of theory) of the title compound.

LC-MS (Method 1): $R_t$=0.85 min; MS (ESIpos): m/z=707 $(M+H)^+$.

Intermediate F205

Trifluoroacetic Acid/1-[(2,5-dioxo-2,5-dihydro-1H-pyrrol-1-yl)acetyl]piperidin-4-yl N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-L-valyl-$N^5$-carbamoyl-L-ornithinate (1:1)

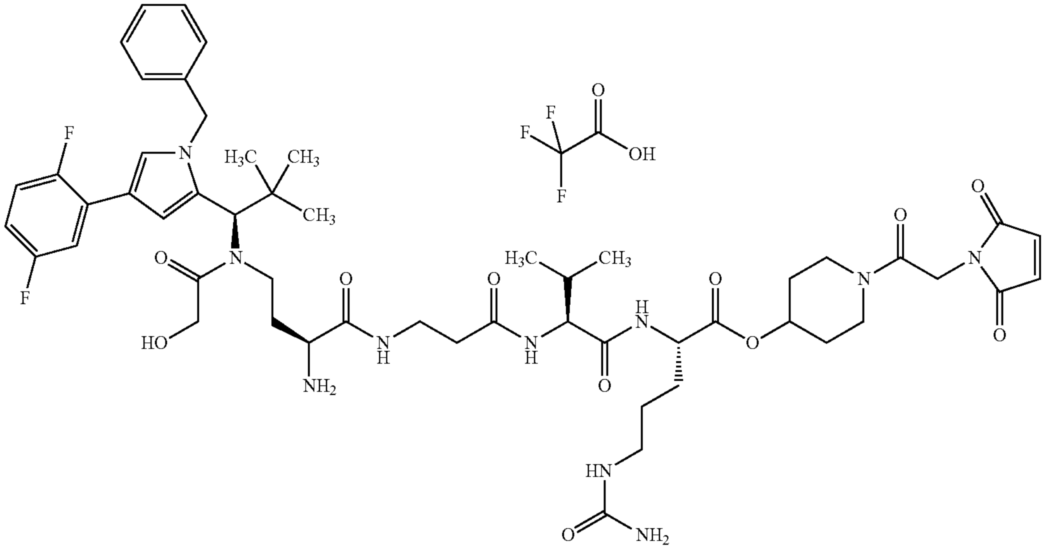 [SMILES: CC(C)[C@H](NC(=O)CCNC(=O)[C@@H](N)CCN(C(=O)CO)[C@@H](c1cc(-c2cc(F)ccc2F)cn1Cc1ccccc1)C(C)(C)C)C(=O)N[C@@H](CCCNC(N)=O)C(=O)OC1CCN(C(=O)CN2C(=O)C=CC2=O)CC1 ; O=C(O)C(F)(F)F]

The synthesis was carried out by coupling of 25 mg (0.034 mmol) of Intermediate C61 and 29 mg (0.041 mmol) of Intermediate L69 in the presence of HATU and N,N-diisopropylethylamine, followed by hydrogenation with palladium on activated carbon (10%) under standard pressure, then coupling with (2,5-dioxo-2,5-dihydro-1H-pyrrol-1-yl) acetic acid in the presence of HATU and N,N-diisopropylethylamine and finally removal of the 2-(trimethylsilyl) ethoxycarbonyl protective group with zinc chloride. HPLC purification gave 11 mg (26% of theory over 4 steps).

LC-MS (Method 1): $R_t$=0.86 min; MS (ESIpos): m/z=1061 $(M+H)^+$.

Intermediate F206

Trifluoroacetic Acid/1-[(2,5-dioxo-2,5-dihydro-1H-pyrrol-1-yl)acetyl]piperidin-4-yl N-{(2S)-2-amino-4-[{(1R)-1-[1-benzyl-4-(2,5-difluorophenyl)-1H-pyrrol-2-yl]-2,2-dimethylpropyl}(glycoloyl)amino] butanoyl}-beta-alanyl-L-valyl-L-alaninate (1:1)

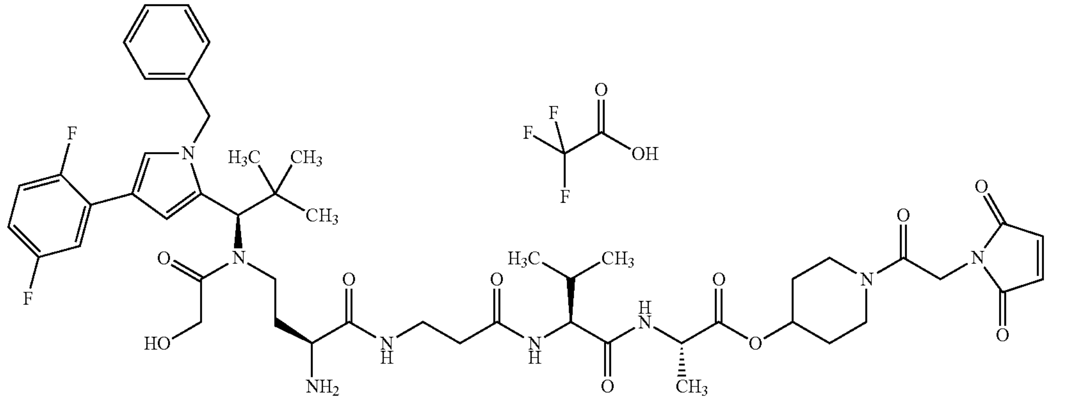 [SMILES: CC(C)[C@H](NC(=O)CCNC(=O)[C@@H](N)CCN(C(=O)CO)[C@@H](c1cc(-c2cc(F)ccc2F)cn1Cc1ccccc1)C(C)(C)C)C(=O)N[C@@H](C)C(=O)OC1CCN(C(=O)CN2C(=O)C=CC2=O)CC1 ; O=C(O)C(F)(F)F]

The synthesis was carried out analogously to Intermediate F205.

LC-MS (Method 1): $R_t$=0.86 min; MS (ESIpos): m/z=975 $(M+H)^+$.

Intermediate F207

$N^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$—{N-[(2,5-dioxo-2,5-dihydro-1H-pyrrol-1-yl)acetyl]-L-valyl-L-alanyl}-L-lysine/trifluoroacetic Acid (1:1)

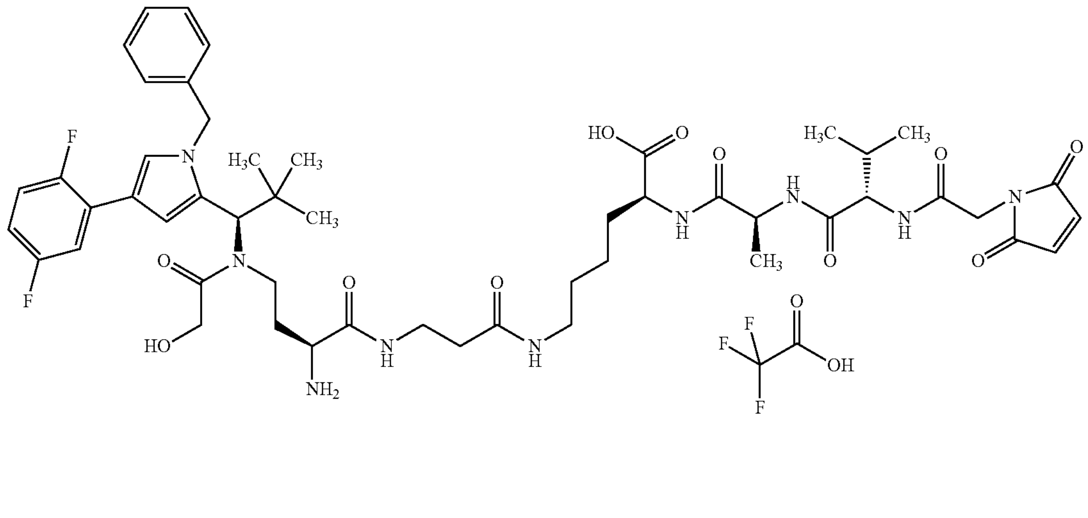

The title compound was prepared analogously to Intermediate F155.

LC-MS (Method 1): $R_t$=0.81 min; MS (ESIpos): m/z=1020 $(M+H)^+$.

Intermediate F209

R-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteine/trifluoroacetic Acid (1:1)

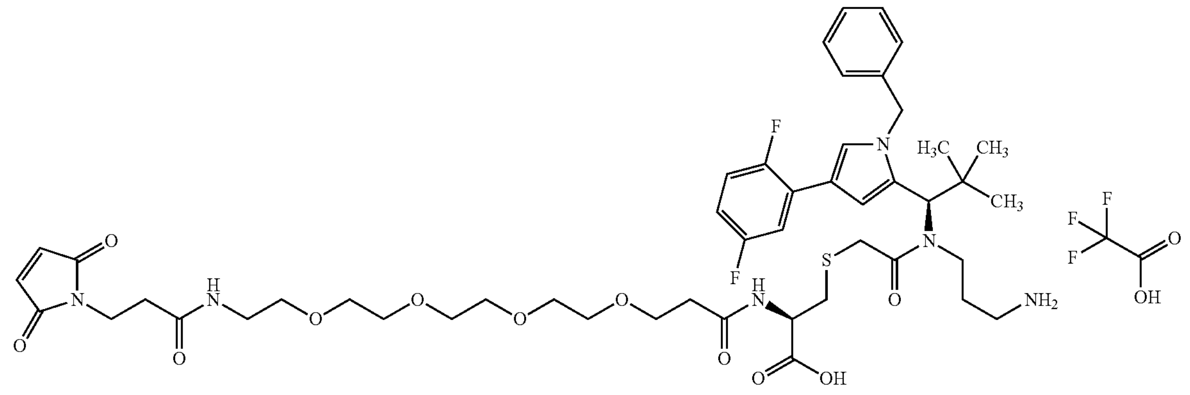 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CCN1C(=O)C=CC1=O)C(=O)O ; O=C(O)C(F)(F)F]

93.9 mg (0.78 mmol) of L-cysteine were suspended in a solution of 93.0 mg (1.11 mmol) of sodium bicarbonate and 0.9 ml of water. 70.0 mg (0.11 mmol) of 2-(trimethylsilyl) ethyl {3-[{(1R)-1-[1-benzyl-4-(2,5-difluorophenyl)-1H-pyrrol-2-yl]-2,2-dimethylpropyl}(chloroacetyl)amino] propyl}carbamate (Intermediate C70), dissolved in 6.0 ml of isopropanol, and 202.3 mg (1.33 mmol) of 1,8-diazabicyclo [5.4.0]undec-7-ene were added. The reaction mixture was stirred at 50° C. for 90 min. Water (0.1% TFA) was added, and the reaction was purified by preparative RP-HPLC (column: Reprosil 125x30; 10μ, flow rate: 50 ml/min, MeCN/water; 0.1% TFA). The solvents were evaporated under reduced pressure and the residue was dried under high vacuum. This gave 53.9 mg (59% of theory) of the compound R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1).

LC-MS (Method 1): $R_t$=1.24 min; MS (ESIpos): m/z=717 $(M+H)^+$.

86.0 mg (0.1 mmol) of R-(1-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) and 58.5 mg (0.11 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were dissolved in 4.0 ml of DMF, and 20.9 mg (0.21 mmol) of 4-methylmorpholine were added. The reaction mixture was stirred at RT overnight. 15.5 mg (0.26 mmol) of HOAc were added and the reaction mixture was purified directly by preparative RP-HPLC (column: Reprosil 125x30; 10μ, flow rate: 50 ml/min, MeCN/water, 0.1% TFA). The solvents were evaporated under reduced pressure and the residue was dried under high vacuum. This gave 68.6 mg (59% of theory) of the compound R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]-L-cysteine.

LC-MS (Method 6): $R_t$=2.88 min; MS (ESIpos): m/z=1115 $(M+H)^+$.

46.4 mg (0.04 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]-L-cysteine were dissolved in 2.0 ml of trifluoroethanol, and 17.0 mg (0.13 mmol) of zinc dichloride were added. The reaction mixture was stirred at 50° C. overnight. Another 8.5 mg (0.07 mmol) of zinc dichloride were added, and the mixture was stirred at 50° C. overnight. 36.5 mg (0.13 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125x30; 10μ, flow rate: 50 ml/min, MeCN/water, 0.1% TFA). The solvents were evaporated under reduced pressure and the residue was dried under high vacuum.

This gave 19.4 mg (43% of theory) of the title compound.

LC-MS (Method 1): $R_t$=0.94 min; MS (ESIpos): m/z=971 $(M+H)^+$.

Intermediate F210

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-D-cysteine/trifluoroacetic Acid (1:1)

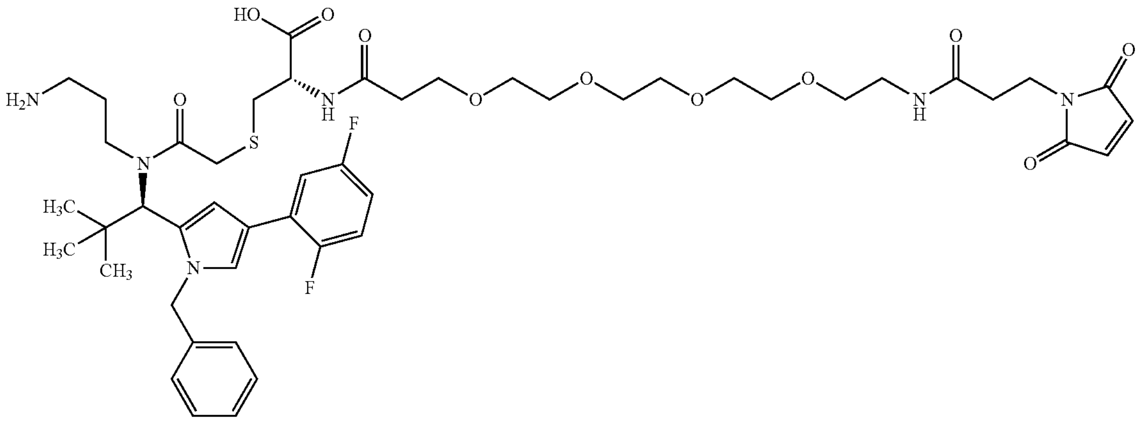 [SMILES: CC(C)(C)[C@H](c1cc(-c2cc(F)ccc2F)cn1Cc1ccccc1)N(CCCN)C(=O)CSC[C@@H](NC(=O)CCOCCOCCOCCOCCNC(=O)CCN1C(=O)C=CC1=O)C(=O)O]

The title compound was prepared analogously to the synthesis of Intermediate F209 using D-cysteine.

LC-MS (Method 1): $R_t$=0.91 min; MS (ESIpos): m/z=971 $(M+H)^+$.

Intermediate F211

Trifluoroacetic Acid/3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-N-[2-(2,5-dioxo-2,5-dihydro-1H-pyrrol-1-yl)ethyl]propanamide (1:1)

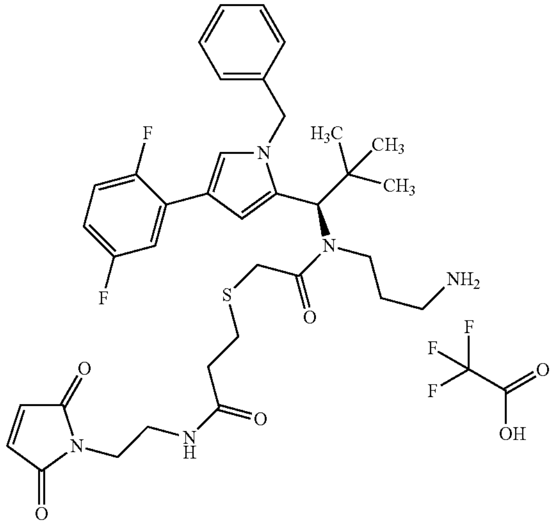

30.0 mg (0.05 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) were initially charged together with 5.5 mg (0.05 mmol) of 3-sulphanylpropanoic acid in 0.5 ml of methanol with a drop of water. 23.0 mg (0.17 mmol) of potassium carbonate were then added, and the reaction mixture was stirred at 50° C. for 4 h. Ethyl acetate was added and the organic phase was washed once with water and once with saturated NaCl solution. The organic phase was dried over magnesium sulphate and the solvent was evaporated under reduced pressure. The residue was used without further purification in the next step of the synthesis. This gave 30.3 mg (86% of theory) of the compound 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid.

LC-MS (Method 1): $R_t$=1.39 min; MS (ESIpos): m/z=702 $(M+H)^+$.

30.0 mg (0.04 mol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid and 9.8 mg (0.06 mmol) of 1-(2-aminoethyl)-1H-pyrrole-2,5-dione hydrochloride (1:1) were initially charged in 2.0 ml of acetonitrile, and 44.2 mg (0.34 mmol) of N,N-diisopropylethylamine were added. 35.4 mg (0.06 mmol) of T3P (50% in ethyl acetate) were added, and the reaction mixture was stirred at RT overnight. Water was added, and purification was carried out directly by preparative RP-HPLC (column: Reprosil 125×30; 10μ, flow rate: 50 ml/min, MeCN/water). The solvents were evaporated under reduced pressure and the residue was dried under high vacuum. This gave 22.0 mg (63% of theory) of the compound 2-(trimethylsilyl)ethyl [3-({(1R)-1-[1-benzyl-4-(2,5-difluorophenyl)-1H-pyrrol-2-yl]-2,2-dimethylpropyl}{[(3-{[2-(2,5-dioxo-2,5-dihydro-1H-pyrrol-1-yl)ethyl]amino}-3-oxopropyl)sulphanyl]acetyl}amino)propyl]carbamate.

LC-MS (Method 1): $R_t$=1.41 min; MS (ESIpos): m/z=824 $(M+H)^+$.

22.0 mg (0.03 mol) of 2-(trimethylsilyl)ethyl [3-({(1R)-1-[1-benzyl-4-(2,5-difluorophenyl)-1H-pyrrol-2-yl]-2,2-dimethylpropyl}{[(3-{[2-(2,5-dioxo-2,5-dihydro-1H-pyrrol-1-yl)ethyl]amino}-3-oxopropyl)sulphanyl]acetyl}amino)propyl]carbamate were dissolved in 1.0 ml of trifluoroethanol, and 9.1 mg (0.07 mmol) of zinc dichloride were added. The reaction mixture was stirred at 50° C. for 5 h. 19.5 mg (0.07 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 15.0 mg (71% of theory) of the title compound.

LC-MS (Method 1): $R_t$=0.88 min; MS (ESIpos): m/z=680 $(M+H)^+$.

Intermediate F212

Trifluoroacetic Acid/N-(3-aminopropyl)-N-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-10-oxo-3,6-dioxa-13-thia-9-azapentadecan-15-amide (1:1)

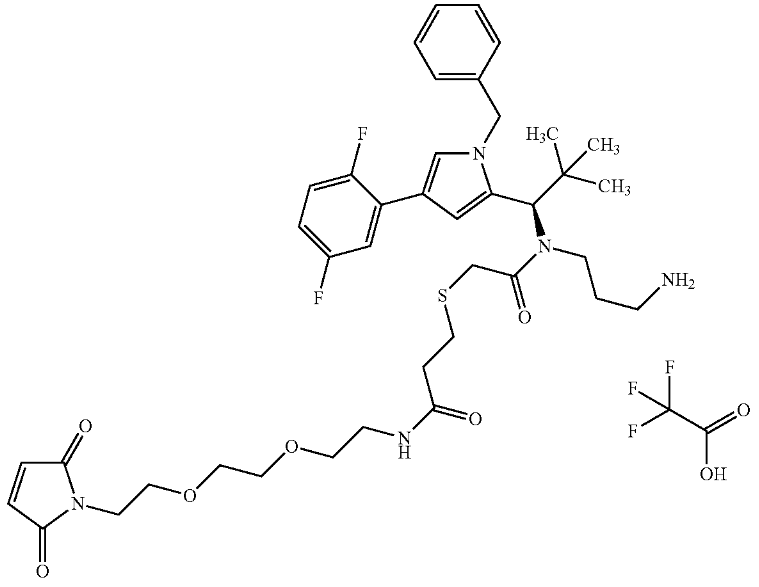 [SMILES: CC(C)(C)[C@H](c1cc(-c2cc(F)ccc2F)cn1Cc1ccccc1)N(CCCN)C(=O)CSCCC(=O)NCCOCCOCCN1C(=O)C=CC1=O ; O=C(O)C(F)(F)F]

28.8 mg (0.04 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 18.3 mg (0.05 mmol) of trifluoroacetic acid/1-{2-[2-(2-aminoethoxy)ethoxy]ethyl}-1H-pyrrole-2,5-dione (1:1) (Intermediate L59) in 1.9 ml of acetonitrile. 42.4 mg (0.33 mmol) of N,N-diisopropylethylamine were then added, and 33.9 mg (0.05 mmol) of T3P (50% in ethyl acetate) were added dropwise. The reaction mixture was stirred at RT overnight. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 10.7 mg (26% of theory) of the compound 2-(trimethylsilyl)ethyl [16-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-10,15-dioxo-3,6-dioxa-13-thia-9,16-diazanonadecan-19-yl]carbamate.

LC-MS (Method 1): $R_t$=1.44 min; MS (ESIpos): m/z=812 $(M+H)^+$.

10.7 mg (0.01 mol) of 2-(trimethylsilyl)ethyl [16-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-10,15-dioxo-3,6-dioxa-13-thia-9,16-diazanonadecan-19-yl]carbamate were dissolved in 0.8 ml of trifluoroethanol, and 8.0 mg (0.06 mmol) of zinc dichloride were added. The reaction mixture was stirred at 50° C. for 5 h. 17.1 mg (0.06 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum.

LC-MS (Method 1): $R_t$=1.03 min; MS (ESIpos): m/z=768 $(M+H)^+$.

Intermediate F213

Trifluoroacetic Acid/3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-N-(2-{[(2,5-dioxo-2,5-dihydro-1H-pyrrol-1-yl)acetyl]amino}ethyl)propanamide (1:1)

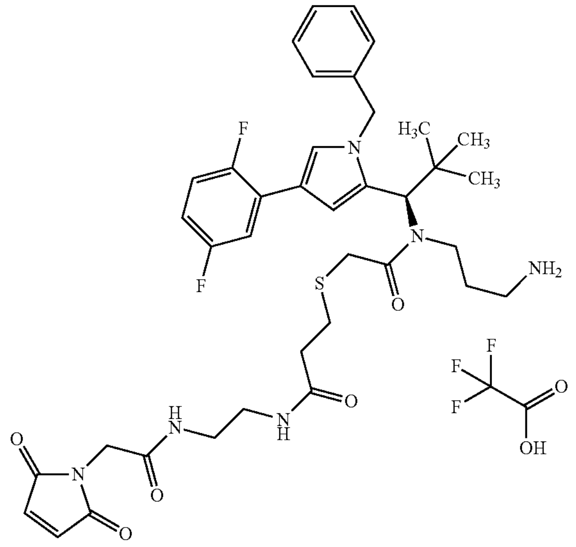

27.5 mg (0.04 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 15.9 mg (0.05 mmol) of trifluoroacetic acid/N-(2-aminoethyl)-2-(2,5-dioxo-2,5-dihydro-1H-pyrrol-1-yl)acetamide (1:1) (Intermediate L1) in 1.8 ml of acetonitrile. 32.4 mg (0.31 mmol) of N,N-diisopropylethylamine were then added, and 32.4 mg (0.05 mmol) of T3P (50% in ethyl acetate) were added dropwise. The reaction mixture was stirred at RT overnight. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 11.9 mg (35% of theory) of the compound 2-(trimethylsilyl)ethyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,7,12-trioxo-10-thia-3,6,13-triazahexadecan-16-yl]carbamate.

LC-MS (Method 1): $R_t$=1.39 min; MS (ESIpos): m/z=881 $(M+H)^+$.

11.9 mg (0.01 mol) of 2-(trimethylsilyl)ethyl-[13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,7,12-trioxo-10-thia-3,6,13-triazahexadecan-16-yl] carbamate were dissolved in 1.0 ml of trifluoroethanol, and 5.5 mg (0.04 mmol) of zinc dichloride were added. The reaction mixture was stirred at 50° C. overnight. 11.8 mg (0.04 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 7.4 mg (60% of theory) of the title compound.

LC-MS (Method 5): $R_t$=2.75 min; MS (ESIpos): m/z=737 $(M+H)^+$.

Intermediate F214

N-[19-(2,5-Dioxo-2,5-dihydro-1H-pyrrol-1-yl)-17-oxo-4,7,10,13-tetraoxa-16-azanonadecan-1-oyl]-L-alpha-glutamyl-S-{2-[(3-aminopropyl) {(1R)-1-[1-benzyl-4-(2,5-difluorophenyl)-1H-pyrrol-2-yl]-2,2-dimethylpropyl}amino]-2-oxoethyl}-L-cysteine/trifluoroacetic Acid (1:1)

111.7 mg (0.30 mmol) of (2S)-5-(benzyloxy)-2-{[(benzyloxy)carbonyl]amino}-5-oxopentanoic acid were initially charged in 3.0 ml of DMF, and 46.1 (0.30 mmol) of HOBt, 96.6 mg (0.30 mmol) of TBTU and 38.9 mg (0.30 mmol) of N,N-diisopropylethylamine were added. The reaction mixture was stirred at RT for 10 min. 250.0 mg (0.30 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) dissolved in 116.3 mg (0.9 mmol) of N,N-diisopropylethylamine and 3.0 ml of DMF were then added. The reaction mixture was stirred at RT overnight. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 257.0 mg (80% of theory) of the compound (16R)-11-{(1R)-1-[1-benzyl-4-(2,5-difluorophenyl)-1H-pyrrol-2-yl]-2,2-dimethylpropyl}-16-{[(2S)-5-(benzyloxy)-2-{[(benzyloxy)carbonyl]amino}-5-oxopentanoyl]amino}-2,2-dimethyl-6,12-dioxo-5-oxa-14-thia-7,11-diaza-2-silaheptadecan-17-oic acid.

LC-MS (Method 1): $R_t$=1.55 min; MS (ESIpos): m/z=1071 $(M+H)^+$.

Under argon, 24.6 mg (0.11 mmol) of palladium(II) acetate were initially charged in 5.0 ml of dichloromethane, and 33.2 mg (0.33 mmol) of triethylamine and 254.3 mg (2.19 mmol) of triethylsilane were added. The reaction mixture was stirred at RT for 5 min, and 234.1 mg (0.22 mmol) of (16R)-11-{(1R)-1-[1-benzyl-4-(2,5-difluorophenyl)-1H-pyrrol-2-yl]-2,2-dimethylpropyl}-16-{[(2S)-5-(benzyloxy)-2-{[(benzyloxy)carbonyl]amino}-5-oxopentanoyl]amino}-2,2-dimethyl-6,12-dioxo-5-oxa-14-thia-7,11-diaza-2-silaheptadecan-17-oic acid dissolved in 5.0 ml of dichloromethane were added. The reaction mixture was stirred at RT overnight. The reaction mixture was filtered through a cardboard filter and the filter cake was washed with dichloromethane. The solvent was evaporated under reduced pressure without heating. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 177.5 mg (85% of theory) of the compound L-alpha-glutamyl-S-(11-{(1R)-1-[1-benzyl-4-(2,5-difluorophenyl)-1H-pyrrol-2-yl]-2,2-dim-

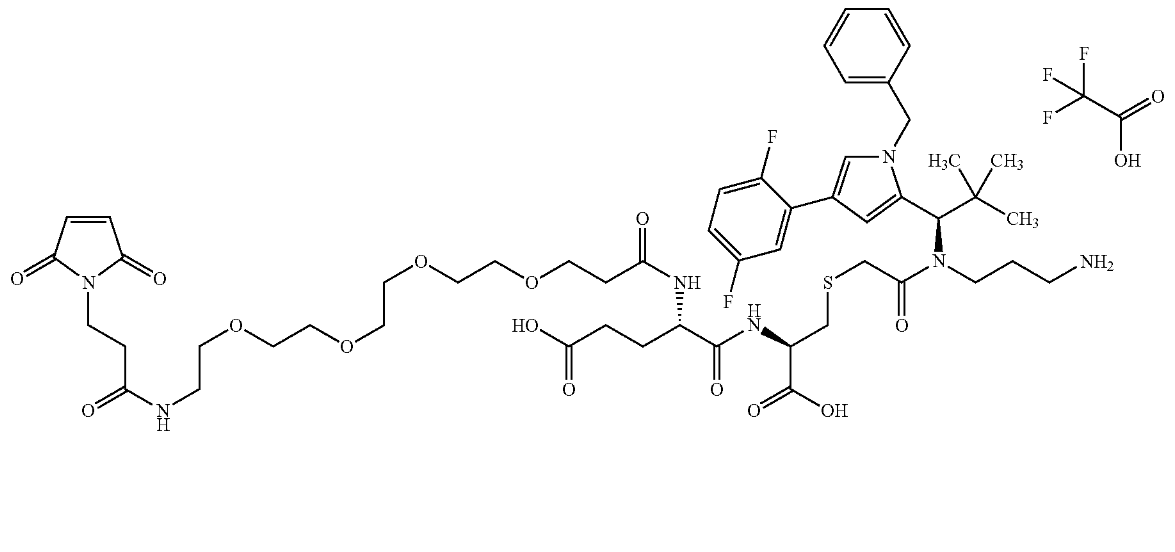 [SMILES: CC(C)(C)[C@H](c1cc(-c2cc(F)ccc2F)cn1Cc1ccccc1)N(CCCN)C(=O)CSC[C@H](NC(=O)[C@H](CCC(=O)O)NC(=O)CCOCCOCCOCCOCCNC(=O)CCN1C(=O)C=CC1=O)C(=O)O ; O=C(O)C(F)(F)F]

ethylpropyl}-2,2-dimethyl-6,12-dioxo-5-oxa-7,11-diaza-2-silatridecan-13-yl)-L-cysteine/trifluoroacetic acid (1:1).

LC-MS (Method 1): $R_t$=1.07 min; MS (ESIpos): m/z=846 $(M+H)^+$.

20.0 mg (20.83 μmol) L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) were initially charged together with 11.8 mg (22.91 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 1.5 ml of DMF, and 6.3 mg (62.49 μmol) of 4-methylmorpholine were added. The reaction mixture was stirred at RT overnight, and 4.4 mg (0.07 mmol) of acetic acid were then added. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 19.1 mg (74% of theory) of the compound N-[19-(2,5-dioxo-2,5-dihydro-1H-pyrrol-1-yl)-17-oxo-4,7,10,13-tetraoxa-16-azanonadecan-1-oyl]-L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 1): $R_t$=1.24 min; MS (ESIpos): m/z=1244 $(M+H)^+$.

17.5 mg (14.06 μmol) of N-[19-(2,5-dioxo-2,5-dihydro-1H-pyrrol-1-yl)-17-oxo-4,7,10,13-tetraoxa-16-azanonadecan-1-oyl]-L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 1.5 ml of trifluoroethanol, and 11.5 mg (84.37 μmol) of zinc dichloride were added. The reaction mixture was stirred at 50° C. for 4 h. 24.7 mg (0.08 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum.

This gave 10.8 mg (63% of theory) of the title compound.

LC-MS (Method 1): $R_t$=0.89 min; MS (ESIpos): m/z=1100 $(M+H)^+$.

Intermediate F215

N-[19-(2,5-Dioxo-2,5-dihydro-1H-pyrrol-1-yl)-17-oxo-4,7,10,13-tetraoxa-16-azanonadecan-1-oyl]-L-valyl-N-{3-[({[(2R)-2-acetamido-2-carboxyethyl]sulphanyl}acetyl){(1R)-1-[1-benzyl-4-(2,5-difluorophenyl)-1H-pyrrol-2-yl]-2,2-dimethylpropyl}amino]propyl}-L-alaninamide

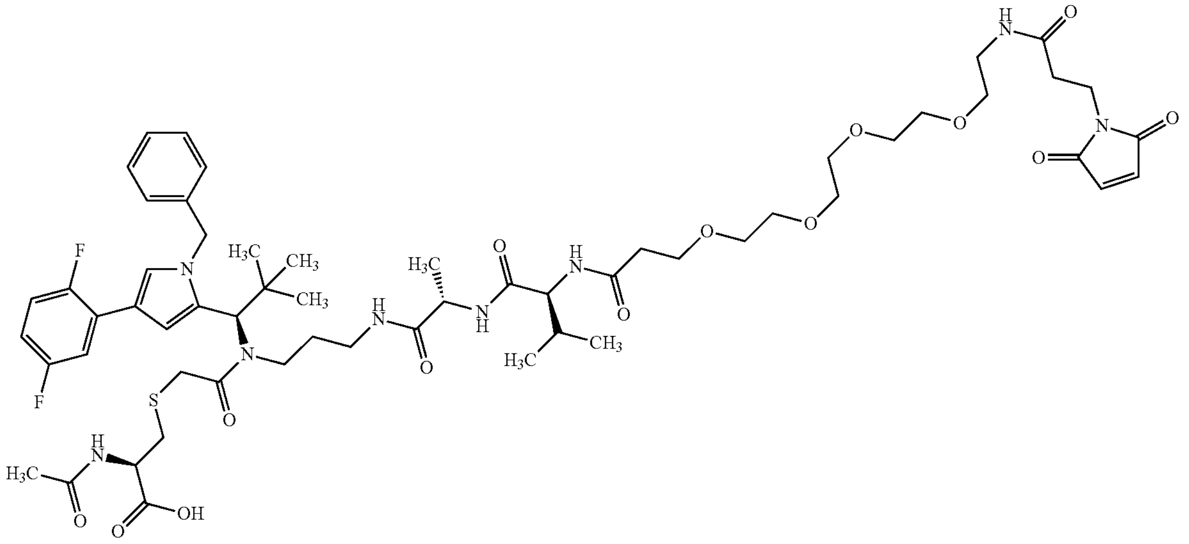 [SMILES: CC(=O)N[C@@H](CSCC(=O)N(CCCNC(=O)[C@H](C)NC(=O)[C@@H](NC(=O)CCOCCOCCOCCOCCNC(=O)CCN1C(=O)C=CC1=O)C(C)C)[C@@H](c1cc(-c2cc(F)ccc2F)cn1Cc1ccccc1)C(C)(C)C)C(=O)O]

14.9 mg (0.02 mmol) of N-acetyl-S-[2-([3-(L-alanylamino)propyl]{(1R)-1-[1-benzyl-4-(2,5-difluorophenyl)-1H-pyrrol-2-yl]-2,2-dimethylpropyl}amino)-2-oxoethyl]-L-cysteine/trifluoroacetic acid (1:1) (Example 229) and 7.1 mg (0.02 mmol) of 2,5-dioxopyrrolidin-1-yl-N-[(benzyloxy)carbonyl]-L-valinate were initially charged in 1.0 ml of DMF, and 5.7 mg (0.06 mmol) of 4-methylmorpholine were added. The reaction mixture was stirred at RT overnight, and 4.5 mg (0.08 mmol) of acetic acid were then added. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 13.3 mg (78% of theory) of the compound N-[(benzyloxy)carbonyl]-L-valyl-N-{3-[({[(2R)-2-acetamido-2-carboxyethyl]sulphanyl}acetyl){(1R)-1-[1-benzyl-4-(2,5-difluorophenyl)-1H-pyrrol-2-yl]-2,2-dimethylpropyl}amino]propyl}-L-alaninamide.

LC-MS (Method 1): $R_t$=1.24 min; MS (ESIpos): m/z=919 $(M+H)^+$.

11.1 mg (0.01 mmol) of N-[(benzyloxy)carbonyl]-L-valyl-N-{3-[({[(2R)-2-acetamido-2-carboxyethyl]sulphanyl}acetyl){(1R)-1-[1-benzyl-4-(2,5-difluorophenyl)-1H-pyrrol-2-yl]-2,2-dimethylpropyl}amino]propyl}-L-alaninamide were dissolved in 5.0 ml of ethanol, 1.0 mg of palladium on activated carbon (10%) was added and the mixture was hydrogenated at RT and standard pressure overnight. The reaction mixture was filtered through Celite and the filter cake was washed with an ethanol/THF/water mixture. The solvents were evaporated under reduced pressure. The residue was purified by preparative RP-HPLC (column: Reprosil 250×30; 10μ, flow rate: 50 ml/min, MeCN/water, 0.1% TFA). The solvents were evaporated under reduced pressure and the residue was lyophilized. This gave 7.5 mg (69% of theory) of the compound L-valyl-N-{3-[({([(2R)-2-acetamido-2-carboxyethyl] sulphanyl}acetyl){(1R)-1-[1-benzyl-4-(2,5-difluorophenyl)-1H-pyrrol-2-yl]-2,2-dimethylpropyl}amino]propyl}-L-alaninamide/trifluoroacetic acid (1:1).

LC-MS (Method 1): $R_t$=0.86 min; MS (ESIpos): m/z=785 $(M+H)^+$.

7.3 mg (8.12 μmol) of L-valyl-N-{3-[({[(2R)-2-acetamido-2-carboxyethyl]sulphanyl}acetyl){(1R)-1-[1-benzyl-4-(2,5-difluorophenyl)-1H-pyrrol-2-yl]-2,2-dimethylpropyl}amino]propyl}-L-alaninamide/trifluoroacetic acid (1:1) were initially charged together with 4.6 mg (8.93 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 0.5 ml of DMF, and 2.5 mg (24.36 μmol) of 4-methylmorpholine were added. The reaction mixture was stirred at RT overnight, and 4.4 mg (0.03 mmol) of acetic acid were then added. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum.

This gave 4.9 mg (50% of theory) of the title compound.

LC-MS (Method 1): $R_t$=1.07 min; MS (ESIpos): m/z=1183 $(M+H)^+$.

Intermediate F216

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteinyl-beta-alanine/trifluoroacetic Acid (1:1)

Under argon, 30.2 mg (0.06 mmol) of N,N'-bis[(benzyloxy)carbonyl]-L-cystine were initially charged in 2.0 ml of water and 2.0 ml of isopropanol, and 56.7 mg (0.20 mmol) of TCEP were added. The reaction mixture was stirred at RT for 30 min. 50.0 mg (0.08 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino] propyl}carbamate (Intermediate C70), dissolved in 2.0 ml of isopropanol, and 122.2 mg (0.48 mmol) of 1,8-diazabicyclo [5.4.0]undec-7-ene were then added, and the reaction mixture was stirred at 50° C. for 7 h. Another 122.2 mg (0.48 mmol) of 1,8-diazabicyclo[5.4.0]undec-7-ene were then added, and the reaction mixture was stirred at 50° C. for 1 h. The mixture was diluted with ethyl acetate and the organic phase was extracted with water and saturated sodium bicarbonate solution and washed with saturated NaCl solution. The organic phase was dried over magnesium sulphate and the solvent was evaporated under reduced pressure. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 43.1 mg (64% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine.

LC-MS (Method 1): $R_t$=1.46 min; MS (ESIpos): m/z=851 $(M+H)^+$.

16.5 mg (0.05 mmol) of 4-methylbenzenesulphonic acid/benzyl beta-alaninate (1:1) were initially charged together with 14.0 mg (0.11 mmol) of N,N-diisopropylethylamine in 1.5 ml of acetonitrile. The reaction mixture was stirred at RT for 3 min, and 30.8 mg (0.04 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine dissolved in 1.5 ml of acetonitrile, 23.4 mg (0.18 mmol) of N,N-diisopropylethylamine and 29.9 mg (0.05 mmol) of T3P (50% in ethyl acetate) were then added. The reaction

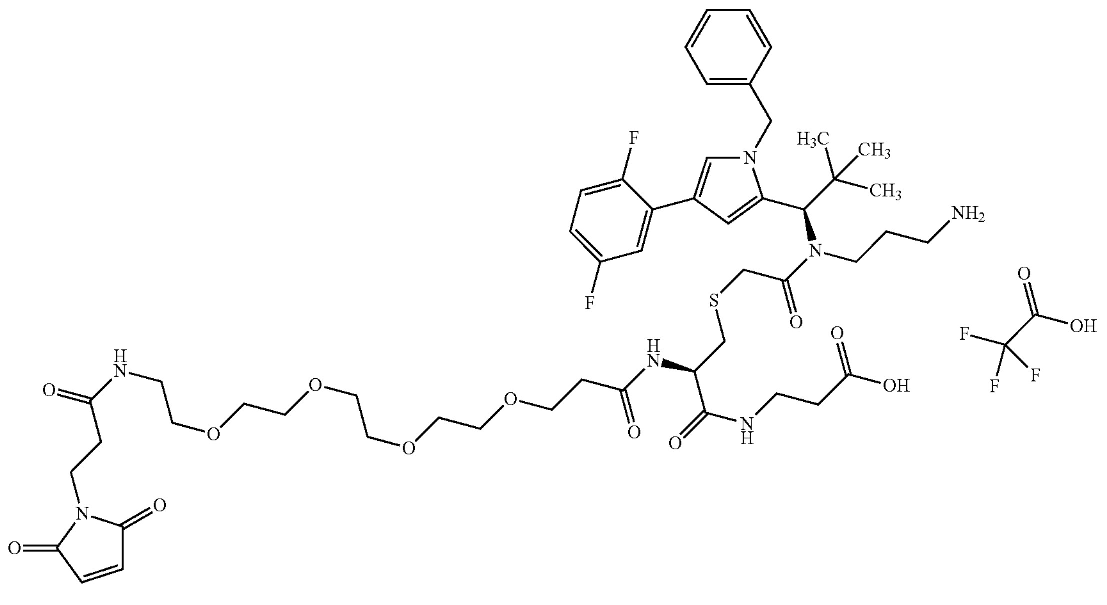 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CCN1C(=O)C=CC1=O)C(=O)NCCC(=O)O ; O=C(O)C(F)(F)F]

mixture was stirred at RT overnight. Water was added, and the reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. The compound obtained was benzyl S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl-beta-alaninate.

LC-MS (Method 1): $R_t$=1.59 min; MS (ESIpos): m/z=1012 $(M+H)^+$.

43.8 mg (43.3 μmol) of benzyl S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl-beta-alaninate were dissolved in 8.0 ml of ethanol, 4.4 mg of palladium on activated carbon (10%) were added and the mixture was hydrogenated at RT and standard pressure overnight. The reaction mixture was filtered through a cardboard filter and the filter cake was washed with ethanol. The solvent was evaporated under reduced pressure. Two more times, the residue was treated as just described. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 4.9 mg (50% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1).

LC-MS (Method 1): $R_t$=1.08 min; MS (ESIpos): m/z=788 $(M+H)^+$.

14.5 mg (16.1 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1) were initially charged together with 9.1 mg (17.7 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 1.0 ml of DMF, and 4.9 mg (48.2 μmol) of 4-methylmorpholine were added. The reaction mixture was stirred at RT overnight, and 3.4 mg (0.06 mmol) of acetic acid were then added. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 4.9 mg (50% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1).

LC-MS (Method 1): $R_t$=1.28 min; MS (ESIpos): m/z=1186 $(M+H)^+$.

14.1 mg (11.9 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]-L-cysteinyl-beta-alanine/trifluoroacetic acid (1:1) were dissolved in 1.5 ml of trifluoroethanol, and 9.7 mg (71.3 μmol) of zinc dichloride were added. The reaction mixture was stirred at 50° C. for 3 h. Another 9.7 mg (71.3 μmol) of zinc dichloride were added, and the reaction mixture was stirred at 50° C. for 3 h. Another 9.7 mg (71.3 μmol) of zinc dichloride were added, and the reaction mixture was stirred at 70° C. for 4 h. 20.8 mg (0.07 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was lyophilized. This gave 6.2 mg (44% of theory) of the title compound.

LC-MS (Method 1): $R_t$=0.82 min; MS (ESIpos): m/z=1042 $(M+H)^+$.

Intermediate F217

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[(2,5-dioxo-2,5-dihydro-1H-pyrrol-1-yl)acetyl]-L-cysteine/trifluoroacetic Acid (1:1)

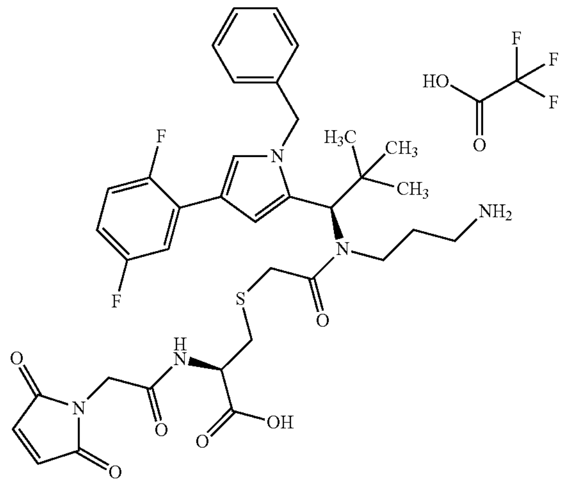 [SMILES: CC(C)(C)[C@H](c1cc(-c2cc(F)ccc2F)cn1Cc1ccccc1)N(CCCN)C(=O)CSC[C@H](NC(=O)CN1C(=O)C=CC1=O)C(=O)O ; O=C(O)C(F)(F)F]

Under argon, 7.5 mg (0.05 mmol) of (2,5-dioxo-2,5-dihydro-1H-pyrrol-1-yl)acetic acid were initially charged in 1.5 ml of DMF, and 7.5 mg (0.05 mmol) of HOBt, 15.5 mg (0.05 mmol) of TBTU and 6.2 mg (0.05 mmol) of N,N-diisopropylethylamine were added. The reaction mixture was stirred at RT for 10 min. 40.0 mg (0.05 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71), dissolved in 1.5 ml of DMF, and 18.7 mg (0.14 mmol) of N,N-diisopropylethylamine were then added, and the reaction mixture was stirred at RT overnight. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 11.2 mg (25% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(2,5-dioxo-2,5-dihydro-1H-pyrrol-1-yl)acetyl]-L-cysteine.

LC-MS (Method 1): $R_t$=1.37 min; MS (ESIpos): m/z=854 $(M+H)^+$.

10.9 mg (12.8 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(2,5-dioxo-2,5-dihydro-1H-pyrrol-1-yl)acetyl]-L-cysteine were dissolved in 2.0 ml of trifluoroethanol, and 10.4 mg (76.6 μmol) zinc dichloride were added. The reaction mixture was stirred at 50° C. for 4 h. 22.4 mg (0.08 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was lyophilized. This gave 7.5 mg (65% of theory) of the title compound.

LC-MS (Method 1): $R_t$=0.92 min; MS (ESIpos): m/z=710 $(M+H)^+$.

Intermediate F218

N-[19-(2,5-Dioxo-2,5-dihydro-1H-pyrrol-1-yl)-17-oxo-4,7,10,13-tetraoxa-16-azanonadecan-1-oyl]-L-gamma-glutamyl-S-{2-[(3-aminopropyl) {(1R)-1-[1-benzyl-4-(2,5-difluorophenyl)-1H-pyrrol-2-yl]-2,2-dimethylpropyl}amino]-2-oxoethyl}-L-cysteine/trifluoroacetic Acid (1:1)

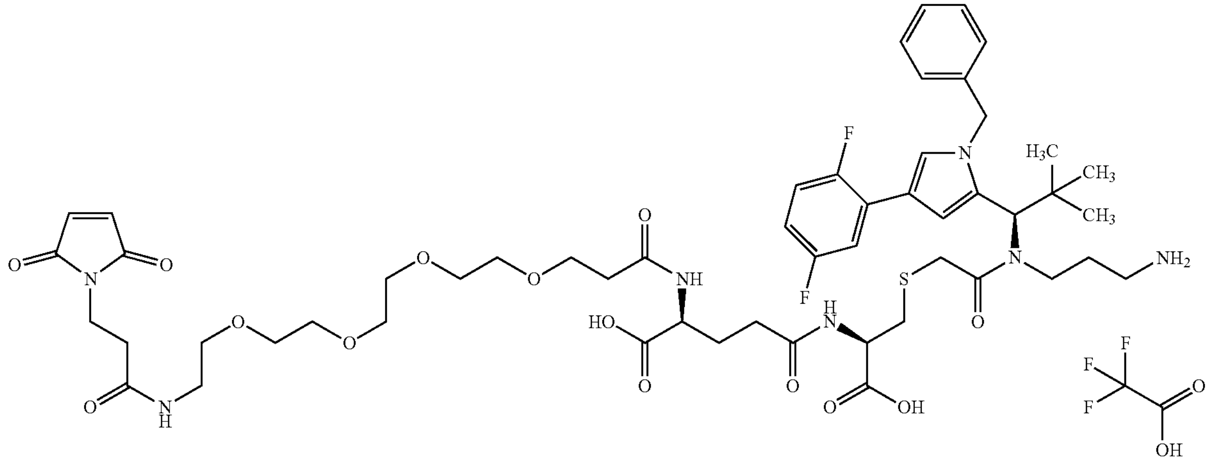 [SMILES: CC(C)(C)[C@H](c1cc(-c2cc(F)ccc2F)cn1Cc1ccccc1)N(CCCN)C(=O)CSC[C@H](NC(=O)CC[C@H](NC(=O)CCOCCOCCOCCOCCNC(=O)CCN1C(=O)C=CC1=O)C(=O)O)C(=O)O ; O=C(O)C(F)(F)F]

Under argon, 22.9 mg (0.06 mmol) of (4S)-5-(benzyloxy)-4-{[(benzyloxy)carbonyl]amino}-5-oxopentanoic acid were initially charged in 2.0 ml of DMF, and 9.4 mg (0.05 mmol) of HOBt, 19.8 mg (0.06 mmol) of TBTU and 8.0 mg (0.06 mmol) of N,N-diisopropylethylamine were added. The reaction mixture was stirred at RT for 10 min. 51.2 mg (0.06 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine (Intermediate C71), dissolved in 1.0 ml of DMF, and 23.9 mg (0.19 mmol) of N,N-diisopropylethylamine were then added, and the reaction mixture was stirred at RT overnight. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 11.2 mg (25% of theory) of the compound (16R)-11-{(1R)-1-[1-benzyl-4-(2,5-difluorophenyl)-1H-pyrrol-2-yl]-2,2-dimethylpropyl}-16-{[(4S)-5-(benzyloxy)-4-{[(benzyloxy)carbonyl]amino}-5-oxopentanoyl]amino}-2,2-dimethyl-6,12-dioxo-5-oxa-14-thia-7,11-diaza-2-silaheptadecan-17-oic acid.

LC-MS (Method 1): $R_t$=1.52 min; MS (ESIpos): m/z=1070 $(M+H)^+$.

Under argon, 3.9 mg (0.02 mmol) of palladium(II) acetate were initially charged in 1.0 ml of dichloromethane, and 5.3 mg (0.05 mmol) of triethylamine and 254.3 mg (2.19 mmol) of triethylsilane were added. The reaction mixture was stirred at RT for 5 min, and 18.6 mg (0.02 mmol) of (16R)-11-{(1R)-1-[1-benzyl-4-(2,5-difluorophenyl)-1H-pyrrol-2-yl]-2,2-dimethylpropyl}-16-{[(4S)-5-(benzyloxy)-4-{[(benzyloxy)carbonyl]amino}-5-oxopentanoyl]amino}-2,2-dimethyl-6,12-dioxo-5-oxa-14-thia-7,11-diaza-2-silaheptadecan-17-oic acid dissolved in 1.0 ml of dichloromethane were added. The solvent was evaporated under reduced pressure without heating. The residue was taken up in acetonitrile, filtered through a syringe filter and purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 11.0 mg (66% of theory) of the compound L-gamma-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1).

LC-MS (Method 1): $R_t$=1.14 min; MS (ESIpos): m/z=846 $(M+H)^+$.

15.0 mg (15.6 μmol) of L-gamma-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) were initially charged together with 8.8 mg (17.2 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 1.0 ml of DMF, and 4.7 mg (46.9 μmol) of 4-methylmorpholine were added. The reaction mixture was stirred at RT overnight, and 3.3 mg (0.06 mmol) of acetic acid were then added. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 14.2 mg (70% of theory) of the compound N-[19-(2,5-dioxo-2,5-dihydro-1H-pyrrol-1-yl)-17-oxo-4,7,10,13-tetraoxa-16- azanonadecan-1-oyl]-L-gamma-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 4) $R_t$=1.24 min; MS (ESIpos): m/z=1244 $(M+H)^+$.

13.8 mg (11.1 μmol) of N-[19-(2,5-dioxo-2,5-dihydro-1H-pyrrol-1-yl)-17-oxo-4,7,10,13-tetraoxa-16-azanonadecan-1-oyl]-L-gamma-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 9.1 mg (66.5 μmol) zinc dichloride were added. The reaction mixture was stirred at 50° C. for 4 h. 19.4 mg (0.07 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 6.9 mg (50% of theory) of the title compound.

LC-MS (Method 1): $R_t$=0.89 min; MS (ESIpos): m/z=1100 $(M+H)^+$.

Intermediate F235

Trifluoroacetic Acid/N-[19-(2,5-dioxo-2,5-dihydro-1H-pyrrol-1-yl)-17-oxo-4,7,10,13-tetraoxa-16-azanonadecan-1-oyl]-L-valyl-N-{4-[(3-aminopropyl){(1R)-1-[1-benzyl-4-(2,5-difluorophenyl)-1H-pyrrol-2-yl]-2,2-dimethylpropyl}carbamoyl]phenyl}-L-alaninamide (1:1)

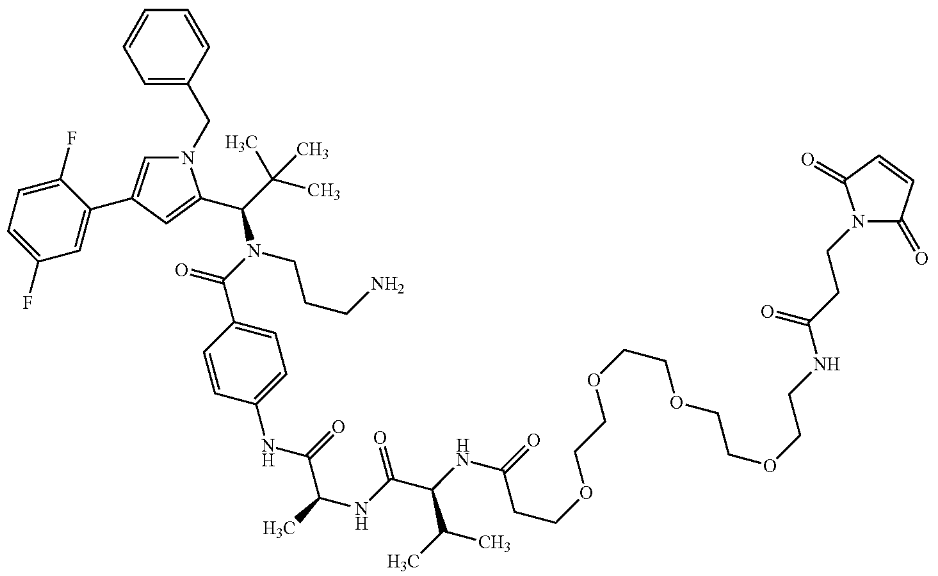 [SMILES: CC(C)[C@H](NC(=O)CCOCCOCCOCCOCCNC(=O)CCN1C(=O)C=CC1=O)C(=O)N[C@@H](C)C(=O)Nc1ccc(C(=O)N(CCCN)[C@@H](c2cc(-c3cc(F)ccc3F)cn2Cc2ccccc2)C(C)(C)C)cc1]

120.0 mg (0.22 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate (see synthesis of Intermediate C11) and 52.1 mg (0.28 mmol) of 4-nitrobenzoyl chloride were dissolved in 8.0 ml of dichloromethane, and 28.4 mg (0.28 mmol) of triethylamine were added. The reaction mixture was stirred at RT overnight. The solvent was evaporated under reduced pressure and the residue was purified by preparative RP-HPLC (column: Reprosil 125×30; 10μ, flow rate: 50 ml/min, MeCN/water, 0.1% TFA). This gave 97.7 mg (64% of theory) of the compound 2-(trimethylsilyl)ethyl {3-[{(1R)-1-[1-benzyl-4-(2,5-difluorophenyl)-1H-pyrrol-2-yl]-2,2-dimethylpropyl}(4-nitrobenzoyl)amino]propyl}carbamate.

LC-MS (Method 1): $R_t$=1.54 min; MS (ESIpos): m/z=705 $(M+H)^+$.

97.0 mg (0.14 mmol) of 2-(trimethylsilyl)ethyl {3-[{(1R)-1-[1-benzyl-4-(2,5-difluorophenyl)-1H-pyrrol-2-yl]-2,2-dimethylpropyl}(4-nitrobenzoyl)amino]propyl}carbamate were dissolved in 5.0 ml of ethanol, 9.7 mg of palladium on activated carbon (10%) were added and the mixture was hydrogenated at standard pressure for 5 h. The reaction mixture was filtered through a cardboard filter and the filter cake was washed with ethanol. The solvent was evaporated under reduced pressure. The residue was used without further purification in the next step of the synthesis. This gave 87.4 mg (88% of theory) of the compound 2-(trimethylsilyl)ethyl {3-[(4-aminobenzoyl){(1R)-1-[1-benzyl-4-(2,5-difluorophenyl)-1H-pyrrol-2-yl]-2,2-dimethylpropyl}amino]propyl}carbamate.

LC-MS (Method 1): $R_t$=1.47 min; MS (ESIpos): m/z=675 $(M+H)^+$.

59.3 mg (0.09 mmol) of 2-(trimethylsilyl)ethyl {3-[(4-aminobenzoyl) {(1R)-1-[1-benzyl-4-(2,5-difluorophenyl)-1H-pyrrol-2-yl]-2,2-dimethylpropyl}amino]propyl}carbamate and 25.5 mg (0.11 mmol) of N-[(benzyloxy)carbonyl]-L-alanine were initially charged together with 68.1 mg (0.53 mmol) of N,N-diisopropylethylamine in 5.0 ml of acetonitrile. 72.7 mg (0.11 mmol) of T3P (50% in ethyl acetate) were added slowly. The reaction mixture was stirred at RT overnight. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 52.2 mg (68% of theory) of the compound benzyl [(2S)-1-{[4-({(1R)-1-[1-benzyl-4-(2,5-difluorophenyl)-1H- pyrrol-2-yl]-2,2-dimethylpropyl}[3-({[2-(trimethylsilyl)ethoxy]carbonyl}amino)propyl]carbamoyl)phenyl]amino}-1-oxopropan-2-yl]carbamate.

LC-MS (Method 1): $R_t$=1.48 min; MS (ESIpos): m/z=880 $(M+H)^+$.

23.9 mg (0.03 mmol) of benzyl [(2S)-1-{[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]amino}-1-oxopropan-2-yl]carbamate were dissolved in 3.0 ml of ethyl acetate, 2.4 mg of palladium on activated carbon (10%) were added and the mixture was hydrogenated at standard pressure for 2 h. The reaction mixture was filtered through a paper filter and the filter cake was washed with ethyl acetate. The solvent was evaporated under reduced pressure. The residue was used without further purification in the next step of the synthesis. This gave 20.1 mg (90% of theory) of the compound 2-(trimethylsilyl)ethyl [3-([4-(L-alanylamino)benzoyl]{(1R)-1-[1-benzyl-4-(2,5-difluorophenyl)-1H-pyrrol-2-yl]-2,2-dimethylpropyl}amino)propyl]carbamate.

LC-MS (Method 1): $R_t$=1.13 min; MS (ESIpos): m/z=746 $(M+H)^+$.

20.0 mg (0.03 mmol) of 2-(trimethylsilyl)ethyl [3-([4-(L-alanylamino)benzoyl]{(1R)-1-[1-benzyl-4-(2,5-difluorophenyl)-1H-pyrrol-2-yl]-2,2-dimethylpropyl}amino)propyl]carbamate were initially charged together with 14.9 mg (0.04 mmol) of 2,5-dioxopyrrolidin-1-yl N-[(benzyloxy)carbonyl]-L-valinate in 2.0 ml of DMF, and 5.4 mg (0.05 mmol) of 4-methylmorpholine were added. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave the compound N-[(benzyloxy)carbonyl]-L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide.

LC-MS (Method 1): $R_t$=1.49 min; MS (ESIpos): m/z=979 $(M+H)^+$.

17.0 mg (17.4 μmol) of N-[(benzyloxy)carbonyl]-L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide were dissolved in 2.5 ml of ethyl acetate, 1.7 mg of palladium on activated carbon (10%) were added and the mixture was hydrogenated at standard pressure overnight. The reaction mixture was filtered through a paper filter and the filter cake was washed with ethyl acetate. The solvent was evaporated under reduced pressure and the residue was dried under high vacuum. This gave 15.3 mg (60% of theory) of the compound L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide.

LC-MS (Method 1): $R_t$=1.15 min; MS (ESIpos): m/z=845 $(M+H)^+$.

15.3 mg (0.01 mmol) of L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide were initially charged together with 7.9 mg (0.02 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 2.4 ml of DMF, and 1.9 mg (0.02 mmol) of 4-methylmorpholine were added. The reaction mixture was stirred at RT overnight, and 1.4 mg (0.02 mmol) of acetic acid were then added. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 11.7 mg (70% of theory) of the compound N-[19-(2,5-dioxo-2,5-dihydro-1H-pyrrol-1-yl)-17-oxo-4,7,10,13-tetraoxa-16-azanonadecan-1-oyl]-L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide.

11.7 mg (0.01 mmol) of N-[19-(2,5-dioxo-2,5-dihydro-1H-pyrrol-1-yl)-17-oxo-4,7,10,13-tetraoxa-16-azanonadecan-1-oyl]-L-gamma-glutamyl-S-(11-{(1R)-1-[1-N-[19-(2,5-dioxo-2,5-dihydro-1H-pyrrol-1-yl)-17-oxo-4,7,10,13-tetraoxa-16-azanonadecan-1-oyl]-L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide were dissolved in 2.0 ml of trifluoroethanol, and 3.9 mg (0.03 mmol) of zinc dichloride were added. The reaction mixture was stirred at 50° C. overnight. 8.3 mg (0.03 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 5.4 mg (47% of theory) of the title compound.

LC-MS (Method 1): $R_t$=0.94 min; MS (ESIpos): m/z=1100 $(M+H)^+$.

Intermediate F236

(2R)-2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)-4-{[(2,5-dioxo-2,5-dihydro-1H-pyrrol-1-yl)acetyl]amino}butanoic Acid/trifluoroacetic Acid (1:1)

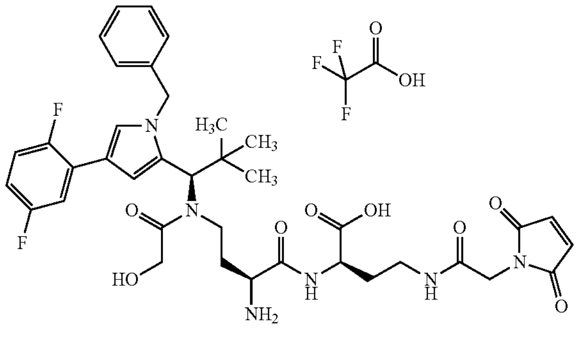 [SMILES: CC(C)(C)[C@H](c1cc(-c2cc(F)ccc2F)cn1Cc1ccccc1)N(CC[C@H](N)C(=O)N[C@H](CCNC(=O)CN1C(=O)C=CC1=O)C(=O)O)C(=O)CO ; O=C(O)C(F)(F)F]

The synthesis of the title compound was carried out analogously to Intermediate F192 from (2R)-4-{[(benzyloxy)carbonyl]amino}-2-[(tert-butoxycarbonyl)amino]butanoic acid/N-cyclohexylcyclohexanamine (1:1).

LC-MS (Method 4): $R_t$=1.1 min; MS (ESIpos): m/z=751 $(M+H)^+$.

Intermediate F238

Trifluoroacetic Acid/N-{(2S)-1-amino-3-[{(1R)-1-[1-benzyl-4-(2,5-difluorophenyl)-1H-pyrrol-2-yl]-2,2-dimethylpropyl}(glycoloyl)amino]propan-2-yl}-N'-[2-(2,5-dioxo-2,5-dihydro-1H-pyrrol-1-yl)ethyl]succinamide (1:1)

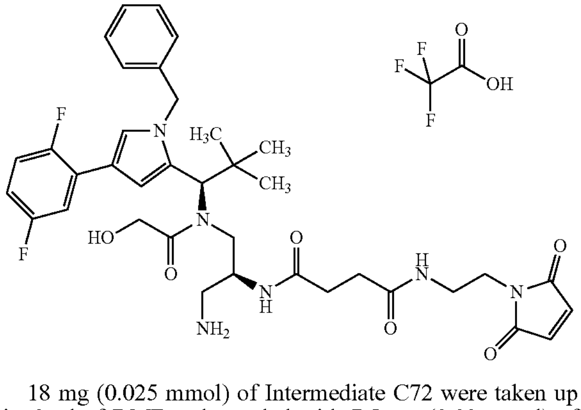

18 mg (0.025 mmol) of Intermediate C72 were taken up in 6 ml of DMF and coupled with 7.5 mg (0.03 mmol) of trifluoroacetic acid/1-(2-aminoethyl)-1H-pyrrole-2,5-dione (1:1) in the presence of 11.3 mg (0.03 mmol) of HATU and 22 μl of N,N-diisopropylethylamine. After 1 h of stirring at RT, the reaction was concentrated and the residue was purified by preparative HPLC. The appropriate fractions were concentrated and the residue was lyophilized from acetonitrile/water 1:1.

This gave 15 mg (67% of theory) of the intermediate.

LC-MS (Method 4): $R_t$=1.71 min; MS (EIpos): m/z=873 $[M+Na]^+$.

The title compound was then prepared from this intermediate by deprotection with zinc chloride in 4 ml of trifluoroethanol as described for Intermediate F119. Purification by preparative HPLC gave 8.5 mg (63% of theory) of the title compound.

LC-MS (Method 1): $R_t$=0.86 min; MS (ESIpos): m/z=707 $(M+Na)^+$.

Intermediate F239

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[(2,5-dioxo-2,5-dihydro-1H-pyrrol-1-yl)acetyl]-L-cysteine/trifluoroacetic Acid (1:1)

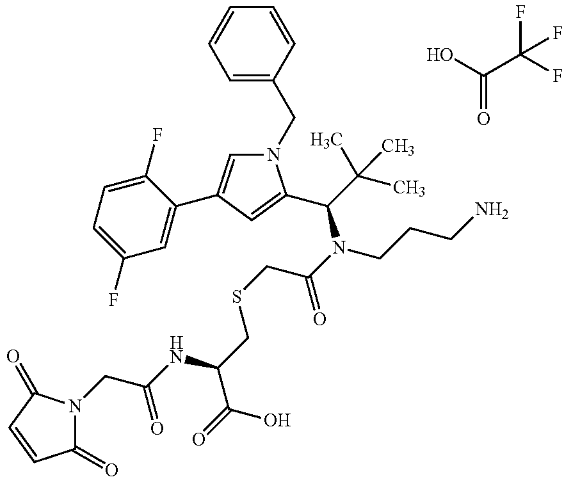 [SMILES: CC(C)(C)[C@H](c1cc(-c2cc(F)ccc2F)cn1Cc1ccccc1)N(CCCN)C(=O)CSC[C@H](NC(=O)CN1C(=O)C=CC1=O)C(=O)O ; O=C(O)C(F)(F)F]

Under argon, 7.5 mg (0.05 mmol) of (2,5-dioxo-2,5-dihydro-1H-pyrrol-1-yl)acetic acid were initially charged in 1.5 ml of DMF, and 7.5 mg (0.05 mmol) of HOBt, 15.5 mg (0.05 mmol) of TBTU and 6.2 mg (0.05 mmol) of N,N-diisopropylethylamine were added. The reaction mixture was stirred at RT for 10 min. 40.0 mg (0.05 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71), dissolved in 1.5 ml of DMF, and 18.7 mg (0.14 mmol) of N,N-diisopropylethylamine were then added, and the reaction mixture was stirred at RT overnight. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 11.2 mg (25% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(2,5-dioxo-2,5-dihydro-1H-pyrrol-1-yl)acetyl]-L-cysteine.

LC-MS (Method 1): $R_t$=1.37 min; MS (ESIpos): m/z=854 $(M+H)^+$.

10.9 mg (12.8 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(2,5-dioxo-2,5-dihydro-1H-pyrrol-1-yl)acetyl]-L-cysteine were dissolved in 2.0 ml of trifluoroethanol, and 10.4 mg (76.6 μmol) zinc dichloride were added. The reaction mixture was stirred at 50° C. for 4 h. 22.4 mg (0.08 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was lyophilized. This gave 7.5 mg (65% of theory) of the title compound.

LC-MS (Method 1): $R_t$=0.92 min; MS (ESIpos): m/z=710 $(M+H)^+$.

Intermediate F240

Trifluoroacetic Acid/3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-N-(2-{[(2,5-dioxo-2,5-dihydro-1H-pyrrol-1-yl)acetyl]amino}ethyl)propanamide (1:1)

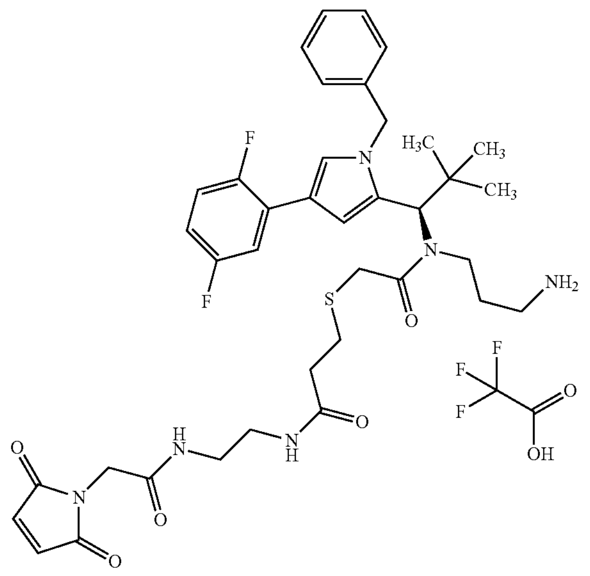

27.5 mg (0.04 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 15.9 mg (0.05 mmol) of trifluoroacetic acid/N-(2-aminoethyl)-2-(2,5-dioxo-2,5-dihydro-1H-pyrrol-1-yl)acetamide (1:1) (Intermediate L1) in 1.8 ml of acetonitrile. 32.4 mg (0.31 mmol) of N,N-diisopropylethylamine were then added, and 32.4 mg (0.05 mmol) of T3P (50% in ethyl acetate) were added dropwise. The reaction mixture was stirred at RT overnight. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 11.9 mg (35% of theory) of the compound 2-(trimethylsilyl)ethyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,7,12-trioxo-10-thia-3,6,13-triazahexadecan-16-yl]carbamate.

LC-MS (Method 1): $R_t$=1.39 min; MS (ESIpos): m/z=881 $(M+H)^+$.

11.9 mg (0.01 mol) of 2-(trimethylsilyl)ethyl-[13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,7,12-trioxo-10-thia-3,6,13-triazahexadecan-16-yl]carbamate were dissolved in 1.0 ml of trifluoroethanol, and 5.5 mg (0.04 mmol) of zinc dichloride were added. The reaction mixture was stirred at 50° C. overnight. 11.8 mg (0.04 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 7.4 mg (60% of theory) of the title compound.

LC-MS (Method 5): $R_t$=2.75 min; MS (ESIpos): m/z=737 $(M+H)^+$.

Intermediate F241

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[N-(bromoacetyl)glycyl]amino}ethyl)butanamide (1:1)

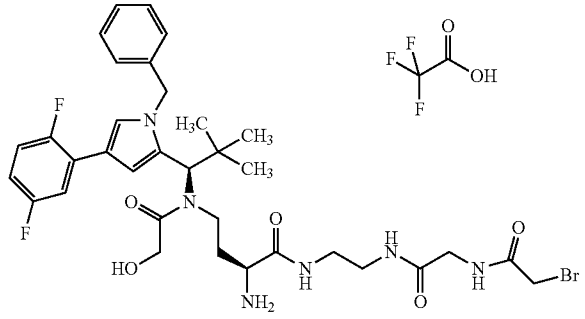 [SMILES: CC(C)(C)[C@H](c1cc(-c2cc(F)ccc2F)cn1Cc1ccccc1)N(CC[C@H](N)C(=O)NCCNC(=O)CNC(=O)CBr)C(=O)CO ; O=C(O)C(F)(F)F]

The title compound was prepared analogously from Intermediate C66 by coupling with commercially available 1-(2-bromoacetoxy)pyrrolidine-2,5-dione and subsequent deblocking with zinc chloride.

LC-MS (Method 1): $R_t$=0.84 min; MS (EIpos): m/z=733 and 735 $[M+H]^+$.

Intermediate F242

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(3-{[(2,5-dioxo-2,5-dihydro-1H-pyrrol-1-yl)acetyl]amino}propyl)butanamide (1:1)

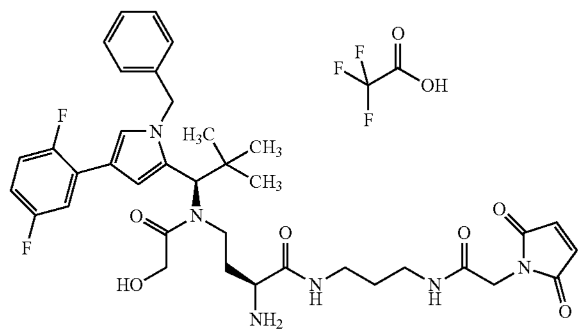 [SMILES: CC(C)(C)[C@H](c1cc(-c2cc(F)ccc2F)cn1Cc1ccccc1)N(CC[C@H](N)C(=O)NCCCNC(=O)CN1C(=O)C=CC1=O)C(=O)CO ; O=C(O)C(F)(F)F]

The synthesis of the title compound was carried out analogously to Intermediate F104.

LC-MS (Method 1): $R_t$=0.84 min; MS (ESIpos): m/z=707 $(M+H)^+$.

Intermediate F243

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[2-(2-{[(2,5-dioxo-2,5-dihydro-1H-pyrrol-1-yl)acetyl]amino}ethoxy)ethyl]butanamide (1:1)

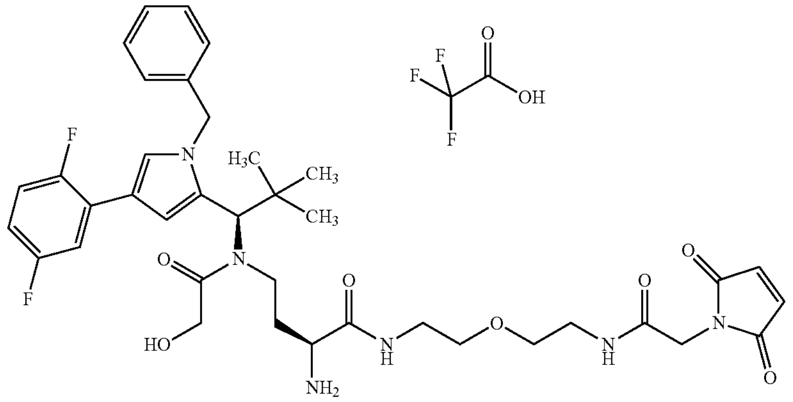 [SMILES: CC(C)(C)[C@H](c1cc(-c2cc(F)ccc2F)cn1Cc1ccccc1)N(CC[C@H](N)C(=O)NCCOCCNC(=O)CN1C(=O)C=CC1=O)C(=O)CO ; O=C(O)C(F)(F)F]

The synthesis of the title compound was carried out analogously to Intermediate F242.

LC-MS (Method 1): $R_t$=0.81 min; MS (ESIpos): m/z=737 $(M+H)^+$.

Intermediate F244

N-{2-[(S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-L-cysteinyl)amino]ethyl}-6-(2,5-dioxo-2,5-dihydro-1H-pyrrol-1-yl)hexanamide

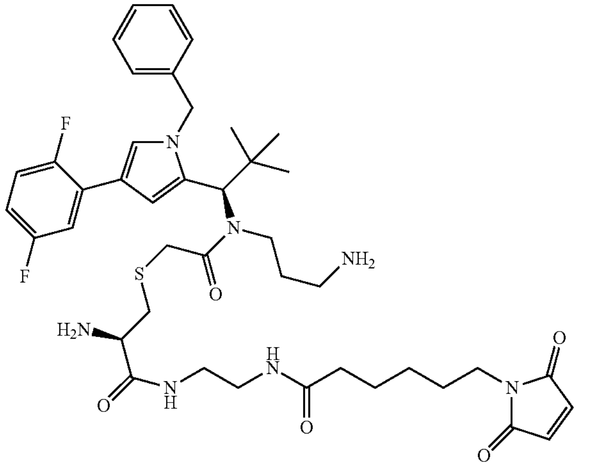 [SMILES: CC(C)(C)[C@H](c1cc(-c2cc(F)ccc2F)cn1Cc1ccccc1)N(CCCN)C(=O)CSC[C@H](N)C(=O)NCCNC(=O)CCCCCN1C(=O)C=CC1=O]

100 mg (about 0.101 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[3-(trimethylsilyl)propanoyl]-L-cysteine (Intermediate C73) were initially charged in 88 ml of dimethylformamide, and with 107 mg (about 0.15 mmol) of N-(2-aminoethyl)-6-(2,5-dioxo-2,5-dihydro-1H-pyrrol-1-yl)hexanamide (Intermediate L73), 46 mg (0.12 mmol) of HATU and 88 μl (0.50 mmol) of were added. The reaction mixture was stirred at RT for 15 minutes. Water/dichloromethane was added to the mixture, and the organic phase was then washed with water and brine, dried over magnesium sulphate, concentrated on a rotary evaporator and dried under high vacuum. The residue was used further without further purification. This gave 92 mg (59%, purity 72%) of the title compound.

LC-MS (Method 1): $R_t$=1.59 min; MS (ESIpos): m/z=1096 $(M+H)^+$.

Under argon, 40 mg (0.30 mmol) of zinc chloride were added to a solution of 91 mg (about 0.06 mmol) of 2-(trimethylsilyl)ethyl [(9R)-4-{(1R)-1-[1-benzyl-4-(2,5-difluorophenyl)-1H-pyrrol-2-yl]-2,2-dimethylpropyl}-20-(2,5-dioxo-2,5-dihydro-1H-pyrrol-1-yl)-5,10,15-trioxo-9-{[3-(trimethylsilyl)propanoyl]amino}-7-thia-4,11,14-triazaicos-1-yl]carbamate in 1.45 ml of trifluoroethanol. The reaction mixture was stirred at 50° C. for 2 h. 30 mg (0.22 mmol) of zinc chloride were then added, and the mixture was stirred at RT for another 1 h. 52 mg (0.18 mmol) of EDTA were added, and after 10 minutes of stirring at RT the mixture was diluted slightly with water/acetonitrile and purified by preparative HPLC (mobile phase: ACN/water+0.1% TFA, gradient). This gave 17 mg (31%) of the title compound.

LC-MS (Method 1): $R_t$=0.80 min; MS (ESIpos): m/z=808 $(M+H)^+$.

Intermediate F245

Trifluoroacetic Acid/N-{(2S)-2-amino-4-[{(1R)-1-[1-benzyl-4-(2,5-difluorophenyl)-1H-pyrrol-2-yl]-2,2-dimethylpropyl}(glycoloyl)amino]butyl}-N'-(2-{[(2,5-dioxo-2,5-dihydro-1H-pyrrol-1-yl)acetyl]amino}ethyl)succinamide (1:1)

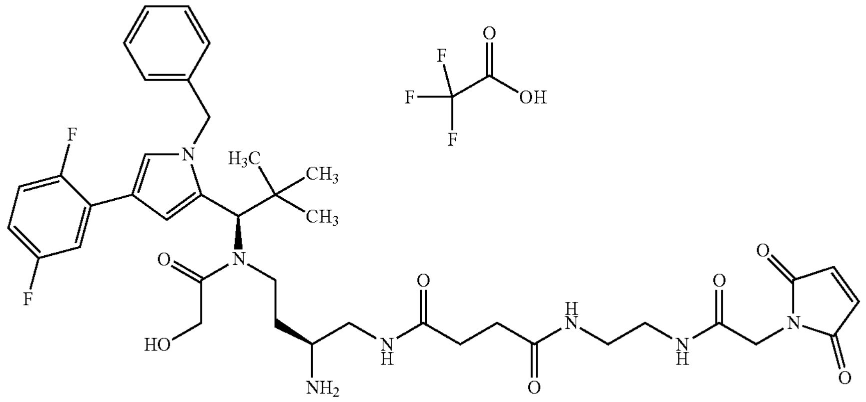 [SMILES: CC(C)(C)[C@H](c1cc(-c2cc(F)ccc2F)cn1Cc1ccccc1)N(CC[C@H](N)CNC(=O)CCC(=O)NCCNC(=O)CN1C(=O)C=CC1=O)C(=O)CO ; O=C(O)C(F)(F)F]

The title compound was prepared by coupling of 10 mg (0.0135 mmol) of Intermediate C65 with 8 mg (0.027 mmol) of Intermediate L1 in 8 ml of DMF in the presence of 15 mg (0.04 mmol) of HATU and 9 µl of N,N-diisopropylethylamine and subsequent deprotection with zinc chloride in trifluoroethanol as described for Intermediate F119. Purification by preparative HPLC gave 8.8 mg (58% of theory over 2 steps) of the title compound.

LC-MS (Method 1): $R_t$=0.84 min; MS (ESIpos): m/z=778 $(M+H)^+$.

Intermediate F247

Trifluoroacetic Acid/methyl 4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-bromo-4-oxobutanoate (1:1)

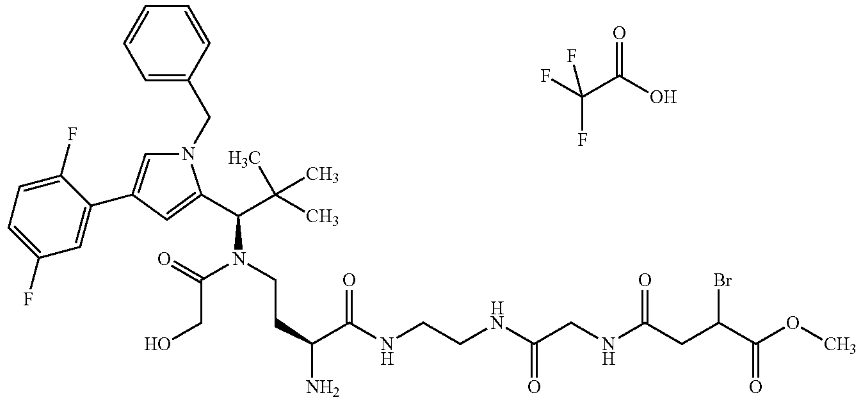 [SMILES: COC(=O)C(Br)CC(=O)NCC(=O)NCCNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

14 mg (0.018 mmol) of Intermediate C66 were dissolved in 14 ml of DCM, and with 10.1 mg (0.037 mmol) of 2-bromo-1-ethylpyridinium tetrafluoroborate (BEP) and, a little at a time, a total of 250 µl of pyridine were added, the pH being kept between 5 and 6. The pH was then adjusted to 4 with acetic acid, the reaction was concentrated and the residue was purified by preparative HPLC. Combination of the appropriate fractions, lyophilization and drying gave 4 mg (21% of theory) of the protected intermediate, which were then deprotected at the amino function with zinc chloride. HPLC purification and lyophilization gave 3 mg (72% of theory) of the title compound as a colourless foam.

LC-MS (Method 1): $R_t$=0.88 min; MS (ESIpos): m/z=805 and 807 $(M+H)^+$.

Intermediate F248

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[2-(2,5-dioxo-2,5-dihydro-1H-pyrrol-1-yl)ethoxy]ethyl}butanamide (1:1)

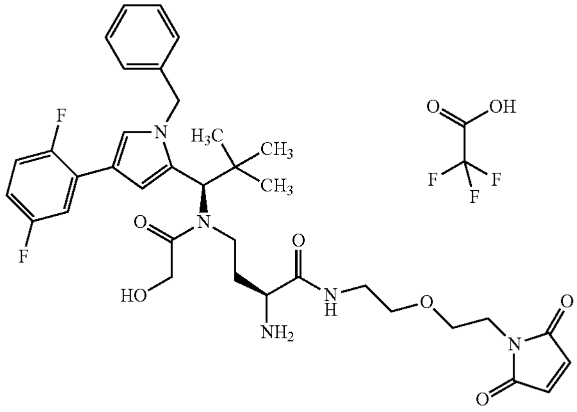 [SMILES: CC(C)(C)[C@H](c1cc(-c2cc(F)ccc2F)cn1Cc1ccccc1)N(CC[C@H](N)C(=O)NCCOCCN1C(=O)C=CC1=O)C(=O)CO ; O=C(O)C(F)(F)F]

The title compound was prepared by coupling of 10 mg (0.015 mmol) of Intermediate C58 with 5 mg (0.017 mmol) of Intermediate L12 in the presence of HATU and subsequent deprotection with zinc chloride. This gave 6.5 mg (52% of theory over 2 steps) of the title compound.

LC-MS (Method 1): $R_t$=0.91 min; MS (ESIpos): m/z=680 $(M+H)^+$.

Intermediate F254

Trifluoroacetic Acid/methyl (3S)-4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-bromo-4-oxobutanoate (1:1)

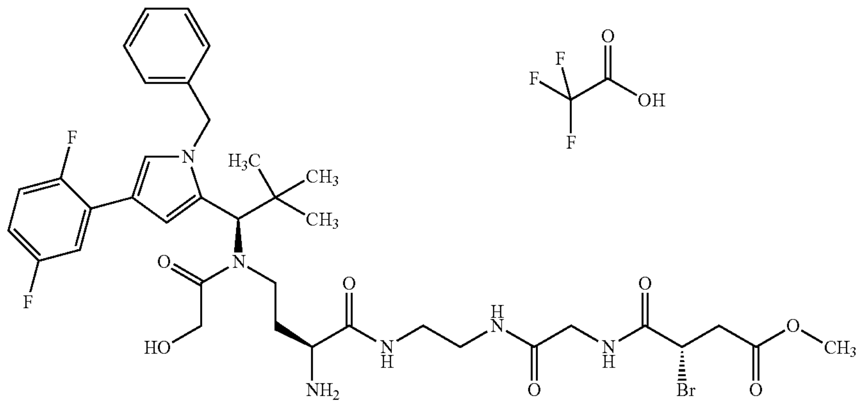 [SMILES: COC(=O)C[C@H](Br)C(=O)NCC(=O)NCCNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

The title compound was prepared analogously to Intermediate 247 by coupling of 15 mg (0.02 mmol) of Intermediate C66 with 21 mg (0.099 mmol) of (2S)-2-bromo-4-methoxy-4-oxobutanoic acid which had been synthesized as described in (J. Org. Chem. 200, 65, 517-522) from (2S)-2-amino-4-methoxy-4-oxobutanoic acid hydrochloride (1:1).

LC-MS (Method 1): $R_t$=0.89 min; MS (ESIpos): m/z=805 and 807 $(M+H)^+$.

Intermediate F255

R/S—(N-[19-(2,5-Dioxo-2,5-dihydro-1H-pyrrol-1-yl)-17-oxo-4,7,10,13-tetraoxa-16-azanonadecan-1-oyl]-L-alpha-glutamyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl})homocysteine/trifluoroacetic Acid (1:1)

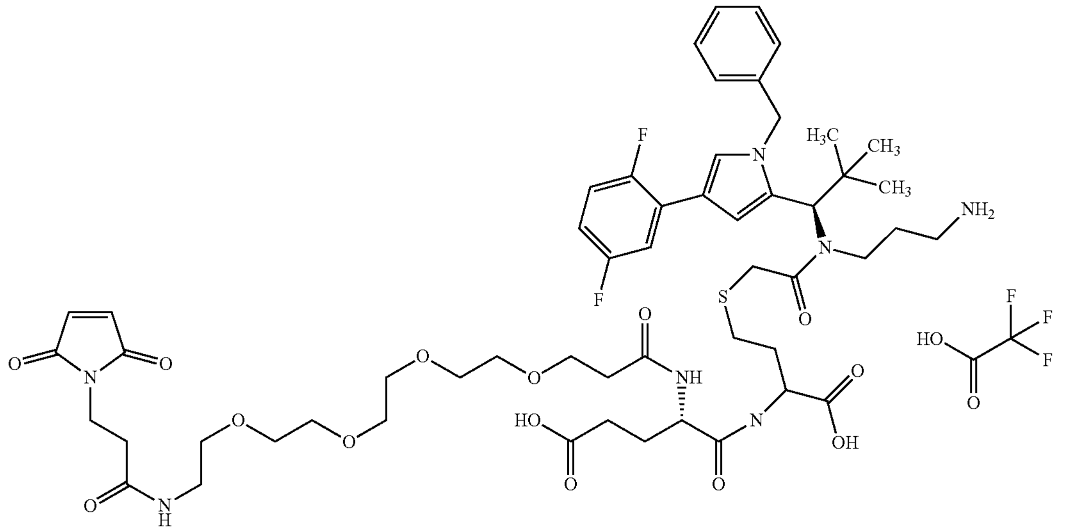 [SMILES: CC(C)(C)[C@H](c1cc(-c2cc(F)ccc2F)cn1Cc1ccccc1)N(CCCN)C(=O)CSCCC(NC(=O)[C@H](CCC(=O)O)NC(=O)CCOCCOCCOCCOCCNC(=O)CCN1C(=O)C=CC1=O)C(=O)O ; O=C(O)C(F)(F)F]

13.1 mg (0.04 mmol) of (2S)-5-(benzyloxy)-2-{[(benzyloxy)carbonyl]amino}-5-oxopentanoic acid were initially charged in 1.0 ml of DMF, and 5.4 mg (0.04 mmol) of HOBt, 11.4 mg (0.04 mmol) of TBTU and 4.6 mg (0.04 mmol) of N,N-diisopropylethylamine were added. The reaction mixture was stirred at RT for 10 min. 30.0 mg (0.04 mmol) of R/S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)homocysteine/trifluoroacetic acid (1:1) (Intermediate C11) dissolved in 12.9 mg (0.1 mmol) of N,N-diisopropylethylamine and 1 ml of DMF were then added. The reaction mixture was stirred at RT overnight. The reaction mixture was purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 32 mg (73%) of the compound 4-[2-[[(1R)-1-[1-benzyl-4-(2,5-difluorophenyl)pyrrol-2-yl]-2,2-dimethylpropyl]-[3-(2-trimethylsilylethoxycarbonylamino)propyl]amino]-2-oxoethyl]sulphanyl-2-[[(2S)-5-benzyloxy-2-(benzyloxycarbonylamino)-5-oxo-pentanoyl]amino]butanoic acid.

LC-MS (Method 1): $R_t$=1.53 min; MS (ESIpos): m/z=1084 $(M+H)^+$.

41.4 mg (0.038 mmol) of 4-[2-[[(1R)-1-[1-benzyl-4-(2,5-difluorophenyl)pyrrol-2-yl]-2,2-dimethylpropyl]-[3-(2-trimethylsilylethoxycarbonylamino)propyl]amino]-2-oxoethyl]sulphanyl-2-[[(2S)-5-benzyloxy-2-(benzyloxycarbonylamino)-5-oxo-pentanoyl]amino]butanoic acid was dissolved in 10 ml of ethanol, 4.2 mg of Pd/C were added and the mixture was hydrogenated under standard pressure. The reaction mixture was filtered through a cardboard filter and the filter cake was washed with ethanol. The solvent was evaporated under reduced pressure without heating. The residue was purified by preparative RP-HPLC (column: Reprosil 250×40; 10μ, flow rate: 50 ml/min, MeCN/water, 0.1% TFA). The solvents were evaporated under reduced pressure and the residue was dried under high vacuum. This gave 21.1 mg (56%) of the compound R/S-(L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl))homocysteine/trifluoroacetic acid (1:1).

LC-MS (Method 1): $R_t$=1.11 min; MS (ESIpos): m/z=860 $(M+H)^+$.

20.4 mg (20.94 μmol) of R/S-(L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl))homocysteine/trifluoroacetic acid (1:1) were initially charged together with 11.8 mg (23.04 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 1.0 ml of DMF, and 4.2 mg (41.88 μmol) of 4-methylmorpholine were added. The reaction mixture was stirred at RT overnight, and 3.1 mg (0.05 mmol) of acetic acid were then added. The reaction mixture was purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 9.5 mg (36%) of the compound R/S—(N-[19-(2,5-dioxo-2,5-dihydro-1H-pyrrol-1-yl)-17-oxo-4,7,10,13-tetraoxa-16-azanonadecan-1-oyl]-L-alpha-glutamyl-S-(11- {(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl))homocysteine.

LC-MS (Method 1): $R_t$=1.66 min; MS (ESIpos): m/z=1259 $(M+H)^+$.

9.4 mg (7.47 μmol) of R/S—(N-[19-(2,5-dioxo-2,5-dihydro-1H-pyrrol-1-yl)-17-oxo-4,7,10,13-tetraoxa-16-azanonadecan-1-oyl]-L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl))homocysteine were dissolved in 1.5 ml of trifluoroethanol, and 6.1 mg (44.81 μmol) of zinc dichloride were added. The reaction mixture was stirred at 50° C. for 3 h. 13.1 mg (0.05 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 6.9 mg (75%) of the title compound.

LC-MS (Method 1): $R_t$=0.87 min; MS (ESIpos): m/z=1114 $(M+H)^+$.

Intermediate F256

Trifluoroacetic Acid/N-({(2S)-2-amino-4-[{(1R)-1-[1-benzyl-4-(2,5-difluorophenyl)-1H-pyrrol-2-yl]-2,2-dimethylpropyl}(glycoloyl)amino]butyl}-N'-[2-(2-{[(2,5-dioxo-2,5-dihydro-1H-pyrrol-1-yl)acetyl]amino}ethoxy)ethyl]succinamide (1:1)

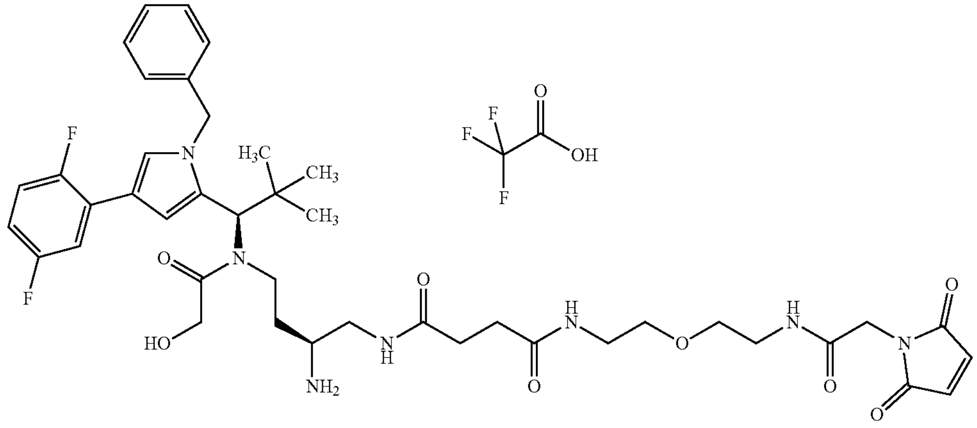 [SMILES: CC(C)(C)[C@H](c1cc(-c2cc(F)ccc2F)cn1Cc1ccccc1)N(CC[C@H](N)CNC(=O)CCC(=O)NCCOCCNC(=O)CN1C(=O)C=CC1=O)C(=O)CO ; O=C(O)C(F)(F)F]

The title compound was prepared by coupling of 10 mg (0.014 mmol) of Intermediate C65 and 9.6 mg (0.027 mmol) of trifluoroacetic acid/N-[2-(2-aminoethoxy)ethyl]-2-(2,5-dioxo-2,5-dihydro-1H-pyrrol-1-yl)acetamide (1:1) in the presence of HATU and N,N-diisopropylethylamine and subsequent deprotection with zinc chloride in trifluoroethanol as described for Intermediate F119. Purification by preparative HPLC gave 8 mg (64% of theory over 2 steps) of the title compound.

LC-MS (Method 1): $R_t$=0.84 min; MS (ESIpos): m/z=822 $(M+H)^+$.

Intermediate F257

R-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[18-(2,5-dioxo-2,5-dihydro-1H-pyrrol-1-yl)-17-oxo-4,7,10,13-tetraoxa-16-azaoctadecan-1-oyl]-L-cysteine/trifluoroacetic Acid (1:1)

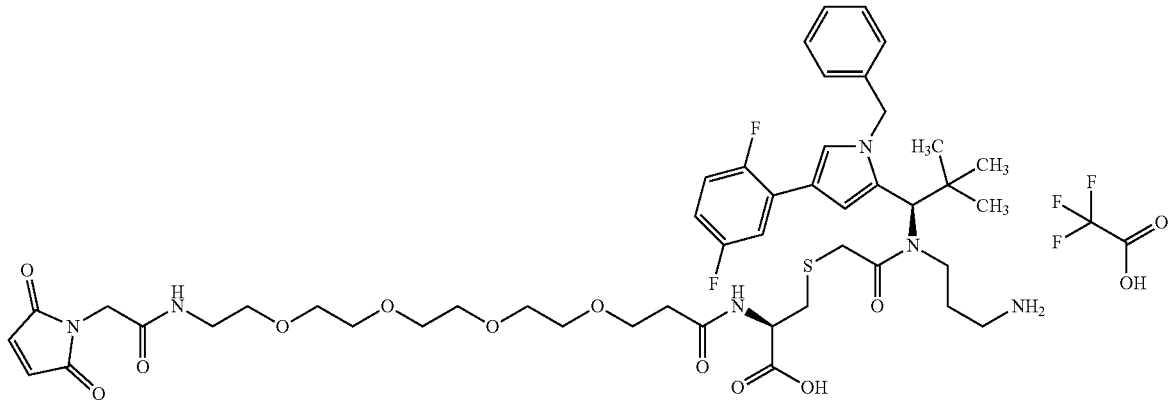 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CN1C(=O)C=CC1=O)C(=O)O ; O=C(O)C(F)(F)F]

50.0 mg (0.06 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) and 29 mg (0.07 mmol) of 3-[2-[2-[2-[2-[[2-(2,5-dioxopyrrol-1-yl)acetyl]amino]ethoxy]ethoxy]ethoxy]ethoxy]propanoic acid (Intermediate L74) were dissolved in 3.0 ml of DMF, and 27.3 mg (0.07 mmol) of HATU and 23.3 mg (0.18 mmol) of N,N-diisopropylethylamine were added. The reaction mixture was stirred at RT for 2 hours. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 17.4 mg (26%) of the compound R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[18-(2,5-dioxo-2,5-dihydro-1H-pyrrol-1-yl)-17-oxo-4,7,10,13-tetraoxa-16-azaoctadecan-1-oyl]-L-cysteine.

LC-MS (Method 6): $R_t$=1.34 min; MS (ESIpos): m/z=1101 $(M+H)^+$.

17 mg (0.02 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[18-(2,5-dioxo-2,5-dihydro-1H-pyrrol-1-yl)-17-oxo-4,7,10,13-tetraoxa-16-azaoctadecan-1-oyl]-L-cysteine were dissolved in 1.0 ml of trifluoroethanol, and 6.3 mg (0.05 mmol) of zinc dichloride were added. The reaction mixture was stirred at 50° C. overnight. 13.5 mg (0.05 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 7.6 mg (46%) of the title compound.

LC-MS (Method 1): $R_t$=0.91 min; MS (ESIpos): m/z=957 $(M+H)^+$.

Intermediate F258

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[3-{2-[(bromoacetyl)amino]ethyl}amino)-3-oxopropyl] butanamide (1:1)

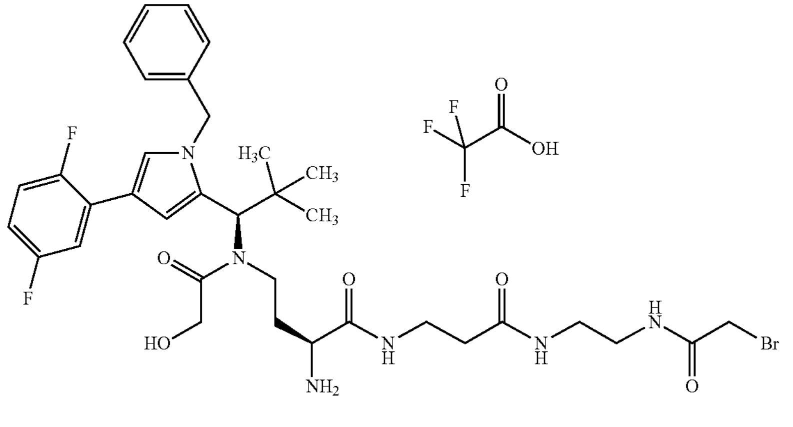 [SMILES: CC(C)(C)[C@H](c1cc(-c2cc(F)ccc2F)cn1Cc1ccccc1)N(CC[C@H](N)C(=O)NCCC(=O)NCCNC(=O)CBr)C(=O)CO ; O=C(O)C(F)(F)F]

The title compound was prepared by coupling of Intermediate C58 with trifluoroacetic acid/benzyl [2-(beta-alanylamino)ethyl]carbamate (1:1) using HATU, subsequent hydrogenolysis, followed by coupling with 1-(2-bromoacetoxy)pyrrolidine-2,5-dione and finally by deprotection with zinc chloride.

LC-MS (Method 1): $R_t$=0.86 min; MS (ESIpos): m/z=747 and 749 $(M+H)^+$.

Intermediate F259

N-{(2S)-2-Amino-4-[{(1R)-1-[1-benzyl-4-(2,5-difluorophenyl)-1H-pyrrol-2-yl]-2,2-dimethyl propyl}(glycoloyl)amino]butanoyl}-3-1 {[N-(bromacetyl)glycyl]amino}-D-alanine/trifluoroacetic Acid (1:1)

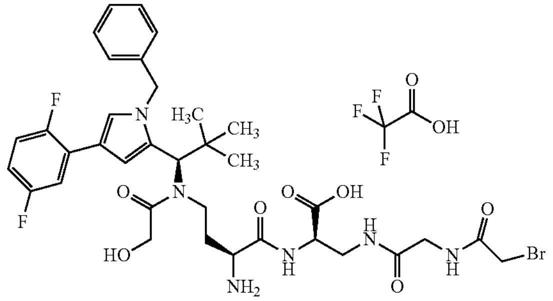 [SMILES: CC(C)(C)[C@H](c1cc(-c2cc(F)ccc2F)cn1Cc1ccccc1)N(CC[C@H](N)C(=O)N[C@H](CNC(=O)CNC(=O)CBr)C(=O)O)C(=O)CO ; O=C(O)C(F)(F)F]

75 mg (0.114 mmol) of Intermediate C58 were taken up in 12.5 ml of DMF and coupled with 78 mg (0.171 mmol) of Intermediate L75 in the presence of 65 mg (0.11 mmol) of HATU and 79 μl of N,N-diisopropylethylamine. After purification by preparative HPLC, the intermediate was taken up in 20 ml of ethanol and hydrogenated over 10% palladium on activated carbon at RT under hydrogen standard pressure for 1 h. The catalyst was then filtered off, the solvent was removed under reduced pressure and the product was purified by preparative HPLC. Lyophilization from acetonitrile/water 1:1 gave 63 mg (64% of theory over 2 steps) of 2-(trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alaninate.

LC-MS (Method 1): $R_t$=1.16 min; MS (EIpos): m/z=844 $[M+H]^+$.

40 mg (0.047 mmol) of this intermediate were then coupled as described above with N-[(benzyloxy)carbonyl] glycine in the presence of HATU and then once more hydrogenolytically deprotected.

The title compound was then prepared by coupling of 10 mg (0.012 mmol) of this intermediate with 7.7 mg (0.032 mmol) of commercially available 1-(2-bromoacetoxy)pyrrolidine-2,5-dione in the presence of 4 μl of N,N-diisopropylethylamine and subsequent deprotection with zinc chloride in trifluoroethanol as described for Intermediate F119. Purification by preparative HPLC gave 1.3 mg of the title compound.

LC-MS (Method 1): $R_t$=0.83 min; MS (ESIpos): m/z=777 and 779 $(M+H)^+$.

Intermediate F260

$N^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$—{N-[(2,5-dioxo-2,5-dihydro-1H-pyrrol-1-yl)acetyl]-L-valyl-L-alanyl}-L-lysine/trifluoroacetic Acid (1:1)

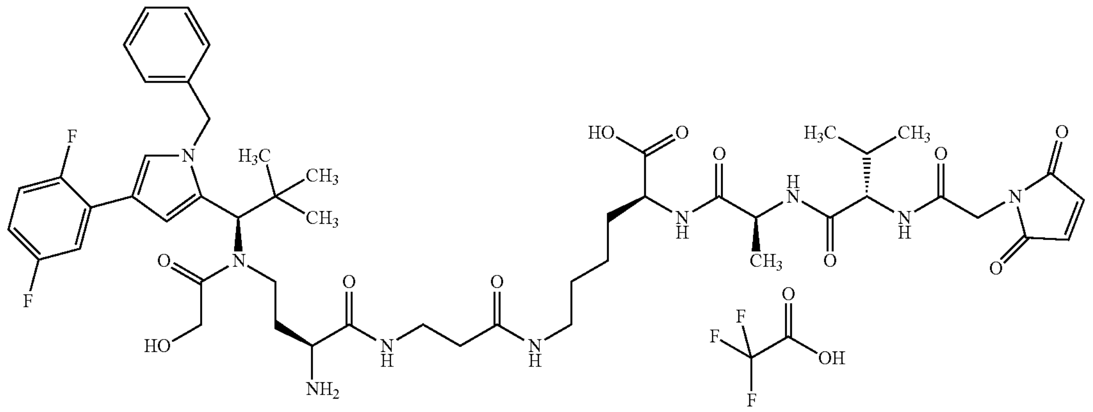

The title compound was prepared analogously to Intermediate F155.

LC-MS (Method 1): $R_t$=0.81 min; MS (ESIpos): m/z=1020 $(M+H)^+$.

Intermediate F261

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{2-[(bromoacetyl)amino]ethoxy}ethyl)butanamide (1:1)

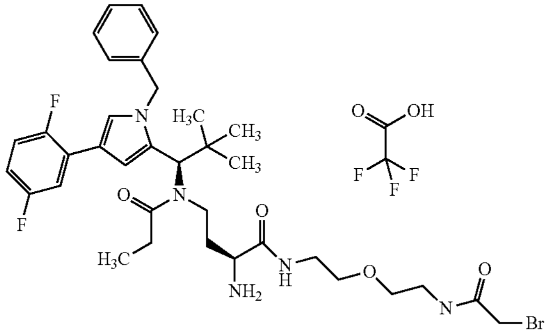 [SMILES: CCC(=O)N(CC[C@H](N)C(=O)NCCOCCNC(=O)CBr)[C@@H](c1cc(-c2cc(F)ccc2F)cn1Cc1ccccc1)C(C)(C)C ; O=C(O)C(F)(F)F]

The title compound was prepared by coupling of 20 mg (0.03 mmol) of Intermediate C58 with 25.8 mg (0.061 mmol) of Intermediate L77 in the presence of HATU and subsequent deprotection with zinc chloride. This gave 11.9 mg (47% of theory over 2 steps) of the title compound.

LC-MS (Method 1): $R_t$=0.84 min; MS (ESIpos): m/z=722 and 720 $(M+H)^+$.

Intermediate F262

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-{3-[2-(2-{[3-(2,5-dioxo-2,5-dihydro-1H-pyrrol-1-yl)propanoyl]amino}ethoxy)ethoxy]propanoyl}-L-cysteine/trifluoroacetic Acid (1:1)

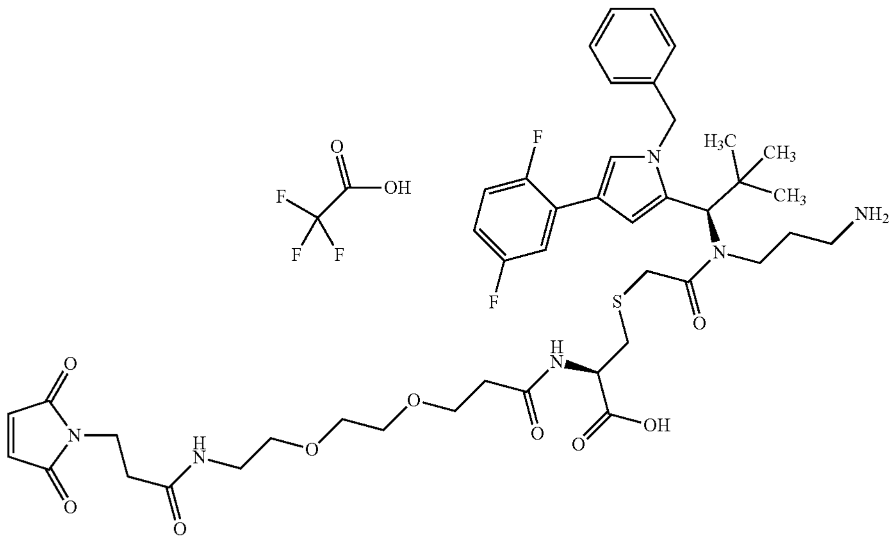 [SMILES: CC(C)(C)[C@H](c1cc(-c2cc(F)ccc2F)cn1Cc1ccccc1)N(CCCN)C(=O)CSC[C@H](NC(=O)CCOCCOCCNC(=O)CCN1C(=O)C=CC1=O)C(=O)O ; O=C(O)C(F)(F)F]

30 mg (36 μmol) of S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1) (Intermediate C71) together with 16.9 mg (40 μmol) of 3-(2,5-dioxo-2,5-dihydro-1H-pyrrol-1-yl)-N-[2-(2-{3-[(2,5-dioxopyrrolidin-1-yl)oxy]-3-oxopropoxy}ethoxy)ethyl]propanamide were initially charged in 1.5 ml of DMF, and 10.9 mg (108 μmol) of 4-methylmorpholine were added. The reaction mixture was stirred at RT overnight, and 7.58 mg (0.13 mmol) of acetic acid were then added. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 33.4 mg (80% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[3-(2,5-dioxo-2,5-dihydro-1H-pyrrol-1-yl)propanoyl]amino}ethoxy)ethoxy]propanoyl}-L-cysteine.

LC-MS (Method 1): $R_t$=1.34 min; MS (ESIpos): m/z=1027 $(M+H)^+$.

32.8 mg (32 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[3-(2,5-dioxo-2,5-dihydro-1H-pyrrol-1-yl)propanoyl]amino}ethoxy)ethoxy]propanoyl}-L-cysteine were dissolved in 3.0 ml of trifluoroethanol, and 26.1 mg (192 μmol) of zinc dichloride were added. The reaction mixture was stirred at 50° C. for 2 h. 56.0 mg (0,192 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was lyophilized. This gave 22.9 mg (71% of theory) of the title compound.

LC-MS (Method 1): $R_t$=0.88 min; MS (ESIpos): m/z=883 $(M+H)^+$.

Intermediate F263

N-[(2,5-Dioxo-2,5-dihydro-1H-pyrrol-1-yl)acetyl]-beta-alanyl-S-{2-[(3-aminopropyl) {(1R)-1-[1-benzyl-4-(2,5-difluorophenyl)-1H-pyrrol-2-yl]-2,2-dimethylpropyl}amino]-2-oxoethyl}-L-cysteine/trifluoroacetic Acid (1:1)

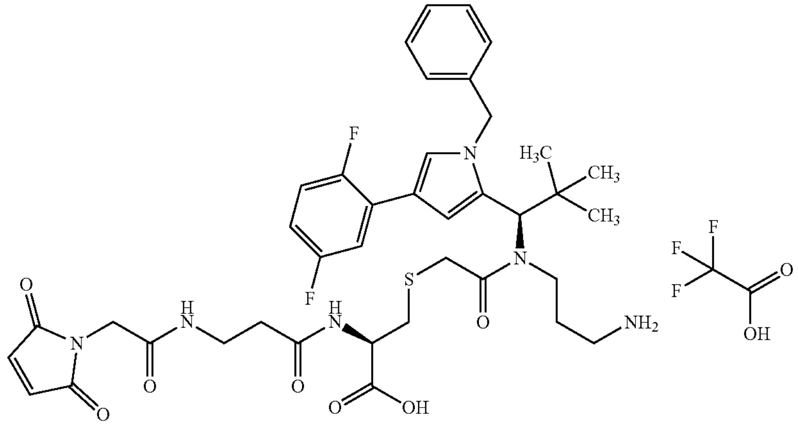

30.0 mg (0.036 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) and 9.8 mg (0.04 mmol) of N-[(2,5-dioxo-2,5-dihydro-1H-pyrrol-1-yl)acetyl]-beta-alanine (Intermediate L78) were dissolved in 1.0 ml of DMF, and 16.4 mg (0.04 mmol) of HATU and 14.0 mg (0.11 mmol) of N,N-diisopropylethylamine were added. The reaction mixture was stirred at RT for 2 hours. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 4.2 mg (13%) of the compound N-[(2,5-dioxo-2,5-dihydro-1H-pyrrol-1-yl)acetyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 6): $R_t$=1.31 min; MS (ESIpos): m/z=925 $(M+H)^+$.

11.3 mg (0.011 mmol) of N-[(2,5-dioxo-2,5-dihydro-1H-pyrrol-1-yl)acetyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 5.0 mg (0.04 mmol) of zinc dichloride were added. The reaction mixture was stirred at 50° C. for 2 hours. 10.7 mg (0.04 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 4.4 mg (40%) of the title compound.

LC-MS (Method 1): $R_t$=0.91 min; MS (ESIpos): m/z=781 $(M+H)^+$.

Intermediate F264

N-[6-(2,5-Dioxo-2,5-dihydro-1H-pyrrol-1-yl)hexanoyl]-beta-alanyl-S-{2-[(3-aminopropyl) {(1R)-1-[1-benzyl-4-(2,5-difluorophenyl)-1H-pyrrol-2-yl]-2,2-dimethylpropyl}amino]-2-oxoethyl}-L-cysteine/trifluoroacetic Acid (1:1)

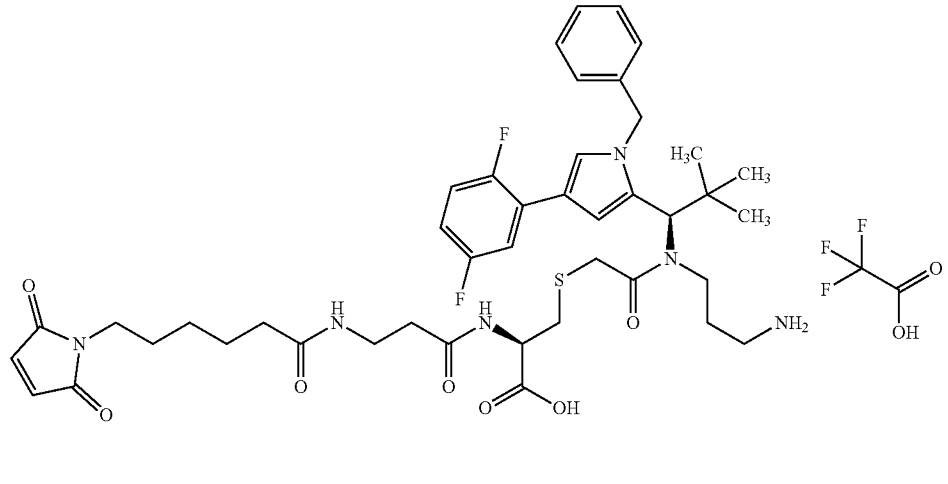

30.0 mg (0.036 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) and 12.2 mg (0.04 mmol) of N-[6-(2,5-dioxo-2,5-dihydro-1H-pyrrol-1-yl)hexanoyl]-beta-alanine (Intermediate L79) were dissolved in 1.0 ml of DMF, and 16.4 mg (0.04 mmol) of HATU and 14.0 mg (0.11 mmol) of N,N-diisopropylethylamine were added. The reaction mixture was stirred at RT for 2 hours. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 8.9 mg (24%) of the compound N-[6-(2,5-dioxo-2,5-dihydro-1H-pyrrol-1-yl)hexanoyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 6): $R_t$=1.38 min; MS (ESIpos): m/z=981 $(M+H)^+$.

15.3 mg (0.015 mmol) of N-[6-(2,5-dioxo-2,5-dihydro-1H-pyrrol-1-yl)hexanoyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 6.3 mg (0.045 mmol) of zinc dichloride were added. The reaction mixture was stirred at 50° C. for 2 hours. 13.5 mg (0.045 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 9.1 mg (62%) of the title compound.

LC-MS (Method 1): $R_t$=0.92 min; MS (ESIpos): m/z=837 $(M+H)^+$.

Intermediate F265

Trifluoroacetic Acid/N-(3-aminopropyl)-N-{(1R)-1-[1-benzyl-4-(2,5-difluorophenyl)-1H-pyrrol-2-yl]-2,2-dimethylpropyl}-22-(2,5-dioxo-2,5-dihydro-1H-pyrrol-1-yl)-6,17-dioxo-10,13-dioxa-3-thia-7,16-diazadocosane-1-amide (1:1)

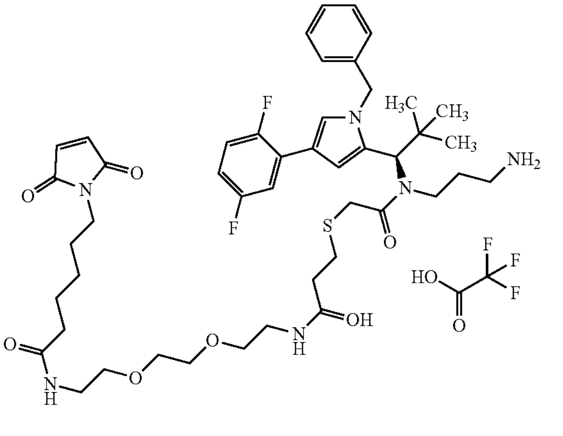 [SMILES: CC(C)(C)[C@H](c1cc(-c2cc(F)ccc2F)cn1Cc1ccccc1)N(CCCN)C(=O)CSCCC(=O)NCCOCCOCCNC(=O)CCCCCN1C(=O)C=CC1=O ; O=C(O)C(F)(F)F]

30.0 mg (42.7 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) and 25.3 mg (55.6 μmol) of trifluoroacetic acid/N-{2-[2-(2-aminoethoxy)ethoxy]ethyl}-6-(2,5-dioxo-2,5-dihydro-1H-pyrrol-1-yl)hexanamide (1:1) (Intermediate L82) were initially charged in 1.9 ml of acetonitrile, and 60 μl (340 μmol) of N,N-diisopropylethylamine and 33 μl (56 μmol) of 2,4,6-tripropyl-1,3,5,2,4,6-trioxatriphosphinane 2,4,6-trioxide 50% in ethyl acetate were added. The reaction mixture was stirred at RT overnight. Water (2.0 ml) was added, and purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 26.7 mg (60% of theory) of the compound 2-(trimethylsilyl)ethyl [4-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-5,10,21-trioxo-14,17-dioxa-7-thia-4,11,20-triazahexacos-1-yl]carbamate.

LC-MS (Method 1): $R_t$=1.40 min; MS (ESIpos): m/z=1025 $(M+H)^+$.

25.3 mg (24.7 μmol) of 2-(trimethylsilyl)ethyl [4-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-5,10,21-trioxo-14,17-dioxa-7-thia-4,11,20-triazahexacos-1-yl]carbamate were dissolved in 2.0 ml of trifluoroethanol, and 20.2 mg (148 μmol) of zinc dichloride were added. The reaction mixture was stirred at 50° C. for 1 h. 43.3 mg (148 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 23.4 mg (95% of theory) of the title compound.

LC-MS (Method 1): $R_t$=0.89 min; MS (ESIpos): m/z=881 $(M+H)^+$.

Intermediate F266

Trifluoroacetic Acid/N-(3-aminopropyl)-N-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,13-dioxo-6,9-dioxa-16-thia-3,12-diazaoctadecan-18-amide (1:1)

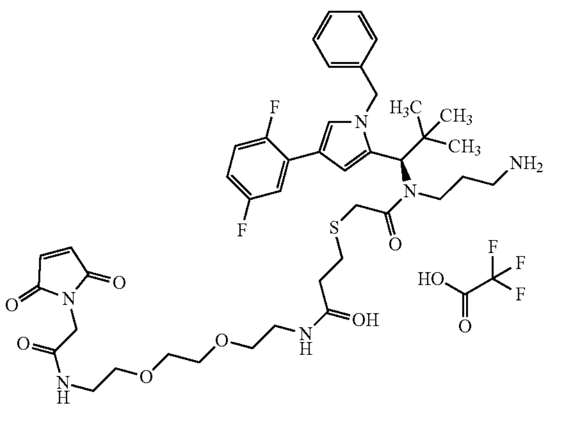 [SMILES: CC(C)(C)[C@H](c1cc(-c2cc(F)ccc2F)cn1Cc1ccccc1)N(CCCN)C(=O)CSCCC(=O)NCCOCCOCCNC(=O)CN1C(=O)C=CC1=O ; O=C(O)C(F)(F)F]

30.0 mg (0.043 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 22.2 mg (0.056 mmol) of trifluoroacetic acid/N-{2-[2-(2-aminoethoxy)ethoxy]ethyl}-2-(2,5-dioxo-2,5-dihydro-1H-pyrrol-1-yl)acetamide (1:1) (Intermediate L83) in 1.9 ml of acetonitrile. 60 µl (0.34 mmol) of N,N-diisopropylethylamine were then added, and 33 µl (0.056 mmol) of T3P (50% in ethyl acetate) were added dropwise. The reaction mixture was stirred at RT overnight. Water (2.0 ml) was added. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 20.5 mg (49% of theory) of the compound 2-(trimethylsilyl)ethyl [19-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,13,18-trioxo-6,9-dioxa-16-thia-3,12,19-triazadocosan-22-yl]carbamate.

LC-MS (Method 1): $R_t$=1.38 min; MS (ESIpos): m/z=969 $(M+H)^+$.

19.1 mg (19.7 µmol) of 2-(trimethylsilyl)ethyl [19-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,13,18-trioxo-6,9-dioxa-16-thia-3,12,19-triazadocosan-22-yl]carbamate were dissolved in 2.0 ml of trifluoroethanol, and 16.1 mg (118 µmol) of zinc dichloride were added. The reaction mixture was stirred at 50° C. for 1 h. 34.6 mg (118 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 13.9 mg (75% of theory) of the title compound.

LC-MS (Method 1): $R_t$=0.86 min; MS (ESIpos): m/z=825 $(M+H)^+$.

Intermediate F267

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,18-dioxo-6,9,12,15-tetraoxa-3-azaoctadecan-18-yl]-L-cysteinyl-beta-alanine/trifluoroacetic Acid (1:1)

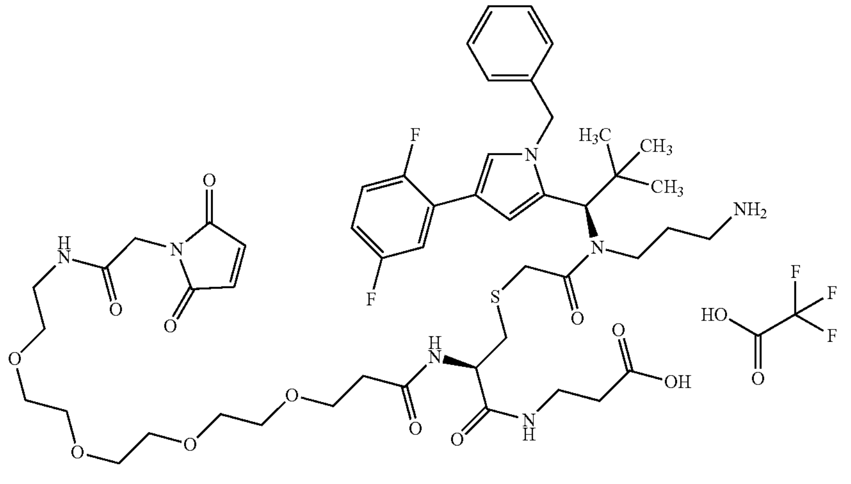 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CN1C(=O)C=CC1=O)C(=O)NCCC(=O)O ; O=C(O)C(F)(F)F]

Under argon, 13.4 mg (33.3 µmol) of 1-(2,5-dioxo-2,5-dihydro-1H-pyrrol-1-yl)-2-oxo-6,9,12,15-tetraoxa-3-azaoctadecan-18-oic acid (Intermediate L74) were initially charged in 1.0 ml of DMF, and 9.3 µl (54.4 µmol) of N,N-diisopropylethylamine and 12.6 mg (33.3 µmol) of HATU were added. The reaction mixture was stirred at RT for 10 min. 25.0 mg (27.7 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1) (see synthesis of Intermediate F216) dissolved in 4.7 µl (27.7 µmol) of N,N-diisopropylethylamine and 1.0 ml of DMF were then added. The reaction mixture was stirred at RT for 90 minutes. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 6.90 mg (19% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,18-dioxo-6,9,12,15-tetraoxa-3-azaoctadecan-18-yl]-L-cysteinyl-beta-alanine.

LC-MS (Method 5): $R_t$=4.44 min; MS (ESIpos): m/z=1172 $(M+H)^+$.

6.70 mg (5.71 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,18-dioxo-6,9,12,15-tetraoxa-3-azaoctadecan-18-yl]-L-cysteinyl-beta-alanine were dissolved in 1.0 ml of trifluoroethanol, and 4.67 mg (34.3 µmol) of zinc dichloride were added. The reaction mixture was stirred at 50° C. for 1 h. 10 mg (34.3 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum.

This gave 4.4 mg (67% of theory) of the title compound.

LC-MS (Method 1): $R_t$=0.85 min; MS (ESIpos): m/z=1028 $(M+H)^+$.

Intermediate F268

Trifluoroacetic Acid/N-(3-aminopropyl)-N-{(1R)-1-[1-benzyl-4-(2,5-difluorophenyl)-1H-pyrrol-2-yl]-2,2-dimethylpropyl}-28-(2,5-dioxo-2,5-dihydro-1H-pyrrol-1-yl)-6,23-dioxo-10,13,16,19-tetraoxa-3-thia-7,22-diazaoctacosane-1-amide (1:1)

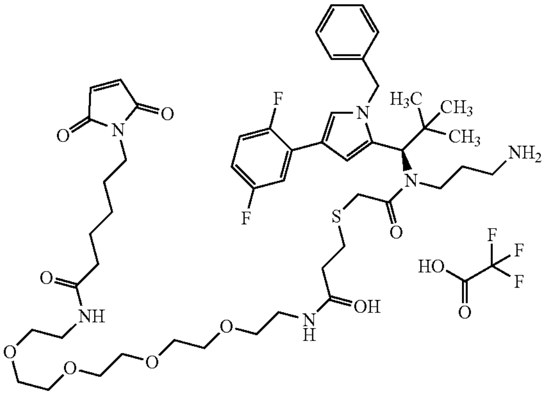 [SMILES: CC(C)(C)[C@H](c1cc(-c2cc(F)ccc2F)cn1Cc1ccccc1)N(CCCN)C(=O)CSCCC(=O)NCCOCCOCCOCCOCCNC(=O)CCCCCN1C(=O)C=CC1=O ; O=C(O)C(F)(F)F]

30.0 mg (0.043 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 30.2 mg (0.056 mmol) of trifluoroacetic acid/N-(14-amino-3,6,9,12-tetraoxatetradec-1-yl)-6-(2,5-dioxo-2,5-dihydro-1H-pyrrol-1-yl)hexanamide (1:1) (Intermediate L84) in 2.0 ml of acetonitrile. 60 μl (0.34 mmol) of N,N-diisopropylethylamine were then added, and 33 μl (0.056 mmol) of T3P (50% in ethyl acetate) were added dropwise. The reaction mixture was stirred at RT overnight. Water (2.0 ml) was added. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 27.9 mg (59% of theory) of the compound 2-(trimethylsilyl)ethyl [4-{(1R)-1-[1-benzyl-4-(2,5-difluorophenyl)-1H-pyrrol-2-yl]-2,2-dimethylpropyl}-32-(2,5-dioxo-2,5-dihydro-1H-pyrrol-1-yl)-5,10,27-trioxo-14,17,20,23-tetraoxa-7-thia-4,11,26-triazadotriacont-1-yl]carbamate.

LC-MS (Method 1): $R_t$=1.41 min; MS (ESIpos): m/z=1114 $(M+H)^+$.

25.6 mg (23.0 μmol) of 2-(trimethylsilyl)ethyl [4-{(1R)-1-[1-benzyl-4-(2,5-difluorophenyl)-1H-pyrrol-2-yl]-2,2-dimethylpropyl}-32-(2,5-dioxo-2,5-dihydro-1H-pyrrol-1-yl)-5,10,27-trioxotrioxo-14,17,20,23-tetraoxa-7-thia-4,11,26-triazadotriacont-1-yl]carbamate were dissolved in 2.5 ml of trifluoroethanol, and 18.8 mg (138 μmol) of zinc dichloride were added. The reaction mixture was stirred at 50° C. for 1 h. 40.3 mg (138 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 22.2 mg (88% of theory) of the title compound.

LC-MS (Method 1): $R_t$=0.94 min; MS (ESIpos): m/z=969 $(M+H)^+$.

Intermediate F269

4-{[(8R,14R)-13-(3-Aminopropyl)-14-[1-benzyl-4-(2,5-difluorophenyl)-1H-pyrrol-2-yl]-1-(2,5-dioxo-2,5-dihydro-1H-pyrrol-1-yl)-15,15-dimethyl-2,7,12-trioxo-10-thia-3,6,13-triazahexadecan-8-yl]amino}-4-oxobutanoic Acid/Trifluoroacetic Acid (1:1)

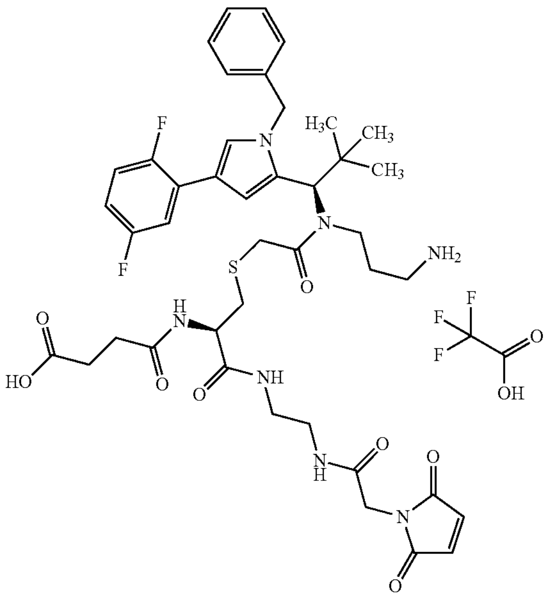

17.0 mg (0.0195 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were initially charged together with 4.99 mg (0.0253 mmol) of N-(2-aminoethyl)-2-(2,5-dioxo-2,5-dihydro-1H-pyrrol-1-yl)acetamide (Intermediate L1) in 1.0 ml of acetonitrile. 27 μl (0.16 mmol) of N,N-diisopropylethylamine were then added, and 15 μl (0.025 mmol) of T3P (50% in ethyl acetate) were added dropwise. The reaction mixture was stirred at RT overnight. Water (2.0 ml) was added. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 9.5 mg (46% of theory) of the compound tert-butyl 4-{[(16R)-11-{(1R)-1-[1-benzyl-4-(2,5-difluorophenyl)-1H-pyrrol-2-yl]-2,2-dimethylpropyl}-23-(2,5-dioxo-2,5-dihydro-1H-pyrrol-1-yl)-2,2-dimethyl-6,12,17,22-tetraoxo-5-oxa-14-thia-7,11,18,21-tetraaza-2-silatricosan-16-yl]amino}-4-oxobutanoate.

LC-MS (Method 1): $R_t$=1.47 min; MS (ESIpos): m/z=1052 $(M+H)^+$.

8.3 mg (7.89 μmol) of tert-butyl 4-{[(16R)-11-{(1R)-1-[1-benzyl-4-(2,5-difluorophenyl)-1H-pyrrol-2-yl]-2,2-dimethylpropyl}-23-(2,5-dioxo-2,5-dihydro-1H-pyrrol-1-yl)-2,2-dimethyl-6,12,17,22-tetraoxo-5-oxa-14-thia-7,11,18,21-tetraaza-2-silatricosan-16-yl]amino}-4-oxobutanoate were dissolved in 1.0 ml of trifluoroethanol, and 6.45 mg (47.3 μmol) of zinc dichloride were added. The reaction mixture was stirred at 50° C. for 6 h. 6.45 mg (47.3 μmol) of zinc dichloride were added and the reaction mixture was stirred at 50° C. overnight. 27.7 mg (94.6 μmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 1.10 mg (14% of theory) of the title compound.

LC-MS (Method 1): $R_t$=0.89 min; MS (ESIpos): m/z=852 $(M+H)^+$.

Intermediate F270

Trifluoroacetic Acid/N-(3-aminopropyl)-N-{(1R)-1-[1-benzyl-4-(2,5-difluorophenyl)-1H-pyrrol-2-yl]-2,2-dimethylpropyl}-N'-(2-{[(2,5-dioxo-2,5-dihydro-1H-pyrrol-1-yl)acetyl]amino}ethyl)succinamide (1:1)

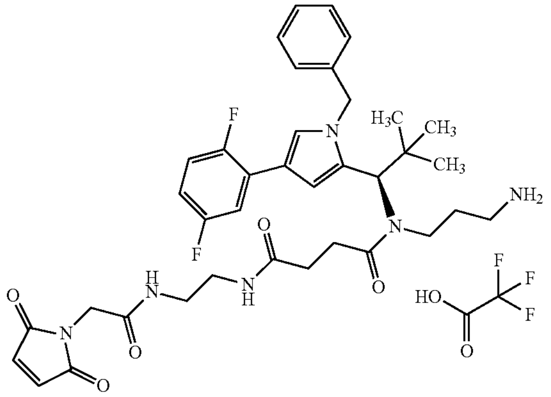

Under argon, 15.0 mg (22.9 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oic acid (Intermediate C78) were initially charged in 1.0 ml of DMF, and 8.0 μl (45.8 μmol) of N,N-diisopropylethylamine and 10.4 mg (27.4 μmol) of HATU were added. The reaction mixture was stirred at RT for 10 min. 8.54 mg (27.4 μmol) of trifluoroacetic acid/N-(2-aminoethyl)-2-(2,5-dioxo-2,5-dihydro-1H-pyrrol-1-yl)acetamide (1:1) (Intermediate L1) dissolved in 4.0 μl (22.9 μmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 14.7 mg (77% of theory) of the compound 2-(trimethylsilyl)ethyl [3-({(1R)-1-[1-benzyl-4-(2,5-difluorophenyl)-1H-pyrrol-2-yl]-2,2-dimethylpropyl}{4-[(2-{[(2,5-dioxo-2,5-dihydro-1H-pyrrol-1-yl)acetyl]amino}ethyl)amino]-4-oxobutanoyl}amino)propyl]carbamate.

LC-MS (Method 5): $R_t$=1.33 min; MS (ESIpos): m/z=835 $(M+H)^+$.

13.2 mg (15.8 μmol) of 2-(trimethylsilyl)ethyl [3-({(1R)-1-[1-benzyl-4-(2,5-difluorophenyl)-1H-pyrrol-2-yl]-2,2-dimethylpropyl}{4-[(2-{[(2,5-dioxo-2,5-dihydro-1H-pyrrol-1-yl)acetyl]amino}ethyl)amino]-4-oxobutanoyl}amino)propyl]carbamate were dissolved in 2.0 ml of trifluoroethanol, and 12.9 mg (94.8 μmol) of zinc dichloride were added. The reaction mixture was stirred at 50° C. for 1 h. 27.7 mg (94.6 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 10.9 mg (83% of theory) of the title compound.

LC-MS (Method 1): $R_t$=0.83 min; MS (ESIpos): m/z=691 $(M+H)^+$.

Intermediate F271

4-{[(20R,26R)-25-(3-Aminopropyl)-26-[1-benzyl-4-(2,5-difluorophenyl)-1H-pyrrol-2-yl]-1-(2,5-dioxo-2,5-dihydro-1H-pyrrol-1-yl)-27,27-dimethyl-2,19,24-trioxo-6,9,12,15-tetraoxa-22-thia-3,18,25-triazaoctacosan-20-yl]amino}-4-oxobutanoic Acid/Trifluoroacetic Acid (1:1)

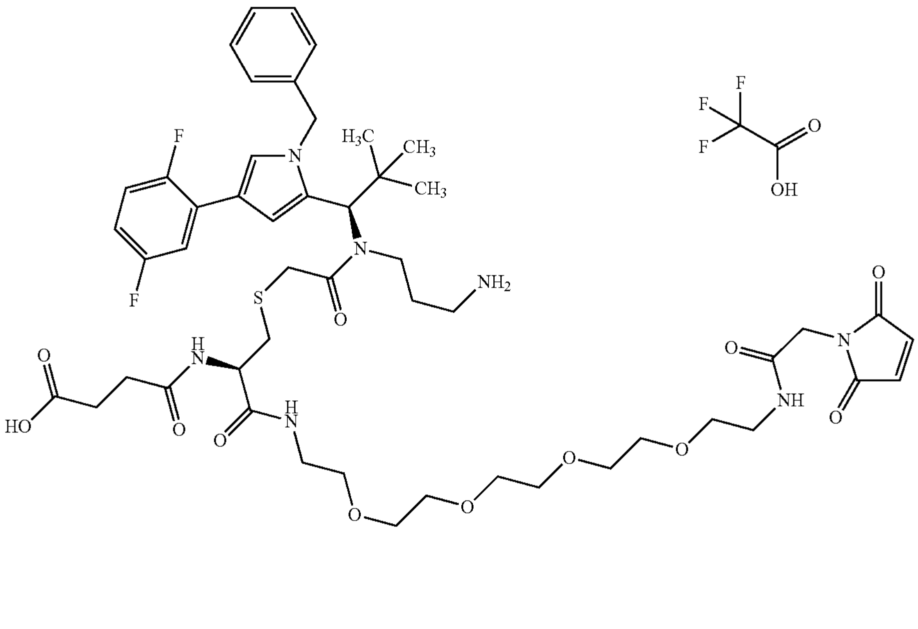 [SMILES: CC(C)(C)[C@H](c1cc(-c2cc(F)ccc2F)cn1Cc1ccccc1)N(CCCN)C(=O)CSC[C@H](NC(=O)CCC(=O)O)C(=O)NCCOCCOCCOCCOCCNC(=O)CN1C(=O)C=CC1=O ; O=C(O)C(F)(F)F]

Under argon, 19.4 mg (22.2 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were initially charged in 2.0 ml of DMF, and 21.7 mg (44.4 μmol) of trifluoroacetic acid/N-(14-amino-3,6,9,12-tetraoxatetradec-1-yl)-2-(2,5-dioxo-2,5-dihydro-1H-pyrrol-1-yl)acetamide (1:1) (Intermediate L74), 12 μl (67 μmol) of N,N-diisopropylethylamine and 16.9 mg (44.4 μmol) of HATU were added. The reaction mixture was stirred at RT for 1 h. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 18.1 mg (66% of theory) of the compound tert-butyl 4-{[(16R)-11-{(1R)-1-[1-benzyl-4-(2,5-difluorophenyl)-1H-pyrrol-2-yl]-2,2-dimethylpropyl}-35-(2,5-dioxo-2,5-dihydro-1H-pyrrol-1-yl)-2,2-dimethyl-6,12,17,34-tetraoxo-5,21,24,27,30-pentaoxa-14-thia-7,11,18,33-tetraaza-2-silapentatriacontan-16-yl]amino}-4-oxobutanoate.

LC-MS (Method 4): $R_t$=1.79 min; MS (ESIpos): m/z=1250 $(M+Na)^+$.

18.1 mg (14.7 μmol) of tert-butyl 4-{[(16R)-11-{(1R)-1-[1-benzyl-4-(2,5-difluorophenyl)-1H-pyrrol-2-yl]-2,2-dimethylpropyl}-35-(2,5-dioxo-2,5-dihydro-1H-pyrrol-1-yl)-2,2-dimethyl-6,12,17,34-tetraoxo-5,21,24,27,30-pentaoxa-14-thia-7,11,18,33-tetraaza-2-silapentatriacontan-16-yl]amino}-4-oxobutanoate were dissolved in 2.0 ml of trifluoroethanol, and 12.0 mg (88.4 μmol) of zinc dichloride were added. The reaction mixture was stirred at 50° C. for 4 h. 25.8 mg (88.4 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 12.3 mg (73% of theory) of the title compound.

LC-MS (Method 1): $R_t$=0.87 min; MS (ESIpos): m/z=1028 $(M+H)^+$.

Intermediate F272

Trifluoroacetic Acid/N-(3-aminopropyl)-N-{(1R)-1-[1-benzyl-4-(2,5-difluorophenyl)-1H-pyrrol-2-yl]-2,2-dimethylpropyl}-N'-[17-(2,5-dioxo-2,5-dihydro-1H-pyrrol-1-yl)-16-oxo-3,6,9,12-tetraoxa-15-azaheptadec-1-yl]succinamide (1:1)

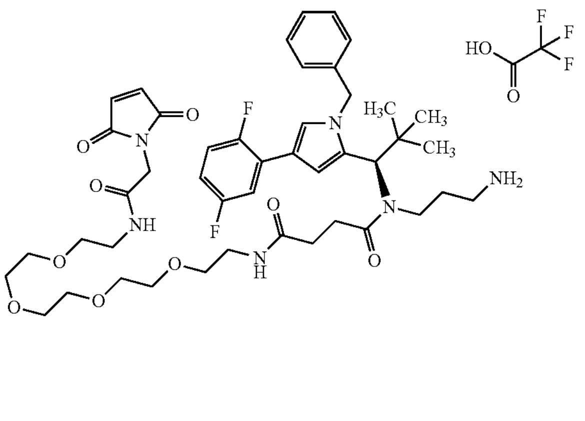 [SMILES: CC(C)(C)[C@H](c1cc(-c2cc(F)ccc2F)cn1Cc1ccccc1)N(CCCN)C(=O)CCC(=O)NCCOCCOCCOCCOCCNC(=O)CN1C(=O)C=CC1=O ; O=C(O)C(F)(F)F]

Under argon, 15.0 mg (22.9 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oic acid (Intermediate C78) were initially charged in 1.0 ml of DMF, and 8.0 μl (45.8 μmol) of N,N-diisopropylethylamine and 10.4 mg (27.4 μmol) of HATU were added. The reaction mixture was stirred at RT for 10 min. 13.4 mg (27.4 μmol) of trifluoroacetic acid/N-(14-amino-3,6,9,12-tetraoxatetradec-1-yl)-2-(2,5-dioxo-2,5-dihydro-1H-pyrrol-1-yl)acetamide (1:1) (Intermediate L85) dissolved in 4.0 μl (22.9 μmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 15.8 mg (68% of theory) of the compound 2-(trimethylsilyl)ethyl [23-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,22-trioxo-6,9,12,15-tetraoxa-3,18,23-triazahexacosan-26-yl]carbamate.

LC-MS (Method 1): $R_t$=1.35 min; MS (ESIpos): m/z=1011 $(M+H)^+$.

15.1 mg (14.9 μmol) of 2-(trimethylsilyl)ethyl [23-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,22-trioxotrioxo-6,9,12,15-tetraoxa-3,18,23-triazahexacosan-26-yl]carbamate were dissolved in 2.0 ml of trifluoroethanol, and 12.2 mg (89.6 μmol) of zinc dichloride were added. The reaction mixture was stirred at 50° C. for 1 h. 26.2 mg (89.6 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 10.3 mg (70% of theory) of the title compound.

LC-MS (Method 1): $R_t$=0.88 min; MS (ESIpos): m/z=867 $(M+H)^+$.

Intermediate F273

Trifluoroacetic Acid/N-(3-aminopropyl)-N-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19-dioxo-6,9,12,15-tetraoxa-22-thia-3,18-diazatetracosane-24-amide (1:1)

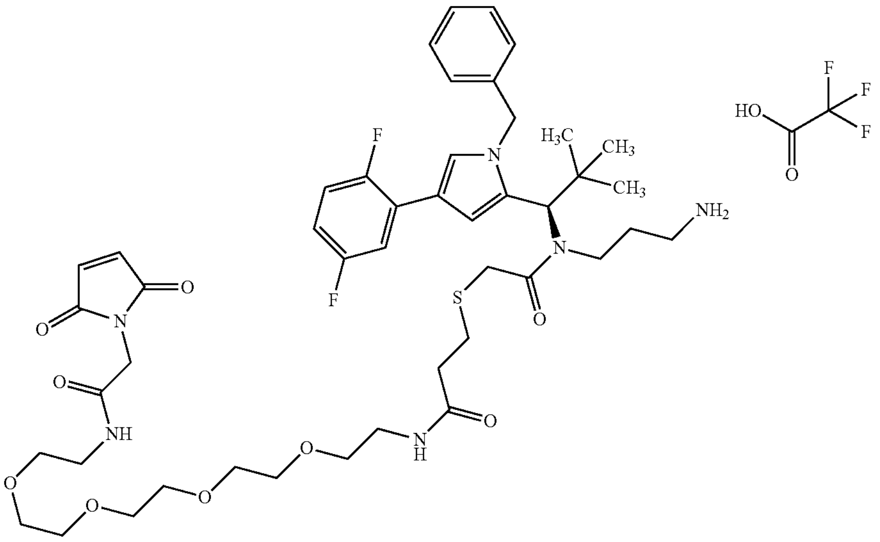 [SMILES: CC(C)(C)[C@H](c1cc(-c2cc(F)ccc2F)cn1Cc1ccccc1)N(CCCN)C(=O)CSCCC(=O)NCCOCCOCCOCCOCCNC(=O)CN1C(=O)C=CC1=O ; O=C(O)C(F)(F)F]

Under argon, 20.0 mg (28.5 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged in 1.0 ml of DMF, and 10.0 μl (57.0 μmol) of N,N-diisopropylethylamine and 13.0 mg (34.2 μmol) of HATU were added. The reaction mixture was stirred at RT for 10 min. 16.7 mg (34.2 μmol) of trifluoroacetic acid/N-(14-amino-3,6,9,12-tetraoxatetradec-1-yl)-2-(2,5-dioxo-2,5-dihydro-1H-pyrrol-1-yl)acetamide (1:1) (Intermediate L85) dissolved in 5.0 μl (28.5 μmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 18.6 mg (62% of theory) of the compound 2-(trimethylsilyl)ethyl [25-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,24-trioxo-6,9,12,15-tetraoxa-22-thia-3,18,25-triazaoctacosan-28-yl] carbamate.

LC-MS (Method 1): $R_t$=1.37 min; MS (ESIpos): m/z=1057 $(M+H)^+$.

17.1 mg (16.2 μmol) of 2-(trimethylsilyl)ethyl [25-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,24-trioxotrioxo-6,9,12,15-tetraoxa-22-thia-3,18,25-triazaoctacosan-28-yl]carbamate were dissolved in 2.0 ml of trifluoroethanol, and 13.2 mg (97.0 μmol) of zinc dichloride were added. The reaction mixture was stirred at 50° C. for 1 h. 28.4 mg (97.0 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 9.80 mg (59% of theory) of the title compound.

LC-MS (Method 1): $R_t$=0.88 min; MS (ESIpos): m/z=913 $(M+H)^+$.

Intermediate F274

N-[(2,5-Dioxo-2,5-dihydro-1H-pyrrol-1-yl)acetyl]-L-valyl-L-alanyl-S-{2-[(3-aminopropyl) {(1R)-1-[1-benzyl-4-(2,5-difluorophenyl)-1H-pyrrol-2-yl]-2,2-dimethylpropyl}amino]-2-oxoethyl}-L-cysteine/trifluoroacetic Acid (1:1)

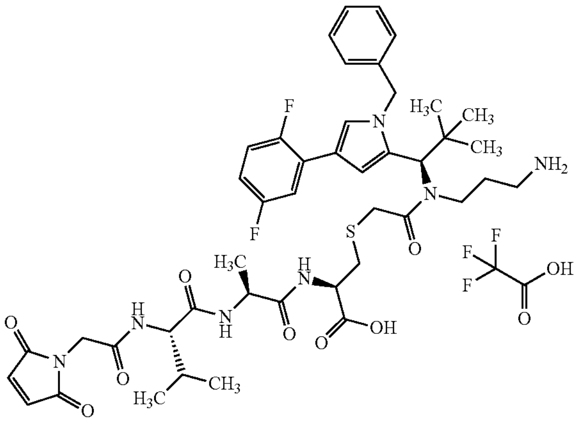 [SMILES: CC(C)[C@H](NC(=O)CN1C(=O)C=CC1=O)C(=O)N[C@@H](C)C(=O)N[C@@H](CSCC(=O)N(CCCN)[C@@H](c1cc(-c2cc(F)ccc2F)cn1Cc1ccccc1)C(C)(C)C)C(=O)O ; O=C(O)C(F)(F)F]

13.9 mg (0.0167 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) were initially charged together with 7.07 mg (0.0217 mmol) of N-[(2,5-dioxo-2,5-dihydro-1H-pyrrol-1-yl)acetyl]-L-valyl-L-alanine (Intermediate L86) in 2.0 ml of acetonitrile. 23 μl (0.13 mmol) of N,N-diisopropylethylamine were then added, and 13 μl (0.022 mmol) of T3P (50% in ethyl acetate)

were added dropwise. The reaction mixture was stirred at RT overnight. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 3.70 mg (19% of theory) of the compound N-[(2,5-dioxo-2,5-dihydro-1H-pyrrol-1-yl)acetyl]-L-valyl-L-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 1): $R_t$=1.34 min; MS (ESIpos): m/z=1024 $(M+H)^+$.

10.6 mg (10.3 μmol) of N-[(2,5-dioxo-2,5-dihydro-1H-pyrrol-1-yl)acetyl]-L-valyl-L-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 8.46 mg (62.1 μmol) of zinc dichloride were added. The reaction mixture was stirred at 50° C. for 1 h. 18.1 mg (62.1 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 5.60 mg (54% of theory) of the title compound.

LC-MS (Method 12): $R_t$=1.69 min; MS (ESIpos): m/z=880 $(M+H)^+$.

Intermediate F275

N-[3-({2-[(3-Aminopropyl) {(1R)-1-[1-benzyl-4-(2,5-difluorophenyl)-1H-pyrrol-2-yl]-2,2-dimethylpropyl}amino]-2-oxoethyl}sulphanyl)propanoyl]-N-(2-{[(2,5-dioxo-2,5-dihydro-1H-pyrrol-1-yl)acetyl]amino}ethyl)-L-alpha-glutamine/trifluoroacetic Acid (1:1)

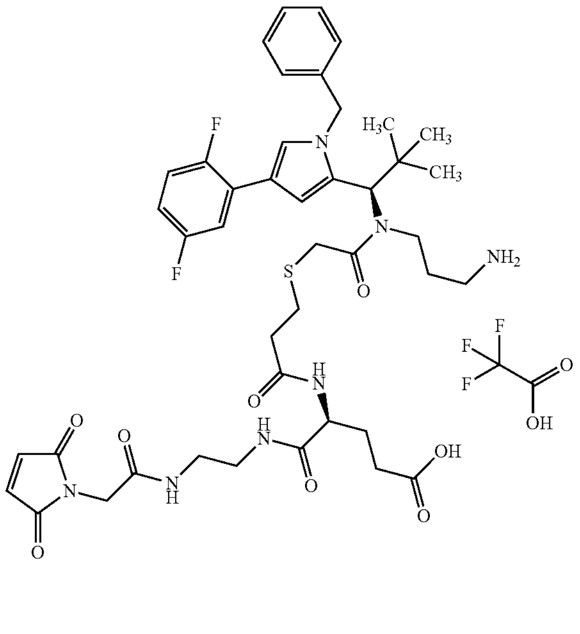

39.0 mg (55.6 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged in 4.0 ml of DMF, 41.6 mg (111 μmol) of 1-benzyl-5-[2-(trimethylsilyl)ethyl]-L-glutamate hydrochloride (1:1) (Intermediate L89), 29 μl (170 μmol) of N,N-diisopropylethylamine and 42.3 mg (111 μmol) of HATU were added and the mixture was stirred at RT for 1 hour. The reaction mixture was stirred at RT for 1 hour, quenched with acetic acid and purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 53.1 mg (93% of theory) of the compound 1-benzyl-5-[2-(trimethylsilyl)ethyl]-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-L-glutamate.

LC-MS (Method 1): $R_t$=1.71 min; MS (ESIpos): m/z=1021 $[M+H]^+$

Under argon, 7.60 mg (33.9 μmol) of palladium(II) acetate were initially charged in 3.0 ml of dichloromethane, and 14 μl (100 μmol) of triethylamine and 110 μl (680 μmol) of triethylsilane were added. The reaction mixture was stirred at RT for 5 min, and 69.2 mg (67.7 μmol) of 1-benzyl-5-[2-(trimethylsilyl)ethyl]-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-L-glutamate dissolved in 3.0 ml of dichloromethane were added. The reaction mixture was stirred at RT overnight. The reaction mixture was filtered through a cardboard filter and the filter cake was washed with dichloromethane. The solvent was evaporated under reduced pressure. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 38.4 mg (61% of theory) of the compound (19S)-11-{(1R)-1-[1-benzyl-4-(2,5-difluorophenyl)-1H-pyrrol-2-yl]-2,2-dimethylpropyl}-2,2-dimethyl-6,12,17-trioxo-19-{3-oxo-3-[2-(trimethylsilyl)ethoxy]propyl}-5-oxa-14-thia-7,11,18-triaza-2-silaicosan-20-oic acid.

LC-MS (Method 1): $R_t$=1.53 min; MS (ESIpos): m/z=931 $(M+H)^+$.

10.0 mg (10.7 μmol) of (19S)-11-{(1R)-1-[1-benzyl-4-(2,5-difluorophenyl)-1H-pyrrol-2-yl]-2,2-dimethylpropyl}-2,2-dimethyl-6,12,17-trioxo-19-{3-oxo-3-[2-(trimethylsilyl)ethoxy]propyl}-5-oxa-14-thia-7,11,18-triaza-2-silaicosan-20-oic acid (Intermediate C69) were initially charged in 1.0 ml of DMF, 6.73 mg (21.5 μmol) of N-(2-aminoethyl)-2-(2,5-dioxo-2,5-dihydro-1H-pyrrol-1-yl)acetamide/2,2,2-trifluoroethane-1,1-diol (1:1) (Intermediate L1), 5.6 μl (32 μmol) of N,N-diisopropylethylamine and 8.17 mg (21.5 μmol) of HATU were added and the mixture was stirred at RT for 1 hour. The reaction mixture was stirred at RT for 3 hour, quenched with acetic acid and purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 6.90 mg (58% of theory) of the compound 2-(trimethylsilyl)ethyl N2-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa- 14-thia-7,11-diaza-2-silaheptadecan-17-yl)-N-(2-{[(2,5-dioxo-2,5-dihydro-1H-pyrrol-1-yl)acetyl]amino}ethyl)-L-alpha-glutaminate.

LC-MS (Method 1): $R_t$=1.57 min; MS (ESIpos): m/z=1110 $[M+H]^+$ 6.90 mg (6.21 μmol) of 2-(trimethylsilyl)ethyl $N^2$-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-N-(2-{[(2,5-dioxo-2,5-dihydro-1H-pyrrol-1-yl)acetyl]amino}ethyl)-L-alpha-glutaminate were dissolved in 2.0 ml of trifluoroethanol, and 5.1 mg (37.2 μmol) zinc dichloride were added. The reaction mixture was stirred at 50° C. for 3 h. 5.1 mg (37.2 μmol) of zinc dichloride were added and the reaction mixture was stirred at 50° C. for 3 h. 5.1 mg (37.2 μmol) of zinc dichloride were added and the reaction mixture was stirred at 50° C. for 3 h. 10.1 mg (74.4 μmol) of zinc dichloride were added and the reaction mixture was stirred at 50° C. overnight and at RT for 72 h. 54.5 mg (186 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 2.4 mg (39% of theory) of the title compound.

LC-MS (Method 1): $R_t$=0.86 min; MS (ESIpos): m/z=866 $(M+H)^+$.

Intermediate F276

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-{3-[2-(2-{[(2,5-dioxo-2,5-dihydro-1H-pyrrol-1-yl)acetyl]amino}ethoxy)ethoxy]propanoyl}-L-cysteine/trifluoroacetic Acid (1:1)

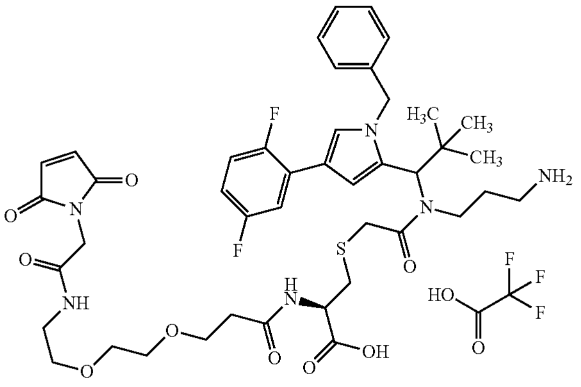

Under argon, 9.08 mg (28.9 μmol) of 3-[2-(2-{[(2,5-Dioxo-2,5-dihydro-1H-pyrrol-1-yl)acetyl]amino}ethoxy)ethoxy]propanoic acid (Intermediate L87) were initially charged in 1.0 ml of DMF, and 8.33 μl (48.2 μmol) of N,N-diisopropylethylamine and 11.0 mg (28.9 μmol) of HATU were added. The reaction mixture was stirred at RT for 10 min. 20.0 mg (27.7 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) dissolved in 4.67 μl (24.1 μmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 4.70 mg (19% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[(2,5-dioxo-2,5-dihydro-1H-pyrrol-1-yl)acetyl]amino}ethoxy)ethoxy]propanoyl}-L-cysteine.

LC-MS (Method 12): $R_t$=2.47 min; MS (ESIpos): m/z=1013 $(M+H)^+$.

13.9 mg (13.7 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[(2,5-dioxo-2,5-dihydro-1H-pyrrol-1-yl)acetyl]amino}ethoxy)ethoxy]propanoyl}-L-cysteine were dissolved in 2.0 ml of trifluoroethanol, and 5.6 mg (41.2 μmol) of zinc dichloride were added. The reaction mixture was stirred at 50° C. for 1 h. 5.6 mg (41.2 μmol) of zinc dichloride were added and the reaction mixture was stirred at 50° C. for 30 minutes. 24.1 mg (82.4 μmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 10.8 mg (80% of theory) of the title compound.

LC-MS (Method 12): $R_t$=1.58 min; MS (ESIpos): m/z=869 $(M+H)^+$.

Intermediate F277

N-[3-({2-[(3-Aminopropyl) {(1R)-1-[1-benzyl-4-(2,5-difluorophenyl)-1H-pyrrol-2-yl]-2,2-dimethylpropyl}amino]-2-oxoethyl}sulphanyl)propanoyl]-3-[(bromoacetyl)amino]-D-alanine/trifluoroacetic Acid (1:1)

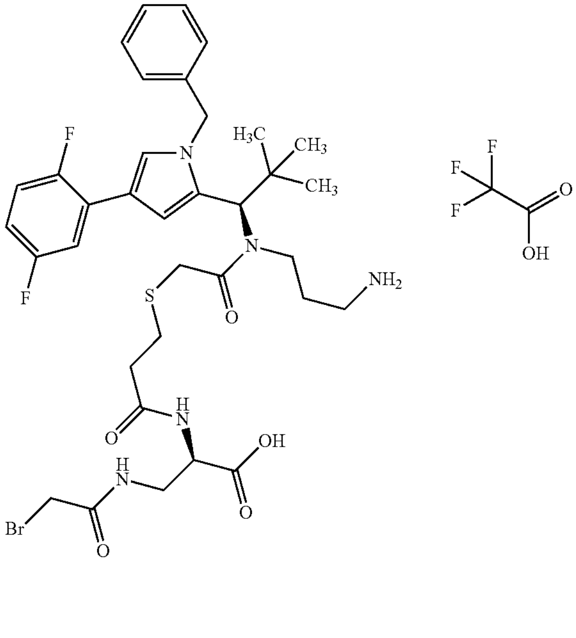 [SMILES: CC(C)(C)[C@H](c1cc(-c2cc(F)ccc2F)cn1Cc1ccccc1)N(CCCN)C(=O)CSCCC(=O)N[C@H](CNC(=O)CBr)C(=O)O ; O=C(O)C(F)(F)F]

8.90 mg (8.88 μmol) of trifluoroacetic acid/2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1) (Intermediate C80) and 2.31 mg (9.77 μmol) of 1-(2-bromoacetoxy)pyrrolidine-2,5-dione were dissolved in 1 ml of dimethylformamide, and 2.9 μl (27 μmol) of N-methylmorpholine were added. The reaction mixture was stirred at RT for 1 h. The reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 5.80 mg (65% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate.

LC-MS (Method 1): $R_t$=1.57 min; MS (ESIpos): m/z=1008 $(M+H)^+$.

5.80 mg (5.75 μmol) of 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate were dissolved in 2.0 ml of trifluoroethanol, and 4.70 mg (34.5 μmol) of zinc dichloride were added. The reaction mixture was stirred at 50° C. for 3 h. 4.70 mg (34.5 μmol) of zinc dichloride were added and the reaction mixture was stirred at 50° C. for 5 h. 20.2 mg (69.0 μmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 1.70 mg (34% of theory) of the title compound.

LC-MS (Method 1): $R_t$=0.90 min; MS (ESIpos): m/z=764 $(M+H)^+$.

Intermediate F278

N-[3-({2-[(3-Aminopropyl) {(1R)-1-[1-benzyl-4-(2,5-difluorophenyl)-1H-pyrrol-2-yl]-2,2-dimethylpropyl}amino]-2-oxoethyl}sulphanyl)propanoyl]-3-{[(2,5-dioxo-2,5-dihydro-1H-pyrrol-1-yl)acetyl]amino}-D-alanine/trifluoroacetic Acid (1:1)

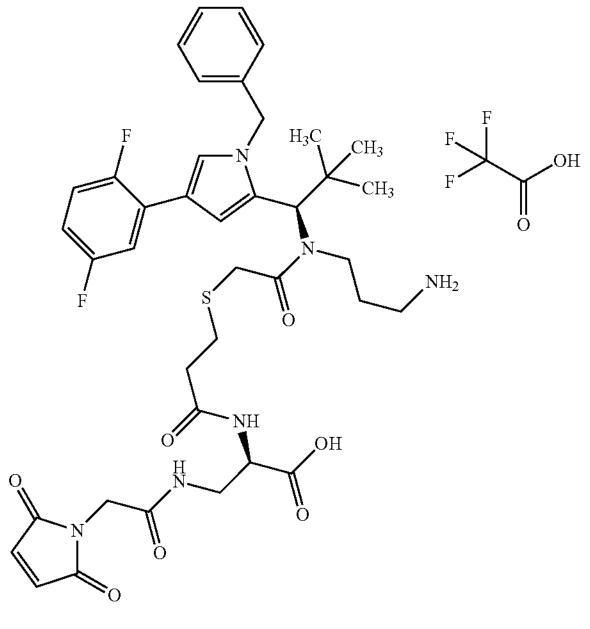 [SMILES: CC(C)(C)[C@H](c1cc(-c2cc(F)ccc2F)cn1Cc1ccccc1)N(CCCN)C(=O)CSCCC(=O)N[C@H](CNC(=O)CN1C(=O)C=CC1=O)C(=O)O ; O=C(O)C(F)(F)F]

10.0 mg (9.98 μmol) of trifluoroacetic acid/2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1) (Intermediate C80) and 2.77 mg (11.0 μmol) of 1-{2-[(2,5-dioxopyrrolidin-1-yl)oxy]-2-oxoethyl}-1H-pyrrole-2,5-dione were dissolved in 1 ml of dimethylformamide, and 3.3 μl (30 μmol) of N-methylmorpholine were added. The reaction mixture was stirred at RT overnight. 2.0 μl (35 μmol) of acetic acid were added, and the reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 5.50 mg (54% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-{[(2,5-dioxo-2,5-dihydro-1H-pyrrol-1-yl)acetyl]amino}-D-alaninate.

LC-MS (Method 1): $R_t$=1.51 min; MS (ESIpos): m/z=1024 $(M+H)^+$.

5.50 mg (5.36 μmol) of 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-{[(2,5-dioxo-2,5-dihydro-1H-pyrrol-1-yl)acetyl]amino}-D-alaninate were dissolved in 1.0 ml of trifluoroethanol, and 4.39 mg (32.2 μmol) of zinc dichloride were added. The reaction mixture was stirred at 50° C. for 1 h. 4.39 mg (32.2 μmol) of zinc dichloride were added and the reaction mixture was stirred at 50° C. for 1 h. 4.39 mg (32.2 μmol) of zinc dichloride were added and the reaction mixture was stirred at 50° C. for 4 h. 28.2 mg (96.5 μmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 2.70 mg (56% of theory) of the title compound.

LC-MS (Method 1): $R_t$=0.89 min; MS (ESIpos): m/z=781 $(M+H)^+$.

Intermediate F279

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({(2R)-2-carboxy-2-[(3-carboxypropanoyl)amino]ethyl}sulphanyl)acetyl]amino)propyl]-L-alaninamide

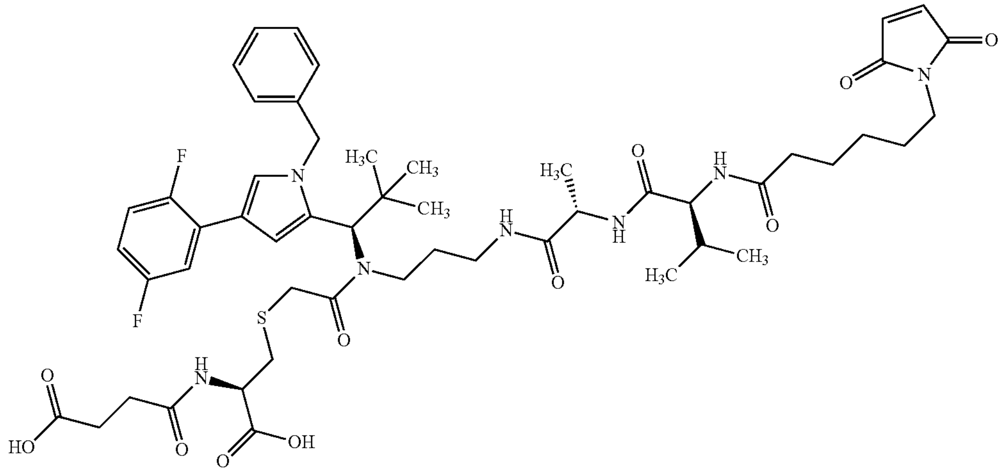 [SMILES: CC(C)[C@H](NC(=O)CCCCCN1C(=O)C=CC1=O)C(=O)N[C@@H](C)C(=O)NCCCN(C(=O)CSC[C@H](NC(=O)CCC(=O)O)C(=O)O)[C@@H](c1cc(-c2cc(F)ccc2F)cn1Cc1ccccc1)C(C)(C)C]

12.2 mg (14 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were dissolved in 2.0 ml of trifluoroethanol, and 11.4 mg (83.8 μmol) of zinc dichloride were added. The reaction mixture was stirred at 50° C. for 3 h. 24.5 mg (83.8 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 4.60 mg (42% of theory) of the compound 4-{[(1R)-2-({2-[(3-aminopropyl) {(1R)-1-[1-benzyl-4-(2,5-difluorophenyl)-1H-pyrrol-2-yl]-2,2-dimethylpropyl}amino]-2-oxoethyl}sulphanyl)-1-carboxyethyl]amino}-4-oxobutanoic acid/trifluoroacetic acid (1:1).

LC-MS (Method 1): $R_t$=0.88 min; MS (ESIpos): m/z=673 $(M+H)^+$.

10.0 mg (12.7 μmol) of 4-{[(1R)-2-({2-[(3-aminopropyl) {(1R)-1-[1-benzyl-4-(2,5-difluorophenyl)-1H-pyrrol-2-yl]-2,2-dimethylpropyl}amino]-2-oxoethyl}sulphanyl)-1-carboxyethyl]amino}-4-oxobutanoic acid/trifluoroacetic acid (1:1) and 7.41 mg (12.7 μmol) of 2,5-dioxopyrrolidin-1-yl N-[6-(2,5-dioxo-2,5-dihydro-1H-pyrrol-1-yl)hexanoyl]-L-valyl-L-alaninate (Intermediate L88) were dissolved in 1.5 ml of dimethylformamide, and 4.4 μl (25 μmol) of N,N-diisopropylethylamine were added. The reaction mixture was stirred at RT for 2 h. 2.0 μl (35 μmol) of acetic acid were added, and the reaction mixture was purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 5.20 mg (39% of theory) of the title compound.

LC-MS (Method 1): $R_t$=1.11 min; MS (ESIpos): m/z=1036 $(M+H)^+$.

Intermediate F280

Trifluoroacetic Acid/N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-3-(2,5-dioxo-2,5-dihydro-1H-pyrrol-1-yl)benzamide (1:1)

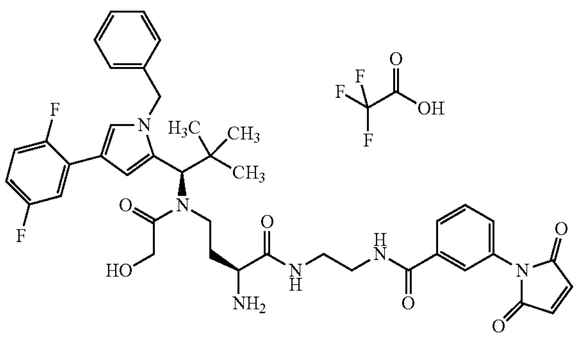 [SMILES: CC(C)(C)[C@H](c1cc(-c2cc(F)ccc2F)cn1Cc1ccccc1)N(CC[C@H](N)C(=O)NCCNC(=O)c1cccc(N2C(=O)C=CC2=O)c1)C(=O)CO ; O=C(O)C(F)(F)F]

The title compound was prepared from Intermediate C64 by coupling with commercially available 1-(3-{[(2,5-dioxopyrrolidin-1-yl)oxy]carbonyl}phenyl)-1H-pyrrole-2,5-dione and subsequent deprotection with zinc chloride.

LC-MS (Method 1): $R_t$=0.88 min; MS (ESIpos): m/z=755 $(M+H)^+$.

Intermediate F281

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[N-(bromoacetyl)-beta-alanyl]amino}-D-alanine/trifluoroacetic Acid (1:1)

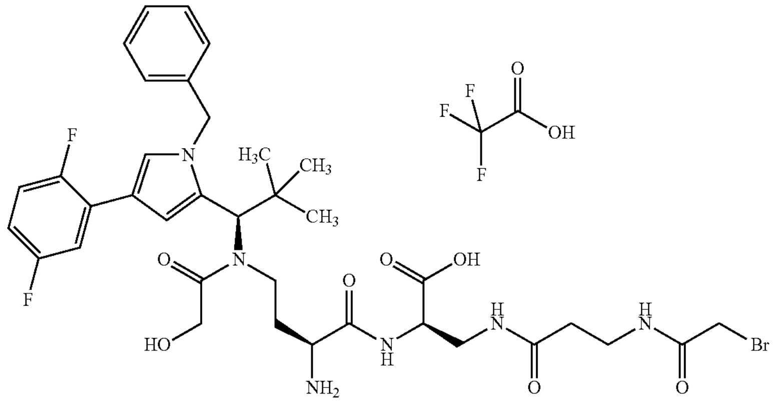 [SMILES: CC(C)(C)[C@H](c1cc(-c2cc(F)ccc2F)cn1Cc1ccccc1)N(CC[C@H](N)C(=O)N[C@H](CNC(=O)CCNC(=O)CBr)C(=O)O)C(=O)CO ; O=C(O)C(F)(F)F]

First, the modified amino acid building blocks N-(bromoacetyl)-beta-alanine and 2-(trimethylsilyl)ethyl-3-amino-N-(tert-butoxycarbonyl)-D-alaninate were prepared by classical methods of peptide chemistry. These were then coupled in the presence of HATU and morpholine. The tert-butoxycarbonyl protective group was then removed using 10% strength trifluoroacetic acid in dichloromethane, giving the intermediate 2-(trimethylsilyl)ethyl 3-{[N-(bromoacetyl)-beta-alanyl]amino}-D-alaninate.

Finally, the title compound was prepared by coupling this intermediate with intermediate C58 in the presence of HATU and 4-methylmorpholine, followed by deprotection with zinc chloride.

LC-MS (Method 1): $R_t$=0.87 min; MS (ESIpos): m/z=791 and 793 $(M+H)^+$.

Intermediate F282

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(3-{[N-(bromoacetyl)glycyl]amino}propyl)butanamide (1:1)

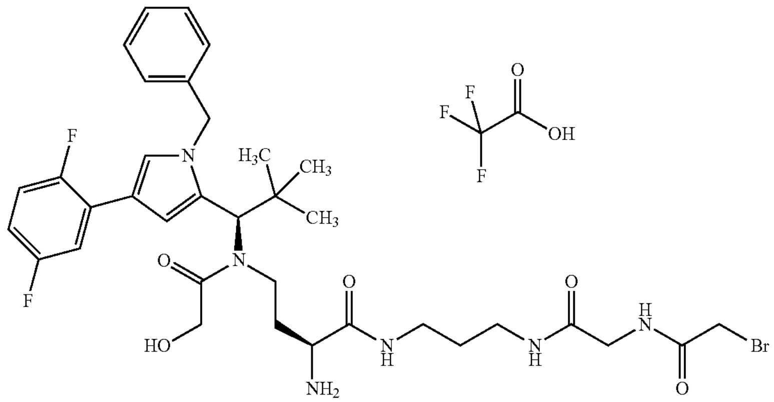 [SMILES: CC(C)(C)[C@H](c1cc(-c2cc(F)ccc2F)cn1Cc1ccccc1)N(CC[C@H](N)C(=O)NCCCNC(=O)CNC(=O)CBr)C(=O)CO ; O=C(O)C(F)(F)F]

First, the intermediate trifluoroacetic acid/N-(3-aminopropyl)-N2-(bromoacetyl)glycinamide (1:1) was prepared from tert-butyl glycinate and bromoacetic anhydride by classical methods of peptide chemistry.

Finally, the title compound was prepared by coupling this intermediate with intermediate C58 in the presence of HATU and 4-methylmorpholine, followed by deprotection with zinc chloride.

LC-MS (Method 1): $R_t$=0.83 min; MS (ESIpos): m/z=747 and 749 $(M+H)^+$.

Intermediate F283

N-[(2R)-2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]-$N^2$-(bromoacetyl)-L-alpha-asparagine/trifluoroacetic Acid (1:1)

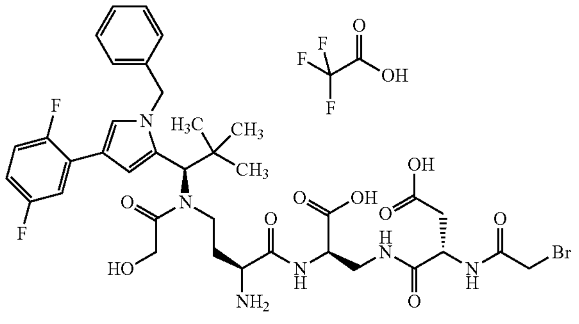 [SMILES: CC(C)(C)[C@H](c1cc(-c2cc(F)ccc2F)cn1Cc1ccccc1)N(CC[C@H](N)C(=O)N[C@H](CNC(=O)[C@H](CC(=O)O)NC(=O)CBr)C(=O)O)C(=O)CO ; O=C(O)C(F)(F)F]

First, the modified amino acid building block (2S)-2-[(bromoacetyl)amino]-4-oxo-4-[2-(trimethylsilyl)ethoxy]butanoic acid and bromoacetic anhydride was prepared from (2S)-2-amino-4-oxo-4-[2-(trimethylsilyl)ethoxy]butanoic acid and bromoacetic anhydride and the amino acid building block 2-(trimethylsilyl)ethyl-3-amino-N-(tert-butoxycarbonyl)-D-alaninate was prepared from commercially available 3-{[(benzyloxy)carbonyl]amino}-N-(tert-butoxycarbonyl)-D-alanine/N-cyclohexylcyclohexanamine (1:1). Both building blocks were coupled in the presence of HATU and morpholine and the tert-butoxycarbonyl protective group was then removed using 5% strength trifluoroacetic acid in dichloromethane, giving the silylethyl ester protective groups and thus the intermediate trifluoroacetic acid/2-(trimethylsilyl)ethyl-N-{(2R)-2-amino-3-oxo-3-[2-(trimethylsilyl)ethoxy]propyl}-N2-(bromoacetyl)-L-alpha-asparaginate (1:1).

Finally, the title compound was prepared by coupling this intermediate with intermediate C58 in the presence of HATU and 4-methylmorpholine, followed by deprotection with zinc chloride.

LC-MS (Method 1): $R_t$=0.84 min; MS (ESIpos): m/z=835 and 837 $(M+H)^+$.

Intermediate F284

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[1-(2,5-dioxo-2,5-dihydro-1H-pyrrol-1-yl)-2,18-dioxo-6,9,12,15-tetraoxa-3-azaoctadecan-18-yl]amino}-D-alanine/trifluoroacetic Acid (1:1)

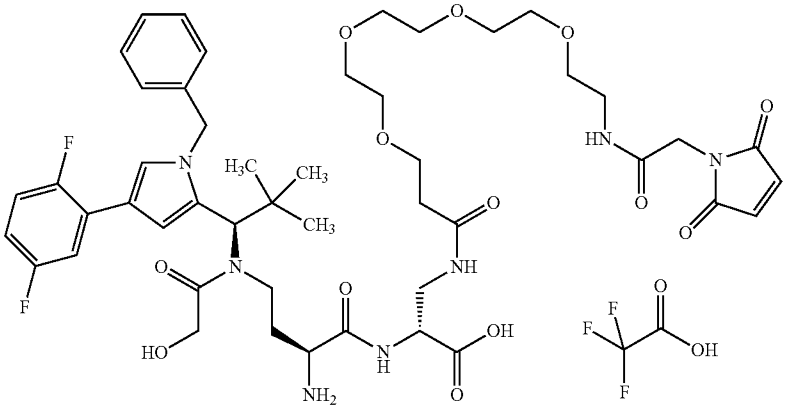

First, intermediate L80 was coupled with commercially available (2,5-dioxo-2,5-dihydro-1H-pyrrol-1-yl)acetic acid in the presence of HATU and N,N-diisopropylethylamine, and the tert-butoxycarbonyl protective group was then removed using 16% strength trifluoroacetic acid in dichloromethane, giving the silylethyl ester protective group.

Finally, the title compound was prepared by coupling this intermediate with intermediate C58 in the presence of HATU and N,N-diisopropylethylamine, followed by deprotection with zinc chloride.

LC-MS (Method 12): $R_t$=1.46 min; MS (ESIpos): m/z=984.45 $(M+H)^+$.

Intermediate F285

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-[(18-bromo-17-oxo-4,7,10,13-tetraoxa-16-azaoctadecan-1-oyl)amino]-D-alanine/trifluoroacetic Acid (1:1)

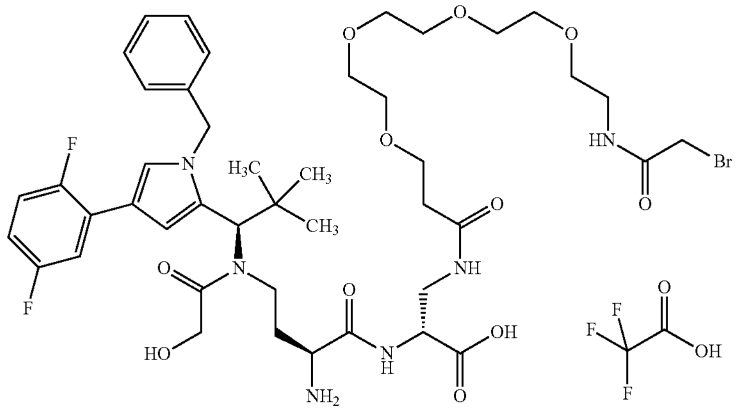 [SMILES: CC(C)(C)[C@H](c1cc(-c2cc(F)ccc2F)cn1Cc1ccccc1)N(CC[C@H](N)C(=O)N[C@H](CNC(=O)CCOCCOCCOCCOCCNC(=O)CBr)C(=O)O)C(=O)CO ; O=C(O)C(F)(F)F]

First, intermediate L80 was acylated with commercially available bromoacetic anhydride, and the tert-butoxycarbonyl protective group was then removed using 20% strength trifluoroacetic acid in dichloromethane, giving the silylethyl ester protective group.

Finally, the title compound was prepared by coupling this intermediate with intermediate C58 in the presence of HATU and N,N-diisopropylethylamine, followed by deprotection with zinc chloride.

LC-MS (Method 1): $R_t$=0.85 min; MS (ESIpos): m/z=967 and 969 $(M+H)^+$.

Intermediate F286

1-[(N-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl) acetyl]amino}-D-alanyl) amino]-3,6,9,12-tetraoxapentadecan-15-oic Acid/Trifluoroacetic Acid (1:1)

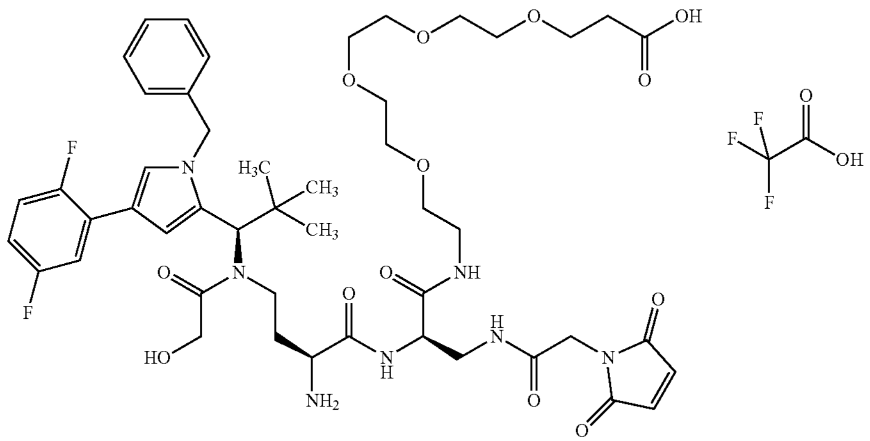 [SMILES: CC(C)(C)[C@H](c1cc(-c2cc(F)ccc2F)cn1Cc1ccccc1)N(CC[C@H](N)C(=O)N[C@H](CNC(=O)CN1C(=O)C=CC1=O)C(=O)NCCOCCOCCOCCOCCC(=O)O)C(=O)CO ; O=C(O)C(F)(F)F]

First, intermediate L91 was coupled with (2,5-dioxo-2,5-dihydro-1H-pyrrol-1-yl)acetic acid in the presence of HATU and N,N-diisopropylethylamine, and the Boc protective group was then removed using 12.5% strength TFA in DCM. The resulting intermediate was coupled with intermediate C58 in the presence of HATU and N,N-diisopropylethylamine and then converted into the title compound by deprotection with zinc chloride.

Intermediate F289

$N^2$-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-$N^6$-[(2,5-dioxo-2,5-dihydro-1H-pyrrol-1-yl)acetyl]-D-lysine/trifluoroacetate (1:1)

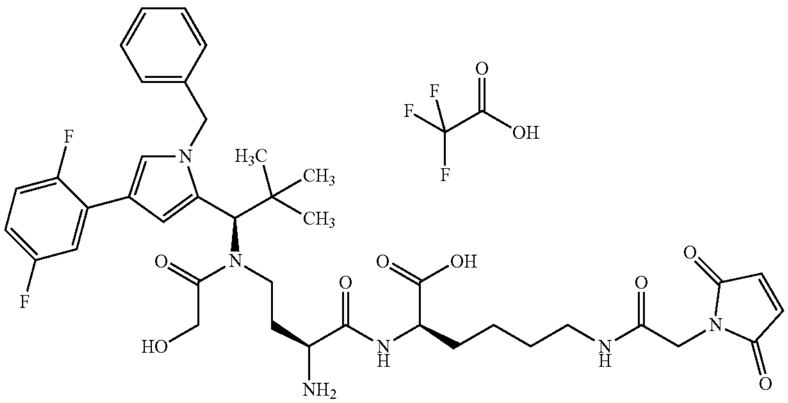

LC-MS (Method 1): $R_t$=0.84 min; MS (ESIpos): m/z=984 $(M+H)^+$.

Intermediate F288

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-({N-[(2,5-dioxo-2,5-dihydro-1H-pyrrol-1-yl)acetyl]-L-seryl}amino)-D-alanine/trifluoroacetic Acid (1:1)

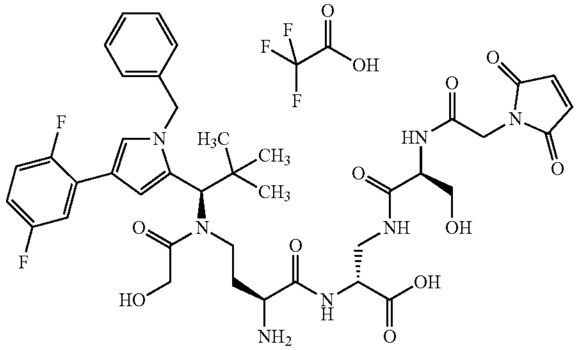 [SMILES: CC(C)(C)[C@H](c1cc(-c2cc(F)ccc2F)cn1Cc1ccccc1)N(CC[C@H](N)C(=O)N[C@H](CNC(=O)[C@H](CO)NC(=O)CN1C(=O)C=CC1=O)C(=O)O)C(=O)CO ; O=C(O)C(F)(F)F]

35 mg (39 µmol) of intermediate C74 were coupled in the presence of HATU and N,N-diisopropyethylamine with N-[(2,5-dioxo-2,5-dihydro-1H-pyrrol-1-yl)acetyl]-L-serine which had been prepared beforehand from tert-butyl O-tert-butyl-L-serinate and (2,5-dioxo-2,5-dihydro-1H-pyrrol-1-yl)acetic acid. Deprotection with zinc chloride and purification by HPLC gave 14 mg (38% of theory) of the title compound.

LC-MS (Method 12): $R_t$=1.43 min; MS (ESIpos): m/z=824.34 $(M+H)^+$.

First, trifluoroacetic acid/2-(trimethylsilyl)ethyl-$N^6$-[(2,5-dioxo-2,5-dihydro-1H-pyrrol-1-yl)acetyl]-D-lysinate (1:1) was prepared by classical methods of peptide chemistry from $N^6$-[(benzyloxy)carbonyl]-$N^2$-(tert-butoxycarbonyl)-D-lysine.

12.5 mg (25 µmol) of this intermediate were then coupled in the presence of HATU and 4-methylmorpholine with 15 mg (23 µmol) of Intermediate C58. Deprotection with zinc chloride and purification by HPLC gave 14 mg (53% of theory) of the title compound.

LC-MS (Method 1): $R_t$=0.83 min; MS (ESIpos): m/z=779 $(M+H)^+$.

Intermediate F290

$N^2$-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-$N^6$-(bromoacetyl)-D-lysine/trifluoroacetic Acid (1:1)

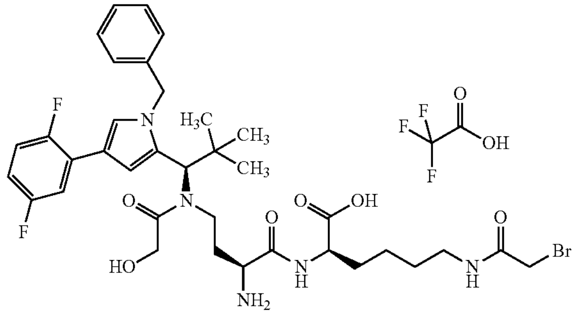 [SMILES: CC(C)(C)[C@H](c1cc(-c2cc(F)ccc2F)cn1Cc1ccccc1)N(CC[C@H](N)C(=O)N[C@H](CCCCNC(=O)CBr)C(=O)O)C(=O)CO ; O=C(O)C(F)(F)F]

First, trifluoroacetic acid/2-(trimethylsilyl)ethyl-N6-(bromoacetyl)-D-lysinate (1:1) was prepared by classical methods of peptide chemistry from $N^6$-[(benzyloxy)carbonyl]-$N^2$-(tert-butoxycarbonyl)-D-lysine.

12 mg (25 µmol) of this intermediate were then coupled in the presence of HATU and 4-methylmorpholine with 15 mg (23 µmol) of Intermediate C58. Deprotection with zinc chloride and purification by HPLC gave 7 mg (36% of theory) of the title compound.

LC-MS (Method 1): $R_t$=0.86 min; MS (ESIpos): m/z=762 and 764 $(M+H)^+$.

Intermediate F291

N-[(2,5-Dioxo-2,5-dihydro-1H-pyrrol-1-yl)acetyl]-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide

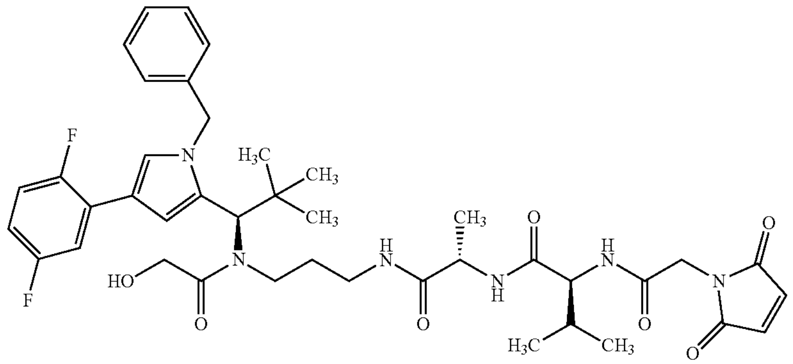 [SMILES: CC(C)[C@H](NC(=O)CN1C(=O)C=CC1=O)C(=O)N[C@@H](C)C(=O)NCCCN(C(=O)CO)[C@@H](c1cc(-c2cc(F)ccc2F)cn1Cc1ccccc1)C(C)(C)C]

The title compound was prepared from Example M9 first by coupling with N-[(benzyloxy)carbonyl]-L-valyl-L-alanine in the presence of HATU and N,N-diisopropylethylamine. In the next step, the Z protective group was removed by hydrogenating for 1 hour over 10% palladium on activated carbon at RT under hydrogen standard pressure and then converting the deprotected intermediate into the title compound by coupling with (2,5-dioxo-2,5-dihydro-1H-pyrrol-1-yl)acetic acid in the presence of HATU and N,N-diisopropylethylamine.

LC-MS (Method 1): $R_t$=1.21 min; MS (ESIpos): m/z=777 $(M+H)^+$.

Intermediate F293

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl)benzoyl]amino}-D-alanine/trifluoroacetic Acid (1:1)

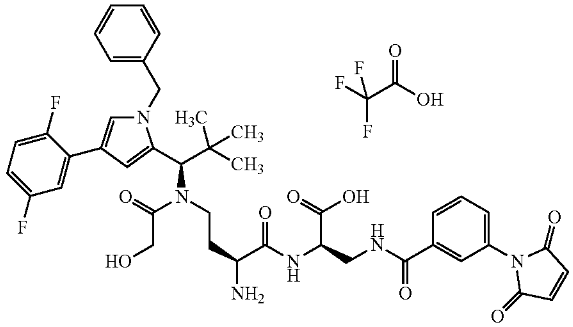 [SMILES: CC(C)(C)[C@H](c1cc(-c2cc(F)ccc2F)cn1Cc1ccccc1)N(CC[C@H](N)C(=O)N[C@H](CNC(=O)c1cccc(N2C(=O)C=CC2=O)c1)C(=O)O)C(=O)CO ; O=C(O)C(F)(F)F]

35 mg (39 μmol) of Intermediate C74 were dissolved in 4 ml of DMF and, in the presence of N,N-diisopropylethylamine, coupled with 13.5 mg (43 μmol) of commercially available 1-(3-{[(2,5-dioxopyrrolidin-1-yl)oxy]carbonyl}phenyl)-1H-pyrrole-2,5-dione. Deprotection with zinc chloride and purification by HPLC gave 12 mg (34% of theory) of the title compound.

LC-MS (Method 12): $R_t$=0.93 min; MS (ESIpos): m/z=799 $(M+H)^+$.

Intermediate F294

N-{5-[(2,5-Dioxopyrrolidin-1-yl)oxy]-5-oxopentanoyl}-L-valyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-alaninamide

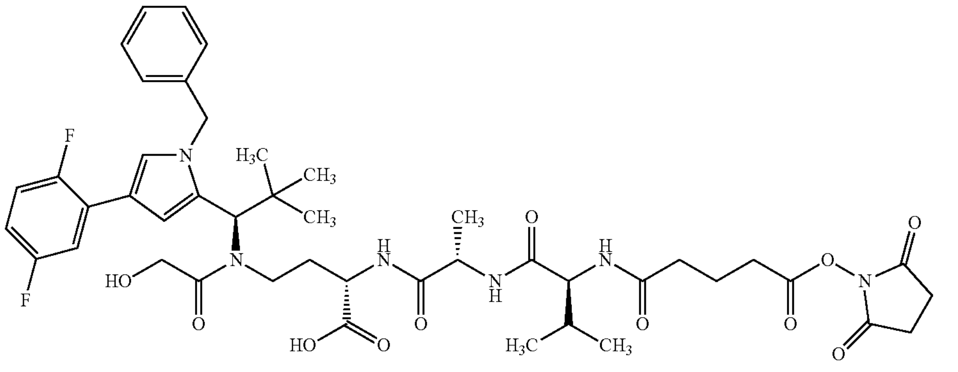 [SMILES: CC(C)[C@H](NC(=O)CCCC(=O)ON1C(=O)CCC1=O)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)O]

41 mg (0.05 mmol) of Intermediate C76 dissolved in 12 ml of methanol were hydrogenated over 10 mg of 10% palladium on activated carbon at RT for 1 h under hydrogen standard pressure. The catalyst was then filtered off and the solvent was removed under reduced pressure. This gave 32 mg (92% of theory) of the deprotected intermediate.

15 mg (0.022 mmol) of this intermediate were dissolved in DMF, and 13 mg (0.039 mmol) of 1,1'-[(1,5-dioxopentan-1,5-diyl)bis(oxy)]dipyrrolidine-2,5-dione and 7 μl of N,N-diisopropylethylamine were added. After 1 h of stirring at RT, the reaction was concentrated and the residue was purified by HPLC. This gave 9 mg (45% of theory) of the title compound.

LC-MS (Method 1): $R_t$=1.08 min; MS (ESIpos): m/z=895 $(M+H)^+$.

Intermediate F295

N-[(2,5-Dioxo-2,5-dihydro-1H-pyrrol-1-yl)acetyl]-L-valyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-alaninamide

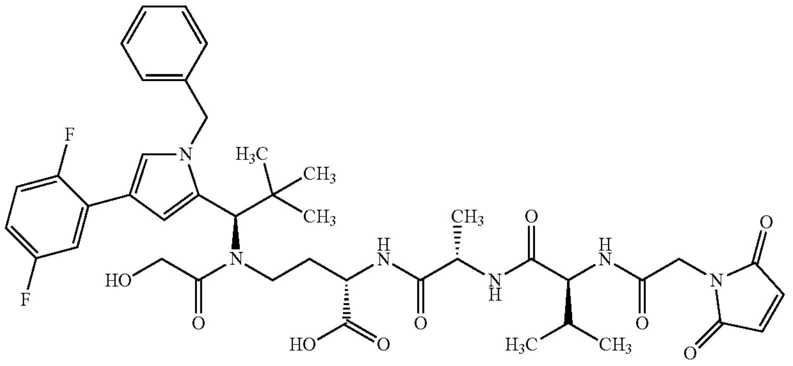 [SMILES: CC(C)[C@H](NC(=O)CN1C(=O)C=CC1=O)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)O]

41 mg (0.05 mmol) of Intermediate C76 dissolved in 12 ml of methanol were hydrogenated over 10 mg of 10% palladium on activated carbon at RT for 1 h under hydrogen standard pressure. The catalyst was then filtered off and the solvent was removed under reduced pressure. This gave 32 mg (92% of theory) of the deprotected intermediate.

15 mg (0.022 mmol) of this intermediate were dissolved in 4 ml of DMF, and 10 mg (0.039 mmol) of 1-{2-[(2,5-dioxopyrrolidin-1-yl)oxy]-2-oxoethyl}-1H-pyrrole-2,5-dione and 7 μl of N,N-diisopropylethylamine were added. After 2 h of stirring at RT, the reaction was concentrated and the residue was purified by HPLC. This gave 10 mg (56% of theory) of the title compound.

LC-MS (Method 1): $R_t$=1.08 min; MS (ESIpos): m/z=821 $(M+H)^+$.

Intermediate F296

Trifluoroacetic Acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[(2-{[(2,5-dioxo-2,5-dihydro-1H-pyrrol-1-yl)acetyl]amino}ethyl)sulphonyl]ethyl}butanamide (1:1)

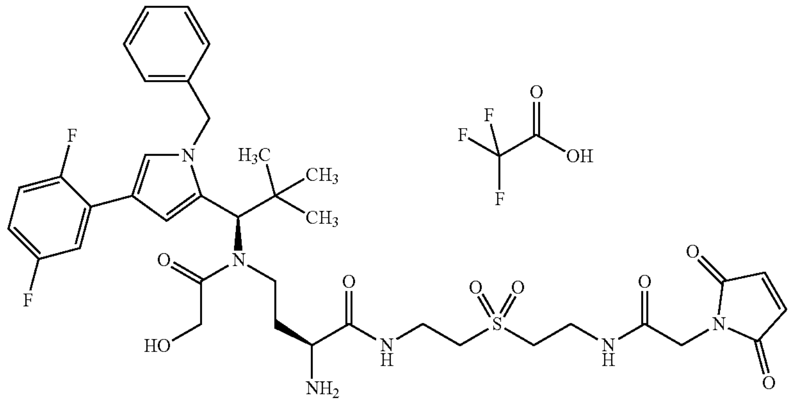 [SMILES: CC(C)(C)[C@H](c1cc(-c2cc(F)ccc2F)cn1Cc1ccccc1)N(CC[C@H](N)C(=O)NCCS(=O)(=O)CCNC(=O)CN1C(=O)C=CC1=O)C(=O)CO ; O=C(O)C(F)(F)F]

The title compound was prepared from Intermediate L81 by coupling with Intermediate C58 in the presence of HATU and N,N-diisopropylethylamine. In the next step, the Z protective group was removed by hydrogenation over 10% palladium on activated carbon in DCM/methanol 1:1 at RT under hydrogen standard pressure for 30 min. The deprotected intermediate was then converted by coupling with (2,5-dioxo-2,5-dihydro-1H-pyrrol-1-yl)acetic acid in the presence of HATU and N,N-diisopropylethylamine and finally by deprotection with zinc chloride into the title compound.

LC-MS (Method 1): $R_t$=0.83 min; MS (ESIpos): m/z=785 $(M+H)^+$.

Intermediate F297

S-{2-[{(1R)-1-[1-Benzyl-4-(2,5-difluorophenyl)-1H-pyrrol-2-yl]-2,2-dimethylpropyl}(pyrrolidin-3-ylmethyl)amino]-2-oxoethyl}-N-[6-(2,5-dioxo-2,5-dihydro-1H-pyrrol-1-yl)hexanoyl]-L-cysteine/trifluoroacetic Acid (1:1) (Isomer 1)

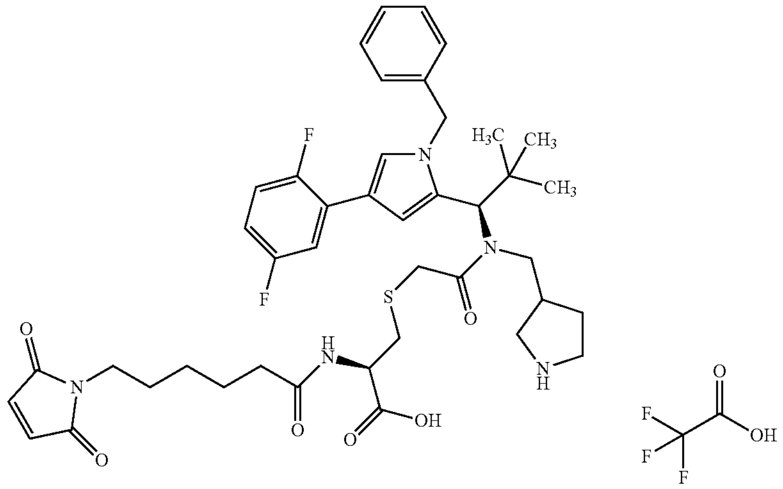 [SMILES: CC(C)(C)[C@H](c1cc(-c2cc(F)ccc2F)cn1Cc1ccccc1)N(CC1CCNC1)C(=O)CSC[C@H](NC(=O)CCCCCN1C(=O)C=CC1=O)C(=O)O ; O=C(O)C(F)(F)F]

Under argon, 15 mg (0.11 mmol) of zinc chloride were added to a solution of 36 mg (0.03 mmol, 68% pure) of S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Intermediate C92) in 0.74 ml of 2,2,2-trifluoroethanol, and the reaction mixture was stirred at 50° C. for 7 h. 32 mg (0.11 mmol) of EDTA were then added and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative HPLC. This gave 6.4 mg (25% of theory) of the title compound.

LC-MS (Method 1): $R_t$=0.95 min; MS (ESIpos): m/z=792 $(M+H-CF_3CO_2H)^+$.

Intermediate F298

S-{2-[{(1R)-1-[1-Benzyl-4-(2,5-difluorophenyl)-1H-pyrrol-2-yl]-2,2-dimethylpropyl}(pyrrolidin-3-ylmethyl)amino]-2-oxoethyl}-N-[6-(2,5-dioxo-2,5-dihydro-1H-pyrrol-1-yl)hexanoyl]-L-cysteine/trifluoroacetic Acid (1:1) (Isomer 2)

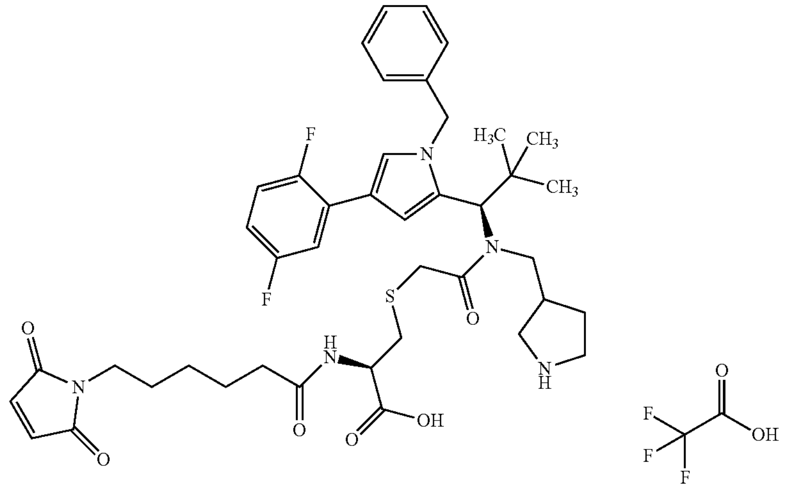 [SMILES: CC(C)(C)[C@H](c1cc(-c2cc(F)ccc2F)cn1Cc1ccccc1)N(CC1CCNC1)C(=O)CSC[C@H](NC(=O)CCCCCN1C(=O)C=CC1=O)C(=O)O ; O=C(O)C(F)(F)F]

Under argon, 19 mg (0.14 mmol) of zinc chloride were added to a solution of 45 mg (0.04 mmol, 71% pure) of S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Intermediate C91) in 0.94 ml of 2,2,2-trifluoroethanol, and the reaction mixture was stirred at 50° C. for 3 h. 42 mg (0.14 mmol) of EDTA were then added and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative HPLC. This gave 5.7 mg (18% of theory) of the title compound.

LC-MS (Method 1): $R_t$=0.96 min; MS (ESIpos): m/z=791 $(M+H-CF_3CO_2H)^+$.

Intermediate F299

S-(2-{(3-Aminopropyl) [(R)-[1-benzyl-4-(2,5-difluorophenyl)-1H-pyrrol-2-yl](cyclohexyl)methyl]amino}-2-oxoethyl)-N-[6-(2,5-dioxo-2,5-dihydro-1H-pyrrol-1-yl)hexanoyl]-L-cysteine/trifluoroacetic Acid (1:1)

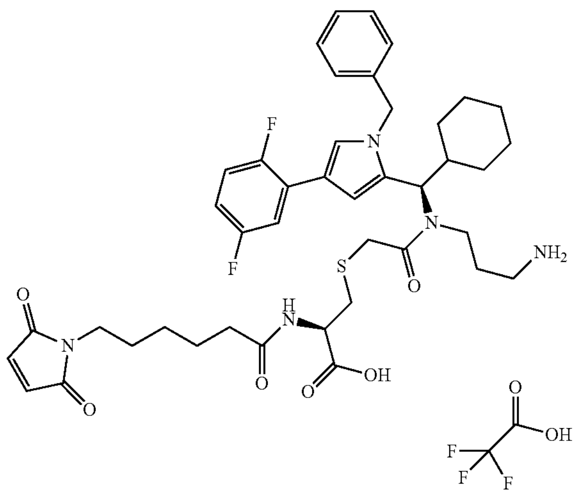 [SMILES: NCCCN(C(=O)CSC[C@H](NC(=O)CCCCCN1C(=O)C=CC1=O)C(=O)O)[C@@H](c1cc(-c2cc(F)ccc2F)cn1Cc1ccccc1)C1CCCCC1 ; O=C(O)C(F)(F)F]

To a solution of 88.0 mg (0.09 mmol) of S-{11-[(R)-[1-benzyl-4-(2,5-difluorophenyl)-1H-pyrrol-2-yl](cyclohexyl)methyl]-2,2-dimethyl-6,12-dioxo-5-oxa-7,11-diaza-2-silatridecan-13-yl}-N-[6-(2,5-dioxo-2,5-dihydro-1H-pyrrol-1-yl)hexanoyl]-L-cysteine (Intermediate C84) in 1.88 ml of 2,2,2-trifluoroethanol was added 76.8 mg (0.57 mmol) of zinc chloride and the reaction mixture was stirred at 50° C. for 3 h. 164.6 mg (0.57 mmol) of EDTA were then added and the mixture was stirred for 15 minutes. Ethyl acetate was added to the reaction mixture and the organic phase was washed repeatedly with water and with saturated NaCl solution. The organic phase was dried over sodium sulphate and the solvent was evaporated under reduced pressure. The residue was purified by preparative HPLC. This gave 31 mg (35% of theory) of the title compound.

LC-MS (Method 12): $R_t$=1.82 min; MS (ESIpos): m/z=792 $(M+H)^+$.

Intermediate F300

(2S)-2-Amino-4-[{(1R)-1-[1-benzyl-4-(2,5-difluorophenyl)-1H-pyrrol-2-yl]-2,2-dimethylpropyl}(glycoloyl)amino]-N-(2-{[(2R)-2-(2,5-dioxo-2,5-dihydro-1H-pyrrol-1-yl)propanoyl]amino}ethyl)butanamide

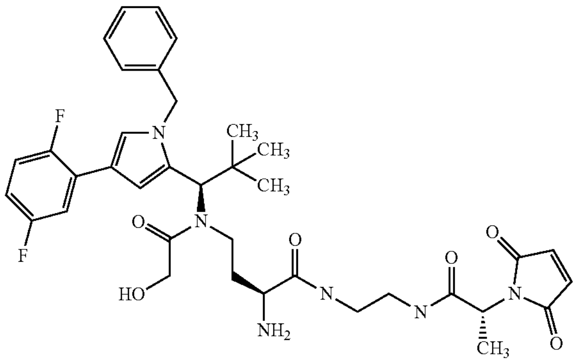 [SMILES: C[C@H](C(=O)NCCNC(=O)[C@@H](N)CCN(C(=O)CO)[C@@H](c1cc(-c2cc(F)ccc2F)cn1Cc1ccccc1)C(C)(C)C)N1C(=O)C=CC1=O]

To a solution of 7 mg (0.08 mmol) of 2-(trimethylsilyl)ethyl {(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2R)-2-(2,5-dioxo-2,5-dihydro-1H-pyrrol-1-yl)propanoyl]amino}ethyl)amino]-1-oxobutan-2-yl}carbamate (Intermediate C100) in 0.2 ml of 2,2,2-trifluoroethanol under argon were added 11 mg (0.08 mmol) of zinc chloride and the reaction mixture was stirred at 50° C. for 8 h. 14 mg (0.05 mmol) of EDTA were then added and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative HPLC. This gave 1.6 mg (27% of theory) of the title compound.

LC-MS (Method 1): $R_t$=0.88 min; MS (ESIpos): m/z=707 $(M+H-CF_3CO_2H)^+$.

Intermediate F302

S-{2-[{(1R)-1-[1-benzyl-4-(2,5-difluorophenyl)-1H-pyrrol-2-yl]-2,2-dimethylpropyl}(pyrrolidin-3-ylmethyl)amino]-2-oxoethyl}-N-[(2,5-dioxo-2,5-dihydro-1H-pyrrol-1-yl)acetyl]-L-cysteine trifluoroacetate (1:1) (Isomer 1)

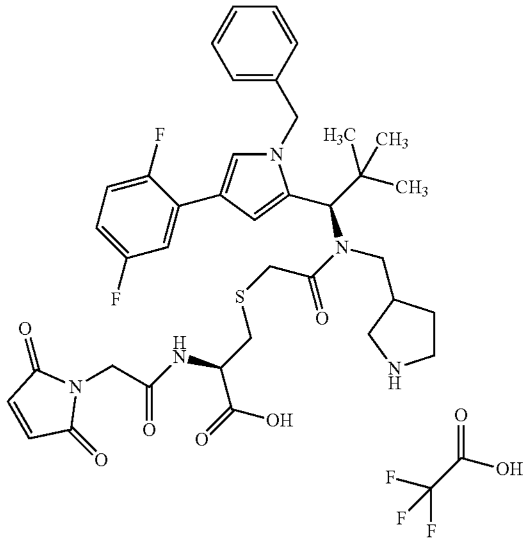 [SMILES: CC(C)(C)[C@H](c1cc(-c2cc(F)ccc2F)cn1Cc1ccccc1)N(CC1CCNC1)C(=O)CSC[C@H](NC(=O)CN1C(=O)C=CC1=O)C(=O)O ; O=C(O)C(F)(F)F]

To a mixture of 56.9 mg (58.2 mmol, 85% purity) of S-[2-({(1R)-1-[1-benzyl-4-(2,5-difluorophenyl)-1H-pyrrol-2-yl]-2,2-dimethylpropyl}{[(1-(tert-butoxycarbonyl)pyrrolidin-3-yl]methyl}amino)-2-oxoethyl]-N-[(2,5-dioxo-2,5-dihydro-1H-pyrrol-1-yl)acetyl]-L-cysteine (Intermediate C94) in 1.4 ml of 2,2,2-trifluoroethanol under argon were added 31.7 mg (0.23 mmol) of zinc chloride and the reaction mixture was stirred at 50° C. for 3 h. 68.0 mg (0.23 mmol) of EDTA were then added and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative HPLC. This gave 7 mg (13% of theory) of the title compound.

LC-MS (Method 1): $R_t$=0.91 min; MS (ESIpos): m/z=736 $(M+H-CF_3CO_2H)^+$.

Intermediate F305

N-{(1R)-1-[1-Benzyl-4-(2,5-difluorophenyl)-1H-pyrrol-2-yl]-2,2-dimethylpropyl}-22-(2,5-dioxo-2,5-dihydro-1H-pyrrol-1-yl)-6,17-dioxo-N-(pyrrolidin-3-ylmethyl)-10,13-dioxa-3-thia-7,16-diazadocosan-1-amide/trifluoroacetic Acid (1:1) (Isomer 2)

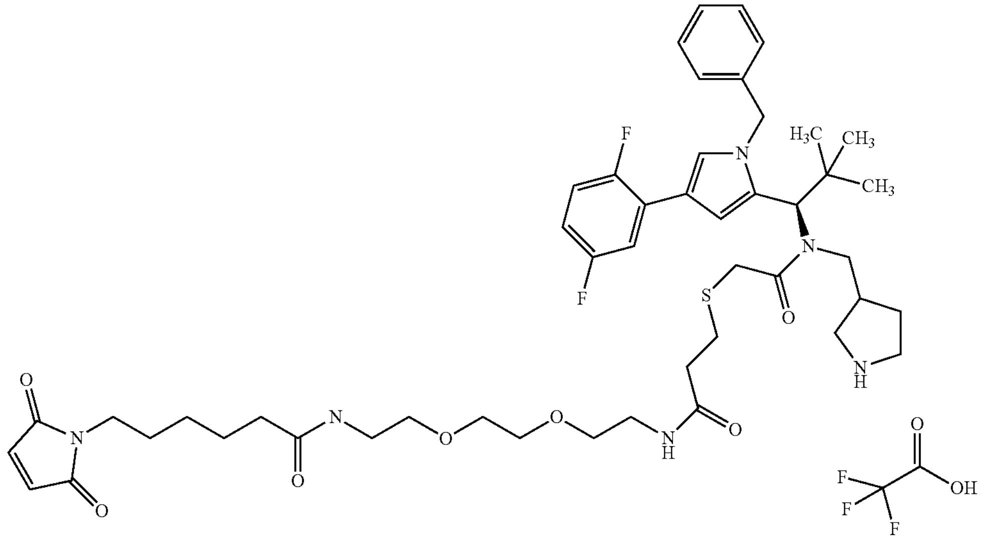 [SMILES: CC(C)(C)[C@H](c1cc(-c2cc(F)ccc2F)cn1Cc1ccccc1)N(CC1CCNC1)C(=O)CSCCC(=O)NCCOCCOCCNC(=O)CCCCCN1C(=O)C=CC1=O ; O=C(O)C(F)(F)F]

To a solution of 24.80 mg (0.02 mmol) of tert-butyl 3-[2-{(1R)-1-[1-benzyl-4-(2,5-difluorophenyl)-1H-pyrrol-2-yl]-2,2-dimethylpropyl}-24-(2,5-dioxo-2,5-dihydro-1H-pyrrol-1-yl)-3,8,19-trioxo-12,15-dioxa-5-thia-2,9,18-triazatetracos-1-yl]pyrrolidine-1-carboxylate (Intermediate C99) in 0.65 ml of 2,2,2-trifluoroethanol were added 13.42 mg (0.10 mmol) of zinc chloride and the reaction mixture was stirred at 50° C. for 8 h. 28.78 mg (0.10 mmol) of EDTA were then added and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative HPLC. This gave 10 mg (44% of theory) of the title compound.

LC-MS (Method 5): $R_t$=3.11 min; MS (ESIpos): m/z=907 $(M+H-CF_3CO_2H)^+$.

Intermediate F306

$N^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-N2-{N-[(2,5-dioxo-2,5-dihydro-1H-pyrrol-1-yl)acetyl]-L-valyl-L-alanyl-beta-alanyl}-L-lysine/trifluoroacetic Acid (1:1)

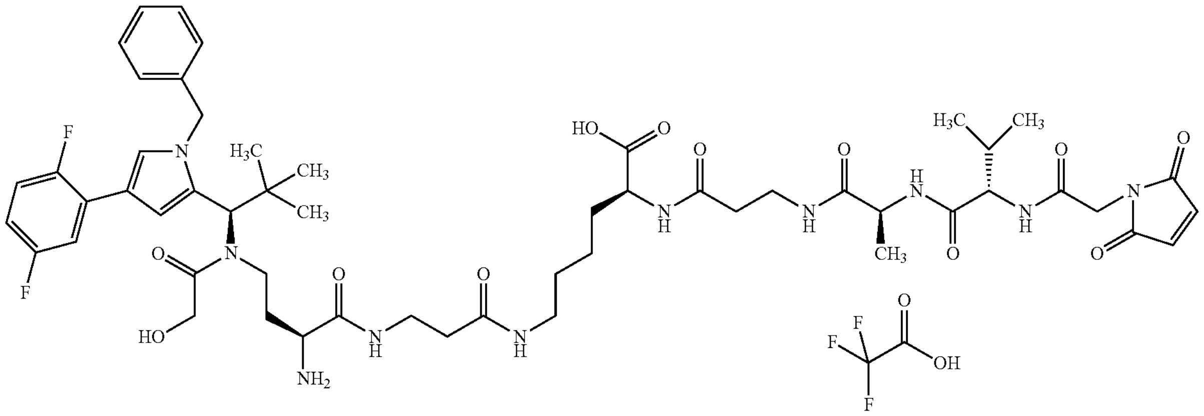

The title compound was prepared by coupling of 24 mg (0.029 mmol) of Intermediate C61 with 30 mg (0.035 mmol) of Intermediate L99 in the presence of 16.7 mg (0.044 mmol) of HATU and 15 μl of N,N-diisopropylethylamine and subsequent deprotection with zinc chloride in trifluoroethanol as described for Intermediate F119. Purification by preparative HPLC gave 19 mg (52% of theory over 2 steps) of the title compound.

LC-MS (Method 1): $R_t$=0.84 min; MS (ESIpos): m/z=1091 $(M+H)^+$.

Intermediate F307

N-[6-(2,5-Dioxo-2,5-dihydro-1H-pyrrol-1-yl)hexanoyl]-L-valyl-L-alanyl-S-{(5R,14R)-13-[(3-aminopropyl)-14-[1-benzyl-4-(2,5-difluorophenyl)-1H-pyrrol-2-yl]-5-carboxy-15,15-dimethyl-2,7,12-trioxo-10-thia-3,6,13-triazahexadec-1-yl}-L-cysteine/trifluoroacetic Acid (1:1)

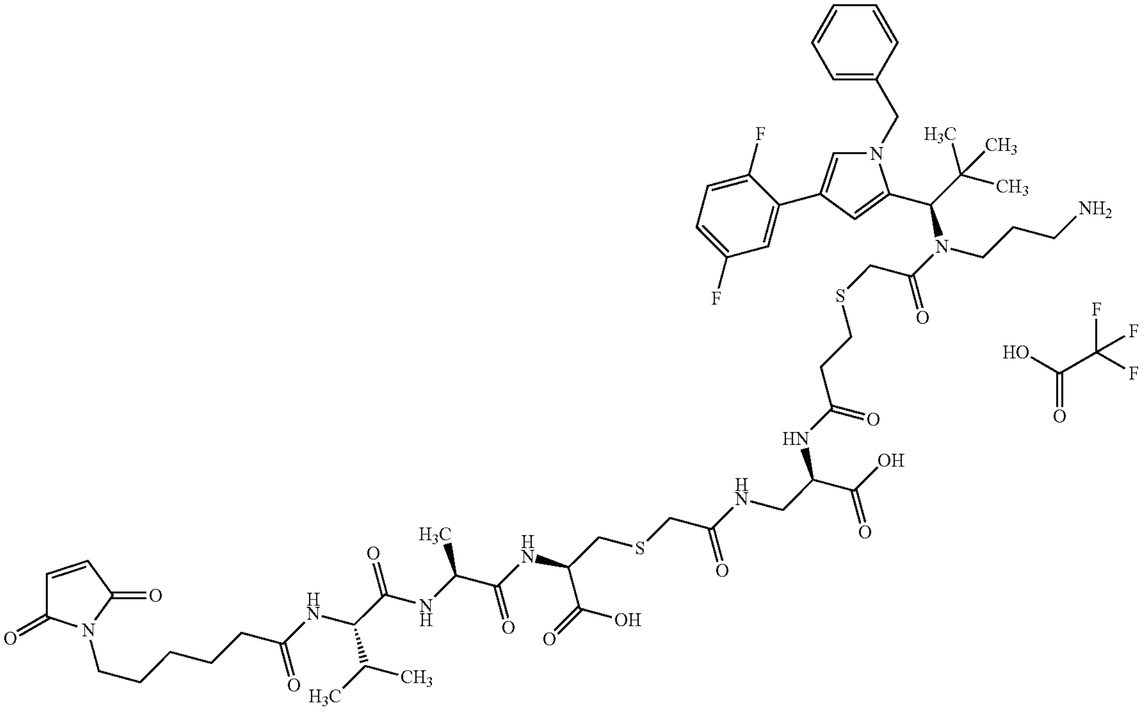 [SMILES: CC(C)[C@H](NC(=O)CCCCCN1C(=O)C=CC1=O)C(=O)N[C@@H](C)C(=O)N[C@@H](CSCC(=O)NC[C@@H](NC(=O)CCSCC(=O)N(CCCN)[C@@H](c1cc(-c2cc(F)ccc2F)cn1Cc1ccccc1)C(C)(C)C)C(=O)O)C(=O)O ; O=C(O)C(F)(F)F]

8.90 mg (8.88 μmol) of trifluoroacetic acid/2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1) (Intermediate C80) and 2.31 mg (9.77 μmol) of 1-(2-bromoacetoxy)pyrrolidine-2,5-dione were dissolved in 1 ml of dimethylformamide, and 2.9 μl (27 μmol) of N-methylmorpholine were added. The reaction mixture was stirred at RT for 1 h. The reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 5.80 mg (65% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate.

LC-MS (Method 1): $R_t$=1.57 min; MS (ESIpos): m/z=1008 $(M+H)^+$.

2-(Trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate (31.9 mg, 31.6 μmol) and L-cysteine (7.66 mg, 63.2 μmol) were dissolved in 3.0 ml of DMF and stirred at RT overnight. The reaction mixture was purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 28.1 mg (76% of theory) of the compound S-[(19R)-11-{(1R)-1-[1-benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine/trifluoroacetic acid (1:1).

LC-MS (Method 12): $R_t$=2.52 min; MS (ESIpos): m/z=1049 $[M+H]^+$

S-[(19R)-11-{(1R)-1-[1-Benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine/trifluoroacetic acid (1:1) (13.5 mg, 11.6 μmol) was dissolved in 1.0 ml of DMF, 2,5-dioxopyrrolidin-1-yl N-[6-(2,5-dioxo-2,5-dihydro-1H-pyrrol-1-yl)hexanoyl]-L-valyl-L-alaninate (6.76 mg, 11.6 μmol) (Intermediate L88) and N,N-diisopropylethylamine (4.0 μl, 23 μmol) were added and the mixture was stirred at RT for 1 h. The reaction mixture was purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 11.1 mg (68% of theory) of the compound N-[6-(2,5-dioxo-2,5-dihydro-1H-pyrrol-1-yl)hexanoyl]-L-valyl-L-alanyl-S-[(19R)-11-{(1R)-1-[1-benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine.

LC-MS (Method 14): $R_t$=7.38 min; MS (ESIpos): m/z=1412 $[M+H]^+$

N-[6-(2,5-Dioxo-2,5-dihydro-1H-pyrrol-1-yl)hexanoyl]-L-valyl-L-alanyl-S-[(19R)-11-{(1R)-1-[1-benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine (9.40 mg, 6.65 μmol) were dissolved in 2.0 ml of trifluoroethanol, and zinc dichloride (5.44 mg, 39.9 μmol) was added. The reaction mixture was stirred at 50° C. for 1 h. Zinc dichloride (5.44 mg, 39.9 μmol) was added and the reaction mixture was stirred at 50° C. for 1 h. Ethylendiamine-N,N,N',N'-tetraacetic acid (23.4 mg, 79.8 μmol) was added to the reaction mixture, which was stirred for 10 min, and then water (0.1% TFA) was added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 5.60 mg (66% of theory) of the title compound.

LC-MS (Method 1): $R_t$=0.93 min; MS (ESIpos): m/z=1168 $(M+H)^+$.

Intermediate F308

N-[6-(2,5-Dioxo-2,5-dihydro-1H-pyrrol-1-yl)hexanoyl]-L-valyl-N-[(12R,19R)-19-amino-4-{(1R)-1-[1-benzyl-4-(2,5-difluorophenyl)-1H-pyrrol-2-yl]-2,2-dimethylpropyl}-12,19-dicarboxy-5,10,15-trioxo-7,17-dithia-4,11,14-triazanonadec-1-yl]-L-alaninamide/trifluoroacetic Acid (1:1)

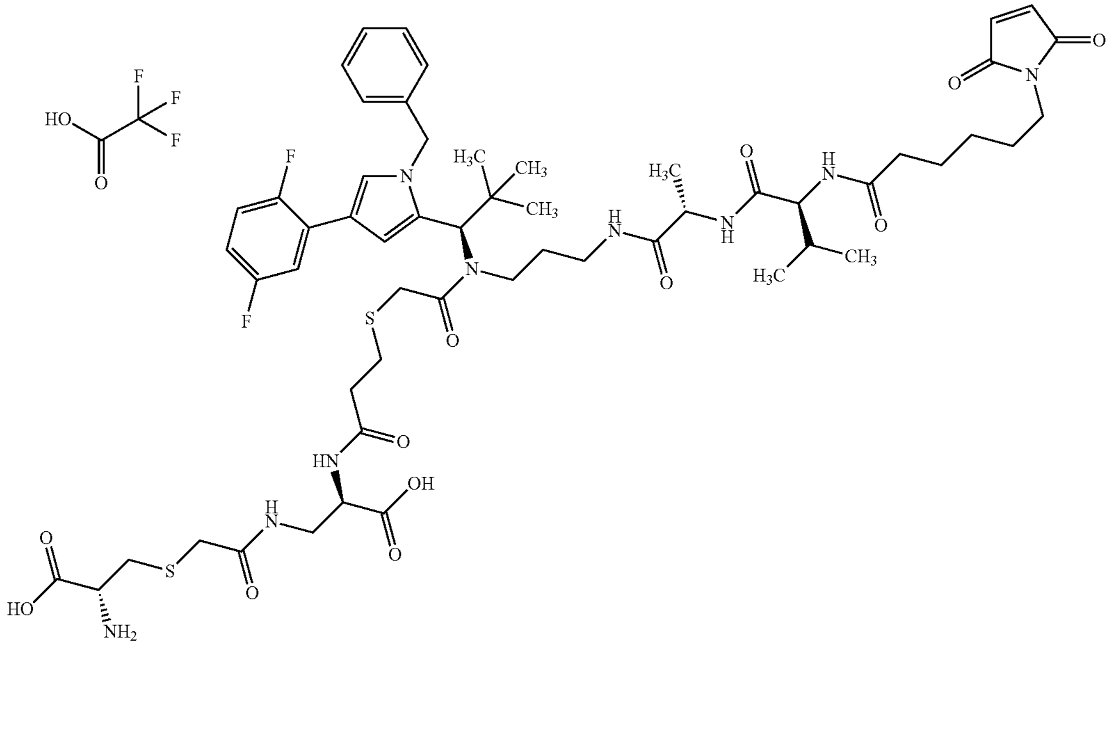 [SMILES: CC(C)[C@H](NC(=O)CCCCCN1C(=O)C=CC1=O)C(=O)N[C@@H](C)C(=O)NCCCN(C(=O)CSCCC(=O)N[C@H](CNC(=O)CSC[C@H](N)C(=O)O)C(=O)O)[C@@H](c1cc(-c2cc(F)ccc2F)cn1Cc1ccccc1)C(C)(C)C ; O=C(O)C(F)(F)F]

N-[3-({2-[(3-Aminopropyl) {(1R)-1-[1-benzyl-4-(2,5-difluorophenyl)-1H-pyrrol-2-yl]-2,2-dimethylpropyl}amino]-2-oxoethyl}sulphanyl)propanoyl]-3-[(bromoacetyl)amino]-D-alanine/trifluoroacetic acid (1:1) (12.7 mg, 14.5 μmol) and N-{[2-(trimethylsilyl)ethoxy]carbonyl}-L-cysteine (3.84 mg, 14.5 μmol) were dissolved in 1.5 ml of DMF and stirred at RT overnight. Then N,N-diisopropylethylamine (2.5 μl, 14 μmol) was added. The reaction mixture was stirred at RT for 3 h and then water (0.1% TFA) was added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 7.40 mg (48% of theory) of the compound S-{(5R,14R)-13-(3-aminopropyl)-14-[1-benzyl-4-(2,5-difluorophenyl)-1H-pyrrol-2-yl]-5-carboxy-15,15-dimethyl-2,7,12-trioxo-10-thia-3,6,13-triazahexadec-1-yl}-N-{[2-(trimethylsilyl)ethoxy]carbonyl}-L-cysteine/trifluoroacetic acid (1:1).

LC-MS (Method 1): $R_t$=1.03 min; MS (ESIpos): m/z=949 $[M+H]^+$

S-{(5R,14R)-13-(3-Aminopropyl)-14-[1-benzyl-4-(2,5-difluorophenyl)-1H-pyrrol-2-yl]-5-carboxy-15,15-dimethyl-2,7,12-trioxo-10-thia-3,6,13-triazahexadec-1-yl}-N-{[2-(trimethylsilyl)ethoxy]carbonyl}-L-cysteine/trifluoroacetic acid (1:1) (7.50 mg, 7.05 μmol) was dissolved in 1.0 ml of DMF, and 2,5-dioxopyrrolidin-1-yl N-[6-(2,5-dioxo-2,5-dihydro-1H-pyrrol-1-yl)hexanoyl]-L-valyl-L-alaninate (4.11 mg, 82% purity, 7.05 μmol) (Intermediate L88) and N,N-diisopropylethylamine (2.5 μl, 14 μmol) were added. The reaction mixture was stirred at RT for 1 h and then purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 4.30 mg (46%) of the compound N-[6-(2,5-dioxo-2,5-dihydro-1H-pyrrol-1-yl)hexanoyl]-L-valyl-N-[(8R,15R)-23-{(1R)-1-[1-benzyl-4-(2,5-difluorophenyl)-1H-pyrrol-2-yl]-2,2-dimethylpropyl}-8,15-dicarboxy-2,2-dimethyl-6,12,17,22-tetraoxo-5-oxa-10,20-dithia-7,13,16,23-tetraaza-2-silahexacosan-26-yl]-L-alaninamide.

LC-MS (Method 14): $R_t$=6.47 min; MS (ESIpos): m/z=1312 $[M+H]^+$

N-[6-(2,5-Dioxo-2,5-dihydro-1H-pyrrol-1-yl)hexanoyl]-L-valyl-N-[(8R,15R)-23-{(1R)-1-[1-benzyl-4-(2,5-difluorophenyl)-1H-pyrrol-2-yl]-2,2-dimethylpropyl}-8,15-dicarboxy-2,2-dimethyl-6,12,17,22-tetraoxo-5-oxa-10,20-dithia-7,13,16,23-tetraaza-2-silahexacosan-26-yl]-L-alaninamide (4.00 mg, 3.05 μmol) were dissolved in 1.0 ml of trifluoroethanol, and zinc dichloride (2.49 mg, 18.3 μmol) was added. The reaction mixture was stirred at 50° C. for 1 h and then ethylendiamine-N,N,N',N'-tetraacetic acid (5.34 mg, 18.3 μmol) was added thereto, the reaction mixture was stirred for 10 min, and then water (0.1% TFA) was added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 2.50 mg (64% of theory) of the title compound.

LC-MS (Method 1): $R_t$=1.00 min; MS (ESIpos): m/z=1168 $[M+H]^+$

Intermediate F309

4-{[(11R,17R)-16-(3-Aminopropyl)-17-[1-benzyl-4-(2,5-difluorophenyl)-1H-pyrrol-2-yl]-1-(2,5-dioxo-2,5-dihydro-1H-pyrrol-1-yl)-18,18-dimethyl-6,6-dioxido-2,10,15-trioxo-6lambda$^6$,13-dithia-3,9,16-triazanonadecan-11-yl]amino}-4-oxobutanoic Acid/Trifluoroacetic Acid (1:1)

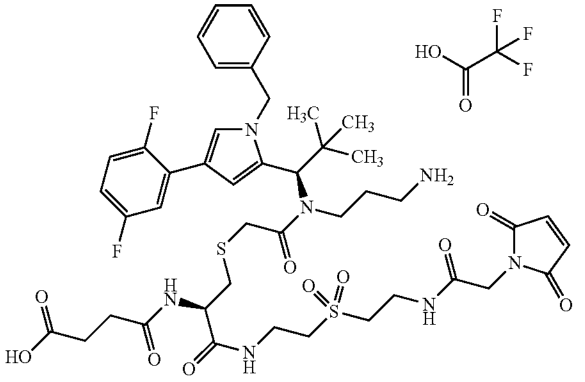 [SMILES: CC(C)(C)[C@H](c1cc(-c2cc(F)ccc2F)cn1Cc1ccccc1)N(CCCN)C(=O)CSC[C@H](NC(=O)CCC(=O)O)C(=O)NCCS(=O)(=O)CCNC(=O)CN1C(=O)C=CC1=O ; O=C(O)C(F)(F)F]

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (50.0 mg, 57.3 μmol) (Intermediate C77) and trifluoroacetic acid/benzyl {2-[(2-aminoethyl)sulphonyl]ethyl}carbamate (1:1) (27.5 mg, 68.7 μmol) (Intermediate L81) were initially charged in 4.0 ml of DMF, and HATU (26.1 mg, 68.7 μmol) and N,N-diisopropylethylamine (30 μl, 170 μmol) were added. The reaction mixture was stirred at RT for 10 min and then purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 53.9 mg (81%) of the compound tert-butyl 4-{[(12R)-17-{(1R)-1-[1-benzyl-4-(2,5-difluorophenyl)-1H-pyrrol-2-yl]-2,2-dimethylpropyl}26,26-dimethyl-7,7-dioxido-3,11,16,22-tetraoxo-1-phenyl-2,23-dioxa-7lambda6,14-dithia-4,10,17,21-tetraaza-26-silaheptacosan-12-yl]amino}-4-oxobutanoate.

LC-MS (Method 1): $R_t$=1.54 min; MS (ESIpos): m/z=1141 $[M+H]^+$

Under argon, palladium(II) acetate (5.12 mg, 22.8 μmol) was initially charged in 3.0 ml of DCM, triethylamine (9.5 μl, 68 μmol) and triethylsilane (73 μl, 460 μmol) were added and the mixture was stirred for 5 min. Then tert-butyl 4-{[(12R)-17-{(1R)-1-[1-benzyl-4-(2,5-difluorophenyl)-1H-pyrrol-2-yl]-2,2-dimethylpropyl}26,26-dimethyl-7,7-dioxido-3,11,16,22-tetraoxo-1-phenyl-2,23-dioxa-7lambda$^6$,14-dithia-4,10,17,21-tetraaza-26-silaheptacosan-12-yl]amino}-4-oxobutanoate (52.1 mg, 45.6 μmol) in 2.0 ml of DCM were added. The reaction mixture was stirred at RT overnight and then admixed with 2.0 ml of water. The solvents were evaporated under reduced pressure. Acetonitrile was added to the residue, and the mixture was filtered and purified by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 43.4 mg (85%) of the compound trifluoroacetic acid/tert-butyl 4-{[(16R)-23-{(1R)-1-[1-benzyl-4-(2,5-difluorophenyl)-1H-pyrrol-2-yl]-2,2-dimethylpropyl}-2,2-dimethyl-21,21-dioxido-6,12,17-trioxo-5-oxa-14,21lambda6-dithia-7,11,18-triaza-2-silatricosan-16-yl]amino}-4-oxobutanoate (1:1).

LC-MS (Method 1): $R_t$=1.21 min; MS (ESIpos): m/z=1007 $[M+H]^+$

Trifluoroacetic acid/tert-butyl 4-{[(16R)-23-amino-11-{(1R)-1-[1-benzyl-4-(2,5-difluorophenyl)-1H-pyrrol-2-yl]-2,2-dimethylpropyl}-2,2-dimethyl-21,21-dioxido-6,12,17-trioxo-5-oxa-14,21lambda$^6$-dithia-7,11,18-triaza-2-silatricosan-16-yl]amino}-4-oxobutanoate (1:1) (20.0 mg, 17.8 μmol) and (2,5-dioxo-2,5-dihydro-1H-pyrrol-1-yl)acetic acid (3.32 mg, 21.4 μmol) were initially charged in 2.0 ml of DMF, and HATU (8.14 mg, 21.4 μmol) and N,N-diisopropylethylamine (9.3 μl, 54 μmol) were added.

The reaction mixture was stirred at RT for 10 min. The reaction mixture was purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 17.4 mg (85%) of the compound tert-butyl 4-{[(16R)-11-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-2,2-dimethyl-21,21-dioxido-6,12,17,25-tetraoxo-5-oxa-14,21lambda6-dithia-7,11,18,24-tetraaza-2-silahexacosan-16-yl]amino}-4-oxobutanoate.

LC-MS (Method 1): $R_t$=1.46 min; MS (ESIpos): m/z=1144 $[M+H]^+$ tert-Butyl 4-{[(16R)-11-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-2,2-dimethyl-21,21-dioxido-6,12,17,25-tetraoxo-5-oxa-14,21lambda$^6$-dithia-7,11,18,24-tetraaza-2-silahexacosan-16-yl]amino}-4-oxobutanoate (15.9 mg, 13.9 μmol) was dissolved in 2.0 ml of trifluoroethanol, and zinc dichloride (11.4 mg, 83.4 μmol) was added. The reaction mixture was stirred at 50° C. for 1 h. Zinc dichloride (11.4 mg, 83.4 μmol) was added and the reaction mixture was stirred at 50° C. for 1 h. Zinc dichloride (11.4 mg, 83.4 μmol) was added and the reaction mixture was stirred at 50° C. for 1 h. Ethylenediamine-N,N,N',N'-tetraacetic acid (73.2 mg, 250 μmol) was added to the reaction mixture, which was stirred for 10 min, and then water (0.1% TFA) was added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 10 mg (68% of theory) of the title compound.

LC-MS (Method 12): $R_t$=1.45 min; MS (ESIpos): m/z=944 $[M+H]^+$

Intermediate F310

Trifluoroacetic Acid/N-[(8R,14R)-13-(3-aminopropyl)-14-[1-benzyl-4-(2,5-difluorophenyl)-1H-pyrrol-2-yl]-1-(2,5-dioxo-2,5-dihydro-1H-pyrrol-1-yl)-15,15-dimethyl-2,7,12-trioxo-10-thia-3,6,13-triazahexadecan-8-yl]-2,5,8,11-tetraoxatetradecan-14-amide (1:1)

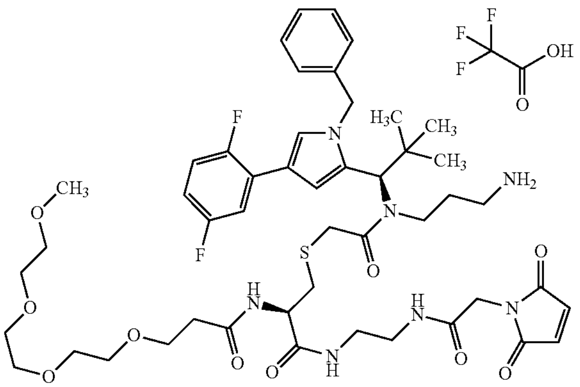 [SMILES: COCCOCCOCCOCCC(=O)N[C@@H](CSCC(=O)N(CCCN)[C@@H](c1cc(-c2cc(F)ccc2F)cn1Cc1ccccc1)C(C)(C)C)C(=O)NCCNC(=O)CN1C(=O)C=CC1=O ; O=C(O)C(F)(F)F]

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (100 mg, 120 μmol) (Intermediate C70) and 1-[(14-oxo-2,5,8,11-tetraoxatetradecan-14-yl)oxy]pyrrolidine-2,5-dione (44.1 mg, 132 μmol) were initially charged in 3.0 ml of DMF, and 4-methylmorpholine (40 μl, 360 μmol) was added. The reaction mixture was stirred at RT overnight, quenched with acetic acid (420 μmol) and purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 69.4 mg (62% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(14-oxo-2,5,8,11-tetraoxatetradecan-14-yl)-L-cysteine.

LC-MS (Method 12): $R_t$=2.61 min; MS (ESIneg): m/z=933 $[M-H]^-$

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(14-oxo-2,5,8,11-tetraoxatetradecan-14-yl)-L-cysteine (27.0 mg, 28.9 μmol) was initially charged in 2.0 ml of DMF, and N-(2-aminoethyl)-2-(2,5-dioxo-2,5-dihydro-1H-pyrrol-1-yl)acetamide (11.4 mg, 57.7 μmol) (Intermediate L1), N,N-diisopropylethylamine (15 μl, 87 μmol) and HATU (22.0 mg, 57.7 μmol) were added. The reaction mixture was stirred at RT for 3 h and purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 13.7 mg (43% of theory) of the compound 2-(trimethylsilyl)ethyl {(16R)-21-{(1R)-1-[1-benzyl-4-(2,5-difluorophenyl)-1H-pyrrol-2-yl]-2,2-dimethylpropyl}-16-[(2-{[(2,5-dioxo-2,5-dihydro-1H-pyrrol-1-yl)acetyl]amino}ethyl)carbamoyl]-14,20-dioxo-2,5,8,11-tetraoxa-18-thia-15,21-diazatetracosan-24-yl}carbamate.

LC-MS (Method 12): $R_t$=2.54 min; MS (ESIpos): m/z=1114 [M+H]$^+$ 2-(Trimethylsilyl)ethyl {(16R)-21-{(1R)-1-[1-benzyl-4-(2,5-difluorophenyl)-1H-pyrrol-2-yl]-2,2-dimethylpropyl}-16-[(2-{[(2,5-dioxo-2,5-dihydro-1H-pyrrol-1-yl)acetyl]amino}ethyl)carbamoyl]-14,20-dioxo-2,5,8,11-tetraoxa-18-thia-15,21-diazatetracosan-24-yl}carbamate (13.7 mg, 12.3 μmol) was dissolved in 2.0 ml of trifluoroethanol, and zinc dichloride (10.1 mg, 73.8 μmol) was added. The reaction mixture was stirred at 50° C. for 4 h. Ethylendiamine-N,N,N',N'-tetraacetic acid (21.6 mg, 73.8 μmol) was added to the reaction mixture, which was stirred for 10 min, and then water (0.1% TFA) was added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 7.30 mg (47% of theory) of the title compound.

LC-MS (Method 1): $R_t$=1.01 min; MS (ESIpos): m/z=970 [M+H]$^+$

Intermediate F311

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,30-dioxo-6,9,12,15,18,21,24,27-octaoxa-3-azatriacontan-30-yl]-L-cysteine/trifluoroacetic Acid (1:1)

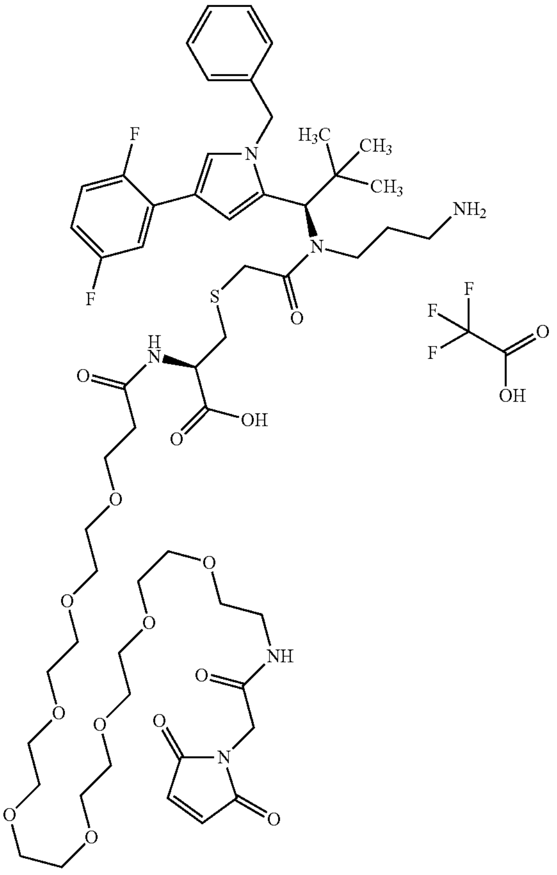 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCOCCOCCOCCOCCNC(=O)CN1C(=O)C=CC1=O)C(=O)O ; O=C(O)C(F)(F)F]

1-(2,5-Dioxo-2,5-dihydro-1H-pyrrol-1-yl)-2-oxo-6,9,12,15,18,21,24,27-octaoxa-3-azatriacontan-30-oic acid (10.8 mg, 18.7 μmol) (Intermediate L97) was initially charged in 1.0 ml of DMF, N,N-diisopropylethylamine (5.4 μl, 31.2 μmol) and HATU (7.10 mg, 18.7 μmol) were added and the mixture was stirred for 10 min. Then S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (12.9 mg, 15.6 μmol) (Intermediate C71) was added, dissolved in 1.0 ml of DMF and N,N-diisopropylethylamine (2.7 μl, 15.6 μmol). The reaction mixture was stirred at RT for 2 h and then purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 3.5 mg (18%) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,30-dioxo-6,9,12,15,18,21,24,27-octaoxa-3-azatriacontan-30-yl]-L-cysteine.

LC-MS (Method 1): $R_t$=1.30 min; MS (ESIneg): m/z=1276 [M−H]$^-$

S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,30-dioxo-6,9,12,15,18,21,24,27-octaoxa-3-azatriacontan-30-yl]-L-cysteine (3.50 mg, 2.74 μmol) was dissolved in 1.0 ml of trifluoroethanol, and zinc dichloride (6.25 mg, 16.4 μmol) was added. The reaction mixture was stirred at 50° C. for 4 h. Ethylenediamine-N,N,N',N'-tetraacetic acid (47 μl, 16 μmol) was added to the reaction mixture, which was stirred for 10 min, and then water (0.1% TFA) was added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 2.0 mg (59% of theory) of the title compound.

LC-MS (Method 1): $R_t$=0.94 min; MS (ESIpos): m/z=1133 (M+H)$^+$.

Intermediate F312

N-[(2,5-Dioxo-2,5-dihydro-1H-pyrrol-1-yl)acetyl]-L-valyl-N-{(2S)-4-[{(1R)-1-[1-benzyl-4-(2,5-difluorophenyl)-1H-pyrrol-2-yl]-2,2-dimethylpropyl}(glycoloyl)amino]-1-{[2-(L-gamma-glutamylamino)ethyl]amino}-1-oxobutan-2-yl]-L-alaninamide/trifluoroacetic Acid (1:1)

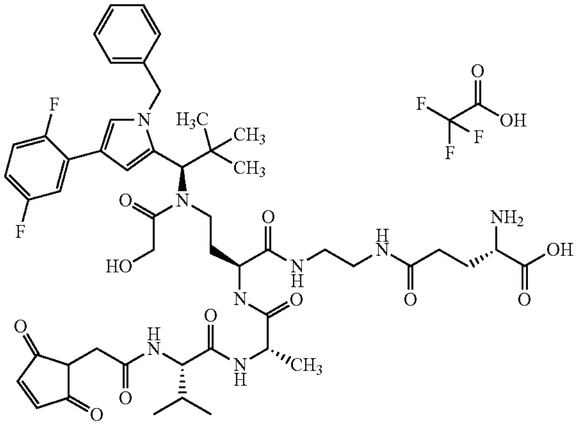 [SMILES: CC(C)[C@H](NC(=O)CC1C(=O)C=CC1=O)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)NCCNC(=O)CC[C@H](N)C(=O)O ; O=C(O)C(F)(F)F]

The title compound was prepared from Intermediate C103 by coupling with N-[(benzyloxy)carbonyl]-L-valyl-L-alanine in the presence of HATU and N,N-diisopropylethylamine. In the next step, the Z protective group was removed by hydrogenation over 10% palladium on activated carbon in DCM/methanol 1:1 at RT under hydrogen standard pressure for 1 hour. The deprotected intermediate was then converted by coupling with (2,5-dioxo-2,5-dihydro-1H-pyrrol-1-yl)acetic acid in the presence of HATU and N,N-diisopropylethylamine and finally by deprotection with zinc chloride and by preparative HPLC to the title compound.

LC-MS (Method 1): $R_t$=0.9 min; MS (ESIpos): m/z=992 $(M+H)^+$.

Intermediate F313

S-[2-({(1R)-1-[1-Benzyl-4-(2,5-difluorophenyl)-1H-pyrrol-2-yl]-2,2-dimethylpropyl}{[(3R,4R)-4-fluoro-pyrrolidin-3-yl]methyl}amino)-2-oxoethyl]-N-[1-(2,5-dioxo-2,5-dihydro-1H-pyrrol-1-yl)-2,18-dioxo-6,9,12,15-tetraoxa-3-azaoctadecan-18-yl]-L-cysteine/trifluoroacetic Acid (1:1)

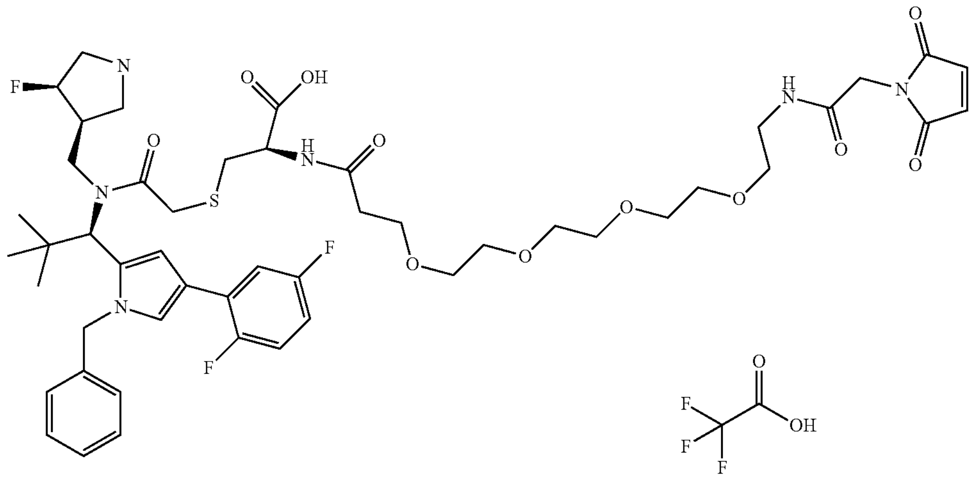 [SMILES: CC(C)(C)[C@H](c1cc(-c2cc(F)ccc2F)cn1Cc1ccccc1)N(C[C@@H]1CNC[C@@H]1F)C(=O)CSC[C@H](NC(=O)CCOCCOCCOCCOCCNC(=O)CN1C(=O)C=CC1=O)C(=O)O ; O=C(O)C(F)(F)F]

To a solution of 55.0 mg (0.14 mmol) of 1-(2,5-dioxo-2,5-dihydro-1H-pyrrol-1-yl)-2-oxo-6,9,12,15-tetraoxa-3-azaoctadecan-18-oic acid in 2.60 ml of DMF under argon were added 16.9 mg (0.13 mmol) of N,N-diisopropylethylamine and 50.0 mg (0.13 mmol) of HATU. The reaction mixture was stirred at RT for 10 minutes. Subsequently, a solution of 40.0 mg (0.05 mmol) of S-[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-L-cysteine (Intermediate C107) was added and the mixture was stirred at RT overnight. Water was added and the mixture was extracted with dichloromethane. The organic phase was dried over magnesium sulphate, the solvent was evaporated under reduced pressure and the residue was dried under high vacuum. The residue was purified by preparative HPLC. This gave 10 mg (13% of theory, 82% purity) of the title compound.

LC-MS (Method 1): $R_t$=1.36 min; MS (ESIpos): m/z=1145 $(M+H)^+$.

To a solution of 10.9 mg (7.8 mmol, 82% purity) of S-[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-N-[1-(2,5-dioxo-2,5-dihydro-1H-pyrrol-1-yl)-2,18-dioxo-6,9,12,15-tetraoxa-3-azaoctadecan-18-yl]-L-cysteine in 0.85 ml of 2,2,2-trifluoroethanol were added 4.3 mg (0.03 mmol) of zinc chloride and the reaction mixture was stirred at 50° C. for 2.5 h. 9.1 mg (0.03 mmol) of EDTA were then added and the mixture was stirred for 15 minutes. The reaction mixture was purified by preparative HPLC. This gave 2.3 mg (26% of theory) of the title compound.

LC-MS (Method 1): $R_t$ 0.89 min; MS (ESIpos): m/z=781 $(M+H-CF_3CO_2H)^+$.

Intermediate F314

Trifluoroacetic Acid/3-{[2-({(1R)-1-[1-benzyl-4-(2,5-difluorophenyl)-1H-pyrrol-2-yl]-2,2-dimethylpropyl}{[(3 S,4R)-4-fluoropyrrolidin-3-yl]methyl}amino)-2-oxoethyl]sulphanyl}-N-(2-{[(2,5-dioxo-2,5-dihydro-1H-pyrrol-1-yl)acetyl]amino}ethyl)propanamide

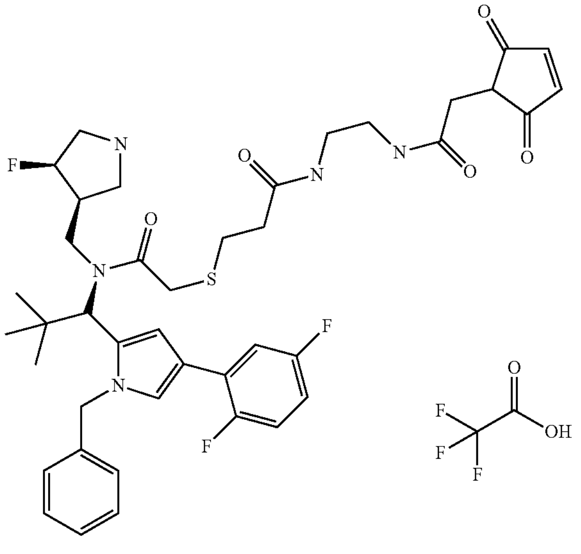

To a solution of 50.0 mg (0.04 mmol) of 3-{[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]sulphanyl}propanoic acid (Intermediate 106) in 3.14 ml of DMF under argon were added 16.89 mg (0.13 mmol) of N,N-diisopropylethylamine and 33.13 mg (0.087 mmol) of HATU. The reaction mixture was stirred at RT for 10 minutes. Subsequently, a solution of 27.29 mg (0.09 mmol) of N-(2-aminoethyl)-2-(2,5-dioxo-2,5-dihydro-1H-pyrrol-1-yl)acetamide-trifluoroacetic acid (1:1) (Intermediate L1) was added, and the mixture was stirred at RT for 15 minutes. Water was added and the mixture was extracted with dichloromethane. The organic phase was dried over magnesium sulphate, the solvent was evaporated under reduced pressure and the residue was dried under high vacuum. The residue was purified by preparative HPLC. This gave 41 mg (68% of theory, 66% purity) of the title compound.

LC-MS (Method 12): $R_t$=2.55 min; MS (ESIneg): m/z=959 $(M-H+Na)^-$.

To a solution of 41.1 mg (0.03 mmol, 66% purity) of 2-(trimethylsilyl)ethyl (3R,4R)-3-[2-{(1R)-1-[1-benzyl-4-(2,5-difluorophenyl)-1H-pyrrol-2-yl]-2,2-dimethylpropyl}-14-(2,5-dioxo-2,5-dihydro-1H-pyrrol-1-yl)-3,8,13-trioxo-5-thia-2,9,12-triazatetradec-1-yl]-4-fluoropyrrolidine-1-carboxylate in 2.54 ml of 2,2,2-trifluoroethanol were added 24.7 mg (0.18 mmol) of zinc chloride, and the reaction mixture was stirred at 50° C. for 2.5 h. 53.0 mg (0.18 mmol) of EDTA were then added and the mixture was stirred for 15 minutes. The reaction mixture was purified by preparative HPLC. This gave 10 mg (36% of theory) of the title compound.

LC-MS (Method 1): $R_t$ 0.89 min; MS (ESIpos): m/z=781 $(M+H-CF_3CO_2H)^+$.

Intermediate F315

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-{3-[5-(2-{[(2,5-dioxo-2,5-dihydro-1H-pyrrol-1-yl)acetyl]amino}ethyl)-1,2,4-oxadiazol-3-yl]propanoyl}-L-cysteine

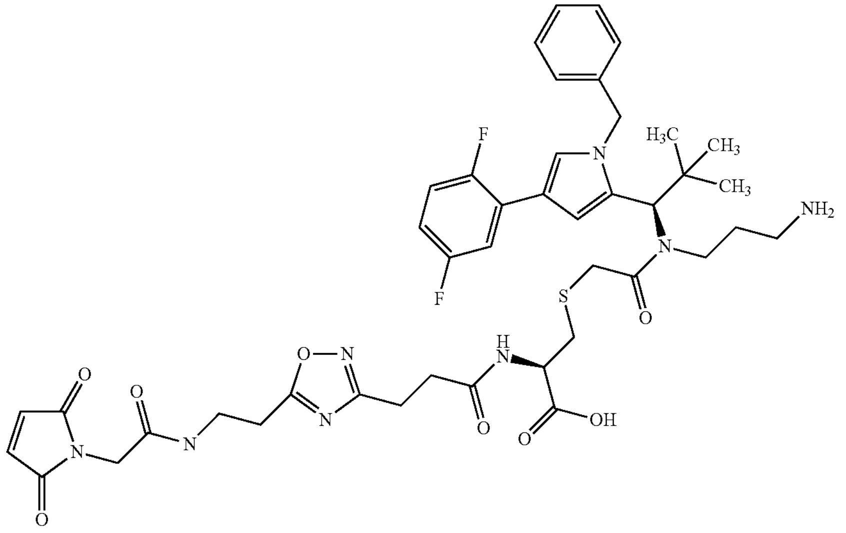 [SMILES: CC(C)(C)[C@H](c1cc(-c2cc(F)ccc2F)cn1Cc1ccccc1)N(CCCN)C(=O)CSC[C@H](NC(=O)CCc1noc(CCNC(=O)CN2C(=O)C=CC2=O)n1)C(=O)O]

To a solution of 50.0 mg (0.07 mmol) of 3-[5-(2-{[(2,5-dioxo-2,5-dihydro-1H-pyrrol-1-yl)acetyl]amino}ethyl)-1,2,4-oxadiazol-3-yl]propanoic acid (Intermediate L100) in 3.5 ml of DMF under argon were added 18.02 mg (0.14 mmol) of N,N-diisopropylethylamine and 31.82 mg (0.09 mmol) of HATU. The reaction mixture was stirred at RT for 10 minutes. Subsequently, a solution of 50.0 mg (0.07 mmol) of N-(2-aminoethyl)-6-(2,5-dioxo-2,5-dihydro-1H-pyrrol-1-yl)hexanamide acetate (1:1) (Intermediate C107) was added, and the mixture was stirred at RT for 2 h. Water was added and the mixture was extracted with dichloromethane. The organic phase was dried over magnesium sulphate, the solvent was evaporated under reduced pressure and the residue was dried under high vacuum. The residue was used further without purification. This gave 49 mg (21% of theory, 31% purity) of the title compound.

LC-MS (Method 1): $R_t$=1.30 min; MS (ESIpos): m/z=1022 (M+H)$^+$.

To a solution of 49.0 mg (0.015 mmol, 31% purity) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[5-(2-{[(2,5-dioxo-2,5-dihydro-1H-pyrrol-1-yl)acetyl]amino}ethyl)-1,2,4-oxadiazol-3-yl]propanoyl}-L-cysteine in 0.5 ml of 2,2,2-trifluoroethanol was added 8.0 mg (0.06 mmol) of zinc chloride and the reaction mixture was stirred at 50° C. for 2 h. 17.2 mg (0.06 mmol) of EDTA were then added and the mixture was stirred for 15 minutes. The reaction mixture was purified by preparative HPLC. This gave 3 mg (21% of theory) of the title compound.

LC-MS (Method 1): $R_t$=0.91 min; MS (ESIpos): m/z=877 (M+H-CF$_3$CO$_2$H)$^+$.

Intermediate F316

Trifluoroacetic Acid/N-{2-[(3-{[2-({(1R)-1-[1-benzyl-4-(2,5-difluorophenyl)-1H-pyrrol-2-yl]-2,2-dimethylpropyl}{[(3S,4R)-4-fluoropyrrolidin-3-yl]methyl}amino)-2-oxoethyl]sulphanyl}propanoyl)amino]ethyl}-6-(2,5-dioxo-2,5-dihydro-1H-pyrrol-1-yl)hexanamide (1:1)

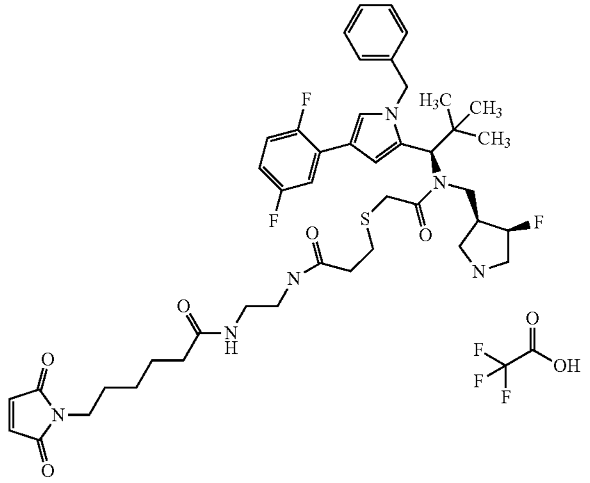 [SMILES: CC(C)(C)[C@H](c1cc(-c2cc(F)ccc2F)cn1Cc1ccccc1)N(C[C@@H]1CNC[C@@H]1F)C(=O)CSCCC(=O)NCCNC(=O)CCCCCN1C(=O)C=CC1=O ; O=C(O)C(F)(F)F]

To a solution of 50.0 mg (0.04 mmol, 65% purity) of 3-{[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]sulphanyl}propanoic acid (Intermediate 106) in 3.0 ml of DMF under argon were added 16.89 mg (0.13 mmol) of N,N-diisopropylethylamine and 33.13 mg (0.087 mmol) of HATU. The reaction mixture was stirred at RT for 10 minutes. Subsequently, a solution of 37.2 mg (0.09 mmol, 70% purity) of N-(2-aminoethyl)-6-(2,5-dioxo-2,5-dihydro-1H-pyrrol-1-yl)hexanamide acetate (1:1) (Intermediate L73) was added, and the mixture was stirred at RT for 7 minutes. Water was added and the mixture was extracted with dichloromethane. The organic phase was dried over magnesium sulphate, the solvent was evaporated under reduced pressure and the residue was dried under high vacuum. The residue was used further without purification. This gave 57 mg (77% of theory, 59% purity) of the title compound.

LC-MS (Method 12): $R_t$=2.60 min; MS (ESIpos): m/z=981 (M+H)$^+$.

To a solution of 56.0 mg (0.03 mmol, 59% purity) of 2-(trimethylsilyl)ethyl (3R,4R)-3-[2-{(1R)-1-[1-benzyl-4-(2,5-difluorophenyl)-1H-pyrrol-2-yl]-2,2-dimethylpropyl}-18-(2,5-dioxo-2,5-dihydro-1H-pyrrol-1-yl)-3,8,13-trioxo-5-thia-2,9,12-triazaoctadec-1-yl]-4-fluoropyrrolidine-1-carboxylate in 2.8 ml of 2,2,2-trifluoroethanol were added 36.0 mg (0.27 mmol) of zinc chloride, and the reaction mixture was stirred at 50° C. for 2 h. 78.3 mg (0.27 mmol) of EDTA were then added and the mixture was stirred for 15 minutes. The reaction mixture was purified by preparative HPLC. This gave 16 mg (44% of theory, 85% purity) of the title compound.

LC-MS (Method 1): $R_t$=0.89 min; MS (ESIpos): m/z=837 (M+H-AcOH)$^+$.

General Method for Synthesis of the APDC or ADC Precursors (Intermediate Series O)

The above-described intermediates of the F series (F1-F305) can be converted to the APDC precursor Q according to Scheme 1. In the case of release of the N-terminal amino group of the legumain-cleavable tripeptide in the APDC precursor molecule, this can be modified in the last step with substituted acyl radicals or alkyl radicals of various structures to improve the profile of properties.

An illustrative method is described here:

0.037 mmol of a suitable intermediate F1-F305 excluding F194 and F294 or a suitably protected precursor thereof is taken up in 1-20 ml, preferably 5-10 ml, of a suitable solvent, for example DMF, DMSO, DCM, chloroform, toluene, THF, methanol or a mixture thereof, and 0.039 mmol of an N-terminally modified tripeptide derivative, for example Intermediate L92, is added, as are 0.041 mmol of a standard coupling reagent, for example HATU, EDCI/HOBT, BEP etc., and 0.11 mmol of a standard base, for example N,N-diisopropylethylamine, triethylamine, 4-methylmorpholine etc. After stirring at RT for 5 min, the mixture is acidified with 2 drops of trifluoroacetic acid and concentrated. The residue is purified by preparative HPLC. The appropriate fractions are concentrated under reduced pressure and the residue is lyophilized from acetonitrile/water.

When said N-terminal modification of the attached tripeptide derivative is a protecting group, this can subsequently, just like any protecting group still present in the precursor molecule, be detached by known methods, for example a Z protecting group preferably by means of hydrogenolysis, a Boc protecting group by means of acid hydrolysis, an Fmoc protecting group by base hydrolysis or a Teoc group by means of fluorides or with zinc chloride.

Finally, the amino group thus released can be acylated or alkylated to improve the profile of properties, for example with amine-reactive groups such as active esters, acid chlorides, isocyanates, etc., or by coupling with carboxylic acid derivatives in the presence of a standard coupling reagent, for example HATU, EDCI/HOBT, BEP etc., and of a standard base, for example N,N-diisopropylethylamine, triethylamine, 4-methylmorpholine etc. If they are still present, further protecting groups in the molecule may be removed in a last step.

Scheme 1:
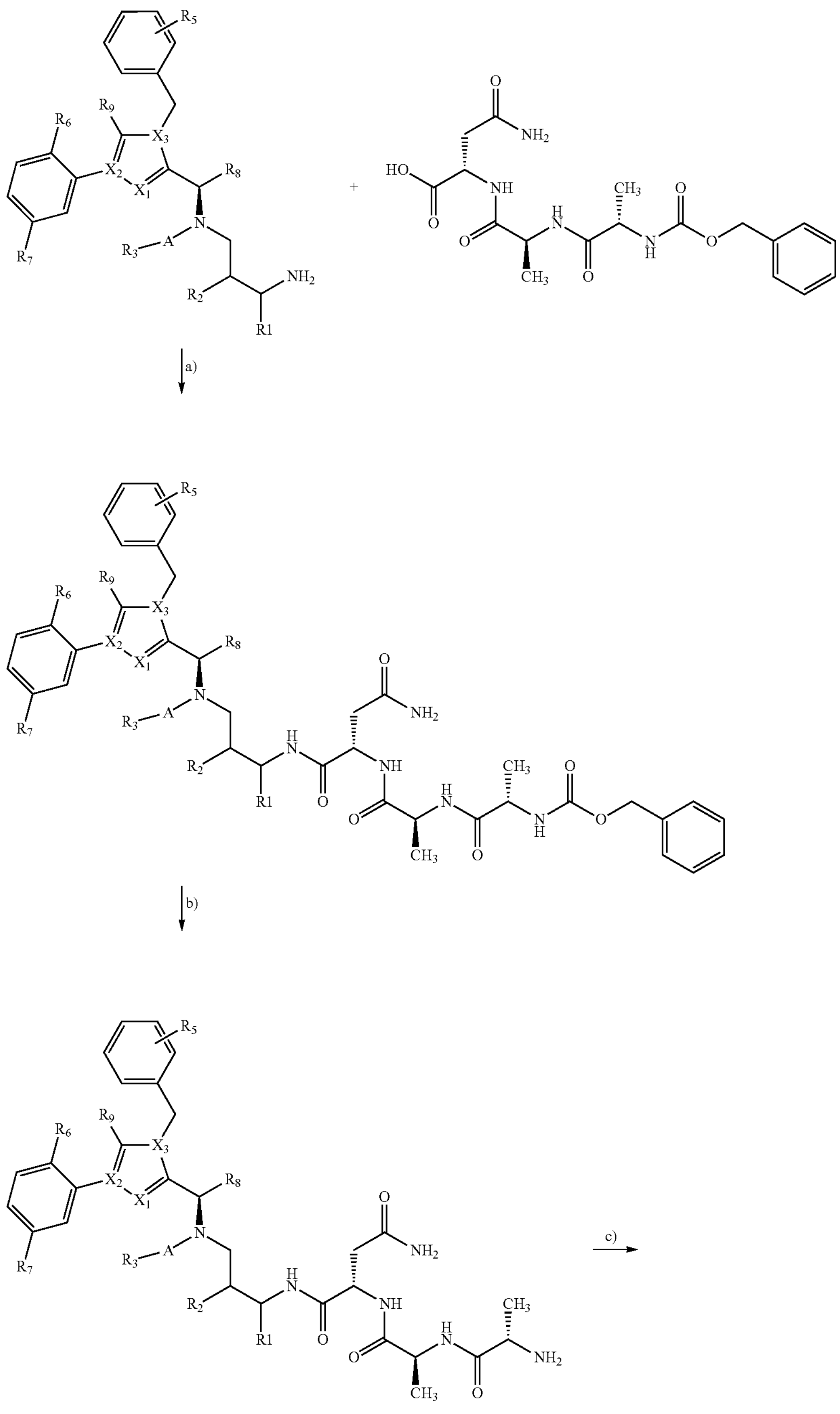

-continued

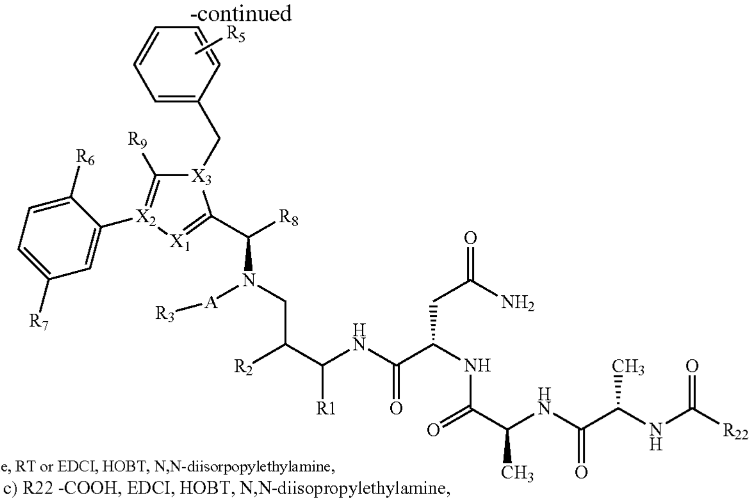

[a]: HATU, DMF, N,N-diisopropylethylamine, RT or EDCI, HOBT, N,N-diisorpopylethylamine, DMF, RT b) $H_2$, 10% Pd—C, MeOH, RT; c) R22 -COOH, EDCI, HOBT, N,N-diisopropylethylamine, DMF, RT or $R^{22}$ -COOH, HATU, N,N-diisopropylethylamine, DMF, RT or $R^{22}$ -COOSu, N,N-diisoproylethylamine, DMF, RT]

In addition, other intermediates according to Schemes 2 and 3 can be converted to legumain-cleavable ADC precursors.

Scheme 2:

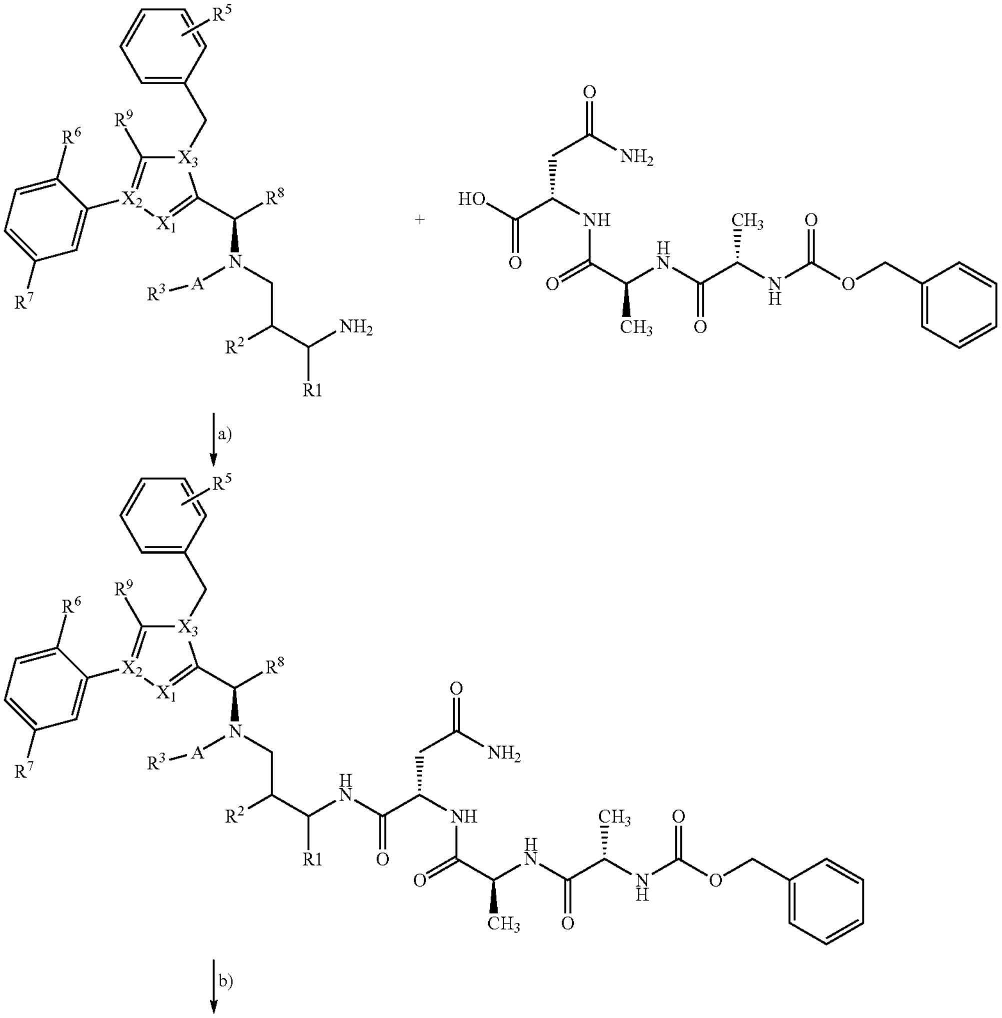

-continued
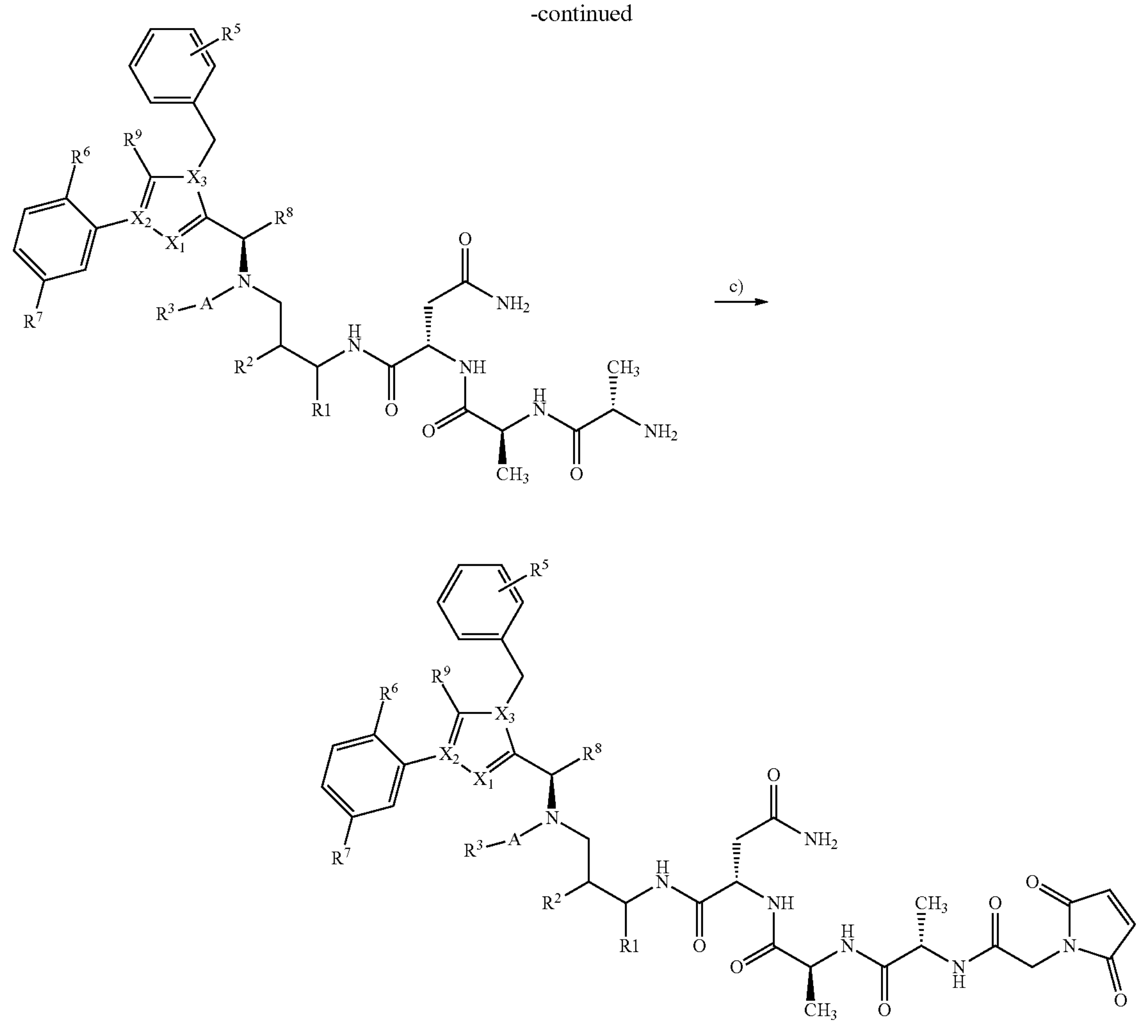
[a): HATU, DMF, N,N-diisopropylethylamine, RT or EDCl, HOBT, N,N-diisorpopylethylamine, DMF, RT b) $H_2$, 10% Pd—C, MeOH, RT; c) 1,1′-[(1,5-dioxopentane-1,5-diyl)bis(oxy)]dipyrrolidine-2,5-dione, N,N-diisopropylethylamine, DMF, RT]
Scheme 3:
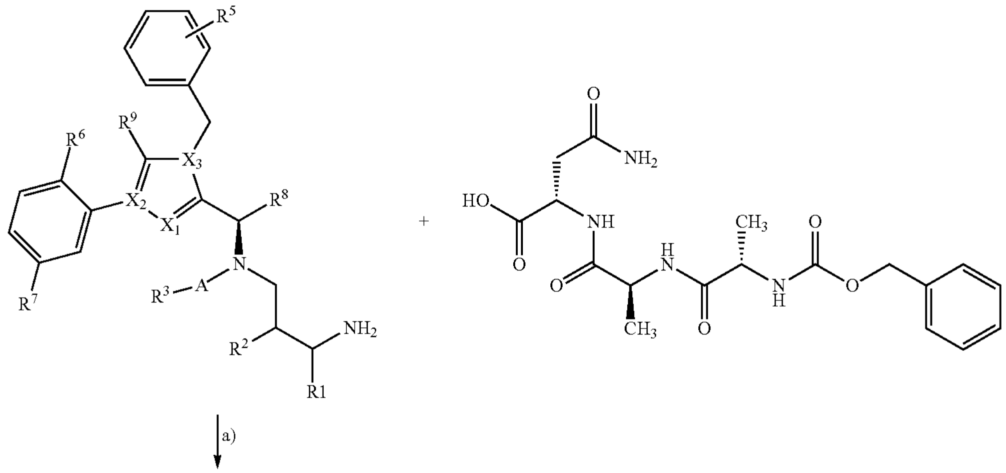

-continued
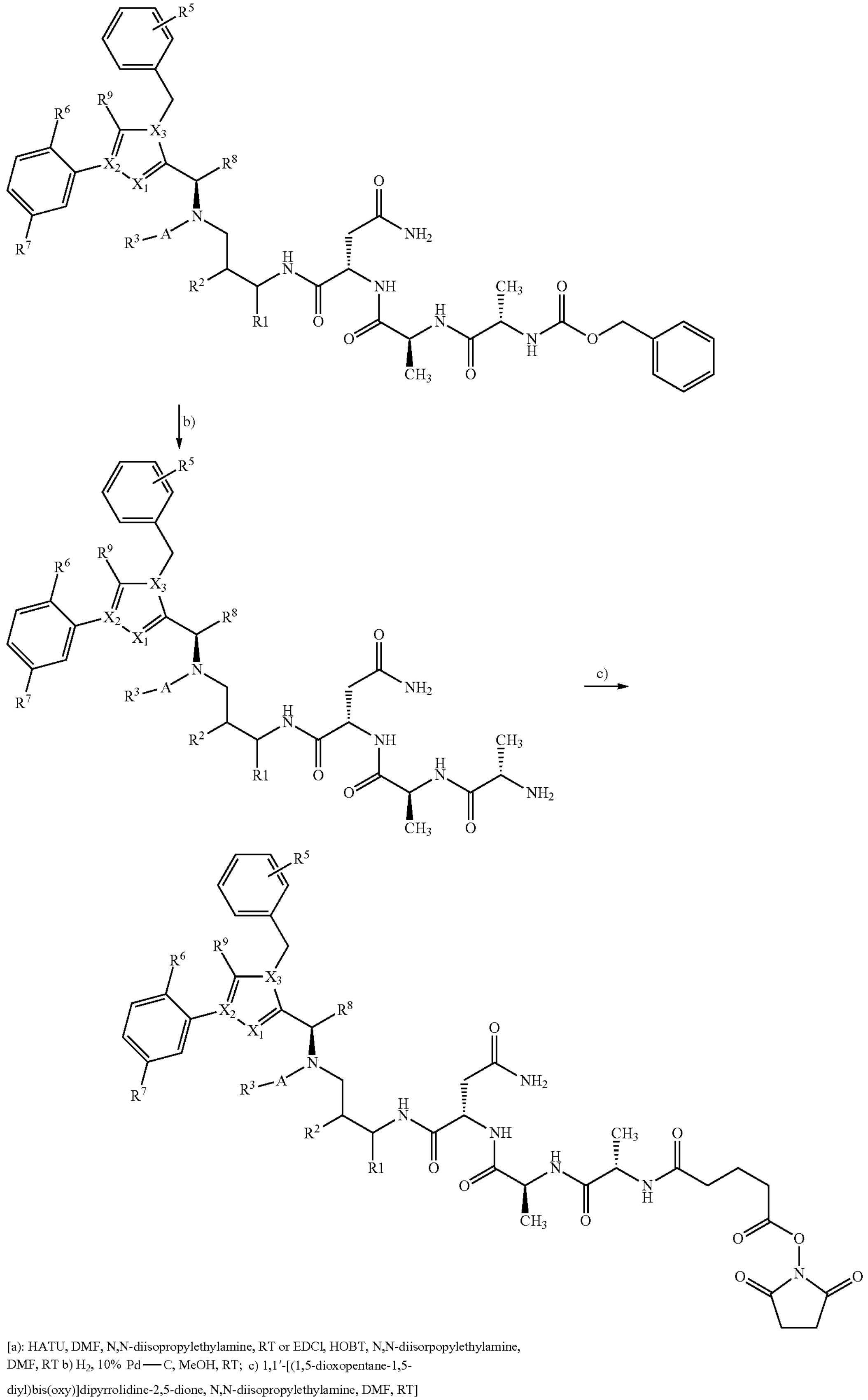
[a): HATU, DMF, N,N-diisopropylethylamine, RT or EDCl, HOBT, N,N-diisorpopylethylamine, DMF, RT b) $H_2$, 10% Pd—C, MeOH, RT; c) 1,1′-[(1,5-dioxopentane-1,5-diyl)bis(oxy)]dipyrrolidine-2,5-dione, N,N-diisopropylethylamine, DMF, RT]

As an alternative to the benzyloxycarbonyl group shown in Schemes 1-3, it is possible to use other protecting groups established in peptide chemistry and attach them by corresponding methods that are likewise known. The selection of the protecting group strategy is made according to requirements known to those skilled in the art relating to compatibility with other structural elements that occur in the molecule. If they are still present, further protecting groups in the molecule may be removed in a last step.

The syntheses may also optionally be rearranged in terms of their sequence.

In addition, the protein-reactive group in the context of the linker structures L1-L2 may be varied within the scope of the claims.

Intermediate Q1

N-[(Benzyloxy)carbonyl]-L-alanyl-L-alanyl-N[1]-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[-(2,5-dioxo-2,5-dihydro-1H-pyrrol-1-yl)acetyl]amino}ethyl)amino]-1-oxobutan-2-yl}-L-aspartamide

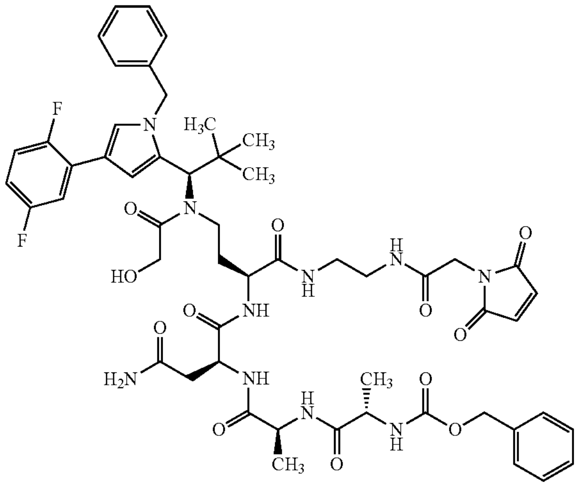 [SMILES: C[C@H](NC(=O)OCc1ccccc1)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

30 mg (0.037 mmol) of Intermediate F104 were taken up in 6 ml of DMF, and 16 mg (0.039 mmol) of Intermediate L92, 15.5 mg (0.041 mmol) of HATU and 0.11 mmol of N,N-diisopropylethylamine were added. After stirring at RT for 5 min, the mixture was acidified with 2 drops of trifluoroacetic acid and concentrated. The residue was purified by preparative HPLC. The appropriate fractions were concentrated and the residue was lyophilized from acetonitrile/water.

This gave 21.5 mg (53% of theory) of the title compound.

LC-MS (Method 1): $R_t$=1.08 min; MS (ESIpos): m/z=1083 $(M+H)^+$.

Intermediate Q2

N-Acetyl-L-alanyl-L-alanyl-N[1]-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[-(2,5-dioxo-2,5-dihydro-1H-pyrrol-1-yl)acetyl]amino}ethyl)amino]-1-oxobutan-2-yl}-L-aspartamide

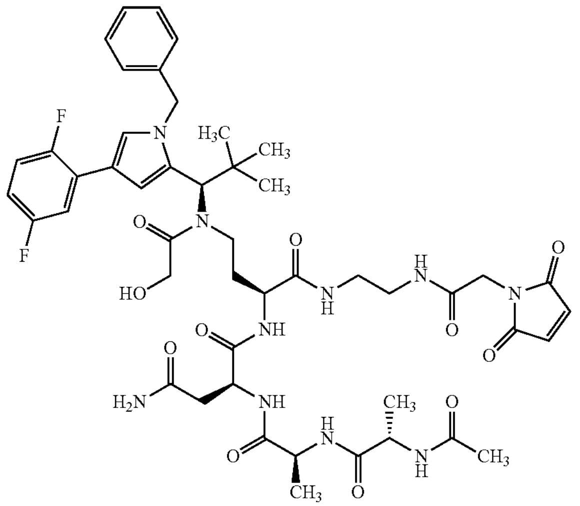 [SMILES: CC(=O)N[C@@H](C)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

30 mg (0.037 mmol) of Intermediate F104 were taken up in 6 ml of DMF, and 14 mg (0.045 mmol) of Intermediate L93, 15.5 mg (0.041 mmol) of HATU and 0.112 mmol of N,N-diisopropylethylamine were added. After stirring at RT for 5 min, another 1.5 mg of HATU and 0.01 mmol of N,N-diisopropylethylamine were added and the mixture was stirred at RT for a further 10 min. Then the mixture was acidified with 2 drops of trifluoroacetic acid and concentrated under reduced pressure. The residue was purified by preparative HPLC. The appropriate fractions were concentrated and the residue was lyophilized from acetonitrile/water. This gave 12.2 mg (33% of theory) of the title compound.

LC-MS (Method 1): $R_t$=0.94 min; MS (ESIpos): m/z=991 $(M+H)^+$.

Intermediate Q3

N-(3-Carboxypropanoyl)-L-alanyl-L-alanyl-N[1]-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[-(2,5-dioxo-2,5-dihydro-1H-pyrrol-1-yl)acetyl]amino}ethyl)amino]-1-oxobutan-2-yl}-L-aspartamide

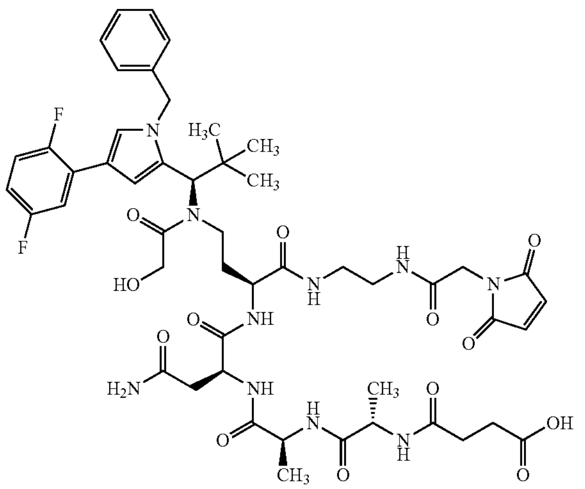 [SMILES: C[C@H](NC(=O)CCC(=O)O)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

15 mg (0.019 mmol) of Intermediate F104 were taken up in 5 ml of DMF, and 9.7 mg (0.02 mmol) of Intermediate L94, 8.5 mg (0.022 mmol) of HATU and 0.056 mol of N,N-diisopropylethylamine were added, and the mixture was stirred at RT for 5 min. Then the mixture was concentrated under reduced pressure, and the residue was purified by preparative HPLC. The appropriate fractions were concentrated and the residue was lyophilized from acetonitrile/water. This gave 5.7 mg (27% of theory) of the title compound.

LC-MS (Method 1): $R_t$=1.17 min; MS (ESIpos): m/z=1149 $(M+H)^+$.

This intermediate was dissolved in 2 ml of 2,2,2-trifluoroethanol. 2.6 mg (0.019 mmol) of zinc chloride were added, and the mixture was stirred at 50° C. for 45 min. Subsequently, 5.6 mg (0.019 mmol) of ethylenediamine-N,N,N',N'-tetraacetic acid were added, and the mixture was diluted with 3 ml of acetonitrile/water 9:1. Then 10 µl of trifluoroacetic acid were added, and the mixture was stirred at RT for 10 min and then concentrated under reduced pressure. The residue was purified by preparative HPLC. Concentration of the appropriate fractions and lyophilization of the residue from acetonitrile/water gave 3.1 mg (62% of theory) of the title compound.

LC-MS (Method 1): $R_t$=0.93 min; MS (ESIpos): m/z=1049 $(M+H)^+$.

Intermediate Q4

Trifluoroacetic Acid/N-[(benzyloxy)carbonyl]-L-alanyl-L-alanyl-N[1]-[(11S,15R)-15-[1-benzyl-4-(2,5-difluorophenyl)-1H-pyrrol-2-yl]-1-(2,5-dioxo-2,5-dihydro-1H-pyrrol-1-yl)-14-glycoloyl-16,16-dimethyl-6,6-dioxido-2,10-dioxo-6lambda$^6$-thia-3,9,14-triazaheptadecan-11-yl]-L-aspartamide (1:1)

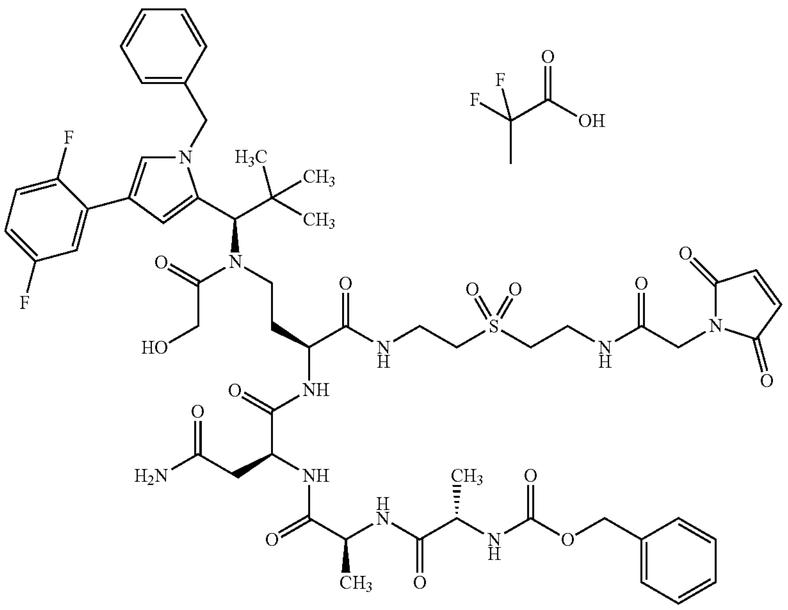

5 mg (0.006 mmol) of Intermediate F296 were taken up in 3 ml of DMF, and 2.8 mg (0.007 mmol) of Intermediate L92 were added, as were 2.3 mg (0.006 mmol) of HATU and 0.017 mmol of N,N-diisopropylethylamine. After stirring at RT for 15 min, the mixture was acidified with 2 drops of trifluoroacetic acid and concentrated. The residue was purified by preparative HPLC. The appropriate fractions were concentrated and the residue was lyophilized from acetonitrile/water. This gave 0.93 mg (13% of theory) of the title compound.

LC-MS (Method 1): $R_t$=1.07 min; MS (ESIpos): m/z=1175 $(M+H)^+$.

Intermediate Q5

N-[(2,5-Dioxo-2,5-dihydro-1H-pyrrol-1-yl)acetyl]-L-alanyl-L-alanyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-aspartamide

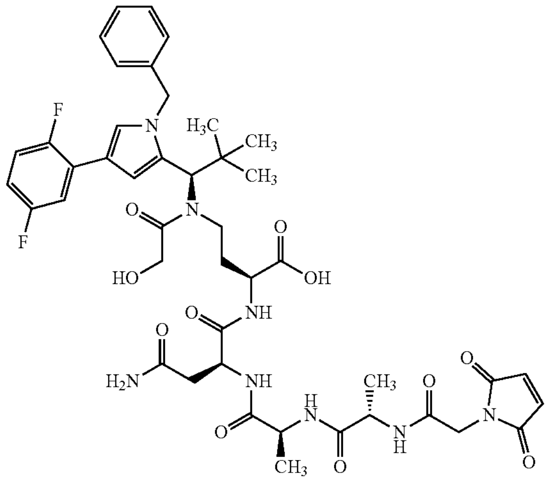 [SMILES: C[C@H](NC(=O)CN1C(=O)C=CC1=O)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)O]

55 mg of the mixture in Intermediate C101 were taken up in 33 ml of DMF, and 27.5 mg (0.067 mmol) of Intermediate L92 were added, as were 28 mg (0.073 mmol) of HATU and 32 μl of N,N-diisopropylethylamine. After 10 min of stirring at RT, the reaction was concentrated and the residue was purified by preparative HPLC.

The crude product thus obtained was initially charged in 4 ml of THF, and 2 ml of water and 0.375 ml of a 2M lithium hydroxide solution were added. The mixture was stirred at RT for 1 h and then neutralized with 1 N hydrochloric acid and concentrated under reduced pressure. The residue was purified by preparative HPLC. The appropriate fractions were concentrated and the residue was lyophilized from acetonitrile/water. 10.2 mg of N-[(benzyloxy)carbonyl]-L-alanyl-L-alanyl-N1-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-aspartamide were obtained.

LC-MS (Method 1): $R_t$=1.09 min; MS (ESIpos): m/z=904 $(M+H)^+$.

In the next step, the Z protecting group was removed by hydrogenation over 10% palladium on activated carbon in methanol at RT under standard hydrogen pressure for 1 hour, and 7.5 mg (87% of theory) of L-alanyl-L-alanyl-N1-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-aspartamide were thus obtained.

LC-MS (Method 1): $R_t$=0.80 min; MS (ESIpos): m/z=770 $(M+H)^+$.

3.75 mg (0.005 mmol) of L-alanyl-L-alanyl-$N^1$-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-aspartamide were taken up in 4 ml of DMF, and 1.72 mg (0.007 mmol) of 1-{2-[(2,5-dioxopyrrolidin-1-yl)oxy]-2-oxoethyl}-1H-pyrrole-2,5-dione and 1.2 μl (0.007 mmol) of N,N-diisopropylethylamine were added. The reaction mixture was stirred at RT for 1 h, then concentrated under reduced pressure, and the residue was purified by preparative RP-HPLC (column: Reprosil 250×30; 10μ, flow rate: 50 ml/min, MeCN/water). The solvents were evaporated under reduced pressure and the residue was dried under high vacuum. This gave 1.3 mg (29% of theory) of the title compound.

LC-MS (Method 1): $R_t$=1.03 min; MS (ESIpos): m/z=907 $(M+H)^+$.

Intermediate Q6

N-{5-[(2,5-Dioxopyrrolidin-1-yl)oxy]-5-oxopentanoyl}-L-alanyl-L-alanyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-aspartamide

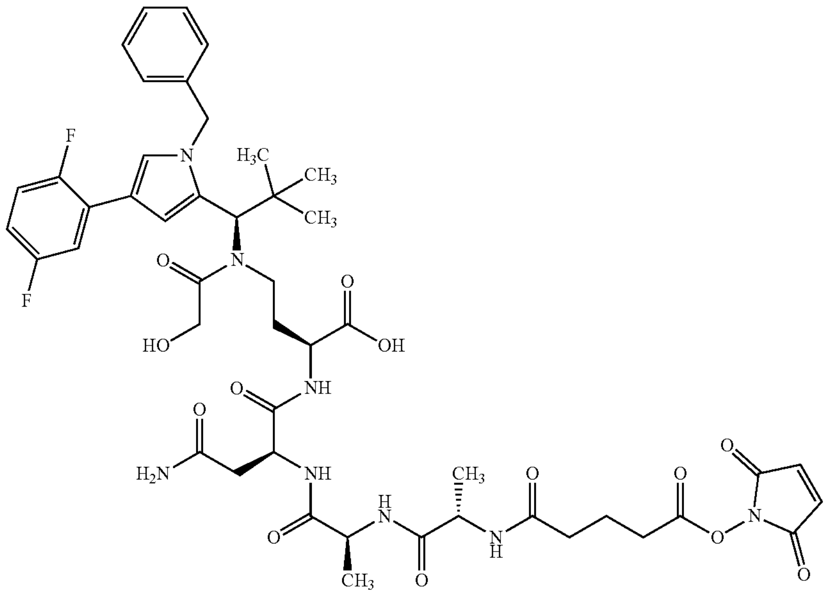 [SMILES: C[C@H](NC(=O)CCCC(=O)ON1C(=O)C=CC1=O)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)O]

3.75 mg (0.005 mmol) of the L-alanyl-L-alanyl-N[1]-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-aspartamide intermediate described in F5 were taken up in 4 ml of DMF, and 2.2 mg (0.007 mmol) of 1,1'-[(1,5-dioxopentane-1,5-diyl)bis(oxy)]dipyrrolidine-2,5-dione and 1.2 μl (0.007 mmol) of N,N-diisopropylethylamine were added. The reaction mixture was stirred at RT for 1 h, then concentrated under reduced pressure, and the residue was purified by preparative RP-HPLC (column: Reprosil 250×30; 10μ, flow rate: 50 ml/min, MeCN/water). The solvents were evaporated under reduced pressure and the residue was dried under high vacuum. This gave 1.9 mg (27% of theory) of the title compound.

LC-MS (Method 1): $R_t$=1.04 min; MS (ESIpos): m/z=981 $(M+H)^+$.

Intermediate Q7

N-Acetyl-L-alanyl-L-alanyl-N[1]-[(2S)-4-[{(1R)-1-[1-benzyl-4-(2,5-difluorophenyl)-1H-pyrrol-2-yl]-2,2-dimethylpropyl}(glycoloyl)amino]-1-({3-[(bromoacetyl)amino]propyl}amino)-1-oxobutan-2-yl]-L-aspartamide

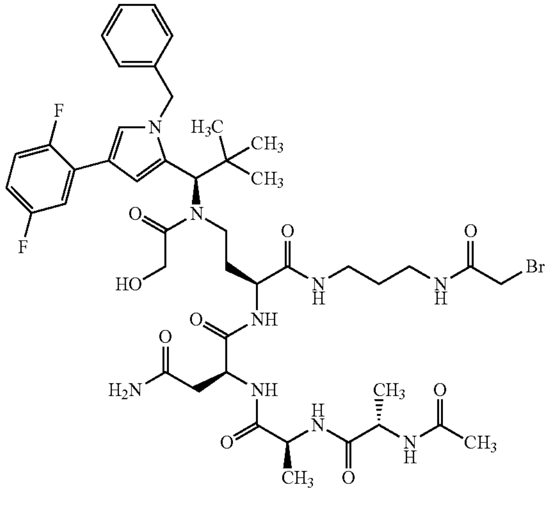 [SMILES: CC(=O)N[C@@H](C)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCCNC(=O)CBr]

4.1 mg (0.005 mmol) of Intermediate F282 were taken up in 1 ml of DMF, and 1.7 mg (0.005 mmol) of Intermediate L93, 2.2 mg (0.006 mmol) of HATU and 0.6 μl of 4-methylmorpholine were added. After 60 min of stirring at RT, the reaction was concentrated and the residue was purified by preparative HPLC. The appropriate fractions were concentrated and the residue was lyophilized from acetonitrile/water. This gave 1.2 mg (24% of theory) of the title compound.

LC-MS (Method 1): $R_t$=0.98 min; MS (ESIpos): m/z=1045 and 1047 $(M+H)^+$.

Intermediate Q8

N-[(Benzyloxy)carbonyl]-L-alanyl-L-alanyl-N[1]-[(20R)-25-{(1R)-1-[1-benzyl-4-(2,5-difluorophenyl)-1H-pyrrol-2-yl]-2,2-dimethylpropyl}-20-carboxy-1-(2,5-dioxo-2,5-dihydro-1H-pyrrol-1-yl)-2,18,24-trioxo-6,9,12,15-tetraoxa-22-thia-3,19,25-triazaoctacosan-28-yl]-L-aspartamide

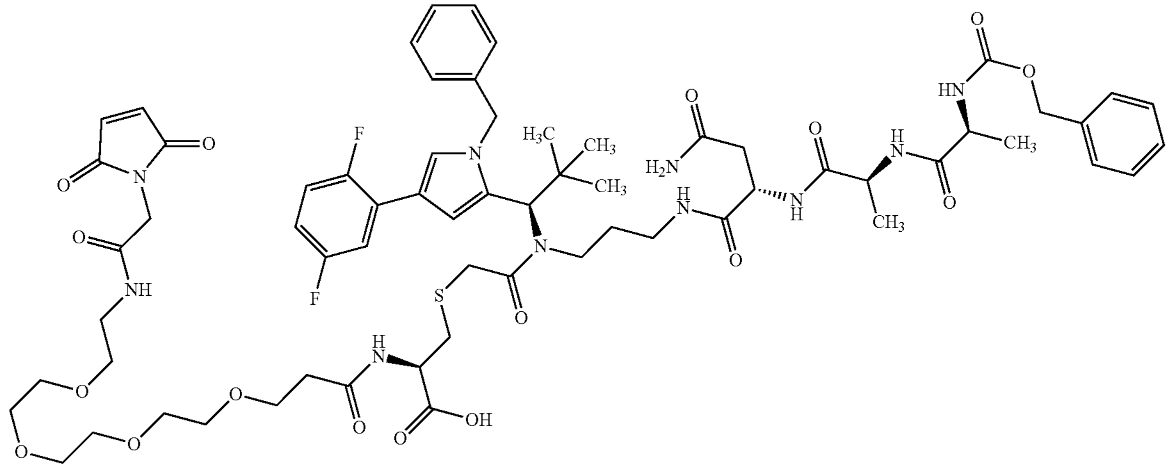 [SMILES: C[C@H](NC(=O)OCc1ccccc1)C(=O)N[C@@H](C)C(=O)N[C@@H](CC(N)=O)C(=O)NCCCN(C(=O)CSC[C@H](NC(=O)CCOCCOCCOCCOCCNC(=O)CN1C(=O)C=CC1=O)C(=O)O)[C@@H](c1cc(-c2cc(F)ccc2F)cn1Cc1ccccc1)C(C)(C)C]

6.80 mg (6.35 μmol) of S-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,18-dioxo-6,9,12,15-tetraoxa-3-azaoctadecan-18-yl]-L-cysteine/trifluoroacetic acid (1:1) (Intermediate F257) and 2.71 mg (6.63 μmol) of N-[(benzyloxy)carbonyl]-L-alanyl-L-alanyl-L-asparagine (Intermediate L92) were dissolved in 1.0 ml of DMF, and 2.66 mg (6.98 μmol) of HATU and 3.3 μl (19 μmol) of N,N-diisopropylethylamine were added. After stirring at RT for 45 min, the mixture was acidified with 4 μl of trifluoroacetic acid and purified by preparative HPLC. The appropriate fractions were concentrated and the residue was lyophilized from acetonitrile/water. This gave 1.20 mg (14% of theory) of the title compound.

LC-MS (Method 1): $R_t$=1.08 min; MS (ESIpos): m/z=1346 $(M+H)^+$.

Intermediate Q9

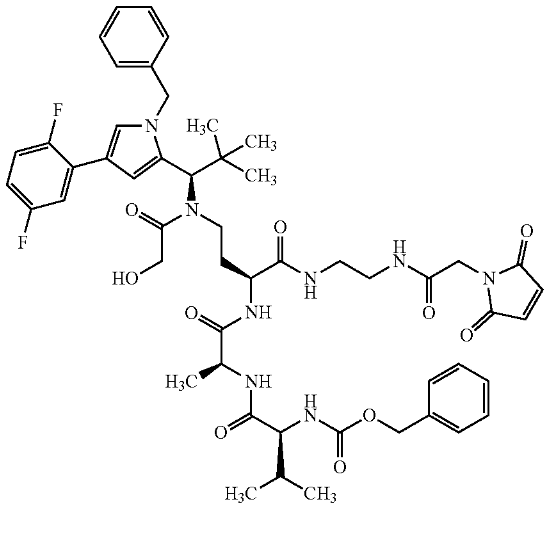 [SMILES: CC(C)[C@H](NC(=O)OCc1ccccc1)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

5 mg (0.0062 mmol) of Intermediate F104 were taken up in 2 ml of DMF, and 2.2 mg (0.0068 mmol) of Intermediate L95, 4.7 mg (0.012 mmol) of HATU and 5 equivalents of N,N-diisopropylethylamine were added. After 1 h of stirring at RT, the reaction was concentrated under reduced pressure and the residue was purified by preparative HPLC. The appropriate fractions were concentrated and the residue was lyophilized from acetonitrile/water. This gave 2 mg (32% of theory) of the title compound.

LC-MS (Method 1): $R_t$=1.28 min; MS (ESIpos): m/z=997 $(M+H)^+$.

Intermediate Q10

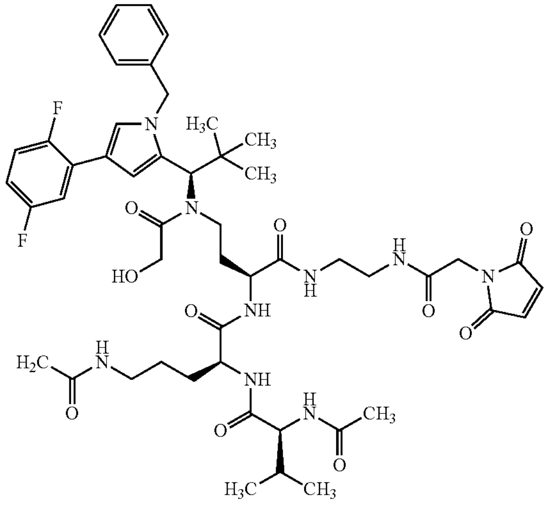 [SMILES: CC(=O)NCCC[C@H](NC(=O)[C@@H](NC(C)=O)C(C)C)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

5 mg (0.0062 mmol) of Intermediate F104 were taken up in 2 ml of DMF, and 2.2 mg (0.0068 mmol) of Intermediate L96, 5.9 mg (0.016 mmol) of HATU and 4 equivalents of 4-methylmorpholine were added. After 2 h of stirring at RT, the mixture was concentrated under reduced pressure and the residue was purified by preparative HPLC. The appropriate fractions were concentrated and the residue was lyophilized from acetonitrile/water. This gave 2.5 mg (41% of theory) of the title compound.

LC-MS (Method 1): $R_t$=0.99 min; MS (ESIpos): m/z=991 $(M+H)^+$.

Intermediate Q11

N-(pyridin-4-ylacetyl)-L-alanyl-L-alanyl-N1-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide Trifluoroacetate (1:1)

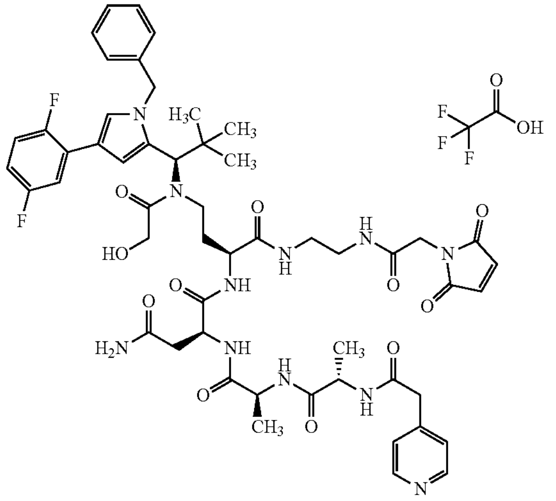 [SMILES: C[C@H](NC(=O)Cc1ccncc1)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O ; O=C(O)C(F)(F)F]

7 mg (0.0087 mmol) of Intermediate F104 were coupled with Intermediate L103 in analogy with Intermediate Q9. This gave 3.5 mg (34% of theory) of the title compound.

LC-MS (Method 1): $R_t$=0.83 min; MS (ESIpos): m/z=1068 $(M+H)^+$.

Intermediate Q12

N-isonicotinoyl-L-alanyl-L-alanyl-N1-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide Trifluoroacetate (1:1)

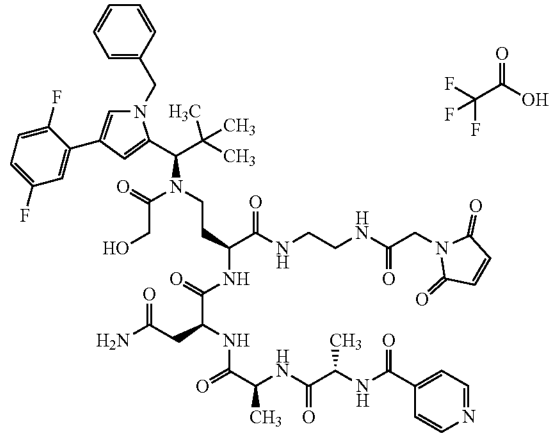 [SMILES: C[C@H](NC(=O)c1ccncc1)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O ; O=C(O)C(F)(F)F]

8 mg (0.0092 mmol) of Intermediate F104 were coupled with Intermediate L104 in analogy with Intermediate Q9. This gave 6 mg (46% of theory) of the title compound.

LC-MS (Method 12): $R_t$=1.71 min; MS (ESIpos): m/z=1054 $(M+H)^+$.

Intermediate Q13

N-{[2-(2-methoxyethoxy)ethoxy]acetyl}-L-alanyl-L-alanyl-N<sup>1</sup>-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide

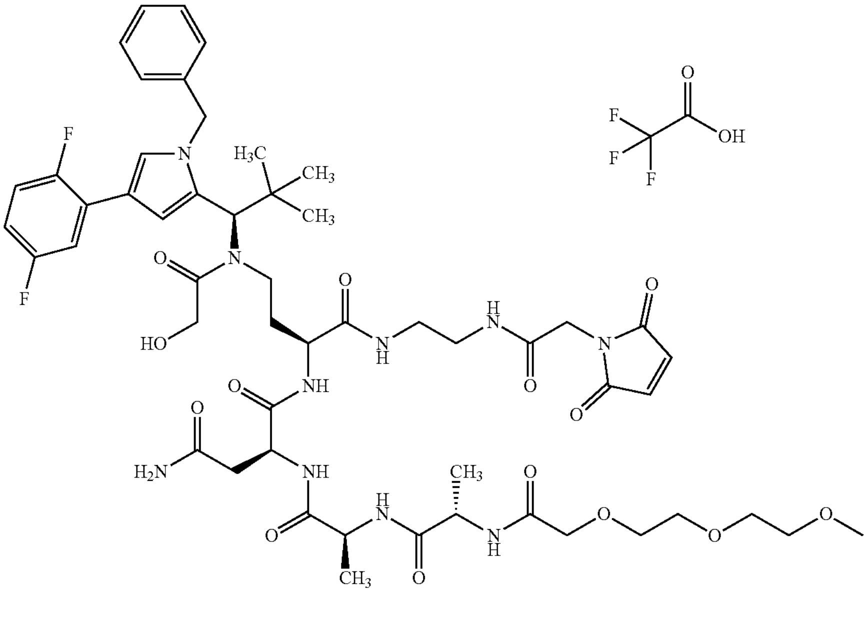 [SMILES: COCCOCCOCC(=O)N[C@@H](C)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O ; O=C(O)C(F)(F)F]

7 mg (0.0087 mmol) of Intermediate F104 were coupled with Intermediate L105 in analogy with Intermediate Q9. This gave 4.6 mg (47% of theory) of the title compound.

LC-MS (Method 1): $R_t$=0.97 min; MS (ESIpos): m/z=1109 $(M+H)^+$.

Intermediate Q14

N-[(Benzyloxy)carbonyl]-L-alanyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[-(2,5-dioxo-2,5-dihydro-1H-pyrrol-1-yl)acetyl]amino}ethyl)amino]-1-oxobutan-2-yl}-L-glutamide

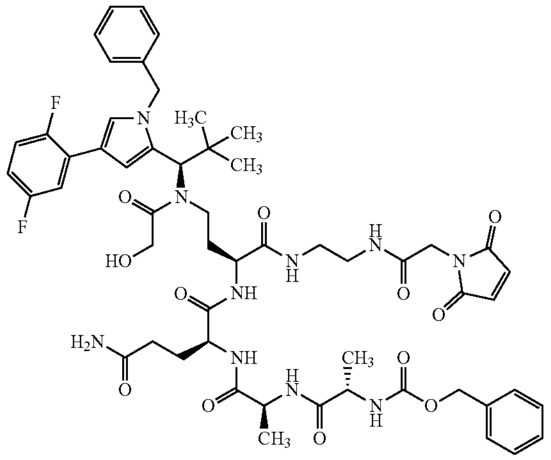 [SMILES: C[C@H](NC(=O)OCc1ccccc1)C(=O)N[C@@H](C)C(=O)N[C@@H](CCC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

LC-MS (Method 1): $R_t$=1.15 min; MS (ESIpos): m/z=1097 $(M+H)^+$.

This intermediate was prepared analogously to Intermediate Q1.

Intermediate Q15

N-[(Benzyloxy)carbonyl]-L-alanyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[-(2,5-dioxo-2,5-dihydro-1H-pyrrol-1-yl)acetyl]amino}ethyl)amino]-1-oxobutan-2-yl}-L-alpha-asparagine

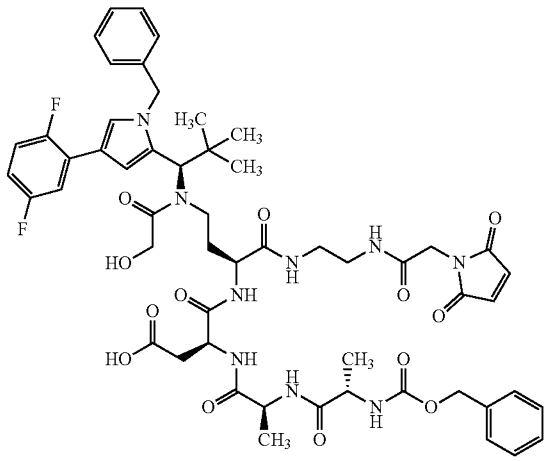 [SMILES: C[C@H](NC(=O)OCc1ccccc1)C(=O)N[C@@H](C)C(=O)N[C@@H](CC(=O)O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

10 mg (0.012 mmol) of Intermediate F104 were coupled with Intermediate L106 in analogy with Intermediate Q1. Subsequently, the title compound was prepared by cleaving the trimethylsilylethyl ester with zinc chloride.

LC-MS (Method 1): $R_t$=1.1 min; MS (ESIpos): m/z=1085 $(M+H)^+$.

In analogy to Intermediate Q1, the following intermediates Q16-Q22 were prepared with corresponding intermediate precursors:

Intermediate Q16

N-[(Benzyloxy)carbonyl]-L-valyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[-(2,5-dioxo-2,5-dihydro-1H-pyrrol-1-yl)acetyl]amino}ethyl)amino]-1-oxobutan-2-yl}-L-aspartamide

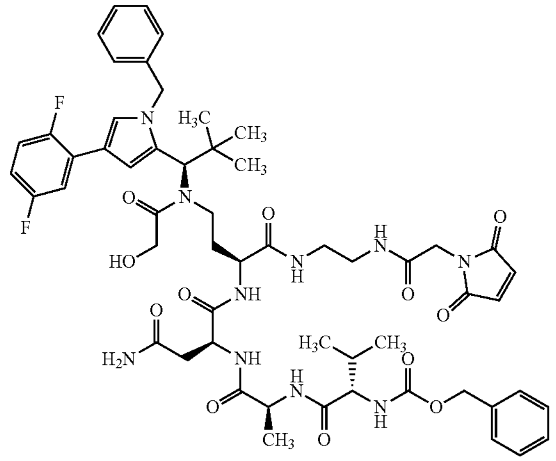 [SMILES: CC(C)[C@H](NC(=O)OCc1ccccc1)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

LC-MS (Method 1): $R_t$=1.13 min; MS (ESIpos): m/z=1111 $(M+H)^+$.

Intermediate Q17

N-[(Benzyloxy)carbonyl]-L-alanyl-L-valyl-N[1]-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[-(2,5-dioxo-2,5-dihydro-1H-pyrrol-1-yl)acetyl]amino}ethyl)amino]-1-oxobutan-2-yl}-L-aspartamide

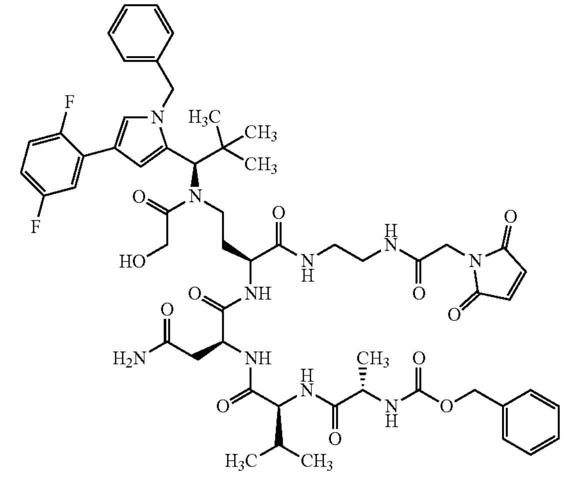 [SMILES: CC(C)[C@H](NC(=O)[C@H](C)NC(=O)OCc1ccccc1)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

LC-MS (Method 1): $R_t$=1.13 min; MS (ESIpos): m/z=1111 $(M+H)^+$.

Intermediate Q18

N-[(2,5-Dioxo-2,5-dihydro-1H-pyrrol-1-yl)acetyl]-L-alanyl-L-alanyl-N-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1S)-1,3-dicarboxypropyl]amino}-3-oxopropyl)amino]-1-oxobutan-2-yl}-L-aspartamide

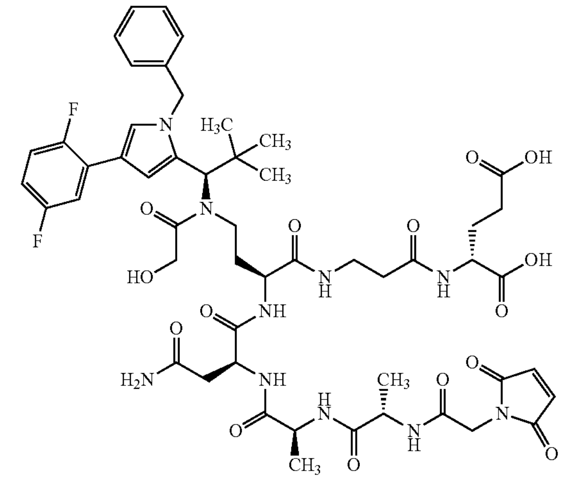 [SMILES: C[C@H](NC(=O)CN1C(=O)C=CC1=O)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@H](CCC(=O)O)C(=O)O]

The title compound was prepared proceeding from compound C111, first by coupling with intermediate L107 in the presence of HATU and N,N-diisopropylethylamine, followed by deprotection by means of zinc chloride in trifluoroethanol.

LC-MS (Method 1): $R_t$=0.89 min; MS (ESIpos): m/z=1107 $[M+H]^+$.

Intermediate Q19

N-[(Benzyloxy)carbonyl]-L-alanyl-glycyl-N[1]-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[-(2,5-dioxo-2,5-dihydro-1H-pyrrol-1-yl)acetyl]amino}ethyl)amino]-1-oxobutan-2-yl}-L-aspartamide

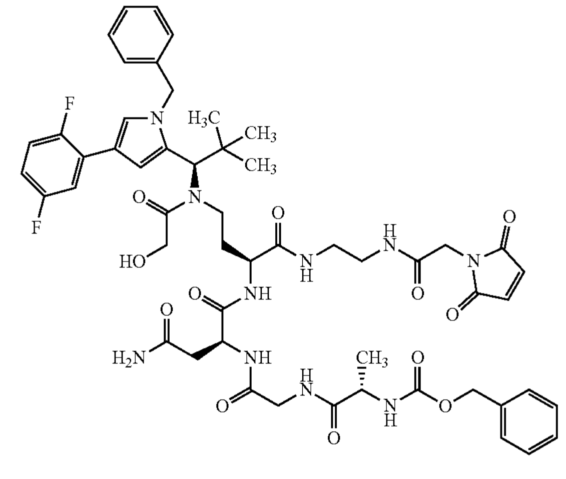 [SMILES: C[C@H](NC(=O)OCc1ccccc1)C(=O)NCC(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

LC-MS (Method 1): $R_t$=1.06 min; MS (ESIpos): m/z=1069 $(M+H)^+$.

Intermediate Q20

N-(38-Oxo-2,5,8,11,14,17,20,23,26,29,32,35-dodecaoxaoctatriacontan-38-yl)-L-alanyl-L-alanyl-N1-[(20R)-25-{(1R)-1-[1-benzyl-4-(2,5-difluorophenyl)-1H-pyrrol-2-yl]-2,2-dimethylpropyl}-20-carboxy-1-(2,5-dioxo-2,5-dihydro-1H-pyrrol-1-yl)-2,18,24-trioxo-6,9,12,15-tetraoxa-22-thia-3,19,25-triazaoctacosan-28-yl]-L-aspartamide

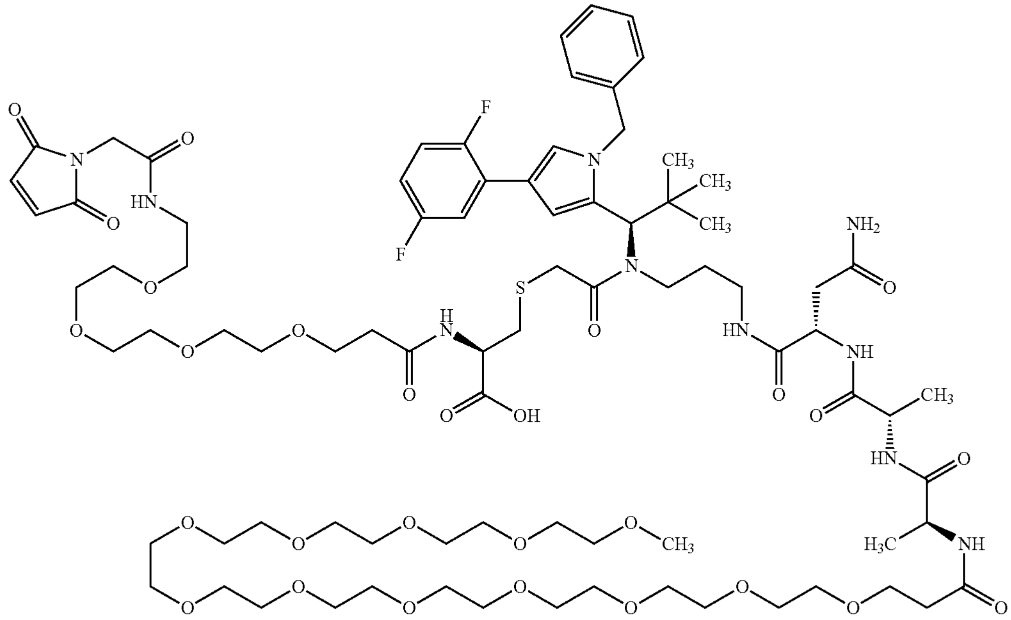 [SMILES: COCCOCCOCCOCCOCCOCCOCCOCCOCCOCCOCCOCCC(=O)N[C@@H](C)C(=O)N[C@@H](C)C(=O)N[C@@H](CC(N)=O)C(=O)NCCCN(C(=O)CSC[C@H](NC(=O)CCOCCOCCOCCOCCNC(=O)CN1C(=O)C=CC1=O)C(=O)O)[C@@H](c1cc(-c2cc(F)ccc2F)cn1Cc1ccccc1)C(C)(C)C]

At 0° C., 47.2 mg (0.0559 mmol) of Intermediate L102 were taken up in 0.50 ml of DMF, and 7.2 mg (0.053 mmol) of HOAt were added, as were 20.2 mg (0.0532 mmol) of HATU and 74.1 µl (0.425 mmol) of N,N-diisopropylethylamine. After stirring at 0° C. for 5 min, 57.0 mg (0.0532 mmol) of Intermediate F257 in DMF (0.5 ml) were added. After stirring at 0° C. for 2 h, water (1.0 ml) and ACN (1.5 ml) were added. The mixture was purified twice by preparative HPLC (mobile phase: ACN/water+0.1% TFA, gradient=1:2→2:1). The appropriate fractions were concentrated and the residue was lyophilized from acetonitrile/water. This gave 9.0 mg (9.5% of theory) of the title compound.

LC-MS (Method 14): $R_t$=5.43 min; MS (ESIpos): m/z=1783.8643 $(M+H)^+$.

Intermediate Q21

N-(38-Oxo-2,5,8,11,14,17,20,23,26,29,32,35-dodecaoxaoctatriacontan-38-yl)-L-alanyl-L-alanyl-N1-[(2S)-4-{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide

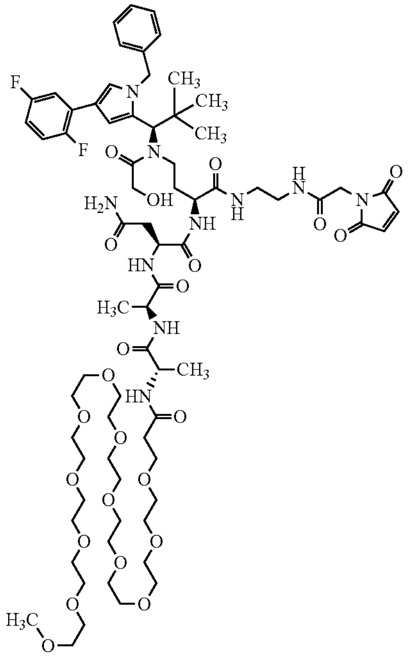 [SMILES: COCCOCCOCCOCCOCCOCCOCCOCCOCCOCCOCCOCCC(=O)N[C@@H](C)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

At 0° C., 57.5 mg (0.0713 mmol) of Intermediate F104 were taken up in 0.80 ml of DMF, and 61.2 mg (0.0727 mmol) of Intermediate L102 were added, as were 27.6 mg (0.0727 mmol) of HATU and 74.5 µl (0.428 mmol) of N,N-diisopropylethylamine. After stirring at 0° C. for 30 min, water (1.0 ml) and ACN (1.5 ml) were added. The mixture was purified by preparative HPLC (mobile phase: ACN/water+0.1% TFA, gradient=45%→85%). The appropriate fractions were concentrated and the residue was lyophilized from acetonitrile/water. This gave 39 mg (36% of theory) of the title compound.

LC-MS (Method 14): $R_t$=5.44 min; MS (ESIpos): m/z=1519.7598 $(M+H)^+$.

Intermediate Q22

N-[(2,5-Dioxo-2,5-dihydro-1H-pyrrol-1-yl)acetyl]-L-alanyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-([2-(L-gamma-glutamylamino)ethyl]amino}-1-oxobutan-2-yl]-L-aspartamide

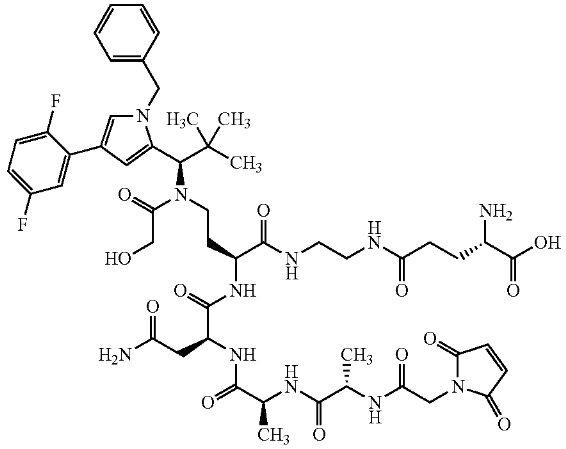 [SMILES: C[C@H](NC(=O)CN1C(=O)C=CC1=O)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CC[C@H](N)C(=O)O]

The title compound was prepared proceeding from compound C103, first by coupling with Intermediate L92 in the presence of HATU and N,N-diisopropylethylamine. In the next step, the Z protecting group was removed by hydrogenation over 10% palladium on activated carbon in ethanol under standard hydrogen pressure at RT for 30 minutes and the deprotected intermediate was then reacted with 1-{6-[(2,5-dioxopyrrolidin-1-yl)oxy]-6-oxohexyl}-1H-pyrrole-2,5-dione in the presence of N,N-diisopropylethylamine in DMF. In the last step, deprotection was effected by means of zinc chloride.

LC-MS (Method 1): $R_t$=0.84 min; MS (ESIpos): m/z=1078 $[M+H]^+$.

Intermediate Q23

N-{5-[(2,5-dioxopyrrolidin-1-yl)oxy]-5-oxopentanoyl}-L-alanyl-L-alanyl-$N^1$-{3-[{(1R)-1-[1-benzyl-4-(2,5-difluorophenyl)-1H-pyrrol-2-yl]-2,2-dimethylpropyl}(glycoloyl)amino]propyl}-L-aspartamide

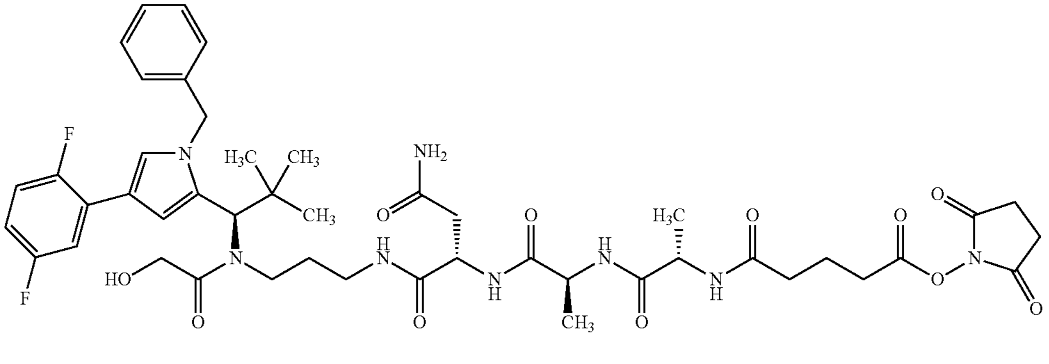 [SMILES: C[C@H](NC(=O)CCCC(=O)ON1C(=O)CCC1=O)C(=O)N[C@@H](C)C(=O)N[C@@H](CC(N)=O)C(=O)NCCCN(C(=O)CO)[C@@H](c1cc(-c2cc(F)ccc2F)cn1Cc1ccccc1)C(C)(C)C]

The title compound was prepared proceeding from compound M9, first by coupling with Intermediate L92 in the presence of HATU and N,N-diisopropylethylamine. In the next step, the Z protecting group was removed by hydrogenation over 10% palladium on activated carbon in ethanol at RT under standard hydrogen pressure for 30 minutes and the deprotected intermediate was then converted to the title compound as described in Intermediate Q6 by reaction with 1,1'-[(1,5-dioxopentane-1,5-diyl)bis(oxy)]dipyrrolidine-2,5-dione.

LC-MS (Method 12): $R_t$=1.89 min; MS (ESIpos): m/z=938 [M+H]$^+$.

Intermediate Q24

N-[(2,5-dioxo-2,5-dihydro-1H-pyrrol-1-yl)acetyl]-L-alanyl-L-alanyl-N<sup>1</sup>-{3-[{(1R)-1-[1-benzyl-4-(2,5-difluorophenyl)-1H-pyrrol-2-yl]-2,2-dimethylpropyl}(glycoloyl)amino]propyl}-L-aspartamide Trifluoroacetate (1:1)

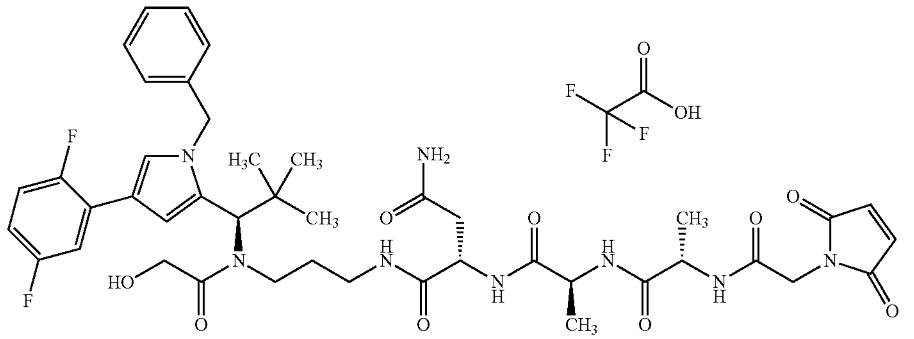 [SMILES: C[C@H](NC(=O)CN1C(=O)C=CC1=O)C(=O)N[C@@H](C)C(=O)N[C@@H](CC(N)=O)C(=O)NCCCN(C(=O)CO)[C@@H](c1cc(-c2cc(F)ccc2F)cn1Cc1ccccc1)C(C)(C)C ; O=C(O)C(F)(F)F]

The title compound was prepared proceeding from compound M9, first by coupling with Intermediate L92 in the presence of HATU and N,N-diisopropylethylamine. In the next step, the Z protecting group was removed by hydrogenation over 10% palladium on activated carbon in ethanol at RT under standard hydrogen pressure for 30 minutes and the deprotected intermediate was then converted to the title compound by reaction with 1-{2-[(2,5-dioxopyrrolidin-1-yl)oxy]-2-oxoethyl}-1H-pyrrole-2,5-dione in the presence of N,N-diisopropylethylamine.

LC-MS (Method 1): $R_t$=1.01 min; MS (ESIpos): m/z=863 [M+H]$^+$.

Intermediate Q25

N-[(2,5-dioxo-2,5-dihydro-1H-pyrrol-1-yl)acetyl]-L-alanyl-L-alanyl-N$^1$-{(2S)-1-[(3-{[(5S)-5-amino-5-carboxypentyl]amino}-3-oxopropyl)amino]-4-[{(1R)-1-[1-benzyl-4-(2,5-difluorophenyl)-1H-pyrrol-2-yl]-2,2-dimethylpropyl}(glycoloyl)amino]-1-oxobutan-2-yl}-L-aspartamide Trifluoroacetate (1:1)

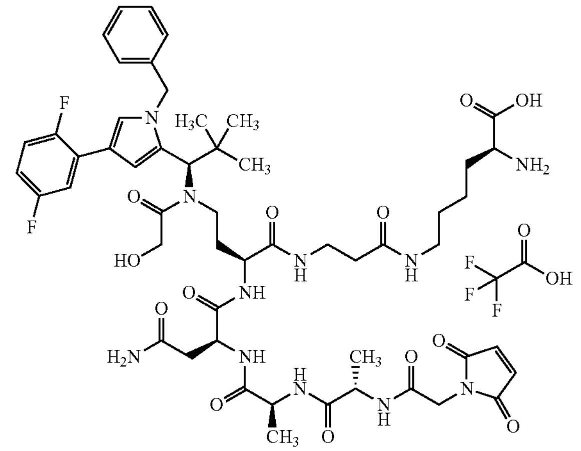

The title compound was prepared proceeding from compound C108, first by coupling with Intermediate L92 in the presence of HATU and N,N-diisopropylethylamine. In the next step, the Z protecting group was removed by hydrogenation over 10% palladium on activated carbon in DCM-methanol 1:1 under standard hydrogen pressure at RT for 1 hour and the deprotected intermediate was then converted to the title compound by reaction with 1-{2-[(2,5-dioxopyrrolidin-1-yl)oxy]-2-oxoethyl}-1H-pyrrole-2,5-dione in the presence of N,N-diisopropylethylamine and finally by deprotection by means of zinc chloride.

LC-MS (Method 12): $R_t$=1.46 min; MS (ESIpos): m/z=1106 [M+H]$^+$.

Intermediate Q26

N-[6-(2,5-dioxo-2,5-dihydro-1H-pyrrol-1-yl)hexanoyl]-L-alanyl-L-alanyl-N[1]-{(2S)-1-[(3-{[(5S)-5-amino-5-carboxypentyl]amino}-3-oxopropyl)amino]-4-[{(1R)-1-[1-benzyl-4-(2,5-difluorophenyl)-1H-pyrrol-2-yl]-2,2-dimethylpropyl}(glycoloyl)amino]-1-oxobutan-2-yl}-L-aspartamide Trifluoroacetate (1:1)

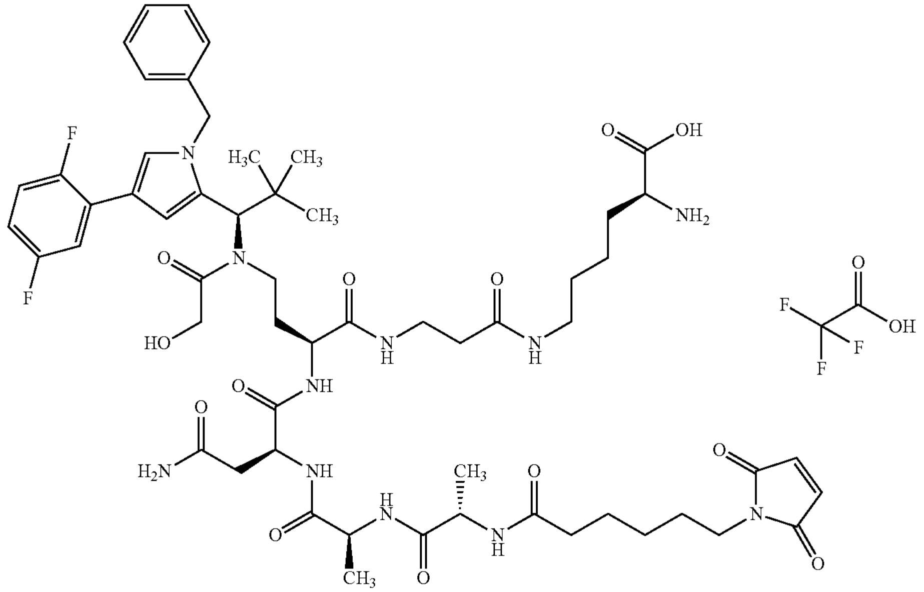 [SMILES: C[C@H](NC(=O)CCCCCN1C(=O)C=CC1=O)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)NCCCC[C@H](N)C(=O)O ; O=C(O)C(F)(F)F]

The title compound was prepared analogously to Intermediate Q25.

LC-MS (Method 12): $R_t$=1.55 min; MS (ESIpos): m/z=1162 $[M+H]^+$.

Intermediate Q27

N-[(2,5-Dioxo-2,5-dihydro-1H-pyrrol-1-yl)acetyl]-L-alanyl-L-alanyl-N[1]-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1S)-1,3-dicarboxypropyl]amino}-3-oxopropyl)amino]-1-oxobutan-2-yl}-L-aspartamide

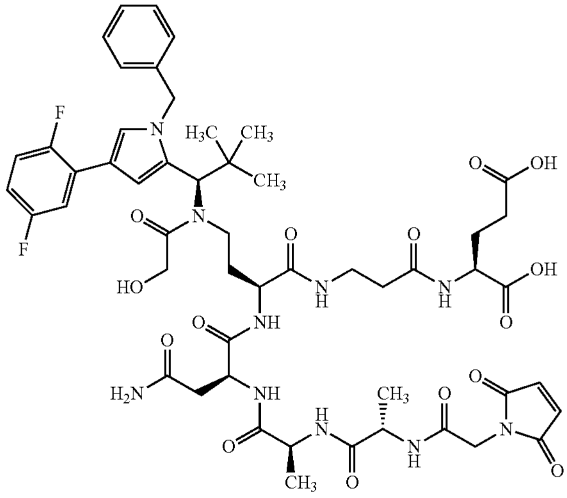 [SMILES: C[C@H](NC(=O)CN1C(=O)C=CC1=O)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@@H](CCC(=O)O)C(=O)O]

The title compound was prepared proceeding from compound C109, first by coupling with Intermediate L107 in the presence of HATU and N,N-diisopropylethylamine, followed by deprotection by means of zinc chloride.

LC-MS (Method 1): $R_t$=0.95 min; MS (ESIpos): m/z=1107 $[M+H]^+$.

Intermediate Q28

N-[(2,5-Dioxo-2,5-dihydro-1H-pyrrol-1-yl)hexanoyl]-L-alanyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1S)-1,3-dicarboxypropyl]amino}-3-oxopropyl)amino]-1-oxobutan-2-yl}-L-aspartamide

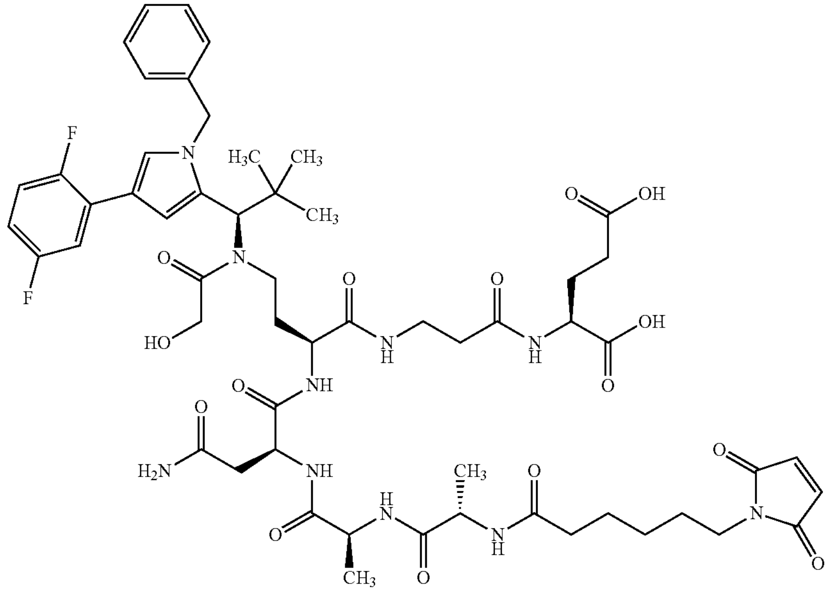 [SMILES: C[C@H](NC(=O)CCCCCN1C(=O)C=CC1=O)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@@H](CCC(=O)O)C(=O)O]

The title compound was prepared proceeding from compound C110, first by coupling with Intermediate L92 in the presence of HATU and N,N-diisopropylethylamine. In the next step, all protecting groups were removed by hydrogenation over 10% palladium on activated carbon in DCM-methanol 1:1 under standard hydrogen pressure at RT for 1 hour and the deprotected intermediate was then converted to the title compound by reaction with 1-{6-[(2,5-dioxopyrrolidin-1-yl)oxy]-6-oxohexyl}-1H-pyrrole-2,5-dione in the presence of N,N-diisopropylethylamine.

LC-MS (Method 12): $R_t$=1.74 min; MS (ESIneg): m/z=1161 $[M-H]^-$.

Intermediate Q29

N-{5-[(2,5-Dioxopyrrolidin-1-yl)oxy]-5-oxopentanoyl}-L-alanyl-L-alanyl-N[1]-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1S)-1,3-dicarboxypropyl]amino}-3-oxopropyl)amino]-1-oxobutan-2-yl}-L-aspartamide

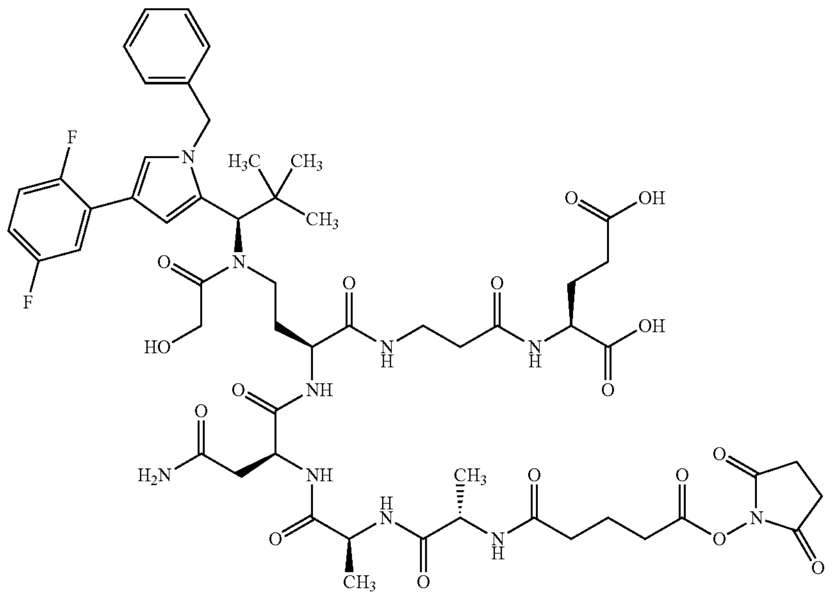 [SMILES: C[C@H](NC(=O)CCCC(=O)ON1C(=O)CCC1=O)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@@H](CCC(=O)O)C(=O)O]

40 mg (39 µmol) of Intermediate C110 in 9 ml of DMF in the presence of 30 mg of HATU and 34 µl of N,N-diisopropylethylamine were coupled with 19.6 mg (47 mmol) of Intermediate L92. Subsequently, all protecting groups were removed by hydrogenation over 10% palladium on activated carbon in methanol under standard hydrogen pressure at RT for 1 hour and the deprotected intermediate was then converted by reaction with 1-{6-[(2,5-dioxopyrrolidin-1-yl)oxy]-6-oxohexyl}-1H-pyrrole-2,5-dione in the presence of N,N-diisopropylethylamine to the title compound, which was purified by preparative HPLC.

LC-MS (Method 1): $R_t$=0.9 min; MS (ESIpos): m/z=1181 $(M+H)^+$.

Intermediate Q30

N-{6-[(2,5-Dioxopyrrolidin-1-yl)oxy]-6-oxohexyl}-N-methyl-L-alanyl-L-alanyl-L-alanyl-N[1]-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1S)-1,3-dicarboxypropyl]amino}-3-oxopropyl)amino]-1-oxobutan-2-yl}-L-aspartamide

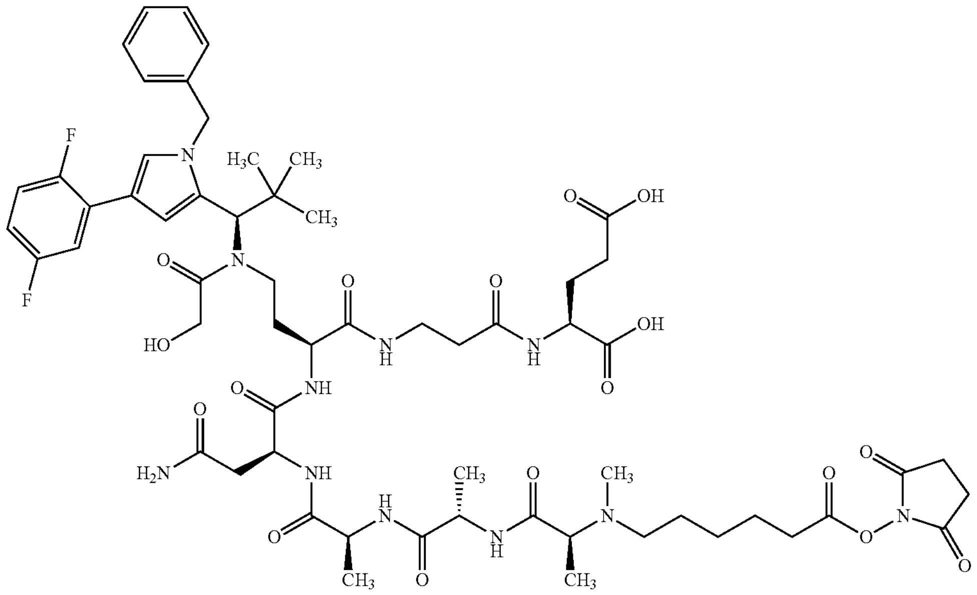 [SMILES: C[C@H](NC(=O)[C@H](C)NC(=O)[C@H](C)N(C)CCCCCC(=O)ON1C(=O)CCC1=O)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@@H](CCC(=O)O)C(=O)O]

First, trifluoroacetic acid/4-nitrobenzyl-L-alanyl-L-alanyl-L-asparaginate (1:1) was prepared by coupling N-(tert-butoxycarbonyl)-L-alanyl-L-alanine with 4-nitrobenzyl L-asparaginate hydrobromide (1:1) in DMF in the presence of HATU and N,N-diisopropylethylamine and then deprotecting the amino group with trifluoroacetic acid in DCM.

LC-MS (Method 1): $R_t$=0.43 min; MS (ESIpos): m/z=410 $(M+H)^+$.

This intermediate was coupled with N-(tert-butoxycarbonyl)-N-methyl-L-alanine in DMF in the presence of HATU and N,N-diisopropylethylamine. Subsequently, the p-nitrobenzyl ester was detached by hydrogenation in DCM-methanol 1:1 over 10% palladium on activated carbon.

LC-MS (Method 1): $R_t$=0.55 min; MS (ESIpos): m/z=460 $(M+H)^+$.

The intermediate thus obtained was coupled with Intermediate C110 in DMF in the presence of HATU and N,N-diisopropylethylamine. Subsequently, the Boc protecting group was detached by stirring with 4 equivalents of zinc chloride in trifluoroethanol at 50° C. for 1 h.

LC-MS (Method 1): $R_t$=1.07 min; MS (ESIpos): m/z=1235 $(M+H)^+$.

44 mg (32 μmol) of this intermediate were combined with 25.4 mg (195 μmol) of 6-oxohexanoic acid, which had been prepared beforehand by a literature method (J. Org. Chem. 1993, 58, 2196), in 20 ml of methanol, and 7.8 μl of acetic acid and 29 mg (313 μmol) of borane-pyridine complex were added. The mixture was stirred at RT for 1 h and then concentrated under reduced pressure and purified by preparative HPLC. 25 mg (56% of theory) of (6S,13S,16S,19S,22S,25S)-16-(2-amino-2-oxoethyl)-13-{2-[{(1R)-1-[1-benzyl-4-(2,5-difluorophenyl)-1H-pyrrol-2-yl]-2,2-dimethylpropyl}(glycoloyl)amino]ethyl}-6-[(benzyloxy)carbonyl]-19,22,25,26-tetramethyl-3,8,12,15,18,21,24-heptaoxo-1-phenyl-2-oxa-7,11,14,17,20,23,26-heptaazadotriacontan-32-oic acid were obtained.

24.5 mg (0.018 mmol) of this intermediate were dissolved in 6 ml of DMF, and 34 mg (0.27 mmol) of 1-hydroxypyrrolidine-2,5-dione, 16 μl of N,N-diisopropylethylamine and, in portions, a total of 50 mg (0.13 mmol) of HATU were added. After stirring at RT for 2 h, the reaction solution was adjusted to pH of 3-4 with TFA and then concentrated and purified by preparative HPLC. 23 mg (87%) of the protected intermediate were obtained, which were then taken up in 10 ml of ethanol. After 10% palladium on activated carbon had been added, the benzyl ester groups were removed under standard hydrogen pressure and, after the catalyst had been filtered off, the remaining solution had been concentrated and then the residue had been lyophilized from acetonitrile/water 9:1, 20 mg (95% of theory) of the title compound were obtained.

LC-MS (Method 1): $R_t$=0.82 min; MS (ESIpos): m/z=1266 $(M+H)^+$.

Intermediate Q31

Trifluoroacetic Acid/N-(pyridin-4-ylacetyl)-L-alanyl-L-alanyl-$N^1$-{(2S)-1-({2-[($N^2$-acetyl-L-lysyl)amino]ethyl}amino)-4-[{(1R)-1-[1-benzyl-4-(2,5-difluorophenyl)-1H-pyrrol-2-yl]-2,2-dimethyl propyl}(glycoloyl)amino]-1-oxobutan-2-yl}-L-aspartamide (1:1)

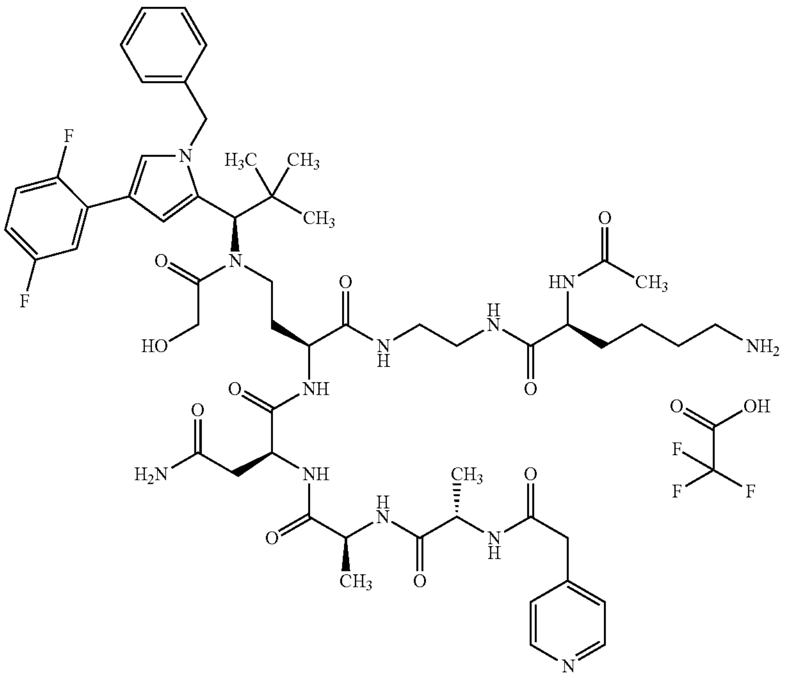 [SMILES: CC(=O)N[C@@H](CCCCN)C(=O)NCCNC(=O)[C@H](CCN(C(=O)CO)[C@@H](c1cc(-c2cc(F)ccc2F)cn1Cc1ccccc1)C(C)(C)C)NC(=O)[C@H](CC(N)=O)NC(=O)[C@H](C)NC(=O)[C@H](C)NC(=O)Cc1ccncc1 ; O=C(O)C(F)(F)F]

The title compound was prepared by HATU coupling of Intermediate C112 with Intermediate L103 in DMF in the presence of N,N-diisopropylethylamine and subsequent detachment of the Boc protecting group by stirring at 50° C. in trifluoroethanol with 6 equivalents of zinc chloride for 30 min.

LC-MS (Method 1): $R_t$=0.76 min; MS (ESIpos): m/z=1101 $(M+H)^+$.

Intermediate Q32

$N^2$-Acetyl-L-lysyl-L-alanyl-L-alanyl-$N^1$-{(2S)-1-[(3-{[(5S)-5-amino-5-carboxypentyl]amino}-3-oxo-propyl)amino]-4-[{(1R)-1-[1-benzyl-4-(2,5-difluoro-phenyl)-1H-pyrrol-2-yl]-2,2-dimethyl propyl}(glycoloyl)amino]-1-oxobutan-2-yl}-L-aspartamide/trifluoroacetic Acid (1:1)

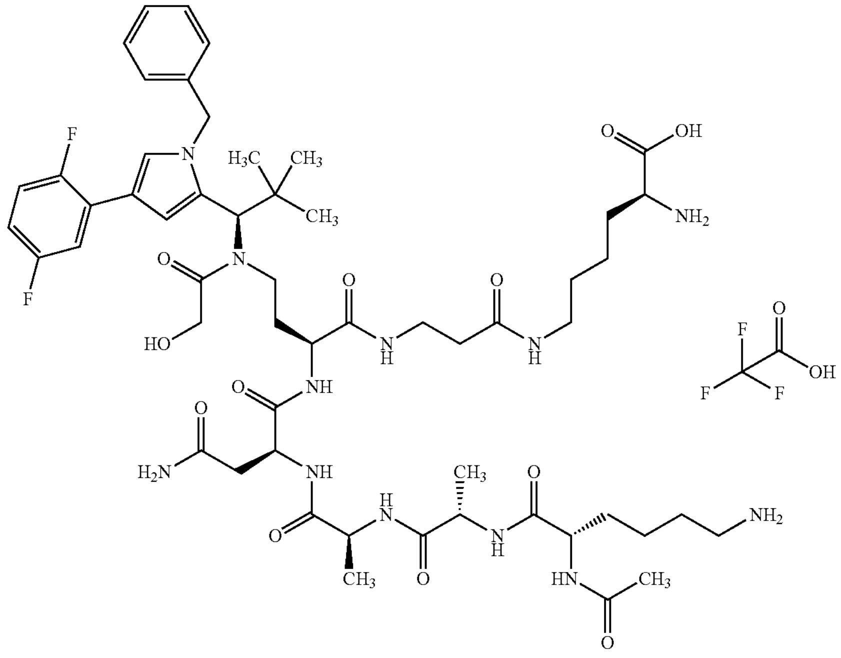 [SMILES: CC(=O)N[C@@H](CCCCN)C(=O)N[C@@H](C)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)NCCCC[C@H](N)C(=O)O ; O=C(O)C(F)(F)F]

First, Intermediate C108 was coupled with Intermediate L92 in DMF in the presence of HATU and N,N-diisopropylethylamine. In the next step, the Z protective group was removed by hydrogenation over 10% palladium on activated carbon in DCM/methanol 1:1 under hydrogen standard pressure at RT for 1 hour. Subsequently, the deprotected intermediate was converted to the title compound by reaction with intermediate L109 in DMF in the presence of HATU and N,N-diisopropylethylamine and subsequent deprotection by stirring with 12 equivalents of zinc chloride in trifluoroethanol at 50° C. for 90 min.

LC-MS (Method 12): $R_t$=1.17 min; MS (ESIneg): m/z=1137 $(M-H)^-$.

Intermediate Q33

$N^2$-Acetyl-L-lysyl-L-alanyl-L-alanyl-N-[(2S)-4-[{(1R)-1-[1-benzyl-4-(2,5-difluorophenyl)-1H-pyrrol-2-yl]-2,2-dimethylpropyl}(glycoloyl)amino]-1-{[2-(L-gamma-glutamylamino)ethyl]amino}-1-oxobutan-2-yl]-L-aspartamide/trifluoroacetic Acid (1:1)

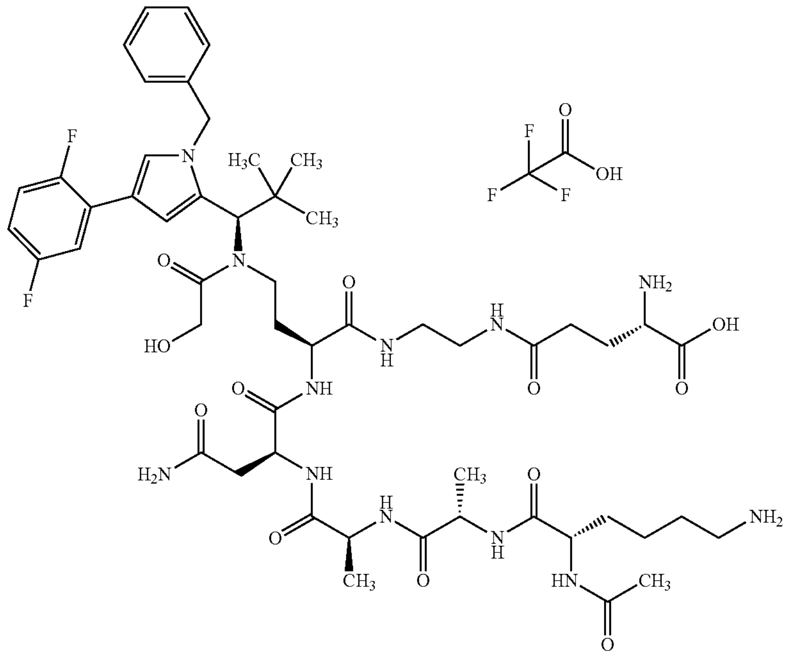 [SMILES: CC(=O)N[C@@H](CCCCN)C(=O)N[C@@H](C)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CC[C@H](N)C(=O)O ; O=C(O)C(F)(F)F]

The title compound was prepared by HATU coupling of Intermediate C103 with Intermediate L110 in DMF in the presence of N,N-diisopropylethylamine and subsequent complete deprotection by stirring at 50° C. in trifluoroethanol with 10 equivalents of zinc chloride for 6 h.

LC-MS (Method 1): $R_t$=0.72 min; MS (ESIpos): m/z=1111 $(M+H)^+$.

Intermediate Q34

$N^2$-Acetyl-L-lysyl-L-alanyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1S)-1,3-dicarboxypropyl]amino}-3-oxopropyl)amino]-1-oxobutan-2-yl}-L-aspartamide/trifluoroacetic Acid (1:1)

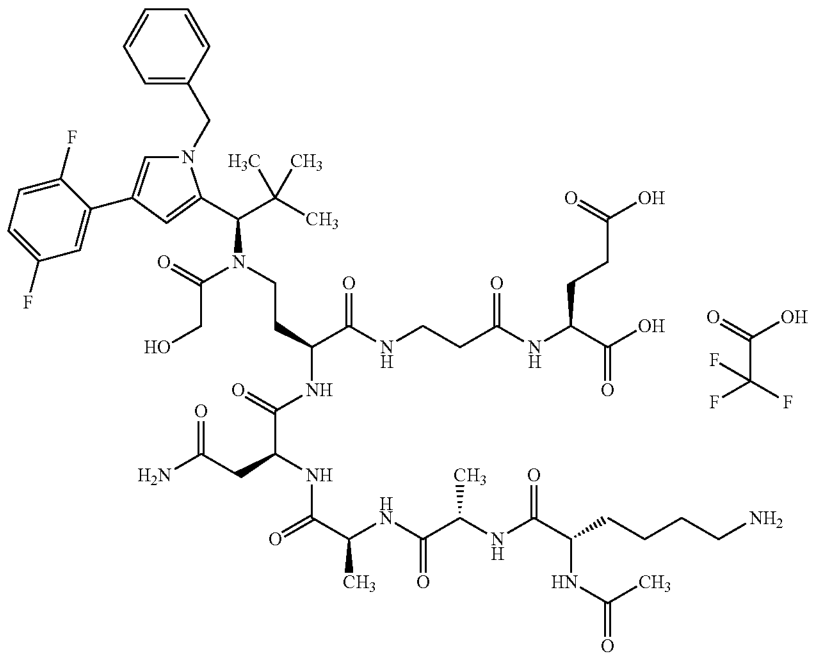 [SMILES: CC(=O)N[C@@H](CCCCN)C(=O)N[C@@H](C)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@@H](CCC(=O)O)C(=O)O ; O=C(O)C(F)(F)F]

The synthesis of the title compound commenced with the HATU coupling of Intermediate C110 with intermediate L110 in DMF in the presence of N,N-diisopropylethylamine. In the next step, the benzyl ester protecting group was removed by hydrogenation over 10% palladium on activated carbon in DCM/methanol 1:1 under hydrogen standard pressure at RT for 1 hour. In the last step, the Teoc protecting group was detached by stirring in trifluoroethanol at 50° C. with 8 equivalents of zinc chloride for 6 h.

LC-MS (Method 12): $R_t$=1.31 min; MS (ESIpos): m/z=1140 $(M+H)^+$.

Intermediate Q35

N-(Pyridin-4-ylacetyl)-L-alanyl-N-methyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide

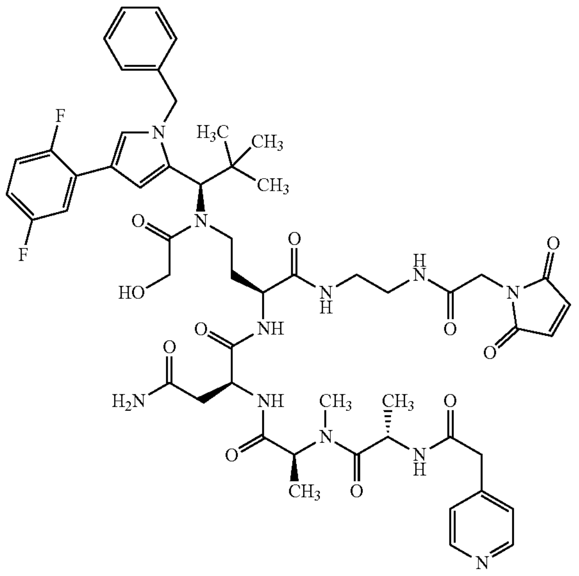 [SMILES: C[C@H](NC(=O)Cc1ccncc1)C(=O)N(C)[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

15 mg (0.019 mmol) of Intermediate F104, in analogy to Intermediate Q1, were coupled to 10 mg (0.024 mmol) of Intermediate L111. After purification by means of preparative HPLC, 4 mg (17% of theory) of the title compound were obtained.

LC-MS (Method 1): $R_t$=0.82 min; MS (ESIpos): m/z=1082 $(M+H)^+$.

Intermediate Q36

N-Acetyl-L-alanyl-N-methyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide

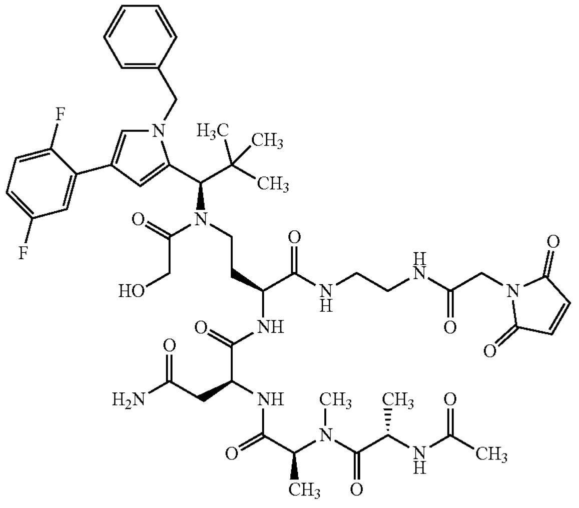 [SMILES: CC(=O)N[C@@H](C)C(=O)N(C)[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

15 mg (0.019 mmol) of Intermediate F104, in analogy to Intermediate Q1, were coupled to 8 mg (0.024 mmol) of Intermediate L112. After purification by means of preparative HPLC, 5.8 mg (28% of theory) of the title compound were obtained.

LC-MS (Method 1): $R_t$=0.95 min; MS (ESIpos): m/z=1005 $(M+H)^+$.

Intermediate Q37

N-(Pyridin-4-ylacetyl)-L-alanyl-L-alanyl-$N^1$-[(2S)-4-[{(1R)-1-[1-benzyl-4-(2,5-difluorophenyl)-1H-pyrrol-2-yl]-2,2-dimethylpropyl}(glycoloyl)amino]-1-({4-[(2,5-dioxopyrrolidin-1-yl)oxy]-4-oxo butyl}amino)-1-oxobutan-2-yl]-L-aspartamide

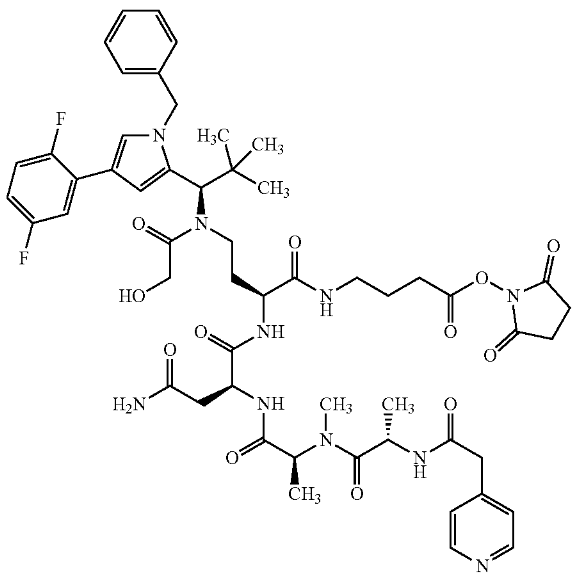 [SMILES: C[C@H](NC(=O)Cc1ccncc1)C(=O)N(C)[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCCC(=O)ON1C(=O)CCC1=O]

20 mg (31 μmol) of Intermediate C114 were initially charged together with 11.6 mg (22.9 μmol) of N-(pyridin-4-ylacetyl)-L-alanyl-L-alanyl-L-asparagine/trifluoroacetic acid (1:1) (Intermediate L104) in 5.0 ml of DMF. Then 11 μl of N,N-diisopropylethylamine and 21 mg (55 μmol) of HATU were added. The reaction mixture was stirred at RT for 60 minutes. The reaction mixture was purified directly by means of preparative RP-HPLC (column: Reprosil 250×30; 10μ, flow rate: 50 ml/min, MeCN/water, 0.1% TFA). The solvents were evaporated under reduced pressure and the residue was dried under high vacuum. This was followed by the detachment of the tert-butyl ester group by stirring at 50° C. in trifluoroethanol with 6 equiv. of zinc chloride for 2 hours. After addition of 6 equiv. of EDTA, purification was effected by preparative HPLC. In the last step, the intermediate obtained was taken up in DMF, 15 equivalents of 1-hydroxypyrrolidine-2,5-dione were added and conversion to the title compound was effected by stirring in the presence of 5 equiv. of HATU and 5 equiv. of N,N-diisopropylethylamine for 60 minutes. The title compound was purified by preparative HPLC.

LC-MS (Method 1): $R_t$=0.87 min; MS (ESIpos): m/z=1071 $(M+H)^+$.

Intermediate Q38

N-Methyl-N-(pyridin-4-ylacetyl)-L-alanyl-L-alanyl-N1-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide

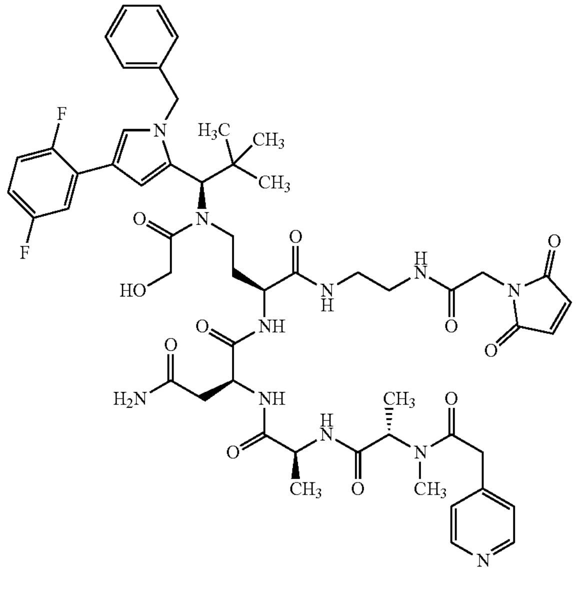 [SMILES: C[C@H](NC(=O)[C@H](C)N(C)C(=O)Cc1ccncc1)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

15 mg (0.019 mmol) of Intermediate F104, in analogy to Intermediate Q1, were coupled to 12.5 mg (0.024 mmol) of Intermediate L113. After purification by means of preparative HPLC, 4 mg (19% of theory) of the title compound were obtained.

LC-MS (Method 1): $R_t$=0.83 min; MS (ESIpos): m/z=1082 $(M+H)^+$.

Intermediate Q39

N-[(2,5-Dioxo-2,5-dihydro-1H-pyrrol-1-yl)acetyl]-L-alanyl-L-alanyl-$N^1$-[(2S)-4-[{(1R)-1-[1-benzyl-4-(2,5-difluorophenyl)-1H-pyrrol-2-yl]-2,2-dimethylpropyl}(glycoloyl)amino]-1-(methylamino)-1-oxobutan-2-yl]-L-aspartamide

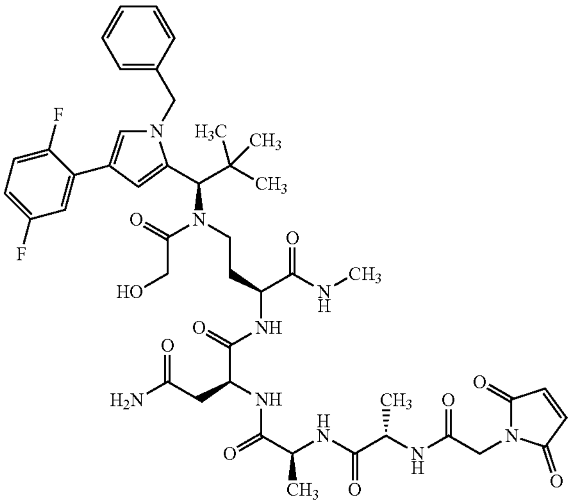 [SMILES: CNC(=O)[C@H](CCN(C(=O)CO)[C@@H](c1cc(-c2cc(F)ccc2F)cn1Cc1ccccc1)C(C)(C)C)NC(=O)[C@H](CC(N)=O)NC(=O)[C@H](C)NC(=O)[C@H](C)NC(=O)CN1C(=O)C=CC1=O]

The title compound was prepared proceeding from compound C115 by coupling to Intermediate L107 in the presence of HATU and N,N-diisopropylethylamine.

LC-MS (Method 1): $R_t$=0.97 min; MS (ESIpos): m/z=920 $[M+H]^+$.

Intermediate Q40

N-{[2-(2-M ethoxyethoxy]acetyl}-L-alanyl-N-methyl-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide

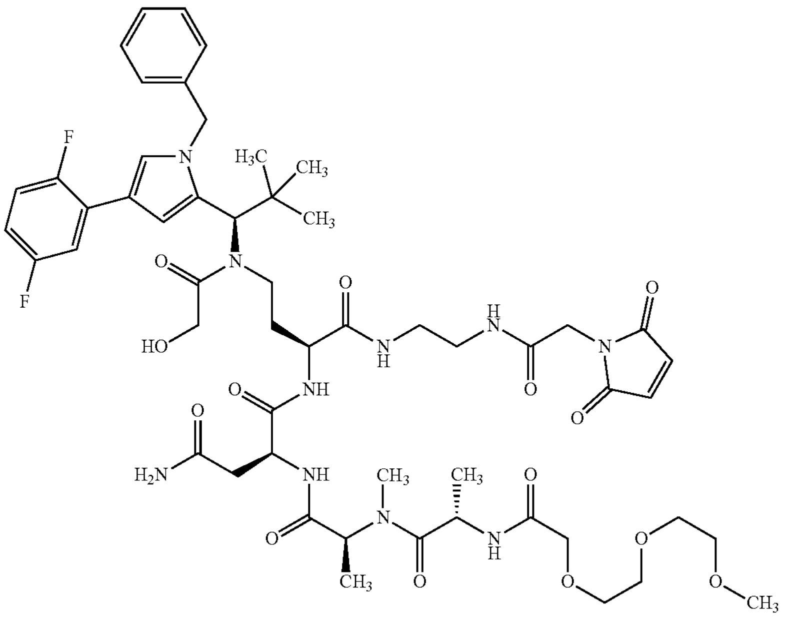 [SMILES: COCCOCCOCC(=O)N[C@@H](C)C(=O)N(C)[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

15 mg (0.019 mmol) of Intermediate F104, in analogy to Intermediate Q1, were coupled to 12.5 mg (0.024 mmol) of Intermediate L114. After purification by means of preparative HPLC, 10.8 mg (50% of theory) of the title compound were obtained.

LC-MS (Method 1): $R_t$=0.99 min; MS (ESIpos): m/z=1123 $(M+H)^+$.

Intermediate Q41

N-[6-(2,5-Dioxo-2,5-dihydro-1H-pyrrol-1-yl)hexanoyl]-L-alanyl-L-alanyl-$N^1$-[(16S)-4-{(1R)-1-[1-benzyl-4-(2,5-difluorophenyl)-1H-pyrrol-2-yl]-2,2-dimethylpropyl}-16,18-dicarboxy-5,10,14-trioxo-7-thia-4,11,15-triazaoctadec-1-yl]-L-aspartamide/trifluoroacetic Acid (1:1)

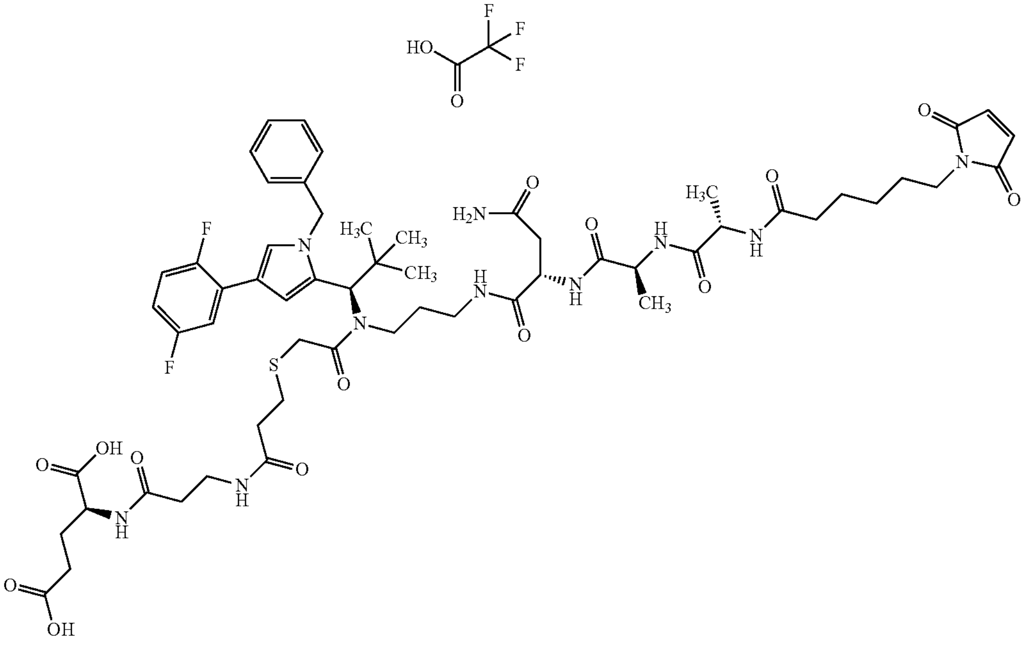 [SMILES: O=C(O)C(F)(F)F ; C[C@H](NC(=O)CCCCCN1C(=O)C=CC1=O)C(=O)N[C@@H](C)C(=O)N[C@@H](CC(N)=O)C(=O)NCCCN(C(=O)CSCCC(=O)NCCC(=O)N[C@@H](CCC(=O)O)C(=O)O)[C@@H](c1cc(-c2cc(F)ccc2F)cn1Cc1ccccc1)C(C)(C)C]

Under argon, 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (174 mg, 94% purity, 234 μmol) (Intermediate C69) and trifluoroacetic acid/dibenzyl beta-alanyl-L-glutamate (1:1) (144 mg, 281 μmol) (Intermediate L115) were initially charged in 4.0 ml of DMF. HATU (107 mg, 281 μmol) and N,N-diisopropylethylamine (120 μl, 700 μmol) were added to the reaction mixture, which was stirred at RT for 10 min. The mixture was diluted with ethyl acetate and the organic phase was washed with water and sat. NaCl solution. The organic phase was dried over magnesium sulphate and the solvent was evaporated under reduced pressure. The residue was purified by means of preparative RP-HPLC (column: Reprosil 250×40; 10μ, flow rate: 50 ml/min, MeCN/water, 0.1% TFA). The solvents were evaporated under reduced pressure and the residue was dried under high vacuum. This gave 229 mg (85% of theory) of the compound dibenzyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-beta-alanyl-L-glutamate.

LC-MS (Method 1): $R_t$=1.55 min; MS (ESIpos): m/z=1082 $[M+H]^+$

Dibenzyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-beta-alanyl-L-glutamate (226 mg, 209 μmol) was dissolved in 10 ml of trifluoroethanol. Zinc chloride (171 mg, 1.25 mmol) was added to the reaction mixture, which was stirred at 50° C. for 1 h. Another two portions each of 6 eq. of $ZnCl_2$ were added and the mixture was stirred at 50° C. for 1 h each time. Ethylenediamine-N,N,N',N'-tetraacetic acid (1.10 g, 3.75 mmol) was added to the mixture and stirred briefly. The reaction mixture was taken up in acetonitrile, filtered through a syringe filter and purified by means of preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 182 mg (83% of theory) of the compound trifluoroacetic acid/dibenzyl N-[3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulfanyl)propanoyl]-beta-alanyl-L-glutamate (1:1).

LC-MS (Method 1): $R_t$=1.07 min; MS (ESIpos): m/z=938 $[M+H]^+$

Under argon, trifluoroacetic acid/dibenzyl N-[3-({2-[(3-aminopropyl) {(1R)-1-[1-benzyl-4-(2,5-difluorophenyl)-1H-pyrrol-2-yl]-2,2-dimethylpropyl}amino]-2-oxoethyl}sulfanyl)propanoyl]-beta-alanyl-L-glutamate (1:1) (55.0 mg, 52.3 μmol) and N-[(benzyloxy)carbonyl]-L-alanyl-L-alanyl-L-asparagine (26.0 mg, 62.7 μmol) (Intermediate L92) were initially charged in 2.5 ml of DMF. To the reaction mixture were added HATU (23.9 mg, 62.7 μmol) and N,N-diisopropylethylamine (27 μl, 160 μmol), and the mixture was stirred at RT for 10 min. 1 ml of water (0.1% TFA) was added to the mixture, which was purified directly by means of preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 54.6 mg (79% of theory) of the compound dibenzyl (2S)-2-{[(5S,8S,11S)-11-(2-amino-2-oxoethyl)-17-{(1R)-1-[1-benzyl-4-(2,5-difluorophenyl)-1H-pyrrol-2-yl]-2,2-dimethylpropyl}-5,8-dimethyl-3,6,9,12,18,23,27-heptaoxo-1-phenyl-2-oxa-20-thia-4,7,10,13,17,24-hexaazaheptacosan-27-yl]amino}pentanedioate.

LC-MS (Method 1): $R_t$=1.32 min; MS (ESIpos): m/z=1328 $[M+H]^+$

Dibenzyl (2S)-2-{[(5S,8S,11S)-11-(2-amino-2-oxoethyl)-17-{(1R)-1-[1-benzyl-4-(2,5-difluorophenyl)-1H-pyrrol-2-yl]-2,2-dimethylpropyl}-5,8-dimethyl-3,6,9,12,18,23,27-heptaoxo-1-phenyl-2-oxa-20-thia-4,7,10,13,17,24-hexaazaheptacosan-27-yl]amino}pentanedioate (53.3 mg, 40.1 μmol) were dissolved in 3.0 ml of ethyl acetate and 3.0 ml of ethanol, and 10% palladium on activated carbon (5.37 mg) was added. The reaction mixture was hydrogenated at RT and standard pressure overnight, and then filtered through a paper filter. The filtercake was washed with ethyl acetate and ethanol. The solvent was evaporated under reduced pressure. The residue was purified by means of preparative RP-HPLC (column: Reprosil 250×30; 10μ, flow rate: 50 ml/min, MeCN/water, 0.1% TFA). The solvents were evaporated under reduced pressure and the residue was lyophilized. This gave 5.6 mg (11% of theory) of the compound L-alanyl-L-alanyl-$N^1$-[(16S)-4-{(1R)-1-[1-benzyl-4-(2,5-difluorophenyl)-1H-pyrrol-2-yl]-2,2-dimethylpropyl}-16,18-dicarboxy-5,10,14-trioxo-7-thia-4,11,15-triazaoctadec-1-yl]-L-aspartamide/trifluoroacetic acid (1:1).

LC-MS (Method 1): $R_t$=0.81 min; MS (ESIpos): m/z=1014 $[M+H]^+$

L-Alanyl-L-alanyl-$N^1$-[(16S)-4-{(1R)-1-[1-benzyl-4-(2,5-difluorophenyl)-1H-pyrrol-2-yl]-2,2-dimethylpropyl}-16,18-dicarboxy-5,10,14-trioxo-7-thia-4,11,15-triazaoctadec-1-yl]-L-aspartamide/trifluoroacetic acid (1:1) (5.40 mg, 4.30 μmol) and 1-{6-[(2,5-dioxopyrrolidin-1-yl)oxy]-6-oxohexyl}-1H-pyrrole-2,5-dione (1.46 mg, 4.73 μmol) were initially charged in 0.49 ml of DMF. N,N-Diisopropylethylamine (2.2 μl, 13 μmol) was added to the reaction mixture, which was stirred at RT for 4 h 30. 0.5 ml of water (0.1% TFA) was added to the mixture, which was purified directly by means of preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 43.1 mg 4.10 mg (72% of theory) of the title compound.

LC-MS (Method 1): $R_t$=0.97 min; MS (ESIpos): m/z=1207 $[M+H]^+$

Intermediate Q42

Trifluoroacetic Acid/N-[(benzyloxy)carbonyl]-L-alanyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide (1:1)

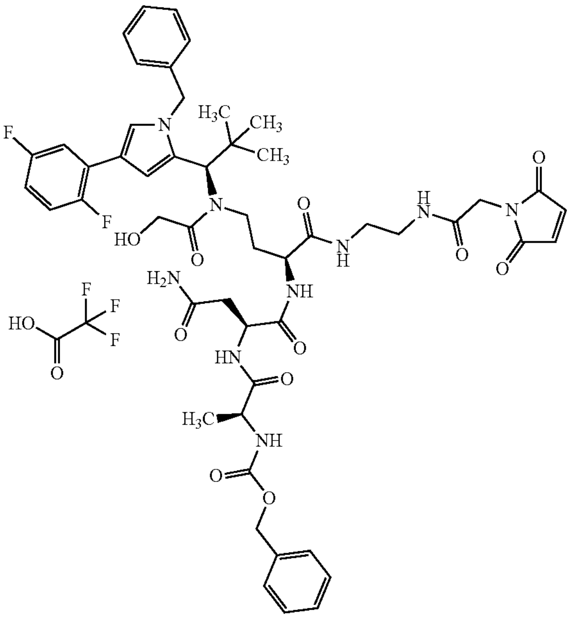 [SMILES: C[C@H](NC(=O)OCc1ccccc1)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O ; O=C(O)C(F)(F)F]

Trifluoroacetic acid/$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}-ethyl)amino]-1-oxobutan-2-yl}-L-aspartamide (1:1) (10.0 mg, 10.9 μmol) (Intermediate C116) and N-[(benzyloxy)carbonyl]-L-alanine (2.42 mg, 10.9 μmol) were initially charged in 1.0 ml of DMF. HATU (4.95 mg, 13.0 μmol) and N,N-diisopropylethylamine (9.5 μl, 54 μmol) were added to the reaction mixture, which was stirred at RT for 10 min. 1.0 ml of water (0.1% TFA) was added to the mixture, which was purified directly by means of preparative RP-HPLC (column: Reprosil 250×30; 10μ, flow rate: 50 ml/min, MeCN/water, 0.1% TFA). The solvents were evaporated under reduced pressure and the residue was lyophilized. This gave 5.6 mg (46% of theory) of the title compound.

LC-MS (Method 1): $R_t$=1.11 min; MS (ESIpos): m/z=1012 $[M+H]^+$

Intermediate Q43

N-[(Benzyloxy)carbonyl]-L-alpha-asparagyl-N¹-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide/trifluoroacetic Acid (1:1)

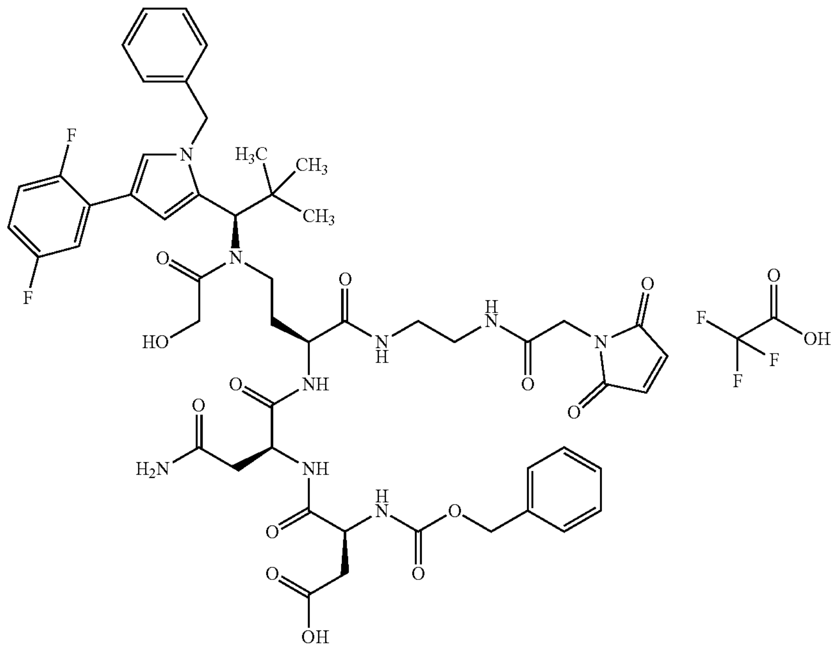

10 mg (0.011 mmol) of Intermediate C116 were taken up in 4 ml of DMF, and 3.9 mg (0.012 mmol) of (2S)-2-{[(benzyloxy)carbonyl]amino}-4-tert-butoxy-4-oxobutanoic acid and 6.2 mg (0.016 mmol) of HATU and 6 µl of N,N-diisopropylethylamine were added. After stirring at RT for 15 min, the mixture was concentrated and the residue was purified by preparative HPLC. The appropriate fractions were concentrated and the residue was lyophilized from acetonitrile/water. 8.2 mg (68% of theory) of the protected intermediate were obtained, which was then deprotected with 6 mg (0.044 mmol) of zinc chloride in 4 ml of trifluoroethanol at 50° C. After addition of 13 mg (0.044 mmol) of EDTA followed by HPLC purification, 3 mg (35% of theory) of the title compound were obtained.

LC-MS (Method 1): $R_t$=1.05 min; MS (ESIpos): m/z=1056 (M+H)⁺.

Intermediate Q44

N-[(Benzyloxy)carbonyl]-L-alanyl-L-alpha-asparagyl-$N^1$-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide/trifluoroacetic Acid (1:1)

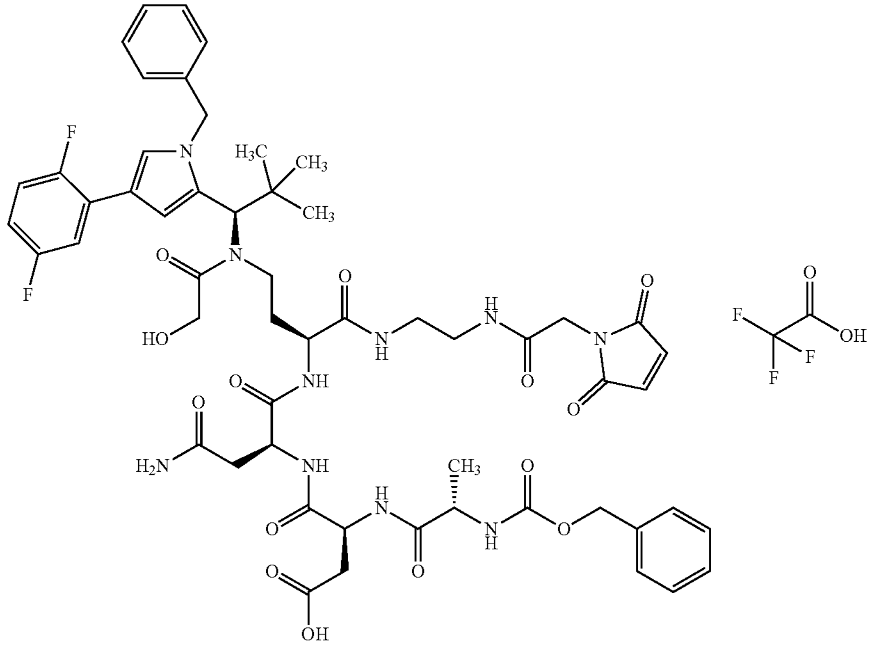 [SMILES: C[C@H](NC(=O)OCc1ccccc1)C(=O)N[C@@H](CC(=O)O)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O ; O=C(O)C(F)(F)F]

10 mg (0.011 mmol) of Intermediate C116 were taken up in 4 ml of DMF, and 5.3 mg (0.013 mmol) of (2S)-2-{[(2S)-2-{[(benzyloxy)carbonyl]amino}propanoyl]amino}-4-tert-butoxy-4-oxobutanoic acid and 6.2 mg (0.016 mmol) of HATU and 6 μl of N,N-diisopropylethylamine were added. After stirring at RT for 15 min, the mixture was concentrated and the residue was purified by preparative HPLC. The appropriate fractions were concentrated and the residue was lyophilized from acetonitrile/water. 8 mg (57% of theory) of the protected intermediate were obtained, which was then deprotected with 5 mg (0.037 mmol) of zinc chloride in 2 ml of trifluoroethanol at 50° C. After addition of 11 mg (0.037 mmol) of EDTA followed by HPLC purification, 3.5 mg (46% of theory) of the title compound were obtained.

LC-MS (Method 1): $R_t$=1.04 min; MS (ESIpos): m/z=1127 $(M+H)^+$.

B: Preparation of Antibody/Drug Conjugates (ADC)

B-1. General Process for Generating Antibodies

A complete human antibody phage library (Hoet R M et al, Nat Biotechnol 2005; 23(3):344-8) was employed to isolate TWEAKR-specific human monoclonal antibodies by protein panning (Hoogenboom H. R., Nat Biotechnol 2005; 23(3):1105-16) using dimeric Fc-fused extracellular domains of human and mouse TWEAKR as immobilized target. Fab phages were identified, and the corresponding antibodies were reformatted to the human IgG1 format. The aglycosylated antibody TPP-2658 was generated by introducing the mutation N297A in the heavy chain of TPP-2090 (Kabat numbering system of immunoglobulins). The antibody thus obtained was used for the working examples described here. In addition, antibodies which bind to TWEAKR are known to the person skilled in the art, see, for example, WO2009/020933(A2) or WO2009140177 (A2).

The commercially available antibodies cetuximab (trade name: Erbitux), trastuzumab (trade name: Herceptin; INN 7637, CAS No: RN: 180288-69-1) and nimotuzumab (trade name: CIMAher) were used for the working examples described here.

For trastuzumab-HC-N297A (corresponding to TPP-7510), a heavy chain with SEQ ID NO: 244 was used. The light chain is identical to the light chain from trastuzumab.

For trastuzumab-HC-N297Q (corresponding to TPP-7511), a heavy chain with SEQ ID NO: 245 was used. The light chain is identical to the light chain from trastuzumab.

B-2. General Process for Expressing Antibodies in Mammalian Cells

The antibodies, for example TPP-2658, TPP-7510 or TPP-7511, were produced in transient mammalian cell cultures as described by Tom et al., Chapter 12 in Methods Express: Expression Systems edited by Micheal R. Dyson and Yves Durocher, Scion Publishing Ltd, 2007.

B-3. General Process for Purifying Antibodies from Cell Supernatants

The antibodies, for example TPP-2658, TPP-7510 or TPP-7511, were obtained from the cell culture supernatants. The cell supernatants were clarified by centrifugation of cells. The cell supernatant was then purified by affinity chromatography on a MabSelect Sure (GE Healthcare) chromatography column. To this end, the column was equilibrated in DPBS pH 7.4 (Sigma/Aldrich), the cell supernatant was applied and the column was washed with about 10 column volumes of DPBS pH 7.4+500 mM sodium chloride. The antibodies were eluted in 50 mM sodium acetate pH 3.5+500 mM sodium chloride and then purified further by gel filtration chromatography on a Superdex 200 column (GE Healthcare) in DPBS pH 7.4.

The commercially available antibodies were purified from the commercial products by standard chromatography methods (protein A chromatography, preparative gel filtration chromatography (SEC—size exclusion chromatography)).

B-4. General Process for Coupling to Cysteine Side Chains

The following antibodies were used in the coupling reactions:

Examples a: cetuximab (anti EGFR AK)
Examples e: trastuzumab (anti-Her2 AK)
Examples i: nimotuzumab (anti-EGFR AK)
Examples k: TPP-2658 (anti-TWEAKR AK)

The coupling reactions were usually carried out under argon.

Between 2 and 5 equivalents of tris(2-carboxyethyl)phosphine hydrochloride (TCEP), dissolved in PBS buffer, were added to a solution of the appropriate antibody in PBS buffer in the concentration range between 1 mg/ml and 20 mg/ml, preferably in the range of about 10 mg/ml to 15 mg/ml, and the mixture was stirred at RT for 1 h. For this purpose, the solution of the respective antibody used can be employed at the concentrations stated in the working examples, or it may optionally also be diluted with PBS buffer to about half of the stated starting concentrations in order to get into the preferred concentration range. Subsequently, depending on the intended loading, from 2 to 12 equivalents, preferably about 5-10 equivalents of the maleinimide precursor compound or halide precursor compound to be coupled were added as a solution in DMSO. Here, the amount of DMSO should not exceed 10% of the total volume. The reaction was stirred in the case of maleinimide precursors for 60-240 min at RT and in the case of halide precursors between 8 and 24 h at RT and then applied to PBS-equilibrated PD 10 columns (Sephadex® G-25, GE Healthcare) and eluted with PBS buffer. Generally, unless indicated otherwise, 5 mg of the antibody in question in PBS buffer were used for the reduction and the subsequent coupling. Purification on the PD10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution. The respective protein concentrations, stated in the working examples, of the ADC solutions were determined. Furthermore, antibody loading (drug/mAb ratio) was determined using the methods described under B-7.

Depending on the linker, the ADCs shown in the examples may also be present to a lesser or higher degree in the form of the hydrolysed open-chain succinamides attached to the antibodies.

In particular the KSP-I-ADCs attached though the linker substructure

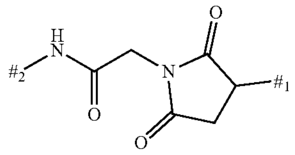

to thiol groups of the antibodies may optionally also be prepared in a targeted manner by rebuffering after the coupling and stirring at pH 8 for about 20-24 h according to Scheme 28 via the ADCs attached via open-chain succinamides.

#1 represents the sulphur bridge to the antibody, and #2 the point of attachment to the modified KSP inhibitor Such ADCs where the linker is attached to the antibodies through hydrolysed open-chain succinamides may optionally also be prepared in a targeted manner by an exemplary procedure as follows:

Small-Scale Coupling:

To a solution of 2-5 mg of the appropriate antibody in PBS buffer in the concentration range between 1 mg/ml and 20 mg/ml, preferably in the range from about 5 mg/ml to 15 mg/ml, were added between 2 und 5 equivalents of tris(2-carboxyethyl)phosphine hydrochloride (TCEP), dissolved in PBS buffer, and the mixture was stirred at RT for 30 min to 1 h. For this purpose, it is possible to use the solution of the antibody used in each case in the concentration specified in the working examples or else, if necessary, to dilute it with PBS buffer down to about half the starting concentration specified in order to arrive in the preferred concentration range. Subsequently, according to the loading desired, between 2 and 12 equivalents, preferably about 5-10 equivalents, of the maleimide precursor compound to be coupled are added as a solution in DMSO. The amount of DMSO here should not exceed 10% of the total volume. The mixture was stirred at RT for 60-240 min and then diluted to a volume of 3-7 ml with PBS buffer which had previously been adjusted to pH 8, and stirred at RT under argon overnight. This solution was then passed through a PD 10 column (Sephadex® G-25, GE Healthcare) equilibrated to pH 7.2 with PBS buffer, and eluted with PBS buffer pH 7.2. This was followed by concentration by ultracentrifugation and redilution with PBS buffer (pH 7.2).

Medium-Scale Coupling:

Under argon, a solution of 0.344 mg TCEP in 100 µl of PBS buffer was added to 60 mg of the antibody in question in 5 ml of PBS buffer (c~12 mg/ml). The reaction was stirred at RT for 30 min, and 0.003 mmol of a maleinimide precursor compound dissolved in 600 µl of DMSO was then added. After a further 1.5 h-2 h of stirring at RT, the reaction was diluted with 1075 µl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was diluted with PBS buffer pH 8 to a total volume of 14 ml. This solution was stirred at RT under argon overnight. If required, the solution was then rebuffered to pH 7.2. The ADC solution was concentrated by ultracentrifugation, rediluted with PBS buffer (pH 7.2) and then optionally concentrated again to a concentration of about 10 mg/ml.

Other potentially hydrolysis-sensitive thianylsuccinimide bridges to the antibody in the working examples contain the following linker substructures, where #1 represents the thioether linkage to the antibody and #1 the point of attachment to the modified KSP inhibitor:

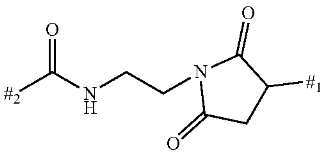

-continued

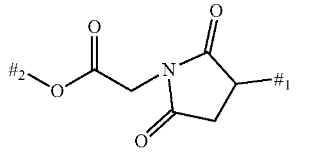

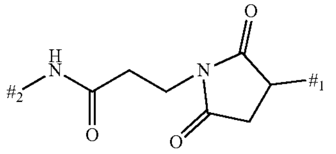

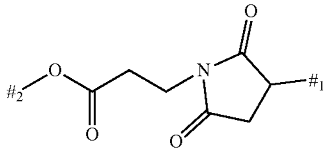

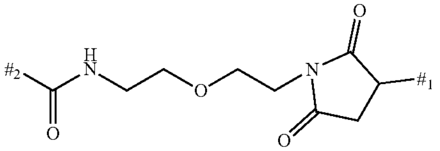

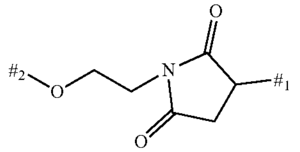

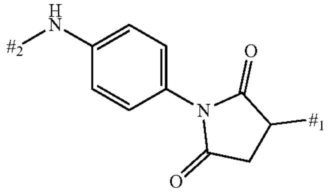

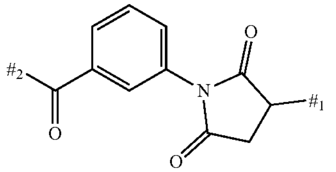

These linker substructures represent the linking unit to the antibody and have (in addition to the further linker composition) a significant effect on the structure and the profile of the metabolites formed in the tumour cells.

In the structural formulae shown, $AK_1$ can mean

Examples a: cetuximab (partially reduced)-S§$^1$

Examples e: trastuzumab (partially reduced)-S§$^1$

Examples i: nimotuzumab (partially reduced)-S§$^1$

Examples k: anti-TWEAKR antibody TPP-2658 (partially reduced)-S§$^1$ where

§$^1$ represents the linkage to the succinimide group or to any isomeric hydrolysed open-chain succinamides or the alkylene radical resulting therefrom, and S represents the sulphur atom of a cysteine residue of the partially reduced antibody.

B-5. General Process for Coupling to Lysine Side Chains

The following antibodies were used for the coupling reactions:

Examples a: cetuximab (anti EGFR AK)

Examples e: trastuzumab (anti-Her2 AK)

Examples i: nimotuzumab (anti-EGFR AK)

Examples k: TPP-2658 (anti-TWEAKR antibody)

The coupling reactions were usually carried out under argon.

From 2 to 8 equivalents of the precursor compound to be coupled were added as a solution in DMSO to a solution of the antibody in question in PBS buffer in a concentration range between 1 mg/ml and 20 mg/ml, preferably about 10 mg/ml, depending on the intended loading. After 30 min to 6 h of stirring at RT, the same amount of precursor compound in DMSO was added again. Here, the amount of DMSO should not exceed 10% of the total volume. After a further 30 min to 6 h of stirring at RT, the reaction was applied to PD 10 columns (Sephadex® G-25, GE Healthcare) equilibrated with PBS and eluted with PBS buffer. Generally, unless indicated otherwise, 5 mg of the antibody in question in PBS buffer were used for the coupling. Purification on the PD10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution.

The respective protein concentrations, stated in the working examples, of the ADC solutions were determined. Furthermore, antibody loading (drug/mAb ratio) was determined using the methods described under B-7.

In the structural formulae shown, $AK_2$ has the meaning

Examples a: cetuximab—NH§$^2$

Examples e: trastuzumab—NH§$^2$

Examples i: nimotuzumab—NH§$^2$

Examples k: anti-TWEAKR antibody TPP-2658—NH—§$^2$ where

§$^2$ represents the linkage to the carbonyl group and

NH represents the side-chain amino group of a lysine residue of the antibody.

B-5a. General Method for ADC Synthesis by Means of Bacterial Transglutaminase

In the coupling reactions in example series t, the antibodies which follow were used (the antibody-HC-N297Z nomenclature which follows means the antibody where the amino acid N297 (Kabat numbering) has been exchanged for the amino acid Z in both heavy chains, the TPP-XXXX-HC-Q295N-HC-N297Q nomenclature means the antibody with the TPP-XXXX where the amino acid Q295 (Kabat numbering) has been exchanged for the amino acid N and the amino acid N297 (Kabat numbering) has been exchanged for the amino acid Q in both heavy chains. The antibody name of the original antibody may either be reported as the name (for example trastuzumab) or as TPP-XXXX (antibody with the TPP number XXXX)):

$AK_{3a}$: anti-TWEAKR antibody TPP-2658 (corresponding to TPP-2090-HC-N297A)

$AK_{3b}$: anti-TWEAKR antibody TPP-5442 (corresponding to TPP-2090-HC-N297Q)

$AK_{3c}$: anti-TWEAKR antibody TPP-8225 (corresponding to TPP-2090-HC-Q295N-HC-N297Q)

$AK_{3d}$: TPP-7510 (corresponding to trastuzumab-HC-N297A)

$AK_{3e}$: TPP-7511 (corresponding to trastuzumab-HC-N297Q)

General Method for Achieving a Maximum DAR of 2:

To a solution of 5 mg of the corresponding aglyco antibody variant (HC-N297A, or HC-Q295N-HC-N297Q) in DPBS pH 7.4 (c~5-15 mg/ml) were added 20 μl (6 equivalents) of a solution of a suitable toxophore linker precursor (e.g. Intermediate Q31-Q34; 10 mM solution in DMSO). After incubation at 37° C. for 5 min, 50 μl of a solution of recombinant bacterial transglutaminase solution in water (product number T001 from Zedira GmbH, Darmstadt, Germany) (25 U/ml) were added and incubation was continued at 37° C. for 24 h. Then the reaction mixture was diluted with DPBS pH 7.4 to a total volume of 2.5 ml and passed by gel filtration through DPBS-equilibrated PD 10 columns (Sephadex® G-25, GE Healthcare) and eluted with DPBS buffer at pH 7.4. Subsequently, the ADC volume was concentrated by means of Amicon Ultracel-30K Zentrifugation (Millipore), and it was rediluted again with DPBS to a volume of 2.5 ml. Finally, 0.00625 μmol of the b-transglutaminase blocker Zedira C100 in 12.5 μl of DPBS was added to the solution. The respective protein concentrations, stated in the working examples, of the ADC solutions were determined. Furthermore, antibody loading (drug/mAb ratio) was determined using the methods described under B-7.

General Method for Achieving a Maximum DAR of 4:

To a solution of 5 mg of the corresponding aglyco antibody variant (HC-N297Q) in DPBS pH 7.4 (c~5-15 mg/ml) were added 16-24 equivalents of a solution of a suitable toxophore linker precursor (e.g. Intermediate Q31-Q34; 10 mM solution in DMSO). After incubation at 37° C. for 5 min, 400 μl (10 U) of a solution of recombinant bacterial transglutaminase solution in water (product number T001 from Zedira GmbH, Darmstadt, Germany) (25 U/ml) were added and incubation was continued at 37° C. for 24 h. Then the reaction mixture was diluted with DPBS pH 7.4 to a total volume of 2.5 ml and passed by gel filtration through DPBS-equilibrated PD 10 columns (Sephadex® G-25, GE Healthcare) and eluted with DPBS buffer at pH 7.4. Subsequently, the ADC volume was concentrated by means of Amicon Ultracel-30K Zentrifugation (Millipore), and it was rediluted again with DPBS to a volume of 2.5 ml. Finally, 0.1 μmol of the b-transglutaminase blocker Zedira C100 in 200 μl of DPBS was added to the solution. The respective protein concentrations, stated in the working examples, of the ADC solutions were determined. Furthermore, antibody loading (drug/mAb ratio) was determined using the methods described under B-7.

General Method for Transglutaminase-Mediated Coupling on a Larger Scale in Order to Achieve a Maximum DAR of 2:

To a solution of 30 mg of the aglycosylated variant (HC-N297A, HC-Q295N-HC-N297Q) of the particular antibody in DPBS pH 7.4 (c~5-15 mg/ml) were added 6 equivalents of a solution of the appropriate toxophore linker precursor (10 mM in DMSO). After incubation at 37° C. for 5 min, 200 μl (7.5 U) of a solution of recombinant bacterial transglutaminase in water (product number T001 from Zedira GmbH, Darmstadt, Germany) (25 U/ml) were added and incubation was continued at 37° C. for a further 24 h. The reaction mixture was purified via gel filtration chromatography on a Superdex 200 column (GE Healthcare) in DPBS pH 7.4 in order to separate small molecules and the transglutaminase from the ADC. Subsequently, the ADC solution was concentrated by means of Amicon Ultracel-30K centrifugation tube (Millipore) to final concentrations of 5-25 mg/ml. The solution was then sterile-filtered.

The respective concentrations of the ADC solutions stated in the working examples were determined. The loading was determined by the methods described in chapter B7. The ADC batches were characterized as indicated in the working examples.

General Method for Transglutaminase-Mediated Coupling on a Larger Scale in Order to Achieve a Maximum DAR of 4:

To a solution of 30 mg of the aglycosylated variant (HC-N297Q) of the particular antibody in DPBS pH 7.4 (c~5-15 mg/ml) were added 16-24 equivalents of a solution of the appropriate toxophore linker precursor (10 mM in DMSO). After incubation at 37° C. for 5 min, 2400 μl (60 U) of a solution of recombinant bacterial transglutaminase in water (product number T001 from Zedira GmbH, Darmstadt, Germany) (25 U/ml) were added and incubation was continued at 37° C. for a further 24 h. The reaction mixture was purified via gel filtration chromatography on a Superdex 200 column (GE Healthcare) in DPBS pH 7.4 in order to separate small molecules and the transglutaminase from the ADC. Subsequently, the ADC solution was concentrated by means of Amicon Ultracel-30K centrifugation tube (Millipore) to final concentrations of 5-25 mg/ml. The solution was then sterile-filtered.

The respective concentrations of the ADC solutions stated in the working examples were determined. The loading was determined by the methods described in chapter B7. The ADC batches were characterized as indicated in the working examples.

In the structural formulae shown for example series t, $AK_3$ in each case has the following meaning:

$AK_{3a}$: anti-TWEAKR antibody (TPP-2658) (corresponding to TPP-2090-HC-N297A)-CO—§ 2

$AK_{3b}$: anti-TWEAKR antibody (TPP-5442) (corresponding to TPP-2090-HC-N297Q)-CO—§ 2

$AK_{3c}$: anti-TWEAKR antibody (TPP-8225) (corresponding to TPP-2090-HC-Q295N-HC-N297Q)-CO—§ 2

$AK_{3d}$: TPP-7510 (corresponding to trastuzumab-HC-N297A)-CO—$§_2$ $AK_{3e}$: TPP-7511 (corresponding to trastuzumab-HC-N297Q)-CO—$§_2$ where $§^2$ means the linkage to the amino group of a toxophore linker precursor, and CO represents the side-chain carbonyl group of a glutamine residue of the antibody.

B-6a. General Process for Preparing Closed Succinimide-Cysteine Adducts:

In an exemplary embodiment, 10 μmol of the maleinimide precursor compounds described above were taken up in 3-5 ml of DMF, and 2.1 mg (20 μmol) of L-cysteine were added. The reaction mixture was stirred at RT for 2 h to 24 h, then concentrated under reduced pressure and then purified by preparative HPLC.

B-6aa. General Process for Preparing Isomeric Open Succinamide-Cysteine Adducts:

In an exemplary embodiment, 68 μmol of the maleinimide precursor compounds described above were taken up in 15 ml of DMF, and with 36 mg (136 μmol) of N-{[2-(trimethylsilyl)ethoxy]carbonyl}-L-cysteine were added. The reaction mixture was stirred at RT for ~20 h, then concentrated under reduced pressure and then purified by preparative HPLC. The appropriate fractions were combined and the solvents were evaporated under reduced pressure, and the residue was then dissolved in 15 ml of THF/water 1:1. 131 μl of a 2M aqueous lithium hydroxide solution were added and the reaction was stirred at RT for 1 h. The reaction was then neutralized with a 1M hydrochloric acid, the solvent was evaporated under reduced pressure and the residue was purified by preparative HPLC. This gave ~50% of theory of the regioisomeric protected intermediates as a colourless foam.

In the last step, 0.023 mmol of these regioisomeric hydrolysis products were dissolved in 3 ml of 2,2,2-trifluoroethanol. 12.5 mg (0,092 mmol) of zinc chloride were added, and the reaction was stirred at 50° C. for 4 h. 27 mg (0.092 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave the hydrolysed open sulphanylsuccinamides as a regioisomer mixture.

Further Purification and Characterization of the Conjugates According to the Invention After the reaction, in some instances the reaction mixture was concentrated, for example by ultrafiltration, and then desalted and purified by chromatography, for example using a Sephadex® G-25 column. Elution was carried out, for example, with phosphate-buffered saline (PBS). The solution was then sterile filtered and frozen. Alternatively, the conjugate can be lyophilized.

B-7. Determination of the Antibody, the Toxophore Loading and the Proportion of Open Cysteine Adducts For protein identification in addition to molecular weight determination after deglycosylation and/or denaturing, a tryptic digestion was carried out which, after denaturing, reduction and derivatization, confirms the identity of the protein via the tryptic peptides found.

The toxophore loading of the PBS buffer solutions obtained of the conjugates described in the working example was determined as follows:

Determination of toxophore loading of lysine-linked ADCs was carried out by mass spectrometric determination of the molecular weights of the individual conjugate species. Here, the antibody conjugates were first deglycosylated with PNGaseF, and the sample was acidified and, after HPLC separation/desalting, analysed by mass spectrometry using ESI-MicroTof$_Q$ (Bruker Daltonik). All spectra over the signal in the TIC (Total Ion Chromatogram) were added and the molecular weight of the different conjugate species was calculated based on MaxEnt deconvolution. The DAR (=drug/antibody ratio) was then calculated after signal integration of the different species.

The toxophore loading of cysteine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 μl) were added to the ADC solution (1 mg/ml, 50 μl). The mixture was incubated at 55° C. for one hour and analysed by HPLC.

HPLC analysis was carried out on an Agilent 1260 HPLC system with detection at 220 nm. A Polymer Laboratories PLRP-S polymeric reversed-phase column (catalogue number PL1912-3802) (2.1×150 mm, 8 μm particle size, 1000 Å) was used at a flow rate of 1 ml/min with the following gradient: 0 min, 25% B; 3 min, 25% B; 28 min, 50% B. Mobile phase A consisted of 0.05% trifluoroacetic acid (TFA) in water, mobile phase B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the light chain with one toxophore (L1) and the heavy chains with one, two and three toxophores (H1, H2, H3).

Average loading of the antibody with toxophores was calculated from the peak areas determined by integration as double the sum of HC load and LC load, where LC load is calculated from the sum of the toxophore number-average weighed integration results of all LC peaks divided by the sum of the singly weighed integration results of all LC peaks, and where the HC-load is calculated from the sum of the toxophore number-average weighed integration results of all HC peaks divided by the sum of the singly weighed integration results of all HC peaks. In individual cases, it may not be possible to determine the toxophore load accurately owing to co-elutions of some peaks.

In the cases where light and heavy chains could not be separated sufficiently by HPLC, determination of toxophore loading of cysteine-linked conjugates was carried out by mass spectrometric determination of the molecular weights of the individual conjugate species at light and heavy chain.

Guanidinium hydrochloride (GuHCl) (28.6 mg) and a solution of DL-dithiothreitol (DTT) (500 mM, 3 μl) were added to the ADC solution (1 mg/ml, 50 μl). The mixture was incubated for one hour at 55° C. and analysed by mass spectrometry after online desalting using ESI-MicroTof$_Q$ (Bruker Daltonik).

For the DAR determination, all spectra were added over the signal in the TIC (Total Ion Chromatogram), and the molecular weight of the different conjugate species at light and heavy chain was calculated based on MaxEnt deconvolution. Average loading of the antibody with toxophores was calculated from the peak areas determined by integration as double the sum of HC load and LC load, where LC load is calculated from the sum of the toxophore number-average weighed integration results of all LC peaks divided by the sum of the singly weighed integration results of all LC peaks, and where the HC-load is calculated from the sum of the toxophore number-average weighed integration results of all HC peaks divided by the sum of the singly weighed integration results of all HC peaks.

To determine the proportion of the open cysteine adduct, the molecular weight area ratio of closed to open cysteine adduct (molecular weight delta 18 Dalton) of all singly conjugated light and heavy chain variants was determined. The mean of all variants yielded the proportion of the open cysteine adduct.

The toxophore loading of glutamine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 μl) were added to the ADC solution (1 mg/ml, 50 μl). The mixture was incubated at 55° C. for one hour and analysed by HPLC.

HPLC analysis was carried out on an Agilent 1260 HPLC system with detection at 220 nm. A Polymer Laboratories PLRP-S polymeric reversed-phase column (catalogue number PL1912-3802) (2.1×150 mm, 8 μm particle size, 1000 Å) was used at a flow rate of 1 ml/min with the following gradient: 0 min, 31% B; 1 min, 31% B; 14 min, 38% B, 16 min, 95% B. Mobile phase A consisted of 0.05% trifluoroacetic acid (TFA) in water, mobile phase B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the light chain with one toxophore (L1) and the heavy chains with one and two toxophores (H1, H2).

Average loading of the antibody with toxophores was calculated from the peak areas determined by integration as double the sum of HC load and LC load, where LC load is calculated from the sum of the toxophore number-average weighed integration results of all LC peaks divided by the sum of the singly weighed integration results of all LC peaks, and where the HC load is calculated from the sum of the toxophore number-average weighed integration results of all HC peaks divided by the sum of the singly weighed integration results of all HC peaks.

Alternatively, determination of toxophore loading of glutamine-linked ADCs was carried out by mass spectrometric determination of the molecular weights of the individual conjugate species. Here, the antibody conjugates were first deglycosylated with PNGaseF, and the sample was acidified and, after HPLC separation/desalting, analysed by mass spectrometry using ESI-MicroTof$_Q$ (Bruker Daltonik). All spectra over the signal in the TIC (Total Ion Chromatogram) were added and the molecular weight of the different conjugate species was calculated based on MaxEnt deconvolution. The DAR (=drug/antibody ratio) was then calculated after signal integration of the different species.

B-8. Checking the Antigen-Binding of the ADCs

The capability of the binder of binding to the target molecule was checked after coupling had taken place. The person skilled in the art is familiar with multifarious methods which can be used for this purpose; for example, the affinity of the conjugate can be checked using ELISA technology or surface plasmon resonance analysis (BIAcore™ measurement). The conjugate concentration can be measured by the person skilled in the art using customary methods, for example for antibody conjugates by protein determination. (see also Doronina et al.; Nature Biotechnol. 2003; 21:778-784 und Polson et al., Blood 2007; 1102:616-623).

Metabolite Embodiments

Example M1

S-[1-(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-2,5-dioxopyrrolidin-3-yl]-L-cysteine/trifluoroacetic Acid (1:1)

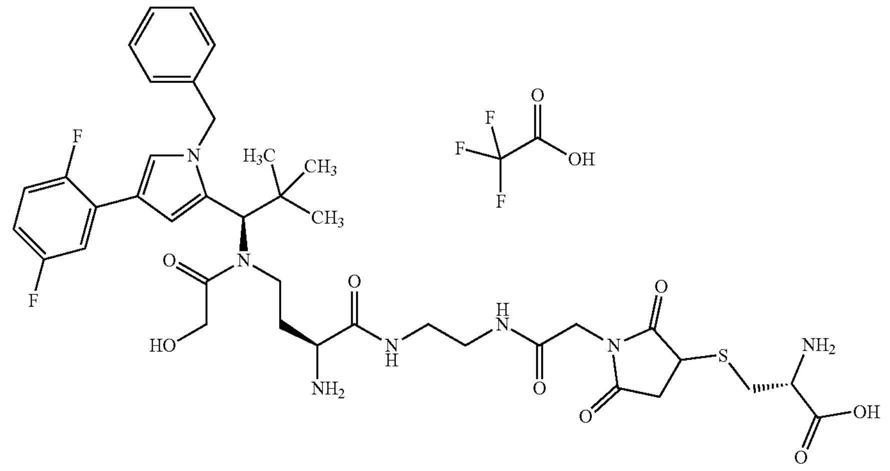 [SMILES: CC(C)(C)[C@H](c1cc(-c2cc(F)ccc2F)cn1Cc1ccccc1)N(CC[C@H](N)C(=O)NCCNC(=O)CN1C(=O)CC(SC[C@H](N)C(=O)O)C1=O)C(=O)CO ; O=C(O)C(F)(F)F]

1.8 mg (2 μmol) of Intermediate F104 were taken up in 1 ml of DMF, and 2.7 mg (22 μmol) of L-cysteine were added. The reaction mixture was stirred at RT for 20 h, then concentrated under reduced pressure and then purified by preparative HPLC. 0.6 mg (26% of theory) of the title compound remained as a colourless foam.

LC-MS (Method 1): $R_t$=0.80 min; MS (EIpos): m/z=814 $[M+H]^+$.

Example M2

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic Acid/Trifluoroacetic Acid (1:1) and 4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic Acid/Trifluoroacetic Acid (1:1)

of intermediate C66 were added to 130 μl of this solution, and the reaction was stirred at RT for 5 min. The mixture was then concentrated under reduced pressure, and the residue was purified by preparative HPLC. The solvent was evaporated under reduced pressure and the residue was dried under high vacuum. This gave 10 mg (89%) of the protected intermediate; it was not possible to separate the regioisomers neither by HPLC nor by LC-MS.

LC-MS (Method 1): $R_t$=1.38 min; MS (EIpos): m/z=1120 $[M+H]^+$.

In the last step, the 10 mg of this intermediate were dissolved in 2 ml of 2,2,2-trifluoroethanol. 12 mg (0.088 mmol) of zinc chloride were added, and the reaction was stirred at 50° C. for 30 min. 26 mg (0.088 mmol) of

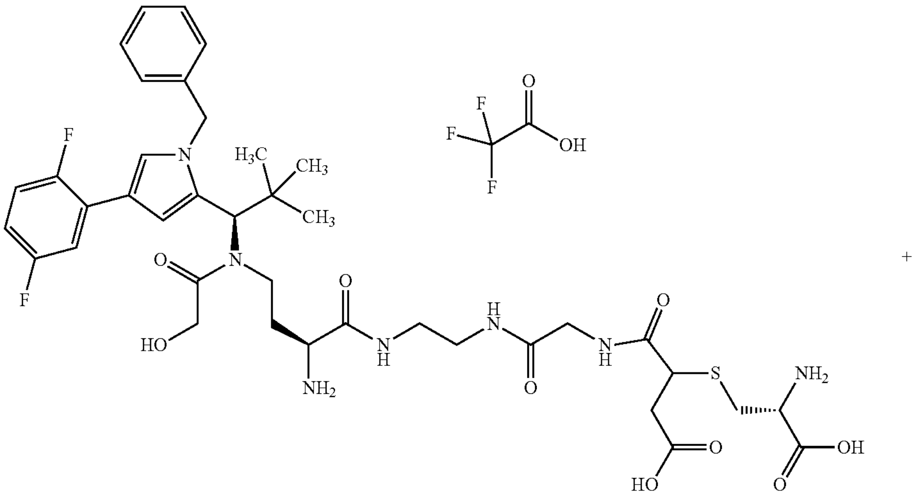

Isomer 1

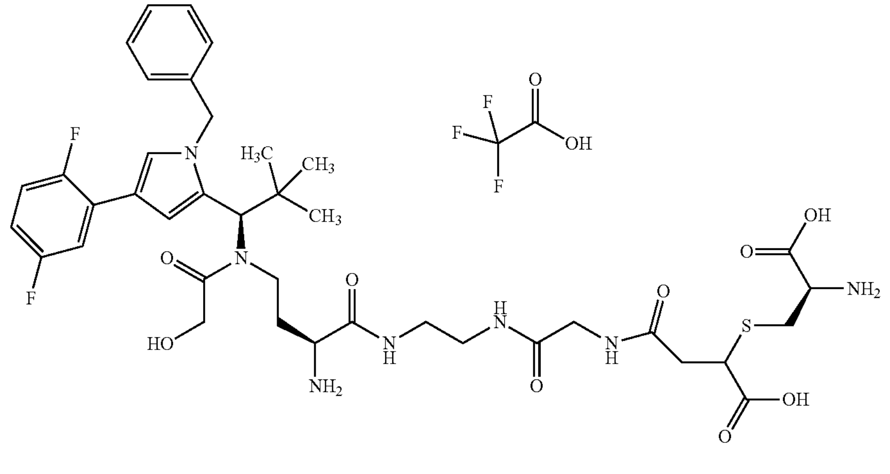

Isomer 2

LC-MS (Method 1): $R_t$=0.80 min; MS (EIpos): m/z=814 $[M+H]^+$.

First, L-cysteine was converted with 1-({[2-(trimethylsilyl)ethoxy]carbonyl}oxy)pyrrolidine-2,5-dione in DMF in the presence of N,N-diisopropylethylamine into N-{[2-(trimethylsilyl)ethoxy]carbonyl}-L-cysteine.

406 mg (1.53 mmol) of N-{[2-(trimethylsilyl)ethoxy]carbonyl}-L-cysteine were dissolved in 10 ml of DMF, 157.5 mg (1.606 mmol) of maleic anhydride were added and the reaction was stirred at RT for 1 hour. 7.5 mg (0.01 mmol) ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 8.3 mg (99% of theory) of the title compound as a regioisomer mixture in a ratio of 87:13.

LC-MS (Method 5): $R_t$=2.3 min and 2.43 min; MS (ESIpos): m/z=832 $(M+H)^+$.

$^1$H-NMR main regioisomer: (500 MHz, DMSO-$d_6$): δ=8.7 (m, 1H), 8.5 (m, 2H), 8.1 (m, 1H), 7.6 (m, 1H), 7.5 (s, 1H) 7.4-7.15 (m, 6H), 6.9-7.0 (m, 1H), 6.85 (s, 1H), 5.61 (s, 1H), 4.9 and 5.2 (2d, 2H), 4.26 and 4.06 (2d, 2H), 3.5-3.8 (m, 5H), 3.0-3.4 (m, 5H), 2.75-3.0 (m, 3H), 2.58 and 2.57 (dd, 1H), 0.77 and 1.5 (2m, 2H), 0.81 (s, 9H).

Alternatively, the regioisomeric title compounds were prepared as follows:

To this end, first L-cysteine was converted with 1-({[2-(trimethylsilyl)ethoxy]carbonyl}oxy)pyrrolidine-2,5-dione in DMF in the presence of N,N-diisopropylethylamine into N-{[2-(trimethylsilyl)ethoxy]carbonyl}-L-cysteine.

55 mg (0.068 mmol) of Intermediate F104 and 36 mg (0.136 mmol) of N-{[2-(trimethylsilyl) ethoxy]carbonyl}-L-cysteine were dissolved in 15 ml of DMF, and the mixture was stirred at RT for 20 h. The mixture was then concentrated and the residue was purified by preparative HPLC. The appropriate fractions were combined and the solvents were evaporated under reduced pressure, and the residue was then dissolved in 15 ml of THF/water 1:1. 131 µl of a 2M aqueous lithium hydroxide solution were added and the reaction was stirred at RT for 1 h. The reaction was then neutralized with a 1M hydrochloric acid, the solvent was evaporated under reduced pressure and the residue was purified by preparative HPLC. This gave 37 mg (50% of theory) of the regioisomeric protected intermediates as a colourless foam.

LC-MS (Method 5): $R_t$=3.33 min and 3.36 min; MS (ESIpos): m/z=976 $(M+H)^+$.

In the last step, 25 mg (0.023 mmol) of this intermediate were dissolved in 3 ml of 2,2,2-trifluoroethanol. 12.5 mg (0.092 mmol) of zinc chloride were added, and the reaction was stirred at 50° C. for 4 h. 27 mg (0.092 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 18.5 mg (85% of theory) of the title compound as a regioisomer mixture in a ratio of 21:79.

LC-MS (Method 5): $R_t$=2.37 min and 3.44 min; MS (ESIpos): m/z=832 $(M+H)^+$.

Example M3

4-[(2-{[(2R)-2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-3-{[(2R)-2-amino-2-carboxyethyl]sulphanyl}-4-oxobutanoic Acid/Trifluoroacetic Acid (1:1) and 4-[(2-{[(2R)-2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-2-{[(2R)-2-amino-2-carboxyethyl]sulphanyl}-4-oxobutanoic Acid/Trifluoroacetic Acid (1:1)

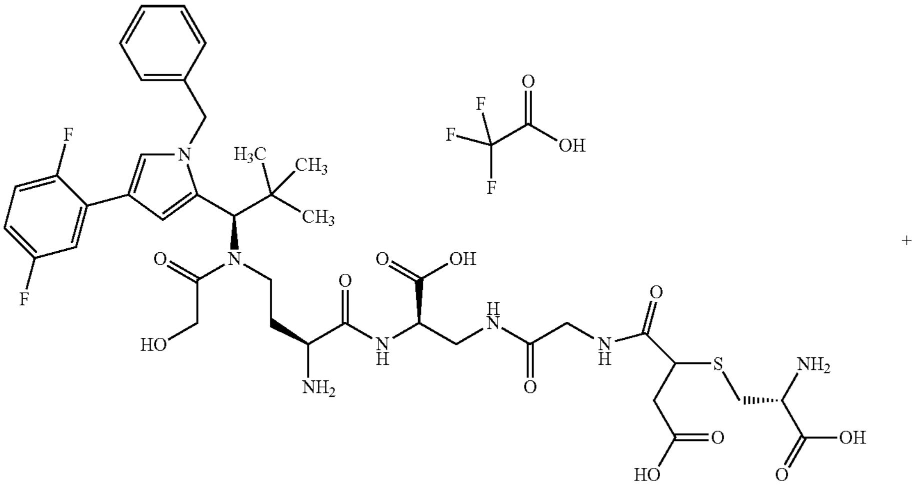

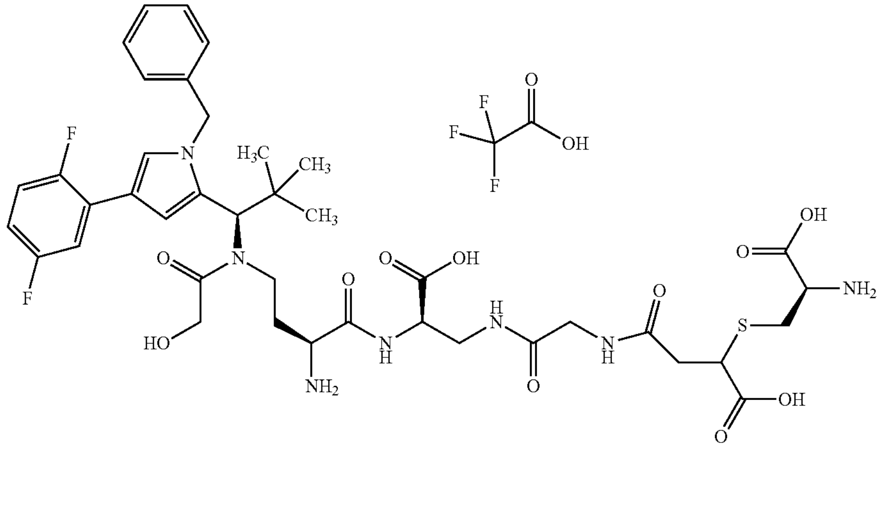

First, L-cysteine was converted with 1-({[2-(trimethylsilyl)ethoxy]carbonyl}oxy)pyrrolidine-2,5-dione in DMF in the presence of N,N-diisopropylethylamine into N-{[2-(trimethylsilyl)ethoxy]carbonyl}-L-cysteine.

11 mg (0.013 mmol) of Intermediate F193 and 8 mg (0.016 mmol) of N-{[2-(trimethylsilyl) ethoxy]carbonyl}-L-cysteine were dissolved in 3 ml of DMF, and the mixture was stirred at RT for 20 h. The mixture was then concentrated and the residue was purified by preparative HPLC.

The appropriate fractions were combined and the solvents were evaporated under reduced pressure, and the residue was then dissolved in 2 ml of THF/water 1:1. 19 μl of a 2M aqueous lithium hydroxide solution were added and the reaction was stirred at RT for 1 h. Another 19 μl of the 2M aqueous lithium hydroxide solution were then added and the reaction was stirred at RT overnight. The mixture was then neutralized with a 1M hydrochloric acid, the solvent was evaporated under reduced pressure and the residue was purified by preparative HPLC. This gave 4.1 mg (38% of theory) of the regioisomeric protected intermediates as a colourless foam.

LC-MS (Method 1): $R_t$=1.03 min (broad); MS (ESIpos): m/z=1020 $(M+H)^+$.

In the last step, 4.1 mg (0.004 mmol) of this intermediate were dissolved in 3 ml of 2,2,2-trifluoroethanol. 3 mg (0.022 mmol) of zinc chloride were added, and the reaction was stirred at 50° C. for 1 h. 6 mg (0.022 mmol) of ethylenediamine-N,N,N',N'-tetraacetic acid and 2 ml of a 0.1% strength aqueous trifluoroacetic acid were then added, and the solvent was evaporated under reduced pressure. The residue was purified by preparative HPLC. Concentration of the appropriate fractions and lyophilization of the residue from acetonitrile/water gave 5 mg (quant.) of the title compound as a regioisomer mixture in a ratio of 20:80.

LC-MS (Method 1): $R_t$=0.78 min (broad); MS (ESIpos): m/z=876 $(M+H)^+$.

LC-MS (Method 5): $R_t$=2.36 min and 2.39 min; MS (ESIpos): m/z=876 $(M+H)^+$.

Example M4

S-(1-{2-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethoxy]ethyl}-2,5-dioxopyrrolidin-3-yl)-L-cysteine/trifluoroacetic Acid (1:1)

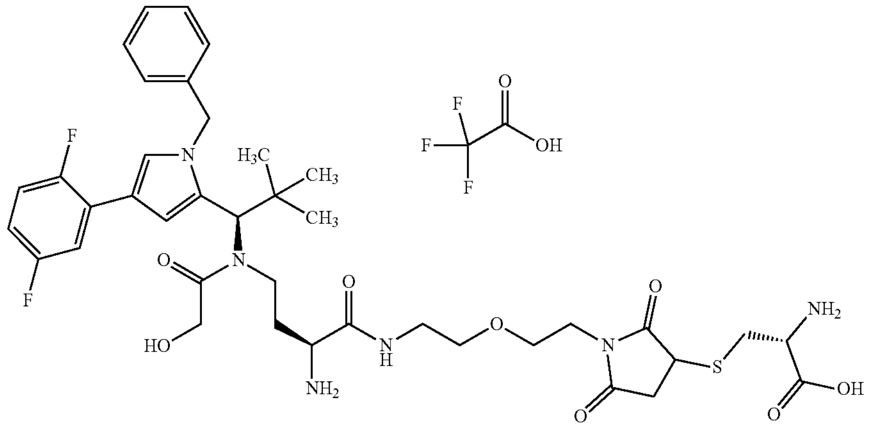 [SMILES: CC(C)(C)[C@H](c1cc(-c2cc(F)ccc2F)cn1Cc1ccccc1)N(CC[C@H](N)C(=O)NCCOCCN1C(=O)CC(SC[C@H](N)C(=O)O)C1=O)C(=O)CO ; O=C(O)C(F)(F)F]

3 mg (4 μmol) of Intermediate F248 were taken up in 2 ml of DMF, and 0.9 mg (8 μmol) of L-cysteine were added. The reaction mixture was stirred at RT for 18 h and then concentrated under reduced pressure. The residue was purified by preparative HPLC. The appropriate fractions were concentrated, giving, after lyophilization of the residue from acetonitrile/water, 1.1 mg (32% of theory) of the title compound as a white solid.

LC-MS (Method 1): $R_t$=0.78 min; MS (EIpos): m/z=801 $[M+H]^+$.

Example M5

(3R,7S)-7-amino-17-{[(2R)-2-amino-2-carboxyethyl]sulphanyl}-3-[1-benzyl-4-(2,5-difluorophenyl)-1H-pyrrol-2-yl]-4-glycoloyl-2,2-dimethyl-8,16-dioxo-12-oxa-4,9,15-triazanonadecan-19-oic Acid/Trifluoroacetic Acid (1:1) and (3R,7S)-7-amino-18-{[(2R)-2-amino-2-carboxyethyl]sulphanyl}-3-[1-benzyl-4-(2,5-difluorophenyl)-1H-pyrrol-2-yl]-4-glycoloyl-2,2-dimethyl-8,16-dioxo-12-oxa-4,9,15-triazanonadecan-19-oic Acid/Trifluoroacetic Acid (1:1)

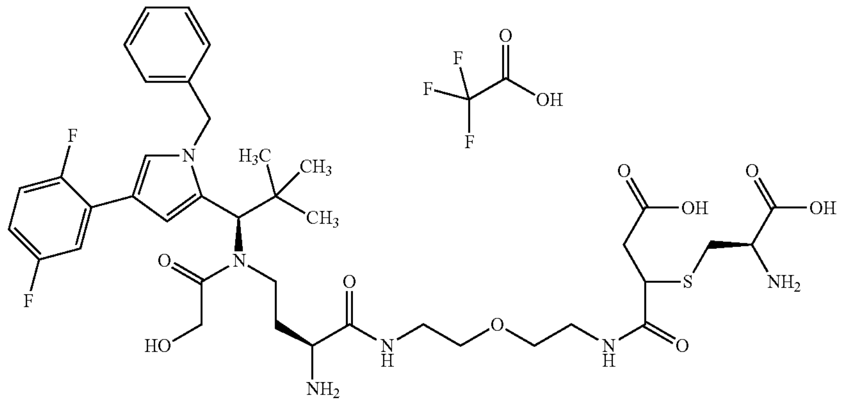

+

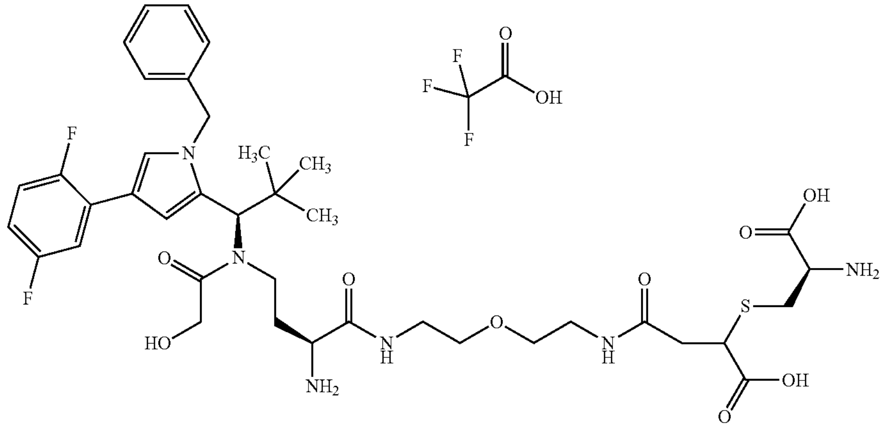

8 mg (0.010 mmol) of the protected intermediate of Intermediate F248 and 5.1 mg (0.02 mmol) of N-{[2-(trimethylsilyl) ethoxy]carbonyl}-L-cysteine were dissolved in 3 ml of DMF, and the mixture was stirred at RT for 18 h and then treated in an ultrasonic bath for 2 h. The mixture was then concentrated and the residue was purified by preparative HPLC. The appropriate fractions were combined and the solvents were evaporated under reduced pressure, and the residue was then dissolved in 2 ml of THF/water 1:1. 15 μl of a 2M aqueous lithium hydroxide solution were added and the reaction was stirred at RT for 15 min. The reaction was then adjusted to a pH of -3 with a 1M hydrochloric acid, diluted with 20 ml of sodium chloride solution and extracted twice with 20 ml of ethyl acetate. The organic phase was dried over magnesium sulphate and concentrated, and the residue was lyophilized from acetonitrile/water. This gave 8.4 mg (78% of theory over 2 steps) of the regioisomeric protected intermediates as a colourless foam.

LC-MS (Method 1): $R_t$=1.44 min and 3.43 min; MS (ESIpos): m/z=1107 $(M+H)^+$.

In the last step, 8 mg (0.007 mmol) of this intermediate were dissolved in 5 ml of 2,2,2-trifluoroethanol. 9.8 mg (0.072 mmol) of zinc chloride were added, and the reaction was stirred at 50° C. for 1.5 h. Ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 4 mg (59% of theory) of the title compound as a regioisomer mixture in a ratio of 31:67.

LC-MS (Method 1): $R_t$=0.79 min and 0.81 min; MS (ESIpos): m/z=819 $(M+H)^+$.

Example M6

2-{[(2R)-2-Amino-2-carboxyethyl]sulphanyl}-4-({(14R)-13-(3-aminopropyl)-14-[1-benzyl-4-(2,5-difluorophenyl)-1H-pyrrol-2-yl]-15,15-dimethyl-2,7,12-trioxo-10-thia-3,6,13-triazahexadec-1-yl}amino)-4-oxobutanoic Acid/Trifluoroacetic Acid (1:2) and 3-{[(2R)-2-amino-2-carboxyethyl]sulphanyl}-4-({(14R)-13-(3-aminopropyl)-14-[1-benzyl-4-(2,5-difluorophenyl)-1H-pyrrol-2-yl]-15,15-dimethyl-2,7,12-trioxo-10-thia-3,6,13-triazahexadec-1-yl}amino)-4-oxobutanoic Acid/Trifluoroacetic Acid (1:2)

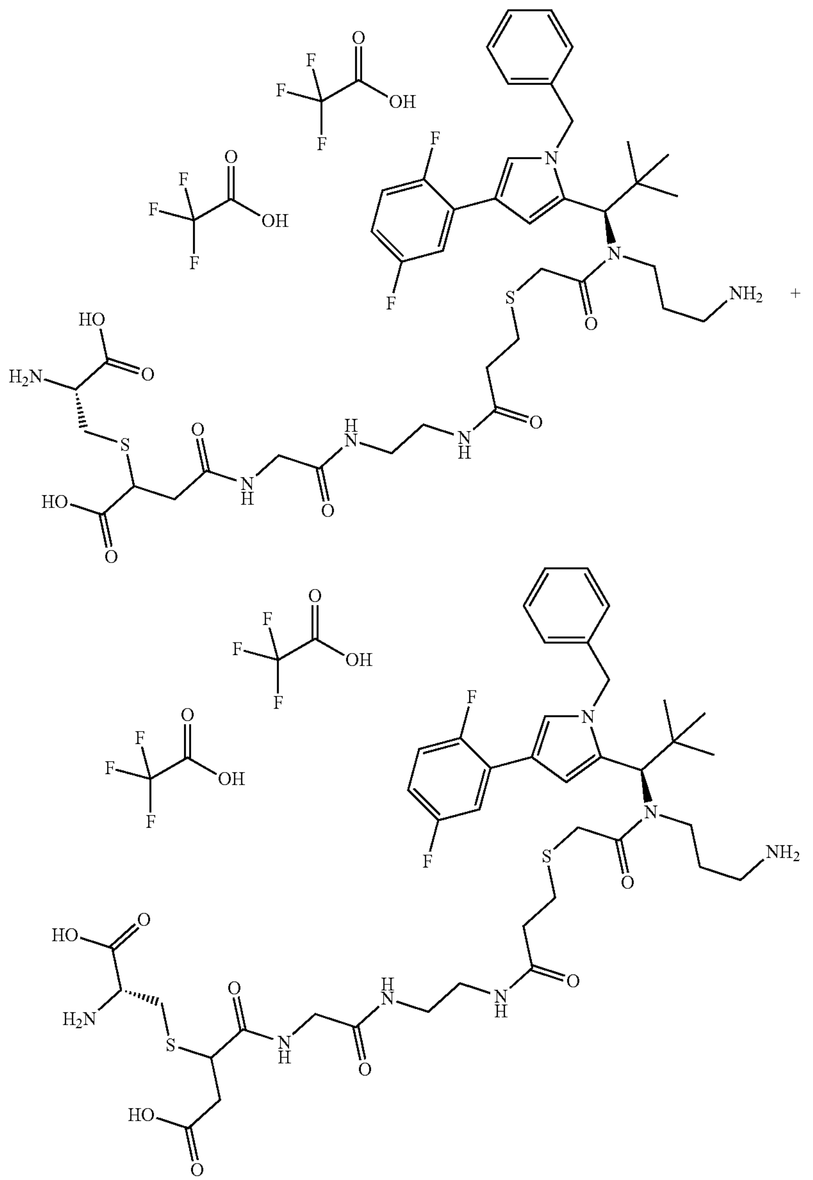

18 mg (0.021 mmol) of Intermediate F213 and 11.2 mg (0.04 mmol) of N-{[2-(trimethylsilyl) ethoxy]carbonyl}-L-cysteine were dissolved in 2 ml of DMF, and the mixture was stirred at RT for 18 h. The reaction mixture was concentrated under reduced pressure. The residue (21.2 mg) was dissolved in 3 ml of THF/water 1:1. 0.04 ml of a 2M aqueous lithium hydroxide solution were added and the reaction was stirred at RT for 3 hours. 0.02 ml of a 2M aqueous lithium hydroxide solution were added and the reaction was stirred at RT for 1 hour. The reaction was then adjusted to a pH of -7 using 7.2 mg (0.12 mmol) of acetic acid. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 13 mg (57% over 2 steps) of the regioisomeric protected intermediates.

LC-MS (Method 1): $R_t$=1.03 min; MS (ESIpos): m/z=1020 $(M+H)^+$.

In the last step, 13 mg (0.01 mmol) of this intermediate were dissolved in 2 ml of 2,2,2-trifluoroethanol. 6.2 mg (0.05 mmol) of zinc chloride were added, and the reaction was stirred at 50° C. for 7 h. 13.3 mg (0.05 mmol) of ethylenediamine-N,N,N',N'-tetraacetic acid were then added, and the product was purified by preparative HPLC. Concentration of the appropriate fractions and lyophilization of the residue from acetonitrile/water gave 10.3 mg (81.4%) of the title compound as a regioisomer mixture.

LC-MS (Method 1): $R_t$=1.03 min; MS (ESIpos): m/z=875 $(M+H)^+$.

Example M7

S-(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-L-cysteine/trifluoroacetic Acid (1:1)

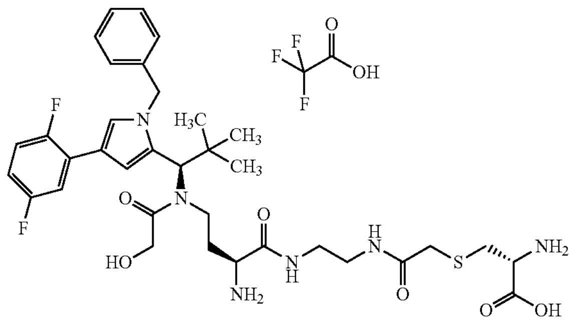 [SMILES: CC(C)(C)[C@H](c1cc(-c2cc(F)ccc2F)cn1Cc1ccccc1)N(CC[C@H](N)C(=O)NCCNC(=O)CSC[C@H](N)C(=O)O)C(=O)CO ; O=C(O)C(F)(F)F]

6 mg (8 μmol) of Intermediate F119 were taken up in 3 ml of DMF, and 1.8 mg (15 μmol) of L-cysteine were added. The reaction mixture was stirred at RT for 6 h and then allowed to stand at RT for 3 days. The reaction was then concentrated under reduced pressure, and the product was purified by preparative HPLC.

LC-MS (Method 1): $R_t$=0.81 min; MS (ESIpos): m/z=717 $(M+H)^+$.

Example M8

(3R)-6-{(11 S,15R)-11-Amino-15-[1-benzyl-4-(2,5-difluorophenyl)-1H-pyrrol-2-yl]-14-glycoloyl-16,16-dimethyl-2,5,10-trioxo-3,6,9,14-tetraazaheptadec-1-yl}-5-oxothiomorpholine-3-carboxylic Acid/Trifluoroacetic Acid (1:1)

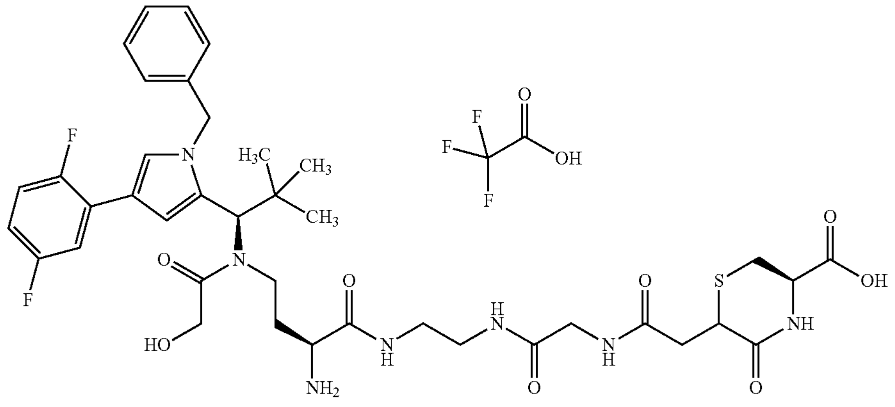

4 mg (0.004 mmol) of the compound from Example 135 were dissolved in 4 ml of THF/water, and 48 μl of a 2-molar aqueous lithium hydroxide solution were added. The reaction was stirred at RT for 1 h and then concentrated and purified by preparative HPLC. Combination, concentration and lyophilization of the appropriate fractions from acetonitrile/water gave 2.4 mg (60% of theory) of the title compound.

LC-MS (Method 1): $R_t$=0.86 min; MS (EIpos): m/z=814 $[M+H]^+$.

Example M9

N-(3-Aminopropyl)-N-{(1R)-1-[1-benzyl-4-(2,5-difluorophenyl)-1H-pyrrol-2-yl]-2,2-dimethylpropyl}-2-hydroxyacetamide

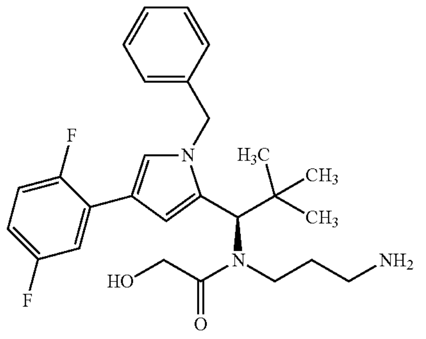 [SMILES: CC(C)(C)[C@H](c1cc(-c2cc(F)ccc2F)cn1Cc1ccccc1)N(CCCN)C(=O)CO]

150.0 mg (0.42 mmol) of (1R)-1-[1-benzyl-4-(2,5-difluorophenyl)-1H-pyrrol-2-yl]-2,2-dimethylpropan-1-amine (Intermediate C52) were initially charged in 2.0 ml of dichloromethane, and 29.2 mg (0.49 mmol) of HOAc and 125.6 mg (0.59 mmol) of sodium triacetoxyborohydride were added and the mixture was stirred at RT for 5 min. 98.9 mg (0.49 mmol) of 3-(1,3-dioxo-1,3-dihydro-2H-isoindol-2-yl)propanal were added. The reaction mixture was stirred at RT overnight. The reaction mixture was diluted with ethyl acetate and the organic phase was washed twice with saturated sodium carbonate solution and once with saturated NaCl solution. After drying over magnesium sulphate, the solvent was evaporated under reduced pressure and the residue was purified on silica gel (mobile phase: dichloromethane/methanol 100:1). The solvents were evaporated under reduced pressure and the residue was dried under high vacuum. This gave 188.6 mg (74%) of the compound 2-[3-({(1R)-1-[1-benzyl-4-(2,5-difluorophenyl)-1H-pyrrol-2-yl]-2,2-dimethylpropyl}amino)propyl]-1H-isoindole-1,3(2H)-dione.

LC-MS (Method 1): $R_t$=1.00 min; MS (ESIpos): m/z=541 $[M+H]^+$.

171.2 mg (0.32 mmol) of 2-[3-({(1R)-1-[1-benzyl-4-(2,5-difluorophenyl)-1H-pyrrol-2-yl]-2,2-dimethylpropyl}amino)propyl]-1H-isoindole-1,3(2H)-dione were initially charged in 5.0 ml of dichloromethane, and 73.6 mg (0.73 mmol) of triethylamine were added. At 0° C., 94.9 mg (0.70 mmol) of acetoxyacetyl chloride were added, and the reaction mixture was stirred at RT overnight. The reaction mixture was diluted with ethyl acetate and the organic phase was washed twice with saturated sodium bicarbonate solution and once with sat. NaCl solution. After drying over magnesium sulphate, the solvent was evaporated under reduced pressure and the residue was purified using Biotage Isolera (silica gel, column 10 g SNAP, flow rate 12 ml/min, ethyl acetate/cyclohexane 1:3). The solvents were evaporated under reduced pressure and the residue was dried under high vacuum. This gave 159.0 mg (77%) of the compound 2-({(1R)-1-[1-benzyl-4-(2,5-difluorophenyl)-1H-pyrrol-2-yl]-2,2-dimethylpropyl}[3-(1,3-dioxo-1,3-dihydro-2H-isoindol-2-yl)propyl]amino)-2-oxoethyl acetate.

LC-MS (Method 1): $R_t$=1.35 min; MS (ESIpos): m/z=642 $[M+H]^+$.

147.2 mg (0.23 mmol) of 2-({(1R)-1-[1-benzyl-4-(2,5-difluorophenyl)-1H-pyrrol-2-yl]-2,2-dimethylpropyl}[3-(1,3-dioxo-1,3-dihydro-2H-isoindol-2-yl)propyl]amino)-2-oxoethyl acetate were initially charged in 4.0 ml of ethanol, and 356.2 mg (4.59 mmol) of methanamine (40% in water) were added. The reaction mixture was stirred at 50° C. overnight. The solvent was evaporated under reduced pressure and the residue co-distilled three times with toluene. The residue was chromatographed by means of silica gel (mobile phase: dichloromethane/methanol 10:1). The solvents were evaporated under reduced pressure and the residue was dried under high vacuum. This gave 67.4 mg (63%) of the title compound.

LC-MS (Method 1): $R_t$=0.91 min; MS (ESIpos): m/z=470 $[M+H]^+$.

Example M10O (2R,28R)-28-Amino-2-[({2-[(3-aminopropyl) {(1R)-1-[1-benzyl-4-(2,5-difluorophenyl)-1H-pyrrol-2-yl]-2,2-dimethylpropyl}amino]-2-oxoethyl}sulphanyl) methyl]-25-(carboxymethyl)-4,20,24-trioxo-7,10,13,16-tetraoxa-26-thia-3,19,23-triazanonacosan-1,29-dioic Acid/Trifluoroacetic Acid (1:2) and (1R,28R,34R)-1-amino-33-(3-aminopropyl)-34-[1-benzyl-4-(2,5-difluorophenyl)-1H-pyrrol-2-yl]-35,35-dimethyl-6,10,26,32-tetraoxo-14,17,20,23-tetraoxa-3,30-dithia-7,11,27,33-tetraazahexatriacontan-1,4,28-tricarboxylic Acid/Trifluoroacetic Acid (1:2)

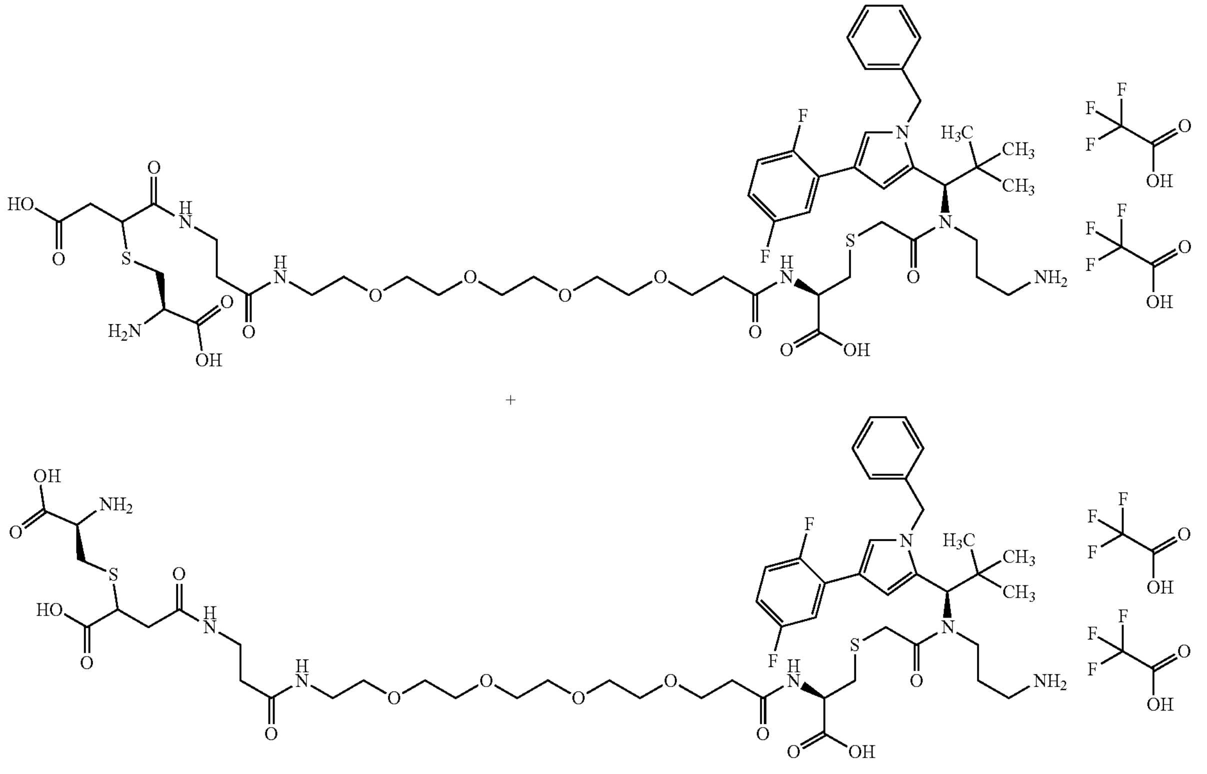

20 mg (0.018 mmol) of R-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteine/trifluoroacetic acid (1:1) (Intermediate F209) and 9.78 mg (0.036 mmol) of N-{[2-(trimethylsilyl) ethoxy]carbonyl}-L-cysteine were dissolved in 2 ml of DMF, and the mixture was stirred at RT for 18 h. The reaction mixture was concentrated under reduced pressure. The residue (47.7 mg) was dissolved in 3 ml of THF/water 1:1. 0.08 ml of a 2M aqueous lithium hydroxide solution were added and the reaction was stirred at RT for 1 hour. The reaction was then adjusted to a pH of -7 using 9.26 mg (0.15 mmol) of acetic acid. The reaction mixture was purified directly by preparative RP-HPLC (column: Reprosil 125×30; 10μ, flow rate: 50 ml/min, MeCN/water, 0.1%

TFA). The solvents were evaporated under reduced pressure and the residue was dried under high vacuum. This gave 15.3 mg (29% over 2 steps) of the regioisomeric protected intermediates.

LC-MS (Method 6): $R_t$=12.26 min and 12.30 min; MS (ESIpos): m/z=1254 $(M+H)^+$.

In the last step, 15.3 mg (0.01 mmol) of this intermediate were dissolved in 2 ml of 2,2,2-trifluoroethanol. 6.1 mg (0.05 mmol) of zinc chloride were added, and the reaction was stirred at 50° C. for 2 h. 13.1 mg (0.05 mmol) of ethylenediamine-N,N,N',N'-tetraacetic acid were then added, and the product was purified by preparative HPLC. Concentration of the appropriate fractions and lyophilization of the residue from acetonitrile/water gave 11.9 mg (79.5%) of the title compound as a regioisomer mixture.

LC-MS (Method 1): $R_t$=0.85 min; MS (ESIpos): m/z=1110 $(M+H)^+$.

Example M11

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-L-cysteine/trifluoroacetic Acid (1:2)

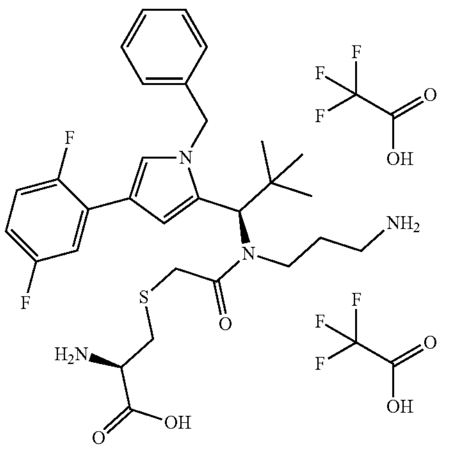

15.0 mg (0.018 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) were dissolved in 1.0 ml of trifluoroethanol, and 7.4 mg (0.054 mmol) of zinc dichloride were added. The reaction mixture was stirred at 50° C. overnight. 15.8 mg (0,054 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 11.1 mg (77%) of the title compound.

LC-MS (Method 1): $R_t$=0.83 min; MS (ESIpos): m/z=573 $(M+H)^+$.

Example M12

4-{[(1R)-2-({2-[(3-Aminopropyl) {(1R)-1-[1-benzyl-4-(2,5-difluorophenyl)-1H-pyrrol-2-yl]-2,2-dimethylpropyl}amino]-2-oxoethyl}sulphanyl)-1-carboxyethyl]amino}-4-oxobutanoic Acid/trifluoroacetic Acid (1:1)

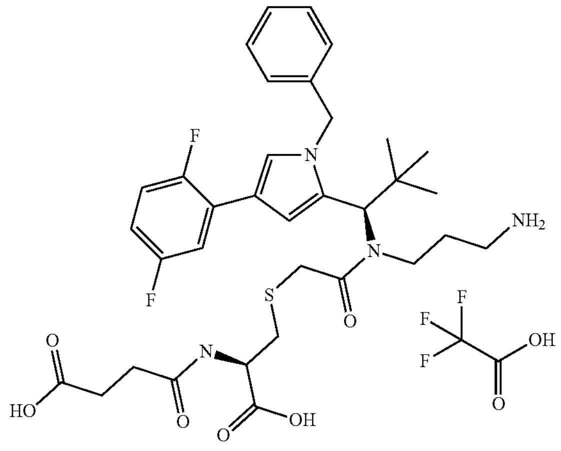

12.2 mg (0.014 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were dissolved in 2.0 ml of trifluoroethanol, and 11.4 mg (0.084 mmol) of zinc dichloride were added. The reaction mixture was stirred at 50° C. for 3 h. 24.5 mg (0,084 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 4.6 mg (42%) of the title compound.

LC-MS (Method 1): $R_t$=0.88 min; MS (ESIpos): m/z=673 $(M+H)^+$.

Example M13

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic Acid/Trifluoroacetic Acid (1:1) Regioisomer 1, Epimer 1 (2R) or (2S)

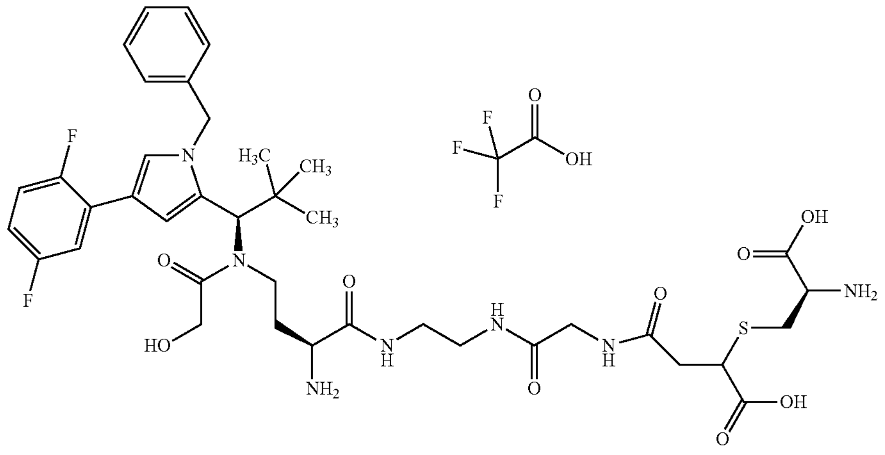 [SMILES: CC(C)(C)[C@H](c1cc(-c2cc(F)ccc2F)cn1Cc1ccccc1)N(CC[C@H](N)C(=O)NCCNC(=O)CNC(=O)CC(SC[C@H](N)C(=O)O)C(=O)O)C(=O)CO ; O=C(O)C(F)(F)F]

LC-MS (Method 5): $R_t$=2.44 min; MS (ESIpos): m/z=832 $[M+H]^+$.

First, methyl L-cysteinate hydrochloride (1:1) was converted with 1-({[2-(trimethylsilyl)ethoxy]carbonyl}oxy)pyrrolidine-2,5-dione in DMF in the presence of N,N-diisopropylethylamine into methyl N-{[2-(trimethylsilyl)ethoxy]carbonyl}-L-cysteinate.

408 mg (1.93 mmol) of commercially available 3-bromo-4-methoxy-4-oxobutanoic acid and 180 mg (0.644 mmol) of methyl N-{[2-(trimethylsilyl)ethoxy]carbonyl}-L-cysteinate were dissolved in 8 ml of DMF, and 147 mg (0.97 mmol) of 1,8-diazabicyclo[5.4.0]undec-7-ene were added. After 18 h of stirring at RT, another 136 mg (0.64 mmol) of 3-bromo-4-methoxy-4-oxobutanoic acid and 147 mg (0.97 mmol) of 1,8-diazabicyclo[5.4.0]undec-7-ene were added, and the mixture was stirred at RT for a further 12 h and then concentrated under reduced pressure. The residue was purified by preparative HPLC. Combination of the appropriate fractions and evaporation of the solvents under reduced pressure gave 151 mg (57% of theory) of 4-methoxy-3-{[(2R)-3-methoxy-3-oxo-2-({[2-(trimethylsilyl)ethoxy]carbonyl}amino)propyl]sulphanyl}-4-oxobutanoic acid.

LC-MS (Method 12): $R_t$=1.74 min; MS (ESIneg): m/z=408 $(M-H)^-$.

Of this intermediate, 145 mg were separated by supercritical fluid chromatography via chiral columns into the individual diastereomers (SFC; column DAICEL, AD-H 5u 250×20 mm; flow rate 80 ml/min; method AD-25% ETOH-80 ml; pressure 100 bar; wavelength 210 nM), giving 63 mg (43%) of Epimer 1 and 58 mg (40%) of Epimer 2.

Epimer 1 was characterized as follows:

LC-MS (Method 5): $R_t$=2.94 min; MS (ESIneg): m/z=408 $(M-H)^-$.

$^1$H-NMR: (400 MHz, DMSO-$d_6$): δ=7.57 (d, 1H), 4.24 (m, 1H), 4.05 (t, 2H), 3.67 (t, 1H), 3.65 (s, 3H), 3.62 (s, 3H), 3.05 (dd, 1H), 2.70-2.88 (m, 2H), 2.59 (dd, 1H), 0.93 (t, 2H), 0.02 (s, 9H).

Epimer 2 was characterized as follows:

LC-MS (Method 5): $R_t$=2.95 min; MS (ESIneg): m/z=408 $(M-H)^-$.

$^1$H-NMR: (400 MHz, DMSO-$d_6$): δ=7.58 (d, 1H), 4.16-4.23 (m, 1H), 4.05 (t, 2H), 3.67 (dd, 1H), 3.65 (s, 3H), 3.64 (s, 3H), 3.04 (dd, 1H), 2.88 (dd, 1H), 2.77 (dd, 1H), 2.61 (dd, 1H), 0.92 (t, 2H), 0.02 (s, 9H).

32.5 mg (0.079 mmol) of Epimer 1 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 43 mg (57% of theory) of the fully protected intermediate methyl 4-{[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9,14-trioxo-5-oxa-7,10,13-triaza-2-silapentadecan-15-yl]amino}-2-{[(2R)-3-methoxy-3-oxo-2-([{2-(trimethylsilyl)ethoxy]carbonyl}amino)propyl]sulphanyl}-4-oxobutanoate. 40 mg (0.035 mmol) of this intermediate were then stirred at RT with 0.9 ml of a 2-molar lithium hydroxide solution in 11 ml of methanol for 20 min, resulting in the cleavage of both methyl ester groups. Purification by HPLC gave 12 mg (31% of theory) of the dicarboxylic acid derivative.

LC-MS (Method 5): $R_t$=4.74 min; MS (ESIpos): m/z=1120 $[M+H]^+$.

Finally, 10 mg (0.009 mmol) of this intermediate were completely deprotected with zinc chloride in trifluoroethanol as described above. The residue was purified by preparative HPLC. Concentration of the appropriate fractions and lyophilization of the residue from acetonitrile/water gave 2.6 mg (30% of theory) of the title compound.

LC-MS (Method 5): $R_t$=2.44 min; MS (ESIpos): m/z=832 $[M+H]^+$.

Example M14

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic Acid/Trifluoroacetic Acid (1:1) Regioisomer 1, Epimer 2 (2R or 2S)

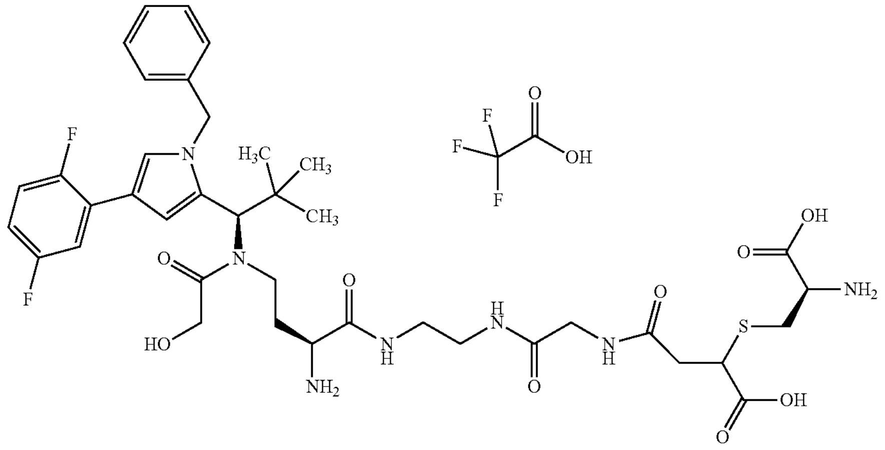 [SMILES: CC(C)(C)[C@H](c1cc(-c2cc(F)ccc2F)cn1Cc1ccccc1)N(CC[C@H](N)C(=O)NCCNC(=O)CNC(=O)CC(SC[C@H](N)C(=O)O)C(=O)O)C(=O)CO ; O=C(O)C(F)(F)F]

LC-MS (Method 5): $R_t$=2.44 min; MS (EIpos): m/z=832 $[M+H]^+$.

The intermediate Epimer 2 described in Example M13 was reacted analogously to the description in Example M13:

32.5 mg (0.079 mmol) of Epimer 2 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 43 mg (57% of theory) of the fully protected intermediate methyl 4-{[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9,14-trioxo-5-oxa-7,10,13-triaza-2-silapentadecan-15-yl]amino}-2-{[(2R)-3-methoxy-3-oxo-2-({[2-(trimethylsilyl)ethoxy]carbonyl}amino)propyl]sulphanyl}-4-oxobutanoate.

40 mg (0.035 mmol) of this intermediate were then stirred at RT with 0.9 ml of a 2-molar lithium hydroxide solution in 11 ml of methanol for 20 min, resulting in the cleavage of both methyl ester groups. Purification by HPLC gave 11 mg (28% of theory) of the dicarboxylic acid derivative.

LC-MS (Method 5): $R_t$=4.74 min; MS (ESIpos): m/z=1120 $[M+H]^+$.

Finally, 10 mg (0.009 mmol) of this intermediate were completely deprotected with zinc chloride in trifluoroethanol as described above. The residue was purified by preparative HPLC. Concentration of the appropriate fractions and lyophilization of the residue from acetonitrile/water gave 4.4 mg (52% of theory) of the title compound.

LC-MS (Method 5): $R_t$=2.44 min; MS (ESIpos): m/z=832 $[M+H]^+$.

Example M15

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic Acid/Trifluoroacetic Acid (1:1) Regioisomer 2, Epimer 1 (3R or 3S)

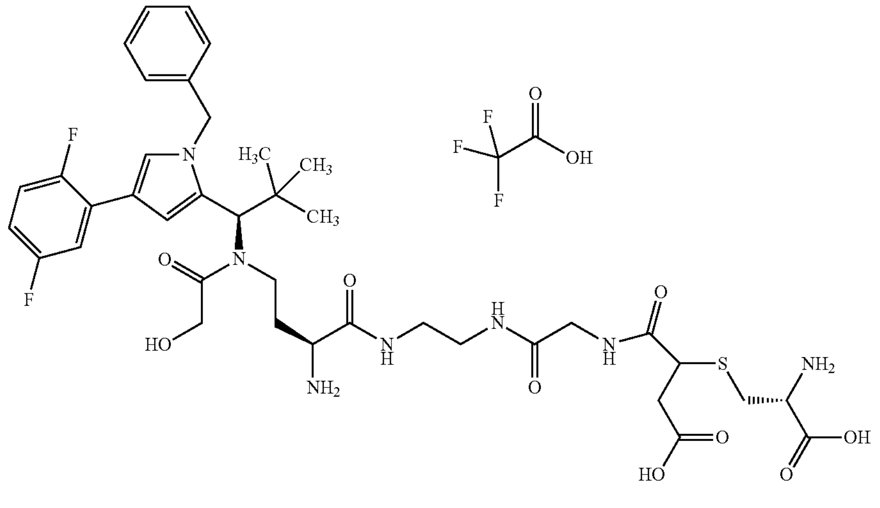 [SMILES: CC(C)(C)[C@H](c1cc(-c2cc(F)ccc2F)cn1Cc1ccccc1)N(CC[C@H](N)C(=O)NCCNC(=O)CNC(=O)C(CC(=O)O)SC[C@H](N)C(=O)O)C(=O)CO ; O=C(O)C(F)(F)F]

LC-MS (Method 5): $R_t$=2.45 min; MS (EIpos): m/z=832 $[M+H]^+$.

742.8 mg (3.3 mmol) of commercially available 2-bromo-4-ethoxy-4-oxobutanoic acid and 802 mg (2.87 mmol) of methyl N-{[2-(trimethylsilyl)ethoxy]carbonyl}-L-cysteinate were dissolved in 32 ml of DMF, and 655.4 mg (4.31 mmol) of 1,8-diazabicyclo[5.4.0]undec-7-ene were added. After 20 h of stirring at RT, the reaction was concentrated under reduced pressure and the residue was purified by preparative HPLC. Combination of the appropriate fractions and evaporation of the solvents under reduced pressure gave 521 mg (43% of theory) of 4-ethoxy-2-{[(2R)-3-methoxy-3-oxo-2-({[2-(trimethylsilyl)ethoxy]carbonyl}amino)propyl]sulphanyl}-4-oxobutanoic acid.

LC-MS (Method 5): $R_t$=3.13 min; MS (ESIpos): m/z=424 $(M+H)^+$.

Of this intermediate, 510 mg were separated by supercritical fluid chromatography via chiral columns into the individual diastereomers (SFC; column DAICEL, AD-H 5u 250×20 mm; flow rate 80 ml/min; method AD-10% ETOH-80 ml; pressure 100 bar; wavelength 210 nM), giving 100 mg (20%) of Epimer 1 and 141 mg (28%) of Epimer 2.

Epimer 1 was characterized as follows:

LC-MS (Method 1): $R_t$=0.99 min; MS (ESIneg): m/z=422 $(M-H)^-$.

$^1$H-NMR: (400 MHz, DMSO-$d_6$): δ=7.60 (d, 1H), 4.18-4.26 (m, 1H), 4.01-4.08 (m, 4H), 3.63 (s, 3H), 3.59 (dd, 1H), 3.04 (dd, 1H), 2.92 (dd, 1H), 2.80 (dd, 1H), 2.63 (dd, 1H), 1.17 (t, 3H), 0.92 (t, 2H), 0.02 (s, 9H).

Epimer 2 was characterized as follows:

LC-MS (Method 5): $R_t$=2.95 min; MS (ESIneg): m/z=408 $(M-H)^-$.

aza-2-silapentadecan-15-yl]amino}-3-{[(2R)-3-methoxy-3-oxo-2-({[2-(trimethylsilyl)ethoxy]carbonyl}amino)propyl]sulphanyl}-4-oxobutanoate.

49 mg (0.042 mmol) of this intermediate were then stirred at RT with 0.5 ml of a 2-molar lithium hydroxide solution in 12 ml of THF/water 1:1 for 30 min, resulting in the cleavage of both methyl ester groups. Acidification and purification by HPLC gave 11 mg (24% of theory) of the dicarboxylic acid derivative.

LC-MS (Method 5): $R_t$=4.68 min; MS (ESIpos): m/z=1120 $[M+H]^+$.

Finally, 11 mg (0.01 mmol) of this intermediate were completely deprotected with zinc chloride in trifluoroethanol as described above. The residue was purified by preparative HPLC. Concentration of the appropriate fractions and lyophilization of the residue from acetonitrile/water gave 3.7 mg (39% of theory) of the title compound.

LC-MS (Method 5): $R_t$=2.45 min; MS (ESIpos): m/z=832 $[M+H]^+$.

Example M16

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic Acid/Trifluoroacetic Acid (1:1) Regioisomer 2, Epimer 2 (3R or 3S)

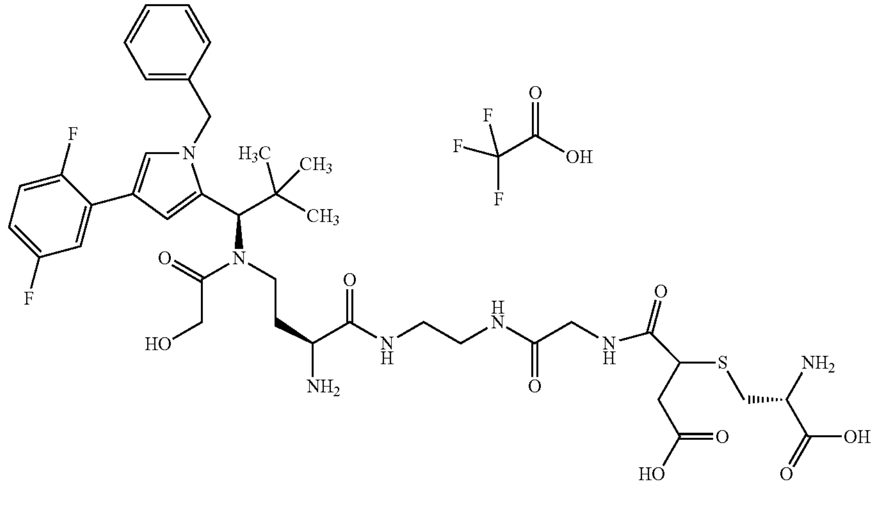 [SMILES: CC(C)(C)[C@H](c1cc(-c2cc(F)ccc2F)cn1Cc1ccccc1)N(CC[C@H](N)C(=O)NCCNC(=O)CNC(=O)C(CC(=O)O)SC[C@H](N)C(=O)O)C(=O)CO ; O=C(O)C(F)(F)F]

$^1$H-NMR: (400 MHz, DMSO-$d_6$): δ=7.56 (d, 1H), 4.21-4.29 (m, 1H), 4.01-4.1 (m, 4H), 3.64 (s, 3H), 3.58 (dd, 1H), 3.08 (dd, 1H), 2.85 (dd, 1H), 2.78 (dd, 1H), 2.60 (dd, 1H), 1.17 (t, 3H), 0.93 (t, 2H), 0.02 (s, 9H).

33.6 mg (0.079 mmol) of Epimer 1 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 51 mg (63% of theory) of the fully protected intermediate ethyl 4-{[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9,14-trioxo-5-oxa-7,10,13-tri- LC-MS (Method 5): $R_t$=2.44 min; MS (EIpos): m/z=832 $[M+H]^+$.

The intermediate Epimer 2 described in Example M15 was reacted analogously to the description in Example M15:

33.6 mg (0.079 mmol) of Epimer 2 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 51 mg (63% of theory) of the fully protected intermediate ethyl 4-{[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9,14-trioxo-5-oxa-7,10,13-triaza-2-silapentadecan-15-yl]amino}-3-{[(2R)-3-methoxy-3-oxo-2-([{2-(trimethylsilyl)ethoxy]carbonyl}amino)propyl] sulphanyl}-4-oxobutanoate.

49 mg (0.042 mmol) of this intermediate were then stirred at RT with 0.5 ml of a 2-molar lithium hydroxide solution in 12 ml of THF/water 1:1 for 30 min, resulting in the cleavage of both methyl ester groups. Acidification and purification by HPLC gave 13.4 mg (28% of theory) of the dicarboxylic acid derivative.

LC-MS (Method 5): $R_t$=4.66 min; MS (ESIpos): m/z=1120 $[M+H]^+$.

Finally, 13.4 mg (0.012 mmol) of this intermediate were completely deprotected with zinc chloride in trifluoroethanol as described above. The residue was purified by preparative HPLC. Concentration of the appropriate fractions and lyophilization of the residue from acetonitrile/water gave 7.5 mg (66% of theory) of the title compound.

LC-MS (Method 5): $R_t$=2.44 min; MS (ESIpos): m/z=832 $[M+H]^+$.

Example M17

(2S)-2-Amino-4-[{(1R)-1-[1-benzyl-4-(2,5-difluorophenyl)-1H-pyrrol-2-yl]-2,2-dimethylpropyl}(glycoloyl)amino]butanoic Acid Hydrochloride (1:1)

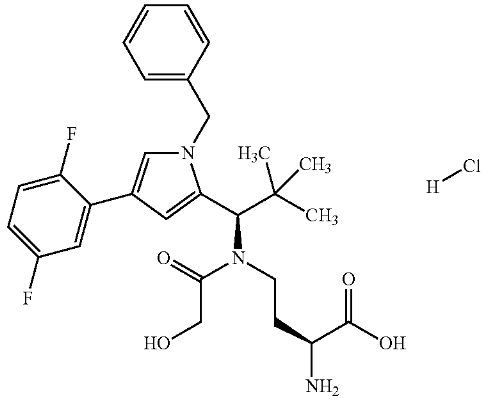 [SMILES: CC(C)(C)[C@H](c1cc(-c2cc(F)ccc2F)cn1Cc1ccccc1)N(CC[C@H](N)C(=O)O)C(=O)CO ; Cl]

150 mg (0.2 mmol) of Intermediate C53 were dissolved in 15 ml of DMF, and 2.29 g (20.39 mmol) of DABCO. The reaction was treated in an ultrasonic bath for 30 min. By addition of 1.17 ml of acetic acid, the reaction was then adjusted to pH 3-4, and the mixture was concentrated under reduced pressure. The residue was purified by preparative HPLC and the appropriate fractions were concentrated at RT under reduced pressure. The residue was taken up in acetonitrile/water 1:1, 5 ml of a 4N hydrochloric acid were added and the mixture was then lyophilized. This gave 81 mg (68% of theory) of the title compound.

LC-MS (Method 5): $R_t$=2.69 min; MS (EIpos): m/z=514 $[M+H]^+$.

Example M18

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine/trifluoroacetic Acid (1:1)

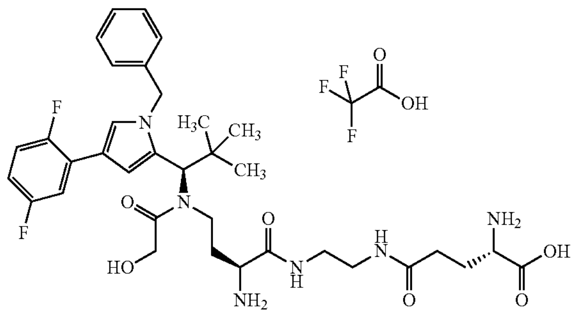 [SMILES: CC(C)(C)[C@H](c1cc(-c2cc(F)ccc2F)cn1Cc1ccccc1)N(CC[C@H](N)C(=O)NCCNC(=O)CC[C@H](N)C(=O)O)C(=O)CO ; O=C(O)C(F)(F)F]

First, trifluoroacetic acid/benzyl N-(2-aminoethyl)-$N^2$-[(benzyloxy)carbonyl]-L-glutaminate (1:1) was prepared using classical methods of peptide chemistry. In the presence of HATU, this intermediate was then coupled with Intermediate C58. Subsequently, first the benzyloxycarbonyl protective group and the benzyl ester were removed by hydrogenolytic cleavage, and then the 2-(trimethylsilyl) ethoxycarbonyl protective group was removed using zinc chloride.

LC-MS (Method 6): $R_t$=1.91 min; MS (EIpos): m/z=685 $[M+H]^+$.

Example M19

$N^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-L-lysine/trifluoroacetic Acid (1:1)

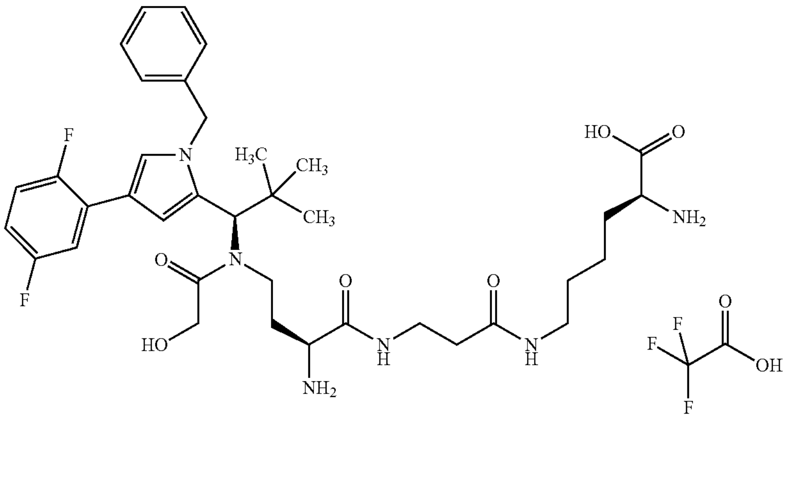 [SMILES: CC(C)(C)[C@H](c1cc(-c2cc(F)ccc2F)cn1Cc1ccccc1)N(CC[C@H](N)C(=O)NCCC(=O)NCCCC[C@H](N)C(=O)O)C(=O)CO ; O=C(O)C(F)(F)F]

Initially, trifluoroacetic acid/2-(trimethylsilyl)ethyl-N2-[(benzyloxy)carbonyl]-L-lysinate (1:1) was prepared using classical protective group operations known in peptide chemistry. In the presence of HATU, this intermediate was then coupled with Intermediate C61. Subsequently, first the 2-(trimethylsilyl)ethoxycarbonyl protective group and the 2-(trimethylsilyl)ethyl ester were cleaved using zinc chloride. Finally, the title compound was obtained by hydrogenolytical cleavage of the benzyloxycarbonyl protective group and purification by preparative HPLC.

HPLC (Method 11): $R_t$=1.65 min;

Example M20

(1R,4R,27R,33R)-1-Amino-32-(3-aminopropyl)-33-[1-benzyl-4-(2,5-difluorophenyl)-1H-pyrrol-2-yl]-34,34-dimethyl-6,9,25,31-tetraoxo-13,16,19,22-tetraoxa-3,29-dithia-7,10,26,32-tetraazapentatriacontane-1,4,27-tricarboxylic Acid/Trifluoroacetic Acid (1:2)

(57% of theory) of 4-methoxy-3-{[(2R)-3-methoxy-3-oxo-2-({[2-(trimethylsilyl)ethoxy]carbonyl}amino)propyl]sulphanyl}-4-oxobutanoic acid.

LC-MS (Method 12): $R_t$=1.74 min; MS (ESIneg): m/z=408 $(M-H)^-$.

3.66 mg (8.93 μmol) of 4-methoxy-3-{[(2R)-3-methoxy-3-oxo-2-({[2-(trimethylsilyl)ethoxy]carbonyl}amino)propyl]sulphanyl}-4-oxobutanoic acid were coupled in the presence of 3.66 mg (8.93 μmol) of HATU and 1.6 μl (15 μmol) of 4-methylmorpholine with 13.0 mg (7.44 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine/trifluoroacetic acid (1:1) (Intermediate C80), giving, after HPLC purification, 3.9 mg (37% of theory) of the fully protected intermediate S-(11-{(1R)-1-[1-benzyl-4-(2,5-difluorophenyl)-1H-pyrrol-2-yl]-2,2-dimethylpropyl}-2,2-dimethyl-6,12-dioxo-

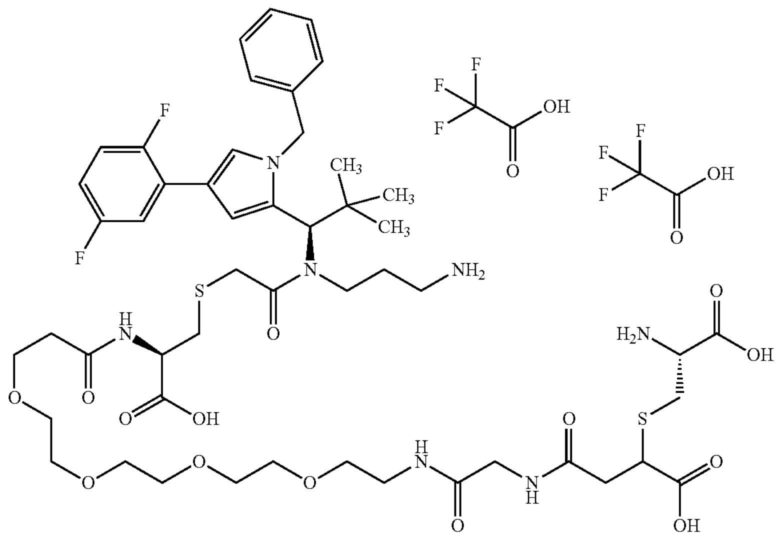 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CNC(=O)CC(SC[C@H](N)C(=O)O)C(=O)O)C(=O)O ; O=C(O)C(F)(F)F ; O=C(O)C(F)(F)F]

First, methyl L-cysteinate hydrochloride (1:1) was converted with 1-({[2-(trimethylsilyl)ethoxy]carbonyl}oxy)pyrrolidine-2,5-dione in DMF in the presence of N,N-diisopropylethylamine into methyl N-{[2-(trimethylsilyl)ethoxy]carbonyl}-L-cysteinate. 408 mg (1.93 mmol) of commercially available 3-bromo-4-methoxy-4-oxobutanoic acid and 180 mg (0.644 mmol) of methyl N-{[2-(trimethylsilyl)ethoxy]carbonyl}-L-cysteinate were dissolved in 8 ml of DMF, and 147 mg (0.97 mmol) of 1,8-diazabicyclo[5.4.0]undec-7-ene were added. After 18 h of stirring at RT, another 136 mg (0.64 mmol) of 3-bromo-4-methoxy-4-oxobutanoic acid and 147 mg (0.97 mmol) of 1,8-diazabicyclo[5.4.0]undec-7-ene were added, and the mixture was stirred at RT for a further 12 h and then concentrated under reduced pressure. The residue was purified by preparative HPLC. Combination of the appropriate fractions and evaporation of the solvents under reduced pressure gave 151 mg 5-oxa-7,11-diaza-2-silatridecan-13-yl)-N-[15-({N-[(8R,11R)-8,11-bis(methoxycarbonyl)-2,2-dimethyl-6,13-dioxo-5-oxa-10-thia-7-aza-2-silatridecan-13-yl]glycyl}amino)-4,7,10,13-tetraoxapentadecan-1-oyl]-L-cysteine. 3.90 mg (2.76 μmol) of this intermediate were then stirred at RT with 35 μl of a 2-molar lithium hydroxide solution in 1.0 ml of THF/water 3:1 for 15 min, resulting in the cleavage of both methyl ester groups. Purification by HPLC gave 3.60 mg (94% of theory) of the dicarboxylic acid derivative.

LC-MS (Method 5): $R_t$=4.83 min; MS (ESIpos): m/z=1385 $[M+H]^+$.

Finally, 3.6 mg (2.6 μmol) of this intermediate were completely deprotected with zinc chloride in trifluoroethanol as described above. The residue was purified by preparative HPLC. Concentration of the appropriate fractions and lyophilization of the residue from acetonitrile/water gave 1.92 mg (55% of theory) of the title compound.

LC-MS (Method 5): $R_t$=2.72 min; MS (ESIneg): m/z=1094 $[M-H]^-$.

Example M21

(2R,24S,27R)-27-Amino-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)methyl]-24-(carboxymethyl)-4,20,23-trioxo-7,10,13,16-tetraoxa-25-thia-3,19,22-triazaoctacosane-1,28-dioic Acid/Trifluoroacetic Acid (1:2)

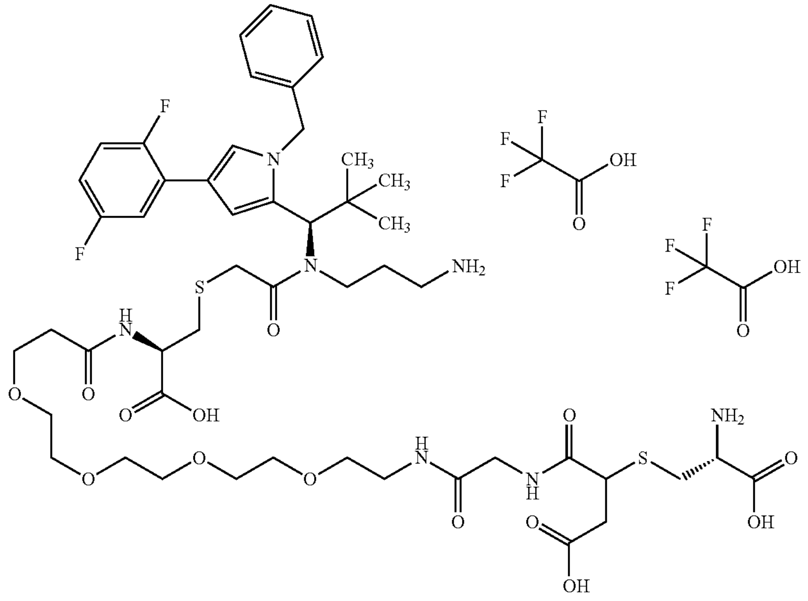 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CNC(=O)C(CC(=O)O)SC[C@H](N)C(=O)O)C(=O)O ; O=C(O)C(F)(F)F ; O=C(O)C(F)(F)F]

742.8 mg (3.3 mmol) of commercially available 2-bromo-4-ethoxy-4-oxobutanoic acid and 802 mg (2.87 mmol) of methyl N-{[2-(trimethylsilyl)ethoxy]carbonyl}-L-cysteinate were dissolved in 32 ml of DMF, and 655.4 mg (4.31 mmol) of 1,8-diazabicyclo[5.4.0]undec-7-ene were added. After 20 h of stirring at RT, the reaction was concentrated under reduced pressure and the residue was purified by preparative HPLC. Combination of the appropriate fractions and evaporation of the solvents under reduced pressure gave 521 mg (43% of theory) of 4-ethoxy-2-{[(2R)-3-methoxy-3-oxo-2-({[2-(trimethylsilyl)ethoxy]carbonyl}amino)propyl]sulphanyl}-4-oxobutanoic acid.

LC-MS (Method 5): $R_t$=3.13 min; MS (ESIpos): m/z=424 $(M+H)^+$.

4.36 mg (10.3 μmol) of 4-ethoxy-2-{[(2R)-3-methoxy-3-oxo-2-({[2-(trimethylsilyl)ethoxy]carbonyl}amino)propyl]sulphanyl}-4-oxobutanoic acid were coupled in the presence of 3.92 mg (10.3 μmol) of HATU and 1.9 μl (17 μmol) of 4-methylmorpholine with 15.0 mg (8.59 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine/trifluoroacetic acid (1:1) (Intermediate C80), giving, after HPLC purification, 3.6 mg (26% of theory) of the fully protected intermediate S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(8R,11S)-11-(2-ethoxy-2-oxoethyl)-8-(methoxycarbonyl)-2,2-dimethyl-6,12-dioxo-5-oxa-10-thia-7-aza-2-siladodecan-12-yl]glycyl}amino)-4,7,10,13-tetraoxapentadecan-1-oyl]-L-cysteine. 6.20 mg (2.82 μmol) of this intermediate were then stirred at RT with 35 μl of a 2-molar lithium hydroxide solution in 1.0 ml of THF/water 1:1 for 15 min, resulting in the cleavage of both ester groups. Acidification and purification by HPLC gave 3.60 mg (92% of theory) of the dicarboxylic acid derivative.

LC-MS (Method 5): $R_t$=4.71 min; MS (ESIpos): m/z=1385 $[M+H]^+$.

Finally, 3.60 mg (1.69 μmol) of this intermediate were completely deprotected with zinc chloride in trifluoroethanol as described above. The residue was purified by preparative HPLC. Concentration of the appropriate fractions and lyophilization of the residue from acetonitrile/water gave 0.88 mg (39% of theory) of the title compound.

LC-MS (Method 5): $R_t$=2.72 min; MS (ESIneg): m/z=1094 $[M-H]^-$.

Example M22

(2R,27R)-27-Amino-2-[({2-[(3-aminopropyl) {(1R)-1-[1-benzyl-4-(2,5-difluorophenyl)-1H-pyrrol-2-yl]-2,2-dimethylpropyl}amino]-2-oxoethyl}sulphanyl) methyl]-24-(carboxymethyl)-4,20,23-trioxo-7,10,13,16-tetraoxa-25-thia-3,19,22-triazaoctacosane-1,28-dioic Acid/Trifluoroacetic Acid (1:2) and (1R,27R,33R)-1-amino-32-(3-aminopropyl)-33-[1-benzyl-4-(2,5-difluorophenyl)-1H-pyrrol-2-yl]-34,34-dimethyl-6,9,25,31-tetraoxo-13,16,19,22-tetraoxa-3,29-dithia-7,10,26,32-tetraazapentatriacontane-1,4,27-tricarboxylic Acid/Trifluoroacetic Acid (1:2)

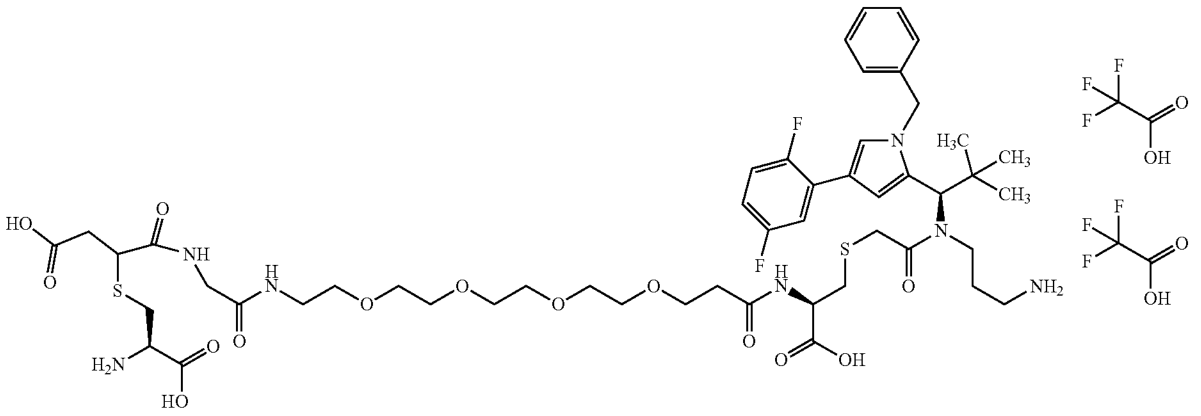

+

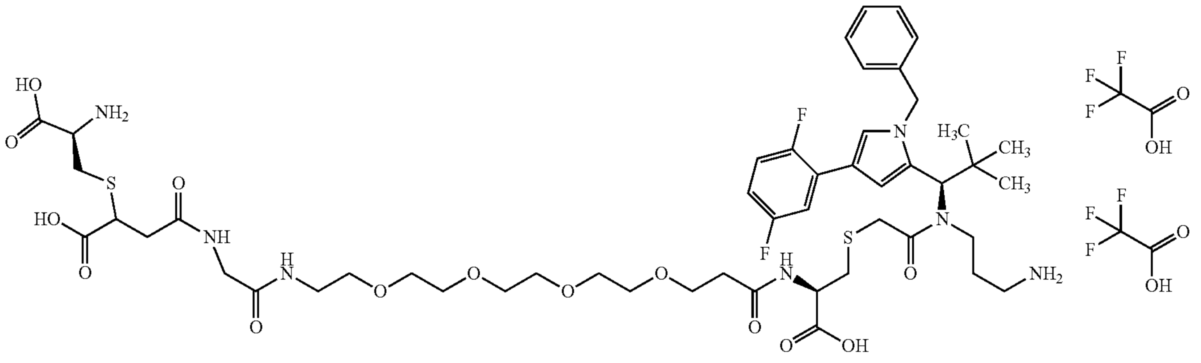

16.5 mg (0.015 mmol) of S-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,18-dioxo-6,9,12,15-tetraoxa-3-azaoctadecan-18-yl]-L-cysteine/trifluoroacetic acid (1:1) (Intermediate F257) and 8.18 mg (0.031 mmol) of N-{[2-(trimethylsilyl) ethoxy]carbonyl}-L-cysteine were dissolved in 2 ml of DMF, and the mixture was stirred at RT for 18 h. The reaction mixture was concentrated under reduced pressure. The residue (28.9 mg) was dissolved in 3 ml of THF/water 1:1. 0.046 ml of a 2M aqueous lithium hydroxide solution were added and the reaction was stirred at RT for 3 hour. The reaction was then adjusted to a pH of -7 using 5.2 µl (0.092 mmol) of acetic acid. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 12.1 mg (58% over 2 steps) of the regioisomeric protected intermediates.

LC-MS (Method 12): $R_t$=1.82 min; MS (ESIpos): m/z=1240 $(M+H)^+$.

In the last step, 12.1 mg (0.009 mmol) of this intermediate were dissolved in 2 ml of 2,2,2-trifluoroethanol. 7.3 mg (0.054 mmol) of zinc chloride were added, and the reaction was stirred at 50° C. for 2 h. 15.7 mg (0.054 mmol) of ethylenediamine-N,N,N',N'-tetraacetic acid were then added, and the product was purified by preparative HPLC. Concentration of the appropriate fractions and lyophilization of the residue from acetonitrile/water gave 6.4 mg (59%) of the title compound as a regioisomer mixture.

LC-MS (Method 1): $R_t$=0.86 min; MS (ESIpos): m/z=1096 $(M+H)^+$.

Example M23

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-L-glutamic Acid/Trifluoroacetic Acid (1:1)

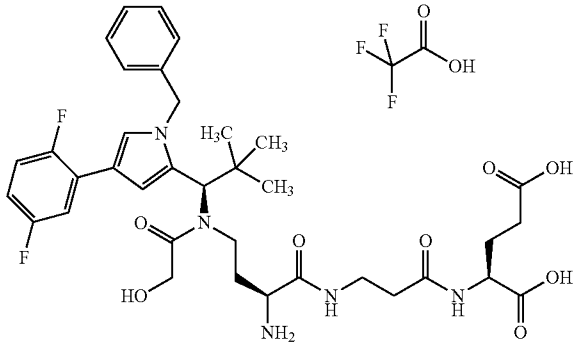 [SMILES: CC(C)(C)[C@H](c1cc(-c2cc(F)ccc2F)cn1Cc1ccccc1)N(CC[C@H](N)C(=O)NCCC(=O)N[C@@H](CCC(=O)O)C(=O)O)C(=O)CO ; O=C(O)C(F)(F)F]

First, di-tert-butyl L-glutamate hydrochloride (1:1) was coupled with Intermediate C61 in the presence of HATU and N,N-diisopropylethylamine. Then the protected intermediate was taken up in trifluoroethanol and fully deprotected by stirring at 50° C. in the presence of zinc chloride overnight. After addition of EDTA, the workup was effected by purification by means of preparative HPLC.

LC-MS (Method 12): $R_t$=1.45 min; MS (ESIpos): m/z=714 $[M+H]^+$.

Example M24

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamic Acid/Trifluoroacetic Acid (1:1)

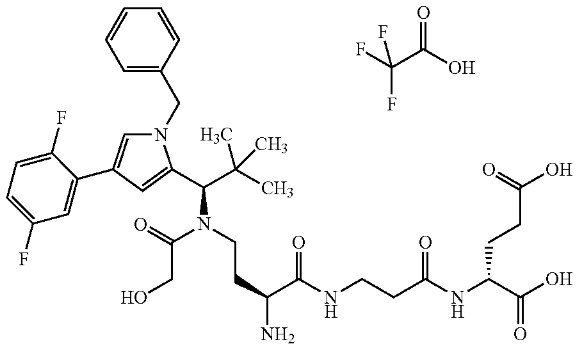 [SMILES: CC(C)(C)[C@H](c1cc(-c2cc(F)ccc2F)cn1Cc1ccccc1)N(CC[C@H](N)C(=O)NCCC(=O)N[C@H](CCC(=O)O)C(=O)O)C(=O)CO ; O=C(O)C(F)(F)F]

First, di-tert-butyl D-glutamate hydrochloride (1:1) was coupled with Intermediate C61 in the presence of HATU and N,N-diisopropylethylamine. Then the protected intermediate was taken up in trifluoroethanol and fully deprotected by stirring at 50° C. in the presence of zinc chloride. After addition of EDTA, the workup was effected by purification by means of preparative HPLC.

LC-MS (Method 12): $R_t$=1.41 min; MS (ESIpos): m/z=714 $[M+H]^+$.

Example M25

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-L-glutamic Acid/Trifluoroacetic Acid (1:1)

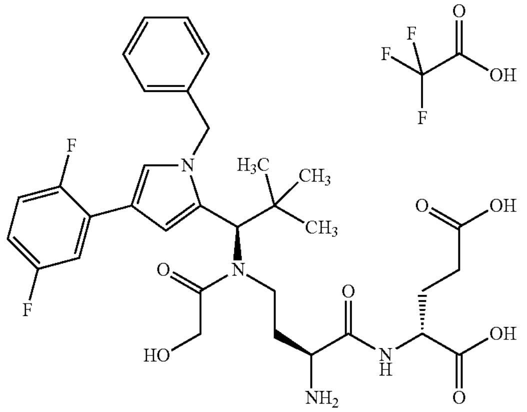 [SMILES: CC(C)(C)[C@H](c1cc(-c2cc(F)ccc2F)cn1Cc1ccccc1)N(CC[C@H](N)C(=O)N[C@H](CCC(=O)O)C(=O)O)C(=O)CO ; O=C(O)C(F)(F)F]

First, di-tert-butyl L-glutamate hydrochloride (1:1) was coupled with Intermediate C61 in the presence of HATU and N,N-diisopropylethylamine. In the next step, the Z protective group was removed by hydrogenation over 10% palladium on activated carbon in methanol at RT under hydrogen standard pressure for 45 min. Then the partially protected intermediate was taken up in trifluoroethanol and fully deprotected by stirring at 50° C. in the presence of zinc chloride for 7 hours. After addition of EDTA, the workup was effected by purification by means of preparative HPLC.

LC-MS (Method 12): $R_t$=1.44 min; MS (ESIpos): m/z=643 $[M+H]^+$.

Example M26

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic Acid/Trifluoroacetic Acid (1:1) Regioisomer 1 Epimer Mixture

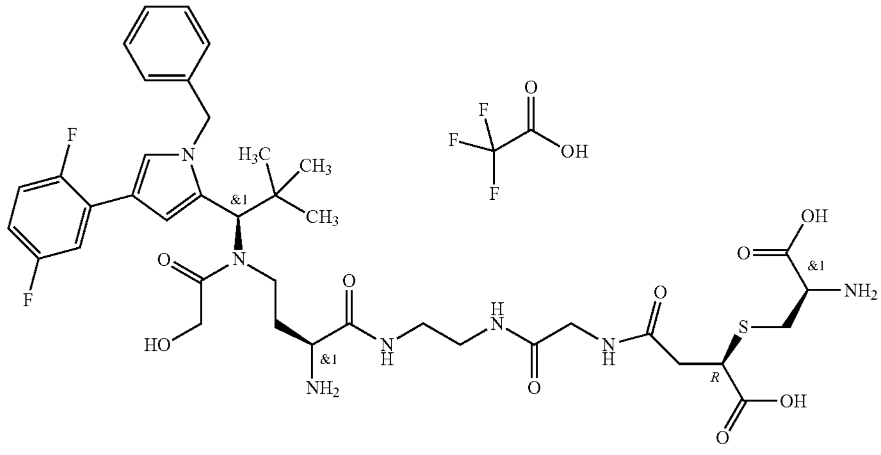

and

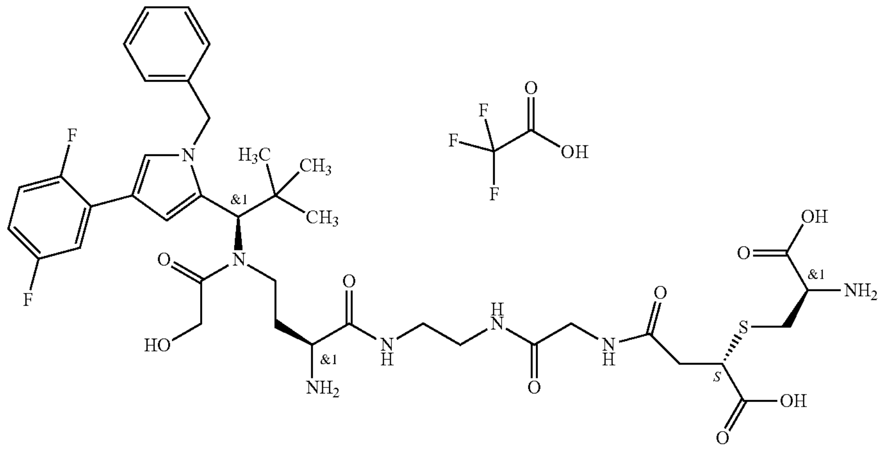

This example describes the epimer mixture of the compounds from Example 13 and Example 14. The synthesis was effected in analogy to Example 13, dispensing with the separation of the two epimers by supercritical fluid chromatography and preparing the title compound as an epimer mixture.

LC-MS (Method 5): $R_t$=2.43 min; MS (ESIpos): m/z=832 $[M+H]^+$.

Example M27

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic Acid/Trifluoroacetic Acid (1:1) Regioisomer 2 Epimer Mixture

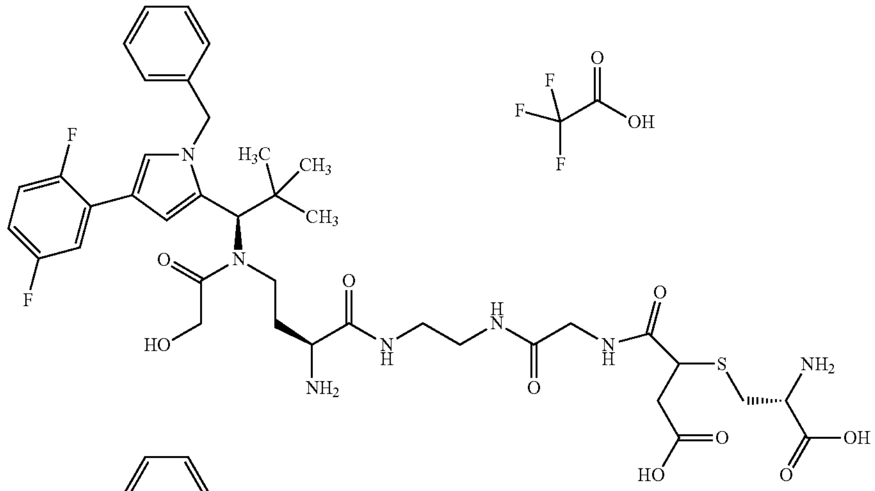

and

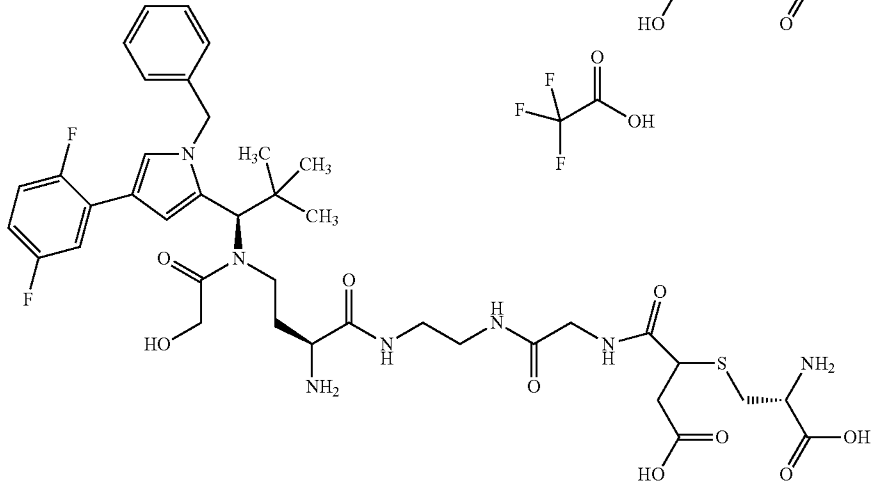

This example describes the epimer mixture of the compounds from Example 15 and Example 16. The synthesis was effected in analogy to Example 15, dispensing with the separation of the two epimers by supercritical fluid chromatography and preparing the title compound as an epimer mixture.

LC-MS (Method 5): $R_t$=2.45 min; MS (EIpos): m/z=832 $[M+H]^+$.

Working examples of APDCs and ADCs

The APDCs and ADCs shown in the structural formulae of the Working examples, which were coupled to the cysteine side chains of the antibodies via maleimide radicals, are, depending on the linker and the coupling procedure, mainly present in the ring-opened or ring-closed forms shown in each case. However, the preparation may comprise a small proportion of the respective other form. The coupling reactions were carried out under argon.

Example 1a

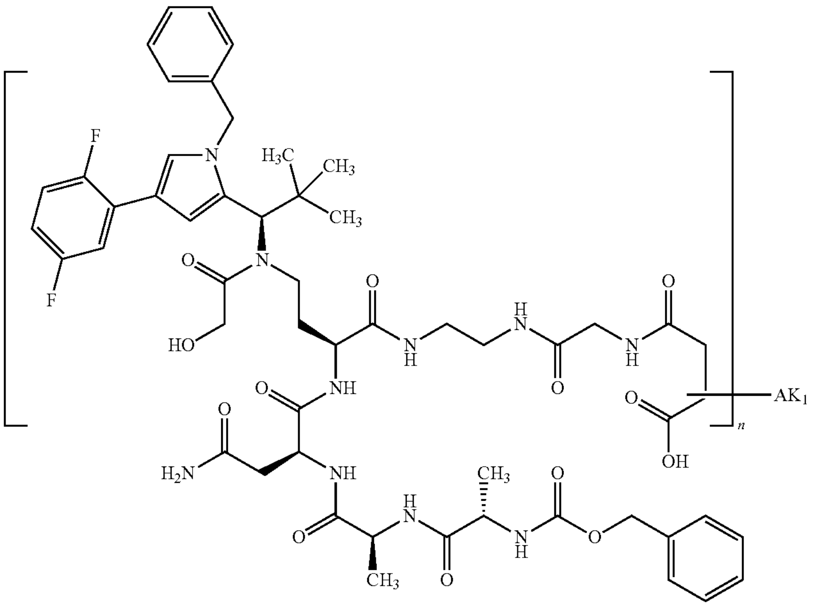

Under argon, a solution of 0.029 mg of TCEP in 0.05 μl of PBS buffer was added to 5 mg of cetuximab in 0.5 ml of PBS (c=10 mg/ml). The reaction was stirred at RT for 30 min, and 0.25 mg (0.00023 mmol) of Intermediate Q1 dissolved in 50 μl of DMSO was then added. After a further 90 min of stirring at RT, the reaction was diluted with 1.95 ml of PBS buffer which had been adjusted to pH 8 beforehand, and stirred at RT under argon overnight.

This solution was then applied to a PD 10 column (Sephadex® G-25, GE Healthcare) which had been equilibrated with PBS buffer pH 7.2 and was eluted with PBS buffer pH 7.2.

The eluate was then concentrated by ultracentrifugation and rediluted with PBS buffer (pH 7.2).

The ADC batch obtained was characterized as follows:

Protein concentration: 1.46 mg/ml

Drug/mAb ratio: 2.7

Example 1e

In an analogous manner, Intermediate Q1 was coupled with 5 mg of trastuzumab. The ADC batch obtained was characterized as follows:

Protein concentration: 1.61 mg/ml

Drug/mAb ratio: 3.3

Example 1i

In an analogous manner, Intermediate Q1 was coupled with 5 mg of nimotuzumab. The ADC batch obtained was characterized as follows:

Protein concentration: 1.75 mg/ml

Drug/mAb ratio: 3.1

Example 1k

In an analogous manner, Intermediate Q1 was coupled with 5 mg of anti-TWEAKR antibody TPP-2658. The ADC batch obtained was characterized as follows:

Protein concentration: 1.26 mg/ml

Drug/mAb ratio: 3.0

Example 1k*

In an analogous manner, Intermediate Q1 was coupled with 50 mg of anti-TWEAKR antibody TPP-2658.

Under argon, a solution of 0.29 mg of TCEP in 0.682 μl of PBS buffer was added to 50 mg of anti-TWEAKR antibody TPP-2658 in 3.07 ml of PBS (c=16.3 mg/ml). The reaction was stirred at RT for 30 min, and 2.53 mg (0.0023 mmol) of Intermediate Q1 dissolved in 357 μl of DMSO were then added. After a further 90 min of stirring at RT, the mixture was diluted to 7.5 ml with 3.391 ml of PBS buffer which had been adjusted to pH 8 beforehand and then passed through a PD 10 column (Sephadex® G-25, GE Healthcare) equilibrated with PBS buffer pH 8, and eluted with PBS buffer pH 8. The eluate was stirred at RT under argon overnight. This solution was then applied to a PD 10 column (Sephadex® G-25, GE Healthcare) which had been equilibrated with PBS buffer pH 7.2 and was eluted with PBS buffer pH 7.2. The eluate was then concentrated by ultracentrifugation and rediluted with PBS buffer (pH 7.2) and reconcentrated again. The ADC batch obtained was characterized as follows:

Protein concentration: 9.56 mg/ml

Drug/mAb ratio: 3.3

Example 2a

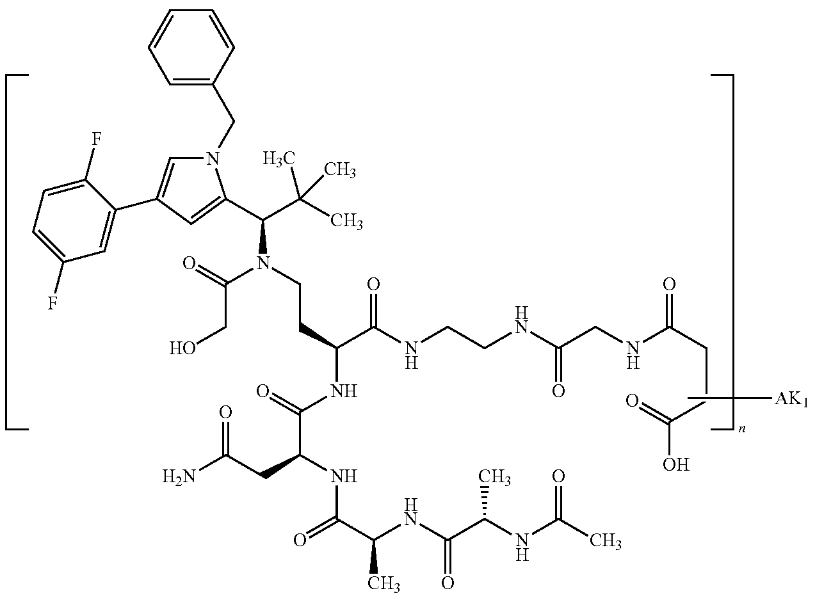

Under argon, a solution of 0.029 mg of TCEP in 0.05 ml of PBS buffer was added to 5 mg of cetuximab in 0.5 ml of PBS (c=10 mg/ml). The reaction was stirred at RT for 30 min, and 0.23 mg (0.00023 mmol) of Intermediate Q2 dissolved in 50 μl of DMSO was then added. After a further 90 min of stirring at RT, the reaction was diluted with 1.9 ml of PBS buffer which had been adjusted to pH 8 beforehand, and stirred at RT under argon overnight.

This solution was then applied to a PD 10 column (Sephadex® G-25, GE Healthcare) which had been equilibrated with PBS buffer pH 7.2 and was eluted with PBS buffer pH 7.2.

This was followed by ultracentrifugation and redilution with PBS buffer (pH 7.2). The ADC batch obtained was characterized as follows:

Protein concentration: 1.87 mg/ml

Drug/mAb ratio: 3.2

Example 2e

In an analogous manner, Intermediate Q2 was coupled with 5 mg of trastuzumab. The ADC batch obtained was characterized as follows:

Protein concentration: 1.41 mg/ml

Drug/mAb ratio: 3.3

Example 2k

In an analogous manner, Intermediate Q2 was coupled with 5 mg of anti-TWEAKR antibody TPP-2658. The ADC batch obtained was characterized as follows: Protein concentration: 1.79 mg/ml Drug/mAb ratio: 3.3

Example 2k*

In an analogous manner to Example 1k*, 2.775 mg (0.0028 mmol) of Intermediate Q2 were coupled with 60 mg of anti-TWEAKR antibody TPP-2658. The ADC batch obtained was characterized as follows:

Protein concentration: 9.97 mg/ml

Drug/mAb ratio: 3.7

Example 3k

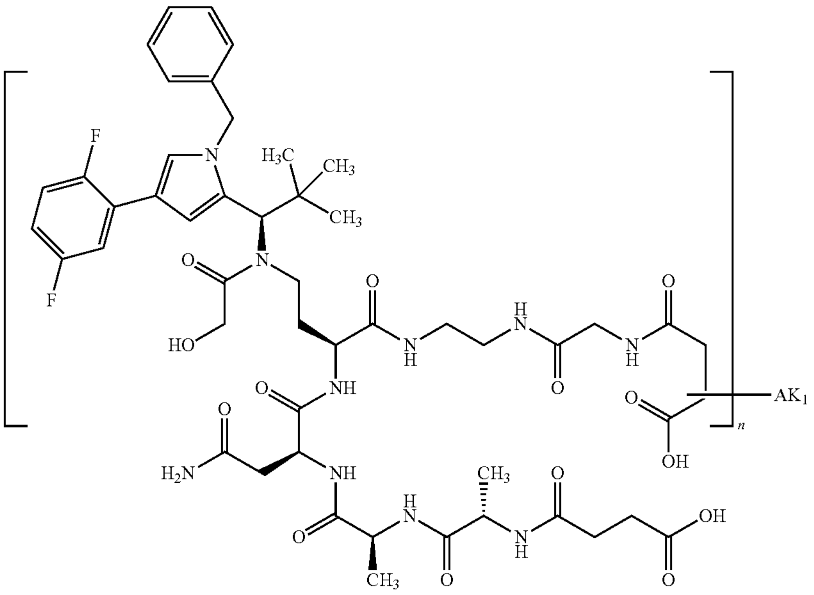

Under argon, a solution of 0.029 mg of TCEP in 0.05 ml of PBS buffer was added to 5 mg of anti-TWEAKR antibody TPP-2658 in 0.5 ml of PBS (c=10 mg/ml). The reaction was stirred at RT for 30 min, and 0.25 mg (0.00023 mmol) of Intermediate Q3 dissolved in 50 μl of DMSO was then added. After a further 90 min of stirring at RT, the reaction was diluted with 1.9 ml of PBS buffer which had been adjusted to pH 8 beforehand, and stirred at RT under argon overnight.

This solution was then applied to a PD 10 column (Sephadex® G-25, GE Healthcare) which had been equilibrated with PBS buffer pH 7.2 and was eluted with PBS buffer pH 7.2.

This was followed by ultracentrifugation and redilution with PBS buffer (pH 7.2). The ADC batch obtained was characterized as follows:

Protein concentration: 1.15 mg/ml

Drug/mAb ratio: 4.3

Example 4a

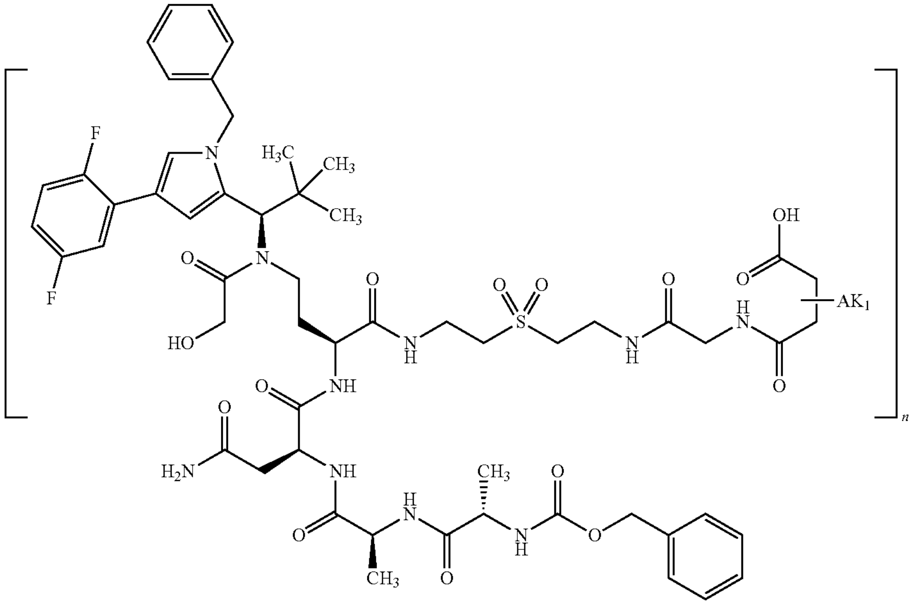

Under argon, a solution of 0.029 mg of TCEP in 0.05 ml of PBS buffer was added to 5 mg of cetuximab in 0.5 ml of PBS (c=10 mg/ml). The reaction was stirred at RT for 30 min, and 0.25 mg (0.00023 mmol) of Intermediate Q4 dissolved in 50 μl of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred at RT under argon overnight. This was followed by ultracentrifugation and redilution with PBS buffer (pH 7.2). The ADC batch obtained was characterized as follows:

Protein concentration: 1.98 mg/ml

Drug/mAb ratio: 2.0

Example 4k

In an analogous manner, Intermediate Q4 was coupled with 5 mg of anti-TWEAKR antibody TPP-2658. The ADC batch obtained was characterized as follows:

Protein concentration: 1.65 mg/ml

Drug/mAb ratio: 3.3

Example 5a

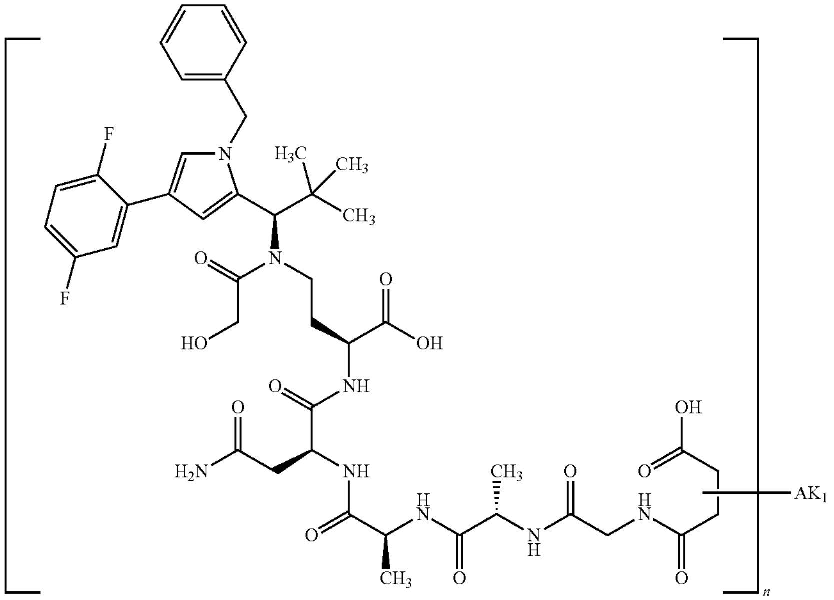

Under argon, a solution of 0.029 mg of TCEP in 0.05 ml of PBS buffer was added to 5 mg of cetuximab in 0.458 ml of PBS (c=10 mg/ml). The reaction was stirred at RT for 30 min, and 0.21 mg (0.00023 mmol) of Intermediate Q5 dissolved in 50 μl of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.91 mg/ml

Drug/mAb ratio: 2.4

Example 5e

In an analogous manner, Intermediate Q5 was coupled with 5 mg of trastuzumab. The ADC batch obtained was characterized as follows:

Protein concentration: 1.55 mg/ml

Drug/mAb ratio: 3.3

Example 5k

In an analogous manner, Intermediate Q5 was coupled with 5 mg of anti-TWEAKR antibody TPP-2658. The ADC batch obtained was characterized as follows:

Protein concentration: 1.54 mg/ml

Drug/mAb ratio: 3.5

Example 6a

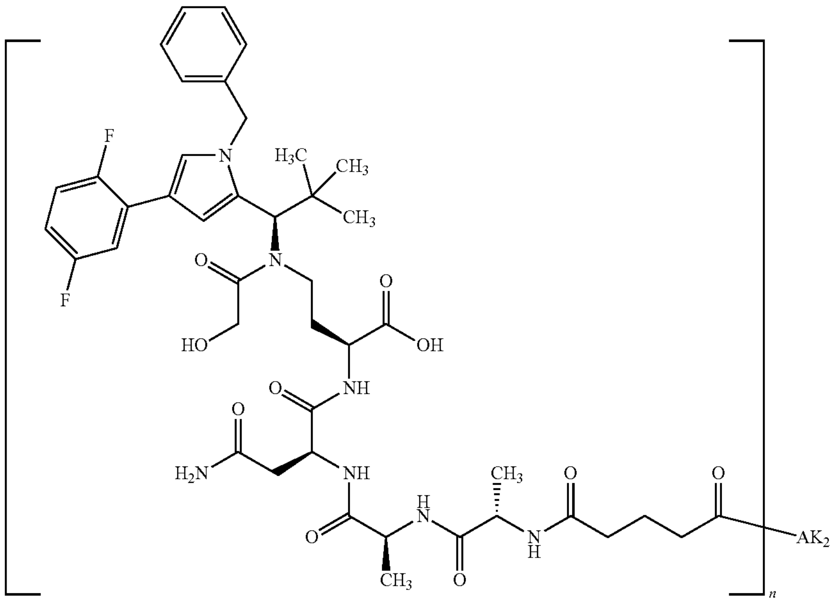

Here, 5 mg of cetuximab in PBS (c=10 mg/ml) were used for coupling with Intermediate Q6. First, 5 eq (0.24 mg) of Intermediate Q6 dissolved in 50 μl of DMSO were added, and after 1 h of stirring at RT the same amount was added again and the reaction was stirred at RT for a further hour. The reaction was subsequently diluted to 2.5 ml with PBS buffer (pH 7.2), purified on a Sephadex column, then concentrated by ultracentrifugation and rediluted with PBS (pH 7.2).

Protein concentration: 2.26 mg/ml

Drug/mAb ratio: 3.7

Example 6e

In an analogous manner, Intermediate Q6 was coupled with 5 mg of trastuzumab. The ADC batch obtained was characterized as follows:

Protein concentration: 1.97 mg/ml

Drug/mAb ratio: 5.4

Example 6k

In an analogous manner, Intermediate Q6 was coupled with 5 mg of anti-TWEAKR antibody TPP-2658. The ADC batch obtained was characterized as follows:

Protein concentration: 2.07 mg/ml

Drug/mAb ratio: 6.7

Example 7a

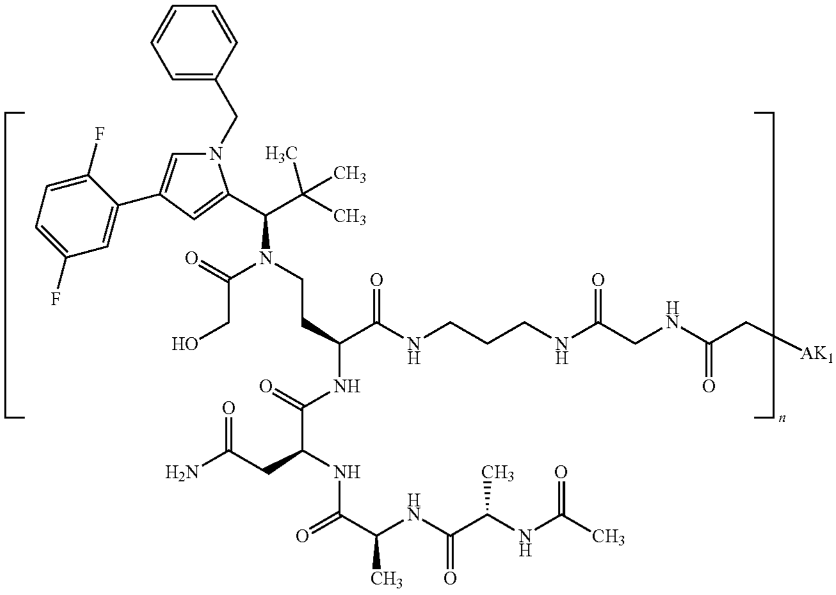

Under argon, a solution of 0.029 mg of TCEP in 0.05 μl of PBS buffer was added to 5 mg of cetuximab in 0.5 ml of PBS (c=10 mg/ml). The reaction was stirred at RT for 30 min. Subsequently, 0.24 mg (0.00023 mmol) of Intermediate Q7 dissolved in 50 μl of DMSO was added and the mixture was stirred at RT overnight. Then the reaction was diluted to 2.5 ml with PBS buffer (pH 7.2), purified on a Sephadex column, and subsequently concentrated by ultracentrifugation and rediluted with PBS (pH 7.2).

Protein concentration: 1.91 mg/ml

Drug/mAb ratio: 1.6

Example 7k

In an analogous manner, Intermediate Q7 was coupled with 5 mg of anti-TWEAKR antibody TPP-2658. The ADC batch obtained was characterized as follows:

Protein concentration: 1.66 mg/ml

Drug/mAb ratio: 2.4

Example 8a

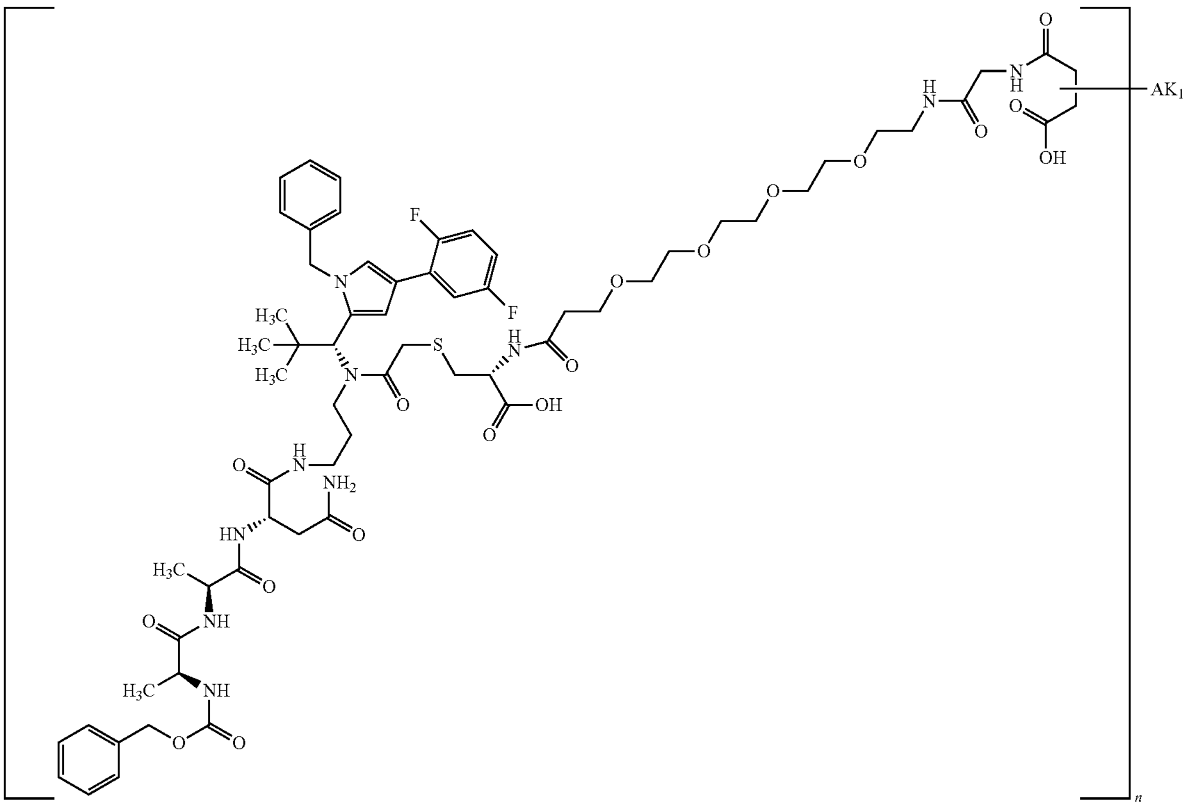

Under argon, a solution of 0.029 mg of TCEP in 50 μl of PBS buffer was added to 5 mg of cetuximab in 458 μl of PBS (c=10.9 mg/ml). The reaction was diluted with 1892 μl of PBS buffer which had been adjusted to pH 8 beforehand and stirred at RT for 1 h. 0.314 mg (0.00023 mmol) of Intermediate Q8 dissolved in 100 μl of DMSO were then added. After a further 90 min of stirring at RT, the reaction was applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:

Protein concentration: 1.15 mg/ml

Drug/mAb ratio: 2.1

Example 8e

In an analogous manner, Intermediate Q8 was coupled with 5 mg of trastuzumab. The ADC batch obtained was characterized as follows:

Protein concentration: 1.21 mg/ml

Drug/mAb ratio: 1.9

Example 8k

In an analogous manner, Intermediate Q8 was coupled with 5 mg of anti-TWEAKR antibody TPP-2658. The ADC batch obtained was characterized as follows:

Protein concentration: 0.65 mg/ml

Drug/mAb ratio: 2.5

Example 9k

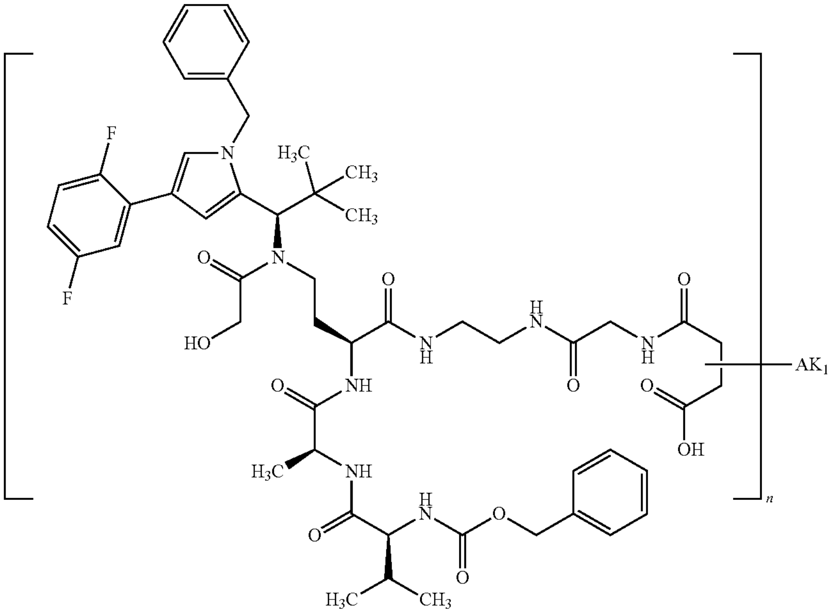

Under argon, a solution of 0.029 mg of TCEP in 0.05 ml of PBS buffer was added to 5 mg of anti-TWEAKR antibody TPP-2658 in 0.450 ml of PBS (c=11.1 mg/ml). The reaction was stirred at RT for 30 min, and 0.24 mg (0.00023 mmol) of Intermediate Q9 dissolved in 50 µl of DMSO was then added. After a further 90 min of stirring at RT, the mixture was diluted with 1.95 ml of PBS buffer which had been adjusted to pH 8 beforehand and then passed through a PD 10 column (Sephadex® G-25, GE Healthcare) equilibrated with PBS buffer pH 8, and eluted with PBS buffer pH 8. The eluate was stirred at RT overnight and then concentrated by ultracentrifugation and rediluted with PBS buffer (pH 7.2). The ADC batch obtained was characterized as follows:

Protein concentration: 0.86 mg/ml

Drug/mAb ratio: 3.1

Example 10a

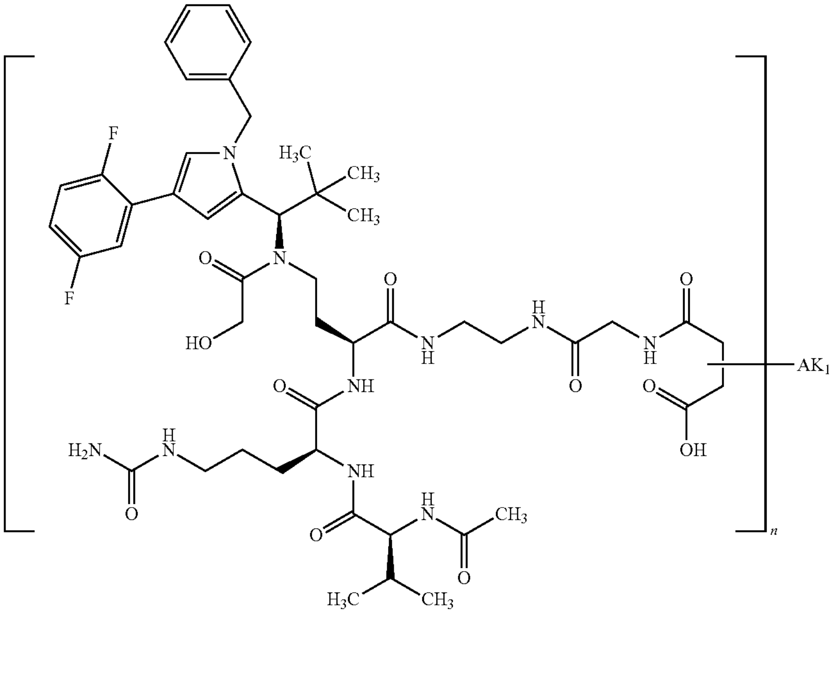

Under argon, a solution of 0.029 mg of TCEP in 0.05 ml of PBS buffer was added to 5 mg of anti-TWEAKR antibody in 0.458 ml of PBS (c=10.9 mg/ml). The reaction was stirred at RT for 30 min, and 0.23 mg (0.00023 mmol) of Intermediate Q10 dissolved in 50 μl of DMSO was then added. After a further 90 min of stirring at RT, the mixture was diluted with 1.95 ml of PBS buffer which had been adjusted to pH 8 beforehand and then passed through a PD 10 column (Sephadex® G-25, GE Healthcare) equilibrated with PBS buffer pH 8, and eluted with PBS buffer pH 8. The eluate was stirred at RT overnight and then concentrated by ultracentrifugation and rediluted with PBS buffer (pH 7.2). The ADC batch obtained was characterized as follows:

Protein concentration: 1.92 mg/ml

Drug/mAb ratio: 2.9

Example 10k

In an analogous manner, Intermediate Q10 was coupled with 5 mg of anti-TWEAKR antibody TPP-2658. The ADC batch obtained was characterized as follows:

Protein concentration: 1.65 mg/ml

Drug/mAb ratio: 3.3

Example 11a

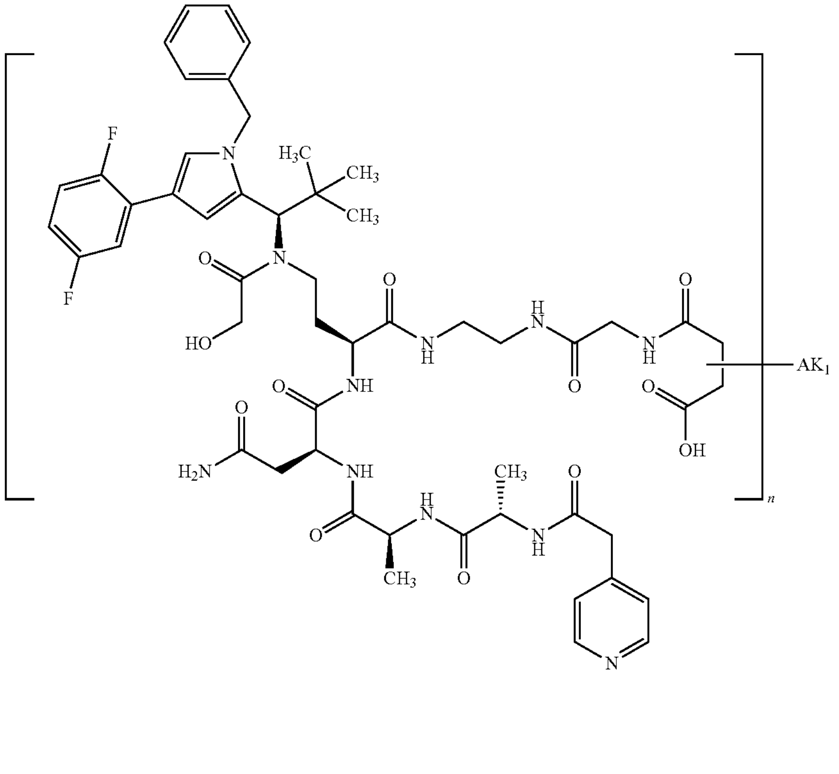

Under argon, a solution of 0.029 mg of TCEP in 0.05 ml of PBS buffer was added to 5 mg of cetuximab in 0.458 ml of PBS (c=10.92 mg/ml). The reaction was stirred at RT for 30 min, and 0.28 mg (0.00023 mmol) of Intermediate Q11 dissolved in 50 μl of DMSO was then added. After a further 90 min of stirring at RT, the reaction was diluted with 1.942 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight.

This solution was then concentrated by ultracentrifugation and rediluted with PBS buffer (pH 7.2). The ADC batch obtained was characterized as follows:

Protein concentration: 1.99 mg/ml

Drug/mAb ratio: 2.6

Example lie

In an analogous manner, Intermediate Q11 was coupled with 5 mg of trastuzumab. The ADC batch obtained was characterized as follows:

Protein concentration: 1.70 mg/ml

Drug/mAb ratio: 3.3

Example 11k

In an analogous manner, Intermediate Q11 was coupled with 5 mg of anti-TWEAKR antibody TPP-2658. The ADC batch obtained was characterized as follows:

Protein concentration: 1.71 mg/ml

Drug/mAb ratio: 3.1

Example 12a

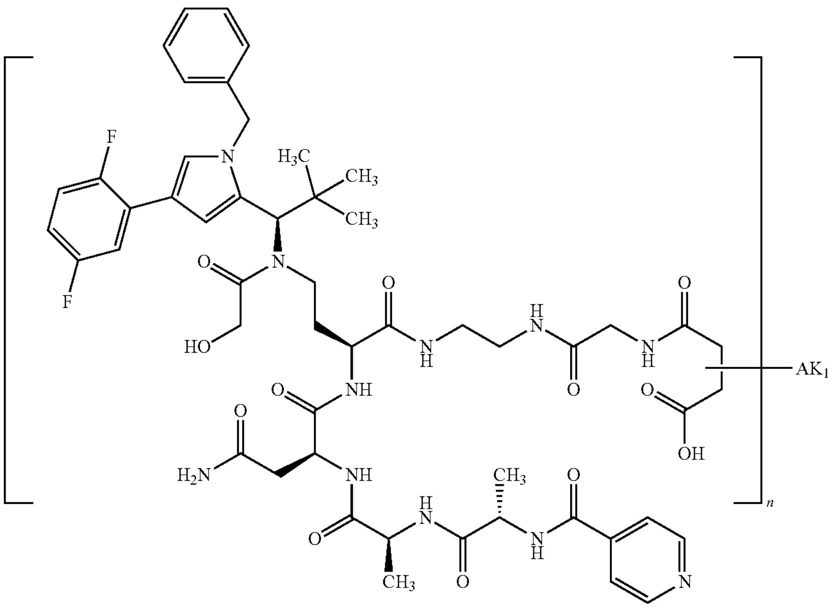

Under argon, a solution of 0.029 mg of TCEP in 0.05 ml of PBS buffer was added to 5 mg of cetuximab in 0.458 ml of PBS (c=10.92 mg/ml). The reaction was stirred at RT for 30 min, and 0.305 mg (0.00023 mmol) of Intermediate Q12 dissolved in 50 µl of DMSO was then added. After a further 90 min of stirring at RT, the reaction was diluted with 1.942 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:
Protein concentration: 2.23 mg/ml
Drug/mAb ratio: 2.5

Example 12e

In an analogous manner, Intermediate Q12 was coupled with 5 mg of trastuzumab. The ADC batch obtained was characterized as follows:
Protein concentration: 1.73 mg/ml
Drug/mAb ratio: 3.1

Example 12k

In an analogous manner, Intermediate Q12 was coupled with 5 mg of anti-TWEAKR antibody TPP-2658. The ADC batch obtained was characterized as follows:
Protein concentration: 1.91 mg/ml
Drug/mAb ratio: 2.8

Example 13a

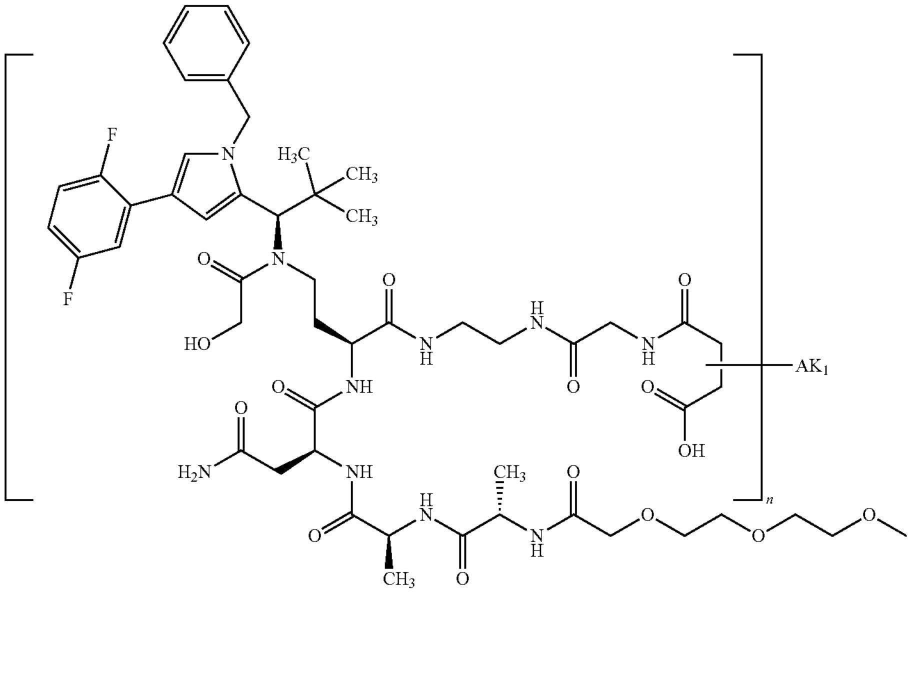

Under argon, a solution of 0.029 mg of TCEP in 0.05 ml of PBS buffer was added to 5 mg of cetuximab in 0.5 ml of PBS (c=10 mg/ml). The reaction was stirred at RT for 30 min, and 0.26 mg (0.00023 mmol) of Intermediate Q13 dissolved in 50 μl of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.98 mg/ml

Drug/mAb ratio: 2.1

Example 13e

In an analogous manner, Intermediate Q13 was coupled with 5 mg of trastuzumab. The ADC batch obtained was characterized as follows:

Protein concentration: 1.83 mg/ml

Drug/mAb ratio: 3.1

Example 13k

In an analogous manner, Intermediate Q13 was coupled with 5 mg of anti-TWEAKR antibody TPP-2658. The ADC batch obtained was characterized as follows:

Protein concentration: 1.54 mg/ml

Drug/mAb ratio: 3.2

Example 14a

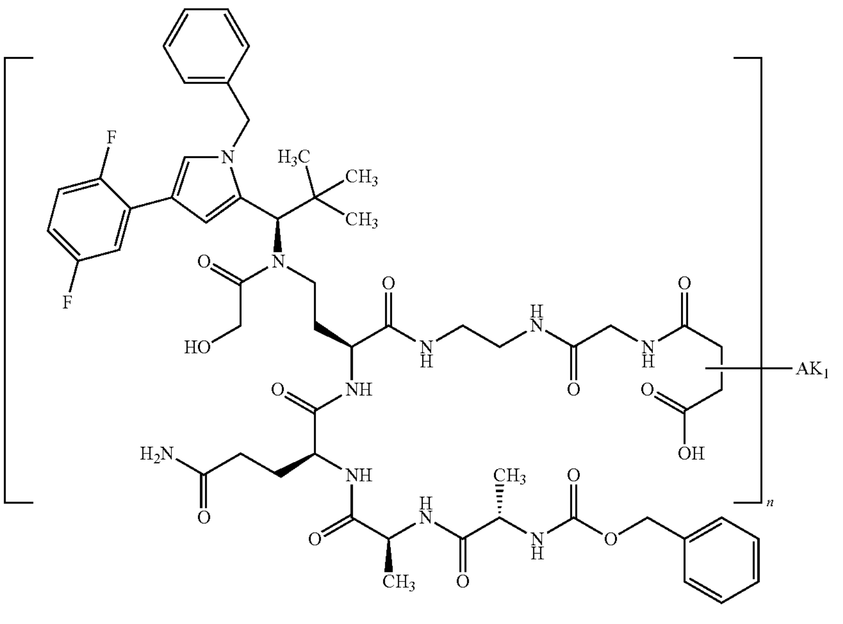

Under argon, a solution of 0.029 mg of TCEP in 0.05 ml of PBS buffer was added to 5 mg of cetuximab in 0.458 ml of PBS (c=10.92 mg/ml). The reaction was stirred at RT for 30 min, and 0.29 mg (0.00023 mmol) of Intermediate Q14 dissolved in 50 μl of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.92 mg/ml

Drug/mAb ratio: 2.9

Example 14e

In an analogous manner, Intermediate Q14 was coupled with 5 mg of trastuzumab. The ADC batch obtained was characterized as follows:

Protein concentration: 1.72 mg/ml

Drug/mAb ratio: 3.4

Example 14k

In an analogous manner, Intermediate Q14 was coupled with 5 mg of anti-TWEAKR antibody TPP-2658. The ADC batch obtained was characterized as follows:

Protein concentration: 1.80 mg/ml

Drug/mAb ratio: 2.9

Example 15a

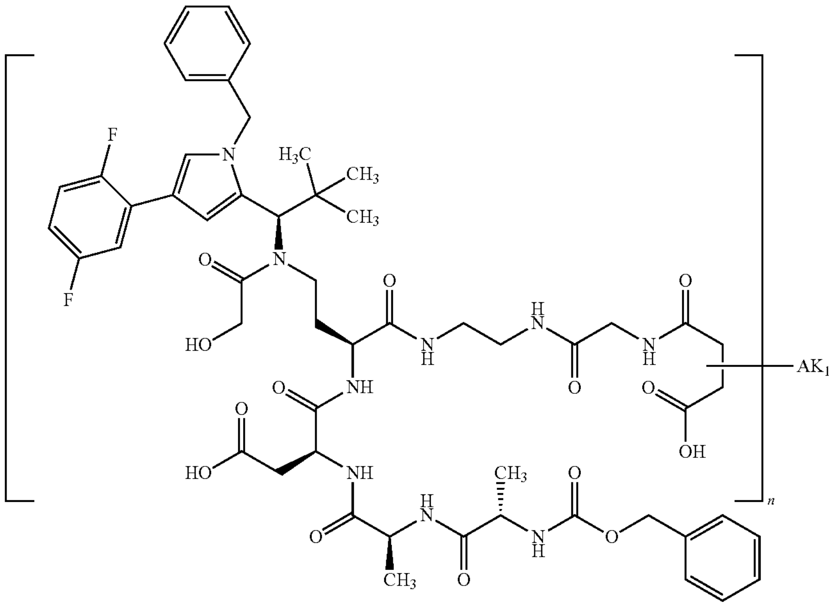

Under argon, a solution of 0.029 mg of TCEP in 0.05 ml of PBS buffer was added to 5 mg of cetuximab in 0.458 ml of PBS (c=10.92 mg/ml). The reaction was stirred at RT for 30 min, and 0.25 mg (0.00023 mmol) of Intermediate Q15 dissolved in 50 μl of DMSO were then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.90 mg/ml

Drug/mAb ratio: 2.8

Example 15k

In an analogous manner, Intermediate Q15 was coupled with 5 mg of anti-TWEAKR antibody TPP-2658. The ADC batch obtained was characterized as follows:

Protein concentration: 1.74 mg/ml

Drug/mAb ratio: 2.9

Example 16a

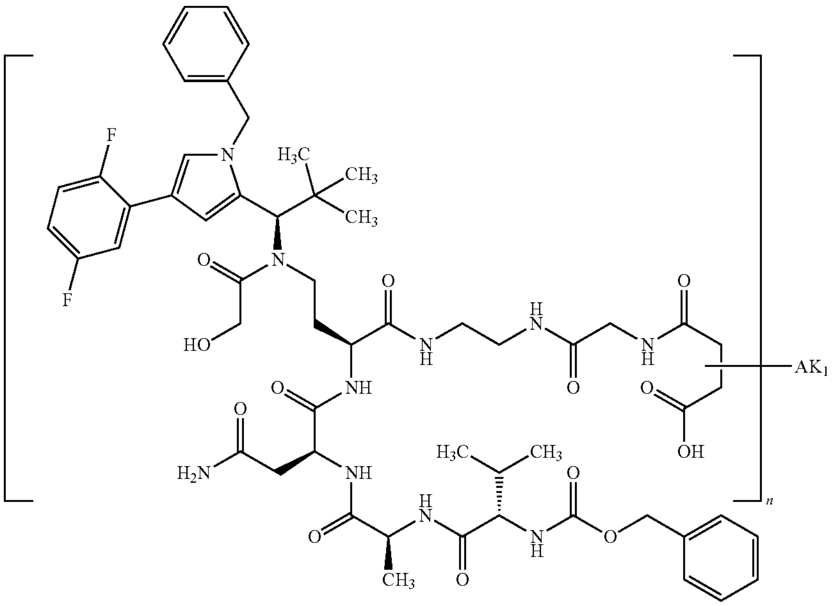

Under argon, a solution of 0.029 mg of TCEP in 0.05 ml of PBS buffer was added to 5 mg of cetuximab in 0.5 ml of PBS (c=10 mg/ml). The reaction was stirred at RT for 30 min, and 0.26 mg (0.00023 mmol) of Intermediate Q16 dissolved in 50 µl of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.74 mg/ml

Drug/mAb ratio: 2.7

Example 16e

In an analogous manner, Intermediate Q16 was coupled with 5 mg of trastuzumab. The ADC batch obtained was characterized as follows:

Protein concentration: 1.61 mg/ml

Drug/mAb ratio: 3.3

Example 16k

In an analogous manner, Intermediate Q16 was coupled with 5 mg of anti-TWEAKR antibody TPP-2658. The ADC batch obtained was characterized as follows:

Protein concentration: 1.75 mg/ml

Drug/mAb ratio: 3.2

Example 17a

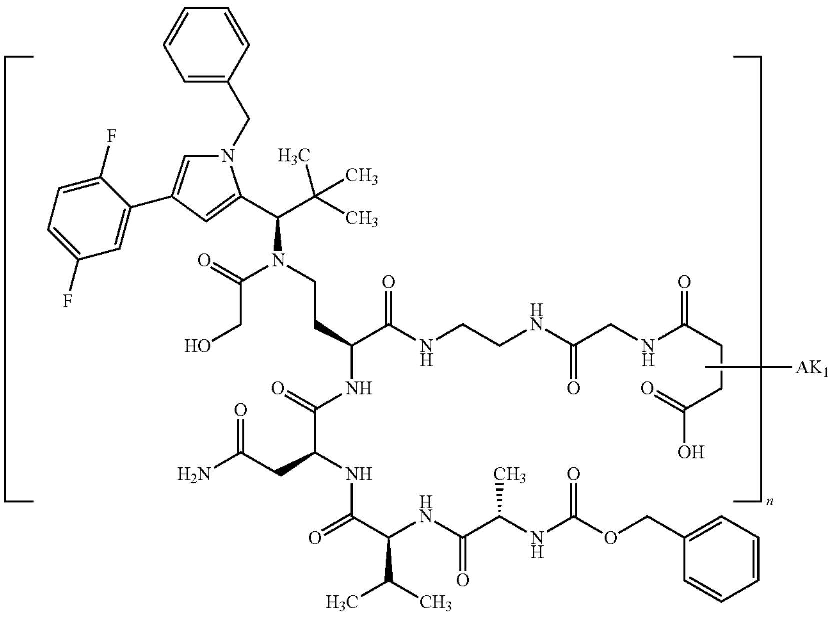

Under argon, a solution of 0.029 mg of TCEP in 0.05 µl of PBS buffer was added to 5 mg of cetuximab in 0.5 ml of PBS (c=10 mg/ml). The reaction was stirred at RT for 30 min, and 0.26 mg (0.00023 mmol) of Intermediate Q17 dissolved in 50 µl of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.93 mg/ml

Drug/mAb ratio: 2.8

Example 17e

In an analogous manner, Intermediate Q17 was coupled with 5 mg of trastuzumab. The ADC batch obtained was characterized as follows:

Protein concentration: 1.83 mg/ml

Drug/mAb ratio: 2.9

Example 17k

In an analogous manner, Intermediate Q17 was coupled with 5 mg of anti-TWEAKR antibody TPP-2658. The ADC batch obtained was characterized as follows:

Protein concentration: 1.34 mg/ml

Drug/mAb ratio: 2.8

Example 18a

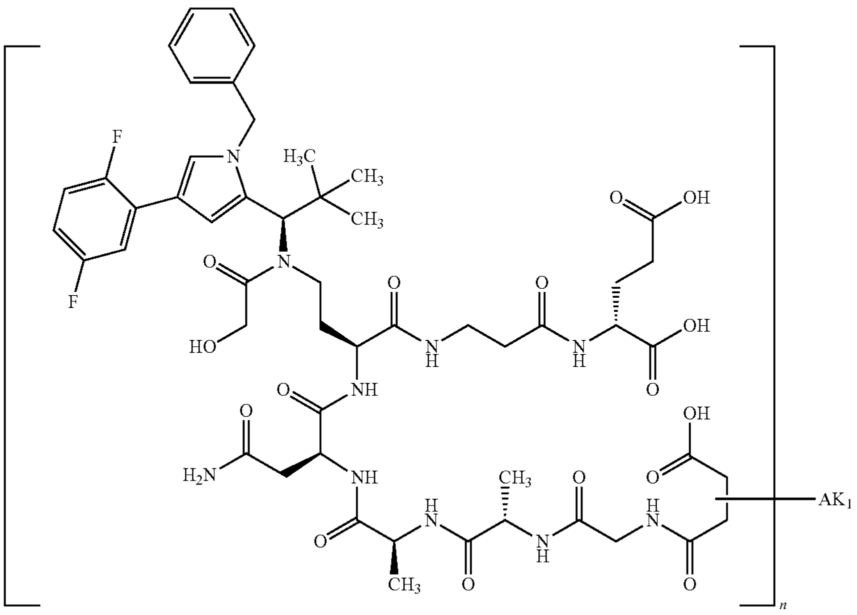

Under argon, a solution of 0.029 mg of TCEP in 0.05 ml of PBS buffer was added to 5 mg of cetuximab in 0.5 ml of PBS (c=10 mg/ml). The reaction was stirred at RT for 30 min, and 0.26 mg (0.00023 mmol) of Intermediate Q18 dissolved in 50 µl of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.57 mg/ml

Drug/mAb ratio: 2.4

Example 18e

In an analogous manner, Intermediate Q18 was coupled with 5 mg of trastuzumab. The ADC batch obtained was characterized as follows:

Protein concentration: 1.79 mg/ml

Drug/mAb ratio: 3.1

Example 18k

In an analogous manner, Intermediate Q18 was coupled with 5 mg of anti-TWEAKR antibody TPP-2658. The ADC batch obtained was characterized as follows:

Protein concentration: 0.68 mg/ml

Drug/mAb ratio: 2.8

Example 19a

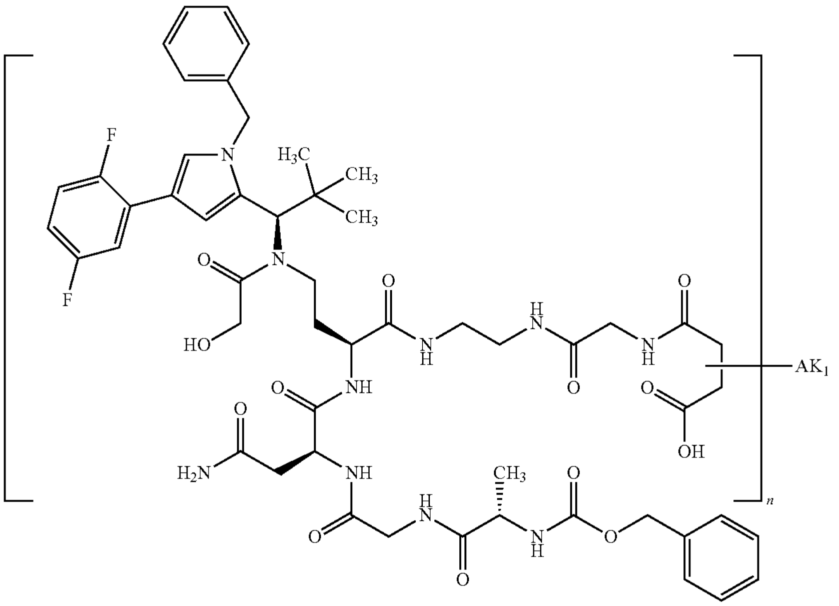

Under argon, a solution of 0.029 mg of TCEP in 0.05 ml of PBS buffer was added to 5 mg of cetuximab in 0.5 ml of PBS (c=10 mg/ml). The reaction was stirred at RT for 30 min, and 0.25 mg (0.00023 mmol) of Intermediate Q19 dissolved in 50 μl of DMSO were then added. After a further 90 min of stirring at RT, the reaction was diluted with 1.95 ml of PBS buffer which had been adjusted to pH 8 beforehand, and stirred at RT under argon overnight.

This solution was then applied to a PD 10 column (Sephadex® G-25, GE Healthcare) which had been equilibrated with PBS buffer pH 7.2 and was eluted with PBS buffer pH 7.2.

This was followed by ultracentrifugation and redilution with PBS buffer (pH 7.2). The ADC batch obtained was characterized as follows:

Protein concentration: 1.85 mg/ml

Drug/mAb ratio: 2.3

Example 19e

In an analogous manner, Intermediate Q19 was coupled with 5 mg of trastuzumab. The ADC batch obtained was characterized as follows:

Protein concentration: 1.88 mg/ml

Drug/mAb ratio: 2.5

Example 19k

In an analogous manner, Intermediate Q19 was coupled with 5 mg of anti-TWEAKR antibody TPP-2658. The ADC batch obtained was characterized as follows:

Protein concentration: 1.80 mg/ml

Drug/mAb ratio: 1.8

Example 20k

Under argon, a solution of 0.131 mg of TCEP in 0.20 ml of PBS buffer was added to 5 mg of anti-TWEAKR antibody TPP-2658 in 0.239 ml of PBS (c=20.90 mg/ml). The reaction was dissolved with 0.461 ml of PBS and stirred at RT for 30 min, and 0.833 mg (0.00040 mmol) of Intermediate Q20 dissolved in 100 μl of DMSO was then added. After a further 120 min of stirring at RT, the reaction was diluted with 1.50 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.96 mg/ml

Drug/mAb ratio: 4.6

Example 20k*

Under argon, a solution of 0.076 mg of TCEP in 0.05 ml of PBS buffer was added to 5 mg of anti-TWEAKR antibody TPP-2658 in 0.239 ml of PBS (c=20.90 mg/ml). The reaction was dissolved with 0.20 ml of PBS and stirred at RT for 150 min, and 0.833 mg (0.00040 mmol) of Intermediate Q20 dissolved in 50 μl of DMSO was then added. After a further 120 min of stirring at RT, the reaction was diluted with 1.96 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by concentration by ultracentrifugation and redilution with PBS buffer (pH 7.2). The ADC batch obtained was characterized as follows:

Protein concentration: 2.17 mg/ml

Drug/mAb ratio: 7.3

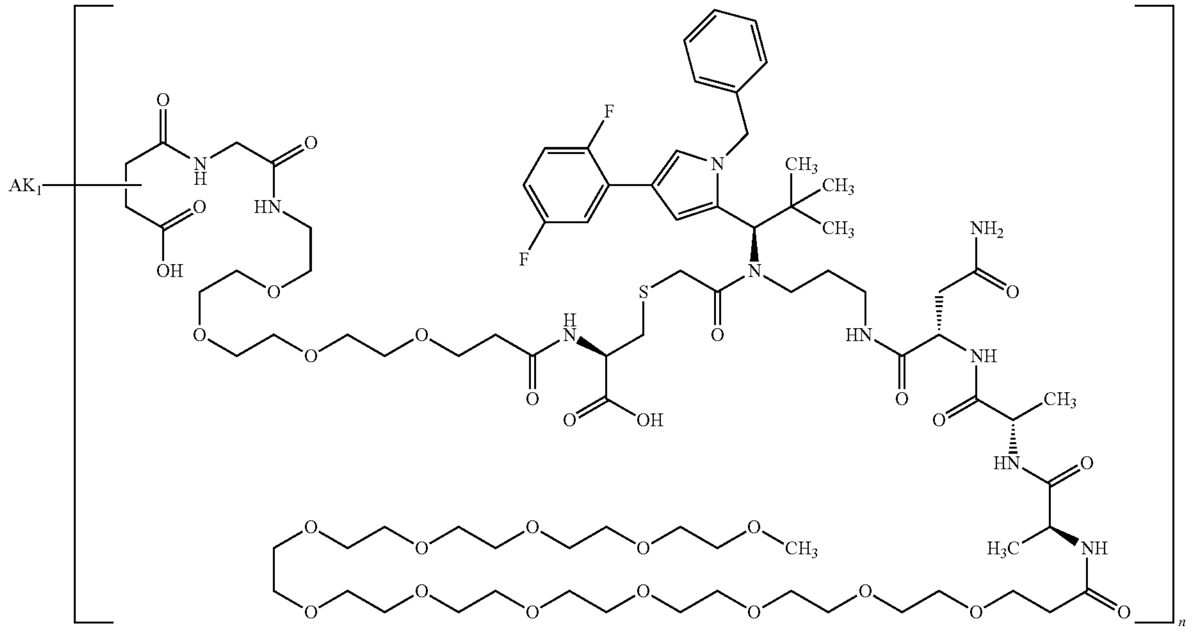

Example 21a

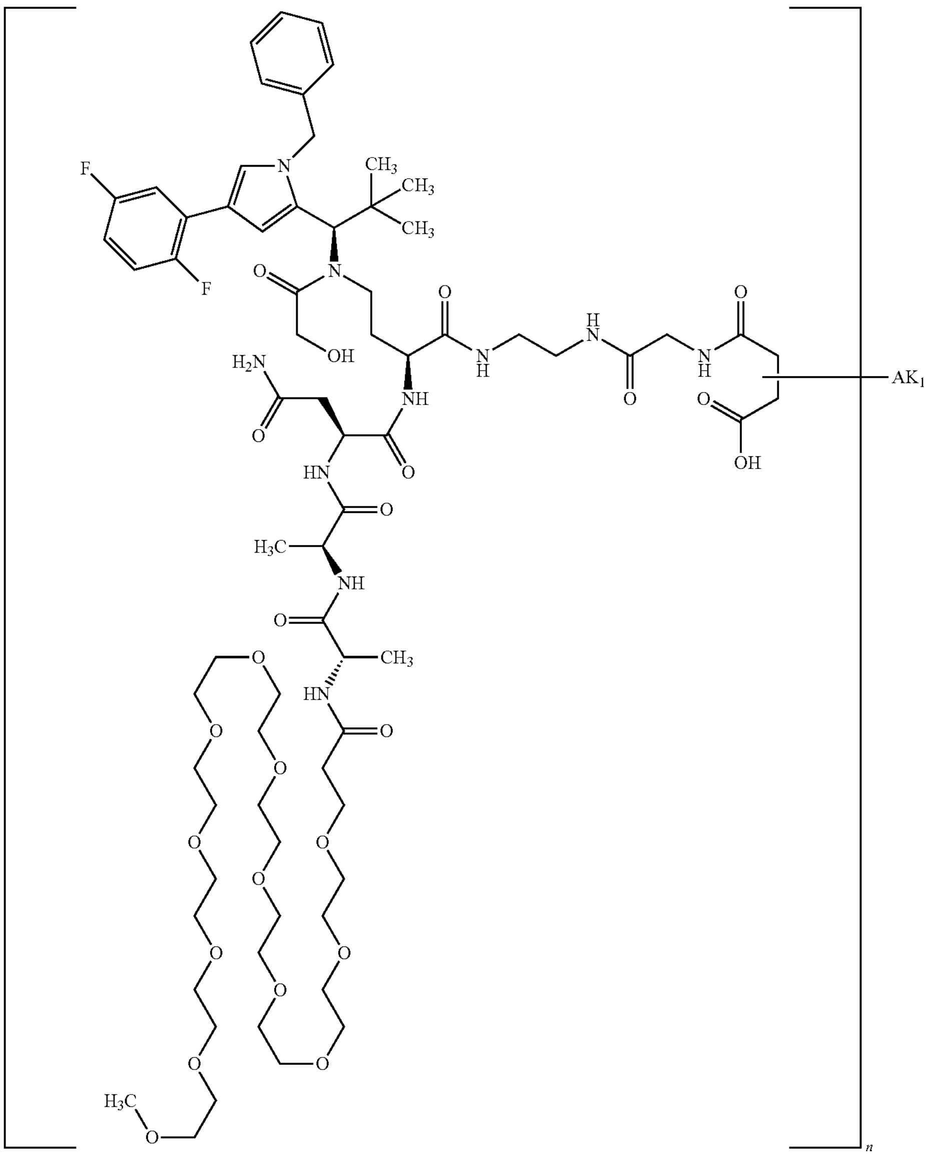

Under argon, a solution of 0.076 mg of TCEP in 0.20 ml of PBS buffer was added to 5 mg of cetuximab antibody in 0.427 ml of PBS (c=11.7 mg/ml). The reaction was stirred at RT for 150 min, and 0.811 mg (0.000533 mmol) of Intermediate Q21 dissolved in 40 μl of DMSO was then added. After a further 120 min of stirring at RT, the reaction was diluted with 1.98 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 2.37 mg/ml

Drug/mAb ratio: 8.1

Example 21e

In an analogous manner, Intermediate Q21 was coupled with 5 mg of trastuzumab. The ADC batch obtained was characterized as follows:

Protein concentration: 2.27 mg/ml

Drug/mAb ratio: 8.0

Example 21k

In an analogous manner, Intermediate Q21 was coupled with 5 mg of anti-TWEAKR antibody TPP-2658. The ADC batch obtained was characterized as follows:

Protein concentration: 2.73 mg/ml

Drug/mAb ratio: 7.9

Example 22a

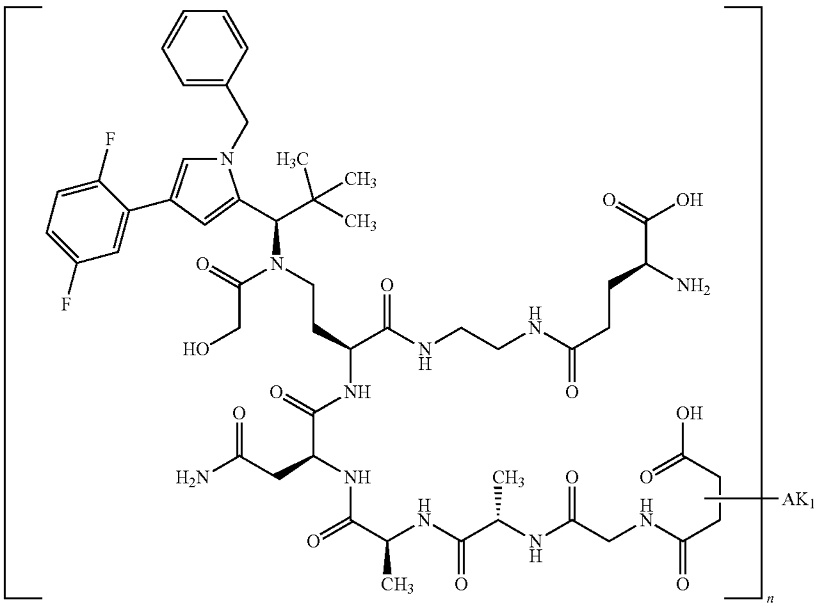

Under argon, a solution of 0.029 mg of TCEP in 0.05 ml of PBS buffer was added to 5 mg of cetuximab in 0.458 ml of PBS (c=10.92 mg/ml). The reaction was stirred at RT for 30 min, and 0.28 mg (0.00023 mmol) of Intermediate Q22 dissolved in 50 l of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.91 mg/ml

Drug/mAb ratio: 2.2

Example 22e

In an analogous manner, Intermediate Q22 was coupled with 5 mg of trastuzumab. The ADC batch obtained was characterized as follows:

Protein concentration: 1.59 mg/ml

Drug/mAb ratio: 1.7

Example 22k

In an analogous manner, Intermediate Q22 was coupled with 5 mg of anti-TWEAKR antibody TPP-2658. The ADC batch obtained was characterized as follows:

Protein concentration: 1.89 mg/ml

Drug/mAb ratio: 2.8

Example 23a

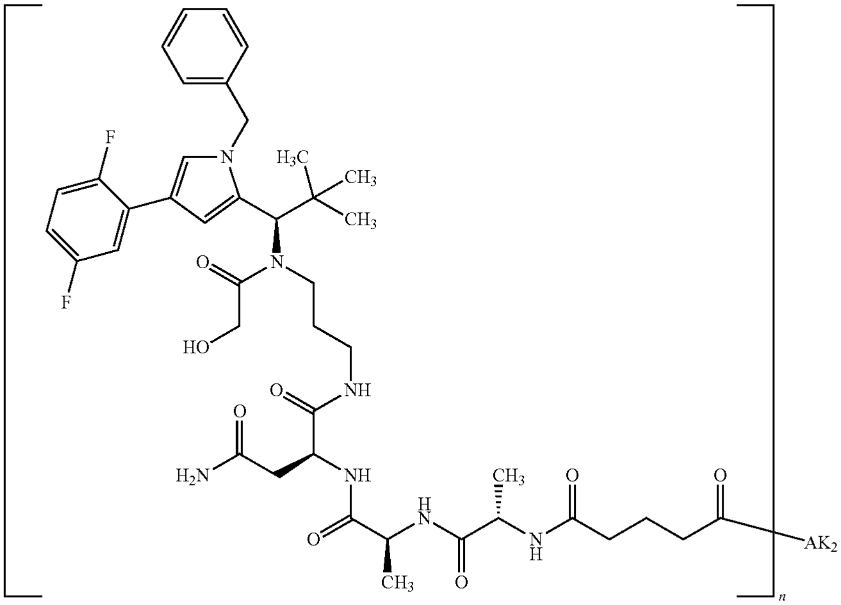

Here, 5 mg of cetuximab in PBS (c=10 mg/ml) were used for coupling with Intermediate Q23. First, 5 eq (0.2 mg) of Intermediate Q23 dissolved in 50 μl of DMSO were added, and after 1 h of stirring at RT the same amount was added again and the reaction was stirred at RT for a further hour. The reaction was subsequently diluted to 2.5 ml with PBS buffer (pH 7.2), purified on a Sephadex column, then concentrated by ultracentrifugation and rediluted with PBS (pH 7.2).

Protein concentration: 1.88 mg/ml

Drug/mAb ratio: 2.6

Example 23e

In an analogous manner, Intermediate Q23 was coupled with 5 mg of trastuzumab. The ADC batch obtained was characterized as follows:

Protein concentration: 1.68 mg/ml

Drug/mAb ratio: 3.7

Example 23k

In an analogous manner, Intermediate Q23 was coupled with 5 mg of anti-TWEAKR antibody TPP-2658. The ADC batch obtained was characterized as follows:

Protein concentration: 1.23 mg/ml

Drug/mAb ratio: 3.9

Example 24a

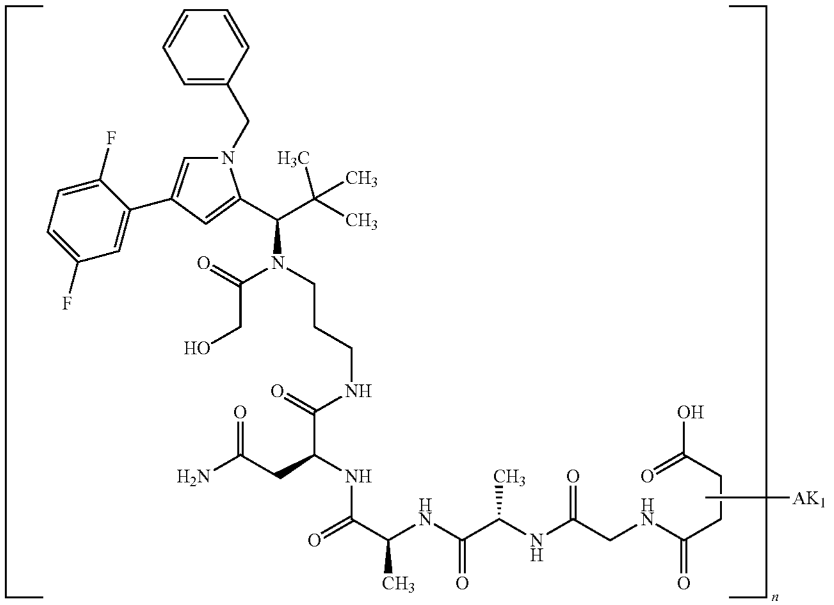

Under argon, a solution of 0.029 mg of TCEP in 0.05 ml of PBS buffer was added to 5 mg of cetuximab in 0.458 ml of PBS (c=10.92 mg/ml). The reaction was stirred at RT for 30 min, and 0.23 mg (0.00023 mmol) of Intermediate Q24 dissolved in 50 μl of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.80 mg/ml

Drug/mAb ratio: 2.2

Example 24e

In an analogous manner, Intermediate Q24 was coupled with 5 mg of trastuzumab. The ADC batch obtained was characterized as follows:

Protein concentration: 1.49 mg/ml

Drug/mAb ratio: 2.3

Example 24k

In an analogous manner, Intermediate Q24 was coupled with 5 mg of anti-TWEAKR antibody TPP-2658. The ADC batch obtained was characterized as follows:

Protein concentration: 1.73 mg/ml

Drug/mAb ratio: 2.2

Example 25a

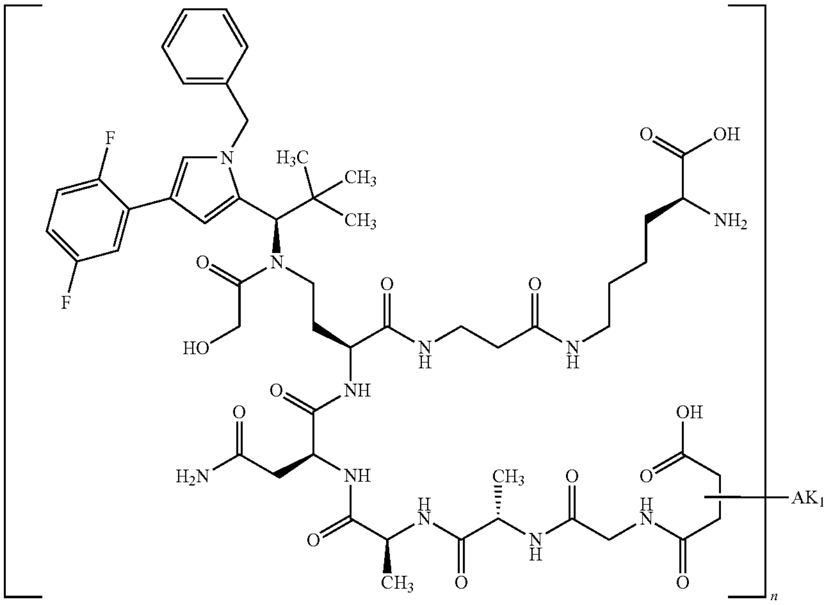

Under argon, a solution of 0.029 mg of TCEP in 0.05 ml of PBS buffer was added to 5 mg of cetuximab in 0.5 ml of PBS (c=10 mg/ml). The reaction was stirred at RT for 30 min, and 0.21 mg (0.00023 mmol) of Intermediate Q25 dissolved in 50 μl of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by ultracentrifugation and redilution with PBS buffer (pH 7.2). The ADC batch obtained was characterized as follows:

Protein concentration: 1.59 mg/ml

Drug/mAb ratio: 2.9

Example 25e

In an analogous manner, Intermediate Q25 was coupled with 5 mg of trastuzumab. The ADC batch obtained was characterized as follows:

Protein concentration: 1.42 mg/ml

Drug/mAb ratio: 3.5

Example 25k

In an analogous manner, Intermediate Q25 was coupled with 5 mg of anti-TWEAKR antibody TPP-2658. The ADC batch obtained was characterized as follows:

Protein concentration: 1.44 mg/ml

Drug/mAb ratio: 3.2

Example 26a

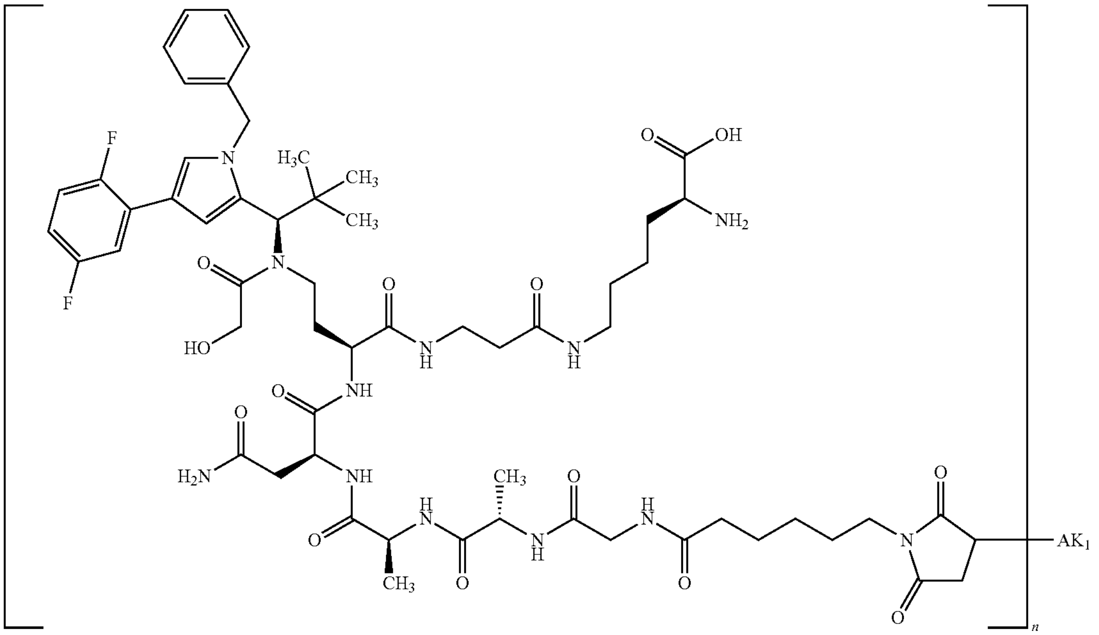

Under argon, a solution of 0.029 mg of TCEP in 0.05 ml of PBS buffer was added to 5 mg of cetuximab in 0.498 ml of PBS (c=10 mg/ml). The reaction was stirred at RT for 30 min, and 0.3 mg (0.00023 mmol) of Intermediate Q26 dissolved in 50 μl of DMSO was then added. After a further 90 min of stirring at RT, the reaction was diluted with 1.9 ml of PBS buffer. This solution was then applied to a PD 10 column (Sephadex® G-25, GE Healthcare) which had been equilibrated with PBS buffer (pH 7.2) and was eluted with PBS buffer (pH 7.2). This was followed by ultracentrifugation and redilution with PBS buffer (pH 7.2). The ADC batch obtained was characterized as follows:

Protein concentration: 2.0 mg/ml

Drug/mAb ratio: 2.9

Example 26e

In an analogous manner, Intermediate Q26 was coupled with 5 mg of trastuzumab. The ADC batch obtained was characterized as follows:

Protein concentration: 1.66 mg/ml

Drug/mAb ratio: 2.9

Example 26k

In an analogous manner, Intermediate Q26 was coupled with 5 mg of anti-TWEAKR antibody TPP-2658. The ADC batch obtained was characterized as follows:

Protein concentration: 1.83 mg/ml

Drug/mAb ratio: 3.4

Example 27a

Under argon, a solution of 0.029 mg of TCEP in 0.05 ml of PBS buffer was added to 5 mg of cetuximab in 0.458 ml of PBS (c=10.92 mg/ml). The reaction was stirred at RT for 30 min, and 0.26 mg (0.00023 mmol) of Intermediate Q27 dissolved in 50 μl of DMSO was then added. After a further 90 min of stirring at RT, the reaction was diluted with 1.9 ml of PBS buffer which had been adjusted to pH 8 beforehand. This solution was then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by concentrated by ultracentrifugation and redilution with PBS buffer (pH 7.2). The ADC batch obtained was characterized as follows:

Protein concentration: 2.02 mg/ml

Drug/mAb ratio: 3.5

Example 27e

In an analogous manner, Intermediate Q27 was coupled with 5 mg of trastuzumab. The ADC batch obtained was characterized as follows:

Protein concentration: 1.72 mg/ml

Drug/mAb ratio: 4.2

Example 27k

In an analogous manner, Intermediate Q27 was coupled with 5 mg of anti-TWEAKR antibody TPP-2658. The ADC batch obtained was characterized as follows:

Protein concentration: 1.79 mg/ml

Drug/mAb ratio: 3.1

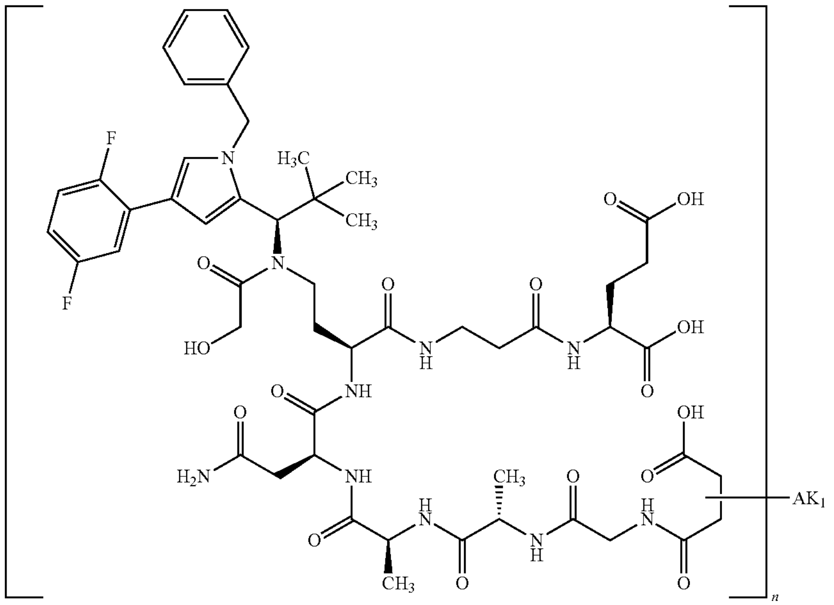

Example 28a

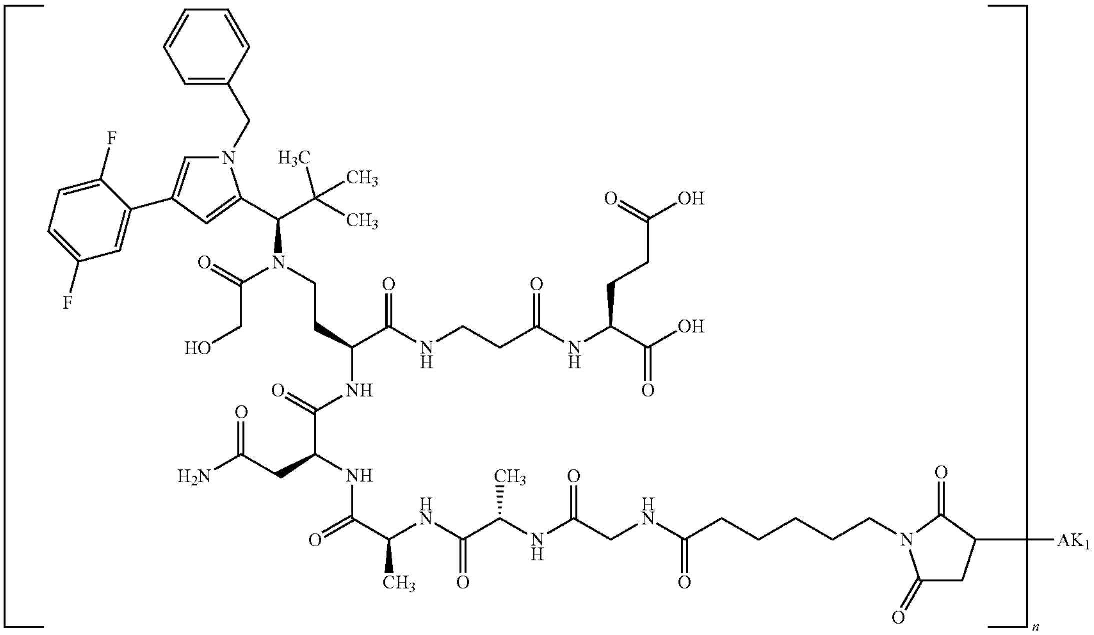

Under argon, a solution of 0.029 mg of TCEP in 0.05 ml of PBS buffer was added to 5 mg of cetuximab in 0.458 ml of PBS (c=10.92 mg/ml). The reaction was stirred at RT for 30 min, and 0.32 mg (0.00023 mmol) of Intermediate Q28 dissolved in 50 μl of DMSO was then added. After a further 90 min of stirring at RT, the reaction was diluted with 1.9 ml of PBS buffer. This solution was then applied to a PD 10 column (Sephadex® G-25, GE Healthcare) which had been equilibrated with PBS buffer (pH 7.2) and was eluted with PBS buffer (pH 7.2). This was followed by ultracentrifugation and redilution with PBS buffer (pH 7.2). The ADC batch obtained was characterized as follows:

Protein concentration: 2.01 mg/ml

Drug/mAb ratio: 2.0

Example 28e

In an analogous manner, Intermediate Q28 was coupled with 5 mg of trastuzumab. The ADC batch obtained was characterized as follows:

Protein concentration: 1.86 mg/ml

Drug/mAb ratio: 3.1

Example 28k

In an analogous manner, Intermediate Q28 was coupled with 5 mg of anti-TWEAKR antibody TPP-2658. The ADC batch obtained was characterized as follows:

Protein concentration: 2.03 mg/ml

Drug/mAb ratio: 2.6

Example 29a

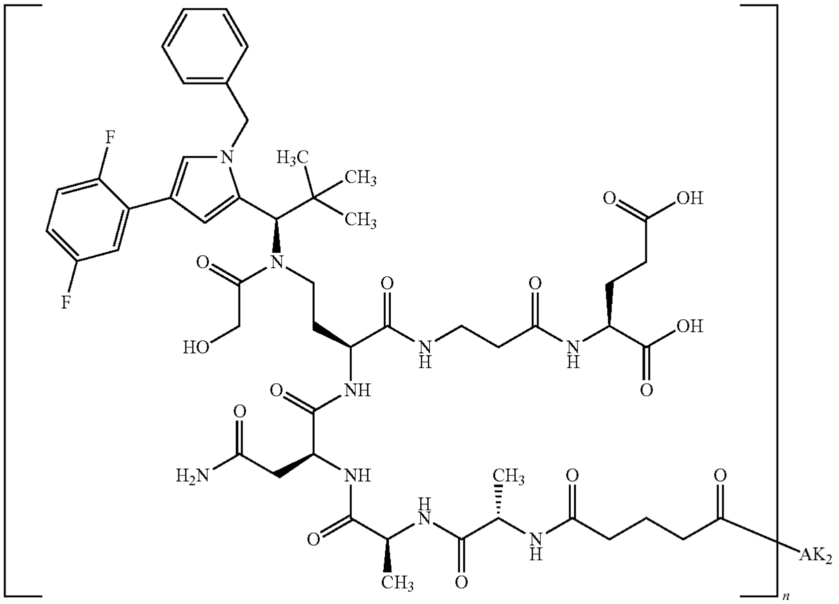

Here, 5 mg of cetuximab in PBS (c=9.1 mg/ml) were used for coupling with Intermediate Q29. First, 5 eq (0.21 mg) of Intermediate Q29 dissolved in 50 μl of DMSO were added under argon, and after 1 h of stirring at RT the same amount was added again and the reaction was stirred at RT for a further hour. The reaction was subsequently diluted to 2.5 ml with PBS buffer (pH 7.2), purified on a Sephadex column, then concentrated by ultracentrifugation and rediluted with PBS (pH 7.2).

Protein concentration: 2.14 mg/ml

Drug/mAb ratio: 2.6

Example 29e

In an analogous manner, Intermediate Q29 was coupled with 5 mg of trastuzumab. The ADC batch obtained was characterized as follows:

Protein concentration: 2.05 mg/ml

Drug/mAb ratio: 3.8

Example 29k

In an analogous manner, Intermediate Q29 was coupled with 5 mg of anti-TWEAKR antibody TPP-2658. The ADC batch obtained was characterized as follows:

Protein concentration: 2.09 mg/ml

Drug/mAb ratio: 3.9

Example 30a

Here, 5 mg of cetuximab in PBS (c=9.1 mg/ml) were used for coupling with Intermediate Q30. First, 5 eq (0.22 mg) of Intermediate Q29 dissolved in 50 μl of DMSO were added under argon, and after 1 h of stirring at RT the same amount was added again and the reaction was stirred at RT for a further hour. The reaction was subsequently diluted to 2.5 ml with PBS buffer (pH 7.2), purified on a Sephadex column, then concentrated by ultracentrifugation and rediluted with PBS (pH 7.2).

Protein concentration: 2.1 mg/ml

Drug/mAb ratio: 4.5

Example 30e

In an analogous manner, Intermediate Q30 was coupled with 5 mg of trastuzumab. The ADC batch obtained was characterized as follows:

Protein concentration: 1.96 mg/ml

Drug/mAb ratio: 5.6

Example 30k

In an analogous manner, Intermediate Q30 was coupled with 5 mg of anti-TWEAKR antibody TPP-2658. The ADC batch obtained was characterized as follows:

Protein concentration: 2.07 mg/ml

Drug/mAb ratio: 5.8

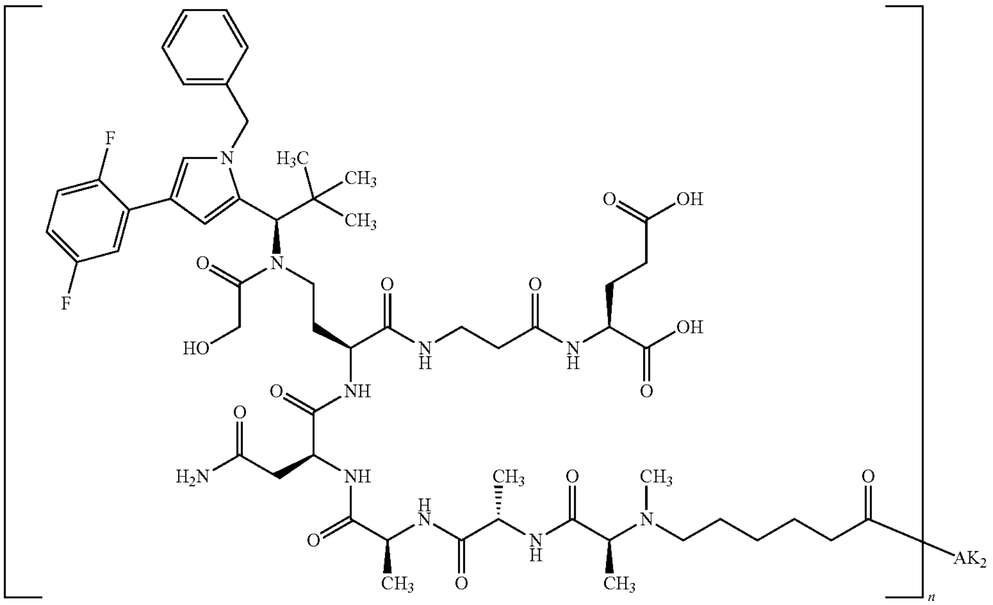

Example 31t

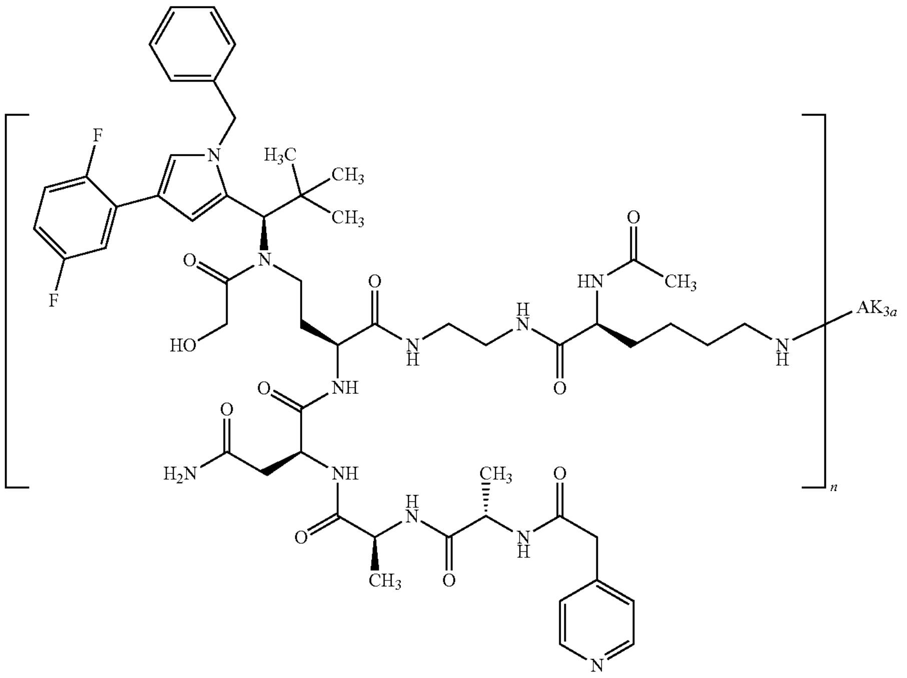

To a solution of 5 mg of the anti-TWEAKR antibody TPP-2658 (corresponding to TPP-2090-HC-N297A) in 530 μl of DPBS pH 7.4 (c~10 mg/ml) were added 20 μl of a 10 mM solution of Intermediate Q31 in DMSO. After incubation at 37° C. for 5 min, 50 μl of a solution of recombinant bacterial transglutaminase solution in water (product number T001 from Zedira GmbH, Darmstadt, Germany) (25 U/ml) were added and incubation was continued at 37° C. for a further 24 h. Then the reaction mixture was diluted with DPBS pH 7.4 to a volume of 2.5 ml and passed by gel filtration through DPBS-equilibrated PD 10 columns (Sephadex® G-25, GE Healthcare) and eluted with DPBS buffer at pH 7.4. Subsequently, the ADC solution was concentrated by means of Amicon Ultracel-30K centrifugation (Millipore), and it was rediluted again with DPBS. Finally, 0.00625 μmol of the b-transglutaminase blocker Zedira C100 in 12.5 μl of DPBS was added to the solution. The ADC solution obtained was characterized as follows:

Protein concentration: 2.11 mg/ml

Drug/mAb ratio: 1.8

Example 31t-4

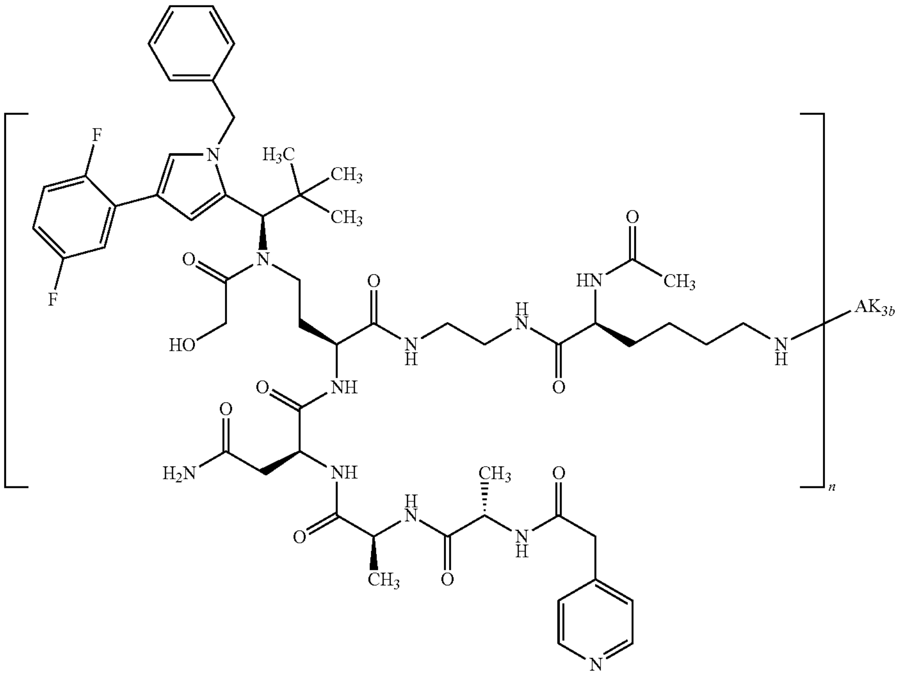

To a solution of 30 mg of the anti-TWEAKR antibody TPP-5442 (corresponding to TPP-2090-HC-N297Q) in DPBS pH 7.4 (c=10 mg/ml) were added 480 μl of a 10 mmol solution of Intermediate Q31 in DMSO. After incubation at 37° C. for 5 min, 2400 μl of a solution of recombinant bacterial transglutaminase solution in water (product number T001 from Zedira GmbH, Darmstadt, Germany) (25 U/ml) were added and incubated at 37° C. for 24 h. The reaction mixture was purified via gel filtration chromatography on a Superdex 200 column (GE Healthcare) in DPBS pH 7.4 in order to separate small molecules and the transglutaminase from the ADC. Subsequently, the ADC solution was concentrated by means of Amicon Ultracel-30K centrifugation tube (Millipore) to the final concentrations of about 12 mg/ml. The solution was then sterile-filtered. The ADC solution obtained was characterized as follows:

Protein concentration: 12.0 mg/ml

Drug/mAb ratio: 3.8

Example 32t

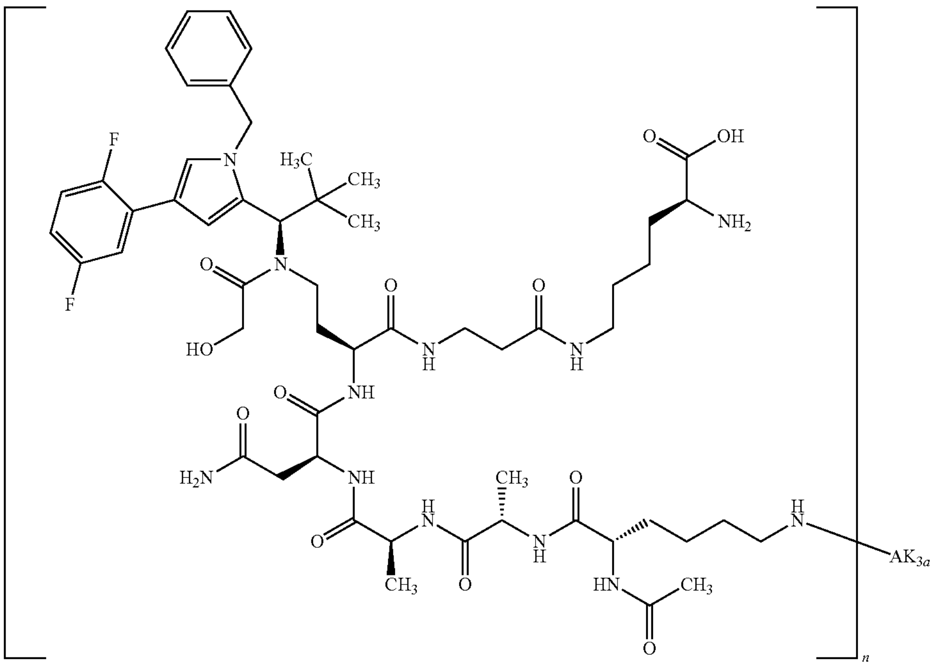

To a solution of 5 mg of the anti-TWEAKR antibody TPP-2658 (corresponding to TPP-2090-HC-N297A) in 530 μl of DPBS pH 7.4 (c~10 mg/ml) were added 20 μl of a 10 mMol solution of Intermediate Q32 in DMSO. After incubation at 37° C. for 5 min, 50 μl of a solution of recombinant bacterial transglutaminase solution in water (product number T001 from Zedira GmbH, Darmstadt, Germany) (25 U/ml) were added and incubation was continued at 37° C. for a further 24 h. Then the reaction mixture was diluted with DPBS pH 7.4 to a volume of 2.5 ml and passed by gel filtration through DPBS-equilibrated PD 10 columns (Sephadex® G-25, GE Healthcare) and eluted with DPBS buffer at pH 7.4. Subsequently, the ADC solution was concentrated by means of Amicon Ultracel-30K centrifugation (Millipore), and it was rediluted again with DPBS. Finally, 0.00625 μmol of the b-transglutaminase blocker Zedira C100 in 12.5 μl of DPBS was added to the solution. The ADC solution obtained was characterized as follows:

Protein concentration: 1.8 mg/ml

Drug/mAb ratio: 2.0

Example 33t

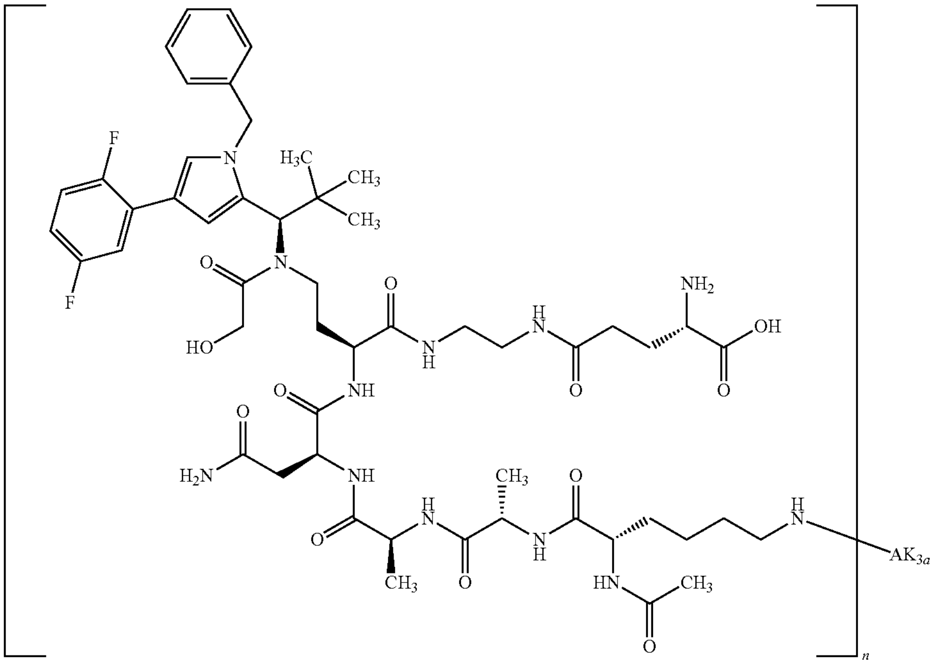

To a solution of 5 mg of the anti-TWEAKR antibody TPP-2658 (corresponding to TPP-2090-HC-N297A) in 530 µl of DPBS pH 7.4 (c~10 mg/ml) were added 20 µl of a 10 mMol solution of Intermediate Q33 in DMSO. After incubation at 37° C. for 5 min, 50 µl of a solution of recombinant bacterial transglutaminase solution in water (product number T001 from Zedira GmbH, Darmstadt, Germany) (25 U/ml) were added and incubation was continued at 37° C. for a further 24 h. Then the reaction mixture was diluted with DPBS pH 7.4 to a volume of 2.5 ml and passed by gel filtration through DPBS-equilibrated PD 10 columns (Sephadex® G-25, GE Healthcare) and eluted with DPBS buffer at pH 7.4. Subsequently, the ADC solution was concentrated by means of Amicon Ultracel-30K centrifugation (Millipore), and it was rediluted again with DPBS. Finally, 0.00625 µmol of the b-transglutaminase blocker Zedira C100 in 12.5 µl of DPBS was added to the solution. The ADC solution obtained was characterized as follows:

Protein concentration: 1.68 mg/ml

Drug/mAb ratio: 1.9

Example 34t

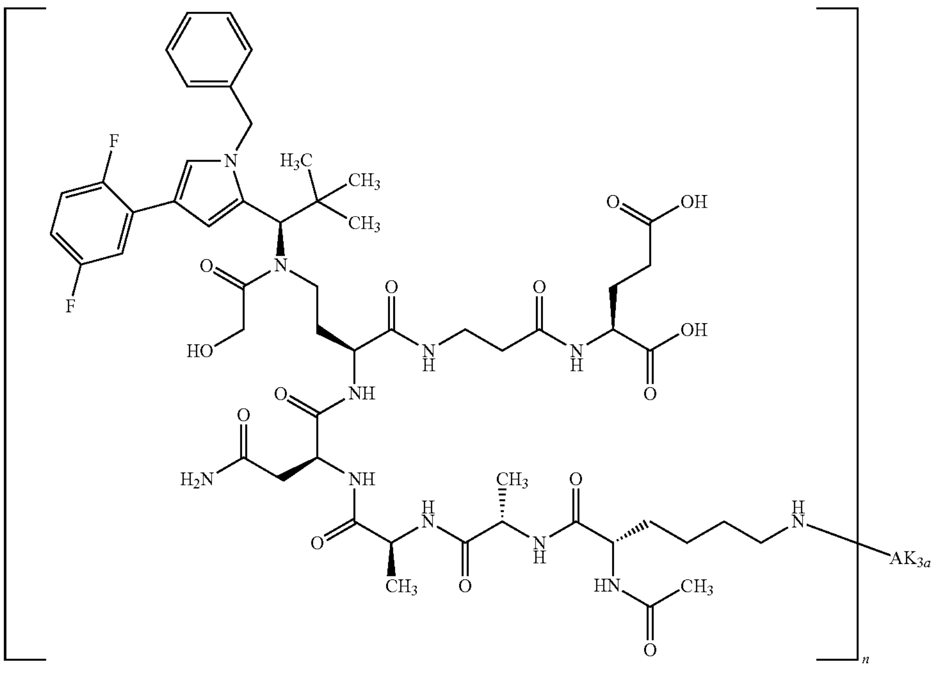

To a solution of 5 mg of the anti-TWEAKR antibody TPP-2658 (corresponding to TPP-2090-HC-N297A) in 530 μl of DPBS pH 7.4 (c~10 mg/ml) were added 20 μl of a 10 mMol solution of Intermediate Q34 in DMSO. After incubation at 37° C. for 5 min, 50 μl of a solution of recombinant bacterial transglutaminase solution in water (product number T001 from Zedira GmbH, Darmstadt, Germany) (25 U/ml) were added and incubation was continued at 37° C. for a further 24 h. Then the reaction mixture was diluted with DPBS pH 7.4 to a volume of 2.5 ml and passed by gel filtration through DPBS-equilibrated PD 10 columns (Sephadex® G-25, GE Healthcare) and eluted with DPBS buffer at pH 7.4. Subsequently, the ADC solution was concentrated by means of Amicon Ultracel-30K centrifugation (Millipore), and it was rediluted again with DPBS. Finally, 0.00625 μmol of the b-transglutaminase blocker Zedira C100 in 12.5 μl of DPBS was added to the solution. The ADC solution obtained was characterized as follows:

Protein concentration: 1.73 mg/ml

Drug/mAb ratio: 1.8

Example 34t-4

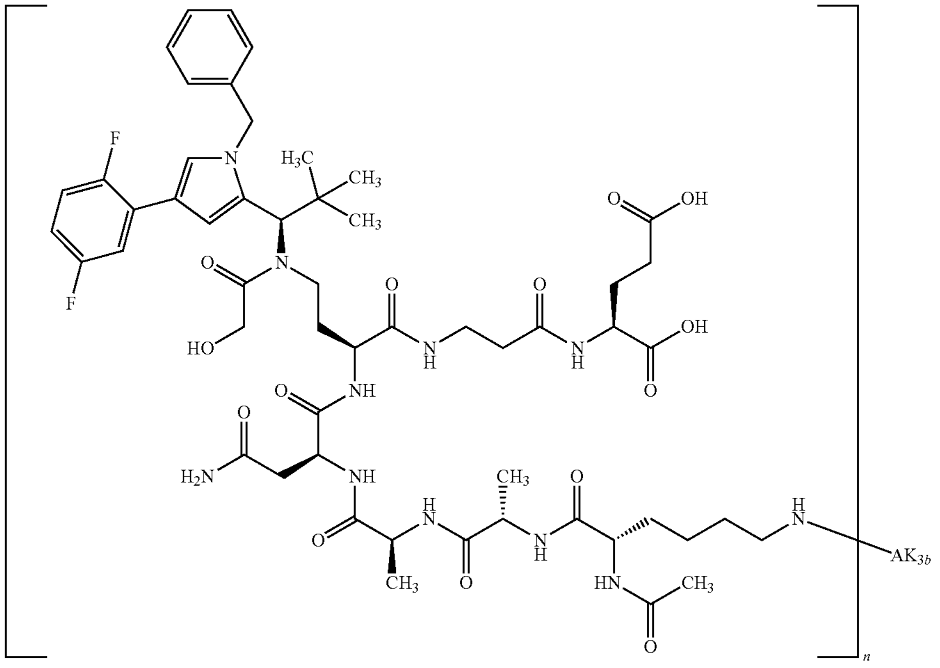

To a solution of 5 mg of the anti-TWEAKR antibody TPP-5442 (corresponding to TPP-2090-HC-N297Q) in DPBS pH 7.4 (c=7.4 mg/ml) were added 83 μl of a 10 mMol solution of Intermediate Q34 in DMSO. After incubation at 37° C. for 5 min, 400 μl of a solution of recombinant bacterial transglutaminase solution in water (product number T001 from Zedira GmbH, Darmstadt, Germany) (25 U/ml) were added and incubation was continued at 37° C. for 24 h. Then the reaction mixture was diluted with DPBS pH 7.4 to a total volume of 2.5 ml and passed by gel filtration through DPBS-equilibrated PD 10 columns (Sephadex® G-25, GE Healthcare) and eluted with DPBS buffer at pH 7.4. Subsequently, the ADC solution was concentrated by means of Amicon Ultracel-30K centrifugation (Millipore), and it was rediluted again with DPBS to a volume of about 2.5 ml. Finally, 0.1 μmol of the b-transglutaminase blocker Zedira C100 in 200 μl of DPBS was added to the solution. The ADC solution obtained was characterized as follows:

Protein concentration: 1.76 mg/ml

Drug/mAb ratio: 3.9

Example 34te-4

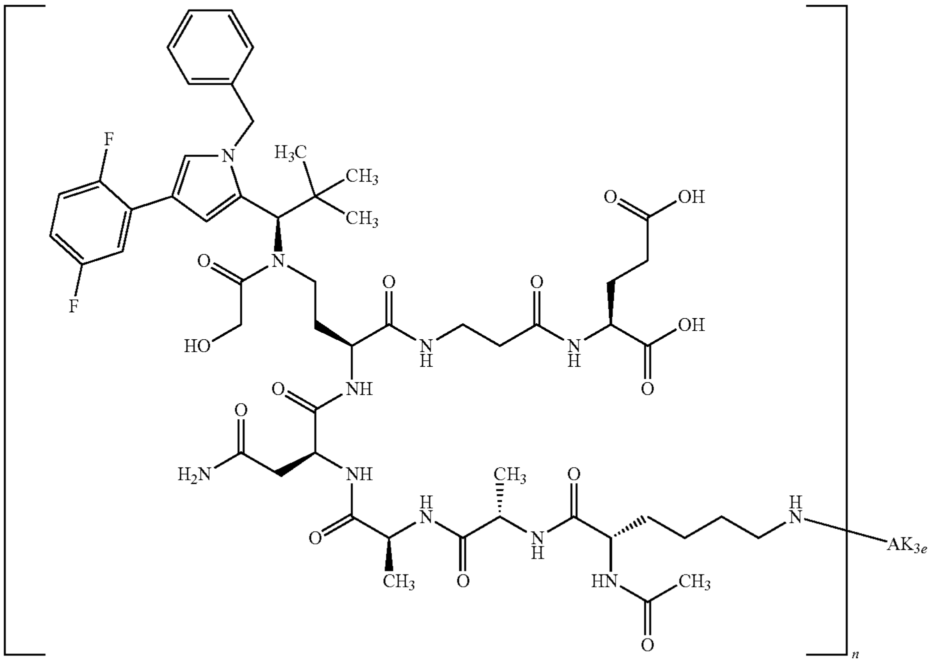

In an analogous manner to Example 34t-4, TPP-7511 (corresponding to trastuzumab-HC-N297Q) was also used and coupled. The ADC solution obtained was characterized as follows:

Protein concentration: 1.56 mg/ml

Drug/mAb ratio: 3.9

Example 35a

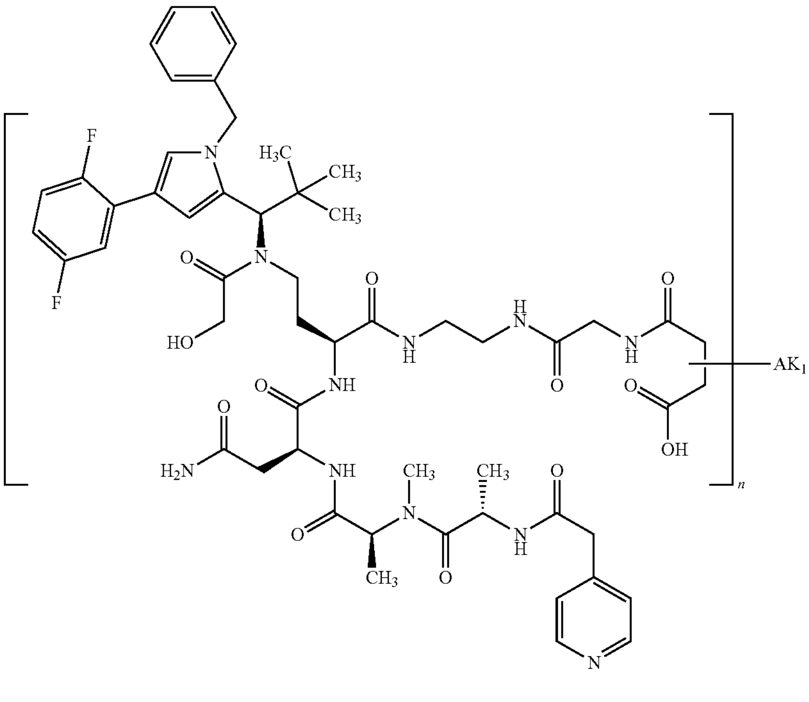

To 5 mg of cetuximab in 0.5 ml of PBS (c=10 mg/ml) under argon was added a solution of 0.029 mg of TCEP in 0.05 ml of PBS buffer. The mixture was stirred at RT for 30 min and then 0.28 mg (0.00023 mmol) of Intermediate Q35 dissolved in 50 μl of DMSO was added. After stirring at RT for a further 90 min, the mixture was diluted to a volume of 2.5 ml with PBS buffer which had been adjusted to pH 8 beforehand. This solution was then passed through a PD 10 column (Sephadex® G-25, GE Healthcare) which had been equilibrated with PBS buffer pH 8 and eluted with PBS buffer pH 8. The eluate was stirred at RT under argon overnight.

This solution was then concentrated by ultracentrifugation and rediluted with PBS buffer (pH 7.2). The ADC batch obtained was characterized as follows:

Protein concentration: 1.94 mg/ml

Drug/mAb ratio: 3.3

Example 35e

In an analogous manner, Intermediate Q35 was coupled to 5 mg of trastuzumab. The ADC batch obtained was characterized as follows:

Protein concentration: 1.89 mg/ml

Drug/mAb ratio: 3.5

Example 35k

In an analogous manner, Intermediate Q35 was coupled to 5 mg of anti-TWEAKR antibody TPP-2658. The ADC batch obtained was characterized as follows:

Protein concentration: 1.78 mg/ml

Drug/mAb ratio: 3.5

Example 36a

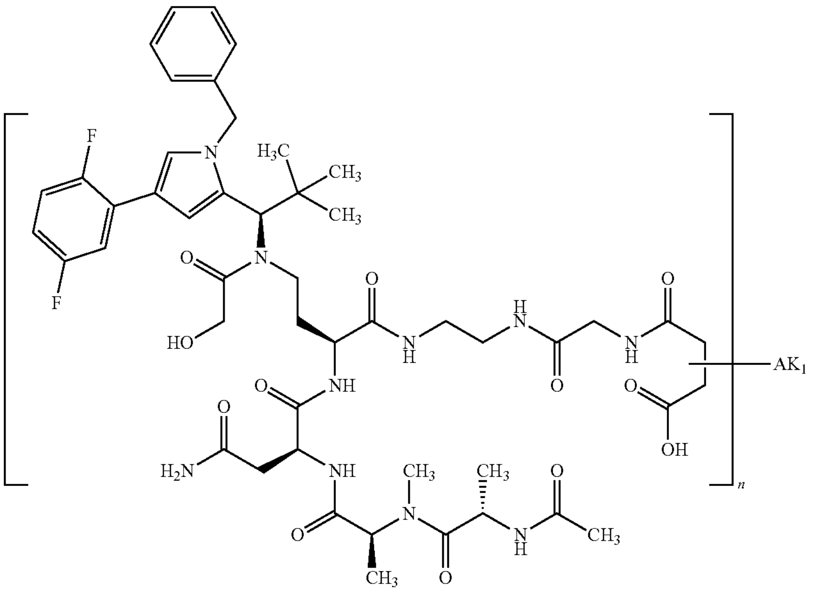

To 5 mg of cetuximab in 0.5 ml of PBS (c=10 mg/ml) under argon was added a solution of 0.029 mg of TCEP in 0.05 ml of PBS buffer. The mixture was stirred at RT for 30 min and then 0.26 mg (0.00023 mmol) of Intermediate Q36 dissolved in 50 μl of DMSO was added. After stirring at RT for a further 90 min, the mixture was diluted to a volume of 2.5 ml with PBS buffer which had been adjusted to pH 8 beforehand. This solution was then passed through a PD 10 column (Sephadex® G-25, GE Healthcare) which had been equilibrated with PBS buffer pH 8 and eluted with PBS buffer pH 8. The eluate was stirred at RT under argon overnight.

This solution was then concentrated by ultracentrifugation and rediluted with PBS buffer (pH 7.2). The ADC batch obtained was characterized as follows:

Protein concentration: 2.0 mg/ml

Drug/mAb ratio: 3.2

Example 36e

In an analogous manner, Intermediate Q36 was coupled to 5 mg of trastuzumab. The ADC batch obtained was characterized as follows:

Protein concentration: 1.84 mg/ml

Drug/mAb ratio: 3.6

Example 36k

In an analogous manner, Intermediate Q36 was coupled to 5 mg of anti-TWEAKR antibody TPP-2658. The ADC batch obtained was characterized as follows:

Protein concentration: 1.75 mg/ml

Drug/mAb ratio: 3.4

Example 37a

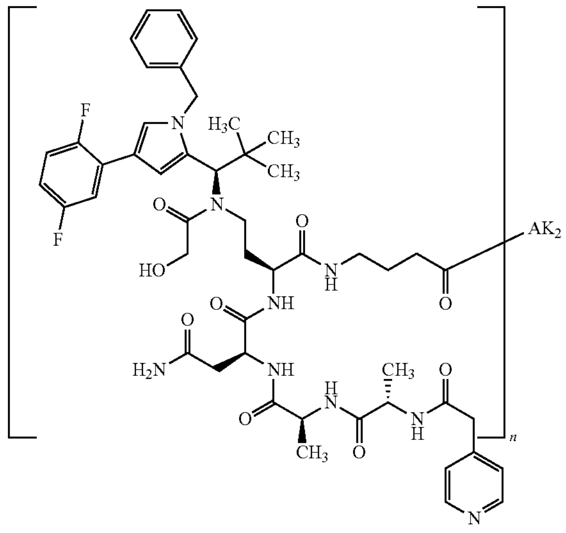

To 5 mg of cetuximab in 0.5 ml of PBS (c=10 mg/ml) under argon was added a solution of 5 eq (0.2 mg) of Intermediate Q37 dissolved in 50 μl of DMSO and, after stirring at RT for 1 h, the same amount again was added and the mixture was stirred at RT for a further hour. Subsequently, the mixture was diluted to 2.5 ml with PBS buffer (pH 7.2), purified using a Sephadex column and then concentrated by ultracentrifugation and rediluted with PBS (pH 7.2).

Protein concentration: 2.2 mg/ml

Drug/mAb ratio: 4.1

Example 37e

In an analogous manner, Intermediate Q37 was coupled to 5 mg of trastuzumab. The ADC batch obtained was characterized as follows:

Protein concentration: 1.64 mg/ml

Drug/mAb ratio: 4.5

Example 37k

In an analogous manner, Intermediate Q37 was coupled to 5 mg of anti-TWEAKR antibody TPP-2658. The ADC batch obtained was characterized as follows:

Protein concentration: 1.6 mg/ml

Drug/mAb ratio: 6.2

Example 38a

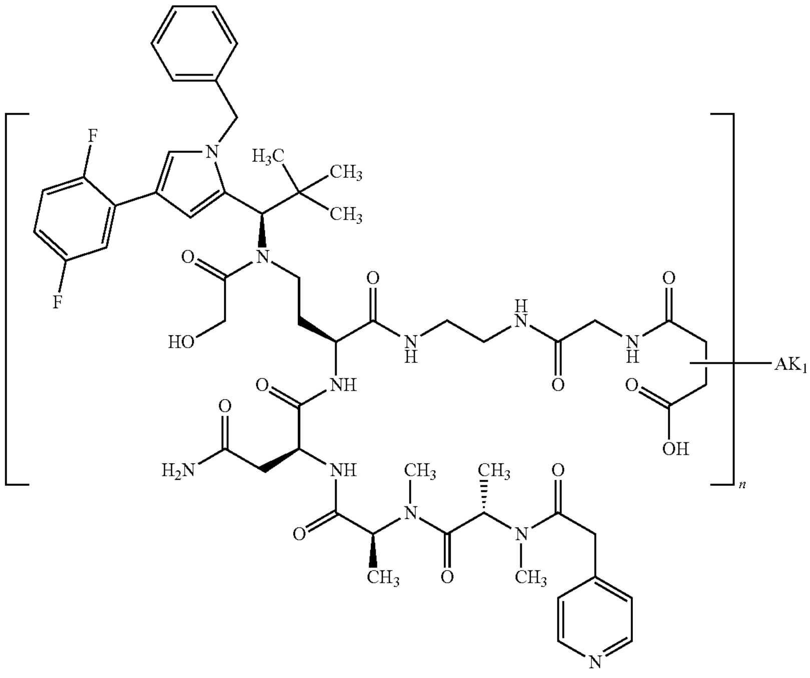

To 5 mg of cetuximab in 0.458 ml of PBS (c=11 mg/ml) under argon was added a solution of 0.029 mg of TCEP in 0.05 ml of PBS buffer. The mixture was stirred at RT for 30 min and then 0.26 mg (0.00023 mmol) of Intermediate Q38 dissolved in 50 μl of DMSO was added. After stirring at RT for a further 90 min, the mixture was diluted to a volume of 2.5 ml with PBS buffer which had been adjusted to pH 8 beforehand. This solution was then passed through a PD 10 column (Sephadex® G-25, GE Healthcare) which had been equilibrated with PBS buffer pH 8 and eluted with PBS buffer pH 8. The eluate was stirred at RT under argon overnight.

This solution was then concentrated by ultracentrifugation and rediluted with PBS buffer (pH 7.2). The ADC batch obtained was characterized as follows:

Protein concentration: 1.94 mg/ml

Drug/mAb ratio: 2.9

Example 38e

In an analogous manner, Intermediate Q38 was coupled to 5 mg of trastuzumab. The ADC batch obtained was characterized as follows:

Protein concentration: 1.82 mg/ml

Drug/mAb ratio: 3.5

Example 38k

In an analogous manner, Intermediate Q38 was coupled to 5 mg of anti-TWEAKR antibody TPP-2658. The ADC batch obtained was characterized as follows:

Protein concentration: 2.01 mg/ml

Drug/mAb ratio: 3.3

Example 39a

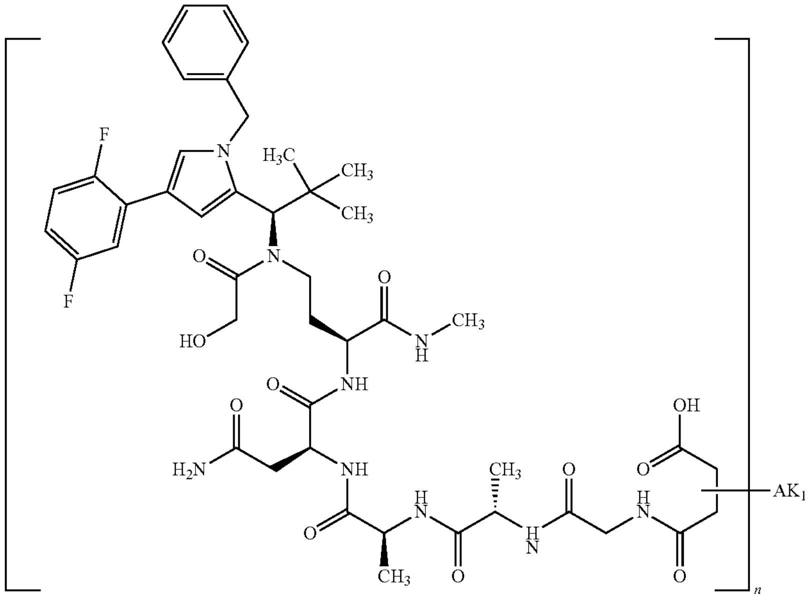

To 5 mg of cetuximab in 0.5 ml of PBS (c=10 mg/ml) under argon was added a solution of 0.029 mg of TCEP in 0.05 ml of PBS buffer. The mixture was stirred at RT for 30 min and then 0.23 mg (0.00023 mmol) of Intermediate Q39 dissolved in 50 µl of DMSO was added. After stirring at RT for a further 90 min, the mixture was diluted with 1.9 ml of PBS buffer which had been adjusted to pH 8 beforehand. This solution was then passed through a PD 10 column (Sephadex® G-25, GE Healthcare) which had been equilibrated with PBS buffer pH 8 and eluted with PBS buffer pH 8. The eluate was stirred at RT under argon overnight. This was followed by concentration by ultracentrifugation and redilution with PBS buffer (pH 7.2). The ADC batch obtained was characterized as follows:

Protein concentration: 1.97 mg/ml

Drug/mAb ratio: 2.8

Example 39e

In an analogous manner, Intermediate Q39 was coupled to 5 mg of trastuzumab. The ADC batch obtained was characterized as follows:

Protein concentration: 1.77 mg/ml

Drug/mAb ratio: 3.3

Example 39k

In an analogous manner, Intermediate Q39 was coupled to 5 mg of anti-TWEAKR antibody TPP-2658. The ADC batch obtained was characterized as follows:

Protein concentration: 1.74 mg/ml

Drug/mAb ratio: 3.4

Example 40a

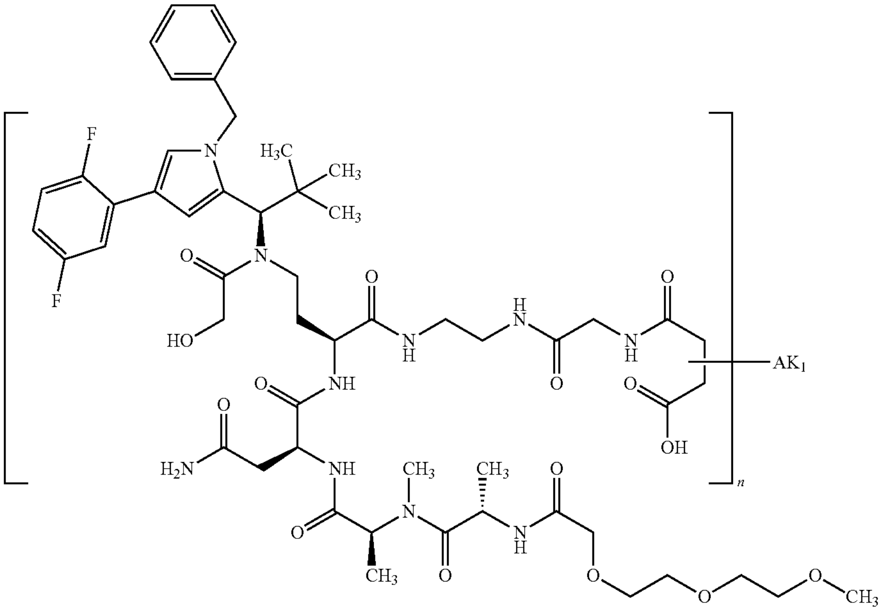

To 5 mg of cetuximab in 0.5 ml of PBS (c=10 mg/ml) under argon was added a solution of 0.029 mg of TCEP in 0.05 ml of PBS buffer. The mixture was stirred at RT for 30 min and then 0.26 mg (0.00023 mmol) of Intermediate Q40 dissolved in 50 μl of DMSO was added. After stirring at RT for a further 90 min, the mixture was diluted to a volume of 2.5 ml with PBS buffer which had been adjusted to pH 8 beforehand. This solution was then passed through a PD 10 column (Sephadex® G-25, GE Healthcare) which had been equilibrated with PBS buffer pH 8 and eluted with PBS buffer pH 8. The eluate was stirred at RT under argon overnight.

This solution was then concentrated by ultracentrifugation and rediluted with PBS buffer (pH 7.2). The ADC batch obtained was characterized as follows:

Protein concentration: 1.95 mg/ml

Drug/mAb ratio: 2.4

Example 40e

In an analogous manner, Intermediate Q40 was coupled to 5 mg of trastuzumab. The ADC batch obtained was characterized as follows:

Protein concentration: 1.84 mg/ml

Drug/mAb ratio: 2.9

Example 40k

In an analogous manner, Intermediate Q40 was coupled to 5 mg of anti-TWEAKR antibody TPP-2658. The ADC batch obtained was characterized as follows:

Protein concentration: 1.93 mg/ml

Drug/mAb ratio: 3.0

Example 41a

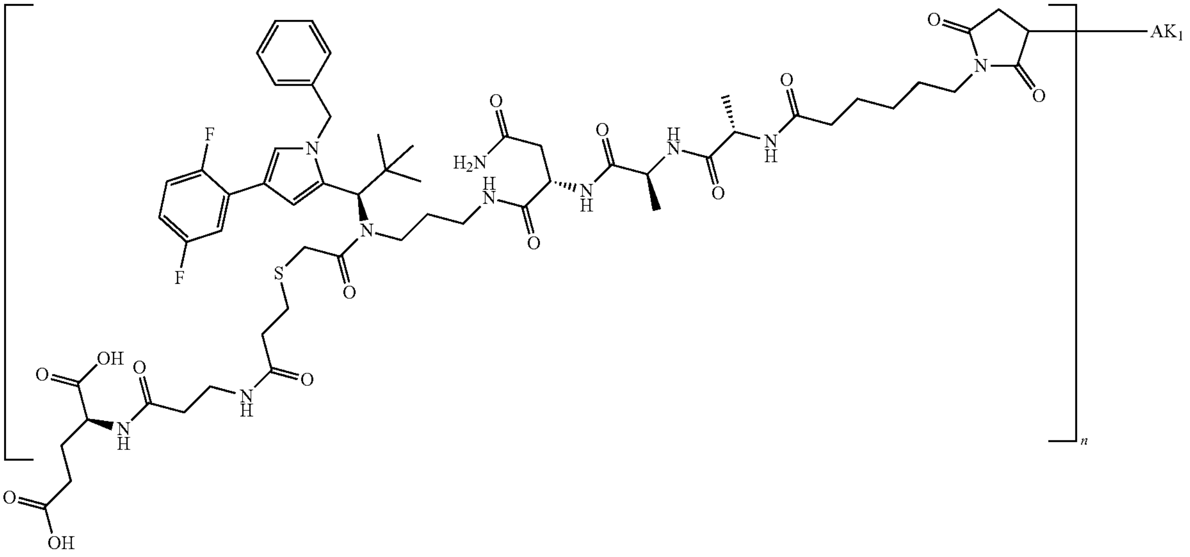

To 5 mg of cetuximab in 0.458 ml of PBS (c=10.9 mg/ml) under argon was added a solution of 0.029 mg of TCEP in 0.05 ml of PBS buffer. The mixture was stirred at RT for 30 min and then 0.308 mg (0.00023 mmol) of Intermediate Q41 dissolved in 50 μl of DMSO was added. After stirring at RT for a further 90 min, the mixture was diluted to a volume of 2.5 ml with PBS buffer. This solution was then purified using a PD 10 column (Sephadex® G-25, GE Healthcare). This solution was then concentrated by ultracentrifugation and rediluted with PBS buffer. The ADC batch obtained was characterized as follows:

Protein concentration: 2.26 mg/ml
Drug/mAb ratio: 3.9

Example 41e

In an analogous manner, Intermediate Q41 was coupled to 5 mg of trastuzumab. The ADC batch obtained was characterized as follows:

Protein concentration: 2.0 mg/ml
Drug/mAb ratio: 4.3

Example 41k

In an analogous manner, Intermediate Q41 was coupled to 5 mg of anti-TWEAKR antibody TPP-2658. The ADC batch obtained was characterized as follows:

Protein concentration: 2.15 mg/ml
Drug/mAb ratio: 4.0

Example 42a

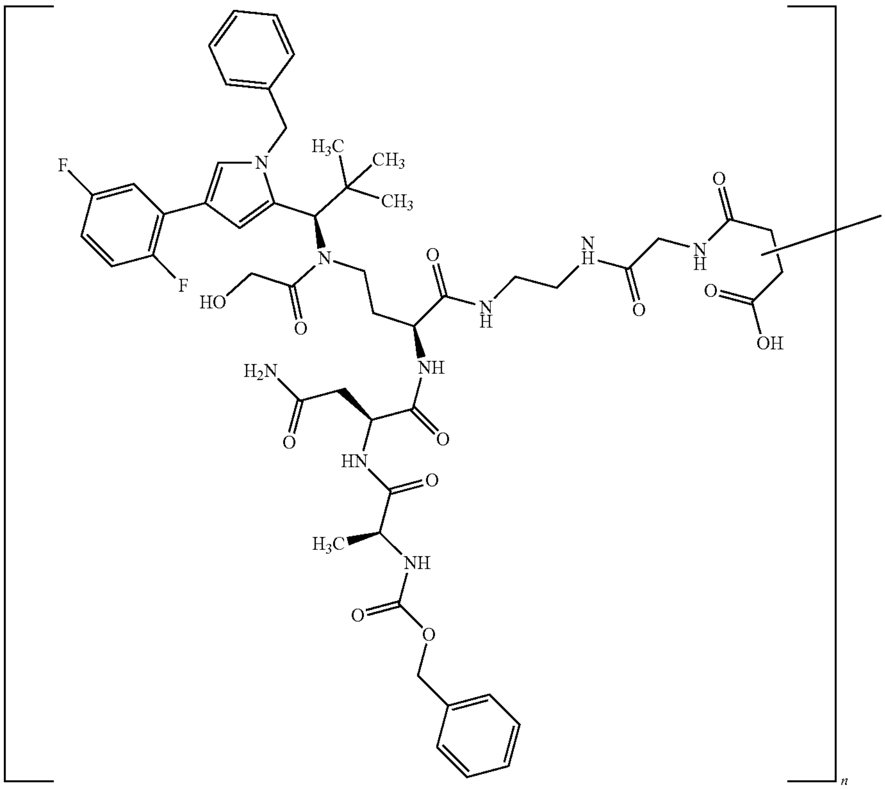

To 5 mg of cetuximab in 0.458 ml of PBS (c=10.9 mg/ml) under argon was added a solution of 0.029 mg of TCEP in 0.05 ml of PBS buffer. The mixture was stirred at RT for 30 min and then 0.263 mg (0.00023 mmol) of Intermediate Q42 dissolved in 50 μl of DMSO was added. After stirring at RT for a further 90 min, the mixture was diluted to a volume of 2.5 ml with PBS buffer which had been adjusted to pH 8 beforehand. This solution was then passed through a PD 10 column (Sephadex® G-25, GE Healthcare) which had been equilibrated with PBS buffer pH 8 and eluted with PBS buffer pH 8. The eluate was stirred at RT under argon overnight.

This solution was then concentrated by ultracentrifugation and rediluted with PBS buffer (pH 7.2). The ADC batch obtained was characterized as follows:

Protein concentration: 0.93 mg/ml
Drug/mAb ratio: 3.5

Example 42e

In an analogous manner, Intermediate Q42 was coupled to 5 mg of trastuzumab. The ADC batch obtained was characterized as follows:

Protein concentration: 0.53 mg/ml
Drug/mAb ratio: 4.2

Example 42k

In an analogous manner, Intermediate Q42 was coupled to 5 mg of anti-TWEAKR antibody TPP-2658. The ADC batch obtained was characterized as follows:

Protein concentration: 0.88 mg/ml
Drug/mAb ratio: 3.7

Example 43a

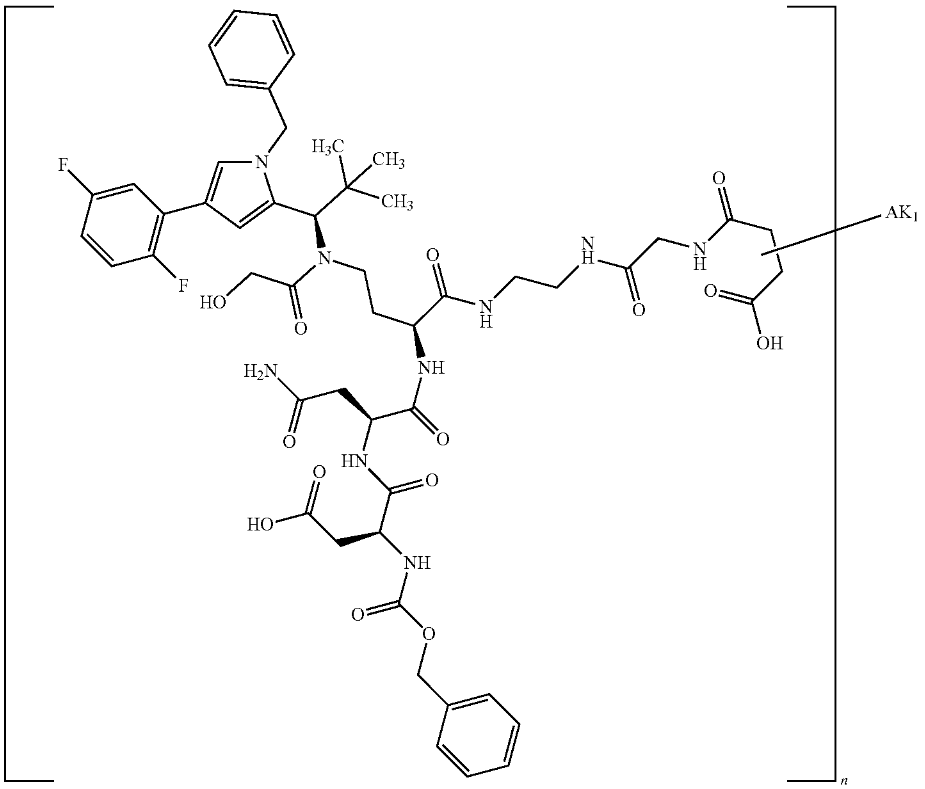

To 5 mg of cetuximab in 0.458 ml of PBS (c=10.9 mg/ml) under argon was added a solution of 0.029 mg of TCEP in 0.05 ml of PBS buffer. The mixture was stirred at RT for 30 min and then 0.27 mg (0.00023 mmol) of Intermediate Q43 dissolved in 50 µl of DMSO was added. After stirring at RT for a further 90 min, the mixture was diluted to a volume of 2.5 ml with PBS buffer which had been adjusted to pH 8 beforehand. This solution was then passed through a PD 10 column (Sephadex® G-25, GE Healthcare) which had been equilibrated with PBS buffer pH 8 and eluted with PBS buffer pH 8. The eluate was stirred at RT under argon overnight.

This solution was then concentrated by ultracentrifugation and rediluted with PBS buffer (pH 7.2). The ADC batch obtained was characterized as follows:

Protein concentration: 1.91 mg/ml

Drug/mAb ratio: 2.6

Example 43e

In an analogous manner, Intermediate Q43 was coupled to 5 mg of trastuzumab. The ADC batch obtained was characterized as follows:

Protein concentration: 1.56 mg/ml

Drug/mAb ratio: 3.6

Example 43k

In an analogous manner, Intermediate Q43 was coupled to 5 mg of anti-TWEAKR antibody TPP-2658. The ADC batch obtained was characterized as follows:

Protein concentration: 1.89 mg/ml

Drug/mAb ratio: 3.6

Example 44a

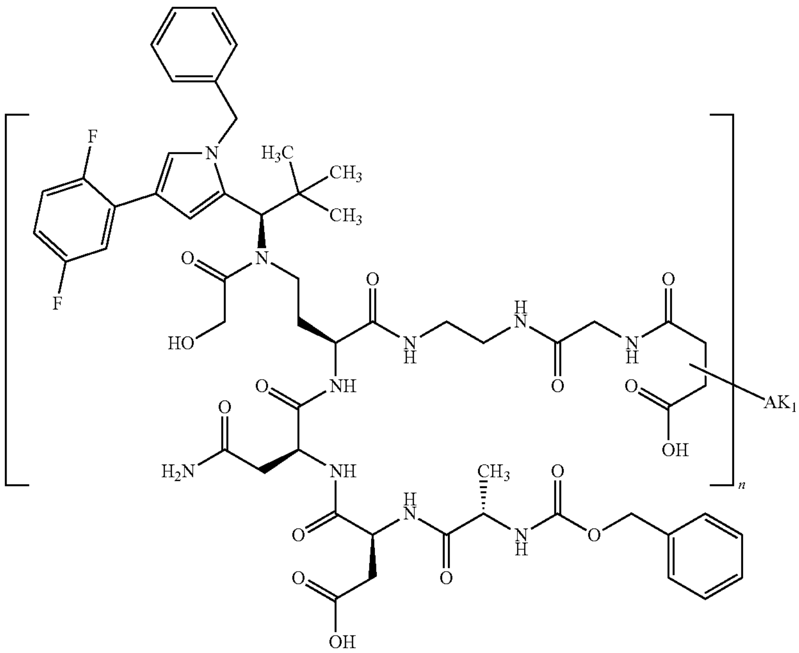

To 5 mg of cetuximab in 0.458 ml of PBS (c=10.9 mg/ml) under argon was added a solution of 0.029 mg of TCEP in 0.05 ml of PBS buffer. The mixture was stirred at RT for 30 min and then 0.29 mg (0.00023 mmol) of Intermediate Q44 dissolved in 50 µl of DMSO was added. After stirring at RT for a further 90 min, the mixture was diluted to a volume of 2.5 ml with PBS buffer which had been adjusted to pH 8 beforehand. This solution was then passed through a PD 10 column (Sephadex® G-25, GE Healthcare) which had been equilibrated with PBS buffer pH 8 and eluted with PBS buffer pH 8. The eluate was stirred at RT under argon overnight.

This solution was then concentrated by ultracentrifugation and rediluted with PBS buffer (pH 7.2). The ADC batch obtained was characterized as follows:
Protein concentration: 1.82 mg/ml
Drug/mAb ratio: 2.6

Example 44e

In an analogous manner, Intermediate Q44 was coupled to 5 mg of trastuzumab. The ADC batch obtained was characterized as follows:
Protein concentration: 1.79 mg/ml
Drug/mAb ratio: 3.4

Example 44k

In an analogous manner, Intermediate Q44 was coupled to 5 mg of anti-TWEAKR antibody TPP-2658. The ADC batch obtained was characterized as follows:
Protein concentration: 1.72 mg/ml
Drug/mAb ratio: 3.7

C: Assessment of Biological Efficacy

The biological activity of the compounds according to the invention can be shown in the assays described below:
a. C-1a Determination of the cytotoxic effect of the ADCs The analysis of the cytotoxic effects of the ADCs was carried out with various cell lines:

NCI-H292: human mucoepidermoid lung carcinoma cells, ATCC-CRL-1848, standard medium: RPMI 1640 (Biochrom; #FG1215, stab. glutamine)+10% FCS (Sigma; #F2442), TWEAKR-positive; EGFR-positive.

BxPC3: human pancreas carcinoma cells, ATCC-CRL-1687, standard medium: RPMI 1640 (Biochrom; #FG1215, stab. glutamine)+10% FCS (Sigma; #F2442), TWEAKR-positive.

LoVo human colorectal cancer cells, ATCC No. CCL-229, cultivation for MTT assay: standard medium: Kaighn's+L-glutamine (Invitrogen 21127)+10% heat inactivated FCS (from Gibco, No. 10500-064). Cultivation for CTG assay: RPMI 1640 (Biochrom; #FG1215, stab. glutamine)+10% FCS (Sigma #F2442). TWEAKR-positive.

KPL4: human breast cancer cell line, Bayer Pharma AG (identity checked and confirmed on 19 Jul. 2012 at DSMZ), standard medium: RPMI 1640 (from Gibco; #21875-059, stab. L-glutamine)+10% heat inactivated FCS (Gibco, No. 10500-064); HER2-positive.

SK-HEP-1: human liver cancer cell line, ATCC No. HTB-52, standard medium: MEM with Earle's salts+Glutamax I (Invitrogen 41090)+10% heat inactivated FCS (from Gibco, No. 10500-064); EGFR-positive, TWEAKR-positive The cells are cultivated by a standard method, as indicated in the American Tissue Type Collection (ATCC) for the respective cell lines.

CTG Assay

The cells were cultivated according to the standard method using the growth media listed under C-1. The test was carried out by detaching the cells with a solution of trypsin (0.05%) and EDTA (0.02%) in PBS (Biochrom AG #L2143), pelleting, resuspending in culture medium, counting and sowing into a 96-well culture plate with white bottom (Costar #3610) (at 75 µl/well, the following cell numbers are per well: NCI-H292: 2500 cells/well, BxPC32500 cells/well, LoVo 3000 cells/well) and incubating in an incubator at 37° C. and 5% carbon dioxide. After 24 h, the antibody drug conjugates were added in 25 µl of culture medium (concentrated four-fold) to the cells to give final antibody drug conjugate concentrations of $3\times10^{-7}$ M to $3\times10^{-11}$ M on the cells (triplicates). The cells were then incubated in an incubator at 37° C. and 5% carbon dioxide. On a parallel plate, the cell activity at the start of the drug treatment (day 0) was determined using the Cell Titer Glow (CTG) luminescent cell viability assay (Promega #G7573 and #G7571). To this end, per cell batch 100 µl of the substrate were added, the plates were then covered with aluminium foil, shaken on the plate shaker at 180 rpm for 2 minutes, allowed to stand on the laboratory bench for 8 minutes and then measured using a luminometer (Victor X2, Perkin Elmer). The substrate detects the ATP content of the living cells generating a luminescence signal whose intensity is directly proportional to the viability of the cells. After 72 h of incubation with the antibody drug conjugates, the viability of these cells was then also determined using the Cell Titer Glow luminescent cell viability assay as described above. From the data measured, the $IC_{50}$ of the growth inhibition was calculated in comparison to day 0 using the DRC (Dose Response Curve) analysis spreadsheets and a 4-parameter fit. The DRC analysis spreadsheet is a biobook spreadsheet developed by Bayer Pharma AG and Bayer Business Services on the IDBS E-WorkBook Suite platform (IDBS: ID Business Solutions Ltd., Guildford, UK).

Table 1a below sets out the $IC_{50}$ values: for representative working examples from this assay:

TABLE 1a

| Example | BxPC3 $IC_{50}$ [M] CTG | NCI-H292 $IC_{50}$ [M] CTG | LoVo $IC_{50}$ [M] CTG |
|---|---|---|---|
| 1k | 1.70E-09 | 2.99E-10 | 1.24E-10 |
| 1k* | 1.27E-09 | 4.66E-10 | 1.25E-10 |
| 2k | 2.94E-09 | 5.84E-10 | 2.04E-10 |
| 2k* | 2.16E-09 | 8.45E-10 | 2.85E-10 |
| 3k | 1.30E-08 | 1.04E-09 | 4.67E-10 |
| 4k | 3.29E-09 | 1.04E-09 | 2.45E-10 |
| 5k | 6.52E-09 | >6.00E-07 | >6.00E-07 |
| 6k | 4.71E-09 | >6.00E-07 | >6.00E-07 |
| 7k | 4.77E-09 | 1.09E-08 | >6.00E-07 |
| 8k | 5.77E-10 | 2.90E-10 | 1.82E-10 |
| 9k | 6.70E-09 | 6.82E-10 | 6.94E-10 |
| 10k | 1.11E-09 | 6.10E-10 | 5.63E-10 |
| D-Asn epimer from Example 1k | >6.0E-07 | >6.0E-07 | >6.0E-07 |
| 11k | 1.43E-09 | 8.16E-10 | 1.66E-10 |

TABLE 1a-continued

| Example | BxPC3 $IC_{50}$ [M] CTG | NCI-H292 $IC_{50}$ [M] CTG | LoVo $IC_{50}$ [M] CTG |
|---|---|---|---|
| 12k | 2.75E-09 | 1.16E-09 | 2.12E-10 |
| 13k | 9.04E-09 | 1.37E-09 | 4.45E-10 |
| 14k | 2.59E-09 | 3.32E-10 | 1.23E-10 |
| 15k | 2.09E-09 | 7.19E-10 | 1.52E-10 |
| 16k | 2.04E-09 | 1.23E-09 | 2.06E-10 |
| 17k | 5.08E-09 | 6.84E-10 | 2.28E-10 |
| 18k | 2.56E-10 | 3.91E-10 | 1.09E-10 |
| 19k | 5.94E-09 | 7.96E-10 | 1.70E-10 |
| 20k | 9.86E-10 | 3.48E-10 | 8.30E-11 |
| 20k* | 4.58E-10 | 6.03E-10 | 1.65E-11 |
| 21k | 2.09E-09 | 1.42E-09 | 2.36E-10 |
| 22k | 4.20E-09 | 4.31E-09 | >6.0E-07 |
| 23k | 1.34E · 09 | 1.27E-09 | 1.56E-08 |
| 24k | 1.72E-09 | 1.99E-09 | 2.41E-07 |
| 25k | 1.37E-09 | 1.96E-09 | >6.0E-07 |
| 26k | 1.99E-09 | 2.54E-09 | >6.0E-07 |
| 27k | 5.34E-10 | 8.61E-10 | 3.46E-10 |
| 28k | 6.18E-10 | 1.17E-09 | 4.33E-10 |
| 29k | 5.66E-10 | 8.06E-10 | 3.13E-10 |
| 30k | 2.56E-10 | 6.83E-10 | 2.13E-10 |
| 35k | 1.65E-08 | 2.29E-08 | 2.86E-10 |
| 36k | 2.33E-08 | 2.26E-08 | 5.24E-10 |
| 37k | 1.69E-09 | 6.00E-09 | 6.00E-07 |
| 38k | 1.32E-08 | 1.69E-08 | 3.06E-10 |
| 39k | 1.46E-09 | 8.07E-08 | >6.00E-07 |
| 40k | 9.95E-09 | 4.65E-09 | 8.78E-10 |
| 41k | 7.36E-10 | 1.15E-09 | 1.06E-09 |
| 42k | 9.80E-10 | 8.36E-10 | 1.22E-10 |
| 43k | 1.08E-09 | 1.11E-09 | 1.43E-10 |
| 44k | 1.40E-09 | 9.09E-10 | 2.31E-10 |

The activity data reported relate to the working examples described in the present experimental section, with the drug/mAB ratios indicated. The values may possibly deviate for different drug/mAB ratios. The IC50 values are means of several independent experiments or individual values. The action of the antibody drug conjugates was selective for the respective isotype control comprising the respective linker and toxophore.

As a further reference compound, in analogy to Example 1k, the D-asparagine epimer of Intermediate Q1 was coupled with the anti-TWEAKR antibody TPP-2658.

Control Example for Example 1k

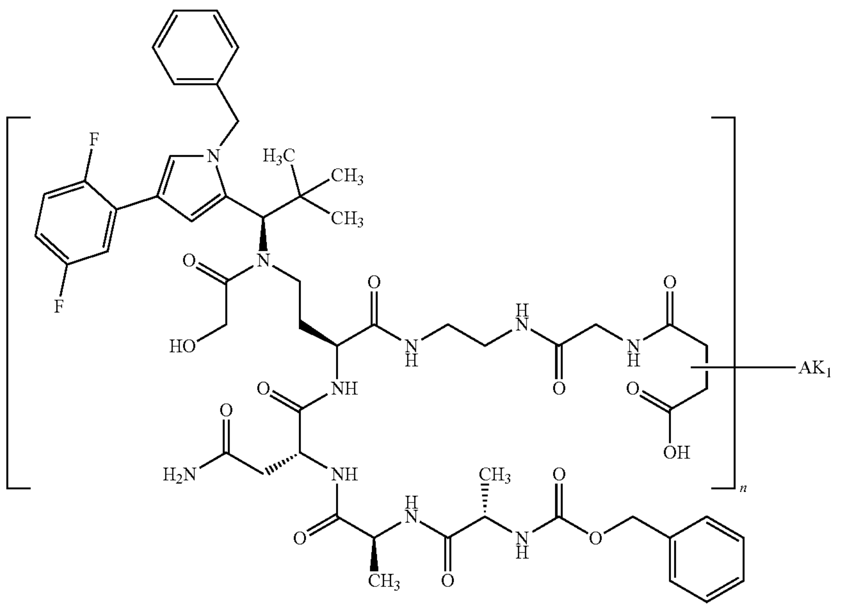

Here, in analogy to Example 1k, the D-asparagine epimer of Q1 was coupled with 60 mg of anti-TWEAKR antibody TPP-2658. The ADC batch obtained was characterized as follows:

Protein concentration: 11.56 mg/ml

Drug/mAb ratio: 3.6

As shown in Table 1a, this control ADC does not show any significant cytotoxic effect on the 3 cell lines.

MTT Assay

The cells were cultivated according to the standard method using the growth media listed under C-1. The test was carried out by detaching the cells with a solution of Accutase in PBS (from Biochrom AG #L2143), pelletizing, resuspending in culture medium, counting and sowing into a 96-well culture plate with white bottom (from Costar #3610) (NCI H292: 2500 cells/well; SK-HEP-1: 1000 cells/well; KPL-4: 1200 cells/well; in total volume 100 μl). The cells were then incubated in an incubator at 37° C. and 5% carbon dioxide. After 48 h, the medium was replaced. The antibody drug conjugates in 10 μl of culture medium in concentrations from $10^{-5}$M to $10^{-13}$M were then pipetted to the cells (in triplicate), and the assay was then incubated in an incubator at 37° C. and 5% carbon dioxide. After 96 h, the cell proliferation was detected using the MTT assay (ATCC, Manassas, Va., USA, catalogue No. 30-1010K). To this end, the MTT reagent was incubated with the cells for 4 h, followed by lysis of the cells overnight by addition of the detergent. The dye formed was detected at 570 nm (Infinite M1000 pro, Tecan). The measured data were used to calculate the $IC_{50}$ of the growth inhibition using the DRC (dose response curve). The proliferation of cells which were not treated with test substance but were otherwise identically treated was defined as the 100% figure.

Tables 1b and 1c below set out the $IC_{50}$ values for representative working examples from this assay:

TABLE 1b

| Example | NCI-H292 $IC_{50}$ [M] MTT assay | SK-HEP-1 $IC_{50}$ [M] MTT assay |
|---|---|---|
| 1a | 1.51E−11 | 1.22E−10 |
| 1i | 4.91E−10 | 3.84E−09 |
| 2a | 6.69E−11 | 1.75E−10 |
| 4a | 1.42E−10 | 9.57E−10 |
| 5a | 6.03E−10 | 5.00E−07 |
| 6a | 2.95E−10 | 5.00E−07 |
| 7a | 2.18E−10 | 5.00E−07 |
| 8a | 9.13E−11 | 1.63E−10 |
| 10a | 4.79E−11 | 9.75E−08 |
| 11a | 2.80E−12 | 3.86E−10 |
| 12a | 7.76E−12 | 6.71E−11 |
| 13a | 7.69E−11 | 1.16E−10 |
| 14a | 9.04E−12 | 1.04E−10 |
| 15a | 2.36E−11 | 9.08E−11 |
| 16a | 4.21E−11 | 2.51E−10 |
| 17a | 6.69E−12 | 4.66E−12 |
| 18a | 1.69E−11 | 2.56E−09 |
| 19a | 2.39E−11 | 1.45E−09 |
| 21a | 7.24E−12 | 2.95E−11 |
| 22a | 2.41E−10 | 9.19E−09 |
| 23a | 1.09E−10 | 7.16E−10 |
| 24a | 2.47E−10 | 5.69E−08 |
| 25a | 4.99E−11 | 6.84E−08 |
| 26a | 7.91E−11 | 5.00E−07 |
| 27a | 3.17E−12 | 4.83E−09 |
| 28a | 6.21E−11 | 4.49E−08 |
| 29a | 1.00E−10 | 1.54E−08 |
| 30a | 1.13E−11 | 3.72E−10 |
| 31t | 1.50E−09 | 1.92E−09 |
| 32t | 2.09E−09 | 2.12E−09 |
| 33t | 3.07E−09 | 1.34E−09 |

TABLE 1b-continued

| Example | NCI-H292 $IC_{50}$ [M] MTT assay | SK-HEP-1 $IC_{50}$ [M] MTT assay |
|---|---|---|
| 34t | 8.16E−10 | 8.87E−10 |
| 34t-4 | 1.84E−10 | 1.71E−10 |
| 35a | 2.04E−12 | 3.06E−09 |
| 36a | 1.83E−12 | 1.35E−09 |
| 37a | 9.22E−11 | 1.09E−08 |
| 38a | 1.32E−10 | 1.27E−10 |
| 39a | 1.15E−09 | 2.66E−08 |
| 40a | 2.05E−11 | 3.10E−10 |
| 41a | 1.58E−10 | 4.88E−12 |
| 42a | 1.49E−12 | 1.04E−11 |
| 43a | 5.42E−12 | 1.50E−09 |
| 44a | 1.52E−11 | 3.58E−10 |

TABLE 1c

| Example | KPL4 $IC_{50}$ [M] MTT assay |
|---|---|
| 1e | 3.75E−10 |
| D-Asn epimer from Example 1e | >1.00E−7 |
| 2e | 3.89E−10 |
| 5e | 2.91E−09 |
| 6e | 3.11E−09 |
| 8e | 6.41E−11 |
| 11e | 9.37E−11 |
| 12e | 1.13E−10 |
| 13e | 5.71E−11 |
| 14e | 2.34E−10 |
| 16e | 1.44E−10 |
| 17e | 9.15E−11 |
| 18e | 8.25E−11 |
| 19e | 4.03E−10 |
| 21e | 1.22E−12 |
| 22e | 5.17E−10 |
| 23e | 5.13E−10 |
| 24e | 7.05E−09 |
| 25e | 7.51E−11 |
| 26e | 5.10E−11 |
| 27e | 4.81E−10 |
| 28e | 4.41E−10 |
| 29e | 9.54E−11 |
| 30e | 2.12E−10 |
| 34te-4 | 3.29E−10 |
| 35e | 7.71E−11 |
| 36e | 4.84E−11 |
| 37e | 9.53E−11 |
| 38e | 1.87E−10 |
| 39e | 4.42E−09 |
| 40e | 1.07E−10 |
| 41e | 7.84E−12 |
| 42e | 1.93E−10 |
| 43e | 1.04E−10 |
| 44e | 2.34E−10 |

The activity data reported relate to the working examples described in the present experimental section, with the drug/mAB ratios indicated. The values may possibly deviate for different drug/mAB ratios. The IC50 values are means of several independent experiments or individual values. The action of the antibody drug conjugates was selective for the respective isotype control comprising the respective linker and toxophore.

Here too, in analogy to Example 1e, the D-asparagine epimer of Q1 was coupled with 5 mg of trastuzumab. The ADC batch obtained was characterized as follows:

Protein concentration: 1.68 mg/ml

Drug/mAb ratio: 3.6

As shown in Table 1c, this control ADC does not show any significant cytotoxic effect on the KPL4 cell line either.

C-1b Determination of the Inhibition of the Kinesin Spindle Protein KSP/Eg5 by Selected Examples The motor domain of the human kinesin spindle protein KSP/Eg5 (tebu-bio/Cytoskeleton Inc, No. 027EG01-XL) was incubated in a concentration of 10 nM with microtubuli (bovine or porcine, tebu-bio/Cytoskeleton Inc) stabilized with 50 μg/ml taxol (Sigma No. T7191-5MG) for 5 min at RT in 15 mM PIPES, pH 6.8 (5 mM $MgCl_2$ and 10 mM DTT, Sigma). The freshly prepared mixture was aliquoted into a 384 MTP (from Corning). The inhibitors to be examined at concentrations of 1.0x10-6 M to 1.0x10-13 M and ATP (final concentration 500 μM, Sigma) were then added. Incubation was at RT for 2 h. ATPase activity was detected by detecting the inorganic phosphate formed using malachite green (Biomol). After addition of the reagent, the assay was incubated at RT for 50 min prior to detection of the absorption at a wavelength of 620 nm. The positive controls used were monastrol (Sigma, M8515-1 mg) and ispinesib (AdooQ Bioscience A10486). The individual data of the dose-activity curve are eight-fold determinations. The $IC_{50}$ values are means of two independent experiments. The 100% control was the sample which had not been treated with inhibitors.

Table 2 below lists the $IC_{50}$ values of representative working examples from the assay described and summarizes the corresponding cytotoxicity data (MTT assay):

TABLE 2

| Examples | KSP assay $IC_{50}$ [M] | NCI-H292 $IC_{50}$ [M] MTT assay | KPL4 $IC_{50}$ [M] MTT assay |
|---|---|---|---|
| M1 | 2.01E−09 | 5.00E−07 | 5.00E−07 |
| M2 | 2.45E−09 | 2.04E−07 | 1.63E−07 |
| M3 | 1.52E−09 | 3.21E−08 | 9.00E−08 |
| M4 | 2.71E−10 | 4.43E−08 | 1.76E−07 |
| M5 | 4.57E−10 | 7.94E−08 | 2.22E−07 |
| M6 | 1.78E−09 | 4.63E−08 | 1.93E−07 |
| M7 | 6.21E−10 | 2.22E−08 | 9.25E−08 |
| M9 | 1.07E−09 | 7.74E−10 | 2.57E−10 |
| M10 | 4.70E−10 | 3.03E−07 | 2.26E−07 |
| M11 | 1.11E−09 | 4.32E−11 | |
| M12 | 4.46E−10 | 3.3E−08 | |
| M13 | 1.50E−09 | 1.52E−07 | 1.69E−07 |
| M14 | 2.16E−09 | 1.74E−07 | 1.82E−07 |
| M15 | 9.64E−10 | 1.33E−07 | 1.69E−07 |
| M16 | 1.48E−09 | 1.43E−07 | 1.95E−07 |
| M17 | 4.17E−09 | 7.35E−09 | |
| M18 | 5.17E−09 | 3.55E−08 | |
| M19 | 2.58E−09 | 1.21E−07 | |
| M20 | 1.50E−09 | 1.49E−07 | 2.13E−07 |
| M21 | 2.31E−09 | | |
| M22 | 8.27E−10 | 2.89E−08 | 1.82E−07 |
| M23 | 1.26E−09 | 5.00E−07 | 5.00E−07 |
| M24 | 2.90E−09 | 1.67E−07 | 5.00E−07 |
| M25 | 2.91E−09 | 5.00E−07 | 5.00E−07 |
| M26 | 9.44E−10 | 6.38E−08 | |
| M27 | 2.03E−09 | 2.76E−07 | |

The activity data reported relate to the working examples described in the present experimental section.

C-1c Enzymatic Assays a: Cathepsin B Assay

For every cathepsin B-cleavable prodrug to be examined, a mixture was made up in a micro reaction vessel (0.5 ml, from Eppendorf). The enzyme used here was obtained from human liver tissue. 2 μg of cathepsin B (Sigma C857125 μg) were initially charged and made up to a total volume of 200 μl with 50 mM Na phosphate buffer, pH6.0, 2 mM DTT. Then 50 μl of the substrate solution to be examined were pipetted in. The mixture was incubated in a thermoblock (from Thermo Fisher Scientific) at 40° C. under constant agitation at 300 rpm. The enzymatic reaction was controlled kinetically. For this purpose, a 10 μl sample was taken at different times. The sample taken was admixed immediately with 20 μl of ice-cold methanol in order to stop the enzymatic reaction and then frozen at −20° C. The times selected for sampling were after 10 min, 2 h, 4 h and 24 h. RP-HPLC analysis examined (reverse phase HPLC, from Agilent Technologies, 1200 Series). The determination of the toxophore released enabled the determination of the half-life $t_{1/2}$ of the enzymatic reaction.

b: Legumain Assay

The legumain assay was conducted with recombinant human enzyme. The rh legumain enzyme solution (catalogue #2199-CY, R&D Systems) was diluted to the desired concentration in 50 mM Na acetate buffer/100 mM NaCl, pH4.0 and preincubated at 37° C. for 2 h. rh legumain was then adjusted to a final concentration of 1 ng/μl in 50 mM MES buffer, 250 mM NaCl, pH 5.0. For every legumain-cleavable prodrug to be examined, a mixture was made up in a micro reaction vessel (0.5 ml, from Eppendorf). For this purpose, the substrate solution was adjusted to the desired concentration (double concentration) with 50 mM MES buffer, 250 mM NaCl, pH 5.0. For the kinetic measurement of the enzymatic reaction, 250 μl of the legumain solution were first initially charged and the enzyme reaction was started by adding 250 μl of the substrate solution (final concentration: single concentration). At different times, 50 μL samples were taken. This sample was admixed immediately with 100 μl of ice-cold methanol in order to stop the enzymatic reaction and then frozen at −20° C. The times selected for sampling were after 0.5 h, 1 h, 3 h and 24 h. The samples were then analysed by means of RP-HPLC analysis and by LC-MS analysis. The determination of the toxophore released enabled the determination of the half-life $t_{1/2}$ of the enzymatic reaction.

As representative examples to show the legumain-mediated cleavage, the substrates produced in the legumain assay were the model compounds A and B.

Reference Example: Model Compound A

N-(Pyridin-4-ylacetyl)-L-alanyl-L-alanyl-$N^1$-[(2S)-4-[{(1R)-1-[1-benzyl-4-(2,5-difluorophenyl)-1H-pyrrol-2-yl]-2,2-dimethylpropyl}(glycoloyl)amino]-1-(methylamino)-1-oxobutan-2-yl]-L-aspartamide

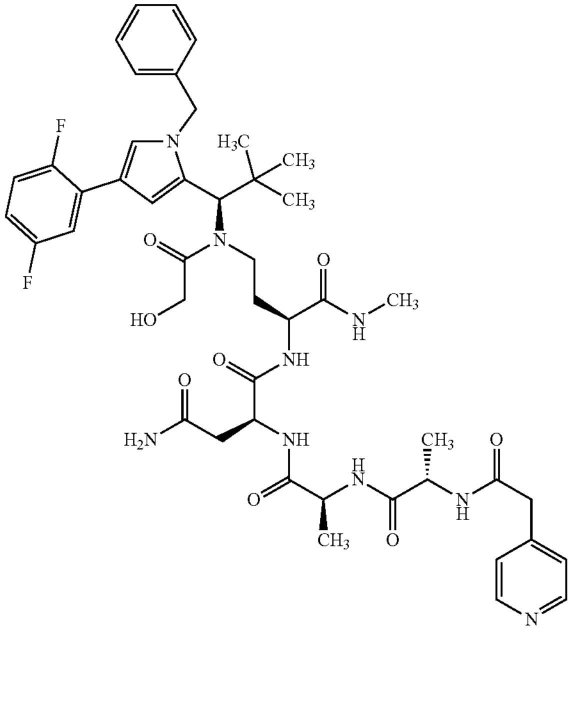 [SMILES: CNC(=O)[C@H](CCN(C(=O)CO)[C@@H](c1cc(-c2cc(F)ccc2F)cn1Cc1ccccc1)C(C)(C)C)NC(=O)[C@H](CC(N)=O)NC(=O)[C@H](C)NC(=O)[C@H](C)NC(=O)Cc1ccncc1]

First of all, trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1) was prepared as described in WO 2015096982 A1. Subsequently, this intermediate was used to prepare the title compound by coupling to Intermediate L103 in DMF in the presence of HATU and of N,N-diisopropylethylamine.

LC-MS (Method 1): $R_t$=0.86 min; MS (ESIpos): m/z=902 $[M+H]^+$.

Reference Example: Model Compound B

N-(Pyridin-4-ylacetyl)-L-alanyl-N-methyl-L-alanyl-$N^1$-[(2S)-4-[{(1R)-1-[1-benzyl-4-(2,5-difluorophenyl)-1H-pyrrol-2-yl]-2,2-dimethylpropyl}(glycoloyl)amino]-1-(methylamino)-1-oxobutan-2-yl]-L-aspartamide

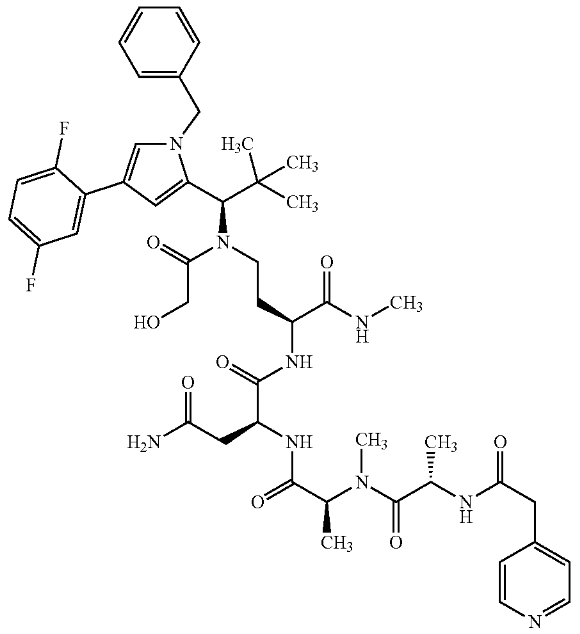 [SMILES: CNC(=O)[C@H](CCN(C(=O)CO)[C@@H](c1cc(-c2cc(F)ccc2F)cn1Cc1ccccc1)C(C)(C)C)NC(=O)[C@H](CC(N)=O)NC(=O)[C@H](C)N(C)C(=O)[C@H](C)NC(=O)Cc1ccncc1]

First of all, trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1) was prepared as described in WO 2015096982 A1. Subsequently, this intermediate was used to prepare the title compound by coupling to Intermediate L119 in DMF in the presence of HATU and of N,N-diisopropylethylamine.

LC-MS (Method 1): $R_t$=0.83 min; MS (ESIpos): m/z=916 $[M+H]^+$.

Compound A was cleaved from legumain under the conditions described above to the target compound with a half-life of 1.1 h.

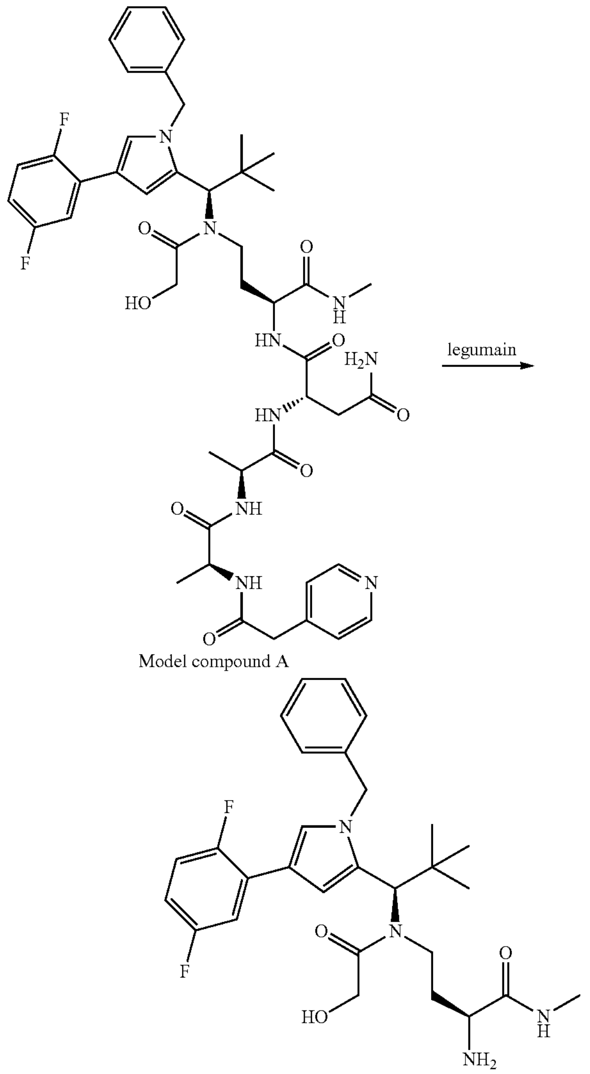

C-2 Internalization Assay

Internalization is a key process which enables specific and efficient provision of the cytotoxic payload in antigen-expressing cancer cells via antibody drug conjugates (ADC). This process is monitored via fluorescent labelling of specific antibodies and an isotype control antibody. First, the fluorescent dye was conjugated to lysines of the antibody. Conjugation was carried out using a two-fold molar excess of CypHer 5E mono NHS ester (Batch 357392, GE Healthcare) at pH 8.3. After the coupling, the reaction mixture was purified by gel chromatography (Zeba Spin Desalting Columns, 40K, Thermo Scientific, No. 87768; elution buffer: DULBECCO'S PBS, Sigma-Aldrich, No. D8537), to eliminate excess dye and to adjust the pH. The protein solution was concentrated using VIVASPIN 500 columns (Sartorius stedim biotec). The dye load of the antibody was determined by means of spectrophotometry analysis (from NanoDrop) and subsequent calculation ($D/P=A_{dye}\ \varepsilon_{protein}:(A_{280}-0.16A_{dye})\varepsilon_{dye}$).

The dye load of the antibodies examined here and the isotype control were of a comparable order of magnitude. In cell binding assays, it was confirmed that the coupling did not lead to any change in the affinity of the antibodies.

The labelled antibodies were used for the internalization assay. Prior to the start of the treatment, cells ($2\times10^4$/well)

were sown in 100 μl medium in a 96-well MTP (fat, black, clear bottom No 4308776, from Applied Biosystems). After 18 h of incubation at 37° C./5% $CO_2$, the medium was replaced and labelled antibodies were added in different concentrations (10, 5, 2.5, 1, 0.1 μg/ml). The same treatment protocol was applied to the labelled isotype control (negative control). The chosen incubation times were 0 h, 0.25 h, 0.5 h, 1 h, 1.5 h, 2 h, 3 h, 6 h and 24 h. The fluorescence measurement was carried out using the InCellAnalyzer 1000 (from GE Healthcare). This was followed by kinetic evaluation via measurement of the parameters granule counts/cell and total granule intensity/cell.

Following binding to the receptor, antibodies were examined for their internalization capacity. For this purpose, cells with different receptor expression levels were chosen. A target-mediated specific internalization was observed with the antibodies, whereas the isotype control showed no internalization.

C-3 In Vitro Tests for Determining Cell Permeability

The cell permeability of a substance can be investigated by means of in vitro testing in a flux assay using Caco-2 cells [M. D. Troutman and D. R. Thakker, *Pharm. Res.* 20 (8), 1210-1224 (2003)]. For this purpose, the cells were cultured for 15-16 days on 24-well filter plates. For the determination of permeation, the respective test substance was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Biblingen, Germany) using reverse phase columns. The HPLC system was coupled via a Turbo Ion Spray Interface to a Triple Quadropol mass spectrometer API 4000 (AB SCIEX Deutschland GmbH, Darmstadt, Germany). The permeability was evaluated on the basis of a $P_{app}$ value, which was calculated using the formula published by Schwab et al. [D. Schwab et al., *J. Med. Chem.* 46, 1716-1725 (2003)]. A substance was classified as actively transported when the ratio of $P_{app}$ (B–A) to $P_{app}$ (A–B) (efflux ratio) was >2 or <0.5.

Of critical importance for toxophores which are released intracellularly is the permeability from B to A [$P_{app}$ (B–A)] and the ratio of $P_{app}$ (B–A) to $P_{app}$ (A–B) (efflux ratio): the lower this permeability, the slower the active and passive transport processes of the substance through the monolayer of Caco-2 cells. If additionally the efflux ratio does not indicate any active transport, the substance may, following intracellular release, remain longer in the cell. Hence, there is also more time available for interaction with the biochemical target (in this case: kinesin spindle protein, KSP/Eg5).

Table 3 below sets out permeability data for representative working examples from this assay:

TABLE 3

| Working Example | $P_{app}$ (B-A) [nm/s] | Efflux ratio |
|---|---|---|
| M1 | 7.8 | 4 |
| M2 | 4.8 | 6.4 |
| M3 | 1.4 | 1.3 |
| M4 | 21.3 | 18.7 |
| M5 | 20.3 | 26.5 |
| M6 | 1.7 | 0.7 |
| M7 | 5.6 | 2.2 |
| M9 | 213 | 16 |
| M11 | 24.3 | 27.7 |
| M12 | 3.3 | 1.8 |
| M13 | 7.1 | 3.6 |

TABLE 3-continued

| Working Example | $P_{app}$ (B-A) [nm/s] | Efflux ratio |
|---|---|---|
| M14 | 12.7 | 6.6 |
| M15 | 6.4 | 4.4 |
| M16 | 9.0 | 7.0 |
| M17 | 93.6 | 81.5 |
| M18 | 1.6 | 2.9 |
| M19 | 1.9 | 2.9 |
| M21 | 0.5 | 1.5 |
| M22 | 0.9 | 0.9 |
| M23 | 2.8 | 2.0 |
| M24 | 3.9 | 1.0 |
| M25 | 8.1 | 3.6 |
| M26 | 13.0 | 9.6 |
| M27 | 13.2 | 11.9 |

C-4 In Vitro Tests for Determining the Substrate Properties for P-Glycoprotein (P-Gp)

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., *J. Clin. Invest.* 96, 1698-1705 (1995)]. For this purpose, the LLC-PK1 cells or L-MDR1 cells were cultured on 96-well filter plates for 3-4 days. For determination of the permeation, the respective test substance, alone or in the presence of an inhibitor (such as ivermectin or verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns. The HPLC system was coupled via a Turbo Ion Spray Interface to a Triple Quadropol mass spectrometer API 3000 (Applied Biosystems Applera, Darmstadt, Germany). The permeability was evaluated on the basis of a $P_{app}$ value, which was calculated using the formula published by Schwab et al. [D. Schwab et al., *J. Med. Chem.* 46, 1716-1725 (2003)]. A substance was classified as P-gp substrate when the efflux ratio of $P_{app}$ (B–A) to $P_{app}$ (A–B) was >2.

As further criteria for the evaluation of the P-gp substrate properties, the efflux ratios in L-MDR1 and LLC-PK1 cells or the efflux ratio in the presence or absence of an inhibitor may be compared. If these values differ by a factor of more than 2, the substance in question is a P-gp substrate.

C-5 Pharmacokinetics

C5a: Identification of the ADC Metabolites after Internalization In Vitro

Description of the Method:

Internalization studies with immunoconjugates are carried out to analyse metabolites formed intracellularly. To this end, human lung tumour cells NCI H292 ($3\times10^5$/well) are sown in 6-well plates and incubated overnight (37° C., 5% $CO_2$). The cells are treated with 10 μg/ml (66 nM) of the ADC to be examined. Internalization was carried out at 37° C. and 5% $CO_2$. At various time points (0, 4, 24, 48, 72 h), cell samples are taken for further analysis. First, the supernatants (about 5 ml) are harvested and, after centrifugation (2 min, RT, 1000 rpm Heraeus Variofuge 3.0R), stored at −80° C. The cells are washed with PBS and detached with Accutase, and the cell number is determined. After another washing, a defined number of cells ($2\times10^5$) is treated with 100 ml of lysis buffer (Mammalian Cell Lysis Kit (Sigma MCL1) and incubated with continuous shaking (Thermomixer, 15 min, 4° C., 650 rpm) in Protein LoBind tubes (Eppendorf Cat. No. 0030 108.116). After the incubation, the lysate is centrifuged (10 min, 4° C., 12000 g, Eppendorf 5415R) and the supernatant is harvested. The supernatant obtained is stored at −80° C. All samples are then analysed as follows.

Measurement of the compounds in the culture supernatant or cell lysate is carried out after precipitation of the proteins with methanol or acetonitrile by high-pressure liquid chromatography (HPLC) coupled to a triple-quadrupole mass spectrometer (MS).

For work-up of 50 µl of culture supernatant/cell lysate, 150 µl of precipitation reagent (generally acetonitrile) are added and the mixture is shaken for 10 seconds. The precipitation reagent contains an internal standard (ISTD) in a suitable concentration (generally in the range of 20-100 ng/ml). After 3 minutes of centrifugation at 16000 g, the supernatant is transferred into an autosampler vial, made up with 500 µl of a buffer suitable for the mobile phase and shaken again.

The two matrix samples are then measured using the HPLC-coupled triple-quadrupol mass spectrometer API6500 from AB SCIEX Deutschland GmbH.

For calibration, concentrations of 0.5-2000 µg/l are added to plasma samples. The detection limit (LOQ) is about 2 µg/l. The linear range extends from 2 to 1000 µg/l.

For calibration of the tumour samples, concentrations of 0.5-200 µg/l are added to the supernatant of untreated tumours. The detection limit is 4 µg/l. The linear range extends from 4 to 200 µg/l.

Quality controls for testing validity contain 5 and 50 µg/l.

C5b: Identification of the ADC Metabolites In Vivo

After i.v. administration of 3-30 mg/kg of different ADCs, the plasma and tumour concentrations of the ADCs and any metabolites occurring can be measured, and the pharmacokinetic parameters such as clearance (CL), area under the curve (AUC) and half-times ($t_{1/2}$) can be calculated.

As a reference example (R10k), an ADC with the agonistic antibody TPP-2658 was prepared with a non-cleavable linker:

Reference Example R10k

To 150 mg of anti-TWEAKR antibody TPP-2658 in 10.5 ml of PBS (c=14.28 mg/ml) under argon was added a solution of 0.86 mg of TCEP in 2 ml of PBS buffer. The antibody TPP-2658 and the production thereof are described in detail in WO 2015/189143 A1.

The mixture was stirred at RT for 30 min and then 6.63 mg (0.008 mmol) of Intermediate F104 dissolved in 1250 µl of DMSO were added. After stirring at RT for a further 90 min, the mixture was diluted with 1250 µl of PBS buffer which had been adjusted to pH 8 beforehand.

This solution was then passed through PD 10 columns (Sephadex® G-25, GE Healthcare) equilibrated with PBS buffer pH 8 and eluted with pH buffer pH 8. The eluate was diluted to a total volume of 22.5 ml with PBS buffer pH 8. This solution was stirred at RT under argon overnight and then rebuffered to pH 7.2 by means of PD-10 columns. This was followed by concentration by ultracentrifugation, redilution with PBS buffer (pH 7.2) and concentration again. The ADC batch obtained was characterized as follows:

Protein concentration: 14.06 mg/ml

Drug/mAb ratio: 3.4

Analysis for Quantification of any Metabolites Occurring

Measurement of the compounds in tumour and tissue was carried out after precipitation of the proteins with methanol or acetonitrile by high-pressure liquid chromatography (HPLC) coupled to a triple-quadrupole mass spectrometer (MS).

During the work-up of a tumour or tissue, the latter was treated with 3 times the amount of extraction buffer. The extraction buffer contained 50 ml of Tissue Protein Extraction Reagent (Pierce, Rockford, Ill.), two pellets of Complete-Protease-Inhibitor-Cocktail (Roche Diagnostics GmbH, Mannheim, Germany) and phenylmethylsulphonyl fluoride (Sigma, St. Louis, Mo.) in a final concentration of 1 mM. The sample is homogenized twice for 20 minutes in a Tissuelyser II (Qiagen), at maximum stroke number. 50 µl of the homogenate were transferred into an autosampler vial and made up with 150 µl of methanol including ISTD. After 3 minutes of centrifugation at 16000 g, 10 µl of the supernatant were made up with 180 µl of a buffer suitable for the mobile phase and shaken again. The tumour sample was then ready for measuring.

The two matrix samples were then measured using the HPLC-coupled triple-quadrupol mass spectrometer API6500 from AB SCIEX Deutschland GmbH.

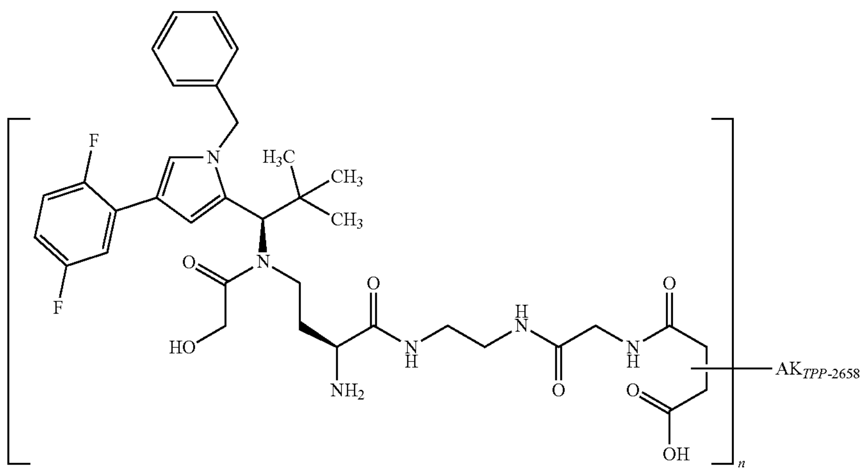

For calibration of the tumour and tissue samples, concentrations of 0.5-200 μg/l were added to the supernatant of untreated tumours or tissue. The detection limit was 3 μg/l. The linear range extends from 3 to 200 μg/l.

Quality controls for testing validity contain 5 and 50 μg/l, in plasma additionally 500 μg/l.

TABLE catabolite concentrations in NCI H292 xenograft of mouse tumour, liver and kidney 24 h after administration of 10 mg/kg of the ADC from Example 1k* (n = 3) or of 10 mg/kg of the ADC from reference example R10k (n = 2). The catabolite measured in both cases was: M26.

| | M26 Mean [μg/l] | M26 SD [μg/l] |
|---|---|---|
| R10k | 98 | 10 |
| Example 1k* | 104 | 12 |
| R10k | 107 | 19 |
| Example 1k* | 63 | 6.9 |
| R10k | 96 | 19 |
| Example 1k* | 72 | 18 |

After administration of the inventive ADC Example 1k* having a legumain-cleavable prodrug residue, concentrations of the active catabolite M26 were measured in the tumour that were comparable to those measured after administration of the ADC with the same antibody but without a legumain-cleavable prodrug residue. By contrast, the measured concentrations of the active metabolite, especially in the liver, after administration of the ADC from Example 1k*, were much lower than after administration of the reference ADC R10k. There is much more selective release of the active ingredient in the target tissue (tumour) compared to other organs when a legumain-cleavable prodrug residue is used in the active ingredient.

Analysis for Quantification of the Antibodies Used

The antibody part of the ADCs was determined using a ligand binding assay (ELISA) as total IgG concentration in plasma samples and tumour lysates. Here, the sandwich ELISA format was used. This ELISA had been qualified and validated for the determination in plasma and tumour samples. The ELISA plates were coated with anti-human goat IgG Fc antibodies. After incubation with the sample, the plates were washed and incubated with a detector conjugate of simian anti-human IgG(H+L) antibody and horseradish peroxidase (HRP). After a further washing step, the HRP substrate was added to OPD and the colour development was monitored via absorption at 490 nm. Standard samples having a known IgG concentration were fitted using a 4-parameter equation. Within the lower (LLOQ) and upper (ULOQ) quantification limits, the unknown concentrations were determined by interpolation.

C-6 Activity Test In Vivo

The activity of the conjugates according to the invention was tested, for example, using xenograft models. The person skilled in the art is familiar with methods in the prior art which allow the activity of the compounds according to the invention to be tested (see, for example, WO 2005/081711; Polson et al., Cancer Res. 2009 Mar. 15; 69(6):2358-64). To this end, a tumour cell line expressing the target molecule of the binder was inoculated into rodents (for example mice). A conjugate according to the invention, an isotype control conjugate, a control antibody or isotonic saline was then administered to the inoculated animals. The administration took place once or more than once. Following an incubation time of several days, the size of the tumour was determined by comparing conjugate-treated animals and the control group. The conjugate-treated animals displayed a smaller tumour size.

C-6a. Growth Inhibition/Regression of Experimental Tumours in the Mouse

Human tumour cells which express the antigen for the antibody-drug conjugate are inoculated subcutaneously into the flank of immunosuppressed mice, for example NMRi nude or SCID mice. 1-10 million cells are detached from the cell culture, centrifuged and resuspended in medium or medium/matrigel. The cell suspension is injected under the skin of the mouse.

Within a few days, a tumour grows. Treatment is commenced after the tumour is established, at a tumour size of approximately 40 $mm^2$. To examine the effect on larger tumours, treatment may be initiated only at a tumour size of 50-100 $mm^2$.

Treatment with APDCs and ADCs is carried out via the intravenous (i.v.) route into the tail vein of the mouse. The ADC is administered in a volume of 5 ml/kg.

The treatment protocol depends on the pharmacokinetics of the antibody. With the conjugates according to the invention, treatment is effected once per week for 2 or 3 weeks as the standard. For a quick assessment, a protocol with a single treatment may be employed. However, the treatment may also be continued, or a second cycle of three treatment days may follow at a later time.

As standard, 8 animals are used per treatment group. In addition to the groups to which the active substances are administered, one group is treated as control group only with the buffer, according to the same protocol.

During the experiment, the tumour area is measured regularly in two dimensions (length/width) using a caliper. The tumour area is determined as length x width. The ratio of the mean tumour area of the treatment group to that of the control group is stated as T/C area.

When, after the end of the treatment, all groups of the experiment are terminated at the same time, the tumours can be removed and weighed. The ratio of the mean tumour weights of the treatment group to that of the control group is stated as T/C weight.

C-6b. Efficacy of the APDCs and ADCs According to the Invention in Various Tumour models The tumour cells are inoculated subcutaneously into the flank of female NMRI nude mice (Janvier). At a tumour size of ~40 $mm^2$, intravenous treatment is effected with the antibody-drug conjugate. After the treatment, monitoring of the tumour growth continues if appropriate.

The treatment with the APDCs according to the invention leads to a distinct and in some cases long-lasting inhibition of tumour growth compared to the control group on the conjugated isotype control antibody. Table 8 shows the T/C values determined for tumour weights and tumour area on the respective day of the end of the experiment, calculated from the start of treatment.

TABLE 8

| Example | Tumour model | Dose | Dose scheme | T/C area |
|---|---|---|---|---|
| 1k* | | 10 mg/kg | Q7dx3 | 0.53 (day 38, final) |
| 2k* | | 10 mg/kg | Q7dx3 | 0.43 (day 38, final) |
| 1k* | | 10 mg/kg | Q7dx2 | 0.38 (day 11, final) |
| 2k* | | 10 mg/kg | Q7dx2 | 0.35 (day 11, final) |
| 1k* | KU-19-19 (human bladder carcinoma) | 10 mg/kg | Q7dx2 | 0.19 (day 9, final) |

The invention claimed is:

1. A conjugate of an antibody or antigen-binding fragment thereof with one or more drug molecules or one or more prodrugs thereof, of the following formula:

BINDER-[-L-KSP]$_n$ wherein

BINDER is the antibody or antigen-binding fragment thereof,

L is a linker, wherein -L- is attached to a cysteine side chain of the antibody or antigen-binding fragment thereof, n is a number from 1 to 50, and KSP is a kinesin spindle inhibitor or prodrug thereof, wherein -L-KSP has the following formula (IIa):

(IIa)

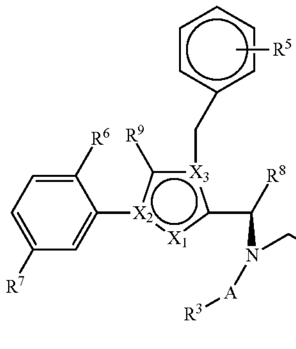

wherein $X_1$ is N, $X_2$ is N and $X_3$ is C; or $X_1$ is CH or CF, $X_2$ is C and $X_3$ is N; or $X_1$ is NH, $X_2$ is C and $X_3$ is C; or $X_1$ is CH, $X_2$ is N and $X_3$ is C;

$R^1$ is —H, -L-#1, -MOD or —$(CH_2)_{0-3}$Z, wherein Z is —H, —$NHY^3$, —$OY^3$, —$SY^3$, halogen, —C(═O)—$NY^1Y^2$ or —CO—$OY^3$, wherein $Y^1$ and $Y^2$ are independently —H, —$NH_2$, —$(CH_2CH2O)_{0-3}$—$(CH_2)_{0-3}$Z' or —$CH(CH_2W)$Z', wherein $Y^3$ is —H or —$(CH_2)_{0-3}$Z', wherein Z' is —H, $NH_2$, $SO_3H$, —COOH, —NH—C(═O)—$CH_2$—$CH_2$—$CH(NH_2)$COOH or —(C(═O)—NH—$CHY^4)_{1-3}$COOH, wherein W is —H or —OH, wherein $Y^4$ is straight-chain or branched $C_{1-6}$-alkyl which is optionally substituted by —NH—C(═O)—$NH_2$, or is aryl or benzyl which are optionally substituted by —$NH_2$;

$R^2$ is -L-#1, —H, -MOD, —C(═O)—$CHY^4$—$NHY^5$ or —$(CH_2)_{0-3}$Z, wherein Z is —H, halogen, —$OY^3$, —$SY^3$, —$NHY^3$, —C(═O)—$NY^1Y^2$ or —C(═O)—$OY^3$, wherein $Y^1$ and $Y^2$ are independently —H, —$NH_2$ or —$(CH_2)_{0-3}$Z', wherein $Y^3$ is —H or —$(CH_2)_{0-3}$Z', wherein Z' is —H, —$SO_3H$, —$NH_2$ or —COOH;

wherein $Y^4$ is straight-chain or branched $C_{1-6}$-alkyl which is optionally substituted by —NH—C(═O)—$NH_2$, or is aryl or benzyl which are optionally substituted by —$NH_2$, wherein $Y^5$ is —H or —C(═O)—$CHY^6$—$NH_2$, wherein $Y^6$ is straight-chain or branched $C_{1-6}$-alkyl;

$R^4$ is -L-#1, —H, —C(═O)—$CHY^4$—$NHY^5$ or —$(CH_2)_{0-3}$Z, wherein Z is —H, halogen, —$OY^3$, —$SY^3$, —$NHY^3$, —C(═O)—$NY^1Y^2$ or —C(═O)—$OY^3$, wherein $Y^1$ and $Y^2$ are independently —H, —$NH_2$ or —$(CH_2)_{0-3}$Z', wherein $Y^3$ is —H or —$(CH_2)_{0-3}$Z', wherein Z' is —H, —$SO_3H$, —$NH_2$ or —COOH;

wherein $Y^4$ is straight-chain or branched $C_{1-6}$-alkyl which is optionally substituted by —NH—C(═O)—$NH_2$, or is aryl or benzyl which are optionally substituted by —$NH_2$, wherein $Y^5$ is —H or —C(═O)—$CHY^6$—$NH_2$, wherein $Y^6$ is straight-chain or branched $C_{1-6}$-alkyl;

or $R^4$ is a group of the formula $R^{21}$—(C(═O))$_{(0-1)}$—(P3)$_{(0-2)}$—P2—NH—CH($CH_2$C(═O)—$NH_2$)—C(═O)— or $R^{21}$—(C(═O))$_{(0-1)}$—(P3)$_{(0-2)}$-P2—NH—CH($CH_2$COOH)—C(═O)—, wherein $R^{21}$ is a $C_{1-10}$-alkyl, $C_5$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by — $NH_2$, —NH-alkyl, —N(alkyl)$_2$, NH—C(═O)-alkyl, —N(alkyl)-C(═O)-alkyl, —$SO_3H$, —S(═O)$_2NH_2$, —S(═O)$_2$—N(alkyl)$_2$, —COOH, —C(═O)$NH_2$, —C(═O)N(alkyl)$_2$, or —OH, —H or an -Ox-$(CH_2CH_2O)_y$—$R^{22}$ group, wherein x is 0 or 1 wherein v is a number from 1 to 20, and wherein $R^{22}$ is —H, -alkyl, —$CH_2$—COOH, —$CH_2$—$CH_2$—COOH, or —$CH_2$—$CH_2$—$NH_2$), wherein P2 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or the respective N-alkyl amino acids;

wherein P3 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or the respective N-alkyl amino acids;

or $R^2$ and $R^4$ together represent (forming a pyrrolidine ring) —$CH_2$—$CHR^{10}$— or #-$CHR^{10}$—$CH_2$—, wherein $R^{10}$ is —H, —$NH_2$, —$SO_3H$, —COOH, —SH, halogen (especially F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl), —OH or $R^{21}$—C(═O)—P3-P2—NH—CH($CH_2$C(═O)—$NH_2$)—C(═O)—SIG-, wherein SIG is a self-immolative group which, after cleavage of the C(═O)—SIG bond, releases the secondary amine;

A is —C(═O)—, —S(═O)—, —S(═O)$_2$—, —S(═O)$_2$NH— or —C(═N—$NH_2$)—;

$R^3$ is -L-#1, -MOD or an optionally substituted alkyl, cycloalkyl, aryl, heteroaryl, heteroalkyl, heterocycloalkyl group, which may in each case be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—C(═O)-alkyl groups, 1-3 —O—C(═O)—NH-alkyl groups, 1-3 —NH—C(═O)-alkyl groups, 1-3 —NH—C(═O)—NH-alkyl groups, 1-3 —$S(O)_n$-alkyl groups, 1-3 —S(═O)$_2$—NH-alkyl groups, 1-3 —NH-alkyl groups, 1-3 —N(alkyl)$_2$ groups, 1-3 —$NH_2$ groups or 1-3 —$(CH_2)_{0-3}$Z groups, wherein Z is —H, halogen, —$OY^3$, —$SY^3$, —$NHY^3$, —C(═O)—$NY^1Y^2$ or —C(═O)—$OY^3$, wherein n is 0, 1 or 2, wherein $Y^1$ and $Y^2$ are independently —H, —$NH_2$ or —$(CH_2)_{0-3}$Z', wherein $Y^3$ is —H, —$(CH_2)_{0-3}$—CH($NHCOCH_3$)Z', —$(CH_2)_{0-3}$—CH($NH_2$)Z' or —$(CH_2)_{0-3}$Z', wherein Z' is —H, —$SO_3H$, —$NH_2$ or —COOH;

$R^5$ is —H, —$NH_2$, —$NO_2$, halogen, —CN, —$CF_3$, —$OCF_3$, —$CH_2F$, —$CH_2F$, —SH or —$(CH_2)_{0-3}$Z, wherein Z is —H, —$OY^3$, —$SY^3$, halogen, —$NHY^3$, —C(═O)—$NY^1Y^2$ or —C(═O)—$OY^3$, wherein $Y^1$ and $Y^2$ are independently —H, —$NH_2$ or —$(CH_2)_{0-3}$Z', wherein $Y^3$ is —H or —$(CH_2)_{0-3}$Z', wherein Z' is —H, —$SO_3H$, —$NH_2$ or —COOH;

$R^6$ and $R^7$ are independently —H, cyano, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy, —$NO_2$, $NH_2$, —COOH or halogen, $R^8$ is $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, $C_{4-10}$-cycloalkyl, fluoro-$C_{4-10}$-cycloalkyl, or —$(CH_2)_{0-2}$—($HZ^2$), wherein $HZ^2$ is a 4- to 7-membered heterocycle having up to two heteroatoms selected from the group consisting of N, O and S, wherein each of these groups may be substituted by —OH, —COOH or —$NH_2$ or -L-#1;

$R^9$ is —H, —F, —$CH_3$, —$CF_3$, —$CH_2F$ or —$CHF_2$;

wherein one of the substituents $R^1$, $R^2$, $R^3$, $R^4$ and $R^8$ is or (in the case of R') contains -L-#1, -L is the linker and #1 is the bond to the antibody or antigen-binding fragment thereof, wherein -MOD is —$(NR^{10})_n$-$(G1)_o$-G2-G3, wherein $R^{10}$ is —H or $C_1$-$C_3$-alkyl;

wherein G1 is —NH—C(═O)—, —C(═O)NH— or

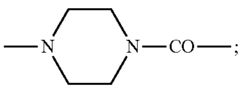;

n is 0 or 1;

o is 0 or 1;

and wherein G2 is a straight-chain and/or branched hydrocarbon group which has 1 to 10 carbon atoms and which may be interrupted once or more than once by one or more of the groups —O—, —S—, —S(═O)—, S(═O)$_2$, —$NR^y$—, —$NR^y$C(═O)—, —C(═O)—$NR^y$—, —$NR^yNR^y$—, —S(═O)$_2$ $NR^yNR^y$—, —C(═O)—$NR^yNR^y$—, —C(═O)—, or —$CR^x$═N—O—, wherein $R^y$ is —H, phenyl, $C_1$-$C_{10}$-alkyl, $C_2$-$C_{10}$-alkenyl or $C_2$-$C_{10}$-alkynyl, each of which may be substituted by —NH—C(═O)—$NH_2$, —COOH, —OH, —$NH_2$, —NH—CN—$NH_2$, sulphonamide, sulphone, sulphoxide or sulphonic acid wherein Rx is —H, $C_1$-$C_3$-alkyl or phenyl, wherein the hydrocarbon chain including a $C_1$-$C_{10}$-alkyl group optionally substituted on the hydrocarbon group as side chain, if present, may be substituted by —NH—C(═O)—$NH_2$, —COOH, —OH, —$NH_2$, —NH—CN—$NH_2$, sulphonamide, sulphone, sulphoxide or sulphonic acid, wherein G3 is —H or —COOH;

wherein -MOD has at least one —COOH group, wherein the conjugate comprises a legumain cleavable group —(C═O)$_{(0-1)}$—$(P3)_{(0-2)}$-P2—NH—CH($CH_2$C(═O)—X)—C(═O)—, wherein X is —$NH_2$ or —COOH;

wherein P2 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or the respective N-alkyl amino acids;

wherein P3 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or the respective N-alkyl amino acids;

or a salt, a solvate, a salt of the solvate, or an epimer thereof.

2. The conjugate according to claim 1, wherein $R^4$ is the group of the formula $R^{21}$—(C(═O))$_{(0-1)}$—$(P3)_{(0-2)}$-P2—NH—CH($CH_2$C(═O)$NH_2$)—C(═O)—.

3. The conjugate according to claim 1, wherein P2 is selected from the group consisting of Ala, Gly, Val, Leu, Ile, Pro, Ser, Thr and Asn, or the respective N-alkyl amino acids.

4. The conjugate according to claim 1, wherein P3 is selected from the group consisting of Pro, Ala, Val, Leu, Ile, Gly, Ser and Gln, or the respective N-alkyl amino acids.

5. The conjugate according to claim 1, wherein P2 is Ala.

6. The conjugate according to claim 1, wherein P3 is Ala.

7. The conjugate according to claim 1, wherein $R^{21}$ is —H, a $C_{1-5}$-alkyl-, $C_{5-10}$-aralkyl-, $C_{1-5}$-alkoxy-, $C_{6-10}$-aryloxy group, $C_{5-10}$-heteroalkyl, $C_{5-10}$-heterocycloalkyl, heteroaryl, heteroarylalkyl, $C_{5-10}$-heteroalkoxy or a $C_{5-10}$-heterocycloalkoxy group, each of which may be substituted by —COOH, —C(═O)—Oalkyl, —C(═O)O—$NH_2$, —$NH_2$ or —N(alkyl)$_2$, or a —$O_x$—$(CH_2CH_2O)_y$—$R^{22}$ group, wherein x is 0 or 1, wherein v is a number from 1 to 20, and $R^{22}$ is —H, -alkyl, —$CH_2$—COOH, —$CH_2$—$CH_2$—COOH, or —$CH_2$—$CH_2$—$NH_2$).

8. The conjugate according to claim 1, wherein $R^4$ is -L-#1 and comprises the group of the formula

—(C═O)$_{(0-1)}$—$(P3)_{(0-2)}$-P2—NH—CH($CH_2$C(═O)—$NH_2$)—C(═O)—, wherein P2 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or the respective N-alkyl amino acids; and wherein P3 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or the respective N-alkyl amino acids.

9. The conjugate according to claim 1, wherein the conjugate is an antibody-prodrug conjugate, wherein $R^4$ is the group of the formula $R^{21}$—(C═O)$_{(0-1)}$—$(P3)_{(0-2)}$-P2—NH—CH($CH_2$C(═O)—$NH_2$)—C(═O)—, wherein $R^{21}$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —N(alkyl)$_2$, —NH—C(═O)-alkyl, —N(alkyl)-C(═O)-alkyl, —$SO_3H$, —S(═O)$_2$—$NH_2$, —S(═O)$_2$—N(alkyl)$_2$, —COOH, —C(═O)—$NH_2$, —C(═O)—N(alkyl)$_2$ or —OH, or —H or a —$O_x$—($CH_2CH_2O$)v-$R^{22}$ group, wherein x is 0 or 1;

wherein v is a number from 1 to 20, and wherein $R^{22}$ is —H, -alkyl, —$CH_2$—COOH, —$CH_2$—$CH_2$—COOH, or —$CH_2$—$CH_2$—$NH_2$, wherein P2 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or the respective N-alkyl amino acids; and wherein each P3 is an amino acid independently selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or the respective N-alkyl amino acids.

10. The conjugate according to claim 1 wherein $R^1$ or $R^3$ is -L-#1.

11. The conjugate according to claim 1, wherein $X_1$ is CH, $X_2$ is C and $X_3$ is N.

12. The conjugate according to claim 1, wherein $R^6$ and $R^7$ are independently —H, $C_{1-3}$-alkyl or halogen.

13. The conjugate according to claim 12, wherein $R^6$ and $R^7$ are —F.

14. The conjugate according to claim 1, wherein $R^8$ is $C_{1-4}$-alkyl or cyclohexyl.

15. The conjugate according to claim 1, wherein $R^9$ is H.

16. The conjugate according to claim 1, wherein the antibody or antigen-binding fragment thereof an antibody.

17. The conjugate according to claim 16, wherein each drug molecule is attached to different amino acids of the antibody via the linker.

18. The conjugate according to claim 1, wherein the conjugate has on average 1.2 to 20 drug molecules or prodrugs per antibody or antigen-binding fragment thereof.

19. The conjugate according to claim 1, wherein the antibody or antigen-binding fragment thereof binds to a cancer target molecule.

20. The conjugate according to claim 19, wherein the antibody or antigen-binding fragment thereof binds to an extracellular target molecule.

21. The conjugate according to claim 20, wherein the antibody or antigen-binding fragment thereof, after binding to the extracellular target molecule, is internalized and processed intracellularly by the cell expressing the target molecule.

22. The conjugate according to claim 16, wherein the antibody or antigen-binding fragment thereof is a human, humanized or chimeric monoclonal antibody or an antigen-binding fragment thereof.

23. The conjugate according to claim 22, wherein the antibody or antigen-binding fragment thereof is an anti-HER2 antibody, an anti-EGFR antibody, an anti-TWEAKR antibody or an antigen-binding fragment thereof.

24. The conjugate according to claim 23, wherein the anti-TWEAKR antibody binds specifically to amino acid D in position 47 (D47) of TWEAKR (SEQ ID NO:169).

25. The conjugate according to claim 23, wherein the anti-TWEAKR antibody is the anti-TWEAKR antibody TPP-2658.

26. The conjugate according to claim 23, wherein the antibody or antigen-binding fragment thereof is an anti-EGFR antibody and $R^3$ is -L-#1.

27. The conjugate according to claim 1, wherein the linker -L- has one of the basic structures (i) to (iv) below:

(i) —(C═O)$_m$-SG1-L1-L2-

(ii) —(C═O)$_m$-L1-SG-L1-L2-

(iii) —(C═O)$_m$-L1-L2-

(iv) —(C═O)$_m$-L1-SG-L2- wherein m is 0 or 1, SG and SG1 are in vivo cleavable groups, each L1 is independently organic groups not cleavable in vivo, and L2 is a coupling group to the antibody or antigen-binding fragment thereof.

28. The conjugate according to claim 27, wherein the in vivo cleavable group SG is a 2-8 oligopeptide group, or a disulphide, a hydrazone, an acetal or an aminal and SG1 is a 2-8 oligopeptide group.

29. The conjugate according to claim 1, wherein the linker is attached to the cysteine side chain and has the following formula:

§ —(C═O)$_m$-L1-L2-§§ wherein m is 0 or 1;

§ represents the bond to the drug molecule and §§ represents the bond to the antibody or antigen-binding fragment thereof, and -L2- is

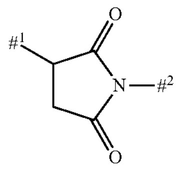
,
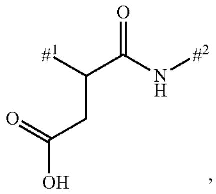
,
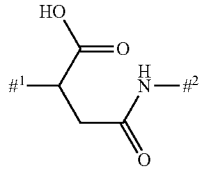
,
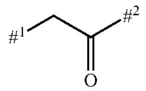
,
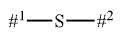
,
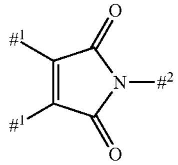
,
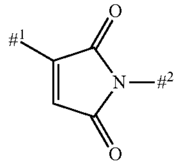
,
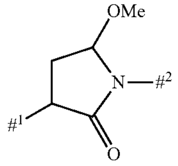
or
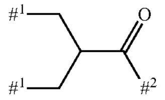

wherein $\#^1$ denotes the point of attachment to the sulphur atom of the antibody or antigen-binding fragment thereof,

#2 denotes the point of attachment to the group L1,

L1 is —$(NR^{10})_n$-(G1)o-G2-, wherein $R^{10}$ is —H, —$NH_2$ or $C_1$-$C_3$-alkyl;

G1 is —NH—C(═O)— or

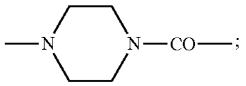

n is 0 or 1;

o is 0 or 1; and

G2 is a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, —S(═O)$_2$—, —NH—, —C(═O)—, —NMe-, —NHNH—, —S(═O)$_2$—NHNH—, —NH—C(═O)—, —C(═O)—NH—, —C(═O)—NHNH— and a 5- to 10-membered aromatic or non-aromatic heterocycle having up to 4 heteroatoms selected from the group consisting of N, O and S, —S(═O)— or —S(═O)$_2$—, wherein the side chains, if present, may be substituted by —NH—C(═O)—$NH_2$, —COOH, —OH, —$NH_2$, —NH—CN—$NH_2$, sulphonamide, sulphone, sulphoxide or sulphonic acid, or is one of the following groups:

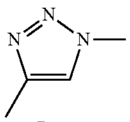

,

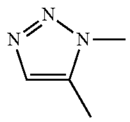

,

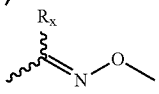

or

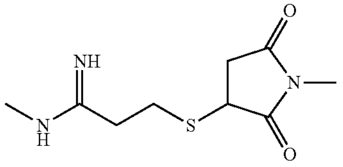

wherein Rx is —H, —$C_1$-$C_3$-alkyl or phenyl.

30. The conjugate according to claim 29, wherein L2 is represented by one or both of the formulae below:

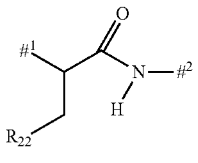

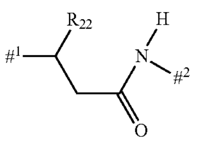

wherein

#$^1$ denotes the point of attachment to the sulphur atom of the antibody or antigen-binding fragment thereof,

#2 denotes the point of attachment to group $L^1$, $R^{22}$ is —COOH, and the bonds to the sulphur atom of the antibody or antigen-binding fragment thereof are present in one of these two structures to an extent of more than 80% (based on the total number of bonds in the linker to the antibody or antigen-binding fragment thereof).

31. The conjugate according to claim 29, wherein $L^1$ has the following formulae:

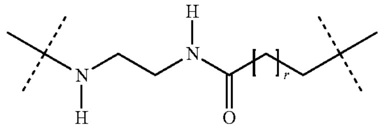

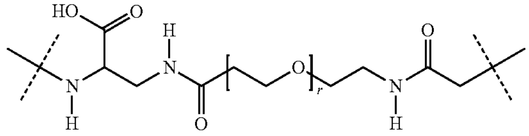

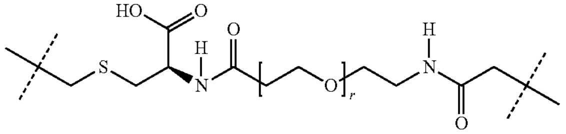

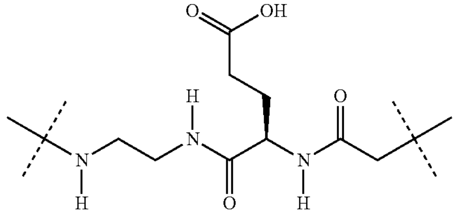

wherein r is a number from 0 to 8.

32. The conjugate according to claim 29, wherein the hydrocarbon chain is interrupted by one group selected from the group consisting of:

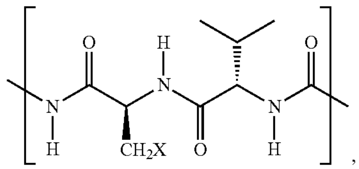

, and

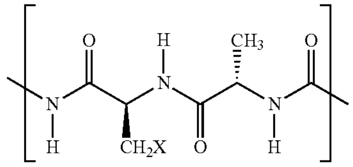

wherein X is —H or a $C_{1-10}$-alkyl group which may optionally be substituted by —NH—C(═O)—$NH_2$, —COOH, —OH, —$NH_2$, —NH—CN—$NH_2$, sulphone, sulphoxide or sulphonic acid.

33. The conjugate according to claim 6, wherein the linker has the formula below:

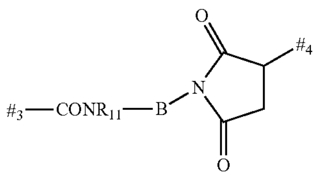

wherein

#3 represents the bond to the drug molecule,

#4 represents the bond to the antibody or antigen-binding fragment thereof, $R^{11}$ is —$NH_2$;
B is —[$(CH_2)_x$—$(X^4)_y$]W—$(CH_2)_z$—,
w is 0 to 20;
x is 0 to 5;
is 0 or 1;
z is 0 to 5; and
$X_4$ is —O—, —C(=O)—NH— or —NH—C(=O)—
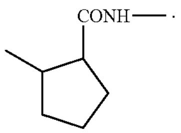
34. The conjugate according to claim 25, wherein the conjugate satisfies one of the following formulae:
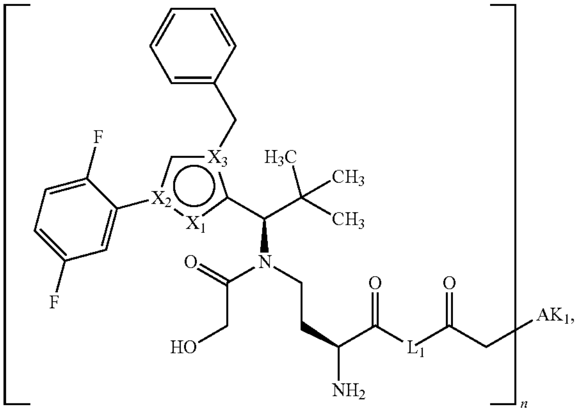
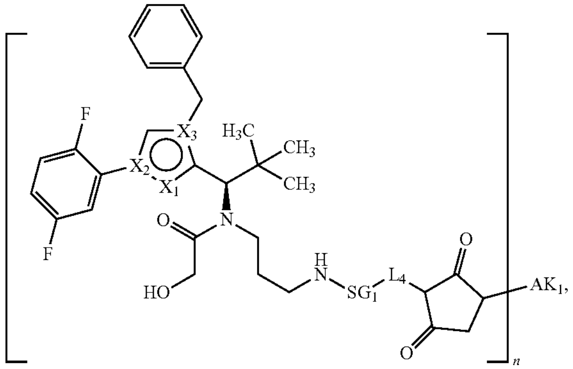
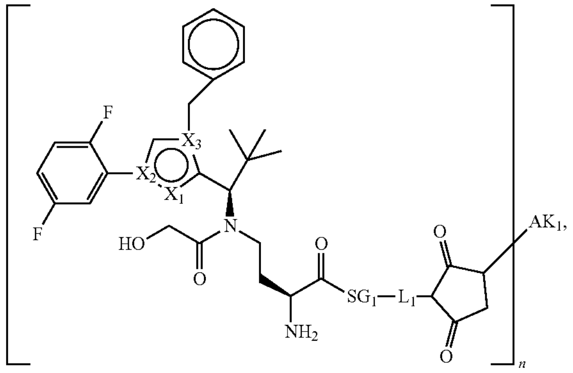
-continued
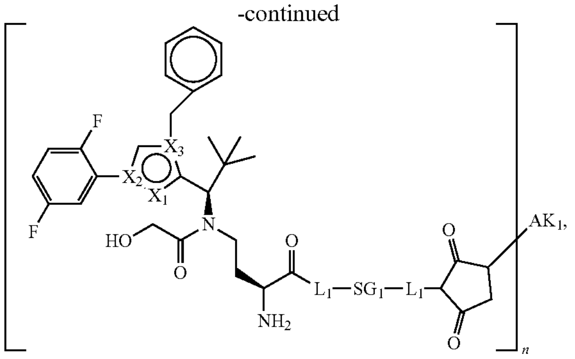
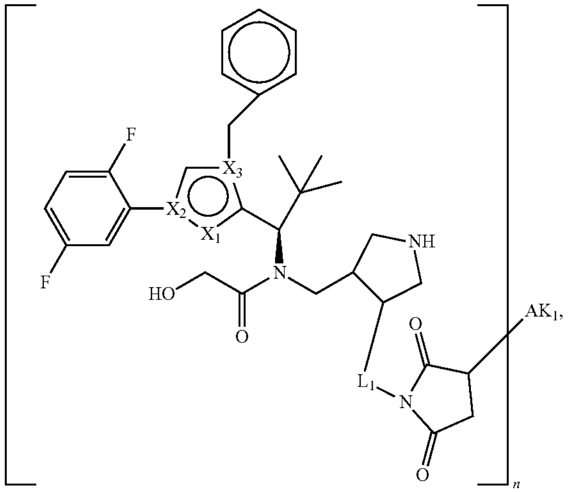
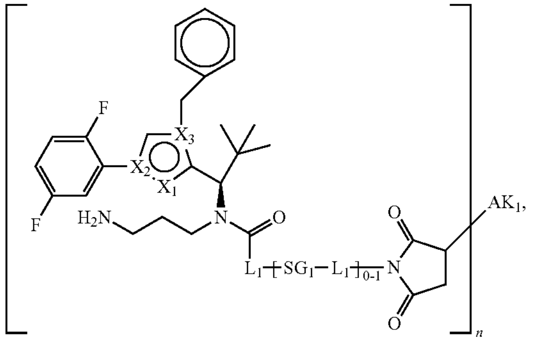
or
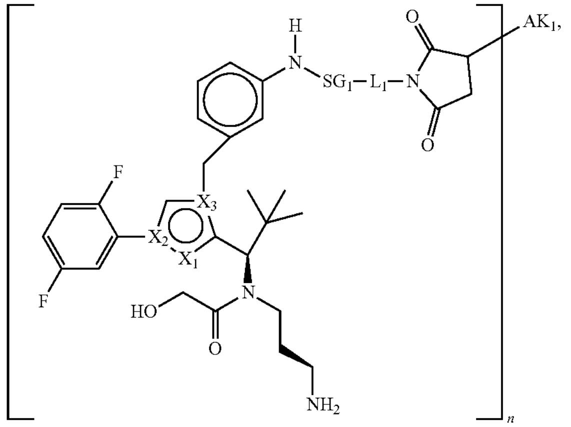
wherein
X1 is N, X2 is N and X3 is C; or
X1 is CH or CF, X2 is C and X3 is N; or
X1 is NH, X2 is C and X3 is C; or
X1 is CH, X2 is N and X3 is C;

$AK_1$ is an antibody or antigen-binding fragment thereof bound via a sulphur atom of the antibody or antigen-binding fragment thereof, n is a number from 1 to 20; and $L_1$ is an optionally branched hydrocarbyl group which has 1 to 70 carbon atoms, or is a straight-chain or branched hydrocarbyl chain having 1 to 100 carbon atoms composed of arylene groups and/or straight-chain and/or branched and/or cyclic alkylene groups, which may be singly or multiply interrupted by one or more of the groups —O—, —S—, —SO—, —$SO_2$—, —NH—, —C(═O)—, —C(═O)—NH—, —NH—C(═O)—, —NMe-, —NHNH—, —S(═O)$_2$—, —NHNH—, —C(═O)—NHNH— and a 5- to 10-membered aromatic or nonaromatic heterocycle having up to 4 heteroatoms selected from the group consisting of N, O and S, —S(═O)— or —S(═O)$_2$—, wherein the side chains, if present, may be substituted by —NH—C(═O)—$NH_2$, —COOH, —OH, —$NH_2$, —NH—CN—$NH_2$, sulphonamide, sulphone, sulphoxide or sulphonic acid, and SG1 is a 2-8 oligopeptide;

L4 is a single bond or a group —(C═O)$_y$-G4-, wherein y is 0 or 1, and wherein G4 is a straight-chain or branched hydrocarbyl chain having 1 to 100 carbon atoms composed of arylene groups and/or straight-chain and/or branched and/or cyclic alkylene groups, which may be singly or multiply interrupted by one or more of the groups —O—, —S—, —S(═O)—, —S(═O)$_2$—, —NH—, —C(═O)—, —NH—C(═O)—, —C(═O)NH—, —Nme-, —NHNH—, —S(═O)$_2$—NHNH—, —C(═O)—NHNH— and a 5- to 10-membered aromatic or nonaromatic heterocycle having up to 4 heteroatoms selected from the group consisting of N, O and S, —S(═O)— or —S(═O)$_2$—, wherein the side chains, if present, may be substituted by —NH—C(═O)—$NH_2$, —COOH, —OH, —$NH_2$, —NH—CN—$NH_2$, sulphonamide, sulphone, sulphoxide or sulphonic acid;

wherein the hydrogen atom in position $R^4$ of formula IIa (i.e. in the —$NH_2$ group) is replaced by legumain-cleavable group of the formula $R^{21}$—(C═O)$_{(0-1)}$—(P3)$_{(0-2)}$-P2—NH—CH($CH_2$C(═O)—$NH_2$)—C(═O)—, wherein $R^{21}$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroaryl-alkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —N(alkyl)$_2$, —NH—C(═O)-alkyl, —N(alkyl)-C(═O)-alkyl, —$SO_3$H, —S(═O)$_2NH_2$, —S(═O)$_2$—N(alkyl)$_2$, —COOH, —C(═O)—$NH_2$, —C(═O)—N(alkyl)$_2$, or —OH, —H or an —$O_x$—($CH_2CH_2O$)$_v$—$R^{22}$ group, wherein x is 0 or 1, wherein v is a number from 1 to 20, and $R^{22}$ is —H, -alkyl, —$CH_2$—COOH, —$CH_2$—$CH_2$—COOH, or —$CH_2$—$CH_2$—$NH_2$;

P2 is an amino acid selected from the group consisting of Gly, Pro, Ala, Val, Leu, Ile, Met, Phe, Tyr, Trp, Ser, Thr, Cys, Asn, Gln, Asp, Glu, Lys, Arg and His or one of the respective N-alkyl amino acids;

P3 is an amino acid selected from the group consisting of Gly, Pro, Ala, Val, Leu, Ile, Met, Phe, Tyr, Trp, Ser, Thr, Cys, Asn, Gln, Asp, Glu, Lys, Arg and His or one of the respective N-alkyl amino acids.

35. A conjugate of an antibody or antigen-binding fragment thereof with one or more drug molecules wherein the conjugate has one or both of the following formulae:

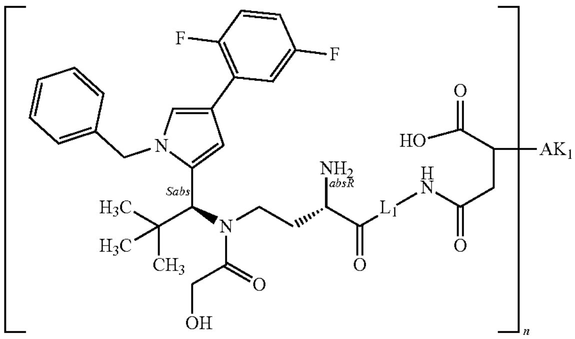

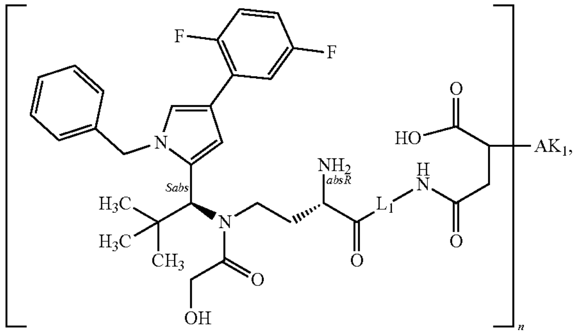

wherein $AK_1$ or $AK_{1A}$ is an antibody or antigen-binding fragment thereof bound via a sulphur atom of the antibody or antigen-binding fragment thereof, n is a number from 1 to 20; and $L_1$ is a straight-chain or branched hydrocarbyl chain having 1 to 100 carbon atoms composed of arylene groups and/or straight-chain and/or branched and/or cyclic alkylene groups, which may be singly or multiply interrupted by one or more of the groups —O—, —S—, —S(═O)—, —S(═O)$_2$—, —NH—, —C(═O)—, —C(═O)—NH—, —NH—C(═O)—, —NMe-, —NHNH—, —S(═O)$_2$—NHNH—, —C(═O)—NHNH— and a 5- to 10-membered aromatic or nonaromatic heterocycle having up to 4 heteroatoms selected from the group consisting of N, O and S, —S(═O)— or —S(═O)$_2$—, wherein the side chains, if present, may be substituted by —NH—C(═O)—$NH_2$, —COOH, —OH, —$NH_2$, —NH—CN—$NH_2$, sulphonamide, sulphone, sulphoxide or sulphonic acid, wherein the hydrogen atom in position $R^4$ of formula IIa (i.e. in the —$NH_2$ group) is replaced by a legumain-cleavable group of the formula $R^{21}$—(C═O)$_{(0-1)}$—(P3)$_{(0-2)}$-P2—NH—CH($CH_2$—C(═O)—$NH_2$)—C(═O)—, wherein $R^{21}$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —N(alkyl)$_2$, —NH—C(═O)-alkyl, —N(alkyl)-C(═O)-alkyl, —$SO_3H$, —S(═O)$_2$—$NH_2$, —S(═O)$_2$—N(alkyl)$_2$, —COOH, —C(═O)—$NH_2$, —C(═O)—N(alkyl)$_2$, or —OH, —H or an —$O_x$—$(CH_2CH_2O)_v$—$R^{22}$ group, wherein x is 0 or 1, wherein v is a number from 1 to 20, and $R^{22}$ is —H, -alkyl, —$CH_2$—COOH, —$CH_2$—$CH_2$—COOH or —$CH_2$—$CH_2$—$NH_2$; P2 is an amino acid selected from the group consisting of Gly, Pro, Ala, Val, Leu, Ile, Met, Phe, Tyr, Trp, Ser, Thr, Cys, Asn, Gln, Asp, Glu, Lys, Arg and His or one of the respective N-alkyl amino acids; and P3 is an amino acid selected from the group consisting of Gly, Pro, Ala, Val, Leu, Ile, Met, Phe, Tyr, Trp, Ser, Thr, Cys, Asn, Gln, Asp, Glu, Lys, Arg and His or one of the respective N-alkyl amino acids.

36. The conjugate according to claim 1 wherein the linker -L- is attached to a cysteine side chain or a cysteine residue and has the formula below:

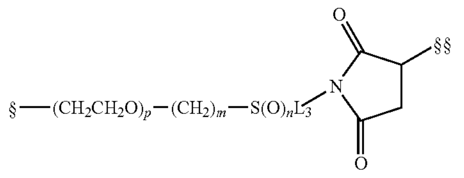

wherein

§ represents the bond to the drug molecule and

§§ represents the bond to the antibody or antigen-binding fragment thereof, m is 0, 1, 2, or 3;

n is 0, 1 or 2;

p is 0 to 20; and

L3 is the group

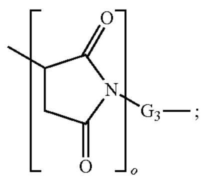

wherein o is 0 or 1; and

G3 is a straight-chain or branched hydrocarbyl chain having 1 to 100 carbon atoms composed of aryl groups and/or straight-chain and/or branched and/or cyclic alkyl groups, which may be singly or multiply interrupted by one or more of the groups —O—, —S—, —S(═O)—, —S(═O)$_2$—, —NH—, —C(═O)—, —NH—C(═O)—, —C(═O)—NH— and a 5- to 10-membered aromatic or nonaromatic heterocycle having up to 4 heteroatoms selected from the group consisting of N, O and S, —NMe-, —NHNH—, —S(═O)$_2$—NHNH—, —C(═O)—NHNH—, —S(═O)— and —S(═O)$_2$—, wherein the side chains, if present, may be substituted by —NH—C(═O)—$NH_2$, —COOH, —OH, -sulphone, sulphoxide or sulphonic acid.

37. The conjugate according to claim 36, wherein the linker -L- is attached to a cysteine side chain or a cysteine residue and has the formula below:

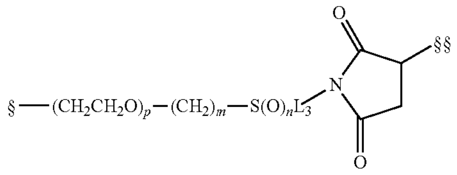

wherein

§ represents the bond to the drug molecule, and

§§ represents the bond to the antibody or antigen-binding fragment thereof, m is 1;

p is 0;

n is 0; and

L3 is the group

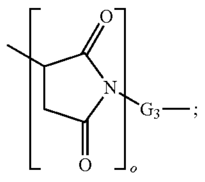

wherein o is 0 or 1; and

G3 is —$(CH_2CH_2O)_s(CH_2)_t(CONH)_u$ $CH_2CH_2O)_v$ $(CH_2)_w$—, wherein s, t, v and w each independently of one another is from 0 to 20 and u is 0 or 1.

38. The conjugate according to claim 1, wherein $R^2$ or $R^3$ is -L-#1.

39. The conjugate according to claim 38, wherein the conjugate has a formula selected from the group consisting of:

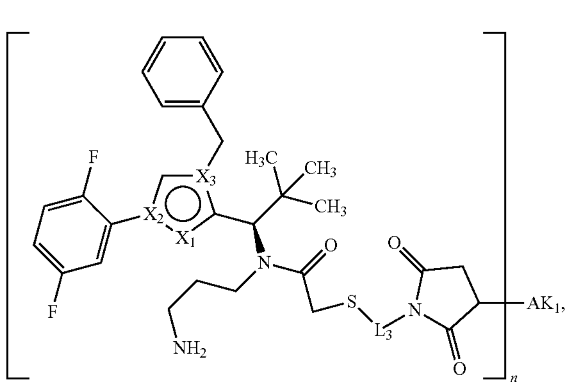

-continued

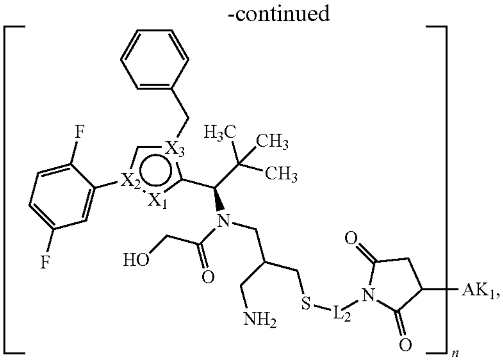

and

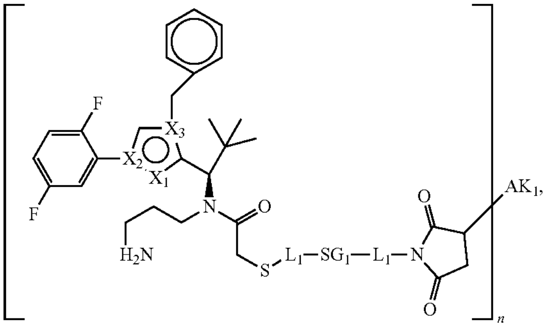

wherein $X_1$ is N, $X_2$ is N and $X_3$ is C; or $X_1$ is CH or CF, $X_2$ is C and $X_3$ is N; or $X_1$ is NH, $X_2$ is C and $X_3$ is C; or $X_1$ is CH, $X_2$ is N and $X_3$ is C;

$AK_1$ is an antibody or antigen-binding fragment thereof attached via a sulphur atom of the antibody or antigen-binding fragment thereof, n is a number from 1 to 20; and $L_1$ is a straight-chain or branched hydrocarbyl chain having 1 to 100 carbon atoms composed of arylene groups and/or straight-chain and/or branched and/or cyclic alkylene groups, which may be interrupted once or more than once by one or more of the —O—, —S—, —S(═O)—, —S(═O)$_2$—, —NH—, —C(═O)—, —C(═O)—NH—, —NH—C(═O)—, —NMe-, —NHNH—, —S(═O)$_2$—NHNH—, —C(═O)—NHNH— groups and a 5- to 10-membered aromatic or nonaromatic heterocycle having up to 4 heteroatoms selected from the group consisting of N, O and S, —S(═O)— or —S(═O)$_2$—, wherein the side chains, if present, may be substituted by —NH—C(═O)—NH$_2$, —COOH, —OH, —NH$_2$, —NH—CN—NH$_2$, sulphonamide, sulphone, sulphoxide or sulphonic acid, L2 and L3 is a straight-chain or branched hydrocarbyl chain having 1 to 100 carbon atoms composed of arylene groups and/or straight-chain and/or branched and/or cyclic alkylene groups, which may be singly or multiply interrupted by one or more of the groups —O—, —S—, —S(═O)—, —S(═O)$_2$—, —NH—, —C(═O)—, —NMe-, —NHNH—, —S(═O)$_2$—NHNH—, —NH—C(═O)—, —C(═O)—NH—, —C(═O)—NHNH— and a 5- to 10-membered aromatic or nonaromatic heterocycle having up to 4 heteroatoms selected from the group consisting of N, O and S, —S(═O)— or —S(═O)$_2$—, wherein the side chains, if present, may be substituted by —NH—C(═O)—NH$_2$, —COOH, —OH, —NH$_2$, —NH—CN—NH$_2$, sulphonamide, sulphone, sulphoxide or sulphonic acid, and wherein the conjugate satisfies one of the following formulae, wherein $SG_1$ is a cleavable group, $AK_1$ is an antibody or antigen-binding fragment thereof joined via cysteine.

40. The conjugate according to claim 23, wherein the anti-TWEAKR antibody is an agonistic antibody.

41. The conjugate according to claim 23, wherein the anti-TWEAKR antibody or the antigen-binding fragment thereof comprises:

a variable heavy chain comprising:

a. a CDR1 of the heavy chain encoded by an amino acid sequence comprising the formula PYPMX (SEQ ID NO: 171), wherein X is I or M;

b. a CDR2 of the heavy chain encoded by an amino acid sequence comprising the formula YISPSGGXTHYADSVKG (SEQ ID NO: 172), wherein X is S or K; and c. a CDR3 of the heavy chain encoded by an amino acid sequence comprising the formula GGDTYFDYFDY (SEQ ID NO: 173);

and a variable light chain comprising:

d. a CDR1 of the light chain encoded by an amino acid sequence comprising the formula RASQSISXYLN (SEQ ID NO: 174), wherein X is G or S;

e. a CDR2 of the light chain encoded by an amino acid sequence comprising the formula XASSLQS (SEQ ID NO: 175), wherein X is Q, A or N; and f. a CDR3 of the light chain encoded by an amino acid sequence comprising the formula QQSYXXPXIT (SEQ ID NO: 176), wherein X at position 5 is T or S, X at position 6 is T or S and X at position 8 is G or F.

42. The conjugate according to claim 23, wherein the anti-TWEAKR antibody or the antigen-binding fragment thereof comprises:

a. a variable sequence of the heavy chain, as shown in SEQ ID NO:10, and also a variable sequence of the light chain, as shown in SEQ ID NO:9, or b. a variable sequence of the heavy chain, as shown in SEQ ID NO:20, and also a variable sequence of the light chain, as shown in SEQ ID NO:19, or c. a variable sequence of the heavy chain, as shown in SEQ ID NO:30, and also a variable sequence of the light chain, as shown in SEQ ID NO:29, or d. a variable sequence of the heavy chain, as shown in SEQ ID NO:40, and also a variable sequence of the light chain, as shown in SEQ ID NO:39, or e. a variable sequence of the heavy chain, as shown in SEQ ID NO:50, and also a variable sequence of the light chain, as shown in SEQ ID NO:49, or f. a variable sequence of the heavy chain, as shown in SEQ ID NO:60, and also a variable sequence of the light chain, as shown in SEQ ID NO:59, or g. a variable sequence of the heavy chain, as shown in SEQ ID NO:70, and also a variable sequence of the light chain, as shown in SEQ ID NO:69, or h. a variable sequence of the heavy chain, as shown in SEQ ID NO:80, and also a variable sequence of the light chain, as shown in SEQ ID NO:79, or i. a variable sequence of the heavy chain, as shown in SEQ ID NO:90, and also a variable sequence of the light chain, as shown in SEQ ID NO:89, or j. a variable sequence of the heavy chain, as shown in SEQ ID NO:100, and also a variable sequence of the light chain, as shown in SEQ ID NO:99, or k. a variable sequence of the heavy chain, as shown in SEQ ID NO:110, and also a variable sequence of the light chain, as shown in SEQ ID NO:109, or l. a variable sequence of the heavy chain, as shown in SEQ ID NO:120, and also a variable sequence of the light chain, as shown in SEQ ID NO:119.

43. The conjugate according to claim 1, wherein the antibody is an IgG antibody.

44. The conjugate according to claim 23, wherein the anti-TWEAKR antibody comprises:

a. a sequence of the heavy chain as shown in SEQ ID NO:2, and a sequence of the light chain as shown in SEQ ID NO:1 or b. a sequence of the heavy chain as shown in SEQ ID NO: 12, and a sequence of the light chain as shown in SEQ ID NO:11 or c. a sequence of the heavy chain as shown in SEQ ID NO:22, and a sequence of the light chain as shown in SEQ ID NO:21 or d. a sequence of the heavy chain as shown in SEQ ID NO:32, and a sequence of the light chain as shown in SEQ ID NO:31 or e. a sequence of the heavy chain as shown in SEQ ID NO:42, and a sequence of the light chain as shown in SEQ ID NO 41 or f. a sequence of the heavy chain as shown in SEQ ID NO: 52, and a sequence of the light chain as shown in SEQ ID NO: 51 or g. a sequence of the heavy chain as shown in SEQ ID NO:62, and a sequence of the light chain as shown in SEQ ID NO:61 or h. a sequence of the heavy chain as shown in SEQ ID NO:72, and a sequence of the light chain as shown in SEQ ID NO:71 or i. a sequence of the heavy chain as shown in SEQ ID NO: 82, and a sequence of the light chain as shown in SEQ ID NO: 81 or j. a sequence of the heavy chain as shown in SEQ ID NO: 92, and a sequence of the light chain as shown in SEQ ID NO: 91 or k. a sequence of the heavy chain as shown in SEQ ID NO:102, and a sequence of the light chain as shown in SEQ ID NO:101 or l. a sequence of the heavy chain as shown in SEQ ID NO: 112, and a sequence of the light chain as shown in SEQ ID NO:111.

45. The conjugate according to claim 1, wherein the conjugate has 1 to 10 drug molecules or prodrug molecules per antibody or antigen-binding fragment thereof.

46. The conjugate according to claim 1, wherein the conjugate is an antibody-prodrug conjugate having a formula selected from the group consisting of:

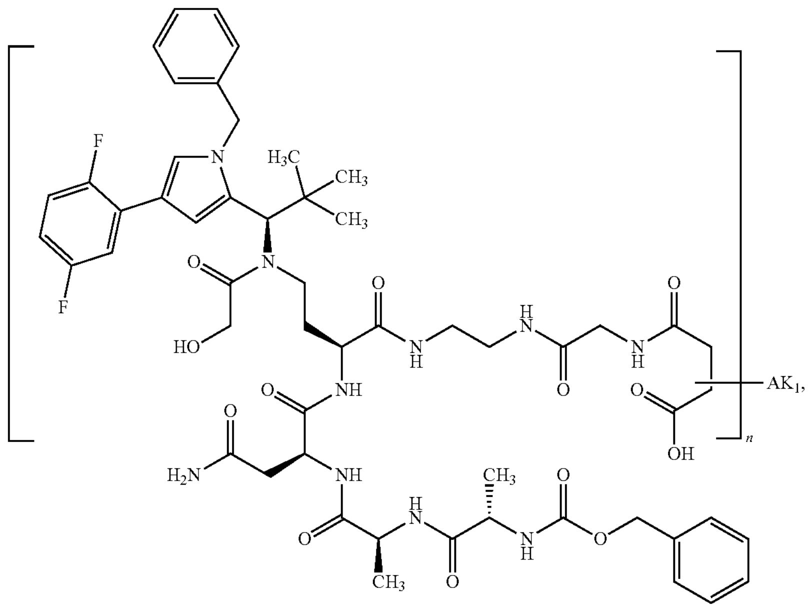

-continued
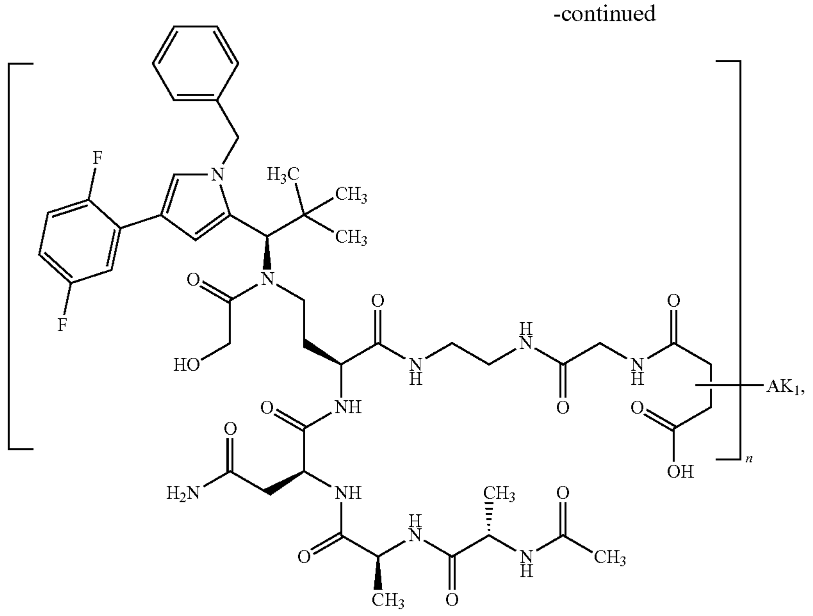
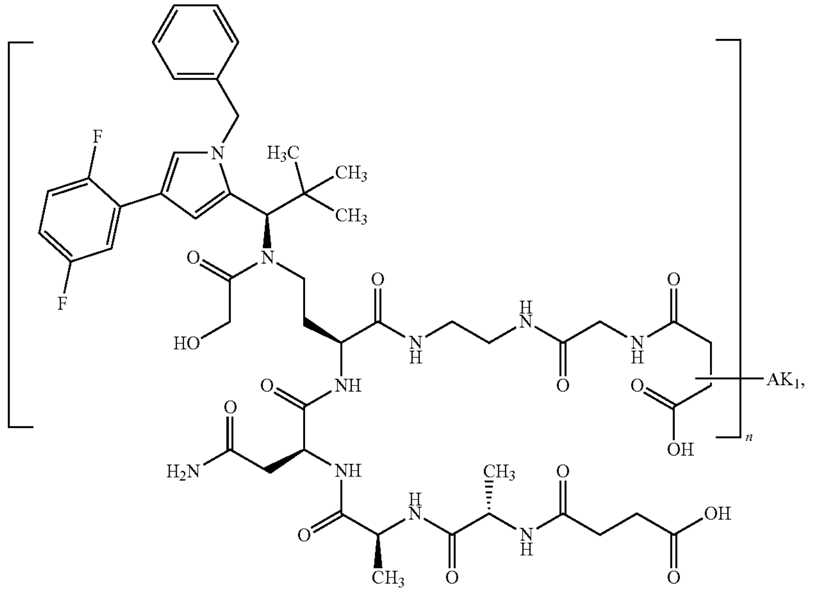

-continued
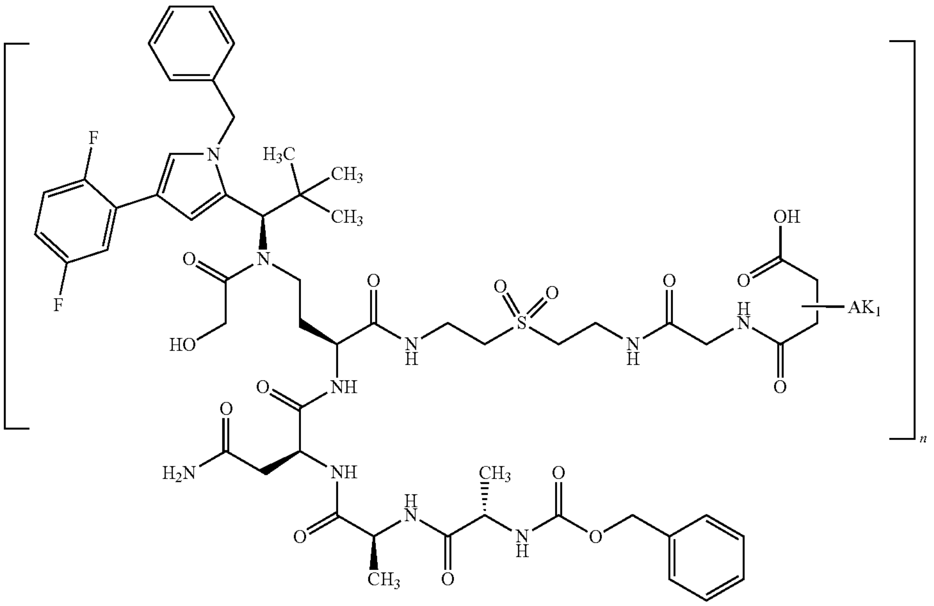
,
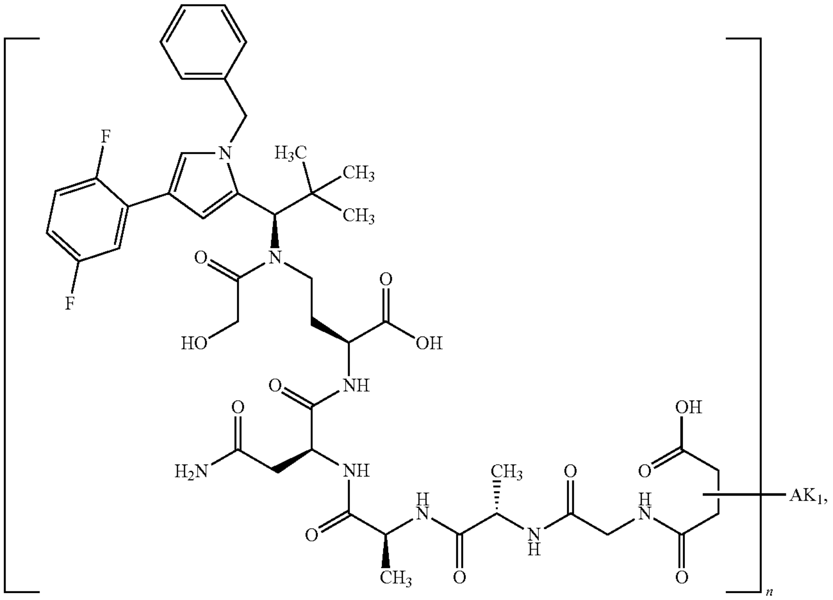

-continued
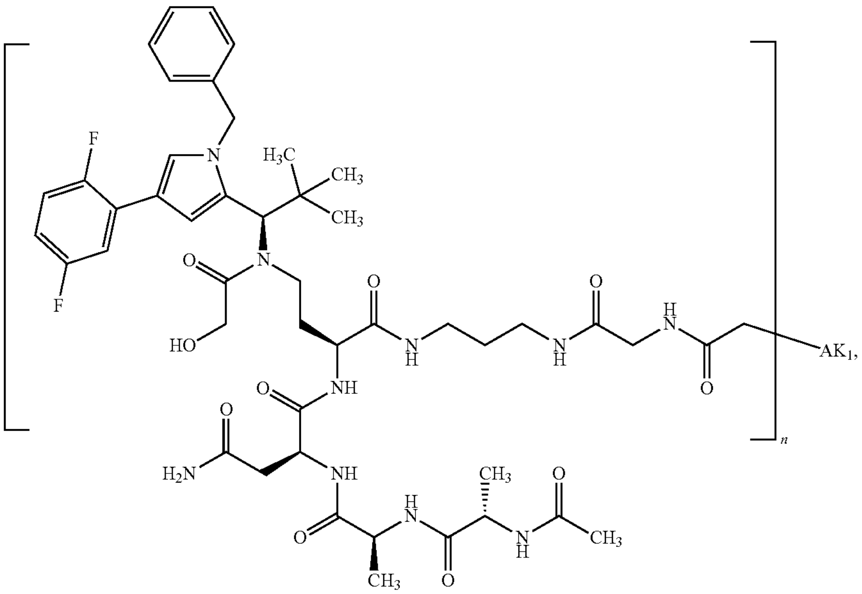
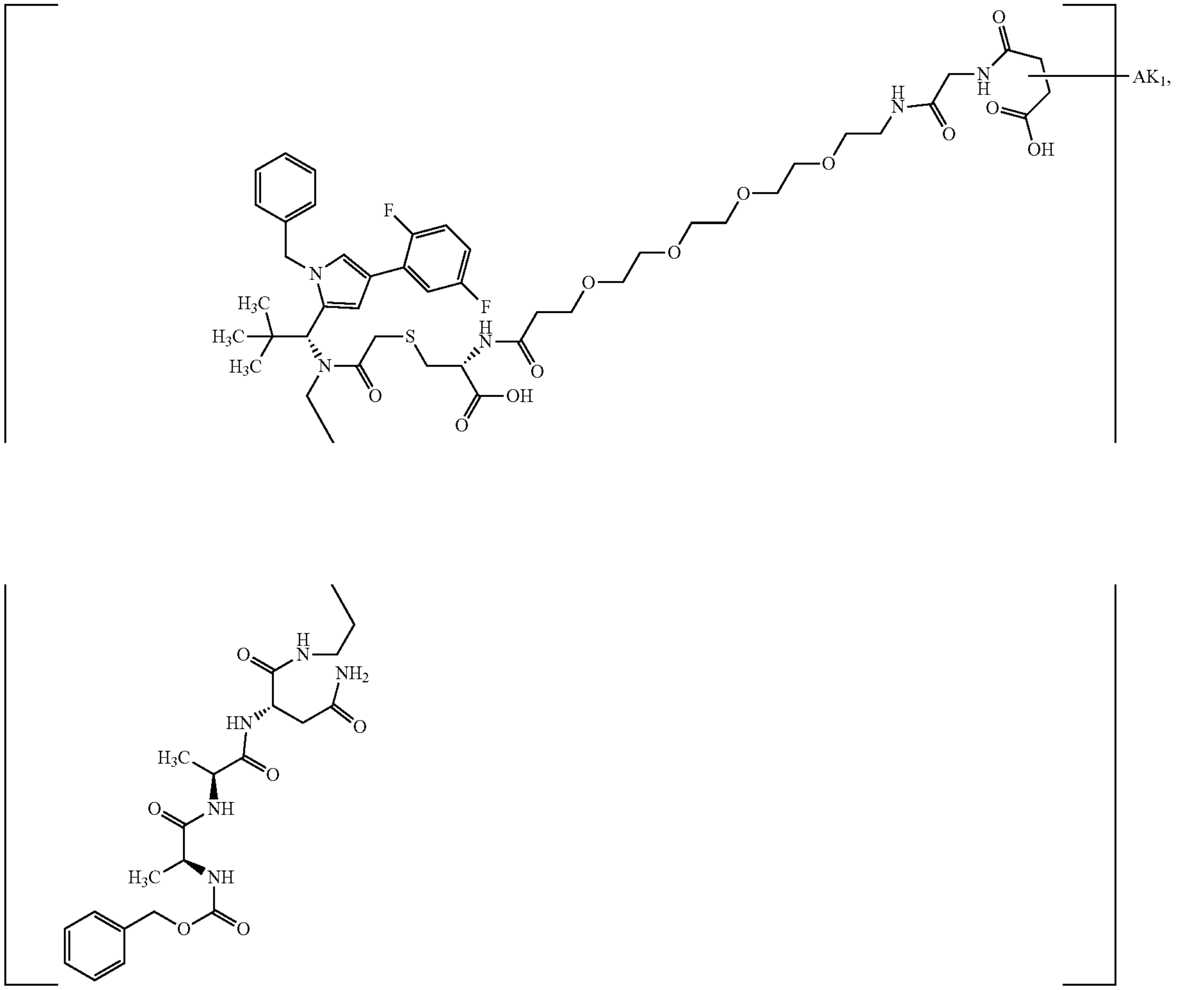

-continued
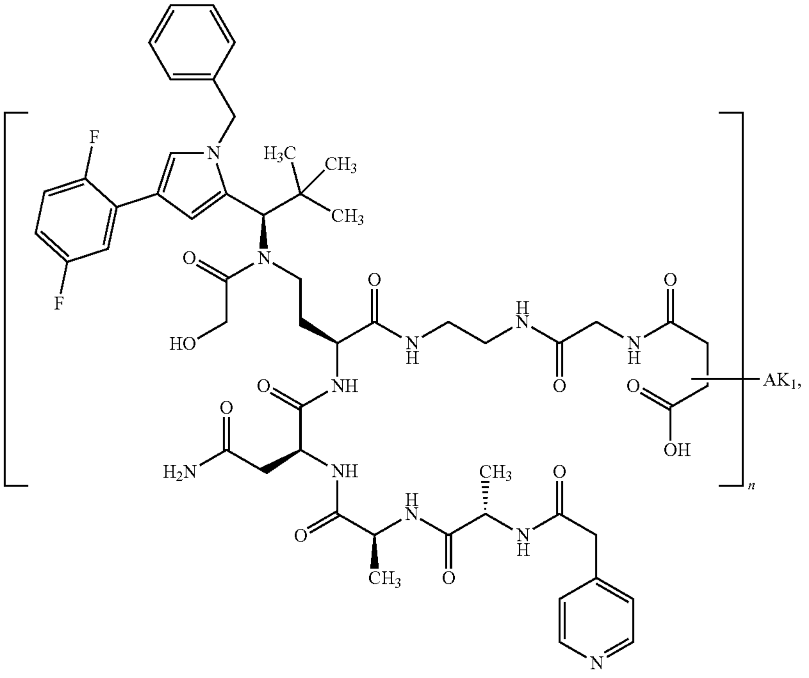
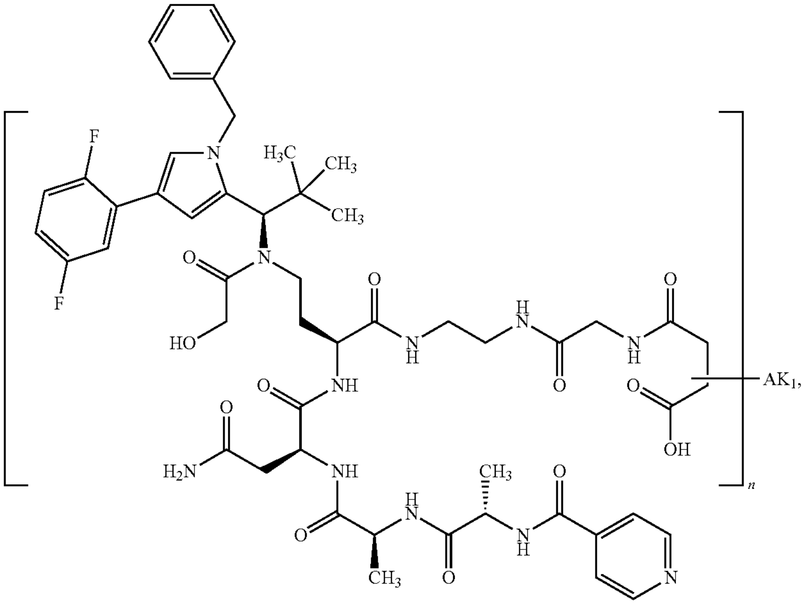

-continued
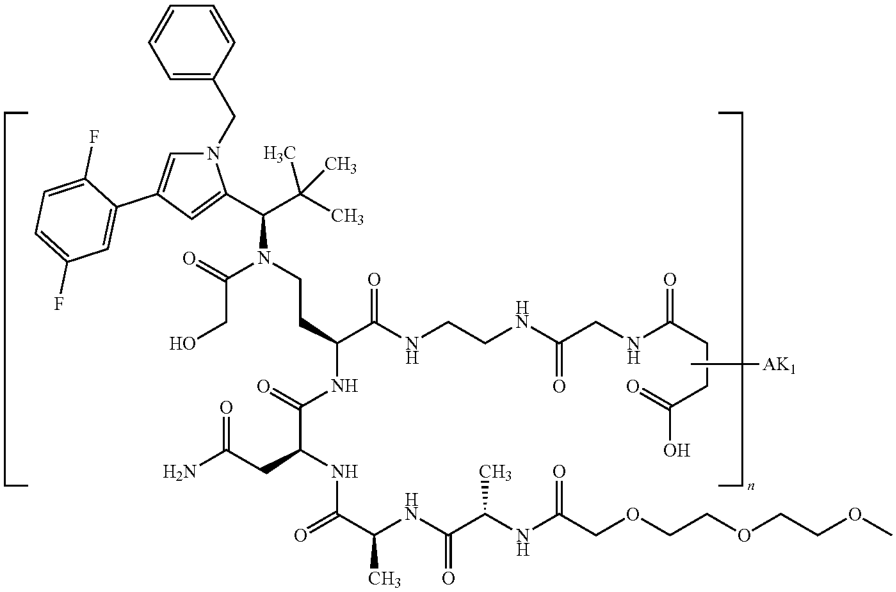
,
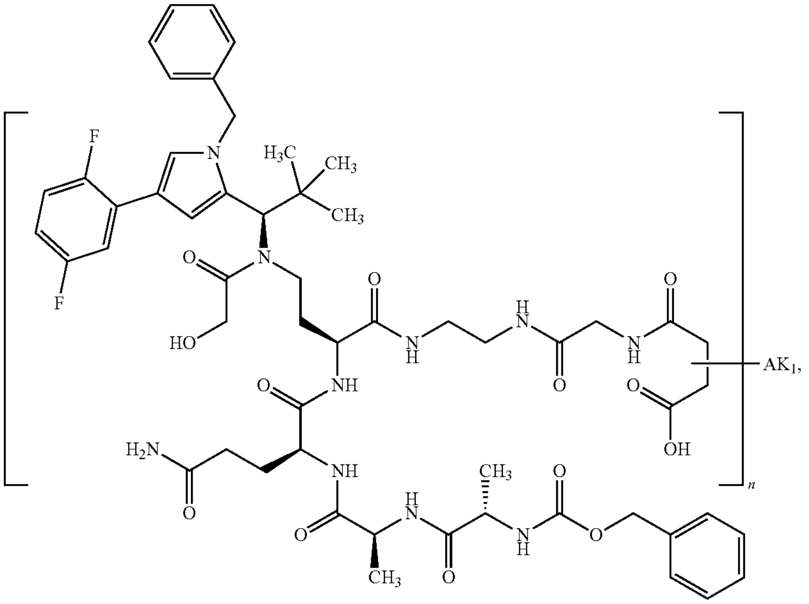

-continued
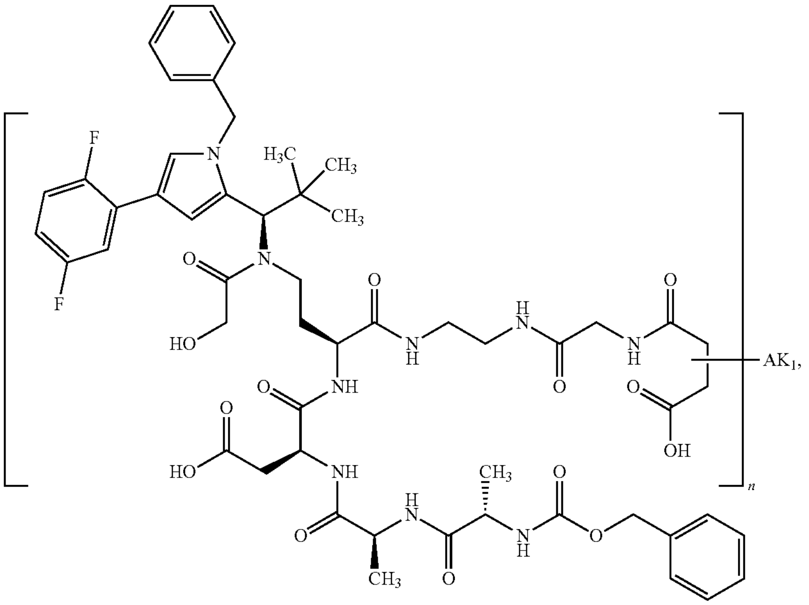
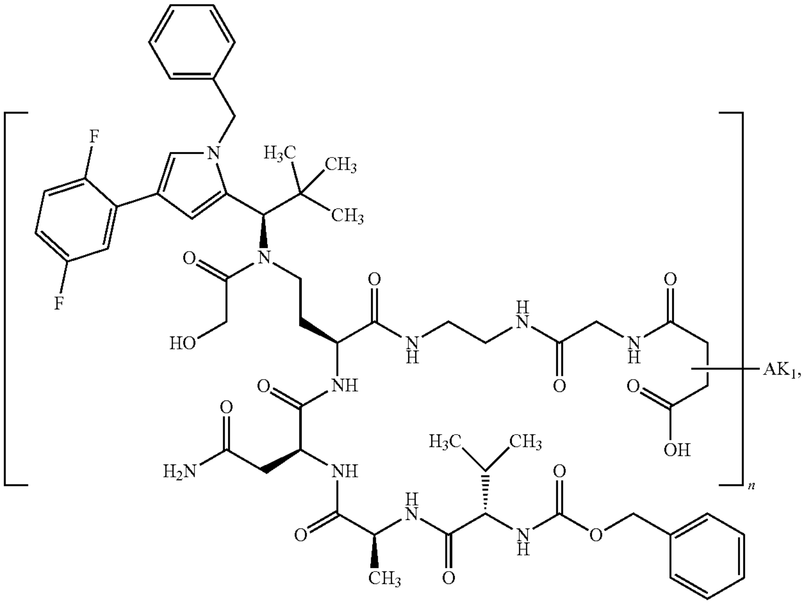

-continued
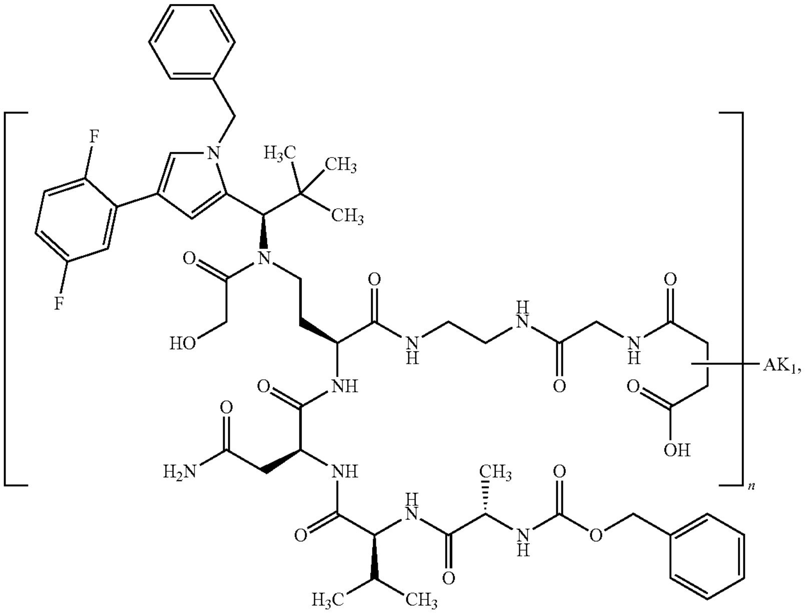
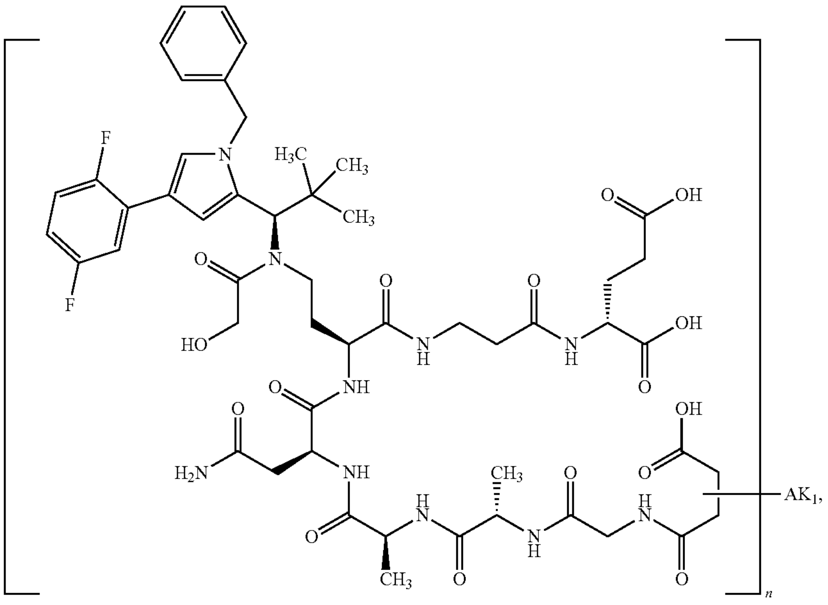

-continued
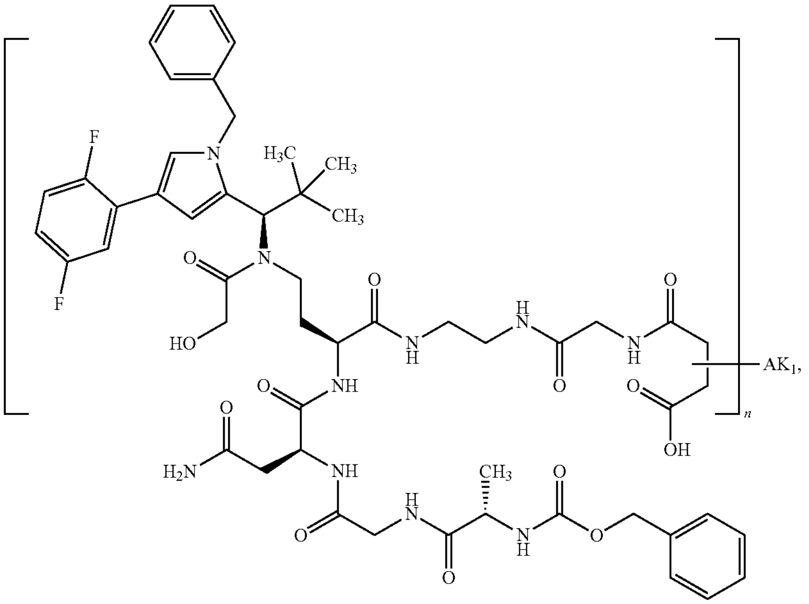
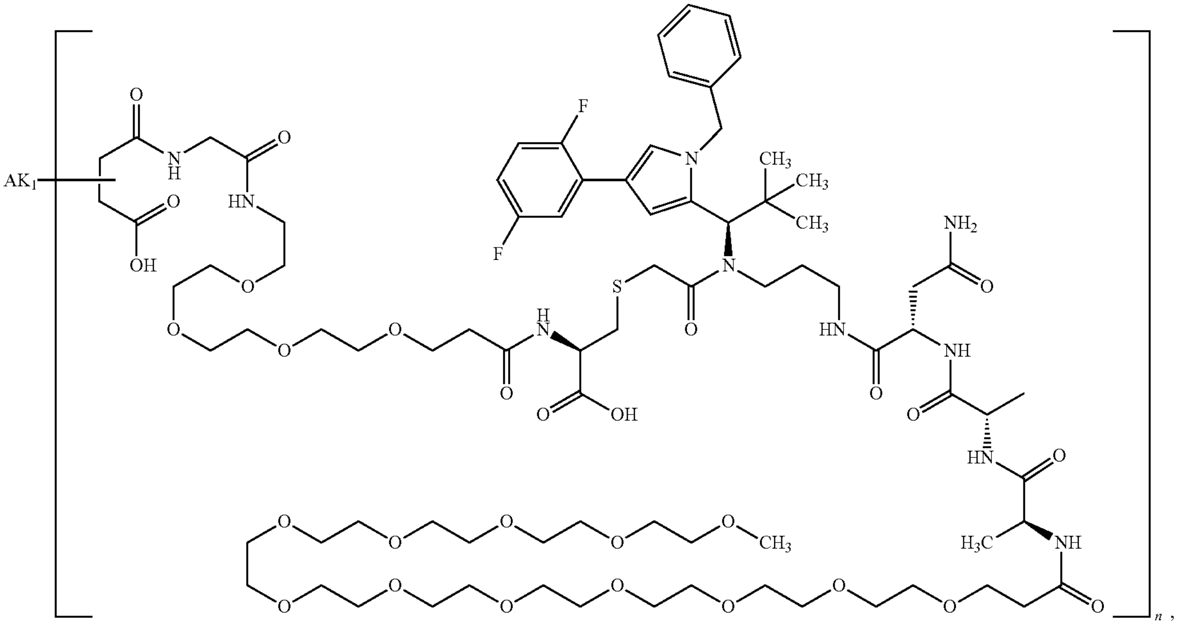

-continued
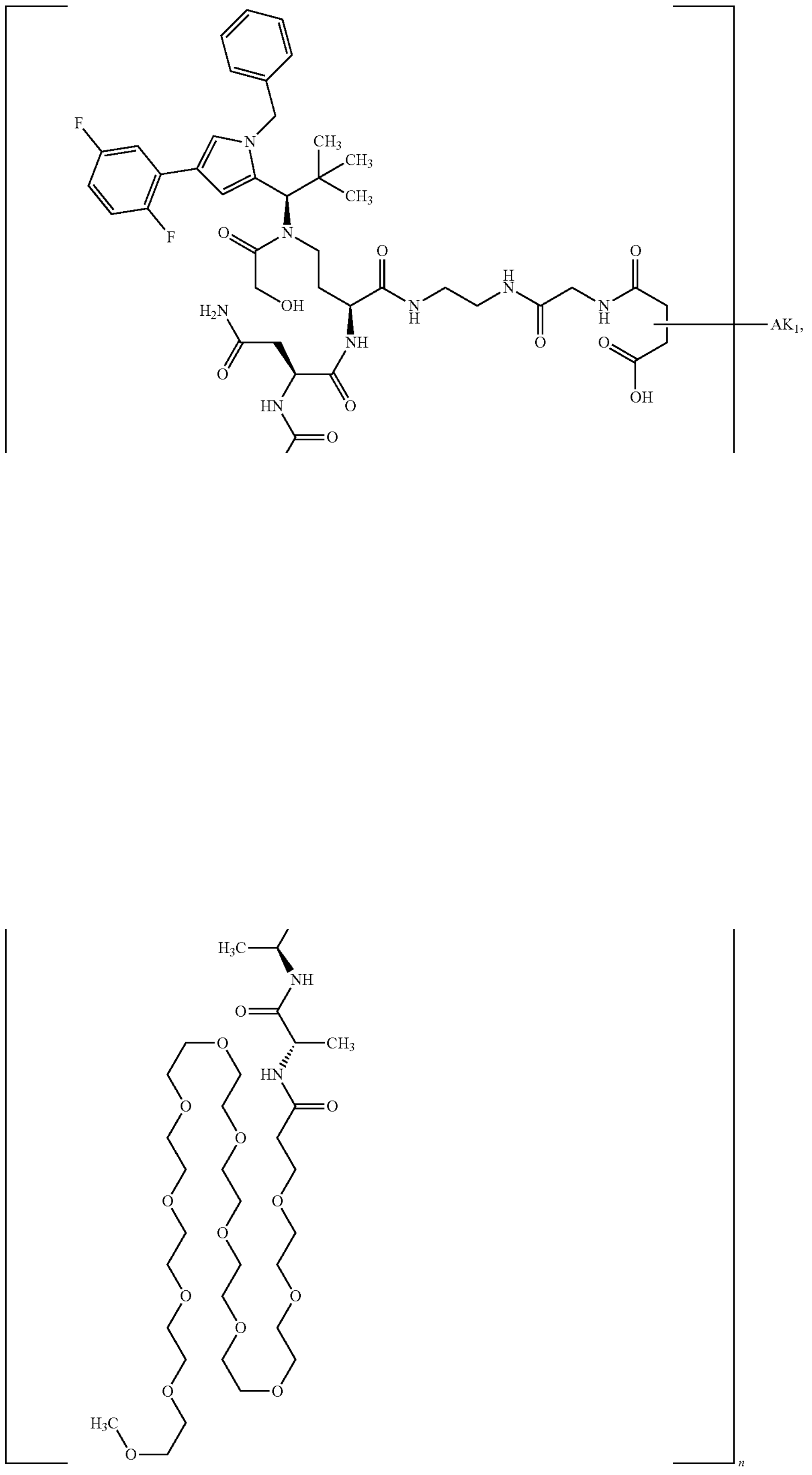

-continued
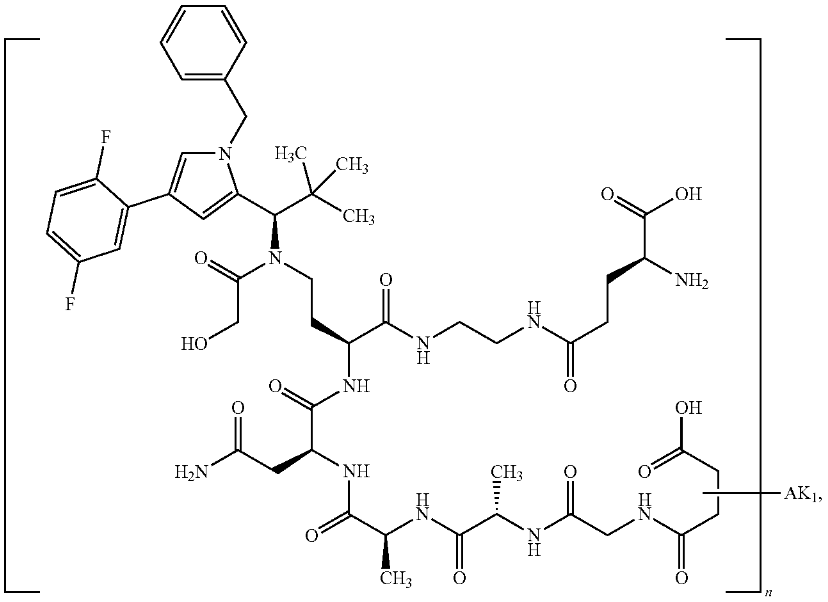
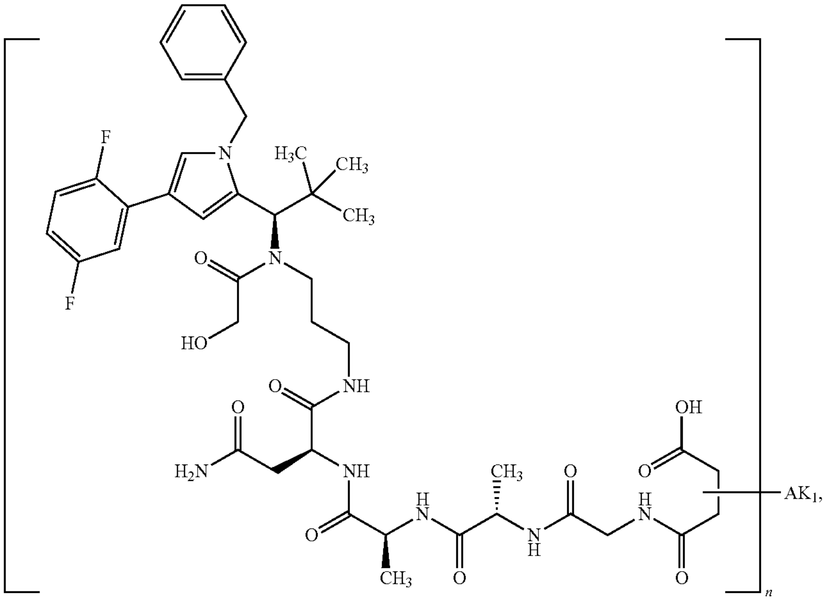

-continued
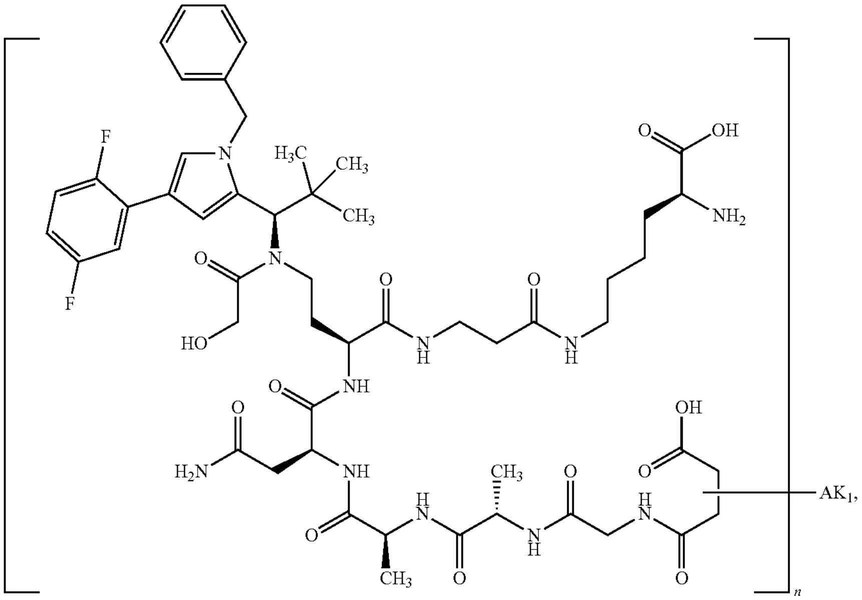
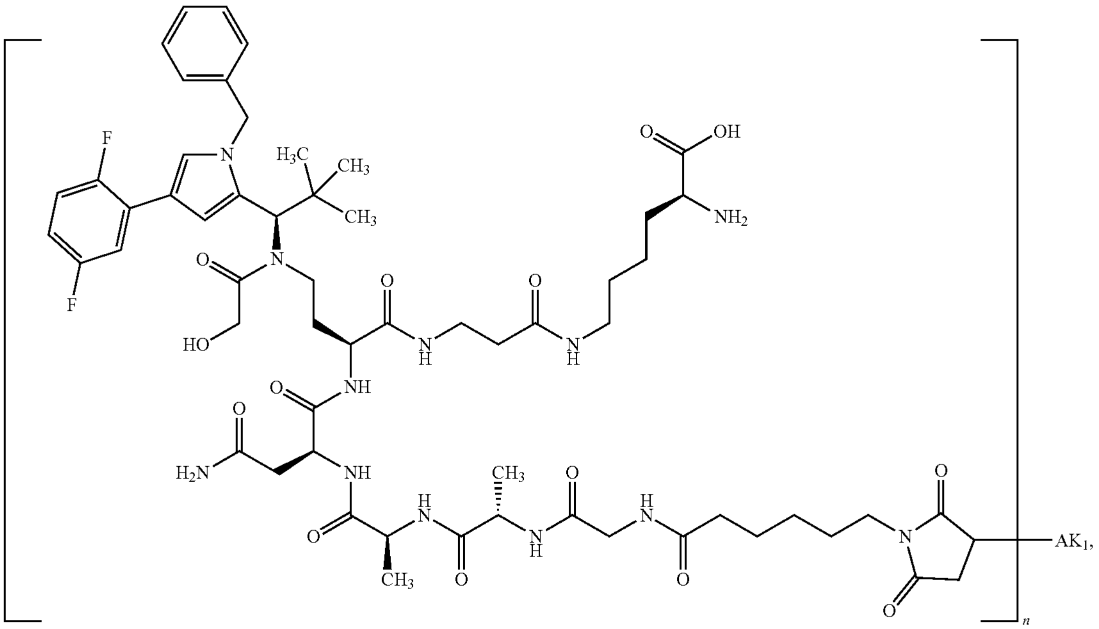

-continued
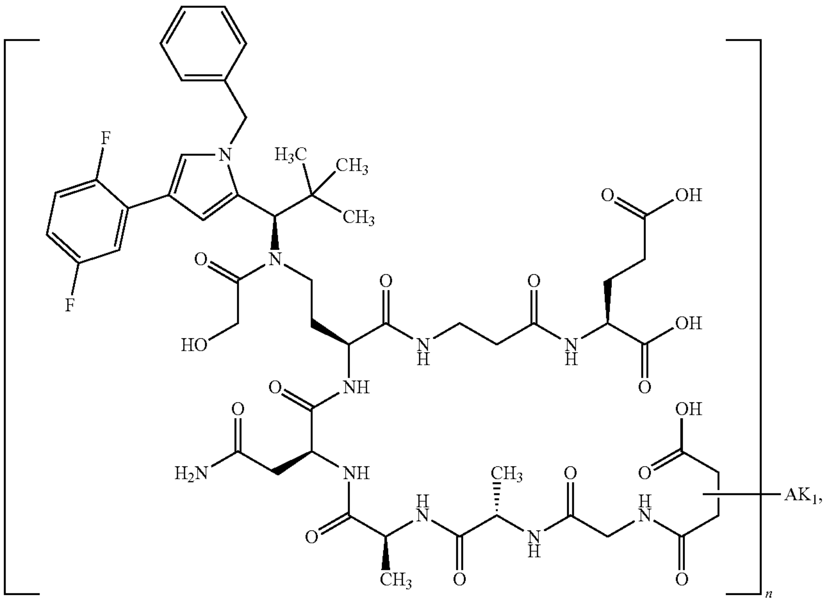
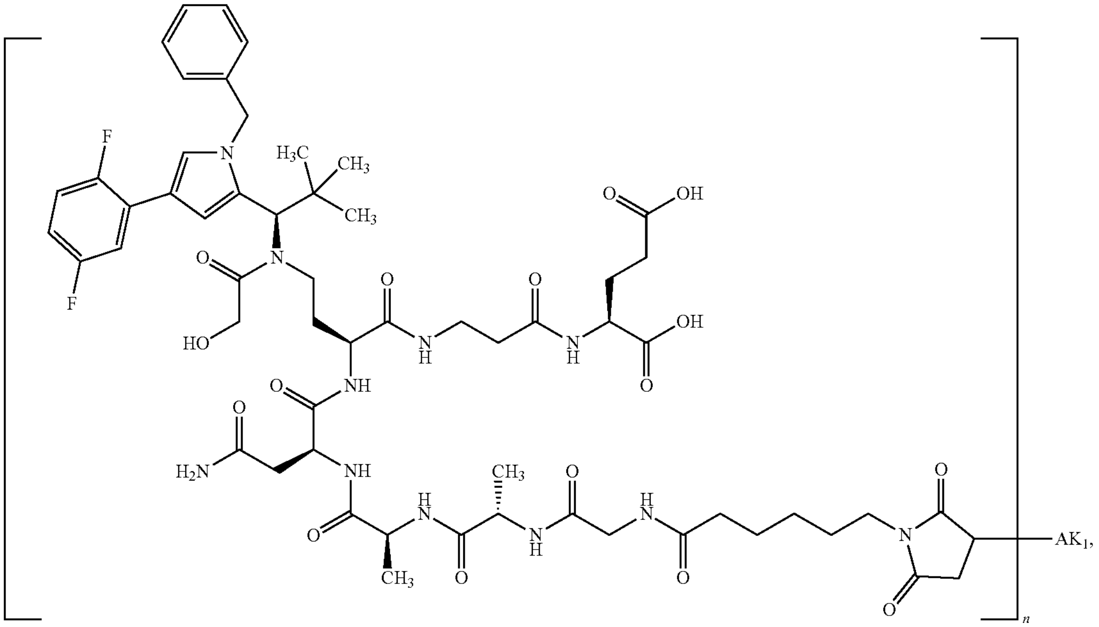

-continued
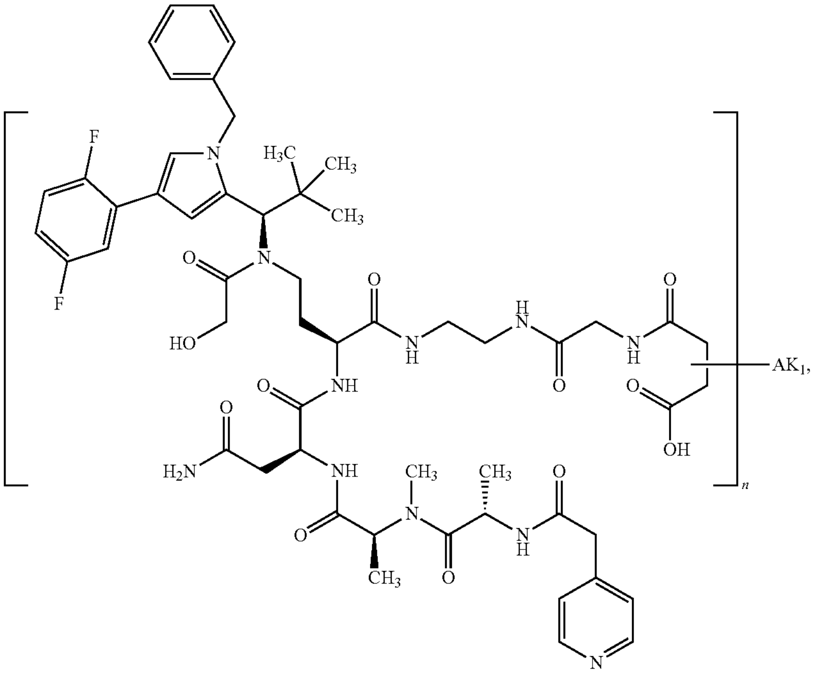
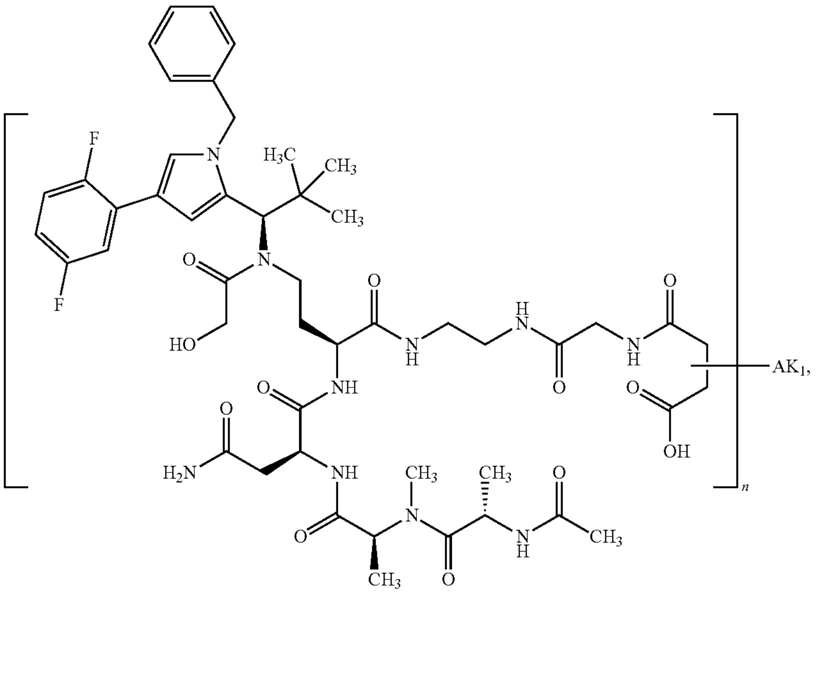

-continued
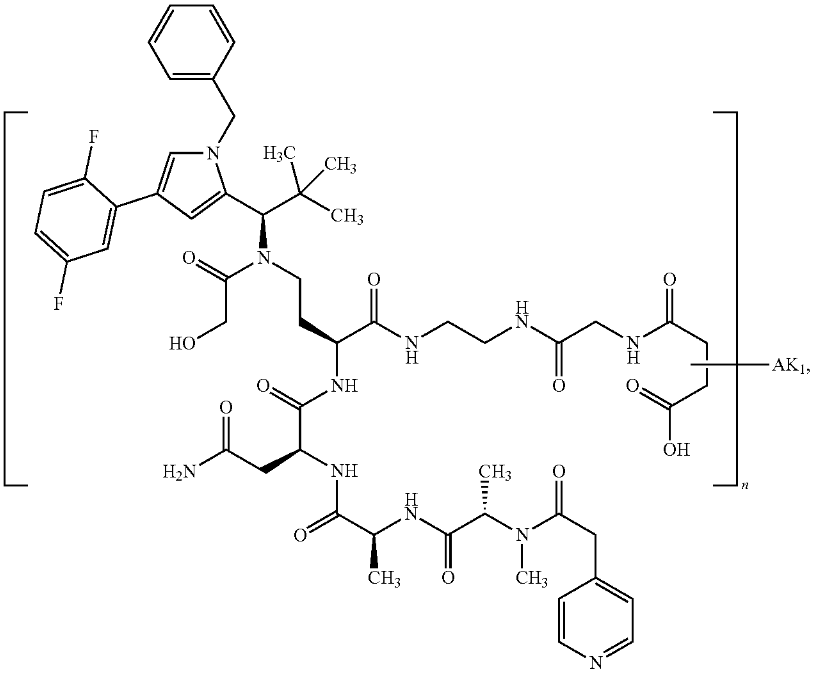
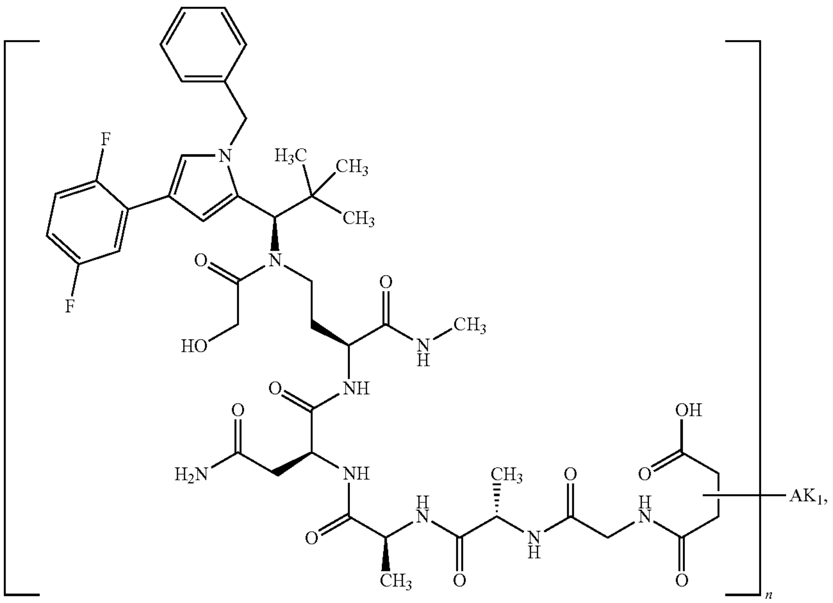

-continued
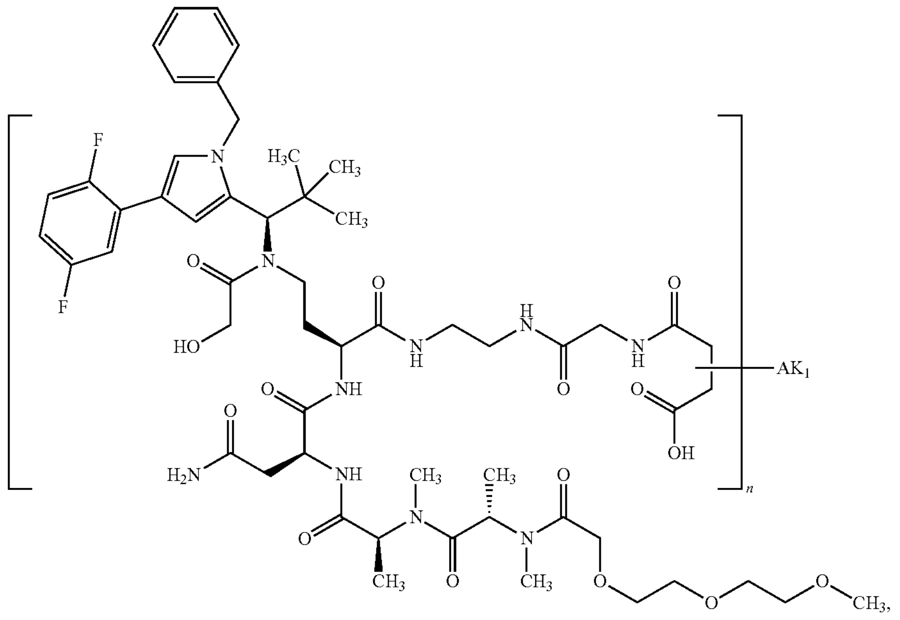
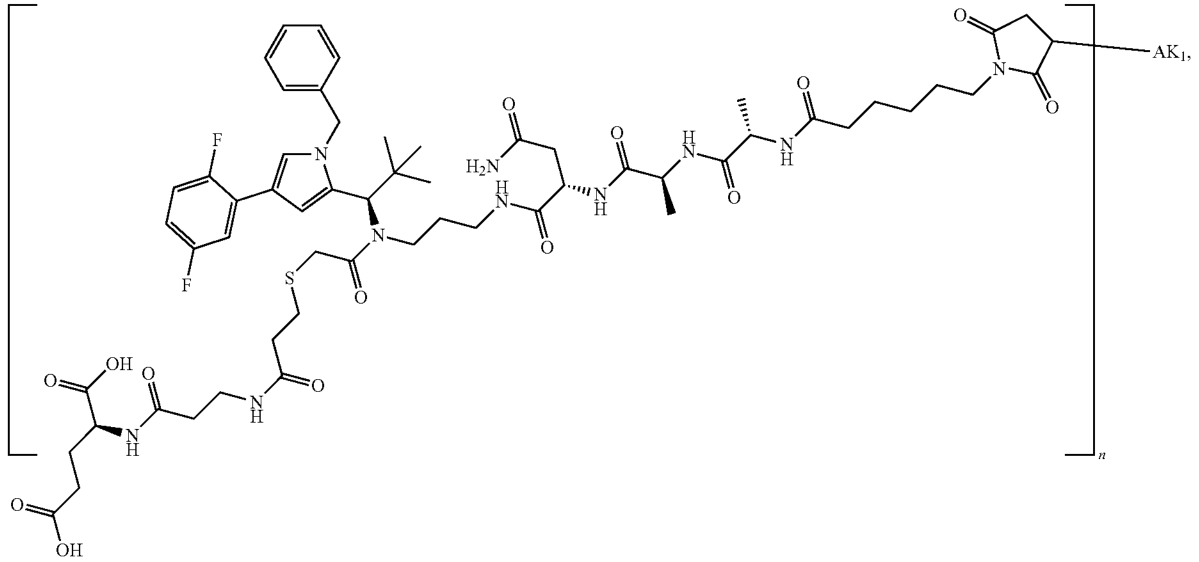

-continued
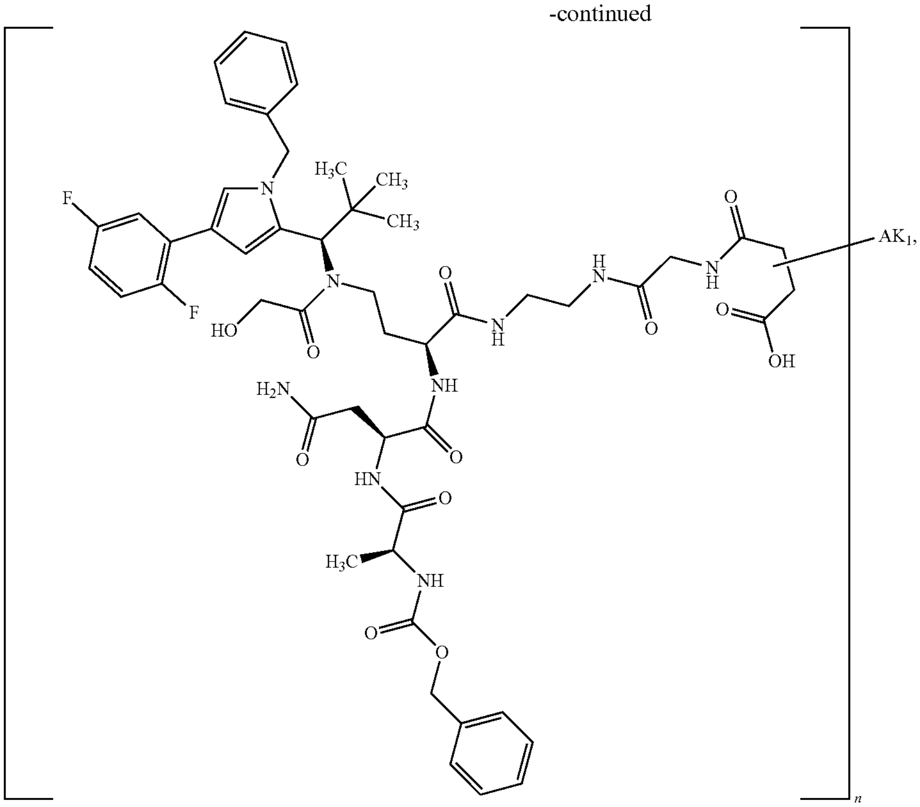
AK1,
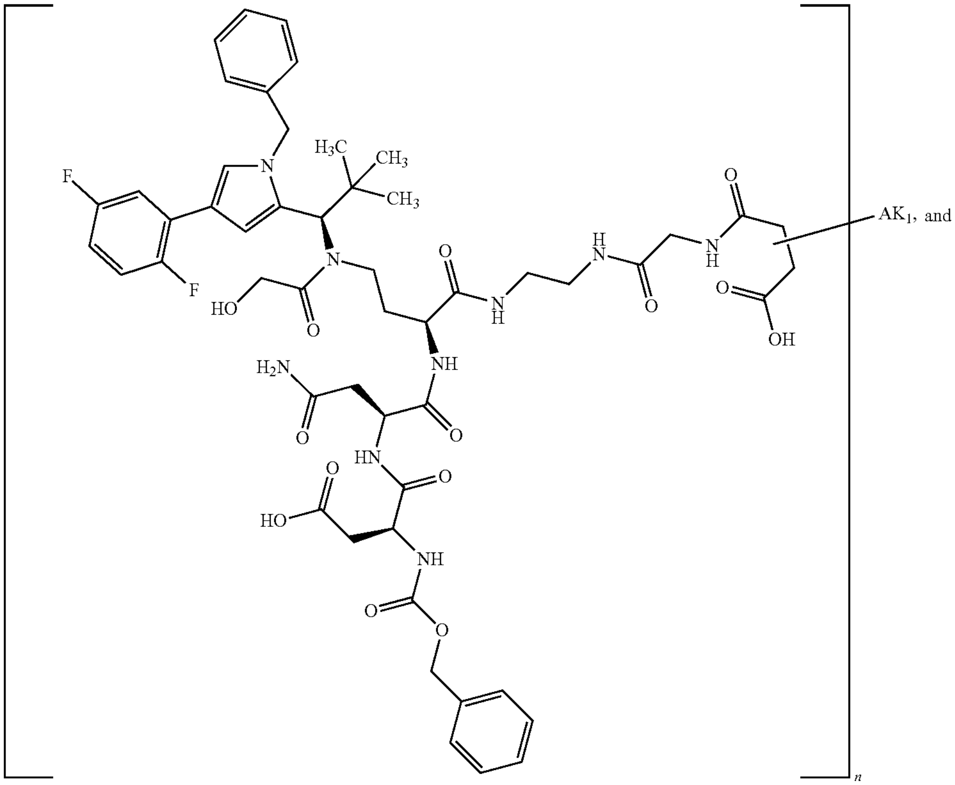
AK1, and

-continued

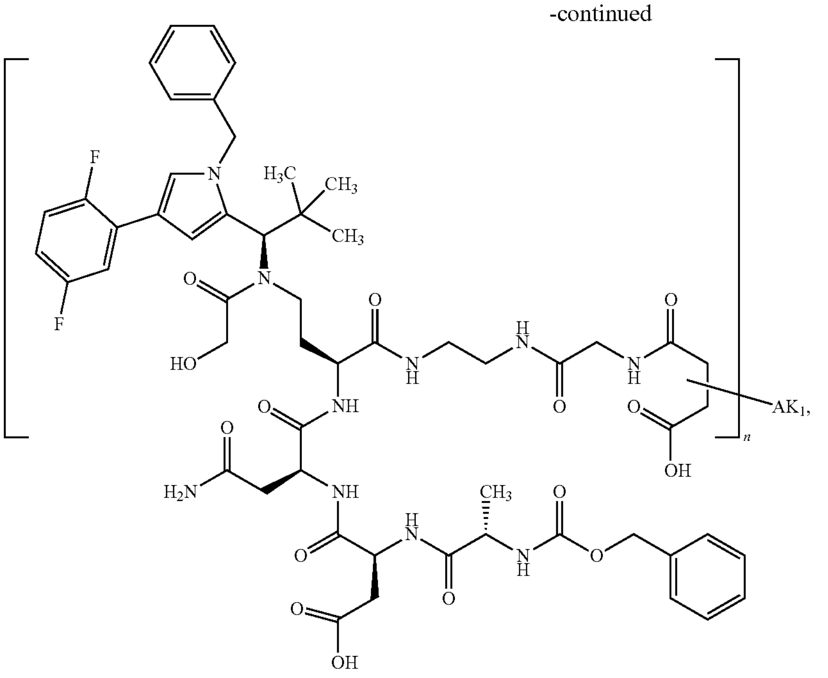

wherein n is a number from 1 to 20, and $AK_1$ is a cysteine-bonded antibody.

47. The conjugate according to claim 1, wherein the conjugate is an antibody-prodrug conjugate, wherein n is a number from 1 to 20, and AK1 is a cysteine-bonded antibody, wherein the antibody-prodrug conjugate, if it has a group

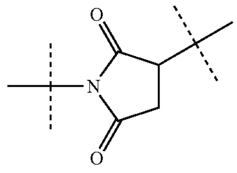

is bonded to the antibody, may also be present instead of this group at least partially in the form of the hydrolysed open-chain succinamides joined to the antibody.

48. A pharmaceutical composition comprising a conjugate according to claim 1 in combination with an inert non-toxic pharmaceutically suitable auxiliary.

49. A method for the treatment or prophylaxis of diseases, the method comprising administering to a patient in need thereof a conjugate according to claim 1.

50. A method for the treatment or prophylaxis of hyperproliferative or angiogenic disorders, the method comprising administering to a patient in need thereof a conjugate according to claim 1.

51. A kinesin spindle protein inhibitor prodrug of the following formula (III):

(III)

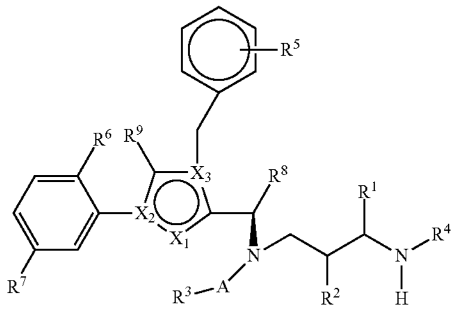

wherein $X_1$ is N, $X_2$ is N and $X_3$ is C; or $X_1$ is CH or CF, $X_2$ is C and $X_3$ is N; or $X_1$ is NH, $X_2$ is C and $X_3$ is C; or $X_1$ is CH, $X_2$ is N and $X_3$ is C;

$R^1$ is —H, -MOD or —$(CH_2)_{0-3}Z$, wherein Z is —H, —$NHY^3$, —$OY^3$, —$SY^3$, halogen, —C(═O)—$NY^1Y^2$ or —C(═O)—$OY^3$, wherein $Y^1$ and $Y^2$ are independently —H, —$NH_2$, —$(CH_2CH_2O)_{0-3}$—$(CH_2)_{0-3}Z'$ or —$CH(CH_2W)Z'$, wherein $Y^3$ is —H or —$(CH_2)_{0-3}Z'$, wherein Z' is —H, $NH_2$, $SO_3H$, —COOH, —NH—C(═O)—$CH_2$—$CH_2$—$CH(NH_2)COOH$ or —(C(═O)—NH—$CHY^4)_{1-3}COOH$, wherein W is —H or —OH, wherein $Y^4$ is straight-chain or branched $C_{1-6}$-alkyl which is optionally substituted by —NH—C(═O)—$NH_2$, or is aryl or benzyl which are optionally substituted by —$NH_2$;

$R^2$ is —H, -MOD, —C(═O)—$CHY^4$—$NHY^5$ or —$(CH_2)_{0-3}Z$, wherein Z is —H, halogen, —$OY^3$, —$SY^3$, —$NHY^3$, —C(═O)—$NY^1Y^2$ or —C(═O)—$OY^3$, wherein $Y^1$ and $Y^2$ are independently —H, —$NH_2$ or —$(CH_2)_{0-3}$Z', wherein $Y^3$ is —H or —$(CH_2)_{0-3}$Z', wherein Z' is —H, —$SO_3H$, —$NH_2$ or —COOH;

wherein $Y^4$ is straight-chain or branched $C_{1-6}$-alkyl which is optionally substituted by —NH—C(═O)—$NH_2$, or is aryl or benzyl which are optionally substituted by —$NH_2$, wherein $Y^5$ is —H or —C(═O)—$CHY^6$—$NH_2$, wherein $Y^6$ is straight-chain or branched $C_{1-6}$-alkyl;

$R^4$ is a legumain cleavable group of the formula $R^{21}$—(C═O)$_{(0-1)}$—(P3)$_{(0-2)}$-P2—NH—CH($CH_2$C(═O)—$NH_2$)—C(═O)—, wherein $R^{21}$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{1-10}$-alkoxy, $C_{6-10}$-aryloxy or $C_{6-10}$-aralkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —N$(alkyl)_2$, —NH—C(═O)-alkyl, —N(alkyl)-C(═O)-alkyl, —$SO_3H$, —S$(═O)_2$—$NH_2$, —S$(═O)_2$—N$(alkyl)_2$, —COOH, —C(═O)—$NH_2$, —C(═O)—N$(alkyl)_2$, or —OH, —H or an —$O_x$—$(CH_2CH_2O)_v$—$R^{22}$ group, wherein x is 0 or 1, wherein v is a number from 1 to 20, wherein $R^{22}$ is —H, -alkyl, —$CH_2$—COOH, —$CH_2$—$CH_2$—COOH, or —$CH_2$—$CH_2$—$NH_2$);

P2 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids;

P3 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or one of the respective N-alkyl amino acids;

A is —C(═O)—, —S(═O)—, —S$(═O)_2$—, —S$(═O)_2$—NH— or —C(═N—$NH_2$)—;

$R^3$ is -MOD or an optionally substituted alkyl, cycloalkyl, aryl, heteroaryl, heteroalkyl, heterocycloalkyl group, a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—CO-alkyl groups, 1-3 —O—C(═O)—NH-alkyl groups, 1-3 —NH—C(═O)-alkyl groups, 1-3 —NH—C(═O)—NH-alkyl groups, 1-3 —S$(═O)_n$-alkyl groups, 1-3 —S$(═O)_2$—NH-alkyl groups, 1-3 —NH-alkyl groups, 1-3 —N$(alkyl)_2$ groups, 1-3 —$NH_2$ groups or 1-3 —$(CH_2)_{0-3}$Z groups, wherein wherein Z is —H, halogen, —$OY^3$, —$SY^3$, —$NHY^3$, —C(═O)—$NY^1Y^2$ or —C(═O)—$OY^3$, wherein n is 0, 1 or 2, wherein $Y^1$ and $Y^2$ are independently —H, —$NH_2$ or —$(CH_2)_{0-3}$Z', wherein $Y^3$ is —H, —$(CH_2)_{0-3}$—CH(NH—C(═O)—$CH_3$)Z', —$(CH_2)_{0-3}$—CH($NH_2$)Z', or —$(CH_2)_{0-3}$Z', wherein Z' is —H, —$SO_3H$, —$NH_2$ or —COOH, $R^5$ is —H, —$NH_2$, —$NO_2$, halogen, —CN, —$CF_3$, —$OCF_3$, —$CH_2F$, —$CH_2F$, —SH or —$(CH_2)_{0-3}$Z, wherein Z is —H, —$OY^3$, —$SY^3$, halogen, —$NHY^3$, —C(═O)—$NY^1Y^2$ or —C(═O)—$OY^3$, wherein $Y^1$ and $Y^2$ are independently —H, —$NH_2$ or —$(CH_2)_{0-3}$Z', wherein $Y^3$ is —H or —$(CH_2)_{0-3}$Z', wherein Z' is —H, —$SO_3H$, —$NH_2$ or —COOH;

$R^6$ and $R^7$ are independently —H, cyano, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy, —$NO_2$, $NH_2$, —COOH or halogen, $R^8$ is $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, $C_{4-10}$-cycloalkyl, fluoro-$C_{4-10}$-cycloalkyl, or —$(CH_2)_{0-2}$—$(HZ^2)$ wherein $HZ^2$ is a 4- to 7-membered heterocycle having up to two heteroatoms selected from the group consisting of N, O and S, wherein each of these groups may be substituted by —OH, —COOH or —$NH_2$;

$R^9$ is —H, —F, —$CH_3$, —$CF_3$, —$CH_2F$ or —$CHF_2$;

MOD is —$(NR^{10})_n$-$(G1)_o$-G2-H, wherein $R^{1o}$ is —H or $C_1$-$C_3$-alkyl;

G1 is —NH—C(═O)—, —C(═O)NH— or

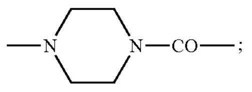—;

n is 0 or 1;

o is 0 or 1; and

G2 is a straight-chain and/or branched hydrocarbon group which has 1 to 10 carbon atoms and which may be interrupted once or more than once identically or differently by the groups —O—, —S—, —S(═O)—, —S$(═O)_2$, —$NR^y$—, —$NR^y$C(═O)—, —C(═O)$NR^y$—, —$NR^yNR^y$—, —S$(═O)_2$—$NR^yNR^y$—, —C(═O)—$NR^yNR^y$—C(═O)—, —$CR^x$═N—O—, wherein Rx is —H, $C_1$-$C_3$-alkyl or phenyl, wherein $R^y$ is —H, phenyl, $C_1$-$C_{10}$-alkyl, $C_2$-$C_{10}$-alkenyl or $C_2$-$C_{10}$-alkynyl, each of which may be substituted by —NH—C(═O)—$NH_2$, —COOH, —OH, —$NH_2$, NH—CN—$NH_2$, sulphonamide, sulphone, sulphoxide or sulphonic acid), wherein the hydrocarbon chain including any side chains may be substituted by —NH—C(═O)—$NH_2$, —COOH, —OH, —$NH_2$, NH—CN—$NH_2$, sulphonamide, sulphone, sulphoxide or sulphonic acid, wherein the group -MOD has at least one group —COOH;

or a salt, a solvate, a salt of the solvate, or an epimer thereof.

* * * * *

SEQUENCE LISTING

<160> NUMBER OF SEQ ID NOS: 245

<210> SEQ ID NO 1
<211> LENGTH: 215
<212> TYPE: PRT
<213> ORGANISM: Homo Sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 2
<211> LENGTH: 449
<212> TYPE: PRT
<213> ORGANISM: Homo Sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln

```
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 3
<211> LENGTH: 11
<212> TYPE: PRT
<213> ORGANISM: Homo Sapiens

<400> SEQUENCE: 3

Arg Ala Ser Gln Ser Ile Ser Gly Tyr Leu Asn
1               5                   10
```

<210> SEQ ID NO 4
<211> LENGTH: 7
<212> TYPE: PRT
<213> ORGANISM: Homo Sapiens

<400> SEQUENCE: 4

Gln Ala Ser Ser Leu Gln Ser
1               5

<210> SEQ ID NO 5
<211> LENGTH: 10
<212> TYPE: PRT
<213> ORGANISM: Homo Sapiens

<400> SEQUENCE: 5

Gln Gln Ser Tyr Thr Ser Pro Phe Ile Thr
1               5                   10

<210> SEQ ID NO 6
<211> LENGTH: 5
<212> TYPE: PRT
<213> ORGANISM: Homo Sapiens

<400> SEQUENCE: 6

Pro Tyr Pro Met Ile
1               5

<210> SEQ ID NO 7
<211> LENGTH: 17
<212> TYPE: PRT
<213> ORGANISM: Homo Sapiens

<400> SEQUENCE: 7

Tyr Ile Ser Pro Ser Gly Gly Ser Thr His Tyr Ala Asp Ser Val Lys
1               5                   10                  15

Gly

<210> SEQ ID NO 8
<211> LENGTH: 11
<212> TYPE: PRT
<213> ORGANISM: Homo Sapiens

<400> SEQUENCE: 8

Gly Gly Asp Thr Tyr Phe Asp Tyr Phe Asp Tyr
1               5                   10

<210> SEQ ID NO 9
<211> LENGTH: 108
<212> TYPE: PRT
<213> ORGANISM: Homo Sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys
            100                 105


<210> SEQ ID NO 10
<211> LENGTH: 121
<212> TYPE: PRT
<213> ORGANISM: Homo Sapiens

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120


<210> SEQ ID NO 11
<211> LENGTH: 215
<212> TYPE: PRT
<213> ORGANISM: Homo Sapiens

<400> SEQUENCE: 11

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

Ser Ser Thr Leu Thr Leu Ser Lys Ala Asp Tyr Glu Lys His Lys Leu
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 12
<211> LENGTH: 449
<212> TYPE: PRT
<213> ORGANISM: Homo Sapiens

<400> SEQUENCE: 12

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Pro Tyr
20 25 30

Pro Met Ile Trp Val Arg Gln Ala Pro Gly Lys Gly Leu Glu Trp Val
35 40 45

Ser Tyr Ile Ser Pro Ser Gly Gly Lys Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Asp Thr Tyr Phe Asp Tyr Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 13
<211> LENGTH: 11
<212> TYPE: PRT
<213> ORGANISM: Homo Sapiens

<400> SEQUENCE: 13

Arg Ala Ser Gln Ser Ile Ser Gly Tyr Leu Asn
1 5 10

<210> SEQ ID NO 14
<211> LENGTH: 7
<212> TYPE: PRT
<213> ORGANISM: Homo Sapiens

<400> SEQUENCE: 14

Gln Ala Ser Ser Leu Gln Ser
1 5

<210> SEQ ID NO 15
<211> LENGTH: 10
<212> TYPE: PRT
<213> ORGANISM: Homo Sapiens

<400> SEQUENCE: 15

Gln Gln Ser Tyr Thr Ser Pro Phe Ile Thr
1 5 10

<210> SEQ ID NO 16
<211> LENGTH: 5
<212> TYPE: PRT
<213> ORGANISM: Homo Sapiens

<400> SEQUENCE: 16

Pro Tyr Pro Met Ile
1 5

<210> SEQ ID NO 17
<211> LENGTH: 17
<212> TYPE: PRT
<213> ORGANISM: Homo Sapiens

<400> SEQUENCE: 17

Tyr Ile Ser Pro Ser Gly Gly Lys Thr His Tyr Ala Asp Ser Val Lys
1 5 10 15

Gly

<210> SEQ ID NO 18
<211> LENGTH: 11
<212> TYPE: PRT
<213> ORGANISM: Homo Sapiens

<400> SEQUENCE: 18

Gly Gly Asp Thr Tyr Phe Asp Tyr Phe Asp Tyr
1               5                   10

<210> SEQ ID NO 19
<211> LENGTH: 108
<212> TYPE: PRT
<213> ORGANISM: Homo Sapiens

<400> SEQUENCE: 19

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys
            100                 105

<210> SEQ ID NO 20
<211> LENGTH: 121
<212> TYPE: PRT
<213> ORGANISM: Homo Sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120

<210> SEQ ID NO 21
<211> LENGTH: 215
<212> TYPE: PRT
<213> ORGANISM: Homo Sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 22
<211> LENGTH: 449
<212> TYPE: PRT
<213> ORGANISM: Homo Sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 23
<211> LENGTH: 11
<212> TYPE: PRT
<213> ORGANISM: Homo Sapiens

<400> SEQUENCE: 23

Arg Ala Ser Gln Ser Ile Ser Ser Tyr Leu Asn
1 5 10

<210> SEQ ID NO 24
<211> LENGTH: 7
<212> TYPE: PRT
<213> ORGANISM: Homo Sapiens

<400> SEQUENCE: 24

```
Gln Ala Ser Ser Leu Gln Ser
1               5


<210> SEQ ID NO 25
<211> LENGTH: 10
<212> TYPE: PRT
<213> ORGANISM: Homo Sapiens

<400> SEQUENCE: 25

Gln Gln Ser Tyr Thr Ser Pro Phe Ile Thr
1               5                   10


<210> SEQ ID NO 26
<211> LENGTH: 5
<212> TYPE: PRT
<213> ORGANISM: Homo Sapiens

<400> SEQUENCE: 26

Pro Tyr Pro Met Met
1               5


<210> SEQ ID NO 27
<211> LENGTH: 17
<212> TYPE: PRT
<213> ORGANISM: Homo Sapiens

<400> SEQUENCE: 27

Tyr Ile Ser Pro Ser Gly Gly Ser Thr His Tyr Ala Asp Ser Val Lys
1               5                   10                  15

Gly


<210> SEQ ID NO 28
<211> LENGTH: 11
<212> TYPE: PRT
<213> ORGANISM: Homo Sapiens

<400> SEQUENCE: 28

Gly Gly Asp Thr Tyr Phe Asp Tyr Phe Asp Tyr
1               5                   10


<210> SEQ ID NO 29
<211> LENGTH: 108
<212> TYPE: PRT
<213> ORGANISM: Homo Sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys
            100                 105
```

<210> SEQ ID NO 30
<211> LENGTH: 121
<212> TYPE: PRT
<213> ORGANISM: Homo Sapiens

<400> SEQUENCE: 30

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120
```

<210> SEQ ID NO 31
<211> LENGTH: 215
<212> TYPE: PRT
<213> ORGANISM: Homo Sapiens

<400> SEQUENCE: 31

```
Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
```

210 215

<210> SEQ ID NO 32
<211> LENGTH: 449
<212> TYPE: PRT
<213> ORGANISM: Homo Sapiens

<400> SEQUENCE: 32

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Pro Tyr
20 25 30

Pro Met Met Trp Val Arg Gln Ala Pro Gly Lys Gly Leu Glu Trp Val
35 40 45

Ser Tyr Ile Ser Pro Ser Gly Gly Lys Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Asp Thr Tyr Phe Asp Tyr Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

-continued

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 33
<211> LENGTH: 11
<212> TYPE: PRT
<213> ORGANISM: Homo Sapiens

<400> SEQUENCE: 33

Arg Ala Ser Gln Ser Ile Ser Ser Tyr Leu Asn
1               5                   10


<210> SEQ ID NO 34
<211> LENGTH: 7
<212> TYPE: PRT
<213> ORGANISM: Homo Sapiens

<400> SEQUENCE: 34

Gln Ala Ser Ser Leu Gln Ser
1               5


<210> SEQ ID NO 35
<211> LENGTH: 10
<212> TYPE: PRT
<213> ORGANISM: Homo Sapiens

<400> SEQUENCE: 35

Gln Gln Ser Tyr Thr Ser Pro Phe Ile Thr
1               5                   10


<210> SEQ ID NO 36
<211> LENGTH: 5
<212> TYPE: PRT
<213> ORGANISM: Homo Sapiens

<400> SEQUENCE: 36

Pro Tyr Pro Met Met
1               5


<210> SEQ ID NO 37
<211> LENGTH: 17
<212> TYPE: PRT
<213> ORGANISM: Homo Sapiens

<400> SEQUENCE: 37

Tyr Ile Ser Pro Ser Gly Gly Lys Thr His Tyr Ala Asp Ser Val Lys
1               5                   10                  15

Gly


<210> SEQ ID NO 38
<211> LENGTH: 11
<212> TYPE: PRT
<213> ORGANISM: Homo Sapiens
```

<400> SEQUENCE: 38

Gly Gly Asp Thr Tyr Phe Asp Tyr Phe Asp Tyr
1               5                   10

<210> SEQ ID NO 39
<211> LENGTH: 108
<212> TYPE: PRT
<213> ORGANISM: Homo Sapiens

<400> SEQUENCE: 39

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys
            100                 105

<210> SEQ ID NO 40
<211> LENGTH: 121
<212> TYPE: PRT
<213> ORGANISM: Homo Sapiens

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120

<210> SEQ ID NO 41
<211> LENGTH: 215
<212> TYPE: PRT
<213> ORGANISM: Homo Sapiens

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr

```
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gly
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 42
<211> LENGTH: 449
<212> TYPE: PRT
<213> ORGANISM: Homo Sapiens

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 43
<211> LENGTH: 11
<212> TYPE: PRT
<213> ORGANISM: Homo Sapiens

<400> SEQUENCE: 43

Arg Ala Ser Gln Ser Ile Ser Ser Tyr Leu Asn
1               5                   10


<210> SEQ ID NO 44
<211> LENGTH: 7
<212> TYPE: PRT
<213> ORGANISM: Homo Sapiens

<400> SEQUENCE: 44

Ala Ala Ser Ser Leu Gln Ser
1               5


<210> SEQ ID NO 45
<211> LENGTH: 10
<212> TYPE: PRT
```

<213> ORGANISM: Homo Sapiens

<400> SEQUENCE: 45

Gln Gln Ser Tyr Ser Thr Pro Gly Ile Thr
1 5 10

<210> SEQ ID NO 46
<211> LENGTH: 5
<212> TYPE: PRT
<213> ORGANISM: Homo Sapiens

<400> SEQUENCE: 46

Pro Tyr Pro Met Met
1 5

<210> SEQ ID NO 47
<211> LENGTH: 17
<212> TYPE: PRT
<213> ORGANISM: Homo Sapiens

<400> SEQUENCE: 47

Tyr Ile Ser Pro Ser Gly Gly Ser Thr His Tyr Ala Asp Ser Val Lys
1 5 10 15

Gly

<210> SEQ ID NO 48
<211> LENGTH: 11
<212> TYPE: PRT
<213> ORGANISM: Homo Sapiens

<400> SEQUENCE: 48

Gly Gly Asp Thr Tyr Phe Asp Tyr Phe Asp Tyr
1 5 10

<210> SEQ ID NO 49
<211> LENGTH: 108
<212> TYPE: PRT
<213> ORGANISM: Homo Sapiens

<400> SEQUENCE: 49

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Gly
85 90 95

Ile Thr Phe Gly Gln Gly Thr Lys Val Glu Ile Lys
100 105

<210> SEQ ID NO 50
<211> LENGTH: 121
<212> TYPE: PRT
<213> ORGANISM: Homo Sapiens

<400> SEQUENCE: 50

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120


<210> SEQ ID NO 51
<211> LENGTH: 215
<212> TYPE: PRT
<213> ORGANISM: Homo Sapiens

<400> SEQUENCE: 51

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Gly
                85                  90                  95

Ile Thr Phe Gly Pro Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 52
<211> LENGTH: 449
<212> TYPE: PRT
<213> ORGANISM: Homo Sapiens
```

-continued

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp

```
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 53
<211> LENGTH: 11
<212> TYPE: PRT
<213> ORGANISM: Homo Sapiens

<400> SEQUENCE: 53

Arg Ala Ser Gln Ser Ile Ser Ser Tyr Leu Asn
1               5                   10


<210> SEQ ID NO 54
<211> LENGTH: 7
<212> TYPE: PRT
<213> ORGANISM: Homo Sapiens

<400> SEQUENCE: 54

Ala Ala Ser Ser Leu Gln Ser
1               5


<210> SEQ ID NO 55
<211> LENGTH: 10
<212> TYPE: PRT
<213> ORGANISM: Homo Sapiens

<400> SEQUENCE: 55

Gln Gln Ser Tyr Ser Ser Pro Gly Ile Thr
1               5                   10


<210> SEQ ID NO 56
<211> LENGTH: 5
<212> TYPE: PRT
<213> ORGANISM: Homo Sapiens

<400> SEQUENCE: 56

Pro Tyr Pro Met Met
1               5


<210> SEQ ID NO 57
<211> LENGTH: 17
<212> TYPE: PRT
<213> ORGANISM: Homo Sapiens

<400> SEQUENCE: 57

Tyr Ile Ser Pro Ser Gly Gly Lys Thr His Tyr Ala Asp Ser Val Lys
1               5                   10                  15

Gly


<210> SEQ ID NO 58
<211> LENGTH: 11
<212> TYPE: PRT
<213> ORGANISM: Homo Sapiens

<400> SEQUENCE: 58

Gly Gly Asp Thr Tyr Phe Asp Tyr Phe Asp Tyr
1               5                   10
```

<210> SEQ ID NO 59
<211> LENGTH: 108
<212> TYPE: PRT
<213> ORGANISM: Homo Sapiens

<400> SEQUENCE: 59

```
Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Gly
                85                  90                  95

Ile Thr Phe Gly Pro Gly Thr Lys Val Glu Ile Lys
            100                 105
```

<210> SEQ ID NO 60
<211> LENGTH: 121
<212> TYPE: PRT
<213> ORGANISM: Homo Sapiens

<400> SEQUENCE: 60

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120
```

<210> SEQ ID NO 61
<211> LENGTH: 217
<212> TYPE: PRT
<213> ORGANISM: Homo Sapiens

<400> SEQUENCE: 61

```
Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60
```

Ser Gly Ser Gly Ser Gly Thr Asp Phe Thr Leu Thr Ile Ser Ser Leu
65 70 75 80

Gln Pro Glu Asp Phe Ala Thr Tyr Tyr Cys Gln Gln Ser Tyr Ser Ser
85 90 95

Pro Gly Ile Thr Phe Gly Pro Gly Thr Lys Val Glu Ile Lys Arg Thr
100 105 110

Val Ala Ala Pro Ser Val Phe Ile Phe Pro Pro Ser Asp Glu Gln Leu
115 120 125

Lys Ser Gly Thr Ala Ser Val Val Cys Leu Leu Asn Asn Phe Tyr Pro
130 135 140

Arg Glu Ala Lys Val Gln Trp Lys Val Asp Asn Ala Leu Gln Ser Gly
145 150 155 160

Asn Ser Gln Glu Ser Val Thr Glu Gln Asp Ser Lys Asp Ser Thr Tyr
165 170 175

Ser Leu Ser Ser Thr Leu Thr Leu Ser Lys Ala Asp Tyr Glu Lys His
180 185 190

Lys Leu Tyr Ala Cys Glu Val Thr His Gln Gly Leu Ser Ser Pro Val
195 200 205

Thr Lys Ser Phe Asn Arg Gly Glu Cys
210 215

<210> SEQ ID NO 62
<211> LENGTH: 449
<212> TYPE: PRT
<213> ORGANISM: Homo Sapiens

<400> SEQUENCE: 62

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Pro Tyr
20 25 30

Pro Met Met Trp Val Arg Gln Ala Pro Gly Lys Gly Leu Glu Trp Val
35 40 45

Ser Tyr Ile Ser Pro Ser Gly Gly Lys Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Asp Thr Tyr Phe Asp Tyr Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp

-continued

```
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 63
<211> LENGTH: 11
<212> TYPE: PRT
<213> ORGANISM: Homo Sapiens

<400> SEQUENCE: 63

Arg Ala Ser Gln Ser Ile Ser Ser Tyr Leu Asn
1               5                   10


<210> SEQ ID NO 64
<211> LENGTH: 7
<212> TYPE: PRT
<213> ORGANISM: Homo Sapiens

<400> SEQUENCE: 64

Ala Ala Ser Ser Leu Gln Ser
1               5


<210> SEQ ID NO 65
<211> LENGTH: 10
<212> TYPE: PRT
<213> ORGANISM: Homo Sapiens

<400> SEQUENCE: 65

Gln Gln Ser Tyr Ser Ser Pro Gly Ile Thr
1               5                   10
```

<210> SEQ ID NO 66
<211> LENGTH: 5
<212> TYPE: PRT
<213> ORGANISM: Homo Sapiens

<400> SEQUENCE: 66

Pro Tyr Pro Met Met
1 5

<210> SEQ ID NO 67
<211> LENGTH: 17
<212> TYPE: PRT
<213> ORGANISM: Homo Sapiens

<400> SEQUENCE: 67

Tyr Ile Ser Pro Ser Gly Gly Lys Thr His Tyr Ala Asp Ser Val Lys
1 5 10 15

Gly

<210> SEQ ID NO 68
<211> LENGTH: 11
<212> TYPE: PRT
<213> ORGANISM: Homo Sapiens

<400> SEQUENCE: 68

Gly Gly Asp Thr Tyr Phe Asp Tyr Phe Asp Tyr
1 5 10

<210> SEQ ID NO 69
<211> LENGTH: 110
<212> TYPE: PRT
<213> ORGANISM: Homo Sapiens

<400> SEQUENCE: 69

Ala Gln Asp Ile Gln Met Thr Gln Ser Pro Ala Thr Leu Ser Ala Ser
1 5 10 15

Val Gly Asp Arg Val Thr Ile Thr Cys Arg Ala Ser Gln Ser Ile Ser
20 25 30

Ser Tyr Leu Asn Trp Tyr Gln Gln Lys Pro Gly Lys Ala Pro Lys Leu
35 40 45

Leu Ile Tyr Ala Ala Ser Ser Leu Gln Ser Gly Val Pro Ser Arg Phe
50 55 60

Ser Gly Ser Gly Ser Gly Thr Asp Phe Thr Leu Thr Ile Ser Ser Leu
65 70 75 80

Gln Pro Glu Asp Phe Ala Thr Tyr Tyr Cys Gln Gln Ser Tyr Ser Ser
85 90 95

Pro Gly Ile Thr Phe Gly Pro Gly Thr Lys Val Glu Ile Lys
100 105 110

<210> SEQ ID NO 70
<211> LENGTH: 121
<212> TYPE: PRT
<213> ORGANISM: Homo Sapiens

<400> SEQUENCE: 70

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Pro Tyr
20 25 30

Pro Met Met Trp Val Arg Gln Ala Pro Gly Lys Gly Leu Glu Trp Val

```
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120
```

<210> SEQ ID NO 71
<211> LENGTH: 217
<212> TYPE: PRT
<213> ORGANISM: Homo Sapiens

<400> SEQUENCE: 71

```
Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Ser
                85                  90                  95

Pro Gly Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 72
<211> LENGTH: 449
<212> TYPE: PRT
<213> ORGANISM: Homo Sapiens

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
```

```
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly

<210> SEQ ID NO 73
<211> LENGTH: 11
<212> TYPE: PRT
<213> ORGANISM: Homo Sapiens

<400> SEQUENCE: 73

Arg Ala Ser Gln Ser Ile Ser Ser Tyr Leu Asn
1 5 10

<210> SEQ ID NO 74
<211> LENGTH: 7
<212> TYPE: PRT
<213> ORGANISM: Homo Sapiens

<400> SEQUENCE: 74

Ala Ala Ser Ser Leu Gln Ser
1 5

<210> SEQ ID NO 75
<211> LENGTH: 10
<212> TYPE: PRT
<213> ORGANISM: Homo Sapiens

<400> SEQUENCE: 75

Gln Gln Ser Tyr Ser Ser Pro Gly Ile Thr
1 5 10

<210> SEQ ID NO 76
<211> LENGTH: 5
<212> TYPE: PRT
<213> ORGANISM: Homo Sapiens

<400> SEQUENCE: 76

Pro Tyr Pro Met Met
1 5

<210> SEQ ID NO 77
<211> LENGTH: 17
<212> TYPE: PRT
<213> ORGANISM: Homo Sapiens

<400> SEQUENCE: 77

Tyr Ile Ser Pro Ser Gly Gly Lys Thr His Tyr Ala Asp Ser Val Lys
1 5 10 15

Gly

<210> SEQ ID NO 78
<211> LENGTH: 11
<212> TYPE: PRT
<213> ORGANISM: Homo Sapiens

<400> SEQUENCE: 78

Gly Gly Asp Gly Tyr Phe Asp Tyr Phe Asp Tyr
1 5 10

<210> SEQ ID NO 79
<211> LENGTH: 110
<212> TYPE: PRT
<213> ORGANISM: Homo Sapiens

<400> SEQUENCE: 79

```
Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Ser
                85                  90                  95

Pro Gly Ile Thr Phe Gly Pro Gly Thr Lys Val Glu Ile Lys
            100                 105                 110


<210> SEQ ID NO 80
<211> LENGTH: 121
<212> TYPE: PRT
<213> ORGANISM: Homo Sapiens

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Phe Asp Tyr Phe Asp Tyr Trp Gly Gln
            100                 105                 110

Gly Thr Leu Val Thr Val Ser Ser Ala
        115                 120


<210> SEQ ID NO 81
<211> LENGTH: 217
<212> TYPE: PRT
<213> ORGANISM: Homo Sapiens

<400> SEQUENCE: 81

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Gly Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95
```

```
Pro Phe Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 82
<211> LENGTH: 449
<212> TYPE: PRT
<213> ORGANISM: Homo Sapiens

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

-continued

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 83
<211> LENGTH: 11
<212> TYPE: PRT
<213> ORGANISM: Homo Sapiens

<400> SEQUENCE: 83

Arg Ala Ser Gln Ser Ile Ser Gly Tyr Leu Asn
1 5 10

<210> SEQ ID NO 84
<211> LENGTH: 7
<212> TYPE: PRT
<213> ORGANISM: Homo Sapiens

<400> SEQUENCE: 84

Asn Ala Ser Ser Leu Gln Ser
1 5

<210> SEQ ID NO 85
<211> LENGTH: 10
<212> TYPE: PRT
<213> ORGANISM: Homo Sapiens

<400> SEQUENCE: 85

Gln Gln Ser Tyr Thr Ser Pro Phe Ile Thr
1 5 10

<210> SEQ ID NO 86
<211> LENGTH: 5
<212> TYPE: PRT
<213> ORGANISM: Homo Sapiens

<400> SEQUENCE: 86

Pro Tyr Pro Met Ile
1 5

<210> SEQ ID NO 87
<211> LENGTH: 17
<212> TYPE: PRT
<213> ORGANISM: Homo Sapiens

<400> SEQUENCE: 87

Tyr Ile Ser Pro Ser Gly Gly Lys Thr His Tyr Ala Asp Ser Val Lys
1 5 10 15

Gly

<210> SEQ ID NO 88
<211> LENGTH: 11
<212> TYPE: PRT
<213> ORGANISM: Homo Sapiens

<400> SEQUENCE: 88

Gly Gly Asp Thr Tyr Phe Asp Tyr Phe Asp Tyr
1 5 10

<210> SEQ ID NO 89
<211> LENGTH: 110
<212> TYPE: PRT
<213> ORGANISM: Homo Sapiens

<400> SEQUENCE: 89

Ala Gln Asp Ile Gln Met Thr Gln Ser Pro Ala Thr Leu Ser Ala Ser
1 5 10 15

Val Gly Asp Arg Val Thr Ile Thr Cys Arg Ala Ser Gln Ser Ile Ser
20 25 30

Gly Tyr Leu Asn Trp Tyr Gln Gln Lys Pro Gly Lys Ala Pro Lys Leu
35 40 45

Leu Ile Tyr Asn Ala Ser Ser Leu Gln Ser Gly Val Pro Ser Arg Phe
50 55 60

Ser Gly Ser Gly Ser Gly Thr Asp Phe Thr Leu Thr Ile Ser Ser Leu
65 70 75 80

Gln Pro Glu Asp Phe Ala Thr Tyr Tyr Cys Gln Gln Ser Tyr Thr Ser
85 90 95

Pro Phe Ile Thr Phe Gly Pro Gly Thr Lys Val Glu Ile Lys
100 105 110

<210> SEQ ID NO 90
<211> LENGTH: 121
<212> TYPE: PRT
<213> ORGANISM: Homo Sapiens

<400> SEQUENCE: 90

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Pro Tyr
20 25 30

Pro Met Ile Trp Val Arg Gln Ala Pro Gly Lys Gly Leu Glu Trp Val
35 40 45

Ser Tyr Ile Ser Pro Ser Gly Gly Lys Thr His Tyr Ala Asp Ser Val
50 55 60

Lys Gly Arg Phe Thr Ile Ser Arg Asp Asn Ser Lys Asn Thr Leu Tyr
65 70 75 80

```
Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120


<210> SEQ ID NO 91
<211> LENGTH: 217
<212> TYPE: PRT
<213> ORGANISM: Homo Sapiens

<400> SEQUENCE: 91

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Gly Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 92
<211> LENGTH: 449
<212> TYPE: PRT
<213> ORGANISM: Homo Sapiens

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 93
<211> LENGTH: 11
<212> TYPE: PRT

<213> ORGANISM: Homo Sapiens

<400> SEQUENCE: 93

Arg Ala Ser Gln Ser Ile Ser Ser Tyr Leu Asn
1 5 10

<210> SEQ ID NO 94
<211> LENGTH: 7
<212> TYPE: PRT
<213> ORGANISM: Homo Sapiens

<400> SEQUENCE: 94

Asn Ala Ser Ser Leu Gln Ser
1 5

<210> SEQ ID NO 95
<211> LENGTH: 10
<212> TYPE: PRT
<213> ORGANISM: Homo Sapiens

<400> SEQUENCE: 95

Gln Gln Ser Tyr Thr Ser Pro Gly Ile Thr
1 5 10

<210> SEQ ID NO 96
<211> LENGTH: 5
<212> TYPE: PRT
<213> ORGANISM: Homo Sapiens

<400> SEQUENCE: 96

Pro Tyr Pro Met Met
1 5

<210> SEQ ID NO 97
<211> LENGTH: 17
<212> TYPE: PRT
<213> ORGANISM: Homo Sapiens

<400> SEQUENCE: 97

Tyr Ile Ser Pro Ser Gly Gly Lys Thr His Tyr Ala Asp Ser Val Lys
1 5 10 15

Gly

<210> SEQ ID NO 98
<211> LENGTH: 11
<212> TYPE: PRT
<213> ORGANISM: Homo Sapiens

<400> SEQUENCE: 98

Gly Gly Asp Thr Tyr Phe Asp Tyr Phe Asp Tyr
1 5 10

<210> SEQ ID NO 99
<211> LENGTH: 110
<212> TYPE: PRT
<213> ORGANISM: Homo Sapiens

<400> SEQUENCE: 99

Ala Gln Asp Ile Gln Met Thr Gln Ser Pro Ala Thr Leu Ser Ala Ser
1 5 10 15

Val Gly Asp Arg Val Thr Ile Thr Cys Arg Ala Ser Gln Ser Ile Ser
20 25 30

Ser Tyr Leu Asn Trp Tyr Gln Gln Lys Pro Gly Lys Ala Pro Lys Leu

```
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Gly Ile Thr Phe Gly Pro Gly Thr Lys Val Glu Ile Lys
            100                 105                 110


<210> SEQ ID NO 100
<211> LENGTH: 121
<212> TYPE: PRT
<213> ORGANISM: Homo Sapiens

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120


<210> SEQ ID NO 101
<211> LENGTH: 217
<212> TYPE: PRT
<213> ORGANISM: Homo Sapiens

<400> SEQUENCE: 101

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Gly Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Gly Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
```

```
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 102
<211> LENGTH: 449
<212> TYPE: PRT
<213> ORGANISM: Homo Sapiens

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 103
<211> LENGTH: 11
<212> TYPE: PRT
<213> ORGANISM: Homo Sapiens

<400> SEQUENCE: 103

Arg Ala Ser Gln Ser Ile Ser Gly Tyr Leu Asn
1               5                   10


<210> SEQ ID NO 104
<211> LENGTH: 7
<212> TYPE: PRT
<213> ORGANISM: Homo Sapiens

<400> SEQUENCE: 104

Asn Ala Ser Ser Leu Gln Ser
1               5


<210> SEQ ID NO 105
<211> LENGTH: 10
<212> TYPE: PRT
<213> ORGANISM: Homo Sapiens

<400> SEQUENCE: 105

Gln Gln Ser Tyr Thr Ser Pro Gly Ile Thr
1               5                   10


<210> SEQ ID NO 106
<211> LENGTH: 5
<212> TYPE: PRT
<213> ORGANISM: Homo Sapiens

<400> SEQUENCE: 106

Pro Tyr Pro Met Met
1               5


<210> SEQ ID NO 107
<211> LENGTH: 17
```

<212> TYPE: PRT
<213> ORGANISM: Homo Sapiens

<400> SEQUENCE: 107

Tyr Ile Ser Pro Ser Gly Gly Lys Thr His Tyr Ala Asp Ser Val Lys
1               5                   10                  15

Gly

<210> SEQ ID NO 108
<211> LENGTH: 11
<212> TYPE: PRT
<213> ORGANISM: Homo Sapiens

<400> SEQUENCE: 108

Gly Gly Asp Thr Tyr Phe Asp Tyr Phe Asp Tyr
1               5                   10

<210> SEQ ID NO 109
<211> LENGTH: 110
<212> TYPE: PRT
<213> ORGANISM: Homo Sapiens

<400> SEQUENCE: 109

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Gly Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Gly Ile Thr Phe Gly Pro Gly Thr Lys Val Glu Ile Lys
            100                 105                 110

<210> SEQ ID NO 110
<211> LENGTH: 121
<212> TYPE: PRT
<213> ORGANISM: Homo Sapiens

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

```
Gly Thr Leu Val Thr Val Ser Ser Ala
        115                 120


<210> SEQ ID NO 111
<211> LENGTH: 217
<212> TYPE: PRT
<213> ORGANISM: Homo Sapiens

<400> SEQUENCE: 111

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Phe Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 112
<211> LENGTH: 449
<212> TYPE: PRT
<213> ORGANISM: Homo Sapiens

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 113
<211> LENGTH: 11
<212> TYPE: PRT
<213> ORGANISM: Homo Sapiens

<400> SEQUENCE: 113

```
Arg Ala Ser Gln Ser Ile Ser Ser Tyr Leu Asn
1               5                   10
```

<210> SEQ ID NO 114
<211> LENGTH: 7
<212> TYPE: PRT
<213> ORGANISM: Homo Sapiens

<400> SEQUENCE: 114

Asn Ala Ser Ser Leu Gln Ser
1               5

<210> SEQ ID NO 115
<211> LENGTH: 10
<212> TYPE: PRT
<213> ORGANISM: Homo Sapiens

<400> SEQUENCE: 115

Gln Gln Ser Tyr Thr Ser Pro Phe Ile Thr
1               5                   10

<210> SEQ ID NO 116
<211> LENGTH: 5
<212> TYPE: PRT
<213> ORGANISM: Homo Sapiens

<400> SEQUENCE: 116

Pro Tyr Pro Met Met
1               5

<210> SEQ ID NO 117
<211> LENGTH: 17
<212> TYPE: PRT
<213> ORGANISM: Homo Sapiens

<400> SEQUENCE: 117

Tyr Ile Ser Pro Ser Gly Gly Lys Thr His Tyr Ala Asp Ser Val Lys
1               5                   10                  15

Gly

<210> SEQ ID NO 118
<211> LENGTH: 11
<212> TYPE: PRT
<213> ORGANISM: Homo Sapiens

<400> SEQUENCE: 118

Gly Gly Asp Thr Tyr Phe Asp Tyr Phe Asp Tyr
1               5                   10

<210> SEQ ID NO 119
<211> LENGTH: 110
<212> TYPE: PRT
<213> ORGANISM: Homo Sapiens

<400> SEQUENCE: 119

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
85 90 95

Pro Phe Ile Thr Phe Gly Pro Gly Thr Lys Val Glu Ile Lys
100 105 110

<210> SEQ ID NO 120
<211> LENGTH: 121
<212> TYPE: PRT
<213> ORGANISM: Homo Sapiens

<400> SEQUENCE: 120

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Pro Tyr
20 25 30

Pro Met Met Trp Val Arg Gln Ala Pro Gly Lys Gly Leu Glu Trp Val
35 40 45

Ser Tyr Ile Ser Pro Ser Gly Gly Lys Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Asp Thr Tyr Phe Asp Tyr Phe Asp Tyr Trp Gly Gln
100 105 110

Gly Thr Leu Val Thr Val Ser Ser Ala
115 120

<210> SEQ ID NO 121
<211> LENGTH: 218
<212> TYPE: PRT
<213> ORGANISM: Mus Musculus

<400> SEQUENCE: 121

Asp Ile Val Leu Thr Gln Ser Pro Ala Ser Leu Ala Val Ser Leu Gly
1 5 10 15

Gln Arg Ala Thr Ile Ser Cys Arg Ala Asn Lys Ser Val Ser Thr Ser
20 25 30

Ser Tyr Ser Tyr Met His Trp Tyr Gln Gln Lys Pro Gly Gln Pro Pro
35 40 45

Lys Leu Leu Ile Lys Tyr Ala Ser Asn Leu Glu Ser Gly Val Pro Ala
50 55 60

Arg Phe Ser Gly Ser Gly Ser Gly Thr Asp Phe Ile Leu Asn Ile His
65 70 75 80

Pro Val Glu Glu Glu Asp Ala Ala Thr Tyr Tyr Cys Gln His Ser Arg
85 90 95

Glu Leu Pro Phe Thr Phe Gly Ser Gly Thr Lys Leu Glu Ile Lys Arg
100 105 110

Ala Asp Ala Ala Pro Thr Val Ser Ile Phe Pro Pro Ser Ser Glu Gln
115 120 125

Leu Thr Ser Gly Gly Ala Ser Val Val Cys Phe Leu Asn Asn Phe Tyr
130 135 140

Pro Lys Asp Ile Asn Val Lys Trp Lys Ile Asp Gly Ser Glu Arg Gln
145 150 155 160

Asn Gly Val Leu Asn Ser Trp Thr Asp Gln Asp Ser Lys Asp Ser Thr
165 170 175

-continued

Tyr Ser Met Ser Ser Thr Leu Thr Leu Thr Lys Asp Glu Tyr Glu Arg
180 185 190

His Asn Ser Tyr Thr Cys Glu Ala Thr His Lys Thr Ser Thr Ser Pro
195 200 205

Ile Val Lys Ser Phe Asn Arg Asn Glu Cys
210 215

<210> SEQ ID NO 122
<211> LENGTH: 450
<212> TYPE: PRT
<213> ORGANISM: Mus Musculus

<400> SEQUENCE: 122

Gln Val Gln Leu Gln Gln Ser Gly Pro Glu Val Val Arg Pro Gly Val
1 5 10 15

Ser Val Lys Ile Ser Cys Lys Gly Ser Gly Tyr Thr Phe Thr Asp Tyr
20 25 30

Gly Ile His Trp Val Lys Gln Ser His Ala Lys Ser Leu Glu Trp Ile
35 40 45

Gly Val Ile Ser Thr Tyr Asn Gly Tyr Thr Asn Tyr Asn Gln Lys Phe
50 55 60

Lys Gly Lys Ala Thr Met Thr Val Asp Lys Ser Ser Ser Thr Ala Tyr
65 70 75 80

Met Glu Leu Ala Arg Leu Thr Ser Glu Asp Ser Ala Ile Tyr Tyr Cys
85 90 95

Ala Arg Ala Tyr Tyr Gly Asn Leu Tyr Tyr Ala Met Asp Tyr Trp Gly
100 105 110

Gln Gly Thr Ser Val Thr Val Ser Ser Ala Lys Thr Thr Ala Pro Ser
115 120 125

Val Tyr Pro Leu Ala Pro Val Cys Gly Asp Thr Thr Gly Ser Ser Val
130 135 140

Thr Leu Gly Cys Leu Val Lys Gly Tyr Phe Pro Glu Pro Val Thr Leu
145 150 155 160

Thr Trp Asn Ser Gly Ser Leu Ser Ser Gly Val His Thr Phe Pro Ala
165 170 175

Val Leu Gln Ser Asp Leu Tyr Thr Leu Ser Ser Ser Val Thr Val Thr
180 185 190

Ser Ser Thr Trp Pro Ser Gln Ser Ile Thr Cys Asn Val Ala His Pro
195 200 205

Ala Ser Ser Thr Lys Val Asp Lys Lys Ile Glu Pro Arg Gly Pro Thr
210 215 220

Ile Lys Pro Cys Pro Pro Cys Lys Cys Pro Ala Pro Asn Leu Leu Gly
225 230 235 240

Gly Pro Ser Val Phe Ile Phe Pro Pro Lys Ile Lys Asp Val Leu Met
245 250 255

Ile Ser Leu Ser Pro Ile Val Thr Cys Val Val Val Asp Val Ser Glu
260 265 270

Asp Asp Pro Asp Val Gln Ile Ser Trp Phe Val Asn Asn Val Glu Val
275 280 285

His Thr Ala Gln Thr Gln Thr His Arg Glu Asp Tyr Asn Ser Thr Leu
290 295 300

Arg Val Val Ser Ala Leu Pro Ile Gln His Gln Asp Trp Met Ser Gly
305 310 315 320

Lys Glu Phe Lys Cys Lys Val Asn Asn Lys Asp Leu Pro Ala Pro Ile

```
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His His Thr Thr Lys Ser Phe Ser Arg Thr
        435                 440                 445

Pro Gly
    450


<210> SEQ ID NO 123
<211> LENGTH: 218
<212> TYPE: PRT
<213> ORGANISM: Mus Musculus

<400> SEQUENCE: 123

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met Gln Trp Tyr Gln Gln Arg Pro Gly Gln Pro Pro
        35                  40                  45

Lys Leu Leu Ile Lys Tyr Ala Thr Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 124
<211> LENGTH: 448
```

<212> TYPE: PRT
<213> ORGANISM: Mus Musculus

<400> SEQUENCE: 124

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Asn Asn Tyr
            20                  25                  30

Trp Met Ser Trp Val Arg Gln Ser Pro Glu Lys Gly Leu Glu Trp Leu
        35                  40                  45

Ala Glu Ile Arg Leu Lys Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Asn Asn Leu Arg Ala Glu Asn Thr Gly Ile Tyr
                85                  90                  95

Tyr Cys Thr Gly Gly Phe Ala Asp Tyr Phe Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400
```

Asp Ser Asp Gly Ser Tyr Phe Met Tyr Ser Lys Leu Arg Val Glu Lys
405 410 415

Lys Asn Trp Val Glu Arg Asn Ser Tyr Ser Cys Ser Val Val His Glu
420 425 430

Gly Leu His Asn His His Thr Thr Lys Ser Phe Ser Arg Thr Pro Gly
435 440 445

<210> SEQ ID NO 125
<211> LENGTH: 218
<212> TYPE: PRT
<213> ORGANISM: Homo Sapiens

<400> SEQUENCE: 125

Asp Ile Val Leu Thr Gln Ser Pro Ala Ser Leu Ala Val Ser Leu Gly
1 5 10 15

Gln Arg Ala Thr Ile Ser Cys Arg Ala Ser Lys Ser Val Ser Thr Ser
20 25 30

Ser Tyr Ser Tyr Met His Trp Tyr Gln Gln Lys Pro Gly Gln Pro Pro
35 40 45

Lys Leu Leu Ile Lys Tyr Ala Ser Asn Leu Glu Ser Gly Val Pro Ala
50 55 60

Arg Phe Ser Gly Ser Gly Ser Gly Thr Asp Phe Ser Leu Asn Ile His
65 70 75 80

Pro Met Glu Glu Asp Asp Thr Ala Met Tyr Phe Cys Gln His Ser Arg
85 90 95

Glu Leu Pro Phe Thr Phe Gly Gly Gly Thr Lys Leu Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 126
<211> LENGTH: 450
<212> TYPE: PRT
<213> ORGANISM: Homo Sapiens

<400> SEQUENCE: 126

Gln Val Gln Leu Val Gln Ser Gly Ala Glu Val Lys Lys Pro Gly Ala
1 5 10 15

Ser Val Lys Val Ser Cys Lys Gly Ser Gly Tyr Thr Phe Thr Asp Tyr
20 25 30

Gly Met His Trp Val Arg Gln Ala Pro Gly Gln Gly Leu Glu Trp Met
35 40 45

Gly Val Ile Ser Thr Tyr Asn Gly Tyr Thr Asn Tyr Asn Gln Lys Phe
50 55 60

Lys Gly Arg Val Thr Met Thr Val Asp Lys Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Ala Tyr Tyr Gly Asn Leu Tyr Tyr Ala Met Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Asp Glu Leu Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly
450

<210> SEQ ID NO 127
<211> LENGTH: 218

<212> TYPE: PRT
<213> ORGANISM: Homo Sapiens

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Ile Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 128
<211> LENGTH: 449
<212> TYPE: PRT
<213> ORGANISM: Homo Sapiens

<400> SEQUENCE: 128

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Glu Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Gly Tyr Tyr Ala Asp Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 129
<211> LENGTH: 218
<212> TYPE: PRT
<213> ORGANISM: Mus Musculus

<400> SEQUENCE: 129

Asp Ile Val Leu Thr Gln Ser Pro Ala Ser Leu Ala Val Ser Leu Gly
1 5 10 15

Gln Arg Ala Thr Ile Ser Cys Lys Ala Ser Gln Ser Val Ser Thr Ser
20 25 30

Thr Tyr Ser Tyr Met Gln Trp Tyr Gln Gln Arg Pro Gly Gln Ser Pro
35 40 45

```
Lys Leu Leu Ile Lys Tyr Ala Ser Lys Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Leu Pro Tyr Thr Phe Gly Gly Gly Thr Arg Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 130
<211> LENGTH: 448
<212> TYPE: PRT
<213> ORGANISM: Mus Musculus

<400> SEQUENCE: 130

Glu Val Lys Leu Gly Glu Ser Gly Gly Gly Leu Val Gln Pro Gly Gly
1               5                   10                  15

Ser Met Lys Leu Ser Cys Val Ala Ser Gly Phe Pro Phe Thr Lys Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
    50                  55                  60

Ser Ala Lys Gly Arg Phe Thr Ile Ser Arg Asp Asp Ser Arg Ser Ser
65                  70                  75                  80

Val Tyr Leu Gln Met Asn Asn Leu Arg Ala Glu Asp Thr Ala Ile Tyr
                85                  90                  95

Tyr Cys Ser Pro Thr Tyr Ala Asp Thr Met Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205
```

```
Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445


<210> SEQ ID NO 131
<211> LENGTH: 218
<212> TYPE: PRT
<213> ORGANISM: Mus Musculus

<400> SEQUENCE: 131

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Thr Ser Asn Leu Glu Ser Gly Val Pro Ala
    50                  55                  60

Arg Phe Ser Gly Ser Gly Ser Gly Thr Asp Phe Ile Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
```

-continued

```
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 132
<211> LENGTH: 451
<212> TYPE: PRT
<213> ORGANISM: Mus Musculus

<400> SEQUENCE: 132

Gln Val Ser Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Gly Pro Asp Tyr Tyr Gly Tyr Tyr Pro Met Asp Tyr
            100                 105                 110

Trp Gly Gln Gly Thr Ser Val Thr Val Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Thr Ser Ser Thr Trp Pro Ser Gln Ser Ile Thr Cys Asn Val Ala His
        195                 200                 205

Pro Ala Ser Ser Thr Lys Val Asp Lys Lys Ile Glu Pro Arg Gly Pro
    210                 215                 220

Thr Ile Lys Pro Cys Pro Pro Cys Lys Cys Pro Ala Pro Asn Leu Leu
225                 230                 235                 240

Gly Gly Pro Ser Val Phe Ile Phe Pro Pro Lys Ile Lys Asp Val Leu
                245                 250                 255

Met Ile Ser Leu Ser Pro Ile Val Thr Cys Val Val Val Asp Val Ser
            260                 265                 270

Glu Asp Asp Pro Asp Val Gln Ile Ser Trp Phe Val Asn Asn Val Glu
        275                 280                 285
```

Val His Thr Ala Gln Thr Gln Thr His Arg Glu Asp Tyr Asn Ser Thr
    290                 295                 300

Leu Arg Val Val Ser Ala Leu Pro Ile Gln His Gln Asp Trp Met Ser
305                 310                 315                 320

Gly Lys Glu Phe Lys Cys Lys Val Asn Asn Lys Asp Leu Pro Ala Pro
                325                 330                 335

Ile Glu Arg Thr Ile Ser Lys Pro Lys Gly Ser Val Arg Ala Pro Gln
            340                 345                 350

Val Tyr Val Leu Pro Pro Pro Glu Glu Glu Met Thr Lys Lys Gln Val
        355                 360                 365

Thr Leu Thr Cys Met Val Thr Asp Phe Met Pro Glu Asp Ile Tyr Val
    370                 375                 380

Glu Trp Thr Asn Asn Gly Lys Thr Glu Leu Asn Tyr Lys Asn Thr Glu
385                 390                 395                 400

Pro Val Leu Asp Ser Asp Gly Ser Tyr Phe Met Tyr Ser Lys Leu Arg
                405                 410                 415

Val Glu Lys Lys Asn Trp Val Glu Arg Asn Ser Tyr Ser Cys Ser Val
            420                 425                 430

Val His Glu Gly Leu His Asn His His Thr Thr Lys Ser Phe Ser Arg
        435                 440                 445

Thr Pro Gly
    450

<210> SEQ ID NO 133
<211> LENGTH: 282
<212> TYPE: PRT
<213> ORGANISM: Macaca fascicularis

<400> SEQUENCE: 133

Glu Gln Ala Pro Gly Thr Ala Pro Cys Ser His Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ser Ala Ala Pro Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

```
Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280


<210> SEQ ID NO 134
<211> LENGTH: 282
<212> TYPE: PRT
<213> ORGANISM: Rattus norvegicus

<400> SEQUENCE: 134

Glu Gln Ala Pro Gly Asn Ala Pro Cys Ser Ser Gly Ser Ser Trp Ser
1               5                   10                  15

Ala Asp Leu Asp Lys Cys Met Asp Cys Ala Ser Cys Pro Ala Arg Pro
            20                  25                  30

His Ser Asp Phe Cys Leu Gly Cys Ala Ala Ala Pro Pro Ala His Phe
        35                  40                  45

Arg Met Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280
```

<210> SEQ ID NO 135
<211> LENGTH: 282
<212> TYPE: PRT
<213> ORGANISM: Sus scrofa

<400> SEQUENCE: 135

```
Glu Arg Val Pro Gly Thr Thr Pro Cys Ser Arg Gly Ser Ser Trp Ser
1               5                   10                  15

Ala Asp Leu Asp Lys Cys Met Asp Cys Ala Ser Cys Pro Ala Arg Pro
            20                  25                  30

His Ser Asp Phe Cys Leu Gly Cys Ala Ala Ala Pro Pro Ala Ser Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280
```

<210> SEQ ID NO 136
<211> LENGTH: 282
<212> TYPE: PRT
<213> ORGANISM: Canis lupus

<400> SEQUENCE: 136

```
Glu Arg Val Pro Gly Thr Thr Pro Cys Pro Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Thr Ala Ala Pro Pro Ala Pro Phe
        35                  40                  45

Arg Leu Leu Trp Pro Arg Ser Asp Lys Thr His Thr Cys Pro Pro Cys
```

```
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280


<210> SEQ ID NO 137
<211> LENGTH: 282
<212> TYPE: PRT
<213> ORGANISM: Mus Musculus

<400> SEQUENCE: 137

Glu Gln Ala Pro Gly Thr Ser Pro Cys Ser Ser Gly Ser Ser Trp Ser
1               5                   10                  15

Ala Asp Leu Asp Lys Cys Met Asp Cys Ala Ser Cys Pro Ala Arg Pro
            20                  25                  30

His Ser Asp Phe Cys Leu Gly Cys Ala Ala Ala Pro Pro Ala His Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140
```

```
His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280


<210> SEQ ID NO 138
<211> LENGTH: 282
<212> TYPE: PRT
<213> ORGANISM: Homo Sapiens

<400> SEQUENCE: 138

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240
```

Leu Tyr Ser Lys Leu Thr Val Asp Lys Ser Arg Trp Gln Gln Gly Asn
245 250 255

Val Phe Ser Cys Ser Val Met His Glu Ala Leu His Asn His Tyr Thr
260 265 270

Gln Lys Ser Leu Ser Leu Ser Pro Gly Lys
275 280

<210> SEQ ID NO 139
<211> LENGTH: 296
<212> TYPE: PRT
<213> ORGANISM: Homo Sapiens

<400> SEQUENCE: 139

Glu Gln Ala Pro Gly Thr Ala Pro Cys Ser Arg Gly Ser Ser Trp Ser
1 5 10 15

Ala Asp Leu Asp Lys Cys Met Asp Cys Ala Ser Cys Arg Ala Arg Pro
20 25 30

His Ser Asp Phe Cys Leu Gly Cys Ala Ala Ala Pro Pro Ala Pro Phe
35 40 45

Arg Leu Leu Trp Pro Ile Glu Gly Arg Met Asp Pro Lys Ser Cys Asp
50 55 60

Lys Thr His Thr Cys Pro Pro Cys Pro Ala Pro Glu Leu Leu Gly Gly
65 70 75 80

Pro Ser Val Phe Leu Phe Pro Pro Lys Pro Lys Asp Thr Leu Met Ile
85 90 95

Ser Arg Thr Pro Glu Val Thr Cys Val Val Val Asp Val Ser His Glu
100 105 110

Asp Pro Glu Val Lys Phe Asn Trp Tyr Val Asp Gly Val Glu Val His
115 120 125

Asn Ala Lys Thr Lys Pro Arg Glu Glu Gln Tyr Asn Ser Thr Tyr Arg
130 135 140

Val Val Ser Val Leu Thr Val Leu His Gln Asp Trp Leu Asn Gly Lys
145 150 155 160

Glu Tyr Lys Cys Lys Val Ser Asn Lys Ala Leu Pro Ala Pro Ile Glu
165 170 175

Lys Thr Ile Ser Lys Ala Lys Gly Gln Pro Arg Glu Pro Gln Val Tyr
180 185 190

Thr Leu Pro Pro Ser Arg Glu Glu Met Thr Lys Asn Gln Val Ser Leu
195 200 205

Thr Cys Leu Val Lys Gly Phe Tyr Pro Ser Asp Ile Ala Val Glu Trp
210 215 220

Glu Ser Asn Gly Gln Pro Glu Asn Asn Tyr Lys Thr Thr Pro Pro Val
225 230 235 240

Leu Asp Ser Asp Gly Ser Phe Phe Leu Tyr Ser Lys Leu Thr Val Asp
245 250 255

Lys Ser Arg Trp Gln Gln Gly Asn Val Phe Ser Cys Ser Val Met His
260 265 270

Glu Ala Leu His Asn His Tyr Thr Gln Lys Ser Leu Ser Leu Ser Pro
275 280 285

Gly Lys His His His His His His
290 295

<210> SEQ ID NO 140
<211> LENGTH: 278
<212> TYPE: PRT

<213> ORGANISM: Homo Sapiens

<400> SEQUENCE: 140

Ala Pro Cys Ser Arg Gly Ser Ser Trp Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 141
<211> LENGTH: 47
<212> TYPE: PRT
<213> ORGANISM: Homo Sapiens

<400> SEQUENCE: 141

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala His His His His His His
        35                  40                  45

<210> SEQ ID NO 142
<211> LENGTH: 282
<212> TYPE: PRT

<213> ORGANISM: Homo Sapiens

<400> SEQUENCE: 142

Glu Gln Ala Pro Gly Thr Ala Pro Cys Ser Arg Gly Ser Ser Trp Ser
1 5 10 15

Ala Asp Leu Asp Lys Cys Met Asp Cys Ala Ser Cys Arg Ala Arg Pro
20 25 30

His Ser Asp Phe Cys Gln Gly Cys Ala Ala Ala Pro Pro Ala Pro Phe
35 40 45

Arg Leu Leu Trp Pro Arg Ser Asp Lys Thr His Thr Cys Pro Pro Cys
50 55 60

Pro Ala Pro Glu Leu Leu Gly Gly Pro Ser Val Phe Leu Phe Pro Pro
65 70 75 80

Lys Pro Lys Asp Thr Leu Met Ile Ser Arg Thr Pro Glu Val Thr Cys
85 90 95

Val Val Val Asp Val Ser His Glu Asp Pro Glu Val Lys Phe Asn Trp
100 105 110

Tyr Val Asp Gly Val Glu Val His Asn Ala Lys Thr Lys Pro Arg Glu
115 120 125

Glu Gln Tyr Asn Ser Thr Tyr Arg Val Val Ser Val Leu Thr Val Leu
130 135 140

His Gln Asp Trp Leu Asn Gly Lys Glu Tyr Lys Cys Lys Val Ser Asn
145 150 155 160

Lys Ala Leu Pro Ala Pro Ile Glu Lys Thr Ile Ser Lys Ala Lys Gly
165 170 175

Gln Pro Arg Glu Pro Gln Val Tyr Thr Leu Pro Pro Ser Arg Glu Glu
180 185 190

Met Thr Lys Asn Gln Val Ser Leu Thr Cys Leu Val Lys Gly Phe Tyr
195 200 205

Pro Ser Asp Ile Ala Val Glu Trp Glu Ser Asn Gly Gln Pro Glu Asn
210 215 220

Asn Tyr Lys Thr Thr Pro Pro Val Leu Asp Ser Asp Gly Ser Phe Phe
225 230 235 240

Leu Tyr Ser Lys Leu Thr Val Asp Lys Ser Arg Trp Gln Gln Gly Asn
245 250 255

Val Phe Ser Cys Ser Val Met His Glu Ala Leu His Asn His Tyr Thr
260 265 270

Gln Lys Ser Leu Ser Leu Ser Pro Gly Lys
275 280

<210> SEQ ID NO 143
<211> LENGTH: 282
<212> TYPE: PRT
<213> ORGANISM: Homo Sapiens

<400> SEQUENCE: 143

Glu Gln Ala Pro Gly Thr Ala Pro Cys Ser Arg Gly Ser Ser Trp Ser
1 5 10 15

Ala Asp Leu Asp Lys Cys Met Asp Cys Ala Ser Cys Arg Ala Arg Pro
20 25 30

Lys Ser Asp Phe Cys Leu Gly Cys Ala Ala Ala Pro Pro Ala Pro Phe
35 40 45

Arg Leu Leu Trp Pro Arg Ser Asp Lys Thr His Thr Cys Pro Pro Cys
50 55 60

Pro Ala Pro Glu Leu Leu Gly Gly Pro Ser Val Phe Leu Phe Pro Pro

```
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280


<210> SEQ ID NO 144
<211> LENGTH: 282
<212> TYPE: PRT
<213> ORGANISM: Homo Sapiens

<400> SEQUENCE: 144

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Pro Ala Arg Pro
            20                  25                  30

His Ser Asp Phe Cys Leu Gly Cys Ala Ala Ala Pro Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160
```

-continued

```
Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280


<210> SEQ ID NO 145
<211> LENGTH: 282
<212> TYPE: PRT
<213> ORGANISM: Homo Sapiens

<400> SEQUENCE: 145

Glu Gln Ala Pro Gly Thr Ala Pro Cys Ser Arg Gly Ser Ser Trp Ser
1               5                   10                  15

Ala Asp Leu Asp Lys Cys Ala Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255
```

```
Val Phe Ser Cys Ser Val Met His Glu Ala Leu His Asn His Tyr Thr
            260                 265                 270

Gln Lys Ser Leu Ser Leu Ser Pro Gly Lys
        275                 280


<210> SEQ ID NO 146
<211> LENGTH: 282
<212> TYPE: PRT
<213> ORGANISM: Homo Sapiens

<400> SEQUENCE: 146

Glu Gln Ala Pro Gly Thr Ala Pro Cys Ser Arg Gly Ser Ser Ala Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280


<210> SEQ ID NO 147
<211> LENGTH: 282
<212> TYPE: PRT
<213> ORGANISM: Homo Sapiens

<400> SEQUENCE: 147

Glu Gln Ala Pro Gly Thr Ala Pro Cys Ser Arg Gly Arg Ser Trp Ser
1               5                   10                  15
```

```
Ala Asp Leu Asp Lys Cys Met Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280


<210> SEQ ID NO 148
<211> LENGTH: 282
<212> TYPE: PRT
<213> ORGANISM: Homo Sapiens

<400> SEQUENCE: 148

Glu Gln Ala Pro Gly Gln Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
```

```
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280


<210> SEQ ID NO 149
<211> LENGTH: 278
<212> TYPE: PRT
<213> ORGANISM: Homo Sapiens

<400> SEQUENCE: 149

Ala Pro Cys Ser Arg Gly Ser Ser Trp Ser Ala Asp Leu Asp Lys Cys
1               5                   10                  15

Met Asp Cys Ala Ser Cys Arg Ala Arg Pro His Ser Asp Phe Cys Ala
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190
```

-continued

```
Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275


<210> SEQ ID NO 150
<211> LENGTH: 278
<212> TYPE: PRT
<213> ORGANISM: Homo Sapiens

<400> SEQUENCE: 150

Ala Pro Cys Ser Arg Gly Ser Ser Trp Ser Ala Asp Leu Asp Lys Cys
1               5                   10                  15

Met Asp Cys Ala Ser Cys Arg Ala Arg Pro His Ser Asp Ala Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275
```

<210> SEQ ID NO 151
<211> LENGTH: 278
<212> TYPE: PRT
<213> ORGANISM: Homo Sapiens

<400> SEQUENCE: 151

```
Ala Pro Cys Ser Arg Gly Ser Ser Trp Ser Ala Asp Leu Asp Lys Cys
1               5                   10                  15

Met Asp Cys Ala Ser Cys Arg Ala Arg Pro His Ser Ala Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275
```

<210> SEQ ID NO 152
<211> LENGTH: 278
<212> TYPE: PRT
<213> ORGANISM: Homo Sapiens

<400> SEQUENCE: 152

```
Ala Pro Cys Ser Arg Gly Ser Ser Trp Ser Ala Asp Leu Asp Lys Cys
1               5                   10                  15

Met Asp Cys Ala Ser Cys Arg Ala Arg Pro His Ala Asp Phe Cys Leu
            20                  25                  30

Gly Cys Ala Ile Glu Gly Arg Met Asp Pro Lys Ser Cys Asp Lys Thr
        35                  40                  45
```

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 153
<211> LENGTH: 278
<212> TYPE: PRT
<213> ORGANISM: Homo Sapiens

<400> SEQUENCE: 153

Ala Pro Cys Ser Arg Gly Ser Ser Trp Ser Ala Asp Leu Asp Lys Cys
1               5                   10                  15

Met Asp Cys Ala Ser Cys Arg Ala Arg Pro Ala Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr

```
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275


<210> SEQ ID NO 154
<211> LENGTH: 278
<212> TYPE: PRT
<213> ORGANISM: Homo Sapiens

<400> SEQUENCE: 154

Ala Pro Cys Ser Arg Gly Ser Ser Trp Ser Ala Asp Leu Asp Lys Cys
1               5                   10                  15

Met Asp Cys Ala Ser Cys Arg Ala Arg Ala His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220
```

```
Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275


<210> SEQ ID NO 155
<211> LENGTH: 278
<212> TYPE: PRT
<213> ORGANISM: Homo Sapiens

<400> SEQUENCE: 155

Ala Pro Cys Ser Arg Gly Ser Ser Trp Ser Ala Asp Leu Asp Lys Cys
1               5                   10                  15

Met Asp Cys Ala Ser Cys Arg Ala Ala Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275


<210> SEQ ID NO 156
<211> LENGTH: 240
<212> TYPE: PRT
<213> ORGANISM: Homo Sapiens
```

<400> SEQUENCE: 156

Ala Pro Cys Ser Arg Gly Ser Ser Trp Ser Ala Asp Leu Asp Lys Cys
1 5 10 15

Met Asp Cys Ala Ser Cys Ala Ala Arg Pro His Ser Asp Phe Cys Leu
20 25 30

Gly Cys Ala Ile Glu Gly Arg Met Asp Pro Lys Ser Cys Asp Lys Thr
35 40 45

His Thr Cys Pro Pro Cys Pro Ala Pro Glu Leu Leu Gly Gly Pro Ser
50 55 60

Val Phe Leu Phe Pro Pro Lys Pro Lys Asp Thr Leu Met Ile Ser Arg
65 70 75 80

Thr Pro Glu Val Thr Cys Val Val Val Asp Val Ser His Glu Asp Pro
85 90 95

Glu Val Lys Phe Asn Trp Tyr Val Asp Gly Val Glu Val His Asn Ala
100 105 110

Lys Thr Lys Pro Arg Glu Glu Gln Tyr Asn Ser Thr Tyr Arg Val Val
115 120 125

Ser Val Leu Thr Val Leu His Gln Asp Trp Leu Asn Gly Lys Glu Tyr
130 135 140

Lys Cys Lys Val Ser Asn Lys Ala Leu Pro Ala Pro Ile Glu Lys Thr
145 150 155 160

Ile Ser Lys Ala Lys Gly Gln Pro Arg Glu Pro Gln Val Tyr Thr Leu
165 170 175

Pro Pro Ser Arg Glu Glu Met Thr Lys Asn Gln Val Ser Leu Thr Cys
180 185 190

Leu Val Lys Gly Phe Tyr Pro Ser Asp Ile Ala Val Glu Trp Glu Ser
195 200 205

Asn Gly Gln Pro Glu Asn Asn Tyr Lys Thr Thr Pro Pro Val Leu Asp
210 215 220

Ser Asp Gly Ser Phe Phe Leu Tyr Ser Lys Leu Thr Val Asp Lys Ser
225 230 235 240

<210> SEQ ID NO 157
<211> LENGTH: 278
<212> TYPE: PRT
<213> ORGANISM: Homo Sapiens

<400> SEQUENCE: 157

Ala Pro Cys Ser Arg Gly Ser Ser Trp Ser Ala Asp Leu Asp Lys Cys
1 5 10 15

Met Asp Cys Ala Ala Cys Arg Ala Arg Pro His Ser Asp Phe Cys Leu
20 25 30

Gly Cys Ala Ile Glu Gly Arg Met Asp Pro Lys Ser Cys Asp Lys Thr
35 40 45

His Thr Cys Pro Pro Cys Pro Ala Pro Glu Leu Leu Gly Gly Pro Ser
50 55 60

Val Phe Leu Phe Pro Pro Lys Pro Lys Asp Thr Leu Met Ile Ser Arg
65 70 75 80

Thr Pro Glu Val Thr Cys Val Val Val Asp Val Ser His Glu Asp Pro
85 90 95

Glu Val Lys Phe Asn Trp Tyr Val Asp Gly Val Glu Val His Asn Ala
100 105 110

Lys Thr Lys Pro Arg Glu Glu Gln Tyr Asn Ser Thr Tyr Arg Val Val
115 120 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 158
<211> LENGTH: 278
<212> TYPE: PRT
<213> ORGANISM: Homo Sapiens

<400> SEQUENCE: 158

Ala Pro Cys Ser Arg Gly Ser Ser Trp Ser Ala Asp Leu Asp Lys Cys
1               5                   10                  15

Met Ala Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp

```
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275
```

<210> SEQ ID NO 159
<211> LENGTH: 278
<212> TYPE: PRT
<213> ORGANISM: Homo Sapiens

<400> SEQUENCE: 159

```
Ala Pro Cys Ser Arg Gly Ser Ser Trp Ser Ala Asp Leu Asp Ala Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275
```

<210> SEQ ID NO 160
<211> LENGTH: 278

<212> TYPE: PRT
<213> ORGANISM: Homo Sapiens

<400> SEQUENCE: 160

Ala Pro Cys Ser Arg Gly Ser Ser Trp Ser Ala Asp Leu Ala Lys Cys
1 5 10 15

Met Asp Cys Ala Ser Cys Arg Ala Arg Pro His Ser Asp Phe Cys Leu
20 25 30

Gly Cys Ala Ile Glu Gly Arg Met Asp Pro Lys Ser Cys Asp Lys Thr
35 40 45

His Thr Cys Pro Pro Cys Pro Ala Pro Glu Leu Leu Gly Gly Pro Ser
50 55 60

Val Phe Leu Phe Pro Pro Lys Pro Lys Asp Thr Leu Met Ile Ser Arg
65 70 75 80

Thr Pro Glu Val Thr Cys Val Val Val Asp Val Ser His Glu Asp Pro
85 90 95

Glu Val Lys Phe Asn Trp Tyr Val Asp Gly Val Glu Val His Asn Ala
100 105 110

Lys Thr Lys Pro Arg Glu Glu Gln Tyr Asn Ser Thr Tyr Arg Val Val
115 120 125

Ser Val Leu Thr Val Leu His Gln Asp Trp Leu Asn Gly Lys Glu Tyr
130 135 140

Lys Cys Lys Val Ser Asn Lys Ala Leu Pro Ala Pro Ile Glu Lys Thr
145 150 155 160

Ile Ser Lys Ala Lys Gly Gln Pro Arg Glu Pro Gln Val Tyr Thr Leu
165 170 175

Pro Pro Ser Arg Glu Glu Met Thr Lys Asn Gln Val Ser Leu Thr Cys
180 185 190

Leu Val Lys Gly Phe Tyr Pro Ser Asp Ile Ala Val Glu Trp Glu Ser
195 200 205

Asn Gly Gln Pro Glu Asn Asn Tyr Lys Thr Thr Pro Pro Val Leu Asp
210 215 220

Ser Asp Gly Ser Phe Phe Leu Tyr Ser Lys Leu Thr Val Asp Lys Ser
225 230 235 240

Arg Trp Gln Gln Gly Asn Val Phe Ser Cys Ser Val Met His Glu Ala
245 250 255

Leu His Asn His Tyr Thr Gln Lys Ser Leu Ser Leu Ser Pro Gly Lys
260 265 270

His His His His His His
275

<210> SEQ ID NO 161
<211> LENGTH: 278
<212> TYPE: PRT
<213> ORGANISM: Homo Sapiens

<400> SEQUENCE: 161

Ala Pro Cys Ser Arg Gly Ser Ser Trp Ser Ala Ala Leu Asp Lys Cys
1 5 10 15

Met Asp Cys Ala Ser Cys Arg Ala Arg Pro His Ser Asp Phe Cys Leu
20 25 30

Gly Cys Ala Ile Glu Gly Arg Met Asp Pro Lys Ser Cys Asp Lys Thr
35 40 45

His Thr Cys Pro Pro Cys Pro Ala Pro Glu Leu Leu Gly Gly Pro Ser
50 55 60

-continued

Val Phe Leu Phe Pro Pro Lys Pro Lys Asp Thr Leu Met Ile Ser Arg
65 70 75 80

Thr Pro Glu Val Thr Cys Val Val Val Asp Val Ser His Glu Asp Pro
85 90 95

Glu Val Lys Phe Asn Trp Tyr Val Asp Gly Val Glu Val His Asn Ala
100 105 110

Lys Thr Lys Pro Arg Glu Glu Gln Tyr Asn Ser Thr Tyr Arg Val Val
115 120 125

Ser Val Leu Thr Val Leu His Gln Asp Trp Leu Asn Gly Lys Glu Tyr
130 135 140

Lys Cys Lys Val Ser Asn Lys Ala Leu Pro Ala Pro Ile Glu Lys Thr
145 150 155 160

Ile Ser Lys Ala Lys Gly Gln Pro Arg Glu Pro Gln Val Tyr Thr Leu
165 170 175

Pro Pro Ser Arg Glu Glu Met Thr Lys Asn Gln Val Ser Leu Thr Cys
180 185 190

Leu Val Lys Gly Phe Tyr Pro Ser Asp Ile Ala Val Glu Trp Glu Ser
195 200 205

Asn Gly Gln Pro Glu Asn Asn Tyr Lys Thr Thr Pro Pro Val Leu Asp
210 215 220

Ser Asp Gly Ser Phe Phe Leu Tyr Ser Lys Leu Thr Val Asp Lys Ser
225 230 235 240

Arg Trp Gln Gln Gly Asn Val Phe Ser Cys Ser Val Met His Glu Ala
245 250 255

Leu His Asn His Tyr Thr Gln Lys Ser Leu Ser Leu Ser Pro Gly Lys
260 265 270

His His His His His His
275

<210> SEQ ID NO 162
<211> LENGTH: 278
<212> TYPE: PRT
<213> ORGANISM: Homo Sapiens

<400> SEQUENCE: 162

Ala Pro Cys Ser Arg Gly Ser Ser Trp Ala Ala Asp Leu Asp Lys Cys
1 5 10 15

Met Asp Cys Ala Ser Cys Arg Ala Arg Pro His Ser Asp Phe Cys Leu
20 25 30

Gly Cys Ala Ile Glu Gly Arg Met Asp Pro Lys Ser Cys Asp Lys Thr
35 40 45

His Thr Cys Pro Pro Cys Pro Ala Pro Glu Leu Leu Gly Gly Pro Ser
50 55 60

Val Phe Leu Phe Pro Pro Lys Pro Lys Asp Thr Leu Met Ile Ser Arg
65 70 75 80

Thr Pro Glu Val Thr Cys Val Val Val Asp Val Ser His Glu Asp Pro
85 90 95

Glu Val Lys Phe Asn Trp Tyr Val Asp Gly Val Glu Val His Asn Ala
100 105 110

Lys Thr Lys Pro Arg Glu Glu Gln Tyr Asn Ser Thr Tyr Arg Val Val
115 120 125

Ser Val Leu Thr Val Leu His Gln Asp Trp Leu Asn Gly Lys Glu Tyr
130 135 140

Lys Cys Lys Val Ser Asn Lys Ala Leu Pro Ala Pro Ile Glu Lys Thr
145 150 155 160

```
Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275


<210> SEQ ID NO 163
<211> LENGTH: 278
<212> TYPE: PRT
<213> ORGANISM: Homo Sapiens

<400> SEQUENCE: 163

Ala Pro Cys Ser Arg Gly Ser Ser Ala Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
```

```
                245                 250                 255

Leu His Asn His Tyr Thr Gln Lys Ser Leu Ser Leu Ser Pro Gly Lys
            260                 265                 270

His His His His His His
        275


<210> SEQ ID NO 164
<211> LENGTH: 278
<212> TYPE: PRT
<213> ORGANISM: Homo Sapiens

<400> SEQUENCE: 164

Ala Pro Cys Ser Arg Gly Ser Ala Trp Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275


<210> SEQ ID NO 165
<211> LENGTH: 278
<212> TYPE: PRT
<213> ORGANISM: Homo Sapiens

<400> SEQUENCE: 165

Ala Pro Cys Ser Arg Gly Ala Ser Trp Ser Ala Asp Leu Asp Lys Cys
```

```
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275


<210> SEQ ID NO 166
<211> LENGTH: 278
<212> TYPE: PRT
<213> ORGANISM: Homo Sapiens

<400> SEQUENCE: 166

Ala Pro Cys Ser Ala Gly Ser Ser Trp Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95
```

```
Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275


<210> SEQ ID NO 167
<211> LENGTH: 278
<212> TYPE: PRT
<213> ORGANISM: Homo Sapiens

<400> SEQUENCE: 167

Ala Pro Cys Ala Arg Gly Ser Ser Trp Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190
```

```
Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275


<210> SEQ ID NO 168
<211> LENGTH: 53
<212> TYPE: PRT
<213> ORGANISM: Homo Sapiens

<400> SEQUENCE: 168

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu Leu Trp Pro
    50


<210> SEQ ID NO 169
<211> LENGTH: 129
<212> TYPE: PRT
<213> ORGANISM: Homo Sapiens

<400> SEQUENCE: 169

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln


<210> SEQ ID NO 170
<211> LENGTH: 959
<212> TYPE: DNA
<213> ORGANISM: Homo Sapiens
```

<400> SEQUENCE: 170

```
atggctcggg gctcgctgcg ccggttgctg cggctcctcg tgctggggct ctggctggcg      60
ttgctgcgct ccgtggccgg ggagcaagcg ccaggcaccg ccccctgctc ccgcggcagc     120
tcctggagcg cggacctgga caagtgcatg gactgcgcgt cttgcagggc gcgaccgcac     180
agcgacttct gcctgggctg cgctgcagca cctcctgccc ccttccggct gctttggccc     240
atccttgggg gcgctctgag cctgaccttc gtgctggggc tgctttctgg ctttttggtc     300
tggagacgat gccgcaggag agagaagttc accacccccca tagaggagac cggcggagag     360
ggctgcccag ctgtggcgct gatccagtga caatgtgccc cctgccagcc ggggctcgcc     420
cactcatcat tcattcatcc attctagagc cagtctctgc ctcccagacg cggcgggagc     480
caagctcctc caaccacaag gggggtgggg ggcggtgaat cacctctgag gcctgggccc     540
agggttcagg ggaaccttcc aaggtgtctg gttgccctgc ctctggctcc agaacagaaa     600
gggagcctca cgctggctca cacaaaacag ctgacactga ctaaggaact gcagcatttg     660
cacaggggag gggggtgccc tccttcctta ggacctgggg gccaggctga cttggggggc     720
agacttgaca ctaggcccca ctcactcaga tgtcctgaaa ttccaccacg gggggtcaccc    780
tggggggtta gggacctatt tttaacacta ggggctggcc cactaggagg gctggcccta     840
agatacagac ccccccaact ccccaaagcg gggaggagat atttattttg ggagagttt     900
ggaggggagg gagaatttat taataaaaga atctttaact ttaaaaaaaa aaaaaaaaa      959
```

<210> SEQ ID NO 171
<211> LENGTH: 5
<212> TYPE: PRT
<213> ORGANISM: Homo Sapiens
<220> FEATURE:
<221> NAME/KEY: VARIANT
<222> LOCATION: 5..5
<223> OTHER INFORMATION: Xaa = Ile or Met

<400> SEQUENCE: 171

```
Pro Tyr Pro Met Xaa
1               5
```

<210> SEQ ID NO 172
<211> LENGTH: 17
<212> TYPE: PRT
<213> ORGANISM: Homo Sapiens
<220> FEATURE:
<221> NAME/KEY: VARIANT
<222> LOCATION: 8..8
<223> OTHER INFORMATION: Xaa = ser or Lys

<400> SEQUENCE: 172

```
Tyr Ile Ser Pro Ser Gly Gly Xaa Thr His Tyr Ala Asp Ser Val Lys
1               5                   10                  15

Gly
```

<210> SEQ ID NO 173
<211> LENGTH: 11
<212> TYPE: PRT
<213> ORGANISM: Homo Sapiens

<400> SEQUENCE: 173

```
Gly Gly Asp Thr Tyr Phe Asp Tyr Phe Asp Tyr
1               5                   10
```

<210> SEQ ID NO 174

<211> LENGTH: 11
<212> TYPE: PRT
<213> ORGANISM: Homo Sapiens
<220> FEATURE:
<221> NAME/KEY: VARIANT
<222> LOCATION: 8..8
<223> OTHER INFORMATION: Xaa = Gly or Ser

<400> SEQUENCE: 174

Arg Ala Ser Gln Ser Ile Ser Xaa Tyr Leu Asn
1 5 10

<210> SEQ ID NO 175
<211> LENGTH: 7
<212> TYPE: PRT
<213> ORGANISM: Homo Sapiens
<220> FEATURE:
<221> NAME/KEY: VARIANT
<222> LOCATION: 1..1
<223> OTHER INFORMATION: Xaa = Gln, Ala or Asn

<400> SEQUENCE: 175

Xaa Ala Ser Ser Leu Gln Ser
1 5

<210> SEQ ID NO 176
<211> LENGTH: 10
<212> TYPE: PRT
<213> ORGANISM: Homo Sapiens
<220> FEATURE:
<221> NAME/KEY: VARIANT
<222> LOCATION: 5..6
<223> OTHER INFORMATION: Xaa = Thr or Ser
<220> FEATURE:
<221> NAME/KEY: VARIANT
<222> LOCATION: 8..8
<223> OTHER INFORMATION: Xaa = Gly or Phe

<400> SEQUENCE: 176

Gln Gln Ser Tyr Xaa Xaa Pro Xaa Ile Thr
1 5 10

<210> SEQ ID NO 177
<211> LENGTH: 645
<212> TYPE: DNA
<213> ORGANISM: Homo Sapiens

<400> SEQUENCE: 177
gacatccaga tgacccagag ccccagcagc ctgagcgcct ccgtgggcga cagagtgacc 60
atcacctgtc gggccagcca gagcatcagc ggctacctga actggtatca gcagaagccc 120
ggcaaggccc ccaagctgct gatctaccag gccagctccc tgcagagcgg cgtgccaagc 180
agattcagcg gcagcggctc cggcaccgac ttcaccctga ccatcagcag cctgcagccc 240
gaggacttcg ccacctacta ctgccagcag agctacacca gccccttcat caccttcggc 300
cagggcacca aggtggaaat caagcggacc gtggccgctc ccagcgtgtt catcttccca 360
cccagcgacg agcagctgaa gtccggcaca gccagcgtgg tctgcctgct gaacaacttc 420
tacccccgcg aggccaaggt gcagtggaag gtggacaacg ccctgcagtc cggcaactcc 480
caggaaagcg tgaccgagca ggacagcaag gactccacct acagcctgag cagcaccctg 540
accctgagca aggccgacta cgagaagcac aaggtgtacg cctgcgaagt gacccaccag 600
ggcctgtcca gccccgtgac caagagcttc aaccggggcg agtgc 645

<210> SEQ ID NO 178

<211> LENGTH: 1347
<212> TYPE: DNA
<213> ORGANISM: Homo Sapiens

<400> SEQUENCE: 178

```
gaagttcaat tgttagagtc cggcggaggc ctggtgcagc ctggcggcag cctgagactg     60
tcttgcgccg ccagcggctt cacattcagc ccctacccca tgatctgggt ccgccaggct    120
ccaggcaagg gcctggaatg ggtgtcctac atcagcccca gcggcggcag cacccactac    180
gccgatagcg tgaagggccg gttcaccatc agccgggaca acagcaagaa caccctgtac    240
ctgcagatga acagcctgcg ggccgaggac accgccgtgt actattgcgc cagaggcggc    300
gacacctact tcgattactt cgactactgg ggccagggca ccctggtgac agtgtccagc    360
gcctccacca agggcccatc ggtcttcccg ctagcaccca gcagcaagag caccagcggc    420
ggaacagccg ccctgggctg cctggtgaaa gactacttcc ccgagcccgt gaccgtgtcc    480
tggaactctg gcgccctgac cagcggagtg cataccttcc ccgccgtgct gcagagcagc    540
ggcctgtaca gcctgagcag cgtggtgaca gtgcccagca gcagcctggg aacccagacc    600
tacatctgca acgtgaacca caagcccagc aacaccaagg tggacaagaa ggtggaaccc    660
aagagctgcg acaagaccca cacctgtccc ccctgccctg cccctgaact gctgggcgga    720
cccagcgtgt tcctgttccc cccaaagccc aaggacaccc tgatgatcag ccggaccccc    780
gaagtgacct gcgtggtggt ggacgtgtcc cacgaggacc cagaagtgaa gtttaattgg    840
tacgtggacg gcgtggaagt gcataacgcc aagaccaagc ccagagagga acagtacaac    900
agcacctacc gggtggtgtc cgtgctgacc gtgctgcacc aggactggct gaacggcaaa    960
gagtacaagt gcaaggtctc caacaaggcc ctgcctgccc ccatcgagaa aaccatcagc   1020
aaggccaagg gccagccccg cgagcctcag gtgtacacac tgccccccag ccgggatgag   1080
ctgaccaaga accaggtgtc cctgacctgt ctggtgaaag gcttctaccc cagcgatatc   1140
gccgtggaat gggagagcaa cggccagccc gagaacaatt acaagaccac ccccccctgtg  1200
ctggacagcg acggctcatt cttcctgtac tccaagctga ccgtggacaa gagccggtgg   1260
cagcagggca acgtgttcag ctgcagcgtg atgcacgagg ccctgcacaa tcactacacc   1320
cagaagtccc tgagcctgag ccccggc                                       1347
```

<210> SEQ ID NO 179
<211> LENGTH: 645
<212> TYPE: DNA
<213> ORGANISM: Homo Sapiens

<400> SEQUENCE: 179

```
gacatccaga tgacccagtc tccagccacc ctgtctgcat ctgtaggaga cagagtcacc     60
atcacttgcc gggcaagtca gagcattagc ggctatttaa attggtatca gcagaaacca    120
gggaaagccc ctaagctcct gatctatcag gcatccagtt tgcaaagtgg ggtcccatca    180
aggttcagtg gcagtggatc tgggacagat ttcactctca ccatcagcag tctgcaacct    240
gaagattttg caacttacta ctgtcaacag agctacacta gtccattcat cactttcggc    300
cctgggacca aggtggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaactctacg cctgcgaagt cacccatcag    600
```

```
ggcctgagct cgcccgtcac aaagagcttc aacaggggag agtgt                   645


<210> SEQ ID NO 180
<211> LENGTH: 1347
<212> TYPE: DNA
<213> ORGANISM: Homo Sapiens

<400> SEQUENCE: 180

gaagttcaat tgttagagtc tggtggcggt cttgttcagc ctggtggttc tttacgtctt     60

tcttgcgctg cttccggatt cactttctct ccttacccta tgatctgggt tcgccaagct    120

cctggtaaag gtttggagtg ggtttcttat atctctcctt ctggtggcaa gactcattat    180

gctgactccg ttaaaggtcg cttcactatc tctagagaca actctaagaa tactctctac    240

ttgcagatga acagcttaag ggctgaggac acggccgtgt attactgtgc gagagggggt    300

gatacttatt tcgactactt tgactactgg ggccagggaa ccctggtcac cgtctcaagc    360

gcctccacca agggcccatc ggtcttcccg ctagcaccca gcagcaagag caccagcggc    420

ggaacagccg ccctgggctg cctggtgaaa gactacttcc ccgagcccgt gaccgtgtcc    480

tggaactctg gcgccctgac cagcggagtg cataccttcc ccgccgtgct gcagagcagc    540

ggcctgtaca gcctgagcag cgtggtgaca gtgcccagca gcagcctggg aacccagacc    600

tacatctgca acgtgaacca caagcccagc aacaccaagg tggacaagaa ggtggaaccc    660

aagagctgcg acaagaccca cacctgtccc ccctgccctg cccctgaact gctgggcgga    720

cccagcgtgt tcctgttccc cccaaagccc aaggacaccc tgatgatcag ccggaccccc    780

gaagtgacct gcgtggtggt ggacgtgtcc cacgaggacc cagaagtgaa gtttaattgg    840

tacgtggacg gcgtggaagt gcataacgcc aagaccaagc ccagagagga acagtacaac    900

agcacctacc gggtggtgtc cgtgctgacc gtgctgcacc aggactggct gaacggcaaa    960

gagtacaagt gcaaggtctc caacaaggcc ctgcctgccc ccatcgagaa aaccatcagc   1020

aaggccaagg gccagccccg cgagcctcag gtgtacacac tgcccccccag ccgggatgag   1080

ctgaccaaga accaggtgtc cctgacctgt ctggtgaaag gcttctaccc cagcgatatc   1140

gccgtggaat gggagagcaa cggccagccc gagaacaatt acaagaccac cccccctgtg   1200

ctggacagcg acggctcatt cttcctgtac tccaagctga ccgtggacaa gagccggtgg   1260

cagcagggca acgtgttcag ctgcagcgtg atgcacgagg ccctgcacaa tcactacacc   1320

cagaagtccc tgagcctgag ccccggc                                       1347


<210> SEQ ID NO 181
<211> LENGTH: 645
<212> TYPE: DNA
<213> ORGANISM: Homo Sapiens

<400> SEQUENCE: 181

gacatccaga tgacccagag ccccagcagc ctgagcgcct ccgtgggcga cagagtgacc     60

atcacctgtc gggccagcca gagcatcagc agctacctga actggtatca gcagaagccc    120

ggcaaggccc ccaagctgct gatctaccag gccagctccc tgcagagcgg cgtgccaagc    180

agattcagcg gcagcggctc cggcaccgac ttcaccctga ccatcagcag cctgcagccc    240

gaggacttcg ccacctacta ctgccagcag agctacacca gccccttcat caccttcggc    300

cagggcacca aggtggaaat caagcggacc gtggccgctc ccagcgtgtt catcttccca    360

cccagcgacg agcagctgaa gtccggcaca gccagcgtgg tctgcctgct gaacaacttc    420
```

```
taccccgcg aggccaaggt gcagtggaag gtggacaacg ccctgcagtc cggcaactcc    480

caggaaagcg tgaccgagca ggacagcaag gactccacct acagcctgag cagcaccctg    540

accctgagca aggccgacta cgagaagcac aaggtgtacg cctgcgaagt gacccaccag    600

ggcctgtcca gccccgtgac caagagcttc aaccggggcg agtgc                    645


<210> SEQ ID NO 182
<211> LENGTH: 1347
<212> TYPE: DNA
<213> ORGANISM: Homo Sapiens

<400> SEQUENCE: 182

gaagttcaat tgttagagtc cggcggaggc ctggtgcagc ctggcggcag cctgagactg     60

tcttgcgccg ccagcggctt cacattcagc ccctacccca tgatgtgggt ccgccaggct    120

ccaggcaagg gcctggaatg ggtgtcctac atcagcccca gcggcggcag cacccactac    180

gccgatagcg tgaagggccg gttcaccatc agccgggaca acagcaagaa caccctgtac    240

ctgcagatga acagcctgcg ggccgaggac accgccgtgt actattgcgc cagaggcggc    300

gacacctact tcgattactt cgactactgg ggccagggca ccctggtgac agtgtccagc    360

gcctccacca agggcccatc ggtcttcccg ctagcaccca gcagcaagag caccagcggc    420

ggaacagccg ccctgggctg cctggtgaaa gactacttcc ccgagcccgt gaccgtgtcc    480

tggaactctg gcgccctgac cagcggagtg cataccttcc ccgccgtgct gcagagcagc    540

ggcctgtaca gcctgagcag cgtggtgaca gtgcccagca gcagcctggg aacccagacc    600

tacatctgca acgtgaacca caagcccagc aacaccaagg tggacaagaa ggtggaaccc    660

aagagctgcg acaagaccca cacctgtccc ccctgccctg cccctgaact gctgggcgga    720

cccagcgtgt tcctgttccc cccaaagccc aaggacaccc tgatgatcag ccggaccccc    780

gaagtgacct gcgtggtggt ggacgtgtcc cacgaggacc cagaagtgaa gtttaattgg    840

tacgtggacg gcgtggaagt gcataacgcc aagaccaagc ccagagagga acagtacaac    900

agcacctacc gggtggtgtc cgtgctgacc gtgctgcacc aggactggct gaacggcaaa    960

gagtacaagt gcaaggtctc caacaaggcc ctgcctgccc ccatcgagaa aaccatcagc   1020

aaggccaagg gccagccccg cgagcctcag gtgtacacac tgccccccag ccgggatgag   1080

ctgaccaaga accaggtgtc cctgacctgt ctggtgaaag gcttctaccc cagcgatatc   1140

gccgtggaat gggagagcaa cggccagccc gagaacaatt acaagaccac cccccctgtg   1200

ctggacagcg acggctcatt cttcctgtac tccaagctga ccgtggacaa gagccggtgg   1260

cagcagggca acgtgttcag ctgcagcgtg atgcacgagg ccctgcacaa tcactacacc   1320

cagaagtccc tgagcctgag ccccggc                                       1347


<210> SEQ ID NO 183
<211> LENGTH: 645
<212> TYPE: DNA
<213> ORGANISM: Homo Sapiens

<400> SEQUENCE: 183

gacatccaga tgacccagtc tccagccacc ctgtctgcat ctgtaggaga cagagtcacc     60

atcacttgcc gggcaagtca gagcattagc agctatttaa attggtatca gcagaaacca    120

gggaaagccc ctaagctcct gatctatcag gcatccagtt tgcaaagtgg ggtcccatca    180

aggttcagtg gcagtggatc tgggacagat ttcactctca ccatcagcag tctgcaacct    240

gaagattttg caacttacta ctgtcaacag agctacacta gtccattcat cactttcggc    300
```

```
cctgggacca aggtggagat caaacgaact gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaactctacg cctgcgaagt cacccatcag    600

ggcctgagct cgcccgtcac aaagagcttc aacaggggag agtgt                    645
```

<210> SEQ ID NO 184
<211> LENGTH: 1347
<212> TYPE: DNA
<213> ORGANISM: Homo Sapiens

<400> SEQUENCE: 184

```
gaagttcaat tgttagagtc tggtggcggt cttgttcagc ctggtggttc tttacgtctt     60

tcttgcgctg cttccggatt cactttctct ccttacccta tgatgtgggt tcgccaagct    120

cctggtaaag gtttggagtg ggtttcttat atctctcctt ctggtggcaa gactcattat    180

gctgactccg ttaaaggtcg cttcactatc tctagagaca actctaagaa tactctctac    240

ttgcagatga acagcttaag ggctgaggac acggccgtgt attactgtgc gagagggggt    300

gatacttatt tcgactactt tgactactgg ggccagggaa ccctggtcac cgtctcaagc    360

gcctccacca agggcccatc ggtcttcccg ctagcaccca gcagcaagag caccagcggc    420

ggaacagccg ccctgggctg cctggtgaaa gactacttcc ccgagcccgt gaccgtgtcc    480

tggaactctg gcgccctgac cagcggagtg cataccttcc ccgccgtgct gcagagcagc    540

ggcctgtaca gcctgagcag cgtggtgaca gtgcccagca gcagcctggg aacccagacc    600

tacatctgca acgtgaacca caagcccagc aacaccaagg tggacaagaa ggtggaaccc    660

aagagctgcg acaagaccca cacctgtccc ccctgccctg cccctgaact gctgggcgga    720

cccagcgtgt tcctgttccc cccaaagccc aaggacaccc tgatgatcag ccggaccccc    780

gaagtgacct gcgtggtggt ggacgtgtcc cacgaggacc cagaagtgaa gtttaattgg    840

tacgtggacg gcgtggaagt gcataacgcc aagaccaagc ccagagagga acagtacaac    900

agcacctacc gggtggtgtc cgtgctgacc gtgctgcacc aggactggct gaacggcaaa    960

gagtacaagt gcaaggtctc caacaaggcc ctgcctgccc ccatcgagaa aaccatcagc   1020

aaggccaagg gccagccccg cgagcctcag gtgtacacac tgccccccag ccgggatgag   1080

ctgaccaaga accaggtgtc cctgacctgt ctggtgaaag gcttctaccc cagcgatatc   1140

gccgtggaat gggagagcaa cggccagccc gagaacaatt acaagaccac ccccccctgtg   1200

ctggacagcg acggctcatt cttcctgtac tccaagctga ccgtggacaa gagccggtgg   1260

cagcagggca acgtgttcag ctgcagcgtg atgcacgagg ccctgcacaa tcactacacc   1320

cagaagtccc tgagcctgag ccccggc                                       1347
```

<210> SEQ ID NO 185
<211> LENGTH: 645
<212> TYPE: DNA
<213> ORGANISM: Homo Sapiens

<400> SEQUENCE: 185

```
gacatccaga tgacccagag ccccagcagc ctgtctgcca gcgtgggcga cagagtgacc     60

atcacctgta gagccagcca gagcatcagc agctacctga actggtatca gcagaagccc    120
```

```
ggcaaggccc ccaagctgct gatctatgcc gccagctctc tgcagagcgg agtgcccagc    180

agattttctg gcagcggcag cggcaccgac ttcaccctga caatcagcag cctgcagccc    240

gaggacttcg ccacctacta ctgccagcag agctacagca cccccggcat cacatttggc    300

cagggcacca aggtggaaat caagcggaca gtggccgctc ccagcgtgtt catcttccca    360

cctagcgacg agcagctgaa gtccggcaca gccagcgtcg tgtgcctgct gaacaacttc    420

tacccccgcg aggccaaggt gcagtggaag gtggacaatg ccctgcagtc cggcaactcc    480

caggaaagcg tcaccgagca ggacagcaag gactccacct acagcctgag cagcaccctg    540

accctgagca aggccgacta cgagaagcac aaggtgtacg cctgcgaagt gacccaccag    600

ggcctgtcta gccccgtgac caagagcttc aaccggggcg agtgt                    645
```

<210> SEQ ID NO 186
<211> LENGTH: 1347
<212> TYPE: DNA
<213> ORGANISM: Homo Sapiens

<400> SEQUENCE: 186

```
gaagttcaat tgttagagtc cggcggaggc ctggtgcagc ctggcggatc tctgagactg     60

agctgtgccg ccagcggctt caccttcagc ccctacccta tgatgtgggt ccgacaggcc    120

cctggcaagg gactggaatg ggtgtcctac atctctccca gcggcggcag cacccactac    180

gccgattctg tgaagggccg gttcaccatc agccgggaca acagcaagaa caccctgtac    240

ctgcagatga acagcctgcg ggccgaggac accgccgtgt actattgtgc cagaggcggc    300

gacacctact tcgattactt cgactactgg ggccagggca ccctggtcac cgtgtcatct    360

gcctccacca agggcccatc ggtcttcccg ctagcaccca gcagcaagag caccagcggc    420

ggaacagccg ccctgggctg cctggtgaaa gactacttcc ccgagcccgt gaccgtgtcc    480

tggaactctg gcgccctgac cagcggagtg cataccttcc ccgccgtgct gcagagcagc    540

ggcctgtaca gcctgagcag cgtggtgaca gtgcccagca gcagcctggg aacccagacc    600

tacatctgca acgtgaacca caagcccagc aacaccaagg tggacaagaa ggtggaaccc    660

aagagctgcg acaagaccca cacctgtccc ccctgccctg cccctgaact gctgggcgga    720

cccagcgtgt tcctgttccc cccaaagccc aaggacaccc tgatgatcag ccggaccccc    780

gaagtgacct gcgtggtggt ggacgtgtcc cacgaggacc cagaagtgaa gtttaattgg    840

tacgtggacg gcgtggaagt gcataacgcc aagaccaagc ccagagagga acagtacaac    900

agcacctacc gggtggtgtc cgtgctgacc gtgctgcacc aggactggct gaacggcaaa    960

gagtacaagt gcaaggtctc caacaaggcc ctgcctgccc ccatcgagaa aaccatcagc   1020

aaggccaagg gccagccccg cgagcctcag gtgtacacac tgccccccag ccgggatgag   1080

ctgaccaaga accaggtgtc cctgacctgt ctggtgaaag gcttctaccc cagcgatatc   1140

gccgtggaat gggagagcaa cggccagccc gagaacaatt acaagaccac cccccctgtg   1200

ctggacagcg acggctcatt cttcctgtac tccaagctga ccgtggacaa gagccggtgg   1260

cagcagggca acgtgttcag ctgcagcgtg atgcacgagg ccctgcacaa tcactacacc   1320

cagaagtccc tgagcctgag ccccggc                                       1347
```

<210> SEQ ID NO 187
<211> LENGTH: 645
<212> TYPE: DNA
<213> ORGANISM: Homo Sapiens

<400> SEQUENCE: 187

```
gacatccaga tgacccagtc tccagccacc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcaacag agctactcta gtccagggat cactttcggc    300

cctgggacca aggtggagat caaacgaact gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaactctacg cctgcgaagt cacccatcag    600

ggcctgagct cgcccgtcac aaagagcttc aacaggggag agtgt                     645
```

<210> SEQ ID NO 188
<211> LENGTH: 1347
<212> TYPE: DNA
<213> ORGANISM: Homo Sapiens

<400> SEQUENCE: 188

```
gaagttcaat tgttagagtc tggtggcggt cttgttcagc ctggtggttc tttacgtctt     60

tcttgcgctg cttccggatt cactttctct ccttacccta tgatgtgggt tcgccaagct    120

cctggtaaag gtttggagtg ggtttcttat atctctcctt ctggtggcaa gactcattat    180

gctgactccg ttaaaggtcg cttcactatc tctagagaca actctaagaa tactctctac    240

ttgcagatga acagcttaag ggctgaggac acggccgtgt attactgtgc gagagggggt    300

gatacgtatt tcgactactt tgactactgg ggccagggaa ccctggtcac cgtctcaagc    360

gcctccacca agggcccatc ggtcttcccg ctagcaccca gcagcaagag caccagcggc    420

ggaacagccg ccctgggctg cctggtgaaa gactacttcc ccgagcccgt gaccgtgtcc    480

tggaactctg gcgccctgac cagcggagtg cataccttcc ccgccgtgct gcagagcagc    540

ggcctgtaca gcctgagcag cgtggtgaca gtgcccagca gcagcctggg aacccagacc    600

tacatctgca acgtgaacca caagcccagc aacaccaagg tggacaagaa ggtggaaccc    660

aagagctgcg acaagaccca cacctgtccc ccctgccctg cccctgaact gctgggcgga    720

cccagcgtgt tcctgttccc cccaaagccc aaggacaccc tgatgatcag ccggaccccc    780

gaagtgacct gcgtggtggt ggacgtgtcc cacgaggacc cagaagtgaa gtttaattgg    840

tacgtggacg gcgtggaagt gcataacgcc aagaccaagc ccagagagga acagtacaac    900

agcacctacc gggtggtgtc cgtgctgacc gtgctgcacc aggactggct gaacggcaaa    960

gagtacaagt gcaaggtctc caacaaggcc ctgcctgccc ccatcgagaa aaccatcagc   1020

aaggccaagg gccagccccg cgagcctcag gtgtacacac tgccccccag ccgggatgag   1080

ctgaccaaga accaggtgtc cctgacctgt ctggtgaaag gcttctaccc cagcgatatc   1140

gccgtggaat gggagagcaa cggccagccc gagaacaatt acaagaccac cccccctgtg   1200

ctggacagcg acggctcatt cttcctgtac tccaagctga ccgtggacaa gagccggtgg   1260

cagcagggca acgtgttcag ctgcagcgtg atgcacgagg ccctgcacaa tcactacacc   1320

cagaagtccc tgagcctgag ccccggc                                       1347
```

<210> SEQ ID NO 189

<211> LENGTH: 651
<212> TYPE: DNA
<213> ORGANISM: Homo Sapiens

<400> SEQUENCE: 189
gcacaagaca tccagatgac ccagtctcca gccaccctgt ctgcatctgt aggagacaga 60
gtcaccatca cttgccgggc aagtcagagc attagcagct atttaaattg gtatcagcag 120
aaaccaggga aagcccctaa gctcctgatc tatgctgcat ccagtttgca aagtggggtc 180
ccatcaaggt tcagtggcag tggatctggg acagatttca ctctcaccat cagcagtctg 240
caacctgaag attttgcaac ttactactgt caacagagct actctagtcc agggatcact 300
ttcggccctg ggaccaaggt ggagatcaaa cgaactgtgg ctgcaccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaac tctacgcctg cgaagtcacc 600
catcagggcc tgagctcgcc cgtcacaaag agcttcaaca ggggagagtg t 651

<210> SEQ ID NO 190
<211> LENGTH: 1347
<212> TYPE: DNA
<213> ORGANISM: Homo Sapiens

<400> SEQUENCE: 190
gaagttcaat tgttagagtc tggtggcggt cttgttcagc ctggtggttc tttacgtctt 60
tcttgcgctg cttccggatt cactttctct ccttacccta tgatgtgggt tcgccaagct 120
cctggtaaag gtttggagtg ggtttcttat atctctcctt ctggtggcaa gactcattat 180
gctgactccg ttaaaggtcg cttcactatc tctagagaca actctaagaa tactctctac 240
ttgcagatga acagcttaag ggctgaggac acggccgtgt attactgtgc gagagggggt 300
gatacgtatt tcgactactt tgactactgg ggccagggaa ccctggtcac cgtctcaagc 360
gcctccacca agggcccatc ggtcttcccg ctagcaccca gcagcaagag caccagcggc 420
ggaacagccg ccctgggctg cctggtgaaa gactacttcc ccgagcccgt gaccgtgtcc 480
tggaactctg gcgccctgac cagcggagtg cataccttcc ccgccgtgct gcagagcagc 540
ggcctgtaca gcctgagcag cgtggtgaca gtgcccagca gcagcctggg aacccagacc 600
tacatctgca acgtgaacca caagcccagc aacaccaagg tggacaagcg ggtggaaccc 660
aagagctgcg acaagaccca cacctgtccc ccctgccctg cccctgaact gctgggcgga 720
cccagcgtgt tcctgttccc cccaaagccc aaggacaccc tgatgatcag ccggaccccc 780
gaagtgacct gcgtggtggt ggacgtgtcc cacgaggacc cagaagtgaa gtttaattgg 840
tacgtggacg gcgtggaagt gcataacgcc aagaccaagc ccagagagga acagtacaac 900
agcacctacc gggtggtgtc cgtgctgacc gtgctgcacc aggactggct gaacggcaaa 960
gagtacaagt gcaaggtctc caacaaggcc ctgcctgccc ccatcgagaa aaccatcagc 1020
aaggccaagg gccagccccg cgagcctcag gtgtacacac tgccccccag ccgggaagag 1080
atgaccaaga accaggtgtc cctgacctgt ctggtgaaag gcttctaccc cagcgatatc 1140
gccgtggaat gggagagcaa cggccagccc gagaacaatt acaagaccac cccccctgtg 1200
ctggacagcg acggctcatt cttcctgtac tccaagctga ccgtggacaa gagccggtgg 1260
cagcagggca acgtgttcag ctgcagcgtg atgcacgagg ccctgcacaa tcactacacc 1320
cagaagtccc tgagcctgag ccccggc 1347

<210> SEQ ID NO 191
<211> LENGTH: 651
<212> TYPE: DNA
<213> ORGANISM: Homo Sapiens

<400> SEQUENCE: 191
gcacaagaca tccagatgac ccagtctcca gccaccctgt ctgcatctgt aggagacaga 60
gtcaccatca cttgccgggc aagtcagagc attagcagct atttaaattg gtatcagcag 120
aaaccaggga aagcccctaa gctcctgatc tatgctgcat ccagtttgca aagtggggtc 180
ccatcaaggt tcagtggcag tggatctggg acagatttca ctctcaccat cagcagtctg 240
caacctgaag attttgcaac ttactactgt caacagagct actctagtcc agggatcact 300
ttcggccctg ggaccaaggt ggagatcaaa cgaactgtgg ctgcaccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaac tctacgcctg cgaagtcacc 600
catcagggcc tgagctcgcc cgtcacaaag agcttcaaca ggggagagtg t 651

<210> SEQ ID NO 192
<211> LENGTH: 1347
<212> TYPE: DNA
<213> ORGANISM: Homo Sapiens

<400> SEQUENCE: 192
gaagttcaat tgttagagtc tggtggcggt cttgttcagc ctggtggttc tttacgtctt 60
tcttgcgctg cttccggatt cactttctct ccttacccta tgatgtgggt tcgccaagct 120
cctggtaaag gtttggagtg ggtttcttat atctctcctt ctggtggcaa gactcattat 180
gctgactccg ttaaaggtcg cttcactatc tctagagaca actctaagaa tactctctac 240
ttgcagatga acagcttaag ggctgaggac acggccgtgt attactgtgc gagagggggt 300
gatggttatt tcgactactt tgactactgg ggccagggaa ccctggtcac cgtctcaagc 360
gcctccacca agggcccatc ggtcttcccg ctagcaccca gcagcaagag caccagcggc 420
ggaacagccg ccctgggctg cctggtgaaa gactacttcc ccgagcccgt gaccgtgtcc 480
tggaactctg gcgccctgac cagcggagtg cataccttcc ccgccgtgct gcagagcagc 540
ggcctgtaca gcctgagcag cgtggtgaca gtgcccagca gcagcctggg aacccagacc 600
tacatctgca acgtgaacca caagcccagc aacaccaagg tggacaagcg ggtggaaccc 660
aagagctgcg acaagaccca cacctgtccc ccctgccctg cccctgaact gctgggcgga 720
cccagcgtgt tcctgttccc cccaaagccc aaggacaccc tgatgatcag ccggaccccc 780
gaagtgacct gcgtggtggt ggacgtgtcc cacgaggacc cagaagtgaa gtttaattgg 840
tacgtggacg gcgtggaagt gcataacgcc aagaccaagc ccagagagga acagtacaac 900
agcacctacc gggtggtgtc cgtgctgacc gtgctgcacc aggactggct gaacggcaaa 960
gagtacaagt gcaaggtctc caacaaggcc ctgcctgccc ccatcgagaa aaccatcagc 1020
aaggccaagg gccagccccg cgagcctcag gtgtacacac tgccccccag ccgggaagag 1080
atgaccaaga accaggtgtc cctgacctgt ctggtgaaag gcttctaccc cagcgatatc 1140

```
gccgtggaat gggagagcaa cggccagccc gagaacaatt acaagaccac ccccctgtg   1200

ctggacagcg acggctcatt cttcctgtac tccaagctga ccgtggacaa gagccggtgg   1260

cagcagggca acgtgttcag ctgcagcgtg atgcacgagg ccctgcacaa tcactacacc   1320

cagaagtccc tgagcctgag ccccggc                                        1347
```

<210> SEQ ID NO 193
<211> LENGTH: 651
<212> TYPE: DNA
<213> ORGANISM: Homo Sapiens

<400> SEQUENCE: 193

```
gcacaagaca tccagatgac ccagtctcca gccaccctgt ctgcatctgt aggagacaga     60

gtcaccatca cttgccgggc aagtcagagc attagcggct atttaaattg gtatcagcag    120

aaaccaggga aagcccctaa gctcctgatc tataacgcat ccagtttgca aagtggggtc    180

ccatcaaggt tcagtggcag tggatctggg acagatttca ctctcaccat cagcagtctg    240

caacctgaag attttgcaac ttactactgt caacagagct acactagtcc attcatcact    300

ttcggccctg ggaccaaggt ggagatcaaa cgaactgtgg ctgcaccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaac tctacgcctg cgaagtcacc    600

catcagggcc tgagctcgcc cgtcacaaag agcttcaaca ggggagagtg t             651
```

<210> SEQ ID NO 194
<211> LENGTH: 1347
<212> TYPE: DNA
<213> ORGANISM: Homo Sapiens

<400> SEQUENCE: 194

```
gaagttcaat tgttagagtc tggtggcggt cttgttcagc ctggtggttc tttacgtctt     60

tcttgcgctg cttccggatt cactttctct ccttacccta tgatctgggt tcgccaagct    120

cctggtaaag gtttggagtg ggtttcttat atctctcctt ctggtggcaa gactcattat    180

gctgactccg ttaaaggtcg cttcactatc tctagagaca actctaagaa tactctctac    240

ttgcagatga acagcttaag ggctgaggac acggccgtgt attactgtgc gagagggggt    300

gatacttatt tcgactactt tgactactgg ggccagggaa ccctggtcac cgtctcaagc    360

gcctccacca agggcccatc ggtcttcccg ctagcaccca gcagcaagag caccagcggc    420

ggaacagccg ccctgggctg cctggtgaaa gactacttcc ccgagcccgt gaccgtgtcc    480

tggaactctg gcgccctgac cagcggagtg catacctttcc ccgccgtgct gcagagcagc    540

ggcctgtaca gcctgagcag cgtggtgaca gtgcccagca gcagcctggg aacccagacc    600

tacatctgca acgtgaacca caagcccagc aacaccaagg tggacaagaa ggtggaaccc    660

aagagctgcg acaagaccca cacctgtccc ccctgccctg cccctgaact gctgggcgga    720

cccagcgtgt tcctgttccc cccaaagccc aaggacaccc tgatgatcag ccggaccccc    780

gaagtgacct gcgtggtggt ggacgtgtcc cacgaggacc cagaagtgaa gtttaattgg    840

tacgtggacg gcgtggaagt gcataacgcc aagaccaagc ccagagagga acagtacaac    900

agcacctacc gggtggtgtc cgtgctgacc gtgctgcacc aggactggct gaacggcaaa    960

gagtacaagt gcaaggtctc caacaaggcc ctgcctgccc ccatcgagaa aaccatcagc   1020
```

```
aaggccaagg gccagccccg cgagcctcag gtgtacacac tgccccccag ccgggatgag   1080

ctgaccaaga accaggtgtc cctgacctgt ctggtgaaag gcttctaccc cagcgatatc   1140

gccgtggaat gggagagcaa cggccagccc gagaacaatt acaagaccac ccccccctgtg  1200

ctggacagcg acggctcatt cttcctgtac tccaagctga ccgtggacaa gagccggtgg   1260

cagcagggca acgtgttcag ctgcagcgtg atgcacgagg ccctgcacaa tcactacacc   1320

cagaagtccc tgagcctgag ccccggc                                       1347


<210> SEQ ID NO 195
<211> LENGTH: 651
<212> TYPE: DNA
<213> ORGANISM: Homo Sapiens

<400> SEQUENCE: 195

gcacaagaca tccagatgac ccagtctcca gccaccctgt ctgcatctgt aggagacaga     60

gtcaccatca cttgccgggc aagtcagagc attagcagct atttaaattg gtatcagcag    120

aaaccaggga aagcccctaa gctcctgatc tataacgcat ccagtttgca aagtggggtc    180

ccatcaaggt tcagtggcag tggatctggg acagatttca ctctcaccat cagcagtctg    240

caacctgaag attttgcaac ttactactgt caacagagct acactagtcc agggatcact    300

ttcggccctg ggaccaaggt ggagatcaaa cgaactgtgg ctgcaccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaac tctacgcctg cgaagtcacc    600

catcagggcc tgagctcgcc cgtcacaaag agcttcaaca ggggagagtg t             651


<210> SEQ ID NO 196
<211> LENGTH: 1347
<212> TYPE: DNA
<213> ORGANISM: Homo Sapiens

<400> SEQUENCE: 196

gaagttcaat tgttagagtc tggtggcggt cttgttcagc ctggtggttc tttacgtctt     60

tcttgcgctg cttccggatt cactttctct ccttacccta tgatgtgggt tcgccaagct    120

cctggtaaag gtttggagtg ggtttcttat atctctcctt ctggtggcaa gactcattat    180

gctgactccg ttaaaggtcg cttcactatc tctagagaca actctaagaa tactctctac    240

ttgcagatga acagcttaag ggctgaggac acggccgtgt attactgtgc gagagggggt    300

gatacttatt tcgactactt tgactactgg ggccagggaa ccctggtcac cgtctcaagc    360

gcctccacca agggcccatc ggtcttcccg ctagcaccca gcagcaagag caccagcggc    420

ggaacagccg ccctgggctg cctggtgaaa gactacttcc ccgagcccgt gaccgtgtcc    480

tggaactctg gcgccctgac cagcggagtg catacettcc ccgccgtgct gcagagcagc    540

ggcctgtaca gcctgagcag cgtggtgaca gtgcccagca gcagcctggg aacccagacc    600

tacatctgca acgtgaacca caagcccagc aacaccaagg tggacaagaa ggtggaaccc    660

aagagctgcg acaagaccca cacctgtccc ccctgccctg cccctgaact gctgggcgga    720

cccagcgtgt tcctgttccc cccaaagccc aaggacaccc tgatgatcag ccggaccccc    780

gaagtgacct gcgtggtggt ggacgtgtcc cacgaggacc cagaagtgaa gtttaattgg    840
```

```
tacgtggacg gcgtggaagt gcataacgcc aagaccaagc ccagagagga acagtacaac    900

agcacctacc gggtggtgtc cgtgctgacc gtgctgcacc aggactggct gaacggcaaa    960

gagtacaagt gcaaggtctc caacaaggcc ctgcctgccc ccatcgagaa aaccatcagc   1020

aaggccaagg gccagccccg cgagcctcag gtgtacacac tgcccccccag ccgggatgag   1080

ctgaccaaga accaggtgtc cctgacctgt ctggtgaaag gcttctaccc cagcgatatc   1140

gccgtggaat gggagagcaa cggccagccc gagaacaatt acaagaccac cccccctgtg   1200

ctggacagcg acggctcatt cttcctgtac tccaagctga ccgtggacaa gagccggtgg   1260

cagcagggca acgtgttcag ctgcagcgtg atgcacgagg ccctgcacaa tcactacacc   1320

cagaagtccc tgagcctgag ccccggc                                         1347
```

<210> SEQ ID NO 197
<211> LENGTH: 651
<212> TYPE: DNA
<213> ORGANISM: Homo Sapiens

<400> SEQUENCE: 197

```
gcacaagaca tccagatgac ccagtctcca gccaccctgt ctgcatctgt aggagacaga     60

gtcaccatca cttgccgggc aagtcagagc attagcggct atttaaattg gtatcagcag    120

aaaccaggga aagcccctaa gctcctgatc tataacgcat ccagtttgca aagtggggtc    180

ccatcaaggt tcagtggcag tggatctggg acagatttca ctctcaccat cagcagtctg    240

caacctgaag attttgcaac ttactactgt caacagagct acactagtcc agggatcact    300

ttcggccctg ggaccaaggt ggagatcaaa cgaactgtgg ctgcaccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaac tctacgcctg cgaagtcacc    600

catcagggcc tgagctcgcc cgtcacaaag agcttcaaca ggggagagtg t             651
```

<210> SEQ ID NO 198
<211> LENGTH: 1347
<212> TYPE: DNA
<213> ORGANISM: Homo Sapiens

<400> SEQUENCE: 198

```
gaagttcaat tgttagagtc tggtggcggt cttgttcagc ctggtggttc tttacgtctt     60

tcttgcgctg cttccggatt cactttctct ccttacccta tgatgtgggt tcgccaagct    120

cctggtaaag gtttggagtg ggtttcttat atctctcctt ctggtggcaa gactcattat    180

gctgactccg ttaaaggtcg cttcactatc tctagagaca actctaagaa tactctctac    240

ttgcagatga acagcttaag ggctgaggac acggccgtgt attactgtgc gagagggggt    300

gatacttatt tcgactactt tgactactgg ggccagggaa ccctggtcac cgtctcaagc    360

gcctccacca agggcccatc ggtcttcccg ctagcaccca gcagcaagag caccagcggc    420

ggaacagccg ccctgggctg cctggtgaaa gactacttcc ccgagcccgt gaccgtgtcc    480

tggaactctg gcgccctgac cagcggagtg cataccttcc ccgccgtgct gcagagcagc    540

ggcctgtaca gcctgagcag cgtggtgaca gtgcccagca gcagcctggg aacccagacc    600

tacatctgca acgtgaacca caagcccagc aacaccaagg tggacaagaa ggtggaaccc    660

aagagctgcg acaagaccca cacctgtccc ccctgccctg cccctgaact gctgggcgga    720
```

```
cccagcgtgt tcctgttccc cccaaagccc aaggacaccc tgatgatcag ccggaccccc    780

gaagtgacct gcgtggtggt ggacgtgtcc cacgaggacc cagaagtgaa gtttaattgg    840

tacgtggacg gcgtggaagt gcataacgcc aagaccaagc ccagagagga acagtacaac    900

agcacctacc gggtggtgtc cgtgctgacc gtgctgcacc aggactggct gaacggcaaa    960

gagtacaagt gcaaggtctc caacaaggcc ctgcctgccc ccatcgagaa aaccatcagc   1020

aaggccaagg gccagccccg cgagcctcag gtgtacacac tgccccccag ccgggatgag   1080

ctgaccaaga accaggtgtc cctgacctgt ctggtgaaag gcttctaccc cagcgatatc   1140

gccgtggaat gggagagcaa cggccagccc gagaacaatt acaagaccac ccccccctgtg   1200

ctggacagcg acggctcatt cttcctgtac tccaagctga ccgtggacaa gagccggtgg   1260

cagcagggca acgtgttcag ctgcagcgtg atgcacgagg ccctgcacaa tcactacacc   1320

cagaagtccc tgagcctgag ccccggc                                       1347
```

```
<210> SEQ ID NO 199
<211> LENGTH: 651
<212> TYPE: DNA
<213> ORGANISM: Homo Sapiens

<400> SEQUENCE: 199

gcacaagaca tccagatgac ccagtctcca gccaccctgt ctgcatctgt aggagacaga     60

gtcaccatca cttgccgggc aagtcagagc attagcagct atttaaattg gtatcagcag    120

aaaccaggga aagcccctaa gctcctgatc tataacgcat ccagtttgca aagtggggtc    180

ccatcaaggt tcagtggcag tggatctggg acagatttca ctctcaccat cagcagtctg    240

caacctgaag attttgcaac ttactactgt caacagagct acactagtcc attcatcact    300

ttcggccctg ggaccaaggt ggagatcaaa cgaactgtgg ctgcaccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaac tctacgcctg cgaagtcacc    600

catcagggcc tgagctcgcc cgtcacaaag agcttcaaca ggggagagtg t             651
```

```
<210> SEQ ID NO 200
<211> LENGTH: 1347
<212> TYPE: DNA
<213> ORGANISM: Homo Sapiens

<400> SEQUENCE: 200

gaagttcaat tgttagagtc tggtggcggt cttgttcagc ctggtggttc tttacgtctt     60

tcttgcgctg cttccggatt cactttctct ccttacccta tgatgtgggt tcgccaagct    120

cctggtaaag gtttggagtg ggtttcttat atctctcctt ctggtggcaa gactcattat    180

gctgactccg ttaaaggtcg cttcactatc tctagagaca actctaagaa tactctctac    240

ttgcagatga acagcttaag ggctgaggac acggccgtgt attactgtgc gagagggggt    300

gatacttatt tcgactactt tgactactgg ggccagggaa ccctggtcac cgtctcaagc    360

gcctccacca agggcccatc ggtcttcccg ctagcaccca gcagcaagag caccagcggc    420

ggaacagccg ccctgggctg cctggtgaaa gactacttcc ccgagcccgt gaccgtgtcc    480

tggaactctg gcgccctgac cagcggagtg catacccttcc ccgccgtgct gcagagcagc    540
```

```
ggcctgtaca gcctgagcag cgtggtgaca gtgcccagca gcagcctggg aacccagacc    600

tacatctgca acgtgaacca caagcccagc aacaccaagg tggacaagaa ggtggaaccc    660

aagagctgcg acaagaccca cacctgtccc ccctgccctg cccctgaact gctgggcgga    720

cccagcgtgt tcctgttccc cccaaagccc aaggacaccc tgatgatcag ccggaccccc    780

gaagtgacct gcgtggtggt ggacgtgtcc cacgaggacc cagaagtgaa gtttaattgg    840

tacgtggacg gcgtggaagt gcataacgcc aagaccaagc ccagagagga acagtacaac    900

agcacctacc gggtggtgtc cgtgctgacc gtgctgcacc aggactggct gaacggcaaa    960

gagtacaagt gcaaggtctc caacaaggcc ctgcctgccc ccatcgagaa aaccatcagc   1020

aaggccaagg gccagccccg cgagcctcag gtgtacacac tgccccccag ccgggatgag   1080

ctgaccaaga accaggtgtc cctgacctgt ctggtgaaag gcttctaccc cagcgatatc   1140

gccgtggaat gggagagcaa cggccagccc gagaacaatt acaagaccac cccccctgtg   1200

ctggacagcg acggctcatt cttcctgtac tccaagctga ccgtggacaa gagccggtgg   1260

cagcagggca acgtgttcag ctgcagcgtg atgcacgagg ccctgcacaa tcactacacc   1320

cagaagtccc tgagcctgag ccccggc                                       1347
```

<210> SEQ ID NO 201
<211> LENGTH: 654
<212> TYPE: DNA
<213> ORGANISM: Mus Musculus

<400> SEQUENCE: 201

```
gatatcgtgc tgacacagtc tcccgccagc ctggccgtgt ctctcggcca gagagccacc     60

atcagctgcc gggccaacaa gagcgtgtcc accagcagct acagctacat gcactggtat    120

cagcagaagc ccggccagcc ccccaagctg ctgattaagt acgccagcaa cctggaaagc    180

ggcgtgcccg ccagattcag cggcagcggc tctggcaccg acttcatcct gaacatccac    240

cccgtggaag aagaggacgc cgccacctac tactgccagc acagcagaga gctgcccttc    300

accttcggca gcggcaccaa gctggaaatc aagcgggccg atgccgcccc taccgtgtcc    360

atcttcccac ccagcagcga gcagctgacc agcggcggag ccagcgtcgt gtgcttcctg    420

aacaacttct accccaagga catcaacgtg aagtggaaga tcgacggcag cgagcggcag    480

aacggcgtgc tgaacagctg gaccgaccag gacagcaagg actccaccta cagcatgagc    540

agcaccctga ccctgaccaa ggacgagtac gagcggcaca acagctacac atgcgaggcc    600

acccacaaga ccagcaccag ccccatcgtg aagtccttca accggaacga gtgc          654
```

<210> SEQ ID NO 202
<211> LENGTH: 1350
<212> TYPE: DNA
<213> ORGANISM: Mus Musculus

<400> SEQUENCE: 202

```
caggtgcagc tgcagcagtc tggccctgaa gtcgtgcggc ctggcgtgtc cgtgaagatc     60

agctgcaagg gcagcggcta caccttcacc gactacggca tccactgggt caagcagagc    120

cacgccaaga gcctggaatg gatcggcgtg atcagcacct acaacggcta caccaactac    180

aaccagaagt tcaagggcaa ggccaccatg accgtggaca agagcagcag caccgcctac    240

atggaactgg cccggctgac cagcgaggac agcgccatct actactgcgc cagagcctac    300

tacggcaacc tgtactacgc catggactac tggggccagg gcaccagcgt gaccgtgtcc    360

tctgccaaga ccaccgcccc tagcgtgtac cctctggccc ctgtgtgtgg cgacaccacc    420
```

ggcagctctg tgactctggg ctgcctggtc aagggctact tccccgagcc cgtgacactg 480
acctggaaca gcggcagcct gagcagcggc gtgcacacct ttccagccgt gctgcagagc 540
gacctgtaca ccctgagcag ctccgtgacc gtgacaagca gcacctggcc cagccagagc 600
atcacctgta acgtggccca ccccgccagc agcaccaagg tggacaagaa gatcgagccc 660
agaggcccca ccatcaagcc ctgccccct tgcaagtgcc cagcccccaa tctgctgggc 720
ggacccagcg tgttcatctt cccacccaag atcaaggacg tgctgatgat cagcctgagc 780
cccatcgtga cctgcgtggt ggtggacgtg tccgaggacg accccgacgt gcagatcagt 840
tggttcgtga acaacgtgga agtgcacacc gcccagaccc agacccacag agaggactac 900
aacagcaccc tgcgggtggt gtccgccctg cccatccagc accaggactg gatgagcggc 960
aaagaattca agtgcaaagt gaacaacaag gacctgcctg cccccatcga gcggaccatc 1020
agcaagccca agggcagcgt gcgggctccc caggtgtacg tgctgccccc acccgaggaa 1080
gagatgacca agaagcaggt cacactgacc tgcatggtca ccgacttcat gcccgaggac 1140
atctacgtgg aatggaccaa caacggcaag accgagctga actacaagaa caccgagcct 1200
gtgctggaca gcgacggcag ctacttcatg tacagcaagc tgcgggtgga aaagaaaaac 1260
tgggtggaac ggaacagcta cagctgcagc gtggtgcacg agggcctgca caaccaccac 1320
accaccaaga gcttcagccg gaccccggc 1350

<210> SEQ ID NO 203
<211> LENGTH: 654
<212> TYPE: DNA
<213> ORGANISM: Mus Musculus

<400> SEQUENCE: 203
gatatcgtgc tgacacagag ccccgccagc ctgaccgtgt ctctcggcca gagagccacc 60
atcagctgcc gggccagcca gagcgtgtcc accagcagct acagctacat gcagtggtat 120
cagcagcggc ctggccagcc ccccaagctg ctgattaagt acgccaccaa cctggacagc 180
ggcgtgcccg ccagattttc tggcagcggc agcggcacag acttcaccct gaacatccac 240
cccgtggaag aagaggacgc cgccacctac tactgccagc acagctggga gatcccttac 300
accttcggcg gaggcaccaa gctggaaatc aagcgggccg atgccgcccc taccgtgtcc 360
atcttcccac ccagcagcga gcagctgacc agcggcggag ccagcgtcgt gtgcttcctg 420
aacaacttct accccaagga catcaacgtg aagtggaaga tcgacggcag cgagcggcag 480
aacggcgtgc tgaacagctg gaccgaccag gacagcaagg actccaccta cagcatgagc 540
agcaccctga ccctgaccaa ggacgagtac gagcggcaca acagctacac atgcgaggcc 600
acccacaaga ccagcaccag ccccatcgtg aagtccttca accggaacga gtgc 654

<210> SEQ ID NO 204
<211> LENGTH: 1344
<212> TYPE: DNA
<213> ORGANISM: Mus Musculus

<400> SEQUENCE: 204
gaagtgaagc tggaagagtc tggcggcgga ctggtccagc ctggcggcag catgaagctg 60
agctgcgtgg ccagcggctt caccttcaac aactactgga tgagctgggt ccgacagagc 120
cccgagaagg gcctggaatg gctggccgag atccggctga agtccgacaa ctacgccacc 180
cactacgccg agagcgtgaa gggcaagttc accatcagcc gggacgacag caagagccgg 240

```
ctgtacctgc agatgaacaa cctgcgggcc gagaacaccg gcatctacta ctgcaccggc    300

ggcttcgccg actacttcga ctactggggc cagggcacca ccctgaccgt gtcctctgcc    360

aagaccaccg cccctagcgt gtaccctctg gcccctgtgt gtggcgacac caccggcagc    420

tctgtgactc tgggctgcct ggtcaagggc tacttccccg agcccgtgac actgacctgg    480

aacagcggca gcctgagcag cggcgtgcac acctttccag ccgtgctgca gagcgacctg    540

tacaccctga gcagctccgt gaccgtgaca agcagcacct ggcccagcca gagcatcacc    600

tgtaacgtgg cccaccccgc cagcagcacc aaggtggaca agaagatcga gcccagaggc    660

cccaccatca agccctgccc cccttgcaag tgcccagccc ccaatctgct gggcggaccc    720

agcgtgttca tcttcccacc caagatcaag gacgtgctga tgatcagcct gagccccatc    780

gtgacctgcg tggtggtgga cgtgtccgag gacgaccccg acgtgcagat cagttggttc    840

gtgaacaacg tggaagtgca caccgcccag acccagaccc acagagagga ctacaacagc    900

accctgcggg tggtgtccgc cctgcccatc cagcaccagg actggatgag cggcaaagaa    960

ttcaagtgca aagtgaacaa caaggacctg cctgccccca tcgagcggac catcagcaag   1020

cccaagggca gcgtgcgggc tccccaggtg tacgtgctgc ccccacccga ggaagagatg   1080

accaagaagc aggtcacact gacctgcatg gtcaccgact tcatgcccga ggacatctac   1140

gtggaatgga ccaacaacgg caagaccgag ctgaactaca agaacaccga gcctgtgctg   1200

gacagcgacg gcagctactt catgtacagc aagctgcggg tggaaaagaa aaactgggtg   1260

gaacggaaca gctacagctg cagcgtggtg cacgagggcc tgcacaacca ccacaccacc   1320

aagagcttca gccggacccc cggc                                          1344
```

```
<210> SEQ ID NO 205
<211> LENGTH: 654
<212> TYPE: DNA
<213> ORGANISM: Homo Sapiens

<400> SEQUENCE: 205

gacattgtgc tgacacagtc tcctgcttcc ctggctgtat ctctggggca gagggccacc     60

atctcatgca gggccagcaa aagtgtcagt acatctagct atagttatat gcactggtac    120

caacagaaac caggacagcc acccaaactc ctcatcaaat atgcatccaa cctagaatct    180

ggggtccctg ccaggttcag tggcagtggg tctgggacag acttctccct caacatccat    240

cccatggagg aggacgatac cgcaatgtat ttctgtcagc acagtaggga gcttccattc    300

acgttcggcg gagggacaaa gttggaaata aaacgtacgg tggccgctcc cagcgtgttc    360

atcttcccac ccagcgacga gcagctgaag tccggcaccg ccagcgtcgt gtgcctgctg    420

aacaacttct acccccgcga ggccaaggtg cagtggaagg tggacaacgc cctgcagagc    480

ggcaacagcc aggaaagcgt caccgagcag gacagcaagg actccaccta cagcctgtcc    540

agcaccctga ccctgagcaa ggccgactac gagaagcaca aggtgtacgc ctgcgaagtg    600

acccaccagg gcctgagcag ccccgtgacc aagagcttca accggggcga gtgc          654
```

```
<210> SEQ ID NO 206
<211> LENGTH: 1350
<212> TYPE: DNA
<213> ORGANISM: Homo Sapiens

<400> SEQUENCE: 206

caggtccagc tggtgcagtc tggggctgag gtgaagaagc ctggggcctc agtgaaggtt     60

tcctgcaagg gttccggcta cacattcact gattatggca tgcactgggt gcggcaggcc    120
```

```
cctggacaag ggctagagtg gatgggagtt attagtactt acaatggtta tacaaactac    180
aaccagaagt ttaagggcag agtcacaatg actgtagaca aatccacgag cacagcctat    240
atggaacttc ggagcttgag atctgacgat acggccgtgt attactgtgc aagagcctac    300
tatggcaacc tttactatgc tatggactac tggggtcaag gaaccctggt caccgtctcc    360
tcagctagca ccaaaggccc gagcgtgttt ccgctggccc cgagcagcaa gagcaccagc    420
ggcggaacag ccgccctggg ctgcctggtg aaagactact tccccgaacc ggtgaccgtg    480
tcctggaact ctggcgccct gaccagcgga gtgcatacct tccccgccgt gctgcagagc    540
agcggcctgt acagcctgag cagcgtggtg acagtgccca gcagcagcct gggaacccag    600
acctacatct gcaacgtgaa ccacaagccc agcaacacca aggtggacaa gaaggtggaa    660
cccaagagct gcgacaagac ccacacctgt ccccccctgcc ctgcccctga actgctgggc    720
ggacccagcg tgttcctgtt cccccccaaag cccaaggaca ccctgatgat cagccggacc    780
cccgaagtga cctgcgtggt ggtggacgtg tcccacgagg acccagaagt gaagtttaat    840
tggtacgtgg acggcgtgga agtgcataac gccaagacca agcccagaga ggaacagtac    900
aacagcacct accgggtggt gtccgtgctg accgtgctgc accaggactg gctgaacggc    960
aaagagtaca agtgcaaggt ctccaacaag gccctgcctg cccccatcga gaaaaccatc   1020
agcaaggcca agggccagcc ccgcgagcct caggtgtaca cactgccccc cagccgggat   1080
gagctgacca agaaccaggt gtccctgacc tgtctggtga aaggcttcta ccccagcgat   1140
atcgccgtgg aatgggagag caacggccag cccgagaaca attacaagac cacccccccct   1200
gtgctggaca gcgacggctc attcttcctg tactccaagc tgaccgtgga caagagccgg   1260
tggcagcagg gcaacgtgtt cagctgcagc gtgatgcacg aggccctgca caatcactac   1320
acccagaagt ccctgagcct gagccccggc                                    1350
```

<210> SEQ ID NO 207
<211> LENGTH: 654
<212> TYPE: DNA
<213> ORGANISM: Homo Sapiens

<400> SEQUENCE: 207

```
gatatccaga tgacccagag ccccagcagc ctgagcgcca gcgtgggcga cagagtgacc     60
atcacctgtc gggccagcca gagcgtgtcc accagcagct acagctacat gcactggtat    120
cagcagaagc ccggcaaggc ccccaagctg ctgattaagt acgccagcaa cctggaaagc    180
ggcgtgccca gccggtttag cggctctggc agcggcaccg acttcaccct gaccatcagc    240
agtctgcagc ccgaggactt cgccacctac tactgccagc acagctggga gatcccttac    300
accttcggcg gaggcaccaa ggtggaaatc aagcgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgtctaa agcagactac gagaaacaca aagtctacgc ctgcgaagtc    600
acccatcagg gcctgagctc gcccgtcaca aagagcttca acaggggaga gtgt          654
```

<210> SEQ ID NO 208
<211> LENGTH: 1347
<212> TYPE: DNA
<213> ORGANISM: Homo Sapiens

<400> SEQUENCE: 208
caggtggaat tggtggaaag cggcggaggc ctggtgcagc ctggcggaag cctgagactg 60
agctgtgccg ccagcggctt caccttcagc agctactgga tgagctgggt ccgacaggct 120
ccaggcaagg gcctggaatg ggtggccgag atccggctga agtccgacaa ctacgccacc 180
cactacgccg agagcgtgaa gggccggttc accatcagcc gggacgacag caagaacagc 240
ctgtacctgc agatgaacag cctgcgggcc gaggacaccg ccgtgtacta ctgcaccggc 300
tactacgccg acgccatgga ctactggggc cagggcaccc tggtcaccgt cagctcagcc 360
tccaccaagg gtccatcggt cttccccctg gcaccctcct ccaagagcac ctctgggggc 420
acagcggccc tgggctgcct ggtcaaggac tacttccccg aaccggtgac ggtgtcgtgg 480
aactcaggcg ccctgaccag cggcgtgcac accttcccgg ctgtcctaca gtcctcagga 540
ctctactccc tcagcagcgt ggtgaccgtg ccctccagca gcttgggcac ccagacctac 600
atctgcaacg tgaatcacaa gcccagcaac accaaggtgg acaagcgggt tgagcccaaa 660
tcttgtgaca aaactcacac atgcccaccg tgcccagcac ctgaactcct ggggggaccg 720
tcagtcttcc tcttcccccc aaaacccaag gacaccctca tgatctcccg gacccctgag 780
gtcacatgcg tggtggtgga cgtgagccac gaagaccctg aggtcaagtt caactggtac 840
gtggacggcg tggaggtgca taatgccaag acaaagccgc gggaggagca gtacaacagc 900
acgtaccggg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tacaccctgc ccccatcccg ggaagagatg 1080
accaagaacc aggtcagcct gacctgcctg gtcaaaggct tctatcccag cgacatcgcc 1140
gtggagtggg agagcaatgg gcagccggag aacaactaca agaccacgcc tcccgtgctg 1200
gactccgacg gctccttctt cctctacagc aagctcaccg tggacaagag caggtggcag 1260
caggggaacg tcttctcatg ctccgtgatg catgaggctc tgcacaacca ctacacgcag 1320
aagagcctct ccctgtctcc gggtaaa 1347

<210> SEQ ID NO 209
<211> LENGTH: 654
<212> TYPE: DNA
<213> ORGANISM: Mus Musculus

<400> SEQUENCE: 209
gatatcgtgc tgacacagtc tcccgccagc ctggccgtgt ctctcggcca gagagccacc 60
atcagctgca aggccagcca gagcgtgtcc accagcacct acagctacat gcagtggtat 120
cagcagcggc ctggacagag ccccaagctg ctgattaagt acgccagcaa gctggacagc 180
ggcgtgcccg ccagattttc tggcagcggc agcggcaccg acttcaccct gaacatccac 240
cccgtggaag aagaggacac cgccacctac tactgccagc acagctggga gctgccctac 300
accttcggcg gaggcacccg gctggaaatc aagagggccg atgccgcccc taccgtgtcc 360
atcttcccac ccagcagcga gcagctgacc agcggcggag ccagcgtcgt gtgcttcctg 420
aacaacttct accccaagga catcaacgtg aagtggaaga tcgacggcag cgagcggcag 480
aacggcgtgc tgaacagctg gaccgaccag gacagcaagg actccaccta cagcatgagc 540
agcaccctga ccctgaccaa ggacgagtac gagcggcaca acagctacac atgcgaggcc 600
acccacaaga ccagcaccag ccccatcgtg aagtccttca accggaacga gtgc 654

<210> SEQ ID NO 210
<211> LENGTH: 1344
<212> TYPE: DNA
<213> ORGANISM: Mus Musculus

<400> SEQUENCE: 210
gaagtgaagc tgggagagtc tggcggcgga ctggtccagc ctggcggcag catgaagctg 60
agctgcgtgg ccagcggctt cccattcacc aaatactgga tgaactgggt ccgacagagc 120
cccgagaagg gcctggaatg ggtggccgag atccggctga agtccgacaa ctacgccacc 180
cactacgccg agagcgccaa gggccggttc accatcagcc gggacgacag ccggtccagc 240
gtgtacctgc agatgaacaa cctgcgggcc gaggacaccg ccatctacta ctgcagcccc 300
acctatgccg acaccatgga ctactggggc cagggcacca gcgtgacagt gtccagcgcc 360
aagaccaccg cccctagcgt gtaccctctg gcccctgtgt gtggcgacac caccggcagc 420
tctgtgactc tgggctgcct ggtcaagggc tacttccccg agcccgtgac actgacctgg 480
aacagcggca gcctgagcag cggcgtgcac acctttccag ccgtgctgca gagcgacctg 540
tacaccctga gcagctccgt gaccgtgaca agcagcacct ggcccagcca gagcatcacc 600
tgtaacgtgg cccaccccgc cagcagcacc aaggtggaca agaagatcga gcccagaggc 660
cccaccatca agccctgccc cccttgcaag tgcccagccc ccaatctgct gggcggaccc 720
agcgtgttca tcttcccacc caagatcaag gacgtgctga tgatcagcct gagccccatc 780
gtgacctgcg tggtggtgga cgtgtccgag gacgaccccg acgtgcagat cagttggttc 840
gtgaacaacg tggaagtgca caccgcccag acccagaccc acagagagga ctacaacagc 900
accctgcggg tggtgtccgc cctgcccatc cagcaccagg actggatgag cggcaaagaa 960
ttcaagtgca aagtgaacaa caaggacctg cctgccccca tcgagcggac catcagcaag 1020
cccaagggca gcgtgcgggc tccccaggtg tacgtgctgc ccccacccga ggaagagatg 1080
accaagaagc aggtcacact gacctgcatg gtcaccgact tcatgcccga ggacatctac 1140
gtggaatgga ccaacaacgg caagaccgag ctgaactaca agaacaccga gcctgtgctg 1200
gacagcgacg gcagctactt catgtacagc aagctgcggg tggaaaagaa aaactgggtg 1260
gaacggaaca gctacagctg cagcgtggtg cacgagggcc tgcacaacca ccacaccacc 1320
aagagcttca gccggacccc cggc 1344

<210> SEQ ID NO 211
<211> LENGTH: 654
<212> TYPE: DNA
<213> ORGANISM: Mus Musculus

<400> SEQUENCE: 211
gatatcgtgc tgacacagtc tcccgccagc ctggccgtgt ctctcggcca gagagccacc 60
atcagctgcc gggccagcaa gagcgtgtcc accagcagct acagctacat gcactggtat 120
cagcagaagc ccggccagcc ccccaagctg ctgatcaagt acaccagcaa cctggaaagc 180
ggcgtgcccg ccagattcag cggaagcggc tccggcaccg acttcatcct gaacatccac 240
cccgtggaag aagaggacgc cgccacctac tactgccagc acagcagaga gctgccctgg 300
accttcggcg gaggcaccaa gctggaaatc aagcgggccg atgccgcccc taccgtgtcc 360
atcttcccac ccagcagcga gcagctgacc agcggcggag ccagcgtcgt gtgcttcctg 420
aacaacttct accccaagga catcaacgtg aagtggaaga tcgacggcag cgagcggcag 480
aacggcgtgc tgaacagctg gaccgaccag gacagcaagg actccaccta cagcatgagc 540

```
agcaccctga ccctgaccaa ggacgagtac gagcggcaca acagctacac atgcgaggcc    600

acccacaaga ccagcaccag ccccatcgtg aagtccttca accggaacga gtgc          654


<210> SEQ ID NO 212
<211> LENGTH: 1353
<212> TYPE: DNA
<213> ORGANISM: Mus Musculus

<400> SEQUENCE: 212

caggtgtccc tgaaagagag cggccctggc atcctgcagc ctagccagac cctgagcctg     60

acctgcagct tcagcggctt cagcctgagc accagcggca tgggcgtgtc ctggatcaga    120

cagcccagcg gcaagggcct ggaatggctg gcccacatct actgggacga cgacaagcgg    180

tacaacccca gcctgaagtc ccggctgacc atctccaagg acaccagccg gaatcaggtg    240

ttcctgaaga tcaccagcgt ggacaccgcc gataccgcca cctactactg cgccagaaga    300

ggccccgact actacggcta ctaccccatg gactattggg gccagggcac cagcgtgacc    360

gtgtctgcca agaccaccgc ccctagcgtg taccctctgg cccctgtgtg tggcgacacc    420

accggcagct ctgtgactct gggctgcctg gtcaagggct acttccccga gcccgtgaca    480

ctgacctgga acagcggcag cctgagcagc ggcgtgcaca cctttccagc cgtgctgcag    540

agcgacctgt acaccctgag cagctccgtg accgtgacaa gcagcacctg gcccagccag    600

agcatcacct gtaacgtggc ccaccccgcc agcagcacca aggtggacaa gaagatcgag    660

cccagaggcc ccaccatcaa gccctgcccc ccttgcaagt gcccagcccc caatctgctg    720

ggcggaccca gcgtgttcat cttcccaccc aagatcaagg acgtgctgat gatcagcctg    780

agccccatcg tgacctgcgt ggtggtggac gtgtccgagg acgaccccga cgtgcagatc    840

agttggttcg tgaacaacgt ggaagtgcac accgcccaga cccagaccca cagagaggac    900

tacaacagca ccctgcgggt ggtgtccgcc ctgcccatcc agcaccagga ctggatgagc    960

ggcaaagaat tcaagtgcaa agtgaacaac aaggacctgc ctgcccccat cgagcggacc   1020

atcagcaagc ccaagggcag cgtgcgggct ccccaggtgt acgtgctgcc cccacccgag   1080

gaagagatga ccaagaagca ggtcacactg acctgcatgg tcaccgactt catgcccgag   1140

gacatctacg tggaatggac caacaacggc aagaccgagc tgaactacaa gaacaccgag   1200

cctgtgctgg acagcgacgg cagctacttc atgtacagca agctgcgggt ggaaaagaaa   1260

aactgggtgg aacggaacag ctacagctgc agcgtggtgc acgagggcct gcacaaccac   1320

cacaccacca agagcttcag ccggaccccc ggc                                1353


<210> SEQ ID NO 213
<211> LENGTH: 1210
<212> TYPE: PRT
<213> ORGANISM: Homo sapiens

<400> SEQUENCE: 213

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
```

```
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495
```

-continued

```
Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910
```

-continued

```
Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
        1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
            1140                1145                1150

Ser Pro Ala His Trp Ala Gln Lys Gly Ser His Gln Ile Ser Leu Asp
        1155                1160                1165

Asn Pro Asp Tyr Gln Gln Asp Phe Phe Pro Lys Glu Ala Lys Pro Asn
    1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
                1205                1210


<210> SEQ ID NO 214
<211> LENGTH: 622
<212> TYPE: PRT
<213> ORGANISM: Homo sapiens

<400> SEQUENCE: 214

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80
```

```
Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495
```

```
Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620


<210> SEQ ID NO 215
<211> LENGTH: 459
<212> TYPE: PRT
<213> ORGANISM: Homo sapiens

<400> SEQUENCE: 215

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
            20                  25                  30

Val Pro Val His Pro Gln Arg Leu Pro Arg Met Gln Glu Asp Ser Pro
        35                  40                  45

Leu Gly Gly Gly Ser Ser Gly Glu Asp Asp Pro Leu Gly Glu Glu Asp
    50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Glu Gly Ser Leu Lys Leu Glu Asp
            100                 105                 110

Leu Pro Thr Val Glu Ala Pro Gly Asp Pro Gln Glu Pro Gln Asn Asn
        115                 120                 125

Ala His Arg Asp Lys Glu Gly Asp Asp Gln Ser His Trp Arg Tyr Gly
    130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
        195                 200                 205

Gly Leu Glu Met Ala Leu Gly Pro Gly Arg Glu Tyr Arg Ala Leu Gln
    210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255
```

Thr Ala Phe Ala Arg Val Asp Glu Ala Leu Gly Arg Pro Gly Gly Leu
260 265 270

Ala Val Leu Ala Ala Phe Leu Glu Glu Gly Pro Glu Glu Asn Ser Ala
275 280 285

Tyr Glu Gln Leu Leu Ser Arg Leu Glu Glu Ile Ala Glu Glu Gly Ser
290 295 300

Glu Thr Gln Val Pro Gly Leu Asp Ile Ser Ala Leu Leu Pro Ser Asp
305 310 315 320

Phe Ser Arg Tyr Phe Gln Tyr Glu Gly Ser Leu Thr Thr Pro Pro Cys
325 330 335

Ala Gln Gly Val Ile Trp Thr Val Phe Asn Gln Thr Val Met Leu Ser
340 345 350

Ala Lys Gln Leu His Thr Leu Ser Asp Thr Leu Trp Gly Pro Gly Asp
355 360 365

Ser Arg Leu Gln Leu Asn Phe Arg Ala Thr Gln Pro Leu Asn Gly Arg
370 375 380

Val Ile Glu Ala Ser Phe Pro Ala Gly Val Asp Ser Ser Pro Arg Ala
385 390 395 400

Ala Glu Pro Val Gln Leu Asn Ser Cys Leu Ala Ala Gly Asp Ile Leu
405 410 415

Ala Leu Val Phe Gly Leu Leu Phe Ala Val Thr Ser Val Ala Phe Leu
420 425 430

Val Gln Met Arg Arg Gln His Arg Arg Gly Thr Lys Gly Gly Val Ser
435 440 445

Tyr Arg Pro Ala Glu Val Ala Glu Thr Gly Ala
450 455

<210> SEQ ID NO 216
<211> LENGTH: 346
<212> TYPE: PRT
<213> ORGANISM: Homo sapiens

<400> SEQUENCE: 216

Met Asp Pro Ala Arg Lys Ala Gly Ala Gln Ala Met Ile Trp Thr Ala
1 5 10 15

Gly Trp Leu Leu Leu Leu Leu Leu Arg Gly Gly Ala Gln Ala Leu Glu
20 25 30

Cys Tyr Ser Cys Val Gln Lys Ala Asp Asp Gly Cys Ser Pro Asn Lys
35 40 45

Met Lys Thr Val Lys Cys Ala Pro Gly Val Asp Val Cys Thr Glu Ala
50 55 60

Val Gly Ala Val Glu Thr Ile His Gly Gln Phe Ser Leu Ala Val Arg
65 70 75 80

Gly Cys Gly Ser Gly Leu Pro Gly Lys Asn Asp Arg Gly Leu Asp Leu
85 90 95

His Gly Leu Leu Ala Phe Ile Gln Leu Gln Gln Cys Ala Gln Asp Arg
100 105 110

Cys Asn Ala Lys Leu Asn Leu Thr Ser Arg Ala Leu Asp Pro Ala Gly
115 120 125

Asn Glu Ser Ala Tyr Pro Pro Asn Gly Val Glu Cys Tyr Ser Cys Val
130 135 140

Gly Leu Ser Arg Glu Ala Cys Gln Gly Thr Ser Pro Pro Val Val Ser
145 150 155 160

Cys Tyr Asn Ala Ser Asp His Val Tyr Lys Gly Cys Phe Asp Gly Asn

-continued

```
                165                 170                 175

Val Thr Leu Thr Ala Ala Asn Val Thr Val Ser Leu Pro Val Arg Gly
            180                 185                 190

Cys Val Gln Asp Glu Phe Cys Thr Arg Asp Gly Val Thr Gly Pro Gly
        195                 200                 205

Phe Thr Leu Ser Gly Ser Cys Cys Gln Gly Ser Arg Cys Asn Ser Asp
    210                 215                 220

Leu Arg Asn Lys Thr Tyr Phe Ser Pro Arg Ile Pro Pro Leu Val Arg
225                 230                 235                 240

Leu Pro Pro Pro Glu Pro Thr Thr Val Ala Ser Thr Thr Ser Val Thr
                245                 250                 255

Thr Ser Thr Ser Ala Pro Val Arg Pro Thr Ser Thr Thr Lys Pro Met
            260                 265                 270

Pro Ala Pro Thr Ser Gln Thr Pro Arg Gln Gly Val Glu His Glu Ala
        275                 280                 285

Ser Arg Asp Glu Glu Pro Arg Leu Thr Gly Gly Ala Ala Gly His Gln
    290                 295                 300

Asp Arg Ser Asn Ser Gly Gln Tyr Pro Ala Lys Gly Gly Pro Gln Gln
305                 310                 315                 320

Pro His Asn Lys Gly Cys Val Ala Pro Thr Ala Gly Leu Ala Ala Leu
                325                 330                 335

Leu Leu Ala Val Ala Ala Gly Val Leu Leu
            340                 345


<210> SEQ ID NO 217
<211> LENGTH: 61
<212> TYPE: PRT
<213> ORGANISM: Homo sapiens

<400> SEQUENCE: 217

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Asn Ile Ser Gly Gly Ile Phe Leu Phe
        35                  40                  45

Phe Val Ala Asn Ala Ile Ile His Leu Phe Cys Phe Ser
    50                  55                  60


<210> SEQ ID NO 218
<211> LENGTH: 1255
<212> TYPE: PRT
<213> ORGANISM: Homo sapiens

<400> SEQUENCE: 218

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
```

```
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510
```

```
Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925
```

```
Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
        1155                1160                1165

Arg Pro Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Pro Ala Phe Ser Pro Ala
                1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
        1235                1240                1245

Leu Gly Leu Asp Val Pro Val
    1250                1255
```

<210> SEQ ID NO 219
<211> LENGTH: 297
<212> TYPE: PRT
<213> ORGANISM: Homo sapiens

<400> SEQUENCE: 219

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45
```

Ser Lys Thr Leu Gly Ala Val Gln Ile Met Asn Gly Leu Phe His Ile
50 55 60

Ala Leu Gly Gly Leu Leu Met Ile Pro Ala Gly Ile Tyr Ala Pro Ile
65 70 75 80

Cys Val Thr Val Trp Tyr Pro Leu Trp Gly Gly Ile Met Tyr Ile Ile
85 90 95

Ser Gly Ser Leu Leu Ala Ala Thr Glu Lys Asn Ser Arg Lys Cys Leu
100 105 110

Val Lys Gly Lys Met Ile Met Asn Ser Leu Ser Leu Phe Ala Ala Ile
115 120 125

Ser Gly Met Ile Leu Ser Ile Met Asp Ile Leu Asn Ile Lys Ile Ser
130 135 140

His Phe Leu Lys Met Glu Ser Leu Asn Phe Ile Arg Ala His Thr Pro
145 150 155 160

Tyr Ile Asn Ile Tyr Asn Cys Glu Pro Ala Asn Pro Ser Glu Lys Asn
165 170 175

Ser Pro Ser Thr Gln Tyr Cys Tyr Ser Ile Gln Ser Leu Phe Leu Gly
180 185 190

Ile Leu Ser Val Met Leu Ile Phe Ala Phe Phe Gln Glu Leu Val Ile
195 200 205

Ala Gly Ile Val Glu Asn Glu Trp Lys Arg Thr Cys Ser Arg Pro Lys
210 215 220

Ser Asn Ile Val Leu Leu Ser Ala Glu Glu Lys Lys Glu Gln Thr Ile
225 230 235 240

Glu Ile Lys Glu Glu Val Val Gly Leu Thr Glu Thr Ser Ser Gln Pro
245 250 255

Lys Asn Glu Glu Asp Ile Glu Ile Ile Pro Ile Gln Glu Glu Glu Glu
260 265 270

Glu Glu Thr Glu Thr Asn Phe Pro Glu Pro Pro Gln Asp Gln Glu Ser
275 280 285

Ser Pro Ile Glu Asn Asp Ser Ser Pro
290 295

<210> SEQ ID NO 220
<211> LENGTH: 595
<212> TYPE: PRT
<213> ORGANISM: Homo sapiens

<400> SEQUENCE: 220

Met Arg Val Leu Leu Ala Ala Leu Gly Leu Leu Phe Leu Gly Ala Leu
1 5 10 15

Arg Ala Phe Pro Gln Asp Arg Pro Phe Glu Asp Thr Cys His Gly Asn
20 25 30

Pro Ser His Tyr Tyr Asp Lys Ala Val Arg Arg Cys Cys Tyr Arg Cys
35 40 45

Pro Met Gly Leu Phe Pro Thr Gln Gln Cys Pro Gln Arg Pro Thr Asp
50 55 60

Cys Arg Lys Gln Cys Glu Pro Asp Tyr Tyr Leu Asp Glu Ala Asp Arg
65 70 75 80

Cys Thr Ala Cys Val Thr Cys Ser Arg Asp Asp Leu Val Glu Lys Thr
85 90 95

Pro Cys Ala Trp Asn Ser Ser Arg Val Cys Glu Cys Arg Pro Gly Met
100 105 110

Phe Cys Ser Thr Ser Ala Val Asn Ser Cys Ala Arg Cys Phe Phe His

```
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Arg Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540
```

```
Glu Pro Glu Leu Glu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
            580                 585                 590

Ser Gly Lys
        595


<210> SEQ ID NO 221
<211> LENGTH: 847
<212> TYPE: PRT
<213> ORGANISM: Homo sapiens

<400> SEQUENCE: 221

Met His Leu Leu Gly Pro Trp Leu Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
```

-continued

```
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
        355                 360                 365

Asn Gly Lys Glu Met Gln Gly Arg Thr Glu Glu Lys Val His Ile Pro
    370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
        435                 440                 445

Pro Ser Val Thr Arg Tyr Glu Trp Lys Pro His Gly Ala Trp Glu Glu
    450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
        515                 520                 525

Cys Asp Phe Ser Ser Ser His Pro Lys Glu Val Gln Phe Phe Trp Glu
    530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
            580                 585                 590

Pro Arg Arg Leu Arg Val Ser Met Ser Pro Gly Asp Gln Val Met Glu
        595                 600                 605

Gly Lys Ser Ala Thr Leu Thr Cys Glu Ser Asp Ala Asn Pro Pro Val
    610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
        675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735
```

```
Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
        755                 760                 765

Glu Met Asn Ile Pro Arg Thr Gly Asp Ala Glu Ser Ser Glu Met Gln
    770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845


<210> SEQ ID NO 222
<211> LENGTH: 364
<212> TYPE: PRT
<213> ORGANISM: Homo sapiens

<400> SEQUENCE: 222

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
```

```
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360


<210> SEQ ID NO 223
<211> LENGTH: 572
<212> TYPE: PRT
<213> ORGANISM: Homo sapiens

<400> SEQUENCE: 223

Met Glu Cys Leu Tyr Tyr Phe Leu Gly Phe Leu Leu Leu Ala Ala Arg
1               5                   10                  15

Leu Pro Leu Asp Ala Ala Lys Arg Phe His Asp Val Leu Gly Asn Glu
            20                  25                  30

Arg Pro Ser Ala Tyr Met Arg Glu His Asn Gln Leu Asn Gly Trp Ser
        35                  40                  45

Ser Asp Glu Asn Asp Trp Asn Glu Lys Leu Tyr Pro Val Trp Lys Arg
    50                  55                  60

Gly Asp Met Arg Trp Lys Asn Ser Trp Lys Gly Gly Arg Val Gln Ala
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
            100                 105                 110

Asn Ile Val Tyr Glu Lys Asn Cys Arg Asn Glu Ala Gly Leu Ser Ala
        115                 120                 125

Asp Pro Tyr Val Tyr Asn Trp Thr Ala Trp Ser Glu Asp Ser Asp Gly
    130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
            180                 185                 190

Arg Val Ser Val Asn Thr Ala Asn Val Thr Leu Gly Pro Gln Leu Met
        195                 200                 205

Glu Val Thr Val Tyr Arg Arg His Gly Arg Ala Tyr Val Pro Ile Ala
    210                 215                 220

Gln Val Lys Asp Val Tyr Val Val Thr Asp Gln Ile Pro Val Phe Val
225                 230                 235                 240

Thr Met Phe Gln Lys Asn Asp Arg Asn Ser Ser Asp Glu Thr Phe Leu
                245                 250                 255

Lys Asp Leu Pro Ile Met Phe Asp Val Leu Ile His Asp Pro Ser His
            260                 265                 270
```

-continued

```
Phe Leu Asn Tyr Ser Thr Ile Asn Tyr Lys Trp Ser Phe Gly Asp Asn
        275                 280                 285

Thr Gly Leu Phe Val Ser Thr Asn His Thr Val Asn His Thr Tyr Val
    290                 295                 300

Leu Asn Gly Thr Phe Ser Leu Asn Leu Thr Val Lys Ala Ala Ala Pro
305                 310                 315                 320

Gly Pro Cys Pro Pro Pro Pro Pro Pro Pro Arg Pro Ser Lys Pro Thr
                325                 330                 335

Pro Ser Leu Ala Thr Thr Leu Lys Ser Tyr Asp Ser Asn Thr Pro Gly
            340                 345                 350

Pro Ala Gly Asp Asn Pro Leu Glu Leu Ser Arg Ile Pro Asp Glu Asn
        355                 360                 365

Cys Gln Ile Asn Arg Tyr Gly His Phe Gln Ala Thr Ile Thr Ile Val
    370                 375                 380

Glu Gly Ile Leu Glu Val Asn Ile Ile Gln Met Thr Asp Val Leu Met
385                 390                 395                 400

Pro Val Pro Trp Pro Glu Ser Ser Leu Ile Asp Phe Val Val Thr Cys
                405                 410                 415

Gln Gly Ser Ile Pro Thr Glu Val Cys Thr Ile Ile Ser Asp Pro Thr
            420                 425                 430

Cys Glu Ile Thr Gln Asn Thr Val Cys Ser Pro Val Asp Val Asp Glu
        435                 440                 445

Met Cys Leu Leu Thr Val Arg Arg Thr Phe Asn Gly Ser Gly Thr Tyr
    450                 455                 460

Cys Val Asn Leu Thr Leu Gly Asp Asp Thr Ser Leu Ala Leu Thr Ser
465                 470                 475                 480

Thr Leu Ile Ser Val Pro Asp Arg Asp Pro Ala Ser Pro Leu Arg Met
                485                 490                 495

Ala Asn Ser Ala Leu Ile Ser Val Gly Cys Leu Ala Ile Phe Val Thr
            500                 505                 510

Val Ile Ser Leu Leu Val Tyr Lys Lys His Lys Glu Tyr Asn Pro Ile
        515                 520                 525

Glu Asn Ser Pro Gly Asn Val Val Arg Ser Lys Gly Leu Ser Val Phe
    530                 535                 540

Leu Asn Arg Ala Lys Ala Val Phe Phe Pro Gly Asn Gln Glu Lys Asp
545                 550                 555                 560

Pro Leu Leu Lys Asn Gln Glu Phe Lys Gly Val Ser
                565                 570
```

<210> SEQ ID NO 224
<211> LENGTH: 848
<212> TYPE: PRT
<213> ORGANISM: Homo sapiens

<400> SEQUENCE: 224

```
Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Asp Ser Ser Ser Thr
65                  70                  75                  80
```

```
Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
    290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Thr Leu Asp Gly His Met Val Val Arg Ser His Ala Arg Val Ser
        355                 360                 365

Ser Leu Thr Leu Lys Ser Ile Gln Tyr Thr Asp Ala Gly Glu Tyr Ile
    370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
            420                 425                 430

Ser Ala Thr Ile Ser Trp Phe Arg Asp Gly Gln Leu Leu Pro Ser Ser
        435                 440                 445

Asn Tyr Ser Asn Ile Lys Ile Tyr Asn Thr Pro Ser Ala Ser Tyr Leu
    450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Leu Glu Phe Ile Leu Val Gln
                485                 490                 495
```

```
Ala Asp Thr Pro Ser Ser Pro Ser Ile Asp Gln Val Glu Pro Tyr Ser
            500                 505                 510

Ser Thr Ala Gln Val Gln Phe Asp Glu Pro Glu Ala Thr Gly Gly Val
        515                 520                 525

Pro Ile Leu Lys Tyr Lys Ala Glu Trp Arg Ala Val Gly Glu Glu Val
    530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
            580                 585                 590

Phe Lys Thr Gln Pro Val Gln Gly Glu Pro Ser Ala Pro Lys Leu Glu
        595                 600                 605

Gly Gln Met Gly Glu Asp Gly Asn Ser Ile Lys Val Asn Leu Ile Lys
    610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
            660                 665                 670

Tyr Val Val Ala Glu Asn Gln Gln Gly Lys Ser Lys Ala Ala His Phe
        675                 680                 685

Val Phe Arg Thr Ser Ala Gln Pro Thr Ala Ile Pro Ala Asn Gly Ser
    690                 695                 700

Pro Thr Ser Gly Leu Ser Thr Gly Ala Ile Val Gly Ile Leu Ile Val
705                 710                 715                 720

Ile Phe Val Leu Leu Leu Val Val Val Asp Ile Thr Cys Tyr Phe Leu
                725                 730                 735

Asn Lys Cys Gly Leu Phe Met Cys Ile Ala Val Asn Leu Cys Gly Lys
            740                 745                 750

Ala Gly Pro Gly Ala Lys Gly Lys Asp Met Glu Glu Gly Lys Ala Ala
        755                 760                 765

Phe Ser Lys Asp Glu Ser Lys Glu Pro Ile Val Glu Val Arg Thr Glu
    770                 775                 780

Glu Glu Arg Thr Pro Asn His Asp Gly Gly Lys His Thr Glu Pro Asn
785                 790                 795                 800

Glu Thr Thr Pro Leu Thr Glu Pro Glu Lys Gly Pro Val Glu Ala Lys
                805                 810                 815

Pro Glu Cys Gln Glu Thr Glu Thr Lys Pro Ala Pro Ala Glu Val Lys
            820                 825                 830

Thr Val Pro Asn Asp Ala Thr Gln Thr Lys Glu Asn Glu Ser Lys Ala
        835                 840                 845


<210> SEQ ID NO 225
<211> LENGTH: 193
<212> TYPE: PRT
<213> ORGANISM: Homo sapiens

<400> SEQUENCE: 225

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30
```

-continued

Cys Leu Val Val Cys Ile Gln Arg Phe Ala Gln Ala Gln Gln Gln Leu
35 40 45

Pro Leu Glu Ser Leu Gly Trp Asp Val Ala Glu Leu Gln Leu Asn His
50 55 60

Thr Gly Pro Gln Gln Asp Pro Arg Leu Tyr Trp Gln Gly Gly Pro Ala
65 70 75 80

Leu Gly Arg Ser Phe Leu His Gly Pro Glu Leu Asp Lys Gly Gln Leu
85 90 95

Arg Ile His Arg Asp Gly Ile Tyr Met Val His Ile Gln Val Thr Leu
100 105 110

Ala Ile Cys Ser Ser Thr Thr Ala Ser Arg His His Pro Thr Thr Leu
115 120 125

Ala Val Gly Ile Cys Ser Pro Ala Ser Arg Ser Ile Ser Leu Leu Arg
130 135 140

Leu Ser Phe His Gln Gly Cys Thr Ile Ala Ser Gln Arg Leu Thr Pro
145 150 155 160

Leu Ala Arg Gly Asp Thr Leu Cys Thr Asn Leu Thr Gly Thr Leu Leu
165 170 175

Pro Ser Arg Asn Thr Asp Glu Thr Phe Phe Gly Val Gln Trp Val Arg
180 185 190

Pro

<210> SEQ ID NO 226
<211> LENGTH: 232
<212> TYPE: PRT
<213> ORGANISM: Homo sapiens

<400> SEQUENCE: 226

Met His Arg Arg Arg Ser Arg Ser Cys Arg Glu Asp Gln Lys Pro Val
1 5 10 15

Met Asp Asp Gln Arg Asp Leu Ile Ser Asn Asn Glu Gln Leu Pro Met
20 25 30

Leu Gly Arg Arg Pro Gly Ala Pro Glu Ser Lys Cys Ser Arg Gly Ala
35 40 45

Leu Tyr Thr Gly Phe Ser Ile Leu Val Thr Leu Leu Leu Ala Gly Gln
50 55 60

Ala Thr Thr Ala Tyr Phe Leu Tyr Gln Gln Gln Gly Arg Leu Asp Lys
65 70 75 80

Leu Thr Val Thr Ser Gln Asn Leu Gln Leu Glu Asn Leu Arg Met Lys
85 90 95

Leu Pro Lys Pro Pro Lys Pro Val Ser Lys Met Arg Met Ala Thr Pro
100 105 110

Leu Leu Met Gln Ala Leu Pro Met Gly Ala Leu Pro Gln Gly Pro Met
115 120 125

Gln Asn Ala Thr Lys Tyr Gly Asn Met Thr Glu Asp His Val Met His
130 135 140

Leu Leu Gln Asn Ala Asp Pro Leu Lys Val Tyr Pro Pro Leu Lys Gly
145 150 155 160

Ser Phe Pro Glu Asn Leu Arg His Leu Lys Asn Thr Met Glu Thr Ile
165 170 175

Asp Trp Lys Val Phe Glu Ser Trp Met His His Trp Leu Leu Phe Glu
180 185 190

Met Ser Arg His Ser Leu Glu Gln Lys Pro Thr Asp Ala Pro Pro Lys
195 200 205

```
Glu Ser Leu Glu Leu Glu Asp Pro Ser Ser Gly Leu Gly Val Thr Lys
    210                 215                 220

Gln Asp Leu Gly Pro Val Pro Met
225                 230


<210> SEQ ID NO 227
<211> LENGTH: 557
<212> TYPE: PRT
<213> ORGANISM: Homo sapiens

<400> SEQUENCE: 227

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
```

```
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Ala
                485                 490                 495

Gly Ser Gln Ser Tyr Glu Asp Met Arg Gly Ile Leu Tyr Ala Ala Pro
            500                 505                 510

Gln Leu Arg Ser Ile Arg Gly Gln Pro Gly Pro Asn His Glu Glu Asp
        515                 520                 525

Ala Asp Ser Tyr Glu Asn Met Asp Asn Pro Asp Gly Pro Asp Pro Ala
    530                 535                 540

Trp Gly Gly Gly Gly Arg Met Gly Thr Trp Ser Thr Arg
545                 550                 555


<210> SEQ ID NO 228
<211> LENGTH: 273
<212> TYPE: PRT
<213> ORGANISM: Homo sapiens

<400> SEQUENCE: 228

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Leu Ser Thr Gly Val Ser Phe Phe Phe Leu Ser
    50                  55                  60

Phe His Ile Ser Asn Leu Gln Phe Asn Ser Ser Leu Glu Asp Pro Ser
65                  70                  75                  80

Thr Asp Tyr Tyr Gln Glu Leu Gln Arg Asp Ile Ser Glu Met Phe Leu
                85                  90                  95

Gln Ile Tyr Lys Gln Gly Gly Phe Leu Gly Leu Ser Asn Ile Lys Phe
            100                 105                 110

Arg Pro Gly Ser Val Val Val Gln Leu Thr Leu Ala Phe Arg Glu Gly
        115                 120                 125

Thr Ile Asn Val His Asp Val Glu Thr Gln Phe Asn Gln Tyr Lys Thr
    130                 135                 140

Glu Ala Ala Ser Arg Tyr Asn Leu Thr Ile Ser Asp Val Ser Val Ser
145                 150                 155                 160
```

```
Asp Val Pro Phe Pro Phe Ser Ala Gln Ser Gly Ala Gly Val Pro Gly
                165                 170                 175

Trp Gly Ile Ala Leu Leu Val Leu Val Cys Val Leu Val Ala Leu Ala
            180                 185                 190

Ile Val Tyr Leu Ile Ala Leu Ala Val Cys Gln Cys Arg Arg Lys Asn
        195                 200                 205

Tyr Gly Gln Leu Asp Ile Phe Pro Ala Arg Asp Thr Tyr His Pro Met
    210                 215                 220

Ser Glu Tyr Pro Thr Tyr His Thr His Gly Arg Tyr Val Pro Pro Ser
225                 230                 235                 240

Ser Thr Asp Arg Ser Pro Tyr Glu Lys Val Ser Ala Gly Asn Gly Gly
                245                 250                 255

Ser Ser Leu Ser Tyr Thr Asn Pro Ala Val Ala Ala Thr Ser Ala Asn
            260                 265                 270

Leu


<210> SEQ ID NO 229
<211> LENGTH: 310
<212> TYPE: PRT
<213> ORGANISM: Homo sapiens

<400> SEQUENCE: 229

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255
```

```
Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310


<210> SEQ ID NO 230
<211> LENGTH: 1048
<212> TYPE: PRT
<213> ORGANISM: Homo sapiens

<400> SEQUENCE: 230

Met Ala Phe Pro Pro Arg Arg Arg Leu Arg Leu Gly Pro Arg Gly Leu
1               5                   10                  15

Pro Leu Leu Leu Ser Gly Leu Leu Leu Pro Leu Cys Arg Ala Phe Asn
            20                  25                  30

Leu Asp Val Asp Ser Pro Ala Glu Tyr Ser Gly Pro Glu Gly Ser Tyr
        35                  40                  45

Phe Gly Phe Ala Val Asp Phe Phe Val Pro Ser Ala Ser Ser Arg Met
    50                  55                  60

Phe Leu Leu Val Gly Ala Pro Lys Ala Asn Thr Thr Gln Pro Gly Ile
65                  70                  75                  80

Val Glu Gly Gly Gln Val Leu Lys Cys Asp Trp Ser Ser Thr Arg Arg
                85                  90                  95

Cys Gln Pro Ile Glu Phe Asp Ala Thr Gly Asn Arg Asp Tyr Ala Lys
            100                 105                 110

Asp Asp Pro Leu Glu Phe Lys Ser His Gln Trp Phe Gly Ala Ser Val
        115                 120                 125

Arg Ser Lys Gln Asp Lys Ile Leu Ala Cys Ala Pro Leu Tyr His Trp
    130                 135                 140

Arg Thr Glu Met Lys Gln Glu Arg Glu Pro Val Gly Thr Cys Phe Leu
145                 150                 155                 160

Gln Asp Gly Thr Lys Thr Val Glu Tyr Ala Pro Cys Arg Ser Gln Asp
                165                 170                 175

Ile Asp Ala Asp Gly Gln Gly Phe Cys Gln Gly Gly Phe Ser Ile Asp
            180                 185                 190

Phe Thr Lys Ala Asp Arg Val Leu Leu Gly Gly Pro Gly Ser Phe Tyr
        195                 200                 205

Trp Gln Gly Gln Leu Ile Ser Asp Gln Val Ala Glu Ile Val Ser Lys
    210                 215                 220

Tyr Asp Pro Asn Val Tyr Ser Ile Lys Tyr Asn Asn Gln Leu Ala Thr
225                 230                 235                 240

Arg Thr Ala Gln Ala Ile Phe Asp Asp Ser Tyr Leu Gly Tyr Ser Val
                245                 250                 255

Ala Val Gly Asp Phe Asn Gly Asp Gly Ile Asp Asp Phe Val Ser Gly
            260                 265                 270

Val Pro Arg Ala Ala Arg Thr Leu Gly Met Val Tyr Ile Tyr Asp Gly
        275                 280                 285

Lys Asn Met Ser Ser Leu Tyr Asn Phe Thr Gly Glu Gln Met Ala Ala
    290                 295                 300

Tyr Phe Gly Phe Ser Val Ala Ala Thr Asp Ile Asn Gly Asp Asp Tyr
305                 310                 315                 320
```

-continued

```
Ala Asp Val Phe Ile Gly Ala Pro Leu Phe Met Asp Arg Gly Ser Asp
                325                 330                 335

Gly Lys Leu Gln Glu Val Gly Gln Val Ser Val Ser Leu Gln Arg Ala
            340                 345                 350

Ser Gly Asp Phe Gln Thr Thr Lys Leu Asn Gly Phe Glu Val Phe Ala
        355                 360                 365

Arg Phe Gly Ser Ala Ile Ala Pro Leu Gly Asp Leu Asp Gln Asp Gly
    370                 375                 380

Phe Asn Asp Ile Ala Ile Ala Ala Pro Tyr Gly Gly Glu Asp Lys Lys
385                 390                 395                 400

Gly Ile Val Tyr Ile Phe Asn Gly Arg Ser Thr Gly Leu Asn Ala Val
                405                 410                 415

Pro Ser Gln Ile Leu Glu Gly Gln Trp Ala Ala Arg Ser Met Pro Pro
            420                 425                 430

Ser Phe Gly Tyr Ser Met Lys Gly Ala Thr Asp Ile Asp Lys Asn Gly
        435                 440                 445

Tyr Pro Asp Leu Ile Val Gly Ala Phe Gly Val Asp Arg Ala Ile Leu
    450                 455                 460

Tyr Arg Ala Arg Pro Val Ile Thr Val Asn Ala Gly Leu Glu Val Tyr
465                 470                 475                 480

Pro Ser Ile Leu Asn Gln Asp Asn Lys Thr Cys Ser Leu Pro Gly Thr
                485                 490                 495

Ala Leu Lys Val Ser Cys Phe Asn Val Arg Phe Cys Leu Lys Ala Asp
            500                 505                 510

Gly Lys Gly Val Leu Pro Arg Lys Leu Asn Phe Gln Val Glu Leu Leu
        515                 520                 525

Leu Asp Lys Leu Lys Gln Lys Gly Ala Ile Arg Arg Ala Leu Phe Leu
    530                 535                 540

Tyr Ser Arg Ser Pro Ser His Ser Lys Asn Met Thr Ile Ser Arg Gly
545                 550                 555                 560

Gly Leu Met Gln Cys Glu Glu Leu Ile Ala Tyr Leu Arg Asp Glu Ser
                565                 570                 575

Glu Phe Arg Asp Lys Leu Thr Pro Ile Thr Ile Phe Met Glu Tyr Arg
            580                 585                 590

Leu Asp Tyr Arg Thr Ala Ala Asp Thr Thr Gly Leu Gln Pro Ile Leu
        595                 600                 605

Asn Gln Phe Thr Pro Ala Asn Ile Ser Arg Gln Ala His Ile Leu Leu
    610                 615                 620

Asp Cys Gly Glu Asp Asn Val Cys Lys Pro Lys Leu Glu Val Ser Val
625                 630                 635                 640

Asp Ser Asp Gln Lys Lys Ile Tyr Ile Gly Asp Asp Asn Pro Leu Thr
                645                 650                 655

Leu Ile Val Lys Ala Gln Asn Gln Gly Glu Gly Ala Tyr Glu Ala Glu
            660                 665                 670

Leu Ile Val Ser Ile Pro Leu Gln Ala Asp Phe Ile Gly Val Val Arg
        675                 680                 685

Asn Asn Glu Ala Leu Ala Arg Leu Ser Cys Ala Phe Lys Thr Glu Asn
    690                 695                 700

Gln Thr Arg Gln Val Val Cys Asp Leu Gly Asn Pro Met Lys Ala Gly
705                 710                 715                 720

Thr Gln Leu Leu Ala Gly Leu Arg Phe Ser Val His Gln Gln Ser Glu
                725                 730                 735
```

```
Met Asp Thr Ser Val Lys Phe Asp Leu Gln Ile Gln Ser Ser Asn Leu
            740                 745                 750

Phe Asp Lys Val Ser Pro Val Val Ser His Lys Val Asp Leu Ala Val
        755                 760                 765

Leu Ala Ala Val Glu Ile Arg Gly Val Ser Ser Pro Asp His Ile Phe
    770                 775                 780

Leu Pro Ile Pro Asn Trp Glu His Lys Glu Asn Pro Glu Thr Glu Glu
785                 790                 795                 800

Asp Val Gly Pro Val Val Gln His Ile Tyr Glu Leu Arg Asn Asn Gly
                805                 810                 815

Pro Ser Ser Phe Ser Lys Ala Met Leu His Leu Gln Trp Pro Tyr Lys
            820                 825                 830

Tyr Asn Asn Asn Thr Leu Leu Tyr Ile Leu His Tyr Asp Ile Asp Gly
        835                 840                 845

Pro Met Asn Cys Thr Ser Asp Met Glu Ile Asn Pro Leu Arg Ile Lys
    850                 855                 860

Ile Ser Ser Leu Gln Thr Thr Glu Lys Asn Asp Thr Val Ala Gly Gln
865                 870                 875                 880

Gly Glu Arg Asp His Leu Ile Thr Lys Arg Asp Leu Ala Leu Ser Glu
                885                 890                 895

Gly Asp Ile His Thr Leu Gly Cys Gly Val Ala Gln Cys Leu Lys Ile
            900                 905                 910

Val Cys Gln Val Gly Arg Leu Asp Arg Gly Lys Ser Ala Ile Leu Tyr
        915                 920                 925

Val Lys Ser Leu Leu Trp Thr Glu Thr Phe Met Asn Lys Glu Asn Gln
    930                 935                 940

Asn His Ser Tyr Ser Leu Lys Ser Ser Ala Ser Phe Asn Val Ile Glu
945                 950                 955                 960

Phe Pro Tyr Lys Asn Leu Pro Ile Glu Asp Ile Thr Asn Ser Thr Leu
                965                 970                 975

Val Thr Thr Asn Val Thr Trp Gly Ile Gln Pro Ala Pro Met Pro Val
            980                 985                 990

Pro Val Trp Val Ile Ile Leu Ala Val Leu Ala Gly Leu Leu Leu Leu
        995                 1000                1005

Ala Val Leu Val Phe Val Met Tyr Arg Met Gly Phe Phe Lys Arg Val
    1010                1015                1020

Arg Pro Pro Gln Glu Glu Gln Glu Arg Glu Gln Leu Gln Pro His Glu
1025                1030                1035                1040

Asn Gly Glu Gly Asn Ser Glu Thr
                1045


<210> SEQ ID NO 231
<211> LENGTH: 188
<212> TYPE: PRT
<213> ORGANISM: Homo sapiens

<400> SEQUENCE: 231

Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Glu Pro Ala Ile Arg Pro Arg Ser Ser
    50                  55                  60
```

Gln Arg Val Pro Pro Met Gly Ile Gln His Ser Lys Glu Leu Asn Arg
65 70 75 80

Thr Cys Cys Leu Asn Gly Gly Thr Cys Met Leu Gly Ser Phe Cys Ala
85 90 95

Cys Pro Pro Ser Phe Tyr Gly Arg Asn Cys Glu His Asp Val Arg Lys
100 105 110

Glu Asn Cys Gly Ser Val Pro His Asp Thr Trp Leu Pro Lys Lys Cys
115 120 125

Ser Leu Cys Lys Cys Trp His Gly Gln Leu Arg Cys Phe Pro Gln Ala
130 135 140

Phe Leu Pro Gly Cys Asp Gly Leu Val Met Asp Glu His Leu Val Ala
145 150 155 160

Ser Arg Thr Pro Glu Leu Pro Pro Ser Ala Arg Thr Thr Thr Phe Met
165 170 175

Leu Val Gly Ile Cys Leu Ser Ile Gln Ser Tyr Tyr
180 185

<210> SEQ ID NO 232
<211> LENGTH: 750
<212> TYPE: PRT
<213> ORGANISM: Homo sapiens

<400> SEQUENCE: 232

Met Trp Asn Leu Leu His Glu Thr Asp Ser Ala Val Ala Thr Ala Arg
1 5 10 15

Arg Pro Arg Trp Leu Cys Ala Gly Ala Leu Val Leu Ala Gly Gly Phe
20 25 30

Phe Leu Leu Gly Phe Leu Phe Gly Trp Phe Ile Lys Ser Ser Asn Glu
35 40 45

Ala Thr Asn Ile Thr Pro Lys His Asn Met Lys Ala Phe Leu Asp Glu
50 55 60

Leu Lys Ala Glu Asn Ile Lys Lys Phe Leu Tyr Asn Phe Thr Gln Ile
65 70 75 80

Pro His Leu Ala Gly Thr Glu Gln Asn Phe Gln Leu Ala Lys Gln Ile
85 90 95

Gln Ser Gln Trp Lys Glu Phe Gly Leu Asp Ser Val Glu Leu Ala His
100 105 110

Tyr Asp Val Leu Leu Ser Tyr Pro Asn Lys Thr His Pro Asn Tyr Ile
115 120 125

Ser Ile Ile Asn Glu Asp Gly Asn Glu Ile Phe Asn Thr Ser Leu Phe
130 135 140

Glu Pro Pro Pro Pro Gly Tyr Glu Asn Val Ser Asp Ile Val Pro Pro
145 150 155 160

Phe Ser Ala Phe Ser Pro Gln Gly Met Pro Glu Gly Asp Leu Val Tyr
165 170 175

Val Asn Tyr Ala Arg Thr Glu Asp Phe Phe Lys Leu Glu Arg Asp Met
180 185 190

Lys Ile Asn Cys Ser Gly Lys Ile Val Ile Ala Arg Tyr Gly Lys Val
195 200 205

Phe Arg Gly Asn Lys Val Lys Asn Ala Gln Leu Ala Gly Ala Lys Gly
210 215 220

Val Ile Leu Tyr Ser Asp Pro Ala Asp Tyr Phe Ala Pro Gly Val Lys
225 230 235 240

Ser Tyr Pro Asp Gly Trp Asn Leu Pro Gly Gly Gly Val Gln Arg Gly

```
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670
```

Arg Ala Phe Ile Asp Pro Leu Gly Leu Pro Asp Arg Pro Phe Tyr Arg
675 680 685

His Val Ile Tyr Ala Pro Ser Ser His Asn Lys Tyr Ala Gly Glu Ser
690 695 700

Phe Pro Gly Ile Tyr Asp Ala Leu Phe Asp Ile Glu Ser Lys Val Asp
705 710 715 720

Pro Ser Lys Ala Trp Gly Glu Val Lys Arg Gln Ile Tyr Val Ala Ala
725 730 735

Phe Thr Val Gln Ala Ala Ala Glu Thr Leu Ser Glu Val Ala
740 745 750

<210> SEQ ID NO 233
<211> LENGTH: 976
<212> TYPE: PRT
<213> ORGANISM: Homo sapiens

<400> SEQUENCE: 233

Met Glu Leu Gln Ala Ala Arg Ala Cys Phe Ala Leu Leu Trp Gly Cys
1 5 10 15

Ala Leu Ala Ala Ala Ala Ala Ala Gln Gly Lys Glu Val Val Leu Leu
20 25 30

Asp Phe Ala Ala Ala Gly Gly Glu Leu Gly Trp Leu Thr His Pro Tyr
35 40 45

Gly Lys Gly Trp Asp Leu Met Gln Asn Ile Met Asn Asp Met Pro Ile
50 55 60

Tyr Met Tyr Ser Val Cys Asn Val Met Ser Gly Asp Gln Asp Asn Trp
65 70 75 80

Leu Arg Thr Asn Trp Val Tyr Arg Gly Glu Ala Glu Arg Ile Phe Ile
85 90 95

Glu Leu Lys Phe Thr Val Arg Asp Cys Asn Ser Phe Pro Gly Gly Ala
100 105 110

Ser Ser Cys Lys Glu Thr Phe Asn Leu Tyr Tyr Ala Glu Ser Asp Leu
115 120 125

Asp Tyr Gly Thr Asn Phe Gln Lys Arg Leu Phe Thr Lys Ile Asp Thr
130 135 140

Ile Ala Pro Asp Glu Ile Thr Val Ser Ser Asp Phe Glu Ala Arg His
145 150 155 160

Val Lys Leu Asn Val Glu Glu Arg Ser Val Gly Pro Leu Thr Arg Lys
165 170 175

Gly Phe Tyr Leu Ala Phe Gln Asp Ile Gly Ala Cys Val Ala Leu Leu
180 185 190

Ser Val Arg Val Tyr Tyr Lys Lys Cys Pro Glu Leu Leu Gln Gly Leu
195 200 205

Ala His Phe Pro Glu Thr Ile Ala Gly Ser Asp Ala Pro Ser Leu Ala
210 215 220

Thr Val Ala Gly Thr Cys Val Asp His Ala Val Val Pro Pro Gly Gly
225 230 235 240

Glu Glu Pro Arg Met His Cys Ala Val Asp Gly Glu Trp Leu Val Pro
245 250 255

Ile Gly Gln Cys Leu Cys Gln Ala Gly Tyr Glu Lys Val Glu Asp Ala
260 265 270

Cys Gln Ala Cys Ser Pro Gly Phe Phe Lys Phe Glu Ala Ser Glu Ser
275 280 285

Pro Cys Leu Glu Cys Pro Glu His Thr Leu Pro Ser Pro Glu Gly Ala

-continued

```
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly Val Ala Val Gly
    530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705                 710                 715                 720
```

```
Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
    770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
    850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
        915                 920                 925

Gly Tyr Thr Ala Ile Glu Lys Val Val Gln Met Thr Asn Asp Asp Ile
    930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975


<210> SEQ ID NO 234
<211> LENGTH: 668
<212> TYPE: PRT
<213> ORGANISM: Homo sapiens

<400> SEQUENCE: 234

Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Thr Val Ile Thr Ser Leu Gln Gln Glu Leu Cys Pro Ser Phe
```

-continued

```
        115                 120                 125

Leu Leu Pro Ser Ala Pro Ala Leu Gly Arg Cys Phe Pro Trp Thr Asn
    130                 135                 140

Val Thr Pro Pro Ala Leu Pro Gly Ile Thr Asn Asp Thr Thr Ile Gln
145                 150                 155                 160

Gln Gly Ile Ser Gly Leu Ile Asp Ser Leu Asn Ala Arg Asp Ile Ser
                165                 170                 175

Val Lys Ile Phe Glu Asp Phe Ala Gln Ser Trp Tyr Trp Ile Leu Val
            180                 185                 190

Ala Leu Gly Val Ala Leu Val Leu Ser Leu Leu Phe Ile Leu Leu Leu
        195                 200                 205

Arg Leu Val Ala Gly Pro Leu Val Leu Val Leu Ile Leu Gly Val Leu
    210                 215                 220

Gly Val Leu Ala Tyr Gly Ile Tyr Tyr Cys Trp Glu Glu Tyr Arg Val
225                 230                 235                 240

Leu Arg Asp Lys Gly Ala Ser Ile Ser Gln Leu Gly Phe Thr Thr Asn
                245                 250                 255

Leu Ser Ala Tyr Gln Ser Val Gln Glu Thr Trp Leu Ala Ala Leu Ile
            260                 265                 270

Val Leu Ala Val Leu Glu Ala Ile Leu Leu Leu Met Leu Ile Phe Leu
        275                 280                 285

Arg Gln Arg Ile Arg Ile Ala Ile Ala Leu Leu Lys Glu Ala Ser Lys
    290                 295                 300

Ala Val Gly Gln Met Met Ser Thr Met Phe Tyr Pro Leu Val Thr Phe
305                 310                 315                 320

Val Leu Leu Leu Ile Cys Ile Ala Tyr Trp Ala Met Thr Ala Leu Tyr
                325                 330                 335

Leu Ala Thr Ser Gly Gln Pro Gln Tyr Val Leu Trp Ala Ser Asn Ile
            340                 345                 350

Ser Ser Pro Gly Cys Glu Lys Val Pro Ile Asn Thr Ser Cys Asn Pro
        355                 360                 365

Thr Ala His Leu Val Asn Ser Ser Cys Pro Gly Leu Met Cys Val Phe
    370                 375                 380

Gln Gly Tyr Ser Ser Lys Gly Leu Ile Gln Arg Ser Val Phe Asn Leu
385                 390                 395                 400

Gln Ile Tyr Gly Val Leu Gly Leu Phe Trp Thr Leu Asn Trp Val Leu
                405                 410                 415

Ala Leu Gly Gln Cys Val Leu Ala Gly Ala Phe Ala Ser Phe Tyr Trp
            420                 425                 430

Ala Phe His Lys Pro Gln Asp Ile Pro Thr Phe Pro Leu Ile Ser Ala
        435                 440                 445

Phe Ile Arg Thr Leu Arg Tyr His Thr Gly Ser Leu Ala Phe Gly Ala
    450                 455                 460

Leu Ile Leu Thr Leu Val Gln Ile Ala Arg Val Ile Leu Glu Tyr Ile
465                 470                 475                 480

Asp His Lys Leu Arg Gly Val Gln Asn Pro Val Ala Arg Cys Ile Met
                485                 490                 495

Cys Cys Phe Lys Cys Cys Leu Trp Cys Leu Glu Lys Phe Ile Lys Phe
            500                 505                 510

Leu Asn Arg Asn Ala Tyr Ile Met Ile Ala Ile Tyr Gly Lys Asn Phe
        515                 520                 525

Cys Val Ser Ala Lys Asn Ala Phe Met Leu Leu Met Arg Asn Ile Val
    530                 535                 540
```

```
Arg Val Val Val Leu Asp Lys Val Thr Asp Leu Leu Leu Phe Phe Gly
545                 550                 555                 560

Lys Leu Leu Val Val Gly Gly Val Gly Val Leu Ser Phe Phe Phe Phe
                565                 570                 575

Ser Gly Arg Ile Pro Gly Leu Gly Lys Asp Phe Lys Ser Pro His Leu
            580                 585                 590

Asn Tyr Tyr Trp Leu Pro Ile Met Thr Ser Ile Leu Gly Ala Tyr Val
        595                 600                 605

Ile Ala Ser Gly Phe Phe Ser Val Phe Gly Met Cys Val Asp Thr Leu
    610                 615                 620

Phe Leu Cys Phe Leu Glu Asp Leu Glu Arg Asn Asn Gly Ser Leu Asp
625                 630                 635                 640

Arg Pro Tyr Tyr Met Ser Lys Ser Leu Leu Lys Ile Leu Gly Lys Lys
                645                 650                 655

Asn Glu Ala Pro Pro Asp Asn Lys Lys Arg Lys Lys
            660                 665


<210> SEQ ID NO 235
<211> LENGTH: 214
<212> TYPE: PRT
<213> ORGANISM: Artificial Sequence
<220> FEATURE:
<223> OTHER INFORMATION: antibody constituent

<400> SEQUENCE: 235

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 236
```

```
<211> LENGTH: 449
<212> TYPE: PRT
<213> ORGANISM: Artificial Sequence
<220> FEATURE:
<223> OTHER INFORMATION: antibody consituent

<400> SEQUENCE: 236

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 237
<211> LENGTH: 214
<212> TYPE: PRT
<213> ORGANISM: Artificial Sequence
<220> FEATURE:
<223> OTHER INFORMATION: antibody constituent

<400> SEQUENCE: 237

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Phe Cys Gln His Phe Asp His Leu Pro Leu
85 90 95

Ala Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 238
<211> LENGTH: 444
<212> TYPE: PRT
<213> ORGANISM: Artificial Sequence
<220> FEATURE:
<223> OTHER INFORMATION: antibody constituent

<400> SEQUENCE: 238

Gln Val Gln Leu Gln Glu Ser Gly Pro Gly Leu Val Lys Pro Ser Glu
1 5 10 15

```
Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430
```

His Tyr Thr Gln Lys Ser Leu Ser Leu Ser Pro Gly
435 440

<210> SEQ ID NO 239
<211> LENGTH: 219
<212> TYPE: PRT
<213> ORGANISM: Artificial Sequence
<220> FEATURE:
<223> OTHER INFORMATION: antibody constituent

<400> SEQUENCE: 239

Asp Ile Gln Met Thr Gln Ser Pro Ser Ser Leu Ser Ala Ser Val Gly
1 5 10 15

Asp Arg Val Thr Ile Thr Cys Arg Ser Ser Gln Asn Ile Val His Ser
20 25 30

Asn Gly Asn Thr Tyr Leu Asp Trp Tyr Gln Gln Thr Pro Gly Lys Ala
35 40 45

Pro Lys Leu Leu Ile Tyr Lys Val Ser Asn Arg Phe Ser Gly Val Pro
50 55 60

Ser Arg Phe Ser Gly Ser Gly Ser Gly Thr Asp Phe Thr Phe Thr Ile
65 70 75 80

Ser Ser Leu Gln Pro Glu Asp Ile Ala Thr Tyr Tyr Cys Phe Gln Tyr
85 90 95

Ser His Val Pro Trp Thr Phe Gly Gln Gly Thr Lys Leu Gln Ile Thr
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 240
<211> LENGTH: 453
<212> TYPE: PRT
<213> ORGANISM: Artificial Sequence
<220> FEATURE:
<223> OTHER INFORMATION: antibody constituent

<400> SEQUENCE: 240

Gln Val Gln Leu Gln Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Ile Tyr Trp Val Arg Gln Ala Pro Gly Gln Gly Leu Glu Trp Ile
35 40 45

Gly Gly Ile Asn Pro Thr Ser Gly Gly Ser Asn Phe Asn Glu Lys Phe
50 55 60

Lys Thr Arg Val Thr Ile Thr Ala Asp Glu Ser Ser Thr Thr Ala Tyr
65 70 75 80

```
Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 241
<211> LENGTH: 449
<212> TYPE: PRT
<213> ORGANISM: Artificial Sequence
<220> FEATURE:

<223> OTHER INFORMATION: antibody constituent

<400> SEQUENCE: 241

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

-continued

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 242
<211> LENGTH: 449
<212> TYPE: PRT
<213> ORGANISM: Artificial Sequence
<220> FEATURE:
<223> OTHER INFORMATION: antibody constituent

<400> SEQUENCE: 242

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
```

305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 243
<211> LENGTH: 449
<212> TYPE: PRT
<213> ORGANISM: Artificial Sequence
<220> FEATURE:
<223> OTHER INFORMATION: antibody constituent

<400> SEQUENCE: 243

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Pro Tyr
20 25 30

Pro Met Ile Trp Val Arg Gln Ala Pro Gly Lys Gly Leu Glu Trp Val
35 40 45

Ser Tyr Ile Ser Pro Ser Gly Gly Ser Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Asp Thr Tyr Phe Asp Tyr Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Asn Tyr Gln Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 244
<211> LENGTH: 449
<212> TYPE: PRT
<213> ORGANISM: Artificial Sequence
<220> FEATURE:
<223> OTHER INFORMATION: antibody constituent

<400> SEQUENCE: 244

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 245
<211> LENGTH: 449
<212> TYPE: PRT
<213> ORGANISM: Artificial Sequence
<220> FEATURE:
<223> OTHER INFORMATION: antibody constituent

<400> SEQUENCE: 245

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

UNITED STATES PATENT AND TRADEMARK OFFICE
CERTIFICATE OF CORRECTION

| | |
|---|---|
| PATENT NO. | : 11,123,439 B2 |
| APPLICATION NO. | : 15/739111 |
| DATED | : September 21, 2021 |
| INVENTOR(S) | : Lerchen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 503 days.

Signed and Sealed this
Thirty-first Day of January, 2023

*Katherine Kelly Vidal*

Katherine Kelly Vidal
*Director of the United States Patent and Trademark Office*